United States Patent
Yang et al.

(10) Patent No.: US 11,548,861 B2
(45) Date of Patent: *Jan. 10, 2023

(54) DRUGS AND COMPOSITIONS FOR THE TREATMENT OF OCULAR DISORDERS

(71) Applicant: Graybug Vision, Inc., Redwood City, CA (US)

(72) Inventors: Ming Yang, Lutherville-Timonium, MD (US); John G. Bauman, El Sobrante, CA (US); Jeffrey L. Cleland, San Carlos, CA (US); Nu Hoang, Annapolis, MD (US); Emmett Cunningham, Hillsboro, CA (US)

(73) Assignee: Graybug Vision, Inc., Redwood City, CA (US)

( * ) Notice: Subject to any disclaimer, the term of this patent is extended or adjusted under 35 U.S.C. 154(b) by 319 days.

This patent is subject to a terminal disclaimer.

(21) Appl. No.: 16/578,003

(22) Filed: Sep. 20, 2019

(65) Prior Publication Data

US 2020/0031783 A1 Jan. 30, 2020

Related U.S. Application Data

(63) Continuation of application No. PCT/US2018/024080, filed on Mar. 23, 2018.

(60) Provisional application No. 62/598,933, filed on Dec. 14, 2017, provisional application No. 62/475,802, filed on Mar. 23, 2017.

(51) Int. Cl.
| | |
|---|---|
| *C07D 271/04* | (2006.01) |
| *C07D 231/12* | (2006.01) |
| *C07D 403/06* | (2006.01) |
| *C07D 403/12* | (2006.01) |
| *C07D 417/04* | (2006.01) |
| *C07D 417/14* | (2006.01) |
| *C07D 487/04* | (2006.01) |
| *C07D 495/04* | (2006.01) |
| *C07D 513/04* | (2006.01) |

(52) U.S. Cl.
CPC ......... *C07D 271/04* (2013.01); *C07D 231/12* (2013.01); *C07D 403/06* (2013.01); *C07D 403/12* (2013.01); *C07D 417/04* (2013.01); *C07D 417/14* (2013.01); *C07D 487/04* (2013.01); *C07D 495/04* (2013.01); *C07D 513/04* (2013.01)

(58) Field of Classification Search
CPC .. C07D 271/04; C07D 231/12; C07D 403/06; C07D 403/12; C07D 417/04; C07D 417/14; C07D 487/04; C07D 495/04; C07D 513/04
See application file for complete search history.

(56) References Cited

U.S. PATENT DOCUMENTS

| | | | |
|---|---|---|---|
| 4,760,057 A | 7/1988 | Alexander | |
| 4,767,784 A | 8/1988 | Zölss et al. | |
| 4,911,920 A | 3/1990 | Jani et al. | |
| 4,997,443 A | 3/1991 | Walthall et al. | |
| 4,997,652 A | 3/1991 | Wong | |
| 5,441,722 A | 8/1995 | Eng et al. | |
| 5,502,092 A | 3/1996 | Barrows et al. | |
| 5,565,215 A | 10/1996 | Gref et al. | |
| 5,624,677 A | 4/1997 | El-Rashidy et al. | |
| 5,650,541 A | 7/1997 | May | |
| 5,681,964 A | 9/1997 | Ashton et al. | |
| 5,866,155 A | 2/1999 | Laurencin et al. | |
| 5,869,103 A | 2/1999 | Yeh et al. | |
| 5,945,126 A | 8/1999 | Thanoo et al. | |
| 6,007,845 A | 12/1999 | Domb et al. | |
| 6,051,576 A | 4/2000 | Ashton et al. | |
| 6,129,761 A | 10/2000 | Hubbell | |
| 6,201,072 B1 | 3/2001 | Rathi et al. | |
| 6,270,802 B1 | 8/2001 | Thanoo et al. | |
| 6,287,588 B1 | 9/2001 | Shih et al. | |
| 6,306,169 B1 | 10/2001 | Lee et al. | |
| 6,375,972 B1 | 4/2002 | Guo et al. | |
| 6,379,962 B1 | 4/2002 | Holy et al. | |
| 6,495,164 B1 | 12/2002 | Ramstack et al. | |
| 6,534,084 B1 | 3/2003 | Vyakamam et al. | |
| 6,573,293 B2 | 6/2003 | Tang et al. | |
| 6,706,289 B2 | 3/2004 | Lewis et al. | |
| 6,765,019 B1 | 7/2004 | Crooks et al. | |
| 6,818,018 B1 | 11/2004 | Sawhney | |
| 6,841,097 B2 | 1/2005 | Andersson et al. | |

(Continued)

FOREIGN PATENT DOCUMENTS

| | | |
|---|---|---|
| CN | 101081206 A | 12/2007 |
| CN | 103833998 B | 6/2014 |

(Continued)

OTHER PUBLICATIONS

Registry No. 1348212-51-0, file Registry on STN, entered STN Dec. 4, 2011.*

(Continued)

*Primary Examiner* — Rebecca L Anderson

(74) *Attorney, Agent, or Firm* — Knowles Intellectual Property Strategies, LLC

(57) ABSTRACT

The present invention provides new prodrugs of therapeutically active compounds, including oligomeric prodrugs, and compositions to treat medical disorders, for example glaucoma, a disorder or abnormality related to an increase in intraocular pressure (IOP), a disorder requiring neuroprotection, age-related macular degeneration, or diabetic retinopathy.

11 Claims, 68 Drawing Sheets

(56) References Cited

U.S. PATENT DOCUMENTS

| | | |
|---|---|---|
| 6,841,617 B2 | 1/2005 | Jeong et al. |
| 7,030,250 B2 | 4/2006 | Losada et al. |
| 7,115,280 B2 | 10/2006 | Hanna et al. |
| 7,125,905 B2 | 10/2006 | Tang et al. |
| 7,163,697 B2 | 1/2007 | Hanes et al. |
| 7,211,600 B2 | 5/2007 | Lipson et al. |
| 7,470,717 B2 | 12/2008 | Ohta et al. |
| 7,501,179 B2 | 3/2009 | Song et al. |
| 7,771,742 B2 | 8/2010 | Hughes et al. |
| 8,008,283 B2 | 8/2011 | Hochman et al. |
| 8,268,342 B2 | 9/2012 | Panda et al. |
| 8,552,139 B2 | 6/2013 | Bezwada |
| 8,492,334 B2 | 7/2013 | Lavik et al. |
| 8,592,427 B2 | 11/2013 | Blumberg et al. |
| 8,623,395 B2 | 1/2014 | de Jean, Jr. et al. |
| 8,628,801 B2 | 1/2014 | Garreta et al. |
| 8,632,809 B2 | 1/2014 | Asgharian et al. |
| 8,663,674 B2 | 3/2014 | Wen et al. |
| 8,685,435 B2 | 4/2014 | Nivaggioli et al. |
| 8,710,069 B2 | 4/2014 | Holtman et al. |
| 8,710,070 B2 | 4/2014 | Holtman et al. |
| 8,815,284 B2 | 8/2014 | Guo et al. |
| 8,871,241 B2 | 10/2014 | Chou et al. |
| 8,889,193 B2 | 11/2014 | McDonnell et al. |
| 8,905,963 B2 | 12/2014 | de Jean, Jr. et al. |
| 8,939,948 B2 | 1/2015 | de Jean, Jr. et al. |
| 8,957,034 B2 | 2/2015 | Hanes et al. |
| 8,962,577 B2 | 2/2015 | Hanes et al. |
| 8,993,615 B2 | 3/2015 | Zack et al. |
| 9,023,896 B2 | 5/2015 | Ashton et al. |
| 9,056,057 B2 | 6/2015 | Popov et al. |
| 9,095,506 B2 | 8/2015 | Spanda et al. |
| 9,107,748 B2 | 8/2015 | de Jean, Jr. et al. |
| 9,125,735 B2 | 9/2015 | de Jean, Jr. et al. |
| 9,161,903 B2 | 10/2015 | Drapeau et al. |
| 9,161,938 B2 | 10/2015 | Huang et al. |
| 9,162,981 B2 | 10/2015 | Zack et al. |
| 9,327,037 B2 | 5/2016 | Suk et al. |
| 9,399,636 B2 | 7/2016 | Cohen et al. |
| 9,415,020 B2 | 8/2016 | Ensign et al. |
| 9,539,239 B1 | 1/2017 | Zack et al. |
| 9,539,259 B2 | 1/2017 | Zack et al. |
| 9,669,136 B2 | 6/2017 | Friedman et al. |
| 9,682,928 B2 | 6/2017 | Partridge et al. |
| 9,789,198 B2 | 10/2017 | Xu et al. |
| 9,808,531 B2 | 11/2017 | Cleland et al. |
| 9,868,720 B2 | 1/2018 | Cohen et al. |
| 9,968,708 B2 | 5/2018 | Spector et al. |
| 10,195,212 B2 | 2/2019 | Hanes et al. |
| 11,160,870 B2 * | 11/2021 | Yang ............... A61K 31/382 |
| 2002/0128224 A1 | 9/2002 | Boyer et al. |
| 2003/0118528 A1 | 6/2003 | Walters et al. |
| 2003/0170286 A1 | 9/2003 | Ashton et al. |
| 2003/0220509 A1 | 11/2003 | Losada et al. |
| 2004/0175429 A1 | 9/2004 | Alavattam |
| 2004/0180036 A1 | 9/2004 | Ashton et al. |
| 2004/0234611 A1 | 11/2004 | Ahlheim et al. |
| 2004/0254182 A1 | 12/2004 | Mulvihill et al. |
| 2005/0048123 A1 | 3/2005 | Su et al. |
| 2005/0164994 A1 | 7/2005 | Ashton et al. |
| 2005/0249773 A1 | 10/2005 | Maspero et al. |
| 2006/0135609 A1 | 6/2006 | Toone et al. |
| 2006/0246145 A1 | 11/2006 | Chang et al. |
| 2006/0260777 A1 | 11/2006 | Rashba-Step et al. |
| 2006/0263335 A1 | 11/2006 | France et al. |
| 2007/0112050 A1 | 5/2007 | Ashton et al. |
| 2008/0118547 A1 | 5/2008 | Huang et al. |
| 2008/0306041 A1 | 12/2008 | Garvey |
| 2009/0163457 A1 | 6/2009 | Ashton et al. |
| 2009/0203709 A1 | 8/2009 | Steinberg et al. |
| 2010/0063035 A1 | 3/2010 | Benedini et al. |
| 2010/0063175 A1 | 3/2010 | Ginty et al. |
| 2010/0152272 A1 | 6/2010 | Bezwada |
| 2010/0143479 A1 | 7/2010 | Thanoo et al. |
| 2010/0215580 A1 | 8/2010 | Hanes et al. |
| 2010/0226985 A1 | 9/2010 | Tomme et al. |
| 2010/0227905 A1 | 9/2010 | Kabra et al. |
| 2010/0247669 A1 | 9/2010 | Eliasof et al. |
| 2010/0227865 A1 | 11/2010 | Riggs-Sauthier et al. |
| 2011/0123446 A1 | 5/2011 | DeSimone et al. |
| 2012/0004225 A1 | 1/2012 | Wanaski et al. |
| 2012/0052041 A1 | 3/2012 | Basu et al. |
| 2012/0063997 A1 | 3/2012 | Hunter et al. |
| 2012/0121718 A1 | 5/2012 | Lai et al. |
| 2012/0259008 A1 | 10/2012 | Ueno |
| 2012/0263803 A1 | 10/2012 | Mashima et al. |
| 2013/0071349 A1 | 3/2013 | Robinston et al. |
| 2013/0183244 A1 | 7/2013 | Hanes et al. |
| 2013/0272994 A1 | 10/2013 | Fu et al. |
| 2013/0281637 A1 | 10/2013 | Ueno et al. |
| 2013/0316006 A1 | 11/2013 | Popov et al. |
| 2013/0331425 A1 | 12/2013 | Culbertson et al. |
| 2014/0039030 A1 | 2/2014 | Kozlowski et al. |
| 2014/0094472 A1 | 4/2014 | Blumberg et al. |
| 2014/0107025 A1 | 4/2014 | Wirostko |
| 2014/0178475 A1 | 6/2014 | Figueiredo et al. |
| 2014/0276482 A1 | 9/2014 | Astafieva et al. |
| 2014/0294986 A1 | 10/2014 | Liu et al. |
| 2014/0329913 A1 | 11/2014 | Hanes et al. |
| 2015/0056300 A1 | 2/2015 | Dewitt et al. |
| 2015/0086484 A1 | 3/2015 | Hanes et al. |
| 2015/0099802 A1 | 4/2015 | Ueno et al. |
| 2015/0140106 A1 | 5/2015 | Mousa |
| 2015/0147406 A1 | 5/2015 | Robinson et al. |
| 2015/0174096 A1 | 6/2015 | Bottger et al. |
| 2016/0310417 A1 | 10/2016 | Prausnitz et al. |
| 2016/0324836 A1 | 11/2016 | Aston et al. |
| 2017/0157147 A1 | 6/2017 | Hanes et al. |
| 2017/0273901 A1 | 9/2017 | Fu et al. |
| 2017/0360750 A1 | 12/2017 | Fu et al. |
| 2018/0008718 A1 | 1/2018 | Fu et al. |

FOREIGN PATENT DOCUMENTS

| | | |
|---|---|---|
| CN | 103897174 A | 7/2014 |
| CN | 104774193 A | 7/2015 |
| EP | 1329453 B1 | 6/2004 |
| EP | 3006050 B1 | 2/2018 |
| GB | 844946 | 8/1960 |
| JP | 2016-132616 A | 7/2016 |
| KR | 2015-0117745 A | 10/2015 |
| WO | WO 1988007044 | 9/1988 |
| WO | WO 1993/23394 A1 | 11/1993 |
| WO | WO 199620698 A2 | 7/1996 |
| WO | WO 1996020698 A2 | 7/1996 |
| WO | WO 1999001498 A1 | 1/1999 |
| WO | WO 2000064953 A1 | 11/2000 |
| WO | WO 2000064977 A1 | 11/2000 |
| WO | WO 2002080910 A1 | 10/2002 |
| WO | WO 2004028583 A2 | 4/2004 |
| WO | WO 2005/072710 A2 | 8/2005 |
| WO | WO 2005/110368 A1 | 11/2005 |
| WO | WO 2005112884 A1 | 12/2005 |
| WO | WO 2006014626 A2 | 2/2006 |
| WO | WO 2006/026215 A1 | 3/2006 |
| WO | WO 2006/047466 A2 | 5/2006 |
| WO | WO 2006133519 A1 | 12/2006 |
| WO | WO 2007062266 A2 | 5/2007 |
| WO | WO 2007090793 A1 | 8/2007 |
| WO | WO 2008030557 A2 | 3/2008 |
| WO | WO 2008041001 A1 | 4/2008 |
| WO | WO 2008075155 A2 | 6/2008 |
| WO | WO 2008132114 A1 | 11/2008 |
| WO | WO 2008157614 A9 | 12/2008 |
| WO | WO 2009019501 A1 | 2/2009 |
| WO | WO 2009030270 A1 | 3/2009 |
| WO | WO 2009035565 A1 | 3/2009 |
| WO | WO 2009089070 A2 | 7/2009 |
| WO | WO 2009/109501 A2 | 9/2009 |
| WO | WO 2011 119777 A3 | 9/2011 |
| WO | WO 2011163594 A2 | 12/2011 |
| WO | WO 2013174780 A1 | 11/2013 |
| WO | WO 2013177367 A2 | 11/2013 |
| WO | WO 2014146486 A1 | 9/2014 |

(56) References Cited

FOREIGN PATENT DOCUMENTS

| | | |
|---|---|---|
| WO | WO 2014177524 A1 | 11/2014 |
| WO | WO 2015035974 A1 | 3/2015 |
| WO | WO 2015172149 A1 | 11/2015 |
| WO | WO 2016100380 A1 | 6/2016 |
| WO | WO 2016100392 A1 | 6/2016 |
| WO | WO 2016118506 A1 | 7/2016 |
| WO | WO 2019210215 A1 | 1/2019 |
| WO | WO 2019118924 A1 | 6/2019 |
| WO | WO 2019209883 A1 | 10/2019 |
| WO | WO 2020/069353 A1 | 4/2020 |
| WO | WO 2020069353 A1 | 4/2020 |
| WO | WO 2020/102758 A1 | 5/2020 |
| WO | WO 2020102758 A1 | 5/2020 |

OTHER PUBLICATIONS

US, 2018/0326078, A1, U.S. Appl. No. 15/976,847, Yang et al., Nov. 15, 2018.
US, 2020/0308162, A1, U.S. Appl. No. 16/899,422, Cleland et al., Oct. 1, 2020.
US, 2021/0040111, A1, U.S. Appl. No. 17/077,853, Yang et al., Feb. 11, 2021.
US, 2021/0085607, A1, U.S. Appl. No. 17/077,856, Saragnese et al., Mar. 25, 2021.
U.S. Appl. No. 17/212,873, filed Mar. 25, 2021, Bauman et al.
U.S. Pat. No. 10,441,548, B2, U.S. Appl. No. 15/349,985, Yu et al., Nov. 15, 2018.
US, 2020/0000734, A1, U.S. Appl. No. 16/566,721, Yu et al., Jan. 2, 2020.
US, 2020/0000735, A1, U.S. Appl. No. 16/566,724, Yu et al., Jan. 2, 2020.
US, 2020/0230246, A1, U.S. Appl. No. 16/821,738, Yang et al., Jul. 23, 2020.
U.S. Pat. No. 11,160,870, B2, U.S. Appl. No. 15/976,847, Yang et al., Nov. 2, 2021.
US, 2021/0214374, A1, U.S. Appl. No. 17/212,873, Bauman et al., Jul. 15, 2021.
US, 2021/0275456, A1, U.S. Appl. No. 17/319,971, Yang et al., Sep. 9, 2021.
Amparo F. et al. "Safety and efficacy of the multitargeted receptor kinase inhibitor pazopanib in the treatment of corneal neovascularization" Invest Ophthalmol Vis Sci. 2013; 54(1), 537-44.
Benny, O. "Local Delivery of Poly Lactic-co-glycolic Acid Microspheres Containing Imatinib Mesylate Inhibits Intracranial Xenograft Glioma Growth" Clin Cancer Res 2009; 15(4), 1222-1231.
Bundgard, H. et al. "N-Sulfonyl Imidates as a Novel Prodrug Form for an Ester Function or a Sulfonamide Group" J. Med. Chem, 1988, 31, 2066-2069.
Cynkowska et al. (2005). "Novel antiglaucoma prodrugs and codrugs of ethacrynic acid" Bioorganic & Medicinal Chemistry Letters 15: 3524-3527.
Fuchs et al. "Sunitinib-eluting beads for chemoembolization: methods for in vitro evaluation of drug release" International Journal of Pharmaceutics 482, 68-74 (2015).
Herrero-Vanrell et al. (2014). "The potential of using biodegradable microspheres in retinal diseases and other intraocular pathologies" Prog Retin Eye Res. 42:27-43.
Li et al. (2008). "Microencapsulation by solvent evaporation: State of the art for process engineering approaches" International Journal of Pharmaceutics 363: 26-39.
Pubchem CID 12805966 (Create Date: Feb. 8, 2007).
Pubchem CID 162349 (Create Date: Aug. 8, 2005).
Pubchem CID 2435 (Create Date: Mar. 25, 2005).
Pubchem CID 2583 (Create Date: Mar. 25, 2005).
Pubchem CID 33624 (Create Date: Jun. 24, 2005).
"Pubchem Substance Record for SID 229019533. Available Date: Feb. 12, 2012".
"Pubchem Substance Record for SID 349991479. Available Date: Dec. 20, 2017".

Qiang Huang, et al.; Prodrug AST-003 Improves the Therapeutic Index of the Multi-Targeted Tyrosine Kinase Inhibitor Sunitinib; PLoS One; 2015; vol. 10 (10); pp. 1-14.
Ramazani et al. (2015) "Sunitinib microspheres based on [PDLLA-PEG-PDLLA]-b-PLLA multi-block copolymers for ocular drug delivery" Eur J Pharm Biopharm. 95(Pt B):368-77.
Rao et al. (1989). "Zur Acylierung von Hydroxy- und Mercapto-carbonsaureestern nach dem Carbodiimid/Acylierungskatalysator—Verfahren" Arch. Pharm. (Weinheim) 322:523-530. Table 3, compound 18.
Welsbie et al. (2013). "Functional genomic screening identifies dual leucine zipper kinase as a key mediator of retinal ganglion cell death" PNAS 110:4045-4050.
Zhao et al. (2014) "Preparation and characterization of sunitinib-loaded microspheres for arterial embolization" Journal of Chinese Pharmaceutical Sciences 23:558-564.
Wagh, et al. "Polymers used in ocular dosage form and drug delivery systems" Asian Journal of Pharmaceutics—Jan. 2008.
U.S. Pat. No. 9,808,531, B2, U.S. Appl. No. 15/273,686, Cleland et al., Nov. 7, 2017.
U.S. Pat. No. 9,956,302, B2, U.S. Appl. No. 15/782,755, Cleland et al., May 1, 2018.
U.S. Pat. No. 10,098,965, B2, U.S. Appl. No. 15/782,744, Cleland et al., Oct. 16, 2018.
U.S. Pat. No. 10,111,964, B2, U.S. Appl. No. 15/842,712, Cleland et al., Oct. 30, 2018.
U.S. Pat. No. 10,117,950, B2, U.S. Appl. No. 15/782,749, Cleland et al., Nov. 6, 2018.
U.S. Pat. No. 10,159,747, B2, U.S. Appl. No. 15/842,684, Cleland et al., Dec. 25, 2018.
U.S. Pat. No. 10,485,876, B2, U.S. Appl. No. 16/162,158, Cleland et al., Nov. 26, 2019.
Barot, et al. "Prodrug Strategies in Ocular Drug Delivery" Med. Chem. 2012, 8(4), 753-768.
Shahzard et al. "Aggregation and clogging phenomena of rigid microparticles in microfluidics" Microfluidics and Nanofluidics, 2018, 22, 1-17.
Tam et al. "Oligo(lactic acid)n-Paclitaxel Prodrugs for Poly(ethylene glycol)-block-poly(lactic acid) Micelles: Loading, Release, and Backbiting Conversion for Anticancer Activity" Supplemental Information J. Am. Chem. Soc. 2016, 138(28), 8674-8677.
US, 2020/0000734, A1, U.S. Appl. No. 15/566,721, Yu et al., Jan. 2, 2020.
U.S. Appl. No. 17/319,971, filed May 13, 2021, Yang et al.
Pech, et al., "Preliminary Evaluation of a Series of Amphiphilic Timolol Prodrug: Possible Evidence for Transcleral Absorption" Journal of Ocular Pharmacology, 1993, 9(2), 141-150.
Sahoo et al., "Residual polyvinyl alcohol associated with polu(D. L-lactide-co-glycolide) nanoparticles affect their physical properties and cellular uptake", Journal of Controlled Release, 2002, 82, 105-114.
Bouligand, et al., "The lyotropic polymorphism of two pharmacologically active molecules", Liquid Crystals, vol. 26, No. 9, 12-1293, 1999.
Chang, et al., "Synthesis and Characterization of Novel PGA and PLA Prodrug with Sulfadiazine and 5-Fluorouracil Terminal Groups", Journal of Macromolecular Science, Part A: Pure and Applied Chemistry, (2007) 44, 887-892.
Chien, et al., "Role of Enzymatic Lability in the Corneal and Conjunctival Penetration of Timolol Ester Prodrugs in the Pigmented Rabbit", Pharmaceutical Research, vol. 8, No. 6, 1991.
Luo, et al., "One-pot preparation of polylactic acid-ibuprofen conjugates and their performance characterization", Polymer Chemistry; Issue 45, 2017.
Pech, et al., "Preliminary Evaluation of a Series of Amphiphilic Timolol Prodrugs: Possible Evidence for Transcleral Absorption" Journal of Ocular Pharmacology, vol. 9, No. 2, 1993.
Bouligand Y. et al., "The lyotropic polymorphism of two pharmacologically active molecules", Liquid Crystals), vol. 26, No. 9, doi:10.1080/026782999203940, pp. 1281-1293, 1999.
Kharkevich D.A., (Pharmacology, 10th ed. M.: GEOTAR-Media, 2010, p. 73-74) Translations.

(56) References Cited

OTHER PUBLICATIONS

Kummerer, K., Pharmaceuticals in the environment, annual review of environment and resources, 2010, V .35, p. 57-75, 35 doi: 10.1146/annurev-environ-052809-161223.

Shi-He Luo et al, "One-pot preparation of polylactic acid-ibuprofen conjugates and their performance characterization", Polymer Chemistry, vol. 8, No. 45, doi:10.1039/C7PY01213F, pp. 7009-7016, 2017.

Yu Tong Tam et al, "Oligo(lactic acid) n-Paclitaxel Prodrugs for Poly(ethylene glycol)-block-poly(lactic acid) Micelles: Loading, Release, and Backbiting Conversion 5 for Anticancer Activity", Journal of The American Chemical Society, vol. 13 8, No. 28, pp. 8674-8677, 2016.

\* cited by examiner

DRUGS AND COMPOSITIONS FOR THE TREATMENT OF OCULAR DISORDERS

CROSS-REFERENCE TO RELATED APPLICATIONS

This application is a continuation of International Application No. PCT/US18/24080 filed in the United States Patent and Trademark Office Receiving Office on Mar. 23, 2018, which claims the benefit of provisional U.S. Application No. 62/475,802 filed Mar. 23, 2017 and U.S. Application No. 62/598,933 filed Dec. 14, 2017. The entirety of these applications is hereby incorporated by reference for all purposes.

BACKGROUND

The eye is a complex organ with unique anatomy and physiology. The structure of the eye can be divided into two parts, the anterior and posterior. The cornea, conjunctiva, aqueous humor, iris, ciliary body and lens are in the anterior portion. The posterior portion includes the sclera, choroid, retinal pigment epithelium, neural retina, optic nerve and vitreous humor. The most important diseases affecting the anterior segment include glaucoma, allergic conjunctivitis, anterior uveitis and cataracts. The most prevalent diseases affecting the posterior segment of the eye are dry and wet age-related macular degeneration (AMD) and diabetic retinopathy.

Typical routes of drug delivery to the eye are topical, systemic, subconjunctival, intravitreal, punctal, intrascleral, transscleral, anterior or posterior sub-Tenon's, suprachoroidal, choroidal, subchoroidal, and subretinal.

To address issues of ocular delivery, a large number of types of delivery systems have been devised. These include conventional (solution, suspension, emulsion, ointment, inserts and gels); vesicular (liposomes, exosomes, niosomes, discomes and pharmacosomes); advanced materials (scleral plugs, gene delivery, siRNA and stem cells); and, controlled release systems (implants, hydrogels, dendrimers, iontophoresis, collagen shields, polymeric solutions, therapeutic contact lenses, cyclodextrin carriers, microneedles and microemulsions and particulates (microparticles and nanoparticles)).

Topical drops are the most widely used non-invasive routes of drug administration to treat anterior ocular diseases. However, a number of barriers exist to effective topical delivery, including tear turnover, nasolacrimal drainage, reflex blinking, and the barrier of the mucosal membrane. It is considered that less than 5% of topically applied dosages reach the deeper ocular tissue.

The patient may be required to instill topical drops up to four times a day. Indeed, certain patients, including corneal transplant recipients, require therapeutic doses of medications to be continuously maintained in the corneal tissues and some patients are required to endure lengthy and arduous dosing regimens that often involve up to hourly application. Each repeat dosing not only requires a further investment of a patient's time, but also increases the chance of irritation and non-compliance.

Drug delivery to the posterior area of the eye usually requires a different mode of administration from topical drops, and is typically achieved via an intravitreal injection, periocular injection or systemic administration. Systemic administration is not preferred given the ratio of volume of the eye to the entire body and thus unnecessary potential systemic toxicity. Therefore, intravitreal injections are currently the most common form of drug administration for posterior disorders. However, intravitreal injections also risk problems due to the common side effect of inflammation to the eye caused by administration of foreign material to this sensitive area, endophthalmitis, hemorrhage, retinal detachment and poor patient compliance.

Transscleral delivery with periocular administration is seen as an alternative to intravitreal injections, however, ocular barriers such as the sclera, choroid, retinal pigment epithelium, lymphatic flow and general blood flow compromise efficacy.

To treat ocular diseases, and in particular diseases of the posterior chamber, the drug must be delivered in an amount and for a duration to achieve efficacy. This seemingly straightforward goal is difficult to achieve in practice.

Examples of common drug classes used for ocular disorders include: prostaglandins, carbonic anhydrase inhibitors, receptor tyrosine kinase inhibitors (RTKIs), Rho kinase (ROCK) inhibitors, beta-blockers, alpha-adrenergic agonists, parasympathomimetics, epinephrine, and hyperosmotic agents.

Although a number of prostaglandin carboxylic acids are effective in treating eye disorders, for example, lowering intraocular pressure (IOP), their hydrophilic nature can lead to rapid clearance from the surface of the eye before effective therapy can be achieved. As a result, prostaglandins are dosed in the form of selected esters to allow entry to the eye and a "prolonged" residence. When in the eye, native esterase enzymes cleave the prostaglandin ester to release the active species. Despite this innovation, current drop administered prostaglandins, for example, latanoprost, bimatoprost, and travoprost, still require daily or several times daily dosing regimens and may cause irritation or hyperemia to the eye in some patients. In addition, nearly half of patients on prostaglandin therapy for glaucoma require a second agent for control of IOP (Physician Drug and Diagnosis Audit (PDDA) from Verispan, L.L.C. January-June, 2003)

Carbonic anhydrase inhibitors (CAIs) are used as an alternative and sometimes in conjunction with prostaglandins to treat eye disorders. Unfortunately, compliancy issues can occur as these medications also require daily or dosing up to four times a day, and may also cause irritation or hyperemia to the eye in some patients.

Another potential avenue for the treatment of ocular disorders involves protecting neurons directly. Preliminary data on receptor tyrosine kinase inhibitors (RTKIs) and dual leucine zipper kinase inhibitors (DLKIs) suggests that instead of treating increasing ocular pressure, molecules such as Sunitinib and Crizotinib can prevent the nerve damage that is associated with it. Unfortunately, Sunitinib has had observed hepatotoxicity in both clinical trials and post-marketing clinical use.

References that describe treatments of ocular disorders and the synthesis of compounds related to treating ocular disorders include the following: Ongini et al., U.S. Pat. No. 8,058,467 titled "Prostaglandin derivatives"; Qlt Plug Delivery Inc, WO2009/035565 titled "Prostaglandin analogues for implant devices and methods"; Allergan Inc, U.S. Pat. No. 5,446,041 titled "Intraocular pressure reducing 11-acyl prostaglandins"; Upjohn Co., DE2263393 titled "9-O-Acylated prostaglandins F2a"; Shionogi & Co. patent publication 948,179 titled "Treatment for hypertension or glaucoma in eyes"; Ragactive, EP1329453 titled "Method for obtaining 4-(n-alkylamine)-5, 6-dihydro-4h-thieno-(2,3-b)-thiopyran-2-sulfonamide-7, 7-dioxides and intermediate products"; and American Cyanamid Co. GB844946 titled "2-(N-Substituted)acylamino-1,3,4-thiadiazole-5-sulfonamides".

Other publications include Vallikivi, I., et al. (2005). "The modelling and kinetic investigation of the lipase-catalyzed acetylation of stereoisomeric prostaglandins." J. Mol. Catal. B: Enzym. 35(1-3): 62-69; Parve, O., et al. (1999). "Lipase-catalyzed acylation of prostanoids." Bioorg. Med. Chem. Lett. 9(13): 1853-1858; and Carmely, S., et al. (1980) "New prostaglandin (PGF) derivatives from the soft coral Lobophyton depressum" Tetrahedron Lett. 21(9): 875-878.

Patent applications that describe DLK inhibitors include: Zhejiang DTRM Biopharma Co., patent publication WO2014146486 titled "Three-level cyclic amine ALK kinase inhibitor for treating cancer"; Kyowa Hakko Kogyo Co., patent publication WO2005012257 titled "Indazole Derivatives"; Genetech, patent publication WO2014177524 titled "C-linked heterocycloalkyl substituted pyrimidines and their uses", and patent publication WO2013174780 titled "Substituted dipyridylamines and uses thereof".

Patent applications that describe derivatives of prostaglandins include: Allergan, U.S. Pat. No. 5,767,154 titled "5-tran-prostaglandins of the F series and their use as ocular hypotensives", U.S. Pat. No. 5,767,154 titled "5-trans-prostaglandins of the F series and their use as ocular hypotensives"; Alcon Laboratories, EP0667160A2 titled "Use of certain prostaglandin analogues to treat glaucoma and ocular hypertension", EP667160 titled "Use of certain prostaglandin analogues to treat glaucoma and ocular hypertension; Asahi glass company and Santen Pharmaceutical Co., EP0850926A2 titled "Difluoroprostaglandin derivatives and their use"; Asahi Glass Co., JP2000080075 titled "Preparation of 15-deoxy-15,15-difluoroprostaglandins as selective and chemically-stable drugs", JP11255740 titled "Preparation of 15-deoxy-15-monofluoroprostaglandin derivatives", JP10087607 titled "Preparation of fluorine-containing prostaglandins as agents for inducing labor and controlling animal sexual cycle", WO9812175 titled "Preparation of fluorinated prostaglandin derivatives for treatment of glaucoma"; Santen Pharmaceutical Co., JP10259179 titled "Preparation of multi-substituted aryloxy-group containing prostaglandins and their use", EP850926 titled "Preparation of difluoroprostaglandin derivatives and their use for treatment of an eye disease".

Johns Hopkins University has filed a number of patents claiming formulations for ocular injections including WO2013/138343 titled "Controlled Release Formulations for the Delivery of HIF-1 Inhibitors", WO2013/138346 titled "Non-linear Multiblock Copolymer-drug Conjugates for the Delivery of Active Agents", WO2011/106702 titled "Sustained Delivery of Therapeutic Agents to an Eye Compartment", WO2016/025215 titled "Glucorticoid-loaded Nanoparticles for Prevention of Corneal Allograft Rejection and Neovascularization", WO2016/100392 titled "Sunitinib Formulations and Methods for Use Thereof in Treatment of Ocular Disorders", WO2016/100380 titled "Sunitinib Formulation and Methods for Use Thereof in Treatment of Glaucoma", WO2016/118506 titled "Compositions for the Sustained Release of Anti-Glaucoma Agents to Control Intraocular Pressure", WO2013/166385 titled "Nanocrystals, Compositions, and Methods that Aid Particle Transport in Mucus", WO2005/072710 titled "Drug and Gene Carrier Particles that Rapidly move Through Mucus Barriers," WO2008/030557 titled "Compositions and Methods for Enhancing Transport through Mucus", WO2012/061703 titled "Compositions and Methods Relating to Reduced Mucoadhesion," WO2012/039979 titled "Large Nanoparticles that Penetrate Tissue," WO2012/109363 titled "Mucus Penetrating Gene Carriers", WO2013/090804 titled "Biodegradable Stealth Nanoparticles Prepared by a Novel Self-Assembly Emulsification Method," WO2013/110028 titled "Nanoparticles Formulations with Enhanced Mucosal Penetration", and WO2013/166498 titled "Lipid-based Drug Carriers for Rapid Penetration through Mucus Linings".

GrayBug Vision, Inc. discloses prodrugs for the treatment of ocular therapy in US 2018-0036416, US 2018-0064823, US 2018-0028673, granted U.S. Pat. No. 9,808,531 and PCT application WO2017/053638. Aggregating microparticles for ocular therapy are described in US 2017-0135960 and WO2017/083779.

U.S. Patent application 2010/227865 titled "Oligomer-Beta Blocker Conjugates" describes beta-blocker mono prodrugs.

The object of this invention is to provide additional compounds, compositions and methods to treat ocular disorders.

SUMMARY

The present invention provides new prodrugs of therapeutically active compounds, including oligomeric prodrugs, and compositions thereof of Formula I, Formula II, Formula III, Formula IV, Formula V, Formula V', Formula VI, Formula VI', Formula VII, Formula VIII, Formula IX, Formula IX', Formula X, Formula X', Formula XI, Formula XII, Formula XIII, Formula XIV, Formula XV, Formula XV', Formula XV'', Formula XVI, Formula XVII, Formula XVII', Formula XVII'', Formula XVII''', Formula XVIII, Formula XVIII', Formula XIX, Formula XIX', Formula XX, Formula XXI, Formula XXII, Formula XXIII, Formula XXIV, Formula XV, Formula XVI, Formula XVII, Formula XVIII, Formula XXIX, Formula XXX, Formula XXXI, Formula XXXII, Formula XXXIII, Formula XXXIV, Formula XXXV, Formula XXXVI, Formula XXXVII, Formula XXXVIII, Formula XXXIX, Formula XL, Formula XLI, Formula XLII, Formula XLIII, Formula XLIV, Formula XLV, Formula XLVI, Formula XLVII, Formula XLVIII, Formula XLIX, Formula L, Formula LI, Formula LII, Formula LIII, or Formula LIV or a pharmaceutically acceptable salt or composition thereof. In one embodiment, an active compound or its salt or composition, as described herein, is used to treat a medical disorder, for example glaucoma, a disorder mediated by carbonic anhydrase, a disorder mediated by a Rho-associated kinase, a disorder mediated by a dual leucine zipper kinase, a disorder mediated by a tyrosine kinase inhibitor, a disorder mediated by VEGF, a disorder mediated by an $\alpha 2$ adrenergic receptor, a disorder or abnormality related to an increase in intraocular pressure (IOP), a disorder mediated by nitric oxide synthase (NOS), or a disorder requiring neuroprotection such as to regenerate/repair optic nerves. In one embodiment, the disorder is ocular. In another embodiment more generally, the disorder treated is allergic conjunctivitis, anterior uveitis, cataracts, dry or wet age-related macular degeneration (AMD), geographic atrophy, or diabetic retinopathy.

In one embodiment the compounds of the present invention have advantageous properties for ocular therapy. In one embodiment, the invention is a method for delivering an active drug to the eye that achieves a controlled release of the active material. This method optionally includes presenting the drug in a sustained delivery system such as a polymeric composition, a hydrophobic liquid, a hydrophobic solid, or a form of slow release reservoir or encapsulation. Often, ocular therapies are delivered to the eye in a form that is hydrophilic to be soluble in ocular fluid. In contrast in this invention, a hydrophobic prodrug of an active compound or a derivative thereof that can be delivered in a polymeric controlled delivery system is provided wherein the hydrophobic compound is more soluble within polymeric material than the ocular fluid, which slows release into ocular aqueous fluid.

In another embodiment, the compounds provided herein are designed to deliver two active compounds with the same, or instead different, but additive or synergistic mechanisms of action for ocular therapy to the eye.

In certain embodiments of the invention, at least one of the active therapeutic agents delivered in modified form is selected from a kinase inhibitor (for example, a tyrosine kinase inhibitor, a VEGF inhibitor, or a dual leucine zipper kinase inhibitor), a prostaglandin, an $\alpha_2$ adrenergic agonist, a carbonic anhydrase inhibitor, a beta blocker, or a Rho-associated kinase (ROCK) inhibitor. Non-limiting examples of active therapeutic agents include Sunitinib or a derivatized version of Sunitinib (for example, with a hydroxyl, amino, thio, carboxy, keto or other functional group instead of fluoro that can be used to covalently connect the hydrophobic moiety), pazopanib, axitinib, sorafenib, ponatinib, lenvatinib, vandetanib, cabozantinib, regorafenib, Latanoprost, dinoprost, travoprost, tafluprost, unoprostone, Timolol, Metipranolol, Brinzolamide, Dorzolamide, Acetazolamide, Methazolamide, Crizotinib, KW-2449, Tozasertib, bimatoprost, brimonidine, SR5834, and SR3677.

In one embodiment compounds of the invention can be used for the controlled administration of active compounds to the eye, over a period of at least two, three, four, five or six months or more in a manner that maintains at least a concentration in the eye that is effective for the disorder to be treated. In some embodiments, the prodrug is provided in a microparticle, microcapsule, vesicle, reservoir, or nanoparticle. In one embodiment, the drug is administered in a polymeric formulation that provides an advantageous release of compound. In one embodiment even the lowest concentration of release over the designated time period is at or above a therapeutically effective dose. In one embodiment, this is achieved by formulating a hydrophobic prodrug of the invention in a polymeric delivery material such as a polymer or copolymer that includes at least moieties of lactic acid, glycolic acid, propylene oxide or ethylene oxide. In a particular embodiment, the polymeric delivery system includes polylactide-co-glycolide, PLA or PGA with or without covalently attached or admixed polyethylene glycol. For example, the hydrophobic drug may be delivered in a mixture of PLGA and PLGA-PEG or PEG.

In certain embodiments, the prodrug of the present invention is delivered in a microparticle or nanoparticle that is a blend of two polymers, for example (i) a PLGA polymer or PLA polymer as described herein and (ii) a PLGA-PEG or PLA-PEG copolymer. In another embodiment, the microparticle or nanoparticle is a blend of three polymers, such as, for example, (i) a PLGA polymer; (ii) a PLA polymer; and, (iii) a copolymer of PLGA-PEG or PLA-PEG. In an additional embodiment, the microparticle or nanoparticle is a blend of (i) a PLA polymer; (ii) a PLGA polymer; (iii) a PLGA polymer that has a different ratio of lactide and glycolide monomers than the PLGA in (ii); and, (iv) a PLGA-PEG or PLA-PEG copolymer. Any ratio of lactide and glycolide in the PLGA can be used that achieves the desired therapeutic effect. In certain illustrative non-limiting embodiments, the ratio of PLA to PLGA by weight in a polymer blend as described is 77/22, 69/30, 49/50, 54/45, 59/40, 64/35, 69/30, 74/25, 79/20, 84/15, 89/10, 94/5, or 99/1.

In certain embodiments, a blend of three polymers that has (i) PLA (ii) PLGA (iii) PLGA with a different ratio of lactide and glycolide monomers than PLGA in (ii) wherein the ratio by weight is 74/20/5 by weight, 69/20/10 by weight, 69/25/5 by weight, or 64/20/15 by weight. In certain embodiments, the PLGA in (ii) has a ratio of lactide to glycolide of 85/15, 75/25, or 50/50. In certain embodiments the PLGA in (iii) has a ratio of lactide to glycolide of 85/15, 75/25, or 50/50.

In certain aspects, the drug may be delivered in a blend of PLGA or PLA and PEG-PLGA, including but not limited to (i) PLGA+approximately by weight 1% PEG-PLGA or (ii) PLA+approximately by weight 1% PEG-PLGA. In certain aspects, the drug may be delivered in a blend of (iii) PLGA/PLA+approximately by weight 1% PEG-PLGA. In certain embodiments, the blend of PLA, PLGA, or PLA/PGA with PLGA-PEG contains approximately from about 0.5% to about 10% by weight of a PEG-PLGA, from about 0.5% to about 5% by weight of a PEG-PLGA, from about 0.5% to about 4% by weight of a PEG-PLGA, from about 0.5% to about 3% by weight of a PEG-PLGA, from about 1.0% to about 3.0% by weight of a PEG-PLGA, from about 0.1% to about 10% of a PEG-PLGA, from about 0.1% to about 5% of a PEG-PLGA, from about 0.1% to about 1% PEG-PLGA, or from about 0.1% to about 2% PEG-PLGA.

In certain non-limiting embodiments, the ratio by weight percent of PLGA to PEG-PLGA in a two polymer blend as described is about 40/1, 45/1, 50/1, 55/1, 60/1, 65/1, 70/1, 75/1, 80/1, 85/1, 90/1, 95/1, 96/1, 97/1, 98/1, 99/1. The PLGA can be acid or ester capped. In non-limiting aspects, the drug can be delivered in a two polymer blend of PLGA75:25 4A+approximately 1% PEG-PLGA50:50; PLGA85:15 5A+approximately 1% PEG-PLGA5050; PLGA75:25 6E+approximately 1% PEG-PLGA50:50; or, PLGA50:50 2A+approximately 1% PEG-PLGA50:50.

In certain non-limiting embodiments, the ratio by weight percent of PLA/PLGA-PEG in a polymer blend as described is about 40/1, 45/1, 50/1, 55/1, 60/1, 65/1, 70/1, 75/1, 80/1, 85/1, 90/1, 95/1, 96/1, 97/1, 98/1, 99/1. The PLA can be acid capped or ester capped. In certain aspects, the PLA is PLA 4.5A. In non-limiting aspects, the drug is delivered in a blend of PLA 4.5A+1% PEG-PLGA.

The PEG segment of the PEG-PLGA may have, for example, in non-limiting embodiments, a molecular weight of at least about 1 kDa, 2 kDa, 3 kDa, 4 kDa, 5 kDa, 6 kDa, 7 kDa, 8 kDa, 9 kDa, or 10 kDa, and typically not greater than 10 kDa, 15 kDa, 20 kDa, or 50 kDa, or in some embodiments, 6 kDa, 7 kDa, 8 kDa, or 9 kDa. In certain embodiment, the PEG segment of the PEG-PLGA has a molecular weight between about 3 kDa and about 7 kDa or between about 2 kDa and about 7 kDa. Non-limiting examples of the PLGA segment of the PEG-PLGA is PLGA50:50, PLGA75:25, or PLGA85:15. In one embodiment, the PEG-PLGA segment is PEG (5 kDa)-PLGA50:50.

When the drug is delivered in a blend of PLGA+PEG-PLGA, any ratio of lactide and glycolide in the PLGA or the PLGA-PEG can be used that achieves the desired therapeutic effect. Non-limiting illustrative embodiments of the ratio of lactide/glycolide in the PLGA or PLGA-PEG are about 5/95, 10/90, 15/85, 20/80, 25/75, 30/70, 35/65, 40/60, 45/55, 50/50, 55/45, 60/40, 65/35, 70/30, 75/25, 80/20, 85/15, 90/10, or 95/5. In one embodiment, the PLGA is a block co-polymer, for example, diblock, triblock, multiblock, or star-shaped block. In one embodiment, the PLGA is a random co-polymer. In certain aspects, the PLGA is PLGA75:25 4A; PLGA85:15 5A; PLGA75:25 6E; or, PLGA50:50 2A.

In another embodiment, the polymer includes a polyethylene oxide (PEO) or polypropylene oxide (PPO). In certain aspects, the polymer can be a random, block, diblock, triblock or multiblock copolymer (for example, a polylactide, a polylactide-co-glycolide, polyglycolide or Pluronic). For injection into the eye, the polymer is pharmaceutically acceptable and typically biodegradable so that it does not have to be removed. As described in Example 9 and shown in FIG. 32, FIG. 33, FIG. 34, and FIG. 35, cumulative drug release of prodrugs of the invention occurs over a period of up to approximately 90 days. Drug release of brinzolamide-acetyl PLA (n=5) (18-3) as shown in FIG. 32 is measured and occurs from day 0 to approximately day 90.

The decreased rate of release of the active material to the ocular compartment may result in decreased inflammation, which has been a significant side effect of ocular therapy to date.

It is also important that the decreased rate of release of the drug while maintaining efficacy over an extended time of up to 2, 3, 4, 5 or 6 months be achieved using a particle that is small enough for administration through a needle without causing significant damage or discomfort to the eye and not to give the illusion to the patient of black spots floating in the eye. This typically means the controlled release particle should be less than approximately 300, 250, 200, 150, 100, 50, 45, 40, 35, or 30 μm, such as less than approximately 30, 29, 28, 27, 26, 25, 24, 23, 22 21, or 20 μm. In one aspect, the particles do not agglomerate in vivo to form larger particles, but instead in general maintain their administered size and decrease in size over time.

The hydrophobicity of the conjugated drug can be measured using a partition coefficient (P; such as Log P in octanol/water), or distribution coefficient (D; such as Log D in octanol/water) according to methods well known to those of skill in the art. Log P is typically used for compounds that are substantially un-ionized in water and Log D is typically used to evaluate compounds that ionize in water. In certain embodiments, the conjugated derivatized drug has a Log P or Log D of greater than approximately 2.5, 3, 3.5, 4, 4.5, 5, 5.5 or 6. In other embodiments, the conjugated derivatized drug has a Log P or Log D which is at least approximately 1, 1.5, 2, 2.5, 3, 3.5 or 4 Log P or Log D units, respectively, higher than the parent hydrophilic drug.

Compounds of Formula I, Formula II, and Formula III are prodrugs or derivatives of prostaglandins.

In certain embodiments, compounds of Formula I Formula II, and Formula III are hydrophobic prodrugs of prostaglandins.

Compound of Formula IV are single agent prodrugs of a prostaglandin and brimonidine allowing release of both compounds in the eye. In one embodiment both compounds are released concurrently.

Compounds of Formula V, Formula VI, Formula V', and Formula VI' are single agent prodrug conjugates of a prostaglandin and one or more Timolol derivatives allowing for the release of both compounds in the eye. In one embodiment both compounds are released concurrently.

Compounds of Formula VII and Formula VIII are hydrophobic prodrugs of the $\alpha_2$ adrenergic agonist brimonidine.

In certain embodiments, compounds of Formula IX and Formula IX' are single agent prodrug conjugates of a prostaglandin and brimonidine allowing release of both compounds in the eye. In one embodiment both compounds are released concurrently.

In alternative embodiments, compounds of Formula IX and Formula IX' are single agent prodrug conjugates of a carbonic anhydrase inhibitor and brimonidine allowing release of both compounds in the eye. In one embodiment both compounds are released concurrently.

In alternative embodiments, compounds of Formula IX and Formula IX' are single agent prodrug conjugates of dual leucine zipper kinase inhibitor and brimonidine allowing release of both compounds in the eye. In one embodiment both compounds are released concurrently.

In alternative embodiments, compounds of Formula IX and Formula IX' are single agent prodrug conjugates of a Rho kinase inhibitor and brimonidine allowing release of both compounds in the eye. In one embodiment both compounds are released concurrently.

In alternative embodiments, compounds of Formula IX and Formula IX' are single agent prodrug conjugates of Sunitinib and brimonidine allowing release of both compounds in the eye. In one embodiment both compounds are released concurrently.

In alternative embodiments, compounds of Formula IX and Formula IX' are single agent prodrug conjugates of a beta-blocker and brimonidine allowing release of both compounds in the eye. In one embodiment both compounds are released concurrently.

In certain embodiments, compounds of Formula X, Formula XI, and Formula XII are single agent prodrug conjugates of a prostaglandin and a Sunitinib derivative allowing release of both compounds in the eye. In one embodiment both compounds are released concurrently.

In alternative embodiments, compounds of Formula X, Formula XI, and Formula XII are single agent prodrug conjugates of brimonidine and a Sunitinib derivative allowing release of both compounds in the eye. In one embodiment both compounds are released concurrently.

In alternative embodiments, compounds of Formula X, Formula XI, and Formula XII are single agent prodrug conjugates of Timolol and a Sunitinib derivative allowing release of both compounds in the eye. In one embodiment both compounds are released concurrently.

Compounds of Formula X' are prodrugs or derivatives of Sunitinib.

In certain embodiments, compounds of Formula X' are hydrophobic prodrugs of Sunitinib.

In other embodiments, compounds of Formula XIII are single agent prodrug conjugates of Timolol and a prostaglandin derivative allowing release of both compounds in the eye. In one embodiment both compounds are released concurrently.

In alternative embodiments, compounds of Formula XIII are single agent prodrug conjugates of Timolol and Brimonidine allowing release of both compounds in the eye. In one embodiment both compounds are released concurrently.

In certain embodiments, compounds of Formula XIV are hydrophobic prodrugs of the beta-blocker Timolol.

In alternative embodiments, compound of Formula XIV are pharmaceutically acceptable salts of hydrophobic prodrugs of the beta-blocker Timolol.

In certain embodiments, compounds of Formula XV, Formula XV', Formula XV", and Formula LIV are single agent prodrug conjugates of a prostaglandin and Timolol allowing release of both compounds in the eye. In one embodiment both compounds are released concurrently.

In alternative embodiments, compounds of Formula XV, Formula XV', Formula XV", and Formula LIV are single agent prodrug conjugates of a carbonic anhydrase inhibitor and Timolol allowing release of both compounds in the eye. In one embodiment both compounds are released concurrently.

In alternative embodiments, compounds of Formula XV, Formula XV', Formula XV", and Formula LIV are single agent prodrug conjugates of dual leucine zipper kinase inhibitor and Timolol allowing release of both compounds in the eye. In one embodiment both compounds are released concurrently.

In alternative embodiments, compounds of Formula XV, Formula XV', Formula XV", and Formula LIV are single agent prodrug conjugates of Brimonidine and Timolol allowing release of both compounds in the eye. In one embodiment both compounds are released concurrently.

In alternative embodiments, compounds of Formula XV, Formula XV', Formula XV", and Formula LIV are single agent prodrug conjugates of Rho kinase inhibitors and Timolol allowing release of both compounds in the eye. In one embodiment both compounds are released concurrently.

In certain embodiments, compounds of Formula XVI and Formula XVII are hydrophobic prodrugs of the beta-blocker Timolol.

In alternative embodiments, compounds of Formula XVI and Formula XVII are pharmaceutically acceptable hydrophobic prodrugs of the beta-blocker Timolol.

In certain embodiments, compounds of Formula XVII', Formula XVII", and Formula XVII''' are hydrophobic prodrugs of Brimonidine.

In alternative embodiments, compounds of Formula XVII', Formula XVII", and Formula XVII''', are pharmaceutically acceptable hydrophobic prodrugs of Brimonidine.

In certain embodiments, compounds of Formula XVIII, Formula XVIII', Formula XIX, Formula XIX', Formula XX, and Formula XXI are single agent prodrug conjugates of a dual leucine zipper kinase and a prostaglandin allowing release of both compounds in the eye. In one embodiment both compounds are released concurrently.

In alternative embodiments, compounds of Formula XVIII, Formula XVIII', Formula XIX, Formula XIX', Formula XX, and Formula XXI are single agent prodrug conjugates of a dual leucine zipper kinase inhibitor and Brimonidine allowing release of both compounds in the eye. In one embodiment both compounds are released concurrently.

In alternative embodiments. compounds of Formula XVIII, Formula XVIII', Formula XIX, Formula XIX', Formula XX, and Formula XXI are single agent prodrug conjugates of a dual leucine zipper kinase inhibitor and Timolol allowing release of both compounds in the eye. In one embodiment both compounds are released concurrently.

In alternative embodiments, compounds of Formula XVIII, Formula XVIII', Formula XIX, Formula XIX', Formula XX, and Formula XXI are single agent prodrug conjugates of a dual leucine zipper kinase inhibitor and Suntinib allowing release of both compounds in the eye. In one embodiment both compounds are released concurrently.

In certain embodiments, compounds of Formula XXII, Formula XXIII, Formula XXIV, Formula XXV, Formula XVI, and Formula XVII are single agent prodrug conjugates of a carbonic anhydride inhibitor and a prostaglandin allowing release of both compounds in the eye. In one embodiment both compounds are released concurrently.

In alternative embodiments, compounds of Formula XXII, Formula XXIII, Formula XXIV, Formula XXV, Formula XVI, and Formula XVII are single agent prodrug conjugates of a carbonic anhydride inhibitor and a beta-blocker allowing release of both compounds in the eye. In one embodiment both compounds are released concurrently.

In alternative embodiments, compounds of Formula XXII, Formula XXIII, Formula XXIV, Formula XXV, Formula XVI, and Formula XVII are single agent prodrug conjugates of a carbonic anhydride inhibitor and a dual leucine zipper kinase inhibitor allowing release of both compounds in the eye. In one embodiment both compounds are released concurrently.

In certain embodiments, compounds of Formula XXVIII, Formula XXVIIIa, Formula XXIX, Formula XXIXa, Formula XXX, and Formula XXXa are single agent prodrug conjugates of a ROCK inhibitor and a prostaglandin allowing release of both compounds in the eye. In one embodiment both compounds are released concurrently.

In alternative embodiments, compounds of Formula XXVIII, Formula XXVIIIa, Formula XXIX, Formula XXIXa, Formula XXX, and Formula XXXa are single agent prodrug conjugates of a ROCK inhibitor and Timolol allowing release of both compounds in the eye. In one embodiment both compounds are released concurrently.

In alternative embodiments, compounds of Formula XXVIII, Formula XXVIIIa, Formula XXIX, Formula XXIXa, Formula XXX, and Formula XXXa are single agent prodrug conjugates of a ROCK inhibitor and a carbonic anhydride inhibitor allowing release of both compounds in the eye. In one embodiment both compounds are released concurrently.

In alternative embodiments, compounds of Formula XXVIII, Formula XXVIIIa, Formula XXIX, Formula XXIXa, Formula XXX, and Formula XXXa are single agent prodrug conjugates of a ROCK inhibitor and a dual leucine zipper kinase inhibitor allowing release of both compounds in the eye. In one embodiment both compounds are released concurrently.

Compounds of Formula XXXI, XXXII, and XXXIII are hydrophobic prodrugs of ROCK inhibitors.

In certain embodiments, compounds of Formula XXXIV are single agent prodrug conjugates of a prostaglandin and Metipranolol allowing release of both compounds in the eye. In one embodiment both compounds are released concurrently.

In alternative embodiments, compounds of Formula XXXIV are single agent prodrug conjugates of a carbonic anhydrase inhibitor and Metipranolol allowing release of both compounds in the eye. In one embodiment both compounds are released concurrently.

In alternative embodiments, compounds of Formula XXXIV are single agent prodrug conjugates of dual leucine zipper kinase inhibitor and Metipranolol allowing release of both compounds in the eye. In one embodiment both compounds are released concurrently.

In alternative embodiments, compounds of Formula XXXIV are single agent prodrug conjugates of Brimonidine and Metipranolol allowing release of both compounds in the eye. In one embodiment both compounds are released concurrently.

In alternative embodiments, compounds of Formula XXXIV are single agent prodrug conjugates of Timolol and Metipranolol allowing release of both compounds in the eye. In one embodiment both compounds are released concurrently.

Compounds of Formula XXXV are hydrophobic prodrugs of Metipranolol.

In certain embodiments, compounds of Formula XXXIV and Formula XXXVIII are single agent prodrug conjugates of a prostaglandin and Levobunolol allowing release of both compounds in the eye. In one embodiment both compounds are released concurrently.

In alternative embodiments, compounds of Formula XXXIV and Formula XXXVIII are single agent prodrug conjugates of a carbonic anhydrase inhibitor and Levobunolol allowing release of both compounds in the eye. In one embodiment both compounds are released concurrently.

In alternative embodiments, compounds of Formula XXXIV and Formula XXXVIII are single agent prodrug conjugates of dual leucine zipper kinase inhibitor and Levobunolol allowing release of both compounds in the eye. In one embodiment both compounds are released concurrently.

In alternative embodiments, compounds of Formula XXXIV and Formula XXXVIII are single agent prodrug conjugates of Brimonidine and Levobunolol allowing release of both compounds in the eye. In one embodiment both compounds are released concurrently.

In alternative embodiments, compounds of Formula XXXIV and Formula XXXVIII are single agent prodrug conjugates of Timolol and Levobunolol allowing release of both compounds in the eye.

Compounds of Formula XXXVII and Formula XXXIX are mono-prodrugs of a Levobunolol derivative.

In certain embodiments, compounds of Formula XL and Formula XLII are single agent prodrug conjugates of a prostaglandin and Carteolol allowing release of both compounds in the eye. In one embodiment both compounds are released concurrently.

In alternative embodiments, compounds of Formula XL and Formula XLII are single agent prodrug conjugates of a carbonic anhydrase inhibitor and Carteolol allowing release of both compounds in the eye. In one embodiment both compounds are released concurrently.

In alternative embodiments, compounds of Formula XL and Formula XLII are single agent prodrug conjugates of dual leucine zipper kinase inhibitor and Carteolol allowing release of both compounds in the eye. In one embodiment both compounds are released concurrently.

In alternative embodiments, compounds of Formula XL and Formula XLII are single agent prodrug conjugates of Brimonidine and Carteolol allowing release of both compounds in the eye.

In one embodiment both compounds are released concurrently.

In alternative embodiments, compounds of Formula XL and Formula XLII are single agent prodrug conjugates of Timolol and Carteolol allowing release of both compounds in the eye.

Compounds of Formula XLI and Formula XLII are mono-prodrugs of Carteolol.

In certain embodiments, compounds of Formula XLIV and Formula XLVI are single agent prodrug conjugates of a prostaglandin and Betaxolol allowing release of both compounds in the eye. In one embodiment both compounds are released concurrently.

In alternative embodiments, compounds of Formula XLIV and Formula XLVI are single agent prodrug conjugates of a carbonic anhydrase inhibitor and Betaxolol allowing release of both compounds in the eye. In one embodiment both compounds are released concurrently.

In alternative embodiments compounds of Formula XLIV and Formula XLVI are single agent prodrug conjugates of dual leucine zipper kinase inhibitor and Betaxolol allowing release of both compounds in the eye. In one embodiment both compounds are released concurrently.

In alternative embodiments, compounds of Formula XLIV and Formula XLVI are single agent prodrug conjugates of Brimonidine and Betaxolol allowing release of both compounds in the eye. In one embodiment both compounds are released concurrently.

In alternative embodiments, compounds of Formula XLIV and Formula XLVI are single agent prodrug conjugates of Timolol and Betaxolol allowing release of both compounds in the eye.

Compounds of Formula XLV and Formula XLVII are mono-prodrugs of Betaxolol.

Compounds of Formula XLVIII are bis-prodrugs of beta blockers.

Compounds of Formula XLIX are mono-prodrugs of beta blockers.

Compounds of Formula L are mono-prodrugs of the ROCK inhibitor SR5834.

Compounds of Formula LI are mono-prodrugs of the ROCK inhibitor SR3677.

In certain embodiments, compounds of Formula LII are prodrug conjugates of the ROCK inhibitor SR5834 and a prostaglandin allowing release of both compounds in the eye. In one embodiment both compounds are released concurrently.

In alternative embodiments, compounds of Formula LII are prodrug conjugates of the ROCK inhibitor SR5834 and Timolol allowing release of both compounds in the eye. In one embodiment both compounds are released concurrently.

In alternative embodiments, compounds of Formula LII are prodrug conjugates of the ROCK inhibitor SR5834 and a carbonic anhydride inhibitor allowing release of both compounds in the eye. In one embodiment both compounds are released concurrently.

In alternative embodiments, compounds of Formula LII are prodrug conjugates of the ROCK inhibitor SR5834 and a dual leucine zipper kinase inhibitor allowing release of both compounds in the eye. In one embodiment both compounds are released concurrently.

In certain embodiments, compounds of Formula LIII are prodrug conjugates of the ROCK inhibitor SR3677 and a prostaglandin allowing release of both compounds in the eye. In one embodiment both compounds are released concurrently.

In alternative embodiments, compounds of Formula LIII are prodrug conjugates of the ROCK inhibitor SR3677 and Timolol allowing release of both compounds in the eye. In one embodiment both compounds are released concurrently.

In alternative embodiments, compounds of Formula LIII are prodrug conjugates of the ROCK inhibitor SR3677 and a carbonic anhydride inhibitor allowing release of both compounds in the eye. In one embodiment both compounds are released concurrently.

In alternative embodiments, compounds of Formula LIII are prodrug conjugates of the ROCK inhibitor SR3677 and a dual leucine zipper kinase inhibitor allowing release of both compounds in the eye. In one embodiment both compounds are released concurrently.

These compounds can be used to treat an ocular disorder in a host, for example a human, in need thereof. In one embodiment, a method for the treatment of such a disorder is provided that includes the administration of an effective amount of a compound of Formula I, Formula II, Formula III, Formula IV, Formula V, Formula V', Formula VI, Formula VI', Formula VII, Formula VIII, Formula IX, Formula IX', Formula X, Formula X', Formula XI, Formula XII, Formula XIII, Formula XIV, Formula XV, Formula XV', Formula XV'', Formula XVI, Formula XVII, Formula XVII', Formula XVII'', Formula XVII''', Formula XVIII, Formula XVIII', Formula XIX, Formula XIX', Formula XX, Formula XXI, Formula XXII, Formula XXIII, Formula XXIV, Formula XV, Formula XVI, Formula XVII, Formula XVIII, Formula XXIX, Formula XXX, Formula XXXI, Formula XXXII, Formula XXXIII, Formula XXXIV, Formula XXXV, Formula XXXVI, Formula XXXVII, Formula XXXVIII, Formula XXXIX, Formula XL, Formula XLI, Formula XLII, Formula XLIII, Formula XLIV, Formula XLV, Formula XLVI, Formula XLVII, Formula XLVIII, Formula XLIX, Formula L, Formula LI, Formula LII, Formula LIII, or Formula LIV or a pharmaceutically acceptable salt or composition thereof, optionally in a pharmaceutically acceptable carrier, including a polymeric carrier, as described in more detail below.

Another embodiment is provided that includes the administration of an effective amount of an active compound or a pharmaceutically acceptable salt thereof, optionally in a pharmaceutically acceptable carrier, including a polymeric carrier, to a host to treat an ocular or other disorder that can benefit from topical or local delivery. The therapy can be delivery to the anterior or posterior chamber of the eye. In specific aspects, the active compound is administered to treat a disorder of the cornea, conjunctiva, aqueous humor, iris, ciliary body, lens sclera, choroid, retinal pigment epithelium, neural retina, optic nerve or vitreous humor.

Any of the compounds described herein (Formula I, Formula II, Formula III, Formula IV, Formula V, Formula V', Formula VI, Formula VI', Formula VII, Formula VIII, Formula IX, Formula IX', Formula X, Formula X', Formula XI, Formula XII, Formula XIII, Formula XIV, Formula XV, Formula XV', Formula XV", Formula XVI, Formula XVII, Formula XVII', Formula XVII", Formula XVII'", Formula XVIII, Formula XVIII', Formula XIX, Formula XIX', Formula XX, Formula XXI, Formula XXII, Formula XXIII, Formula XXIV, Formula XV, Formula XVI, Formula XVII, Formula XVIII, Formula XXIX, Formula XXX, Formula XXXI, Formula XXXII, Formula XXXIII, Formula XXXIV, Formula XXXV, Formula XXXVI, Formula XXXVII, Formula XXXVIII, Formula XXXIX, Formula XL, Formula XLI, Formula XLII, Formula XLIII, Formula XLIV, Formula XLV, Formula XLVI, Formula XLVII, Formula XLVIII, Formula XLIX, Formula L, Formula LI, Formula LII, Formula LIII, or Formula LIV) can be administered to the eye in a composition as described further herein in any desired form of administration, including via intravitreal, intrastromal, intracameral, sub-tenon, sub-retinal, retro-bulbar, peribulbar, suprachoroidal, choroidal, subchoroidal, conjunctival, subconjunctival, episcleral, posterior juxtascleral, circumcorneal, and tear duct injections, or through a mucus, mucin, or a mucosal barrier, in an immediate or controlled release fashion.

In any of the Formulas described herein (Formula I, Formula II, Formula III, Formula IV, Formula V, Formula V', Formula VI, Formula VI', Formula VII, Formula VIII, Formula IX, Formula IX', Formula X, Formula X', Formula XI, Formula XII, Formula XIII, Formula XIV, Formula XV, Formula XV', Formula XV", Formula XVI, Formula XVII, Formula XVII', Formula XVII", Formula XVII'", Formula XVIII, Formula XVIII', Formula XIX, Formula XIX', Formula XX, Formula XXI, Formula XXII, Formula XXIII, Formula XXIV, Formula XV, Formula XVI, Formula XVII, Formula XVIII, Formula XXIX, Formula XXX, Formula XXXI, Formula XXXII, Formula XXXIII, Formula XXXIV, Formula XXXV, Formula XXXVI, Formula XXXVII, Formula XXXVIII, Formula XXXIX, Formula XL, Formula XLI, Formula XLII, Formula XLIII, Formula XLIV, Formula XLV, Formula XLVI, Formula XLVII, Formula XLVIII, Formula XLIX, Formula L, Formula LI, Formula LII, Formula LIII, or Formula LIV) if the stereochemistry of a chiral carbon is not specifically designated in the Formula it is intended that the carbon can be used as an R enantiomer, an S enantiomer, or a mixture of enantiomers including a racemic mixture. Timolol as used Formula V, Formula VI, Formula V', Formula VI', Formula X, Formula XI, Formula XII, Formula XIII, Formula XIV, Formula XV, Formula XV', Formula XVI, Formula XVII, Formula XVIII, Formula XVIII', Formula XIX, Formula XIX', Formula XX, Formula XXI, Formula XXVIII, Formula XXVIIIa, Formula XXIX, Formula XXIXa, Formula XXX, Formula XXXa, XXXIV, Formula XXXIV, Formula XXXVIII, Formula XL, Formula XLII, Formula LII, and Formula LII has (S)-stereochemistry as used in commercial Timolol maleate ophthalmic solutions, such as Istalol® and Timoptic®. On both U.S. FDA labels, Timolol maleate is described as a single enantiomer ((−)-1-(tert-butylamino)-3-[(4-morpholino-1,2,5-thiadiazol-3-yl)oxy]-2-propanol maleate) that "possesses an asymmetric carbon atom in its structure and is provided as the levo-isomer." The (S)-enantiomer has CAS No. 26839-75-8 and the (R)-enantiomer has CAS No. 26839-76-9, but only the (S)-enantiomer is described as "Timolol". Likewise, compounds presented which are or are analogs of commercial products are provided in their approved stereochemistry for regulatory use, unless otherwise instructed.

In addition, moieties that have repetitive units, for example including but not limited to an oligomer of polylactic acid, polypropylene oxide, and polylactide-coglycolide that has a chiral carbon can be used with the chiral carbons all having the same stereochemistry, random stereochemistry, or ordered but different stereochemistry such as a block of S enantiomer units followed by a block of R enantiomer units in each oligomeric unit. In some embodiments lactic acid is used in its naturally occurring S enantiomeric form.

In certain embodiments, the conjugated active drug is delivered in a biodegradable microparticle or nanoparticle that has at least approximately 5, 7.5, 10, 12.5, 15, 20, 25 or 30% or more by weight conjugated active drug. In some embodiments, the biodegradable microparticle degrades over a period of time and in any event provides controlled delivery that lasts at least approximately 2 months, 3 months, 4 months, 5 months or 6 months or more. In some embodiments, the loaded microparticles are administered via subconjunctival or subchoroidal injection.

In certain embodiments, the conjugated active drug is delivered as the pharmaceutically acceptable salt form. Salt forms of a compound will exhibit distinctive solution and solid-state properties compared to their respective free base or free acid form, and for this reason pharmaceutical salts are used in drug formulations to improve aqueous solubility, chemical stability, and physical stability issues. Lipophilic salt forms of compounds, which have enhanced solubility in lipidic vehicles relative to the free acid or free base forms of compounds, are often advantageous in terms of pharmacological properties due in part to their low melting points. Lipophilic salt forms of compounds are used to increase aqueous solubility for oral and parenteral drug delivery, enhance permeation across hydrophobic barriers, and enhance drug loading in lipid-based formulations. As discussed in Example 7, lipophilic salt forms of Timolol prodrugs were soluble in water and DMSO and as discussed in Example 9, the theoretical drug loading of Timolol salt forms was 13.8%. FIG. 35 shows the drug release kinetics of salt forms of Timolol and irrespective of the salt, Timolol prodrugs were released within 25 days.

In all of the polymer moieties described in this specification, where the structures are depicted as block copolymers (for example, blocks of "x" followed by blocks of "y"), it is intended that the polymer can alternately be a random or alternating copolymer (for example, "x" and "y" are either randomly distributed or alternate). Unless stereochemistry is specifically indicated, each individual moiety of each oligomer that has a chiral center can be presented at the chiral carbon in (R) or (S) configuration or a mixture there of, including a racemic mixture.

Various Formulas below use R groups defined in other Formulas, each of which R group is meant to have the definition as presented in the first Formula that it was presented in unless explicitly changed by context.

In most of the Formulas presented herein, the prodrugs are depicted as one or several active moieties covalently bound to or through a described prodrug moiety(ies) with a defined variable range of each of the active moiety and the prodrug moiety, typically through the use of descriptors n, m, o, x, y, z, u, v, w, x', y' or zz. As indicated below, these descriptors can independently have numerical ranges provided below, and in most embodiments, are typically within a smaller range, also as provided below. Each variable is independent such that any of the integers of one variable can be used with any of the integers of the other variable, and each combination is considered separately and independently disclosed, and set out below like this only for space considerations.

For example, n, m, and o can independently be any integer between 0 and 29 (0, 1, 2, 3, 4, 5, 6, 7, 8, 9, 10, 11, 12, 13, 14, 15, 16, 17, 18, 19, 20, 21, 22, 23, 24, 25, 26, 27, 28 or 29). In certain embodiments, n or m or o can independently be 0, 1, 2, 3, 4, 5, 6, 7 or 8, and in certain aspects, 1, 2, 3 or 4.

Likewise, x, y, and z can independently be any integer between 1 and 30 (1, 2, 3, 4, 5, 6, 7, 8, 9, 10, 11, 12, 13, 14, 15, 16, 17, 18, 19, 20, 21, 22, 23, 24, 25, 26, 27, 28, 29 or 30). In certain embodiments, x or y or z can independently be 1, 2, 3, 4, 5, 6, 7, 8, 9, 10, 11, or 12 and in certain aspects, 1, 2, 3, 4, 5, or 6. In certain embodiments, x is 1, 2, 3, 4, 5, 6, 7, or 8. In certain embodiments, y is 1, 2, 3, 4, 5, 6, 7, or 8. In certain embodiments, x is 1, 2, 3, 4, 5, or 6. In certain embodiments, y is 1, 2, 3, 4, 5, or 6. In certain embodiments, z is 1, 2, 3, 4, 5, or 6. In certain embodiments, y is 1, 2, or 3. In certain embodiments, x is 1, 2, or 3. In certain embodiments, x is an integer selected from 1, 2, 3, or 4 and y is 1. In certain embodiments, x is an integer selected from 1, 2, 3, or 4 and y is 2. In certain embodiments, x is in integer selected from 1, 2, 3, or 4 and y is 3.

Where x, y, or z is used in connection with a single atom, such as

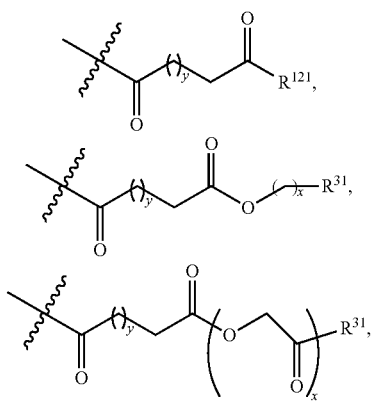

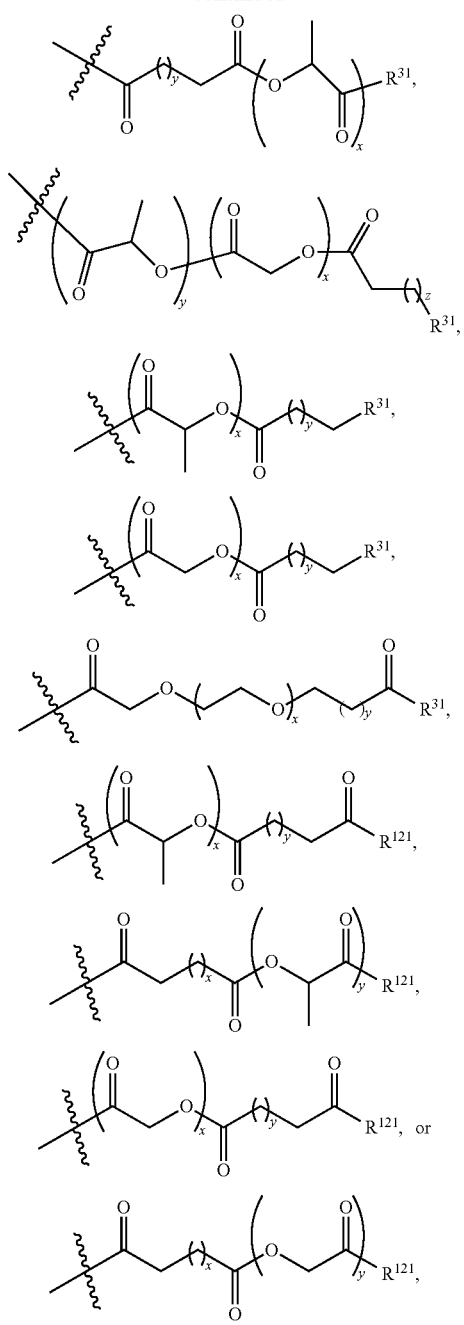

x, y, or z are typically independently 1, 2, 3, 4, 5, 6, 7, 8, 9, 10, 11 or 12, and more typically 1, 2, 3, 4, 5 or 6, and even 1, 2, 3 or 4 or 1 or 2.

Where x, y, or z is used in connection with the monomeric residue in an oligomer, including for example but not limited to:

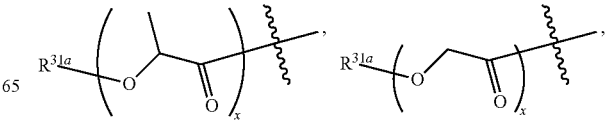

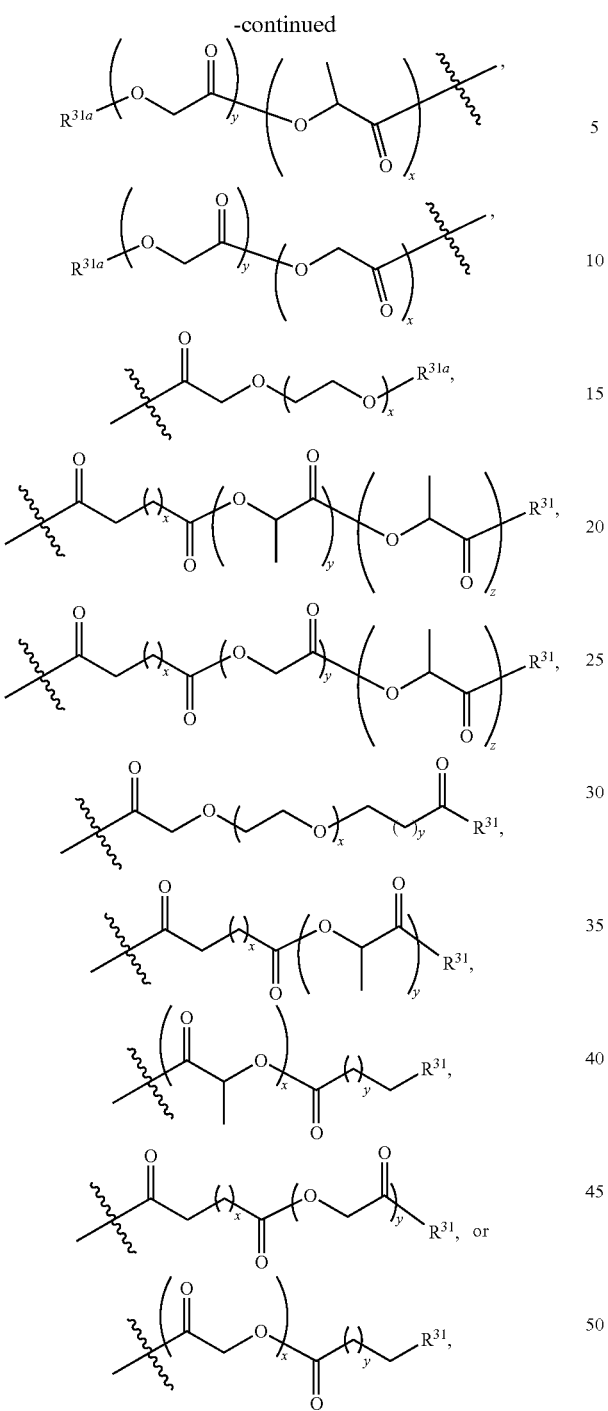

The variable zz is selected from 1, 2, 3, 4, 5, or 6, and in some embodiments, 1, 2, 3 or 4, and in additional embodiments zz is selected from 7, 8, or 9. In additional embodiments, zz can be 0 if it results in a sufficiently stable compound.

Non-limiting examples of Formula I and Formula II include at least hydrophobic prodrugs or derivatives of the following prostaglandins:

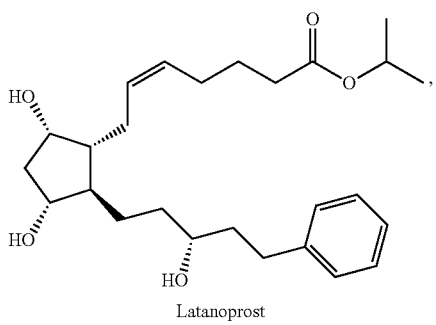
Latanoprost

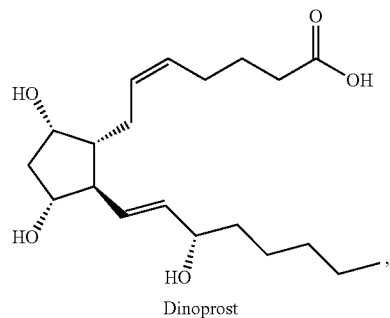
Dinoprost

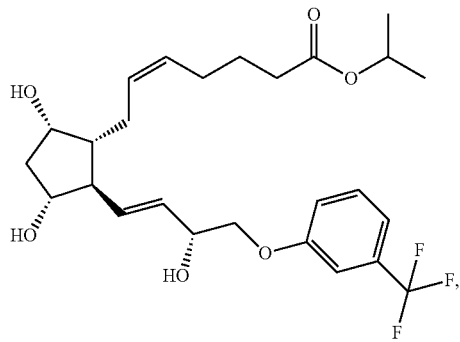
Travoprost

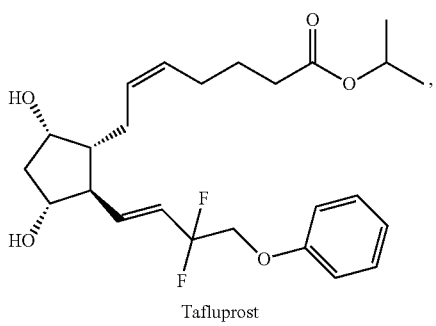
Tafluprost then x, y or z is in some embodiments are independently 1, 2, 3, 4, 5, 6, 7 or 8, and even for example, 2, 4 or 6 residues.

Similarly, u, v, and w can independently be any integer between 0 and 29 (1, 2, 3, 4, 5, 6, 7, 8, 9, 10, 11, 12, 13, 14, 15, 16, 17, 18, 19, 20, 21, 22, 23, 24, 25, 26, 27, 28 or 29) wherein u+v+w is 20 to 30 carbons. In certain embodiments, u or v or w can independently be 0, 1, 2, 3, 4, 5, 6, 7 or, and in certain aspects, 1, 2, 3 or 4.

Also, x' and y' are independently selected from 0, 1, 2, 3, 4, 5, 6, 7, 8, 9, and 10, and wherein if x' and y' are within the linker then x' and y' cannot both be 0. In some embodiments, x' and y' are independently 0, 1, 2, 3, 4, 5, 6 or 7, or even, 1, 2, 3, or 4.

-continued

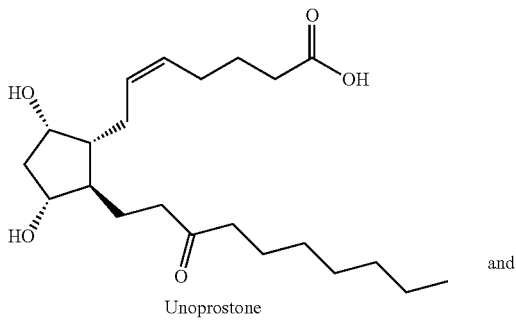
Unoprostone and

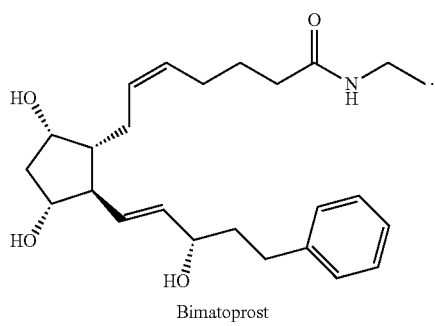 [SMILES: CCNC(=O)CCC/C=C\C[C@@H]1[C@@H](/C=C/[C@@H](O)CCc2ccccc2)[C@H](O)C[C@@H]1O ; "."]
Bimatoprost

The disclosure provides a compound of Formula I:

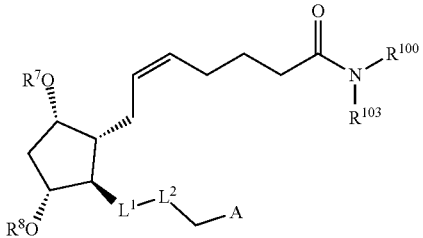
(I)

or a pharmaceutically acceptable composition, salt, or isotopic derivative thereof.

L¹ is selected from:

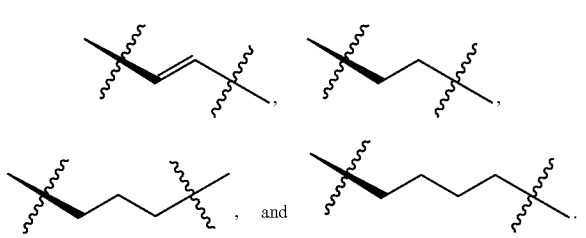

L² is selected from:

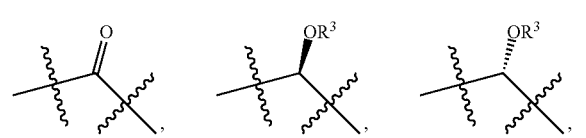

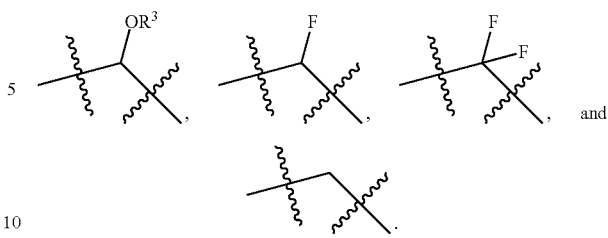

A is selected from: H, alkyl, cycloalkyl, cycloalkylalkyl, heterocycle, heterocycloalkyl, aryl, arylalkyl, heteroaryl, heteroarylalkyl, aryloxy, and alkyloxy wherein each group can be optionally substituted with another desired substituent group which is pharmaceutically acceptable and sufficiently stable under the conditions of use, for example selected from $R^5$.

$R^{103}$ is selected from: H, alkyl, cycloalkyl, cycloalkylalkyl, heterocycle, heterocycloalkyl, aryl, arylalkyl, heteroaryl, heteroarylalkyl, aryloxy, and alkyloxy wherein each group can be optionally substituted with another desired substituent group which is pharmaceutically acceptable and sufficiently stable under the conditions of use, for example selected from $R^5$.

$R^3$ is selected from —C(O)$R^4$, —C(O)A, and hydrogen.

Non-limiting examples of Formula I include:

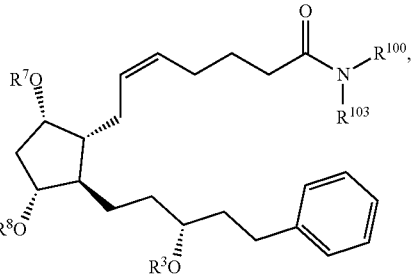

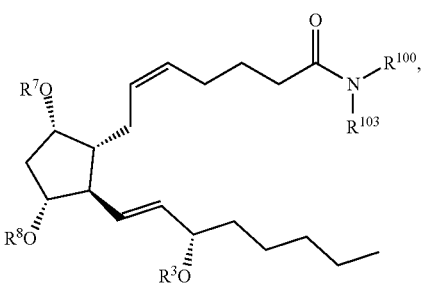

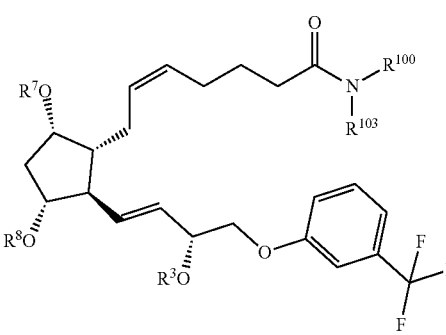

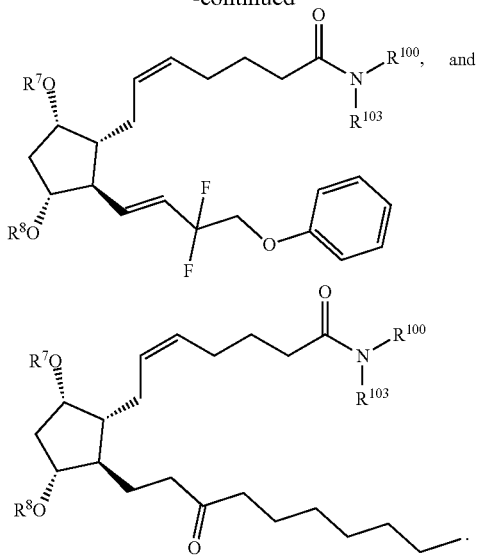

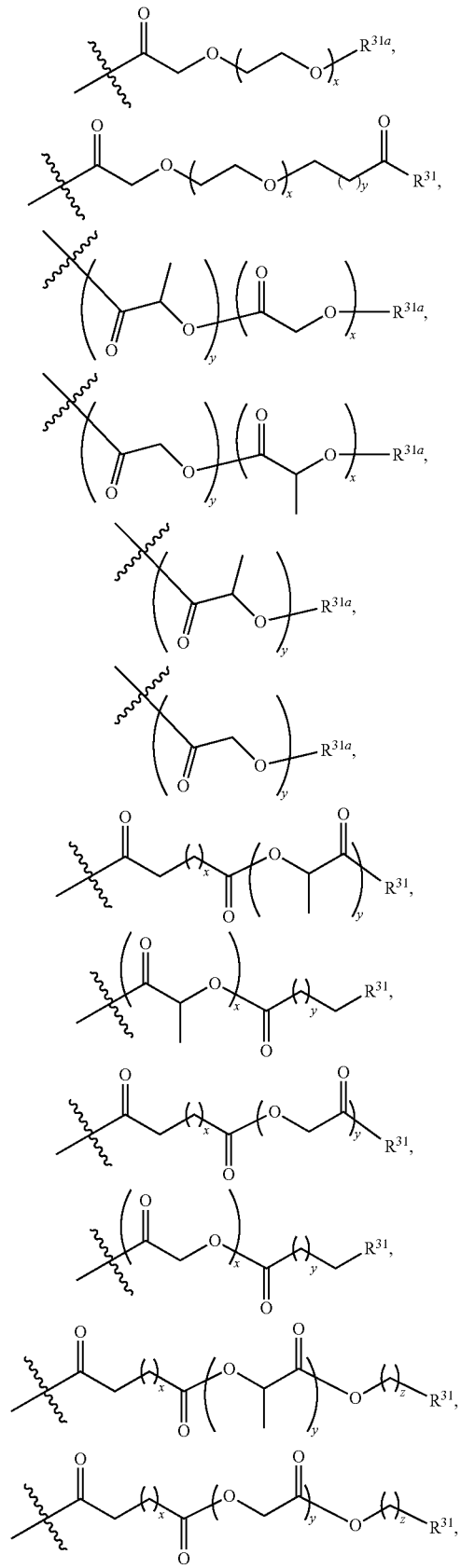

or $R^{50}$ is selected from:

$R^{100}$ is selected from:
(i) $C_1$-$C_{10}$alkyl, —$C_0$-$C_{10}$alkyl($C_3$-$C_7$cycloalkyl), heterocycle, —$C_0$-$C_{10}$alkyl($C_3$-$C_7$heterocycloalkyl), -aryl$C_0$-$C_{10}$alkyl, -heteroarylalkyl, —$C_0$-$C_{10}$alkyl$C_2$-$C_{10}$alkenyl, and $C_2$-$C_{10}$alkynyl;
(ii) an unsaturated fatty acid residue including but not limited the carbon fragment taken from linoleic acid (—$(CH_2)_8(CH)_2CH_2(CH)_2(CH_2)_4CH_3$)), docosahexaenoic acid (—$(CH_2)_3(CHCHCH_2)_6CH_3$)), eicosapentaenoic acid (—$(CH_2)_4(CHCHCH_2)_5CH_3$)), alpha-linolenic acid (—$(CH_2)_8(CHCHCH_2)_3CH_3$)) stearidonic acid, y-linolenic acid, arachidonic acid, docosatetraenoic acid, palmitoleic acid, vaccenic acid, paullinic acid, oleic acid, elaidic acid, gondoic acid, euric acid, nervonic acid and mead acid;
(iii) -$C_{10}$-$C_{30}$alkyl$R^5$, —$C_{10}$-$C_{30}$alkenyl$R^5$, —$C_{10}$-$C_{30}$alkynyl$R^5$, —$C_{10}$-$C_{30}$alkenylalkynyl$R^5$, —$C_{10}$-$C_{30}$alkyl, —$C_{10}$-$C_{30}$alkenyl, —$C_{10}$-$C_{30}$alkynyl, —$C_{10}$-$C_{30}$alkenylalkynyl; and (iv) $R^{50}$;

In one embodiment, —$C_{10}$-$C_{30}$ as used in the definition of $R^{100}$ is —$C_{12}$-$C_{28}$, —$C_{12}$-$C_{26}$, —$C_{12}$-$C_{24}$, —$C_{14}$-$C_{22}$, —$C_{14}$-$C_{20}$, —$C_{14}$-$C_{18}$, —$C_{14}$-$C_{16}$, or —$C_{12}$-$C_{14}$.

wherein in Formula I, $R^{100}$ can only be selected from (i), (ii), and (iii) above if at least one of $R^7$ and $R^8$, is selected to be $R^{50}$.

$R^5$ is selected from: halogen, hydroxyl, cyano, mercapto, amino, alkoxy, cycloalkyl, cycloalkylalkyl, heterocyclyl, heterocycloalkyl, aryl, arylalkyl, heteroaryl, heteroarylalkyl, aryloxy, —S(O)$_2$alkyl, —S(O)alkyl, —P(O)(Oalkyl)$_2$, B(OH)$_2$, —Si(CH$_3$)$_3$, —COOH, —COOalkyl, and —CONH$_2$, each of which except halogen, cyano, and —Si(CH$_3$)$_3$ may be optionally substituted, for example with halogen, alkyl, aryl, heterocycle or heteroaryl if desired and if the resulting compound is stable and achieves the desired purpose, wherein the group cannot be substituted with itself, for example alkyl would not be substituted with alkyl;

$R^7$ and $R^8$, are independently selected from: —C(O)$R^4$, —C(O)A, hydrogen, and $R^{50}$;

$R^{50}$ is selected from carbonyl derivatives of polyethylene glycol, polypropylene glycol, polypropylene oxide, polylactic acid, poly(lactic-co-glycolic acid), polyglycolic acid, polyester, polyamide, and other biodegradable polymers, each of which $R^{50}$ can be optionally capped or substituted with a $R^{31}$;

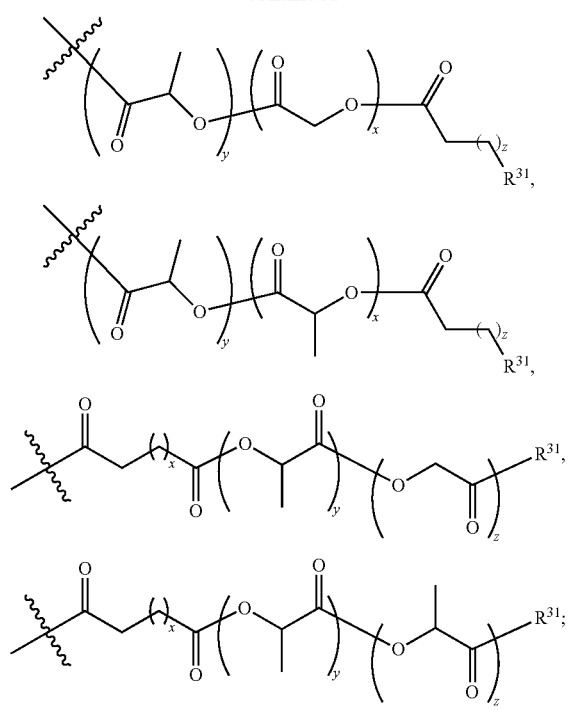

or R⁵⁰ is

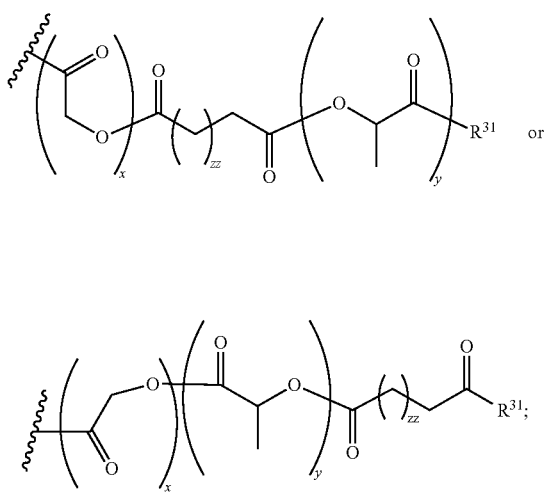

In some embodiments, the compound can be capped with hydrogen, or can be capped to create a terminal ester or ether. For example, the moiety can be capped with a terminal hydroxyl or carboxy which can be further derivatized to an ether or ester; and $R^{31}$ is hydrogen, hydroxy, amino, A, alkyl, alkoxy, alkenyl, alkynyl cycloalkyl, cycloalkylalkyl, heterocyclyl, heterocycloalkyl, aryl, arylalkyl, heteroaryl, heteroarylalkyl, aryloxy, or polyethylene glycol;

$R^{31a}$ is hydrogen, A, —C(O)alkyl, aryl, alkyl, cycloalkyl, cycloalkylalkyl, heterocyclyl, heterocycloalkyl, arylalkyl, heteroaryl, heteroarylalkyl, polylactic acid, polygylcolic acid, polyethylene glycol, stearoyl, or

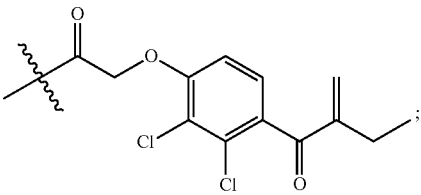 [SMILES: *C(=O)COc1ccc(C(=O)C(=C)CC)c(Cl)c1Cl]

$R^4$ is selected from:

(i) —$C_{20}$-$C_{30}$alkyl$R^5$, —$C_{20}$-$C_{30}$alkenyl$R^5$, —$C_{20}$-$C_{30}$alkynyl$R^5$, —$C_{20}$-$C_{30}$alkenylalkynyl$R^5$, —$C_{20}$-$C_{30}$alkyl, —$C_{20}$-$C_{30}$alkenyl, —$C_{20}$-$C_{30}$alkynyl, —$C_{20}$-$C_{30}$alkenylalkynyl;

(ii) an unsaturated fatty acid residue containing at least 20 carbon atoms including but not limited to the carbon chains from docosahexaenoic acid (—$(CH_2)_3$ $(CHCHCH_2)_6CH_3$)), eicosapentaenoic acid (—$(CH_2)_4$ $(CHCHCH_2)_5CH_3$)), docosatetraenoic acid, and nervonic acid, and wherein, if desired, each of which can be substituted with $R^5$.

x, y, and z can independently be any integer between 1 and 30 (1, 2, 3, 4, 5, 6, 7, 8, 9, 10, 11, 12, 13, 14, 15, 16, 17, 18, 19, 20, 21, 22, 23, 24, 25, 26, 27, 28, 29 or 30).

Non-limiting examples of $R^{50}$ include:

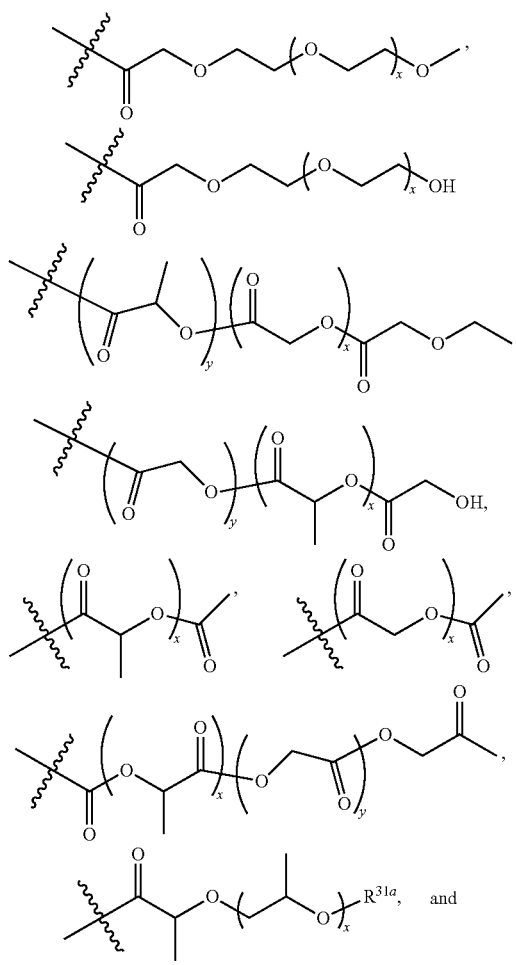

-continued
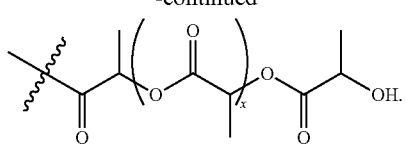
Additional non-limiting examples of $R^{50}$ include:
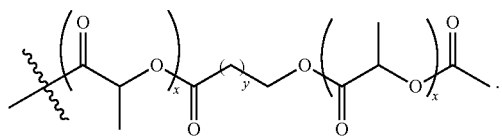
Non-limiting examples of $R^4$ include:
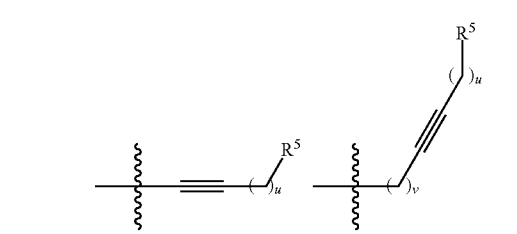
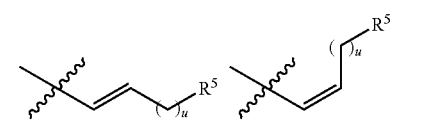
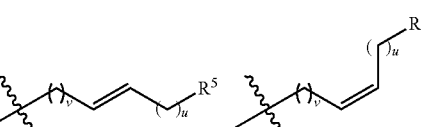
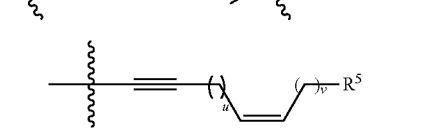
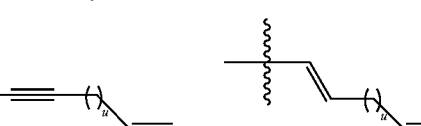
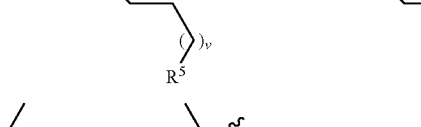

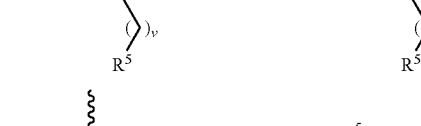
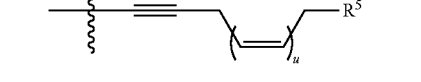
-continued
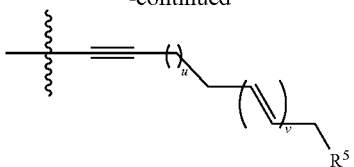
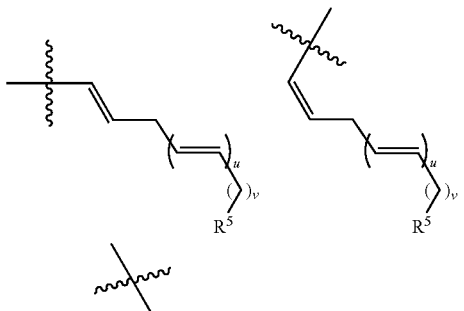
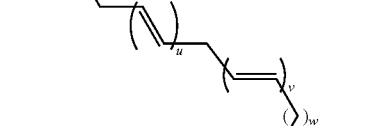
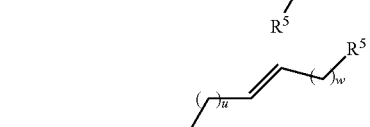
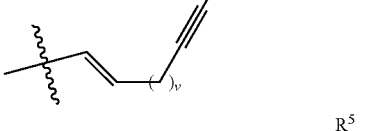
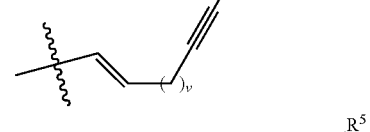
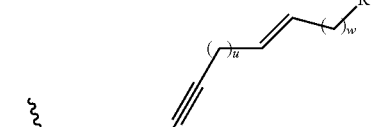
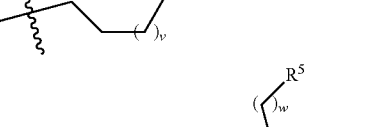
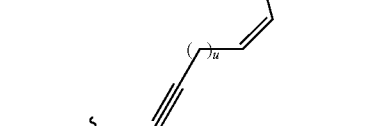
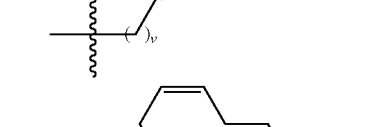
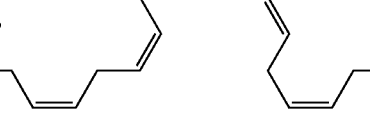

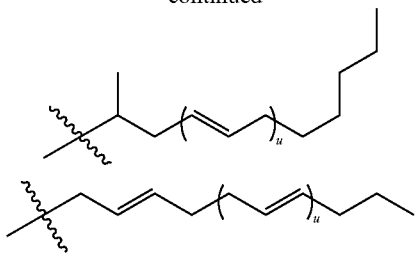

n, m, and o can independently be any integer between 0 and 29 (0, 1, 2, 3, 4, 5, 6, 7, 8, 9, 10, 11, 12, 13, 14, 15, 16, 17, 18, 19, 20, 21, 22, 23, 24, 25, 26, 27, 28 or 29);

wherein as used in $R^4$ above n+m+o is 18 to 30 carbons;

In one embodiment x, y, and z are independently selected from the following ranges: 1 to 5, 6 to 11, 12 to 17, 18 to 23, and 24 to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30).

Additional non-limiting examples of $R^{50}$ include:

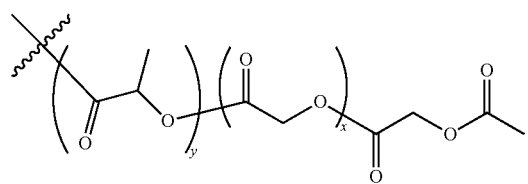

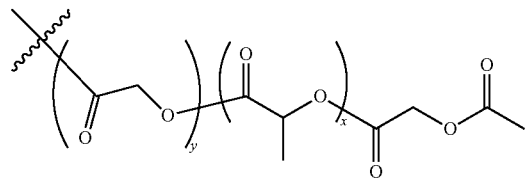

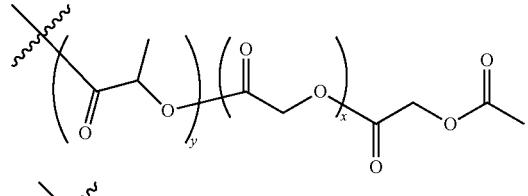

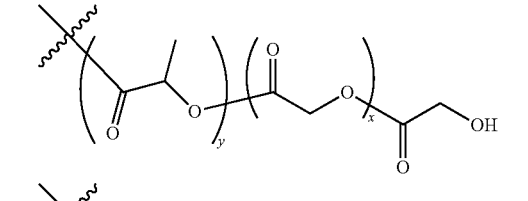

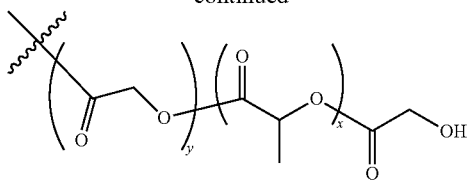

wherein x and y are as defined above.

In one embodiment $R^{100}$ is ethyl and $R^{103}$ is hydrogen.

In one embodiment a compound of Formula I or Formula II is hydrolysable by an enzyme in vivo, such as an esterase.

The disclosure also provides a compound of Formula II:

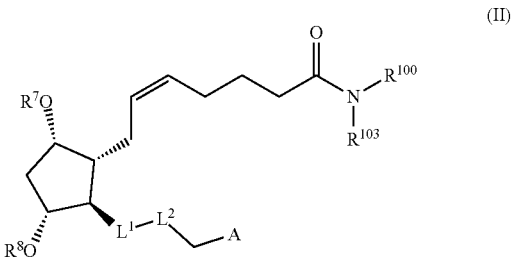

(II)

or a pharmaceutically acceptable composition, salt, or isotopic derivative thereof.

$L^3$ is selected from:

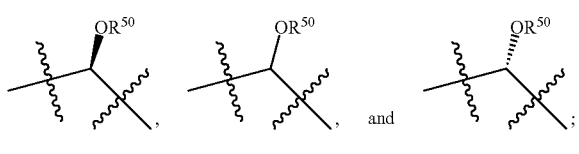

and wherein all other variables are as defined herein.

Non-limiting examples of Formula II include:

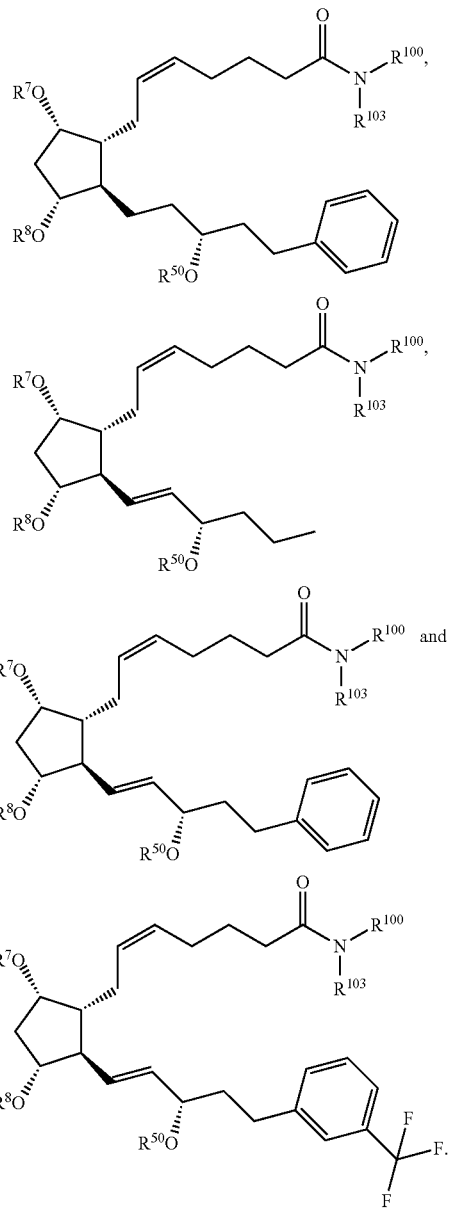

In one embodiment, $R^{100}$ is ethyl and $R^{103}$ is hydrogen.

In one embodiment, $R^{50}$ is X

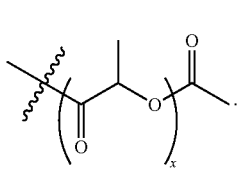

In one embodiment the disclosure provides a prodrug of a carbonic anhydrase inhibitor for ocular therapy, which can be released from a therapeutic, including a polymeric, delivery system while maintaining efficacy over an extended time such as up to 4, 5 or 6 months.

The disclosure provides a prostaglandin prodrug of Formula III:

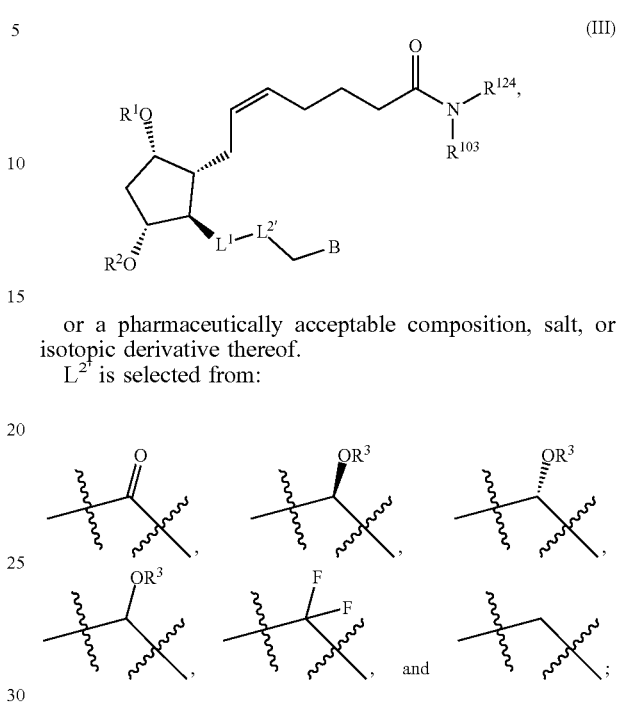

(III)

or a pharmaceutically acceptable composition, salt, or isotopic derivative thereof.

$L^{2'}$ is selected from:

B is selected from: heterocycle, heterocycloalkyl, aryl, arylalkyl, heteroaryl, heteroarylalkyl, aryloxy, and alkyloxy wherein each group can be optionally substituted with another desired substituent group which is pharmaceutically acceptable and sufficiently stable under the conditions of use, for example selected from $R^5$; and $R^1$, $R^2$, and $R^3$ are independently at each instance selected from: —C(O)$R^4$, C(O)A, and hydrogen,
 wherein in Formula III, $R^1$ or $R^2$ is —C(O)$R^4$;

$R^{124}$ is selected from:
(i) an unsaturated fatty acid residue containing at least 22 carbon atoms including but not limited to the carbon chains from docosahexaenoic acid (—(CH$_2$)$_3$(CHCHCH$_2$)$_6$CH$_3$)), alpha-linolenic acid (—(CH$_2$)$_8$(CHCHCH$_2$)$_3$CH$_3$)), docosatetraenoic acid, and nervonic acid,
(ii) —C$_{22}$-C$_{30}$alkylR$^5$, —C$_{22}$-C$_{30}$alkenylR$^5$, —C$_{22}$-C$_{30}$alkynylR$^5$, —C$_{22}$-C$_{30}$alkenylalkynylR$^5$, —C$_{22}$-C$_{30}$alkyl, —C$_{22}$-C$_{30}$alkenyl, —C$_{22}$-C$_{30}$alkynyl, —C$_{22}$-C$_{30}$alkenylalkynyl; and wherein, if desired, each $R^{124}$ can be substituted with $R^5$.

Non-limiting examples of $R^{124}$ include:

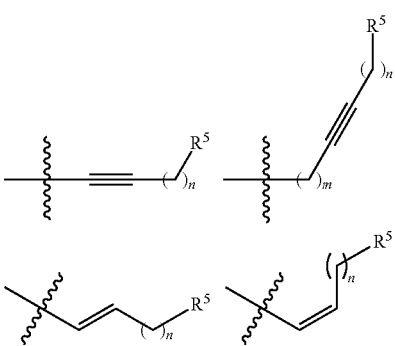

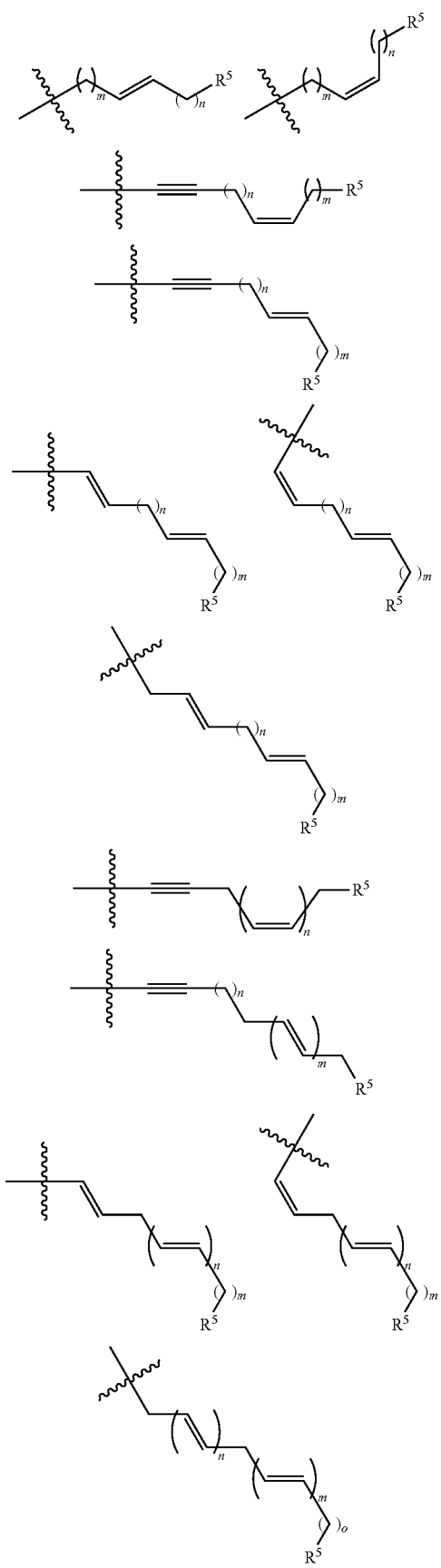
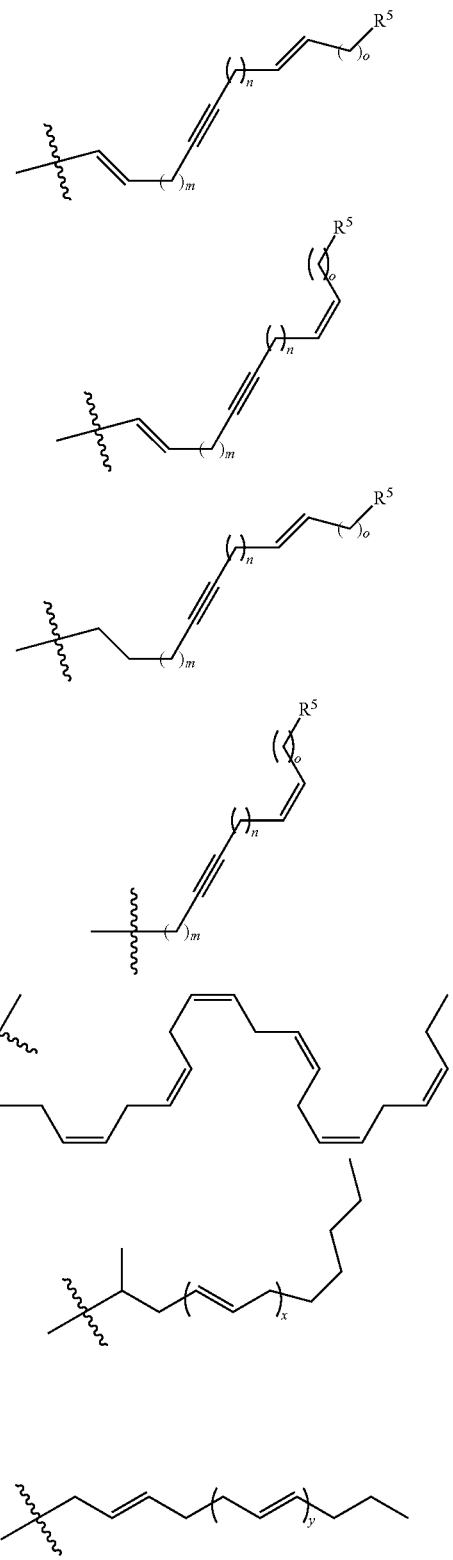
wherein u, v, and w can independently be any integer between 0 and 29 (1, 2, 3, 4, 5, 6, 7, 8, 9, 10, 11, 12, 13, 14, 15, 16, 17, 18, 19, 20, 21, 22, 23, 24, 25, 26, 27, 28 or 29) wherein u+v+w is 20 to 30 carbons; and
wherein all other variables are as defined herein.

Non-limiting examples of Formula III include:

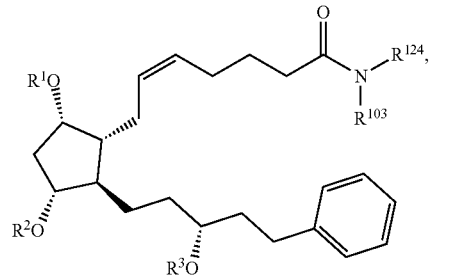

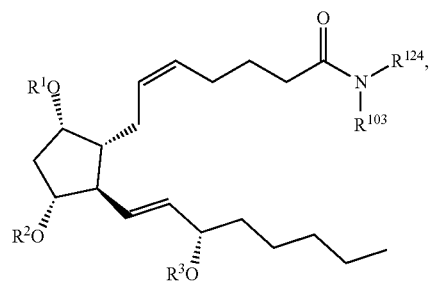

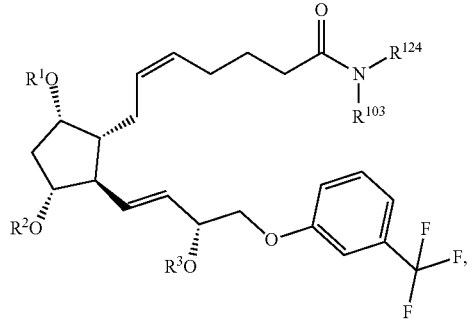

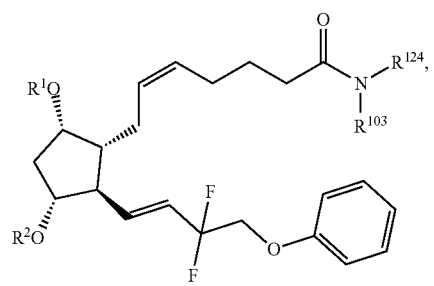

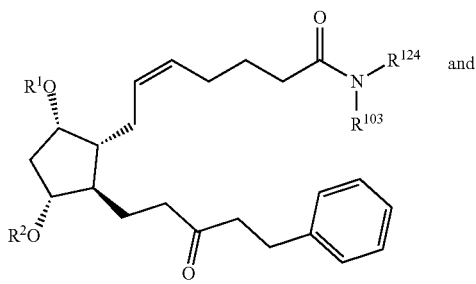 and

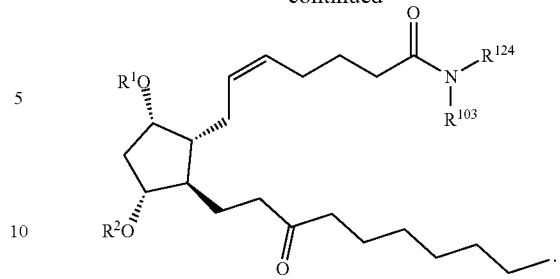

In one embodiment, —$C_{22}$-$C_{30}$ as used in the definition of $R^4$ is —$C_{22}$-$C_{28}$, —$C_{22}$-$C_{26}$, or —$C_{22}$-$C_{24}$.

While various structures are depicted as block copolymers (i.e., blocks of "x" followed by blocks of "y"), in some embodiments, the polymer can be a random or alternating copolymer ("x" and "y" are either randomly distributed or alternate).

In another embodiment a compound of Formula I, Formula II, or Formula III or a composition thereof is for use in the cosmetic enhancement of eyelash hair or eyebrow hair.

In another embodiment a compound of Formula I, Formula II, or Formula III or a composition thereof is used for the growth of eyelash or eyebrow hair.

The disclosure also provides a prodrug of Formula IV:

(IV)

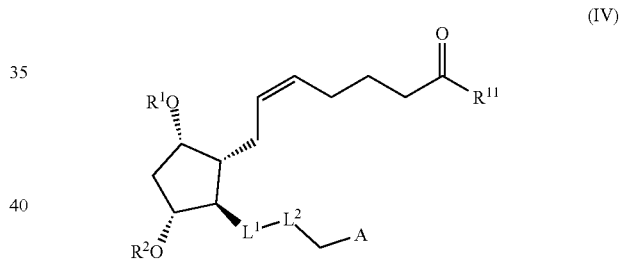

or a pharmaceutically acceptable composition, salt, or isotopic derivative thereof.

$R^{11}$ is selected from:

(i) $R^{102}$;

(ii) —NH—$C_2$-$C_{30}$alkenyl-C(O)$R^{102}$, —NH—$C_2$-$C_{30}$alkynyl-C(O)$R^{102}$, —NH—$C_2$-$C_{30}$alkenylalkynyl-C(O)$R^{102}$, —NH—$C_1$-$C_{30}$alkyl-C(O)$R^{102}$, —O—$C_2$-$C_{30}$alkenyl-C(O)$R^{102}$, —O—$C_2$-$C_{30}$alkynyl-C(O)$R^{102}$, —O—$C_2$-$C_{30}$alkenylalkynyl-C(O)$R^{102}$, and —O—$C_1$-$C_{30}$alkyl-C(O)$R^{102}$;

(iii)

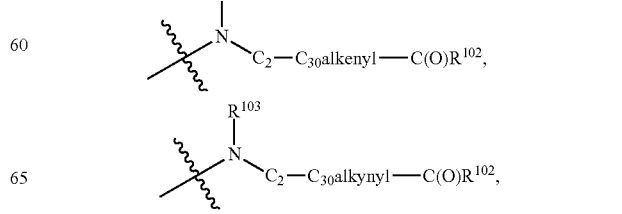

-continued
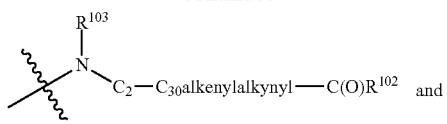
and
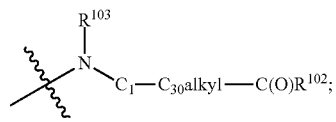
(iv) polyethylene glycol, polypropylene glycol, polypropylene oxide, polylactic acid, and poly(lactic-co-glycolic acid) capped with $R^{102}$
(v)
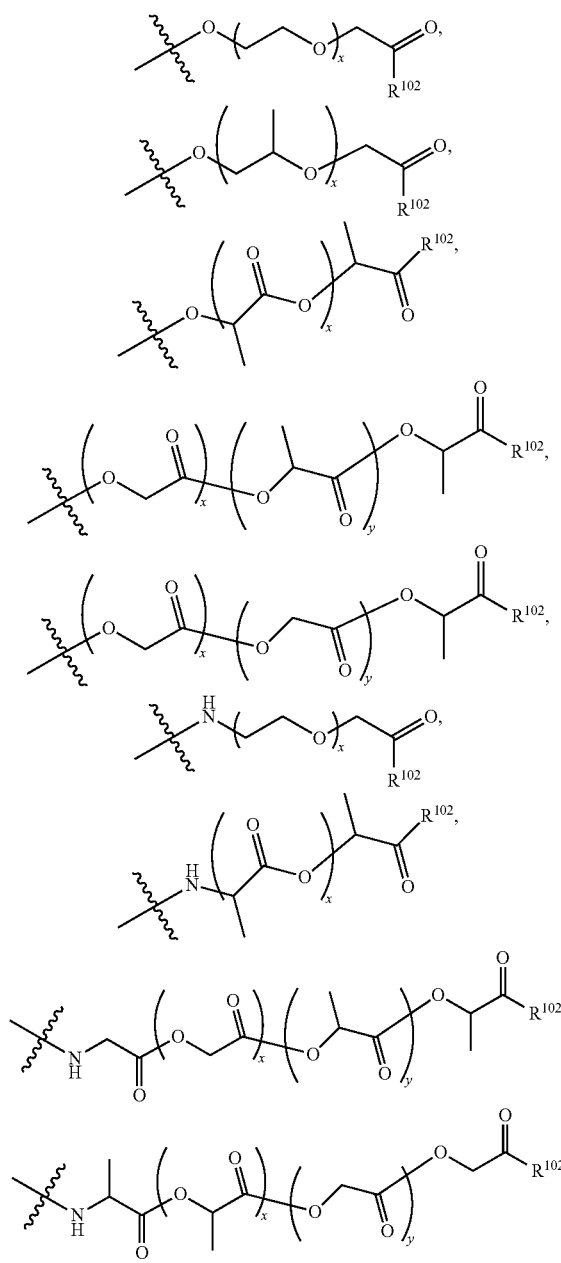
-continued
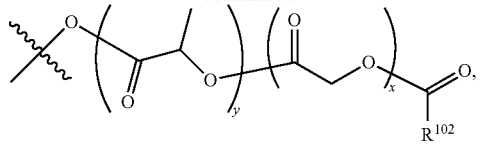
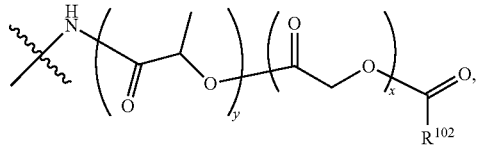
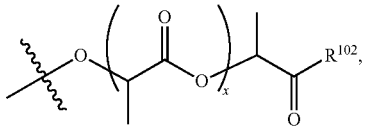
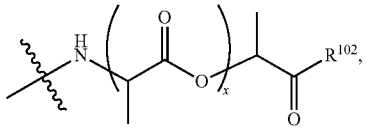
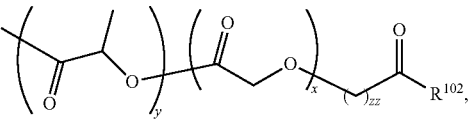
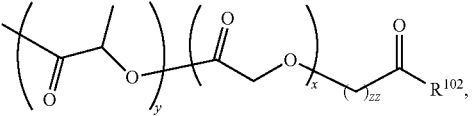
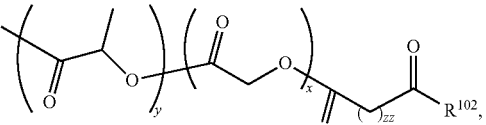
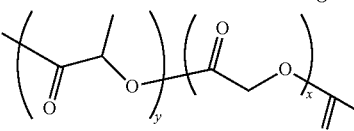
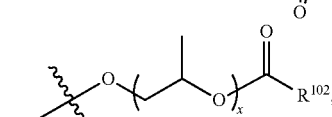
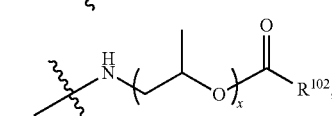
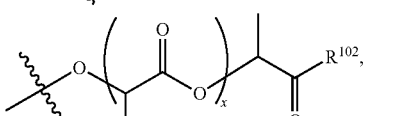
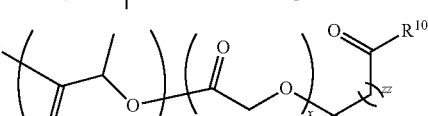
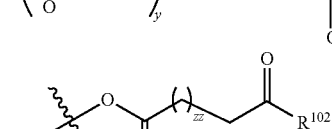

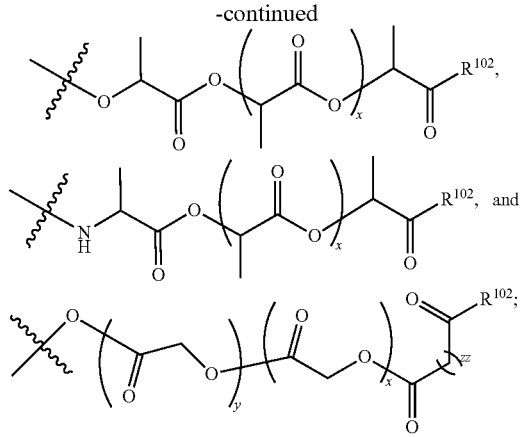
or R[11] is
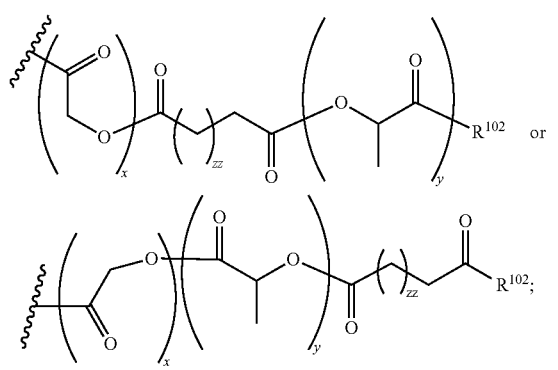
wherein R[11] can be further substituted with R[5] if valence permits, a stable compound is formed, and the resulting compound is pharmaceutically acceptable;
zz is selected from 1, 2, 3, 4, 5, or 6;
or zz is selected from at 7, 8, or 9;
or zz is 0 if the resulting compound is sufficiently stable.
Non-limiting examples of R[11] include:
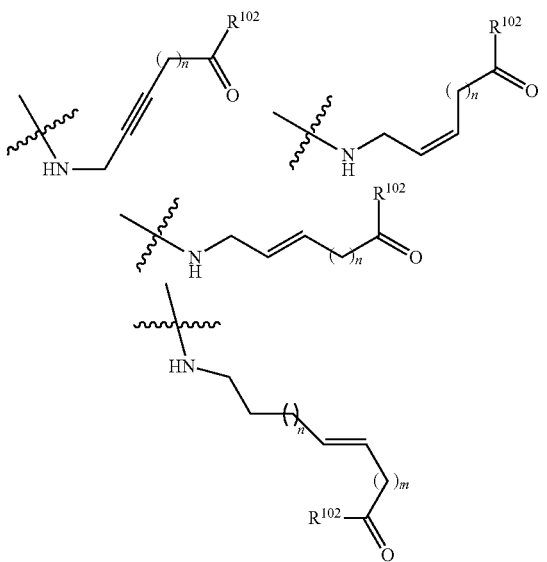
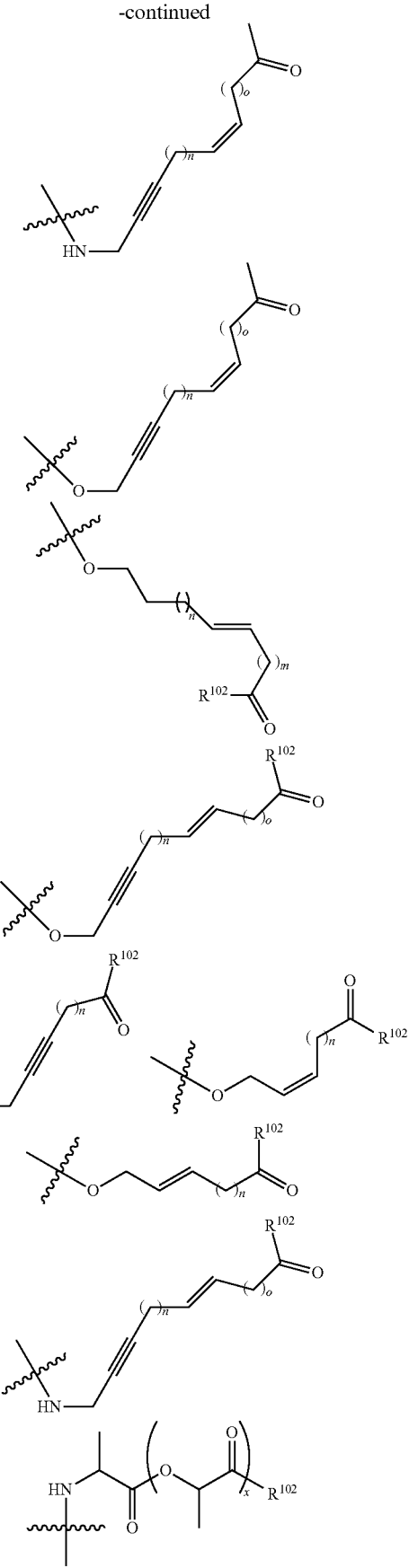

-continued
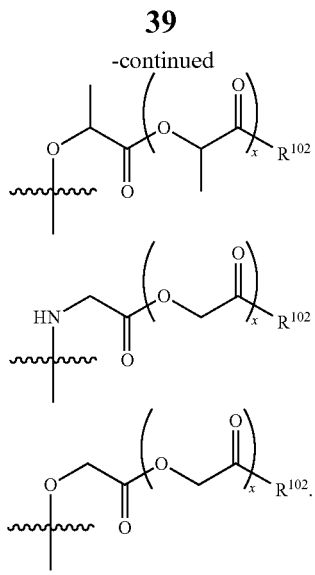
Additional non-limiting examples of $R^{11}$ include:
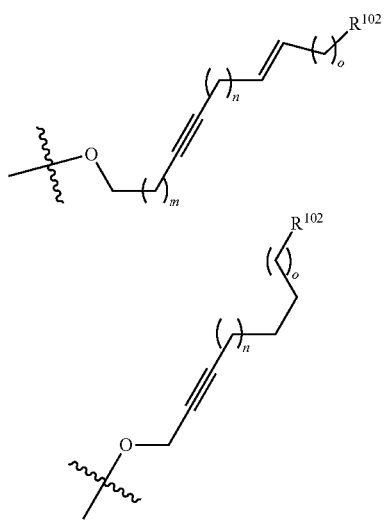
wherein n, m, o, x, and y are as defined above; $R^{102}$ is
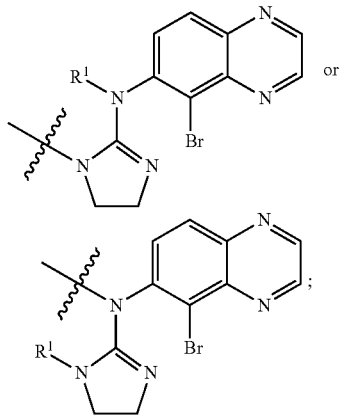
or $R^{102}$ is
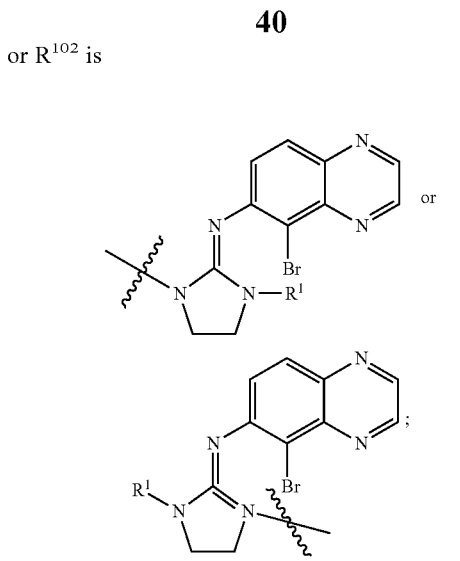
wherein all other variables are as defined herein.
In various different embodiments, $-C_2-C_{30}$ as used in the definition of $R^{11}$ may be $-C_2-C_{28}$, $-C_4-C_{26}$, $-C_4-C_{24}$, $-C_6-C_{22}$, $-C_6-C_{20}$, $-C_8-C_{18}$, $-C_8-C_{16}$, $-C_5-C_{14}$, $-C_8-C_{12}$, $-C_5-C_{20}$, or $-C_6-C_{24}$
Non-limiting examples of Formula IV include:
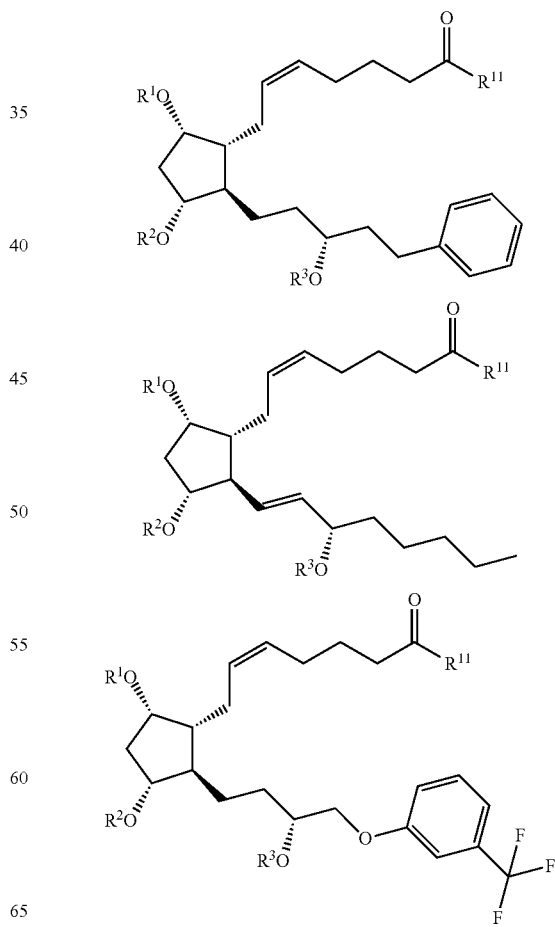

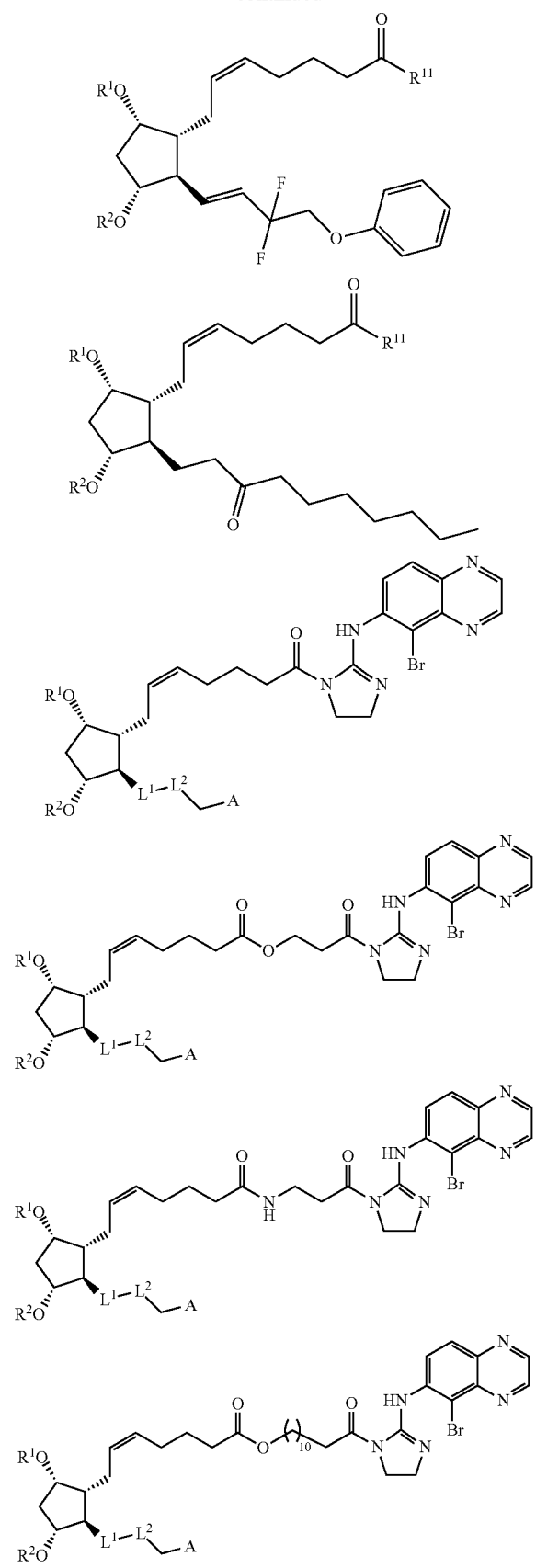
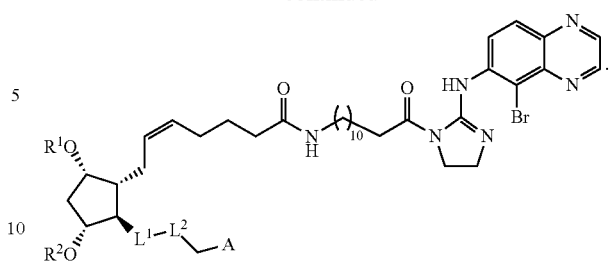
The disclosure also provides a compound of Formula V and VI:
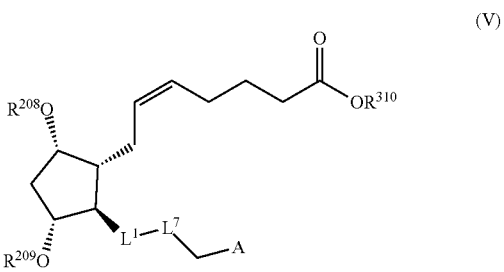
(V)
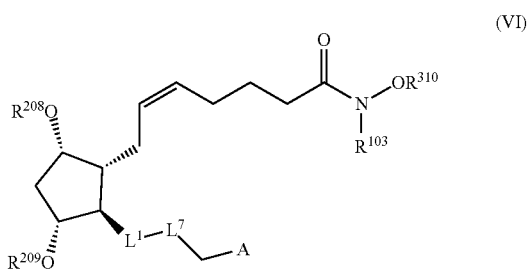
(VI)
or a pharmaceutically acceptable composition, salt, or isotopic derivative thereof.
$R^{310}$ is alkyl or hydrogen;
$L^7$ is selected from:
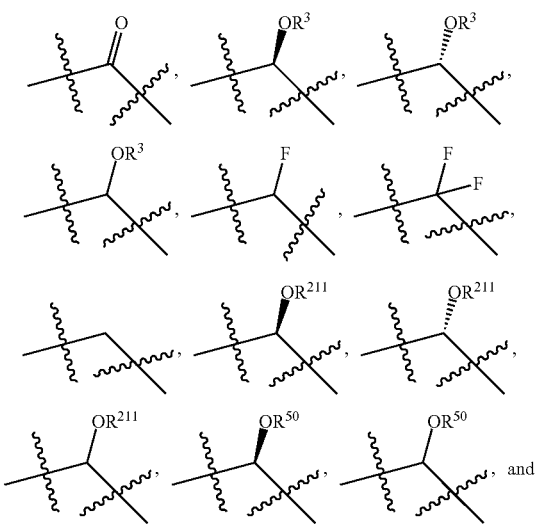

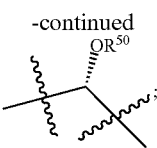

$R^{208}$ and $R^{209}$ are independently selected from: —C(O)$R^{4b}$, —C(O)A, hydrogen, $R^{21}$, and $L^8$-$R^{212}$;

$R^{4b}$ is selected from:

(i) —$C_{10}$-$C_{30}$alkyl$R^5$, —$C_{10}$-$C_{30}$alkenyl$R^5$, —$C_{10}$-$C_{30}$alkynyl$R^5$, —$C_{10}$-$C_{30}$alkenylalkynyl$R^5$, —$C_{10}$-$C_{30}$alkyl, —$C_{10}$-$C_{30}$alkenyl, —$C_{10}$-$C_{30}$alkynyl, —$C_{10}$-$C_{30}$alkenylalkynyl;

(ii) an unsaturated fatty acid residue including but not limited to the carbon chains from linoleic acid (—$(CH_2)_8(CH)_2CH_2(CH)_2(CH_2)_4CH_3$)), docosahexaenoic acid (—$(CH_2)_3(CHCHCH_2)_6CH_3$)), eicosapentaenoic acid (—$(CH_2)_4(CHCHCH_2)_5CH_3$)), alpha-linolenic acid (—$(CH_2)_8(CHCHCH_2)_3CH_3$)) stearidonic acid, y-linolenic acid, arachidonic acid, docosatetraenoic acid, palmitoleic acid, vaccenic acid, paullinic acid, oleic acid, elaidic acid, gondoic acid, euric acid, nervonic acid or mead acid, and wherein, if desired, each of which can be substituted with $R^5$.

wherein either at least one of $R^{208}$ and $R^{209}$ is $R^{211}$ or $L^8$-$R^{212}$; or $L^7$ is selected from

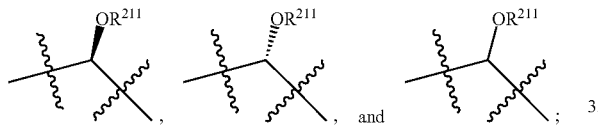

$L^8$ is —C(O)-alkyl-C(O)— or $L^8$ is —C(O)-alkenyl-C(O)—;

$R^{211}$ is selected from:

polyethylene glycol, polypropylene glycol, polypropylene oxide, polylactic acid, a biodegradable polymer and poly(lactic-co-glycolic acid) each of which is optionally linked by a carbonyl and each is capped with $R^{212}$ including:

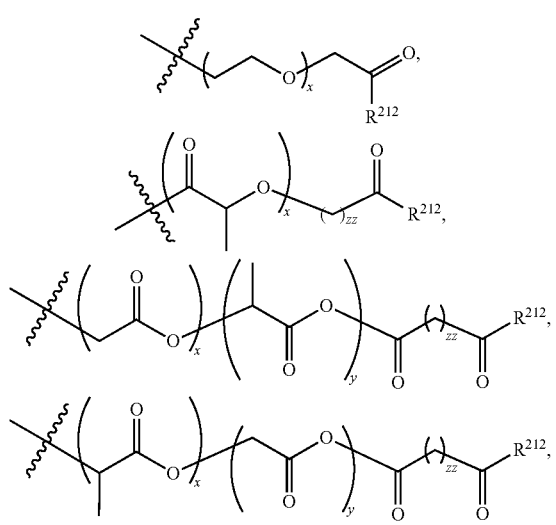

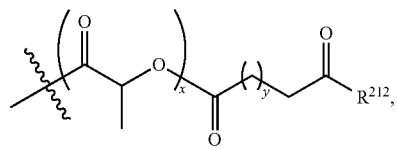

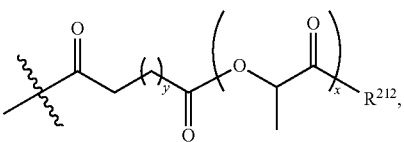

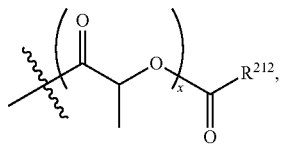

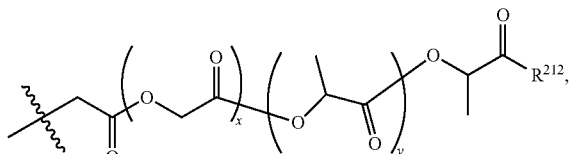

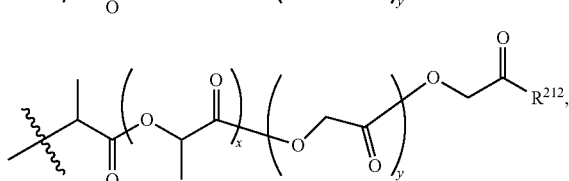

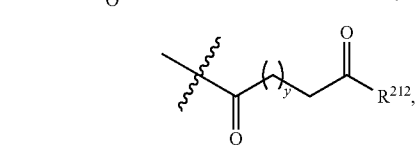

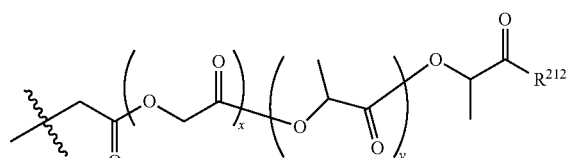

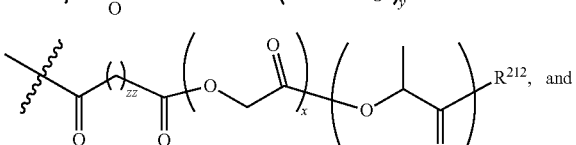, and

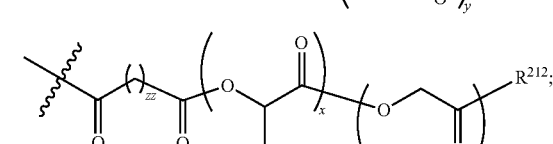;

or $R^{211}$ is selected from:

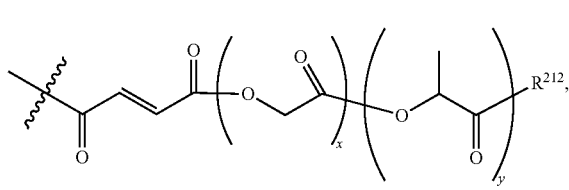

-continued
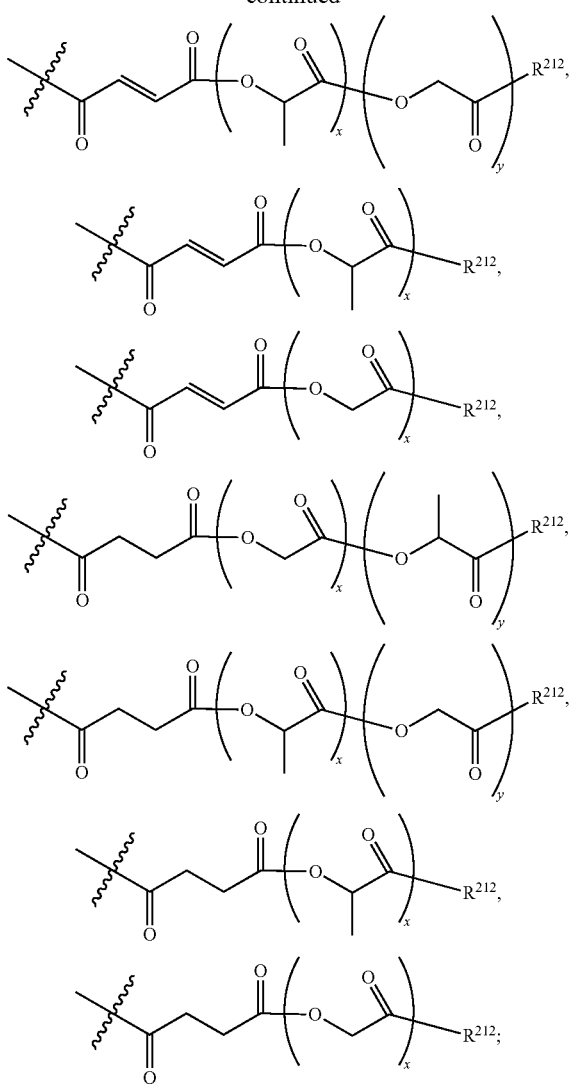
or R²¹¹ is
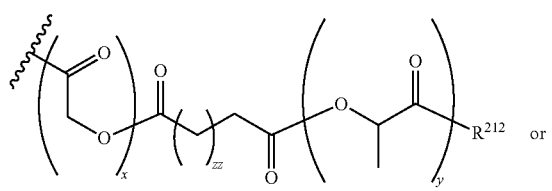
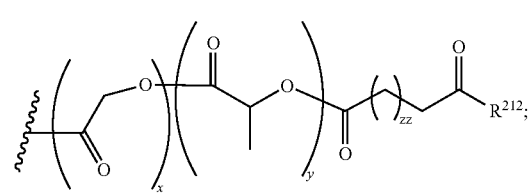
R²¹² is selected from:
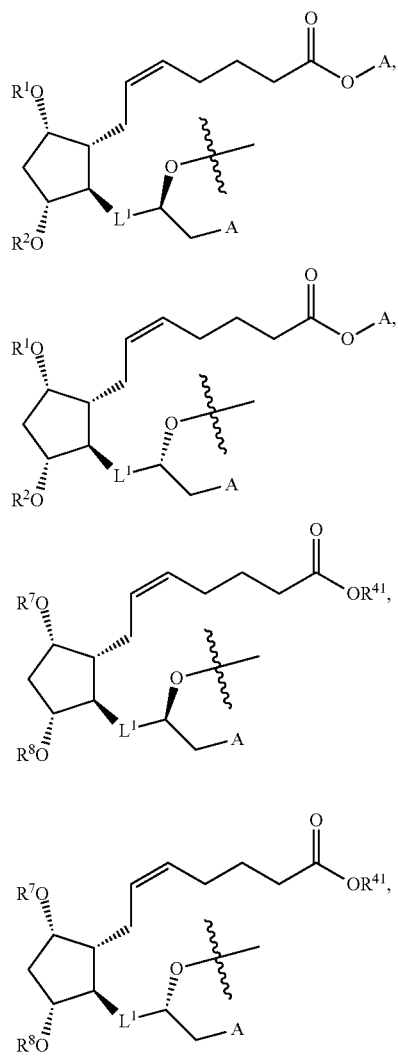
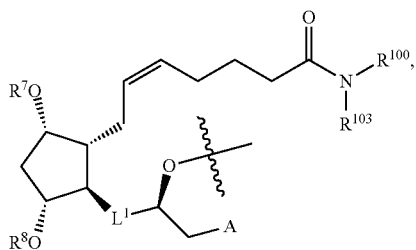
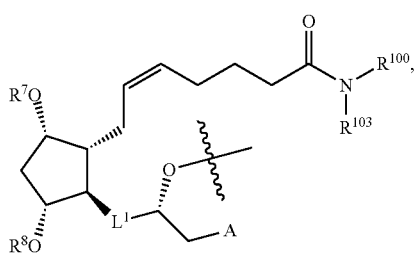

-continued

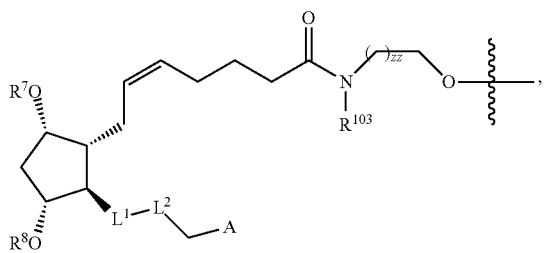

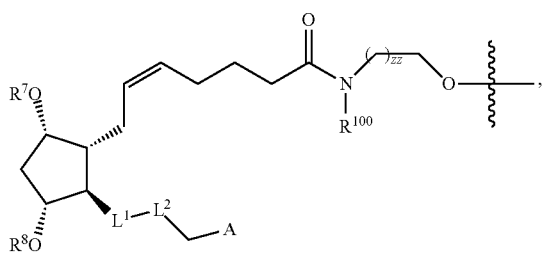

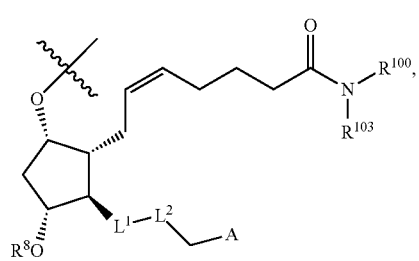

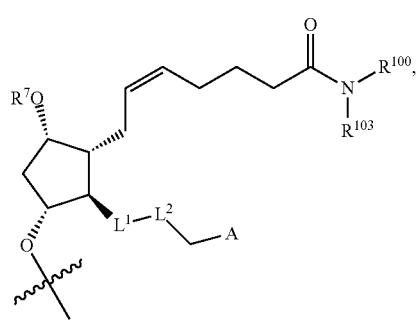

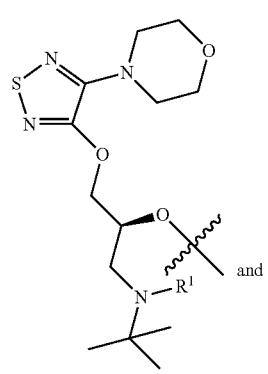 and

-continued

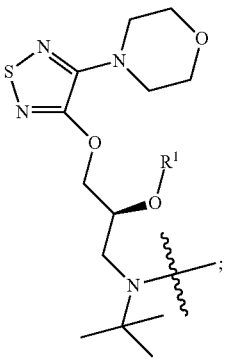

$R^{41}$ is selected from:

(i) polyethylene glycol, polypropylene glycol, polypropylene oxide, polylactic acid, poly(lactic-co-glycolic acid), polyglycolic acid, a polyester, a polyamide, or other biodegradable polymer,

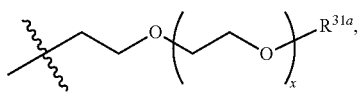

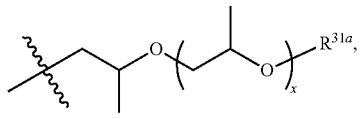

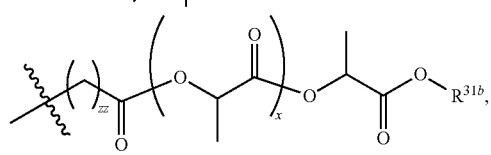

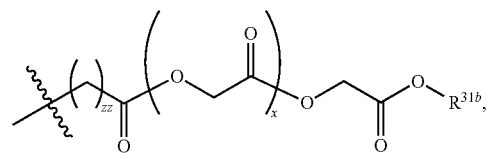

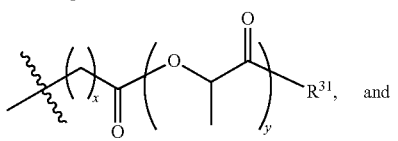, and

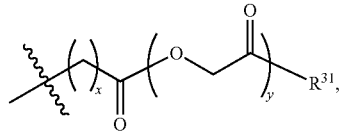

wherein in some embodiments a terminal hydroxy or carboxy group can be substituted to create an ether or ester;

(ii) —$C_{10}$-$C_{30}$alkyl$R^5$, —$C_{10}$-$C_{30}$alkenyl$R^5$, —$C_{10}$-$C_{30}$alkynyl$R^5$, —$C_{10}$-$C_{30}$alkenylalkynyl$R^5$, —$C_{10}$-$C_{30}$alkyl, —$C_{10}$-$C_{30}$alkenyl, —$C_{10}$-$C_{30}$alkynyl, and —$C_{10}$-$C_{30}$alkenylalkynyl;

(iii) an unsaturated fatty acid residue; and (iv) alkyl, cycloalkyl, cycloalkylalkyl, heterocycle, heterocycloalkyl, arylalkyl, and heteroarylalkyl; and wherein all other variables are as defined herein.

In one embodiment $R^{212}$ is
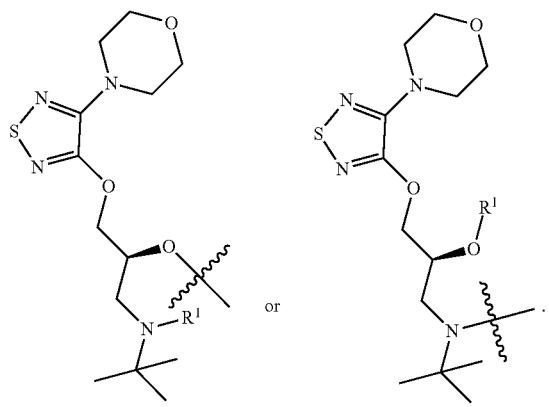
or
Non-limiting examples of $R^{41}$ include:
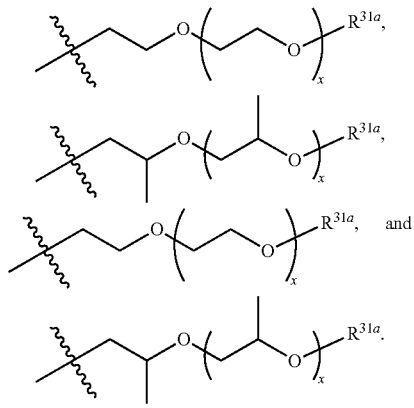
The disclosure also provides a compound of Formula V' and VI':
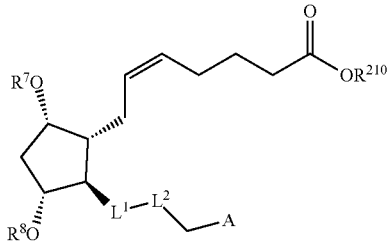
(V')
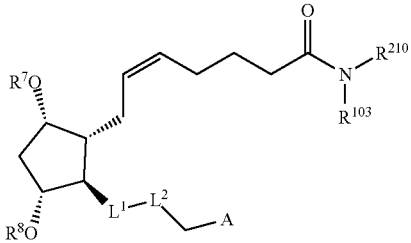
(VI')
or a pharmaceutically acceptable composition, salt, or isotopic derivative thereof.
$R^{210}$ is $L^9$-$R^{212}$;
$L^9$ is selected from:
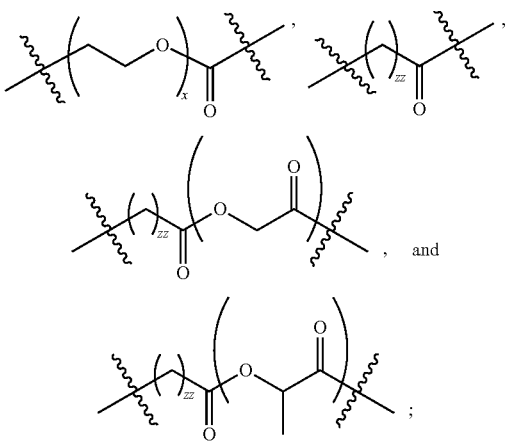
$R^{212}$ is selected from:
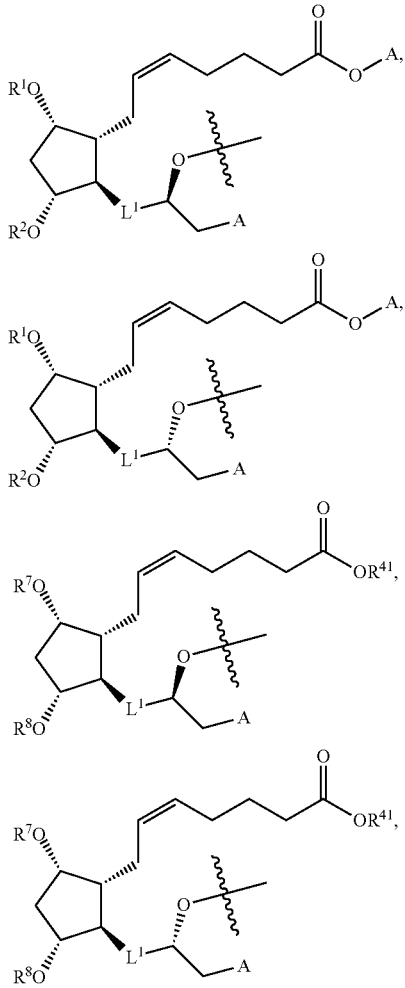

51
-continued
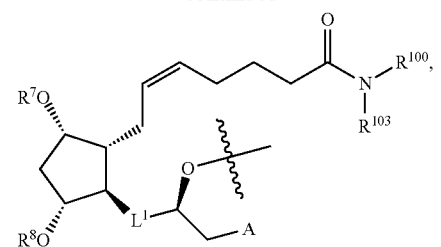
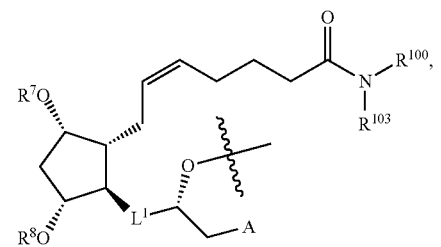
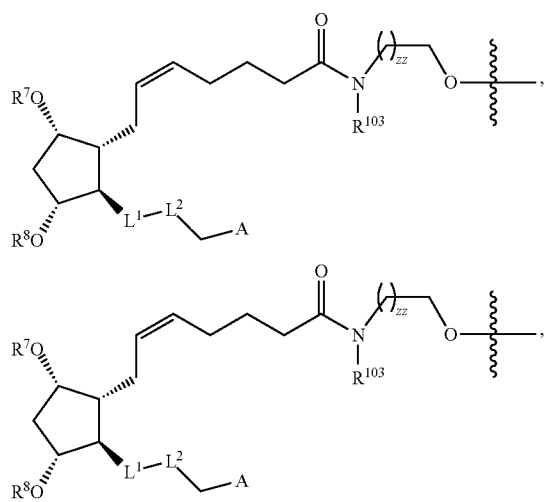
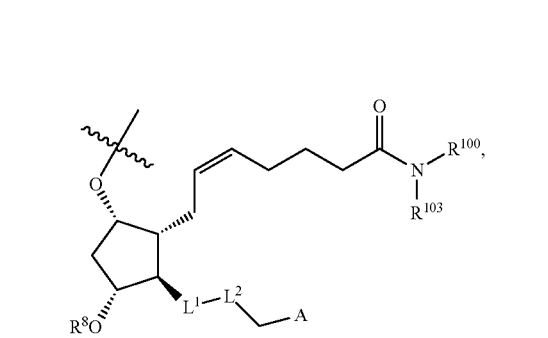
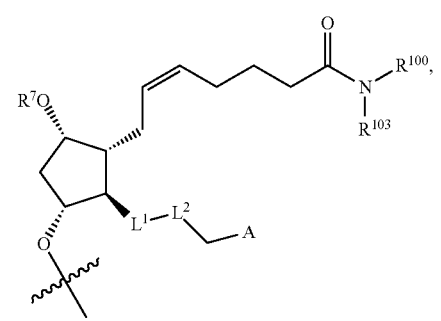
52
-continued
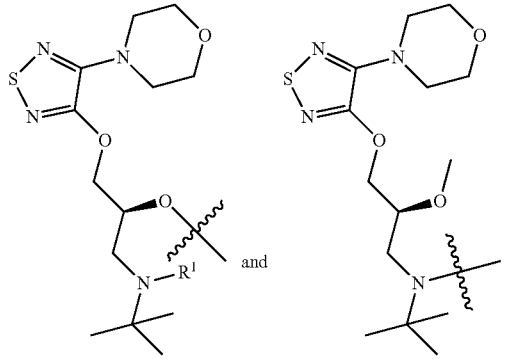
and
wherein all other variables are as defined herein.
In one embodiment $R^{212}$ is
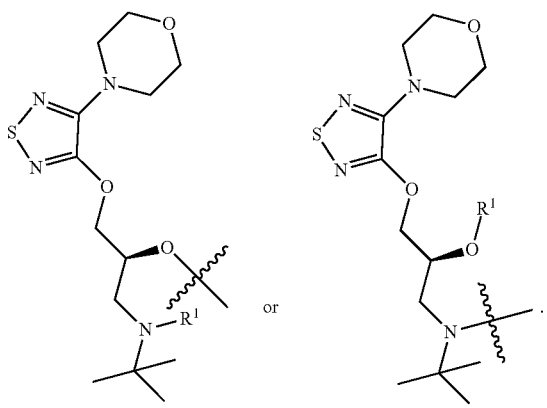
The disclosure also provides a prodrug of Formula VII, Formula VIII, or Formula VIII':
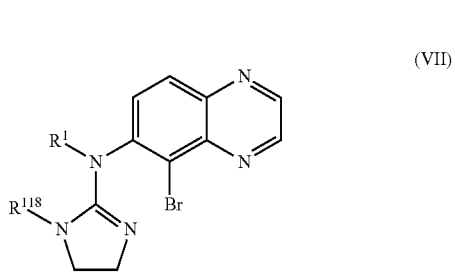
(VII)
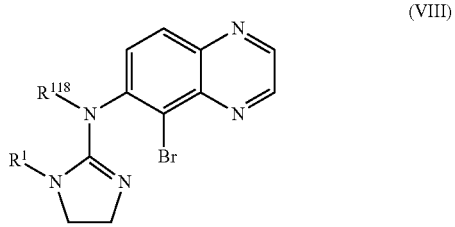
(VIII)

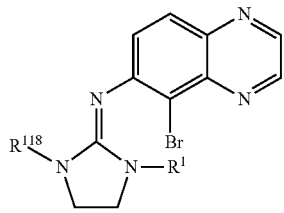

(VIII')

or a pharmaceutically acceptable composition, salt, or isotopic derivative thereof.

$R^{118}$ is selected from:
(i) —C(O)C$_5$-C$_{30}$alkylR$^5$, —C(O)C$_2$-C$_{30}$alkenylR$^5$, —C(O)C$_2$-C$_{30}$alkynylR$^5$, —C(O)C$_4$-C$_{30}$alkenylalkynylR$^5$, —C(O)C$_5$-C$_{30}$alkyl, —C(O)C$_2$-C$_{30}$alkenyl, —C(O)C$_2$-C$_{30}$alkynyl, and —C(O)C$_4$-C$_{30}$alkenylalkynyl;
(ii) —C(O)(C$_{1-30}$alkyl with at least one R$^5$ substituent on the alkyl chain), —C(O)(C$_{1-30}$alkenyl, with at least one R$^5$ substituent on the alkenyl chain), —C(O)(C$_{1-30}$alkynyl, with at least one R$^5$ substituent on the alkynyl chain), -(lactic acid)$_{1-20}$C(O)C$_{1-30}$alkyl, -(lactic acid)$_{1-10}$C(O)C$_{1-30}$alkyl, -(lactic acid)$_{4-20}$C(O)C$_{1-30}$alkyl, -(lactic acid)$_{1-20}$C(O)C$_{1-10}$alkyl, -(lactic acid)$_{1-20}$C(O)C$_{4-10}$alkyl, -(lactic acid)$_{1-20}$C(O)OH, -(lactic acid)$_{1-10}$C(O)OH, -(lactic acid)$_{4-20}$C(O)OH, -(lactic acid)$_{1-10}$C(O)OH, -(lactic acid)$_{4-10}$C(O)OH, -(lactide-co-glycolide)$_{1-10}$C(O)C$_{1-30}$alkyl, -(lactide-co-glycolide)$_{4-10}$C(O)C$_{1-30}$alkyl, -(lactide-co-glycolide)$_{1-10}$C(O)C$_{1-12}$alkyl, -(lactide-co-glycolide)$_{1-10}$C(O)C$_{4-22}$alkyl, -(glycolic acid)$_{1-10}$C(O)C$_{1-10}$alkyl, -(glycolic acid)$_{4-10}$C(O)C$_{1-10}$alkyl, -(lactic acid)$_{4-10}$C(O)C$_{1-10}$alkyl, -(lactic acid)$_{1-10}$C(O)C$_{1-10}$alkyl, -(lactic acid)$_{1-10}$C(O)C$_{4-10}$alkyl, -(lactic acid)$_{1-10}$C(O)C$_{4-10}$alkyl, and -(lactic acid)$_{1-10}$C(O)C$_{4-10}$alkyl;
(iii) an unsaturated fatty acid residue including but not limited to the carbonyl fragment taken from linoleic acid (—(CH$_2$)$_8$(CH)$_2$CH$_2$(CH)$_2$(CH$_2$)$_4$CH$_3$), docosahexaenoic acid (—(CH$_2$)$_3$(CHCHCH$_2$)$_6$CH$_3$)), eicosapentaenoic acid (—(CH$_2$)$_4$(CHCHCH$_2$)$_5$CH$_3$)), alpha-linolenic acid (—(CH$_2$)$_8$(CHCHCH$_2$)$_3$CH$_3$)), stearidonic acid, y-linolenic acid, arachidonic acid, docosatetraenoic acid, palmitoleic acid, vaccenic acid, paullinic acid, oleic acid, elaidic acid, gondoic acid, euric acid, nervonic acid and mead acid, each of which can be further optionally further substituted with R$^5$ (including for example a second R$^5$) if valence permits, a stable compound is formed, and the resulting compound is pharmaceutically acceptable;
(iv) polyethylene glycol, polypropylene glycol, polypropylene oxide, polylactic acid, poly(lactic-co-glycolic acid), polyglycolic acid, polyester, polyamide, and other biodegradable polymers, each of which can be capped to complete the terminal valence or to create a terminal ether or ester; and (v)

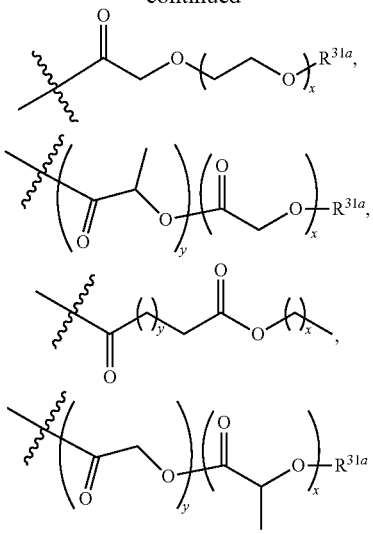

or $R^{118}$ is selected from:
(vi) —(C(O)CH$_2$O)$_{1-20}$C(O)C$_{1-30}$alkyl, —(C(O)CH(CH$_3$)O)$_{1-20}$C(O)C$_{1-30}$alkyl, —(C(O)CH$_2$O)$_{1-10}$C(O)C$_{1-30}$alkyl, —(C(O)CH(CH$_3$)O)$_{1-10}$C(O)C$_{1-30}$alkyl, —(C(O)CH$_2$O)$_{4-20}$C(O)C$_{1-30}$alkyl, —(C(O)CH(CH$_3$)O)$_{4-20}$C(O)C$_{1-30}$alkyl, —(C(O)CH$_2$O)$_{1-20}$C(O)C$_{1-10}$alkyl, —(C(O)CH(CH$_3$)O)$_{1-20}$C(O)C$_{1-10}$alkyl, —(C(O)CH$_2$O)$_{1-20}$C(O)C$_{4-10}$alkyl, —(C(O)CH(CH$_3$)O)$_{1-20}$C(O)C$_{4-10}$alkyl, —(C(O)CH(CH$_3$)O)$_{4-10}$C(O)C$_{1-10}$alkyl, —(C(O)CH$_2$O)$_{4-10}$C(O)C$_{1-10}$alkyl, —(C(O)CH(CH$_3$)O)$_{1-10}$C(O)C$_{1-10}$alkyl, —(C(O)CH$_2$O)$_{1-10}$C(O)C$_{1-10}$alkyl, —(C(O)CH(CH$_3$)O)$_{1-10}$C(O)C$_{4-10}$alkyl, (C(O)CH$_2$O)$_{1-10}$C(O)C$_{4-10}$alkyl, —(C(O)CH$_2$O)$_{1-10}$C(O)C$_{4-10}$alkyl, —(C(O)CH(CH$_3$)O)$_{1-10}$C(O)C$_{4-10}$alkyl, —(C(O)CH$_2$O)$_{1-11}$C(O)C$_{4-10}$alkyl, —(C(O)CH(CH$_3$)O)$_{1-10}$C(O)C$_{4-10}$alkyl, —(C(O)CH$_2$O)$_{1-10}$(C(O)CH(CH$_3$)O)$_{1-10}$C(O)C$_{1-30}$alkyl, —(C(O)CH$_2$O)$_{2-10}$ (C(O)CH(CH$_3$)O)$_{2-10}$C(O)C$_{1-30}$alkyl, —(C(O)CH$_2$O)$_{1-10}$(C(O)CH(CH$_3$)O)$_{1-10}$C(O)C$_{1-12}$alkyl, —(C(O)CH$_2$O)$_{1-10}$(C(O)CH(CH$_3$)O)$_{1-10}$C(O)C$_{4-22}$alkyl, —(C(O)CH(CH$_3$)O)$_{1-10}$(C(O)CH$_2$O)$_{1-10}$C(O)C$_{1-30}$alkyl, —(C(O)CH(CH$_3$)O)$_{2-10}$(C(O)CH$_2$O)$_{2-10}$C(O)C$_{1-30}$alkyl, —(C(O)CH(CH$_3$)O)$_{1-10}$(C(O)CH$_2$O)$_{1-10}$C(O)C$_{1-12}$alkyl, and —(C(O)CH(CH$_3$)O)$_{1-10}$(C(O)CH$_2$O)$_{1-10}$C(O)C$_{4-22}$alkyl;
or $R^{118}$ is

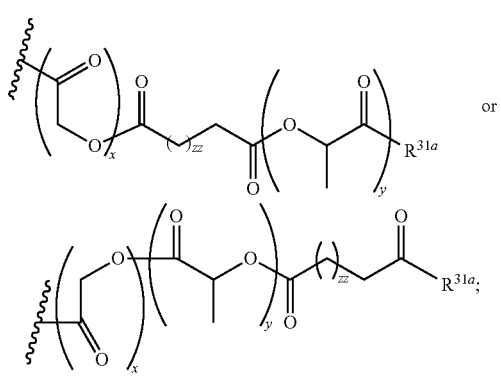

wherein all other variables are as defined herein.

In various different embodiments, —$C_{10}$-$C_{30}$ as used in the definition of $R^{118}$ is —$C_{10}$-$C_{18}$, —$C_{10}$-$C_{16}$, —$C_{10}$-$C_{14}$, —$C_{10}$-$C_{12}$, —$C_{19}$-$C_{28}$, —$C_{19}$-$C_{26}$, —$C_{19}$-$C_{24}$, —$C_{19}$-$C_{22}$, —$C_{19}$-$C_{20}$, —$C_{20}$-$C_{28}$, —$C_{20}$-$C_{26}$, —$C_{20}$-$C_{24}$, —$C_{20}$-$C_{22}$, —$C_{22}$-$C_{28}$, —$C_{22}$-$C_{26}$, —$C_{22}$-$C_{24}$, or —$C_{26}$-$C_{28}$.

Non-limiting examples of Formula VII include:

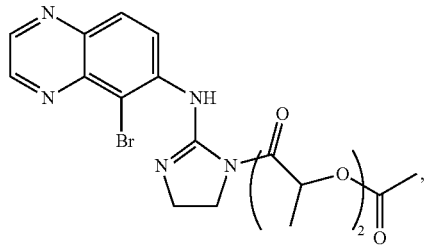

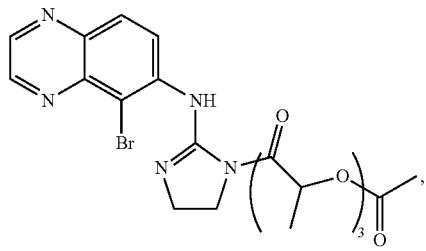

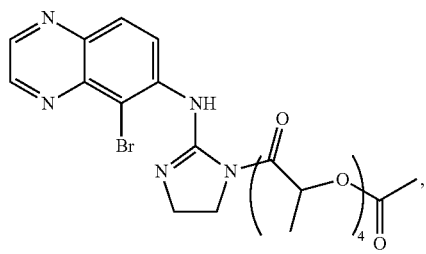

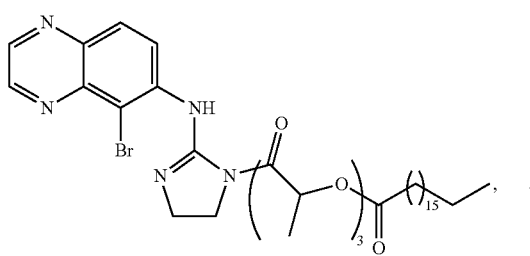

and

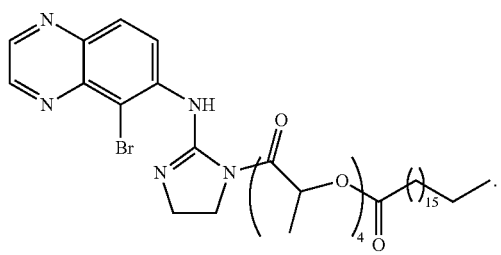

Compounds of Formula VIII' are drawn as

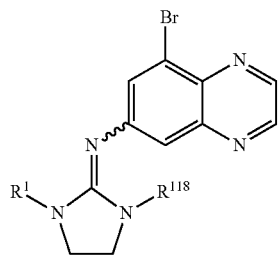

where the bond between the aromatic ring and the imidazole ring is drawn as a wavy line. In one embodiment, compounds of Formula VIII' are the Z isomer. In one embodiment, compounds of Formula VIII' are the E isomer. For example, Compound 115-1 is drawn as

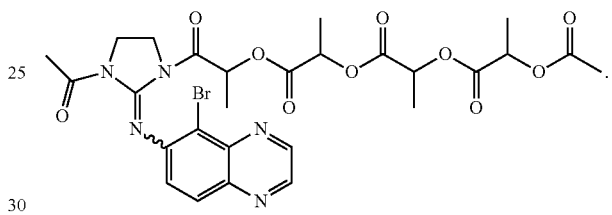

In one embodiment, Compound 115-1 is the Z isomer:

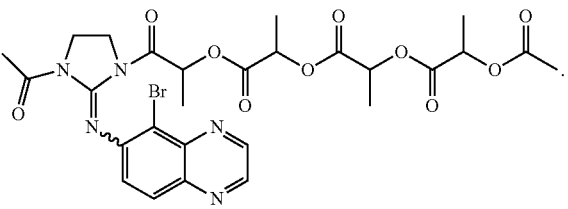 [SMILES: CC(=O)OC(C)C(=O)OC(C)C(=O)OC(C)C(=O)OC(C)C(=O)N1CCN(C(C)=O)C1=Nc1ccc2nccnc2c1Br]

In one embodiment, Compound 115-1 is the E isomer:

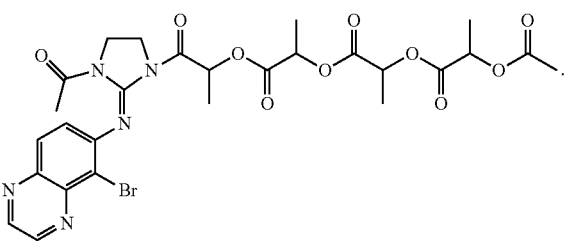 [SMILES: CC(=O)OC(C)C(=O)OC(C)C(=O)OC(C)C(=O)OC(C)C(=O)N1CCN(C(C)=O)/C1=N\c1ccc2nccnc2c1Br]

The disclosure also provides a prodrug of Formula IX, IX', or IX":

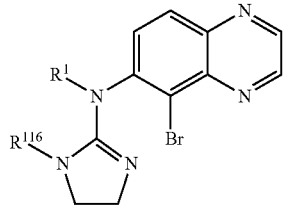
(IX)

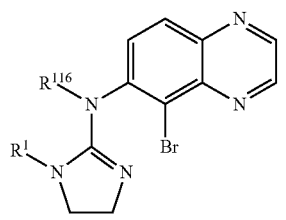
(IX')

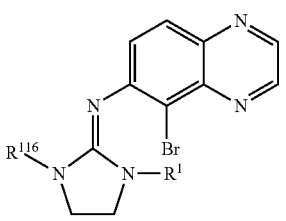
(IX")

or a pharmaceutically acceptable composition, salt, or isotopic derivative thereof.

$R^{116}$ is selected from: $R^{117}$, alkyl, alkyloxy, acyl, polyethylene glycol, polypropylene glycol, polypropylene oxide, polylactic acid, poly(lactic-co-glycolic acid), a polyglycolic acid, a polyester, polyamide, or other biodegradable polymer, wherein each $R^{116}$ other than $R^{17}$ is substituted with at least one $L^4$-$R^{110}$;

wherein $R^{116}$ can be further substituted with $R^5$ if valence permits, a stable compound is formed, and the resulting compound is pharmaceutically acceptable.

$R^{117}$ is selected from:

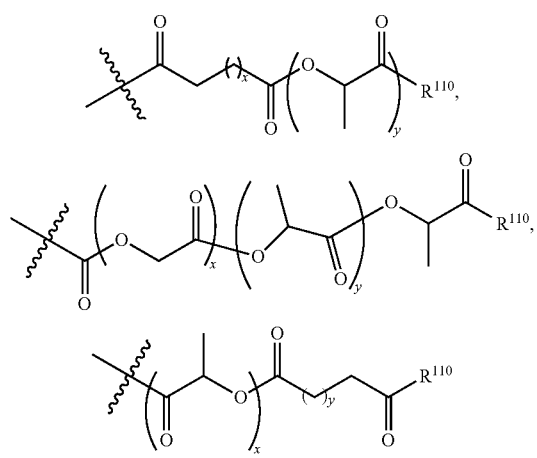

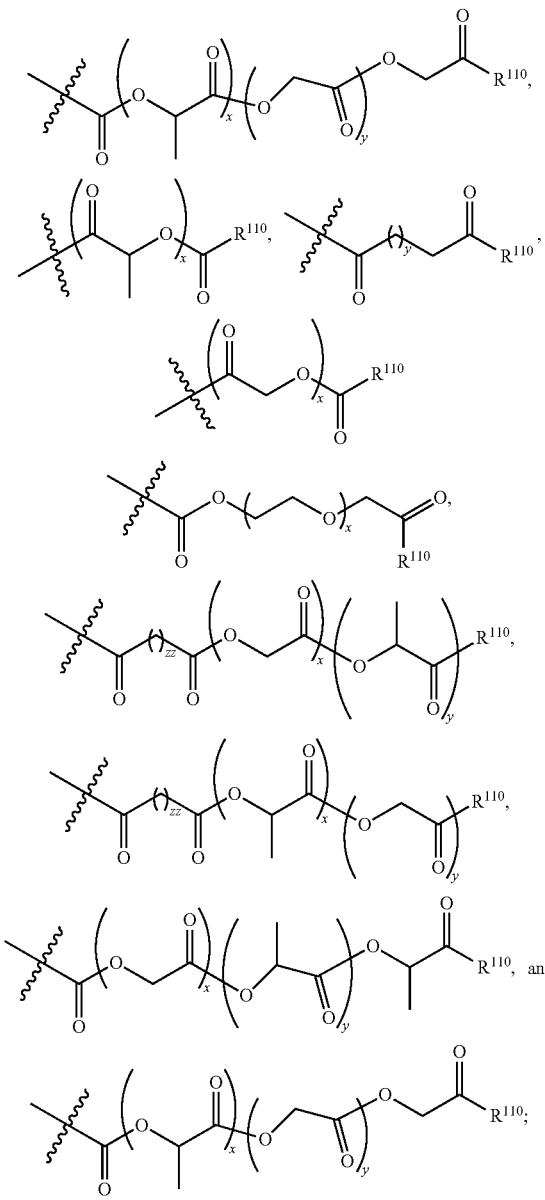

or $R^{117}$ is

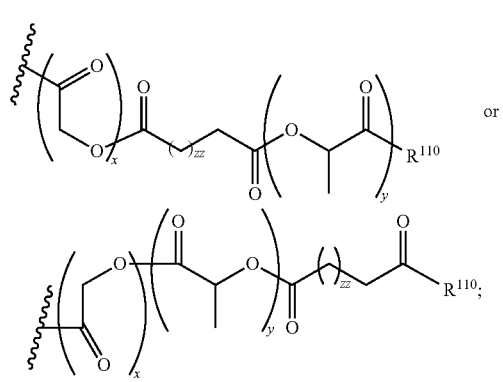

$R^{110}$ is selected from
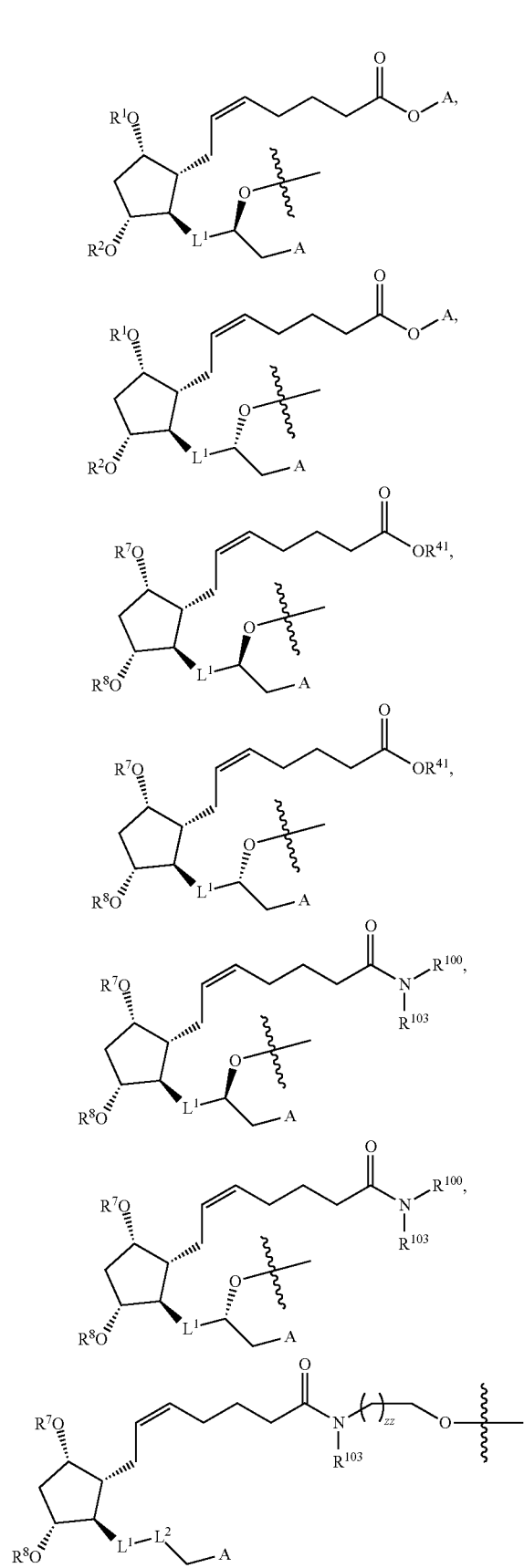
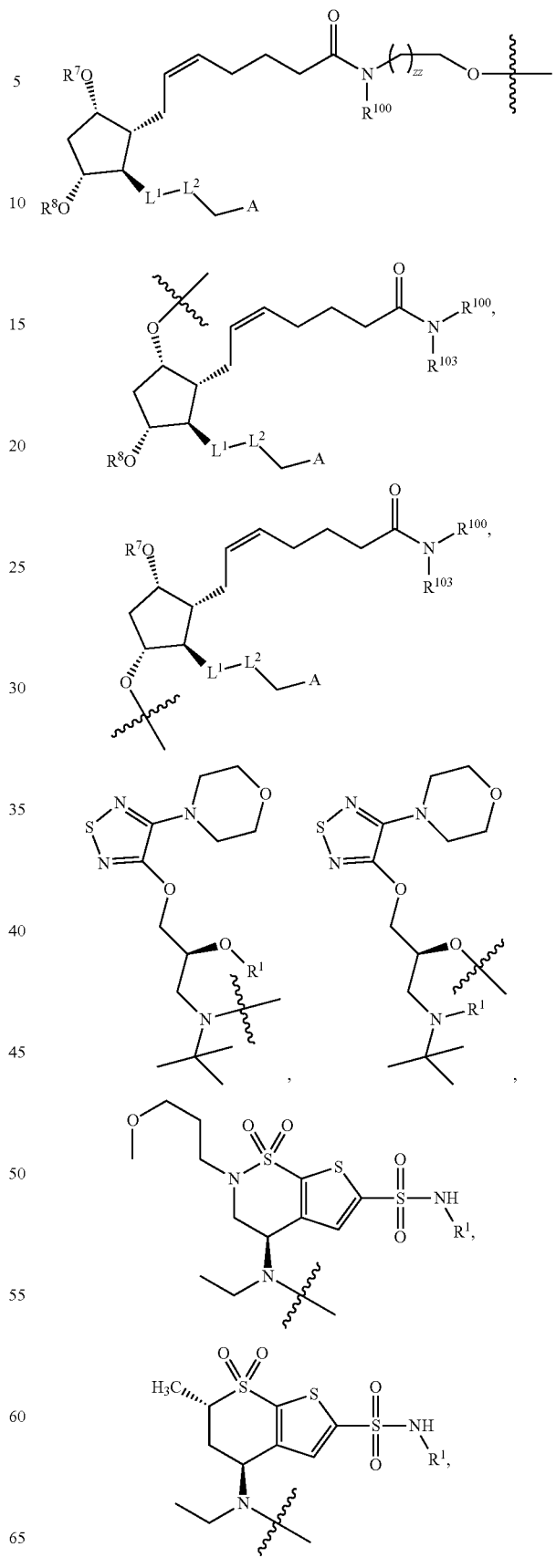

61
-continued
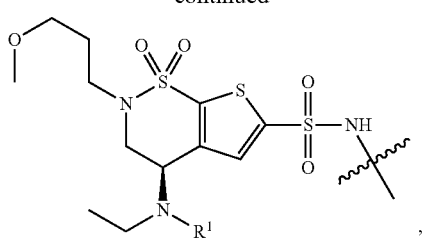
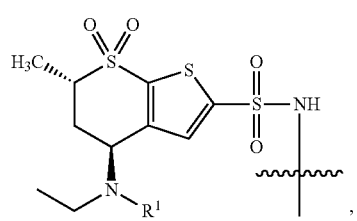
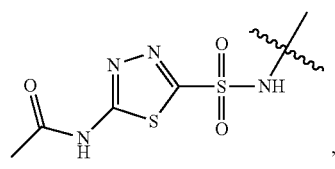
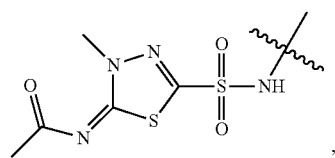
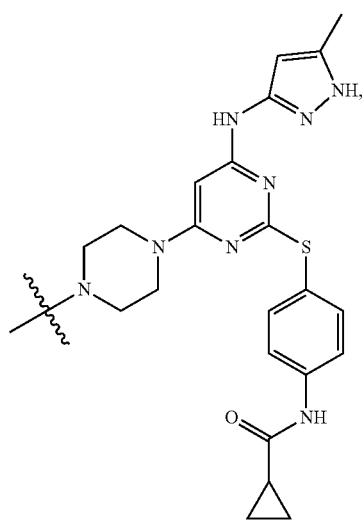
62
-continued
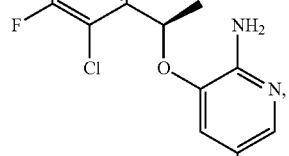
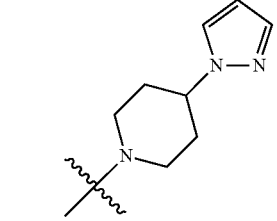
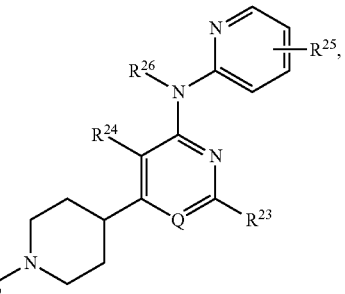
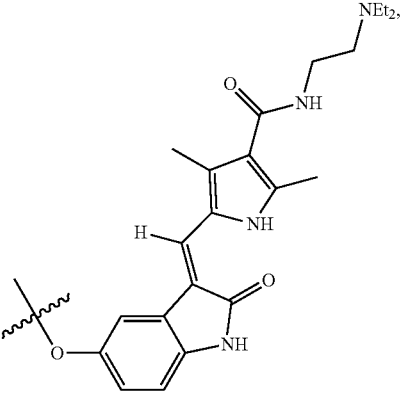
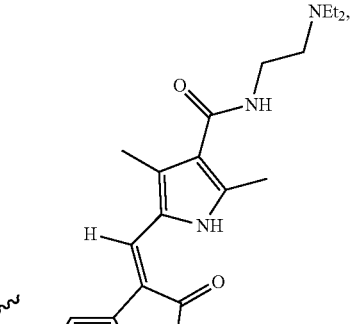

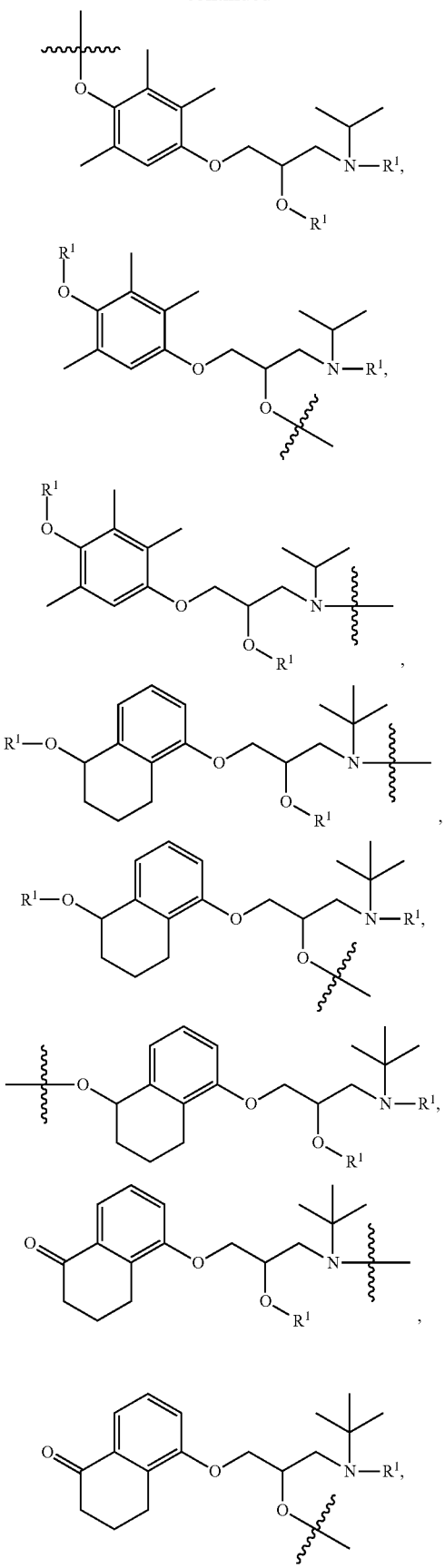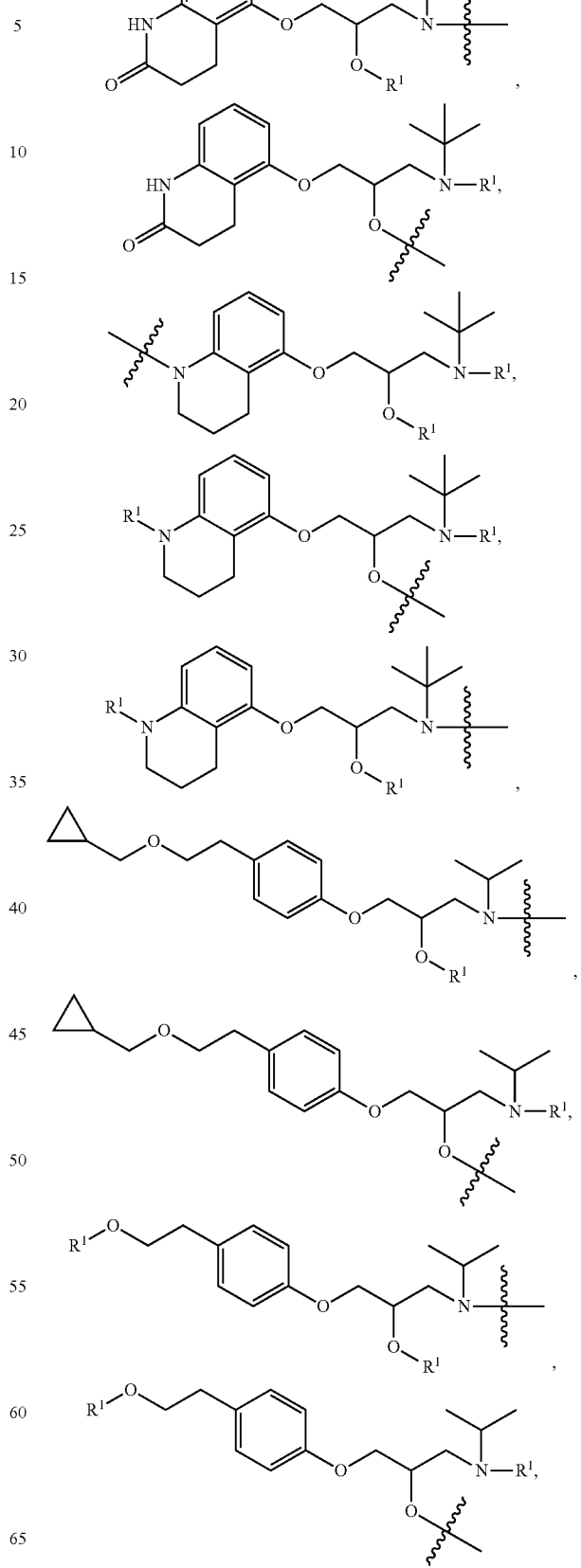

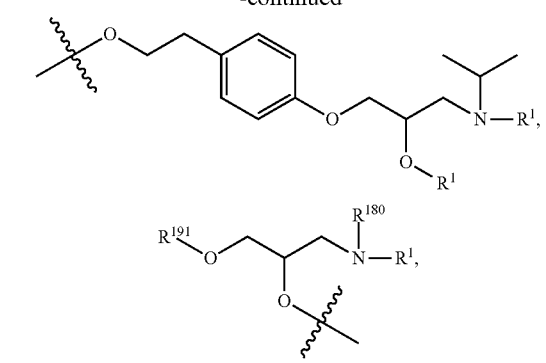
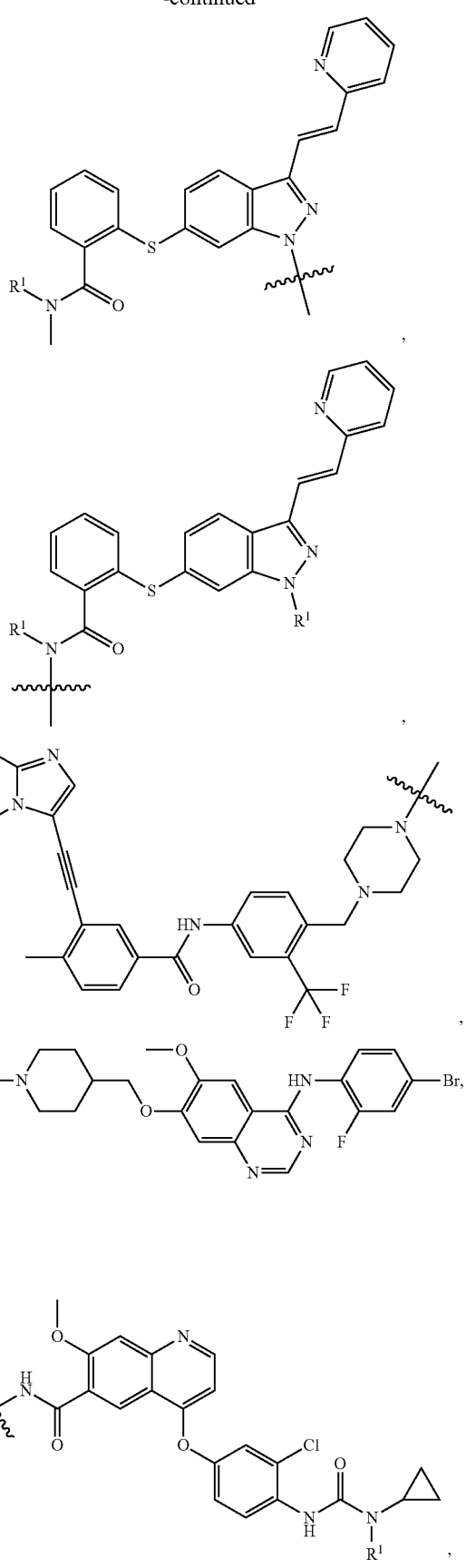

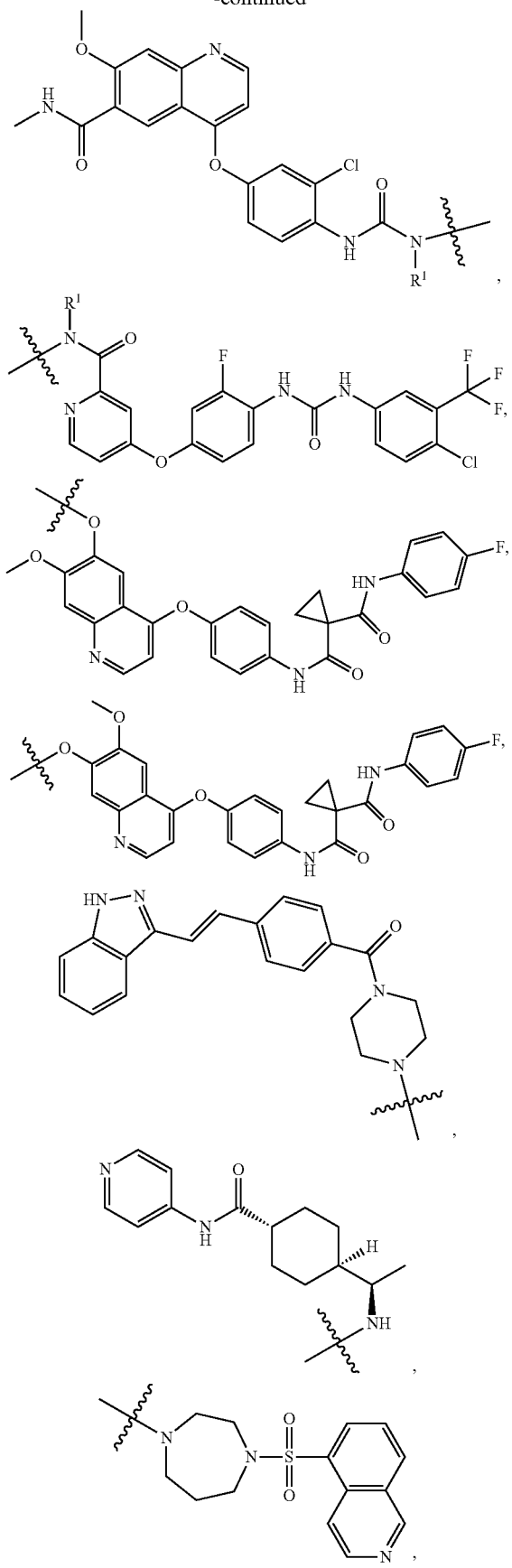

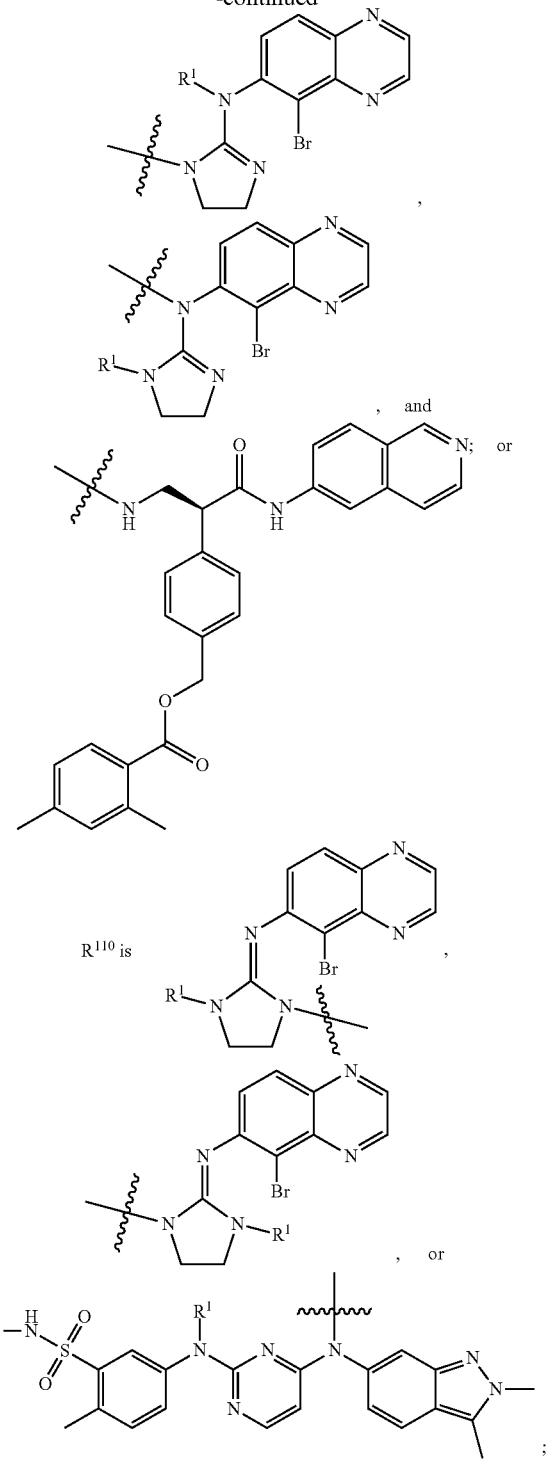

L⁴ is selected from: bond, alkyl, alkenyl, alkynyl, —C(O)—, —C(S)—, —NH—, —N(alkyl)-, —O—, and alkyl-C(O)—;

R³¹ᵇ is hydrogen, aryl, alkyl, cycloalkyl, cycloalkylalkyl, heterocyclyl, heterocycloalkyl, arylalkyl, heteroaryl, heteroarylalkyl, polyethylene glycol, polylactic acid, polygylcolic acid, or stearoyl;

Q is selected from: N, CH, and CR²³;

R²³, R²⁴, and R²⁵ are independently selected from: hydrogen, halogen, hydroxyl, cyano, mercapto, nitro, amino, aryl, alkyl, alkoxy, alkenyl, alkynyl cycloalkyl, cycloalkylalkyl, heterocyclyl, heterocycloalkyl, aryl, arylalkyl, heteroaryl, heteroarylalkyl, aryloxy, —S(O)$_2$alkyl, —S(O)alkyl, —P(O)(Oalkyl)$_2$, B(OH)$_2$, —Si(CH$_3$)$_3$, —COOH, —COOalkyl, —CONH$_2$,

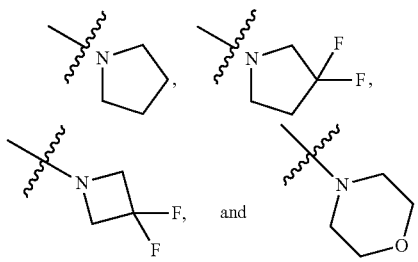

each of which except halogen, nitro, and cyano, may be optionally substituted, for example with halogen, alkyl, aryl, heterocycle or heteroaryl;

$R^{26}$ is selected from H, C(O)A, —C$_0$-C$_{10}$alkylR$^5$, —C$_2$-C$_{10}$alkenylR$^5$, —C$_2$-C$_{10}$alkynylR$^5$, —C$_2$-C$_{10}$alkenyl, and —C$_2$-C$_{10}$alkynyl;

$R^{180}$ is C$_1$-C$_6$ alkyl, acyl, or hydrogen;

$R^{191}$ is selected from:

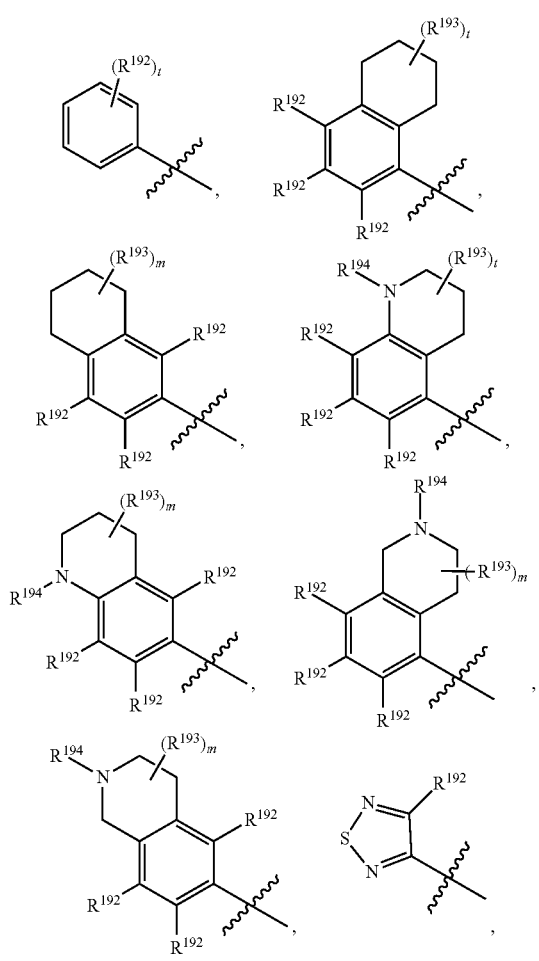

and $R^{195}$;

or in an alternative embodiment, $R^{191}$ is selected from

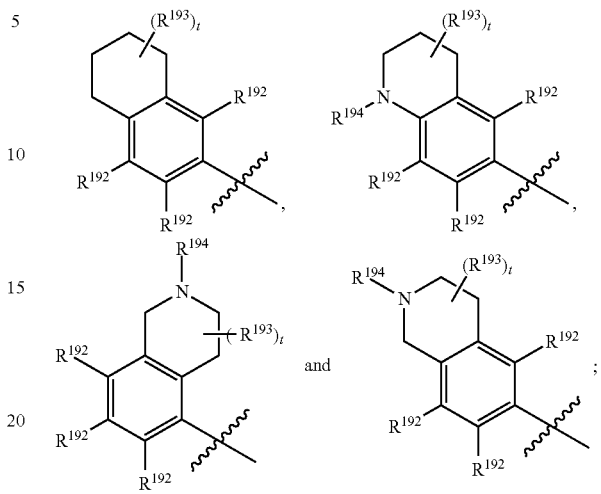

t is independently selected from 0, 1, 2, 3, and 4;

$R^{192}$ is independently selected from alkyl, cycloalkyl, aryl, heteroaryl, heterocycle, cyano, amino, hydroxyl, and acyl, each of which R$^{192}$ is optionally substituted with a R$^{175}$ group;

$R^{193}$ is independently selected from alkyl, cycloalkyl, aryl, heteroaryl, heterocycle, amino, hydroxyl, and acyl;

or two $R^{193}$ groups with the carbon to which they are linked form a carbonyl group;

or two $R^{193}$ groups with the carbon(s) to which they are linked form a fused or spirocyclic ring;

$R^{194}$ is selected from alkyl, cycloalkyl, R$^{175}$, and acyl; and $R^{195}$ is selected from aryl, heteroaryl, cycloalkyl, and heterocycle, wherein each R$^{195}$ is optionally substituted with 1, 2, 3, or 4 R$^{192}$ groups;

$R^{175}$ is selected from: C(O)A, C(O)R$^4$, and R$^{178}$;

$R^{178}$ is selected from:

(i) carbonyl linked polyethylene glycol, carbonyl linked polypropylene glycol, carbonyl linked polypropylene oxide, polylactic acid, poly(lactic-co-glycolic acid), polyglycolic acid, polyester, polyamide,

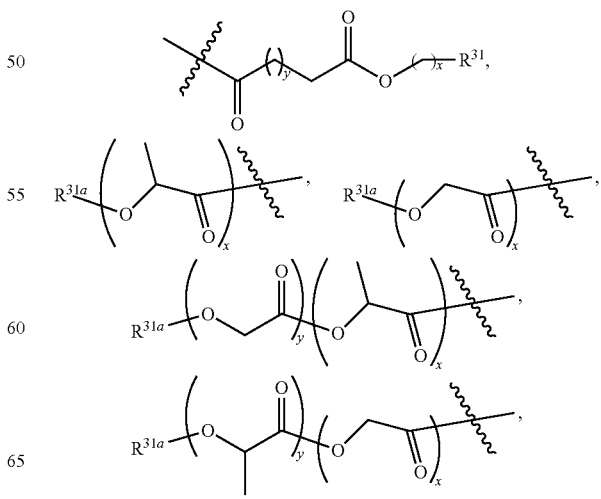

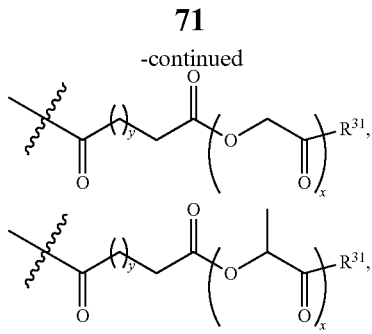

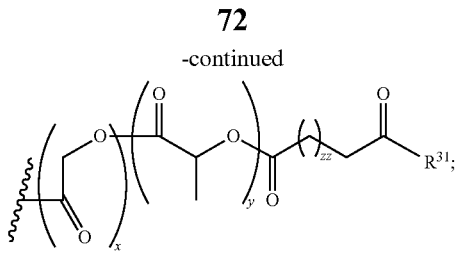

wherein all other variables are as defined herein.

The disclosure also provides a prodrug of Formula X:

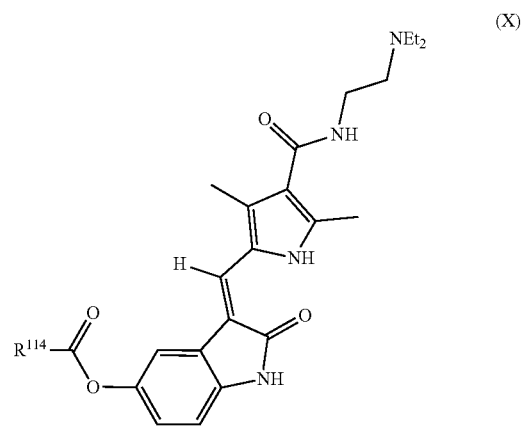

and other biodegradable polymer, wherein each $R^{178}$ is optionally substituted with $R^{31}$, and wherein each of $R^{178}$ with a terminal hydroxy or carboxy group can be substituted to create an ether or ester;

(ii) -(lactic acid) $1\text{-}20C(O)C_{1\text{-}22}$alkyl, -(lactic acid)$_{1\text{-}10}$C(O)C$_{1\text{-}22}$alkyl, -(lactic acid)$_{4\text{-}20}$C(O)C$_{1\text{-}22}$alkyl, -(lactic acid)$_{1\text{-}20}$C(O)C$_{1\text{-}10}$alkyl, -(lactic acid)$_{1\text{-}20}$C(O)C$_{4\text{-}10}$alkyl, -(lactic acid)$_{1\text{-}20}$C(O)OH, -(lactic acid)$_{1\text{-}10}$C(O)OH, -(lactic acid)$_{4\text{-}20}$C(O)OH, -(lactic acid)$_{1\text{-}10}$C(O)OH, -(lactic acid)$_{4\text{-}10}$C(O)OH, -(lactide-co-glycolide)$_{1\text{-}10}$C(O)C$_{1\text{-}22}$alkyl, -(lactide-co-glycolide)$_{4\text{-}10}$C(O)C$_{1\text{-}22}$alkyl, -(lactide-co-glycolide)$_{1\text{-}10}$C(O)C$_{1\text{-}12}$alkyl, -(lactide-co-glycolide)$_{1\text{-}10}$C(O)C$_{4\text{-}22}$alkyl, -(glycolic acid)$_{1\text{-}10}$C(O)C$_{1\text{-}10}$alkyl, -(glycolic acid)$_{4\text{-}10}$C(O)C$_{1\text{-}10}$alkyl, -(lactic acid)$_{4\text{-}10}$C(O)C$_{1\text{-}10}$alkyl, -(lactic acid)$_{1\text{-}10}$C(O)C$_{1\text{-}10}$alkyl, -(lactic acid)$_{1\text{-}10}$C(O)C$_{4\text{-}10}$alkyl, -(lactic acid)$_{1\text{-}10}$C(O)C$_{4\text{-}10}$alkyl, or -(lactic acid)$_{1\text{-}10}$C(O)C$_{4\text{-}10}$alkyl;

or $R^{78}$ is selected from:

(i) —(C(O)CH$_2$O)$_{1\text{-}20}$C(O)C$_{1\text{-}30}$alkyl, —(C(O)CH(CH$_3$)O)$_{1\text{-}20}$C(O)C$_{1\text{-}30}$alkyl, —(C(O)CH$_2$O)$_{1\text{-}10}$C(O)C$_{1\text{-}30}$alkyl, —(C(O)CH(CH$_3$)O)$_{1\text{-}10}$C(O)C$_{1\text{-}30}$alkyl, —(C(O)CH$_2$O)$_{4\text{-}20}$C(O)C$_{1\text{-}30}$alkyl, —(C(O)CH(CH$_3$)O)$_{4\text{-}20}$C(O)C$_{1\text{-}30}$alkyl, —(C(O)CH$_2$O)$_{1\text{-}20}$C(O)C$_{1\text{-}10}$alkyl, —(C(O)CH(CH$_3$)O)$_{1\text{-}20}$C(O)C$_{1\text{-}10}$alkyl, —(C(O)CH$_2$O)$_{1\text{-}20}$C(O)C$_{4\text{-}10}$alkyl, —(C(O)CH(CH$_3$)O)$_{1\text{-}20}$C(O)C$_{4\text{-}10}$alkyl, —(C(O)CH(CH$_3$)O)$_{4\text{-}10}$C(O)C$_{1\text{-}10}$alkyl, —(C(O)CH$_2$O)$_{4\text{-}10}$C(O)C$_{1\text{-}10}$alkyl, —(C(O)CH(CH$_3$)O)$_{1\text{-}10}$C(O)C$_{1\text{-}10}$alkyl, —(C(O)CH$_2$O)$_{1\text{-}10}$C(O)C$_{1\text{-}10}$alkyl, —(C(O)CH(CH$_3$)O)$_{1\text{-}10}$C(O)C$_{1\text{-}10}$alkyl, (C(O)CH$_2$O)$_{1\text{-}10}$C(O)C$_{4\text{-}10}$alkyl, —(C(O)CH$_2$O)$_{1\text{-}10}$C(O)C$_{4\text{-}10}$alkyl, —(C(O)CH(CH$_3$)O)$_{1\text{-}10}$C(O)C$_{4\text{-}10}$alkyl, —(C(O)CH$_2$O)$_{1\text{-}10}$C(O)C$_{4\text{-}10}$alkyl, —(C(O)CH(CH$_3$)O)$_{1\text{-}10}$C(O)C$_{4\text{-}10}$alkyl, —(C(O)CH$_2$O)$_{1\text{-}10}$(C(O)CH(CH$_3$)O)$_{1\text{-}10}$C(O)C$_{1\text{-}30}$alkyl, —(C(O)CH$_2$O)$_{2\text{-}10}$(C(O)CH(CH$_3$)O)$_{2\text{-}10}$C(O)C$_{1\text{-}30}$alkyl, —(C(O)CH$_2$O)$_{1\text{-}10}$(C(O)CH(CH$_3$)O)$_{1\text{-}10}$C(O)C$_{1\text{-}12}$alkyl, —(C(O)CH$_2$O)$_{1\text{-}10}$(C(O)CH(CH$_3$)O)$_{1\text{-}10}$C(O)C$_{4\text{-}22}$alkyl, —(C(O)CH(CH$_3$)O)$_{1\text{-}10}$(C(O)CH$_2$O)$_{1\text{-}10}$C(O)C$_{1\text{-}30}$alkyl, —(C(O)CH(CH$_3$)O)$_{2\text{-}10}$(C(O)CH$_2$O)$_{2\text{-}10}$C(O)C$_{1\text{-}30}$alkyl, —(C(O)CH(CH$_3$)O)$_{1\text{-}10}$(C(O)CH$_2$O)$_{1\text{-}10}$C(O)C$_{1\text{-}12}$alkyl, and —(C(O)CH(CH$_3$)O)$_{1\text{-}10}$(C(O)CH$_2$O)$_{1\text{-}10}$C(O)C$_{4\text{-}22}$alkyl; and or $R^{178}$ is

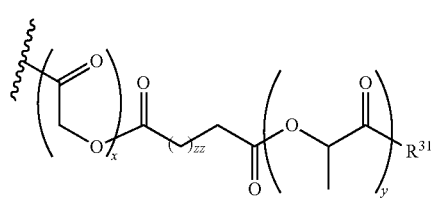

or

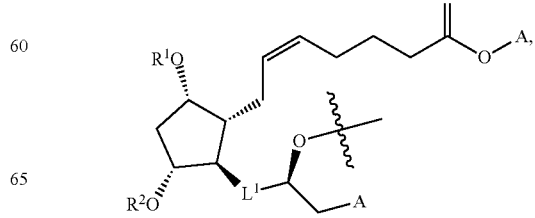

or a pharmaceutically acceptable composition, salt, or isotopic derivative thereof. This structure is related to Sunitinib (marketed in the form of the (−)-malic acid salt as SUTENT® by Pfizer, and previously known as SU 11248), which is an oral, small-molecule, multi-targeted receptor tyrosine kinase (RTK) inhibitor that was approved by the FDA for the treatment of renal cell carcinoma (RCC) and imatinib-resistant gastrointestinal stromal tumor (GIST) on Jan. 26, 2006. Sunitinib was the first cancer drug simultaneously approved for two different indications. Sunitinib inhibits cellular signaling by targeting multiple receptor tyrosine kinases (RTKs). These include all receptors for platelet-derived growth factor (PDGF-Rs) and vascular endothelial growth factor receptors (VEGFRs), which play a role in both tumor angiogenesis and tumor cell proliferation. The simultaneous inhibition of these targets leads to both reduced tumor vascularization and cancer cell death, and, ultimately, tumor shrinkage. Sunitinib and derivatives thereof are described in U.S. Pat. Nos. 7,211,600; 6,573,293; and 7,125,905, the entirety of which is incorporated by reference.

$R^{114}$ is selected from:

73
-continued
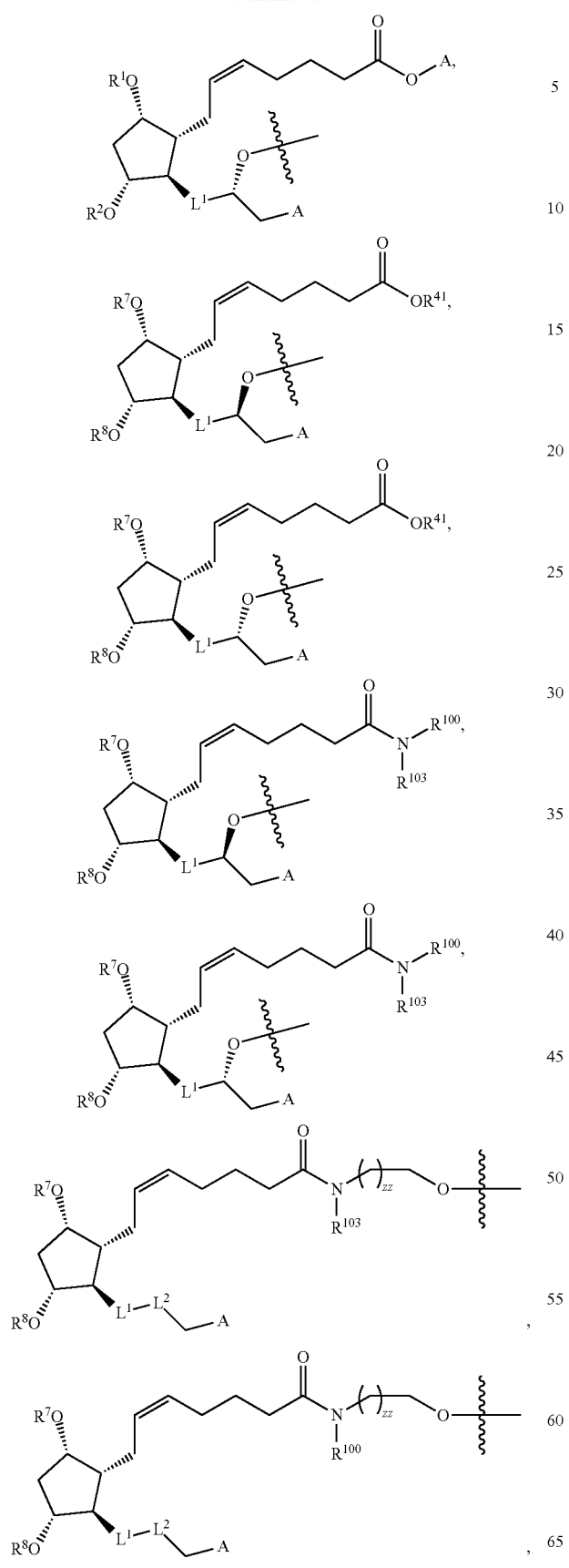
74
-continued
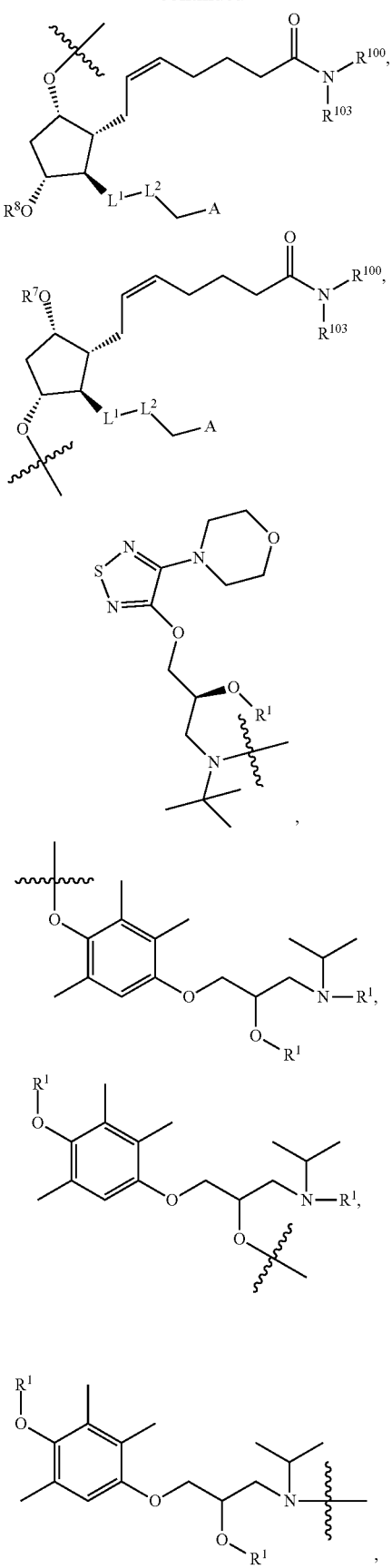

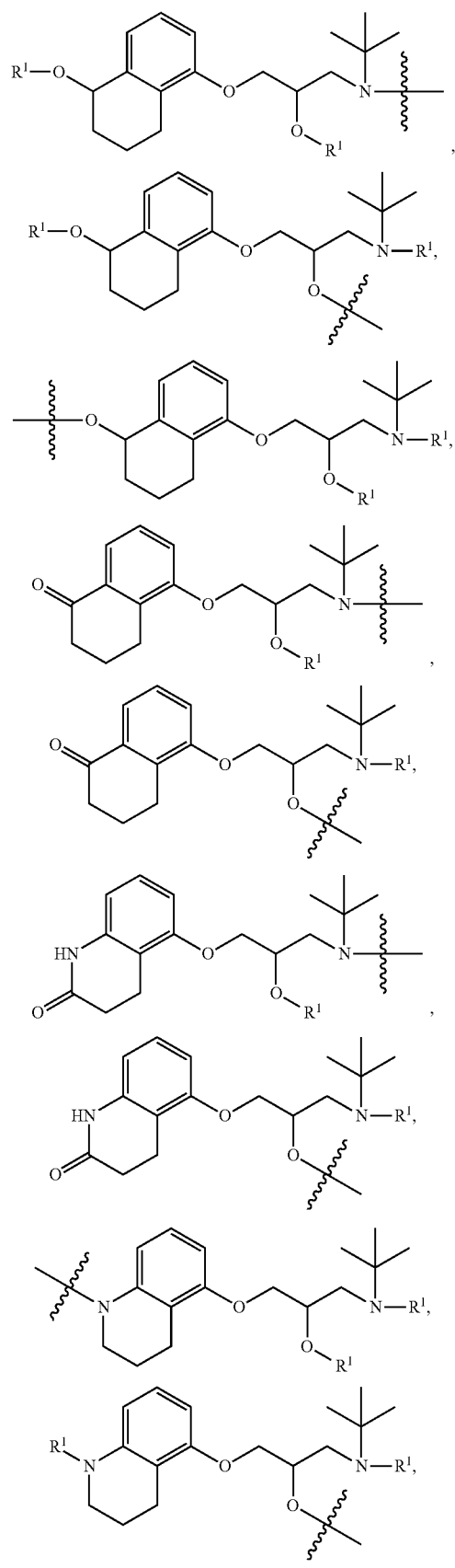
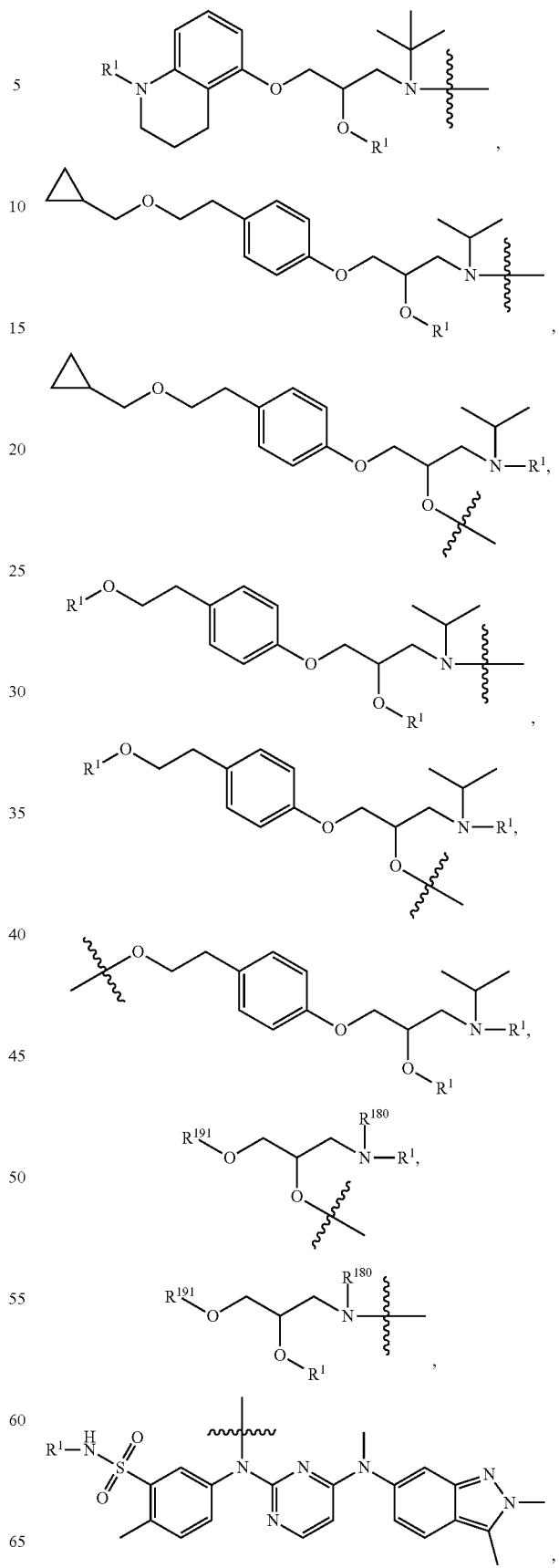

-continued
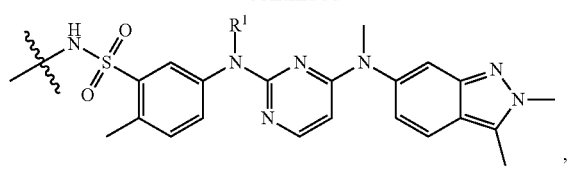,
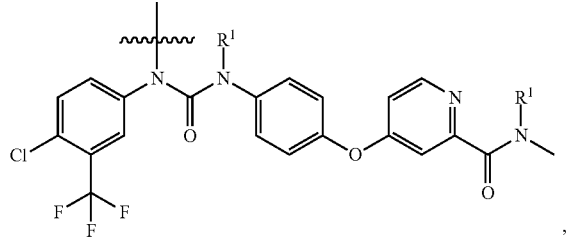,
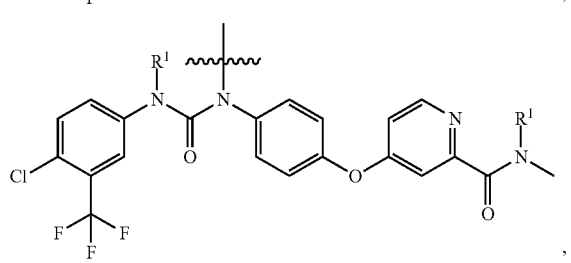,
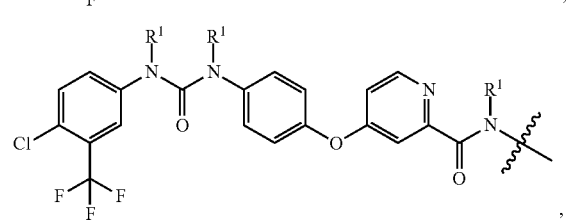,
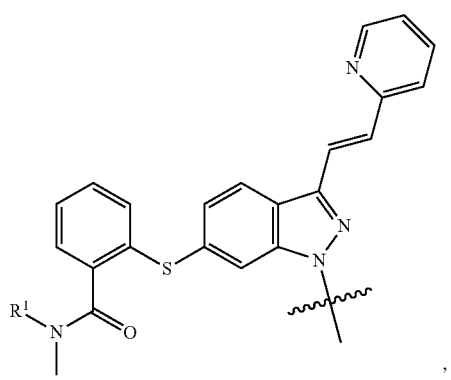,
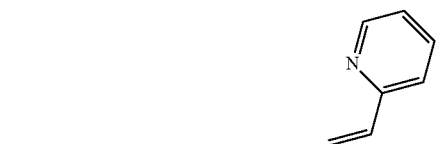
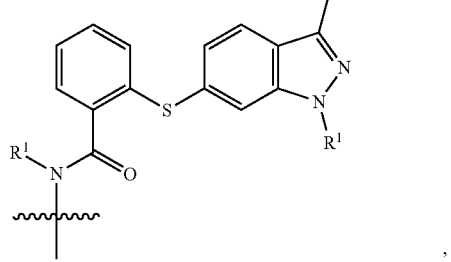,
-continued
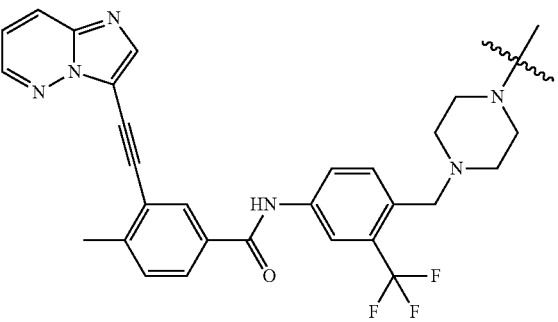,
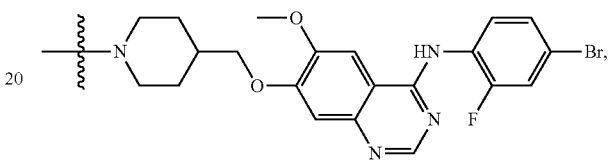,
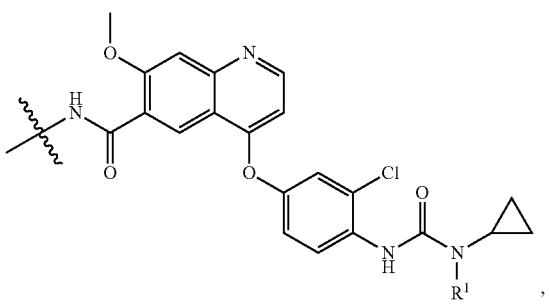,
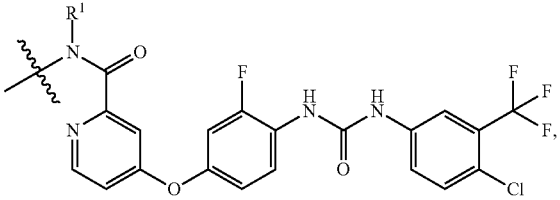,
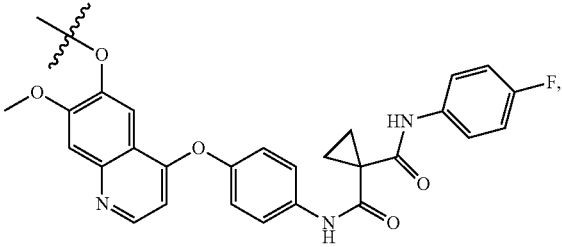

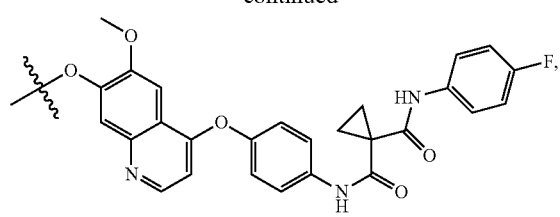
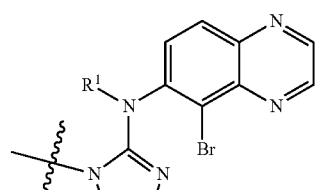
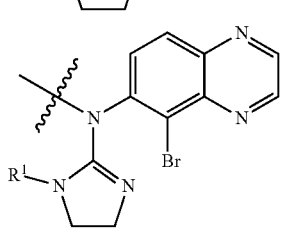
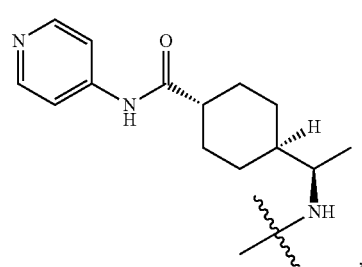
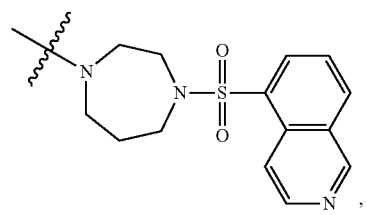
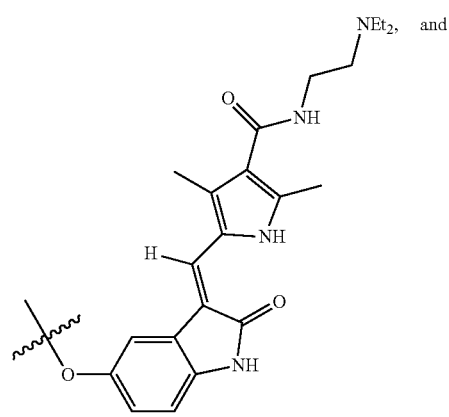
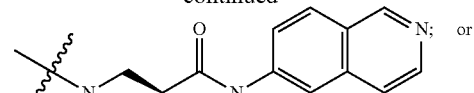
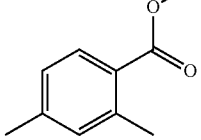
R[114] is
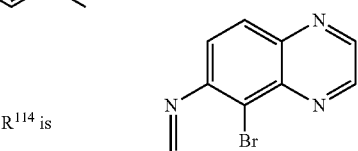
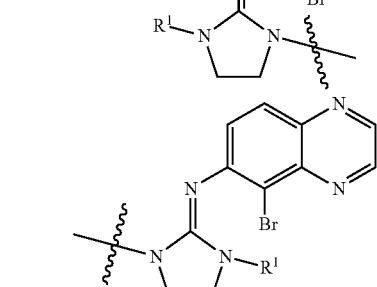
, or
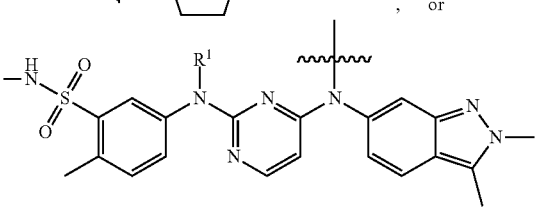
;
and
wherein all other variables are as defined herein.
In one embodiment, L² is L²′ wherein L²′ is defined above.
In one embodiment, A is B wherein B is defined above.
In an alternative embodiment, the disclosure provides a prodrug of Formula X′:
(X′)
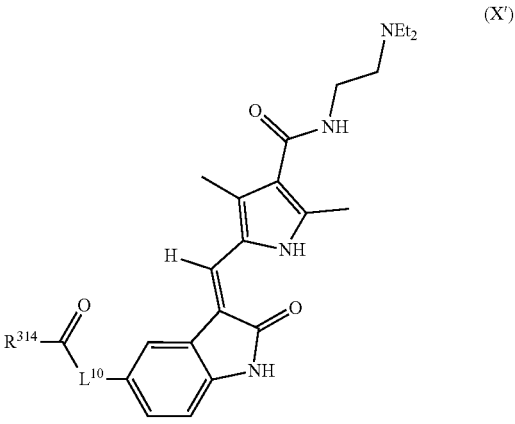

or a pharmaceutically acceptable composition, salt, or isotopic derivative thereof.

wherein $L^{10}$ is —O—, —NH—, or —N(alkyl)-;

$R^{314}$ is an unsaturated fatty acid residue including but not limited to the carbon chains from linoleic acid (—$(CH_2)_8(CH)_2CH_2(CH)_2(CH_2)_4CH_3$)), docosahexaenoic acid (—$(CH_2)_3(CHCHCH_2)_6CH_3$)), eicosapentaenoic acid (—$(CH_2)_4(CHCHCH_2)_5CH_3$)), alphalinolenic acid (—$(CH_2)_8(CHCHCH_2)_3CH_3$)), stearidonic acid, y-linolenic acid, arachidonic acid, docosatetraenoic acid, palmitoleic acid, vaccenic acid, paullinic acid, oleic acid, elaidic acid, gondoic acid, euric acid, nervonic acid and mead acid, and wherein, if desired, each of which can be substituted with $R^5$; and $R^5$ is defined above.

In one embodiment, $R^{314}$ is

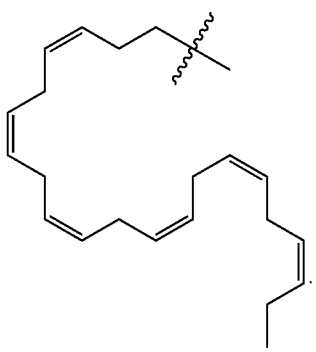 [SMILES: *CC/C=C\C/C=C\C/C=C\C/C=C\C/C=C\C/C=C\CC]

The disclosure also provides a prodrug of Formula XI:

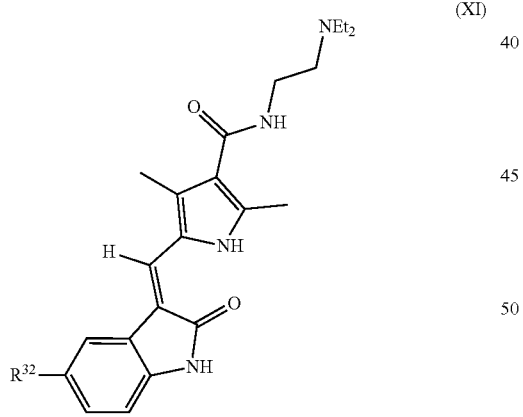

(XI)

or a pharmaceutically acceptable composition, salt, or isotopic derivative thereof.

$R^{32}$ is selected from: $R^{35}$, alkyl, alkyloxy, acyl, polyethylene glycol, polypropylene glycol, polypropylene oxide, polylactic acid, poly(lactic-co-glycolic acid), a polyglycolic acid, a polyester, polyamide, or other biodegradable polymer, wherein each $R^{32}$ other than $R^{35}$ is substituted with at least one $L^4$-$R^{10}$;

wherein $R^{32}$ can be further substituted with $R^5$ if valence permits, a stable compound is formed, and the resulting compound is pharmaceutically acceptable.

$R^{35}$ is selected from:

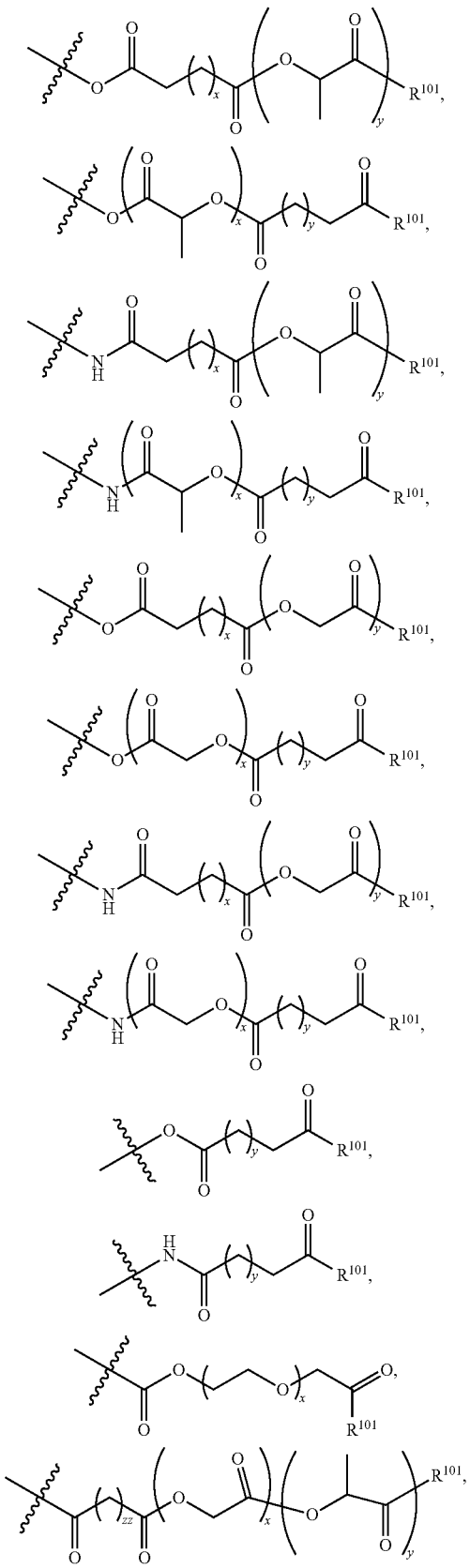

83
-continued
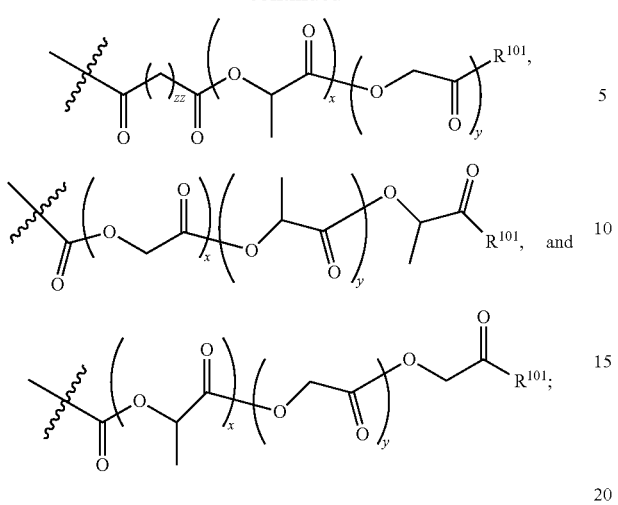
or R³⁵ is
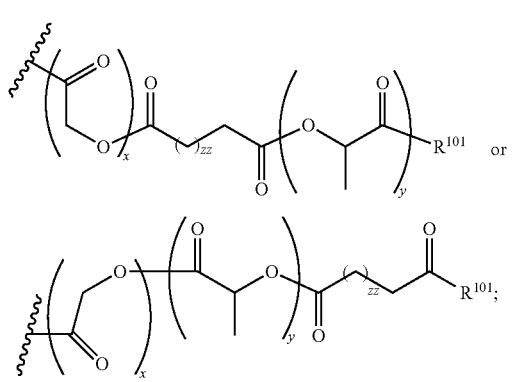
R¹⁰¹ is selected from
84
-continued
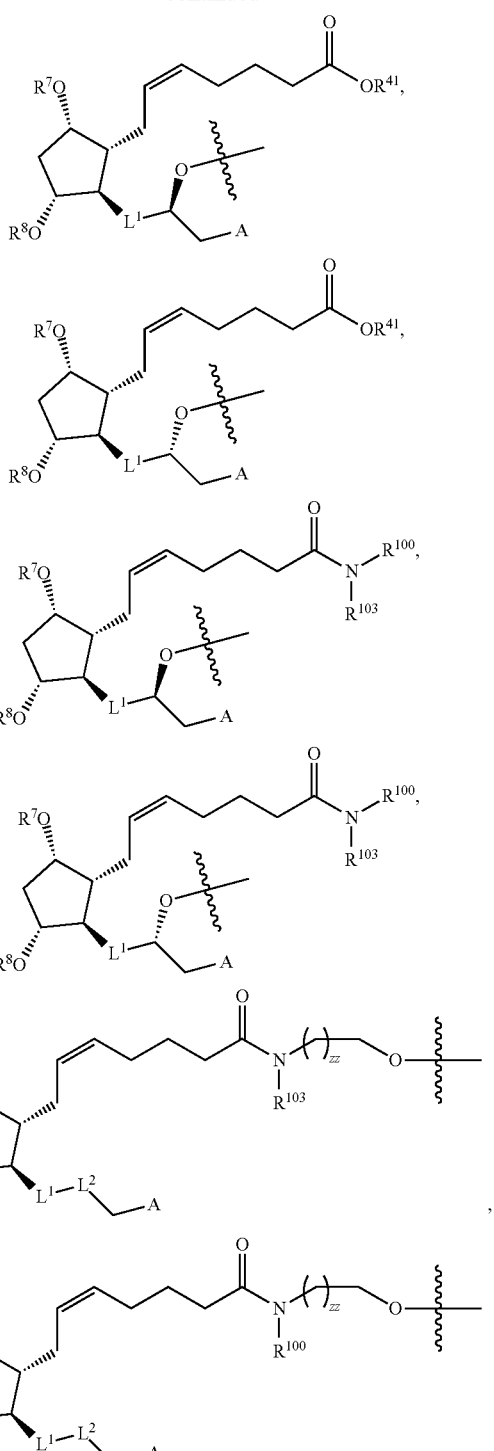

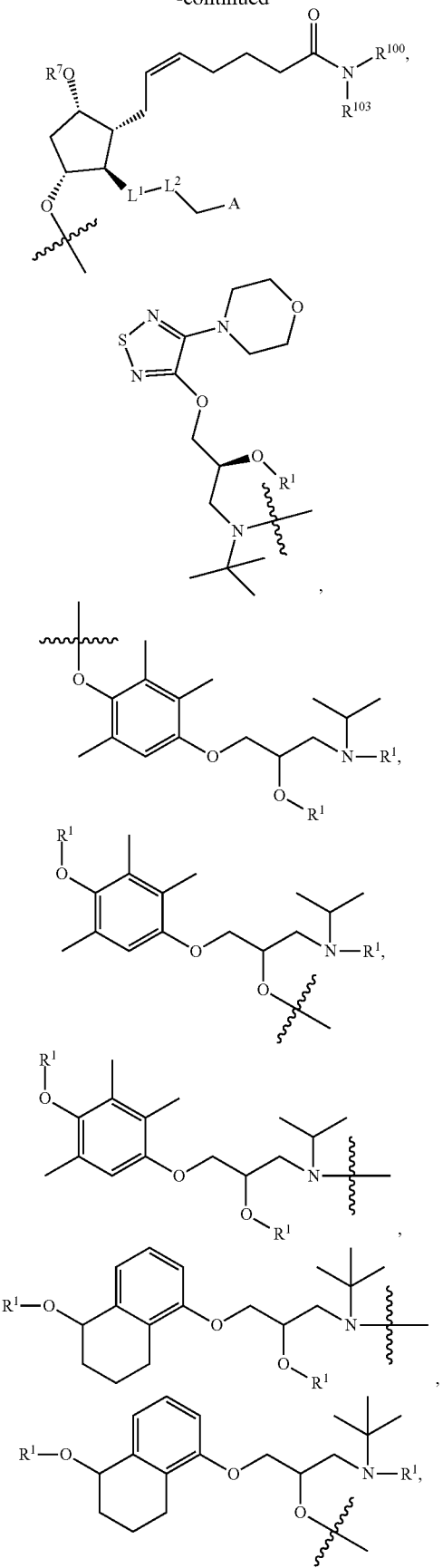
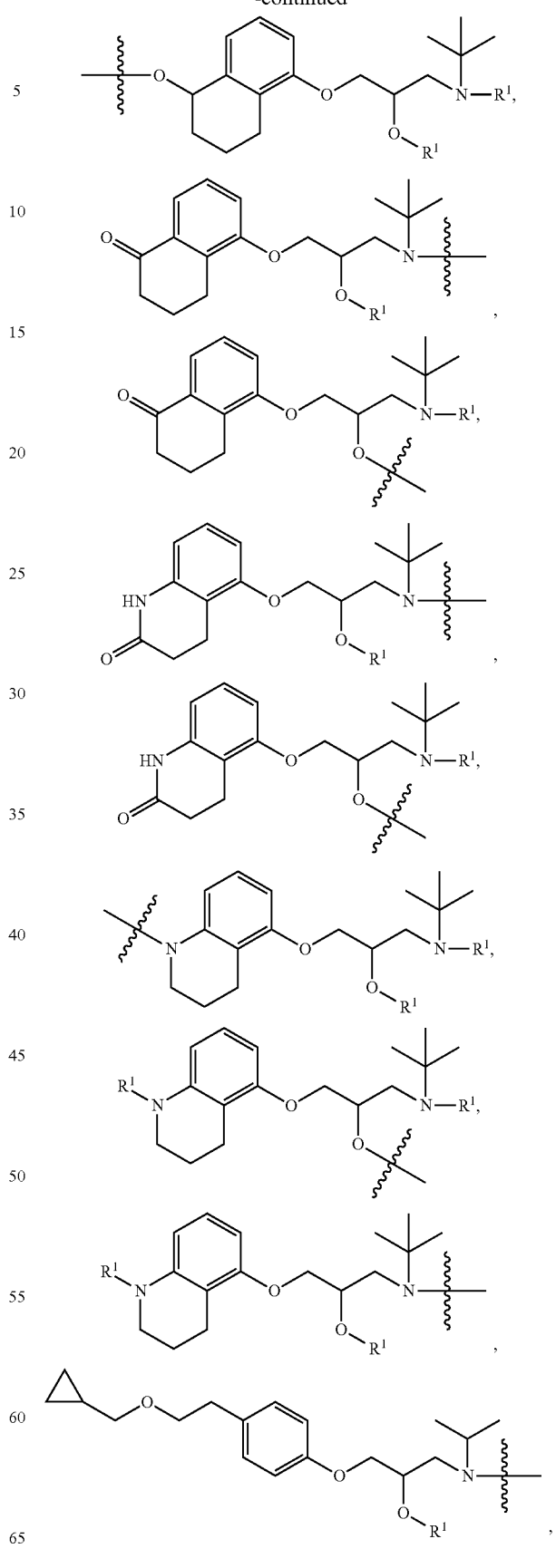

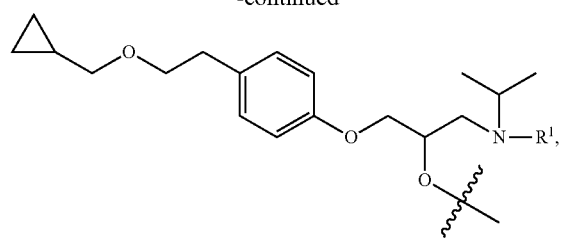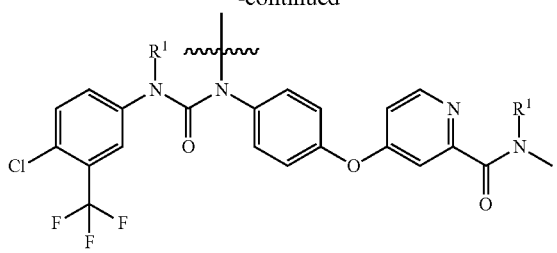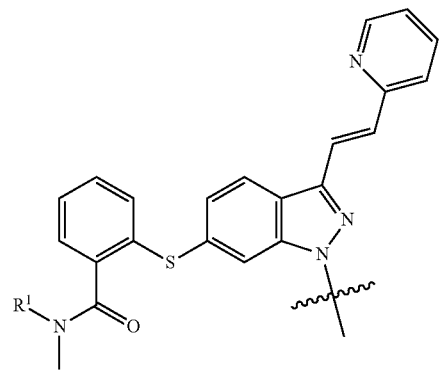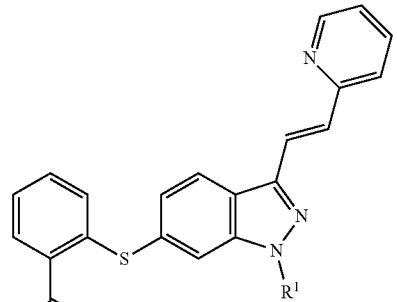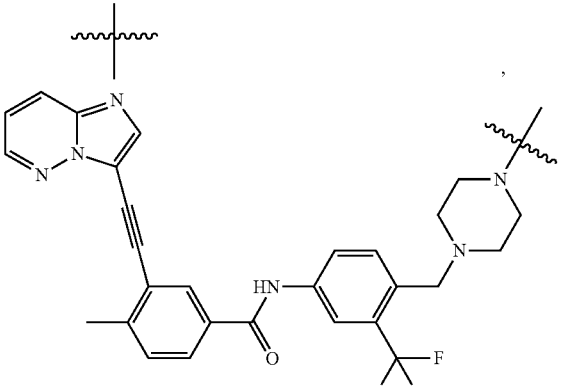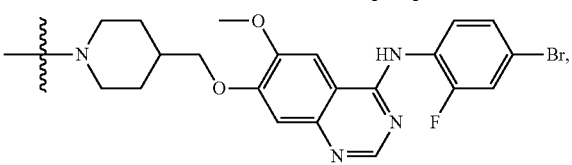

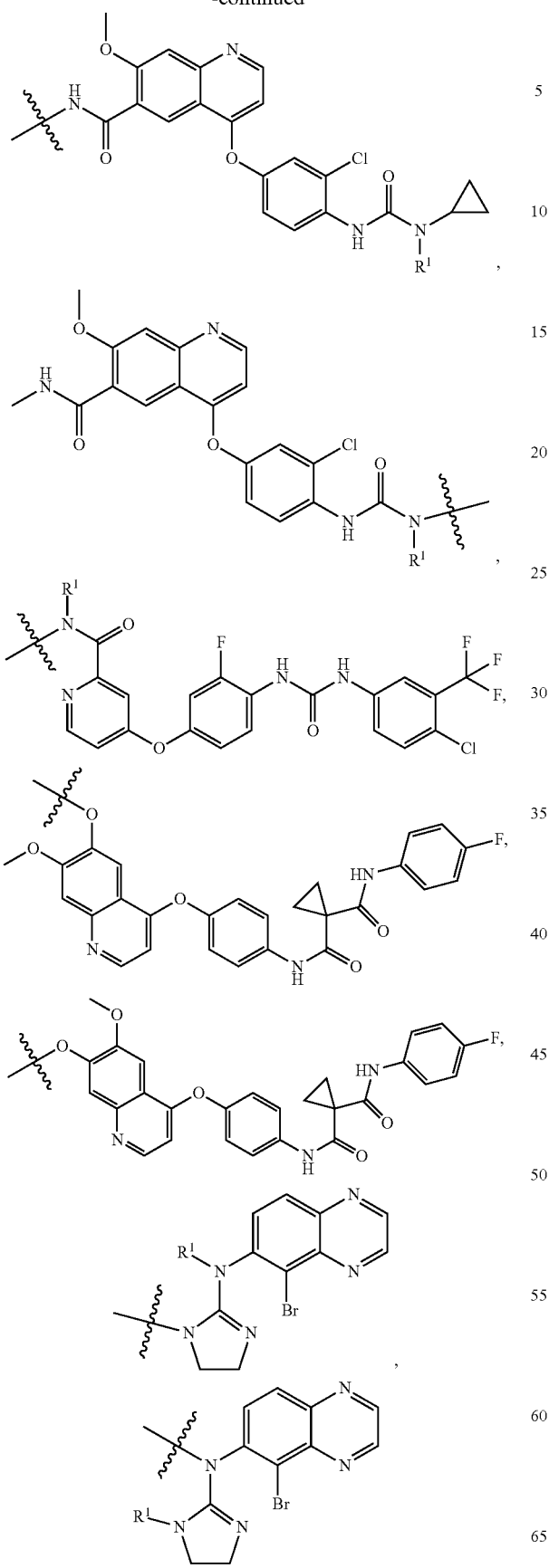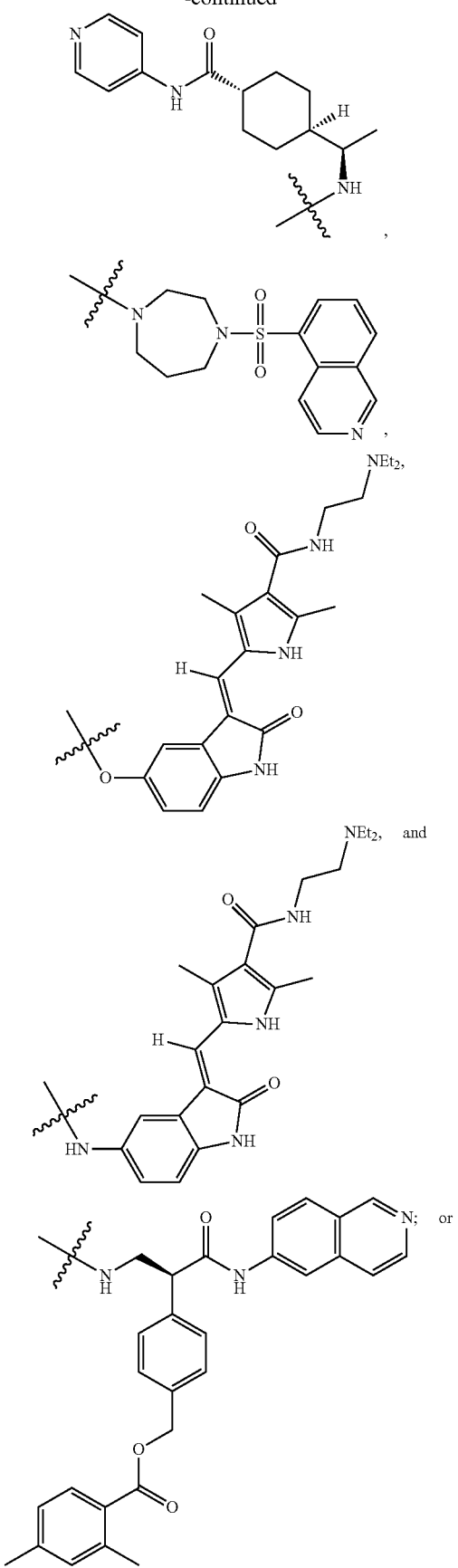

$R^{101}$ is 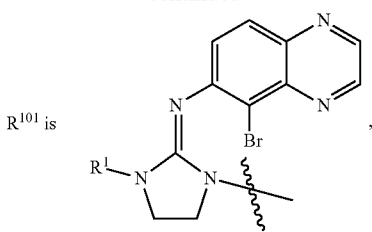,
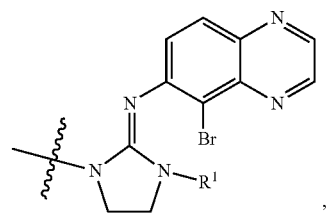,
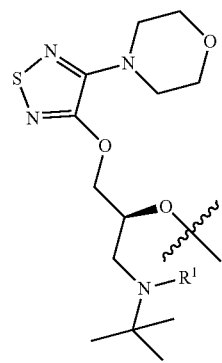
or
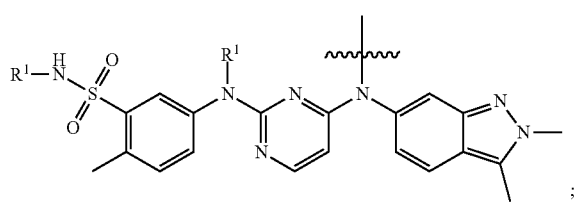;
and
wherein all other variables are as defined herein.
Non-limiting examples of Formula XI include
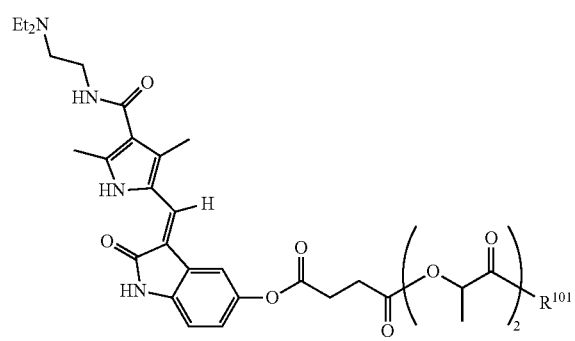
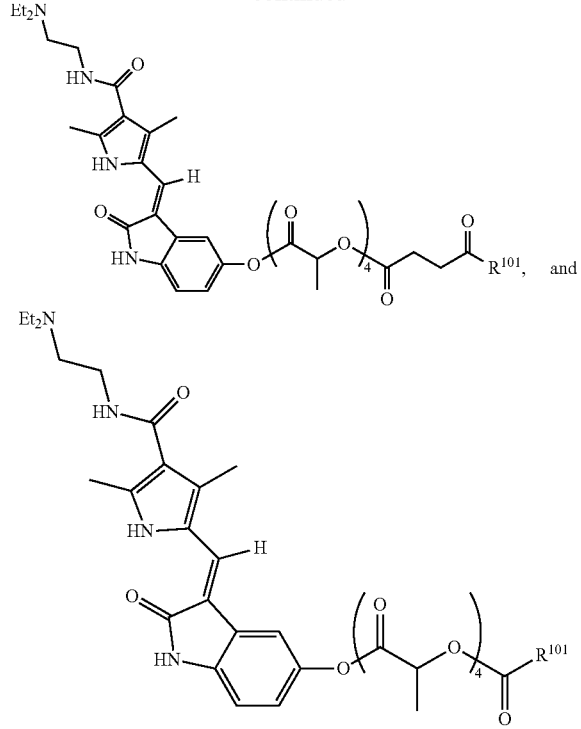, and
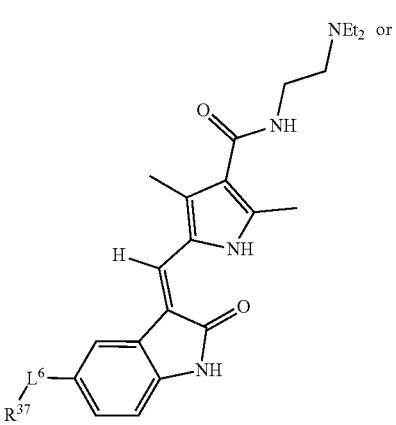
The disclosure also provides a prodrug of Formula XII or Formula XIII:
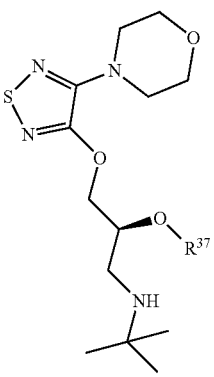 (XII)
(XIII)

or a pharmaceutically acceptable composition, salt, or isotopic derivative thereof.

$R^{37}$ is selected from: $R^{38}$, polyethylene glycol, polypropylene glycol, polypropylene oxide, polylactic acid, poly(lactic-co-glycolic acid), a polyglycolic acid, a polyester, a polyamide, or other biodegradable polymer, wherein each $R^{37}$ other than $R^{38}$ is substituted with at least one $L^4$-$R^{108}$;

$L^6$ is selected from —O—, —NH—, —S—, —C(O)— and —OC(O)—;

$R^{38}$ is selected from:

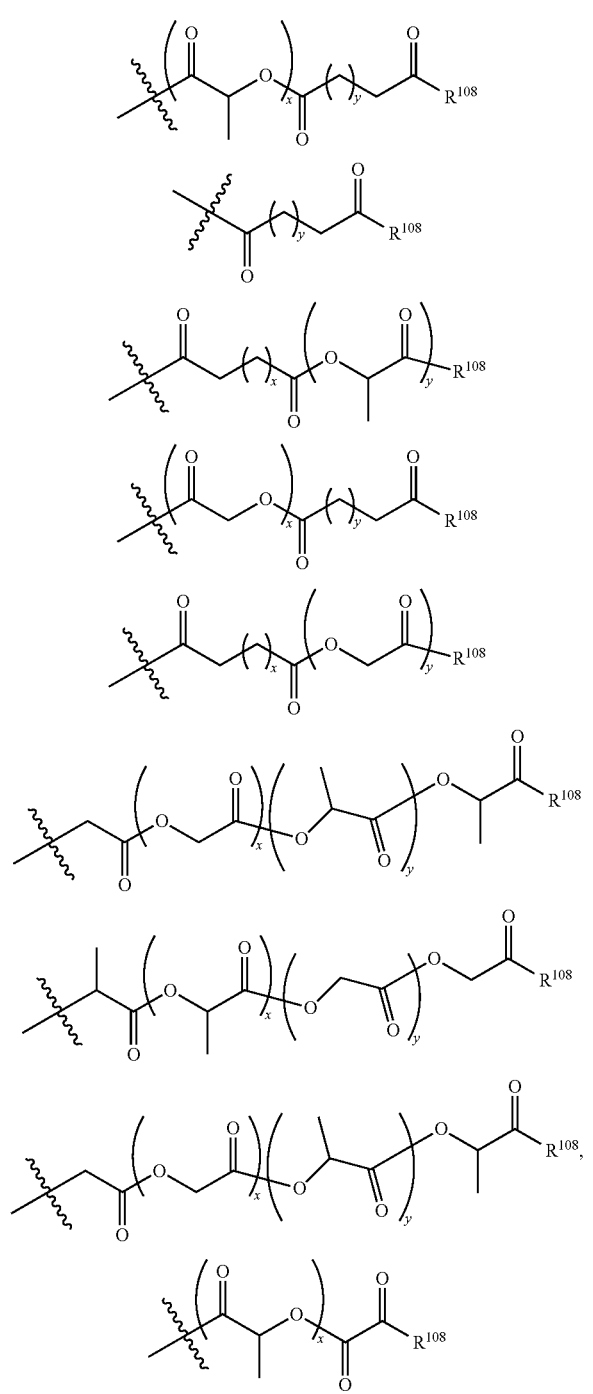

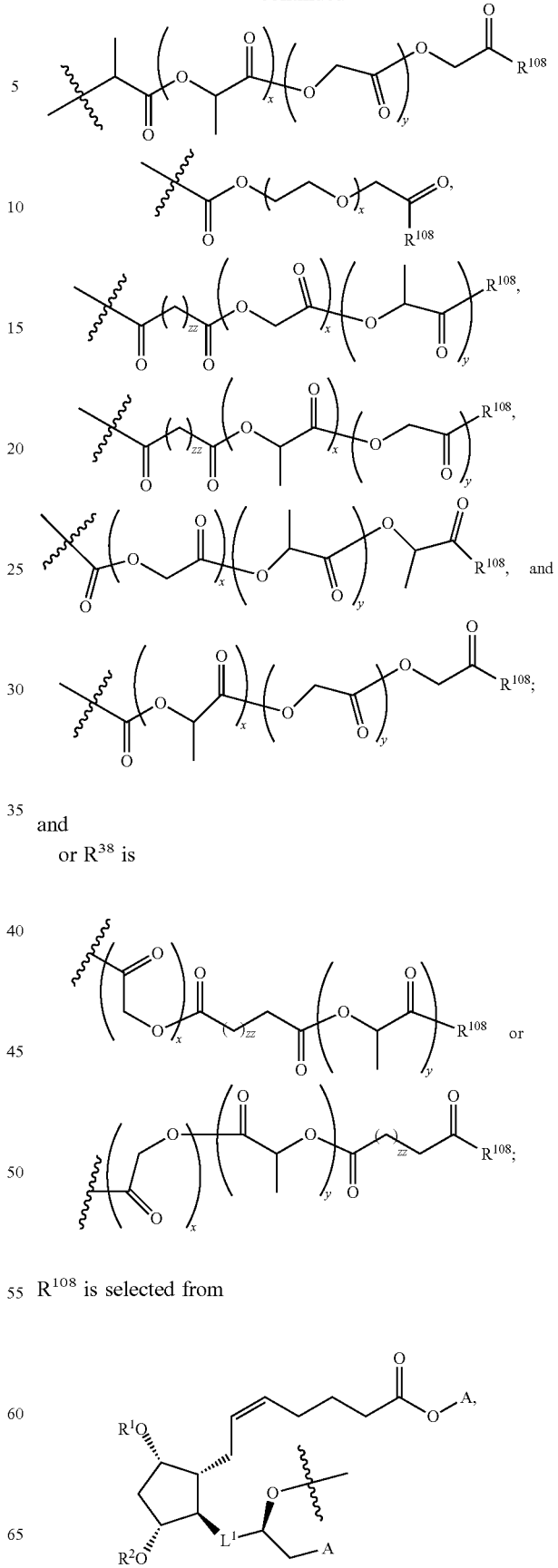

and or $R^{38}$ is $R^{108}$ is selected from

-continued
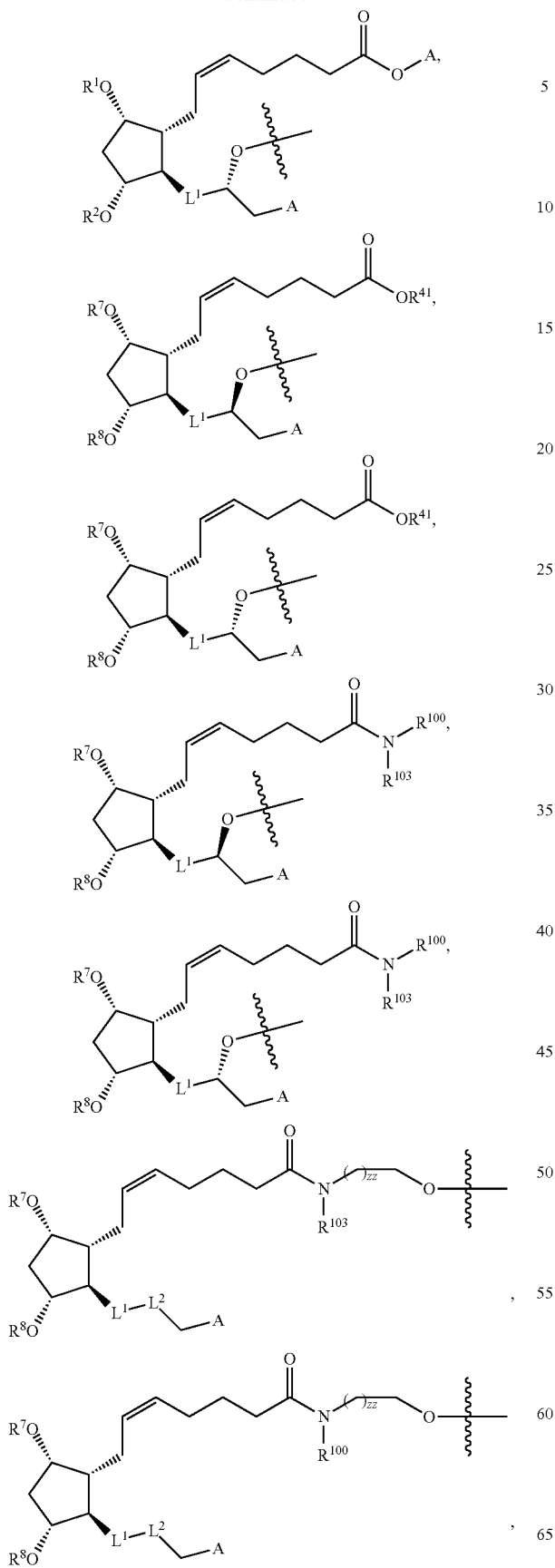
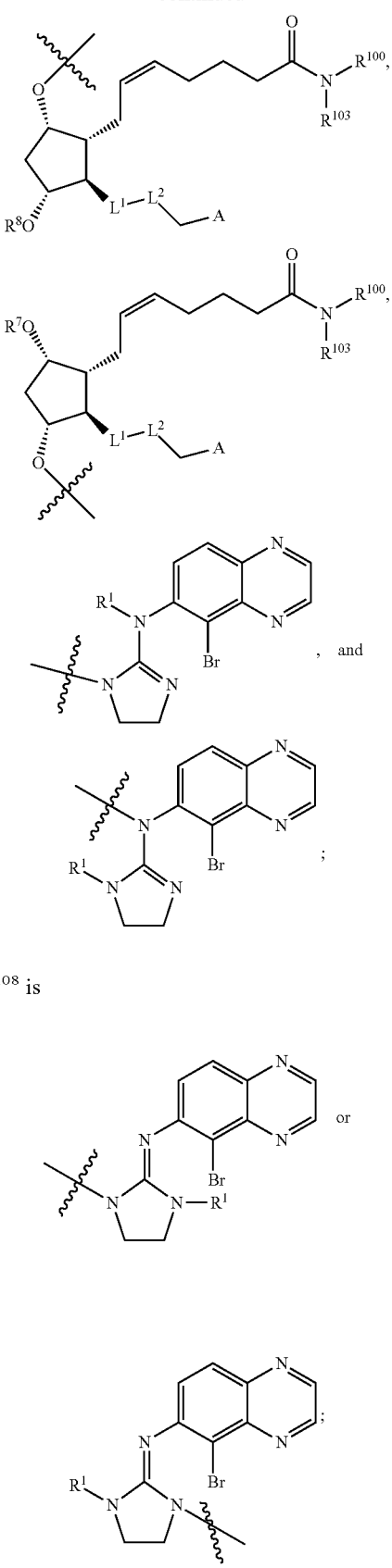
or $R^{108}$ is or in an alternative embodiment, $R^{108}$ is

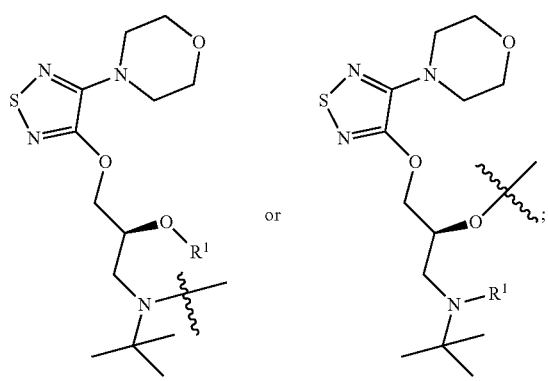

and
wherein all other variables are as defined herein.

The disclosure also provides a prodrug of Formula XIV:

(XIV)

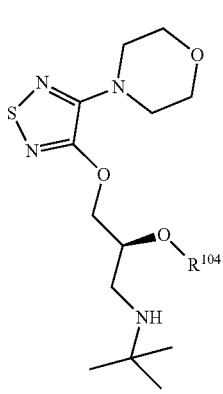

or a pharmaceutically acceptable composition, salt, or isotopic derivative thereof.

$R^{104}$ is selected from —C(O)C$_{17-30}$alkyl, —C(O)C$_{10-30}$alkenyl, —C(O)C$_{10-30}$alkynyl, —C(O)(C$_{10-30}$alkyl with at least one $R^5$ substituent on the alkyl chain), —C(O)(C$_{10-30}$alkenyl, with at least one $R^5$ substituent on the alkenyl chain), and —C(O)(C$_{10-30}$alkynyl, with at least one $R^5$ substituent on the alkynyl chain);

wherein $R^5$ is defined above.

In one embodiment, $R^{104}$ is —C(O)(CH$_2$)$_{16}$CH$_3$.

In one embodiment, $R^{104}$ is

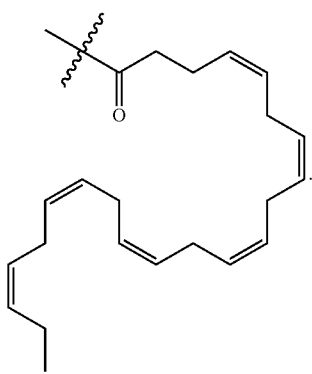 [SMILES: *C(=O)CC/C=C\C/C=C\C/C=C\C/C=C\C/C=C\C/C=C\CC]

In one embodiment, a compound of Formula XIV is the pharmaceutically acceptable HCl salt.

In one embodiment, a compound of Formula XIV is the pharmaceutically acceptable maleic salt.

In one embodiment, a compound of Formula XIV is the pharmaceutically acceptable succinic salt.

In one embodiment, a compound of Formula XIV is the pharmaceutically acceptable fumaric salt.

The disclosure also provides a prodrug of Formula XV:

(XV)

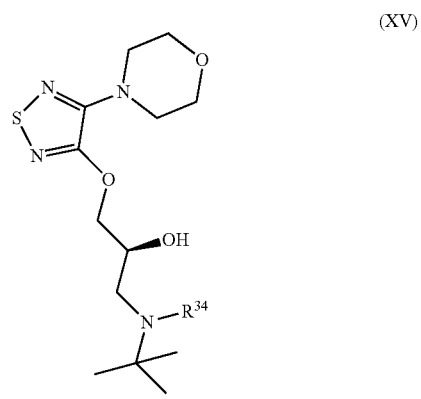

or a pharmaceutically acceptable composition, salt, or isotopic derivative thereof.

$R^{34}$ is selected from: acyl, $R^{36}$, carbonyl linked polyethylene glycol, carbonyl linked polypropylene glycol, carbonyl linked polypropylene oxide, polylactic acid, and poly(lactic-co-glycolic acid), a polyglycolic acid, a polyester, polyamide,

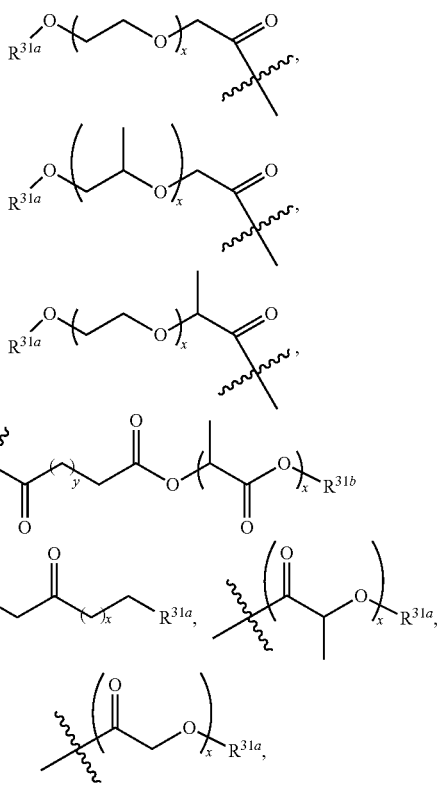

-continued
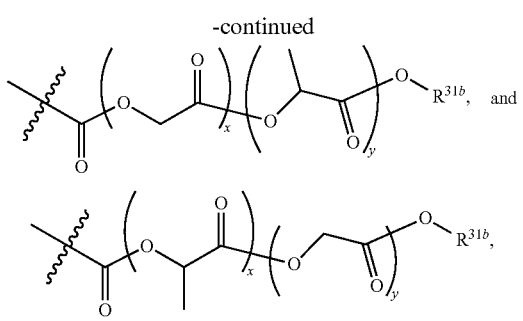
or other biodegradable polymer, wherein each $R^{34}$ other than $R^{36}$ is substituted with at least one $L^4$-$R^{115}$;
or $R^{34}$ is
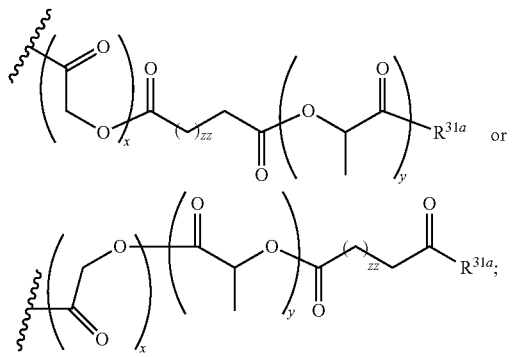
In one embodiment $R^{34}$ is selected from:
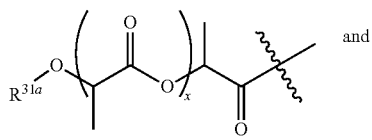
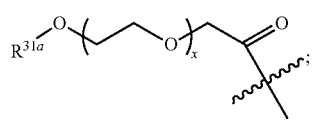
In one embodiment $R^{31a}$ is selected from —C(O)A, stearoyl, and
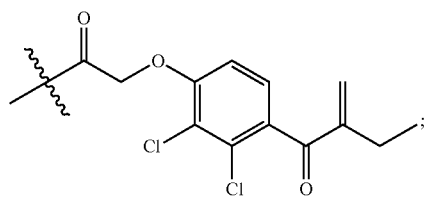 [SMILES: *C(=O)COc1ccc(C(=O)C(=C)CC)c(Cl)c1Cl]
In an alternative embodiment, $R^{31b}$ is selected from —C(O)A, stearoyl, and
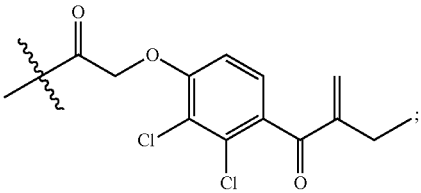 [SMILES: *C(=O)COc1ccc(C(=O)C(=C)CC)c(Cl)c1Cl]
$R^{31}$ is selected from:
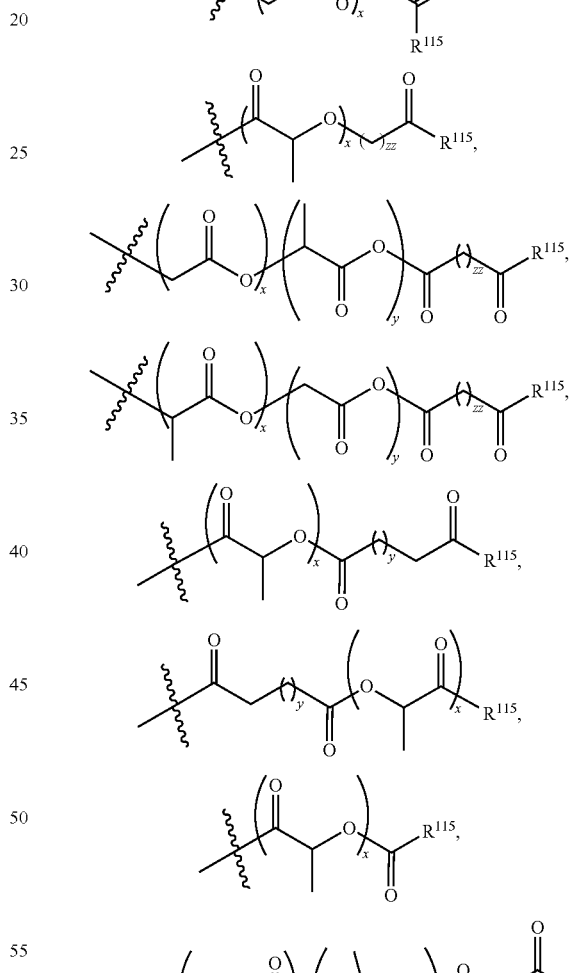
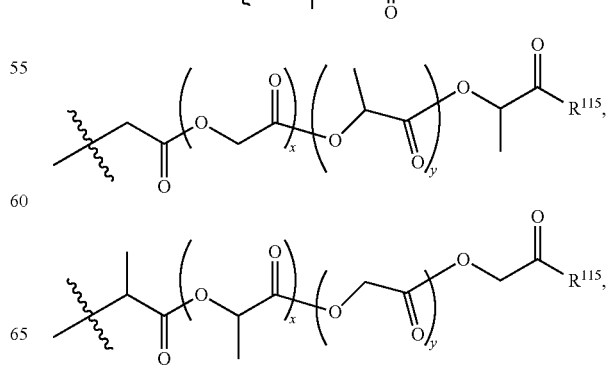

101
-continued
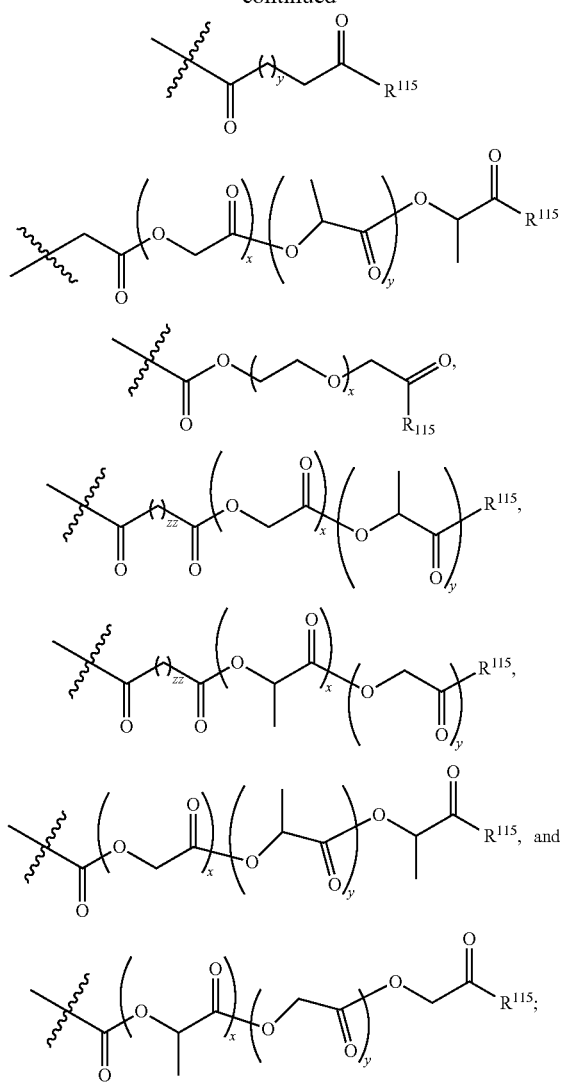
or R³⁶ is
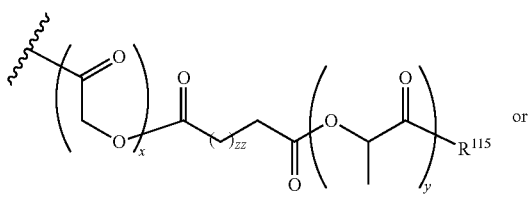
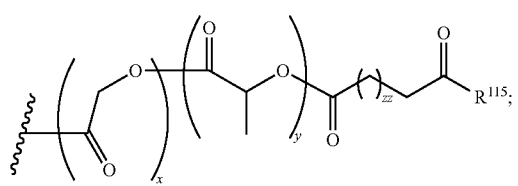
102
R¹¹⁵ is selected from
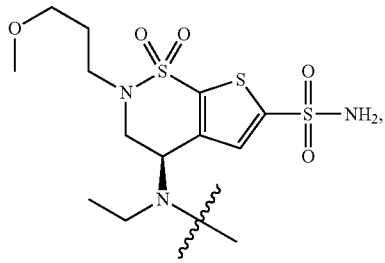
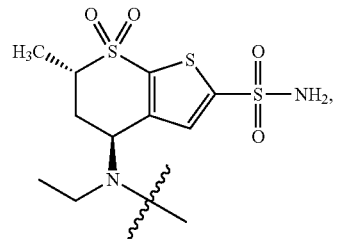
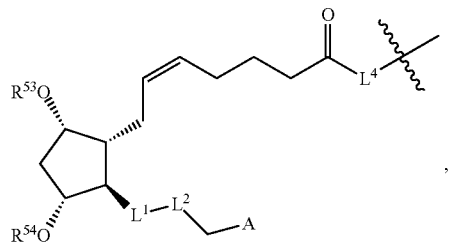
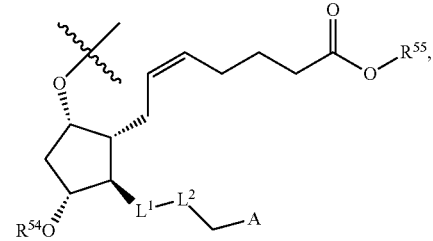
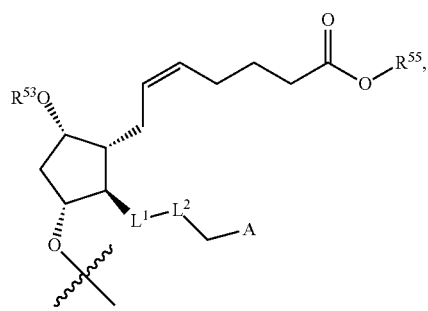
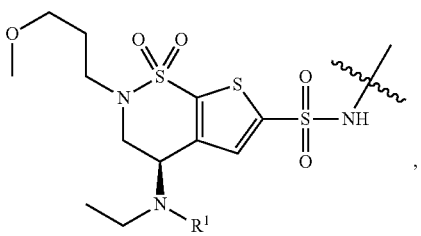

103
-continued
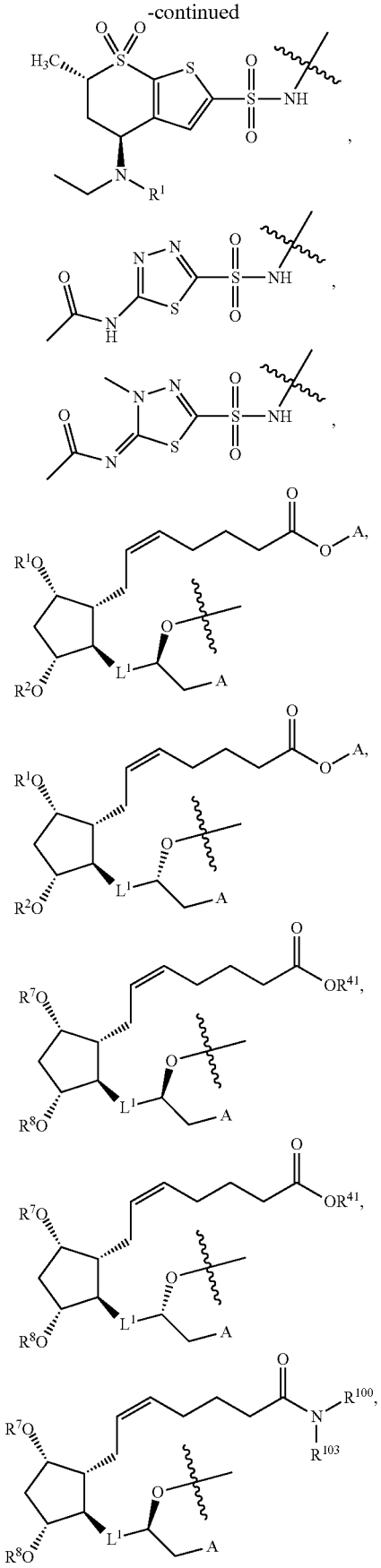
104
-continued
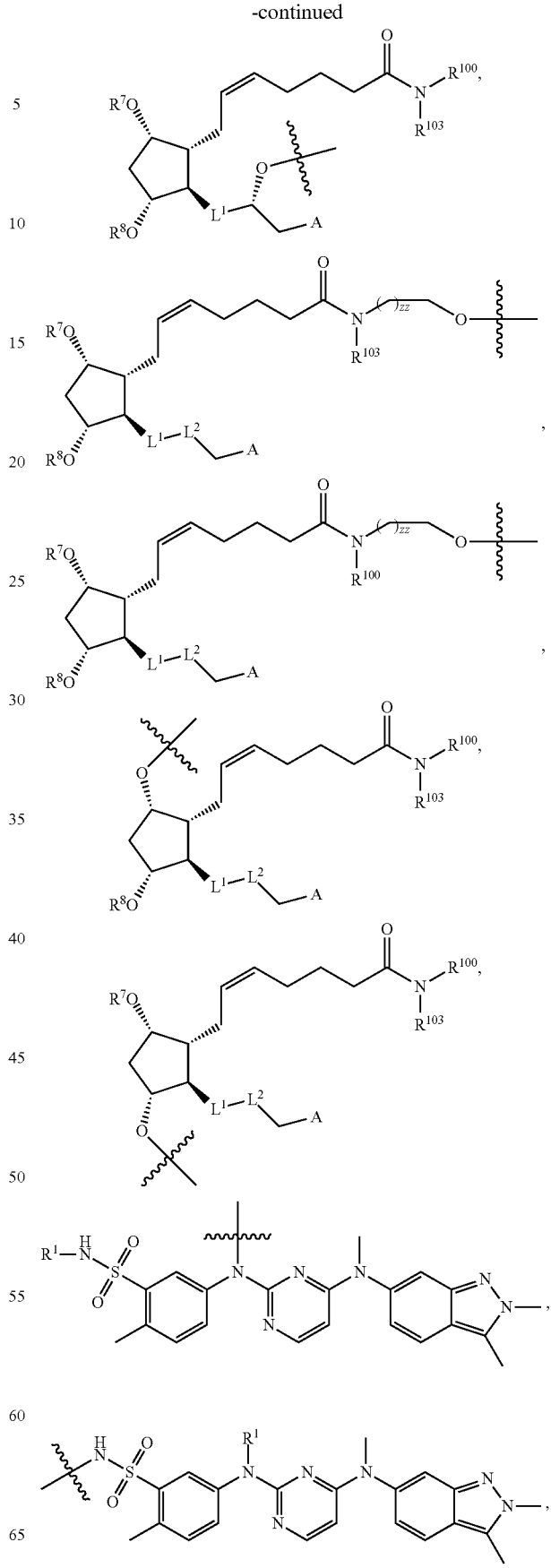

105
-continued
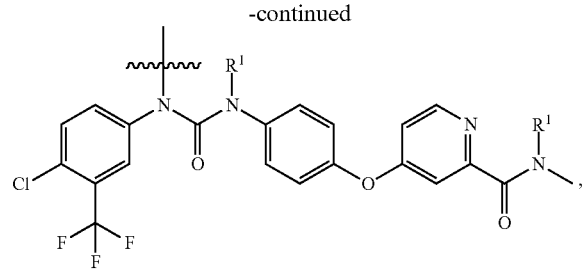
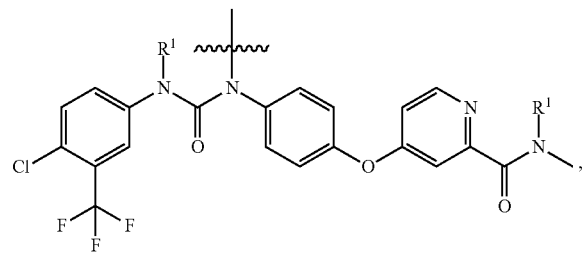
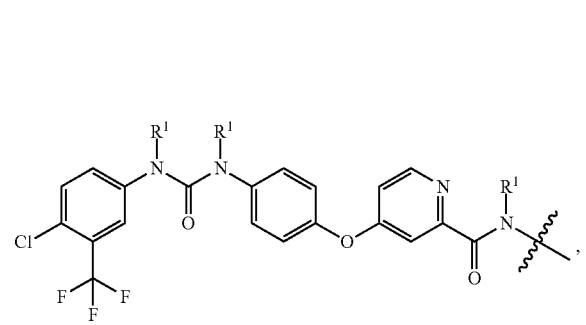
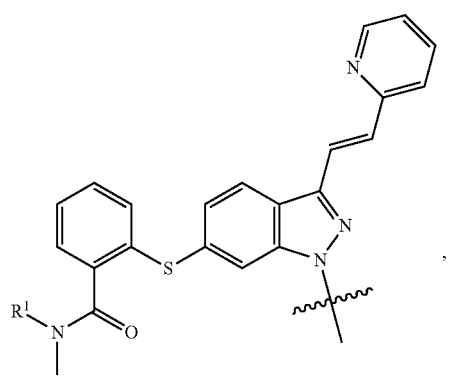
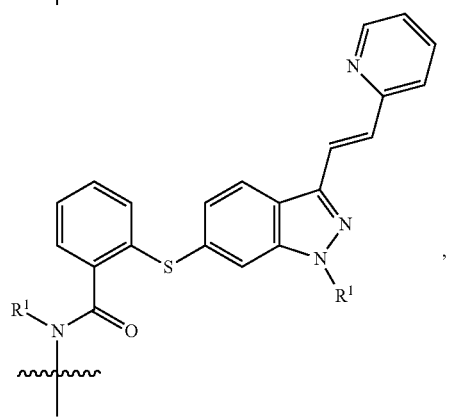
106
-continued
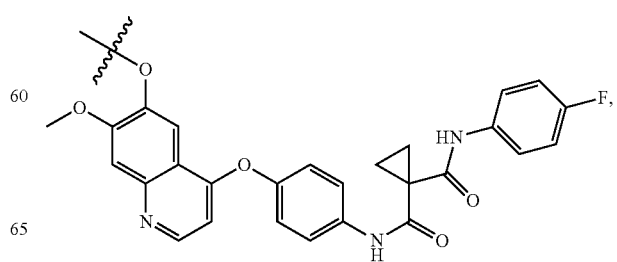

-continued
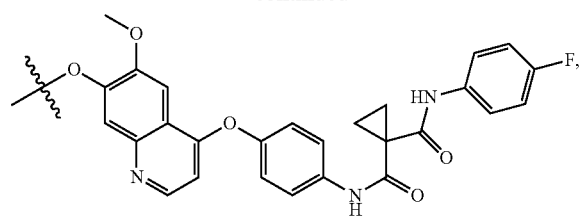
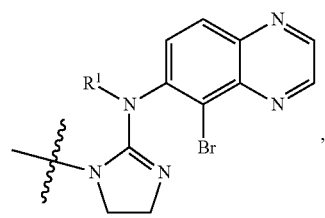
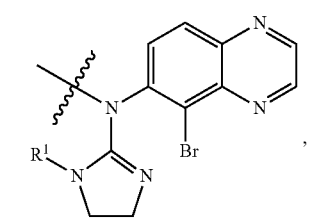
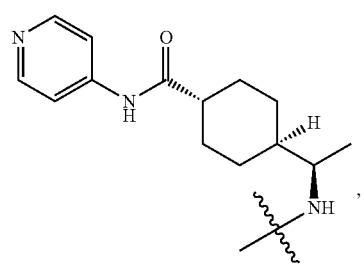
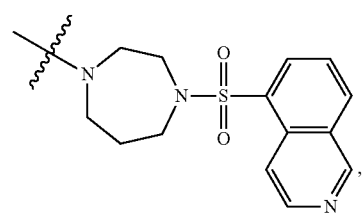
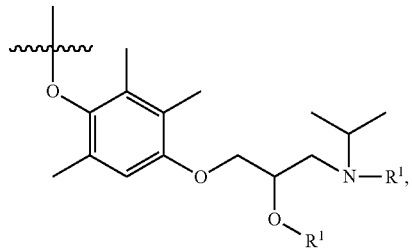
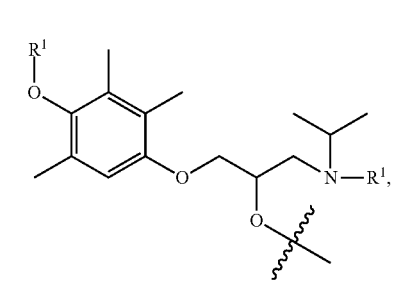
-continued
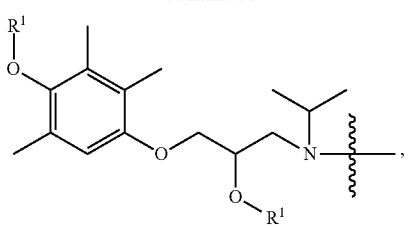
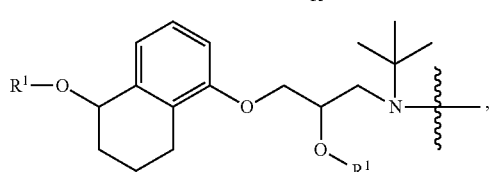
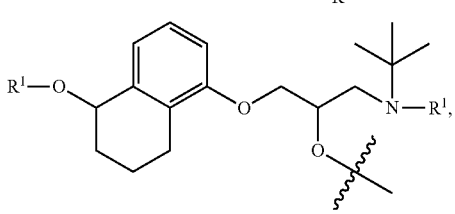
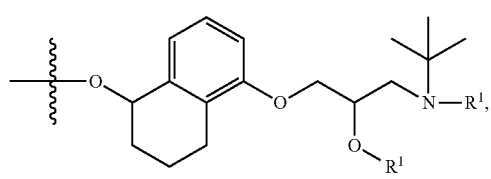
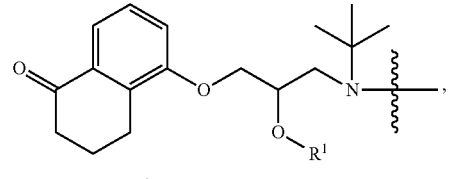
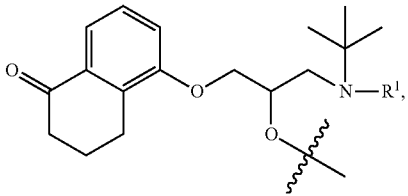
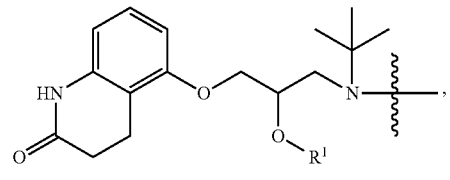
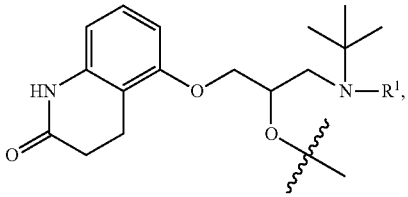
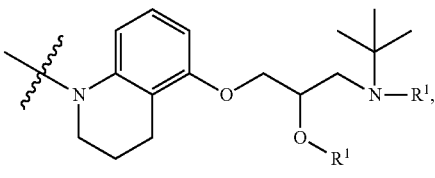

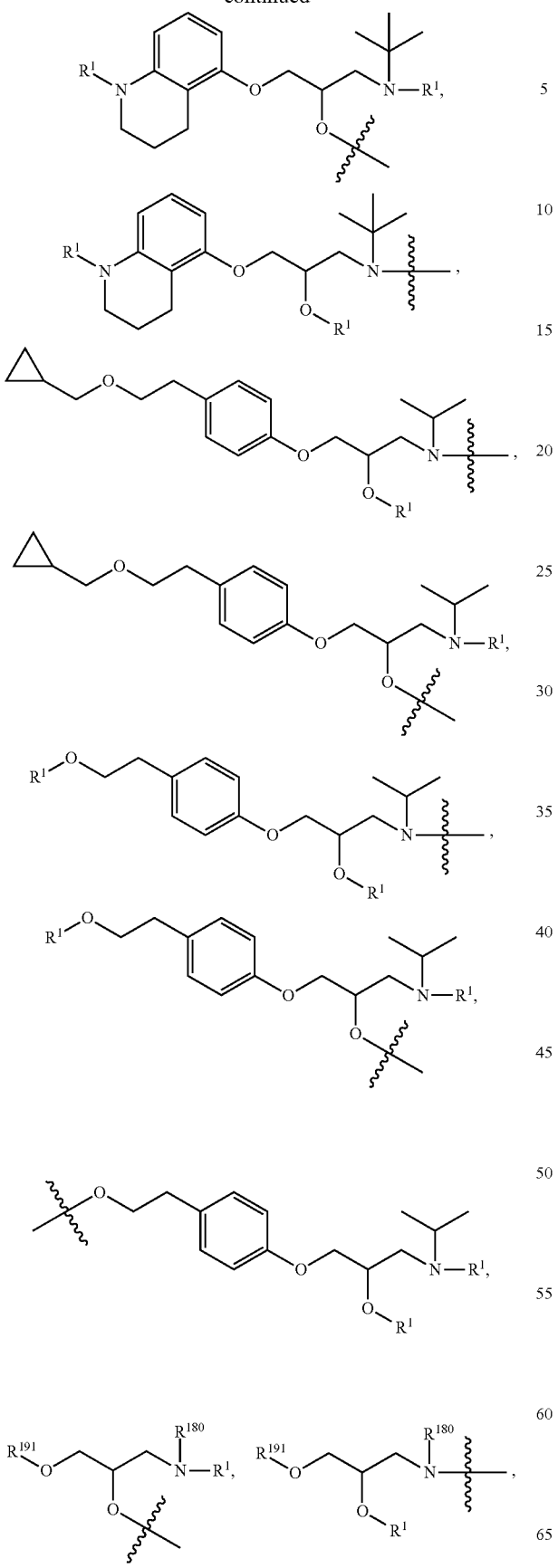
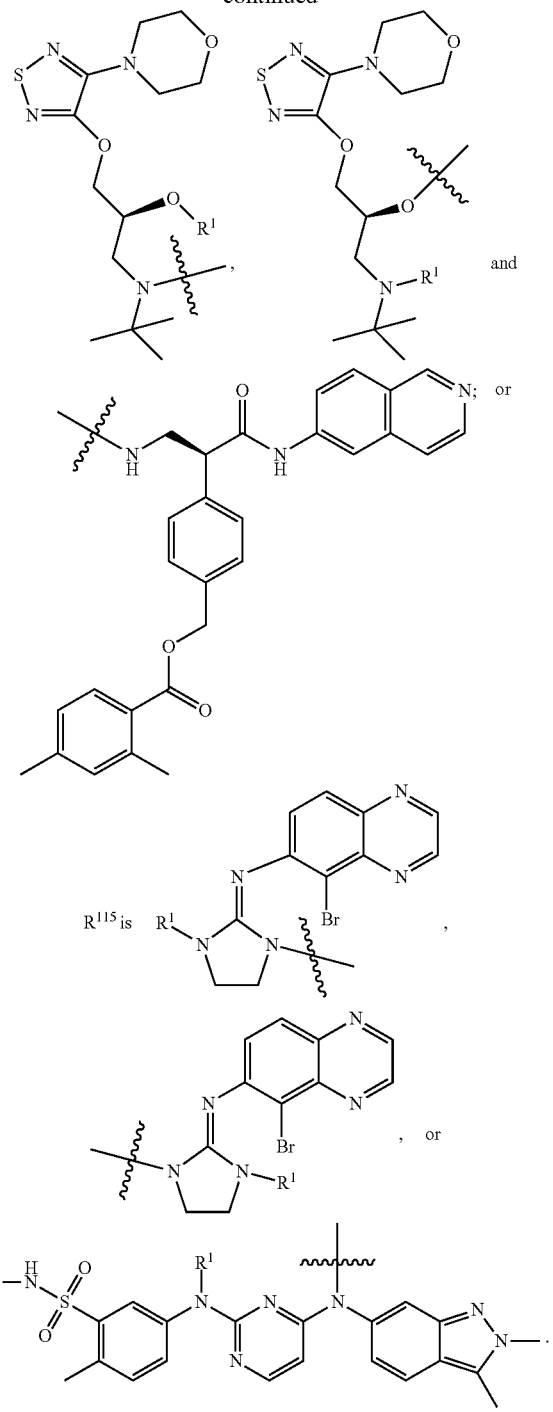

wherein

R[53] and R[54] are independently selected from —C(O)R[4], —C(O)A, and hydrogen; and R[55] is selected from (i) polyethylene glycol, polypropylene glycol, polypropylene oxide, polylactic acid, and poly(lactic-co-glycolic acid), polyglycolic acid, or a polyester, a polyamide, or other biodegradable polymer, wherein a terminal hydroxy or carboxy group can be substituted to create an ether or ester, respectively;

(ii) —$C_{10}$-$C_{30}$alkyl$R^5$, —$C_{10}$-$C_{30}$alkenyl$R^5$, —$C_{10}$-$C_{30}$alkynyl$R^5$, —$C_{10}$-$C_{30}$alkenylalkynyl$R^5$, —$C_{10}$-$C_{30}$alkyl, —$C_{10}$-$C_{30}$alkenyl, —$C_{10}$-$C_{30}$alkynyl, and —$C_{10}$-$C_{30}$alkenylalkynyl;

(iii) an unsaturated fatty acid residue including but not limited the carbon fragment taken from linoleic acid (—$(CH_2)_8(CH)_2CH_2(CH)_2(CH_2)_4CH_3$)), docosahexaenoic acid (—$(CH_2)_3(CHCHCH_2)_6CH_3$)), eicosapentaenoic acid (—$(CH_2)_4(CHCHCH_2)_5CH_3$)), alpha-linolenic acid (—$(CH_2)_8(CHCHCH_2)_3CH_3$)) stearidonic acid, y-linolenic acid, arachidonic acid, docosatetraenoic acid, palmitoleic acid, vaccenic acid, paullinic acid, oleic acid, elaidic acid, gondoic acid, euric acid, nervonic acid and mead acid;

(iv) alkyl, cycloalkyl, cycloalkylalkyl, heterocycle, heterocycloalkyl, arylalkyl, and heteroarylalkyl; and wherein all other variables are as defined herein.

In an alternative embodiment, the disclosure also provides a prodrug of Formula XV'

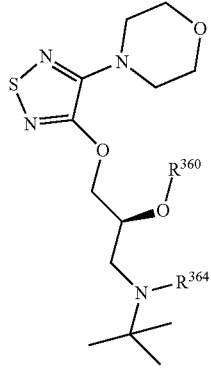

(XV')

or a pharmaceutically acceptable composition, salt, or isotopic derivative thereof.

$R^{364}$ is selected from: acyl, carbonyl linked polyethylene glycol, carbonyl linked polypropylene glycol, carbonyl linked polypropylene oxide, polylactic acid, poly(lactic-co-glycolic acid), polyglycolic acid, polyester, polyamide,

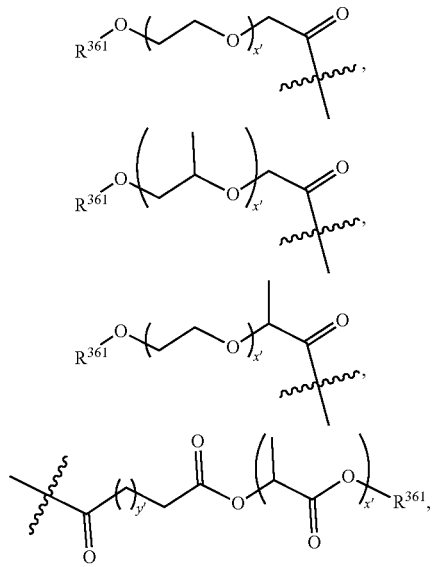

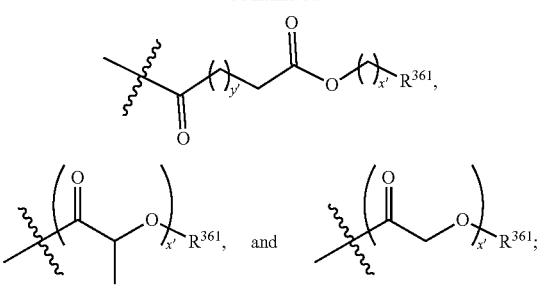

or $R^{364}$ is

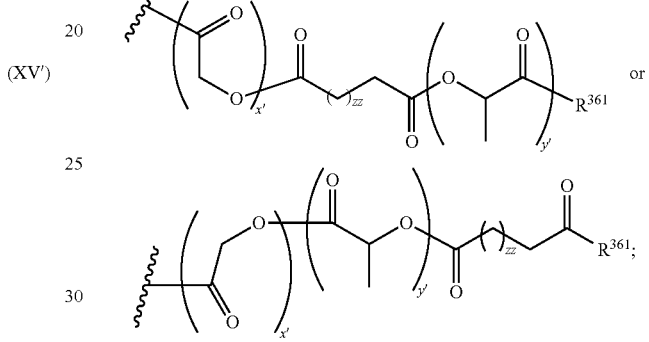

$R^{361}$ is selected from hydrogen, A, —C(O)alkyl, —C(O)A, aryl, alkyl, cycloalkyl, cycloalkylalkyl, heterocyclyl, heterocycloalkyl, arylalkyl, heteroaryl, heteroarylalkyl, polylactic acid, polygylcolic acid, polyethylene glycol, and stearoyl;

$R^{360}$ is selected from

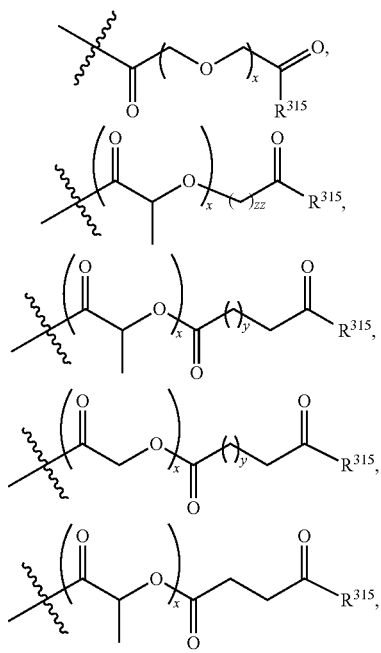

113
-continued
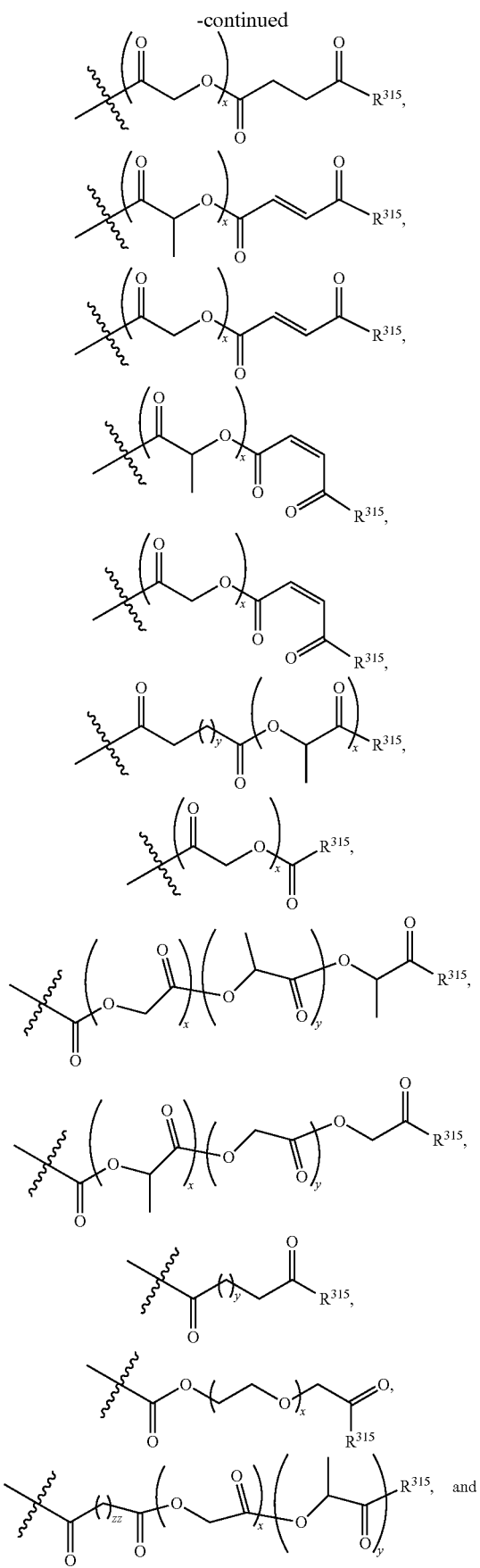
114
-continued
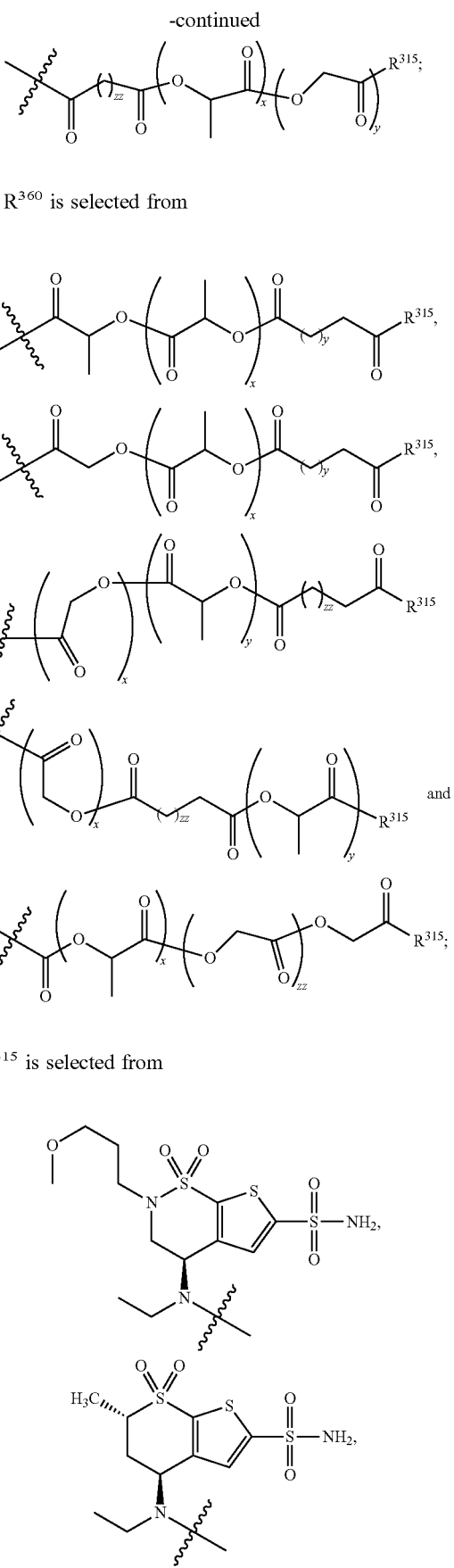
or R³⁶⁰ is selected from
R³¹⁵ is selected from -continued
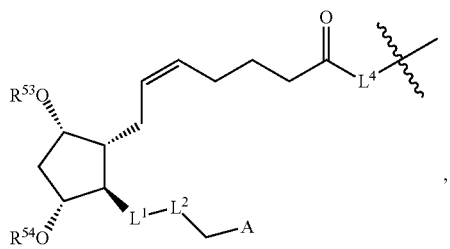
,
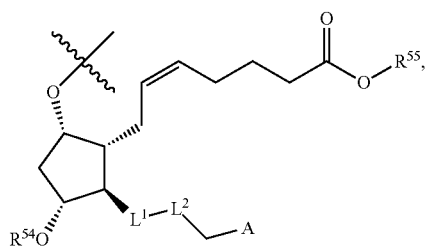
,
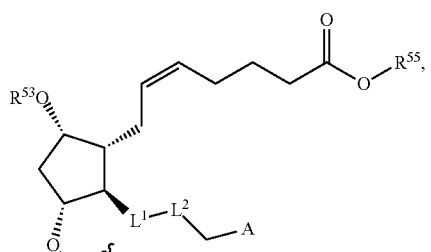
,
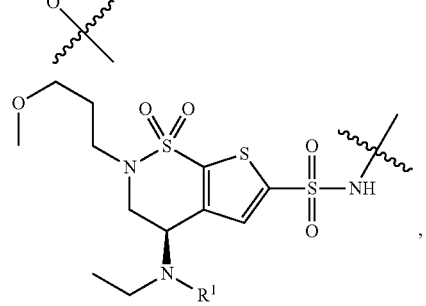
,
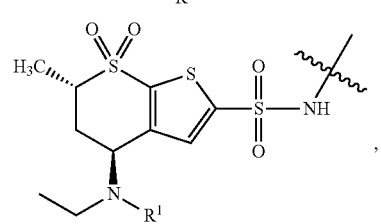
,
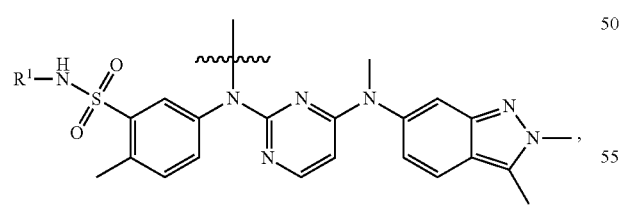
,
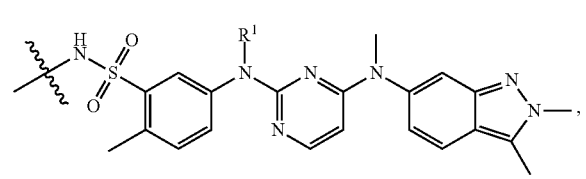
-continued
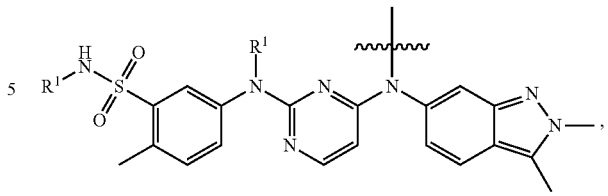
,
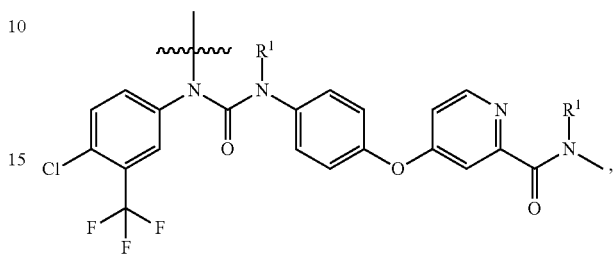
,
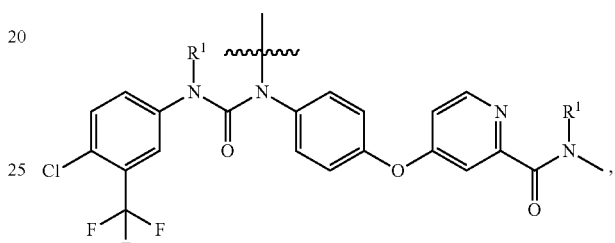
,
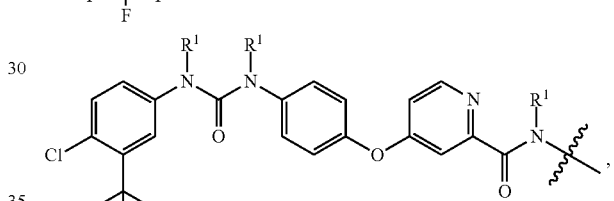
,
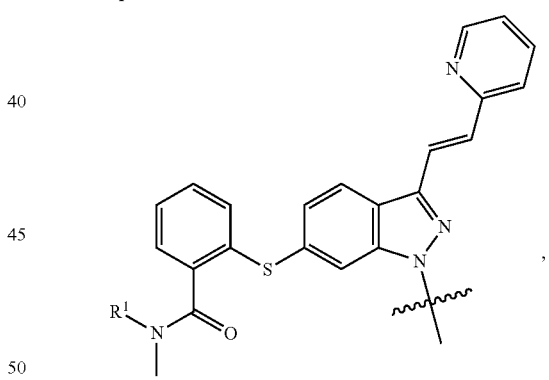
,
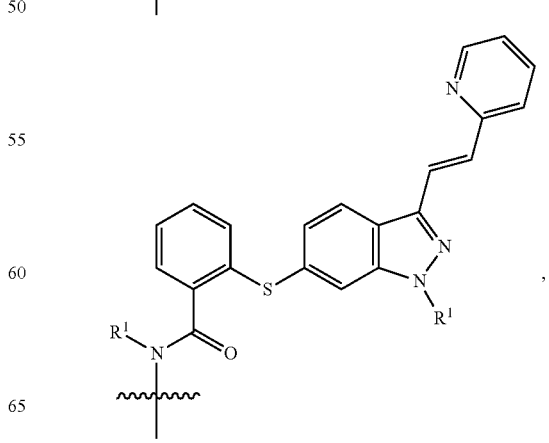
,

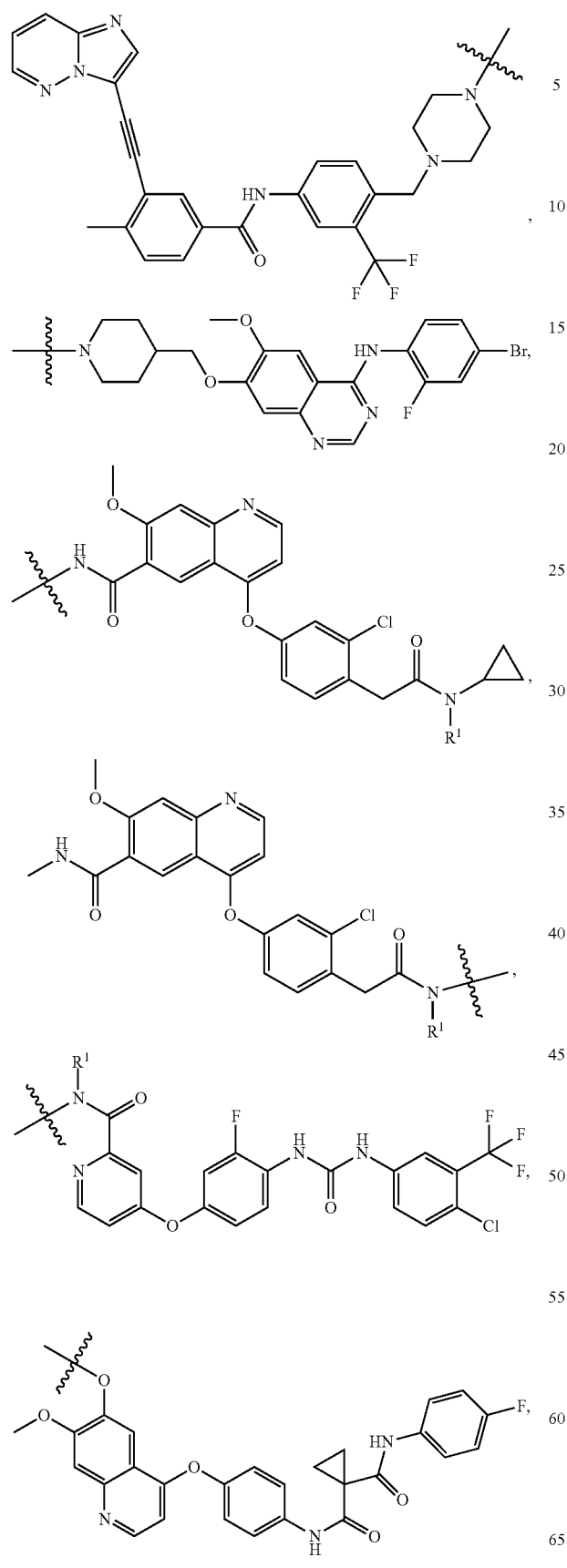
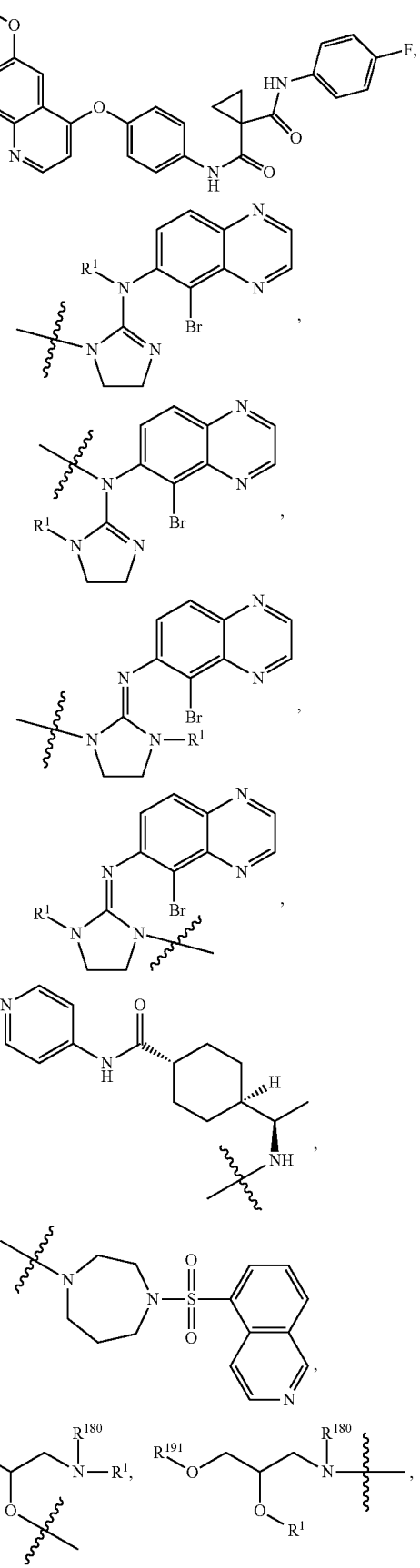

119
-continued

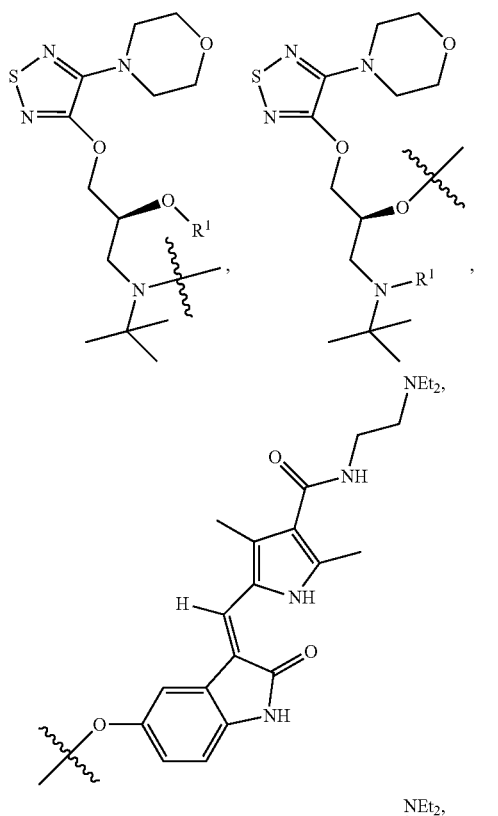

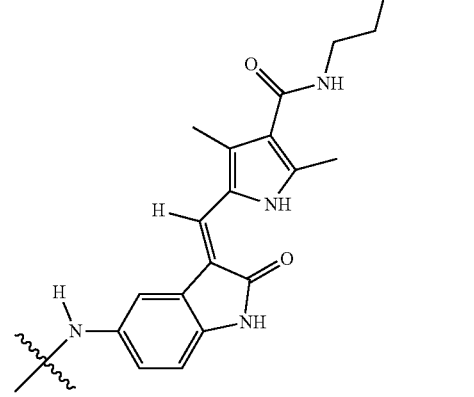

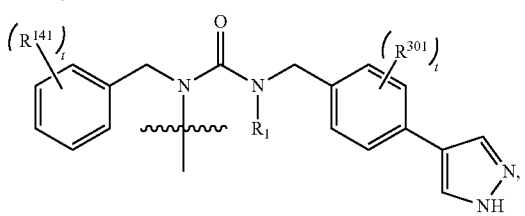

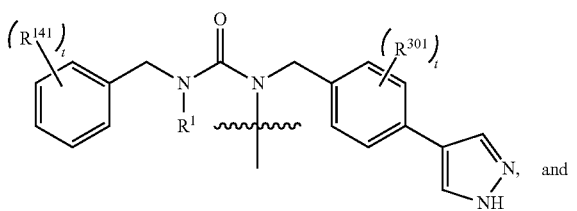

120
-continued

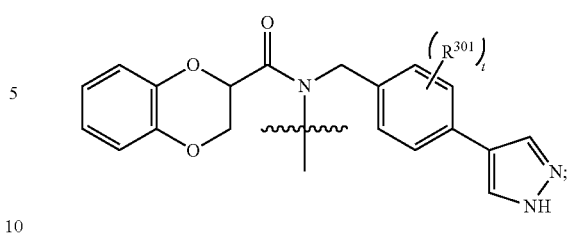

x', and y' are independently selected from 0, 1, 2, 3, 4, 5, 6, 7, 8, 9, and 10, and wherein if x' and y' are within the linker then x' and y' cannot both be 0;

$R^{141}$ is selected from hydrogen, —C(O)NR$^1$R$^2$, —C(O)R$^1$, —C(O)OR$^1$, nitro, amino, —NR$^{134}$R$^{135}$, alkyl, alkoxy, alkylalkoxy, alkoxyalkoxy, haloalkoxy, cycloalkyl, heterocycloalkyl, heteroaryl, aryl, and halogen;

$R^{134}$ and $R^{135}$ are independently selected from H, alkyl, —SO$_2$CH$_3$, —C(O)CH$_3$, and —C(O)NH$_2$;

$R^{301}$ is selected from hydrogen, —C(O)NR$^1$R$^2$, —C(O)R$^1$, —C(O)OR$^1$, nitro, amino, —NR$^{134}$R$^{135}$, alkyl, alkoxy, alkylalkoxy, alkoxyalkoxy, haloalkoxy, cycloalkyl, heterocycloalkyl, heteroaryl, aryl, halogen, —O(CH$_2$)$_2$NR$^{334}$R$^{335}$, and —N(CH$_3$)(CH$_2$)$_2$NR$^{334}$R$^{335}$;

$R^{334}$ and $R^{335}$ are independently selected from H, alkyl, —SO$_2$CH$_3$, —C(O)CH$_3$, and —C(O)NH$_2$;

or $R^{334}$ and $R^{335}$ can together form a heterocycloalkyl; and wherein all other variables are as defined herein.

In one embodiment, $R^{364}$ is

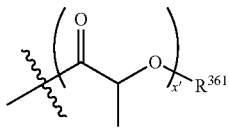

and $R^{361}$ is —C(O)alkyl;

In one embodiment, $R^{364}$ is

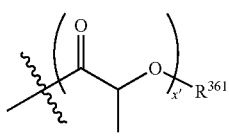

and $R^{361}$ is —C(O)Me;

In one embodiment, $R^{364}$ is

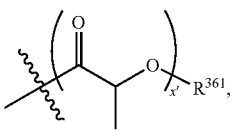

$R^{361}$ is —C(O)Me, and x' is an integer between 1 and 6 (1, 2, 3, 4, 5, or 6);

In one embodiment, $R^{364}$ is
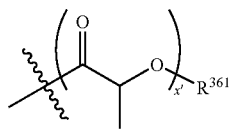
and $R^{361}$ is stearoyl;
In one embodiment, $R^{364}$ is
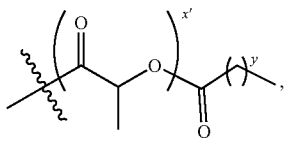
x' is an integer between 1 and 6 (1, 2, 3, 4, 5, or 6), and y is 11 or 17, or in an alternative embodiment, y is 10 or 16.
In one embodiment, $R^{360}$ is
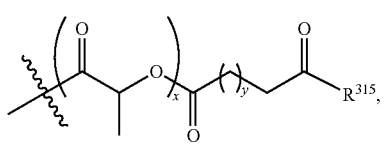
$R^{315}$ is
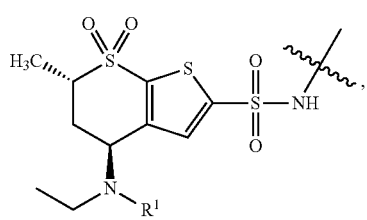
and $R^1$ is hydrogen.
In one embodiment, $R^{360}$ is
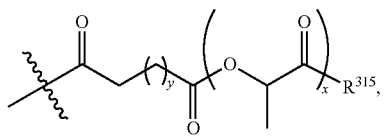
$R^{315}$ is
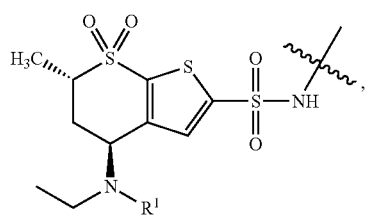
and $R^1$ is hydrogen.
In one embodiment, $R^{360}$ is
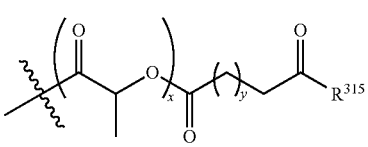
$R^{315}$ is
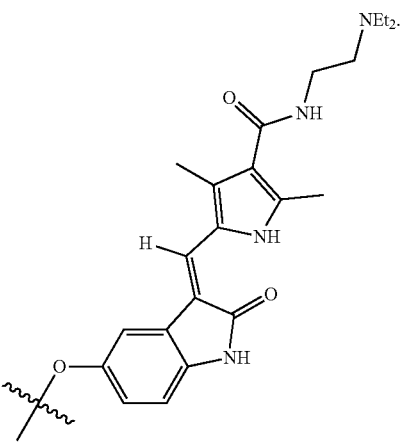
In certain embodiments, $R^{360}$ is
and $R^{315}$ is
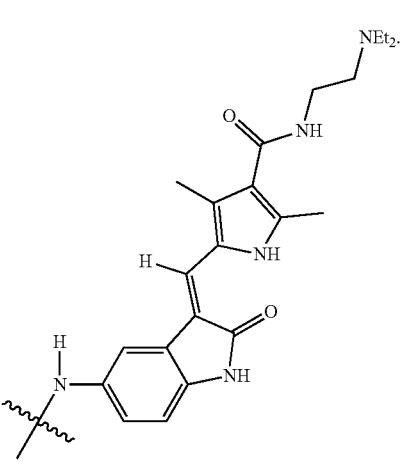

In certain embodiments, $R^{360}$ is

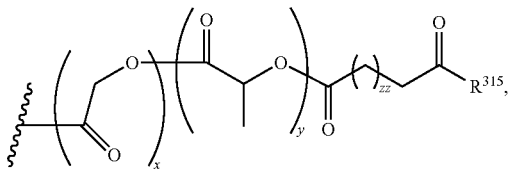

x, x and y are independently selected from 1, 2, 3, 4, 5, or 6, and zz is 1, 2, or 3.

In certain embodiments, $R^{360}$ is

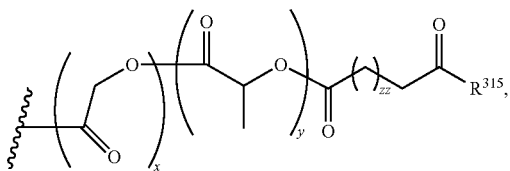

x, x and y are independently selected from 1, 2, or 3, and zz is 1, 2, or 3.

In certain embodiments, $R^{360}$ is

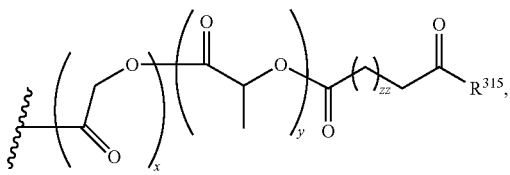

x and y are independently selected from 1, 2, or 3, zz is 1, 2, or 3, and $R^{360}$ is

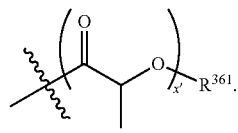

In certain embodiments, x' and x are 1 and y and y' are independently selected from 1, 2, 3, 4, 5, and 6.

In certain embodiments, x' and x are 2 and y and y' are independently selected from 1, 2, 3, 4, 5, and 6.

In certain embodiments, x' and x are 3 and y and y' are independently selected from 1, 2, 3, 4, 5, and 6.

In certain embodiments, x' and x are 1 and y and y' are independently selected from 1, 2, or 3.

In certain embodiments, x' and x are 2 and y and y' are independently selected from 1, 2, or 3.

In certain embodiments, y' and y are 1 and x and x' are independently selected from 1, 2, 3, 4, 5, and 6.

In certain embodiments, y' and y are 2 and x and x' are independently selected from 1, 2, 3, 4, 5, and 6.

In certain embodiments, y' and y are 3 and x and x' are independently selected from 1, 2, 3, 4, 5, and 6.

In certain embodiments, y' and y are 1 and x and x' are independently selected from 1, 2, and 3.

In certain embodiments, y' and y are 2 and x and x' are independently selected from 1, 2, and 3.

Non-limiting examples of compounds of Formula XV' include

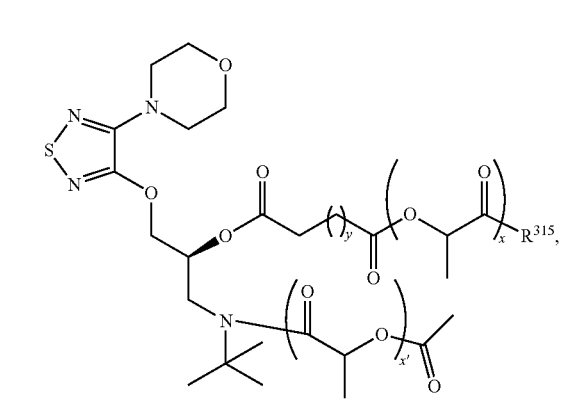

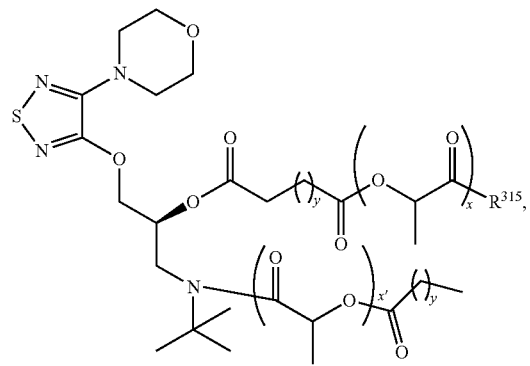

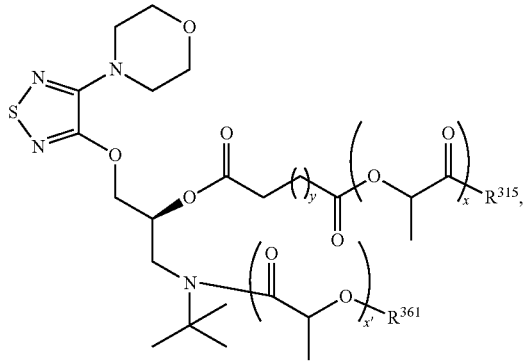

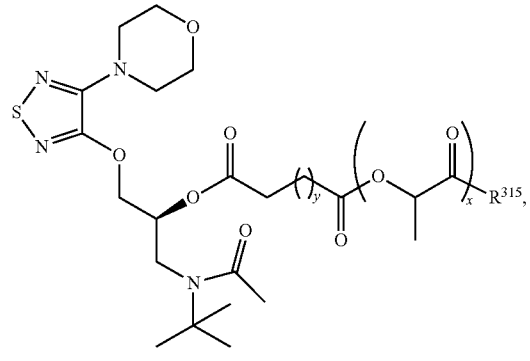

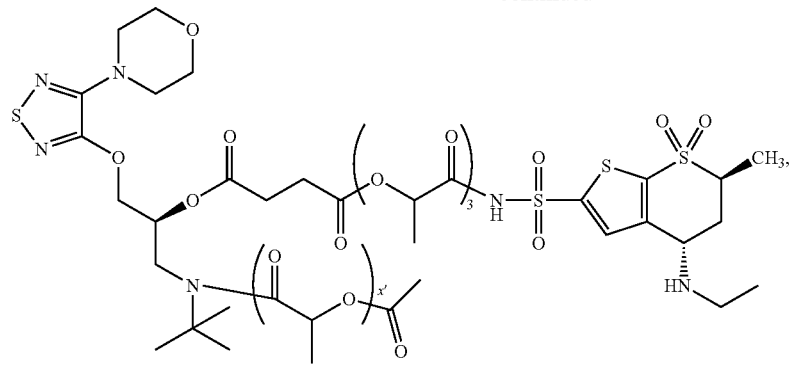
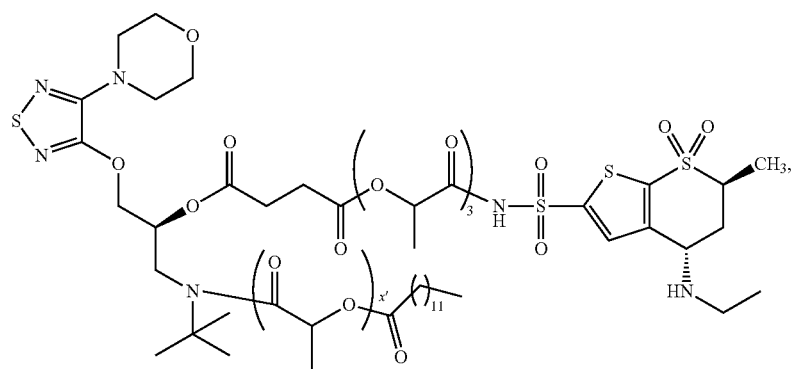
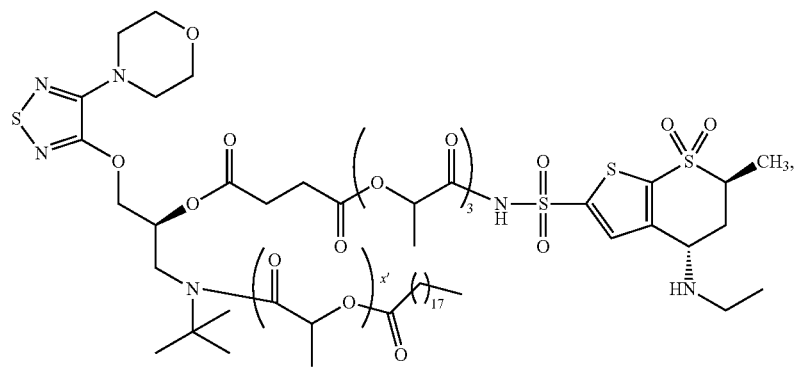

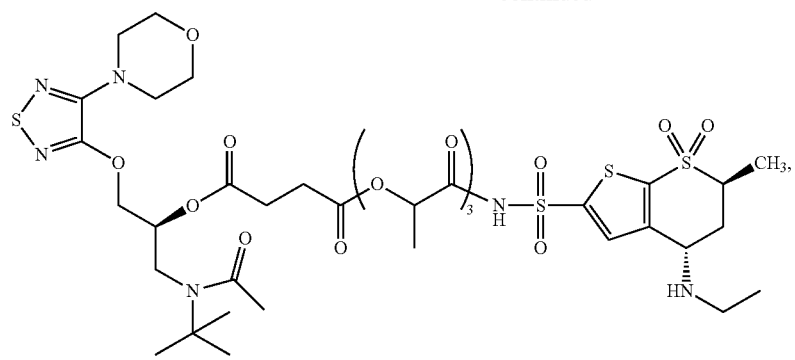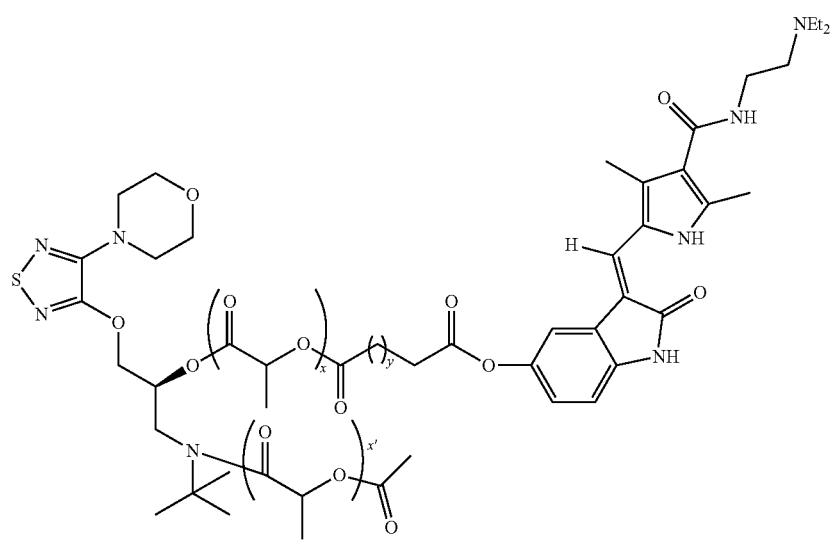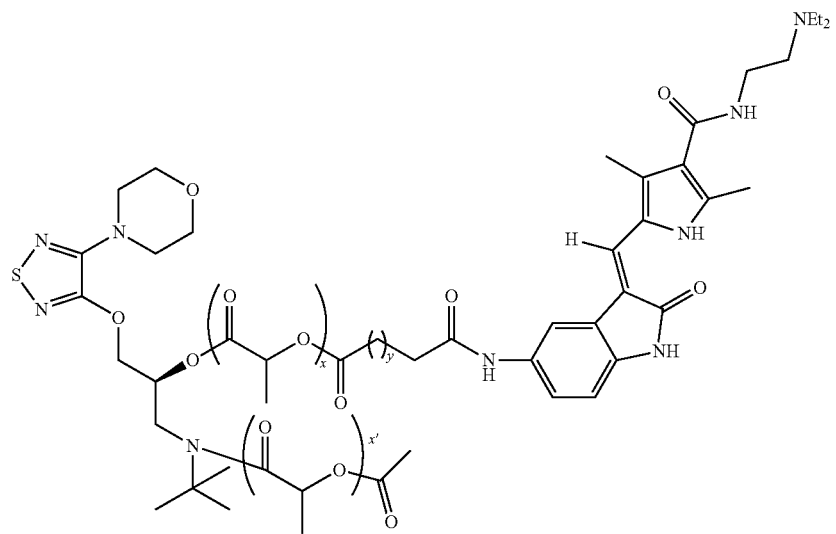

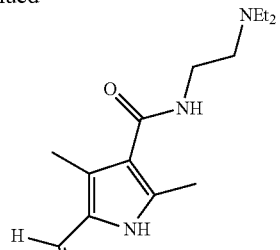
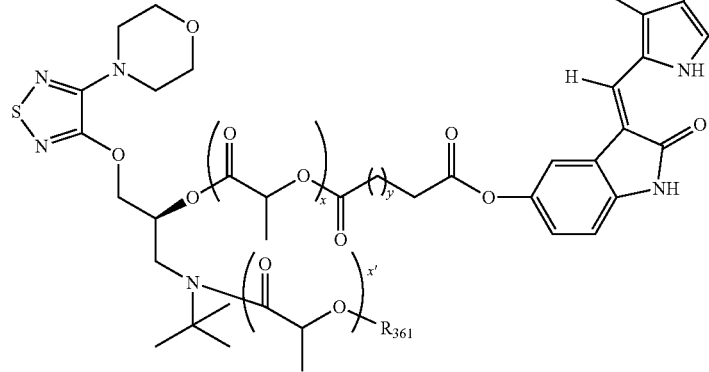
Additional non-limiting examples of Formula XV' include
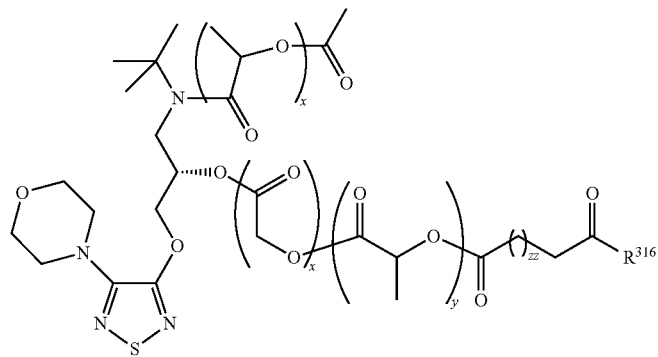
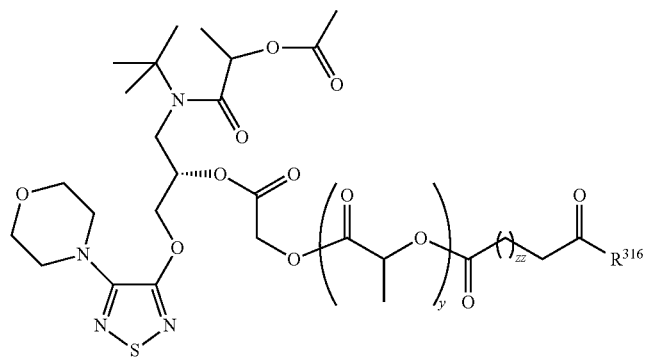

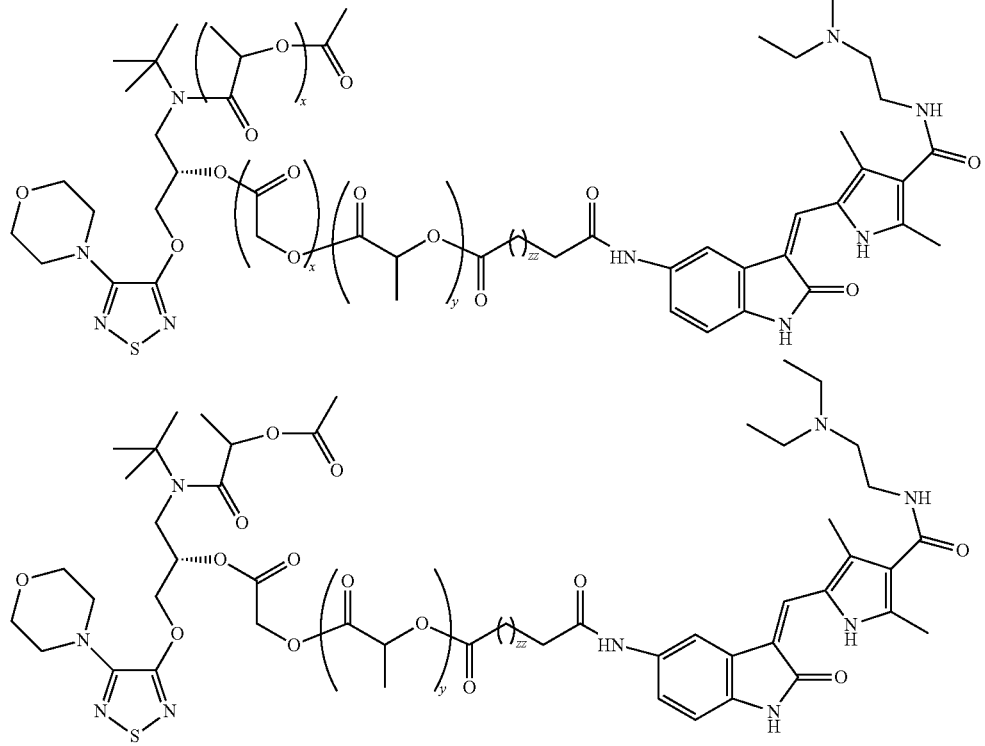
In an alternative embodiment, the disclosure also provides a prodrug of Formula XV":
(XV")
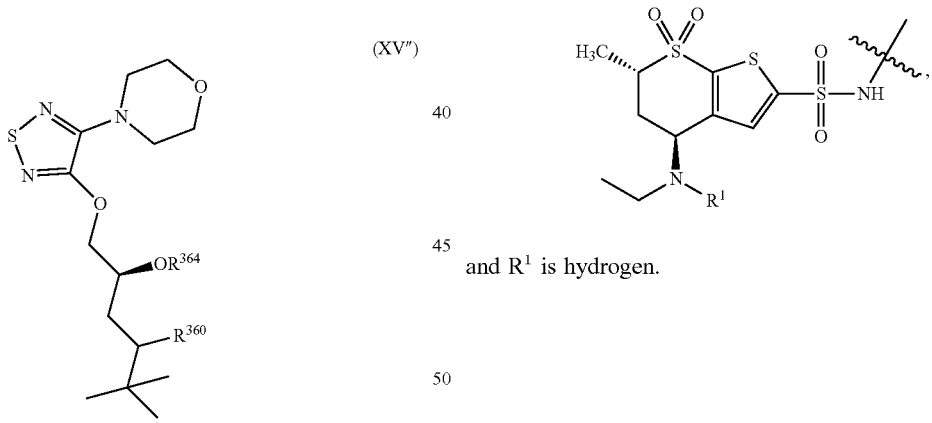
or a pharmaceutically acceptable composition, salt, or isotopic derivative thereof.
wherein $R^{360}$ and $R^{364}$ are defined above.
In one embodiment, $R^{360}$ is
$R^{315}$ is
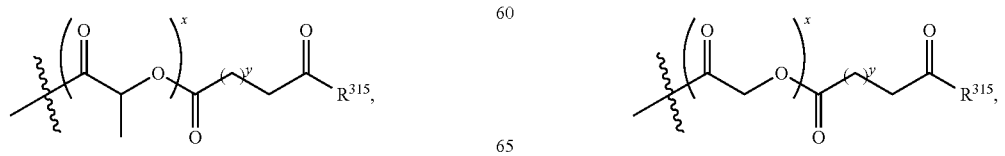
and $R^1$ is hydrogen.
In one embodiment, $R^{360}$ is $R^{315}$ is

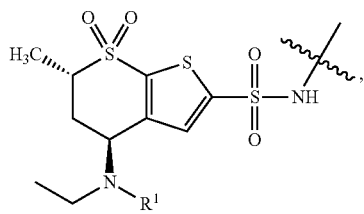

and $R^1$ is hydrogen.

In one embodiment, $R^{360}$ is

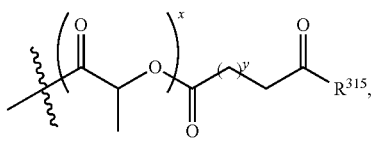

$R^{315}$ is

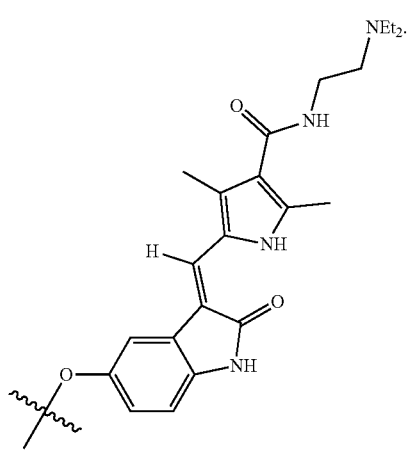

In one embodiment, $R^{360}$ is

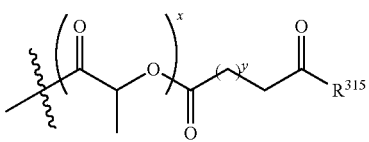

and $R^{315}$ is

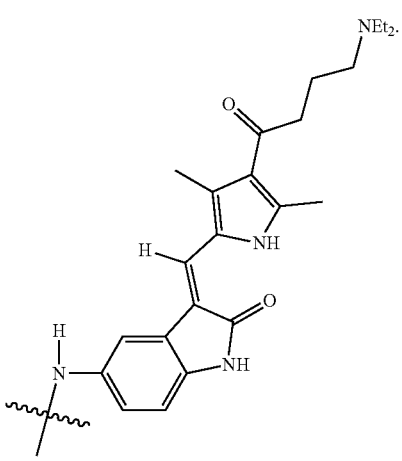

In certain embodiments, x' and x are 1 and y and y' are independently selected from 1, 2, 3, 4, 5, and 6.

In certain embodiments, x' and x are 2 and y and y' are independently selected from 1, 2, 3, 4, 5, and 6.

In certain embodiments, x' and x are 3 and y and y' are independently selected from 1, 2, 3, 4, 5, and 6.

In certain embodiments, x' and x are 1 and y and y' are independently selected from 1, 2, or 3.

In certain embodiments, x' and x are 2 and y and y' are independently selected from 1, 2, or 3.

In certain embodiments, y' and y are 1 and x and x' are independently selected from 1, 2, 3, 4, 5, and 6.

In certain embodiments, y' and y are 2 and x and x' are independently selected from 1, 2, 3, 4, 5, and 6.

In certain embodiments, y' and y are 3 and x and x' are independently selected from 1, 2, 3, 4, 5, and 6.

In certain embodiments, y' and y are 1 and x and x' are independently selected from 1, 2, and 3.

In certain embodiments, y' and y are 2 and x and x' are independently selected from 1, 2, and 3.

Non-limiting Examples of Compound of Formula XV" include:

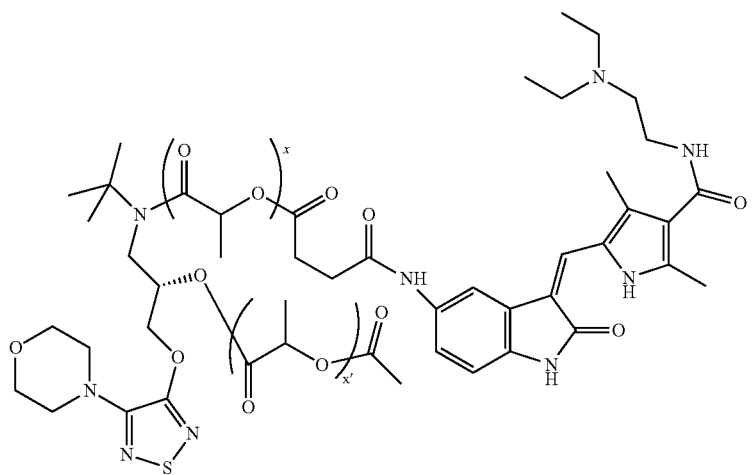
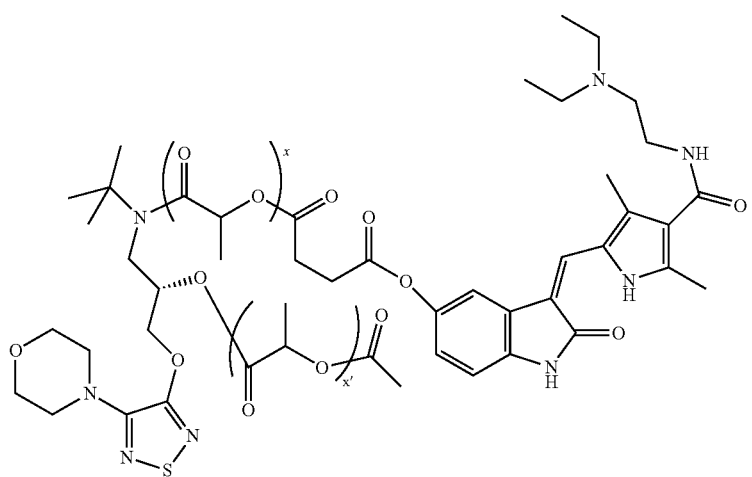
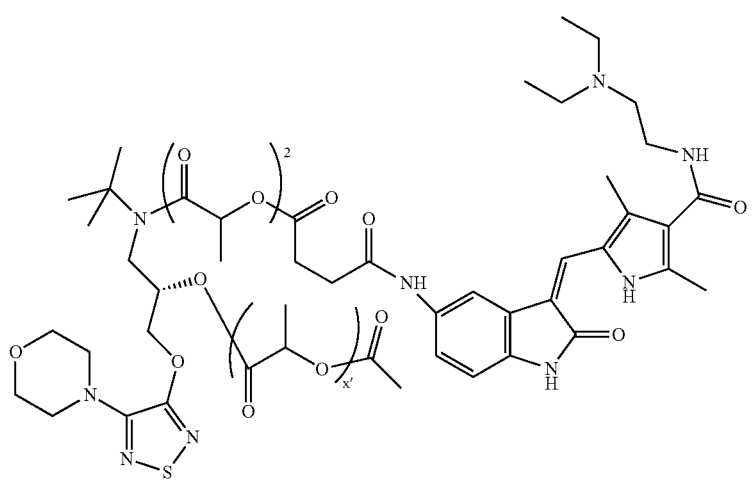

-continued
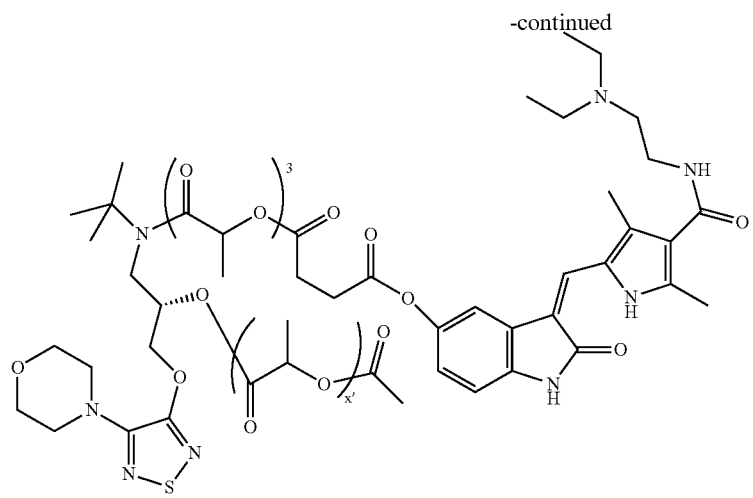
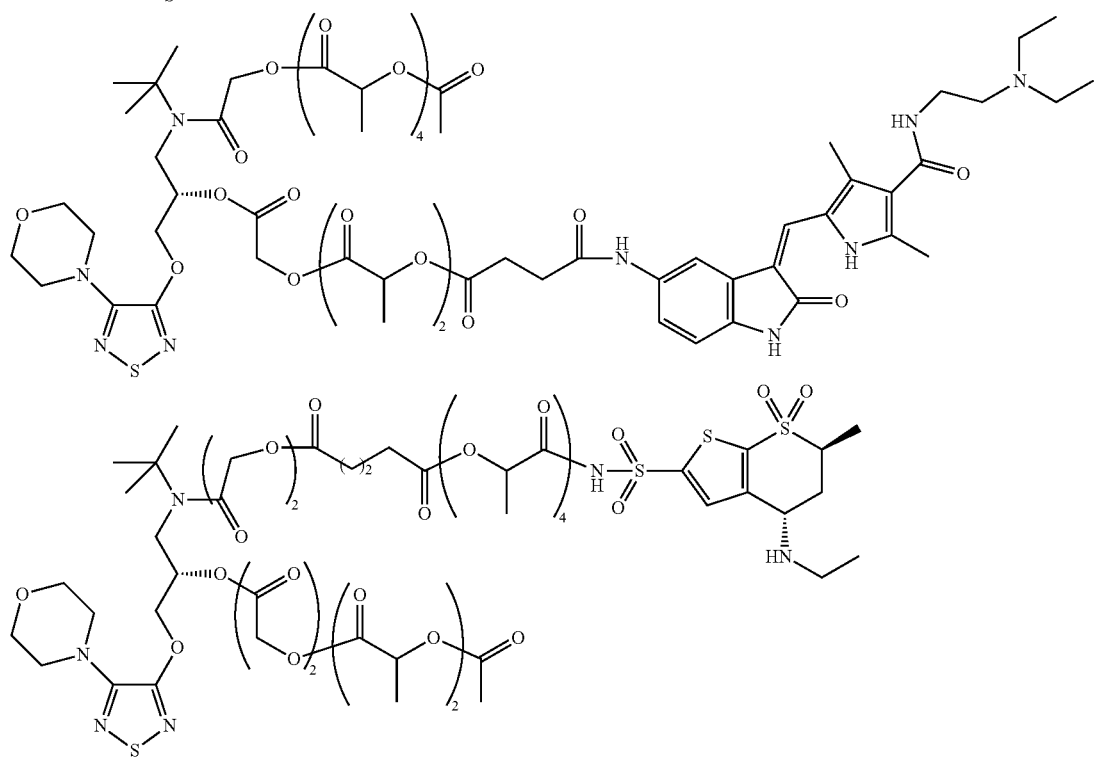
The disclosure also provides a prodrug of Formula XVI:
(XVI)
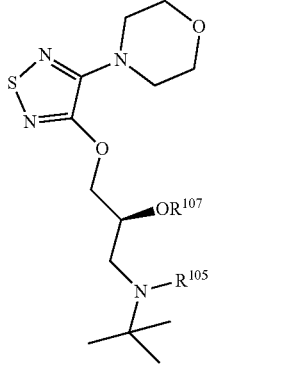
or a pharmaceutically acceptable composition, salt, or isotopic derivative thereof.
$R^{105}$ is selected from:
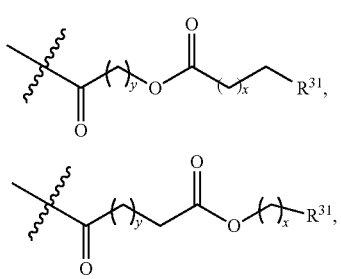

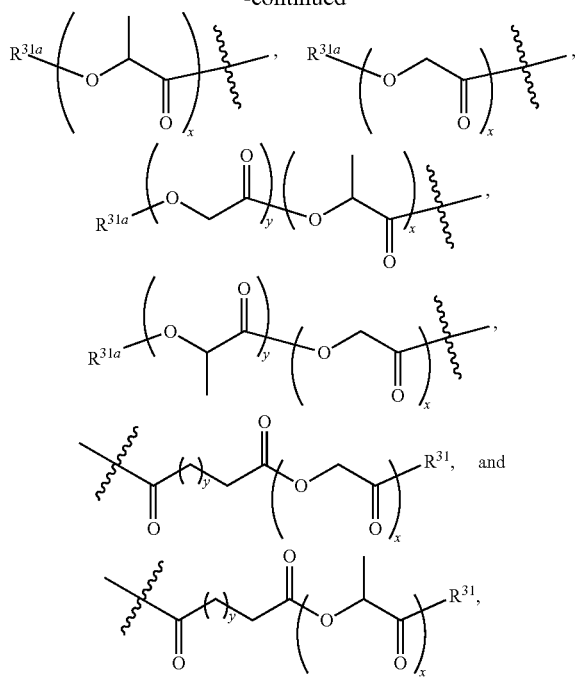

and wherein each $R^{105}$ is optionally substituted with $R^{31}$;

(ii) —C(O)C$_{10\text{-}30}$alkyl, —C(O)C$_{10\text{-}30}$alkenyl, —C(O)C$_{10\text{-}30}$alkynyl, —C(O)(C$_{10\text{-}30}$alkyl with at least one $R^5$ substituent on the alkyl chain), —C(O)(C$_{10\text{-}30}$alkenyl, with at least one $R^5$ substituent on the alkenyl chain) —C(O)(C$_{10\text{-}30}$alkynyl, with at least one $R^5$ substituent on the alkynyl chain), -(lactic acid)$_{1\text{-}20}$C(O)C$_{1\text{-}30}$alkyl, -(lactic acid)$_{1\text{-}10}$C(O)C$_{1\text{-}30}$alkyl, -(lactic acid)$_{4\text{-}20}$C(O)C$_{1\text{-}30}$alkyl, -(lactic acid)$_{1\text{-}20}$C(O)C$_{1\text{-}10}$alkyl, -(lactic acid)$_{1\text{-}20}$C(O)C$_{4\text{-}10}$alkyl, -(lactic acid)$_{1\text{-}20}$C(O)OH, -(lactic acid)$_{1\text{-}10}$C(O)OH, -(lactic acid)$_{4\text{-}20}$C(O)OH, -(lactic acid)$_{1\text{-}10}$C(O)OH, -(lactic acid)$_{4\text{-}10}$C(O)OH, -(lactide-co-glycolide)$_{1\text{-}10}$C(O)$_{C1\text{-}22}$alkyl, -(lactide-co-glycolide)$_{4\text{-}10}$C(O)$_{C1\text{-}22}$alkyl, -(lactide-co-glycolide)$_{1\text{-}10}$C(O)$_{C1\text{-}12}$alkyl, -(lactide-co-glycolide)$_{1\text{-}10}$C(O)$_{C4\text{-}22}$alkyl, -(glycolic acid)$_{1\text{-}10}$C(O)$_{C1\text{-}10}$alkyl, -(glycolic acid)$_{4\text{-}10}$C(O)$_{C1\text{-}10}$alkyl, -(lactic acid)$_{4\text{-}10}$C(O)C$_{1\text{-}10}$alkyl, -(lactic acid)$_{1\text{-}10}$C(O)C$_{1\text{-}10}$alkyl, -(lactic acid)$_{1\text{-}10}$C(O)C$_{4\text{-}10}$alkyl, -(lactic acid)$_{1\text{-}10}$C(O)C$_{4\text{-}10}$alkyl, or -(lactic acid)$_{1\text{-}10}$C(O)C$_{4\text{-}10}$alkyl;

or $R^{105}$ is selected from:

(iii) —(C(O)CH$_2$O)$_{1\text{-}20}$C(O)C$_{1\text{-}30}$alkyl, —(C(O)CH(CH$_3$)O)$_{1\text{-}20}$C(O)C$_{1\text{-}30}$alkyl, —(C(O)CH$_2$O)$_{1\text{-}10}$C(O)C$_{1\text{-}30}$alkyl, —(C(O)CH(CH$_3$)O)$_{1\text{-}10}$C(O)C$_{1\text{-}30}$alkyl, —(C(O)CH$_2$O)$_{4\text{-}20}$C(O)C$_{1\text{-}30}$alkyl, —(C(O)CH(CH$_3$)O)$_{4\text{-}20}$C(O)C$_{1\text{-}30}$alkyl, —(C(O)CH$_2$O)$_{1\text{-}20}$C(O)C$_{1\text{-}10}$alkyl, —(C(O)CH(CH$_3$)O)$_{1\text{-}20}$C(O)C$_{1\text{-}10}$alkyl, —(C(O)CH$_2$O)$_{1\text{-}20}$C(O)C$_{4\text{-}10}$alkyl, —(C(O)CH(CH$_3$)O)$_{1\text{-}20}$C(O)C$_{4\text{-}10}$alkyl, —(C(O)CH(CH$_3$)O)$_{4\text{-}10}$C(O)C$_{1\text{-}10}$alkyl, —(C(O)CH$_2$O)$_{4\text{-}10}$C(O)C$_{1\text{-}10}$alkyl, —(C(O)CH(CH$_3$)O)$_{1\text{-}10}$C(O)C$_{1\text{-}10}$alkyl, —(C(O)CH$_2$O)$_{1\text{-}10}$C(O)C$_{1\text{-}10}$alkyl, —(C(O)CH(CH$_3$)O)$_{1\text{-}10}$C(O)C$_{4\text{-}10}$alkyl, (C(O)CH$_2$O)$_{1\text{-}10}$C(O)C$_{4\text{-}10}$alkyl, —(C(O)CH$_2$O)$_{1\text{-}10}$C(O)C$_{4\text{-}10}$alkyl, —(C(O)CH(CH$_3$)O)$_{1\text{-}10}$C(O)C$_{4\text{-}10}$alkyl, —(C(O)CH$_2$O)$_{1\text{-}10}$C(O)C$_{4\text{-}10}$alkyl, —(C(O)CH(CH$_3$)O)$_{1\text{-}10}$C(O)C$_{4\text{-}10}$alkyl, —(C(O)CH$_2$O)$_{1\text{-}10}$(C(O)CH(CH$_3$)O)$_{1\text{-}10}$C(O)C$_{1\text{-}30}$alkyl, —(C(O)CH$_2$O)$_{2\text{-}10}$(C(O)CH(CH$_3$)O)$_{2\text{-}10}$C(O)C$_{1\text{-}30}$alkyl, —(C(O)CH$_2$O)$_{1\text{-}10}$(C(O)CH(CH$_3$)O)$_{1\text{-}10}$C(O)C$_{1\text{-}12}$alkyl, —(C(O)CH$_2$O)$_{1\text{-}10}$(C(O)CH(CH$_3$)O)$_{1\text{-}10}$C(O)C$_{4\text{-}22}$alkyl, —(C(O)CH(CH$_3$)O)$_{1\text{-}10}$(C(O)CH$_2$O)$_{1\text{-}10}$C(O)C$_{1\text{-}30}$alkyl, —(C(O)CH(CH$_3$)O)$_{2\text{-}10}$(C(O)CH$_2$O)$_{2\text{-}10}$C(O)C$_{1\text{-}30}$alkyl, —(C(O)CH(CH$_3$)O)$_{1\text{-}10}$(C(O)CH$_2$O)$_{1\text{-}10}$C(O)C$_{1\text{-}12}$alkyl, and —(C(O)CH(CH$_3$)O)$_{1\text{-}10}$(C(O)CH$_2$O)$_{1\text{-}10}$C(O)C$_{4\text{-}22}$alkyl;

or $R^{105}$ is

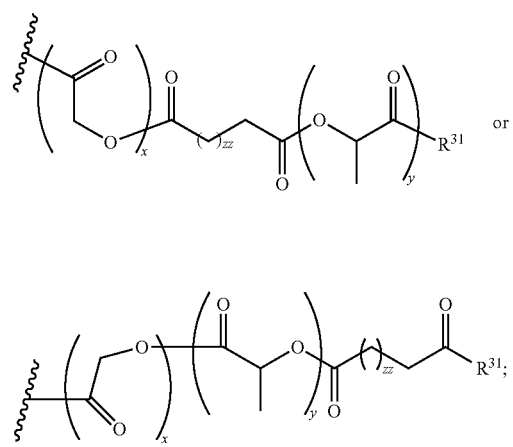

$R^{107}$ is selected from: hydrogen, —C(O)A, aryl, alkyl, alkenyl, alkynyl cycloalkyl, cycloalkylalkyl, heterocyclyl, heterocycloalkyl, aryl, arylalkyl, heteroaryl, and heteroarylalkyl; and wherein all other variables are as defined herein.

In one embodiment, $R^{105}$ is —C(O)(CH$_2$)$_{16}$CH$_3$.

In one embodiment, $R^{105}$ is

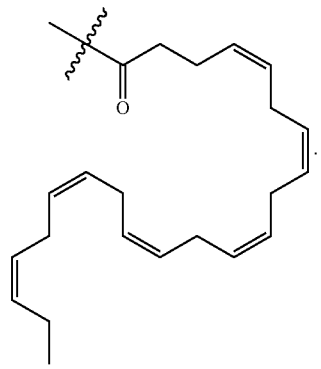 [SMILES: *C(=O)CC/C=C\C/C=C\C/C=C\C/C=C\C/C=C\C/C=C\CC]

In an alternative embodiment, $R^{105}$ is

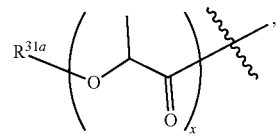

x is 1, and $R^{107}$ is —C(O)A.

In an alternative embodiment, $R^{105}$ is

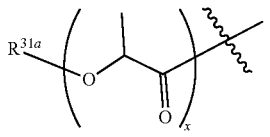

and $R^{31a}$ is —C(O)alkyl.

In an alternative embodiment, $R^{105}$ is

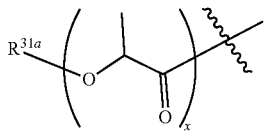

and $R^{31a}$ is —C(O)alkyl
wherein alkyl is methyl.

Alternative non-limiting examples of Formula XVI include

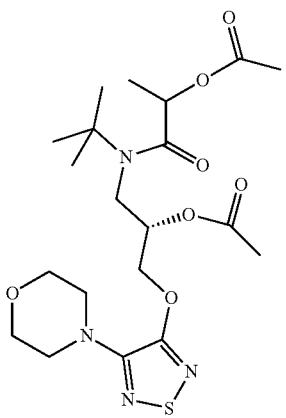

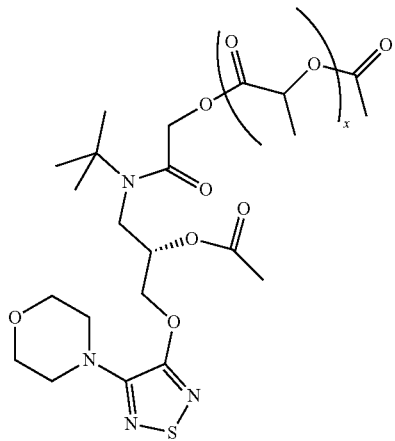

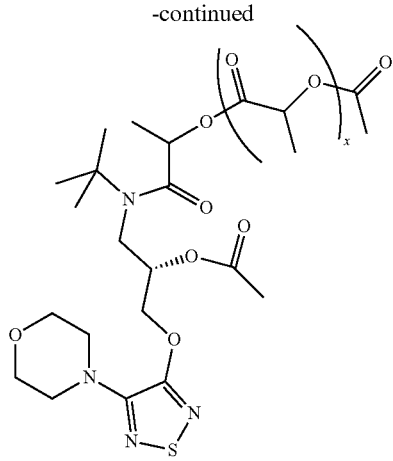

The disclosure also provides a prodrug of Formula XVII:

(XVII)

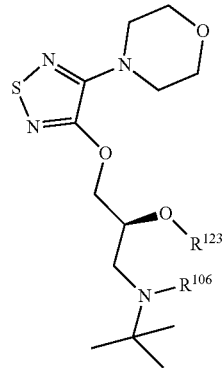

or a pharmaceutically acceptable composition, salt, or isotopic derivative thereof.

$R^{123}$ is selected from:
(i) polyethylene glycol, polypropylene glycol, polypropylene oxide, polylactic acid, poly(lactic-co-glycolic acid), polyglycolic acid, polyester, polyamide,

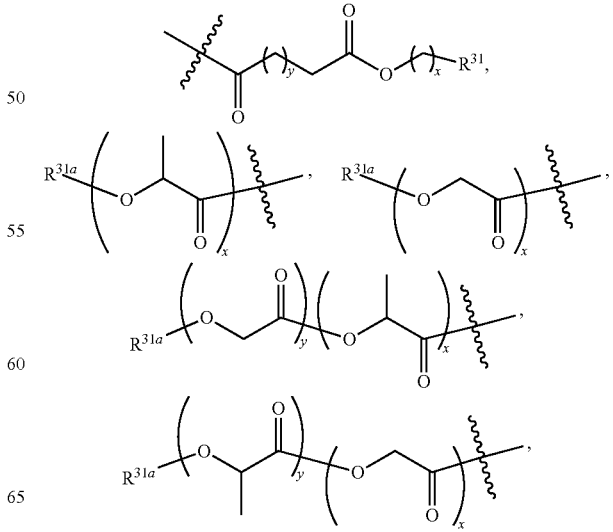

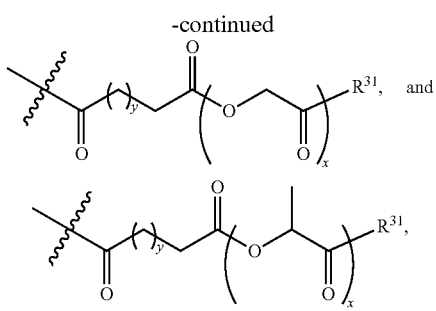

wherein each $R^{123}$ is optionally substituted with $R^{31}$, and wherein each of $R^{123}$ with a terminal hydroxy or carboxy group can be substituted to create an ether or ester;

(ii) —C(O)C$_{17-30}$alkyl, —C(O)C$_{10-30}$alkenyl, —C(O)C$_{10-30}$alkynyl, —C(O)(C$_{10-30}$alkyl with at least one $R^5$ substituent on the alkyl chain), —C(O)(C$_{10-30}$alkenyl, with at least one $R^5$ substituent on the alkenyl chain) —C(O)(C$_{10-30}$alkynyl, with at least one $R^5$ substituent on the alkynyl chain), -(lactic acid)$_{1-20}$C(O)C$_{1-30}$alkyl, -(lactic acid)$_{1-10}$C(O)C$_{1-30}$alkyl, -(lactic acid)$_{4-20}$C(O)C$_{1-30}$alkyl, -(lactic acid)$_{1-20}$C(O)C$_{1-10}$alkyl, -(lactic acid)$_{1-20}$C(O)C$_{4-10}$alkyl, -(lactic acid)$_{1-20}$C(O)OH, -(lactic acid)$_{1-10}$C(O)OH, -(lactic acid)$_{4-20}$C(O)OH, -(lactic acid)$_{1-10}$C(O)OH, -(lactic acid)$_{4-10}$C(O)OH, -(lactide-co-glycolide)$_{1-10}$C(O)C$_{1-22}$alkyl, -(lactide-co-glycolide)$_{4-10}$C(O)C$_{1-22}$alkyl, -(lactide-co-glycolide)$_{1-10}$C(O)C$_{1-12}$alkyl, -(lactide-co-glycolide)$_{1-10}$C(O)C$_{4-22}$alkyl, -(glycolic acid)$_{1-10}$C(O)C$_{1-10}$alkyl, -(glycolic acid)$_{4-10}$C(O)C$_{1-10}$alkyl, -(lactic acid)$_{4-10}$C(O)C$_{1-10}$alkyl, -(lactic acid)$_{1-10}$C(O)C$_{1-10}$alkyl, -(lactic acid)$_{1-10}$C(O)C$_{4-10}$alkyl, -(lactic acid)$_{1-10}$C(O)C$_{4-10}$alkyl, or -(lactic acid)$_{1-10}$C(O)C$_{4-10}$alkyl;

or $R^{123}$ is selected from:

(iii) —(C(O)CH$_2$O)$_{1-20}$C(O)C$_{1-30}$alkyl, —(C(O)CH(CH$_3$)O)$_{1-20}$C(O)C$_{1-30}$alkyl, —(C(O)CH$_2$O)$_{1-10}$C(O)C$_{1-30}$alkyl, —(C(O)CH(CH$_3$)O)$_{1-10}$C(O)C$_{1-30}$alkyl, —(C(O)CH$_2$O)$_{4-20}$C(O)C$_{1-30}$alkyl, —(C(O)CH(CH$_3$)O)$_{4-20}$C(O)C$_{1-30}$alkyl, —(C(O)CH$_2$O)$_{1-20}$C(O)C$_{1-10}$alkyl, —(C(O)CH(CH$_3$)O)$_{1-20}$C(O)C$_{1-10}$alkyl, —(C(O)CH$_2$O)$_{1-20}$C(O)C$_{4-10}$alkyl, —(C(O)CH(CH$_3$)O)$_{1-20}$C(O)C$_{4-10}$alkyl, —(C(O)CH(CH$_3$)O)$_{4-10}$C(O)C$_{1-10}$alkyl, —(C(O)CH$_2$O)$_{4-10}$C(O)C$_{1-10}$alkyl, —(C(O)CH(CH$_3$)O)$_{1-10}$C(O)C$_{1-10}$alkyl, —(C(O)CH$_2$O)$_{1-10}$C(O)C$_{1-10}$alkyl, —(C(O)CH(CH$_3$)O)$_{1-10}$C(O)C$_{4-10}$alkyl, (C(O)CH$_2$O)$_{1-10}$C(O)C$_{4-10}$alkyl, —(C(O)CH$_2$O)$_{1-10}$C(O)C$_{4-10}$alkyl, —(C(O)CH(CH$_3$)O)$_{1-10}$C(O)C$_{4-10}$alkyl, —(C(O)CH$_2$O)$_{1-10}$C(O)C$_{4-10}$alkyl, —(C(O)CH(CH$_3$)O)$_{1-10}$C(O)C$_{4-10}$alkyl, —(C(O)CH$_2$O)$_{1-10}$(C(O)CH(CH$_3$)O)$_{1-10}$C(O)C$_{1-30}$alkyl, —(C(O)CH$_2$O)$_{2-10}$ (C(O)CH(CH$_3$)O)$_{2-10}$ C(O)C$_{1-30}$alkyl, —(C(O)CH$_2$O)$_{1-10}$(C(O)CH(CH$_3$)O)$_{1-10}$C(O)C$_{1-12}$alkyl, —(C(O)CH$_2$O)$_{1-10}$(C(O)CH(CH$_3$)O)$_{1-10}$C(O)C$_{4-22}$alkyl, —(C(O)CH(CH$_3$)O)$_{1-10}$(C(O)CH$_2$O)$_{1-10}$C(O)C$_{1-30}$alkyl, —(C(O)CH(CH$_3$)O)$_{2-10}$ (C(O)CH$_2$O)$_{2-10}$C(O)C$_{1-30}$alkyl, —(C(O)CH(CH$_3$)O)$_{1-10}$(C(O)CH$_2$O)$_{1-10}$C(O)C$_{1-12}$alkyl, and —(C(O)CH(CH$_3$)O)$_{1-10}$(C(O)CH$_2$O)$_{1-10}$C(O)C$_{4-22}$alkyl;

or $R^{123}$ is

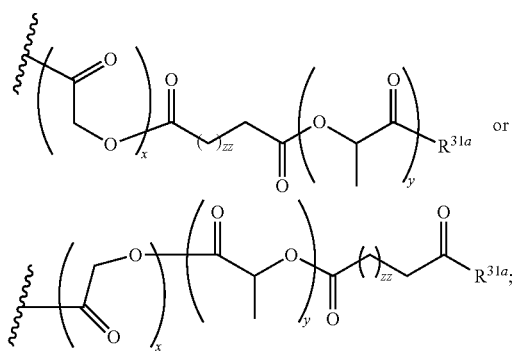

$R^{106}$ is selected from:

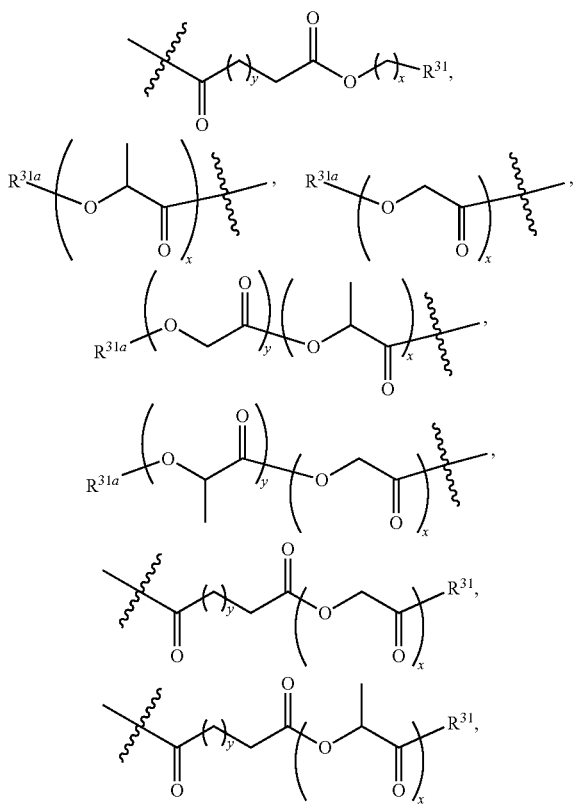

acyl, aryl, alkyl, alkenyl, alkynyl cycloalkyl, cycloalkylalkyl, heterocyclyl, heterocycloalkyl, aryl, arylalkyl, heteroaryl, and heteroarylalkyl, and in one embodiment, $R^{106}$ is —C(O)(CH$_2$)$_{16}$CH$_3$; and or $R^{106}$ is

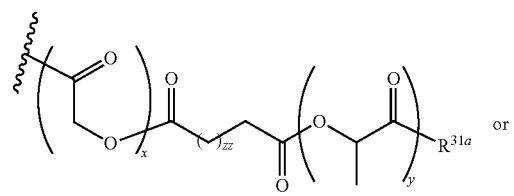

-continued
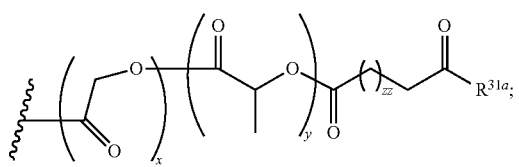
wherein all other variables are as defined herein.
In an alternative embodiment, $R^{106}$ is selected form
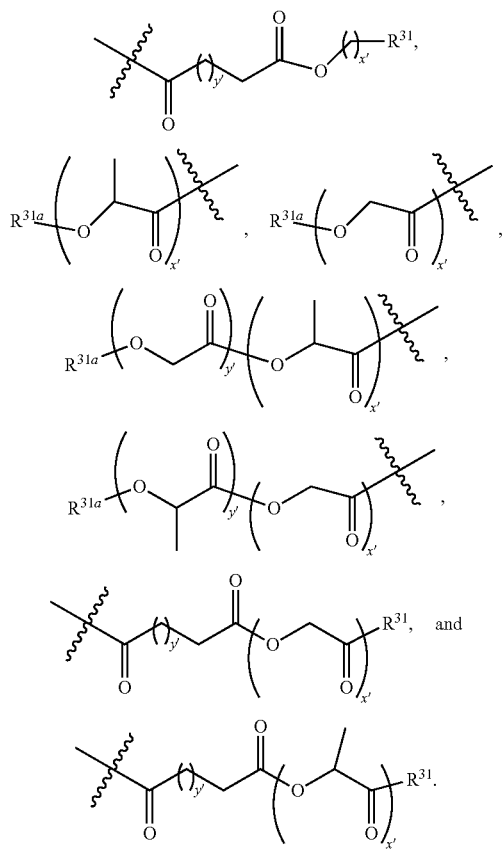
In one embodiment, $R^{123}$ is
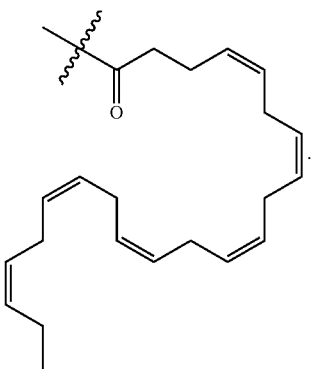 [SMILES: *C(=O)CC/C=C\C/C=C\C/C=C\C/C=C\C/C=C\C/C=C\CC]
In one embodiment, $R^{123}$ is
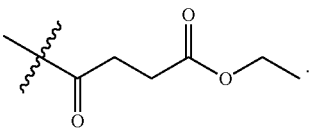 [SMILES: *C(=O)CCC(=O)OCC]
In an alternative embodiment, $R^{123}$ is
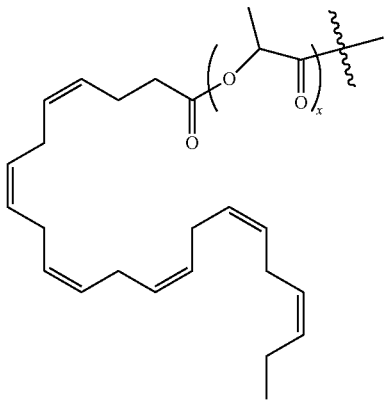
Non-limiting Examples of Formula XVII include
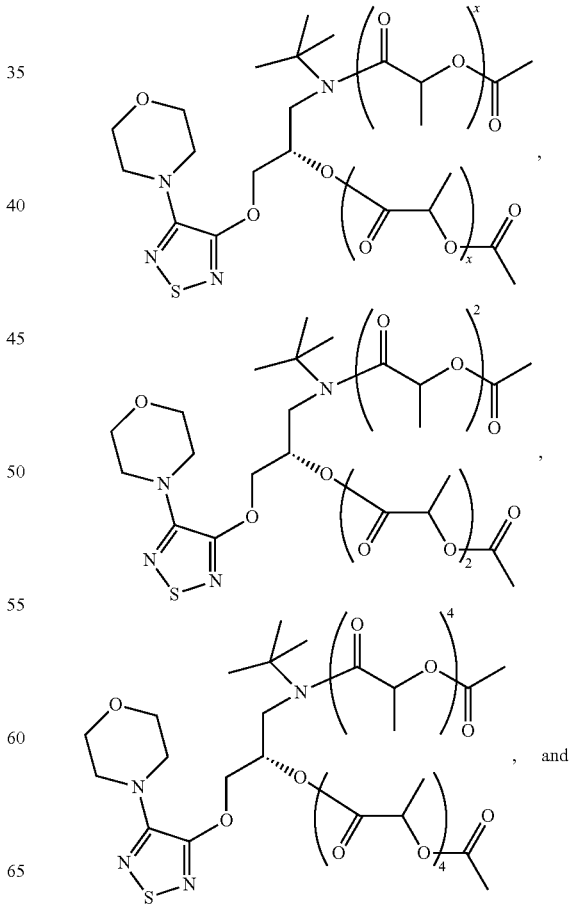

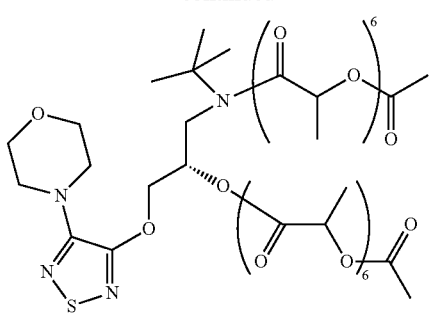
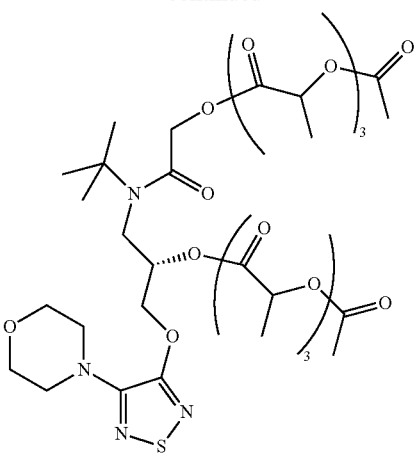
Additional non-limiting Examples of Formula XVII include
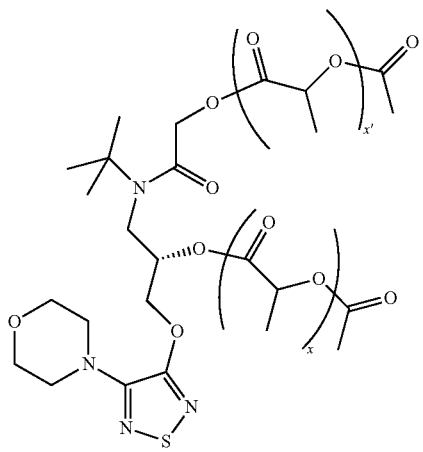
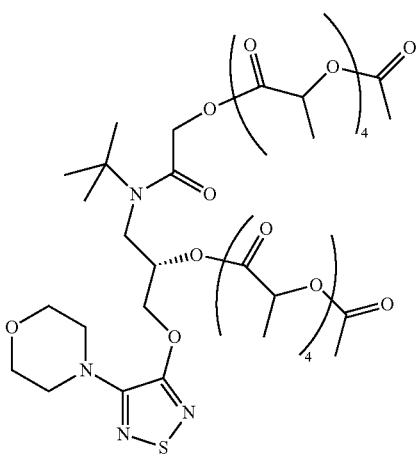
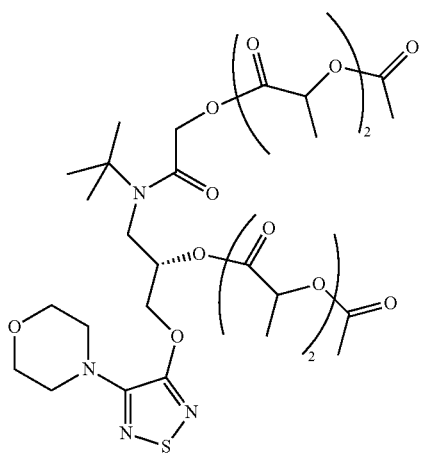
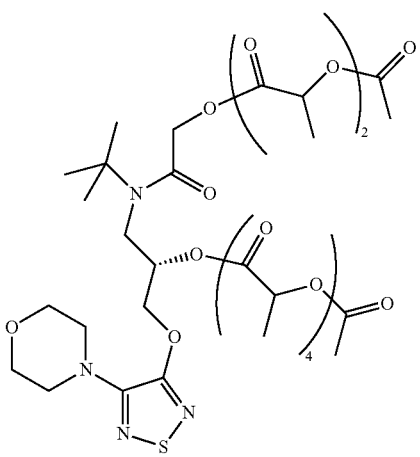

149
-continued
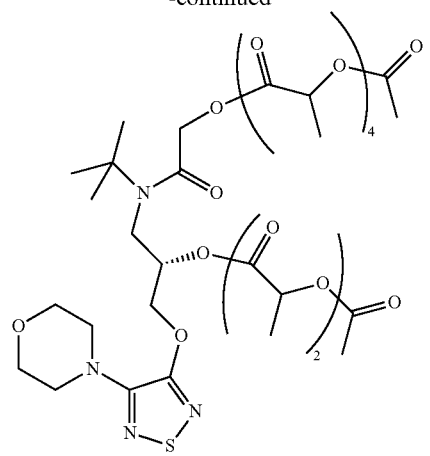
150
-continued
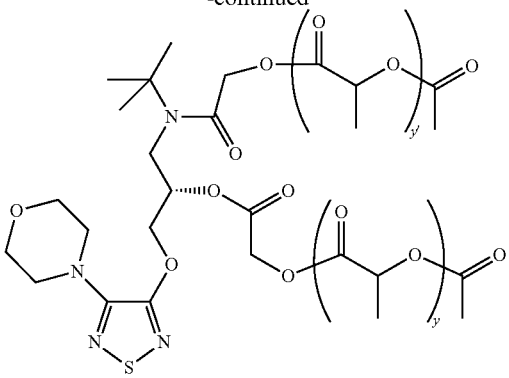
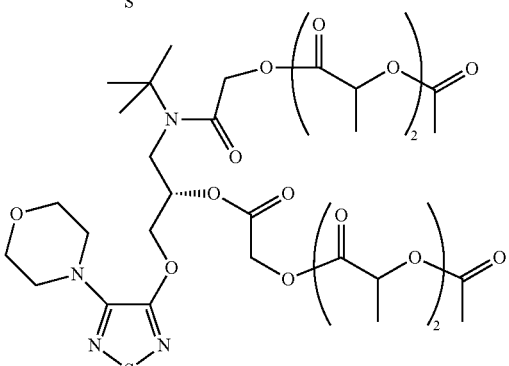
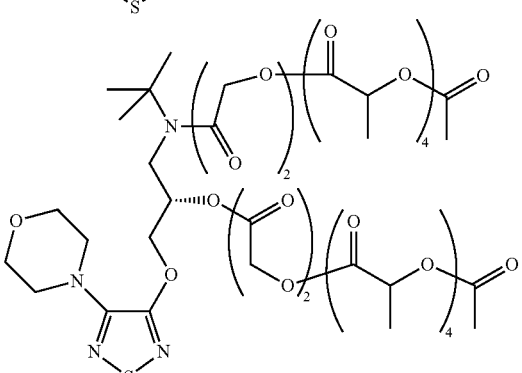
In an alternative embodiment, the disclosure also provides a prodrug of Formula XVII′ XVII″, or XVII‴
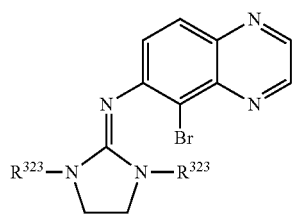
(XVII′)
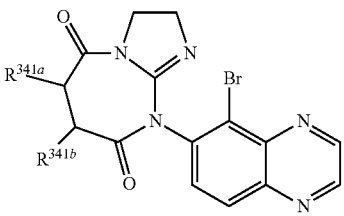
(XVII″)

-continued (XVII''')

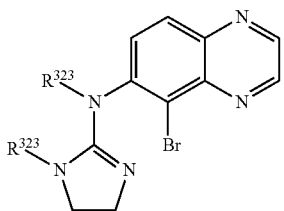

or a pharmaceutically acceptable composition, salt, or isotopic derivative thereof.

wherein $R^{323}$ is independently selected from polyethylene glycol, polypropylene glycol, polypropylene oxide, polylactic acid, poly(lactic-co-glycolic acid), polyglycolic acid, polyester, polyamide,

[structures with $R^{31a}$ groups]

or $R^{323}$ is

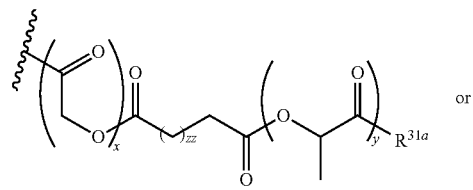

-continued

[structure with $R^{31a}$ group]

$R^{341a}$ and $R^{341b}$ are independently selected from hydrogen and alkyl; and
wherein all other variables are as defined herein.
In one embodiment of Formula XVII', $R^{323}$ is

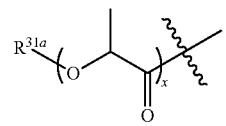

and $R^{31a}$ is —C(O)alkyl.
In one embodiment of Formula XVII', $R^{323}$ is

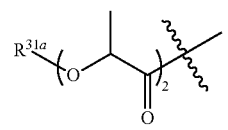

and $R^{31a}$ is —C(O)alkyl.
In one embodiment of Formula XVII', $R^{323}$ is

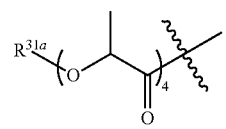

and $R^{31a}$ is —C(O)alkyl.
In one embodiment of Formula XVII'', $R^{341a}$ and $R^{341b}$ are hydrogen.
In one embodiment of Formula XVII'', $R^{341a}$ is hydrogen and $R^{341b}$ is methyl.
In one embodiment of Formula XVII'', $R^{341a}$ is methyl and $R^{341b}$ is hydrogen.
In one embodiment of Formula XVII'', Formula XVIII' is the malic salt.
In one embodiment of Formula XVII'', Formula XVIII' is the maleate salt.
Non-limiting Examples of Formula XVII' include

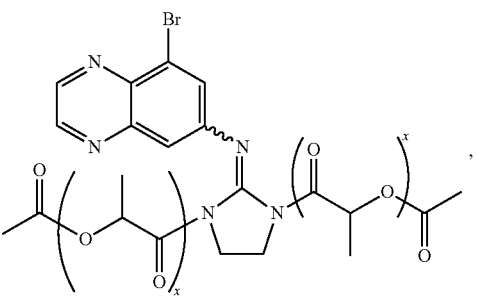

-continued

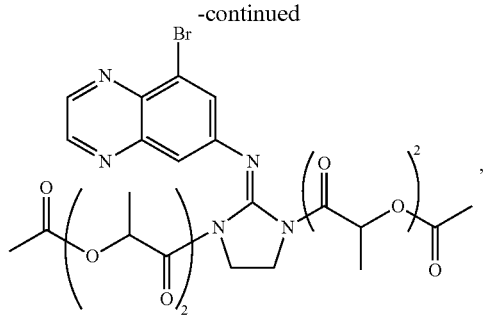

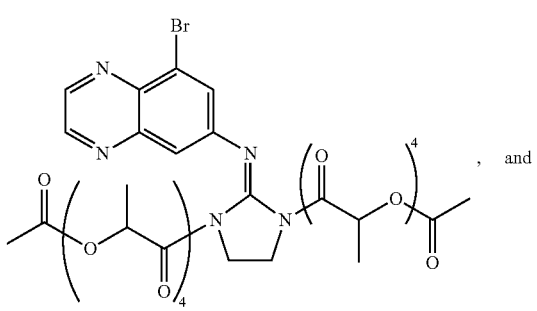

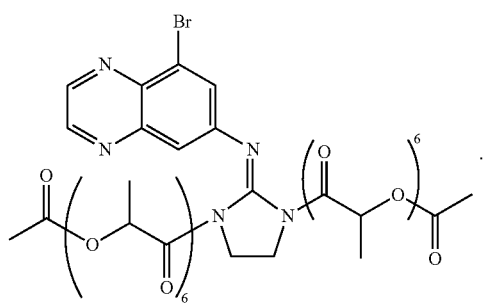

Compounds of Formula XVII' are drawn as

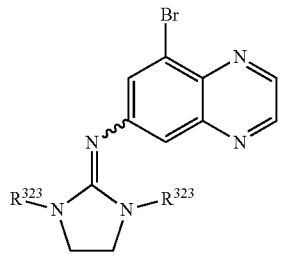

where the bond between the aromatic ring and the imidazole ring is drawn as a wavy line. In one embodiment, compounds of Formula XVII' are the Z isomer. In one embodiment, compounds of Formula XVII' are the E isomer.

The disclosure also provides a prodrug of Formula XVIII, Formula XVIII', Formula XIX, Formula XIX', Formula XX, and Formula XXI:

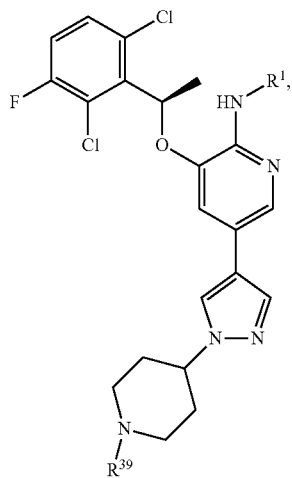

(XVIII)

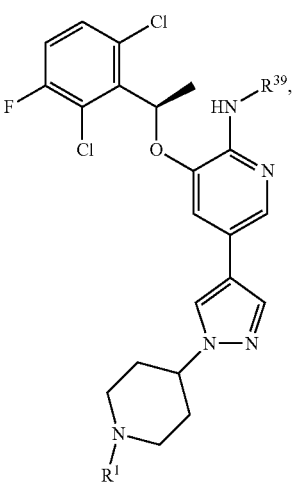

(XVIII')

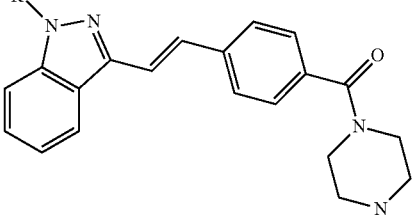

(XIX)

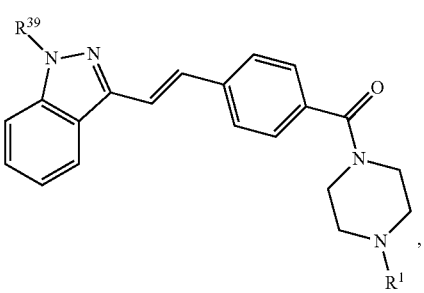

(XIX')

-continued (XX)

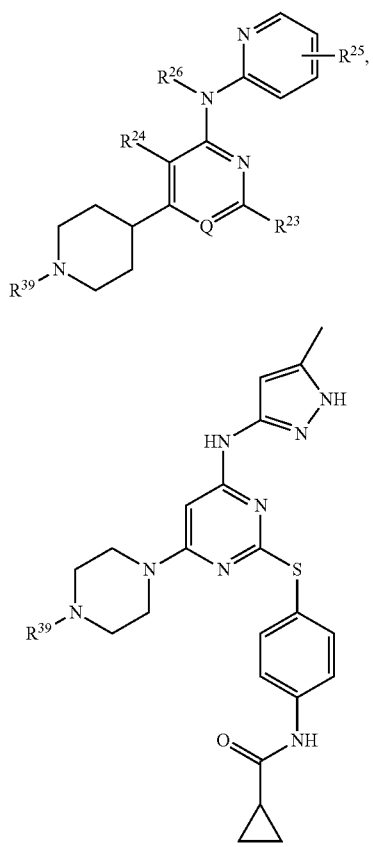

(XXI)

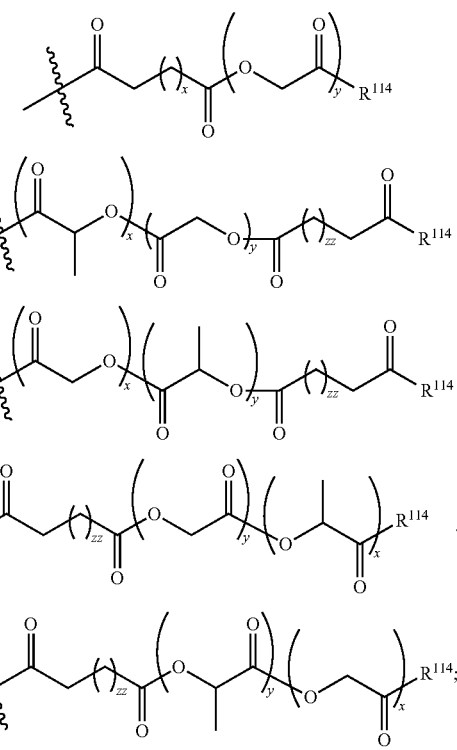

or a pharmaceutically acceptable salt thereof.

$R^{39}$ is selected from: $R^{40}$, carbonyl linked polyethylene glycol, carbonyl linked polypropylene glycol, carbonyl linked polypropylene oxide, polylactic acid, and poly(lactic-co-glycolic acid), a polyglycolic acid, a polyester, polyamide, or other biodegradable polymer, wherein each $R^{39}$ other than $R^{40}$ is substituted with at least one $L^4$-$R^{114}$;

$R^{40}$ is selected from:

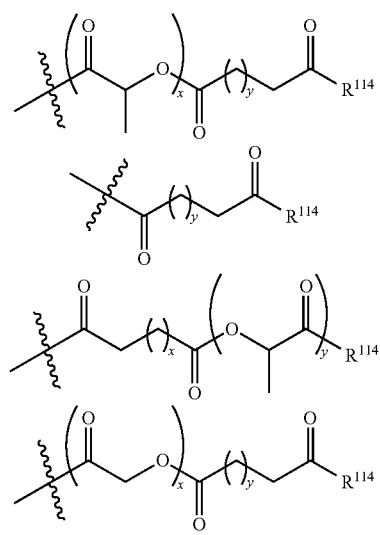

or $R^{40}$ is

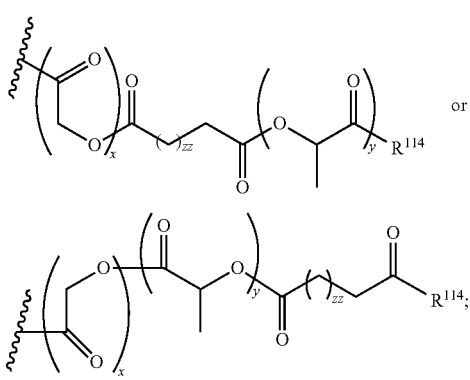

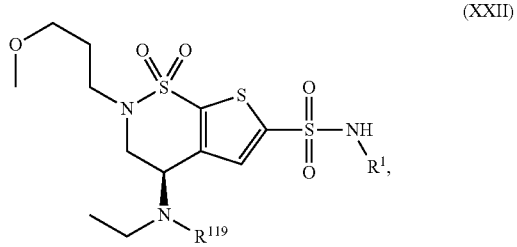

wherein all other variables are as defined herein.

The disclosure also provides prodrugs of Formula XXII, Formula XXIII, Formula XXIV, Formula XXV, Formula XXVI, and Formula XXVII:

(XXII)

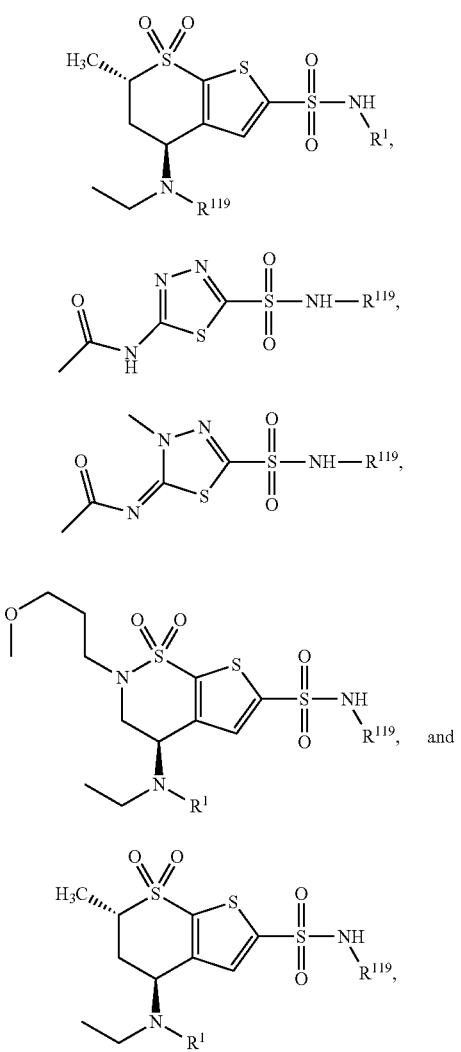

or a pharmaceutically acceptable composition, salt, or isotopic derivative thereof.

$R^{119}$ is selected from: acyl, $R^{120}$, polyethylene glycol, polypropylene glycol, polypropylene oxide, polylactic acid, poly(lactic-co-glycolic acid), a polyglycolic acid, a polyester, polyamide, or other biodegradable polymer, wherein each $R^{119}$ other than $R^{120}$ is substituted with at least one $L^4$-$R^{121}$;

$R^{120}$ is selected from:

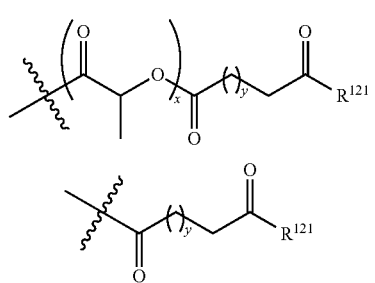

or R¹²⁰ is
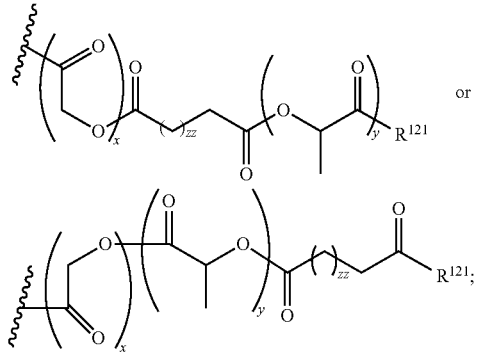
R¹²¹ is selected from:
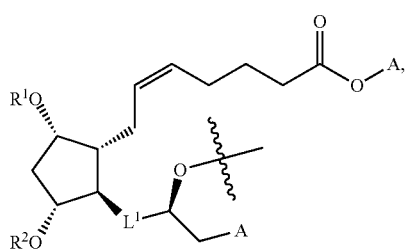
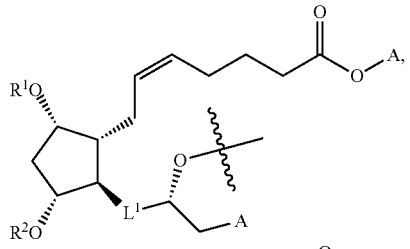
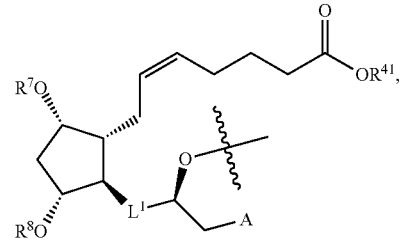
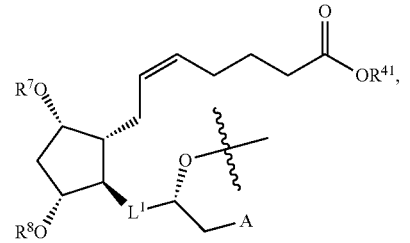
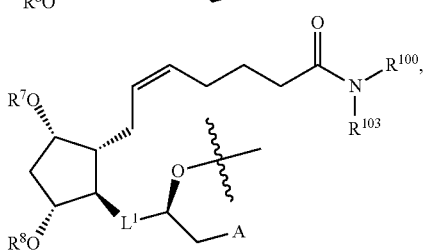
-continued
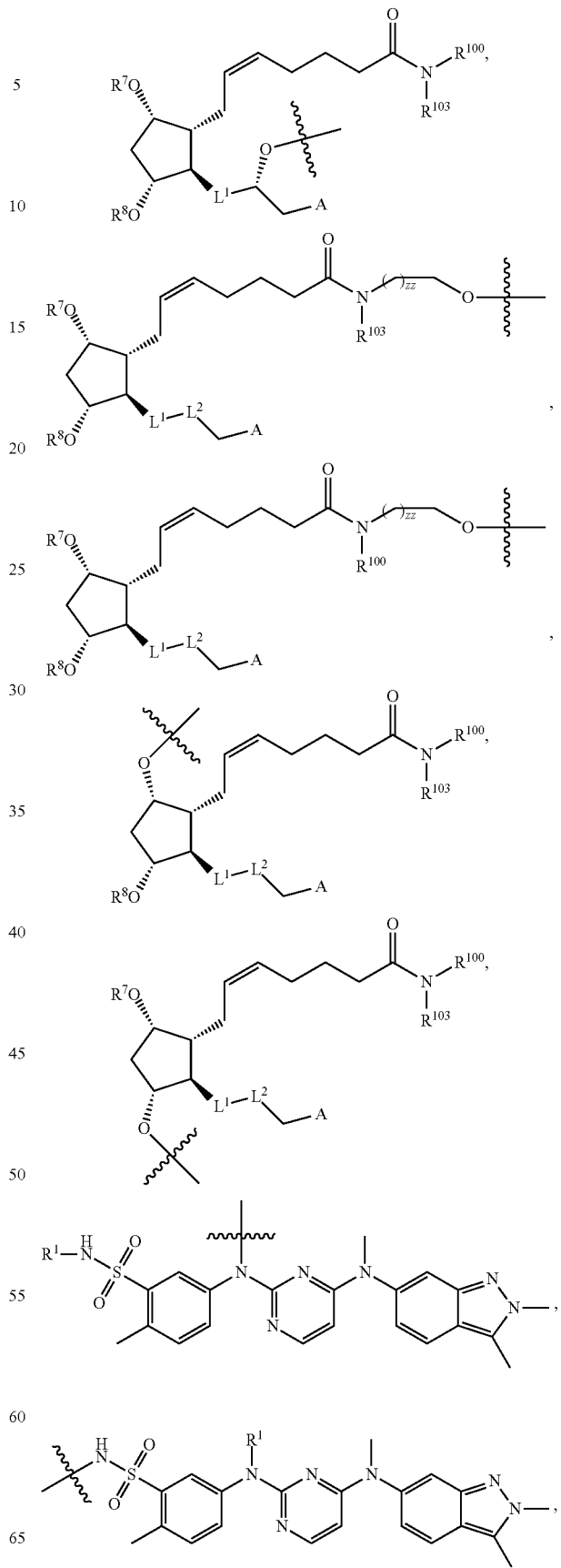

161
-continued
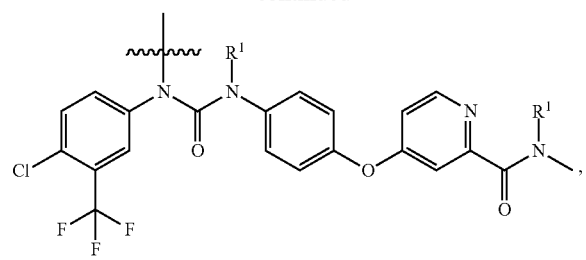
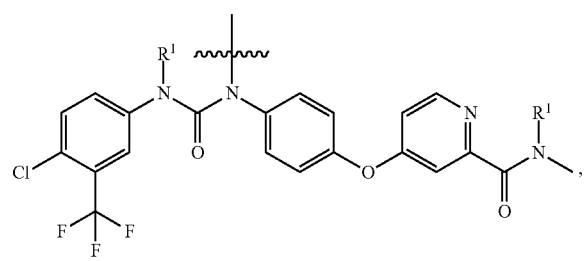
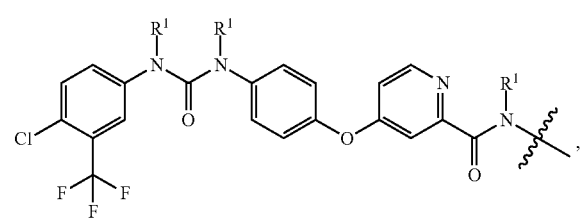
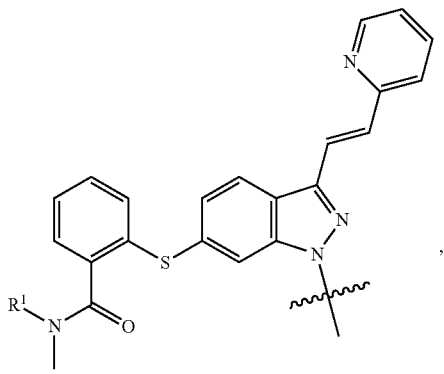
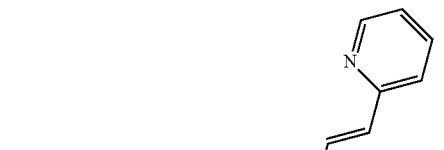
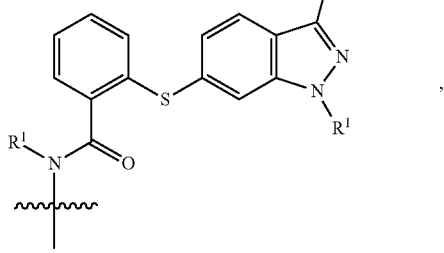
162
-continued
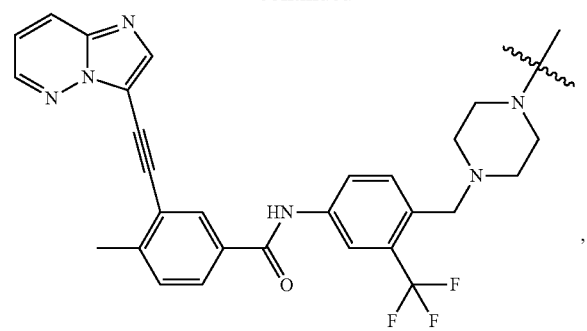
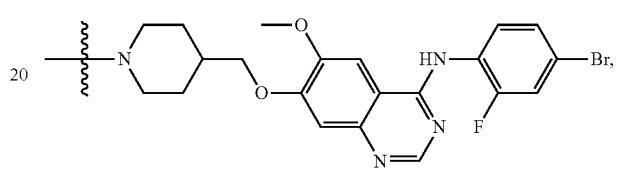
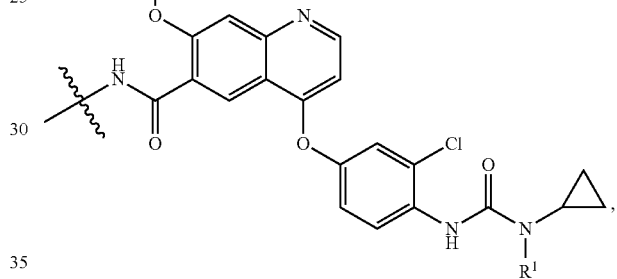
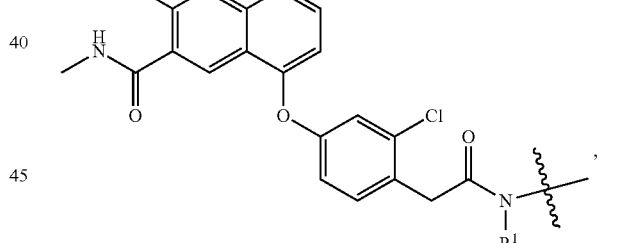
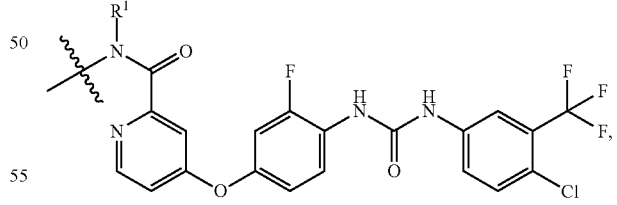
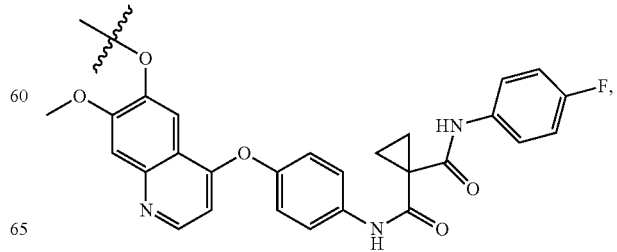

-continued
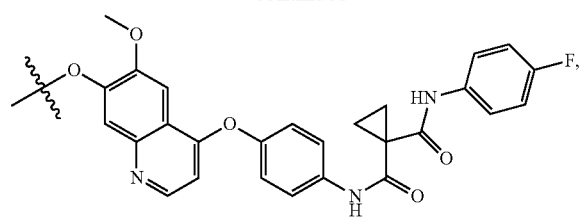
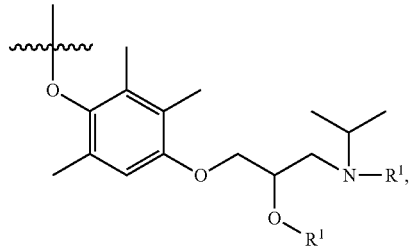
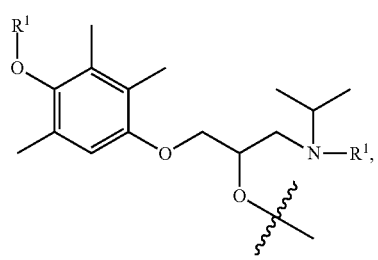
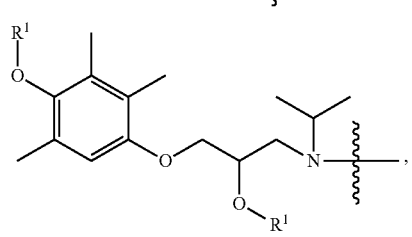
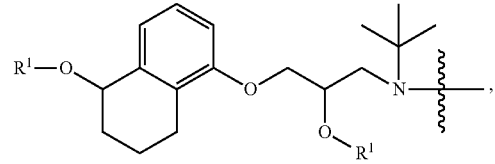
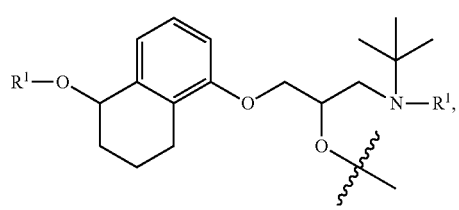
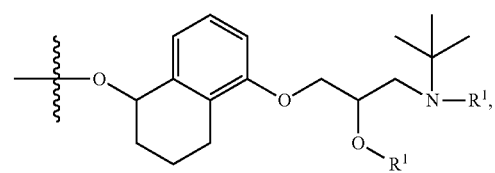
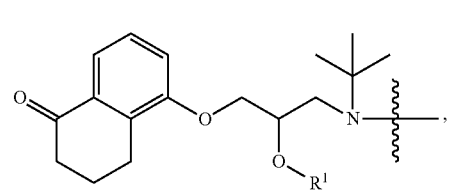
-continued
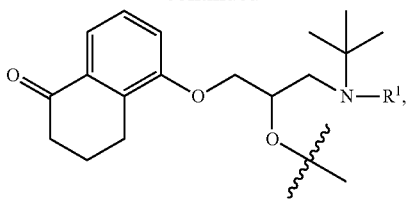
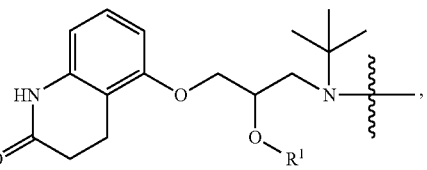
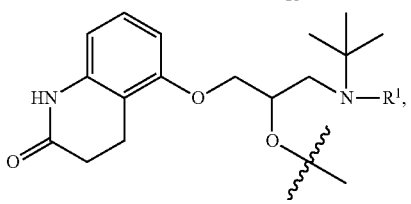
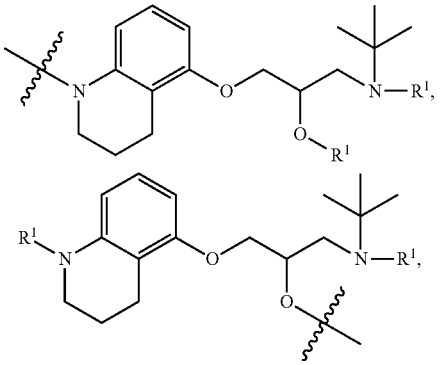
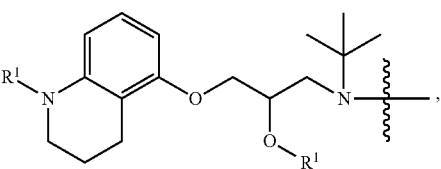
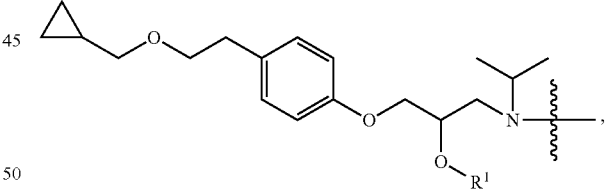
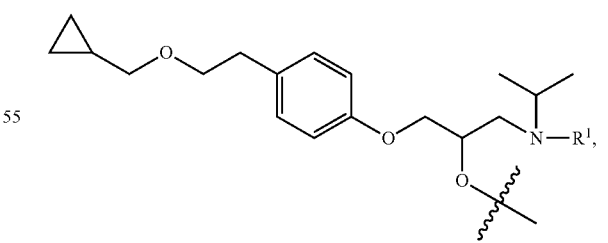
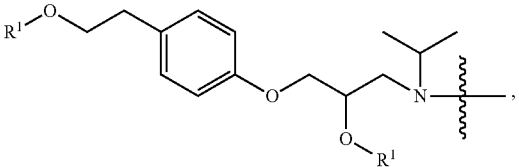

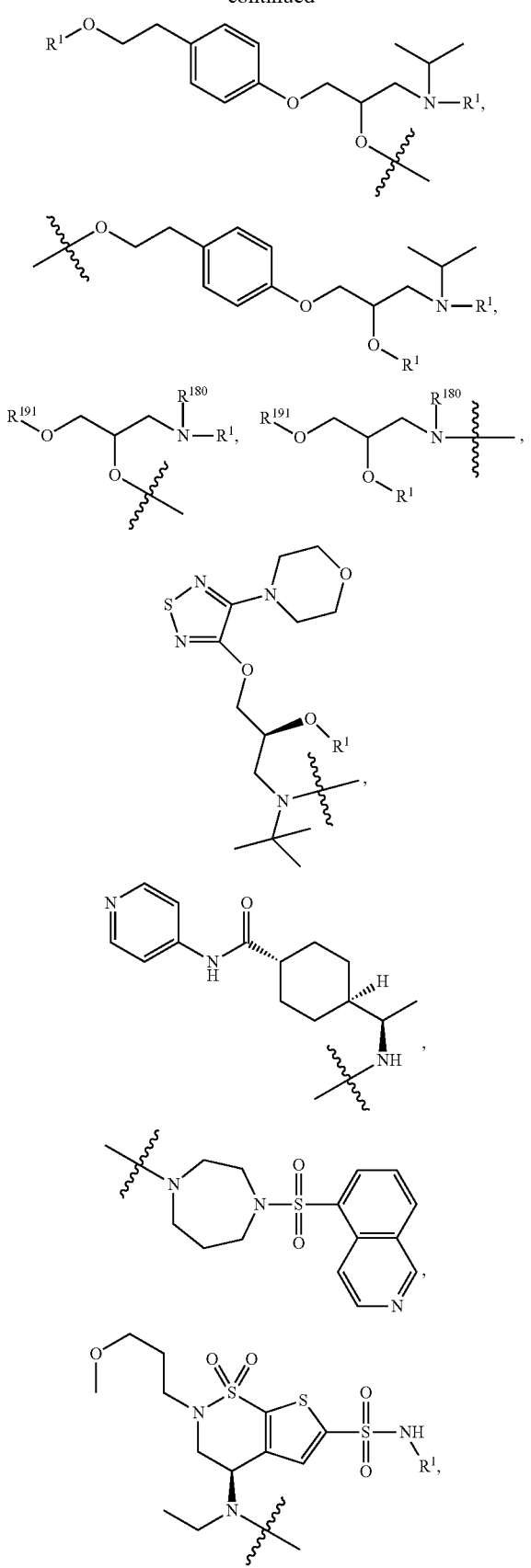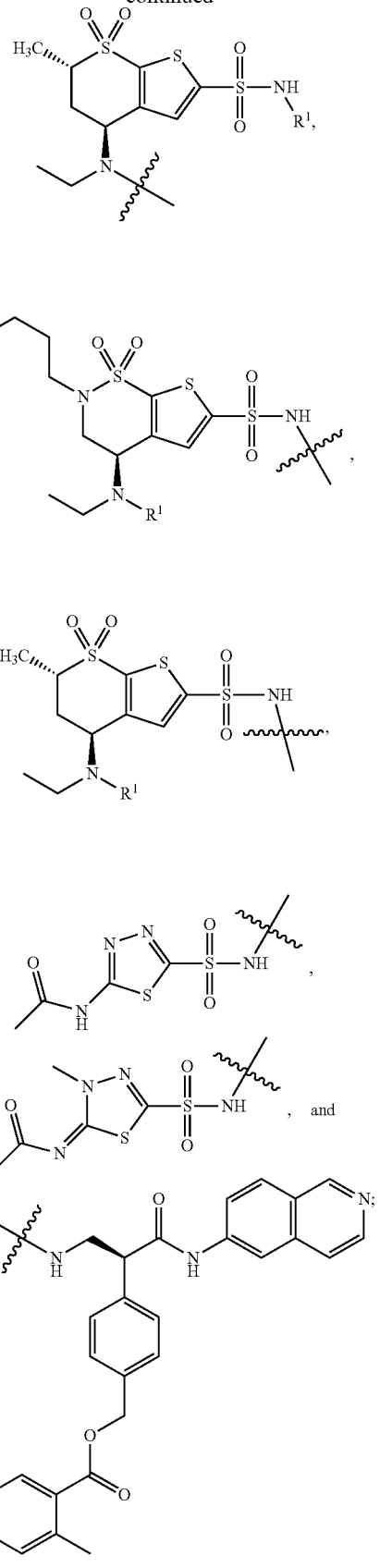
wherein all other variables are as defined herein.

The disclosure also provides prodrugs of Formula XXVIII, XXIX, XXX, XXX' and XXX"

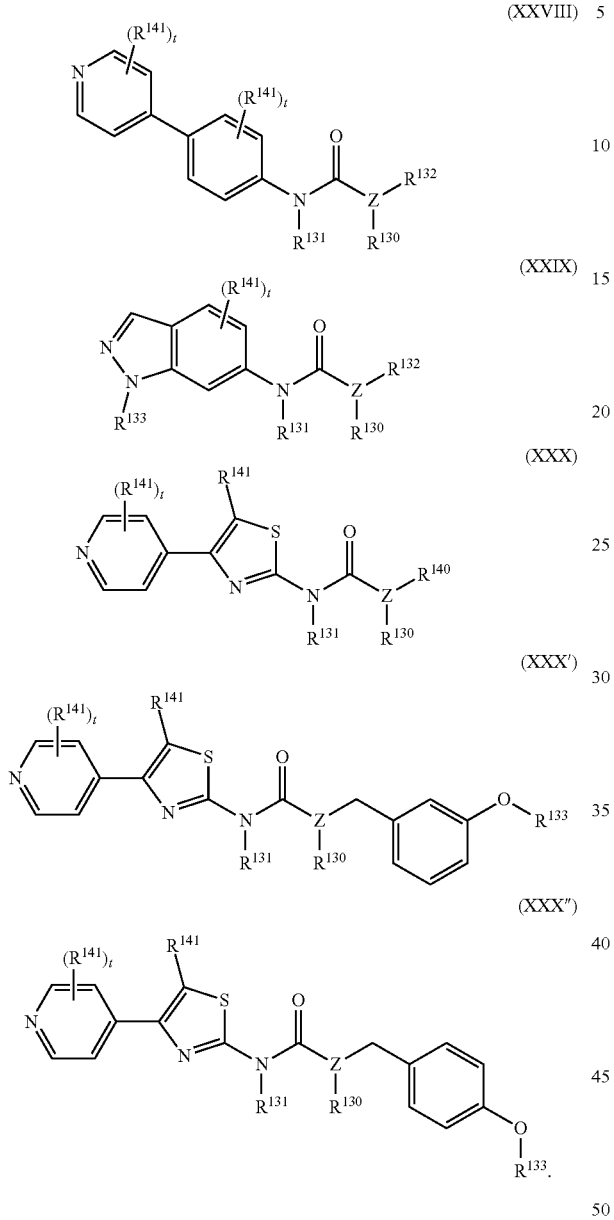

or a pharmaceutically acceptable composition, salt, or isotopic derivative thereof.

Z is $CR^{130}$ or N;

t is independently selected from 0, 1, 2, 3, and 4;

$R^{130}$, $R^{131}$, and $R^{133}$ are independently selected at each occurrence from H, $C_1$-$C_{30}$alkyl, —C(O)$C_1$-$C_{30}$alkyl, $C_1$-$C_{30}$heteroalkyl, and $R^{136}$;

$R^{132}$ is selected from $R^{136}$, $C_1$-$C_{30}$alkyl, $C_1$-$C_{30}$cycloalkyl, heterocycloalkyl, aryl, heteroaryl, and alkylaryl, any of which can be optionally substituted with one or more of hydroxyl, —CH$_2$OH, —C(O)NH$_2$, acetyl, carbonyl, alkyl, cycloalkyl, heterocycloalkyl, aryl, and heteroaryl, any of which can be optionally substituted with one or more of hydroxyl, nitro, amino, —NR$^{134}$R$^{135}$, alkyl, alkoxy, alkylalkoxy, alkoxylalkoxy, haloalkoxy, heteroarylcarbonyl, heteroaryl, —OCH$_3$, —OCF$_3$, —OCHF$_2$, —OCH$_2$F, —OSO$_2$CH$_3$, tosyl, or halogen;

$R^{140}$ is selected from $R^{136}$, hydrogen, alkyl, cycloalkyl, heterocycloalkyl, and aryl, any of which except hydrogen can be optionally substituted with one or more of hydroxyl, —CH$_2$OH, —C(O)NH$_2$, acetyl, carbonyl, alkyl, cycloalkyl, heterocycloalkyl, aryl, and heteroaryl, any of which can be optionally substituted with one or more of hydroxyl, nitro, amino, —NR$^{134}$R$^{135}$, alkyl, alkoxy, alkylalkoxy, alkoxylalkoxy, haloalkoxy, heteroarylcarbonyl, heteroaryl, —OCH$_3$, —OCF$_3$, —OCHF$_2$, —OCH$_2$F, —OSO$_2$CH$_3$, tosyl, or halogen;

$R^{136}$ is selected from: $R^{137}$, acyl, alkyl, alkyloxy, polyethylene glycol, polypropylene glycol, polypropylene oxide, polylactic acid, poly(lactic-co-glycolic acid), a polyglycolic acid, a polyester, polyamide, or other biodegradable polymer, wherein each $R^{136}$ other than $R^{137}$ is substituted with at least one $L^4$-$R^{138}$.

or $R^{136}$ is $L^4$-$R^{138}$ or $R^{138}$;

wherein at least one of $R^{130}$, $R^{131}$, and $R^{133}$ in Formula XXVIII, Formula XXIX, Formula XXX, Formula XXX' and Formula XXX" is $R^{136}$;

$R^{137}$ is selected from:

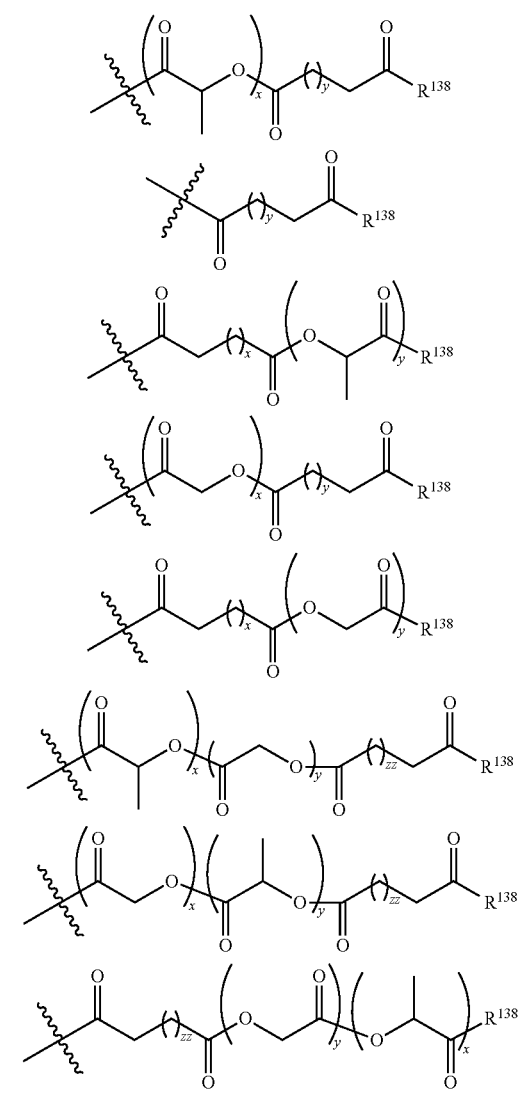

169
-continued
170
-continued
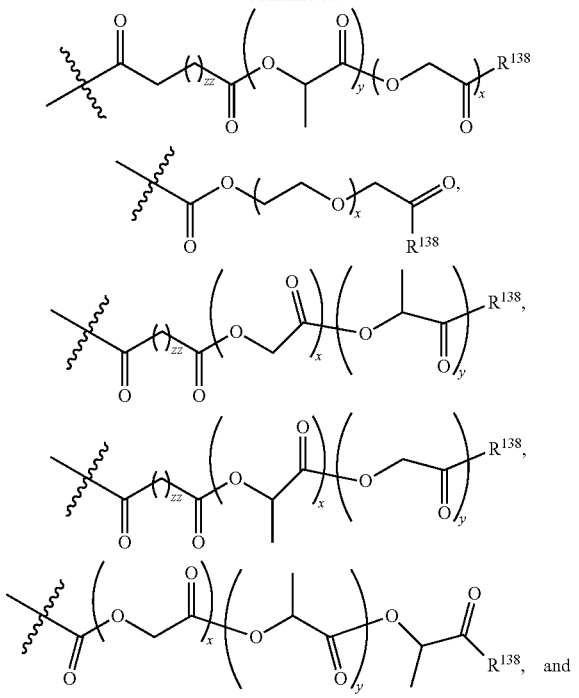
or $R^{137}$ is
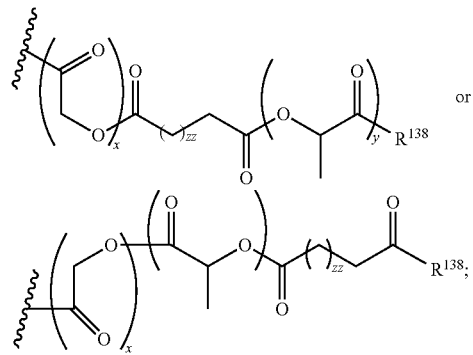
$R^{138}$ is selected from:
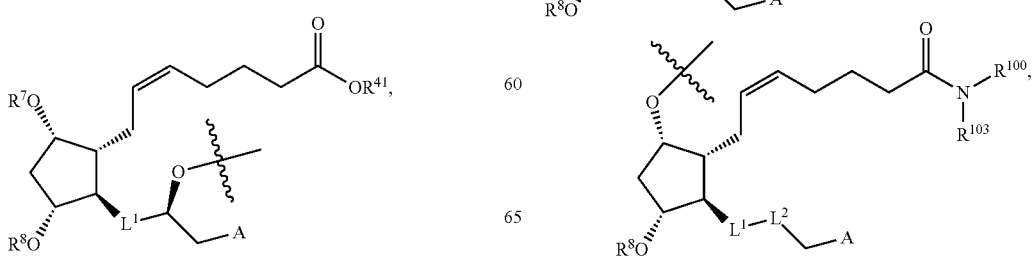

171
-continued
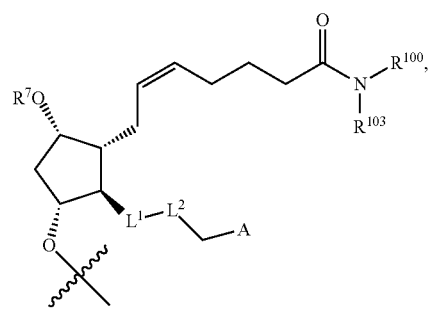
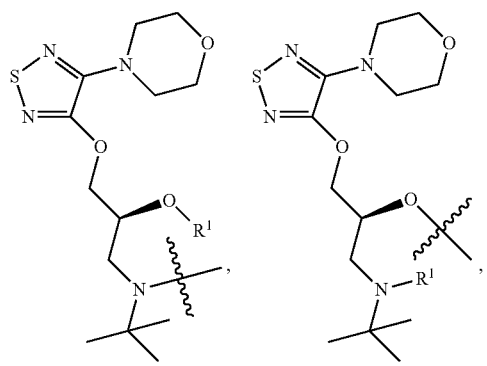
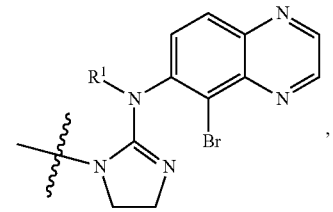
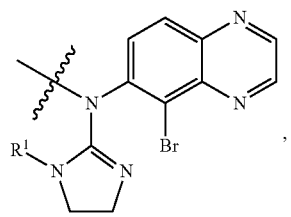
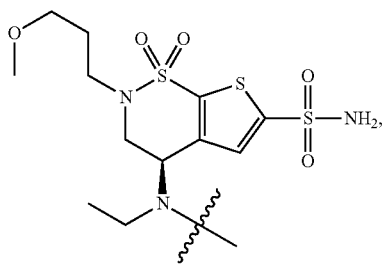
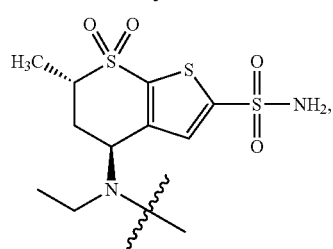
172
-continued
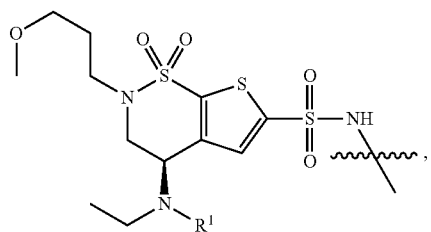
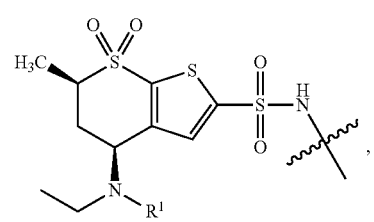
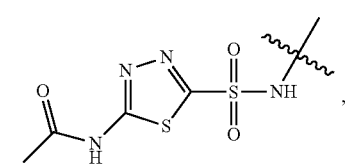
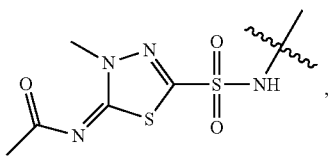
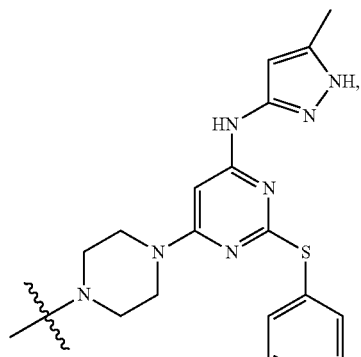

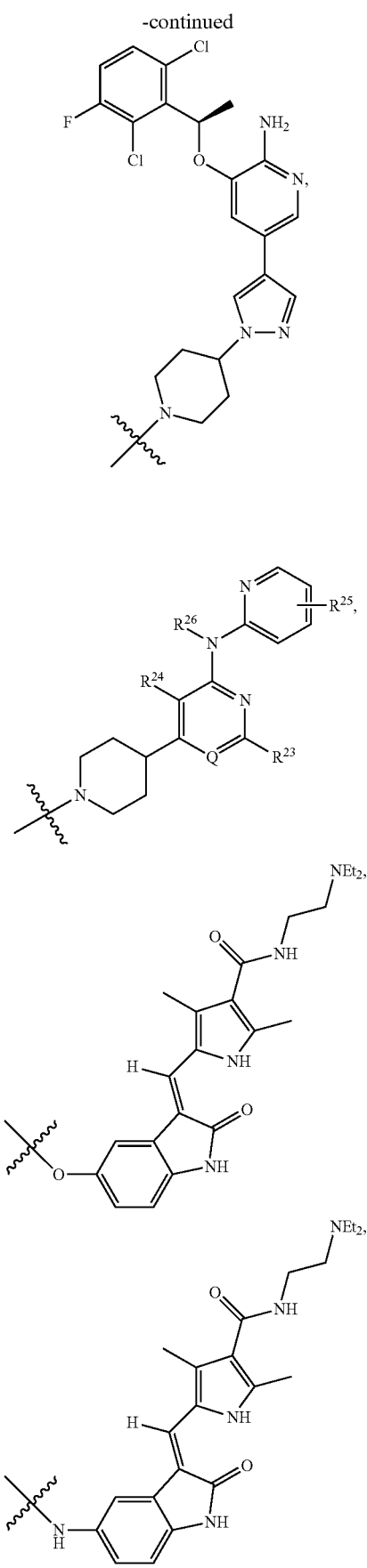
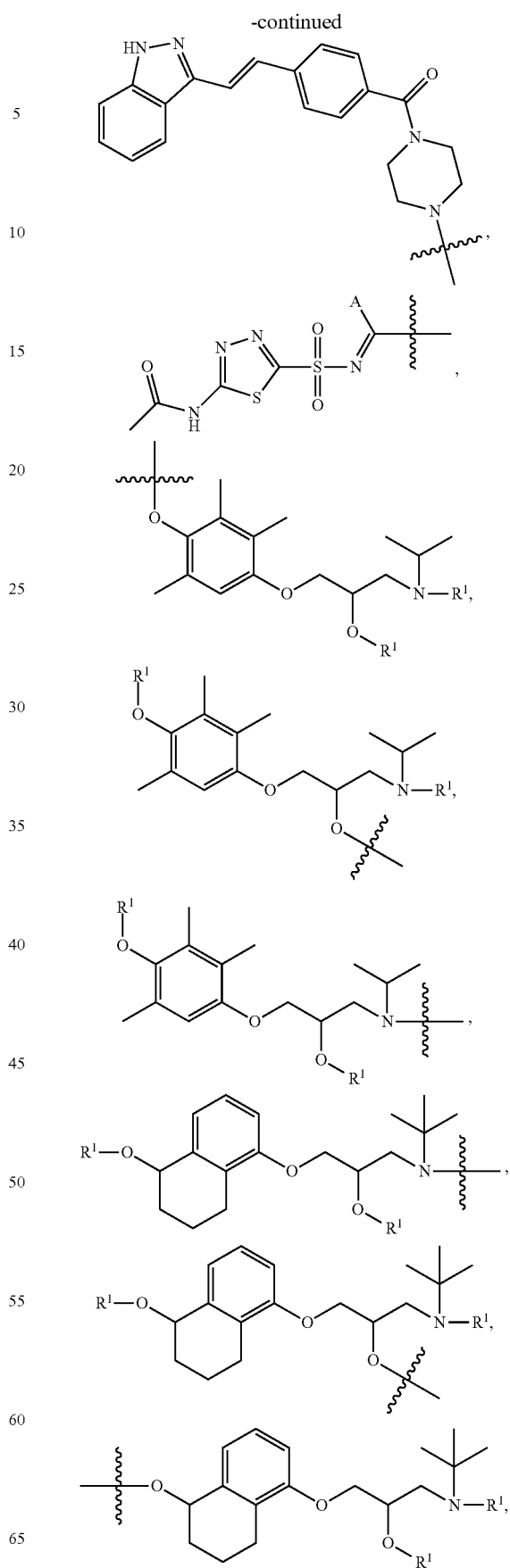

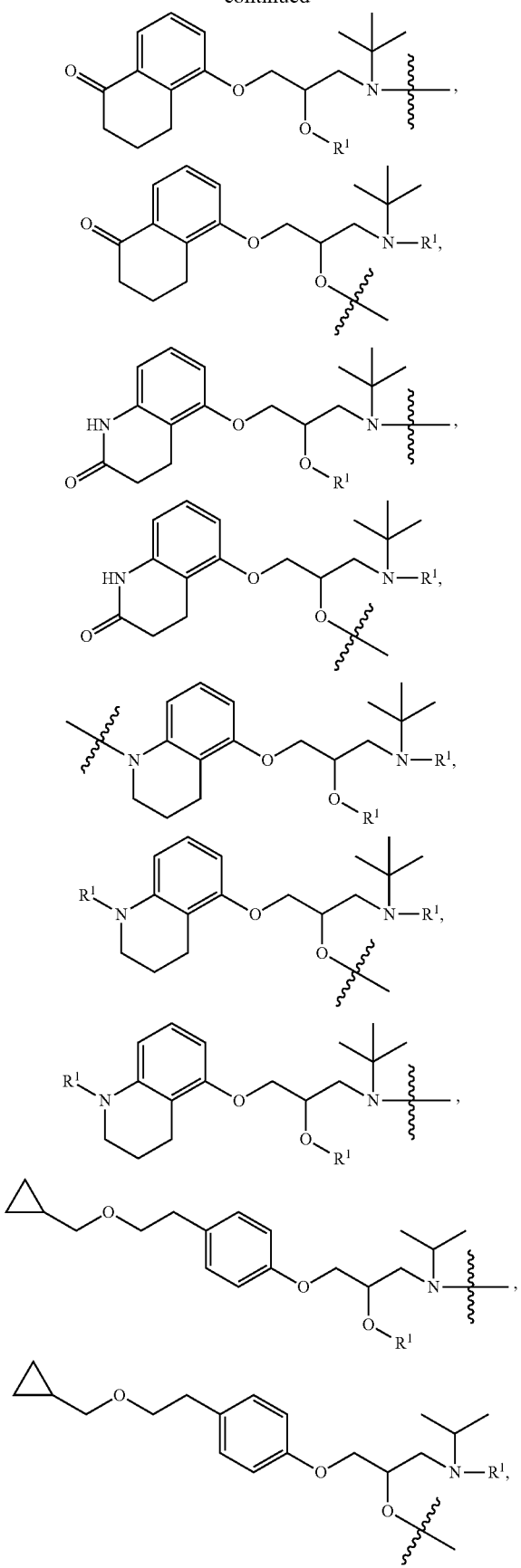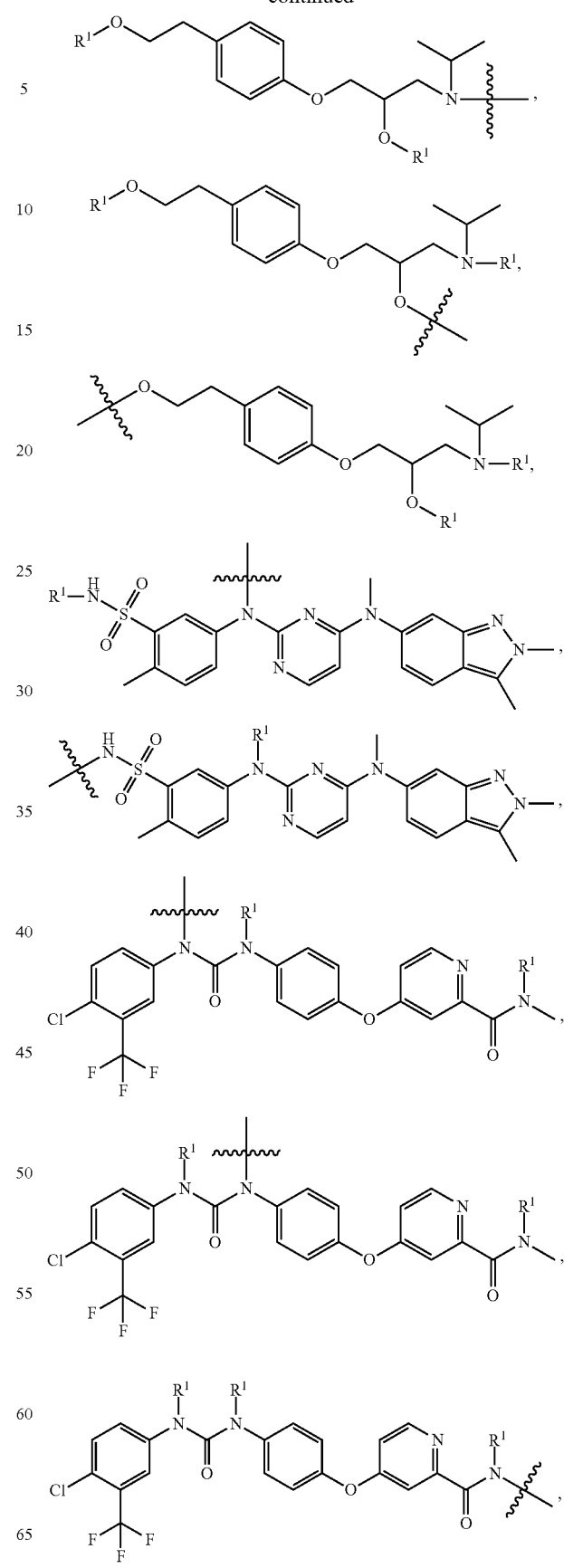

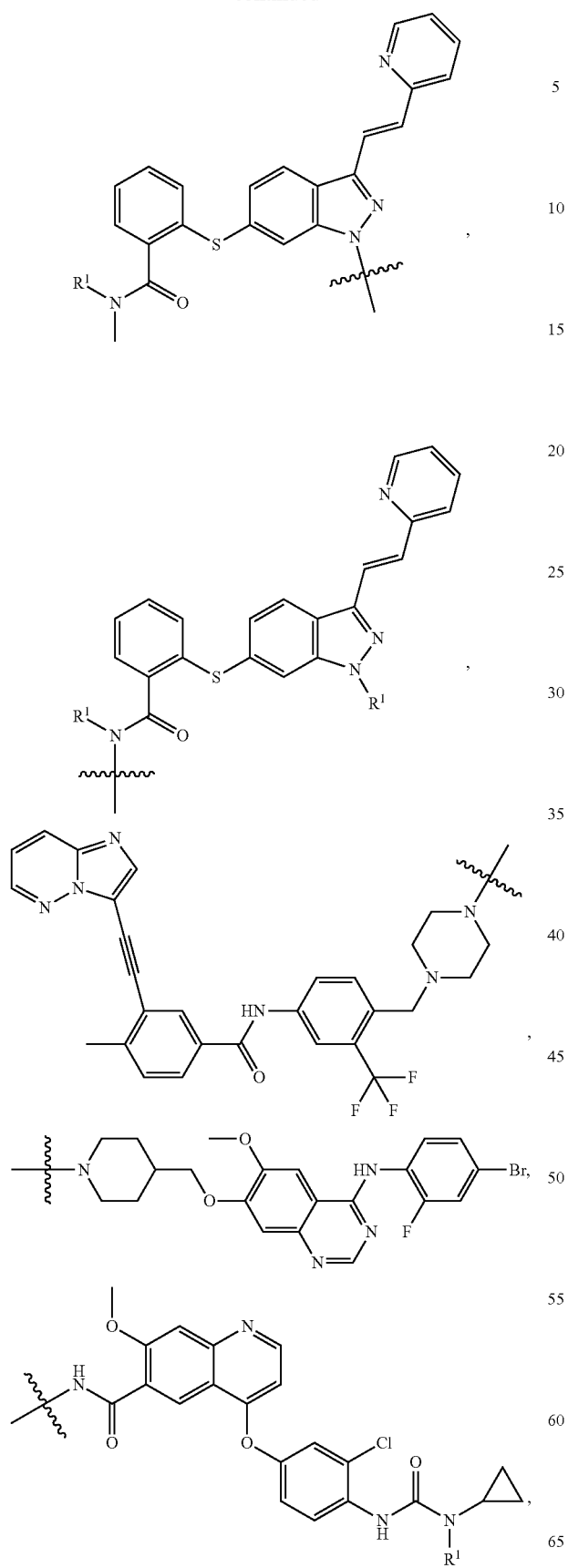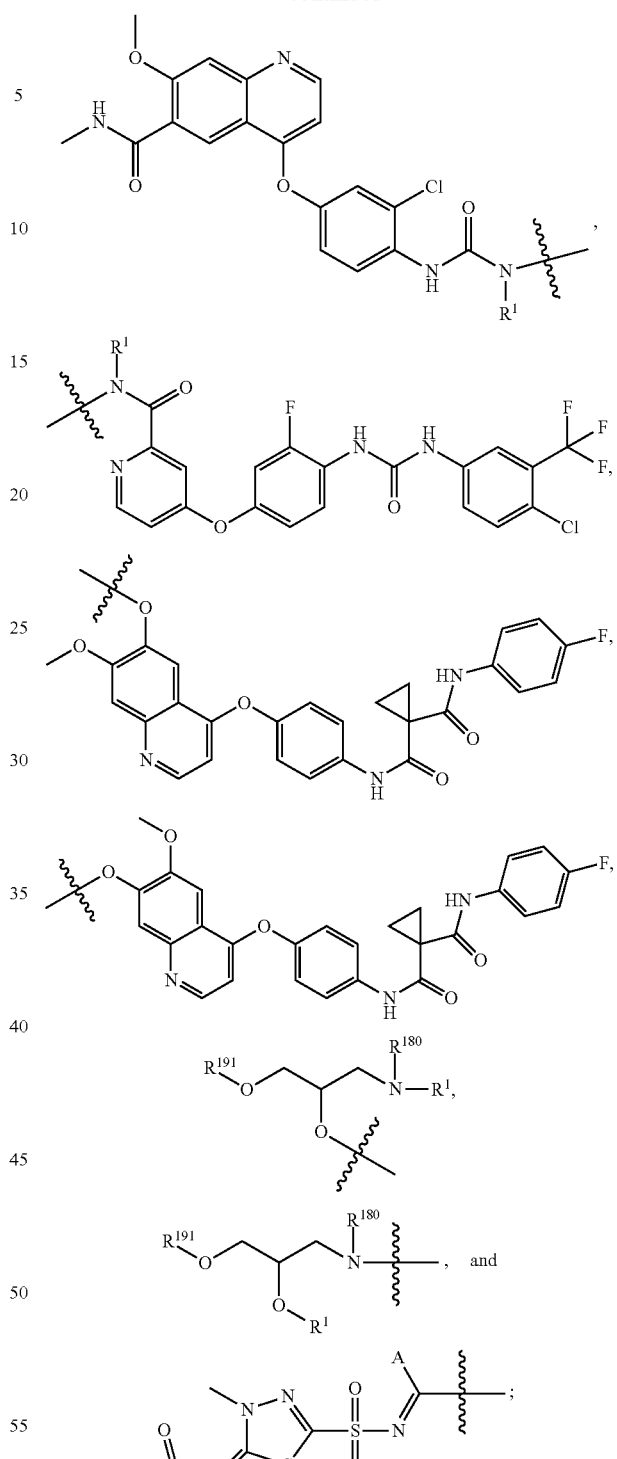

-continued

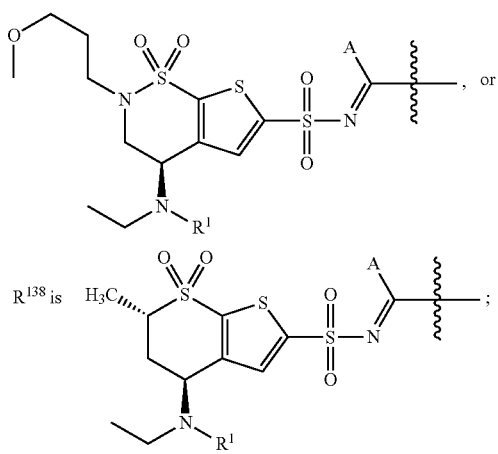

Or in an alternative embodiment, $R^{138}$ is selected from

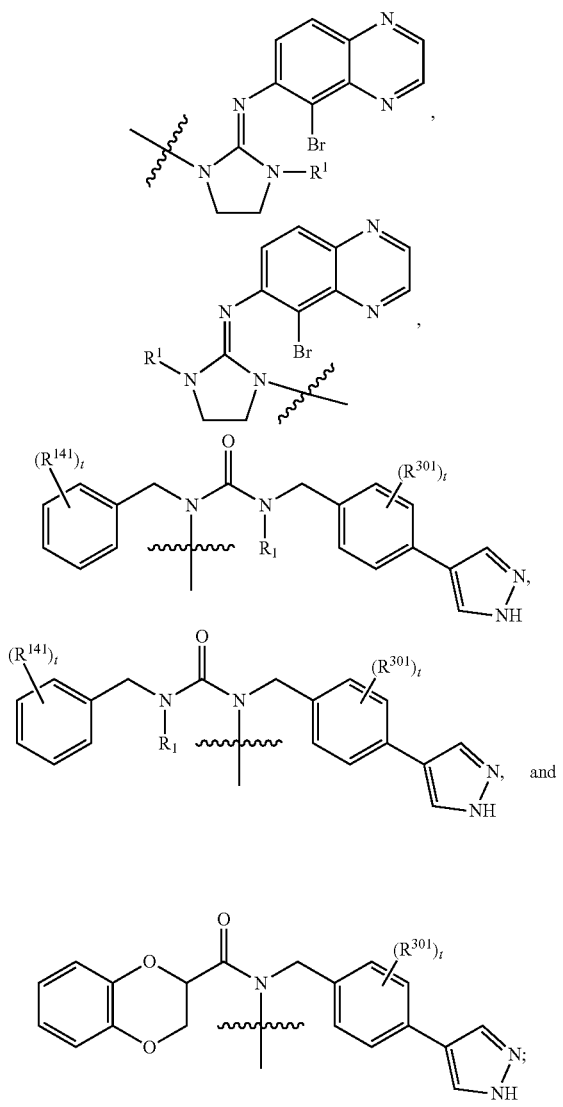

wherein all other variables are as defined herein.

In an alternative embodiment, Formula XXVIII is Formula XXVIIIa

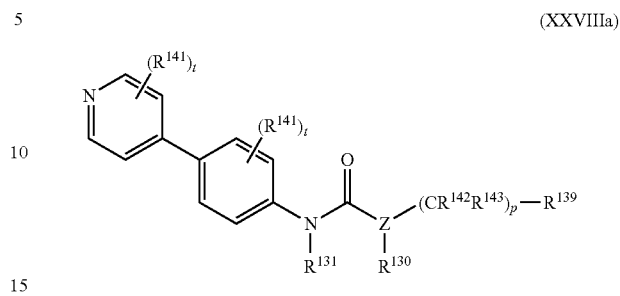
(XXVIIIa)

wherein:

$R^{142}$ and $R^{143}$ are independently selected from H, —OH, acetyl, —C(O)NH$_2$, C$_1$-C$_6$alkyl, C$_1$-C$_6$cycloalkyl, hereterocycloalkyl, aryl, or heteroaryl, wherein any one of the C$_1$-C$_6$alkyl, C$_1$-C$_6$cycloalkyl, hereteroC$_1$-C$_6$cycloalkyl, aryl, or heteroaryl groups is optionally substituted with one or more of hydroxyl, —CH$_2$OH, —C(O)NH$_2$, acetyl, carbonyl, alkyl, cycloalkyl, heterocycloalkyl, aryl, and heteroaryl, any of which can be optionally substituted with one or more of hydroxyl, nitro, amino, —NR$^{134}$R$^{135}$, alkyl, alkyl-O—R$^{136}$, alkoxy, alkylalkoxy, alkoxylalkoxy, heteroarylcarbonyl, heteroaryl, —OCH$_3$, —OCF$_3$, —OCHF$_2$, —OCH$_2$F;

$R^{139}$ is selected from cycloalkyl, heterocycloalkyl, aryl, or heteroaryl, any of which is optionally substituted with one or more of hydroxyl, —CH$_2$OH, —C(O)NH$_2$, acetyl, carbonyl, alkyl, cycloalkyl, heterocycloalkyl, aryl, and heteroaryl, any of which can be optionally substituted with one or more of hydroxyl, nitro, amino, —NR$^{134}$R$^{135}$, alkyl, alkoxy, alkylalkoxy, alkoxylalkoxy, haloalkoxy, heteroarylcarbonyl, heteroaryl, —OCH$_3$, —OCF$_3$, —OCHF$_2$, —OCH$_2$F, —OSO$_2$CH$_3$, tosyl, or halogen;

p is 1, 2, or 3; and wherein all other variables are as defined herein.

In an alternative embodiment, Formula XXVIII is Formula XXVIIIb

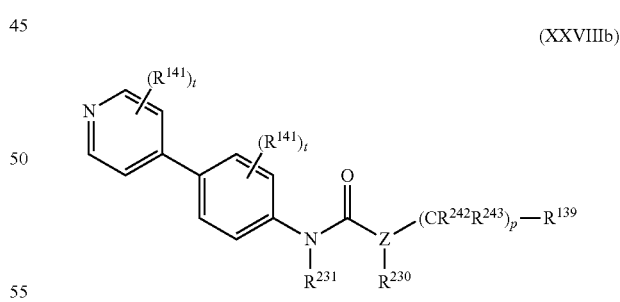
(XXVIIIb)

wherein:

$R^{230}$ and $R^{231}$ are independently selected at each occurrence from H, C$_1$-C$_{30}$alkyl, —C(O)C$_1$-C$_{30}$alkyl, C$_1$-C$_{30}$heteroalkyl, and R$^{136}$;

$R^{242}$ and $R^{243}$ are independently selected at each instance from H, —OH, acetyl, —C(O)NH$_2$, C$_1$-C$_6$alkyl, C$_1$-C$_6$cycloalkyl, hereterocycloalkyl, aryl, or heteroaryl, wherein any one of the C$_1$-C$_6$alkyl, C$_1$-C$_6$cycloalkyl, hereteroC$_1$-C$_6$cycloalkyl, aryl, or heteroaryl groups is optionally substituted with one or more substituents selected from hydroxyl, nitro, amino, —NR$^{134}$R$^{135}$, alkyl, alkyl-O—R$^{136}$, —O—$R^{136}$, alkoxy, alkylalkoxy, alkoxylalkoxy, heteroarylcarbonyl, heteroaryl, —$OCH_3$, —$OCF_3$, —$OCHF_2$, —$OCH_2F$;

wherein at least one instance of $R^{230}$, $R^{231}$, $R^{242}$, or $R^{243}$ is $R^{136}$ or contains a O—$R^{136}$ substitutent; and wherein all other variables are as defined herein.

In one embodiment the compound is:

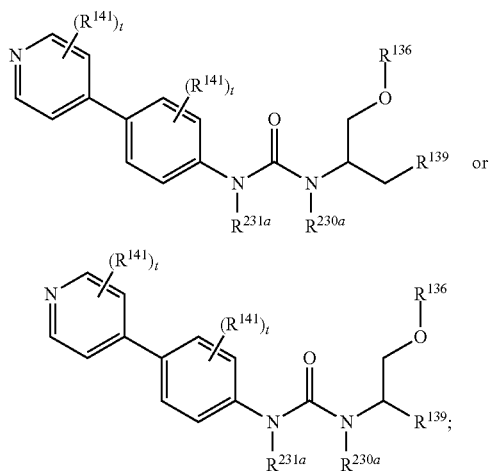

wherein:

$R^{230a}$ and $R^{231a}$ are independently selected at each occurrence from H, $C_1$-$C_{30}$alkyl, —$C(O)C_1$-$C_{30}$alkyl, and $C_1$-$C_{30}$heteroalkyl; and wherein all other variables are as defined herein.

Non-limiting examples of Formula XXVIII include

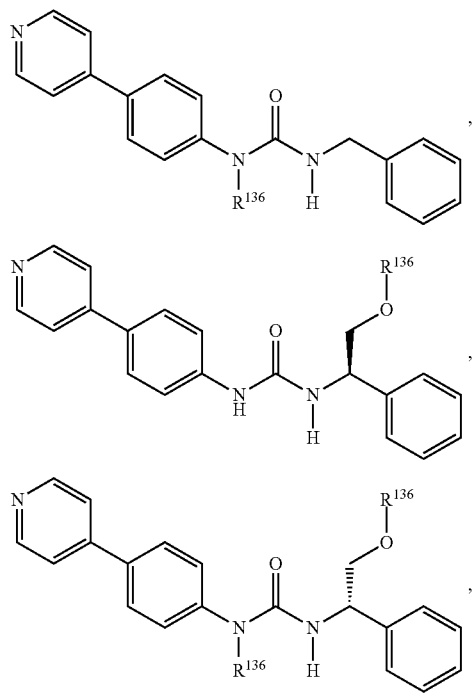

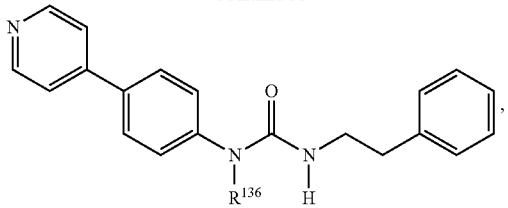

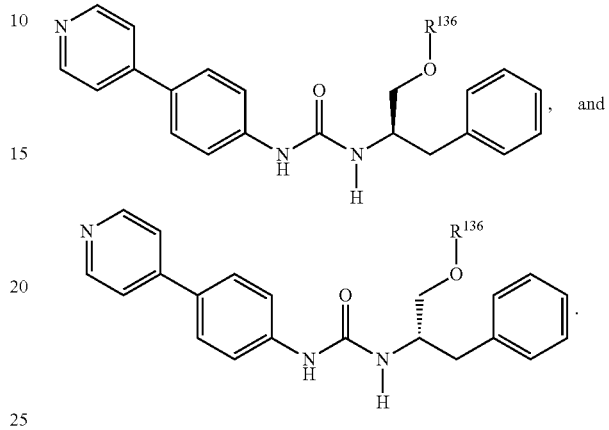

In an alternative embodiment, Formula XXIX is Formula XXIXa

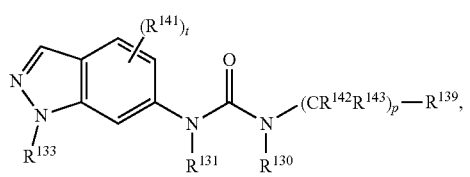

(XXIXa)

wherein all other variables are as defined herein.

In an alternative embodiment, Formula XXIX is Formula XXIXb

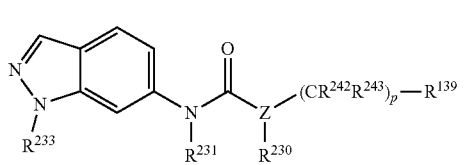

(XXIXb)

wherein:

$R^{230}$, $R^{231}$, and $R^{233}$ are independently selected at each occurrence from H, $C_1$-$C_{30}$alkyl, —$C(O)C_1$-$C_{30}$alkyl, $C_1$-$C_{30}$heteroalkyl, and $R^{136}$;

wherein at least one instance of $R^{230}$, $R^{231}$, $R^{233}$, $R^{242}$, or $R^{243}$ is $R^{136}$ or contains a 0-R substitutent;

wherein all other variables are as defined herein.

Non-limiting examples of Formula XXIX include

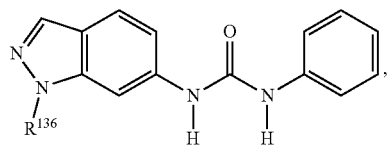

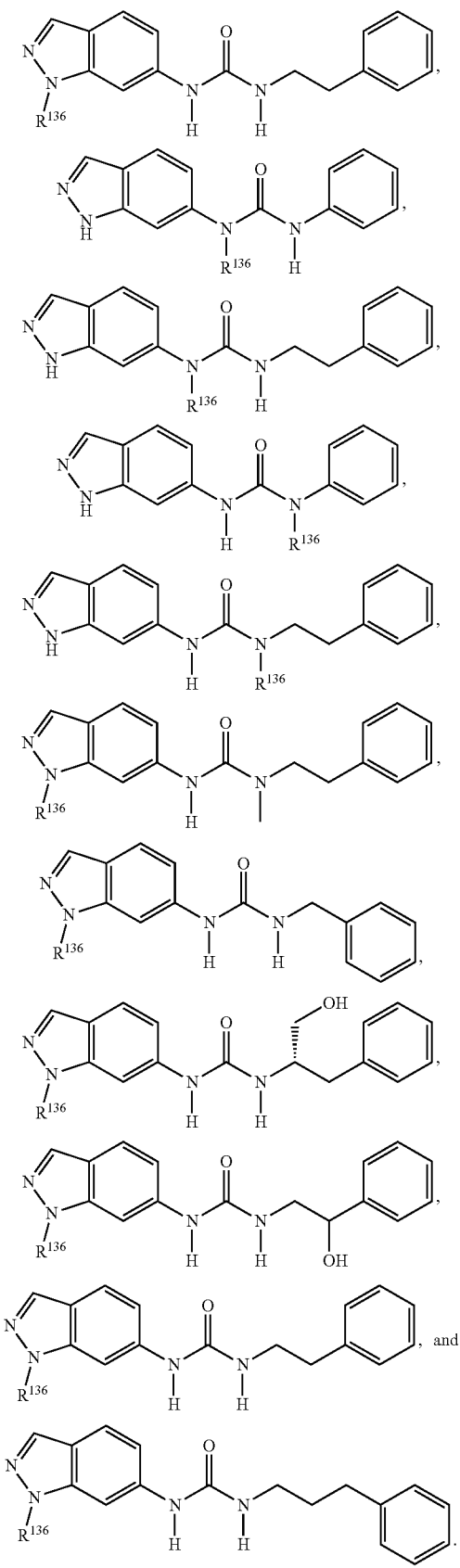

In an alternative embodiment, Formula XXX is Formula XXXa


wherein all other variables are as defined herein.

In an alternative embodiment, Formula XXX is Formula XXXb


wherein at least one instance of $R^{230}$, $R^{231}$, $R^{242}$, or $R^{243}$ is $R^{136}$ or contains a O-$R^{136}$ substitutent; and wherein all other variables are as defined herein.

In one embodiment the compound is:

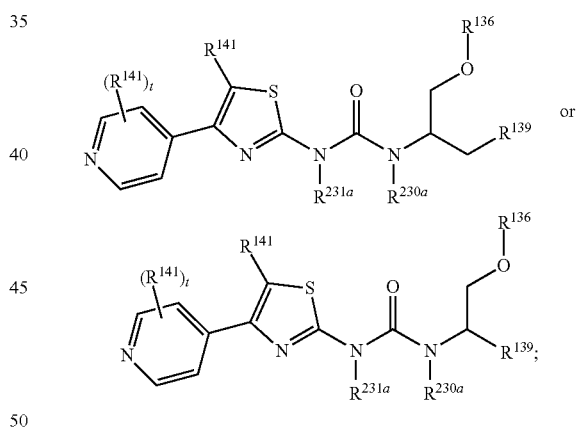

wherein all variables are as defined herein.

Non-limiting examples of Formula XXX include

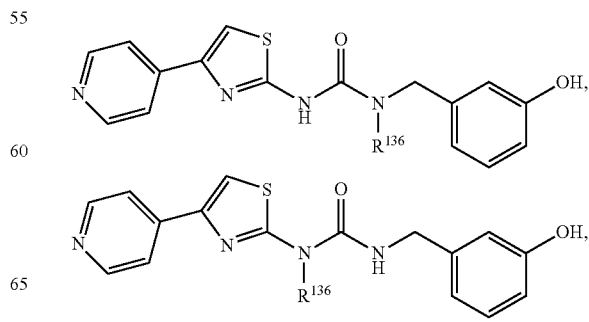

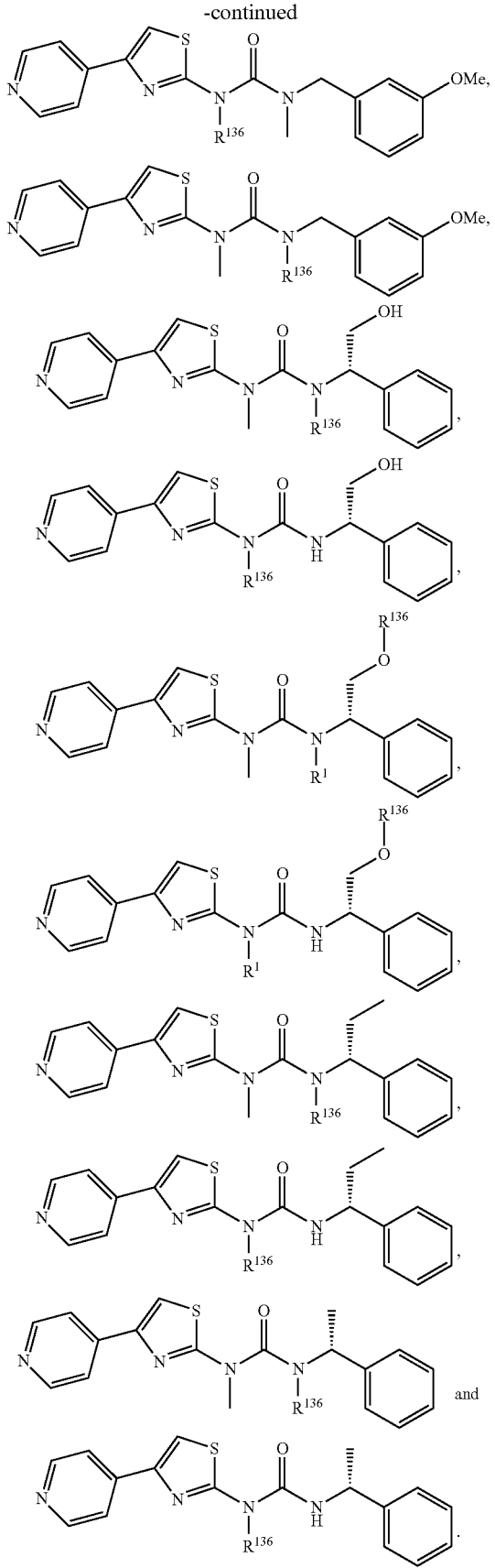

The disclosure also provides prodrugs of Formula XXXI, XXXII, and XXXIII:

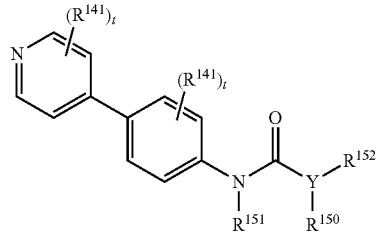
(XXXI)

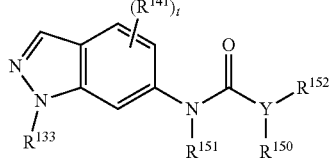
(XXXII)

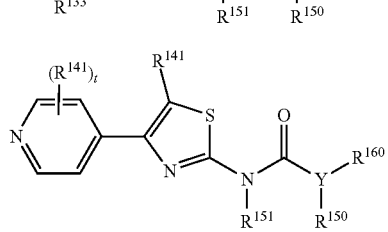
(XXXIII)

or a pharmaceutically acceptable composition, salt, or isotopic derivative thereof.

Y is $CR^{150}$ or N;

$R^{150}$ and $R^{151}$ are independently selected at each occurrence from H, $C_1$-$C_{30}$alkyl, —C(O)$C_1$-$C_{30}$alkyl, $C_1$-$C_{30}$heteroalkyl, and $R^{156}$;

in one embodiment the heteroalkyl contains at least one heteroatom in the chain, for example, an amine, carbonyl, carboxy, oxo, thio, phosphate, phosphonate, nitrogen, phosphorus, silicon, or boron atoms in place of a carbon atom. In one embodiment, the only heteroatom is oxygen. "Nonlimiting examples of heteroalkyl moieties are polyethylene glycol, polyalkylene glycol, amide, polyamide, polylactide, polyglycolide, thioether, ether, alkyl-heterocycle-alkyl, —O—alkyl-O-alkyl, and alkyl-O-haloalkyl.

$R^{152}$ is selected from $C_1$-$C_{30}$alkyl, $C_1$-$C_{30}$cycloalkyl, heterocycloalkyl, aryl, heteroaryl, or alkylaryl, any of which can be optionally substituted with one or more of hydroxyl, —CH$_2$OH, —C(O)NH$_2$, acetyl, carbonyl, alkyl, cycloalkyl, heterocycloalkyl, aryl, and heteroaryl, any of which can be optionally substituted with one or more of hydroxyl, nitro, amino, —NR$^{134}$R$^{135}$, alkyl, alkoxy, alkylalkoxy, alkoxylalkoxy, haloalkoxy, heteroarylcarbonyl, heteroaryl, —OCH$_3$, —OCF$_3$, —OCHF$_2$, —OCH$_2$F, —OSO$_2$CH$_3$, tosyl, or halogen;

or $R^{151}$ and $R^{152}$ can together form a cycloalkyl or heterocycloalkyl;

$R^{160}$ is selected from H, $C_1$-$C_{30}$alkyl, $C_1$-$C_{30}$cycloalkyl, heterocycloalkyl, and aryl, any of which except hydrogen can be optionally substituted with one or more of hydroxyl, —CH$_2$OH, —C(O)NH$_2$, acetyl, carbonyl, alkyl, cycloalkyl, heterocycloalkyl, aryl, and heteroaryl, any of which can be optionally substituted with one or more of hydroxyl, nitro, amino, —NR$^{134}$R$^{135}$, alkyl, alkoxy, alkylalkoxy, alkoxylalkoxy, haloalkoxy, heteroarylcarbonyl, heteroaryl, —OCH$_3$, —OCF$_3$, —OCHF$_2$, —OCH$_2$F, —OSO$_2$CH$_3$, tosyl, or halogen; or $R^{151}$ and $R^{152}$ can together form a cycloalkyl or heterocycloalkyl;

wherein at least one of $R^{150}$ and $R^{151}$ is $R^{156}$;

$R^{156}$ is selected from:

(i) polyethylene glycol, polypropylene glycol, polypropylene oxide, polylactic acid, poly(lactic-co-glycolic acid) polyglycolic acid, polyester, polyamide, and other biodegradable polymers, each of which can be capped to complete the terminal valence or to create a terminal ether or ester, in one embodiment the capping group is selected from $R^{31}$; and (ii)

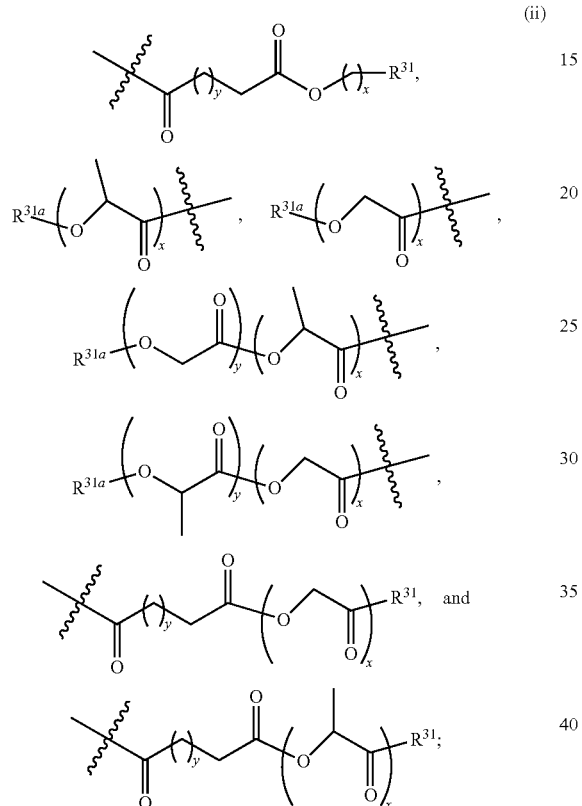

or $R^{156}$ is

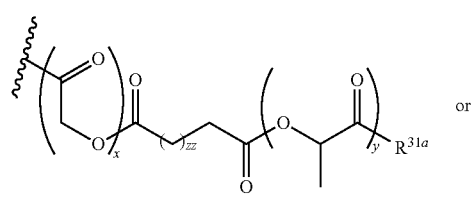

or

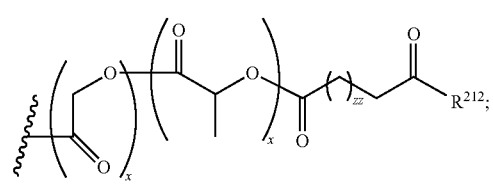

wherein all other variables are as defined herein.

In one embodiment $R^{156}$ is selected from:

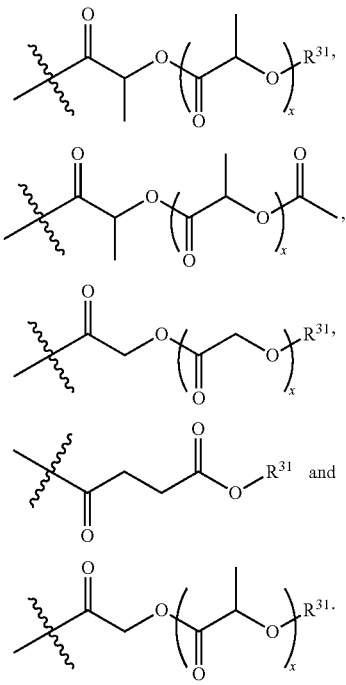

In one embodiment $R^{56}$ is selected from:

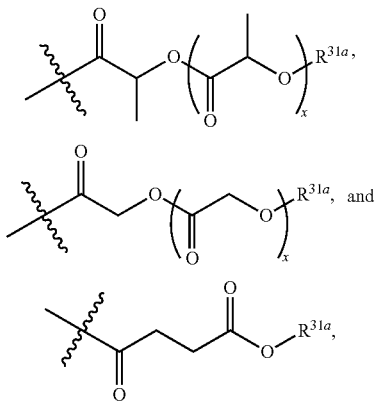

The disclosure also provides prodrugs of Formula XXXIV, Formula XXXVI, Formula XXXVIII, Formula XL, Formula XLII, Formula XLIV, Formula XLVI, and Formula XLVIII:

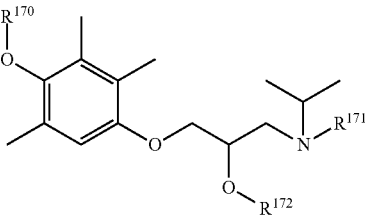

(XXXIV)

-continued (XXXVI)
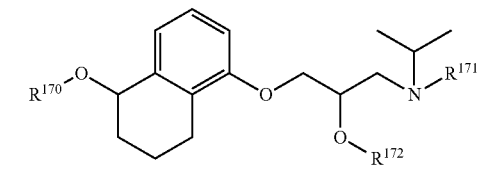

(XXXVIII)
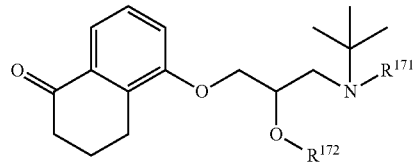

(XL)
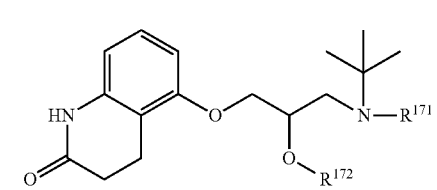

(XLII)
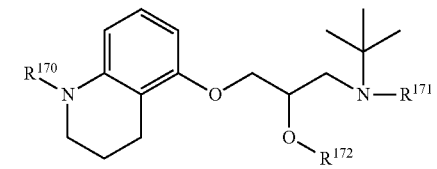

(XLIV)
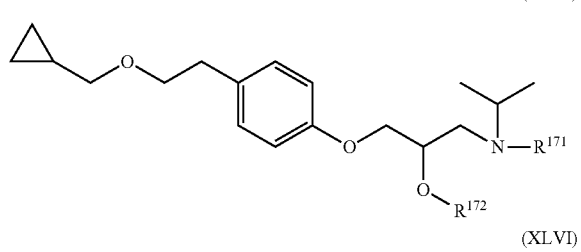

(XLVI)
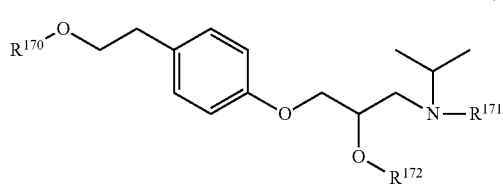

(XLVIII)
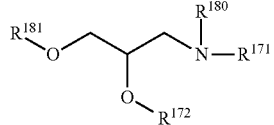

or a pharmaceutically acceptable composition, salt, or isotopic derivative thereof.

$R^{70}$, $R^{711}$, and $R^{172}$ are independently selected from: $R^1$, $R^{173}$, acyl, carbonyl linked polyethylene glycol, carbonyl linked polypropylene glycol, carbonyl linked polypropylene oxide, polylactic acid, poly(lactic-co-glycolic acid), polyglycolic acid, polyester, polyamide, or other biodegradable polymer, each of which $R^{170}$, $R^{171}$, and $R^{172}$ other than $R^{173}$ are optionally substituted with $L^8$-$R^{174}$;

wherein at least one of $R^{170}$, $R^{171}$, and $R^{172}$ is $R^{173}$ or substituted with $L^8$-$R^{174}$ $R^{181}$ is selected from:

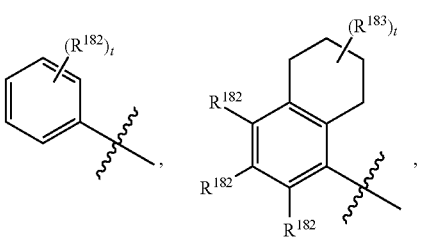

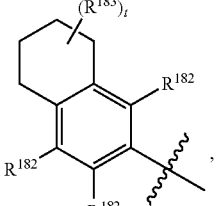

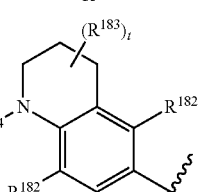

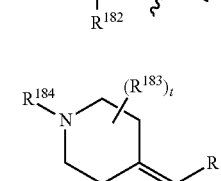

$R^{185}$;

$R^{182}$ is independently selected from alkyl, cycloalkyl, aryl, heteroaryl, heterocycle, cyano, amino, hydroxyl, and acyl, each of which $R^{182}$ is optionally substituted with a $R^{170}$ group;

$R^{183}$ is independently selected from alkyl, cycloalkyl, aryl, heteroaryl, heterocycle, amino, hydroxyl, and acyl;

or two $R^{183}$ groups with the carbon to which they are linked form a carbonyl group;

or two $R^{183}$ groups with the carbon(s) to which they are linked form a fused or spirocyclic ring;

$R^{184}$ is selected from alkyl, cycloalkyl, $R^{170}$, and acyl;

$R^{185}$ is selected from aryl, heteroaryl, cycloalkyl, and heterocycle, wherein each $R^{185}$ is optionally substituted with 1, 2, 3, or 4 $R^{182}$ groups;

$R^{173}$ is selected from:

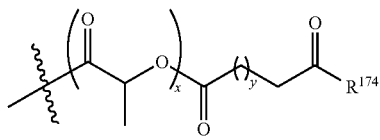

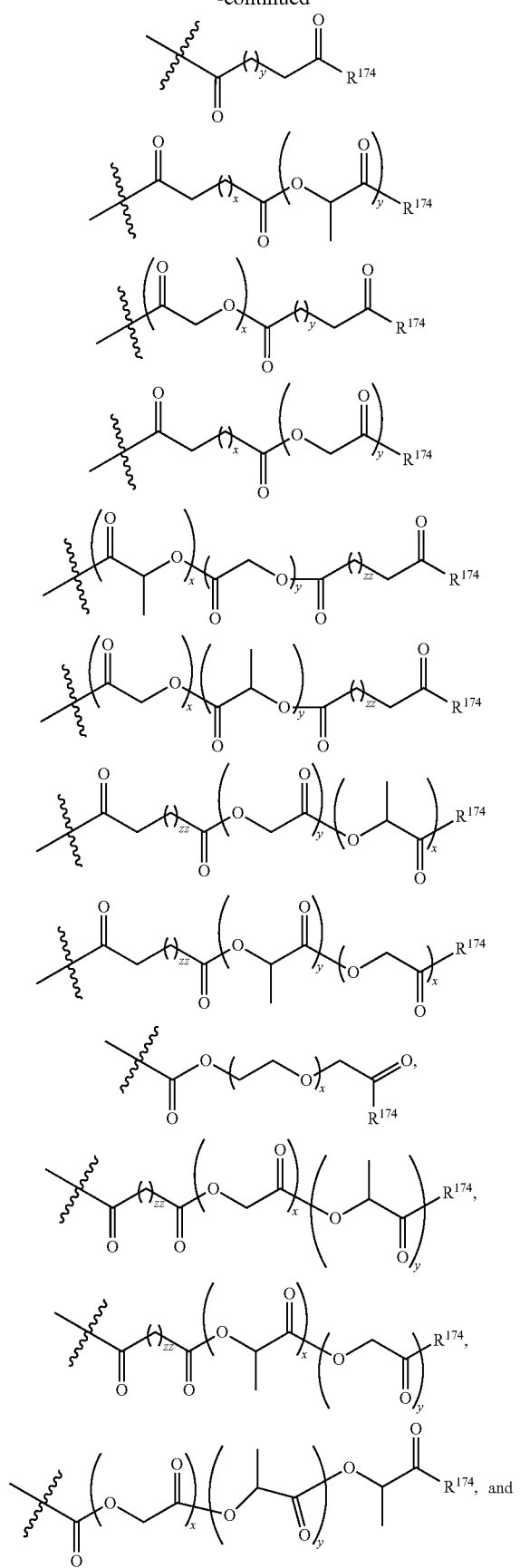
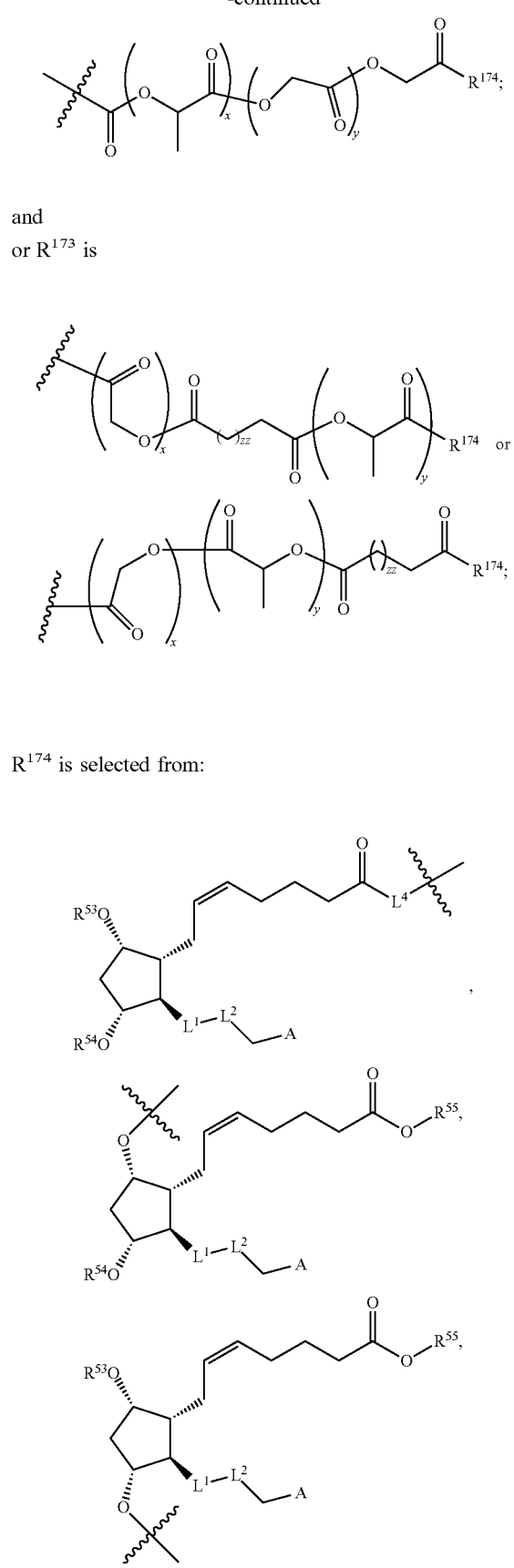
and
or $R^{173}$ is
$R^{174}$ is selected from:

193
-continued
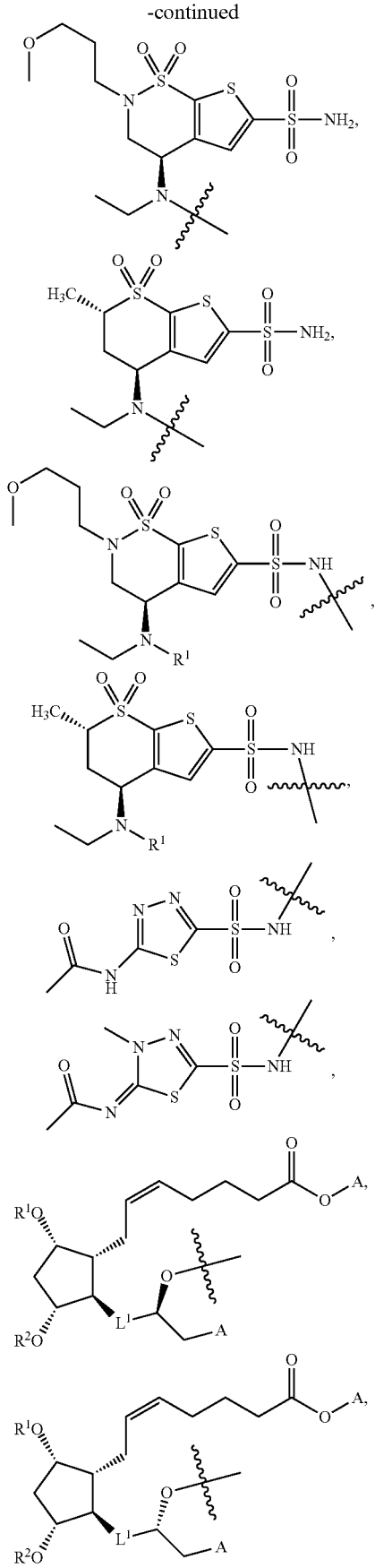
194
-continued
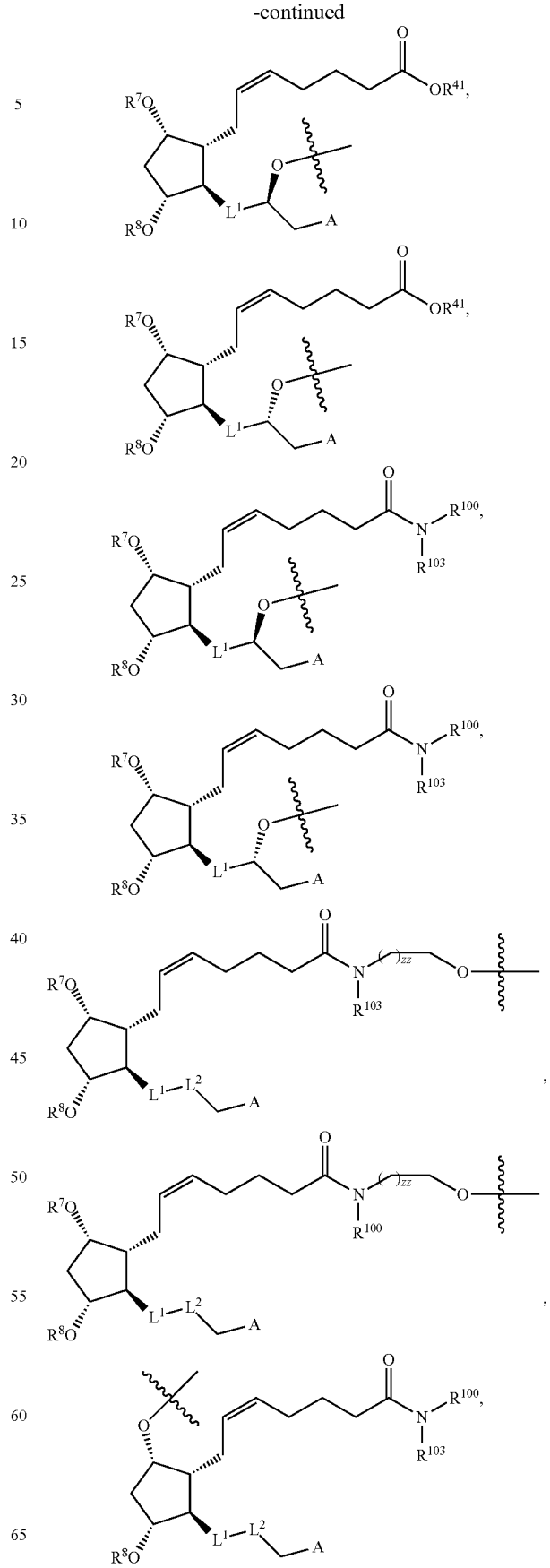

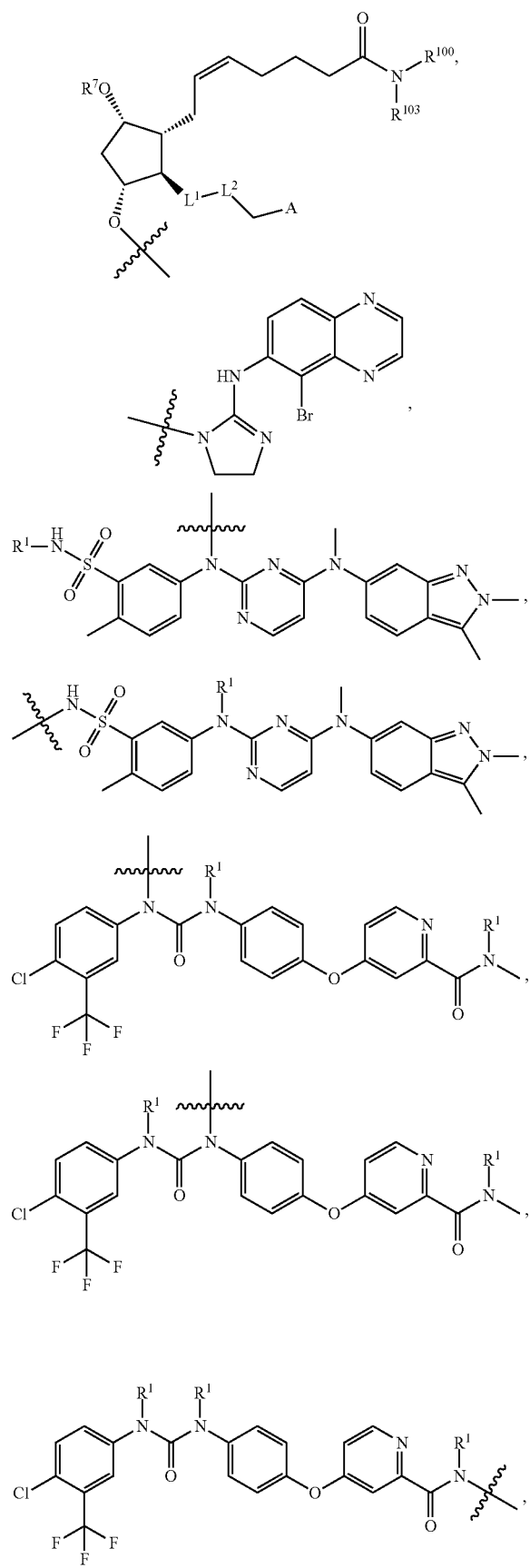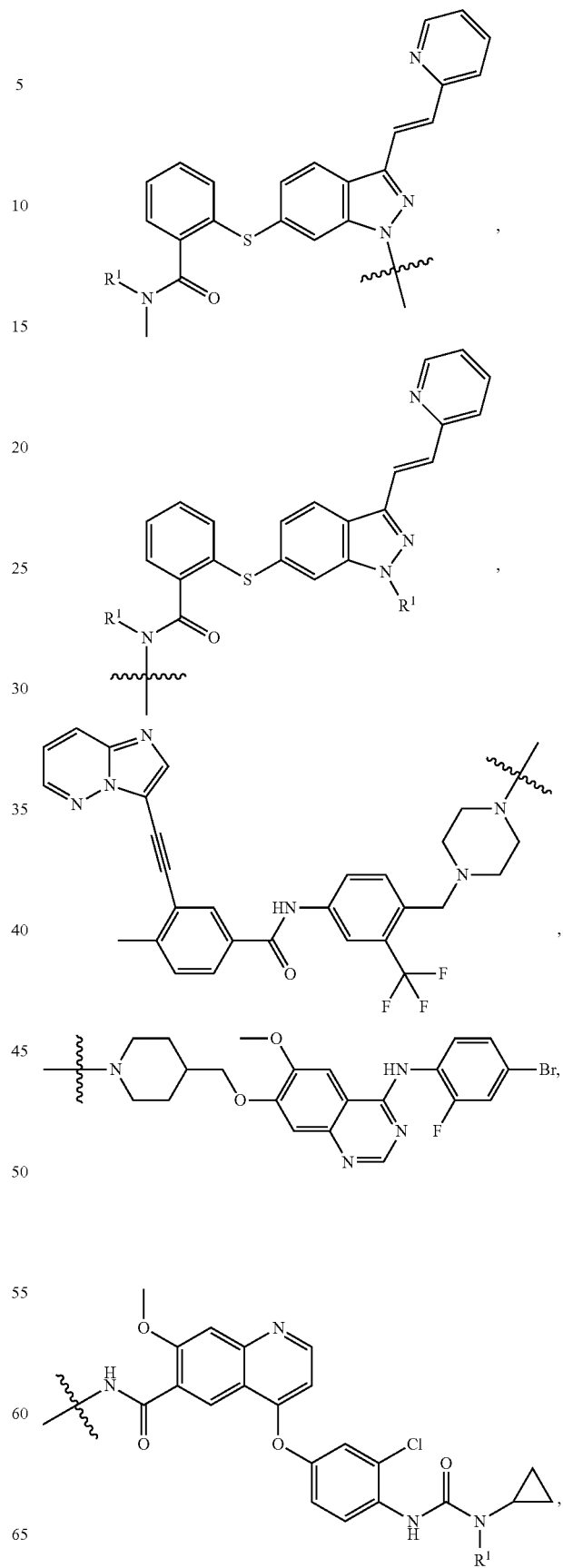

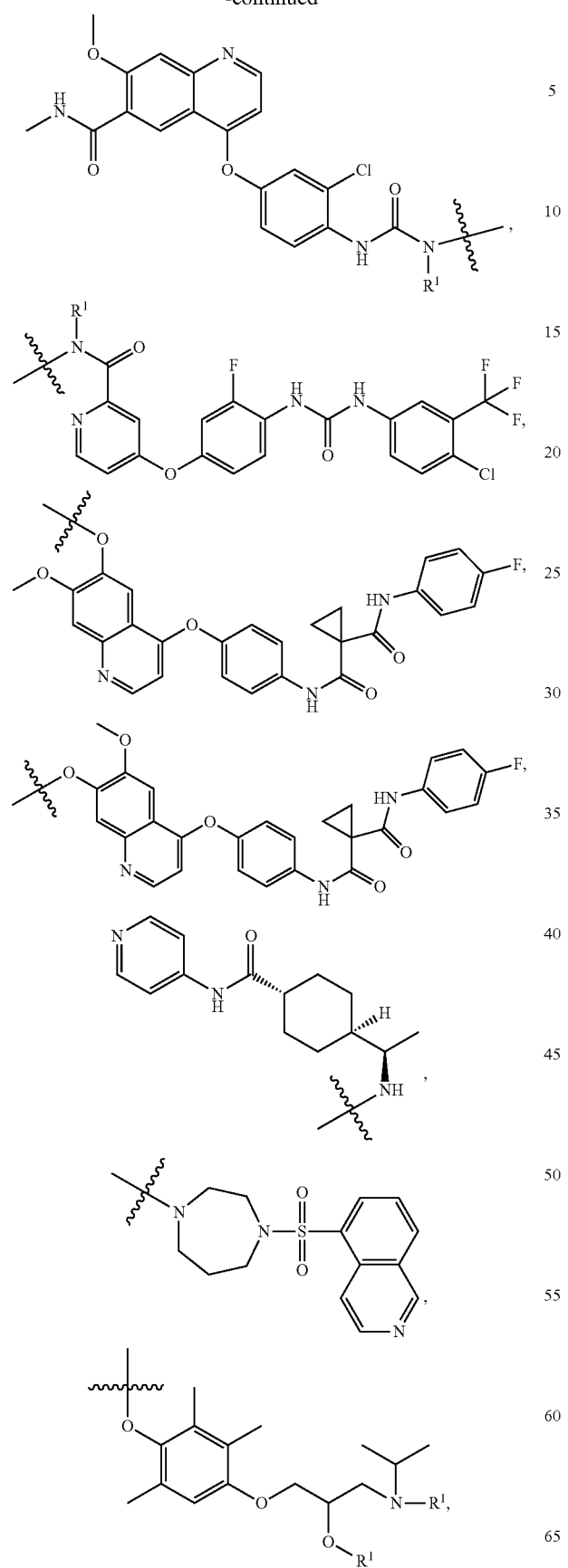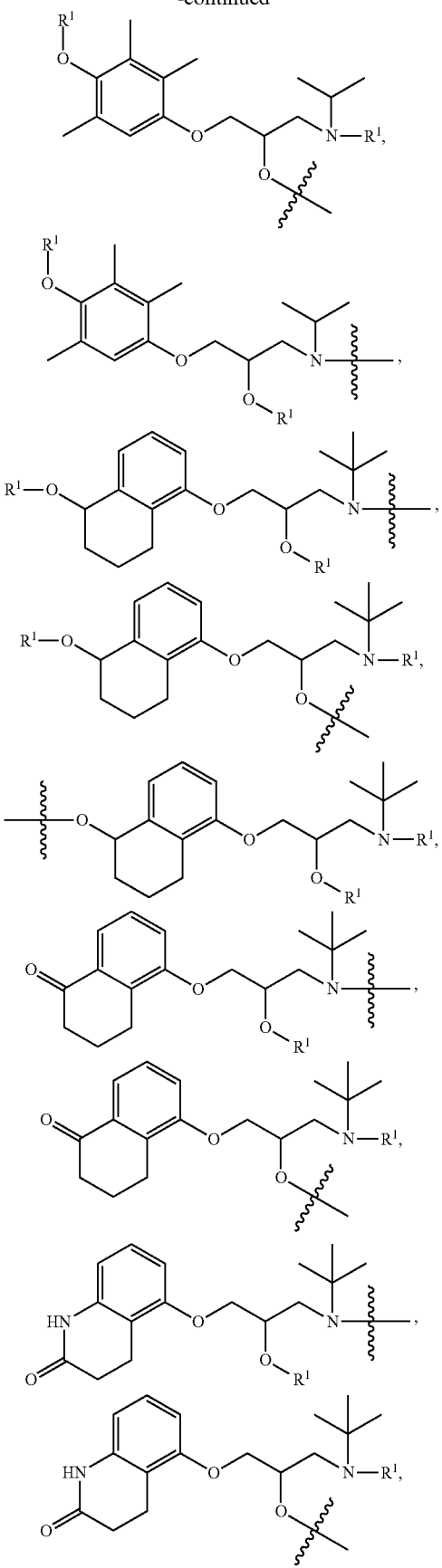

-continued
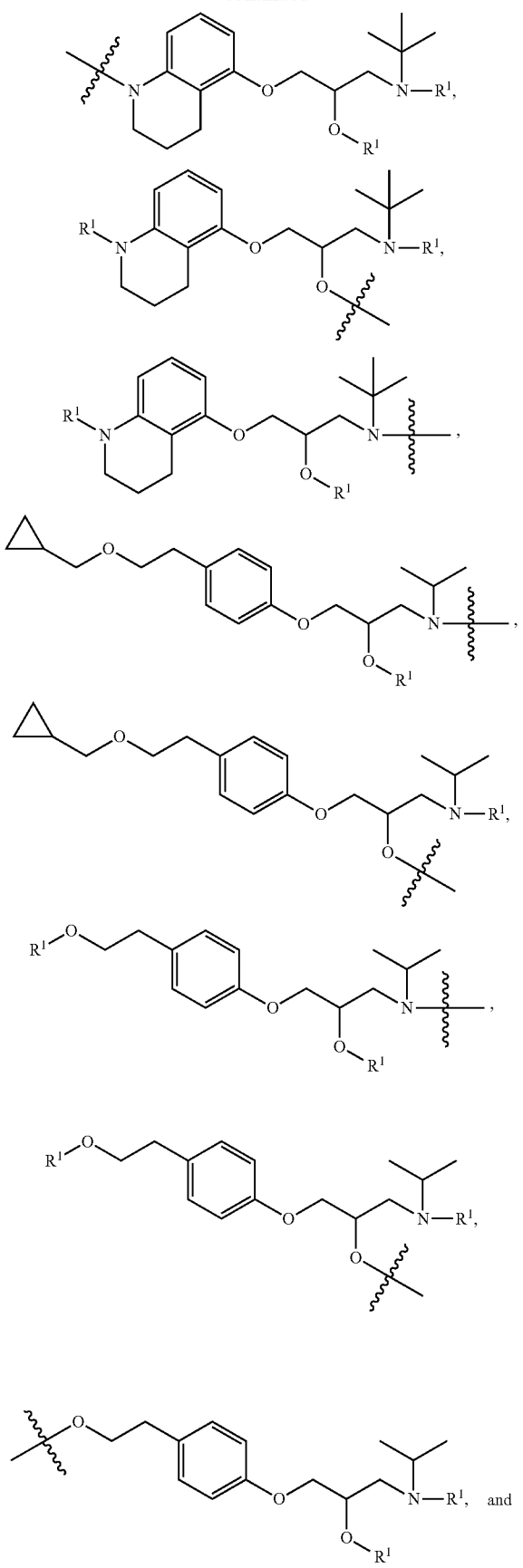
or $R^{174}$ is
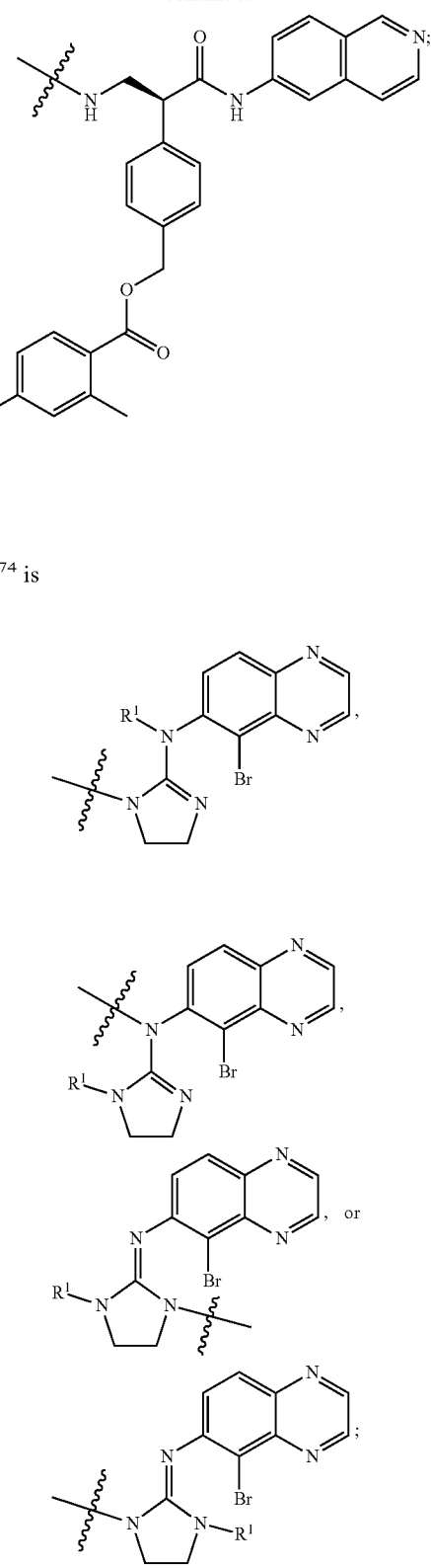
wherein all other variables are as defined herein.
The disclosure also provides prodrugs of Formula XXXV, Formula XXXVII, Formula XXXIX, Formula XLI, Formula XLIII, Formula XLV, Formula XLVII, and Formula XLIX:

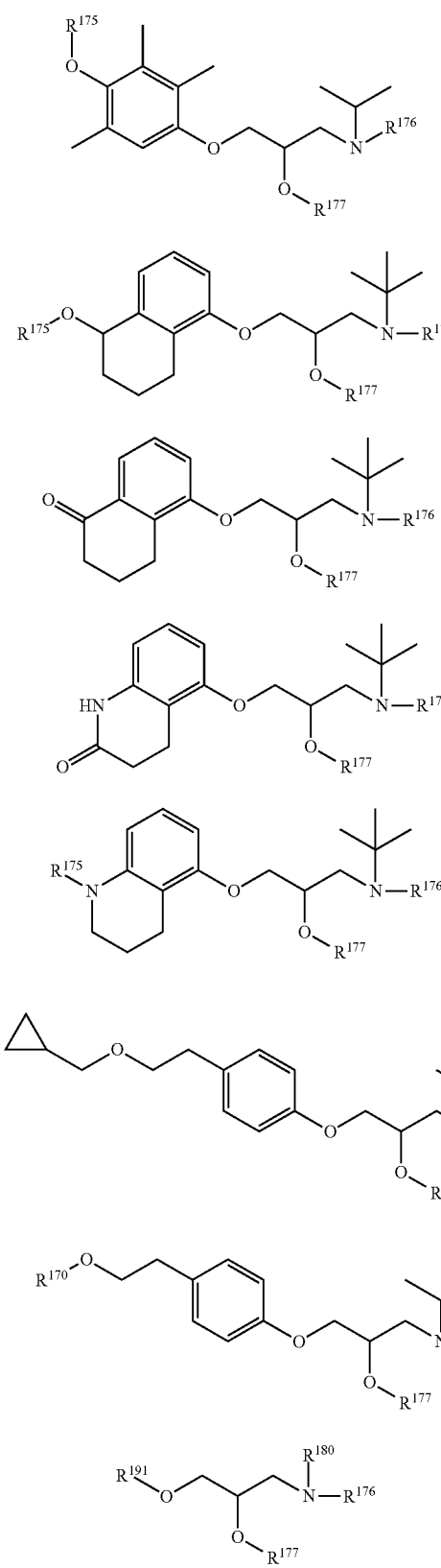

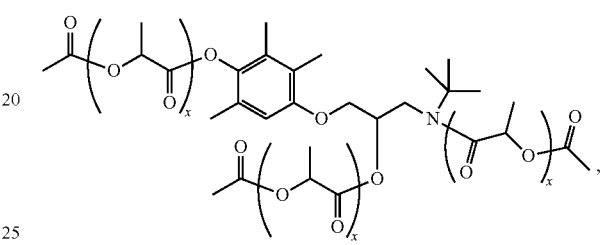

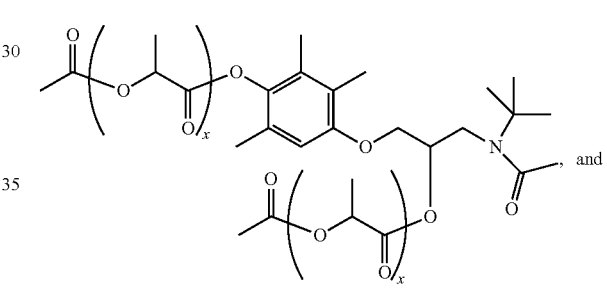

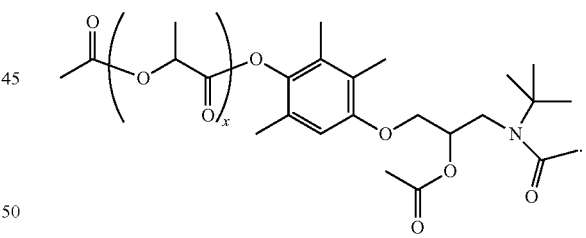

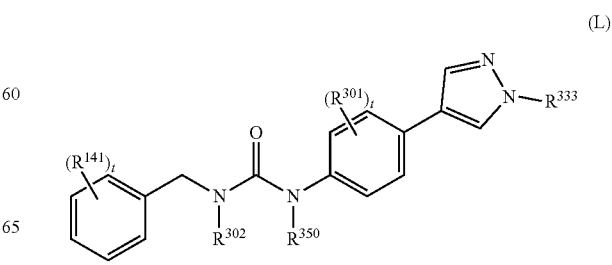

or a pharmaceutically acceptable composition, salt, or isotopic derivative thereof.

In some embodiments the compounds of Formula XXXIV to Formula XLIX can be used in the form of an R enantiomer, an S enantiomer, or a mixture of enantiomers including a racemic mixture.

In some embodiments the compounds of Formula XXXIV to Formula XLIX have the same stereochemistry as the corresponding commercial drug.

$R^{175}$, $R^{176}$, and $R^{177}$ are independently selected from: $C(O)A$, $C(O)R^4$, and $R^{178}$;

wherein at least one of $R^{175}$, $R^{176}$, and $R^{177}$ is $R^{178}$; and wherein all other variables are as defined herein.

Non-limiting examples of Formula XXXV include:

In an alternative embodiment, this disclosure provides prodrugs of Formula (L), (L'), and (LI):

-continued

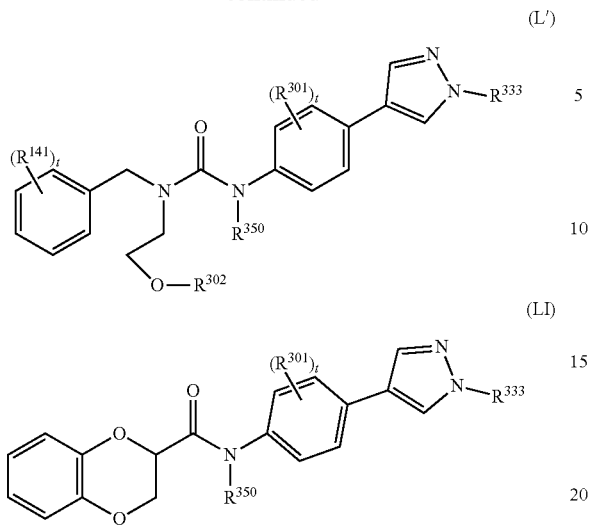

or a pharmaceutically acceptable composition, salt, or isotopic derivative thereof.

wherein $R^{302}$ and $R^{333}$ are independently selected from H, $C_1$-$C_{30}$alkyl, —C(O)$C_1$-$C_{30}$alkyl, $C_1$-$C_{30}$heteroalkyl, $C_2$-$C_{30}$alkenyl, and $R^{356}$;

$R^{350}$ is selected from H, $C_1$-$C_{30}$alkyl, —C(O)$C_1$-$C_{30}$alkyl, $C_1$-$C_{30}$heteroalkyl, $C_2$-$C_{30}$alkenyl, and $R^{356}$;

$R^{356}$ is selected from (i) polyethylene glycol, polypropylene glycol, polypropylene oxide, polylactic acid, poly(lactic-co-glycolic acid) polyglycolic acid, polyester, polyamide, and other biodegradable polymers, each of which can be capped to complete the terminal valence or to create a terminal ether or ester;

(ii)

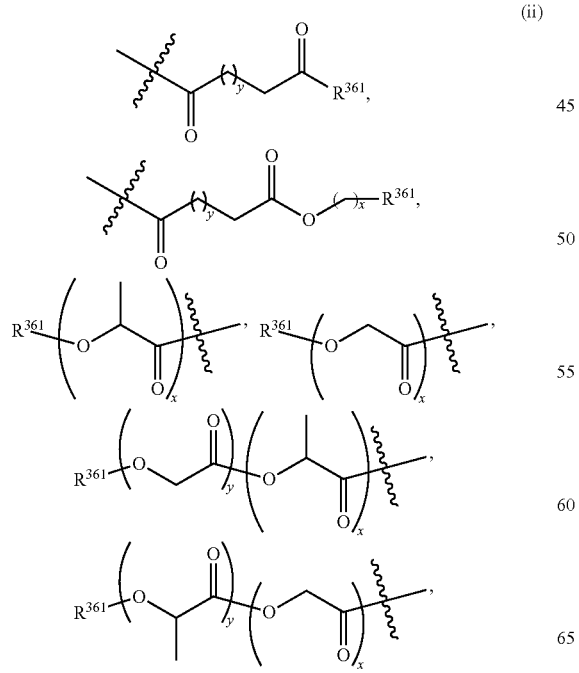

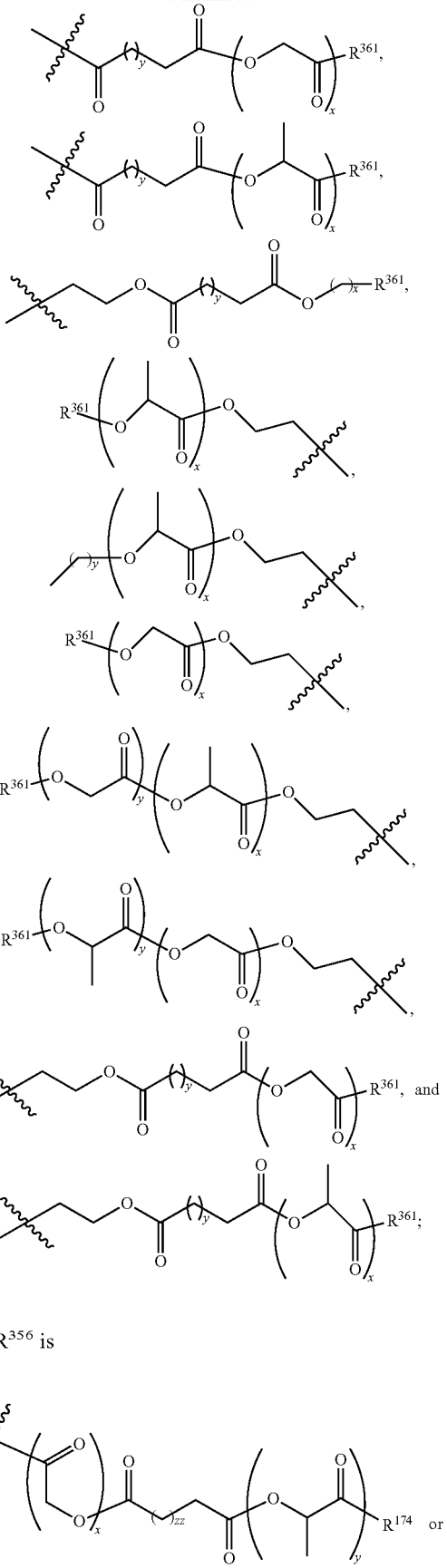

or $R^{356}$ is

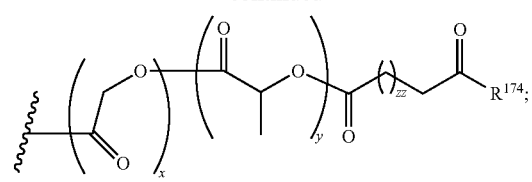

wherein at least one of $R^{302}$, $R^{333}$ and $R^{350}$ is $R^{356}$; and wherein all other variables are as defined herein.

In one embodiment, $R^{141}$ is $OCH_3$.

In one embodiment, $R^{301}$ is selected from $-N(CH_3)_2$,

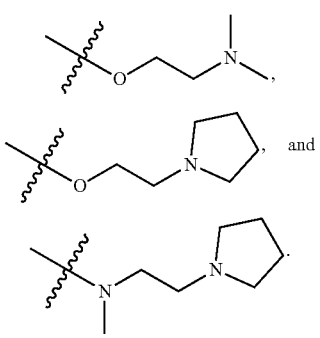

In one embodiment, $R^{301}$ is

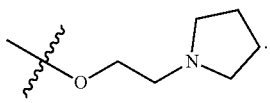

In one embodiment, $R^{301}$ is $-OCH_3$.
In one embodiment, $R^{301}$ is selected from F and Cl.
In one embodiment, $R^{350}$ is hydrogen.
In one embodiment, $R^{310}$ is $CH_3$.
In one embodiment, $R^{350}$ is $CH_2H_5$.
In one embodiment, $R^{356}$ is

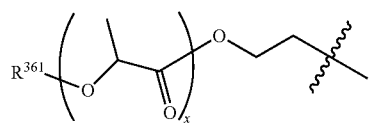

and $R^{361}$ is $-C(O)CH_3$.
In one embodiment, $R^{356}$ is

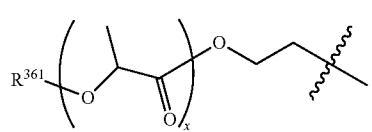

and $R^{361}$ is stearoyl.

In one embodiment, $R^{356}$ is

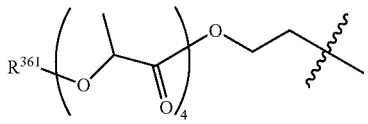

and $R^{361}$ is $-C(O)CH_3$.
In one embodiment, $R^{356}$ is

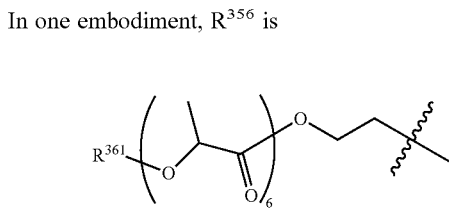

and $R^{361}$ is $-C(O)CH_3$.
In one embodiment, $R^{356}$ is

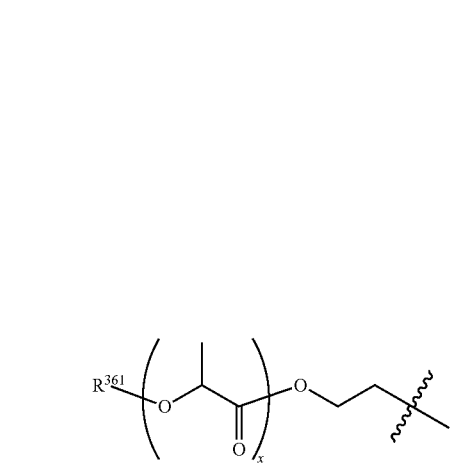

and x is an integer between 1 and 6.
In one embodiment, $R^{356}$ is

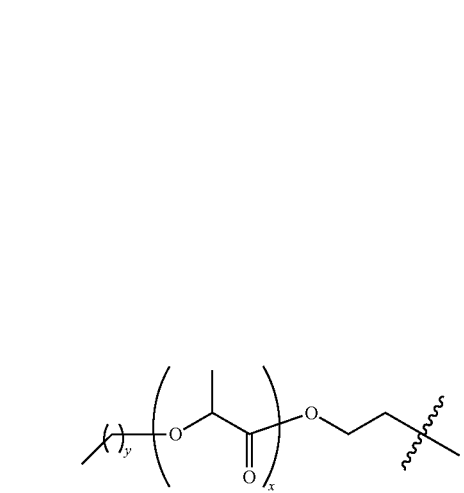

and y is 11, or in an alternative embodiment, y is 10.

In one embodiment, $R^{356}$ is
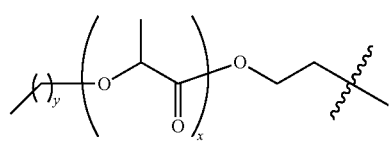
and y is 17, or in an alternative embodiment, y is 16.
In one embodiment, $R^{333}$ is
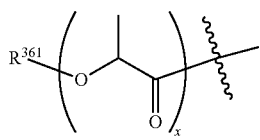
and $R^{361}$ is —C(O)alkyl.
Non-limiting Examples of Formula L and Formula LI include
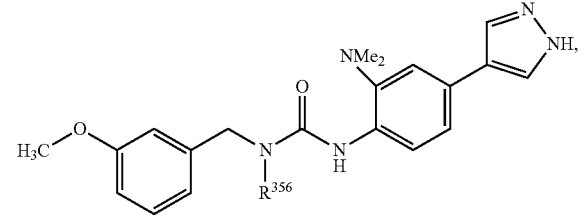
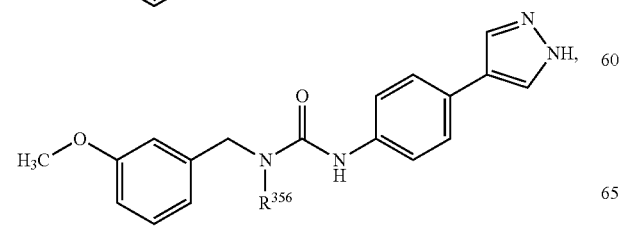
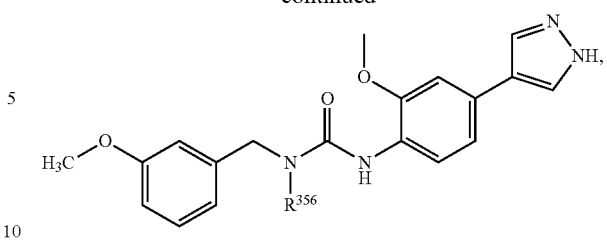
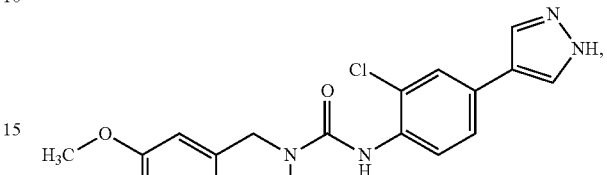
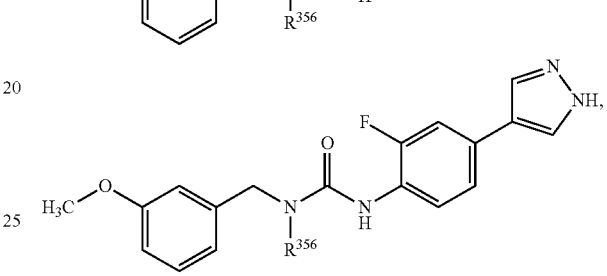
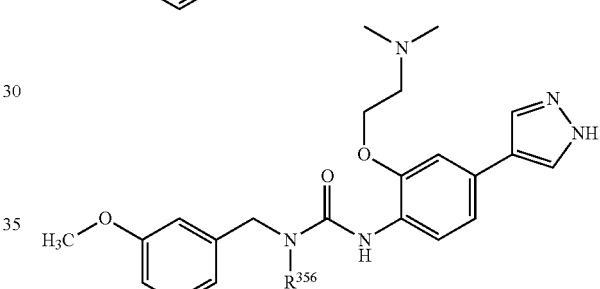
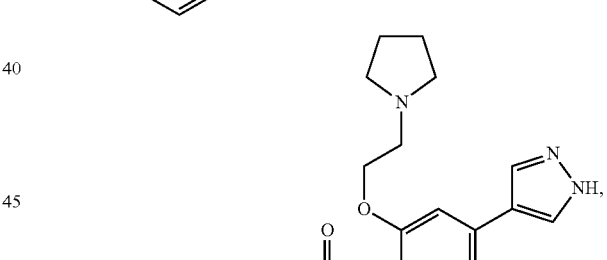
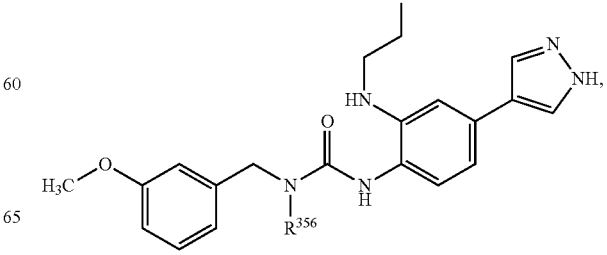

-continued

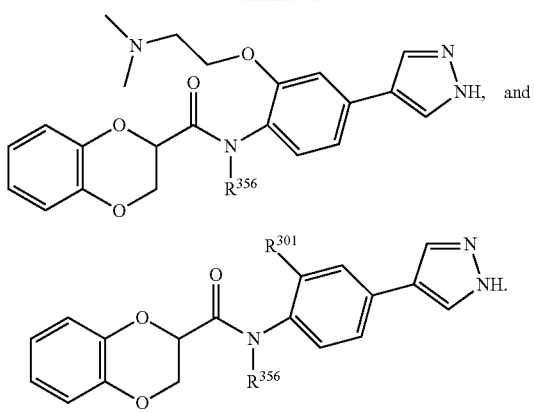

In an alternative embodiment, this disclosure provides prodrugs of Formula (LII) and (LIII):

(LII)

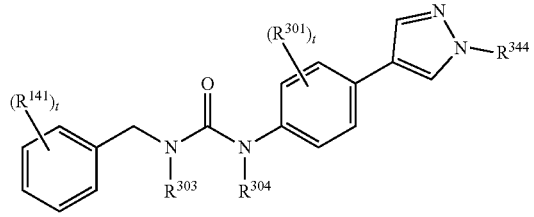

(LII')

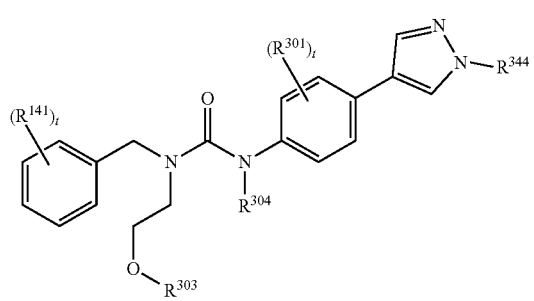

(LIII)

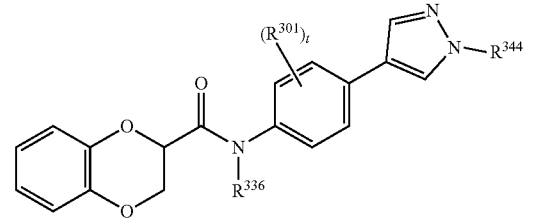

or a pharmaceutically acceptable composition, salt, or isotopic derivative thereof wherein $R^{303}$, $R^{304}$, and $R^{344}$ are independently selected at each occurrence from H, $C_1$-$C_{30}$alkyl, —C(O)$C_1$-$C_{30}$alkyl, $C_2$-$C_{30}$alkenyl, $C_1$-$C_{30}$heteroalkyl, and $R^{336}$;

wherein at least one of $R^{303}$, $R^{304}$, and $R^{344}$ is $R^{336}$;

$R^{336}$ is selected from:

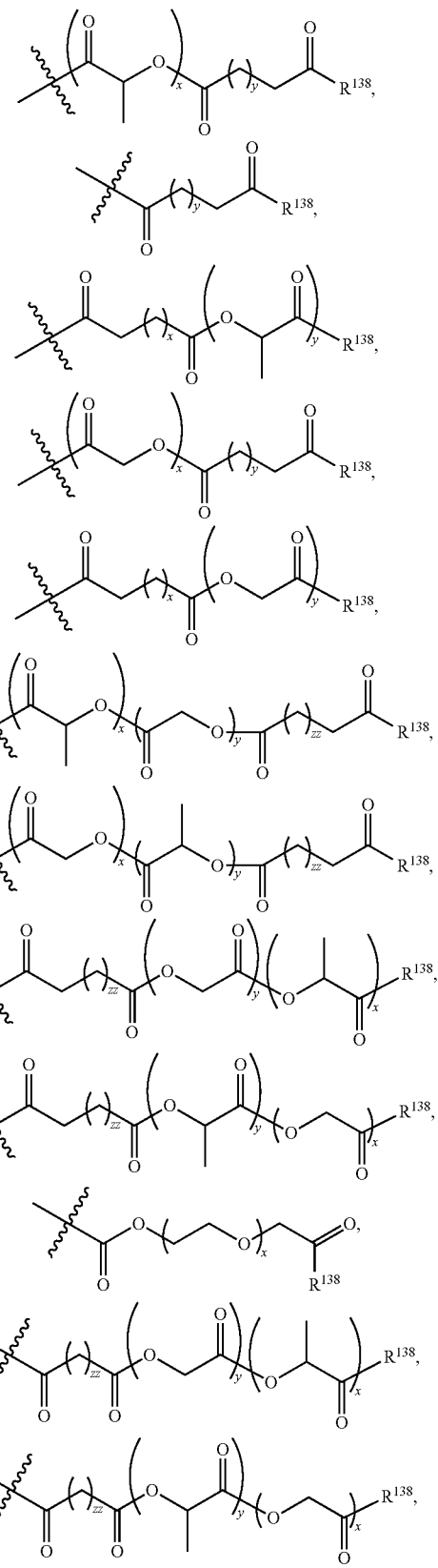

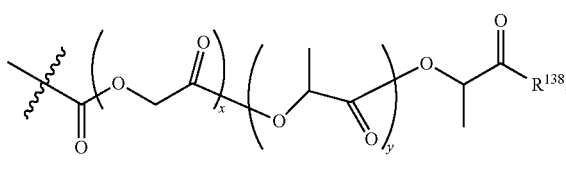
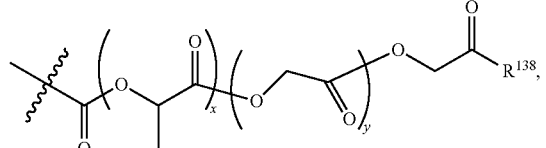
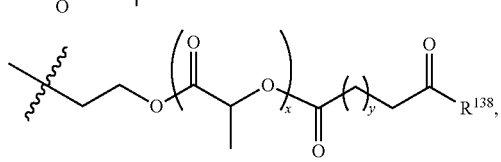
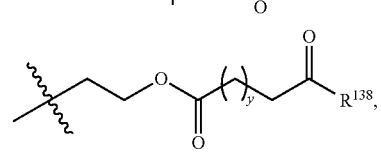
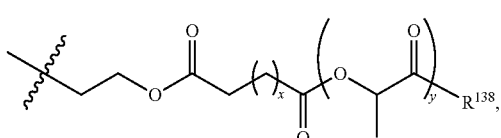
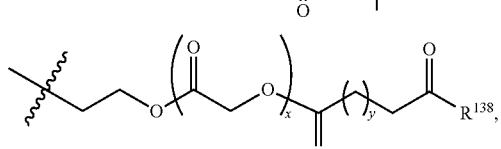
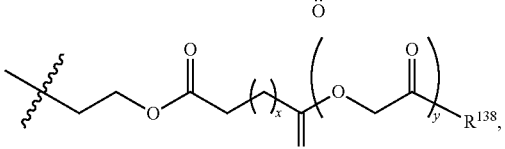
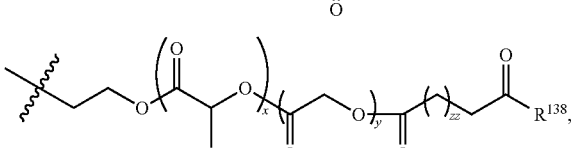
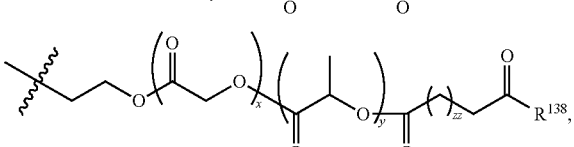
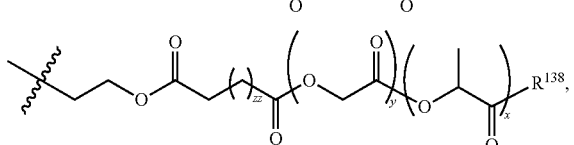
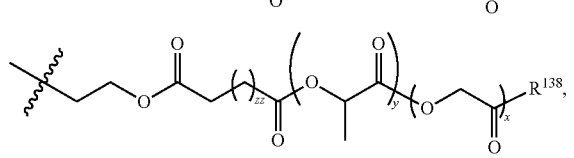
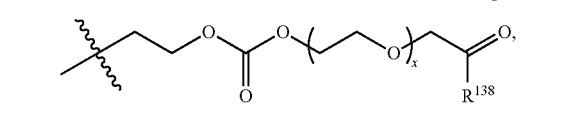
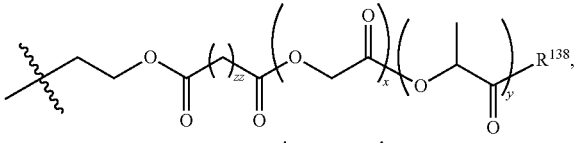
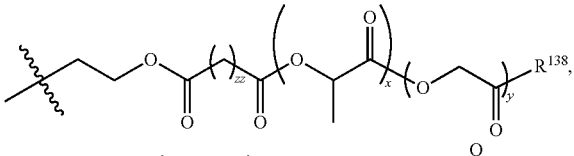
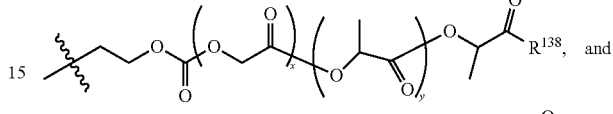
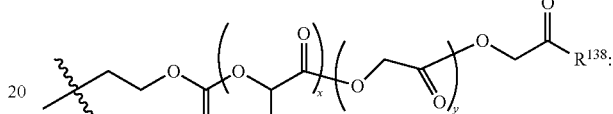
and
or $R^{336}$ is
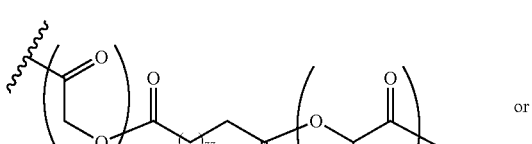
or
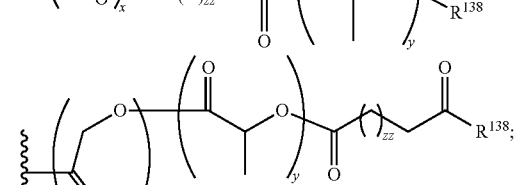
wherein all other variables are as defined herein.
In one embodiment, $R^{141}$ is $OCH_3$.
In one embodiment, $R^{301}$ is selected from $—N(CH_3)_2$,
, 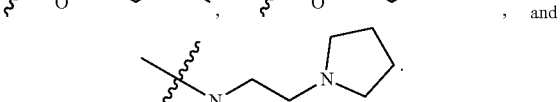, and
In one embodiment, $R^{301}$ is
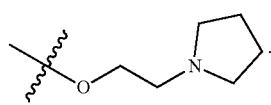

In one embodiment, $R^{301}$ is —OCH$_3$.
In one embodiment, $R^{301}$ is selected from F and Cl.
In one embodiment, $R^{304}$ is hydrogen.
In one embodiment, $R^{304}$ is CH$_3$.
In one embodiment, $R^{304}$ is CH$_2$H$_5$.
In one embodiment, $R^{303}$ is

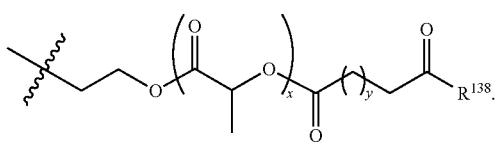

In one embodiment, $R^{303}$ is

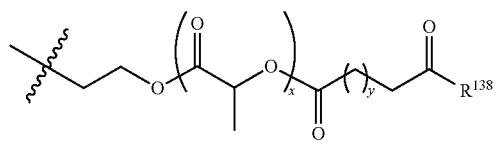

and $R^{138}$ is

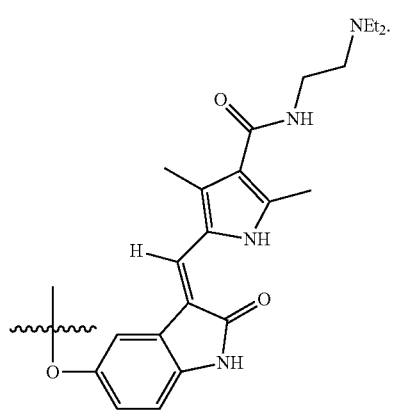

In one embodiment, $R^{303}$ is

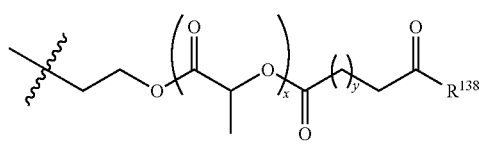

$R^{138}$ is

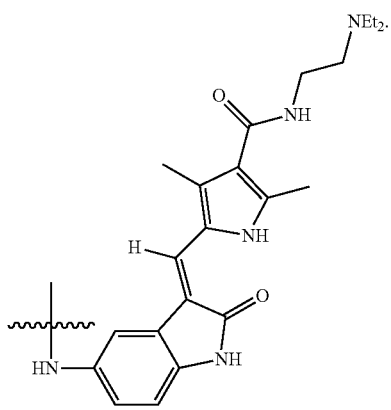

In a further embodiment, x is 2 and y is 2.

Non-limiting Examples of Formula LII and Formula LIII include

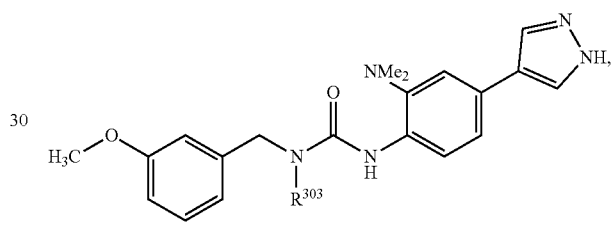

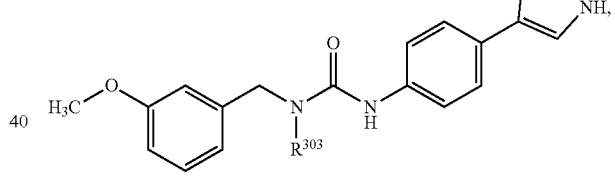

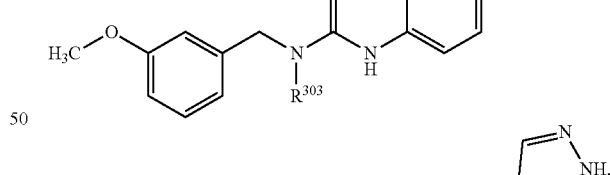

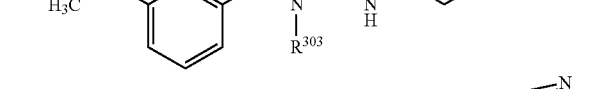

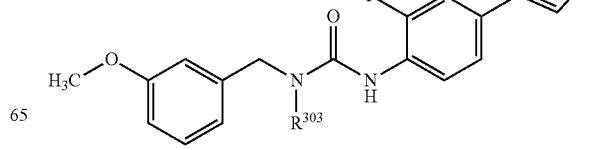

-continued
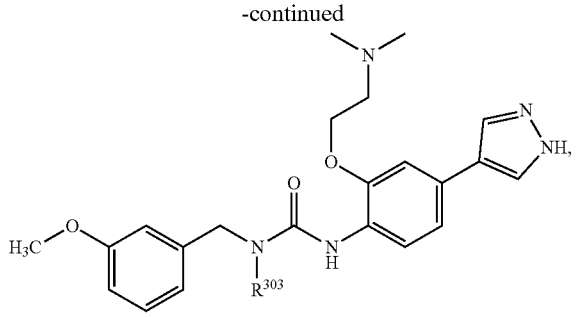
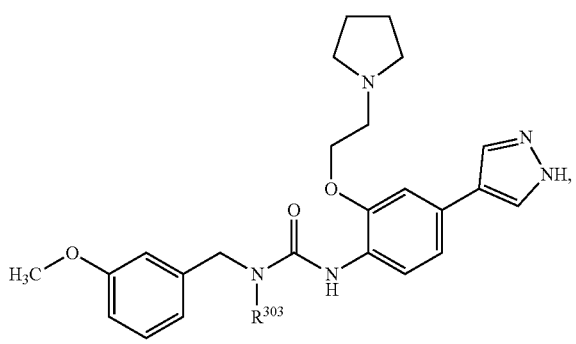
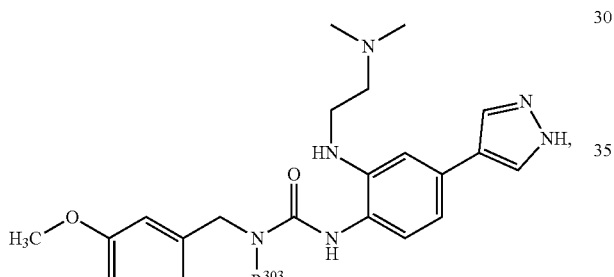
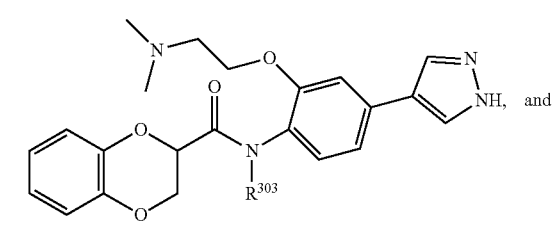
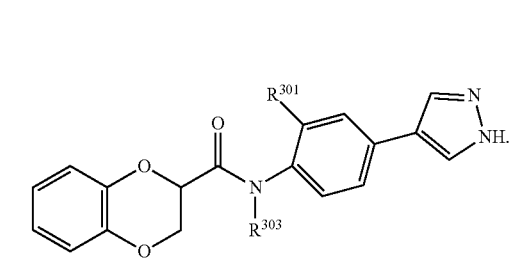
In an alternative embodiment, this disclosure provides prodrugs of Formula (LIV):
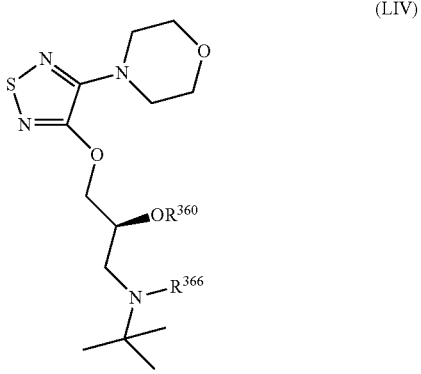
(LIV)
or a pharmaceutically acceptable composition, salt, or isotopic derivative thereof
wherein
$R^{366}$ is selected from
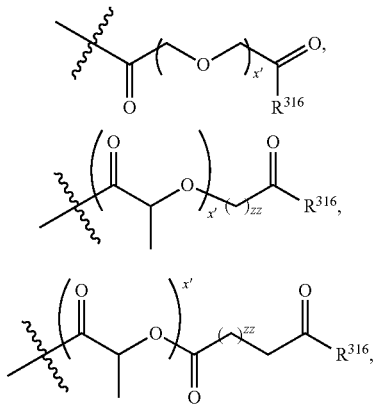
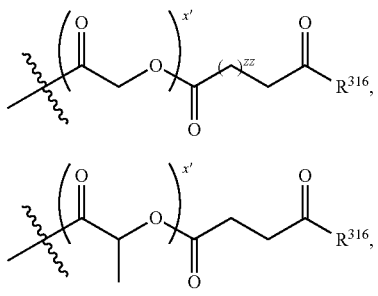
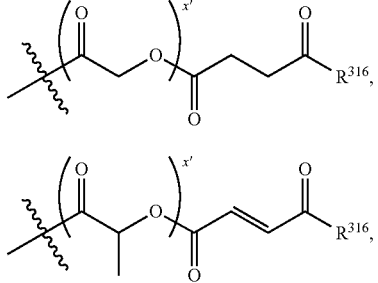

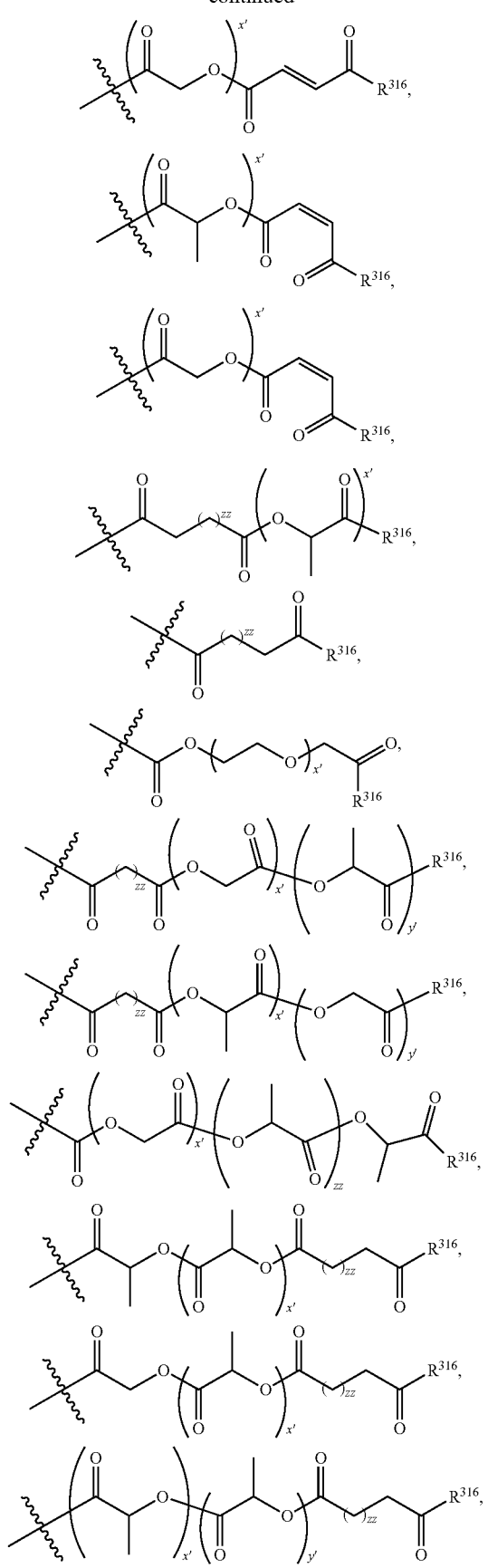
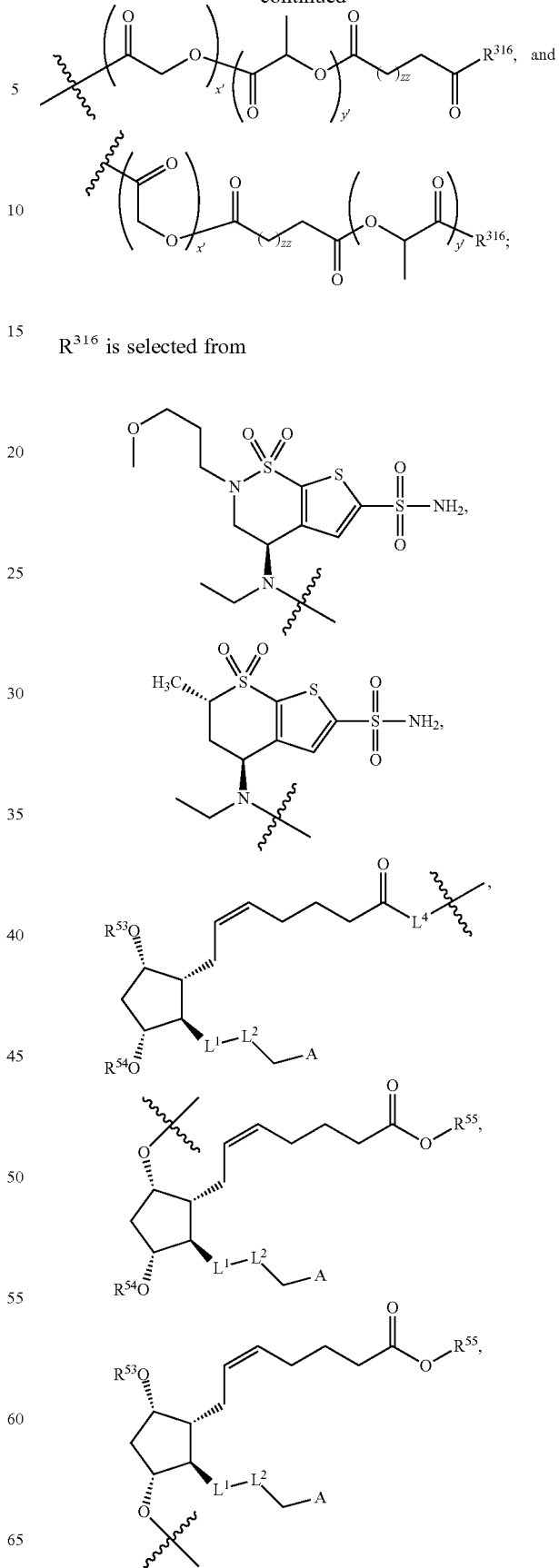
R³¹⁶ is selected from

219
-continued
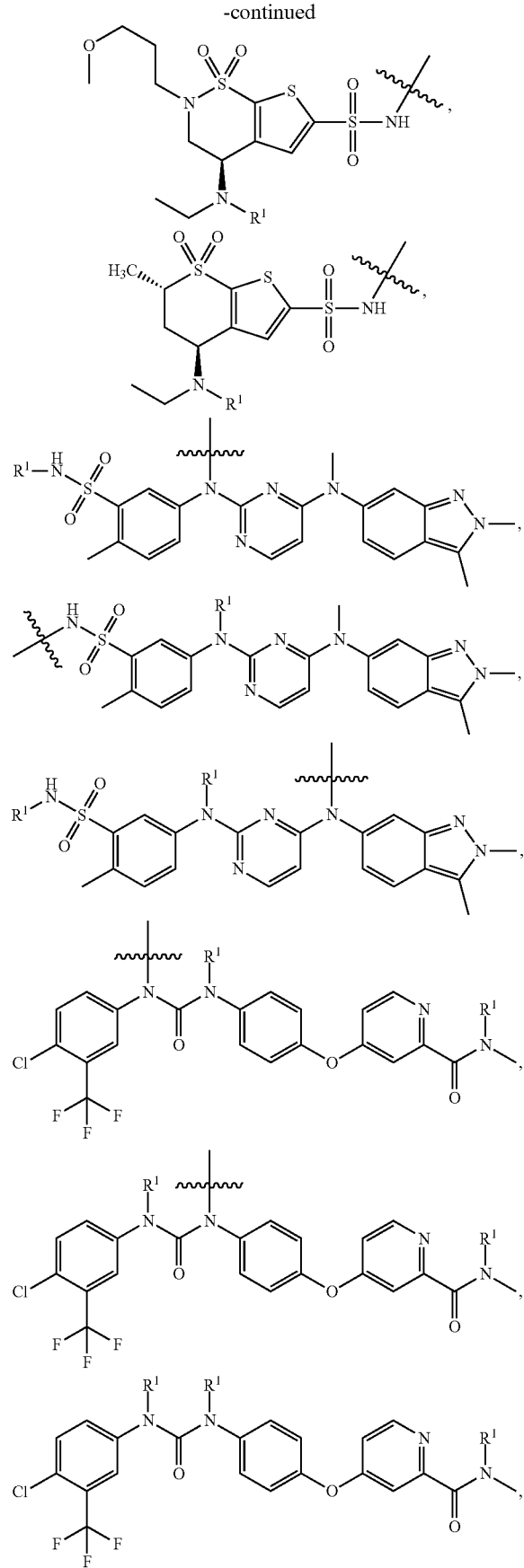
220
-continued
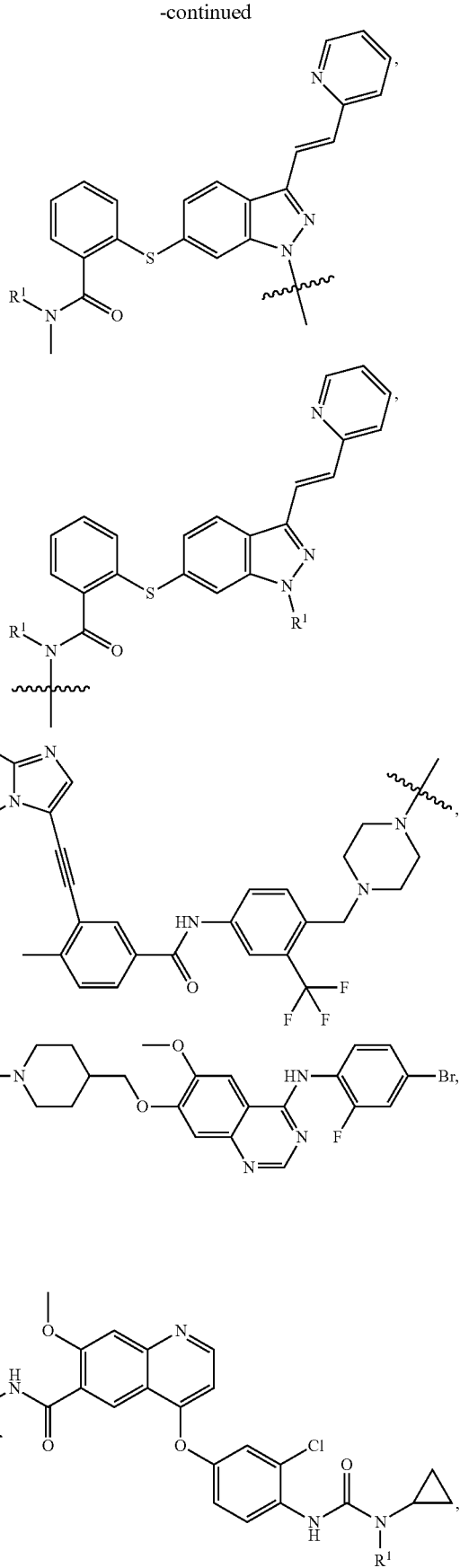

221
-continued
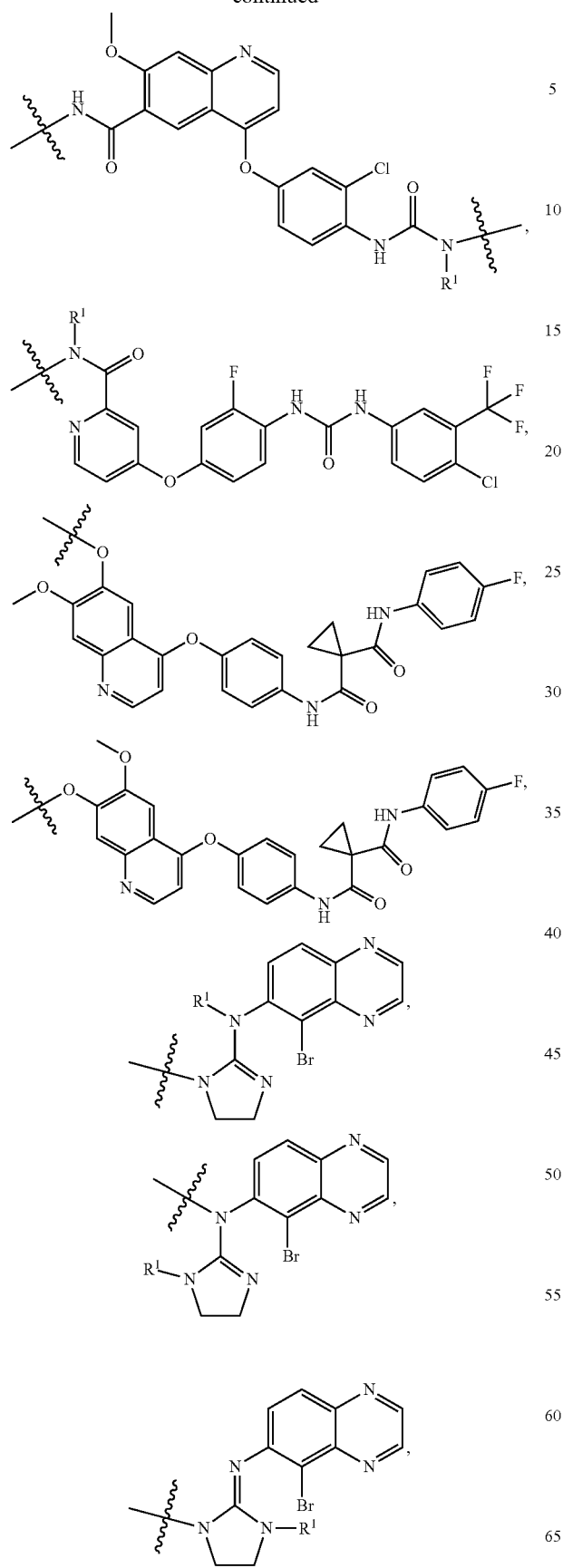
222
-continued
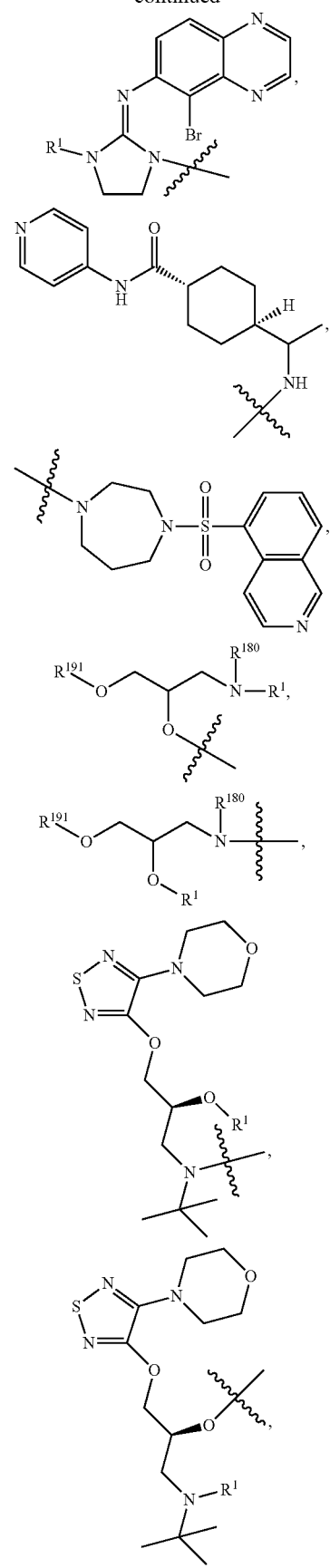

-continued
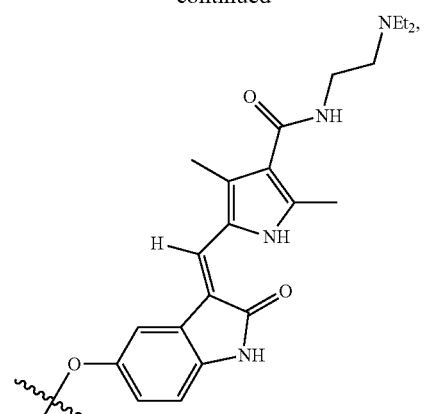
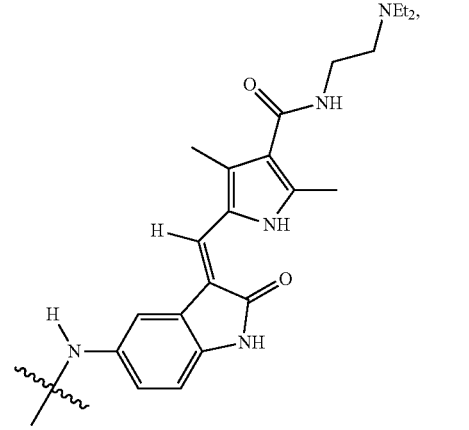
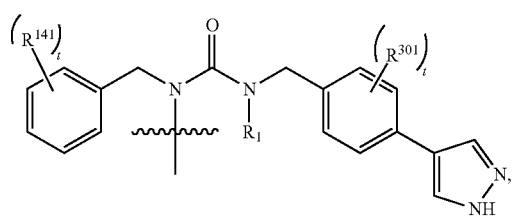
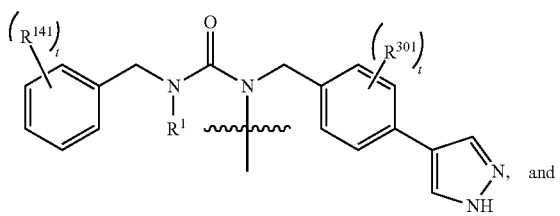
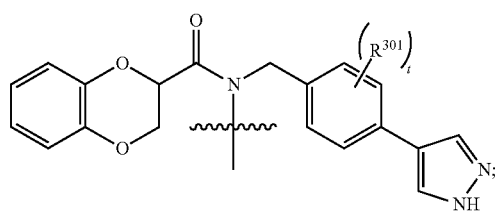
and
wherein all other variables are as defined herein.
In one embodiment, $R^{360}$ is
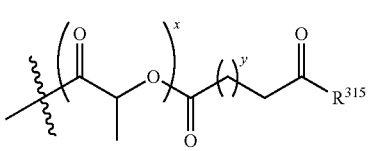
and $R^{366}$ is
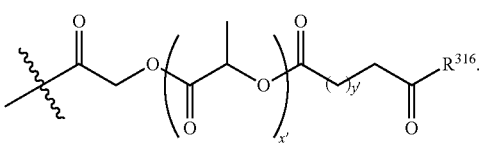
In one embodiment, $R^{360}$ is
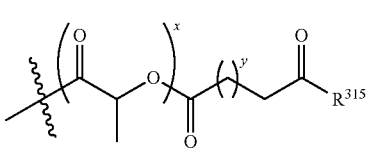
and $R^{366}$ is
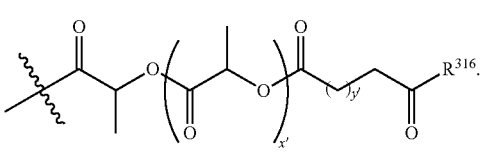
In one embodiment, $R^{360}$ is
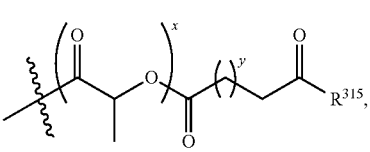
x is 1, 2, 3, or 4, and y is 1, 2, 3, or 4.
In one embodiment, $R^{366}$ is
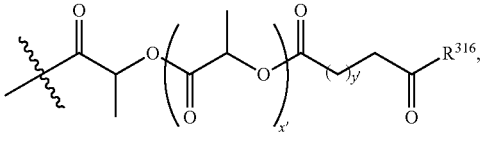
and x' and y' are independently selected from an integer between 0 and 4.

In one embodiment, $R^{360}$ is
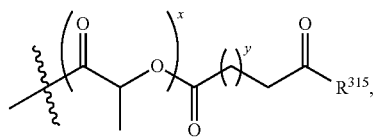
$R^{366}$
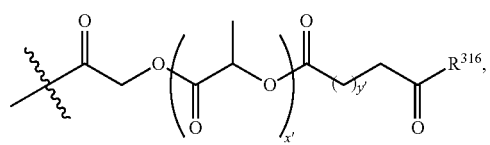
$R^{315}$ is
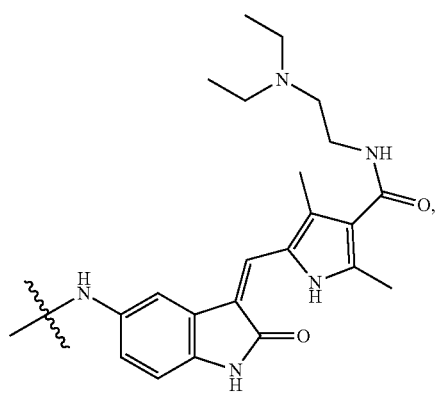 [SMILES: *Nc1ccc2c(c1)/C(=C/c1[nH]c(C)c(C(=O)NCCN(CC)CC)c1C)C(=O)N2]
and $R^{316}$ is
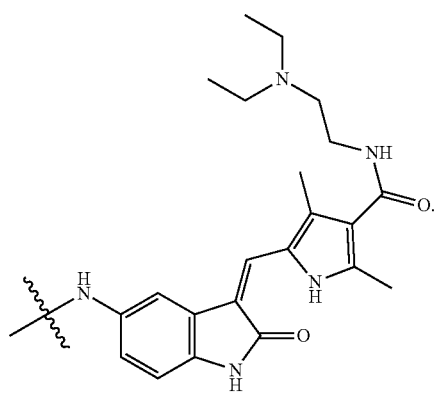 [SMILES: *Nc1ccc2c(c1)/C(=C/c1[nH]c(C)c(C(=O)NCCN(CC)CC)c1C)C(=O)N2]
In one embodiment, $R^{360}$ is
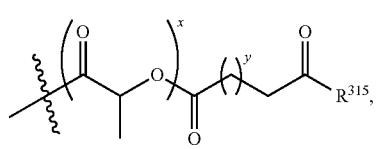
$R^{366}$ is
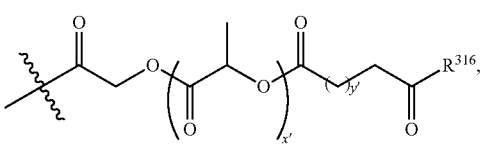
$R^{315}$ is
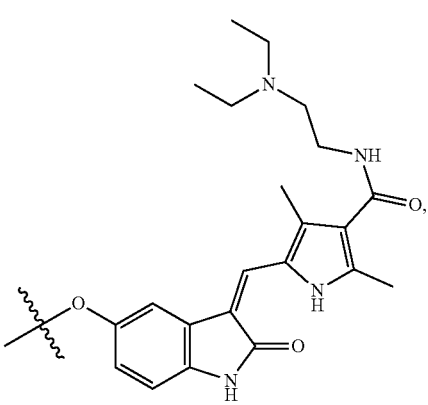 [SMILES: *Oc1ccc2c(c1)/C(=C/c1[nH]c(C)c(C(=O)NCCN(CC)CC)c1C)C(=O)N2]
and $R^{316}$ is
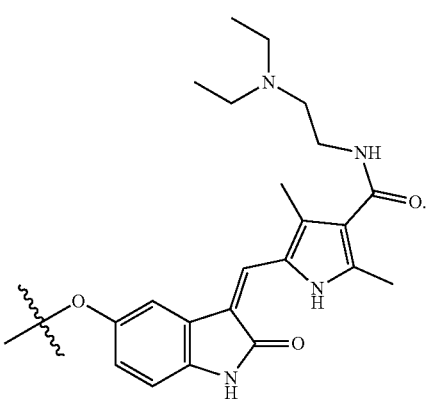 [SMILES: *Oc1ccc2c(c1)/C(=C/c1[nH]c(C)c(C(=O)NCCN(CC)CC)c1C)C(=O)N2]
Non-limiting Examples of Compounds of Formula (LIV) include:
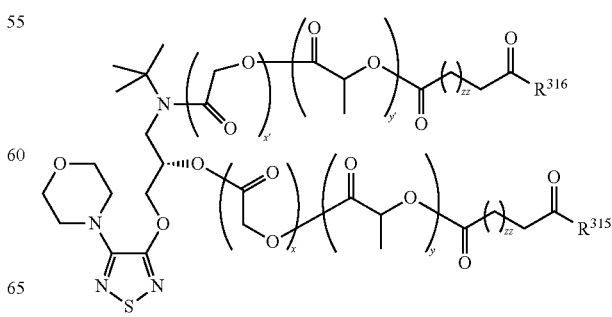

227
-continued
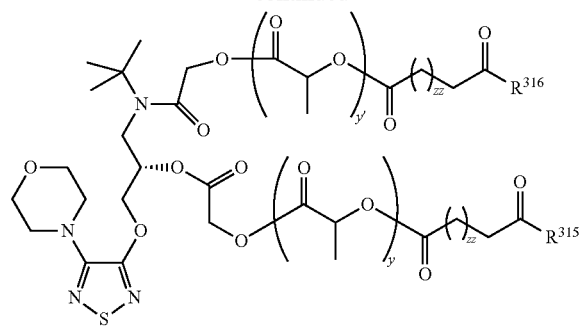
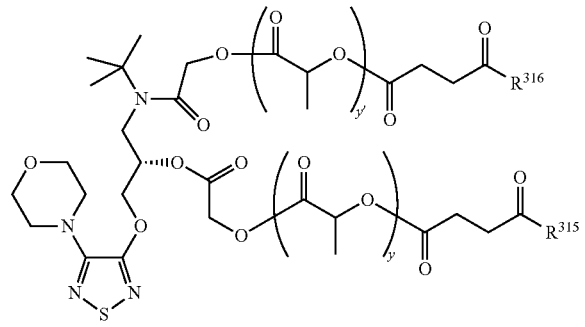
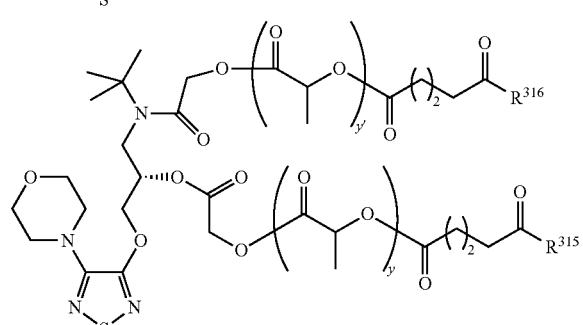
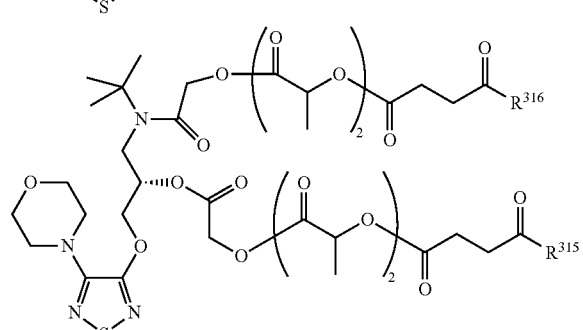
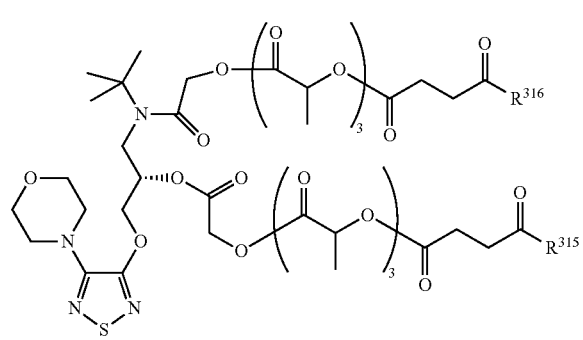
228
-continued
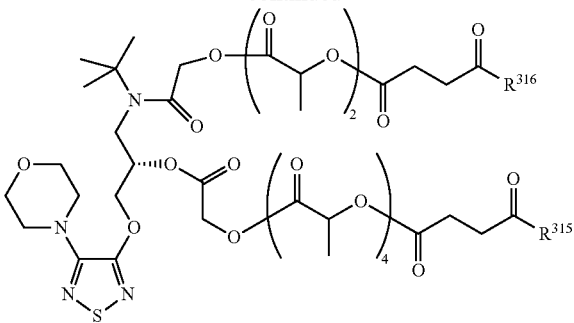
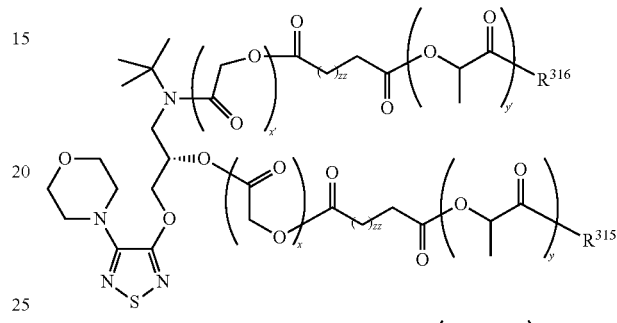
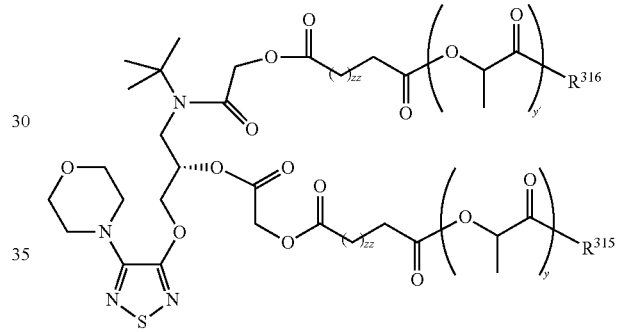
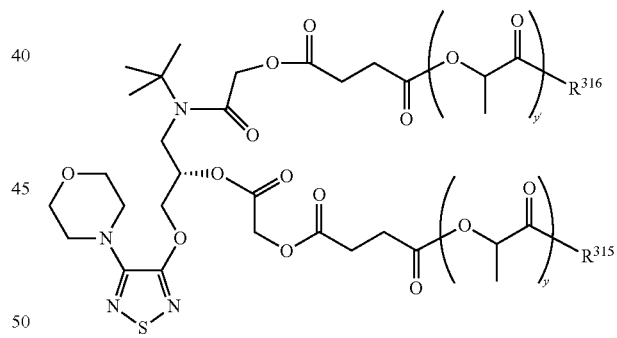
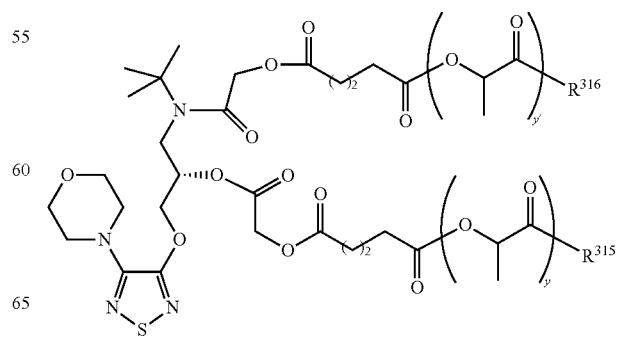

-continued

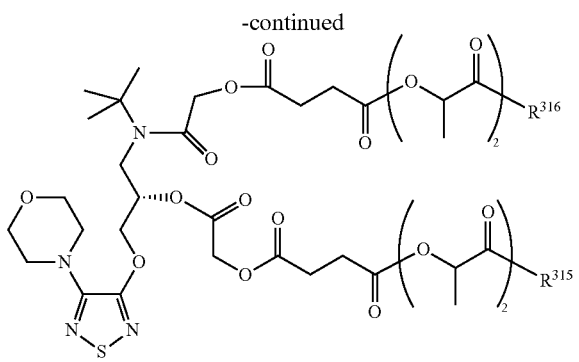

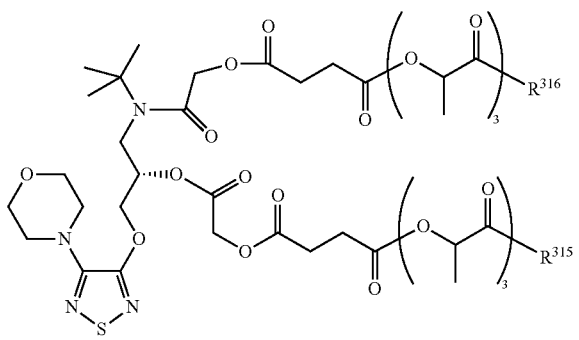

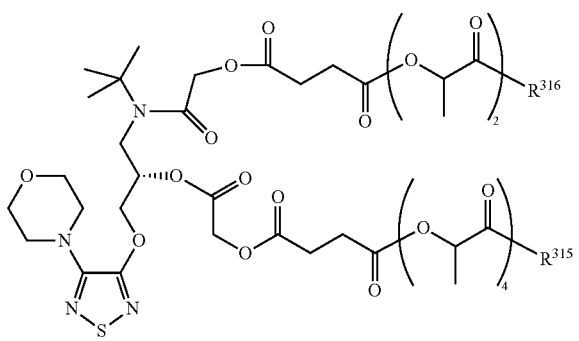

In certain embodiments of Formula LIV, x and x' are independently selected from 1, 2, 3, 4, 5, or 6; y and y' are independently selected from 1, 2, 3, 4, 5, or 6; and zz in at least one instance is selected from 1, 2, or 3.

In certain embodiments of Formula LIV, x and x' are independently selected from 1, 2, or 3; y and y' are independently selected from 1, 2, or 3; and zz in at least one instance is selected from 1, 2, or 3.

In certain embodiments of Formula LIV, x and x' are independently selected from 1, 2, or 3; y and y' are independently selected from 1, 2, or 3; and zz in at least one instance is 1.

In certain embodiments of Formula LIV, x and x' are independently selected from 1, 2, or 3; y and y' are independently selected from 1, 2, or 3; and zz in at least one instance is 2.

In certain embodiments of Formula LIV, x and x' are independently selected from 1, 2, or 3; y and y' are independently selected from 1, 2, or 3; and zz in at least one instance is 3.

In certain embodiments of Formula LIV, x and x' are 1; y and y' are independently selected from 1, 2, or 3; and zz in at least one instance is selected from 1, 2, or 3.

In certain embodiments of Formula LIV, x and x' are 2; y and y' are independently selected from 1, 2, or 3; and zz in at least one instance is selected from 1, 2, or 3.

In certain embodiments of Formula LIV, x and x' are 3; y and y' are independently selected from 1, 2, or 3; and zz in at least one instance is selected from 1, 2, or 3.

In certain embodiments of Formula LIV, x and x' are independently selected from 1, 2, or 3; y and y' are 1; and zz in at least one instance is selected from 1, 2, or 3.

In certain embodiments of Formula LIV, x and x' are independently selected from 1, 2, or 3; y and y' are 2; and zz in at least one instance is selected from 1, 2, or 3.

In certain embodiments of Formula LIV, x and x' are independently selected from 1, 2, or 3; y and y' are 3; and zz in at least one instance is selected from 1, 2, or 3.

Additional compounds of the present invention include:

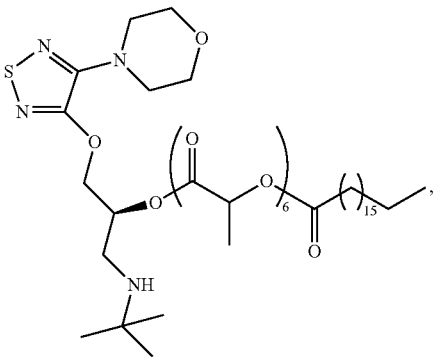

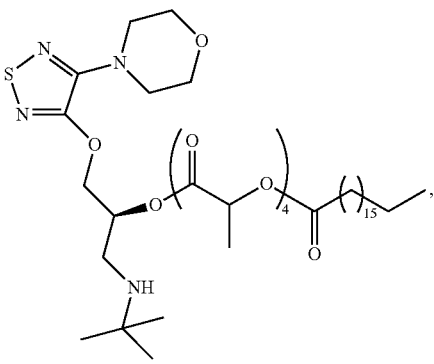

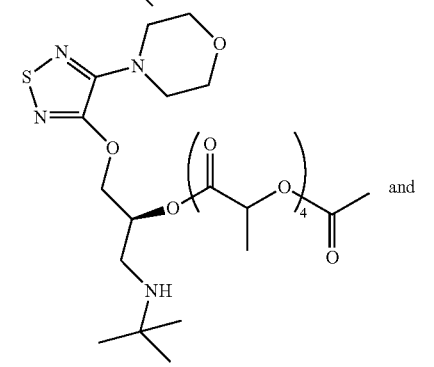

and

-continued

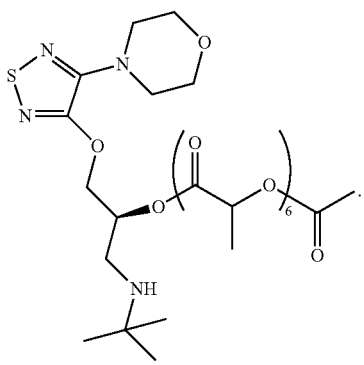

In one embodiment of any of the above formulas a

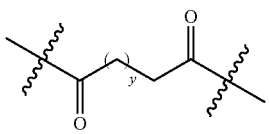

subunit is replaced with

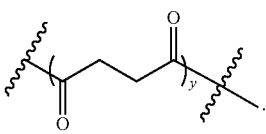

In one embodiment of any of the above formulas a

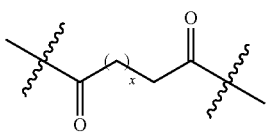

subunit is replaced with

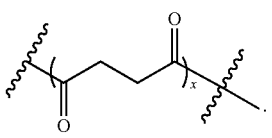

In an alternative embodiment, a

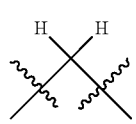 [SMILES: *C*]

moiety in an R group that can be substituted with $R^5$ as defined herein is instead substituted with oxo to form

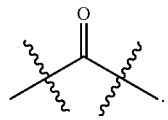 [SMILES: *C(*)=O]

Pharmaceutical compositions comprising a compound or salt of Formula I, Formula II, Formula III, Formula IV, Formula V, Formula V', Formula VI, Formula VI', Formula VII, Formula VIII, Formula IX, Formula IX', Formula X, Formula X', Formula XI, Formula XII, Formula XIII, Formula XIV, Formula XV, Formula XV', Formula XV'', Formula XVI, Formula XVII, Formula XVII', Formula XVII'', Formula XVII''', Formula XVIII, Formula XVIII', Formula XIX, Formula XIX', Formula XX, Formula XXI, Formula XXII, Formula XXIII, Formula XXIV, Formula XV, Formula XVI, Formula XVII, Formula XVIII, Formula XXIX, Formula XXX, Formula XXXI, Formula XXXII, Formula XXXIII, Formula XXXIV, Formula XXXV, Formula XXXVI, Formula XXXVII, Formula XXXVIII, Formula XXXIX, Formula XL, Formula XLI, Formula XLII, Formula XLIII, Formula XLIV, Formula XLV, Formula XLVI, Formula XLVII, Formula XLVIII, Formula XLIX, Formula L, Formula LI, Formula LII, Formula LIII, or Formula LIV together with a pharmaceutically acceptable carrier are also disclosed.

Methods of treating or preventing ocular disorders, including glaucoma, a disorder mediated by carbonic anhydrase, a disorder mediated by a Rho-associated kinase, a disorder mediated by a dual leucine zipper kinase, a disorder mediated by an α2 adrenergic receptor, a disorder mediated a disorder or abnormality related to an increase in intraocular pressure (IOP), a disorder mediated by nitric oxide synthase (NOS), a disorder requiring neuroprotection such as to regenerate/repair optic nerves, allergic conjunctivitis, anterior uveitis, cataracts, dry or wet age-related macular degeneration (AMD), geographic atrophy, or diabetic retinopathy are disclosed comprising administering a therapeutically effective amount of a compound or salt or Formula I, Formula II, Formula III, Formula IV, Formula V, Formula V', Formula VI, Formula VI', Formula VII, Formula VIII, Formula IX, Formula IX', Formula X, Formula X', Formula XI, Formula XII, Formula XIII, Formula XIV, Formula XV, Formula XV', Formula XV'', Formula XVI, Formula XVII, Formula XVII', Formula XVII'', Formula XVII''', Formula XVIII, Formula XVIII', Formula XIX, Formula XIX', Formula XX, Formula XXI, Formula XXII, Formula XXIII, Formula XXIV, Formula XV, Formula XVI, Formula XVII, Formula XVIII, Formula XXIX, Formula XXX, Formula XXXI, Formula XXXII, Formula XXXIII, Formula XXXIV, Formula XXXV, Formula XXXVI, Formula XXXVII, Formula XXXVIII, Formula XXXIX, Formula XL, Formula XLI, Formula XLII, Formula XLIII, Formula XLIV, Formula XLV, Formula XLVI, Formula XLVII, Formula XLVIII, Formula XLIX, Formula L, Formula LI, Formula LII, Formula LIII, or Formula LIV to a host, including a human, in need of such treatment.

In another embodiment, an effective amount of a compound of Formula I, Formula II, Formula III, Formula IV, Formula V, Formula V', Formula VI, Formula VI', Formula VII, Formula VIII, Formula IX, Formula IX', Formula X, Formula X', Formula XI, Formula XII, Formula XIII, Formula XIV, Formula XV, Formula XV', Formula XV'', Formula XVI, Formula XVII, Formula XVII', Formula XVII", Formula XVII''', Formula XVIII, Formula XVIII', Formula XIX, Formula XIX', Formula XX, Formula XXI, Formula XXII, Formula XXIII, Formula XXIV, Formula XV, Formula XVI, Formula XVII, Formula XVIII, Formula XXIX, Formula XXX, Formula XXXI, Formula XXXII, Formula XXXIII, Formula XXXIV, Formula XXXV, Formula XXXVI, Formula XXXVII, Formula XXXVIII, Formula XXXIX, Formula XL, Formula XLI, Formula XLII, Formula XLIII, Formula XLIV, Formula XLV, Formula XLVI, Formula XLVII, Formula XLVIII, Formula XLIX, Formula L, Formula LI, Formula LII, Formula LIII, or Formula LIV is provided to decrease intraocular pressure (IOP) caused by glaucoma. In an alternative embodiment, the compound of Formula I, Formula II, Formula III, Formula IV, Formula V, Formula V', Formula VI, Formula VI', Formula VII, Formula VIII, Formula IX, Formula IX', Formula X, Formula X', Formula XI, Formula XII, Formula XIII, Formula XIV, Formula XV, Formula XV', Formula XV", Formula XVI, Formula XVII, Formula XVII', Formula XVII", Formula XVII''', Formula XVIII, Formula XVIII', Formula XIX, Formula XIX', Formula XX, Formula XXI, Formula XXII, Formula XXIII, Formula XXIV, Formula XV, Formula XVI, Formula XVII, Formula XVIII, Formula XXIX, Formula XXX, Formula XXXI, Formula XXXII, Formula XXXIII, Formula XXXIV, Formula XXXV, Formula XXXVI, Formula XXXVII, Formula XXXVIII, Formula XXXIX, Formula XL, Formula XLI, Formula XLII, Formula XLIII, Formula XLIV, Formula XLV, Formula XLVI, Formula XLVII, Formula XLVIII, Formula XLIX, Formula L, Formula LI, Formula LII, Formula LIII, or Formula LIV be used to decrease intraocular pressure (IOP), regardless of whether it is associated with glaucoma.

In one embodiment, the disorder is associated with an increase in intraocular pressure (IOP) caused by potential or previously poor patient compliance to glaucoma treatment. In yet another embodiment, the disorder is associated with potential or poor neuroprotection through neuronal nitric oxide synthase (NOS). The active compound or its salt or prodrug provided herein may thus dampen or inhibit glaucoma in a host, by administration of an effective amount in a suitable manner to a host, typically a human, in need thereof.

Methods for the treatment of a disorder associated with glaucoma, increased intraocular pressure (IOP), and optic nerve damage caused by either high intraocular pressure (IOP) or neuronal nitric oxide synthase (NOS) are provided that includes the administration of an effective amount of a compound Formula I, Formula II, Formula III, Formula IV, Formula V, Formula V', Formula VI, Formula VI', Formula VII, Formula VIII, Formula IX, Formula IX', Formula X, Formula X', Formula XI, Formula XII, Formula XIII, Formula XIV, Formula XV, Formula XV', Formula XV", Formula XVI, Formula XVII, Formula XVII', Formula XVII", Formula XVII''', Formula XVIII, Formula XVIII', Formula XIX, Formula XIX', Formula XX, Formula XXI, Formula XXII, Formula XXIII, Formula XXIV, Formula XV, Formula XVI, Formula XVII, Formula XVIII, Formula XXIX, Formula XXX, Formula XXXI, Formula XXXII, Formula XXXIII, Formula XXXIV, Formula XXXV, Formula XXXVI, Formula XXXVII, Formula XXXVIII, Formula XXXIX, Formula XL, Formula XLI, Formula XLII, Formula XLIII, Formula XLIV, Formula XLV, Formula XLVI, Formula XLVII, Formula XLVIII, Formula XLIX, Formula L, Formula LI, Formula LII, Formula LIII, or Formula LIV or a pharmaceutically acceptable salt thereof, optionally in a pharmaceutically acceptable carrier are also disclosed.

Methods for the treatment of a disorder associated with age-related macular degeneration (AMD) and geographic atrophy are provided that includes the administration of an effective amount of a compound Formula I, Formula II, Formula III, Formula IV, Formula V, Formula V', Formula VI, Formula VI', Formula VII, Formula VIII, Formula IX, Formula IX', Formula X, Formula X', Formula XI, Formula XII, Formula XIII, Formula XIV, Formula XV, Formula XV', Formula XV", Formula XVI, Formula XVII, Formula XVII', Formula XVII", Formula XVII''', Formula XVIII, Formula XVIII', Formula XIX, Formula XIX', Formula XX, Formula XXI, Formula XXII, Formula XXIII, Formula XXIV, Formula XV, Formula XVI, Formula XVII, Formula XVIII, Formula XXIX, Formula XXX, Formula XXXI, Formula XXXII, Formula XXXIII, Formula XXXIV, Formula XXXV, Formula XXXVI, Formula XXXVII, Formula XXXVIII, Formula XXXIX, Formula XL, Formula XLI, Formula XLII, Formula XLIII, Formula XLIV, Formula XLV, Formula XLVI, Formula XLVII, Formula XLVIII, Formula XLIX, Formula L, Formula LI, Formula LII, Formula LIII, or Formula LIV or a pharmaceutically acceptable salt thereof, optionally in a pharmaceutically acceptable carrier are also disclosed.

Methods for treatment of a disorder mediated by a carbonic anhydrase are provided to treat a patient in need thereof wherein a prodrug of a carbonic anhydrase inhibitor as described herein is provided.

Methods for treatment of a disorder mediated by a Rho-associated kinase are provided to treat a patient in need thereof wherein a prodrug of a Rho-associated kinase inhibitor as described herein is provided.

Methods for treatment of a disorder mediated by a beta-blocker are provided to treat a patient in need thereof wherein a prodrug of a beta blocker as described herein is provided.

Methods for treatment of a disorder mediated by a dual leucine zipper kinase are provided to treat a patient in need thereof wherein a prodrug of a dual leucine zipper kinase inhibitor as described herein is provided.

Methods for treatment of a disorder mediated by a $\alpha_2$ adrenergic are provided to treat a patient in need thereof also disclosed wherein a prodrug of a $\alpha_2$ adrenergic agonist as described herein is provided.

The present invention includes at least the following features:

(a) a compound of Formula I, Formula II, Formula III, Formula IV, Formula V, Formula V', Formula VI, Formula VI', Formula VII, Formula VIII, Formula IX, Formula IX', Formula X, Formula X', Formula XI, Formula XII, Formula XIII, Formula XIV, Formula XV, Formula XV', Formula XV", Formula XVI, Formula XVII, Formula XVII', Formula XVII", Formula XVII''', Formula XVIII, Formula XVIII', Formula XIX, Formula XIX', Formula XX, Formula XXI, Formula XXII, Formula XXIII, Formula XXIV, Formula XV, Formula XVI, Formula XVII, Formula XVIII, Formula XXIX, Formula XXX, Formula XXXI, Formula XXXII, Formula XXXIII, Formula XXXIV, Formula XXXV, Formula XXXVI, Formula XXXVII, Formula XXXVIII, Formula XXXIX, Formula XL, Formula XLI, Formula XLII, Formula XLIII, Formula XLIV, Formula XLV, Formula XLVI, Formula XLVII, Formula XLVIII, Formula XLIX, Formula L, Formula LI, Formula LII, Formula LIII, or Formula LIV as described herein, or a pharmaceutically acceptable salt or prodrug thereof (each of which and all subgenuses and species thereof are considered individually and specifically described);

(b) a compound of Formula I, Formula II, Formula III, Formula IV, Formula V, Formula V', Formula VI, Formula VI', Formula VII, Formula VIII, Formula IX, Formula IX', Formula X, Formula X', Formula XI, Formula XII, Formula XIII, Formula XIV, Formula XV, Formula XV', Formula XV", Formula XVI, Formula XVII, Formula XVII', Formula XVII", Formula XVII''', Formula XVIII, Formula XVIII', Formula XIX, Formula XIX', Formula XX, Formula XXI, Formula XXII, Formula XXIII, Formula XXIV, Formula XV, Formula XVI, Formula XVII, Formula XVIII, Formula XXIX, Formula XXX, Formula XXXI, Formula XXXII, Formula XXXIII, Formula XXXIV, Formula XXXV, Formula XXXVI, Formula XXXVII, Formula XXXVIII, Formula XXXIX, Formula XL, Formula XLI, Formula XLII, Formula XLIII, Formula XLIV, Formula XLV, Formula XLVI, Formula XLVII, Formula XLVIII, Formula XLIX, Formula L, Formula LI, Formula LII, Formula LIII, or Formula LIV as described herein, or a pharmaceutically acceptable salt or prodrug thereof, for use in treating or preventing an ocular disorder as further described herein;

(c) a compound of Formula I, Formula II, Formula III, Formula IV, Formula V, Formula V', Formula VI, Formula VI', Formula VII, Formula VIII, Formula IX, Formula IX', Formula X, Formula X', Formula XI, Formula XII, Formula XIII, Formula XIV, Formula XV, Formula XV', Formula XV", Formula XVI, Formula XVII, Formula XVII', Formula XVII", Formula XVII''', Formula XVIII, Formula XVIII', Formula XIX, Formula XIX', Formula XX, Formula XXI, Formula XXII, Formula XXIII, Formula XXIV, Formula XV, Formula XVI, Formula XVII, Formula XVIII, Formula XXIX, Formula XXX, Formula XXXI, Formula XXXII, Formula XXXIII, Formula XXXIV, Formula XXXV, Formula XXXVI, Formula XXXVII, Formula XXXVIII, Formula XXXIX, Formula XL, Formula XLI, Formula XLII, Formula XLIII, Formula XLIV, Formula XLV, Formula XLVI, Formula XLVII, Formula XLVIII, Formula XLIX, Formula L, Formula LI, Formula LII, Formula LIII, or Formula LIV as described herein, or a pharmaceutically acceptable salt or prodrug thereof for use in treating or preventing disorders related to an ocular disorder such as glaucoma, a disorder mediated by carbonic anhydrase, a disorder or abnormality related to an increase in intraocular pressure (IOP), a disorder mediated by nitric oxide synthase (NOS), a disorder requiring neuroprotection such as to regenerate/repair optic nerves, allergic conjunctivitis, anterior uveitis, cataracts, dry or wet age-related macular degeneration (AMD), geographic atrophy or diabetic retinopathy;

(d) use of a compound of Formula I, Formula II, Formula III, Formula IV, Formula V, Formula V', Formula VI, Formula VI', Formula VII, Formula VIII, Formula IX, Formula IX', Formula X, Formula X', Formula XI, Formula XII, Formula XIII, Formula XIV, Formula XV, Formula XV', Formula XV", Formula XVI, Formula XVII, Formula XVII', Formula XVII", Formula XVII''', Formula XVIII, Formula XVIII', Formula XIX, Formula XIX', Formula XX, Formula XXI, Formula XXII, Formula XXIII, Formula XXIV, Formula XV, Formula XVI, Formula XVII, Formula XVIII, Formula XXIX, Formula XXX, Formula XXXI, Formula XXXII, Formula XXXIII, Formula XXXIV, Formula XXXV, Formula XXXVI, Formula XXXVII, Formula XXXVIII, Formula XXXIX, Formula XL, Formula XLI, Formula XLII, Formula XLIII, Formula XLIV, Formula XLV, Formula XLVI, Formula XLVII, Formula XLVIII, Formula XLIX, Formula L, Formula LI, Formula LII, Formula LIII, or Formula LIV or a pharmaceutically acceptable salt or prodrug thereof in the manufacture of a medicament for use in treating or preventing glaucoma and disorders involving increased intraocular pressure (IOP) or nerve damage related to either IOP or nitric oxide synthase (NOS) and other disorders described further herein;

(e) use of a compound of Formula I, Formula II, Formula III, Formula IV, Formula V, Formula V', Formula VI, Formula VI', Formula VII, Formula VIII, Formula IX, Formula IX', Formula X, Formula X', Formula XI, Formula XII, Formula XIII, Formula XIV, Formula XV, Formula XV', Formula XV", Formula XVI, Formula XVII, Formula XVII', Formula XVII", Formula XVII''', Formula XVIII, Formula XVIII', Formula XIX, Formula XIX', Formula XX, Formula XXI, Formula XXII, Formula XXIII, Formula XXIV, Formula XV, Formula XVI, Formula XVII, Formula XVIII, Formula XXIX, Formula XXX, Formula XXXI, Formula XXXII, Formula XXXIII, Formula XXXIV, Formula XXXV, Formula XXXVI, Formula XXXVII, Formula XXXVIII, Formula XXXIX, Formula XL, Formula XLI, Formula XLII, Formula XLIII, Formula XLIV, Formula XLV, Formula XLVI, Formula XLVII, Formula XLVIII, Formula XLIX, Formula L, Formula LI, Formula LII, Formula LIII, or Formula LIV or a pharmaceutically acceptable salt or prodrug thereof in the manufacture of a medicament for use in treating or preventing age-related macular degeneration (AMD) and other disorders described further herein;

(f) a process for manufacturing a medicament intended for the therapeutic use for treating or preventing glaucoma and disorders involving nerve damage related to both (IOP) and nitric oxide synthase (NOS) and other disorders described further herein characterized in that a compound of Formula I, Formula II, Formula III, Formula IV, Formula V, Formula V', Formula VI, Formula VI', Formula VII, Formula VIII, Formula IX, Formula IX', Formula X, Formula X', Formula XI, Formula XII, Formula XIII, Formula XIV, Formula XV, Formula XV', Formula XV", Formula XVI, Formula XVII, Formula XVII', Formula XVII", Formula XVII''', Formula XVIII, Formula XVIII', Formula XIX, Formula XIX', Formula XX, Formula XXI, Formula XXII, Formula XXIII, Formula XXIV, Formula XV, Formula XVI, Formula XVII, Formula XVIII, Formula XXIX, Formula XXX, Formula XXXI, Formula XXXII, Formula XXXIII, Formula XXXIV, Formula XXXV, Formula XXXVI, Formula XXXVII, Formula XXXVIII, Formula XXXIX, Formula XL, Formula XLI, Formula XLII, Formula XLIII, Formula XLIV, Formula XLV, Formula XLVI, Formula XLVII, Formula XLVIII, Formula XLIX, Formula L, Formula LI, Formula LII, Formula LIII, or Formula LIV as described herein is used in the manufacture;

(g) a pharmaceutical formulation comprising an effective host-treating amount of the a compound of Formula I, Formula II, Formula III, Formula IV, Formula V, Formula V', Formula VI, Formula VI', Formula VII, Formula VIII, Formula IX, Formula IX', Formula X, Formula X', Formula XI, Formula XII, Formula XIII, Formula XIV, Formula XV, Formula XV', Formula XV", Formula XVI, Formula XVII, Formula XVII', Formula XVII", Formula XVII''', Formula XVIII, Formula XVIII', Formula XIX, Formula XIX', Formula XX, Formula XXI, Formula XXII, Formula XXIII, Formula XXIV, Formula XV, Formula XVI, Formula XVII, Formula XVIII, Formula XXIX, Formula XXX, Formula XXXI, Formula XXXII, Formula XXXIII, Formula XXXIV, Formula XXXV, Formula XXXVI, Formula XXXVII, Formula XXXVIII, Formula XXXIX, Formula XL, Formula XLI, Formula XLII, Formula XLIII, Formula XLIV, Formula XLV, Formula XLVI, Formula XLVII, Formula XLVIII, Formula XLIX, Formula L, Formula LI, Formula LII, Formula LIII, or Formula LIV or a pharmaceutically acceptable salt or prodrug thereof together with a pharmaceutically acceptable carrier or diluent;

(h) a compound of Formula I, Formula II, Formula III, Formula IV, Formula V, Formula V', Formula VI, Formula VI', Formula VII, Formula VIII, Formula IX, Formula IX', Formula X, Formula X', Formula XI, Formula XII, Formula XIII, Formula XIV, Formula XV, Formula XV', Formula XV", Formula XVI, Formula XVII, Formula XVII', Formula XVII", Formula XVII''', Formula XVIII, Formula XVIII', Formula XIX, Formula XIX', Formula XX, Formula XXI, Formula XXII, Formula XXIII, Formula XXIV, Formula XV, Formula XVI, Formula XVII, Formula XVIII, Formula XXIX, Formula XXX, Formula XXXI, Formula XXXII, Formula XXXIII, Formula XXXIV, Formula XXXV, Formula XXXVI, Formula XXXVII, Formula XXXVIII, Formula XXXIX, Formula XL, Formula XLI, Formula XLII, Formula XLIII, Formula XLIV, Formula XLV, Formula XLVI, Formula XLVII, Formula XLVIII, Formula XLIX, Formula L, Formula LI, Formula LII, Formula LIII, or Formula LIV as described herein in substantially pure form, (e.g., at least 90 or 95%);

(i) processes for the manufacture of a compound of Formula I, Formula II, Formula III, Formula IV, Formula V, Formula V', Formula VI, Formula VI', Formula VII, Formula VIII, Formula IX, Formula IX', Formula X, Formula X', Formula XI, Formula XII, Formula XIII, Formula XIV, Formula XV, Formula XV', Formula XV", Formula XVI, Formula XVII, Formula XVII', Formula XVII", Formula XVII''', Formula XVIII, Formula XVIII', Formula XIX, Formula XIX', Formula XX, Formula XXI, Formula XXII, Formula XXIII, Formula XXIV, Formula XV, Formula XVI, Formula XVII, Formula XVIII, Formula XXIX, Formula XXX, Formula XXXI, Formula XXXII, Formula XXXIII, Formula XXXIV, Formula XXXV, Formula XXXVI, Formula XXXVII, Formula XXXVIII, Formula XXXIX, Formula XL, Formula XLI, Formula XLII, Formula XLIII, Formula XLIV, Formula XLV, Formula XLVI, Formula XLVII, Formula XLVIII, Formula XLIX, Formula L, Formula LI, Formula LII, Formula LIII, or Formula LIV or a pharmaceutically acceptable salt or prodrug thereof; and (j) processes for the preparation of therapeutic products including drug delivery agents that contain an effective amount a compound of Formula I, Formula II, Formula III, Formula IV, Formula V, Formula V', Formula VI, Formula VI', Formula VII, Formula VIII, Formula IX, Formula IX', Formula X, Formula X', Formula XI, Formula XII, Formula XIII, Formula XIV, Formula XV, Formula XV', Formula XV", Formula XVI, Formula XVII, Formula XVII', Formula XVII", Formula XVII''', Formula XVIII, Formula XVIII', Formula XIX, Formula XIX', Formula XX, Formula XXI, Formula XXII, Formula XXIII, Formula XXIV, Formula XV, Formula XVI, Formula XVII, Formula XVIII, Formula XXIX, Formula XXX, Formula XXXI, Formula XXXII, Formula XXXIII, Formula XXXIV, Formula XXXV, Formula XXXVI, Formula XXXVII, Formula XXXVIII, Formula XXXIX, Formula XL, Formula XLI, Formula XLII, Formula XLIII, Formula XLIV, Formula XLV, Formula XLVI, Formula XLVII, Formula XLVIII, Formula XLIX, Formula L, Formula LI, Formula LII, Formula LIII, or Formula LIV as described herein.

DETAILED DESCRIPTION

I. Terminology

Figure 1:
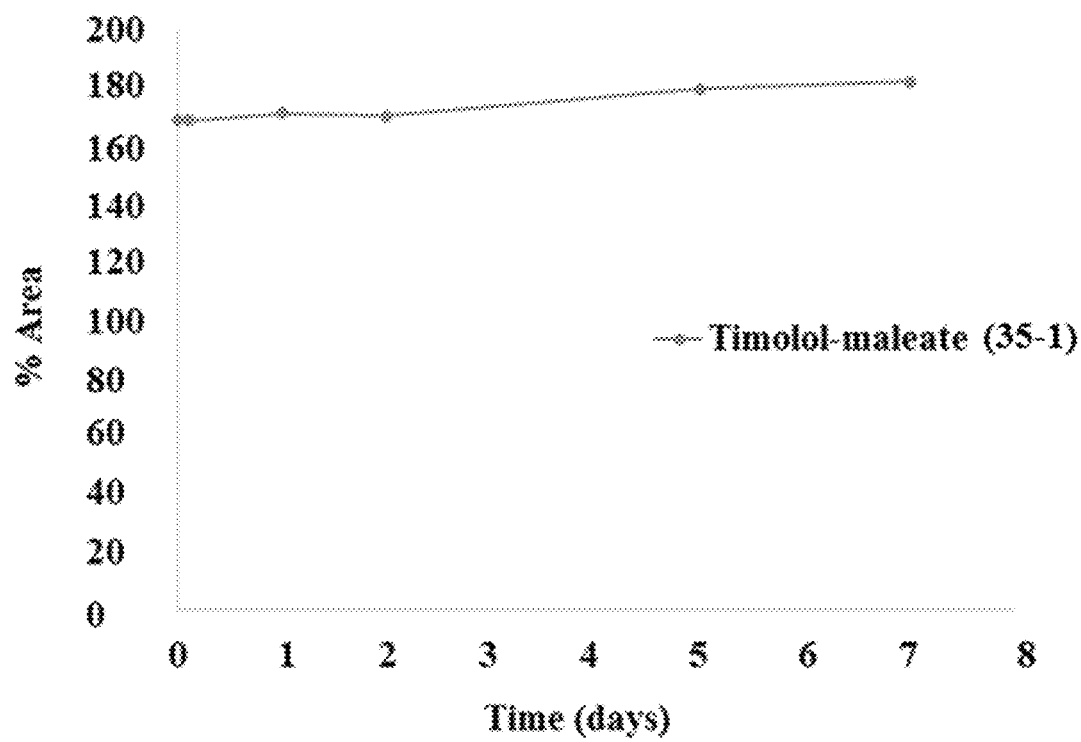
FIG. 1 is a graph depicting the stability of Timolol-maleate (35-1) over the course of 8 days as described in Example 8. The x-axis represents time measured in days and the y-axis represents the amount of undegraded Timolol-maleate as a percentage of the total amount of Timolol-maleate.

The presently disclosed subject matter may be embodied in many different forms and should not be construed as limited to the embodiments set forth herein. Indeed, many modifications and other embodiments of the presently disclosed subject matter will come to mind for one skilled in the art to which the presently disclosed subject matter pertains having the benefit of the teachings presented in the descriptions included herein. Therefore, it is to be understood that the presently disclosed subject matter is not to be limited to the specific embodiments disclosed and that modifications and other embodiments are intended to be included within the scope of the disclosed subject matter.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Compounds are described using standard nomenclature. Unless defined otherwise, all technical and scientific terms used herein have the same meaning as is commonly understood by one of skill in the art to which this invention belongs.

The compounds in any of the Formulas described herein include enantiomers, mixtures of enantiomers, diastereomers, cis/trans isomers, tautomers, racemates and other isomers, such as rotamers, as if each is specifically described.

The compounds in any of the Formulas may be prepared by chiral or asymmetric synthesis from a suitable optically pure precursor or obtained from a racemate or mixture of enantiomers or diastereomers by any conventional technique, for example, by chromatographic resolution using a chiral column, TLC or by the preparation of diastereoisomers, separation thereof and regeneration of the desired enantiomer or diastereomer. See, e.g., "Enantiomers, Racemates and Resolutions," by J. Jacques, A. Collet, and S. H. Wilen, (Wiley-Interscience, New York, 1981); S. H. Wilen, A. Collet, and J. Jacques, *Tetrahedron,* 2725 (1977); E. L. Eliel *Stereochemistry of Carbon Compounds* (McGraw-Hill, N Y, 1962); and S. H. Wilen *Tables of Resolving Agents and Optical Resolutions* 268 (E. L. Eliel ed., Univ. of Notre Dame Press, Notre Dame, Ind., 1972, *Stereochemistry of Organic Compounds,* Ernest L. Eliel, Samuel H. Wilen and Lewis N. Manda (1994 John Wiley & Sons, Inc.), and *Stereoselective Synthesis A Practical Approach,* Mihíly Nógrádi (1995 VCH Publishers, Inc., NY, NY).

The terms "a" and "an" do not denote a limitation of quantity, but rather denote the presence of at least one of the referenced item. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and are independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed.

The present invention includes compounds of Formula I, Formula II, Formula III, Formula IV, Formula V, Formula V', Formula VI, Formula VI', Formula VII, Formula VIII, Formula IX, Formula IX', Formula X, Formula X', Formula XI, Formula XII, Formula XIII, Formula XIV, Formula XV, Formula XV', Formula XV'', Formula XVI, Formula XVII, Formula XVII', Formula XVII'', Formula XVII''', Formula XVIII, Formula XVIII', Formula XIX, Formula XIX', Formula XX, Formula XXI, Formula XXII, Formula XXIII, Formula XXIV, Formula XV, Formula XVI, Formula XVII, Formula XVIII, Formula XXIX, Formula XXX, Formula XXXI, Formula XXXII, Formula XXXIII, Formula XXXIV, Formula XXXV, Formula XXXVI, Formula XXXVII, Formula XXXVIII, Formula XXXIX, Formula XL, Formula XLI, Formula XLII, Formula XLIII, Formula XLIV, Formula XLV, Formula XLVI, Formula XLVII, Formula XLVIII, Formula XLIX, Formula L, Formula LI, Formula LII, Formula LIII, or Formula LIV and the use of compounds with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, phosphorus, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes isotopically modified compounds of Formula I, Formula II, Formula III, Formula IV, Formula V, Formula V', Formula VI, Formula VI', Formula VII, Formula VIII, Formula IX, Formula IX', Formula X, Formula X', Formula XI, Formula XII, Formula XIII, Formula XIV, Formula XV, Formula XV', Formula XV'', Formula XVI, Formula XVII, Formula XVII', Formula XVII'', Formula XVII''', Formula XVIII, Formula XVIII', Formula XIX, Formula XIX', Formula XX, Formula XXI, Formula XXII, Formula XXIII, Formula XXIV, Formula XV, Formula XVI, Formula XVII, Formula XVIII, Formula XXIX, Formula XXX, Formula XXXI, Formula XXXII, Formula XXXIII, Formula XXXIV, Formula XXXV, Formula XXXVI, Formula XXXVII, Formula XXXVIII, Formula XXXIX, Formula XL, Formula XLI, Formula XLII, Formula XLIII, Formula XLIV, Formula XLV, Formula XLVI, Formula XLVII, Formula XLVIII, Formula XLIX, Formula L, Formula LI, Formula LII, Formula LIII, or Formula LIV. Isotopically labeled compounds of this invention and prodrugs thereof can generally be prepared by carrying out the procedures disclosed in the schemes or in the examples and preparations described below by substituting an isotopically labeled reagent for a non-isotopically labeled reagent.

By way of general example and without limitation, isotopes of hydrogen, for example, deuterium ($^2H$) and tritium ($^3H$) may be used anywhere in described structures that achieves the desired result. Alternatively or in addition, isotopes of carbon, e.g., $^{13}C$ and $^{14}C$, may be used. In one embodiment, the isotopic substitution is deuterium for hydrogen at one or more locations on the molecule to improve the performance of the drug, for example, the pharmacodynamics, pharmacokinetics, biodistribution, half-life, stability, AUC, $T_{max}$, $C_{max}$, etc. For example, the deuterium can be bound to carbon in a location of bond breakage during metabolism (an α-deuterium kinetic isotope effect) or next to or near the site of bond breakage (a β-deuterium kinetic isotope effect).

Isotopic substitutions, for example deuterium substitutions, can be partial or complete. Partial deuterium substitution means that at least one hydrogen is substituted with deuterium. In certain embodiments, the isotope is 90, 95 or 99% or more enriched at any location of interest. In one embodiment deuterium is 90, 95 or 99% enriched at a desired location.

In one embodiment, the substitution of a hydrogen atom for a deuterium atom can be provided in any of A, $L^1$, or $L^2$. In one embodiment, the substitution of a hydrogen atom for a deuterium atom occurs within an R group selected from any of $R^1$, $R^2$, $R^3$, $R^4$, $R^5$, $R^7$, $R^8$, $R^{11}$, $R^{16}$, $R^{17}$, $R^{23}$, $R^{24}$, $R^{25}$, $R^{26}$, $R^{31}$, $R^{32}$, $R^{34}$, $R^{35}$, $R^{36}$, $R^{37}$, $R^{38}$, $R^{39}$, $R^{40}$, $R^{41}$, $R^{50}$, $R^{100}$, $R^{101}$, $R^{102}$, $R^{103}$, $R^{104}$, $R^{105}$, $R^{106}$, $R^{107}$, $R^{108}$, $R^{110}$, $R^{114}$, $R^{116}$, $R^{17}$, $R^{118}$, $R^{119}$, $R^{120}$, $R^{12}$, $R^{23}$, $R^{124}$, $R^{130}$, $R^{131}$, $R^{132}$, $R^{133}$, $R^{134}$, $R^{135}$, $R^{136}$, $R^{137}$, $R^{138}$, $R^{139}$, $R^{140}$, $R^{141}$, $R^{142}$, $R^{143}$, $R^{50}$, $R^{151}$, $R^{152}$, $R^{153}$, $R^{156}$, $R^{160}$, $R^{170}$, $R^{171}$, $R^{172}$, $R^{173}$, $R^{174}$, $R^{175}$, $R^{176}$, $R^{177}$, $R^{178}$, $R^{182}$, $R^{183}$, $R^{192}$, $R^{193}$, $R^{194}$, $R^{208}$, $R^{209}$, $R^{210}$, $R^{21}$, $R^{212}$, $R^{301}$, $R^{302}$, $R^{303}$, $R^{304}$, $R^{334}$, $R^{33}$, $R^{336}$, and $R^{356}$. For example, when any of R groups are, or contain for example through substitution, methyl, ethyl, or methoxy, the alkyl residue may be deuterated (in non-limiting embodiments, $CD_3$, $CH_2CD_3$, $CD_2CD_3$, $CDH_2$, $CD_2H$, $CD_3$, $CHDCH_2D$, $CH_2CD_3$, $CHDCHD_2$, $OCDH_2$, $OCD_2H$, or $OCD_3$ etc.

The compound of the present invention may form a solvate with a solvent (including water). Therefore, in one embodiment, the invention includes a solvated form of the active compound. The term "solvate" refers to a molecular complex of a compound of the present invention (including salts thereof) with one or more solvent molecules. Examples of solvents are water, ethanol, dimethyl sulfoxide, acetone and other common organic solvents. The term "hydrate" refers to a molecular complex comprising a compound of the invention and water. Pharmaceutically acceptable solvates in accordance with the invention include those wherein the solvent may be isotopically substituted, e.g. $D_2O$, $d_6$-acetone, $d_6$-DMSO. A solvate can be in a liquid or solid form.

A dash ("-") is defined by context and can in addition to its literary meaning indicate a point of attachment for a substituent. For example, —(C=O)NH$_2$ is attached through carbon of the keto (C=O) group. A dash ("-") can also indicate a bond within a chemical structure. For example —C(O)—NH$_2$ is attached through carbon of the keto group which is bound to an amino group (NH$_2$).

An equal sign ("=") is defined by context and can in addition to its literary meaning indicate a point of attachment for a substituent wherein the attachment is through a double bond. For example, =CH$_2$ represents a fragment that is doubly bonded to the parent structure and consists of one carbon with two hydrogens bonded in a terminal fashion. =CHCH$_3$ on the other hand represents a fragment that is doubly bonded to the parent structure and consists of two carbons. In the above example it should be noted that the stereoisomer is not delineated and that both the cis and trans isomer are independently represented by the group.

The term "substituted", as used herein, means that any one or more hydrogens on the designated atom or group is replaced with a moiety selected from the indicated group, provided that the designated atom's normal valence is not exceeded. For example, when the substituent is oxo (i.e., =O), then in one embodiment, two hydrogens on the atom are replaced. When an oxo group replaces two hydrogens in an aromatic moiety, the corresponding partially unsaturated ring replaces the aromatic ring. For example a pyridyl group substituted by oxo is a pyridone. Combinations of substituents and/or variables are permissible only if such combinations result in stable compounds or useful synthetic intermediates.

A stable compound or stable structure refers to a compound with a long enough residence time to either be used as a synthetic intermediate or as a therapeutic agent, as relevant in context.

"Alkyl" is a straight chain saturated aliphatic hydrocarbon group. In certain embodiments, the alkyl is $C_1$-$C_2$, $C_1$-$C_3$, $C_1$-$C_6$, or $C_1$-$C_{30}$ (i.e., the alkyl chain can be 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbons in length). The specified ranges as used herein indicate an alkyl group with length of each member of the range described as an independent species. For example, the term $C_1$-$C_6$ alkyl as used herein indicates a straight alkyl group having from 1, 2, 3, 4, 5, or 6 carbon atoms and is intended to mean that each of these is described as an independent species. For example, the term $C_1$-$C_4$alkyl as used herein indicates a straight or branched alkyl group having from 1, 2, 3, or 4 carbon atoms and is intended to mean that each of these is described as an independent species. When $C_0$-$C_4$ alkyl is used herein in conjunction with another group, for example, ($C_3$-$C_7$cycloalkyl)$C_0$-$C_4$ alkyl, or —$C_0$-$C_4$alkyl($C_3$-$C_7$cycloalkyl), the indicated group, in this case cycloalkyl, is either directly bound by a single covalent bond ($C_0$alkyl), or attached by an alkyl chain in this case 1, 2, 3, or 4 carbon atoms. Alkyls can also be attached via other groups such as heteroatoms as in —O—$C_0$-$C_4$alkyl($C_3$-$C_7$cycloalkyl). Alkyls can be further substituted with alkyl to make branched alkyls. Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane and 2,3-dimethylbutane. In one embodiment, the alkyl group is optionally substituted as described above.

"Alkenyl" is a straight chain aliphatic hydrocarbon group having one or more carbon-carbon double bonds each of which is independently either cis or trans that may occur at a stable point along the chain. In one embodiment, the double bond in a long chain similar to a fatty acid has the stereochemistry as commonly found in nature. Non-limiting examples are $C_2$-$C_{30}$alkenyl, $C_{10}$-$C_{30}$alkenyl (i.e., having 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbons), and $C_2$-$C_4$alkenyl. The specified ranges as used herein indicate an alkenyl group having each member of the range described as an independent species, as described above for the alkyl moiety. Examples of alkenyl include, but are not limited to, ethenyl and propenyl. Alkenyls can be further substituted with alkyl to make branched alkenyls. In one embodiment, the alkenyl group is optionally substituted as described above.

"Alkynyl" is a straight chain aliphatic hydrocarbon group having one or more carbon-carbon triple bonds that may occur at any stable point along the chain, for example, $C_2$-$C_8$alkynyl or $C_{10}$-$C_{30}$alkynyl (i.e., having 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbons). The specified ranges as used herein indicate an alkynyl group having each member of the range described as an independent species, as described above for the alkyl moiety. Alkynyls can be further substituted with alkyl to make branched alkynyls. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. In one embodiment, the alkynyl group is optionally substituted as described above.

"Alkylene" is a bivalent saturated hydrocarbon. Alkylenes, for example, can be a 1 to 8 carbon moiety, 1 to 6 carbon moiety, or an indicated number of carbon atoms, for example $C_1$-$C_4$alkylene, $C_1$-$C_3$alkylene, or $C_1$-$C_2$alkylene.

"Alkenylene" is a bivalent hydrocarbon having at least one carbon-carbon double bond. Alkenylenes, for example, can be a 2 to 8 carbon moiety, 2 to 6 carbon moiety, or an indicated number of carbon atoms, for example $C_2$-$C_4$alkenylene.

"Alkynylene" is a bivalent hydrocarbon having at least one carbon-carbon triple bond. Alkynylenes, for example, can be a 2 to 8 carbon moiety, 2 to 6 carbon moiety, or an indicated number of carbon atoms, for example $C_2$-$C_4$alkynylene.

"Alkenylalkynyl" in one embodiment is a bivalent hydrocarbon having at least one carbon-carbon double bond and at least one carbon-carbon triple bond. It will be recognized to one skilled in the art that the bivalent hydrocarbon will not result in hypervalency, for example, hydrocarbons that include —C═C═C—C or —C≡C≡C—C, and must be stable. Alkenylalkynyls, for example, can be a 4 to 8 carbon moiety, 4 to 6 carbon moiety, or an indicated number of carbon atoms, for example $C_4$-$C_6$alkenylalkynyls.

"Alkoxy" is an alkyl group as defined above covalently bound through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Similarly an "alkylthio" or a "thioalkyl" group is an alkyl group as defined above with the indicated number of carbon atoms covalently bound through a sulfur bridge (—S—). In one embodiment, the alkoxy group is optionally substituted as described above.

"Alkenyloxy" is an alkenyl group as defined covalently bound to the group it substitutes by an oxygen bridge (—O—).

"Amide" or "carboxamide" is —C(O)NR$^a$R$^b$ wherein R$^a$ and R$^b$ are each independently selected from hydrogen, alkyl, for example, $C_1$-$C_6$alkyl, alkenyl, for example, $C_2$-$C_6$alkenyl, alkynyl, for example, $C_2$-$C_6$alkynyl, —$C_0$-$C_4$alkyl($C_3$-$C_7$cycloalkyl), —$C_0$-$C_4$alkyl($C_3$-$C_7$heterocycloalkyl), —$C_0$-$C_4$alkyl(aryl), and —$C_0$-$C_4$alkyl(heteroaryl); or together with the nitrogen to which they are bonded, R$^a$ and R$^b$ can form a $C_3$-$C_7$heterocyclic ring. In one embodiment, the R$^a$ and R$^b$ groups are each independently optionally substituted as described above.

"Carbocyclic group", "carbocyclic ring", or "cycloalkyl" is a saturated or partially unsaturated (i.e., not aromatic) group containing all carbon ring atoms. A carbocyclic group typically contains 1 ring of 3 to 7 carbon atoms or 2 fused rings each containing 3 to 7 carbon atoms. Cycloalkyl substituents may be pendant from a substituted nitrogen or carbon atom, or a substituted carbon atom that may have two substituents can have a cycloalkyl group, which is attached as a spiro group. Examples of carbocyclic rings include cyclohexenyl, cyclohexyl, cyclopentenyl, cyclopentyl, cyclobutenyl, cyclobutyl and cyclopropyl rings. In one embodiment, the carbocyclic ring is optionally substituted as described above. In one embodiment, the cycloalkyl is a partially unsaturated (i.e., not aromatic) group containing all carbon ring atoms. In another embodiment, the cycloalkyl is a saturated group containing all carbon ring atoms. In another embodiment, a carbocyclic ring comprises a caged carbocyclic group. In one embodiment, a carbocyclic ring comprises a bridged carbocyclic group. An example of a caged carbocyclic group is adamantane. An example of a bridged carbocyclic group includes bicyclo[2.2.1]heptane (norbomane). In one embodiment, the caged carbocyclic group is optionally substituted as described above. In one embodiment, the bridged carbocyclic group is optionally substituted as described above.

"Hydroxyalkyl" is an alkyl group as previously described, substituted with at least one hydroxyl substituent.

"Halo" or "halogen" indicates independently any of fluoro, chloro, bromo, and iodo.

"Aryl" indicates aromatic groups containing only carbon in the aromatic ring or rings. In one embodiment, the aryl groups contain 1 to 3 separate or fused rings and is 6 to about 14 or 18 ring atoms, without heteroatoms as ring members. When indicated, such aryl groups may be further substituted with carbon or non-carbon atoms or groups. Such substitution may include fusion to a 4 to 7-membered saturated cyclic group that optionally contains 1 or 2 heteroatoms independently chosen from N, O, B, and S, to form, for example, a 3,4-methylenedioxyphenyl group. Aryl groups include, for example, phenyl and naphthyl, including 1-naphthyl and 2-naphthyl. In one embodiment, aryl groups are pendant. An example of a pendant ring is a phenyl group substituted with a phenyl group. In one embodiment, the aryl group is optionally substituted as described above. In one embodiment, aryl groups include, for example, dihydroindole, dihydrobenzofuran, isoindoline-1-one and indolin-2-one that can be optionally substituted.

The term "heterocycle," or "heterocyclic ring" as used herein refers to a saturated or a partially unsaturated (i.e., having one or more double and/or triple bonds within the ring without aromaticity) carbocyclic radical of 3 to about 12, and more typically 3, 5, 6, 7 to 10 ring atoms in which at least one ring atom is a heteroatom selected from nitrogen, oxygen, phosphorus, silicon, boron and sulfur, the remaining ring atoms being C, where one or more ring atoms is optionally substituted independently with one or more substituents described above. A heterocycle may be a monocycle having 3 to 7 ring members (2 to 6 carbon atoms and 1 to 4 heteroatoms selected from N, O, P, and S) or a bicycle having 5 to 10 ring members (4 to 9 carbon atoms and 1 to 6 heteroatoms selected from N, O, P, and S), for example: a bicyclo [4,5], [5,5], [5,6], or [6,6] system. In one embodiment, the only heteroatom is nitrogen. In one embodiment, the only heteroatom is oxygen. In one embodiment, the only heteroatom is sulfur. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. Spiro moieties are also included within the scope of this definition. Examples of a heterocyclic group wherein 1 or 2 ring carbon atoms are substituted with oxo (=O) moieties are pyrimidinonyl and 1,1-dioxo-thiomorpholinyl. The heterocycle groups herein are optionally substituted independently with one or more substituents described herein.

"Heteroaryl" indicates a stable monocyclic aromatic ring which contains from 1 to 3, or in some embodiments from 1 to 2, heteroatoms chosen from N, O, and S, with remaining ring atoms being carbon, or a stable bicyclic or tricyclic system containing at least one 5- to 7-membered aromatic ring which contains from 1, 2, 3, or 4, or in some embodiments from 1 or 2, heteroatoms chosen from N, O, B, and S, with remaining ring atoms being carbon. In one embodiment, the only heteroatom is nitrogen. In one embodiment, the only heteroatom is oxygen. In one embodiment, the only heteroatom is sulfur. Monocyclic heteroaryl groups typically have from 5 to 7 ring atoms. In some embodiments bicyclic heteroaryl groups are 9- to 10-membered heteroaryl groups, that is, groups containing 9 or 10 ring atoms in which one 5- to 7-member aromatic ring is fused to a second aromatic or non-aromatic ring. When the total number of S and O atoms in the heteroaryl group exceeds 1, these heteroatoms are not adjacent to one another. In one embodiment, the total number of S and O atoms in the heteroaryl group is not more than 2. In another embodiment, the total number of S and O atoms in the aromatic heterocycle is not more than 1. Heteroaryl groups are optionally substituted independently with one or more substituents described herein.

"Heterocycloalkyl" is a saturated ring group. It may have, for example, 1, 2, 3, or 4 heteroatoms independently chosen from N, S, and O, with remaining ring atoms being carbon. In a typical embodiment, nitrogen is the heteroatom. Monocyclic heterocycloalkyl groups typically have from 3 to about 8 ring atoms or from 4 to 6 ring atoms. Examples of heterocycloalkyl groups include morpholinyl, piperazinyl, piperidinyl, and pyrrolinyl.

The term "esterase" refers to an enzyme that catalyzes the hydrolysis of an ester. As used herein, the esterase can catalyze the hydrolysis of prostaglandins described herein. In certain instances, the esterase includes an enzyme that can catalyze the hydrolysis of amide bonds of prostaglandins.

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, and the like. A "dosage form" can also include an implant, for example an optical implant.

A "pharmaceutical composition" is a composition comprising at least one active agent, such as a compound or salt of Formula I, Formula II, Formula III, Formula IV, Formula V, Formula V', Formula VI, Formula VI', Formula VII, Formula VIII, Formula IX, Formula IX', Formula X, Formula X', Formula XI, Formula XII, Formula XIII, Formula XIV, Formula XV, Formula XV', Formula XV'', Formula XVI, Formula XVII, Formula XVII', Formula XVII'', Formula XVII''', Formula XVIII, Formula XVIII', Formula XIX, Formula XIX', Formula XX, Formula XXI, Formula XXII, Formula XXIII, Formula XXIV, Formula XV, Formula XVI, Formula XVII, Formula XVIII, Formula XXIX, Formula XXX, Formula XXXI, Formula XXXII, Formula XXXIII, Formula XXXIV, Formula XXXV, Formula XXXVI, Formula XXXVII, Formula XXXVIII, Formula XXXIX, Formula XL, Formula XLI, Formula XLII, Formula XLIII, Formula XLIV, Formula XLV, Formula XLVI, Formula XLVII, Formula XLVIII, Formula XLIX, Formula L, Formula LI, Formula LII, Formula LIII, or Formula LIV and at least one other substance, such as a pharmaceutically acceptable carrier. "Pharmaceutical combinations" are combinations of at least two active agents which may be combined in a single dosage form or provided together in separate dosage forms with instructions that the active agents are to be used together to treat any disorder described herein.

A "pharmaceutically acceptable salt" includes a derivative of the disclosed compound in which the parent compound is modified by making inorganic and organic, non-toxic, acid or base addition salts thereof. The salts of the present compounds can be synthesized from a parent compound that contains a basic or acidic moiety by conventional chemical methods. Generally, such salt can be prepared by reacting free acid forms of these compounds with a stoichiometric amount of the appropriate base (such as Na, Ca, Mg, or K hydroxide, carbonate, bicarbonate, or the like), or by reacting a free base form of the compound with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like.

Additional non-limiting examples of salts include 1-hydroxy-2-naphthoic acid, 2,2-dichloroacetic acid, 2-oxoglutaric acid, 4-acetamidobenzoic acid, 4-aminosalicylic acid, adipic acid, aspartic acid, benzenesulfonic acid, camphoric acid, camphor-10-sulfonic acid, capric acid, caproic acid, caprylic acid, carbonic acid, cinnamic acid, cyclamic acid, dodecylsulfuric acid, ethane-1,2-disulfonic acid, ethanesulfonic acid, formic acid, galactaric acid, gentisic acid, glucoheptonic acid, gluconic acid, glucuronic acid, glutaric acid, glycerophosphoric acid, hippuric acid, isobutyric acid, lactobionic acid, lauric acid, malonic acid, mandelic acid, naphthalene-1,5-disulfonic acid, naphthalene-2-sulfonic acid, nicotinic acid, nitric acid, oleic acid, palmitic acid, pyroglutamic acid, sebacic acid, thiocyanic acid, and undecylenic acid. Lists of additional suitable salts may be found, e.g., in *Remington's Pharmaceutical Sciences*, 17th ed., Mack Publishing Company, Easton, Pa., p. 1418 (1985).

The term "carrier" refers to a diluent, excipient, or vehicle with which an active compound is provided.

A "patient" or "host" or "subject" is typically a human, however, may be more generally a mammal. In an alternative embodiment it can refer to for example, a cow, sheep, goat, horses, dog, cat, rabbit, rat, mice, fish, bird and the like.

A "prodrug" as used herein, means a compound which when administered to a host in vivo is converted into a parent drug. As used herein, the term "parent drug" means the active form of the compounds that renders the biological effect to treat any of the disorders described herein, or to control or improve the underlying cause or symptoms associated with any physiological or pathological disorder described herein in a host, typically a human. Prodrugs can be used to achieve any desired effect, including to enhance properties of the parent drug or to improve the pharmaceutic or pharmacokinetic properties of the parent. Prodrug strategies exist which provide choices in modulating the conditions for in vivo generation of the parent drug, all of which are deemed included herein. Non-limiting examples of prodrug strategies include covalent attachment of removable groups, or removable portions of groups, for example, but not limited to acylation, phosphorylation, phosphonylation, phosphoramidate derivatives, amidation, reduction, oxidation, esterification, alkylation, other carboxy derivatives, sulfoxy or sulfone derivatives, carbonylation or anhydride, among others. In certain aspects of the present invention, at least one hydrophobic group is covalently bound to the parent drug to slow release of the parent drug in vivo.

A "therapeutically effective amount" of a pharmaceutical composition/combination of this invention means an amount effective, when administered to a patient, to provide a therapeutic benefit such as an amelioration of symptoms of the selected disorder, typically an ocular disorder In certain aspects, the disorder is glaucoma, a disorder mediated by carbonic anhydrase, a disorder or abnormality related to an increase in intraocular pressure (IOP), a disorder mediated by nitric oxide synthase (NOS), a disorder requiring neuroprotection such as to regenerate/repair optic nerves, allergic conjunctivitis, anterior uveitis, cataracts, dry or wet age-related macular degeneration (AMD) or diabetic retinopathy.

"γ-linolenic acid" is gamma-linolenic acid.

The term "polymer" as used herein includes oligomers.

II. Detailed Description of the Active Compounds

In certain embodiments, compounds for ocular delivery are provided that are lipophilic monoprodrugs of, for example, Timolol, Metipranolol, Levobunolol, Carteolol, Betaxolol, Brinzolamide, Dorzolamide, acetazolamide, Methazolamide, Brimonidine, apraclonidine, Sunitinib, Latanoprost, dinoprost, travoprost, tafluprost, unoprostone, SR8165, SR5834, axitinib, bosutinib, neratinib, Crizotinib, Tozasertib, lestautinib, foretinib, TAE-684, KW-2449, Y-27637, AMA0076, AR-13324, RKI-1447, RKI-1313, Wf536, CID 5056270, K-I 15, fasudil, pazopanib, axitinib, sorafenib, ponatinib, lenvatinib, vandetanib, cabzantinib, or regorafenib, covalently linked to a biodegradable oligomer, as described in more detail herein.

In various embodiments, two biologically active compounds are covalently linked (optionally with a biodegradable linker(s), for example, that includes a linking ester, amide, etc. bond as exemplified throughout this specification in detail, e.g., —""linked through to"—) for ocular combination therapy. In some embodiments, the bis-prodrug is in a biodegradable polymeric delivery system, such as a biodegradable microparticle or nanoparticle, for controlled delivery. In one embodiment, a β-blocker (for example, Timolol, Metipranolol, Levobunolol, Carteolol or Betaxolol) is covalently linked to a carbonic anhydrase inhibitor (for example, Brinzolamide, Dorzolamide, acetazolamide or Methazolamide). In another embodiment, an α-agonist (for example Brimonidine or apraclonidine) is covalently linked to a β-blocker (for example, Timolol, Metipranolol, Levobunolol, Carteolol or Betaxolol). Alternatively, an α-agonist (for example Brimonidine or apraclonidine) is covalently linked to a carbonic anhydrase inhibitor (for example, Brinzolamide, Dorzolamide, Acetazolamide or Methazolamide). This invention includes the specific combination of each of the named actives with each other named active in the bis-prodrug, as if each combination were individually described (and is only written like this for efficiency of space).

In yet another embodiment, a Rho associated kinase inhibitor (for example Y-27637, AMA0076, AR-13324, RKI-1447, RKI-1313, Wf536, CID 5056270, K-115, fasudil, or SR5834) (ROCK inhibitor) is covalently linked to a β-blocker (for example, Timolol, Metipranolol, Levobunolol, Carteolol or Betaxolol). In yet another embodiment, a ROCK inhibitor (for example Y-27637, AMA0076, AR-13324, RKI-1447, RKI-1313, Wf536, CID 5056270, K-115, fasudil, or SR5834) is covalently linked to a carbonic anhydrase inhibitor (for example, Brinzolamide, Dorzolamide, acetazolamide or Methazolamide). In yet another embodiment, ROCK inhibitor (for example Y-27637, AMA0076, AR-13324, RKI-1447, RKI-1313, Wf536, CID 5056270, K-115, SR5834, or fasudil) is covalently linked to an α-agonist (for example Brimonidine or apraclonidine). Alternatively, a neuroprotectant DLK inhibitor (for example, Sunitinib, SR8165, axitinib, bosutinib, neratinib, Crizotinib, Tozasertib, lestautinib, foretinib or TAE-684) is covalently linked to a ROCK inhibitor (for example Y-27637, AMA0076, AR-13324, RKI-1447, RKI-1313, Wf536, CID 5056270, K-115, fasudil, or SR5834). In alternative embodiments, a ROCK inhibitor can be selected for these embodiments selected from those disclosed in Pireddu, et. al., "Pyridylthiazole-based urease as inhibitors of Rho associated protein kinases (ROCK 1 and 2)" *Med. Chem. Comm.* 2012, 3, 699; Patel, et al., "Identification of novel ROCK inhibitors with anti-migratory and anti-invasive activities" *Oncogene* 2014, 33, 550-555; Patel, et al, "RKI-1447 is a potent inhibitor of the Rho-Associated ROCK Kinase with anti-Invasive and Antitumor Activities in Breast Cancer" *Cancer Research*, online Jul. 30, 2012, 5025-5033); Yin et al., "Discovery of Potent and Selective Urea-Based ROCK Inhibitors and Their Effects on Intraocular Pressure in Rats" *ACS Med. Chem. Lett.* 2010, 1, 175-179; or, Mei, et al. "Discovery of potent and selective urea-based ROCK inhibitors: Exploring the inhibitor's potency and ROCK2/PKA selectivity by 3D-QSAR, molecular docking and molecular dynamics simulations" *Bioorganic & Medicinal Chemistry* 2015, 23, 2505-2517. See also U.S. Pat. Nos. 9,221,808 and 9,409,868, herein incorporated in their entirety by reference. Again, this invention includes the specific combination of each of the named actives with each other named active in the bis-prodrug, as if each combination were individually (and is only written like this for efficiency of space).

In other embodiments, a small molecule VEGF inhibitor (for example, pazopanib, axitinib, sorafenib, ponatinib, lenvatinib, vandetanib, cabzantinib, or regorafenib) is covalently linked to a ROCK inhibitor (for example Y-27637, AMA0076, AR-13324, RKI-1447, RKI-1313, Wf536, CID 5056270, K-115, fasudil, or SR5834), a β-blocker (for example, as named above), an α-agonist (for example, as named above), a carbonic anhydrase inhibitor (for example, as named above), a prostaglandin (for example Latanoprost, dinoprost, travoprost, tafluprost or unoprostone), or a neuroprotective DLK inhibitor such as SR8165, axitinib, bosutinib, neratinib, Crizotinib, toazaertib, lestautinib, foretinib, TAE-684 or KW-2449. As above, this invention includes the specific combination of each of the named actives with each other named active in the bis-prodrug, as if each combination were individually (and is only written like this for efficiency of space).

In specific embodiments, Sunitinib is covalently linked to one of the β-blockers named above. In another embodiment, Sunitinib is covalently linked to a carbonic acid inhibitor named above. Alternatively, Sunitinib is covalently linked to an α-agonist above. In certain embodiments, Sunitinib is covalently linked to a prostaglandin (for example Latanoprost, dinoprost, travoprost, tafluprost or unoprostone). Alternatively, instead of Sunitinib, a TKI neuroprotectant DLK inhibitor such as SR8165, axitinib, bosutinib, neratinib, Crizotinib, Tozasertib, lestautinib, foretinib, TAE-684 or KW-2449 is covalently linked to a β-blocker, an α-agonist, ROCK inhibitor, a carbonic anhydrase inhibitor, VEGR inhibitor or prostaglandin, as named above. Again, this invention includes the specific combination of each of the named actives with each other named active in the bis-prodrug, as if each combination were individually (and is only written like this for efficiency of space).

In other various embodiments, the biologically active compound as described herein for ocular therapy is covalently linked (optionally with a biodegradable linker(s) that include a linking ester, amide, etc. bond as exemplified throughout this specification in detail) to a second same biologically active compound, to create a biodegradable dimer for ocular combination therapy. The dimer is more lipophilic and thus will enhance the controlled delivery of the active compound over time, in particular in a polymeric delivery system, for example, when administered in a hydrophilic intravitreal fluid of the eye. Biologically active compounds that can be dimerized with a biodegradable linker for use in a biodegradable polymeric composition include, but are not limited to, Timolol, Metipranolol, Levobunolol, Carteolol, Betaxolol, Brinzolamide, Dorzolamide, acetazolamide, Methazolamide, Brimonidine, apraclonidine, Sunitinib, Latanoprost, dinoprost, travoprost, tafluprost, unoprostone, SR8165, axitinib, bosutinib, neratinib, Crizotinib, Tozasertib, lestautinib, foretinib, TAE-684, KW-2449, Y-27637, AMA0076, AR-13324, RKI-1447, RKI-1313, Wf536, CID 5056270, K-115, fasudil, SR5834, pazopanib, axitinib, sorafenib, ponatinib, lenvatinib, vandetanib, cabzantinib, or regorafenib. Methods to dimerize these compounds with a biodegradable linker are exemplified throughout this specification.

According to the present invention, compounds of Formula I, Formula II, Formula III, Formula IV, Formula V, Formula V', Formula VI, Formula VI', Formula VII, Formula VIII, Formula IX, Formula IX', Formula X, Formula X', Formula XI, Formula XII, Formula XIII, Formula XIV, Formula XV, Formula XV', Formula XV", Formula XVI, Formula XVII, Formula XVII', Formula XVII", Formula XVII''', Formula XVIII, Formula XVIII', Formula XIX, Formula XIX', Formula XX, Formula XXI, Formula XXII, Formula XXIII, Formula XXIV, Formula XV, Formula XVI, Formula XVII, Formula XVIII, Formula XXIX, Formula XXX, Formula XXXI, Formula XXXII, Formula XXXIII, Formula XXXIV, Formula XXXV, Formula XXXVI, Formula XXXVII, Formula XXXVIII, Formula XXXIX, Formula XL, Formula XLI, Formula XLII, Formula XLIII, Formula XLIV, Formula XLV, Formula XLVI, Formula XLVII, Formula XLVIII, Formula XLIX, Formula L, Formula LI, Formula LII, Formula LIII, or Formula LIV are provided:

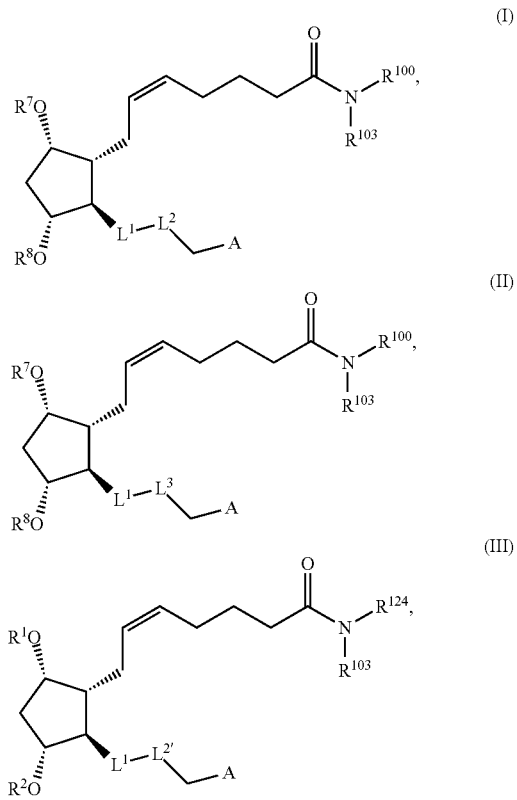

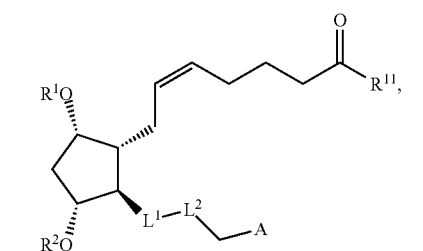
(IV)
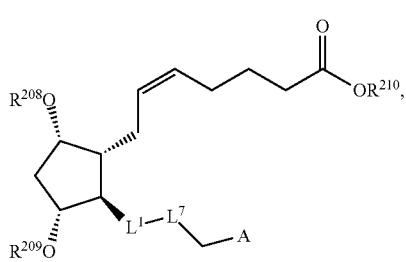
(V)
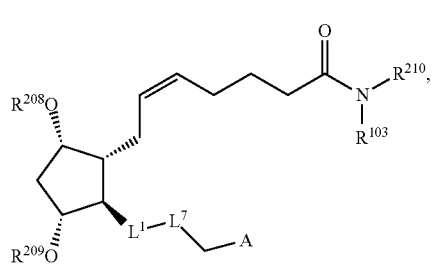
(VI)
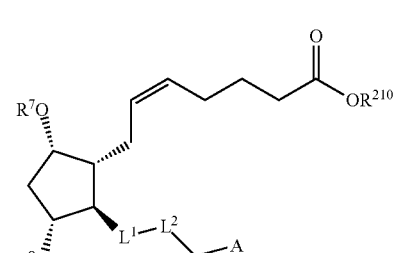
(V')
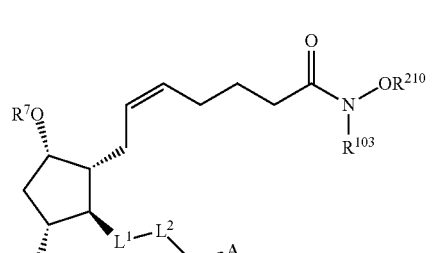
(VI')
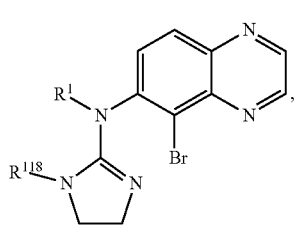
(VII)
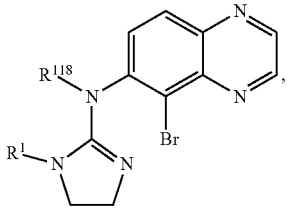
(VIII)
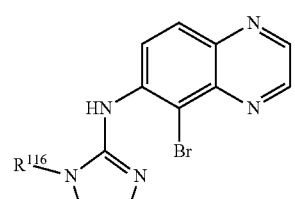
(IX)
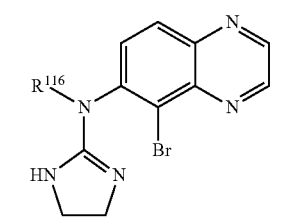
(IX')
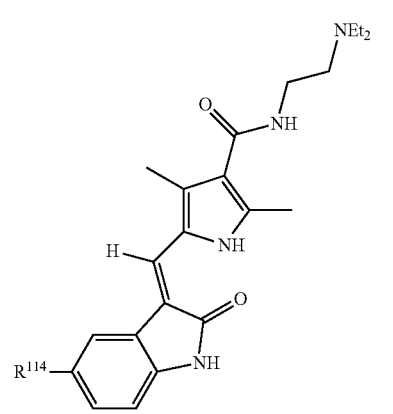
(X)
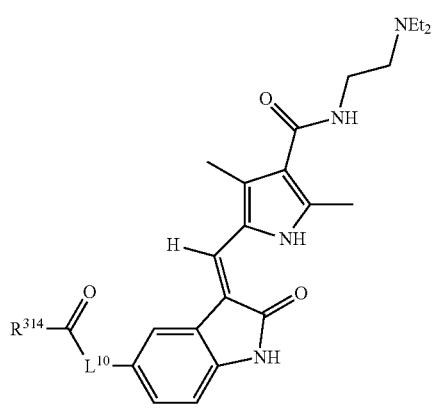
(X')

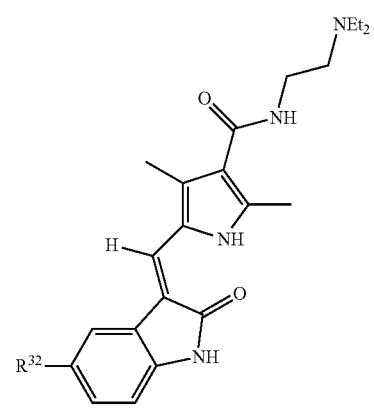 (XI)
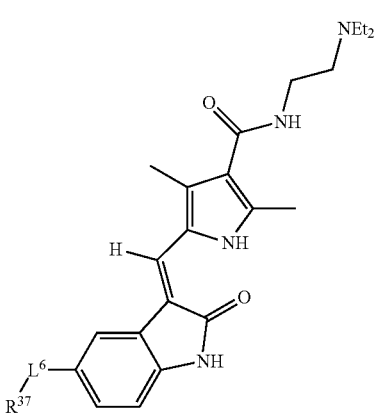 (XII)
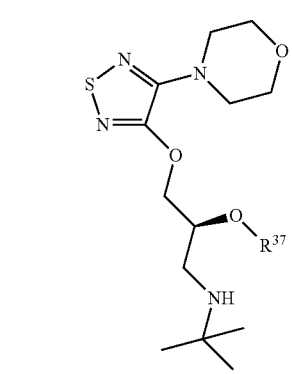 (XIII)
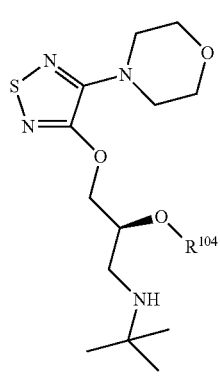 (XIV)
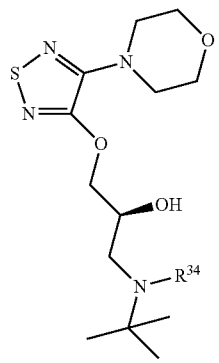 (XV)
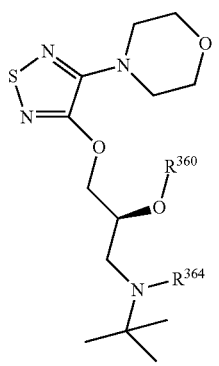 (XV')
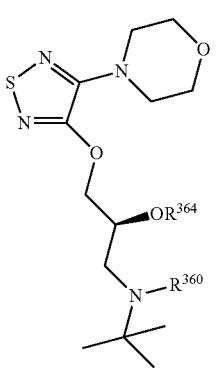 (XV'')
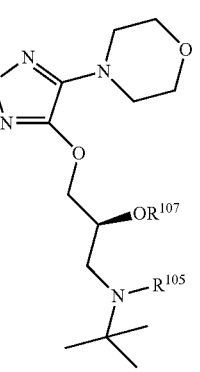 (XVI)

(XVII)
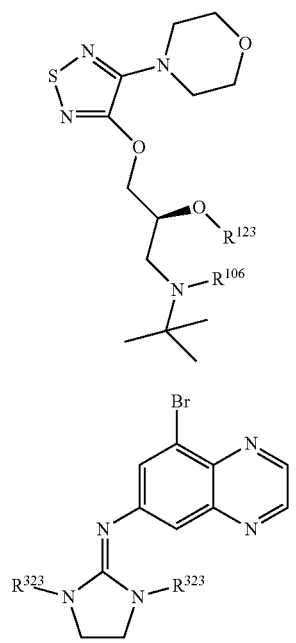
(XVII')
(XVII'')
(XVII''')
(XVIII)
(XVIII')
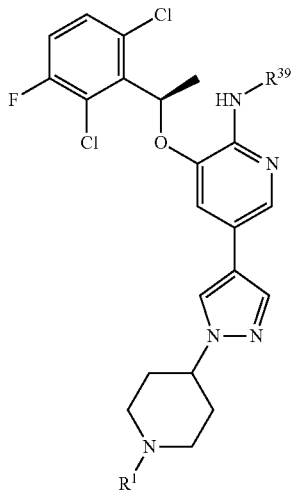
(XIX)
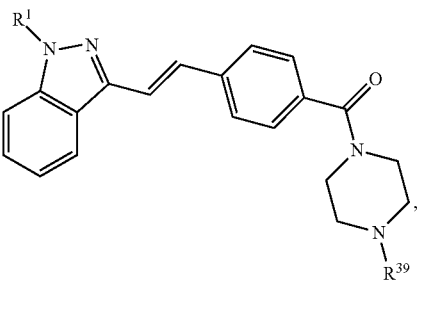
(XIX')
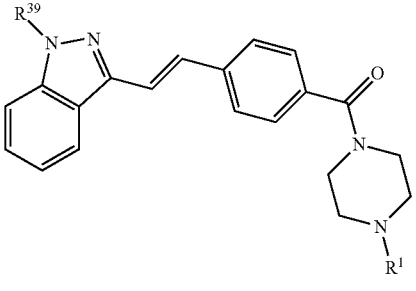
(XX)

(XXI)
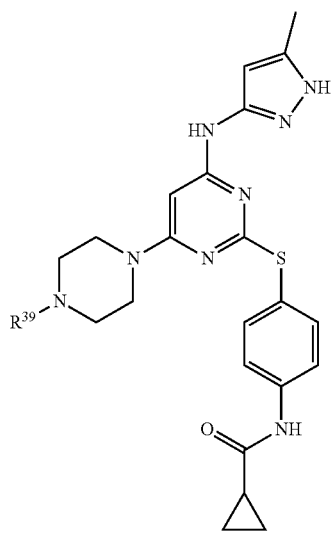
(XXII)
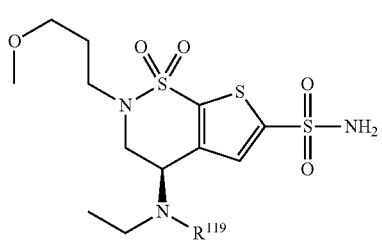
(XXIII)
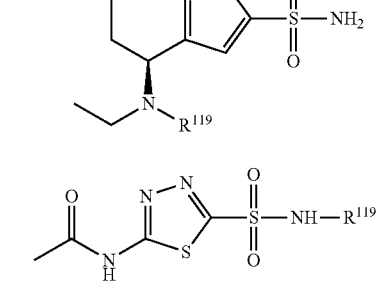
(XXIV)
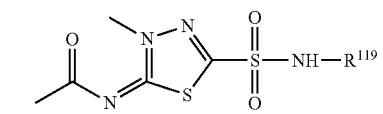
(XXV)
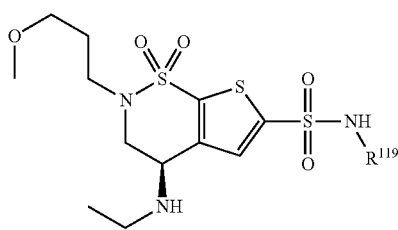
(XXVI)
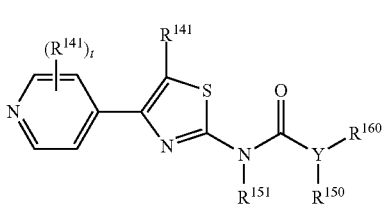
(XXVII)
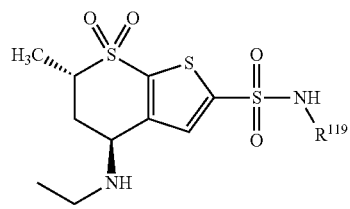
(XXVIII)
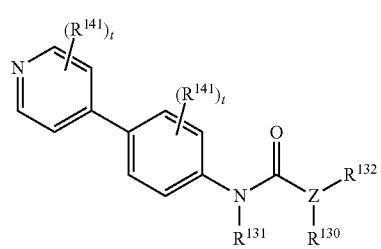
(XXIX)
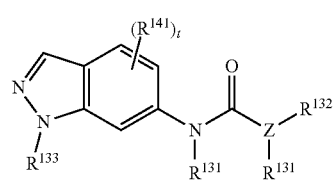
(XXX)
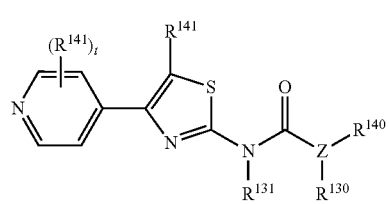
(XXXI)
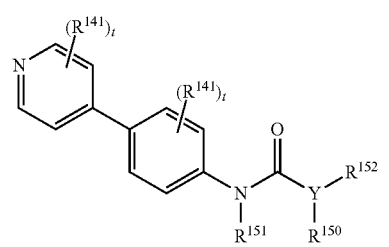
(XXXII)
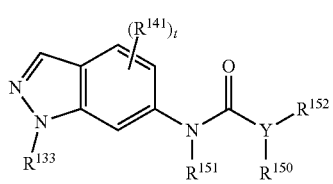
(XXXIII)

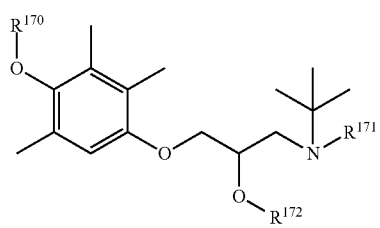 (XXXIV)
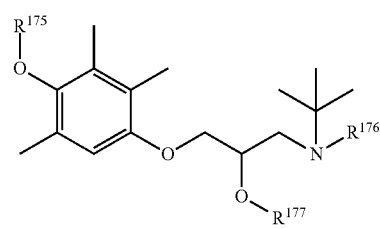 (XXXV)
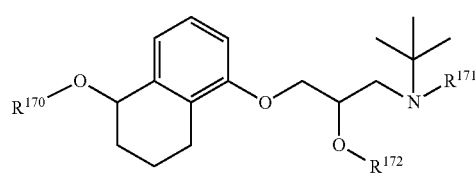 (XXXVI)
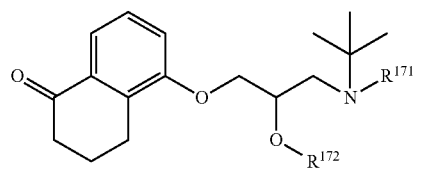 (XXXVIII)
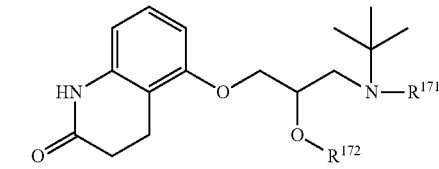 (XL)
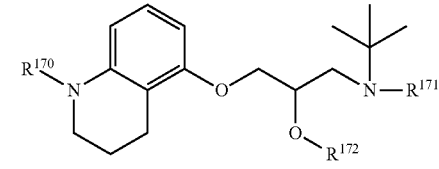 (XLII)
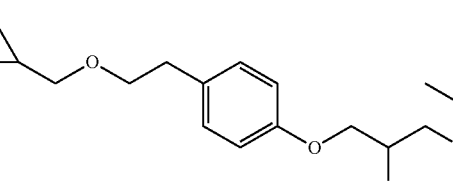 (XLIV)
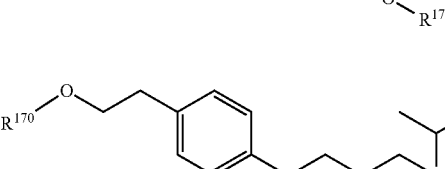 (XLVI)
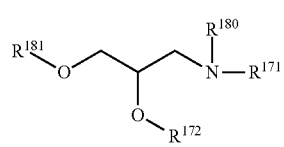 (XLVIII)
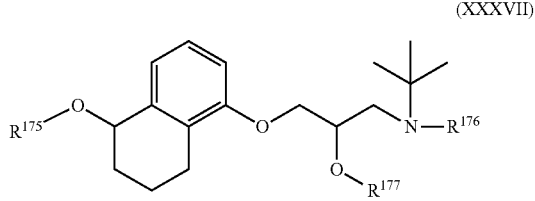 (XXXVII)
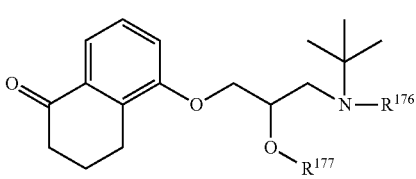 (XXXIX)
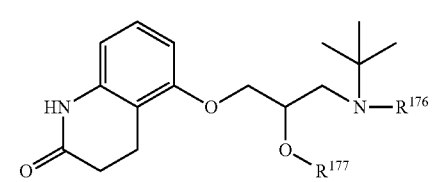 (XLI)
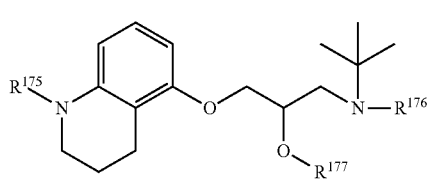 (XLIII)
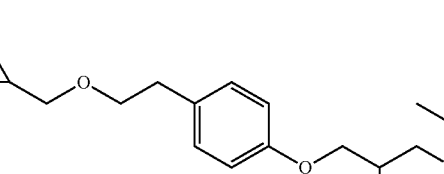 (XLV)
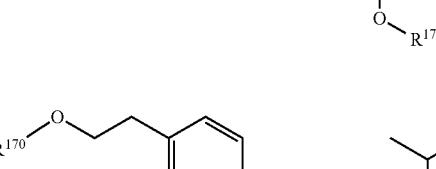 (XLVII)
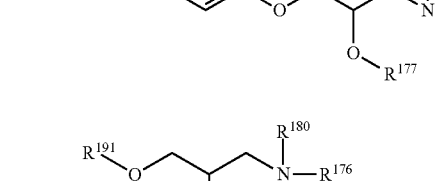 (XLIX)

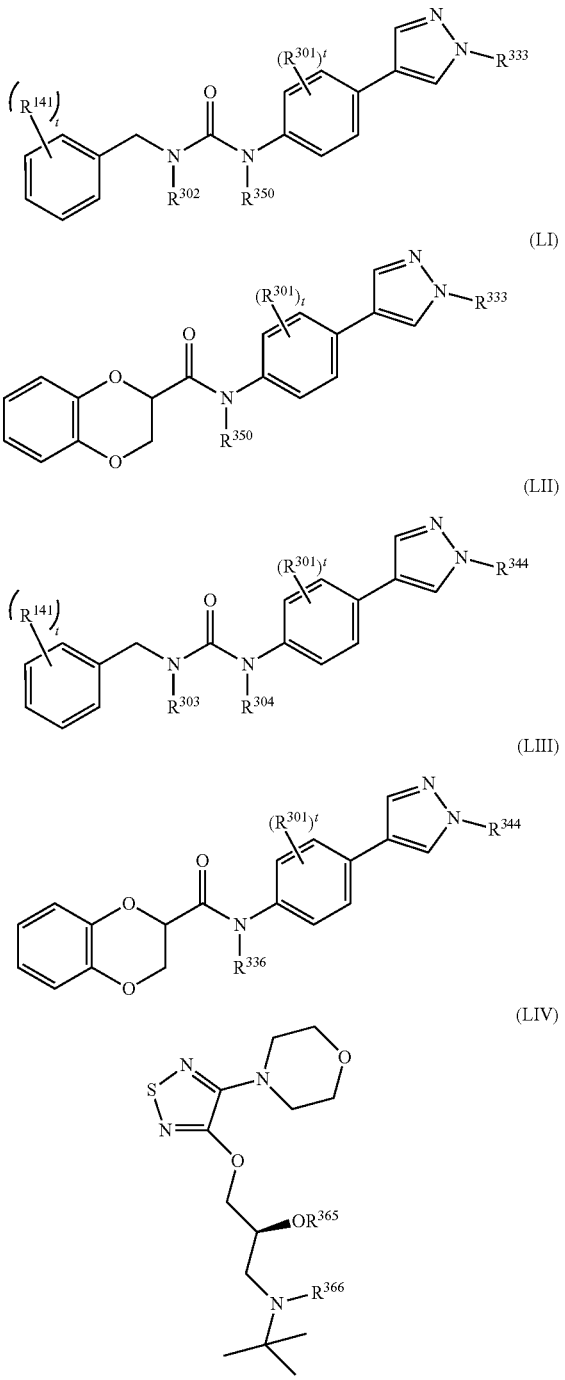

as well as the pharmaceutically acceptable salts and compositions thereof. Formula I, Formula II, and Formula III can be considered a prostaglandin covalently bound to a hydrophobic moiety through an ester or amide linkage that may be metabolized in the eye to afford the parent prostaglandin. Formula IV can be considered a prostaglandin covalently bound to Brimonidine through either a direct bond or a connecting fragment bound to both species that may be metabolized in the eye to afford the parent prostaglandin and Brimonidine. Formula V, Formula V', Formula VI, and Formula VI' can be considered a prostaglandin covalently bound to Timolol through either a direct bond or a connecting fragment bound to both species that may be metabolized in the eye to afford the parent prostaglandin and one, two, or three moieties of Timolol per prostaglandin. Formula VII and Formula VIII can be considered Brimonidine covalently bound to a hydrophobic moiety through an amide linkage that may be metabolized in the eye to afford Brimonidine. Formula IX and IX' can be considered Brimonidine covalently bound to a prostaglandin, Timolol, a carbonic anhydrase inhibitor, or a duel leucine zipper kinase through a connecting fragment bound to both species that may be metabolized in the eye to afford Brimonidine as well as either prostaglandin, Timolol, a carbonic anhydrase inhibitor, or a duel leucine zipper kinase. Formula X can be considered a derivative of Sunitinib covalently bound to either a prostaglandin, Brimonidine, or Timolol through an ester or amide linkage that may be metabolized in the eye to afford the parent Sunitinib derivative as well as either a prostaglandin, Brimonidine, or Timolol. Formula X' can be considered a derivative of Sunitinib covalently bound to a hydrophobic moiety through an ester or amide linkage that may be metabolized in the eye to afford the parent Sunitinib. Formula XI can be considered a derivative of Sunitinib covalently bound to either a prostaglandin, Brimonidine, or Timolol through an ester or amide linkage that may be metabolized in the eye to afford the parent Sunitinib derivative as well as either a prostaglandin, Brimonidine, or Timolol. Formula XII can be considered a derivative of Sunitinib covalently bound to either a prostaglandin, Brimonidine, or Timolol through an ester or amide linkage that may be metabolized in the eye to afford the parent Sunitinib derivative as well as either a prostaglandin, Brimonidine, or Timolol. Formula XIII can be considered Timolol covalently bound to either a prostaglandin or Brimonidine that may be metabolized in the eye to afford Timolol as well as either a prostaglandin or Brimonidine. Formula XIV can be considered Timolol covalently bound to a hydrophobic moiety through an ester linkage that may be metabolized in the eye to afford the Timolol. Formula XV, Formula XV', Formula XV'' and Formula LIV can be considered Timolol covalently bound to a prostaglandin, Brimonidine, a carbonic anhydrase inhibitor, or a duel leucine zipper kinase that may be metabolized in the eye to afford Timolol as well as either prostaglandin, Brimonidine, a carbonic anhydrase inhibitor, or a duel leucine zipper kinase. Formula XVI can be considered Timolol covalently bound to a hydrophobic moiety through an ester linkage that may be metabolized in the eye to afford Timolol. Formula XVII can be considered Timolol covalently bound to a hydrophobic moiety through an ester linkage that may be metabolized in the eye to afford Timolol. Formula XVIII and Formula XVIII' can be considered Crizotinib covalently bound to either a prostaglandin, Brimonidine, or Timolol through a connecting fragment bound to both species that may be metabolized in the eye to release Crizotinib as well as either a prostaglandin, Brimonidine, or Timolol. Formula XIX and Formula XIX' can be considered KW-2449 covalently to either a prostaglandin, Brimonidine, or Timolol through a connecting fragment bound to both species that may be metabolized in the eye to release KW-2449 as well as a prostaglandin, Brimonidine, or Timolol. Formula XX can be considered an active DLK inhibitor covalently bound to either a prostaglandin, Brimonidine, or Timolol through a connecting fragment bound to both species that may be metabolized in the eye to release the active DLK inhibitor as well as a prostaglandin, Brimonidine, or Timolol. Formula XXI can be considered a derivative of Tozasertib covalently bound to either a prostaglandin, Brimonidine, or Timolol through a connecting fragment bound to both species that may be metabolized in the eye to release Tozasertib as well as a prostaglandin, Brimonidine, or Timolol. Formula XXII can be considered Brinzolamide covalently bound to a prostaglandin through a connecting fragment bound to both species that may be metabolized in the eye to afford Brinzolamide and a prostaglandin. Formula XXIII can be considered Dorzolamide covalently bound to a prostaglandin through a connecting fragment bound to both species that may be metabolized in the eye to afford Dorzolamide and a prostaglandin. Formula XXIV can be considered Acetazolamide covalently bound to a prostaglandin through a connecting fragment bound to both species that may be metabolized in the eye to afford Acetazolamide and a prostaglandin. Formula XXV can be considered Methazolamide covalently bound to a prostaglandin through a connecting fragment bound to both species that may be metabolized in the eye to afford Methazolamide and a prostaglandin. Formula XXVI can be considered Brinzolamide covalently bound to a prostaglandin through a connecting fragment bound to both species that may be metabolized in the eye to afford Brinzolamide and a prostaglandin. Formula XXVII can be considered Dorzolamide covalently bound to a prostaglandin through a connecting fragment bound to both species that may be metabolized in the eye to afford Dorzolamide and a prostaglandin. Formula XXVIII can be considered an active ROCK inhibitor covalently bound to either a prostaglandin, Brimonidine, Timolol, a carbonic anhydrase inhibitor, a duel leucine zipper kinase through a connecting fragment bound to both species that may be metabolized in the eye to release the active ROCK inhibitor. Formula XXIX can be considered an active ROCK inhibitor covalently bound to either a prostaglandin, Brimonidine, Timolol, a carbonic anhydrase inhibitor, a duel leucine zipper kinase through a connecting fragment bound to both species that may be metabolized in the eye to release the active ROCK inhibitor. Formula XXX can be considered an active ROCK inhibitor covalently bound to either a prostaglandin, Brimonidine, Timolol, a carbonic anhydrase inhibitor, a duel leucine zipper kinase through a connecting fragment bound to both species that may be metabolized in the eye to release the active ROCK inhibitor. Formula XXXI can be considered a ROCK inhibitor covalently bound to a hydrophobic moiety through an amide linkage that may be metabolized in the eye to afford the parent ROCK inhibitor. Formula XXXII can be considered a ROCK inhibitor covalently bound to a hydrophobic moiety through an amide linkage to both species that may be metabolized in the eye to afford the parent ROCK inhibitor. Formula XXXIII can be considered a ROCK inhibitor covalently bound to a hydrophobic moiety through an amide linkage bound to both species that may be metabolized in the eye to afford the parent ROCK inhibitor. Formula XXXIV can be considered Metipranolol covalently bound to a prostaglandin, Brimonidine, a carbonic anhydrase inhibitor, or a duel leucine zipper kinase through a connecting fragment bound to both species that may be metabolized in the eye to afford Metipranolol as well as either prostaglandin, Brimonidine, a carbonic anhydrase inhibitor, or a duel leucine zipper kinase. Formula XXXV can be considered a Metipranolol covalently bound to a hydrophobic moiety through an amide or ester linkage that may be metabolized in the eye to afford Metipranolol. Formula XXXIV and Formula XXXVIII can be considered Levobunolol covalently bound to a prostaglandin, Brimonidine, a carbonic anhydrase inhibitor, or a duel leucine zipper kinase through a connecting fragment bound to both species that may be metabolized in the eye to afford Levobunolol as well as either prostaglandin, Brimonidine, a carbonic anhydrase inhibitor, or a duel leucine zipper kinase. Formula XXXVII and Formula XXXIX can be considered Levobunolol covalently bound to a hydrophobic moiety through an amide or ester linkage that may be metabolized in the eye to afford Levobunolol. Formula XL and Formula XLII can be considered Carteolol covalently bound to a prostaglandin, Brimonidine, a carbonic anhydrase inhibitor, or a duel leucine zipper kinase through a connecting fragment bound to both species that may be metabolized in the eye to afford Carteolol as well as either prostaglandin, Brimonidine, a carbonic anhydrase inhibitor, or a duel leucine zipper kinase. Formula XLI and Formula XLII can be considered Carteolol covalently bound to a hydrophobic moiety through an amide or ester linkage that may be metabolized in the eye to afford Carteolol. Formula XLIV and Formula XLVI can be considered Betaxolol covalently bound to a prostaglandin, Brimonidine, a carbonic anhydrase inhibitor, or a duel leucine zipper kinase through a connecting fragment bound to both species that may be metabolized in the eye to afford Betaxolol as well as either prostaglandin, Brimonidine, a carbonic anhydrase inhibitor, or a duel leucine zipper kinase. Formula XLV and Formula XLVII can be considered Carteolol covalently bound to a hydrophobic moiety through an amide or ester linkage that may be metabolized in the eye to afford Betaxolol. Formula XLVIII can be considered a beta-blocker covalently bound to a prostaglandin, Brimonidine, a carbonic anhydrase inhibitor, or a duel leucine zipper kinase through a connecting fragment bound to both species that may be metabolized in the eye to afford the beta-blocker as well as either prostaglandin, Brimonidine, a carbonic anhydrase inhibitor, or a duel leucine zipper kinase. Formula XLIX can be considered a beta-blocker covalently bound to a hydrophobic moiety through an amide or ester linkage that may be metabolized in the eye to afford the beta-blocker. Formula L can be considered SR5834 covalently bound to a hydrophobic moiety through an amide or amine linkage that may be metabolized in the eye to afford SR5834. Formula LI can be considered SR3677 covalently bound to a hydrophobic moiety through an amide or amine linkage that may be metabolized in the eye to afford SR3677. Formula LII can be considered SR5834 covalently bound to a prostaglandin, Brimonidine, a carbonic anhydrase inhibitor, or a duel leucine zipper kinase through a connecting fragment bound to both species that may be metabolized in the eye to afford SR5834 as well as either prostaglandin, Brimonidine, a carbonic anhydrase inhibitor, or a duel leucine zipper kinase. Formula LIII LII can be considered SR3677 covalently bound to a prostaglandin, Brimonidine, a carbonic anhydrase inhibitor, or a duel leucine zipper kinase through a connecting fragment bound to both species that may be metabolized in the eye to afford SR3677 as well as either prostaglandin, Brimonidine, a carbonic anhydrase inhibitor, or a duel leucine zipper kinase.

In one embodiment, the compound is a treatment for glaucoma, and therefore can be used as an effective amount to treat a host in need of glaucoma treatment. In another embodiment, the compound acts through a mechanism other than those associated with glaucoma to treat a disorder described herein in a host, typically a human.

The compounds, as described herein, may include, for example, prodrugs, which are hydrolysable to form the active carboxylic acid compound. Thus, when a compound of Formula I, Formula II, Formula III, Formula IV, Formula V, Formula VI, Formula V', or Formula VI' is administered to a mammalian subject, typically a human, the amide or ester modifications may be cleaved to release the parent free acid compound:

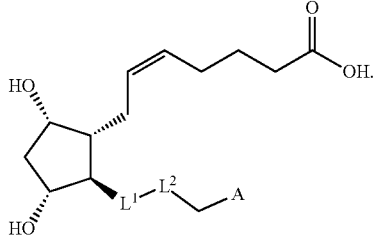

The compounds, as described herein, may include, for example, prodrugs, which are hydrolysable to form the active imidazole compound. Thus when a compound of Formula VII, Formula VIII, Formula IX, Formula IX', Formula XVII', Formula XVII", or Formula XVII'" is administered to a mammalian subject, typically a human, the amide modifications may be cleaved to release Brimonidine.

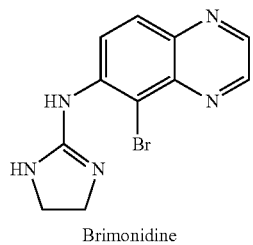 [SMILES: Brc1c(NC2=NCCN2)ccc2nccnc12]

Brimonidine

The compounds, as described herein, may include, for example, prodrugs, which are hydrolysable to form the active beta-blockers Timolol, Metipranolol, Levobunolol, Carteolol, or Betaxolol. Thus when a compound of Formula III, Formula IV, Formula XV, Formula XV', Formula XV", Formula XVI, Formula XVII, or Formula LIV is administered to a mammalian subject, typically a human, the amide or ester modifications may be cleaved to release Timolol. When a compound of Formula XXXIV or Formula XXXV is administered to a mammalian subject, typically a human, the amide or ester modifications may be cleaved to release Metipranolol. When a compound of Formula XXXVI or Formula XXXVIII is administered to a mammalian subject, typically a human, the amide or ester modifications may be cleaved to release Levobunolol. When a compound of Formula XL or Formula XLII is administered to a mammalian subject, typically a human, the amide or ester modifications may be cleaved to release careolol. When a compound of Formula XLIV or Formula XLVI is administered to a mammalian subject, typically a human, the amide or ester modifications may be cleaved to release Betaxolol.

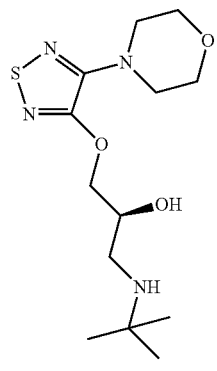

Timolol

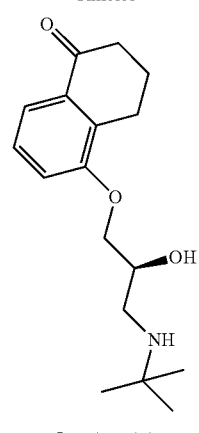

Levobunolol

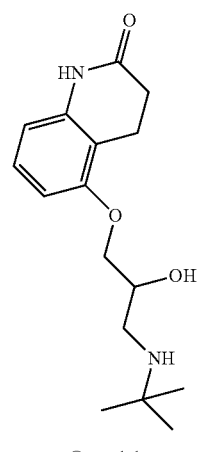

Carteolol

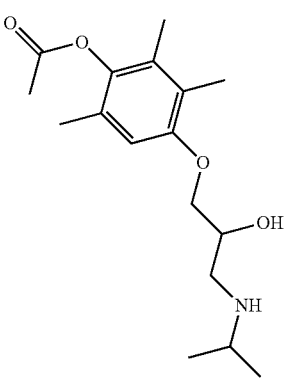

Metipranolol

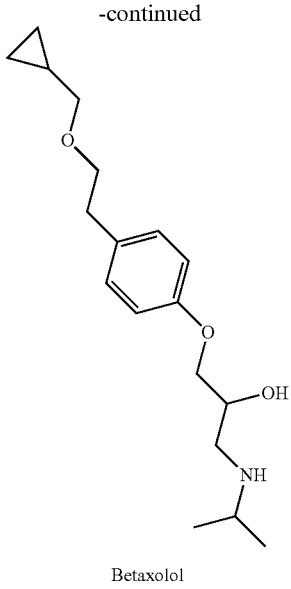

Betaxolol

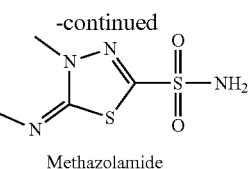

Methazolamide

The compounds, as described herein, may include, for example, prodrugs, which are hydrolysable to form the active sulfonamide compound. Thus when a compound of Formula XII or Formula XXIV is administered to a mammalian subject, typically a human, the amide or sulfonamide modification may be cleaved to release Brinzolamide. When a compound of Formula XXIII or Formula XXVII is administered to a mammalian subject, typically a human, the amide or sulfonamide modification may be cleaved to release Dorzolamide. When a compound of Formula XXIV is administered to a mammalian subject, typically a human, the amide modifications may be cleaved to release Acetazolamide. When a compound of Formula XXV is administered to a mammalian subject, typically a human, the amide modifications may be cleaved to release Methazolamide.

The compounds, as described herein, may include, for example, prodrugs, which are hydrolysable to form the active Sunitinib derivative and an active carboxylic acid or an active sulfonamide compound. Thus when a compound of Formula X, Formula X', Formula XI, or Formula XII is administered to a mammalian subject, typically a human, the prodrug may be cleaved to release the parent Sunitinib derivative. The active Sunitinib derivative is a phenol compound that has been demonstrated in the literature to be an active RTKI (Kuchar, M., et al. (2012). "Radioiodinated Sunitinib as a potential radiotracer for imaging angiogenesis-radiosynthesis and first radiopharmacological evaluation of 5-[125I]Iodo-Sunitinib." Bioorg Med Chem Lett 22(8): 2850-2855. Formulations of Sunitinib for the treatment of ocular disorders and glaucoma have been described in WO2016/100392 and WO2016/100380, respectively.

The compounds, as described herein, may include, for example, prodrugs, which are hydrolysable to release the active DLK inhibitor. Thus when a compound of Formula XVIII or Formula XVIII' is administered to a mammalian subject, typically a human, the amide bond may be cleaved to release Crizotinib. When a compound of Formula XIX or XIX' is administered to a mammalian subject, typically a human, the amide bond may be cleaved to release KW-2449. When a compound of Formula XX is administered to a mammalian subject, typically a human, the amide bond may be cleaved to release a piperidino DLK inhibitor. When a compound of Formula XXI is administered to a mammalian subject, typically a human, the amide bond may be cleaved to release a Tozasertib derivative.

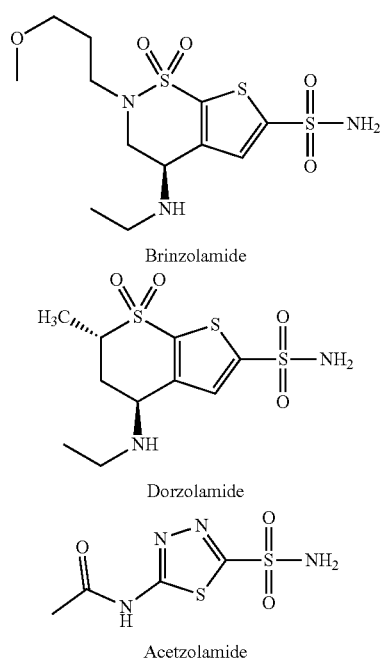

Brinzolamide

Dorzolamide

Acetzolamide

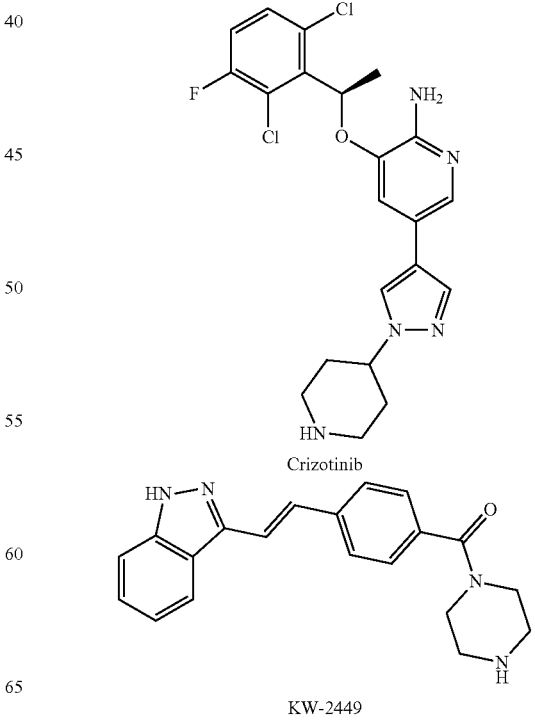

Crizotinib

KW-2449

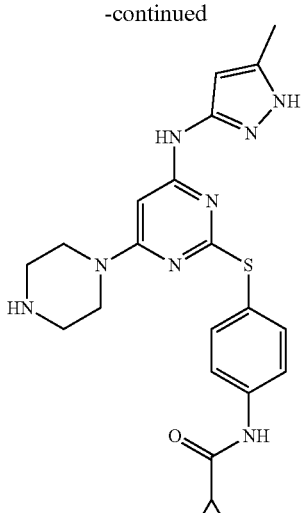

Tozasertib derivative

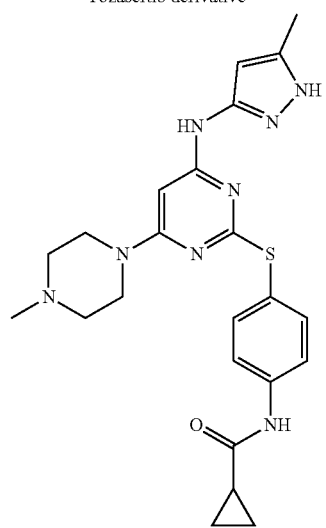

Tozasertib

The compounds, as described herein, may include, for example, prodrugs, which are hydrolysable to release the active ROCK inhibitor. Thus when a compound of Formula XXX or XXXIII is administered to a mammalian subject, typically a human, the amide modifications may be cleaved to release RKI-1447 or RKI-1313. When a compound of Formula XXIX or XXXII is administered to a mammalian subject, typically a human, the amide modifications may be cleaved to release RKI-11 or RKI-18. When a compound of Formula L or LII is administered to a mammalian subject, typically a human, the amide modifications may be cleaved to release SR5834 (1-(2-hydroxyethyl)-1-[(3-methoxyphenyl)methyl]-3-[4-(1H-pyrazol-4-yl)phenyl]urea), RKI-H-1y (1-(2-hydroxyethyl)-1-[(3-methoxyphenyl)methyl]-3-[4-(1H-pyrazol-4-yl)-2-[2-(pyrrolidin-1-yl)ethoxy]phenyl] urea), or RKI-1y (3-(4-(1H-pyrazol-4-yl)-2-(2-(pyrrolidin-1-yl)ethoxy)phenyl)-1-ethyl-1-(3-methoxybenzyl)urea).

When a compound of Formula LI or Formula LIII is administered to a mammalian subject, typically a human, the amide modifications may be cleaved to release SR3677.

RKI-1447

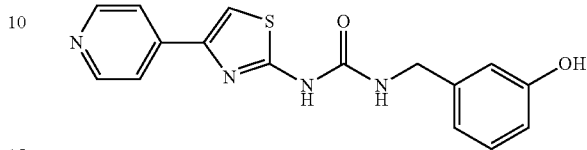

RKI-1313

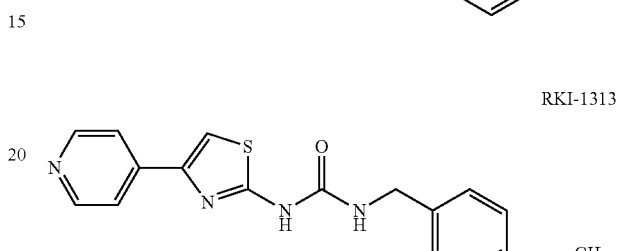

RKI-11

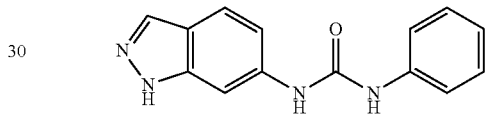

RKI-18

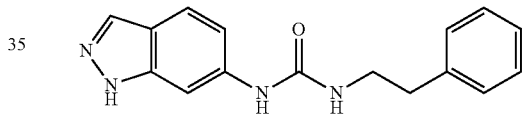

SR5834

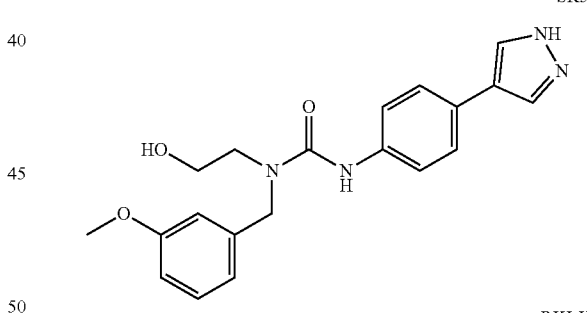

RKI-H-1y

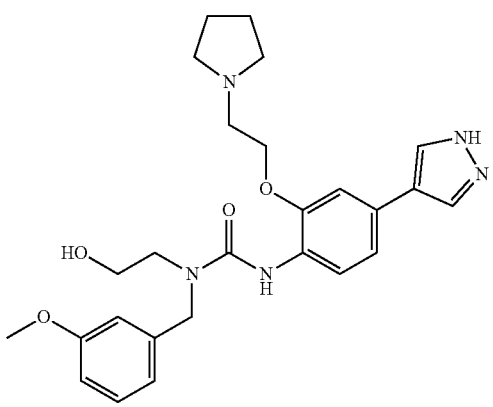

RKI-1y

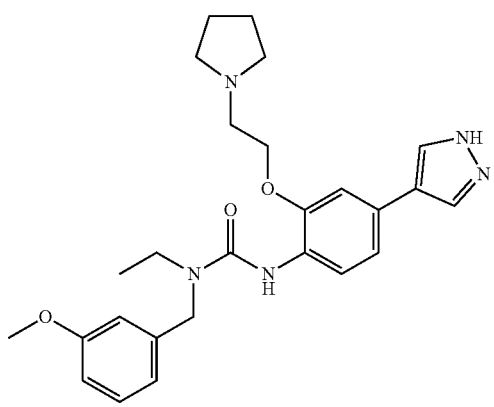

SR3677

The amides and esters of commercial prostaglandins are believed to act as prodrugs in the eye, in that the ester or amide form, is hydrolyzed by an endogenous ocular enzyme, releasing the parent compound as a free acid which is the active pharmacologic agent. However, this also releases a potentially toxic and potentially irritating small aliphatic alcohol, for example, isobutanol into the eye. While effective in reducing intraocular pressure, most drugs currently in use, including Latanoprost, bimatoprost, travoprost, may cause a significant level of eye irritation in some patients.

In addition to the foregoing, the isopropyl esters of prostaglandins, for example, Latanoprost and fluprostenol, are highly viscous, glassy oils, which can be difficult to handle and to formulate into ophthalmic solutions. In addition, these compounds can be prone to the retention of potentially toxic process solvents. The higher alkyl esters or amides of prostaglandins can be easier to handle and may not release as irritating of an alcohol or amine upon hydrolysis.

In addition to the irritation caused by the prostaglandins themselves, and particularly the naturally-occurring and synthetic prostaglandins of the type presently on the market, the preservatives typically used in ophthalmic solutions are known to potentially irritate a percentage of the population. Thus, despite the fact that the prostaglandins represent an important class of potent therapeutic agents for the treatment of glaucoma, the unwanted side effects of these drugs, particularly ocular irritation and inflammation, may limit patient use and can be related to patient withdrawal from the use of these drugs. The higher alkyl esters and amides of prostaglandins as disclosed herein, can be less irritating to patients yet therapeutically effective.

Non-limiting examples of compounds of Formula I, Formula II, Formula III, Formula IV, Formula V, Formula V', Formula VI, Formula VI', Formula VII, Formula VIII, Formula IX, Formula IX', Formula X, Formula X', Formula XI, Formula XII, Formula XIII, Formula XIV, Formula XV, Formula XV', Formula XVI, Formula XVII, Formula XVII', Formula XVII'', Formula XVII''', Formula XVIII, Formula XVIII', Formula XIX, Formula XIX', Formula XX, Formula XXI, Formula XXII, Formula XXIII, Formula XXIV, Formula XV, Formula XVI, Formula XVII, Formula XVIII, Formula XXIX, Formula XXX, Formula XXXI, Formula XXXII, Formula XXXIII, Formula XXXIV, Formula XXXV, Formula XXXVI, Formula XXXVII, Formula XXXVIII, Formula XXXIX, Formula XL, Formula XLI, Formula XLII, Formula XLIII, Formula XLIV, Formula XLV, Formula XLVI, Formula XLVII, Formula XLVIII, Formula XLIX, Formula L, Formula LI, Formula LII, or Formula LIII with variations in the variables e.g., $L^1$, $L^2$, $R^1$-$R^{27}$, and A, are illustrated below. The disclosure includes all combinations of these definitions so long as a stable compound results.

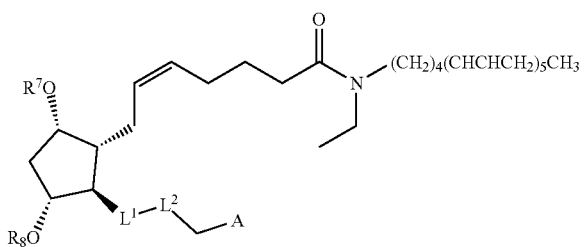

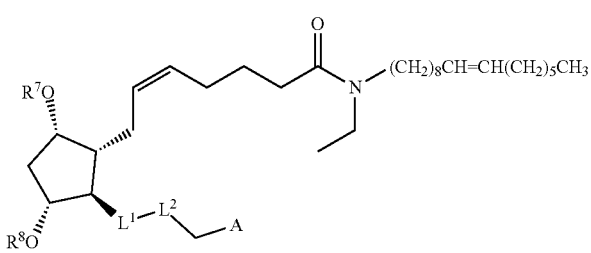

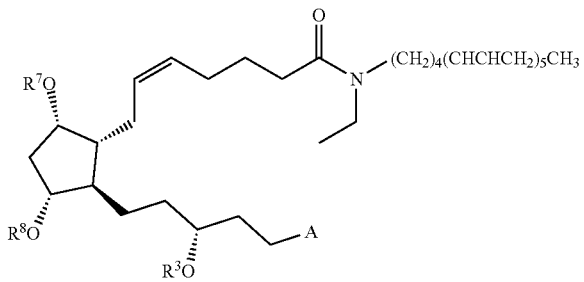

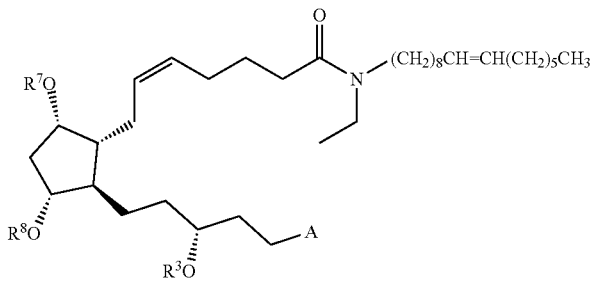

279 280
-continued
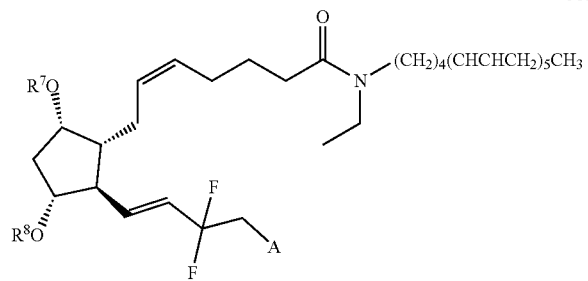
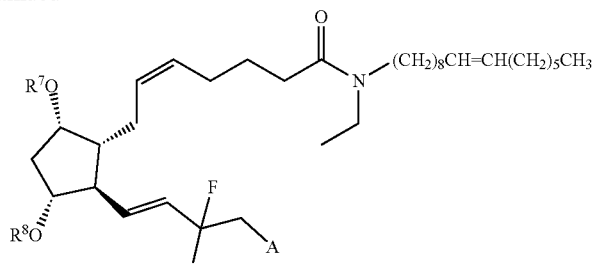
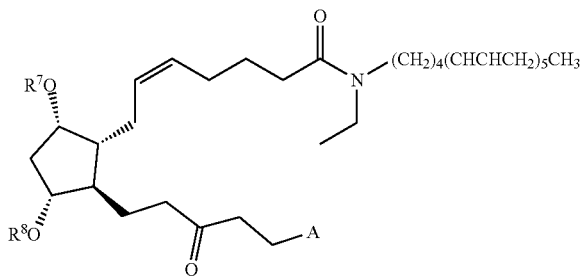
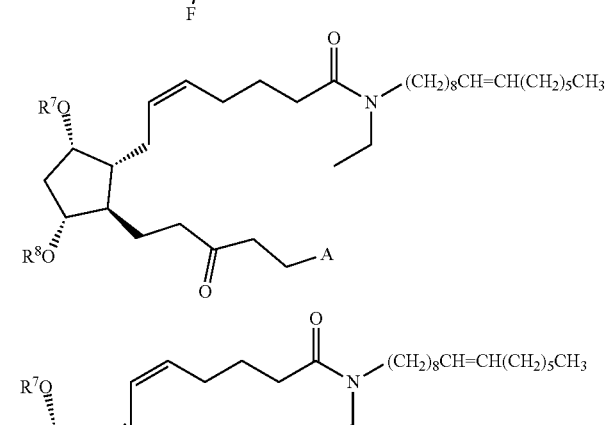
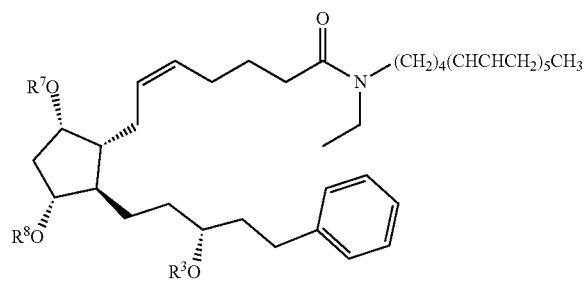
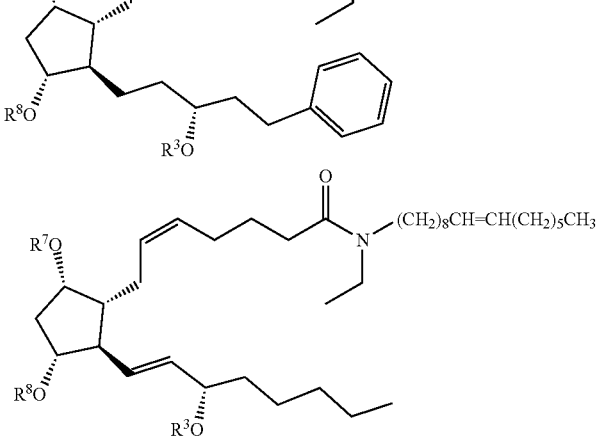
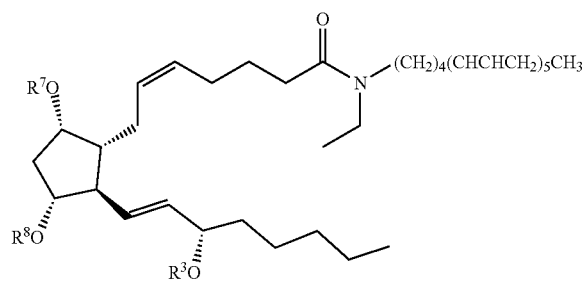
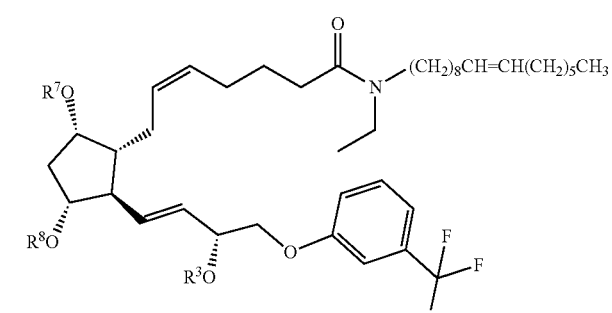
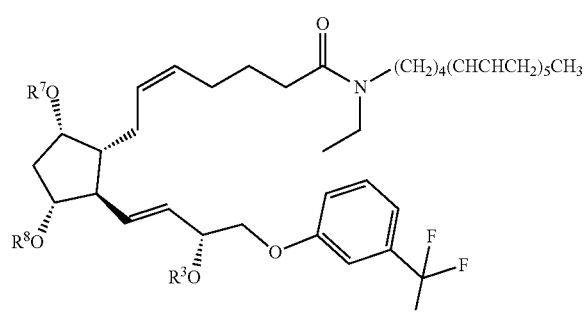
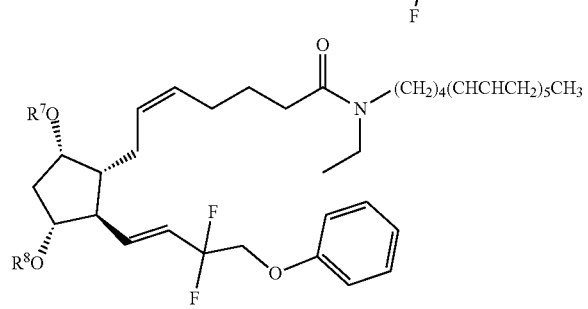
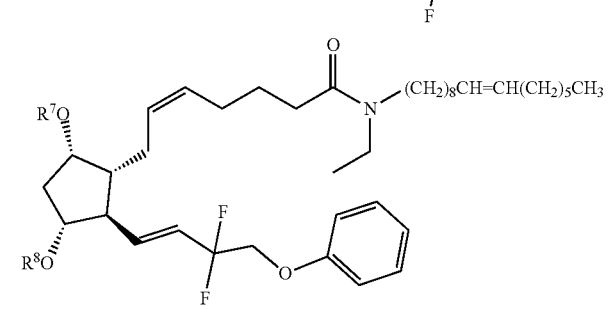

281
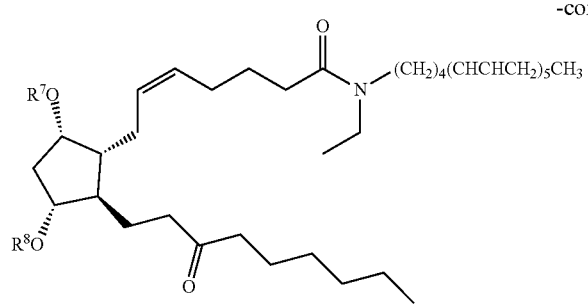
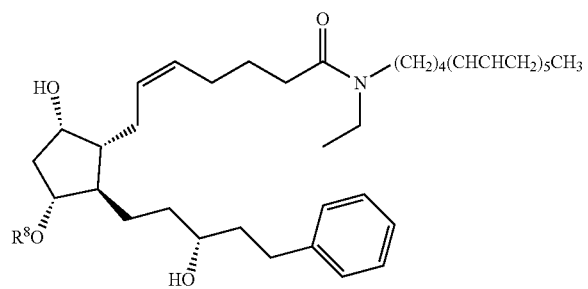
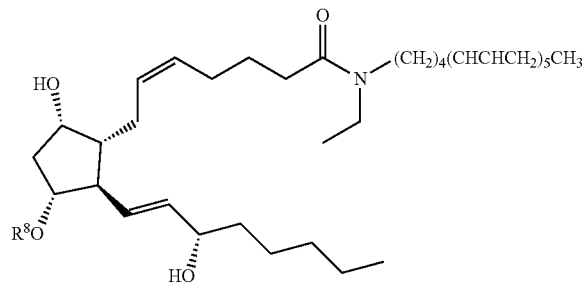
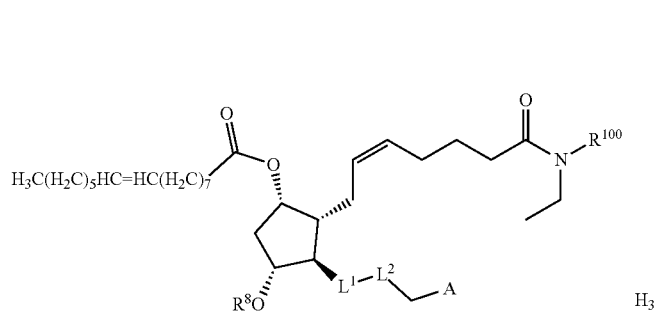
282
-continued
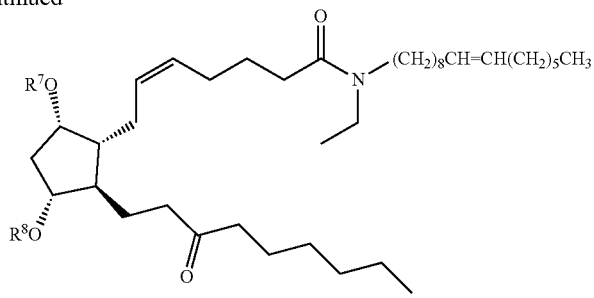
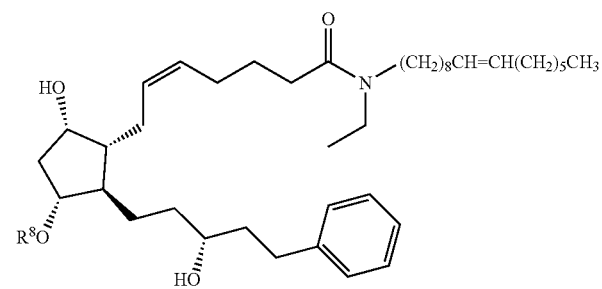
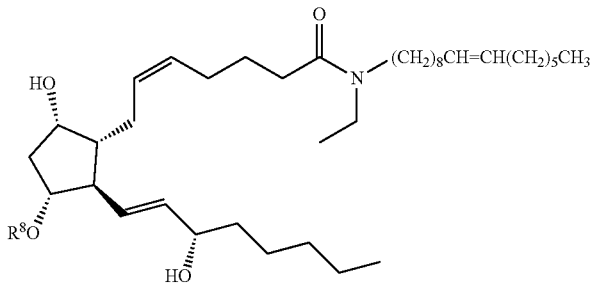
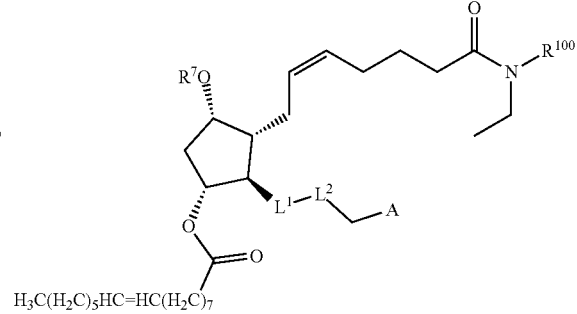
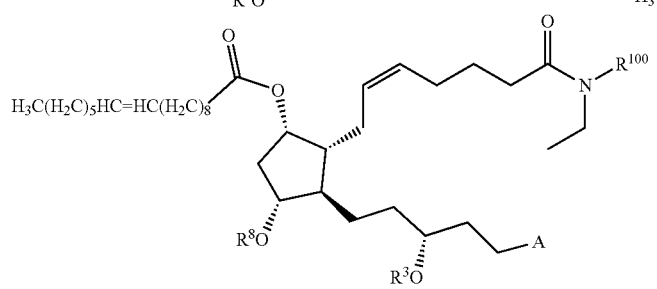

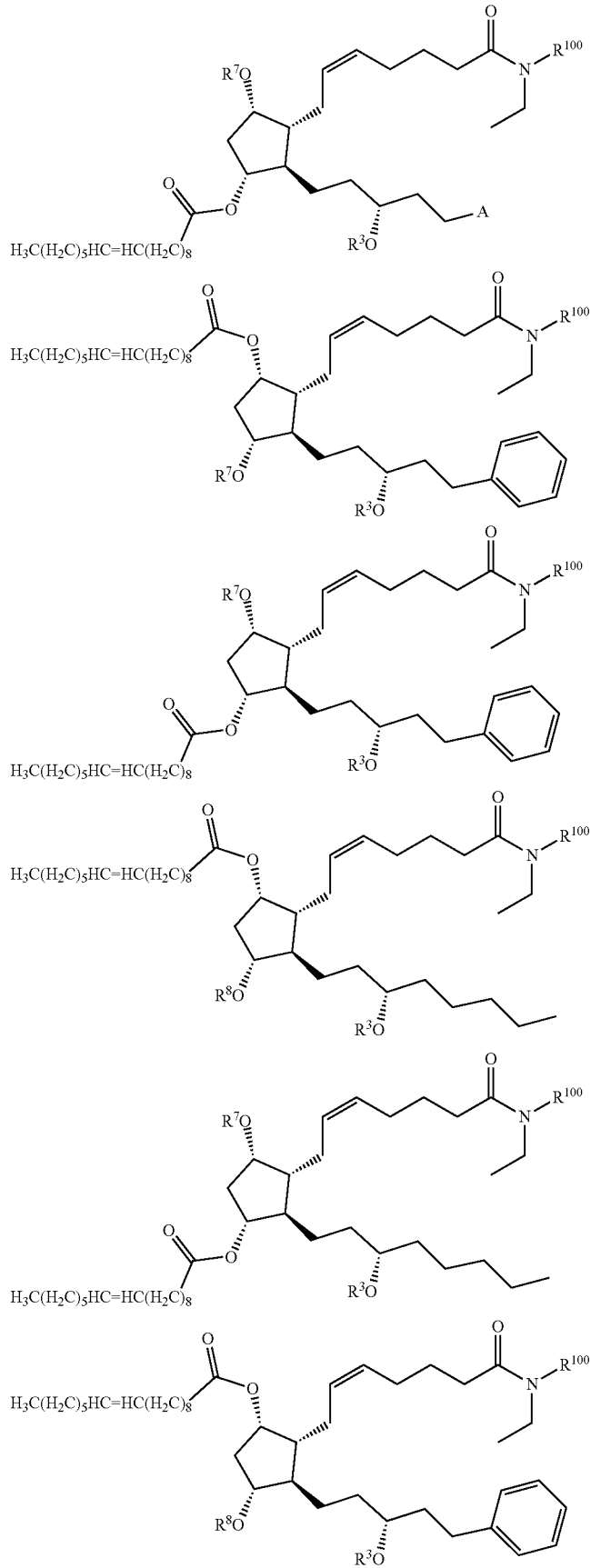

-continued
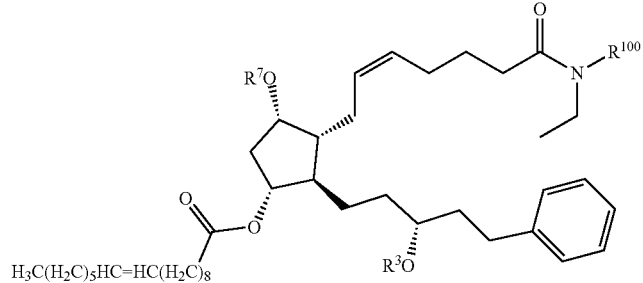
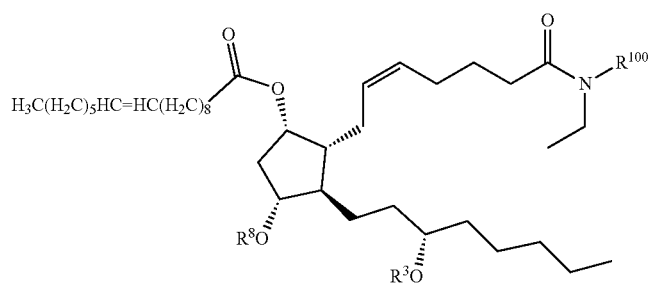
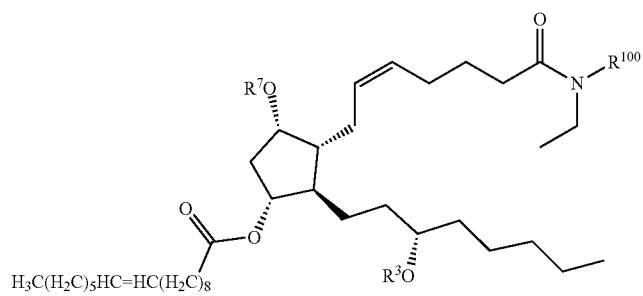
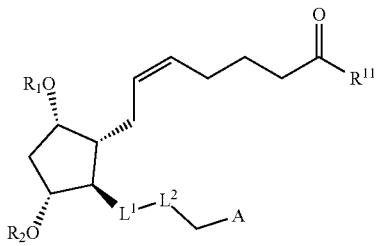
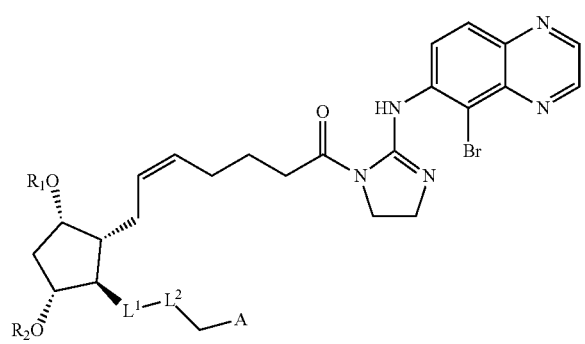
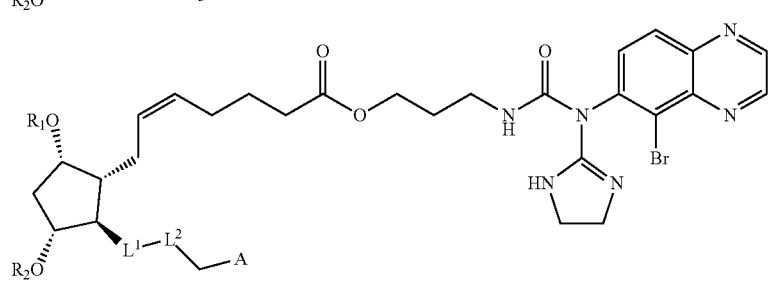

-continued
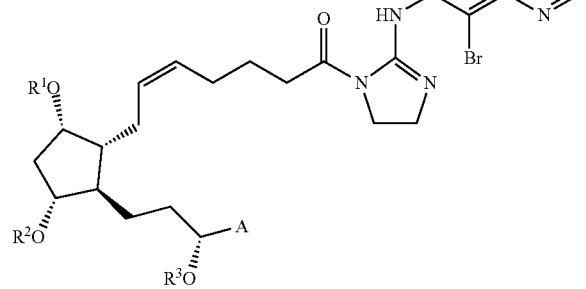
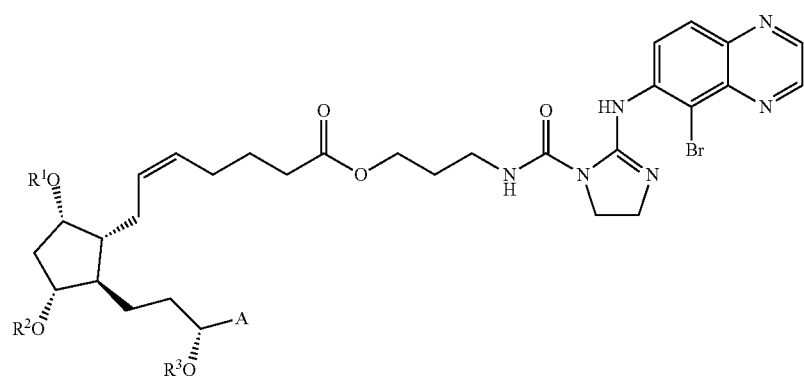
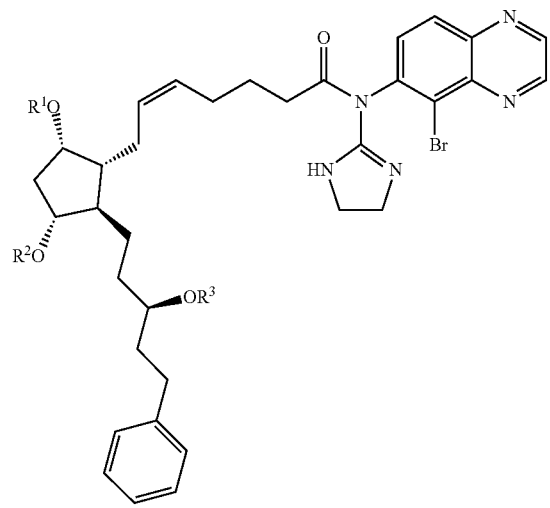
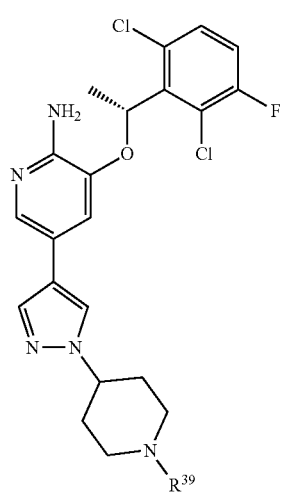
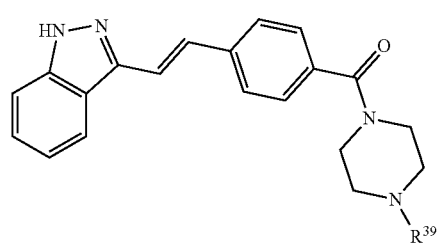
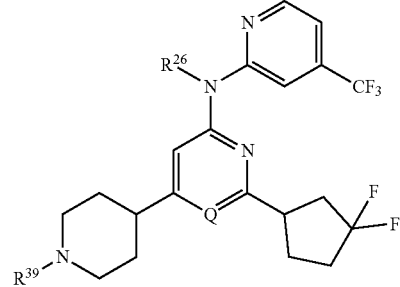

289
-continued
290
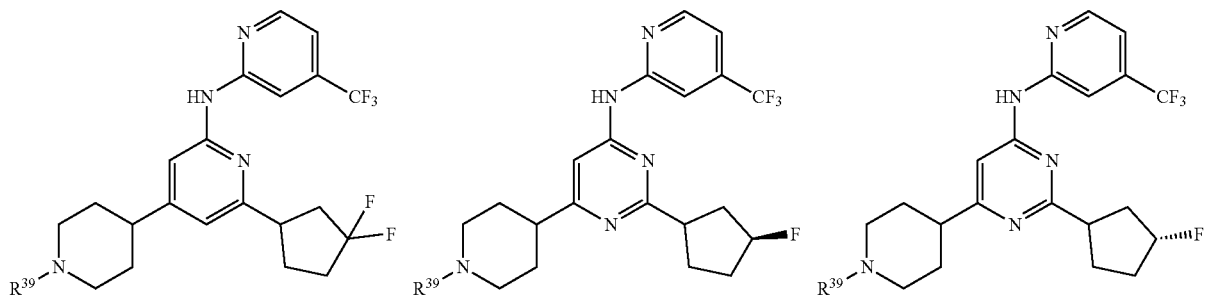
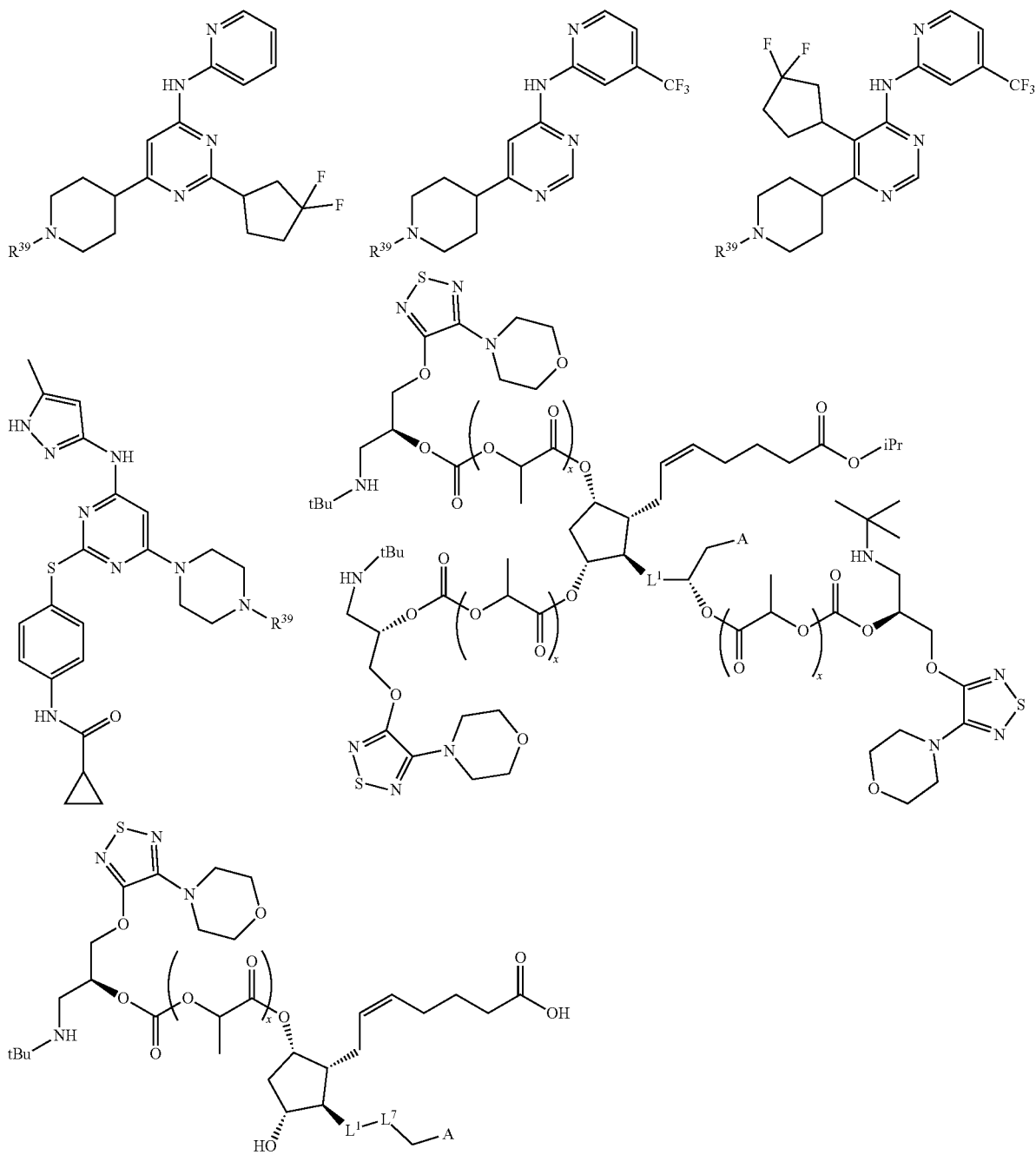

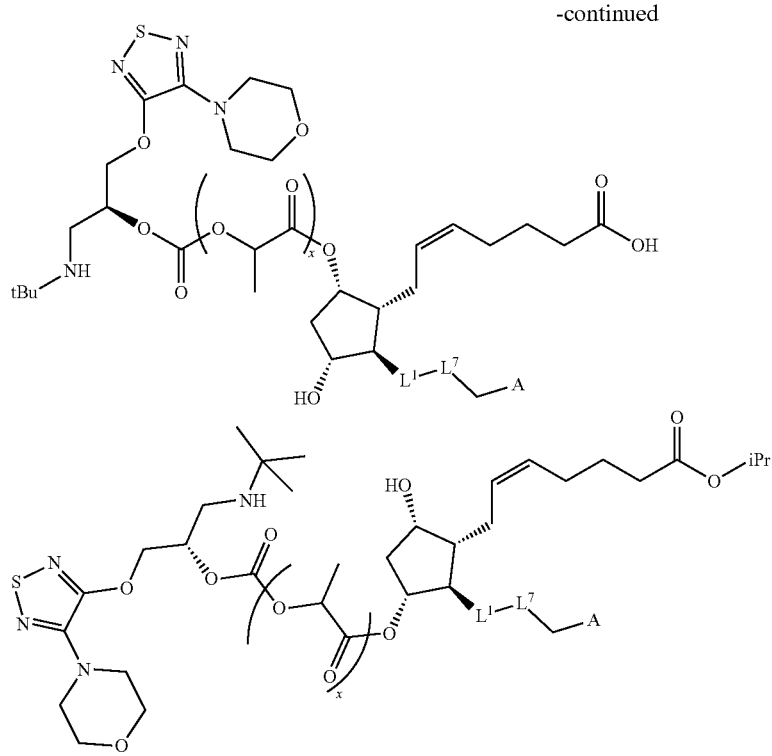

Embodiments of x and y

In embodiments provided herein, each of the below is considered individually and specifically described.
In one embodiment x is 1 and y is 1.
In one embodiment x is 1 and y is 2.
In one embodiment x is 1 and y is 3.
In one embodiment x is 1 and y is 4.
In one embodiment x is 1 and y is 5.
In one embodiment x is 1 and y is 6.
In one embodiment x is 1 and y is 7.
In one embodiment x is 1 and y is 8.
In one embodiment x is 2 and y is 1.
In one embodiment x is 2 and y is 2.
In one embodiment x is 2 and y is 3.
In one embodiment x is 2 and y is 4.
In one embodiment x is 2 and y is 5.
In one embodiment x is 2 and y is 6.
In one embodiment x is 2 and y is 7.
In one embodiment x is 2 and y is 8.
In one embodiment x is 3 and y is 1.
In one embodiment x is 3 and y is 2.
In one embodiment x is 3 and y is 3.
In one embodiment x is 3 and y is 4.
In one embodiment x is 3 and y is 5.
In one embodiment x is 3 and y is 6.
In one embodiment x is 3 and y is 7.
In one embodiment x is 3 and y is 8.
In one embodiment x is 4 and y is 1.
In one embodiment x is 4 and y is 2.
In one embodiment x is 4 and y is 3.
In one embodiment x is 4 and y is 4.
In one embodiment x is 4 and y is 5.
In one embodiment x is 4 and y is 6.
In one embodiment x is 4 and y is 7.
In one embodiment x is 4 and y is 8.
In one embodiment x is 5 and y is 1.
In one embodiment x is 5 and y is 2.
In one embodiment x is 5 and y is 3.
In one embodiment x is 5 and y is 4.
In one embodiment x is 5 and y is 5.
In one embodiment x is 5 and y is 6.
In one embodiment x is 5 and y is 7.
In one embodiment x is 5 and y is 8.
In one embodiment x is 6 and y is 1.
In one embodiment x is 6 and y is 2.
In one embodiment x is 6 and y is 3.
In one embodiment x is 6 and y is 4.
In one embodiment x is 6 and y is 5.
In one embodiment x is 6 and y is 6.
In one embodiment x is 6 and y is 7.
In one embodiment x is 6 and y is 8.
In one embodiment x is 7 and y is 1.
In one embodiment x is 7 and y is 2.
In one embodiment x is 7 and y is 3.
In one embodiment x is 7 and y is 4.
In one embodiment x is 7 and y is 5.
In one embodiment x is 7 and y is 6.
In one embodiment x is 7 and y is 7.
In one embodiment x is 7 and y is 8.
In one embodiment x is 8 and y is 1.
In one embodiment x is 8 and y is 2.
In one embodiment x is 8 and y is 3.
In one embodiment x is 8 and y is 4.
In one embodiment x is 8 and y is 5.
In one embodiment x is 8 and y is 6.
In one embodiment x is 8 and y is 7.
In one embodiment x is 8 and y is 8.

III. Pharmaceutical Preparations

One embodiment provides compositions including the compounds described herein. In certain embodiments, the composition includes a compound of Formula I, Formula II, Formula III, Formula IV, Formula V, Formula V', Formula VI, Formula VI', Formula VII, Formula VIII, Formula IX, Formula IX', Formula X, Formula X', Formula XI, Formula XII, Formula XIII, Formula XIV, Formula XV, Formula XV', Formula XV'', Formula XVI, Formula XVII, Formula XVII', Formula XVII'', Formula XVII''', Formula XVIII, Formula XVIII', Formula XIX, Formula XIX', Formula XX, Formula XXI, Formula XXII, Formula XXIII, Formula XXIV, Formula XV, Formula XVI, Formula XVII, Formula XVIII, Formula XXIX, Formula XXX, Formula XXXI, Formula XXXII, Formula XXXIII, Formula XXXIV, Formula XXXV, Formula XXXVI, Formula XXXVII, Formula XXXVIII, Formula XXXIX, Formula XL, Formula XLI, Formula XLII, Formula XLIII, Formula XLIV, Formula XLV, Formula XLVI, Formula XLVII, Formula XLVIII, Formula XLIX, Formula L, Formula LI, Formula LII, Formula LIII, or Formula LIV in combination with a pharmaceutically acceptable carrier, excipient or diluent. In one embodiment, the composition is a pharmaceutical composition for treating an eye disorder or eye disease. Non-limiting exemplary eye disorder or disease treatable with the composition includes age related macular degeneration, alkaline erosive keratoconjunctivitis, allergic conjunctivitis, allergic keratitis, anterior uveitis, Behcet's disease, blepharitis, blood-aqueous barrier disruption, chorioiditis, chronic uveitis, conjunctivitis, contact lens-induced keratoconjunctivitis, corneal abrasion, corneal trauma, corneal ulcer, crystalline retinopathy, cystoid macular edema, dacryocystitis, diabetic keratophathy, diabetic macular edema, diabetic retinopathy, dry eye disease, dry age-related macular degeneration, geographic atrophy, eosinophilic granuloma, episcleritis, exudative macular edema, Fuchs' Dystrophy, giant cell arteritis, giant papillary conjunctivitis, glaucoma, glaucoma surgery failure, graft rejection, herpes zoster, inflammation after cataract surgery, iridocorneal endothelial syndrome, iritis, keratoconjunctiva sicca, keratoconjunctival inflammatory disease, keratoconus, lattice dystrophy, map-dot-fingerprint dystrophy, necrotic keratitis, neovascular diseases involving the retina, uveal tract or cornea, for example, neovascular glaucoma, corneal neovascularization, neovascularization resulting following a combined vitrectomy and lensectomy, neovascularization of the optic nerve, and neovascularization due to penetration of the eye or contusive ocular injury, neuroparalytic keratitis, non-infectious uveitisocular herpes, ocular lymphoma, ocular rosacea, ophthalmic infections, ophthalmic pemphigoid, optic neuritis, panuveitis, papillitis, pars planitis, persistent macular edema, phacoanaphylaxis, posterior uveitis, post-operative inflammation, proliferative diabetic retinopathy, proliferative sickle cell retinopathy, proliferative vitreoretinopathy, retinal artery occlusion, retinal detachment, retinal vein occlusion, retinitis pigmentosa, retinopathy of prematurity, rubeosis iritis, scleritis, Stevens-Johnson syndrome, sympathetic ophthalmia, temporal arteritis, thyroid associated ophthalmopathy, uveitis, vernal conjunctivitis, vitamin A insufficiency-induced keratomalacia, vitreitis, and wet age-related macular degeneration.

Compounds of Formula I, Formula II, Formula III, Formula IV, Formula V, Formula V', Formula VI, Formula VI', Formula VII, Formula VIII, Formula IX, Formula IX', Formula X, Formula X', Formula XI, Formula XII, Formula XIII, Formula XIV, Formula XV, Formula XV', Formula XV''', Formula XVI, Formula XVII, Formula XVII', Formula XVII'', Formula XVII''', Formula XVIII, Formula XVIII', Formula XIX, Formula XIX', Formula XX, Formula XXI, Formula XXII, Formula XXIII, Formula XXIV, Formula XV, Formula XVI, Formula XVII, Formula XVIII, Formula XXIX, Formula XXX, Formula XXXI, Formula XXXII, Formula XXXIII, Formula XXXIV, Formula XXXV, Formula XXXVI, Formula XXXVII, Formula XXXVIII, Formula XXXIX, Formula XL, Formula XLI, Formula XLII, Formula XLIII, Formula XLIV, Formula XLV, Formula XLVI, Formula XLVII, Formula XLVIII, Formula XLIX, Formula L, Formula LI, Formula LII, Formula LIII, or Formula LIV or its salt, can be delivered by any method known for ocular delivery. Methods include but are not limited to conventional (solution, suspension, emulsion, ointment, inserts and gels); vesicular (liposomes, niosomes, discomes and pharmacosomes), particulates (microparticles and nanoparticles), advanced materials (scleral plugs, gene delivery, siRNA and stem cells); and controlled release systems (implants, hydrogels, dendrimers, iontoporesis, collagen shields, polymeric solutions, therapeutic contact lenses, cyclodextrin carriers, microneedles and microemulsions).

In certain aspects, a delivery system is used including but not limited to the following; i) a degradable polymeric composition; ii) a non-degradable polymeric composition; (iii) a gel, including, a hydrogel; (iv) a depot; (v) a particle containing a core; vi) a surface-coated particle; vii) a multi-layered polymeric or non-polymeric or mixed polymeric and non-polymeric particle; viii) a polymer blend and/or ix) a particle with a coating on the surface of the particle. The polymers can include, for example, hydrophobic regions. In some embodiments, at least about 30, 40 or 50% of the hydrophobic regions in the coating molecules have a molecular mass of least about 2 kDa. In some embodiments, at least about 30, 40 or 50% of the hydrophobic regions in the coating molecules have a molecular mass of least about 3 kDa. In some embodiments, at least about 30, 40 or 50% of the hydrophobic regions in the coating molecules have a molecular mass of least about 4 kDa. In some embodiments, at least about 30, 40 or 50% of the hydrophobic regions in the coating molecules have a molecular mass of least about 5 kDa. In certain embodiments, up to 5, 10, 20, 30, 40, 50, 60, 70, 80, 90 or even 95% or more of a copolymer or polymer blend consists of a hydrophobic polymer or polymer segment. In some embodiments, the polymeric material includes up to 2, 3, 4, 5, 6, 7, 8, 9, or 10% or more hydrophilic polymer. In one embodiment, the hydrophobic polymer is a polymer or copolymer of lactic acid or glycolic acid, including PLGA. In one embodiment, the hydrophilic polymer is polyethylene glycol. In certain embodiments a triblock polymer such as a Pluronic is used. The drug delivery system can be suitable for administration into an eye compartment of a patient, for example by injection into the eye compartment. In some embodiments, the core includes a biocompatible polymer. As used herein, unless the context indicates otherwise, "drug delivery system", "carrier", and "particle composition" can all be used interchangeably. In a typical embodiment this delivery system is used for ocular delivery.

The particle in the drug delivery system can be of any desired size that achieves the desired result. The appropriate particle size can vary based on the method of administration, the eye compartment to which the drug delivery system is administered, the therapeutic agent employed and the eye disorder to be treated, as will be appreciated by a person of skill in the art in light of the teachings disclosed herein. For example, in some embodiments the particle has a diameter of at least about 1 nm, or from about 1 nm to about 50 microns. The particle can also have a diameter of, for example, from about 1 nm to about 15, 16, 17, 18, 19, 2, 21, 22, 23, 24, 25, 26, 27, 28, 29 or 30 microns; or from about 10 nm to about less than 30, 35, 40, 45 or 50 microns; or from about 10 nm to about less than 28 microns; from about 1 nm to about 5 microns; less than about 1 nm; from about 1 nm to about 3 microns; or from about 1 nm to about 1000 nm; or from about 25 nm to about 75 nm; or from about 20 nm to less than or about 30 nm; or from about 100 nm to about 300 nm. In some embodiments, the average particle size can be about up to 1 nm, 10 nm, 25 nm, 30 nm, 50 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, 1000 nm, or more. In some embodiments, the particle size can be about 100 microns or less, about 50 microns or less, about 30 microns or less, about 10 microns or less, about 6 microns or less, about 5 microns or less, about 3 microns or less, about 1000 nm or less, about 800 nm or less, about 600 nm or less, about 500 nm or less, about 400 nm or less, about 300 nm or less, about 200 nm or less, or about 100 nm or less. In some embodiments, the particle can be a nanoparticle or a microparticle. In some embodiments, the drug delivery system can contain a plurality of sizes particles. The particles can be all nanoparticles, all microparticles, or a combination of nanoparticles and microparticles.

When delivering the active material in a polymeric delivery composition, the active material can be distributed homogeneously, heterogeneously, or in one or more polymeric layers of a multi-layered composition, including in a polymer coated core or a bare uncoated core.

In some embodiments, the drug delivery system includes a particle comprising a core. In some embodiments a compound of Formula I, Formula II, Formula III, Formula IV, Formula V, Formula V', Formula VI, Formula VI', Formula VII, Formula VIII, Formula IX, Formula IX', Formula X, Formula X', Formula XI, Formula XII, Formula XIII, Formula XIV, Formula XV, Formula XV', Formula XV", Formula XVI, Formula XVII, Formula XVII', Formula XVII", Formula XVII''', Formula XVIII, Formula XVIII', Formula XIX, Formula XIX', Formula XX, Formula XXI, Formula XXII, Formula XXIII, Formula XXIV, Formula XV, Formula XVI, Formula XVII, Formula XVIII, Formula XXIX, Formula XXX, Formula XXXI, Formula XXXII, Formula XXXIII, Formula XXXIV, Formula XXXV, Formula XXXVI, Formula XXXVII, Formula XXXVIII, Formula XXXIX, Formula XL, Formula XLI, Formula XLII, Formula XLIII, Formula XLIV, Formula XLV, Formula XLVI, Formula XLVII, Formula XLVIII, Formula XLIX, Formula L, Formula LI, Formula LII, Formula LIII, or Formula LIV can be present in the core in a suitable amount, e.g., at least about 1% weight (wt), at least about 5% wt, at least about 10% wt, at least about 20% wt, at least about 30% wt, at least about 40% wt, at least about 50% wt, at least about 60% wt, at least about 70% wt, at least about 80% wt, at least about 85% wt, at least about 90% wt, at least about 95% wt, or at least about 99% wt of the core. In one embodiment, the core is formed of 100% wt of the pharmaceutical agent. In some cases, the pharmaceutical agent may be present in the core at less than or equal to about 100% wt, less than or equal to about 90% wt, less than or equal to about 80% wt, less than or equal to about 70% wt, less than or equal to about 60% wt, less than or equal to about 50% wt, less than or equal to about 40% wt, less than or equal to about 30% wt, less than or equal to about 20% wt, less than or equal to about 10% wt, less than or equal to about 5% wt, less than or equal to about 2% wt, or less than or equal to about 1% wt. Combinations of the above-referenced ranges are also possible (e.g., present in an amount of at least about 80% wt and less than or equal to about 100% wt). Other ranges are also possible.

In embodiments in which the core particles comprise relatively high amounts of a pharmaceutical agent (e.g., at least about 50% wt of the core particle), the core particles generally have an increased loading of the pharmaceutical agent compared to particles that are formed by encapsulating agents into polymeric carriers. This is an advantage for drug delivery applications, since higher drug loadings mean that fewer numbers of particles may be needed to achieve a desired effect compared to the use of particles containing polymeric carriers.

In some embodiments, the core is formed of a solid material having a relatively low aqueous solubility (i.e., a solubility in water, optionally with one or more buffers), and/or a relatively low solubility in the solution in which the solid material is being coated with a surface-altering agent. For example, the solid material may have an aqueous solubility (or a solubility in a coating solution) of less than or equal to about 5 mg/mL, less than or equal to about 2 mg/mL, less than or equal to about 1 mg/mL, less than or equal to about 0.5 mg/mL, less than or equal to about 0.1 mg/mL, less than or equal to about 0.05 mg/mL, less than or equal to about 0.01 mg/mL, less than or equal to about 1 µg/mL, less than or equal to about 0.1 µg/mL, less than or equal to about 0.01 µg/mL, less than or equal to about 1 ng/mL, less than or equal to about 0.1 ng/mL, or less than or equal to about 0.01 ng/mL at 25° C. In some embodiments, the solid material may have an aqueous solubility (or a solubility in a coating solution) of at least about 1 pg/mL, at least about 10 pg/mL, at least about 0.1 ng/mL, at least about 1 ng/mL, at least about 10 ng/mL, at least about 0.1 µg/mL, at least about 1 µg/mL, at least about 5 µg/mL, at least about 0.01 mg/mL, at least about 0.05 mg/mL, at least about 0.1 mg/mL, at least about 0.5 mg/mL, at least about 1.0 mg/mL, at least about 2 mg/mL. Combinations of the above-noted ranges are possible (e.g., an aqueous solubility or a solubility in a coating solution of at least about 10 µg/mL and less than or equal to about 1 mg/mL). Other ranges are also possible. The solid material may have these or other ranges of aqueous solubilities at any point throughout the pH range (e.g., from pH 1 to pH 14).

In some embodiments, the core may be formed of a material within one of the ranges of solubilities classified by the U.S. Pharmacopeia Convention: e.g., very soluble: >1,000 mg/mL; freely soluble: 100-1,000 mg/mL; soluble: 33-100 mg/mL; sparingly soluble: 10-33 mg/mL; slightly soluble: 1-10 mg/mL; very slightly soluble: 0.1-1 mg/mL; and practically insoluble: <0.1 mg/mL.

Although a core may be hydrophobic or hydrophilic, in many embodiments described herein, the core is substantially hydrophobic. "Hydrophobic" and "hydrophilic" are given their ordinary meaning in the art and, as will be understood by those skilled in the art, in many instances herein, are relative terms. Relative hydrophobicities and hydrophilicities of materials can be determined by measuring the contact angle of a water droplet on a planar surface of the substance to be measured, e.g., using an instrument such as a contact angle goniometer and a packed powder of the core material.

In some embodiments, the core particles described herein may be produced by nanomilling of a solid material (e.g., a compound of Formula I, Formula II, Formula III, Formula IV, Formula V, Formula V', Formula VI, Formula VI', Formula VII, Formula VIII, Formula IX, Formula IX', Formula X, Formula X', Formula XI, Formula XII, Formula XIII, Formula XIV, Formula XV, Formula XV', Formula XV", Formula XVI, Formula XVII, Formula XVII', Formula XVII", Formula XVII''', Formula XVIII, Formula XVIII', Formula XIX, Formula XIX', Formula XX, Formula XXI, Formula XXII, Formula XXIII, Formula XXIV, Formula XV, Formula XVI, Formula XVII, Formula XVIII, Formula XXIX, Formula XXX, Formula XXXI, Formula XXXII, Formula XXXIII, Formula XXXIV, Formula XXXV, Formula XXXVI, Formula XXXVII, Formula XXXVIII, Formula XXXIX, Formula XL, Formula XLI, Formula XLII, Formula XLIII, Formula XLIV, Formula XLV, Formula XLVI, Formula XLVII, Formula XLVIII, Formula XLIX, Formula L, Formula LI, Formula LII, Formula LIII, or Formula LIV) in the presence of one or more stabilizers/surface-altering agents. Small particles of a solid material may require the presence of one or more stabilizers/surface-altering agents, particularly on the surface of the particles, in order to stabilize a suspension of particles without agglomeration or aggregation in a liquid solution. In some such embodiments, the stabilizer may act as a surface-altering agent, forming a coating on the particle.

In a wet milling process, milling can be performed in a dispersion (e.g., an aqueous dispersion) containing one or more stabilizers (e.g., a surface-altering agent), a grinding medium, a solid to be milled (e.g., a solid pharmaceutical agent), and a solvent. Any suitable amount of a stabilizer/surface-altering agent can be included in the solvent. In some embodiments, a stabilizer/surface-altering agent may be present in the solvent in an amount of at least about 0.001% (wt or % weight to volume (w:v)), at least about 0.01, at least about 0.1, at least about 0.5, at least about 1, at least about 2, at least about 3, at least about 4, at least about 5, at least about 6, at least about 7, at least about 8, at least about 10, at least about 12, at least about 15, at least about 20, at least about 40, at least about 60, or at least about 80% of the solvent. In some cases, the stabilizer may be present in the solvent in an amount of about 100% (e.g., in an instance where the stabilizer/surface-altering agent is the solvent). In other embodiments, the stabilizer may be present in the solvent in an amount of less than or equal to about 100, less than or equal to about 80, less than or equal to about 60, less than or equal to about 40, less than or equal to about 20, less than or equal to about 15, less than or equal to about 12, less than or equal to about 10, less than or equal to about 8, less than or equal to about 7%, less than or equal to about 6%, less than or equal to about 5%, less than or equal to about 4%, less than or equal to about 3%, less than or equal to about 2%, or less than or equal to about 1% of the solvent. Combinations of the above-referenced ranges are also possible (e.g., an amount of less than or equal to about 5% and at least about 1% of the solvent). Other ranges are also possible. The particular range chosen may influence factors that may affect the ability of the particles to penetrate mucus such as the stability of the coating of the stabilizer/surface-altering agent on the particle surface, the average thickness of the coating of the stabilizer/surface-altering agent on the particles, the orientation of the stabilizer/surface-altering agent on the particles, the density of the stabilizer/surface altering agent on the particles, stabilizer/drug ratio, drug concentration, the size and polydispersity of the particles formed, and the morphology of the particles formed.

The compound of Formula I, Formula II, Formula III, Formula IV, Formula V, Formula V', Formula VI, Formula VI', Formula VII, Formula VIII, Formula IX, Formula IX', Formula X, Formula X', Formula XI, Formula XII, Formula XIII, Formula XIV, Formula XV, Formula XV', Formula XV", Formula XVI, Formula XVII, Formula XVII', Formula XVII", Formula XVII', Formula XVIII, Formula XVIII', Formula XIX, Formula XIX', Formula XX, Formula XXI, Formula XXII, Formula XXIII, Formula XXIV, Formula XV, Formula XVI, Formula XVII, Formula XVIII, Formula XXIX, Formula XXX, Formula XXXI, Formula XXXII, Formula XXXIII, Formula XXXIV, Formula XXXV, Formula XXXVI, Formula XXXVII, Formula XXXVIII, Formula XXXIX, Formula XL, Formula XLI, Formula XLII, Formula XLIII, Formula XLIV, Formula XLV, Formula XLVI, Formula XLVII, Formula XLVIII, Formula XLIX, Formula L, Formula LI, Formula LII, Formula LIII, or Formula LIV (or salt thereof) may be present in the solvent in any suitable amount. In some embodiments, the pharmaceutical agent (or salt thereof) is present in an amount of at least about 0.001% (wt % or % weight to volume (w:v)), at least about 0.01%, at least about 0.1%, at least about 0.5%, at least about 1%, at least about 2%, at least about 3%, at least about 4%, at least about 5%, at least about 6%, at least about 7%, at least about 8%, at least about 10%, at least about 12%, at least about 15%, at least about 20%, at least about 40%, at least about 60%, or at least about 80% of the solvent. In some cases, the pharmaceutical agent (or salt thereof) may be present in the solvent in an amount of less than or equal to about 100%, less than or equal to about 90%, less than or equal to about 80%, less than or equal to about 60%, less than or equal to about 40%, less than or equal to about 20%, less than or equal to about 15%, less than or equal to about 12%, less than or equal to about 10%, less than or equal to about 8%, less than or equal to about 7%, less than or equal to about 6%, less than or equal to about 5%, less than or equal to about 4%, less than or equal to about 3%, less than or equal to about 2%, or less than or equal to about 1% of the solvent. Combinations of the above-referenced ranges are also possible (e.g., an amount of less than or equal to about 20% and at least about 1% of the solvent). In some embodiments, the pharmaceutical agent is present in the above ranges but in w:v.

The ratio of stabilizer/surface-altering agent to pharmaceutical agent (or salt thereof) in a solvent may also vary. In some embodiments, the ratio of stabilizer/surface-altering agent to pharmaceutical agent (or salt thereof) may be at least 0.001:1 (weight ratio, molar ratio, or w:v ratio), at least 0.01:1, at least 0.01:1, at least 1:1, at least 2:1, at least 3:1, at least 5:1, at least 10:1, at least 25:1, at least 50:1, at least 100:1, or at least 500:1. In some cases, the ratio of stabilizer/surface-altering agent to pharmaceutical agent (or salt thereof) may be less than or equal to 1000:1 (weight ratio or molar ratio), less than or equal to 500:1, less than or equal to 100:1, less than or equal to 75:1, less than or equal to 50:1, less than or equal to 25:1, less than or equal to 10:1, less than or equal to 5:1, less than or equal to 3:1, less than or equal to 2:1, less than or equal to 1:1, or less than or equal to 0.1:1. Combinations of the above-referenced ranges are possible (e.g., a ratio of at least 5:1 and less than or equal to 50:1). Other ranges are also possible.

Stabilizers/surface-altering agents may be, for example, polymers or surfactants. Examples of polymers are those suitable for use in coatings, as described in more detail below. Non-limiting examples of surfactants include L-a-phosphatidylcholine (PC), 1,2-dipalmitoylphosphatidycholine (DPPC), oleic acid, sorbitan trioleate, sorbitan monooleate, sorbitan monolaurate, polyoxyethylene sorbitan monolaurate, polyoxyethylene sorbitan monooleate, natural lecithin, oleyl polyoxyethylene ether, stearyl polyoxyethylene ether, lauryl polyoxyethylene ether, block copolymers of oxyethylene and oxypropylene, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol 400, cetyl pyridinium chloride, benzalkonium chloride, olive oil, glyceryl monolaurate, corn oil, cotton seed oil, and sunflower seed oil. Derivatives of the above-noted compounds are also possible. Combinations of the above-noted compounds and others described herein may also be used as surface-altering agents in the inventive particles. As described herein, in some embodiments a surface-altering agent may act as a stabilizer, a surfactant, and/or an emulsifier. In some embodiments, the surface altering agent may aid particle transport in mucus.

It should be appreciated that while in some embodiments the stabilizer used for milling forms a coating on a particle surface, which coating renders particle mucus penetrating, in other embodiments, the stabilizer may be exchanged with one or more other surface-altering agents after the particle has been formed. For example, in one set of methods, a first stabilizer/surface-altering agent may be used during a milling process and may coat a surface of a core particle, and then all or portions of the first stabilizer/surface-altering agent may be exchanged with a second stabilizer/surface-altering agent to coat all or portions of the core particle surface. In some cases, the second stabilizer/surface-altering agent may render the particle mucus penetrating more than the first stabilizer/surface-altering agent. In some embodiments, a core particle having a coating including multiple surface-altering agents may be formed.

In other embodiments, core particles may be formed by a precipitation technique. Precipitation techniques (e.g., microprecipitation techniques, nanoprecipitation techniques) may involve forming a first solution comprising a compound of Formula I, Formula II, Formula III, Formula IV, Formula V, Formula V', Formula VI, Formula VI', Formula VII, Formula VIII, Formula IX, Formula IX', Formula X, Formula X', Formula XI, Formula XII, Formula XIII, Formula XIV, Formula XV, Formula XV', Formula XV'', Formula XVI, Formula XVII, Formula XVII', Formula XVII'', Formula XVII''', Formula XVIII, Formula XVIII', Formula XIX, Formula XIX', Formula XX, Formula XXI, Formula XXII, Formula XXIII, Formula XXIV, Formula XV, Formula XVI, Formula XVII, Formula XVIII, Formula XXIX, Formula XXX, Formula XXXI, Formula XXXII, Formula XXXIII, Formula XXXIV, Formula XXXV, Formula XXXVI, Formula XXXVII, Formula XXXVIII, Formula XXXIX, Formula XL, Formula XLI, Formula XLII, Formula XLIII, Formula XLIV, Formula XLV, Formula XLVI, Formula XLVII, Formula XLVIII, Formula XLIX, Formula L, Formula LI, Formula LII, Formula LIII, or Formula LIV and a solvent, wherein the material is substantially soluble in the solvent. The solution may be added to a second solution comprising another solvent in which the material is substantially insoluble, thereby forming a plurality of particles comprising the material. In some cases, one or more surface-altering agents, surfactants, materials, and/or bioactive agents may be present in the first and/or second solutions. A coating may be formed during the process of precipitating the core (e.g., the precipitating and coating steps may be performed substantially simultaneously). In other embodiments, the particles are first formed using a precipitation technique, following by coating of the particles with a surface-altering agent.

In some embodiments, a precipitation technique may be used to form particles (e.g., nanocrystals) of a salt of a compound of Formula I, Formula II, Formula III, Formula IV, Formula V, Formula V', Formula VI, Formula VI', Formula VII, Formula VIII, Formula IX, Formula IX', Formula X, Formula X', Formula XI, Formula XII, Formula XIII, Formula XIV, Formula XV, Formula XV', Formula XV'', Formula XVI, Formula XVII, Formula XVII', Formula XVII'', Formula XVII''', Formula XVIII, Formula XVIII', Formula XIX, Formula XIX', Formula XX, Formula XXI, Formula XXII, Formula XXIII, Formula XXIV, Formula XV, Formula XVI, Formula XVII, Formula XVIII, Formula XXIX, Formula XXX, Formula XXXI, Formula XXXII, Formula XXXIII, Formula XXXIV, Formula XXXV, Formula XXXVI, Formula XXXVII, Formula XXXVIII, Formula XXXIX, Formula XL, Formula XLI, Formula XLII, Formula XLIII, Formula XLIV, Formula XLV, Formula XLVI, Formula XLVII, Formula XLVIII, Formula XLIX, Formula L, Formula LI, Formula LII, Formula LIII, or Formula LIV. Generally, a precipitation technique involves dissolving the material to be used as the core in a solvent, which is then added to a miscible anti-solvent with or without excipients to form the core particle. This technique may be useful for preparing particles of pharmaceutical agents that are soluble in aqueous solutions (e.g., agents having a relatively high aqueous solubility). In some embodiments, pharmaceutical agents having one or more charged or ionizable groups can interact with a counter ion (e.g., a cation or an anion) to form a salt complex.

As described herein, in some embodiments, a method of forming a core particle involves choosing a stabilizer that is suitable for both nanomilling and for forming a coating on the particle and rendering the particle mucus penetrating. For example, as described in more detail below, it has been demonstrated that 200-500 nm nanoparticles of a model compound pyrene produced by nanomilling of pyrene in the presence of Pluronic® F127 resulted in particles that can penetrate physiological mucus samples at the same rate as well-established polymer-based MPP. Interestingly, it was observed that only a handful of stabilizers/surface-altering agents tested fit the criteria of being suitable for both nanomilling and for forming a coating on the particle that renders the particle mucus penetrating, as described in more detail below.

IV. Description of Polymeric Delivery Materials

The particles of the drug delivery system can include a biocompatible polymer. As used herein, the term "biocompatible polymer" encompasses any polymer than can be administered to a patient without an unacceptable adverse effect to the patient.

Examples of biocompatible polymers include but are not limited to polystyrenes; poly(hydroxy acid); poly(lactic acid); poly(glycolic acid); poly(lactic acid-co-glycolic acid); poly(lactic-co-glycolic acid); poly(lactide); poly(glycolide); poly(lactide-co-glycolide); polyanhydrides; polyorthoesters; polyamides; polycarbonates; polyalkylenes; polyethylenes; polypropylene; polyalkylene glycols; poly(ethylene glycol); polyalkylene oxides; poly(ethylene oxides); polyalkylene terephthalates; poly(ethylene terephthalate); polyvinyl alcohols; polyvinyl ethers; polyvinyl esters; polyvinyl halides; poly(vinyl chloride); polyvinylpyrrolidone; polysiloxanes; poly(vinyl alcohols); poly(vinyl acetate); polyurethanes; co-polymers of polyurethanes; derivativized celluloses; alkyl cellulose; hydroxyalkyl celluloses; cellulose ethers; cellulose esters; nitro celluloses; methyl cellulose; ethyl cellulose; hydroxypropyl cellulose; hydroxy-propyl methyl cellulose; hydroxybutyl methyl cellulose; cellulose acetate; cellulose propionate; cellulose acetate butyrate; cellulose acetate phthalate; carboxylethyl cellulose; cellulose triacetate; cellulose sulfate sodium salt; polymers of acrylic acid; methacrylic acid; copolymers of methacrylic acid; derivatives of methacrylic acid; poly(methyl methacrylate); poly(ethyl methacrylate); poly(butylmethacrylate); poly(isobutyl methacrylate); poly(hexylmethacrylate); poly(isodecyl methacrylate); poly(lauryl methacrylate); poly(phenyl methacrylate); poly(methyl acrylate); poly(isopropyl acrylate); poly(isobutyl acrylate); poly(octadecyl acrylate); poly(butyric acid); poly(valeric acid); poly(lactide-co-caprolactone); copolymers of poly(lactide-co-caprolactone); blends of poly(lactide-co-caprolactone); hydroxyethyl methacrylate (HEMA); copolymers of HEMA with acrylate; copolymers of HEMA with polymethylmethacrylate (PMMA); polyvinylpyrrolidone/vinyl acetate copolymer (PVP/VA); acrylate polymers/copolymers; acrylate/carboxyl polymers; acrylate hydroxyl and/or carboxyl copolymers; polycarbonate-urethane polymers; silicone-urethane polymers; epoxy polymers; cellulose nitrates; polytetramethylene ether glycol urethane; polymethylmethacrylate-2-hydroxyethylmethacrylate copolymer; polyethylmethacrylate-2-hydroxyethylmethacrylate copolymer; polypropylmethacrylate-2-hydroxyethylmethacrylate copolymer; polybutylmethacrylate-2-hydroxyethylmethacrylate copolymer; polymethylacrylate-2-hydroxyethylmethacrylate copolymer; polyethylacrylate-2-hydroxyethylmethacrylate copolymer; polypropylacrylate-2-hydroxymethacrylate copolymer; polybutylacrylate-2-hydroxyethylmethacrylate copolymer; copolymermethylvinylether maleicanhydride copolymer; poly (2-hydroxyethyl methacrylate) polymer/copolymer; acrylate carboxyl and/or hydroxy copolymer; olefin acrylic acid copolymer; ethylene acrylic acid copolymer; polyamide polymers/copolymers; polyimide polymers/copolymers; ethylene vinylacetate copolymer; polycarbonate urethane; silicone urethane; polyvinylpyridine copolymers; polyether sulfones; polygalactin, poly-(isobutyl cyanoacrylate), and poly(2-hydroxyethyl-L-glutamine); polydimethyl siloxane; poly(caprolactones); poly(ortho esters); polyamines; polyethers; polyesters; polycarbamates; polyureas; polyimides; polysulfones; polyacetylenes; polyethyeneimines; polyisocyanates; polyacrylates; polymethacrylates; polyacrylonitriles; polyarylates; and combinations, copolymers and/or mixtures of two or more of any of the foregoing. In some cases, the particle includes a hydrophobic material and at least one bioactive agent. In certain embodiments, the hydrophobic material is used instead of a polymer. In other embodiments, the hydrophobic material is used in addition to a polymer.

An active compound as described herein can be physically mixed in the polymeric material, including in an interpenetrating polymer network or can be covalently bound to the polymeric material Linear, non-linear or linear multiblock polymers or copolymers can be used to form nanoparticles, microparticles, and implants (e.g., rods, discs, wafers, etc.) useful for the delivery to the eye. The polymers can contain one or more hydrophobic polymer segments and one or more hydrophilic polymer segments covalently connected through a linear link or multivalent branch point to form a non-linear multiblock copolymer containing at least three polymeric segments. The polymer can be a conjugate further containing one or more therapeutic, prophylactic, or diagnostic agents covalently attached to the one or more polymer segments. By employing a polymer-drug conjugate, particles can be formed with more controlled drug loading and drug release profiles. In addition, the solubility of the conjugate can be controlled so as to minimize soluble drug concentration and, therefore, toxicity.

The one or more hydrophobic polymer segments, independently, can be any biocompatible hydrophobic polymer or copolymer. In some cases, the one or more hydrophobic polymer segments are also biodegradable. Examples of suitable hydrophobic polymers include polyesters such as polylactic acid, polyglycolic acid, or polycaprolactone, polyanhydrides, such as polysebacic anhydride, and copolymers thereof. In certain embodiments, the hydrophobic polymer is a polyanhydride, such as polysebacic anhydride or a copolymer thereof. The one or more hydrophilic polymer segments can be any hydrophilic, biocompatible, non-toxic polymer or copolymer. The hydrophilic polymer segment can be, for example, a poly(alkylene glycol), a polysaccharide, poly(vinyl alcohol), polypyrrolidone, a polyoxyethylene block copolymer (PLURONIC®) or a copolymers thereof. In preferred embodiments, the one or more hydrophilic polymer segments are, or are composed of, polyethylene glycol (PEG).

WO 2016/100380A1 and WO 2016/100392 A1 describe certain Sunitinib delivery systems, which can also be used in the present invention to deliver Sunitinib or another active agent provided by the current invention, and as described further herein. For example, WO 2016/100380A1 and WO 2016/100392 A1 describe that a polymeric Sunitinib drug formulation can be prepared by: (i) dissolving or dispersing Sunitinib or its salt in an organic solvent optionally with an alkaline agent; (ii) mixing the solution/dispersion of step (i) with a polymer solution that has a viscosity of at least about 300 cPs (or perhaps at least about 350, 400, 500, 600, 700 or 800 or more cPs); (iii) mixing the drug polymer solution/dispersion of step (ii) with an aqueous non-acidic or alkaline solution (for example at least approximately a pH of 7, 8, or 9 and typically not higher than about 10) optionally with a surfactant or emulsifier, to form a solvent-laden Sunitinib encapsulated microparticle, (iv) isolating the microparticles. When Sunitinib malate or another pharmaceutically acceptable salt of Sunitinib is used, it was reported that it may be useful to include the alkaline agent in the organic solvent. However, when Sunitinib free base is used, then it was reported that adding an acid to the organic solvent can improve drug loading of the microparticle. Examples were provided demonstrating that polyesters such as PLGA, PEG-PLGA(PLA) and PEG-PLGA/PLGA blend microparticles display sustained release of Sunitinib or its analog or pharmaceutically acceptable salt. The PCT references describe that polymer microparticles composed of PLGA and PEG covalently conjugated to PLGA ($M_w$ 45 kDa) (PLGA45k-PEG5k) loaded with Sunitinib malate were prepared using a single emulsion solvent evaporation method. Loading improvement was achieved by increasing the alkalinity of Sunitinib malate in solution, up to 16.1% with PEG-PLGA, which could be further increased by adding DMF, compared to only 1% with no alkaline added. Sunitinib malate loading was further increased by increasing the pH of the aqueous solution as well as the polymer solution. Still further significant increases in Sunitinib malate loading in the microparticles was achieved by increasing polymer concentration or viscosity. It was reported in these PCT applications that the loading of Sunitinib can be increased by increasing the alkalinity of the Sunitinib in solution during encapsulation. This can be achieved by selection of the solvent, adding alkalizing agents to the solvent, or including alkaline drugs with the Sunitinib. Examples of compounds that can be added for this purpose include solvents or solvent additives such as dimethylacetamide (DMA), DMTA, triethylamine (TEA), aniline, ammonium, and sodium hydroxide, drugs such as Vitamin B4, caffeine, alkaloids, nicotine, the analgesic morphine, the antibacterial berberine, the anticancer compound vincristine, the antihypertension agent reserpine, the cholinomimetic galantamine, the anticholinergic agent atropine, the vasodilator vincamine, the antiarrhythmia compound quinidine, the antiasthma therapeutic ephedrine, and the antimalarial drug quinine. Surfactants include anionic, cationic and non-ionic surfactants, such as, but not limited to, polyvinyl alcohol, F-127, lectin, fatty acids, phospholipids, polyoxyethylene sorbitan fatty acid derivatives, tocopherols and castor oil. The PCTs also reported that drug loading in the particle is significantly affected by the acid value. For example, raising the pH by addition of alkaline significantly increases the amount of Sunitinib malate incorporated. Loading also can be increased by changing the water phase pH. For example, when water phase (such as PBS) pH is raised from 6.8 to 7.4. Drug loading can also be increased by increasing both polymer and drug concentration, polymer molecular weight. The preferred aqueous pH is higher than 6 and lower than 10, more for example between pH 6 and 8. According to WO 2016/100380A1 and WO 2016/100392 A1, polymer concentration and viscosity can affect encapsulation efficiency. For example, it was reported that for the same formulation composition (99% PLGA 75:25 4A and 1% PLGA-PEG (PEG MW 5 Kd, PLGA MW~ 45 Kd)) at different polymer concentrations in dichloromethane (DCM), the encapsulation efficiency increases to over 50% at 100 mg/mL polymer concentration. The dynamic viscosity of this polymer solution in DCM, prior to mixing with Sunitinib malate solution in DMSO, is estimated to be around 350 cPs. The preferred minimal viscosity of polymer solution in DCM is about 350 cPs. In a preferred embodiment, the polymer concentration in DCM is 140 mg/mL, which is approximately 720 cPs by calculation. Particles made of 99% PLGA 7525 6E and 1% PLGA-PEG (PEG MW 5 Kd, PLGA MW~ 45 Kd) can have a polymer concentration in DCM ranging from 100-200 mg/mL. Since PLGA 7525 6E is a polymer with higher Mw than that of PLGA 7525 4A, the polymer solution in DCM is more viscous with a dynamic viscosity of about 830 cPs. Drug loading is also significantly affected by the method of making and the solvent used. For example, S/O/W single emulsion method will yield a higher loading than O/W single emulsion method even without control the acid value. In addition, W/O/W double emulsions have been shown to significantly improve drug loading of less hydrophobic salt forms over single O/W emulsions. The ratio of continuous phase to dispersed phase can also significantly alter the encapsulation efficiency and drug loading by modulation of the rate of particle solidification. The rate of polymer solidification with the evaporation of solvent affects the degree of porosity within microparticles. A large CP:DP ratio results in faster polymer precipitation, less porosity, and higher encapsulation efficiency and drug loading. However, decreasing the rate of evaporation of the solvent during particle preparation can also lead to improvements in drug loading of highly polar compounds. As the organic phase evaporates, highly polar compounds within the organic phase is driven to the surface of the particles resulting in poor encapsulation and drug loading. By decreasing the rate of solvent evaporation by decreasing the temperature or rate of stirring, encapsulation efficiency and % drug loading can be increased for highly polar compounds.

These technologies can be used by one of skill in the art to deliver any of the active compounds as described generally in this specification.

U.S. Pat. No. 8,889,193 and PCT/US2011/026321 disclose, for example, a method for treating an eye disorder in a patient in need thereof, comprising administering into the eye, for example, by intravitreal injection into the vitreous chamber of the eye, an effective amount of a drug delivery system which comprises: (i) a microparticle including a core which includes the biodegradable polymer polylactide-co-glycolide; (ii) a coating associated with the core which is non-covalently associated with the microparticle particle; wherein the coating molecule has a hydrophilic region and a hydrophobic region, and wherein the hydrophilic region is polyethylene glycol; and (iii) a therapeutically effective amount of a therapeutic agent, wherein the drug delivery system provides sustained release of the therapeutic agent into the vitreous chamber over a period of time of at least three months; and wherein the vitreous chamber of the eye exhibits at least 10% less inflammation or intraocular pressure than if the particle were uncoated. In certain embodiments, the microparticle can be about 50 or 30 microns or less. The delivery system described in U.S. Pat. No. 8,889,193 and PCT/US2011/026321 can be used to deliver any of the active agents described herein.

In some embodiments, the drug delivery systems contain a particle with a coating on the surface, wherein the coating molecules have hydrophilic regions and, optionally, hydrophobic regions, The drug delivery system can include a coating. The coating can be disposed on the surface of the particle, for example by bonding, adsorption or by complexation. The coating can also be intermingled or dispersed within the particle as well as disposed on the surface of the particle.

The homogeneous or heterogenous polymer or polymeric coating can be, for example, polyethylene glycol, polyvinyl alcohol (PVA), or similar substances. The coating can be, for example, vitamin E-PEG 1k or vitamin E-PEG 5k or the like. Vitamin E-PEG 5k can help present a dense coating of PEG on the surface of a particle. The coating can also include nonionic surfactants such as those composed of polyalkylene oxide, e.g., polyoxyethylene (PEO), also referred to herein as polyethylene glycol; or polyoxypropylene (PPO), also referred to herein as polypropylene glycol (PPG), and can include a copolymer of more than one alkylene oxide.

The polymer or copolymer can be, for example, a random copolymer, an alternating copolymer, a block copolymer or graft copolymer.

In some embodiments, the coating can include a polyoxyethylene-polyoxypropylene copolymer, e.g., block copolymer of ethylene oxide and propylene oxide. (i.e., poloxamers). Examples of poloxamers suitable for use in the present invention include, for example, poloxamers 188, 237, 338 and 407. These poloxamers are available under the trade name Pluronic® (available from BASF, Mount Olive, N.J.) and correspond to Pluronic® F-68, F-87, F-108 and F-127, respectively. Poloxamer 188 (corresponding to Pluronic® F-68) is a block copolymer with an average molecular mass of about 7,000 to about 10,000 Da, or about 8,000 to about 9,000 Da, or about 8,400 Da. Poloxamer 237 (corresponding to Pluronic® F-87) is a block copolymer with an average molecular mass of about 6,000 to about 9,000 Da, or about 6,500 to about 8,000 Da, or about 7,7000 Da. Poloxamer 338 (corresponding to Pluronic® F-108) is a block copolymer with an average molecular mass of about 12,000 to about 18,000 Da, or about 13,000 to about 15,000 Da, or about 14,600 Da. Poloxamer 407 (corresponding to Pluronic® F-127) is a polyoxyethylene-polyoxypropylene triblock copolymer in a ratio of between about $E_{101} P_{56} E_{101}$ to about $E_{106} P_{70} E_{106}$, or about $E_{101} P_{56} E_{101}$, or about $E_{106} P_{70} E_{106}$, with an average molecular mass of about 10,000 to about 15,000 Da, or about 12,000 to about 14,000 Da, or about 12,000 to about 13,000 Da, or about 12,600 Da. For example, the NF forms of poloxamers or Pluronic® polymers can be used.

In some embodiments, the polymer can be, for example Pluronic® P103 or Pluronic® P105. Pluronic® P103 is a block copolymer with an average molecular mass of about 3,000 Da to about 6,000 Da, or about 4,000 Da to about 6,000 Da, or about 4,950 Da. Pluronic® P105 is a block copolymer with an average molecular mass of about 5,000 Da to about 8,000 Da, or about 6,000 Da to about 7,000 Da, or about 6,500 Da.

In some embodiments, the polymer can have an average molecular weight of about 9,000 Da or greater, about 10,000 Da or greater, about 11,000 Da or greater or about 12,000 Da or greater. In exemplary embodiments, the polymer can have an average molecular weight of from about 10,000 to about 15,000 Da, or about 12,000 to about 14,000 Da, or about 12,000 to about 13,000 Da, or about 12,600 Da. In some embodiments, the polymer can be selected from Pluronic® P103, P105, F-68, F-87, F-108 and F-127, from Pluronic® P103, P105, F-87, F-108 and F-127, or from Pluronic® P103, P105, F-108 and F-127, or from Pluronic® P103, P105 and F-127. In some embodiments, the polymer can be Pluronic® F-127. In representative embodiments, the polymer is associated with the particles. For example, the polymer can be covalently attached to the particles. In representative embodiments, the polymer comprises polyethylene glycol, which is covalently attached to a selected polymer, yielding what is commonly referred to as a PEGylated particle.

In some embodiments, a coating is non-covalently associated with a core particle. This association can be held together by any force or mechanism of molecular interaction that permits two substances to remain in substantially the same positions relative to each other, including intermolecular forces, dipole-dipole interactions, van der Waals forces, hydrophobic interactions, electrostatic interactions and the like. In some embodiments, the coating is adsorbed onto the particle. According to representative embodiments, a non-covalently bound coating can be comprised of portions or segments that promote association with the particle, for example by electrostatic or van der Waals forces. In some embodiments, the interaction is between a hydrophobic portion of the coating and the particle. Embodiments include particle coating combinations which, however attached to the particle, present a hydrophilic region, e.g. a PEG rich region, to the environment around the particle coating combination. The particle coating combination can provide both a hydrophilic surface and an uncharged or substantially neutrally-charged surface, which can be biologically inert.

Suitable polymers for use according to the compositions and methods disclosed herein can be made up of molecules having hydrophobic regions as well as hydrophilic regions. Without wishing to be bound by any particular theory, when used as a coating, it is believed that the hydrophobic regions of the molecules are able to form adsorptive interactions with the surface of the particle, and thus maintain a non-covalent association with it, while the hydrophilic regions orient toward the surrounding, frequently aqueous, environment. In some embodiments the hydrophilic regions are characterized in that they avoid or minimize adhesive interactions with substances in the surrounding environment. Suitable hydrophobic regions in a coatings can include, for example, PPO, vitamin E and the like, either alone or in combination with each other or with other substances. Suitable hydrophilic regions in the coatings can include, for example, PEG, heparin, polymers that form hydrogels and the like, alone or in combination with each other or with other substances.

Representative coatings according to the compositions and methods disclosed herein can include molecules having, for example, hydrophobic segments such as PPO segments with molecular weights of at least about 1.8 kDa, or at least about 2 kDa, or at least about 2.4 kDa, or at least about 2.8 kDa, or at least about 3.2 kDa, or at least about 3.6 kDa, or at least about 4.0 kDa, or at least about 4.4 kDa, or at least about 4.8 kDa or at least about 5.2 kDa, or at least 5.6 kDa, or at least 6.0 kDa, or at least 6.4 kDa or more. In some embodiments, the coatings can have PPO segments with molecular weights of from about 1.8 kDa to about 10 kDa, or from about 2 kDa to about 5 kDa, or from about 2.5 kDa to about 4.5 kDa, or from about 2.5 kDa to about 3.5 kDa, or from about 3.0 kDa to about 5.0 kDa, or from about 3.0 kDa to about 6.0 kDa, or from about 4 kDa to about 6 kDa, or from 4.0 kDa to about 7.0 kDa. In some embodiments, at least about 10%, or at least about 25%, or at least about 50%, or at least about 75%, or at least about 90%, or at least about 95%, or at least about 99% or more of the hydrophobic regions in these coatings have molecular weights within these ranges. In some embodiments, the coatings are biologically inert. Compounds that generate both a hydrophilic surface and an uncharged or substantially neutrally-charged surface can be biologically inert.

Representative coatings according to the compositions and methods disclosed herein can include molecules having, for example, hydrophobic segments such as PEG segments with molecular weights of at least about 1.8 kDa, or at least about 2 kDa, or at least about 2.4 kDa, or at least about 2.8 kDa, or at least about 3.2 kDa, or at least about 3.6 kDa, or at least about 4.0 kDa, or at least about 4.4 kDa, or at least about 4.8 kDa, or at least about 5.2 kDa, or at least 5.6 kDa, or at least 6.0 kDa, or at least 6.4 kDa or more. In some embodiments, the coatings can have PEG segments with molecular weights of from about 1.8 kDa to about 10 kDa, or from about 2 kDa to about 5 kDa, or from about 2.5 kDa to about 4.5 kDa, or from about 2.5 kDa to about 3.5 kDa. In some embodiments, at least about 10%, or at least about 25%, or at least about 50%, or at least about 75%, or at least about 90%, or at least about 95%, or at least about 99% or more of the hydrophobic regions in these coatings have molecular weights within these ranges. In some embodiments, the coatings are biologically inert. Compounds that generate both a hydrophilic surface and an uncharged or substantially neutrally-charged surface can be biologically inert.

Representative coatings according to the compositions and methods disclosed herein can include molecules having, for example, segments such as PLGA segments with molecular weights of at least about 4 kDa, or at least about 8 kDa, or at least about 12 kDa, or at least about 16 kDa, or at least about 20 kDa, or at least about 24 kDa, or at least about 28 kDa, or at least about 32 kDa, or at least about 36 kDa, or at least about 40 kDa, or at least about 44 kDa, of at least about 48 kDa, or at least about 52 kDa, or at least about 56 kDa, or at least about 60 kDa, or at least about 64 kDa, or at least about 68 kDa, or at least about 72 kDa, or at least about 76 kDa, or at least about 80 kDa, or at least about 84 kDa, or at least about 88 kDa or more. In some embodiments, at least about 10%, or at least about 25%, or at least about 50%, or at least about 75%, or at least about 90%, or at least about 95%, or at least about 99% or more of the regions in these coatings have molecular weights within these ranges. In some embodiments, the coatings are biologically inert. Compounds that generate both a hydrophilic surface and an uncharged or substantially neutrally-charged surface can be biologically inert.

In some embodiments, s coating can include, for example, one or more of the following: anionic proteins (e.g., bovine serum albumin), surfactants (e.g., cationic surfactants such as for example dimethyldioctadecyl-ammonium bromide), sugars or sugar derivatives (e.g., cyclodextrin), nucleic acids, polymers (e.g., heparin), mucolytic agents, N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin β4, dornase alfa, neltenexine, erdosteine, various DNases including rhDNase, agar, agarose, alginic acid, amylopectin, amylose, beta-glucan, callose, carrageenan, cellodextrins, cellulin, cellulose, chitin, chitosan, chrysolaminarin, curdlan, cyclodextrin, dextrin, ficoll, fructan, fucoidan, galactomannan, gellan gum, glucan, glucomannan, glycocalyx, glycogen, hemicellulose, hydroxyethyl starch, kefiran, laminarin, mucilage, glycosaminoglycan, natural gum, paramylon, pectin, polysaccharide peptide, schizophyllan, sialyl lewis x, starch, starch gelatinization, sugammadex, xanthan gum, xyloglucan, L-phosphatidylcholine (PC), 1,2-dipalmitoylphosphatidylcholine (DPPC), oleic acid, sorbitan trioleate, sorbitan monooleate, sorbitan monolaurate, polyoxyethylene (20) sorbitan monolaurate, polyoxyethylene (20) sorbitan monooleate, natural lecithin, oleyl polyoxyethylene (2) ether, stearyl polyoxyethylene (2) ether, polyoxyethylene (4) lauryl ether, block copolymers of oxyethylene and oxypropylene, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol 400, cetyl pyridinium chloride, benzalkonium chloride, olive oil, glyceryl monolaurate, corn oil, cotton seed oil, sunflower seed oil, lecithin, oleic acid, sorbitan trioleate, and combinations of two or more of any of the foregoing.

A particle-coating combinations can be made up of any combination of particle and coating substances disclosed or suggested herein. Examples of such combinations include, for example, polystyrene-PEG, or PLGA-Pluronic® F-127.

In one aspect of the present invention, an effective amount of an active compound as described herein is incorporated into a nanoparticle, e.g. for convenience of delivery and/or extended release delivery. The use of materials in nanoscale provides one the ability to modify fundamental physical properties such as solubility, diffusivity, blood circulation half-life, drug release characteristics, and/or immunogenicity. These nanoscale agents may provide more effective and/or more convenient routes of administration, lower therapeutic toxicity, extend the product life cycle, and ultimately reduce health-care costs. As therapeutic delivery systems, nanoparticles can allow targeted delivery and controlled release.

In another aspect of the present invention, the nanoparticle or microparticle is coated with a surface agent that facilitates passage of the particle through mucus. Said nanoparticles and microparticles have a higher concentration of surface agent than has been previously achieved, leading to the unexpected property of extremely fast diffusion through mucus. The present invention further comprises a method of producing said particles. The present invention further comprises methods of using said particles to treat a patient.

A number of companies have developed microparticles for treatment of eye disorders that can be used in conjunction with the present invention. For example, Allergan has disclosed a biodegradable microsphere to deliver a therapeutic agent that is formulated in a high viscosity carrier suitable for intraocular injection or to treat a non-ocular disorder (see U.S. publication 2010/0074957 and U.S. publication 2015/0147406). In one embodiment, the '957 application describes a biocompatible, intraocular drug delivery system that includes a plurality of biodegradable microspheres, a therapeutic agent, and a viscous carrier, wherein the carrier has a viscosity of at least about 10 cps at a shear rate of 0.1/second at 25° C. Allergan has also disclosed a composite drug delivery material that can be injected into the eye of a patient that includes a plurality of microparticles dispersed in a media, wherein the microparticles contain a drug and a biodegradable or bioerodible coating and the media includes the drug dispersed in a depot-forming material, wherein the media composition may gel or solidify on injection into the eye (see WO 2013/112434 A1, claiming priority to Jan. 23, 2012). Allergan states that this invention can be used to provide a depot means to implant a solid sustained drug delivery system into the eye without an incision. In general, the depot on injection transforms to a material that has a viscosity that may be difficult or impossible to administer by injection. In addition, Allergan has disclosed biodegradable microspheres between 40 and 200 µm in diameter, with a mean diameter between 60 and 150 µm that are effectively retained in the anterior chamber of the eye without producing hyperemia, see, US 2014/0294986. The microspheres contain a drug effective for an ocular condition with greater than seven day release following administration to the anterior chamber of the eye. The administration of these large particles is intended to overcome the disadvantages of injecting 1-30 µm particles which are generally poorly tolerated.

In another embodiment any of the above delivery systems can be used to facilitate or enhance delivery through mucus.

Common techniques for preparing particles include, but are not limited to, solvent evaporation, solvent removal, spray drying, phase inversion, coacervation, and low temperature casting. Suitable methods of particle formulation are briefly described below. Pharmaceutically acceptable excipients, including pH modifying agents, disintegrants, preservatives, and antioxidants, can optionally be incorporated into the particles during particle formation.

Solvent Evaporation

In this method, the drug (or polymer matrix and one or more Drugs) is dissolved in a volatile organic solvent, such as methylene chloride. The organic solution containing the drug is then suspended in an aqueous solution that contains a surface active agent such as poly(vinyl alcohol). The resulting emulsion is stirred until most of the organic solvent evaporated, leaving solid nanoparticles. The resulting nanoparticles are washed with water and dried overnight in a lyophilizer. Nanoparticles with different sizes and morphologies can be obtained by this method.

Drugs which contain labile polymers, such as certain polyanhydrides, may degrade during the fabrication process due to the presence of water. For these polymers, the following two methods, which are performed in completely anhydrous organic solvents, can be used.

Solvent Removal

Solvent removal can also be used to prepare particles from drugs that are hydrolytically unstable. In this method, the drug (or polymer matrix and one or more Drugs) is dispersed or dissolved in a volatile organic solvent such as methylene chloride. This mixture is then suspended by stirring in an organic oil (such as silicon oil) to form an emulsion. Solid particles form from the emulsion, which can subsequently be isolated from the supernatant. The external morphology of spheres produced with this technique is highly dependent on the identity of the drug.

In one embodiment a compound of the present invention is administered to a patient in need thereof as particles formed by solvent removal. In another embodiment the present invention provides particles formed by solvent removal comprising a compound of the present invention and one or more pharmaceutically acceptable excipients as defined herein. In another embodiment the particles formed by solvent removal comprise a compound of the present invention and an additional therapeutic agent. In a further embodiment the particles formed by solvent removal comprise a compound of the present invention, an additional therapeutic agent, and one or more pharmaceutically acceptable excipients. In another embodiment any of the described particles formed by solvent removal can be formulated into a tablet and then coated to form a coated tablet. In an alternative embodiment the particles formed by solvent removal are formulated into a tablet but the tablet is uncoated.

Spray Drying

In this method, the drug (or polymer matrix and one or more Drugs) is dissolved in an organic solvent such as methylene chloride. The solution is pumped through a micronizing nozzle driven by a flow of compressed gas, and the resulting aerosol is suspended in a heated cyclone of air, allowing the solvent to evaporate from the micro droplets, forming particles. Particles ranging between 0.1-10 microns can be obtained using this method.

In one embodiment a compound of the present invention is administered to a patient in need thereof as a spray dried dispersion (SDD). In another embodiment the present invention provides a spray dried dispersion (SDD) comprising a compound of the present invention and one or more pharmaceutically acceptable excipients as defined herein. In another embodiment the SDD comprises a compound of the present invention and an additional therapeutic agent. In a further embodiment the SDD comprises a compound of the present invention, an additional therapeutic agent, and one or more pharmaceutically acceptable excipients. In another embodiment any of the described spray dried dispersions can be coated to form a coated tablet. In an alternative embodiment the spray dried dispersion is formulated into a tablet but is uncoated.

Phase Inversion

Particles can be formed from drugs using a phase inversion method. In this method, the drug (or polymer matrix and one or more Drugs) is dissolved in a "good" solvent, and the solution is poured into a strong non solvent for the drug to spontaneously produce, under favorable conditions, microparticles or nanoparticles. The method can be used to produce nanoparticles in a wide range of sizes, including, for example, about 100 nanometers to about 10 microns, typically possessing a narrow particle size distribution.

In one embodiment a compound of the present invention is administered to a patient in need thereof as particles formed by phase inversion. In another embodiment the present invention provides particles formed by phase inversion comprising a compound of the present invention and one or more pharmaceutically acceptable excipients as defined herein. In another embodiment the particles formed by phase inversion comprise a compound of the present invention and an additional therapeutic agent. In a further embodiment the particles formed by phase inversion comprise a compound of the present invention, an additional therapeutic agent, and one or more pharmaceutically acceptable excipients. In another embodiment any of the described particles formed by phase inversion can be formulated into a tablet and then coated to form a coated tablet. In an alternative embodiment the particles formed by phase inversion are formulated into a tablet but the tablet is uncoated.

Coacervation

Techniques for particle formation using coacervation are known in the art, for example, in GB-B-929 406; GB-B-929 40 1; and U.S. Pat. Nos. 3,266,987, 4,794,000, and 4,460, 563. Coacervation involves the separation of a drug (or polymer matrix and one or more Drugs) solution into two immiscible liquid phases. One phase is a dense coacervate phase, which contains a high concentration of the drug, while the second phase contains a low concentration of the drug. Within the dense coacervate phase, the drug forms nanoscale or microscale droplets, which harden into particles. Coacervation may be induced by a temperature change, addition of a non-solvent or addition of a micro-salt (simple coacervation), or by the addition of another polymer thereby forming an interpolymer complex (complex coacervation).

In one embodiment a compound of the present invention is administered to a patient in need thereof as particles formed by coacervation. In another embodiment the present invention provides particles formed by coacervation comprising a compound of the present invention and one or more pharmaceutically acceptable excipients as defined herein. In another embodiment the particles formed by coacervation comprise a compound of the present invention and an additional therapeutic agent. In a further embodiment the particles formed by coacervation comprise a compound of the present invention, an additional therapeutic agent, and one or more pharmaceutically acceptable excipients. In another embodiment any of the described particles formed by coacervation can be formulated into a tablet and then coated to form a coated tablet. In an alternative embodiment the particles formed by coacervation are formulated into a tablet but the tablet is uncoated.

Low Temperature Casting

Methods for very low temperature casting of controlled release microspheres are described in U.S. Pat. No. 5,019, 400 to Gombotz et al. In this method, the drug (or polymer matrix and Sunitinib) is dissolved in a solvent. The mixture is then atomized into a vessel containing a liquid non-solvent at a temperature below the freezing point of the drug solution which freezes the drug droplets. As the droplets and non-solvent for the drug are warmed, the solvent in the droplets thaws and is extracted into the non-solvent, hardening the microspheres.

In one embodiment a compound of the present invention is administered to a patient in need thereof as particles formed by low temperature casting. In another embodiment the present invention provides particles formed by low temperature casting comprising a compound of the present invention and one or more pharmaceutically acceptable excipients as defined herein. In another embodiment the particles formed by low temperature casting comprise a compound of the present invention and an additional therapeutic agent. In a further embodiment the particles formed by low temperature casting comprise a compound of the present invention, an additional therapeutic agent, and one or more pharmaceutically acceptable excipients. In another embodiment any of the described particles formed by low temperature casting can be formulated into a tablet and then coated to form a coated tablet. In an alternative embodiment the particles formed by low temperature casting are formulated into a tablet but the tablet is uncoated.

V. Controlled Release of Therapeutic Agent

The rate of release of the therapeutic agent can be related to the concentration of therapeutic agent dissolved in polymeric material. In many embodiments, the polymeric composition includes non-therapeutic agents that are selected to provide a desired solubility of the therapeutic agent. The selection of polymer can be made to provide the desired solubility of the therapeutic agent in the matrix, for example, a hydrogel may promote solubility of hydrophilic material. In some embodiments, functional groups can be added to the polymer to increase the desired solubility of the therapeutic agent in the matrix. In some embodiments, additives may be used to control the release kinetics of therapeutic agent, for example, the additives may be used to control the concentration of therapeutic agent by increasing or decreasing solubility of the therapeutic agent in the polymer so as to control the release kinetics of the therapeutic agent. The solubility may be controlled by including appropriate molecules and/or substances that increase and/or decrease the solubility of the dissolved from of the therapeutic agent to the matrix. The solubility of the therapeutic agent may be related to the hydrophobic and/or hydrophilic properties of the matrix and therapeutic agent. Oils and hydrophobic molecules and can be added to the polymer to increase the solubility of hydrophobic treatment agent in the matrix.

Instead of or in addition to controlling the rate of migration based on the concentration of therapeutic agent dissolved in the matrix, the surface area of the polymeric composition can be controlled to attain the desired rate of drug migration out of the composition. For example, a larger exposed surface area will increase the rate of migration of the active agent to the surface, and a smaller exposed surface area will decrease the rate of migration of the active agent to the surface. The exposed surface area can be increased in any number of ways, for example, by any of castellation of the exposed surface, a porous surface having exposed channels connected with the tear or tear film, indentation of the exposed surface, protrusion of the exposed surface. The exposed surface can be made porous by the addition of salts that dissolve and leave a porous cavity once the salt dissolves. In the present invention, these trends can be used to decrease the release rate of the active material from the polymeric composition by avoiding these paths to quicker release. For example, the surface area can be minimized, or channels avoided.

Further, an implant may be used that includes the ability to release two or more drugs in combination, for example, the structure disclosed in U.S. Pat. No. 4,281,654 (Shell), for example, in the case of glaucoma treatment, it may be desirable to treat a patient with multiple prostaglandins or a prostaglandin and a cholinergic agent or an adrenergic antagonist (beta blocker), for example, Alphagan (Allegan, Irvine, Calif., USA), or a prostaglandin and a carbonic anhydrase inhibitor.

In addition, drug impregnated meshes may be used, for example, those disclosed in U.S. Patent Application Publication No. 2002/0055701 or layering of biostable polymers as described in U.S. Patent Application Publication No. 2005/0129731. Certain polymer processes may be used to incorporate drug into the devices, as described herein, for example, so-called "self-delivering drugs" or Polymer Drugs (Polymerix Corporation, Piscataway, N.J., USA) are designed to degrade only into therapeutically useful compounds and physiologically inert linker molecules, further detailed in U.S. Patent Application Publication No. 2005/0048121 (East), hereby incorporated by reference in its entirety. Such delivery polymers may be employed in the devices, as described herein, to provide a release rate that is equal to the rate of polymer erosion and degradation and is constant throughout the course of therapy. Such delivery polymers may be used as device coatings or in the form of microspheres for a drug depot injectable (for example, a reservoir described herein). A further polymer delivery technology may also be adapted to the devices, as described herein, for example, that described in U.S. Patent Application Publication No. 2004/0170685 (Carpenter), and technologies available from Medivas (San Diego, Calif., USA).

VI. Process of Preparation of Compounds of Formula I, Formula II, Formula III, Formula IV, Formula V, Formula V', Formula VI, Formula VI', Formula VII, Formula VIII, Formula IX, Formula IX', Formula X, Formula X', Formula XI, Formula XII, Formula XIII, Formula XIV, Formula XV, Formula XV', Formula XV", Formula XVI, Formula XVII, Formula XVII', Formula XVII", Formula XVII''', Formula XVIII, Formula XVIII', Formula XIX, Formula XIX', Formula XX, Formula XXI, Formula XXII, Formula XXIII, Formula XXIV, Formula XV, Formula XVI, Formula XVII, Formula XVIII, Formula XXIX, Formula XXX, Formula XXXI, Formula XXXII, Formula XXXIII, Formula XXXIV, Formula XXXV, Formula XXXVI, Formula XXXVII, Formula XXXVIII, Formula XXXIX, Formula XL, Formula XLI, Formula XLII, Formula XLIII, Formula XLIV, Formula XLV, Formula XLVI, Formula XLVII, Formula XLVIII, Formula XLIX, Formula L, Formula LI, Formula LII, Formula LIII, or Formula LIV Abbreviations CAN Acetonitrile
Ac Acetyl
$Ac_2O$ Acetic anhydride
AcOEt, EtOAc ethyl acetate
AcOH Acetic acid
$Boc_2O$ di-tert-butyl dicarbonate
Bu Butyl
CAN Ceric ammonium nitrate
CBz Carboxybenzyl
CDI Carbonyldiimidazole
$CH_3OH$, MeOH Methanol
CsF Cesium fluoride
CuI Cuprous iodide
DCM, $CH_2Cl_2$ Dichloromethane
DIEA, DIPEA N,N-diisopropylethylamine
DMA N,N-dimethylacetamide DMAP 4-Dimethylaminopyridine
DMF N,N-dimethylformamide
DMS Dimethyl sulfide
DMSO Dimethylsulfoxide
DPPA Diphenyl phosphoryl azide
EDCI 1-Ethyl-3-(3-dimethylaminopropyl)carbodiimide
Et Ethyl
$Et_3N$, TEA Triethylamine
EtOAc Ethyl acetate
EtOH Ethanol
HATU 1-[Bis(dimethylamino)methylene]-1H-1,2,3-triazolo[4,5-b]pyridinium3-oxide hexafluorophosphate
HCl Hydrochloric acid
HOBT Hydroxybenzotriazole
iBu, i-Bu, isoBu Isobutyl
iPr, i-Pr, isoPr Isopropyl
$iPr_2NEt$ N,N-diisopropylethylamine
$K_2CO_3$ Potassium carbonate
$K_2CO_3$ Potassium carbonate
LiOH Lithium hydroxide
Me Methyl
MeI Methyl iodide
Ms Mesyl
MsCl Mesylchloride
MTBE Methyl tbutylether
$Na_2SO_4$ Sodium sulfate
NaCl Sodium chloride
NaH Sodium hydride
$NaHCO_3$ Sodium bicarbonate
NBS N-bromo succinimide
NCS N-chloro succinimide
$NEt_3$ Trimethylamine
NMP N-Methyl-2-pyrrolidone
PCC Pyridinium chlorochromate
Pd $(OAc)_2$ Palladium acetate
Pd(dppf)$Cl_2$ [1,1'-Bis(diphenylphosphino) ferrocene]dichloropalladium(II)
Pd$(PPh_3)_2Cl_2$ Bis(triphenylphosphine)palladium(II) dichloride
Pd$(PPh_3)_4$ Tetrakis(triphenylphosphine)palladium(O)
Pd/C Palladium on carbon
$Pd_2(dba)_3$ Tris(dibenzylideneacetone)dipalladium(O)
PMB 4-Methoxybenzyl ether
$PPh_3$ Triphenylphosphine
Pr Propyl
Py, py Pyridine
RT Room temperature
TBAF Tetra-n-butylammonium fluoride
TBAT Tetrabutylammonium difluorotriphenylsilicate
tBu, t-Bu Tertbutyl
tBuOK Potassium tert-butoxide
TEA Trimethylamine
$Tf_2O$ Trifluoromethanesulfonic anhydride
TFA Trifluoroacetic acid
THF Tetrahydrofuran
TMS Trimethylsilane
TMSBr Bromotrimethylsilane
$t_R$ Retention time
Troc 2,2,2-Trichlorethoxycarbonyl chloride
Zn $(CN)_2$ Zinc cyanide General Methods All nonaqueous reactions were performed under an atmosphere of dry argon or nitrogen gas using anhydrous solvents. The progress of reactions and the purity of target compounds were determined using one of the two liquid chromatography (LC) methods listed below. The structure of starting materials, intermediates, and final products was confirmed by standard analytical techniques, including NMR spectroscopy and mass spectrometry.

The compounds described herein can be prepared by methods known by those skilled in the art. In one non-limiting example the disclosed compounds can be made by the schemes below.

Compounds of the present invention with stereocenters may be drawn without stereochemistry for convenience. One skilled in the art will recognize that pure enantiomers and diastereomers can be prepared by methods known in the art. Examples of methods to obtain optically active materials include at least the following.

i) Physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) Simultaneous crystallization—a technique whereby the individual enantiomers are separately crystallized from a solution of the racemate, possible only if the latter is a conglomerate in the solid state;

iii) Enzymatic resolutions—a technique whereby partial or complete separation of a racemate by virtue of differing rates of reaction for the enantiomers with an enzyme;

iv) Enzymatic asymmetric synthesis—a synthetic technique whereby at least one step of the synthesis uses an enzymatic reaction to obtain an enantiomerically pure or enriched synthetic precursor of the desired enantiomer;

v) Chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) Diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) First- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) Kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) Enantiospecific synthesis from non-racemic precursors—a synthetic technique whereby the desired enantiomer is obtained from non-chiral starting materials and where the stereochemical integrity is not or is only minimally compromised over the course of the synthesis;

x) Chiral liquid chromatography—a technique whereby the enantiomers of a racemate are separated in a liquid mobile phase by virtue of their differing interactions with a stationary phase (including via chiral HPLC). The stationary phase can be made of chiral material or the mobile phase can contain an additional chiral material to provoke the differing interactions;

xi) Chiral gas chromatography—a technique whereby the racemate is volatilized and enantiomers are separated by virtue of their differing interactions in the gaseous mobile phase with a column containing a fixed non-racemic chiral adsorbent phase;

xii) Extraction with chiral solvents—a technique whereby the enantiomers are separated by virtue of preferential dissolution of one enantiomer into a particular chiral solvent;

xiii) Transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

xiv) Simulated moving bed chromatography, is used in one embodiment. A wide variety of chiral stationary phases are commercially available.

Example 1. Synthesis of PLA Linkers

Scheme 1: Synthesis of Octadecanoic acid (S)-1-carboxy-ethyl ester (1-4):

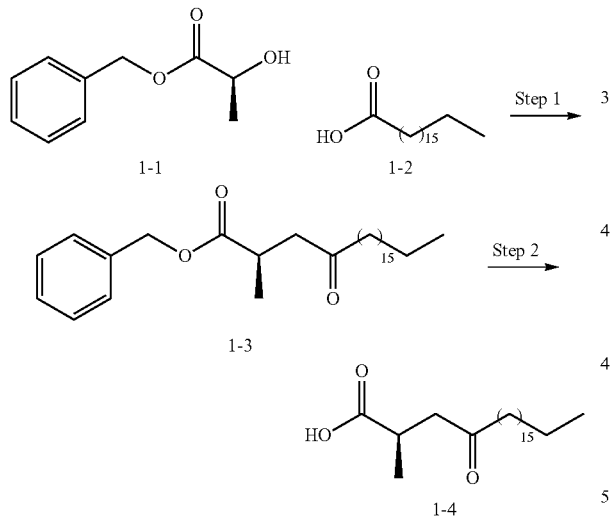

Step-1: Preparation of Octadecanoic acid (S)-1-benzyloxycarbonyl-ethyl ester (1-2)

To a solution of octadecanoic acid (1-2, 14.2 g, 50.00 mmol) in dichloromethane (100 mL) was added EDC.HCl (15.9 g, 83.20 mmol), (S)-2-hydroxy-propionic acid benzyl ester (1-1, 10.0 g, 55.50 mmol) and 4-dimethylaminopyridine (680 mg, 5.5 mmol) at 0° C. The reaction mixture was allowed to stir at 25-30° C. over a period of 2 hours. The resulting reaction mass was quenched with water (750 mL), extracted with dichloromethane (800×3 mL), dried over sodium sulfate and concentrated under reduced pressure. The crude product obtained upon evaporation of volatiles was purified through silica gel (230-400) column (3% ethyl acetate in hexane) to obtain product 1-3 as a colorless liquid (13 g, 53%). $^1$H-NMR (400 MHz, DMSO-d6) δ 7.39-7.32 (m, 5H), 5.14 (s, 2H), 5.04 (q, J=7.2 Hz, 1H), 2.32 (t, 2H), 1.51-1.47 (m, 2H), 1.40 (d, J=7.2 Hz, 3H), 1.22 (bs, 28H), 0.84 (t, J=7.2 Hz, 3H); MS m/z (M+H)$^+$ 445.1

Step-2: Preparation of Octadecanoic acid (S)-1-carboxy-ethyl ester (1-4)

To a 250 mL autoclave vessel, a solution of octadecanoic acid (S)-1-benzyloxycarbonyl-ethyl ester (1-3.13 g, 27.86 mmol) in methanol (70 mL) and 10% Pd/C (2.6 g, 50% wet) were added at 25-30° C. The reaction mixture was stirred at room temperature under hydrogen pressure (5 kg/cm$^2$) over a period of 2 hours. After completion of the reaction, the reaction mixture was filtered through celite bed. Then volatiles were evaporated under reduced pressure to obtain product 1-4 as an off white solid (7.5 g, 78%). $^1$H-NMR (400 MHz, DMSO-d6) δ 12.25 (s, 1H), 4.86 (q, J=7.2 Hz, 1H), 2.31 (t, 2H), 1.53-1.49 (m, 2H), 1.36 (d, J=7.2 Hz, 3H), 1.23 (bs, 28H), 0.84 (t, J=7.2 Hz, 3H); MS m/z (M-H)$^-$ 355.4

Scheme 2: Synthesis of Octadecanoic acid (S)-1-[(S)-1-((S)-1-carboxy-ethoxycarbonyl)-ethoxycarbonyl]-ethyl ester (2-3):

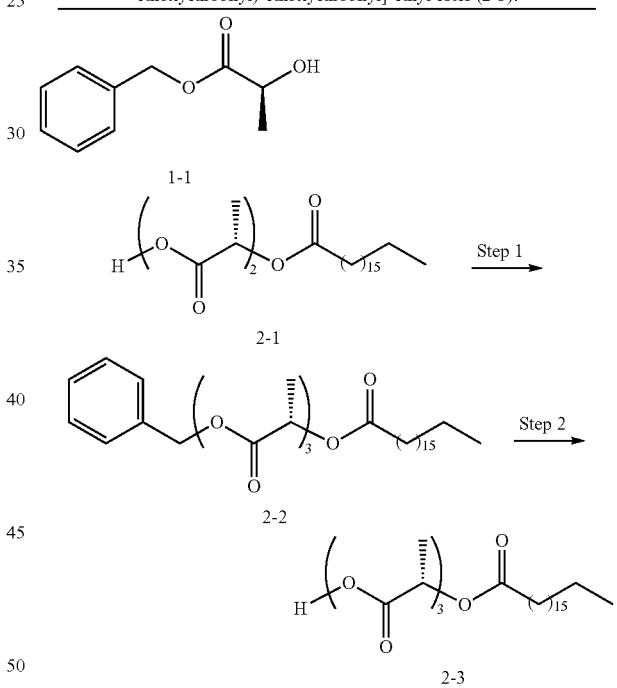

Step-1: Preparation of Octadecanoic acid (S)-1-[(S)-1-((S)-1-benzyloxycarbonyl-ethoxycarbonyl)-ethoxycarbonyl]-ethyl ester (2-2)

To a solution of octadecanoic acid (S)-1-((S)-1-carboxy-ethoxycarbonyl)-ethyl ester (2-1, 16.6 g, 41.66 mmol) in dichloromethane (50 mL) was added EDC.HCl (10.6 g, 55.54 mmol), (S)-2-hydroxy-propionic acid benzyl ester (1-1, 5 g, 27.77 mmol) and 4-dimethylaminopyridine (338 mg, 2.77 mmol) and at 0° C. The reaction mixture was allowed to stir at 25-30° C. over a period of 1 hour. The resulting reaction mass was quenched with water (250 mL), extracted with dichloromethane (250×3 mL), dried over sodium sulfate and concentrated under reduced pressure.

The crude product obtained upon evaporation of volatiles was purified through silica gel (230-400) column (4% ethyl acetate in hexane) to obtain product 2-2 as a colorless liquid (11 g, 70%). $^1$H-NMR (400 MHz, DMSO-d6) δ 7.40-7.32 (m, 5H), 5.20-5.14 (m, 4H), 5.05 (q, J=7.2 Hz, 1H), 2.33 (t, 2H), 1.52-1.47 (m, 2H), 1.45-1.40 (m, 9H), 1.22 (bs, 28H), 0.86 (t, J=7.2 Hz, 3H); MS m/z (M+H)$^+$ 590.79, (M+NH$_4$)$^+$ 609

Step-2: Preparation of Octadecanoic acid (S)-1-[(S)-1-((S)-1-carboxy-ethoxycarbonyl)-ethoxycarbonyl]-ethyl ester (2-3)

To a 100 mL autoclave vessel, a solution of octadecanoic acid (R)-1-[(R)-1-((R)-1-benzyloxycarbonyl-ethoxycarbonyl)-ethoxycarbonyl]-ethyl ester (2-2, 11 g, 19.57 mmol) in methanol (60 mL) and 10% Pd/C (2.2 g, 50% wet) was added at 25-30° C. The reaction mixture was stirred at room temperature under hydrogen pressure (5 kg/cm$^2$) over a period of 2 hours. After completion of the reaction, the reaction mixture was filtered through celite bed and the volatiles were evaporated under reduced pressure to obtain product 2-3 as a white solid (7.7 g, 83%).

Scheme 3: Synthesis of Octadecanoic acid (S)-1-((S)-1-{(S)-1-[(S)-1-((S)-1-carboxy-ethoxycarbonyl)-ethoxycarbonyl]-ethoxycarbonyl}-ethoxycarbonyl)-ethyl ester (3-3):

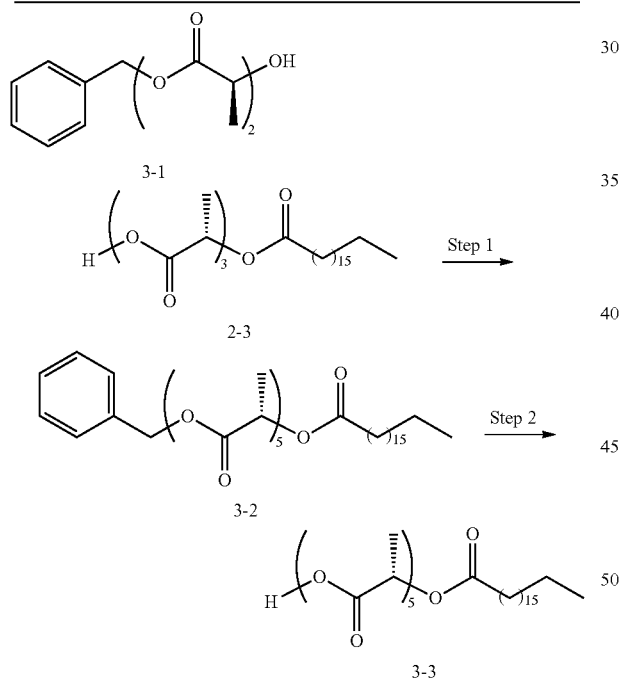

Step-1: Preparation of Octadecanoic acid (S)-1-((S)-1-{(S)-1-[(S)-1-((S)-1-benzyloxycarbonyl-ethoxycarbonyl)-ethoxycarbonyl]-ethoxycarbonyl}-ethoxycarbonyl)-ethyl ester (3-2)

To a solution of octadecanoic acid (S)-1-[(S)-1-((S)-1-carboxy-ethoxycarbonyl)-ethoxycarbonyl]-ethyl ester (2-3, 8.92 g, 17.85 mmol) in dichloromethane (30 mL) was added EDC.HCl (4.54 g, 23.8 mmol), (S)-2-hydroxy-propionic acid (S)-1-benzyloxycarbonyl-ethyl ester (3-1, 3 g, 11.90 mmol) and 4-dimethylaminopyridine (145 mg, 1.19 mmol) at 0° C. The reaction mixture was allowed to stir at 25-30° C. over a period of 1 hour. The resulting reaction mass was quenched with water (200 mL), extracted with dichloromethane (250×3 mL), dried over sodium sulfate and concentrated under reduced pressure. The crude product obtained upon evaporation of volatiles was purified through silica gel (230-400) column (4% ethyl acetate in hexane) to obtain product 3-2 as a colorless liquid (6.2 g, 71%). $^1$H-NMR (400 MHz, DMSO-d6) δ 7.38-7.34 (m, 5H), 5.21-5.15 (m, 6H), 5.05 (q, J=7.2 Hz, 1H), 2.33 (t, J=7.2 Hz, 2H), 1.51-1.39 (m, 17H), 1.27 (bs, 28H), 0.86 (t, J=7.2 Hz, 3H); MS m/z (M+H)$^+$ 736, (M+NH$_4$)$^+$ 754

Step-2: Preparation of Octadecanoic acid (S)-1-((S)-1-{(S)-1-[(S)-1-((S)-1-carboxy-ethoxycarbonyl)-ethoxycarbonyl]-ethoxycarbonyl}-ethoxycarbonyl)-ethyl ester (3-3)

To a 100 mL autoclave vessel, a solution of octadecanoic acid (R)-1-[(R)-1-((R)-1-benzyloxycarbonyl-ethoxycarbonyl)-ethoxycarbonyl]-ethyl ester (3-2, 6.2 g, 19.57 mmol) in methanol (60 mL) and 20% Pd/C (1.24 g, 50% wet) were added at 25-30° C. The reaction mixture was stirred at room temperature under hydrogen pressure (5 kg/cm$^2$) over a period of 2 hours. After completion of the reaction, the reaction mixture was filtered through celite bed and the volatiles were evaporated under reduced pressure to obtain product 3-3 as a white solid (4.2 g, 77%). $^1$H-NMR (400 MHz, DMSO-d6) δ 5.23-5.14 (m, 3H), 5.05 (q, J=7.2 Hz, 1H), 4.98 (q, J=7.2 Hz, 1H), 2.32 (m, 2H), 1.53-1.39 (m, 17H), 1.23 (bs, 28H), 0.84 (t, J=7.2 Hz, 3H); MS m/z (M−H)$^-$ 643.9

Scheme 4: Synthesis of Octadecanoic acid (S)-1-{(S)-1-[(S)-1-((S)-1-{(S)-1-[(S)-1-((S)-1-carboxy-ethoxycarbonyl)-ethoxycarbonyl]-ethoxycarbonyl}-ethoxycarbonyl)-ethoxycarbonyl]-ethoxycarbonyl}-ethyl ester (4-3):

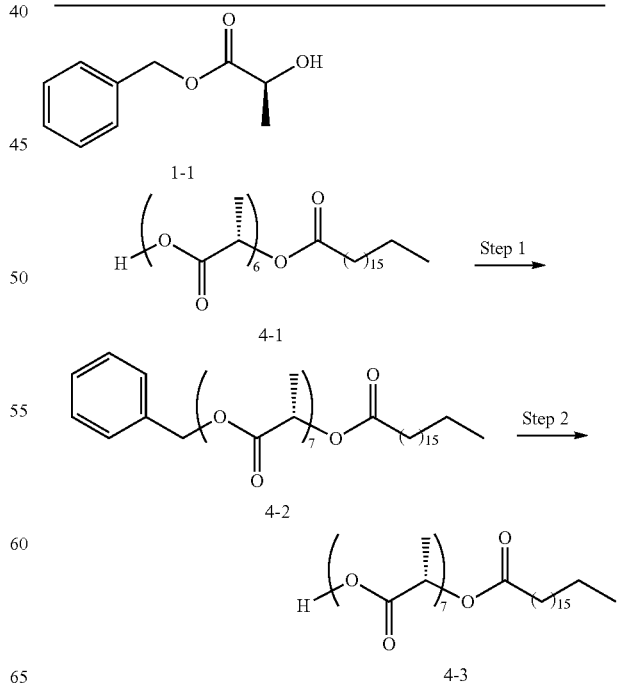

Step-1: Preparation of Octadecanoic acid (S)-1-{(S)-1-[(S)-1-((S)-1-{(S)-1-[(S')-1-((S)-1-benzyloxy-carbonyl-ethoxycarbonyl)-ethoxycarbonyl]-ethoxycarbonyl}-ethoxycarbonyl)-ethoxycarbonyl]-ethoxycarbonyl}-ethyl ester (4-2)

To a solution of octadecanoic acid (S)-1-[(S)-1-((S)-1-{(S)-1-[(S)-1-((S)-1-carboxy-ethoxycarbonyl)-ethoxycarbonyl]-ethoxycarbonyl}-ethoxycarbonyl)-ethoxycarbonyl]-ethyl ester (4-1, 11.9 g, 16.66 mmol) in dichloromethane (50 mL) was added EDC.HCl (4.2 g, 22.22 mmol), (S)-2-hydroxy-propionic acid benzyl ester (1-1, 2.0 g, 11.11 mmol) and 4-dimethylaminopyridine (135 mg, 1.11 mmol) at 0° C. The reaction mixture was allowed to stir at 25-30° C. over a period of 1 hour. The resulting reaction mass was quenched with water (100 mL), extracted with dichloromethane (250×3 mL), dried over sodium sulfate and concentrated under reduced pressure. The crude product obtained upon evaporation of volatiles was purified through silica gel (230-400) column (5% ethyl acetate in hexane) to obtain product 4-2 as a colorless liquid (7.1 g, 73%). $^1$H-NMR (400 MHz, DMSO-d6) δ 7.38-7.34 (m, 5H), 5.20-5.15 (m, 8H), 5.05 (q, J=7.2 Hz, 1H), 2.35-2.31 (m, 2H), 1.50-1.39 (m, 23H), 1.24 (bs, 28H), 0.86 (t, J=7.2 Hz, 3H); MS m/z (M+H)$^+$ 879.9; (M+NH$_4$)$^+$ 897

Step-2: Preparation of Octadecanoic acid (S)-1-{(S)-1-[(S)-1-((S)-1-{(S)-1-[(S)-1-((S)-1-carboxy-ethoxycarbonyl)-ethoxycarbonyl]- ethoxycarbonyl}-ethoxycarbonyl)-ethoxycarbonyl]-ethoxycarbonyl}-ethyl ester (4-3)

To a 100 mL autoclave vessel, a solution of octadecanoic acid (S)-1-{(5)-1-[(S)-1-((S)-1-{(S)-1-[(S)-1-((S)-1-benzyloxycarbonyl-ethoxycarbonyl)-ethoxycarbonyl]-ethoxycarbonyl}-ethoxycarbonyl)-ethoxycarbonyl]-ethoxycarbonyl}-ethyl ester (4-2, 7.1 g, 8.08 mmol) in methanol (20 mL) and 10% Pd/C (1.42 g, 50% wet) were added at 25-30° C. The reaction mixture was stirred at room temperature under hydrogen pressure (5 kg/cm$^2$) over a period of 2 hours. After completion of the reaction, the reaction mixture was filtered through celite bed and the volatiles were evaporated under reduced pressure to obtain product 4-3 as a colorless low melting solid (4.8 g, 75%). $^1$H-NMR (400 MHz, DMSO-d6) δ 5.25-5.12 (m, 2H), 5.05 (q, J=7.2 Hz, 1H), 4.97 (q, J=7.2 Hz, 1H), 2.33 (m, 2H), 1.52-1.39 (m, 23H), 1.23 (bs, 28H), 0.85 (t, J=7.2 Hz, 3H); MS m/z (M−H)$^−$ 787.1

Step-1: Preparation of Compound 5-2

To a solution of octadecanoic acid (S)-1-[(S)-1-((S)-1-{(S)-1-[(S)-1-((S)-1-carboxy-ethoxycarbonyl)-ethoxycarbonyl]-ethoxycarbonyl}-ethoxycarbonyl)-ethoxycarbonyl]-ethyl ester (4-1, 3.9 g, 5.55 mmol) in dichloromethane (15 mL) was added EDC.HCl (1.4 g, 7.40 mmol), (R)-2-hydroxy-propionic acid (R)-1-((R)-1-{(R)-1-[(R)-1-((R)-1-benzyloxycarbonyl-ethoxycarbonyl)-ethoxycarbonyl]-ethoxycarbonyl}-ethoxycarbonyl)-ethyl ester (5-1, 2.0 g, 3.70 mmol) and 4-dimethylaminopyridine (45 mg, 0.37 mmol) at 0° C. The reaction mixture was allowed to stir at 25-30° C. over a period of 1 hour. The resulting reaction mass was quenched with water (100 mL), extracted with dichoromethane (250×3 mL), dried over sodium sulfate and concentrated under reduced pressure. The crude product obtained upon evaporation of volatiles was purified through silica gel (230-400) column (6% ethyl acetate in hexane) to obtain product 5-2 as a pale yellow liquid 3.1 g (67%). $^1$H-NMR (400 MHz, DMSO-d6) δ 7.37-7.35 (m, 5H), 5.21-5.15 (m, 13H), 5.05 (q, J=7.2 Hz, 1H), 2.35-2.31 (m, 2H), 1.47-1.41 (m, 38H), 1.24 (bs, 28H), 0.86 (t, J=7.2 Hz, 3H); MS m/z (M+H)$^+$ 1240.3; (M+NH$_4$)$^+$ 1257.3

Step-2: Preparation Compound 5-3

To a 100 mL autoclave vessel, a solution of compound (5-2, 3.1 g, 2.50 mmol) in methanol (20 mL) and 20% Pd/C (0.62 g, 50% wet) were added at 25-30° C. The reaction mixture was stirred at room temperature under hydrogen pressure (5 kg/cm$^2$) over a period of 2 hours. After completion of the reaction, the reaction mixture was filtered through celite bed and the volatiles were evaporated under reduced pressure to obtain product 5-3 as a off white solid (2.3 g, 80%). $^1$H-NMR (400 MHz, DMSO-d6) δ 13.11 (bs, 1H), 5.23-5.17 (m, 10H), 5.09-4.95 (m, 2H), 1.47-1.40 (m, 36H), 1.23 (bs, 32H), 0.82 (t, J=8.8 Hz, 3H), 2.35-2.31 (m, 2H), 1.47-1.41 (m, 38H), 1.24 (bs, 28H), 0.86 (t, J=7.2 Hz, 3H); MS m/z (M+H)$^+$ 1240.3; (M+NH$_4$)$^+$ 1257.3

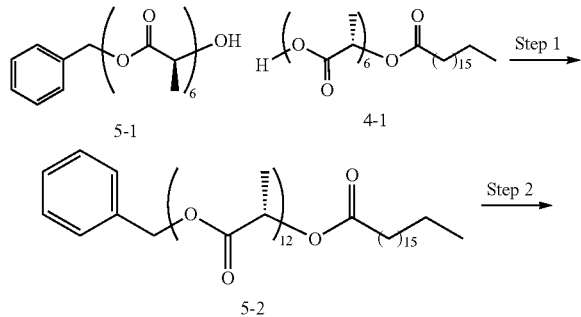

Scheme 5: Synthesis of Compound 5-3:

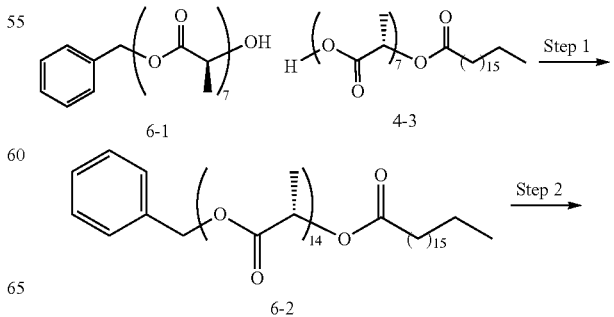

Scheme 6: Synthesis of Compound 6-3:

-continued

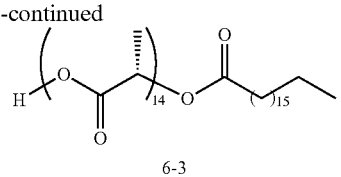

6-3

Step-1: Preparation of Compound 6-2

To a solution of octadecanoic acid (S)-1-{(S)-1-[(S)-1-((S)-1-{(S)-1-[(S)-1-((S)-1-carboxy-ethoxycarbonyl)-ethoxycarbonyl]-ethoxycarbonyl}-ethoxycarbonyl)-ethoxycarbonyl]-ethoxycarbonyl}-ethyl ester (4-3, 6.75 g, 8.57 mmol) in dichloromethane (40 mL) was added EDC.HCl (2.18 g, 11.43 mmol), (S)-2-hydroxy-propionic acid (S)-1-[(S)-1-((S)-1-{(S)-1-[(S)-1-((S)-1-benzyloxycarbonyl-ethoxycarbonyl)-ethoxycarbonyl]-ethoxycarbonyl}-ethoxycarbonyl)-ethoxycarbonyl]-ethyl ester (6-1, 3.5 g, 5.71 mmol) and 4-dimethylaminopyridine (69 mg, 0.57 mmol) at 0° C. The reaction mixture was allowed to stir at 25-30° C. over a period of 1 hour. The resulting reaction mass was quenched with water (250 mL), extracted with dichloromethane (350×3 mL), dried over sodium sulfate and concentrated under reduced pressure. The crude product obtained upon evaporation of volatiles was purified through silica gel (230-400) column (6% ethyl acetate in hexane) to obtain product 6-2 as a pale yellow liquid (6.2 g, 78%).

Step-2: Preparation Compound 6-3

To a 250 mL autoclave vessel, a solution of compound 6-2, 6.2 g, 4.48 mmol) in methanol (60 mL) and 20% Pd/C (1.24 g, 50% wet) were added at 25-30° C. The reaction mixture was stirred at room temperature under hydrogen pressure (5 kg/cm²) over a period of 2 hours. After completion of the reaction, the reaction mixture was filtered through celite bed and the volatiles were evaporated under reduced pressure to obtain product 6-3 as an off white solid (4.2 g, 72%). ¹H-NMR (400 MHz, DMSO-d6) δ 13.20 (s, 1H), 5.23-5.15 (m, 12H), 5.08-4.97 (m, 2H), 2.33 t, J=7.2 Hz, 2H), 1.50-1.41 (m, 44H), 1.23 (bs, 28H), 0.85 (t, J=7.2 Hz, 3H); MS m/z (M−H)⁻ 1147.7

Scheme 7: Synthesis of Succinic acid mono-((S)-1-benzyloxycarbonyl-ethyl) ester (7-1):

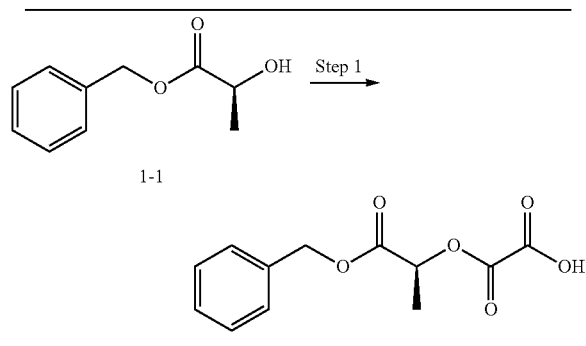

Step-1: Preparation of Succinic acid mono-((S)-1-benzyloxycarbonyl-ethyl) ester (7-1)

To a solution of succinic acid (6.56 g, 55.55 mmol) in dichloromethane (50 mL) was added EDC.HCl (15.9 g, 83.33 mmol), hydroxybenzotriazole (0.766 g, 5.55 mmol), (S)-2-Hydroxy-propionic acid benzyl ester (1-1, 5.0 g, 27.77 mmol) and 4-dimethylaminopyridine (338 mg, 2.77 mmol) at 0° C. The reaction mixture was allowed to stir at 25-30° C. over a period of 1 hour. The resulting reaction mixture was quenched with water (150 mL), extracted with dichloromethane (250×3 mL), dried over sodium sulfate and concentrated under reduced pressure. The crude product obtained upon evaporation of volatiles was purified through silica gel (230-400) column (30% ethyl acetate in hexane) to obtain 7-1 as a pale yellow liquid (1.0 g, 71%). ¹H-NMR (400 MHz, DMSO-d6) δ 12.25 (bs, 1H), 7.38-7.33 (m, 5H), 5.15 (s, 2H), 5.05 (q, J=7.2 Hz, 1H), 2.58-2.46 (m, 4H), 1.40 (d, J=7.2 Hz, 3H); MS m/z (M+H)⁺ 281.6

Scheme 8: Synthesis of Succinic acid mono-[(S)-1-((S)-1-benzyloxycarbonyl-ethoxycarbonyl)-ethyl] ester (8-1):

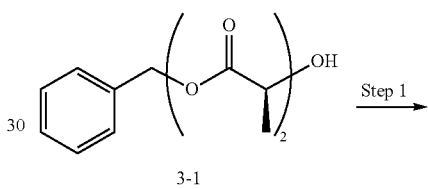

3-1

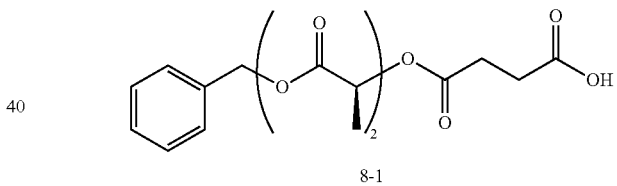

8-1

Step-1: Preparation of Succinic acid mono-[(S)-1-((S)-1-benzyloxycarbonyl-ethoxycarbonyl)-ethyl] ester (8-1)

To a solution of succinic acid (5.6 g, 47.61 mmol) in dichloromethane (60 mL) was added EDC.HCl (13.6 g, 71.4 mmol), hydroxybenzotriazole (0.697 g, 4.76 mmol), (S)-2-hydroxy-propionic acid benzyl ester (3-1, 6.0 g, 23.80 mmol) and 4-dimethylaminopyridine (290 mg, 2.38 mmol) at 0° C. The reaction mixture was allowed to stir at 25-30° C. over a period of 1 hour. The resulting reaction mixture was quenched with water (250 mL), extracted with dichloromethane (400×3 mL), dried over sodium sulfate and concentrated under reduced pressure. The crude product obtained upon evaporation of volatiles was purified through silica gel (230-400) column (35% ethyl acetate in hexane) to obtain 8-1 as a pale, yellow liquid 4.3 g (51%). ¹H-NMR (400 MHz, DMSO-d6) δ 12.24 (bs, 1H), 7.38-7.33 (m, 5H), 5.16-5.15 (m, 3H), 5.04 (q, J=7.2 Hz, 1H), 2.57-2.45 (m, 4H), 1.40 (d, J=7.2 Hz, 3H), 1.35 (d, J=7.2 Hz, 3H)

Scheme 9: Synthesis of Succinic acid mono-((S)-1-{(S)-1-[(S)-1-((S)-1-benzyloxycarbonyl-ethox ycarbonyl)-ethoxycarbonyl]-ethoxycarbonyl}-ethyl) ester (9-3):

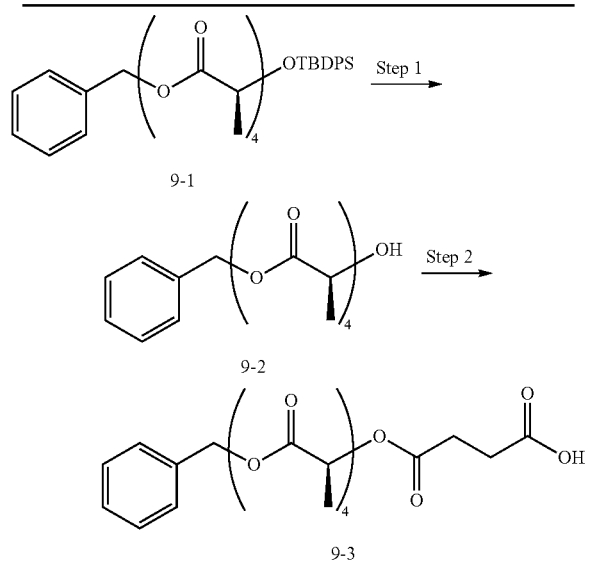

Scheme 10: Synthesis of Succinic acid mono-[(S)-1-((S)-1-allyloxycarbonyl-ethoxycarbonyl)-ethyl] ester (10-3):

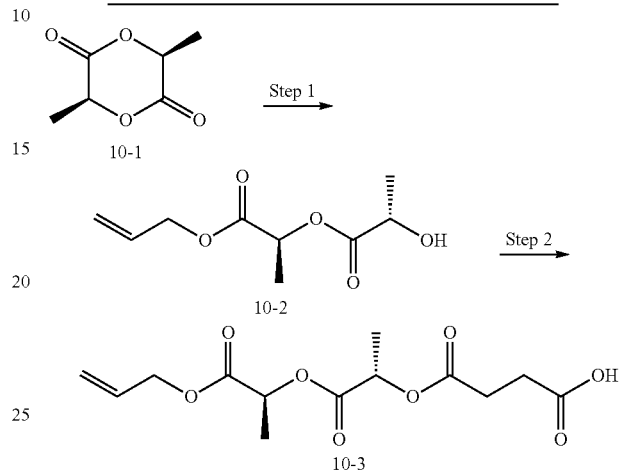

Step-1: Preparation of (S)-2-Hydroxy-propionic acid (S)-1-[(S)-1-((S)-1-benzyloxycarbonyl-ethoxycarbonyl)-ethoxycarbonyl]-ethyl ester (9-2)

To a solution of (S)-2-(tert-butyl-diphenyl-silanyloxy)-propionic acid (S)-1-[(S)-1-((S)-1-benzyloxycarbonyl-ethoxycarbonyl)-ethoxycarbonyl]-ethyl ester (9-1, 14 g, 22.05 mmol) in tetrahydrofuran (1400 mL) was added tetra-n-butylammonium fluoride (33.08 mL, 1.0 M, 33.08 mmol) and acetic acid (1.98 g, 33.08 mmol) at 0° C. The reaction mixture was allowed to stir at room temperature over a period of 1 hour. The resulting reaction mixture was concentrated under reduced pressure and crude product obtained upon evaporation of the volatiles was purified through silica gel column chromatography (20% ethyl acetate in hexane) to afford product 9-2 as colorless liquid (4.7 g, 53%). $^1$H-NMR (400 MHz, DMSO-d6) δ 7.40-7.33 (m, 5H), 5.47 (d, J=7.2 Hz, 1H), 5.20-5.07 (m, 5H), 4.22-4.177 (m, 1H), 1.46-1.39 (m, 9H), 1.26 (d, J=7.2 Hz, 311); MS m/z (M+H)$^+$ 396.8

Step-2: Preparation of Succinic acid mono-((S)-1-{(S)-1-[(S)-1-((S)-1-benzyloxycarbonyl-ethoxycarbonyl)-ethoxycarbonyl]-ethoxycarbonyl}-ethyl) ester (9-3)

To a solution of succinic acid (2.8 g, 23.71 mmol) in dichloromethane (50 mL) was added EDC.HCl (6.79 g, 35.55 mmol), hydroxybenzotriazole (0.327 g, 2.37 mmol), (S)-2-hydroxy-propionic acid (S)-1-[(S)-1-((S)-1-benzyloxycarbonyl-ethoxycarbonyl)-ethoxycarbonyl]-ethyl ester 9-2, 4.7 g, 11.85 mmol) and 4-dimethylaminopyridine (144 mg, 1.18 mmol) at 0° C. The reaction mixture was allowed to stir at 25-30° C. over a period of 1 hour. The resulting reaction mixture was quenched with water (250 mL), extracted with dichloromethane (500×3 mL), dried over sodium sulfate and concentrated under reduced pressure. The crude product obtained upon evaporation of volatiles was purified through silica gel (230-400) column (40% ethyl acetate in hexane) to obtain product 9-3 as a pale yellow liquid (3.1 g, 53%). $^1$H-NMR (400 MHz, DMSO-d6) δ 12.24 (bs, 1H), 7.38-7.35 (m, 5H), 5.21-5.15 (m, 5H), 5.05 (q, J=7.2 Hz, 1H), 2.7-2.5 (m, 4H), 1.46-1.40 (m, 12H); MS m/z (M−H)$^−$ 494.6

Step-1: Preparation of (S)-2-Hydroxy-propionic acid (S)-1-allyloxycarbonyl-ethyl ester (10-2)

To a solution of (3S,6S)-3,6-dimethyl-[1,4]dioxane-2,5-dione 10-1, 5.0 g, 34.72 mmol) in toluene (100 mL) was added allyl alcohol (2.24 mL, 32.98 mmol) and camphorsulfonic acid (0.8 g, 3.47 mmol) at 25-30° C. The reaction mixture was allowed to stir at 80° C. over a period of 16 hours. The resulting reaction mixture was diluted with ethyl acetate (800 mL) and washed with water (2×400 mL). The crude product obtained upon evaporation of volatiles was purified through silica gel (230-400) column chromatography (5% methanol in dichloromethane) to obtain product 10-2 as a pale yellow liquid (3.6 g, 51%). $^1$H-NMR (400 MHz, DMSO-d6) δ 5.93-5.87 (m, 1H), 5.46 (d, J=7.2 Hz, 1H), 5.34-5.21 (m, 2H), 5.07 (q, J=7.2 Hz, 1H), 4.62-4.60 (d, J=7.2 Hz, 1H), 4.22-4.18 (m, 1H), 1.43 (d, J=7.2 Hz, 3H), 1.28 (d, J=7.2 Hz, 3H); MS m/z (M+H)$^+$ 203.0

Step-2: Preparation of Succinic acid mono-[(S)-1-((S)-1-allyloxycarbonyl-ethoxycarbonyl)-ethyl] ester (10-3)

To a solution of (S)-2-hydroxy-propionic-acid (S)-1-allyloxycarbonyl-ethyl ester 10-2, 3.6 g, 17.82 mmol) in dichloromethane (40 mL) was added 4-dimethylaminopyridine (338 mg, 2.77 mmol) and dihydro-furan-2,5-dione (3.2 g, 32.07 mmol) at 0° C. The reaction mixture was allowed to stir at 25-30° C. over a period of 16 hours. The resulting reaction mixture was quenched with water (150 mL), extracted with dichloromethane (250×3 mL), dried over sodium sulfate and concentrated under reduced pressure. The crude product obtained upon evaporation of volatiles was purified through silica gel (230-400) column (2% methanol in dichloromethane) to obtain product 10-3 as a pale yellow liquid (2.9 g, 53%). $^1$H-NMR (400 MHz, DMSO-d6) δ 12.25 (bs, 1H), 5.94-5.84 (m, 1H), 5.33-5.04

(m, 4H), 4.61 (m, 2H) 2.66-2.54 (m, 4H), 1.41 (m, 6H); (M+H)⁺ 302.9 (M+NH₄)⁺ 319.9

Scheme 11: Synthesis of Succinic acid mono-((S)-1-{(S)-1-[(S)-1-((S)-1-allyloxycarbonyl-ethoxycarbonyl)-ethoxycarbonyl]-ethoxycarbonyl}-ethyl) ester (11-4):

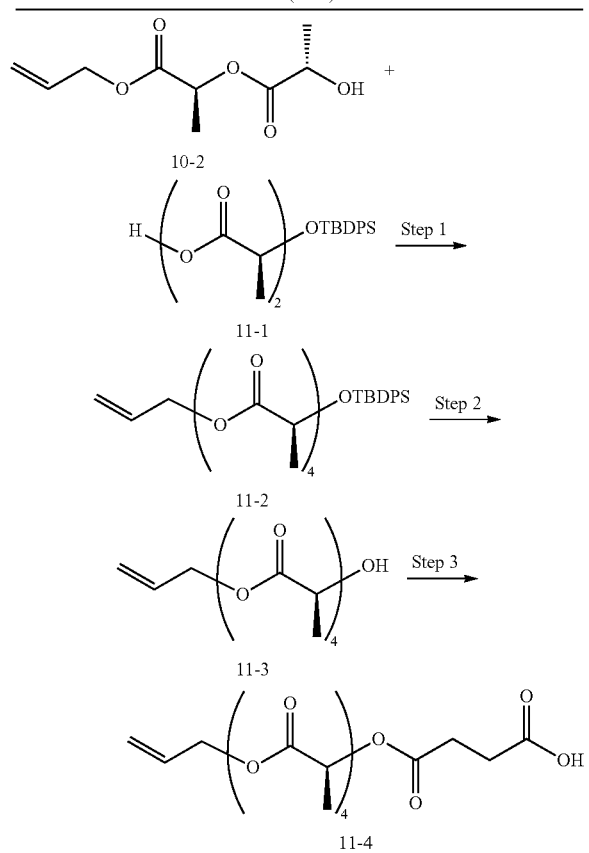

Step-1: Preparation of (S)-2-(tert-Butyl-diphenyl-silanyloxy)-propionic acid (S)-1-[(S)-1-((S)-1-allyloxycarbonyl-ethoxycarbonyl)-ethoxycarbonyl]-ethyl ester (11-2)

To a solution of (S)-2-(tert-butyl-diphenyl-silanyloxy)-propionic acid (S)-1-carboxy-ethyl ester 11-1, 2.75 g, 6.43 mmol) in dichloromethane (10 mL) was added EDC.HCl (1.88 g, 9.88 mmol), (S)-2-hydroxy-propionic acid (S)-1-allyloxycarbonyl-ethyl ester 10-2, 1.0 g, 4.94 mmol) and 4-dimethylaminopyridine (59 mg, 0.49 mmol) at 0° C. The reaction mixture was allowed to stir at 25-30° C. over a period of 1 hour. The resulting reaction mass was quenched with water (100 mL), extracted with dichloromethane (150×3 mL), dried over sodium sulfate and concentrated under reduced pressure. The crude product obtained upon evaporation of volatiles was purified through silica gel (230-400) column (3% ethyl acetate in hexane) to obtain product 11-2 as a colorless liquid (1.8 g, 62%). ¹H-NMR (400 MHz, DMSO-d6) δ 7.61-7.39 (m, 10H), 5.92-5.85 (m, 1H), 5.32-5.13 (m, 4H), 4.95 (q, J=6.8 Hz, 1H), 4.61-4.59 (m, 2H), 4.29 (q, J=6.8 Hz, 1H), 1.5-1.4 (m, 6H), 1.35-1.28 (m, 6H) 1.02 (s, 9H); MS m/z (M+H)⁺ 585.7, (M+NH₄)⁺ 602.7

Step-2: Preparation of (S)-2-Hydroxy-propionic acid (S)-1-[(S)-1-((S)-1-allyloxycarbonyl-ethoxycarbonyl)-ethoxycarbonyl]-ethyl ester (11-3)

To a solution of (S)-2-(tert-butyl-diphenyl-silanyloxy)-propionic acid (S)-1-[(S)-1-((S)-1-allyloxycarbonyl-ethoxycarbonyl)-ethoxycarbonyl]-ethyl ester 11-2, 2.0 g, 3.42 mmol) in tetrahydrofuran (20 mL) was added tetra-n-butylammonium fluoride (5.1 mL, 1.0 M, 5.13 mmol) and acetic acid (0.30 g, 5.13 mmol) at 0° C. The reaction mixture was allowed to stir at room temperature over a period of 1 hour at 0° C. The resulting reaction mixture was concentrated under reduced pressure and crude product obtained upon evaporation of the volatiles was purified through silica gel column chromatography (18% ethyl acetate in hexane) to afford product 11-3 as a colorless liquid (0.6 g, 50%). ¹H-NMR (400 MHz, DMSO-d6) δ 5.93-5.86 (m, 1H), 5.48 (d, J=6.4 Hz, 1H), 5.34-5.09 (m, 5H), 4.62-4.60 (m, 2H), 4.20 (q, J=6.4 Hz, 1H), 1.48-1.40 (m, 9H), 1.29-1.25 (m, 3H); MS m/z (M+H)⁺ 347.7, (M+NH₄)⁺ 364.7

Step-3: Preparation of Succinic acid mono-((S)-1-{(S)-1-[(S)-1-((S)-1-allyloxycarbonyl-ethoxycarbonyl)-ethoxycarbonyl]-ethoxycarbonyl}-ethyl) ester (11-4)

To a solution of (S)-2-hydroxy-propionic acid (S)-1-[(S)-1-((S)-1-allyloxycarbonyl-ethoxycarbonyl)-ethoxycarbonyl]-ethyl ester 11-3, 0.6 g, 1.73 mmol) in dichloromethane (6 mL) was added 4-dimethylaminopyridine (42 mg, 0.34 mmol) and dihydro-furan-2,5-dione (0.31 g, 3.11 mmol) at 0° C. The reaction mixture was allowed to stir at 25-30° C. over a period of 16 hours. The resulting reaction mixture was quenched with water (50 mL), extracted with dichloromethane (150×3 mL), dried over sodium sulfate and concentrated under reduced pressure. The crude product obtained upon evaporation of volatiles was purified through silica gel (230-400) column (2% methanol in dichloromethane) to obtain product 11-4 as a colorless liquid (0.4 g, 51%). ¹H-NMR (400 MHz, DMSO-d6) δ 5.93-5.86 (m, 1H), 5.34-5.04 (m, 6H), 4.62-4.60 (m, 2H), 2.60-2.44 (m, 4H), 1.47-1.42 (m, 12H); MS m/z (M−H)⁻ 445.5.

Example 2. Synthesis of Mono-Prodrugs

Synthesis of Dorzolamide Mono-Prodrugs

Scheme 12: Synthesis of Octadecanoic acid (S)-1-((S)-1-{(S)-1-[(S)-2-(4-ethylamino-6-methyl-7,7-dioxo-4,5,6,7-tetrahydro-7λ*6*-thieno[2,3-b]thiopyran-2-sulfonylamino-1-methyl-2-oxo-ethoxycarbonyl]-ethoxycarbonyl}-ethoxycarbonyl)-ethyl ester (12-3):

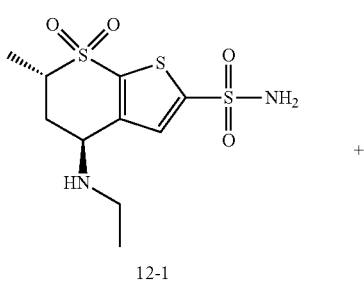

12-1

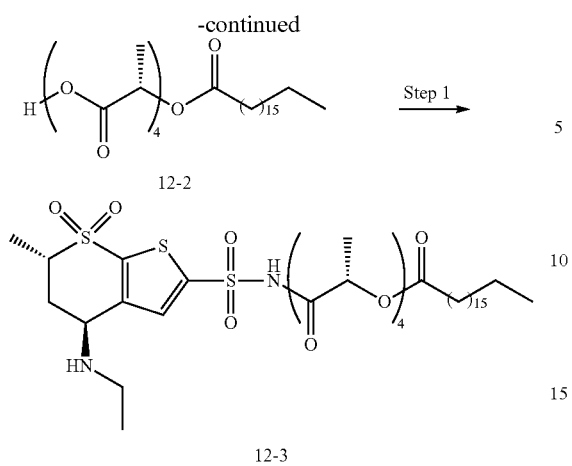

12-2

12-3

Step-1: Preparation of Octadecanoic acid (S)-1-
((S)-1-{(S)-1-[(S)-2-(4-ethylamino-6-methyl-7,7-
dioxo-4,5,6,7-tetrahydro-7λ*6*-thieno[2,3-b]thiopy-
ran-2-sulfonylamino)-1-methyl-2-oxo-
ethoxycarbonyl]-ethoxycarbonyl}-ethoxycarbonyl)-
ethyl ester (12-3)

To a solution of Dorzolamide (12-1, 0.3 g, 0.83 mmol) in dichloromethane (3 mL) was added N,N-diisopropylethylamine (0.3 mL, 1.66 mmol) at 0° C. After 30 minutes, octadecanoic acid (S)-1-{(S)-1-[(S)-1-((S)-1-carboxyethoxycarbonyl)-ethoxycarbonyl]-ethoxycarbonyl}-ethyl ester (12-2, 0.715 g, 1.25 mmol), EDC.HCl (0.317 g, 1.66 mmol) and 4-dimethylaminopyridine (0.01 g, 0.08 mmol) were added at 0° C. The reaction mixture was allowed to stir at 25-30° C. over a period of 1 hour. The resulting reaction mass was quenched with water (100 mL) and extracted with dichloromethane (250×2 mL). The dichloromethane was dried over sodium sulfate, filtered and concentrated under reduced pressure. The crude product obtained upon evaporation of volatiles was purified through silica gel (230-400) column (3% methanol in DCM) to obtain product 12-3 as an off-white solid (0.3 g, 41%). $^{1}$H-NMR (400 MHz, DMSO-d6 with TFA) 6 8.85 (m, 2H), 8.14 (s, 1H), 5.2-5.1 (m, 2H), 5.1-4.9 (m, 2H), 4.75-4.65 (m, 1H), 4.15-4.0 (m. 1H), 3.30-2.9 (m, 2H), 2.7-2.4 (m, 2H), 2.30 (t, 2H), 1.55-1.3 (m, 17H), 1.3-1.1 (m, 31H), m, 0.85-0.75 (m, 3H); MS m/z [M+H]$^{+}$ 880.3.

Scheme 13: Synthesis of Compound 13-2:

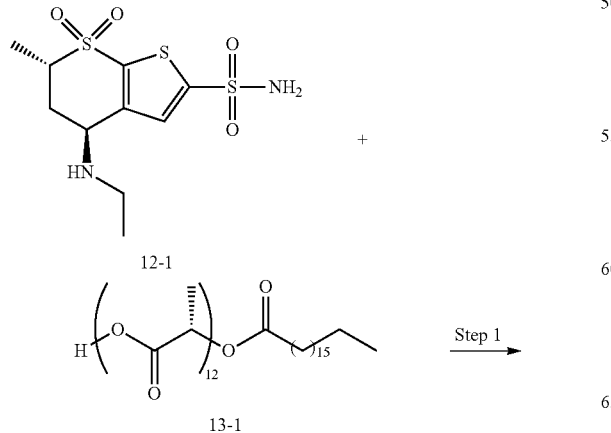

13-1

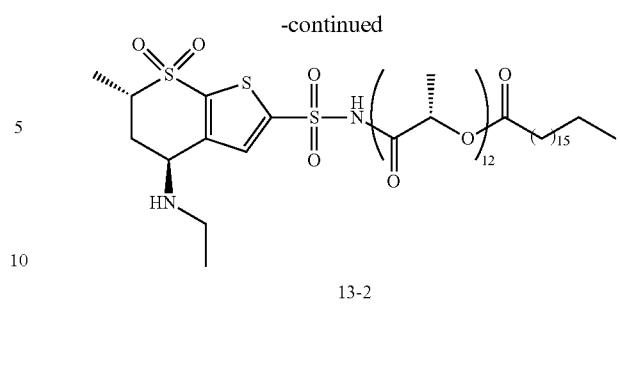

13-2

Step-1: Preparation of Compound 13-2

To a solution of Dorzolamide (12-1, 0.25 g, 0.69 mmol) in dichloromethane (2.5 mL) was added N,N-diisopropylethylamine (0.25 mL, 1.38 mmol) at 0° C. After 30 minutes, compound 13-1 (1.03 g, 0.89 mmol), EDC.HCl (0.263 g, 1.38 mmol) and 4-dimethylaminopyridine (0.008 g, 0.07 mmol) were added at 0° C. The reaction mixture was allowed to stir at 25-30° C. over a period of 1 hour. The resulting reaction mass was quenched with water (100 mL), extracted with dichloromethane (250×2 mL). The dichloromethane was dried over sodium sulfate, filtered and concentrated under reduced pressure. The crude product obtained upon evaporation of volatiles was purified through silica gel (230-400) column (3.5% methanol in DCM) to obtain 13-2 as an off-white solid 0.35 g (34.6%). $^{1}$H-NMR (400 MH z, DMSO-d6) δ 7.43 (bs, 1H), 5.26-5.15 (m, 9H), 5.15-5.0 (m, 2H), 4.79 (q, 1H), 3.95-3.8 (m. 2H), 2.6-2.4 (m, 2H), 2.33 (t, 2H), 1.55-1.38 (m, 33H), 1.38-1.15 (m, 38H), 1.15-0.95 (m, 3H), 0.83 (t, 3H); MS m/z [M+H]$^{+}$ 1456.5.

Scheme 14: Synthesis of Compound 14-2:

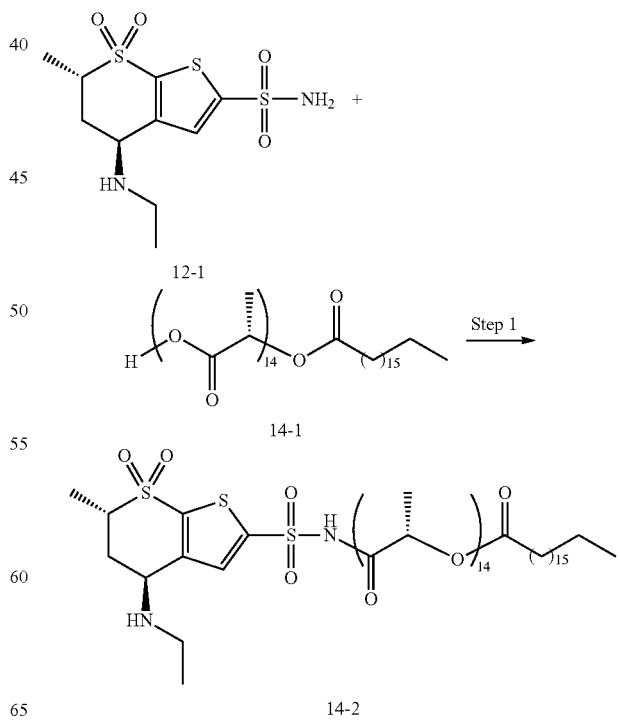

14-2

Step-1: Preparation of Compound 14-2

To a solution of Dorzolamide (12-1, 0.25 g, 0.69 mmol) in dichloromethane (2.5 mL) was added N,N-diisopropylethylamine (0.25 mL, 1.38 mmol) at 0° C. After 30 minutes, compound 14-1 (1.168 g, 0.9 mmol), EDC.HCl (0.263 g, 1.38 mmol) and 4-dimethylaminopyridine (0.008 g, 0.07 mmol) were added at 0° C. The reaction mixture was allowed to stir at 25-30° C. over a period of 1 hour. The resulting reaction mass was quenched with water (100 mL), extracted with dichloromethane (250×2 mL). The dichloromethane was dried over sodium sulfate, filtered and concentrated under reduced pressure. The crude product obtained upon evaporation of volatiles was purified through silica gel (230-400) column (2% methanol in DCM) to obtain 14-2 as an off-white solid (0.15 g, 13.6%). $^1$H-NMR (400 MHz, DMSO-d6 with TFA) δ 9.0-8.75 (m, 2H), 8.13 (s, 1H), 5.24-5.1 (m, 12H), 5.03 (q, 2H), 4.97 (q, 2H), 4.73-4.65 (m, 1H), 4.15-4.0 (m, 1H), 2.7-2.4 (m, 2H), 2.33 (t, 2H), 1.6-1.3 (m, 47H), 1.3-1.1 (m, 31H), 0.81 (t, 3H).

Synthesis of Brinzolamide Mono-Prodrugs

Scheme 15: Synthesis of Octadecanoic acid (S)-1-[(S)-1-((S)-1-{(S)-2-[4-ethylamino-2-(3-methoxy-propyl)-1,1-dioxo-1,2,3,4-tetrahydro-1λ*6*-thieno[3,2-e][1,2]thiazine-6-sulfonylamino]-1-methyl-2-oxo-ethoxycarbonyl}-ethoxycarbonyl)-ethoxycarbonyl]-ethyl ester (15-2):

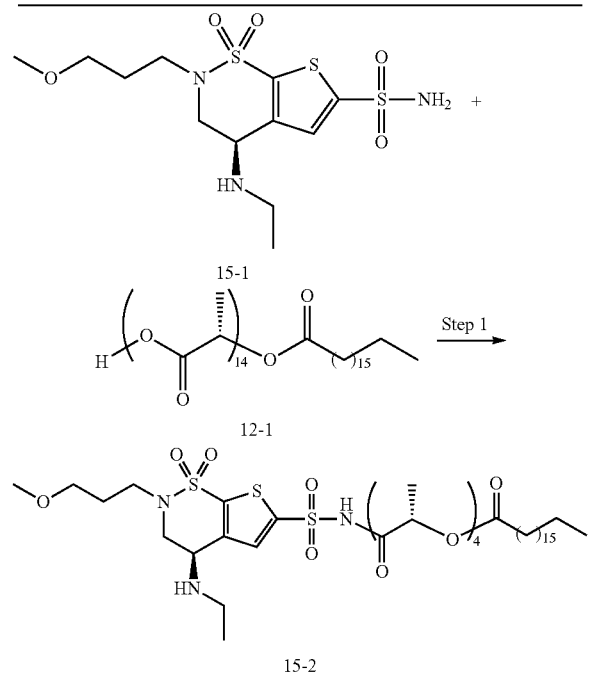

Step-1: Preparation of Octadecanoic acid (S)-1-[(S)-1-((S)-1-{(S)-2-[4-ethylamino-2-(3-methoxy-propyl)-1,1-dioxo-1,2,3,4-tetrahydro-1λ*6*-thieno[3,2-e][1,2]thiazine-6-sulfonylamino]-1-methyl-2-oxo-ethoxycarbonyl}-ethoxycarbonyl)-ethoxycarbonyl]-ethyl ester (15-2)

To a solution of Brinzolamide (15-1, 0.3 g, 0.78 mmol) and octadecanoic acid (S)-1-{(S)-1-[(S)-1-((S)-1-carboxy-ethoxycarbonyl)-ethoxycarbonyl]-ethoxycarbonyl}-ethyl ester (12-2, 0.671 g, 1.17 mmol) in dichloromethane (3 mL) was added EDC.HCl (0.298 g, 1.56 mmol), 4-dimethylaminopyridine (9 mg, 0.08 mmol) at 0° C. The reaction mixture was allowed to stir at 25-30° C. over a period of 1 hour. The resulting reaction mass was quenched with water (100 mL) and extracted with dichloromethane (250×2 mL). The dichloromethane was dried over sodium sulfate, filtered and concentrated under reduced pressure. The crude product obtained upon evaporation of volatiles was purified through silica gel (230-400) column (4% methanol in DCM) to obtain product 15-2 as an off white solid (0.2 g, 27.3%). $^1$H-NMR (400 MHz, DMSO-d6) δ 9.2-8.9 (m, 2H), 7.89 (s, 1H), 5.21-5.01 (m, 3H), 4.90-4.79 (m, 2H), 4.13-3.99 (m, 2H), 3.42-3.31 (m, 3H), 3.24-3.0 (m, 6H), 2.33 (t, 2H), 1.83 (quintet, 2H), 1.57-1.37 (m, 11H), 1.34-1.15 (m, 31H), 0.83 (t, 3H). MS m/z [M+H]$^+$ 939.1.

Scheme 16: Synthesis of Compound 16-1:

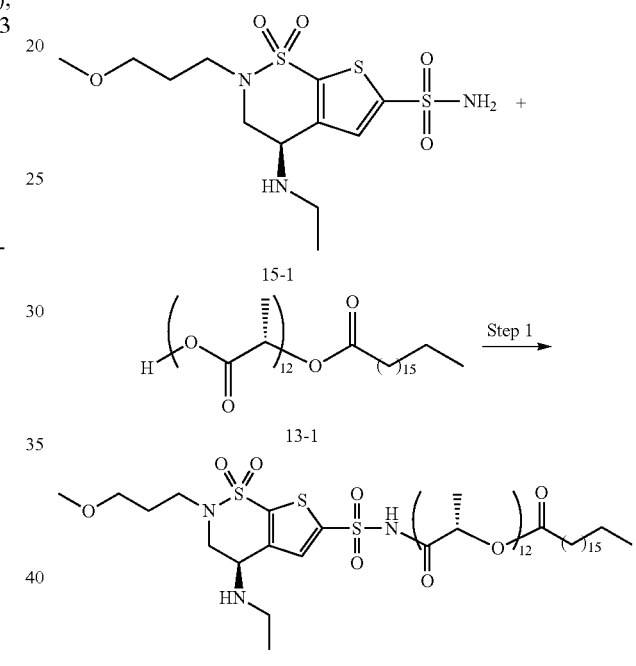

Step-1: Preparation of Compound 16-1

To a solution of Brinzolamide (15-1, 0.3 g, 0.78 mmol) and compound (13-1, 1.165 g, 1.01 mmol) in dichloromethane (3 mL) was added EDC.HCl (0.298 g, 1.56 mmol) and 4-dimethylaminopyridine (9 mg, 0.08 mmol) at 0° C. The reaction mixture was allowed to stir at 25-30° C. over a period of 1 hour. The resulting reaction mass was quenched with water (100 mL) and extracted with dichloromethane (250×2 mL). The dichloromethane was dried over sodium sulfate, filtered and concentrated under reduced pressure. The crude product obtained upon evaporation of volatiles was purified through silica gel (230-400) column (4% methanol in DCM) to obtain 16-1 as an off white solid (0.2 g, 19.4%). $^1$H-NMR (400 MHz, DMSO-d6) δ 9.2-8.9 (m, 2H), 7.84 (bs, 1H), 5.25-5.0 (m, 11H), 5.14-4.89-4.75 (m, 2H), 4.1-3.9 (m, 2H), 3.41-3.32 (m, 3H), 3.24-3.0 (m, 6H), 2.35-2.25 (m, 2H), 1.82 (quintet, 2H), 1.55-1.39 (m, 32H), 1.34-1.16 (m, 34H), 0.83 (t, 3H). MS m/z [M+H]$^+$ 1515.7.

Scheme 17: Synthesis of compound 17-1:

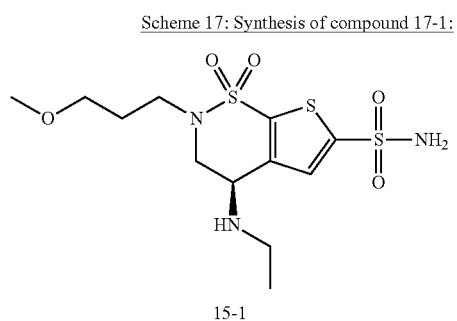

15-1

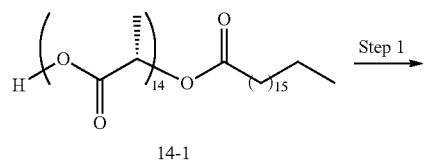

14-1

Step 1

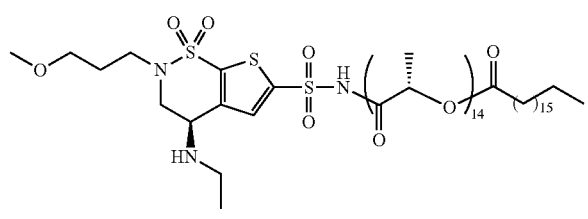

17-1

Step-1: Preparation of Compound 17-1

To a solution of Brinzolamide (15-1, 0.25 g, 0.65 mmol) and compound (14-1, 1.18 g, 9.1 mmol) in dichloromethane (2.5 mL) was added EDC.HCl (0.248 g, 1.3 mmol) and 4-dimethylaminopyridine (8 mg, 0.06 mmol) at 0° C. The reaction mixture was allowed to stir at 25-30° C. over a period of 1 hour. The resulting reaction mass was quenched with water (100 mL) and extracted with dichloromethane (250×2 mL). The dichloromethane was dried over sodium sulfate, filtered and concentrated under reduced pressure. The crude product obtained upon evaporation of volatiles was purified through silica gel (230-400) column (3% methanol in DCM) to obtain crude 17-1, which was further purified by preparative HPLC to afford 17-1 as an off white solid (0.08 g, 8%). $^1$H-NMR (400 MHz, DMSO-d6) δ 9.2-8.9 (m, 2H), 7.79 (s, 1H), 5.25-5.15 (m, 11H), 5.14-5.01 (m, 2H), 4.89-4.73 (m, 2H), 4.1-3.9 (m, 2H), 3.41-3.30 (m, 3H), 3.24-3.0 (m, 6H), 2.33 (t, 2H), 1.81 (quintet, 2H), 1.54-1.37 (m, 39H), 1.36-1.15 (m, 34H), 0.82 (t, 3H). MS m/z [M+H]$^+$ 1658.4.

Scheme 18: Synthesis of (S)-2-Hydroxy-propionic acid (S)-1-[(S)-1-((S)-1-{(S)-2-[4-ethylamino-2-(3-methoxy-propyl)-1,1-dioxo-1,2,3,4-tetrahydro-1λ*6*-thieno[3.2-e][1,2]thiazine-6-sulfonylamino]-1-methyl-2-oxo-ethoxycarbonyl}-ethoxycarbonyl)-ethoxycarbonyl]-ethyl ester (18-3):

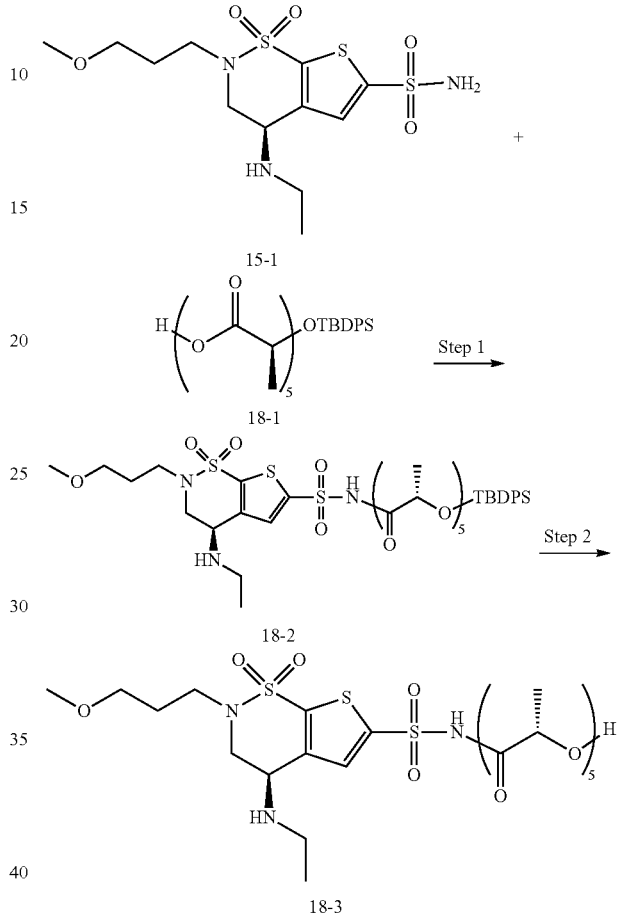

Step-1: Preparation of Compound 18-2

To a solution of Brinzolamide (15-1, 0.8 g, 2.09 mmol) and (S)-2-(tert-butyl-diphenyl-silanyloxy)-propionic acid, (S)-1-{(S)-1-[(S)-1-((S)-1-carboxy-ethoxycarbonyl)-ethoxycarbonyl]-ethoxycarbonyl}-ethyl ester (18-1, 1.933 g, 3.13 mmol) in dichloromethane (8 mL) was added EDC.HCl (0.798 g, 4.18 mmol) and 4-dimethylaminopyridine (25 mg, 0.21 mmol) at 0° C. The reaction mixture was allowed to stir at 25-30° C. over a period of 1 hour. The resulting reaction mass was quenched with water (100 mL) and extracted with dichloromethane (300×2 mL). The dichloromethane was dried over sodium sulfate, filtered and concentrated under reduced pressure. The crude product obtained upon evaporation of volatiles was purified through silica gel (230-400) column (3% methanol in DCM) to obtain product 18-2 as an off-white solid (1.4 g, 68.6%). 1H NMR (400 MHz, DMSO-d6) δ 7.64-7.57 (m, 4H), 7.53-7.37 (m, 6H), 5.11 (dq, J=34.1, 7.0 Hz, 2H), 4.94 (q, J=7.0 Hz, 2H), 4.29 (q, J=6.7 Hz, 1H), 4.03 (bs, 1H), 3.74 (s, 2H), 3.45-3.34 (m, 3H), 3.22 (m, 2H), 1.80 (m, J=6.8 Hz, 2H), 1.46 (dd, J=10.1, 7.0 Hz, 7H), 1.38-1.20 (m, 18H), 1.02 (s, 14H). MS m/z (M+H) 983.2

Step-2: Preparation of (S)-2-Hydroxy-propionic acid (S)-1-[(S)-1-((S)-1-{(S)-2-[4-ethylamino-2-(3-methoxy-propyl)-1,1-dioxo-1,2,3,4-tetrahydro-1λ*6*-thieno[3,2-e][1,2]thiazine-6-sulfonylamino]-1-methyl-2-oxo-ethoxycarbonyl}-ethoxycarbonyl)-ethoxycarbonyl]-ethyl ester (18-3)

To a solution of compound 18-2 (1.4 g, 1.42 mmol) in tetrahydrofuran (14 mL) was added tetra butyl ammonium fluoride (2.13 mL, 1.0M, 2.13 mmol) and acetic acid (0.128 ml, 2.13 mmol) at 0° C. The reaction mixture was allowed to stir at room temperature over a period of 12 hours. The resulting reaction mixture was concentrated under reduced pressure and crude product obtained upon evaporation of the volatiles was purified through silica gel column chromatography (5% methanol in ethyl acetate) to afford product 18-3 as an off white solid (500 mg, 47%). $^1$H-NMR (400 MHz, DMSO-d6) δ 9.2-8.8 (m, 2H), 7.76 (bs, 1H), 5.45 (d, 1H), 5.19-5.03 (m, 3H), 4.79 (q, 1H), 4.18 (quintet, 1H), 4.1-3.95 (m, 2H), 3.40-3.28 (m, 3H), 3.21-2.9 (m, 6H), 1.80 (quintet, 2H), 1.48-1.39 (m, 9H), 1.29-1.22 (m, 6H), 1.16 (t, 3H). MS m/z [M+H]$^+$ 744.6.

[(2S)-2-{[(2S)-2-{[(2S)-2-{[(2S)-2-[(tertbutyldiphenylsilyl)oxy]propanoyl]oxy}propanoyl]oxy}propanoyl]oxy}propanoyl]oxy}propanoyl]oxy}propanoyl]oxy}propanoyl]oxy}propanoyl]oxy}propanoic acid (19-1, 1.33 g, 1.36 mmol) in dichloromethane (3.5 mL) was added EDC.HCl (0.348 g, 1.82 mmol) and 4-dimethylaminopyridine (11 mg, 0.09 mmol) at 0° C. The reaction mixture was allowed to stir at 25-30° C. over a period of 1 hour. The resulting reaction mass was quenched with water (100 mL) and extracted with dichloromethane (200×2 mL). The dichloromethane was dried over sodium sulfate, filtered and concentrated under reduced pressure. The crude product obtained upon evaporation of volatiles was purified through silica gel (230-400) column (4.5% methanol in DCM) to obtain product 19-2 as an off-white solid (0.54 g, 44.3%). 1H NMR (400 MHz, DMSO-d6) δ 7.61-7.59 (m, 4H), 7.48-7.39 (m, 6H), 5.22-5.15 (m, 6H), 5.08 (q, J=7.2 Hz, 1H), 4.94 (q, J=7.2 Hz, 1H), 4.79 (q, J=7.2 Hz, 2H), 3.40-3.33 (m, 4H), 3.22 (s, 2H), 1.48-1.40 (m, 21H), 1.33-1.29 (m, 16H), 1.01 (s, 10H). MS m/z (M+H)$^+$ 1343.0

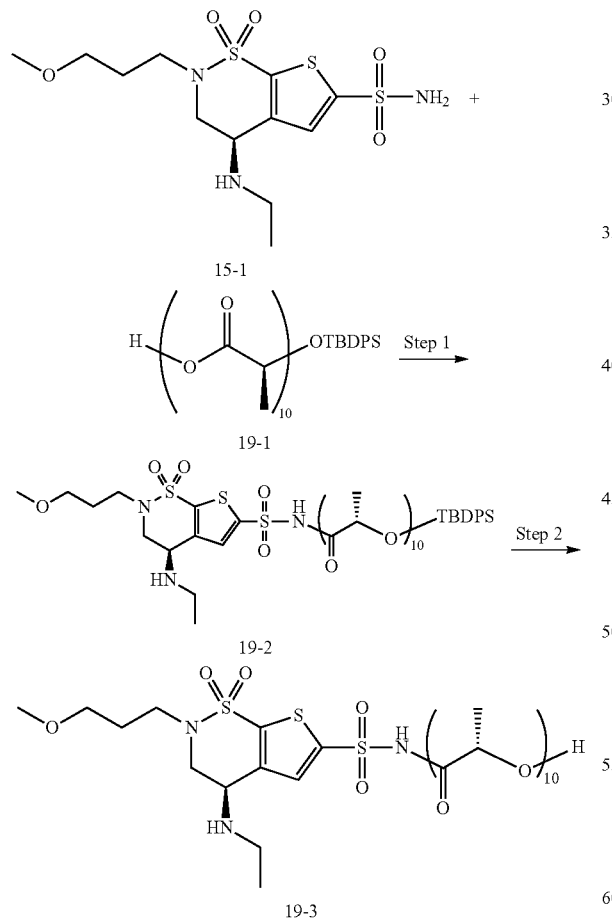

Scheme 19: Synthesis of Compound 19-3:

Step-2: Preparation Compound 19-3

To a solution of compound (19-2, 0.54 g, 0.4 mmol) in tetrahydrofuran (5.4 mL) was added tetra butyl ammonium fluoride (0.8 mL, 1.0M, 0.8 mmol) and acetic acid (0.048 ml, 0.8 mmol) at 0° C. The reaction mixture was allowed to stir at room temperature over a period of 12 hours. The resulting reaction mixture was concentrated under reduced pressure. The crude product obtained upon evaporation of volatiles was purified through silica gel (230-400) column (5.5% methanol in ethyl acetate) and further purified by preparative HPLC to obtain 19-3 as an off white solid (55 mg, 12.5%). $^1$H-NMR (400 MHz, DMSO-d6) δ 9.2-8.9 (m, 2H), 7.82 (s, 1H), 5.76 (s, 1H), 5.48 (d, 1H), 5.25-5.05 (m, 7H), 4.9-4.77 (m, 2H), 4.21 (quintet, 1H), 4.13-3.98 (m, 2H), 3.45-3.35 (m, 3H), 3.24-3.0 (m, 6H), 1.82 (quintet, 2H), 1.50-1.41 (m, 24H), 1.33-1.25 (m, 6H), 1.24 (t, 3H). MS m/z [M+H]$^+$ 1105.0.

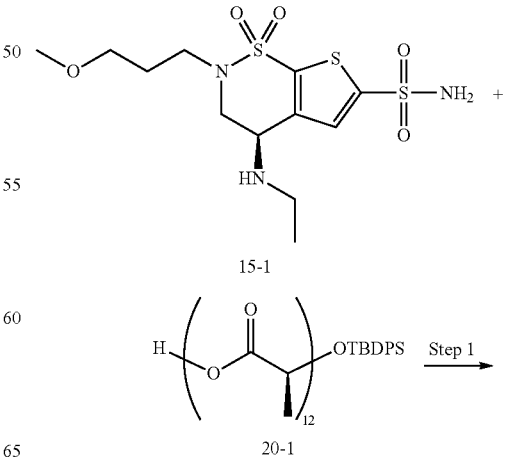

Scheme 20: Synthesis of Compound 20-3:

Step-1: Preparation of Compound 19-2

To a solution of Brinzolamide (15-1, 0.35 g, 0.91 mmol) and (2S)-2-{[(2S)-2-{[(2S)-2-{[(2S)-2-{[(2S)-2-{

335

-continued

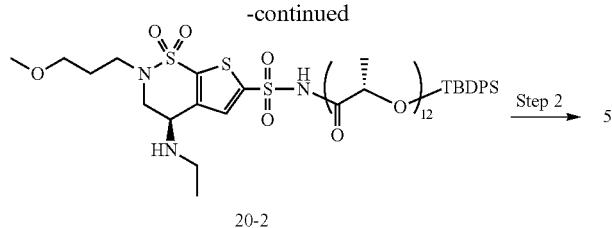

20-2

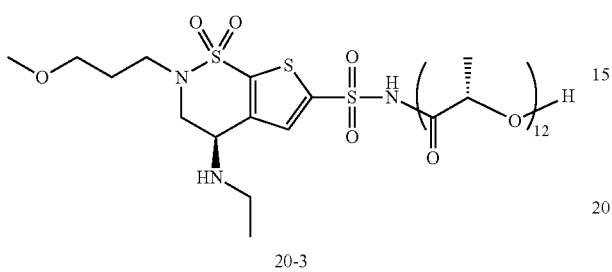

20-3

Step-1: Preparation of Compound 20-2

To a solution of Brinzolamide (15-1, 0.35 g, 0.91 mmol) and (2S)-2-{[(2S)-2-{[(2S)-2-{[(2S)-2-{[(2S)-2-{[(2S)-2-{[(2S)-2-{[(2S)-2-{[(2S)-2-{[(2S)-2-{[(2S)-2-[(tert-butyldiphenylsilyl)oxy]propanoyl]oxy}propanoyl]oxy}propanoyl]oxy}propanoyl]oxy}propanoyl]oxy}propanoyl]oxy}propanoyl]oxy}propanoyl]oxy}propanoyl]oxy}propanoyl]oxy}propanoic acid (20-1, 1.53 g, 1.36 mmol) in dichloromethane (3.5 mL) was added EDC.HCl (0.348 g, 1.82 mmol) and 4-dimethylaminopyridine (11 mg, 0.09 mmol) at 0° C. The reaction mixture was allowed to stir at 25-30° C. over a period of 1 hour. The resulting reaction mass was quenched with water (100 mL) and extracted with dichloromethane (200×2 mL). The dichloromethane was dried over sodium sulfate, filtered and concentrated under reduced pressure. The crude product obtained upon evaporation of volatiles was purified through silica gel (230-400) column (4% methanol in DCM) to obtain product 20-2 as an off-white solid (1 g, 74%).

Step-2: Preparation of Compound 20-3

To a solution of compound 20-2 (1 g, 0.67 mmol) in tetrahydrofuran (10 mL) was added tetra butyl ammonium fluoride (1.34 mL, 1.0M, 1.34 mmol) and acetic acid (0.08 ml, 1.34 mmol) at 0° C. The reaction mixture was allowed to stir at room temperature over a period of 12 hours. The resulting reaction mixture was concentrated under reduced pressure. The crude product obtained upon evaporation of volatiles was purified through silica gel (230-400) column (4% methanol in ethyl acetate) and further purified by preparative HPLC to obtain product 20-3 as an off white solid (120 mg, 14.3%). $^1$H-NMR (400 MHz, DMSO-d6) δ 9.2-8.9 (m, 2H), 7.73 (s, 1H), 5.73 (s, 1H), 5.44 (d, 1H), 5.25-5.15 (m, 9H), 5.15-5.02 (m, 2H), 4.81-4.73 (m, 2H), 4.17 (quintet, 1H), 4.1-3.9 (m, 2H), 3.48-3.29 (m, 3H), 3.24-2.952 (m, 6H), 1.80 (quintet, 2H), 1.50-1.40 (m, 30H), 1.30-1.22 (m, 6H), 1.18 (t, 3H). MS m/z [M+H]$^+$ 1248.9.0.

336

Synthesis of Bis-PLA-Dorzolamide Mono-Prodrugs

Scheme 21: Synthesis of Compound 21:

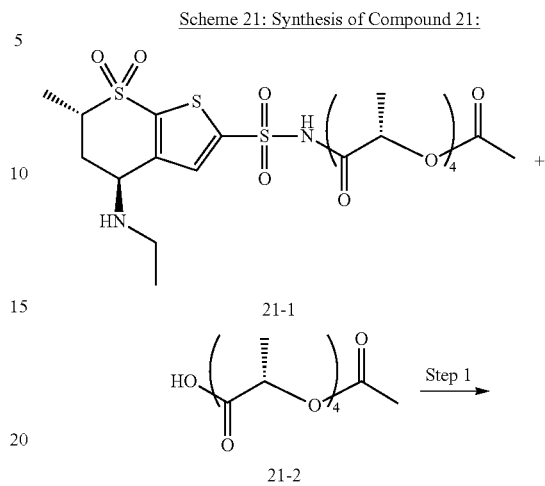

21-1

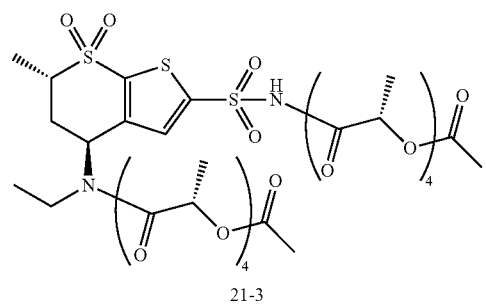

21-2

21-3

Step-1: Preparation of Compound 21-3

To a solution of (S)-2-{(S)-2-[(S)-2-((S)-2-acetoxy-propionyloxy)-propionyloxy]-propionyloxy}-propionic acid (21-2, 0.636 g, 1.83 mmol) in dichloromethane (8 mL) was added triethyamine (0.5 ml, 3.66 mmol), ethyl chloroformate (0.25 ml, 2.44 mmol), (S)-2-((S)-2-acetoxy-propionyloxy)-propionic acid (S)-1-{(S)-2-[(S)-4-ethylamino-2-(3-methoxy-propyl)-1,1-dioxo-1,2,3,4-tetrahydro-lambda*6*-thieno[3,2-e][1,2]thiazine-6-sulfonylamino]-1-methyl-2-oxo-ethoxycarbonyl}-ethylester (27-1, 0.8 g, 1.22 mmol), 4-dimethylaminopyridine (14.8 mg, 0.12 mmol) at 0° C. The reaction mixture was allowed to stir at 25-30° C. over a period of 1 hour. The resulting reaction mass was quenched with water (100 mL) and extracted with dichloromethane (200×2 mL). The dichloromethane was dried over sodium sulfate, filtered and concentrated under reduced pressure. The crude product obtained upon evaporation of volatiles was purified by preparative HPLC. The recovered solid was washed with water and dried to obtain product 27-3 as an off white solid (60 mg, 5%). $^1$H-NMR (400 MHz, DMSO-d6) (2 rotamers observed) δ 7.33 and 7.02 (2s, 1H), 5.9-5.0 (m, 7H), 4.77 (q, 1H), 3.77 (t, 1H), 3.5-3.0 (m, 2H), 2.8-2.3 (m, 3H), 2.07 (s, 3H), 2.06 (s, 3H), 1.55-1.2 (m, 27H), 1.16 and 0.97 (2t, 3H); MS m/z (M−H)$^−$ 984.2.

Synthesis of Bis-PLA-Brinzolamide Mono-Prodrugs

Scheme 22: Synthesis of (S)-2-Acetoxy-propionic acid (S)-2-[4{[(S)-2-((S)-2-acetoxy-propionyloxy)-propionyl]-ethyl-amino}-2-(3-methoxy propyl)-1,1-dioxo-1,2,3,4-tetrahydro-λ*6*-thieno[3,2-e][1,2]thiazine-6-sulfonylamino]-1-methyl-2-oxo-ethyl ester (22-3):

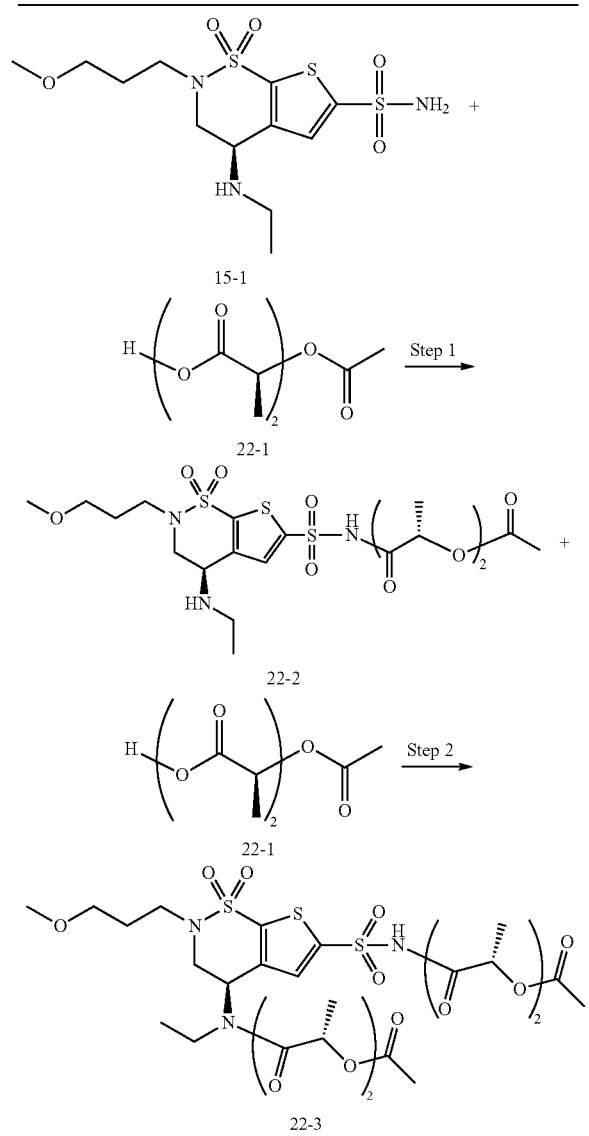

Step-1: Preparation of (S)-2-Acetoxy-propionic acid (S)-2-[4-ethylamino-2-(3-methoxy-propyl)-1,1-dioxo-1,2,3,4-tetrahydro-1λ*6*-thieno[3,2-e][1,2]thiazine-6-sulfonylamino]-1-methyl-2-oxo-ethyl ester (22-2)

To a solution of Brinzolamide (15-1, 1 g, 2.61 mmol) and (S)-2-((S)-2-acetoxy-propionyloxy)-propionic acid (22-1, 0.797 g, 3.91 mmol) in dichloromethane (10 mL) was added EDC.HCl (0.997 g, 5.22 mmol) and 4-dimethylaminopyridine (32 mg, 0.26 mmol) at 0° C. The reaction mixture was allowed to stir at 25-30° C. over a period of 1 hour. The resulting reaction mass was quenched with water (100 mL) and extracted with dichloromethane (150×3 mL). The dichloromethane was dried over sodium sulfate, filtered and concentrated under reduced pressure. The crude product obtained upon evaporation of volatiles was purified through silica gel (230-400) column (3% methanol in DCM) to obtain product 22-2 as an off white solid (550 mg, 37%). $^1$H NMR (400 MHz, DMSO-d6) δ 7.57 (s, 1H), 5.06-4.89 (m, 1H), 4.78 (dd, J=12.2, 7.0 Hz, 1H), 3.38 (q, J=6.4 Hz, 4H), 3.25-3.10 (m, 3H), 2.09-2.03 (m, 2H), 2.05 (s, 2H), 1.85-1.77 (m, 2H), 1.48-1.36 (m, 4H), 1.29 (dd, J=7.0, 4.0 Hz, 3H), 1.09 (dd, J=7.2, 4.5 Hz, 2H). MS m/z (M+H)$^+$ 570.0.

Step-2: Preparation of (S)-2-Acetoxy-propionic acid (S)-2-[4-{[(S)-2-((S)-2-acetoxy-propionyloxy)-propionyl]-ethyl-amino}-2-(3-methoxy-propyl)-1,1-dioxo-1,2,3,4-tetrahydro-1lambda*6*-thieno[3,2-e][1,2]thiazine-6-sulfonylamino]-1-methyl-2-oxo-ethyl ester (22-3)

To a solution of (S)-2-((S)-2-acetoxy-propionyloxy)-propionic acid (22-1, 0.294 g, 1.44 mmol) in dichloromethane (5.5 mL) was added triethyamine (0.394 ml, 2.88 mmol), ethyl chloroformate (0.252 ml, 2.4 mmol), (S)-2-acetoxy-propionic acid (S)-2-[4-ethylamino-2-(3-methoxy-propyl)-1,1-dioxo-1,2,3,4-tetrahydro-1λ*6*-thieno[3,2-e][1,2]thiazine-6-sulfonylamino]-1-methyl-2-oxo-ethyl ester (22-2, 0.550 g, 0.96 mmol), and 4-dimethylaminopyridine (11.7 mg, 0.09 mmol) at 0° C. The reaction mixture was allowed to stir at 25-30° C. over a period of 1 hour. The resulting reaction mass was quenched with water (100 mL) and extracted with dichloromethane (200×2 mL). The dichloromethane was dried over sodium sulfate, filtered, and concentrated under reduced pressure. The crude product obtained upon evaporation of volatiles was purified by preparative HPLC to obtain product 22-3 as an off white solid (75 mg, 10%). $^1$H-NMR (400 MHz, DMSO-d6) δ (2 rotamers observed) 6 7.63 and 7.29 (2s, 1H), 5.9-4.8 (m, 4H), 4.2-2.6 (m, 12H), 2.09-2.03 (4s, 6H), 1.88-1.78 (m, 2H), 1.48-0.8 (m, 15H), MS m/z (M−H)$^−$ 755.8.

Scheme 23: Synthesis of Compound 23-3:

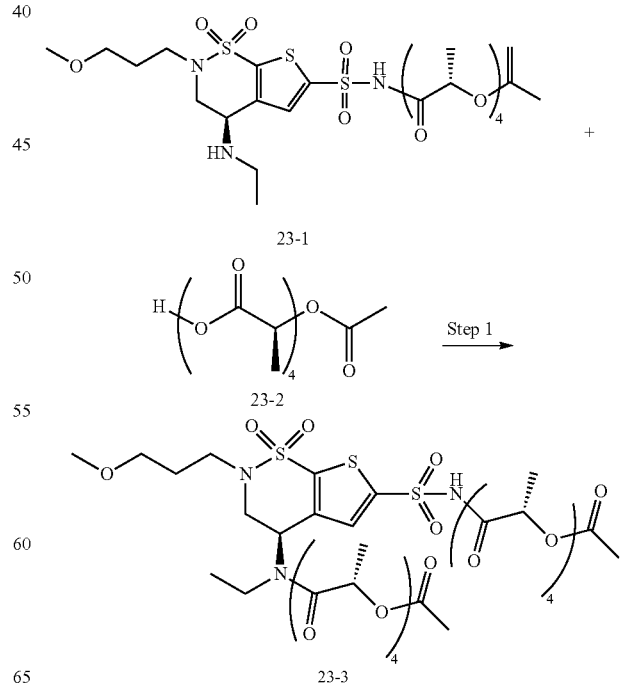

Step-1: Preparation of Compound 23-3

To a solution of (S)-2-{(S)-2-[(S)-2-((S)-2-Acetoxy-propionyloxy)-propionyloxy]-propionyloxy}-propionic acid (23-2, 0.439 g, 1.26 mmol) in dichloromethane (6 mL) was added triethyamine (0.34 ml, 2.52 mmol), ethyl chloroformate (0.17 ml, 1.68 mmol), (S)-2-((S)-2-acetoxy-propionyloxy)-propionic acid (S)-1-{(S)-2-[(S)-4-ethylamino-2-(3-methoxy-propyl)-1,1-dioxo-1,2,3,4-tetrahydro-1λ*6*-thieno[3,2-e][1,2]thiazine-6-sulfonylamino]-1-methyl-2-oxo-ethoxycarbonyl}-ethyl ester (23-1, 0.6 g, 0.84 mmol), and 4-dimethylaminopyridine (10 mg, 0.08 mmol) at 0° C. The reaction mixture was allowed to stir at 25-30° C. over a period of 1 hour. The resulting reaction mass was quenched with water (100 mL) and extracted with dichloromethane (200×2 mL). The dichloromethane was dried over sodium sulfate, filtered and concentrated under reduced pressure. The crude product obtained upon evaporation of volatiles was purified by preparative HPLC to obtain product 23-3 as an off white solid (50 mg, 5.7%). $^1$H-NMR (400 MHz, DMSO-d6) δ (2 rotamers observed) 6 7.63 and 7.26 (2s, 1H), 5.9-4.8 (m, 8H), 4.2-2.6 (m, 12H), 2.07 (s, 6H), 1.81 (q, 2H), 1.55-0.9 (m, 27H), MS m/z (M−H)⁻ 1044.1.

Synthesis of Brimonidine Mono-Prodrugs

Scheme 24: Synthesis of Free Brimonidine (24-2):

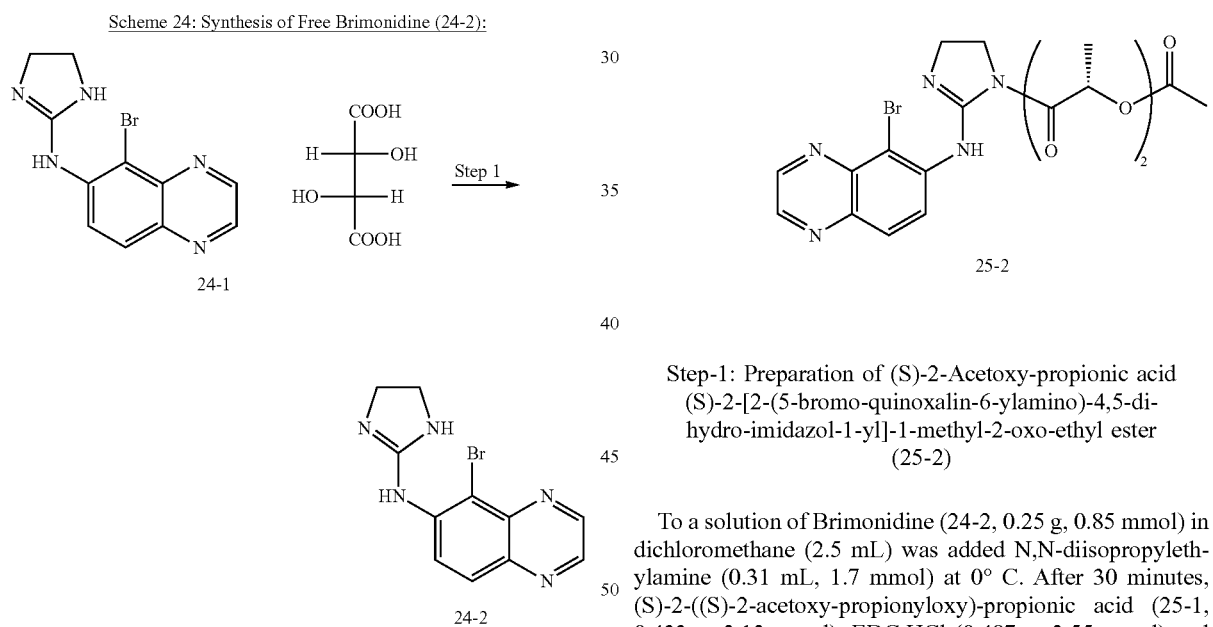

Step-1: Preparation of Free Brimonidine (24-2)

To a solution of Brimonidine tartarate (24-1, 5 g, 11.3 mmol) in water (50 ml) was added NaOH pellets (1.13 g, 28.27 mmol) slowly at 0° C. The reaction mixture was allowed to stir at 0-5° C. over a period of 15 minutes. The resulting reaction mass was filtered and the collected solid was dried under high vacuum to obtain product 24-2 as a pale yellow solid (2 g, 60%). $^1$H-NMR (400 MHz, DMSO-d6) δ 8.85 (d, J=2 Hz, 1H), 8.69 (d, J=2 Hz, 1H), 7.83 (d, J=9 Hz, 1H), 7.56 (d, J=9 Hz, 1H), 6.56 (s, 2H), 3.50 (s, 4H). MS m/z [M+H]⁺ 292.1/294.1.

Scheme 25: Synthesis of (S)-2-Acetoxy-propionic acid (S)-2-[2-(5-bromo-quinoxzlin-6-ylamino)-4,5-dihydro-imidazol-1-yl]-1-methyl-2-oxo-ethyl ester (25-2):

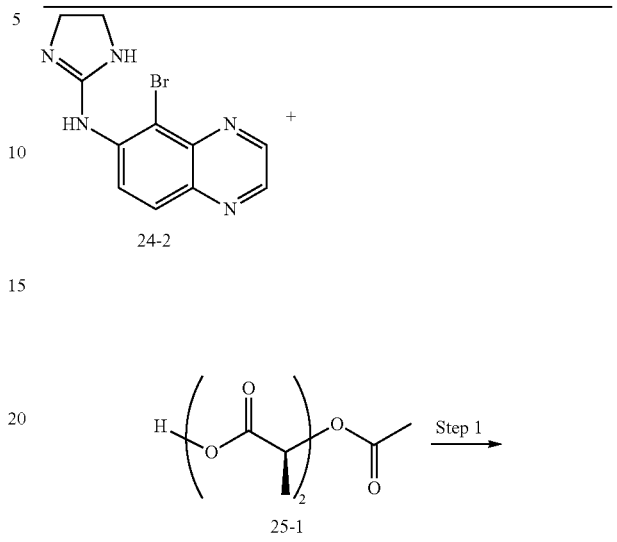

Step-1: Preparation of (S)-2-Acetoxy-propionic acid (S)-2-[2-(5-bromo-quinoxalin-6-ylamino)-4,5-dihydro-imidazol-1-yl]-1-methyl-2-oxo-ethyl ester (25-2)

To a solution of Brimonidine (24-2, 0.25 g, 0.85 mmol) in dichloromethane (2.5 mL) was added N,N-diisopropylethylamine (0.31 mL, 1.7 mmol) at 0° C. After 30 minutes, (S)-2-((S)-2-acetoxy-propionyloxy)-propionic acid (25-1, 0.433 g, 2.12 mmol), EDC.HCl (0.487 g, 2.55 mmol) and 4-dimethylaminopyridine (10 mg, 0.08 mmol) were added at 0° C. The reaction mixture was allowed to stir at 25-30° C. over a period of 1 hour. The resulting reaction mass was quenched with water (50 mL) and extracted with dichloromethane (100×2 mL). The dichloromethane was dried over sodium sulfate, filtered and concentrated under reduced pressure. The crude product obtained upon evaporation of volatiles was purified through silica gel (230-400) column (2% methanol in DCM) and further purified by prep-HPLC to obtain product 25-2 as a pale yellow solid (60 mg, 14.7%). 1H-NMR (400 MHz, DMSO-d6) δ 8.96 (d, J=2 Hz, 1H), 8.85 (d, J=2 Hz, 1H), 7.99 (d, J=9 Hz, 1H), 7.59 (d, J=9 Hz, 1H), 7.29 (s, 1H), 6.53 (q, 1H), 5.05 (q, 1H), 3.96-3.84 (m, 2H), 3.44-3.34 (m, 2H), 2.06 (s, 3H), 1.63 (d, 3H), 1.47 (d, 3H). MS m/z [M+H]⁺ 480.3.

Scheme 26: Synthesis of (S)-2-((S)-2-Acetoxy-propionyloxy)-propionic acid (S)-2-[2-(5-bromo-quinoxalin-6-ylamino)-4,5-dihydro-imidazol-1-yl]-1-methyl-2-oxo-ethyl ester (26-2):

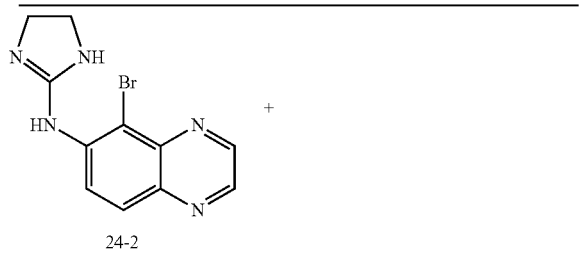

24-2

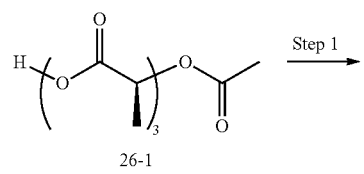

26-1

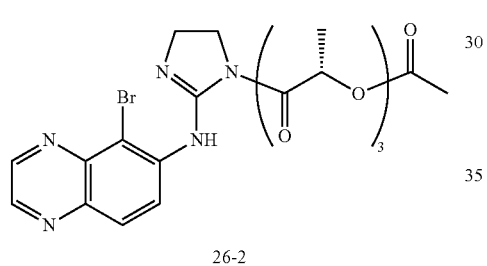

26-2

Scheme 27: Synthesis of (S)-2-[(S)-2-((S)-2-Acetoxy-propionyloxy)-propionyloxy]-propionic acid (S)-2-[2-(5-bromo-quinoxalin-6-ylamino)-4,5-dihydro-imidazol-1-yl]-1-methyl-2-oxo-ethyl ester (27-2):

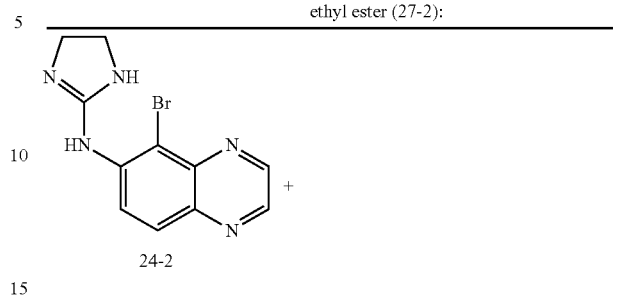

24-2

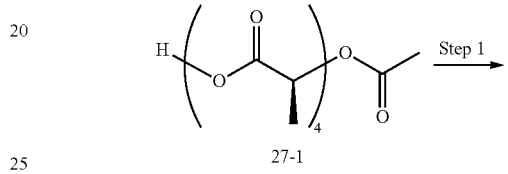

27-1

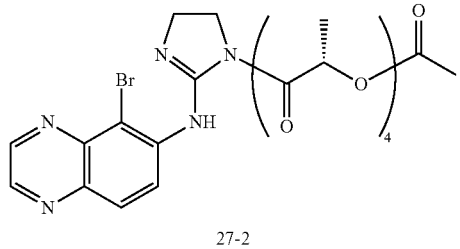

27-2

Step-1: Preparation of (S)-2-((S)-2-Acetoxy-propionyloxy)-propionic acid (S)-2-[2-(5-bromo-quinoxalin-6-ylamino)-4,5-dihydro-imidazol-1-yl]-1-methyl-2-oxo-ethyl ester (26-2)

To a solution of Brimonidine (24-2, 0.25 g, 0.85 mmol) in dichloromethane (2.5 mL) was added N,N-diisopropylethylamine (0.31 mL, 1.7 mmol) at 0° C. After 30 minutes, (S)-2-[(S)-2-((S)-2-acetoxy-propionyloxy)-propionyloxy]-propionic acid (26-1, 0.586 g, 2.12 mmol), EDC.HCl (0.487 g, 2.55 mmol) and 4-dimethylaminopyridine (10 mg, 0.08 mmol) were added at 0° C. The reaction mixture was allowed to stir at 25-30° C. over a period of 1 hour. The resulting reaction mass was quenched with water (50 mL) and extracted with dichloromethane (100×2 mL). The dichloromethane was dried over sodium sulfate, filtered and concentrated under reduced pressure. The crude product obtained upon evaporation of volatiles was purified through silica gel (230-400) column (2% methanol in DCM) to obtain product 26-2 as a pale yellow solid (100 mg, 21.7%). $^1$H-NMR (400 MHz, DMSO-d6) δ 8.96 (d, J=2 Hz, 1H), 8.85 (d, J=2 Hz, 1H), 7.99 (d, J=9 Hz, 1H), 7.60 (d, J=9 Hz, 1H), 7.30 (s, 1H), 6.52 (q, 1H), 5.18 (q, 1H), 5.0 (q, 1H), 3.96-3.83 (m, 2H), 3.45-3.34 (m, 2H), 2.06 (s, 3H), 1.64 (d, 3H), 1.50 (d, 3H), 1.44 (d, 3H). MS m/z [M+H]$^+$ 551.2.

Step-1: Preparation of (S)-2-[(S)-2-((S)-2-Acetoxy-propionyloxy)-propionyloxy]-propionic acid (S)-2-[2-(5-bromo-quinoxalin-6-ylamino)-4,5-dihydro-imidazol-1-yl]-1-methyl-2-oxo-ethyl ester (27-2)

To a solution of Brimonidine (24-2, 0.25 g, 0.85 mmol) in dichloromethane (2.5 mL) was added N,N-diisopropylethylamine (0.31 mL, 1.7 mmol) at 0° C. After 30 minutes, ((S)-2-{(S)-2-[(S)-2-((S)-2-acetoxy-propionyloxy)-propionyloxy]-propionyloxy}-propionic acid (27-1, 0.739 g, 2.12 mmol), EDC.HCl (0.487 g, 2.55 mmol) and 4-dimethylaminopyridine (10 mg, 0.08 mmol) were added at 0° C. The reaction mixture was allowed to stir at 25-30° C. over a period of 1 hour. The resulting reaction mass was quenched with water (50 mL) and extracted with dichloromethane (100×2 mL). The dichloromethane was dried over sodium sulfate, filtered and concentrated under reduced pressure. The crude product obtained upon evaporation of volatiles was purified through silica gel (230-400) column (2.5% methanol in DCM) to obtain product 27-2 as a pale yellow solid (100 mg, 18.9%). $^1$H-NMR (400 MHz, DMSO-d6) δ 8.96 (d, J=2 Hz, 1H), 8.85 (d, J=2 Hz, 1H), 7.99 (d, J=9 Hz, 1H), 7.60 (d, J=9 Hz, 1H), 7.30 (s, 1H), 6.52 (q, 1H), 5.23-5.15 (m, 2H), 5.04 (q, 1H), 3.95-3.83 (m, 2H), 3.45-3.34 (m, 2H), 2.06 (s, 3H), 1.64 (d, 3H), 1.50 (d, 3H), 1.48 (d, 3H), 1.42 (d, 3H). MS m/z [M+H]$^+$ 622.9.

Scheme 28: Synthesis of Octadecanoic acid (R)-1-((R)-1-{(R)-2-[2-(5-bromo-quinoxalin-6-ylamino)-4,5-dihydro-imidazol-1-yl]-1-methyl-2-oxo-ethoxycarbonyl}-ethoxycarbonyl)-ethyl ester (28-2):

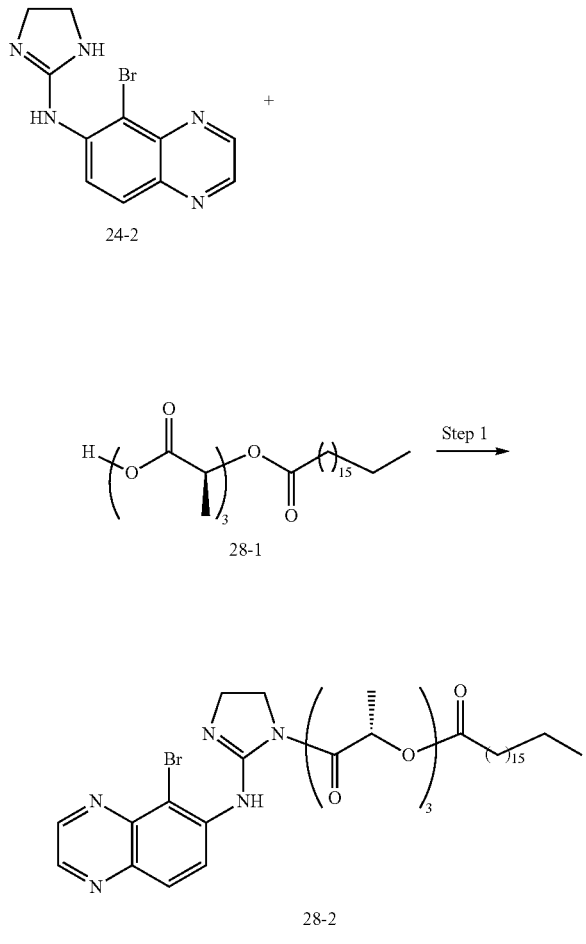

Scheme 29: Synthesis of Octadecanoic acid (S)-1-[(S)-1-((S)-1-{(S)-2-[2-(5-bromo-quinoxalin-6-ylamino)-4,5-dihydro-imidazol-1-yl]-1-methyl-2-oxo-ethoxycarbonyl}-ethoxycarbonyl)-ethoxycarbonyl]-ethyl ester (29-2):

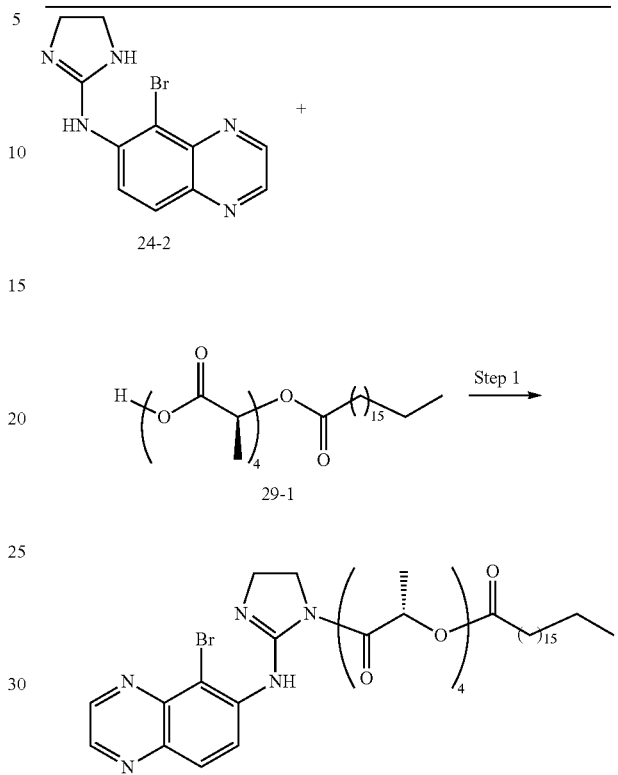

Step-1: Preparation of Octadecanoic acid (R)-1-((R)-1-{(R)-2-[2-(5-bromo-quinoxalin-6-ylamino)-4,5-dihydro-imidazol-1-yl]-1-methyl-2-oxo-ethoxycarbonyl}-ethoxycarbonyl)-ethyl ester (28-2)

To a solution of Brimonidine (24-2, 0.25 g, 0.85 mmol) in dichloromethane (2.5 mL) was added N,N-diisopropylethylamine (0.31 mL, 1.7 mmol) at 0° C. After 30 minutes, octadecanoic acid (R)-1-[(R)-1-((R)-1-carboxy-ethoxycarbonyl)-ethoxycarbonyl]-ethyl ester (28-1, 1.062 g, 2.12 mmol), EDC.HCl (0.487 g, 2.55 mmol) and 4-dimethylaminopyridine (10 mg, 0.08 mmol) were added at 0° C. The reaction mixture was allowed to stir at 25-30° C. over a period of 1 hour. The resulting reaction mass was quenched with water (50 mL) and extracted with dichloromethane (100×2 mL). The dichloromethane was dried over sodium sulfate, filtered sulfate and concentrated under reduced pressure. The crude product obtained upon evaporation of volatiles was purified through silica gel (230-400) column (40% ethyl acetate in hexane) to obtain product 28-2 as a pale yellow solid (100 mg, 15%). $^1$H-NMR (400 MHz, DMSO-d6) δ 8.96 (d, J=2 Hz, 1H), 8.84 (d, J=2 Hz, 1H), 7.99 (d, J=9 Hz, 1H), 7.59 (d, J=9 Hz, 1H), 7.29 (s, 1H), 6.52 (q, 1H), 5.17 (q, 1H), 5.06 (q, 1H), 3.95-3.84 (m, 2H), 3.44-3.34 (m, 2H), 2.32 (t, 2H), 1.63 (d, 3H), 1.52-1.38 (m, 14H), 1.30-1.14 (m, 28H), 0.83 (t, 3H). MS m/z [M+H]$^+$ 775.2.

Step-1: Preparation of Octadecanoic acid (S)-1-[(S)-1-((S)-1-{(S)-2-[2-(5-bromo-quinoxalin-6-ylamino)-4,5-dihydro-imidazol-1-yl]-1-methyl-2-oxo-ethoxycarbonyl}-ethoxycarbonyl)-ethoxycarbonyl]-ethyl ester (29-2)

To a solution of Brimonidine (24-2, 0.25 g, 0.85 mmol) in dichloromethane (2.5 mL) was added N,N-diisopropylethylamine (0.31 mL, 1.7 mmol) at 0° C. After 30 minutes, octadecanoic acid (S)-1-{(S)-1-[(S)-1-((S)-1-carboxy-ethoxycarbonyl)-ethoxycarbonyl]-ethoxycarbonyl}-ethyl ester (29-1, 1.212 g, 2.12 mmol), EDC.HCl (0.487 g, 2.55 mmol) and 4-dimethylaminopyridine (10 mg, 0.08 mmol) were added at 0° C. The reaction mixture was allowed to stir at 25-30° C. over a period of 1 hour. The resulting reaction mass was quenched with water (50 mL) and extracted with dichloromethane (100×2 mL). The dichloromethane was dried over sodium sulfate, filtered and concentrated under reduced pressure. The crude product obtained upon evaporation of volatiles was purified through silica gel (230-400) column (37% ethyl acetate in hexane) to obtain product 29-2 as a pale yellow solid 220 mg (30%). $^1$H-NMR (400 MHz, DMSO-d6) δ 8.95 (d, J=2 Hz, 1H), 8.84 (d, J=2 Hz, 1H), 7.99 (d, J=9 Hz, 1H), 7.59 (d, J=9 Hz, 1H), 7.29 (s, 1H), 6.52 (q, 1H), 5.24-5.16 (m, 2H), 5.05 (q, 1H), 3.94-3.83 (m, 2H), 3.44-3.34 (m, 2H), 2.33 (t, 2H), 1.63 (d, 3H), 1.54-1.44 (m, 8H), 1.41 (d, 3H), 1.30-1.14 (m, 28H), 0.83 (t, 3H). MS m/z [M+H]$^+$ 847.4.

Synthesis of Tris-PLA-Bimatoprost Prodrugs (Compounds of Formula II)

Scheme 30: Synthesis of (S)-2-Acetoxy-propionic acid (1S,2R,3R,4R)-4-((S)-2-acetoxy-propionyloxy)-3-[(E)-(S)-3-((S)-2-acetoxy-propionyloxy)-5-phenyl-pent-1-enyl]-2-((Z)-6-ethylcarbamoyl-hex-2-enyl)-cyclopentyl ester (30-3):

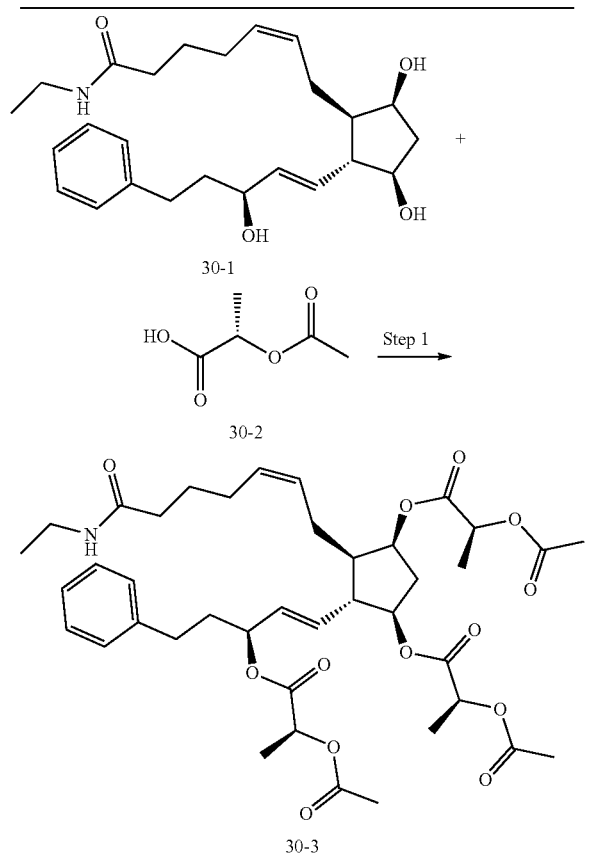

Scheme 31: Synthesis of compound 31-2:

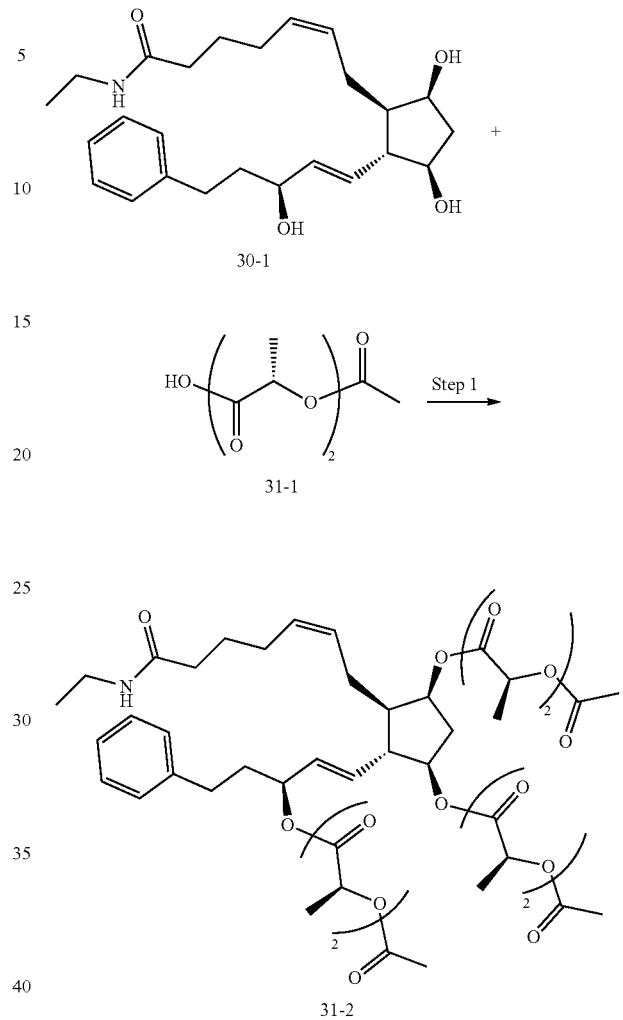

Step-1: Preparation of (S)-2-Acetoxy-propionic acid (1S,2R,3R,4R)-4-((S)-2-acetoxy-propionyloxy)-3-[(E)-(S)-3-((S)-2-acetoxy-propionyloxy)-5-phenyl-pent-1-enyl]-2-((Z)-6-ethylcarbamoyl-hex-2-enyl)-cyclopentyl ester (30-3)

To a solution of bimatoprost (30-1, 0.1 g, 0.24 mmol) and (S)-2-acetoxy-propionic acid (30-2, 0.19 g, 1.44 mmol) in dichloromethane (1 mL) was added EDC.HCl (0.367 g, 1.92 mol) and 4-dimethylaminopyridine (9 mg, 0.07 mmol) at 0° C. The reaction mixture was allowed to stir at 25-30° C. over a period of 2 hours. The resulting reaction mass was quenched with water (50 mL) and extracted with dichloromethane (50×4 mL). The dichloromethane was dried over sodium sulfate, filtered and concentrated under reduced pressure. The crude product obtained upon evaporation of volatiles was purified through silica gel (230-400) column (50% ethyl acetate in hexane) to obtain product 30-3 as a colorless wax (130 mg, 72%). $^1$H-NMR (400 MHz, DMSO-d6) δ 7.69 (t, 1H), 7.30-7.23 (m, 2H), 7.20-7.12 (m, 3H), 5.66-5.56 (m, 2H), 5.36-5.22 (m, 2H), 5.21-5.13 (m, 1H), 5.05-4.85 (m, 5H), 3.02 (quintet, 2H), 2.65-2.5 (m, 2H), 2.08 (s, 6H), 2.07-1.78 (m, 13H), 1.52-1.32 (m, 13H), 0.97 (t, 3H); MS m/z [M+H-AcOCH(Me)COOH]+626.6, (M+Formate)$^+$ 802.9.

Step-1: Preparation of Compound 31-2

To a solution of bimatoprost (30-1, 0.1 g, 0.24 mmol) and (S)-2-((S)-2-acetoxy-propionyloxy)-propionic acid (31-1, 0.294 g, 1.44 mmol) in dichloromethane (1 mL) was added EDC.HCl (0.367 g, 1.92 mol) and 4-dimethylaminopyridine (9 mg, 0.07 mmol) at 0° C. The reaction mixture was allowed to stir at 25-30° C. over a period of 2 hour. The resulting reaction mass was quenched with water (50 mL) and extracted with dichloromethane (50×4 mL). The dichloromethane was dried over sodium sulfate, filtered and concentrated under reduced pressure. The crude product obtained upon evaporation of volatiles was purified through silica gel (230-400) column (55% ethyl acetate in hexane) to obtain product 31-2 as a colorless wax (120 mg, 52%). $^1$H-NMR (400 MHz, DMSO-d6) δ 7.69 (t, 1H), 7.30-7.23 (m, 2H), 7.21-7.13 (m, 3H), 5.67-5.52 (m, 2H), 5.36-5.22 (m, 2H), 5.21-5.14 (m, 1H), 5.14-4.98 (m, 7H), 4.94-4.86 (m, 1H), 3.02 (quintet, 2H), 2.63-2.5 (m, 2H), 2.09-1.78 (m, 19H), 1.52-1.32 (m, 22H), 0.97 (t, 3H); MS m/z [M+H]$^+$ 975.0, [M+H-AcOCH(Me)COOCH(Me)COOH]+770.9, [M+Formate]$^-$ 1019.3.

Scheme 32: Synthesis of compound 32-2:

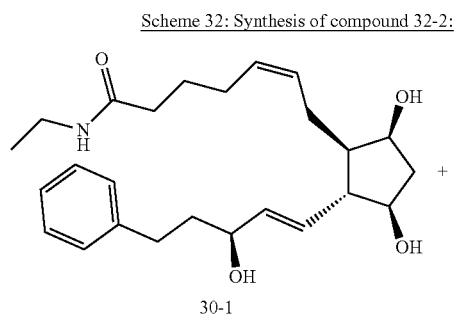

Scheme 33: Synthesis of compound 33-2:

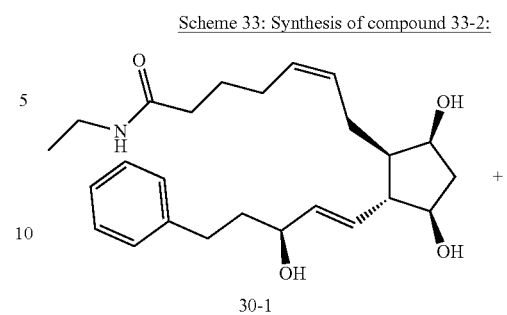

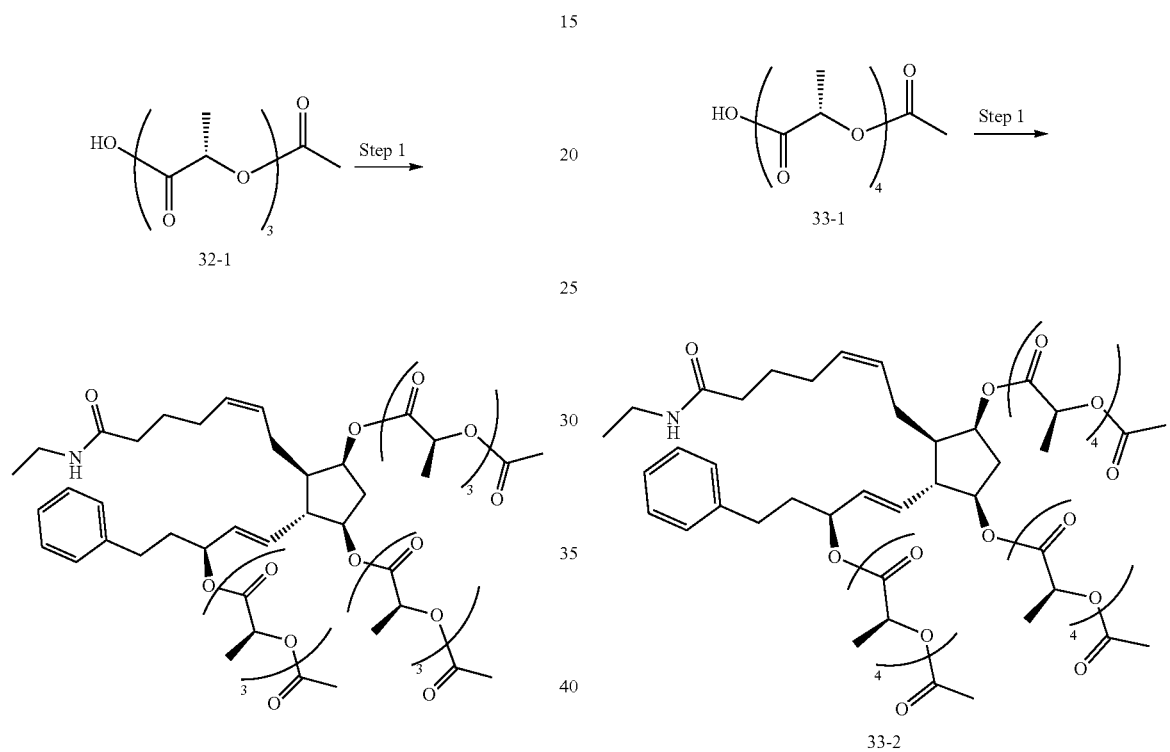

Step-1: Preparation of Compound 32-2

To a solution of bimatoprost (30-1, 0.1 g, 0.24 mmol) and (S)-2-[(S)-2-((S)-2-acetoxy-propionyloxy)-propionyloxy]-propionic acid (32-1, 0.397 g, 1.44 mmol) in dichloromethane (1 mL) was added EDC.HCl (0.367 g, 1.92 mol) and 4-dimethylaminopyridine (9 mg, 0.07 mmol) at 0° C. The reaction mixture was allowed to stir at 25-30° C. over a period of 2 hours. The resulting reaction mass was quenched with water (50 mL) and extracted with dichloromethane (50×4 mL). The dichloromethane was dried over sodium sulfate, filtered and concentrated under reduced pressure. The crude product obtained upon evaporation of volatiles was purified through silica gel (230-400) column (52% ethyl acetate in hexane) to obtain product 32-2 as a colorless wax (120 mg, 42%). $^1$H-NMR (400 MHz, DMSO-d6) δ 7.69 (t, 1H), 7.30-7.23 (m, 2H), 7.21-7.13 (m, 3H), 5.65-5.55 (m, 2H), 5.36-4.98 (m, 13H), 4.95-4.86 (m, 1H), 3.02 (quintet, 2H), 2.63-2.5 (m, 2H), 2.06 (s, 9H), 2.05-1.78 (m, 10H), 1.52-1.33 (m, 31H), 0.97 (t, 3H); MS m/z [M+H]$^+$ 1191.2, [M+H-AcOCH(Me) COOCH(Me)COOCH(Me)COOH]$^+$ 915.2, [M+Formate]$^-$ 1235.7.

Step-1: Preparation of Compound 33-2

To a solution of bimatoprost (30-1, 0.2 g, 0.48 mmol) and (S)-2-{(S)-2-[(S)-2-((S)-2-acetoxy-propionyloxy)-propionyloxy]-propionyloxy}-propionic acid (33-1, 1.002 g, 2.88 mmol) in dichloromethane (2 mL) was added EDC.HCl (0.733 g, 3.84 mol) and 4-dimethylaminopyridine (17 mg, 0.14 mmol) at 0° C. The reaction mixture was allowed to stir at 25-30° C. over a period of 2 hours. The resulting reaction mass was quenched with water (100 mL) and extracted with dichloromethane (200×2 mL). The dichloromethane was dried over sodium sulfate, filtered and concentrated under reduced pressure. The crude product obtained upon evaporation of volatiles was purified through silica gel (230-400) column (50% ethyl acetate in hexane) to obtain product 33-2 as a colorless wax (320 mg, 47%). $^1$H-NMR (400 MHz, DMSO-d6) δ 7.68 (t, 1H), 7.30-7.23 (m, 2H), 7.21-7.13 (m, 3H), 5.65-5.54 (m, 2H), 5.37-5.00 (m, 16H), 4.95-4.86 (m, 1H), 3.01 (quintet, 2H), 2.62-2.5 (m, 2H), 2.06 (s, 9H), 2.05-1.78 (m, 10H), 1.51-1.34 (m, 40H), 0.97 (t, 3H); MS m/z [M+H]$^+$ 1407.4, [M+H-AcOCH(Me)COOCH(Me) COOCH(Me)COOCH(Me)COOH]+1059.6.

349

Scheme 34: Synthesis of compound 34-2:

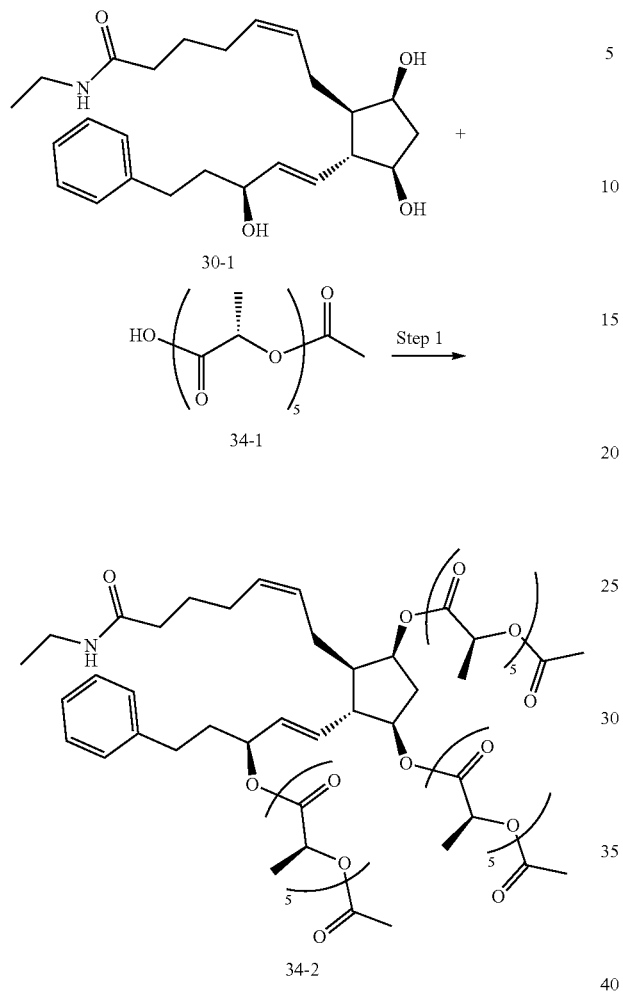

Step-1: Preparation of Compound 34-2

To a solution of bimatoprost (30-1, 0.15 g, 0.36 mmol) and (S)-2-((S)-2-{(S)-2-[(S)-2-((S)-2-acetoxy-propionyloxy)-propionyloxy]-propionyloxy}-propionyloxy)-propionic acid (34-1, 0.907 g, 2.16 mmol) in dichloromethane (1.5 mL) was added EDC.HCl (0.55 g, 2.88 mol) and 4-dimethylaminopyridine (13 mg, 0.11 mmol) at 0° C. The reaction mixture was allowed to stir at 25-30° C. over a period of 2 hours. The resulting reaction mass was quenched with water (100 mL) and extracted with dichloromethane (200×2 mL). The dichloromethane was dried over sodium sulfate, filtered and concentrated under reduced pressure. The crude product obtained upon evaporation of volatiles was purified through silica gel (230-400) column (50% ethyl acetate in hexane) to obtain product 34-2 as a colorless wax (350 mg, 59%). $^1$H-NMR (400 MHz, DMSO-d$_6$) δ 7.68 (t, 1H), 7.30-7.23 (m, 2H), 7.21-7.14 (m, 3H), 5.66-5.52 (m, 2H), 5.37-4.99 (m, 19H), 4.95-4.86 (m, 1H), 3.01 (quintet, 2H), 2.62-2.5 (m, 2H), 2.06 (s, 9H), 2.05-1.78 (m, 10H), 1.51-1.35 (m, 49H), 0.97 (t, 3H); MS m/z [M+H-AcOCH(Me)COOCH(Me)COOCH(Me)COOCH(Me)CO—OCH(Me)COOH]+1203.4.

350

Synthesis of Timolol Mono-Prodrugs

Scheme 35: Synthesis of Acetic acid (S)-1-(tert-butylamino-methyl)-2-(4-morpholin-4-yl-[1,2,5]thiadiazol-3-yloxy)-ethyl ester maleate (35-4):

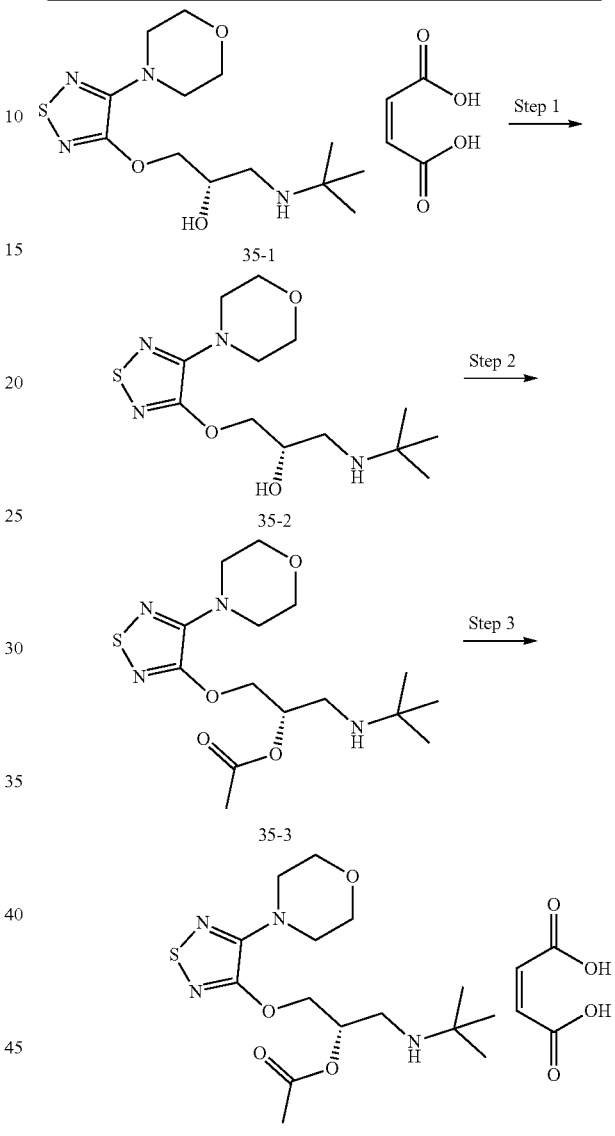

Step-1: Preparation of Free-Timolol (35-2)

To a solution of Timolol maleate (35-1, 1.6 g, 4.60 mmol) in water (16 mL) was added NaOH pellets (0.46 g, 11.5 mmol) slowly at 0° C. The reaction mixture was allowed to stir at 0-5° C. over a period of 15 minutes. The resulting reaction mixture was diluted with dichloromethane (500 mL) and washed with water (2×200 mL). The product obtained upon evaporation of volatiles afforded 35-2 as a colorless liquid (1.0 g, 85%). $^1$H NMR (400 MHz, DMSO-d6) δ 5.01 (bs, 1H), 4.39 (dd, J=4.0 Hz, J=10.5 Hz 2H), 4.29 (dd, J=6.4 Hz, J=10.5 Hz 2H), 3.88-3.78 (m, 1H), 3.74-3.66 (m, 4H), 3.50-3.40 (m, 4H), 2.6-2.5 (m, 2H), 1.4 (bs, 1H), 1.00 (s, 9H); MS m/z (M+H)$^+$ 317.6.

Step-2: Preparation of Acetic acid (S)-1-(tert-butylamino-methyl)-2-(4-morpholin-4-yl-[1,2,5]thiadiazol-3-yloxy)-ethyl ester (35-3)

To a solution of Timolol (35-2, 1.0 g, 3.16 mmol) in dichloromethane (10 mL) was added acetic anhydride (0.8 mL, 7.90 mmol) and 4-dimethylaminopyridine (0.077 g, 0.316 mmol) at 0° C. The reaction mixture was stirred at 25-30° C. over a period of 2 hours. The resulting reaction mixture was quenched with water (200 mL), extracted with dichloromethane (2×200 mL) and dried over sodium sulfate. The dried solution was filtered and volatiles were evaporated under reduced pressure to obtain product 35-3 as an off-white solid (1.2 g, 80%).

Step-3: Preparation of Acetic acid (S)-1-(tert-butylamino-methyl)-2-(4-morpholin-4-yl-[1,2,5]thiadiazol-3-yloxy)-ethyl ester maleate (35-4)

To a solution of acetic acid (S)-1-(tert-butylamino-methyl)-2-(4-morpholin-4-yl-[1,2,5]thiadiazol-3-yloxy)-ethyl ester (35-3, 1.2 g, 2.52 mmol) in acetone (6 mL) was added maleic acid (0.264 g, 2.27 mmol) at 0° C. The reaction mixture was allowed to stir at room temperature over a period of 20 minutes. The resulting reaction mixture was concentrated under reduced pressure to give product 35-4 as white solid (0.3 g, 21%). $^1$H-NMR (400 MHz, DMSO-d6) δ 8.57 (bs, 1H), 8.29 (bs, 1H), 6.02 (s, 2H), 5.45-5.35 (m, 1H), 4.66 (dd, 1H), 4.45 (dd, 1H), 3.72-3.65 (m, 4H), 3.48-3.29 (m, 5H), 3.25-3.12 (m, 1H), 2.08 (s, 3H), 1.29 (s, 9H). MS m/z [M+H]$^+$ 359.1.

Step-1: Preparation of Carbonic acid tert-butyl ester (S)-1-(tert-butylamino-methyl)-2-(4-morpholin-4-yl-[1,2,5]thiadiazol-3-yloxy)-ethyl ester (36-2)

To a solution of Timolol (35-2, 4.0 g, 12.65 mmol) in dichloromethane (40 mL) was added di-tert-butyl dicarbonate (36-1, 4.36 mL, 18.99 mmol) and 4-dimethylaminopyridine (0.155 g, 1.26 mmol) at 0° C. The reaction mixture stirred at 25-30° C. over a period of 2 hours. The resulting reaction mixture was quenched with water (300 mL), extracted with dichloromethane (2×500 mL) and dried over sodium sulfate and concentrated under reduced pressure. The crude product obtained upon evaporation of volatiles was purified through silica gel (230-400) column (2% methanol in dichloromethane) to obtain product 36-2 as a colorless liquid (0.7 g, 58%). $^1$H-NMR (400 MHz, DMSO-d6) δ 4.94-4.85 (m, 1H), 4.64 (dd, 1H), 4.46 (dd, 1H), 3.69-3.63 (m, 4H), 3.43-3.38 (m, 4H), 2.72-2.63 (m, 2H), 1.40 (s, 9H), 0.97 (s, 9H). MS m/z [M+H]$^+$ 417.1.

Scheme 36: Synthesis of Carbonic acid tert-butyl ester (S)-1-(tert-butylamino-methyl)-2-(4-morpholin-4-yl-[1,2,5]thiadiazol-3-yloxy)-ethyl ester (36-2):

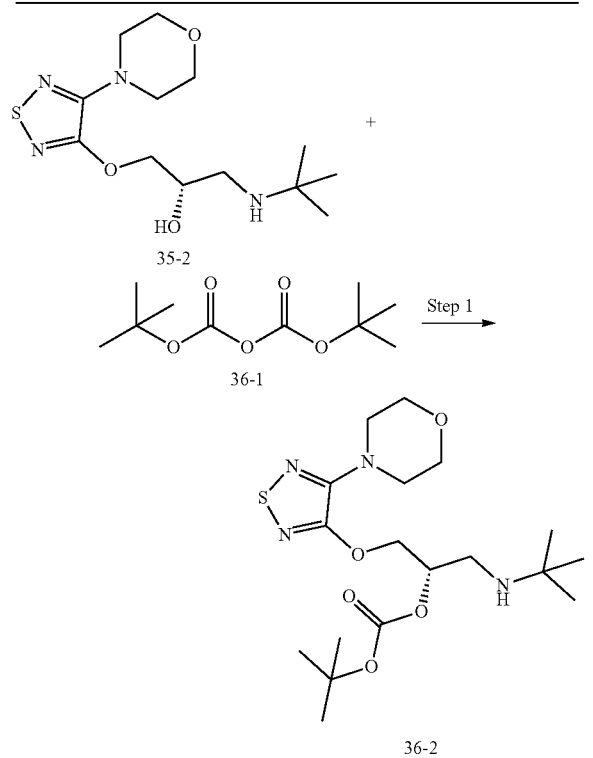

Scheme 37: Synthesis of Carbonic acid (S)-1-[(acetyl-tert-butyl-amino)-methyl]-2-(4-morpholin-4-yl-[1,2,5]thiadiazol-3-yloxy)-ethyl ester (37-2):

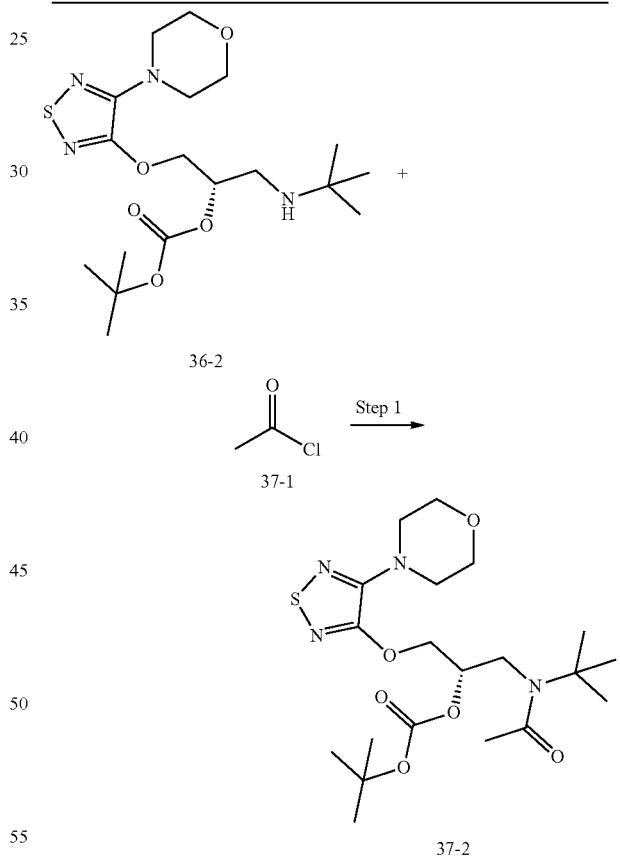

Step-1: Preparation of Carbonic acid (S)-1-[(acetyl-tert-butyl-amino)-methyl]-2-(4-morpholin-4-yl-[1,2,5]thiadiazol-3-yloxy)-ethyl ester tert-butyl ester (37-2)

To a solution of carbonic acid tert-butyl ester (S)-1-(tert-butylamino-methyl)-2-(4-morpholin-4-yl-[1,2,5]thiadiazol-3-yloxy)-ethyl ester (36-2, 0.6 g, 1.44 mmol) in dichloromethane (6 mL) was added N,N-diisopropylethylamine (0.7 mL, 4.32 mmol) and acetyl chloride (37-1, 0.11 mL, 3.60 mmol) at 0° C. The reaction mixture stirred at 25-30° C. over a period of 2 hours. The resulting reaction mixture was quenched with water (200 mL), extracted with dichloromethane (2×200 mL) and dried over sodium sulfate and concentrated under reduced pressure. The crude product obtained upon evaporation of volatiles was purified through silica gel (230-400) column (25% ethyl acetate in hexane) to obtain product 37-2 as a colorless liquid (0.24 g, 36%). $^1$H-NMR (400 MHz, DMSO-d6) δ 5.22-5.14 (m, 1H), 4.60 (dd, 1H), 4.44 (dd, 1H), 3.70-3.61 (m, 6H), 3.41-3.35 (m, 4H), 2.05 (s, 3H), 1.37 (s, 9H), 1.33 (s, 9H). MS m/z [M+H]$^+$ 459.2.

Scheme 38: Synthesis of Octadecanoic acid (R)-1-[(S)-1-(tert-butylamino-methyl)-2-(4-morpholin-4-yl-[1,2,5]thiadiazol-3-yloxy)-ethoxycarbonyl]-ethyl ester maleate (38-2):

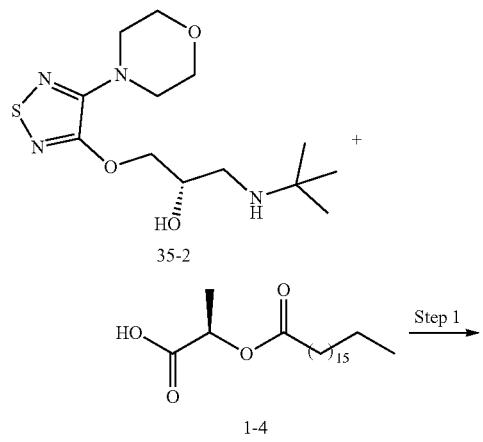

Step-1: Preparation of Octadecanoic acid (R)-1-[(S)-1-(tert-butylamino-methyl)-2-(4-morpholin-4-yl-[1,2,5]thiadiazol-3-yloxy)-ethoxycarbonyl]-ethyl ester (38-1)

To a solution of octadecanoic acid (R)-1-carboxy-ethyl ester (1-4, 0.84 g, 2.36 mmol) in dichloromethane (5 mL) was added EDC.HCl (0.604 g, 3.16 mmol), Timolol (35-2, 0.5 g, 1.57 mmol) and 4-dimethylaminopyridine (19 mg, 0.157 mmol) at 0° C. The reaction mixture was allowed to stir at 25-30° C. over a period of 2 hours. The reaction was quenched with water (100 mL) and extracted with dichloromethane (200×3 mL). The dichloromethane was dried over sodium sulfate, filtered and concentrated under reduced pressure. The crude product obtained upon evaporation of volatiles was purified through silica gel (230-400) column (25% ethyl acetate in hexane) to obtain product 38-1 as colorless liquid (0.7 g, 70%).

Step-2: Preparation of Octadecanoic acid (R)-1-[(S)-1-(tert-butylamino-methyl)-2-(4-morpholin-4-yl-[1,2,5]thiadiazol-3-yloxy)-ethoxycarbonyl]-ethyl ester maleate (38-2)

To a solution of octadecanoic acid (R)-1-[(S)-1-(tert-butylamino-methyl)-2-(4-morpholin-4-yl-[1,2,5]thiadiazol-3-yloxy)-ethoxycarbonyl]-ethyl ester (38-1, 0.5 g, 0.763 mmol) in acetone (2.5 mL) was added maleic acid (0.08 g, 0.687 mmol) at 0° C. The reaction mixture was allowed to stir at room temperature over a period of 20 minutes. The resulting mixture was filtered and the solid was dried under reduced pressure to give product 38-2 as white solid (0.45 g, 77%). $^1$H-NMR (400 MHz, DMSO-d6) δ 8.57 (bs, 1H), 8.41 (bs, 1H), 6.02 (s, 2H), 5.51-5.42 (m, 1H), 5.18 (q, 1H), 4.67 (dd, 1H), 4.49 (dd, 1H), 3.73-3.62 (m, 4H), 3.48-3.12 (m, 6H), 2.32 (t, 2H), 1.50 (quintet, 2H), 1.40 (d, 3H), 1.35-1.15 (m, 37H), 0.85 (t, 3H). MS m/z [M+H]$^+$ 656.1.

Scheme 39: Synthesis of Octadecanoic acid (R)-1-[(S)-1-(tert-butylamino-methyl)-2-(4-morpholin-4-yl-[1,2,5]thiadiazol-3-yloxy)-ethoxycarbonyl]-ethyl ester hydrochloride (39-1):

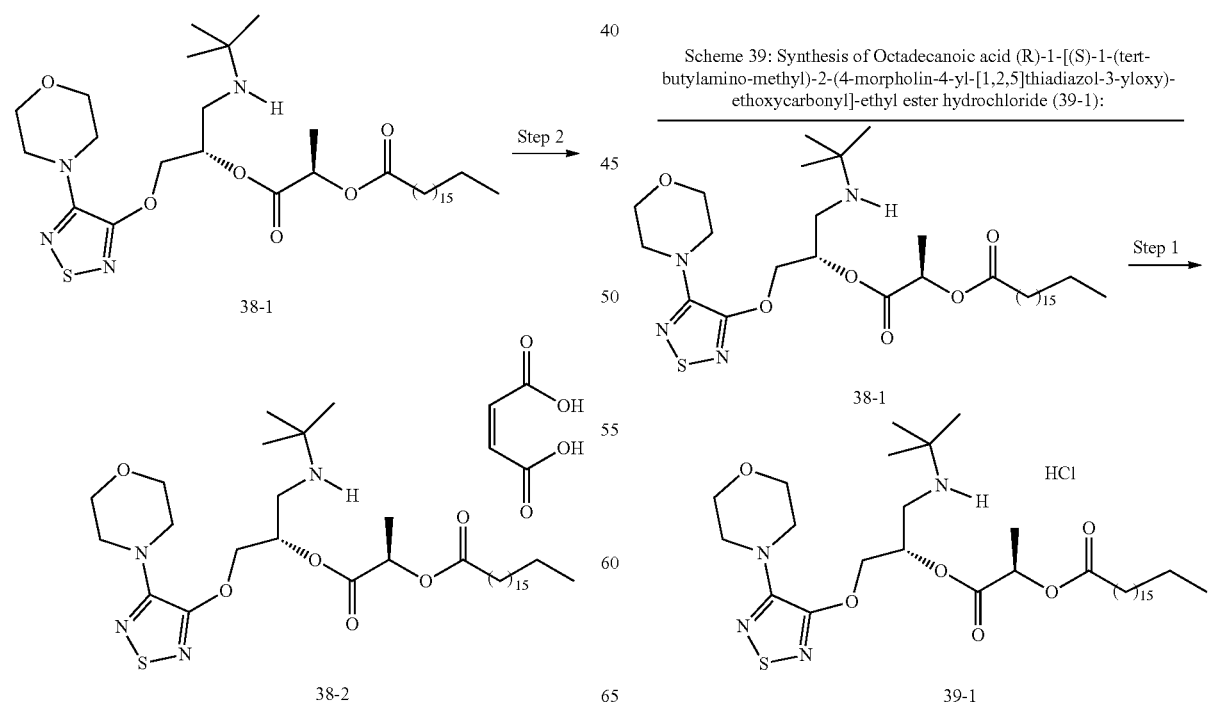

Step-1: Preparation of Octadecanoic acid (R)-1-[(S)-1-(tert-butylamino-methyl)-2-(4-morpholin-4-yl-[1,2,5]thiadiazol-3-yloxy)-ethoxycarbonyl]-ethyl ester hydrochloride (39-1)

To a solution of octadecanoic acid (R)-1-[(S)-1-(tert-butylamino-methyl)-2-(4-morpholin-4-yl-[1,2,5]thiadiazol-3-yloxy)-ethoxycarbonyl]-ethyl ester (38-1, 0.2 g, 0.305 mmol) in dioxane (0.4 mL) was added 4M HCl in dioxane (0.15 mL, 0.61 mmol) at 0° C. The mixture was allowed to stir at room temperature over a period of 20 minutes. The resulting mixture was concentrated under reduced pressure to give product 39-1 as waxy solid (0.15 g, 71%). $^1$H-NMR (400 MHz, DMSO-d6) δ 9.18 (bs, 1H), 8.82 (bs, 1H), 5.53-5.46 (m, 1H), 5.23 (q, 1H), 4.69 (dd, 1H), 4.51 (dd, 1H), 3.74-3.63 (m, 4H), 3.48-3.3 (m, 5H), 3.25-3.12 (m, 1H), 2.33 (t, 2H), 1.51 (quintet, 2H), 1.37 (d, 3H), 1.35-1.15 (m, 37H), 0.83 (t, 3H). MS m/z [M+H]$^+$ 656.0.

Scheme 40: Synthesis of Octadecanoic acid (S)-1-[(S)-1-((S)-1-{(S)-1-[(S)-1-(tert-butylamino-methyl)-2-(4-morpholin-4-yl-[1,2,5]thiadiazol-3-yloxy)-ethoxycarbonyl]-ethoxycarbonyl}-ethoxycarbonyl)-ethoxycarbonyl]-ethyl ester maleate (40-2):

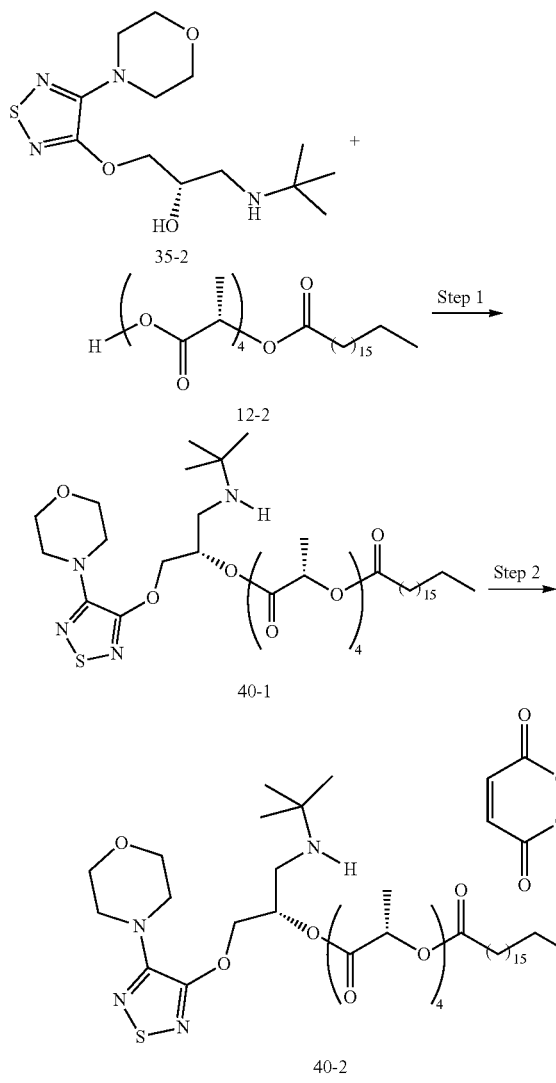

Step-1: Preparation of Octadecanoic acid (S)-1-[(S)-1-((S)-1-{(S)-1-[(S)-1-(tert-butylamino-methyl)-2-(4-morpholin-4-yl-[1,2,5]thiadiazol-3-yloxy)-ethoxycarbonyl]-ethoxycarbonyl}-ethoxycarbonyl)-ethoxycarbonyl]-ethyl ester (40-1)

To a solution of octadecanoic acid (S)-1-{(S)-1-[(S)-1-((S)-1-carboxy-ethoxycarbonyl)-ethoxycarbonyl]-ethoxycarbonyl}-ethyl ester (12-2, 1.62 g, 2.84 mmol) in dichloromethane (6 mL) was added EDC.HCl (0.725 g, 3.79 mmol), Timolol (35-2, 0.6 g, 1.89 mmol) and 4-dimethylaminopyridine (23 mg, 0.189 mmol) at 0° C. The reaction mixture was allowed to stir at 25-30° C. over a period of 2 hours. The resulting reaction mass was quenched with water (100 mL), extracted with dichloromethane (200×3 mL), dried over sodium sulfate and concentrated under reduced pressure. The crude product obtained upon evaporation of volatiles was purified through silica gel (230-400) column (25% ethyl acetate in hexane) to obtain product 40-1 as colorless liquid (1.0 g, 62%). $^1$H NMR (400 MHz, DMSO-d6) δ 5.23-5.11 (m, 3H), 515-5.07 (m, 2H), 4.62 (dd, J=11.5, 2.5 Hz, 1H), 4.46 (dd, J=11.6, 7.4 Hz, 1H), 3.67 (t, J=4.7 Hz, 4H), 3.40 (s, 4H), 2.71 (s, 2H), 2.33-2.30 (m, 3H), 1.48-1.36 (m, 12H), 1.23 (s, 32H), 1.00 (s, 9H), 0.89-0.77 (m, 3H); MS m/z (M+H) 872.1

Step-2: Preparation of Octadecanoic acid (S)-1-[(S)-1-((S)-1-{(S)-1-[(S)-1-(tert-butylamino-methyl)-2-(4-morpholin-4-yl-[1,2,5]thiadiazol-3-yloxy)-ethoxycarbonyl]-ethoxycarbonyl}-ethoxycarbonyl)-ethoxycarbonyl]-ethyl ester maleate (40-2)

To a solution of octadecanoic acid (S)-1-[(S)-1-((S)-1-{(S)-1-[(S)-1-(tert-butylamino-methyl)-2-(4-morpholin-4-yl-[1,2,5]thiadiazol-3-yloxy)-ethoxycarbonyl]-ethoxycarbonyl}-ethoxycarbonyl)-ethoxycarbonyl]-ethyl ester (40-1, 0.8 g, 0.918 mmol) in acetone (4 mL) was added maleic acid (0.095 g, 0.826 mmol) at 0° C. The reaction mixture was allowed to stir at room temperature over a period of 20 minutes. The resulting reaction mixture was filtered and dried under reduced pressure to give product 40-2 as waxy solid (0.8 g, 88%). $^1$H-NMR (400 MHz, DMSO-d6) δ 8.7-8.3 (m, 2H), 6.04 (s, 2H), 5.55-5.44 (m, 1H), 5.27 (q, 1H), 5.25-5.13 (m, 2H), 5.06 (q, 1H), 4.68 (dd, 1H), 4.49 (dd, 1H), 3.73-3.64 (m, 4H), 3.48-3.15 (m, 6H), 2.33 (t, 2H), 1.56-1.38 (m, 14H), 1.32-1.14 (m, 37H), 0.85 (t, 3H). MS m/z [M+H]$^+$ 872.1.

Scheme 41: Synthesis of Octadecanoic acid (S)-1-[(S)-1-((S)-1-{(S)-1-[(S)-1-(tert-butylamino-methyl)-2-(4-morpholin-4-yl-[1,2,5]thiadiazol-3-yloxy)-ethoxycarbonyl]-ethoxycarbonyl}-ethoxycarbonyl)-ethoxycarbonyl]-ethyl ester hydrochloride (40-1):

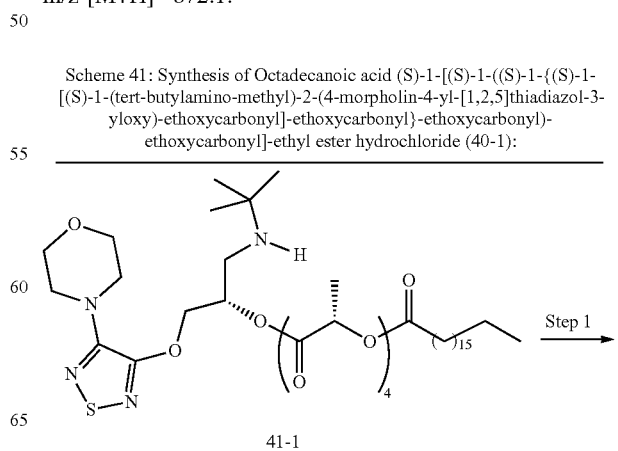

-continued

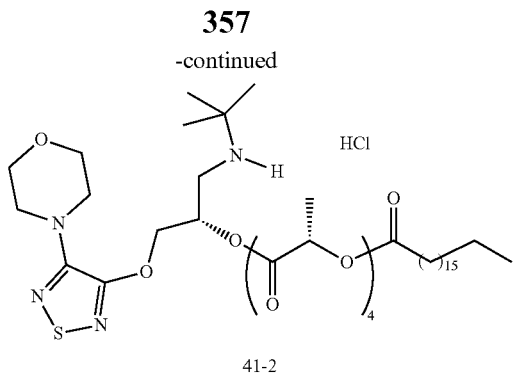

41-2

Step-1: Preparation of Octadecanoic acid (S)-1-
[(S)-1-((S)-1-{(S)-1-[(S)-1-(tert-butylamino-
methyl)-2-(4-morpholin-4-yl-[1,2,5]thiadiazol-3-
yloxy)-ethoxycarbonyl]-ethoxycarbonyl}-
ethoxycarbonyl)-ethoxycarbonyl]-ethyl ester
hydrochloride (41-2)

To a solution of octadecanoic acid (R)-1-[(S)-1-(tert-butylamino-methyl)-2-(4-morpholin-4-yl-[1,2,5]thiadiazol-3-yloxy)-ethoxycarbonyl]-ethylester (40-1, 0.2 g, 0.229 mmol) in dioxane (0.4 mL) was added 4M HCl in dioxane (0.11 mL, 0.459 mmol) at 0° C. The mixture was allowed to stir at room temperature over a period of 20 minutes and concentrated under reduced pressure to afford product 40-2 as waxy solid (0.15 g, 71%). $^1$H-NMR (400 MHz, DMSO-d6) δ 9.09 (bs, 1H), 8.80 (bs, 1H), 5.56-5.47 (m, 1H), 5.32 (q, 1H), 5.22-5.13 (m, 2H), 5.05 (q, 1H), 4.68 (dd, 1H), 4.50 (dd, 1H), 3.72-3.64 (m, 4H), 3.48-3.32 (m, 5H), 3.26-3.12 (m, 1H), 2.33 (t, 2H), 1.56-1.38 (m, 14H), 1.32-1.14 (m, 37H), 0.85 (t, 3H). MS m/z [M+H]$^+$ 872.2.

Scheme 42: Synthesis of Octadecanoic acid (S)-1-((S)-1-{(S)-1-[(S)-1-((S)-1-{(S)-1-[(S)-1-(tert-butylamino-methyl)-2-(4-morpholin-4-yl-[1,2,5]thiadiazol-3-yloxy)-ethoxycarbonyl]-ethoxycarbonyl}-ethoxycarbonyl)-ethoxycarbonyl]-ethoxycarbonyl}-ethoxycarbonyl)-ethyl ester maleate (42-2):

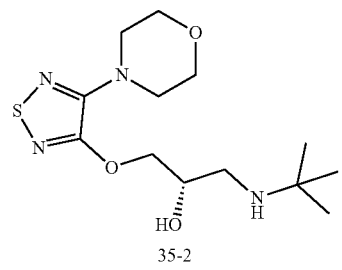

35-2

+

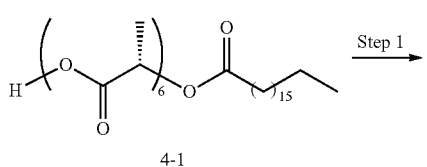

4-1

Step 1

-continued

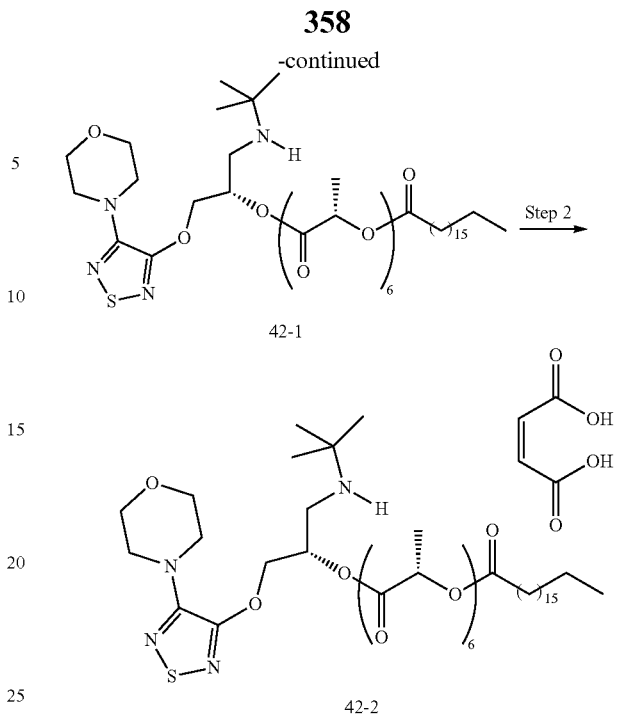

42-1

42-2

Step-1: Preparation of Octadecanoic acid (S)-1-
((S)-1-{(S)-1-[(S)-1-((S)-1-{(S)-1-[(S)-1-(tert-buty-
lamino-methyl)-2-(4-morpholin-4-yl-[1,2,5]thiadi-
azol-3-yloxy)-ethoxycarbonyl]-ethoxycarbonyl}-
ethoxycarbonyl)-ethoxycarbonyl]-ethoxycarbonyl}-
ethoxycarbonyl)-ethyl ester (42-1)

To a solution of octadecanoic acid (S)-1-[(S)-1-((S)-1-{(S)-1-[(S)-1-((S)-1-carboxy-ethoxycarbonyl)-ethoxycarbonyl]-ethoxycarbonyl}-ethoxycarbonyl)-ethoxycarbonyl]-ethyl ester (4-1, 1.69 g, 2.37 mmol) in dichloromethane (5 mL) was added EDC.HCl (0.603 g, 3.16 mmol), Timolol (35-2, 0.5 g, 1.58 mmol) and 4-dimethylaminopyridine (19 mg, 0.158 mmol) at 0° C. The reaction mixture was allowed to stir at 25-30° C. over a period of 2 hours. The reaction was quenched with water (100 mL) and extracted with dichloromethane (200×3 mL). The dichloromethane was dried over sodium sulfate, filtered and concentrated under reduced pressure. The crude product obtained upon evaporation of volatiles was purified through silica gel (230-400) column (25% ethyl acetate in hexane) to obtain product 42-1 as colorless liquid (0.7 g, 43%).

Step-2: Preparation of Octadecanoic acid (S)-1-
((S)-1-{(S)-1-[(S)-1-((S)-1-{(S)-1-[(S)-1-(tert-buty-
lamino-methyl)-2-(4-morpholin-4-yl-[1,2,5]thiadi-
azol-3-yloxy)-ethoxycarbonyl]-ethoxycarbonyl}-
ethoxycarbonyl)-ethoxycarbonyl]-ethoxycarbonyl}-
ethoxycarbonyl)-ethyl ester maleate (42-2)

To a solution of octadecanoic acid (S)-1-((S)-1-{(S)-1-[(S)-1-((S)-1-{(S)-1-[(S)-1-(tert-butylamino-methyl)-2-(4-morpholin-4-yl-[1,2,5]thiadiazol-3-yloxy)-ethoxycarbonyl]-ethoxycarbonyl}-ethoxycarbonyl)-ethoxycarbonyl]-ethoxycarbonyl}-ethoxycarbonyl)-ethyl ester (42-1, 0.5 g, 0.492 mmol) in acetone (2.5 mL) was added maleic acid (0.051 g, 0.443 mmol) at 0° C. The reaction mixture was allowed to stir at room temperature over a period of 20 minutes. The resulting reaction mixture was concentrated under reduced pressure to afford product 42-2 as waxy solid (0.45 g, 81%). ¹H-NMR (400 MHz, DMSO-d6) δ 8.7-8.3 (m, 2H), 6.11 (s, 2H), 5.54-5.44 (m, 1H), 5.29 (q, 1H), 5.24-5.13 (m, 4H), 5.06 (q, 1H), 4.68 (dd, 1H), 4.49 (dd, 1H), 3.73-3.62 (m, 4H), 3.5-3.1 (m, 6H), 2.33 (t, 2H), 1.56-1.38 (m, 20H), 1.35-1.15 (m, 37H), 0.85 (t, 3H). MS m/z [M+H]⁺ 1016.2.

Scheme 43: Synthesis of Octadecanoic acid (S)-1-((S)-1-{(S)-1-[(S)-1-((S)-1-{(S)-1-[(S)-1-(tert-butylamino-methyl)-2-(4-morpholin-4-yl-[1,2,5]thiadiazol-3-yloxy)-ethoxycarbonyl]-ethoxycarbonyl}-ethoxycarbonyl)-ethoxycarbonyl]-ethoxycarbonyl}-ethoxycarbonyl)-ethyl ester hydrochloride (43-1):

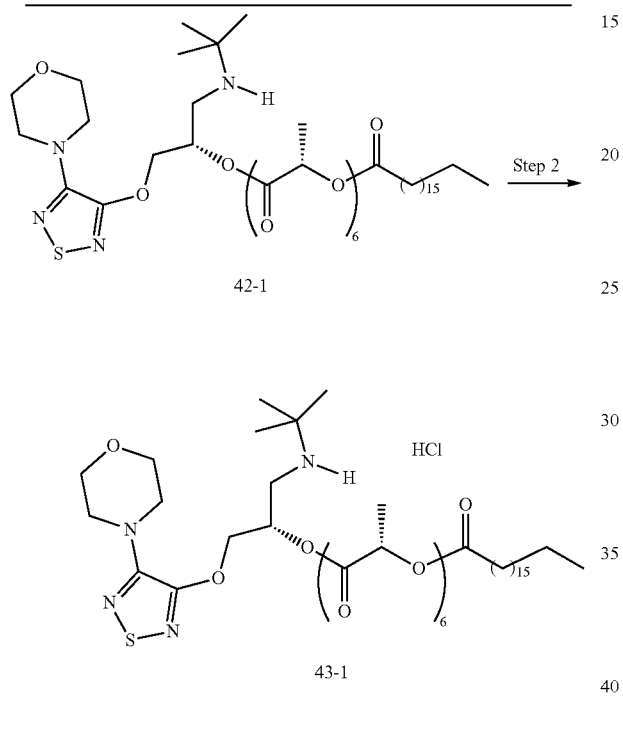

Step-1: Preparation of Octadecanoic acid (S)-1-((S)-1-{(S)-1-[(S)-1-((S)-1-{(S)-1-[(S)-1-(tert-butylamino-methyl)-2-(4-morpholin-4-yl-[1,2,5]thiadiazol-3-yloxy)-ethoxycarbonyl]-ethoxycarbonyl}-ethoxycarbonyl)-ethoxycarbonyl]-ethoxycarbonyl}-ethoxycarbonyl)-ethyl ester hydrochloride (43-1)

To a solution of octadecanoic acid (S)-1-((S)-1-{(S)-1-[(S)-1-((S)-1-{(S)-1-[(S)-1-(tert-butylamino-methyl)-2-(4-morpholin-4-yl-[1,2,5]thiadiazol-3-yloxy)-ethoxycarbonyl]-ethoxycarbonyl}-ethoxycarbonyl)-ethoxycarbonyl]-ethoxycarbonyl}-ethoxycarbonyl)-ethyl ester (42-1, 0.2 g, 0.196 mmol) in dioxane (0.4 mL) was added 4M HCl in dioxane (0.095 mL, 0.393 mmol) at 0° C. The reaction mixture was allowed to stir at room temperature over a period of 20 minutes. The resulting reaction mixture was concentrated under reduced pressure to give product 43-1 as a waxy solid (0.15 g, 72%). ¹H-NMR (400 MHz, DMSO-d6) δ 9.06 (bs, 1H), 8.77 (bs, 1H), 5.56-5.46 (m, 1H), 5.32 (q, 1H), 5.24-5.13 (m, 4H), 5.04 (q, 1H), 4.69 (dd, 1H), 4.51 (dd, 1H), 3.73-3.64 (m, 4H), 3.48-3.32 (m, 5H), 3.26-3.12 (m, 1H), 2.33 (t, 2H), 1.56-1.38 (m, 20H), 1.38-1.14 (m, 37H), 0.85 (t, 3H). MS m/z [M+H]⁺ 1016.3.

Scheme 44: Synthesis of (R)-2-Acetoxy-propionic acid (S)-1-(tert-butylamino)-methyl)-2-(4-morpholin-4-yl-[1,2,5]thiadiazol-3-yloxy)-ethyl ester maleate (44-2):

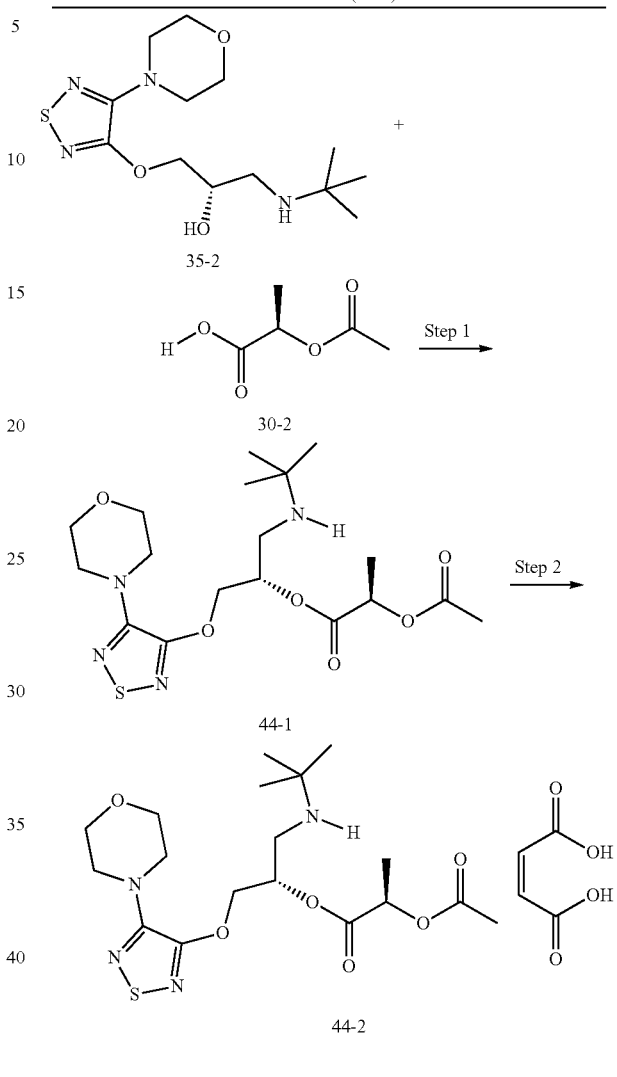

Step-1: Preparation of (R)-2-Acetoxy-propionic acid (S)-1-(tert-butylamino-methyl)-2-(4-morpholin-4-yl-[1,2,5]thiadiazol-3-yloxy)-ethyl ester (44-1)

To a solution of (R)-2-acetoxy-propionic acid (30-2, 0.63 g, 4.74 mmol) in dichloromethane (10 mL) was added EDC.HCl (1.2 g, 6.32 mmol), Timolol (35-2, 1.0 g, 3.16 mmol) and 4-dimethylaminopyridine (38 mg, 0.316 mmol) at 0° C. The reaction mixture was allowed to stir at 25-30° C. over a period of 2 hours. The resulting reaction mass was quenched with water (100 mL) and extracted with dichloromethane (200×3 mL). The dichloromethane was dried over sodium sulfate, filtered and concentrated under reduced pressure. The crude product obtained upon evaporation of volatiles was purified through silica gel (230-400) column (30% ethyl acetate in hexane) to obtain product 44-1 as colorless liquid (0.3 g, 26%). ¹H NMR (400 MHz, DMSO-d6) δ 5.20-4.12 (m, 1H), 4.96 (q, J=7.0 Hz, 1H), 4.63 (dd, 1H), 4.50 (dd, 1H), 3.73-3.64 (m, 4H), 3.43-3.38 (m, 4H), 2.76-2.68 (m, 2H), 2.04 (s, 3H), 1.35 (d, J=7.0 Hz, 3H), 1.00 (s, 9H); MS m/z (M+H)⁺ 431.6

Step-2: Preparation of (R)-2-Acetoxy-propionic acid (S)-1-(tert-butylamino-methyl)-2-(4-morpholin-4-yl-[1,2,5]thiadiazol-3-yloxy)-ethyl ester maleate (44-2)

To a solution of (R)-2-acetoxy-propionic acid (S)-1-(tert-butylamino-methyl)-2-(4-morpholin-4-yl-[1,2,5]thiadiazol-3-yloxy)-ethyl ester (44-1, 0.3 g, 0.697 mmol) in acetone (1.5 mL) was added maleic acid (0.072 g, 0.627 mmol) at 0° C. The reaction mixture was allowed to stir at room temperature over a period of 20 minutes. The resulting suspension was filtered and the collected solid was dried under reduced pressure to give product 44-2 as white solid (0.32, 84%). $^1$H-NMR (400 MHz, DMSO-d6) δ 8.58 (bs, 1H), 8.39 (bs, 1H), 6.02 (s, 2H), 5.52-5.41 (m, 1H), 5.18 (q, 1H), 4.67 (dd, 1H), 4.50 (dd, 1H), 3.72-3.62 (m, 4H), 3.48-3.31 (m, 5H), 3.29-3.12 (m, 1H), 2.08 (s, 3H), 1.40 (d, 3H), 1.28 (s, 9H). MS m/z [M+H]+ 431.6.

Scheme 45: Synthesis of (S)-2-[(S)-2-((S)-2-Acetoxy-propionyloxy)-propionyloxy]propionic acid (S)-1-[(S)-1-(tert-butylamino-methyl)-2-(4-morpholin-4-yl-[1,2,5]thiadiazol-3-yloxy)-ethoxy carbonyl]-ethyl ester maleate (45-2):

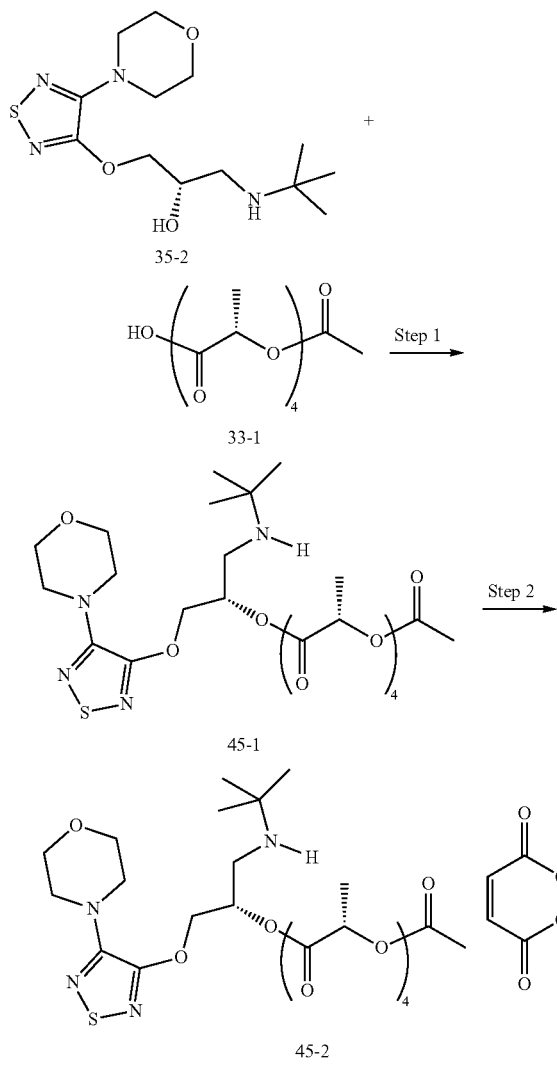

Step-1: Preparation of (S)-2-[(S)-2-((S)-2-Acetoxy-propionyloxy)-propionyloxy]-propionic acid (S)-1-[(S)-1-(tert-butylamino-methyl)-2-(4-morpholin-4-yl-[1,2,5]thiadiazol-3-yloxy)-ethoxycarbonyl]-ethyl ester (45-1)

To a solution of (S)-2-{(S)-2-[(S)-2-((S)-2-acetoxy-propionyloxy)-propionyloxy]-propionyloxy}-propionic acid (33-1, 3.3 g, 9.49 mmol) in dichloromethane (20 mL) was added EDC.HCl (2.41 g, 12.65 mmol), Timolol (35-2, 2.0 g, 6.32 mmol) and 4-dimethylaminopyridine (77 mg, 0.632 mmol) at 0° C. The reaction mixture was allowed to stir at 25-30° C. over a period of 2 hours. The resulting reaction mass was quenched with water (200 mL), extracted with dichloromethane (400×3 mL), dried over sodium sulfate and concentrated under reduced pressure. The crude product obtained upon evaporation of volatiles was purified through silica gel (230-400) column (40% ethyl acetate in hexane) to obtain product 45-1 as colorless liquid 1.2 g (29%). $^1$H NMR (400 MHz, DMSO-d6) δ 5.24-4.99 (m, 5H), 4.62 (dd, 1H), 4.47 (dd, 1H), 3.70-3.64 (m, 4H), 3.45-3.38 (m, 4H), 2.76-2.66 (m, 2H), 2.06 (s, 3H), 1.50-1.37 (m, 12H), 1.00 (s, 9H); MS m/z (M+H)+ 647.6

Step-2: Preparation of (S)-2-[(S)-2-((S)-2-Acetoxy-propionyloxy)-propionyloxy]-propionic acid (S)-1-[(S)-1-(tert-butylamino-methyl)-2-(4-morpholin-4-yl-[1,2,5]thiadiazol-3-yloxy)-ethoxy carbonyl]-ethyl ester maleate (45-2)

To a solution of (S)-2-[(S)-2-((S)-2-acetoxy-propiony-loxy)-propionyloxy]-propionic acid (S)-1-[(S)-1-(tert-butylamino-methyl)-2-(4-morpholin-4-yl-[1,2,5]thiadiazol-3-yloxy)-ethoxy carbonyl]-ethyl ester (45-1, 1.2 g, 1.85 mmol) in acetone (6 mL) was added maleic acid (0.193 g, 1.66 mmol) at 0° C. The reaction mixture was allowed to stir at room temperature over a period of 20 minutes. The resulting reaction mixture was concentrated under reduced pressure to give product 45-2 as white solid (1.3 g, 92%).

Scheme 46: Synthesis of N-tert-Butyl-N-[(S)-2-hydroxy-3-(4-morpholin-4-yl-[1,2,5]thiadiazol-3-yloxy)-propyl]-acetamide (46-4):

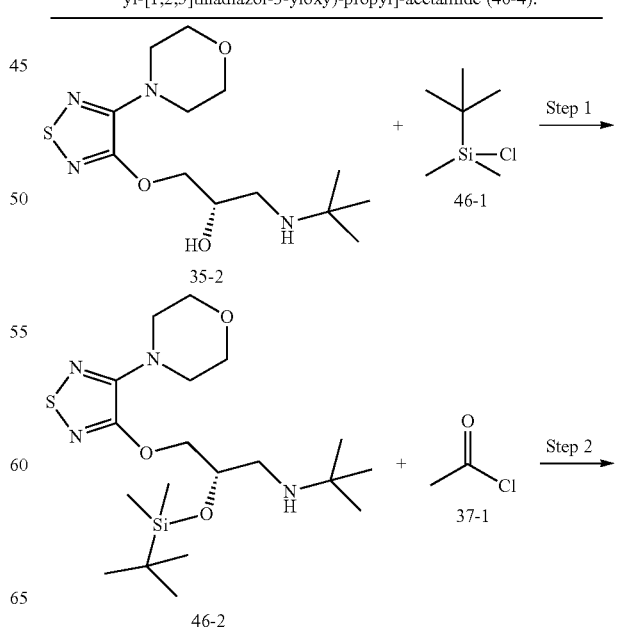

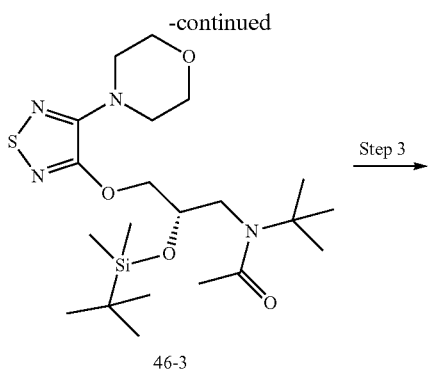

46-3

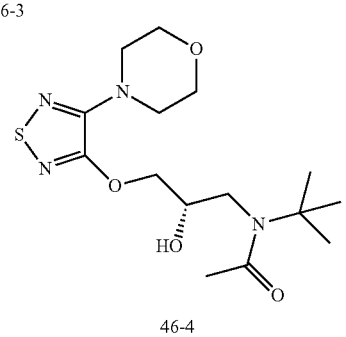

46-4

Step-1: Preparation of tert-Butyl-[(S)-2-(tert-butyl-dimethyl-silanyloxy)-3-(4-morpholin-4-yl-[1,2,5]thiadiazol-3-yloxy)-propyl]-amine (46-2)

To a solution of Timolol (35-2, 5 g, 15.8 mmol) in dimethylformamide (50 mL) was added imidazole (2.69 g, 39.0 mmol) and TBDMS-Cl (2.86 mL, 18.9 mmol) at 0° C. The reaction mixture was stirred at room temperature over period of 12 hours and the resulting reaction mixture was removed under reduced pressure. The crude product obtained upon evaporation of volatiles was purified through silica gel (230-400) column (2% isopropyl alcohol in chloroform) to obtain product 46-2 as a colorless liquid (4 g, 58.8%). $^1$H NMR (400 MHz, DMSO-d6) δ 4.49-4.36 (m, 2H), 4.03 (bs, 1H), 3.74-3.63 (m, 4H), 3.51-3.35 (m, 4H), 2.65-2.5 (m, 2H), 1.23 (bs, 1H), 1.01 (s, 9H), 0.84 (s, 9H), 0.07 (s, 3H), 0.02 (s, 3H); MS m/z (M+H)$^+$ 431.7

Step-2: Preparation of N-tert-Butyl-N—[(S)-2-(tert-butyl-dimethyl-silanyloxy)-3-(4-morpholin-4-yl-[1,2,5]thiadiazol-3-yloxy)-propyl]-acetamide (46-3)

To a solution of tert-butyl-[(S)-2-(tert-butyl-dimethyl-silanyloxy)-3-(4-morpholin-4-yl-[1,2,5]thiadiazol-3-yloxy)-propyl]-amine (46-2, 4 g, 9.29 mmol) in chloroform (40 mL) was added triethylamine (1.9 ml, 13.93 mmol) and acetyl chloride (37-1, 0.99 mL, 13.93 mmol) at 0° C. The reaction mixture was stirred at 25-30° C. over a period of 12 hours, quenched with water (100 mL) and extracted with dichloromethane (2×200 mL). The dichloromethane was dried over sodium sulfate, filtered and evaporated under reduced pressure to obtain product 46-3 as a colorless liquid (3.3 g, 75%). $^1$H NMR (400 MHz, DMSO-d6) δ 4.40 (dd, 1H), 4.32 (dd, 1H), 4.26-4.18 (m, 1H), 3.74-3.64 (m, 4H), 3.6-3.35 (m, 6H), 2.08 (s, 2H), 1.83 (s, 9H), 0.82 (s, 9H), 0.06 (s, 3H), 0.04 (s, 3H); MS m/z (M+H) 473.7

Step-3: Preparation of N-tert-Butyl-N—[(S)-2-hydroxy-3-(4-morpholin-4-yl-[1,2,5]thiadiazol-3-yloxy)-propyl]-acetamide (46-4)

To a solution of N-tert-butyl-N—[(S)-2-(tert-butyl-dimethyl-silanyloxy)-3-(4-morpholin-4-yl-[1,2,5]thiadiazol-3-yloxy)-propyl]-acetamide (46-3, 3.3 g, 6.98 mmol) in tetrahydrofuran (33 mL) was added tetra butyl ammonium fluoride (10.4 mL, 1.0 M, 10.47 mmol) at 0° C. The reaction mixture was allowed to stir at room temperature over a period of 1 hour. The resulting reaction mixture was concentrated under reduced pressure and crude product obtained upon evaporation of the volatiles was purified through silica gel column chromatography (60% ethyl acetate in hexane) to afford product 46-4 as an off white solid (1.3 g, 52%). $^1$H NMR (400 MHz, DMSO-d6) δ 5.46 (d, J=5.3 Hz, 1H), 4.36-4.23 (m, 2H), 4.03-3.97 (m, 1H), 3.72-3.66 (m, 4H), 3.46-3.37 (m, 6H), 2.06 (s, 3H), 1.38 (s, 9H); MS m/z (M+H)$^+$ 359.6.

Scheme 47: Synthesis of (R)-2-Acetoxy-propionic acid (S)-1-[(acetyl-tert-butyl-amino)-methyl]-2-(4-morpholin-4-yl-[1,2,5]thiadiazol-3-yloxy)-ethyl ester (47-1):

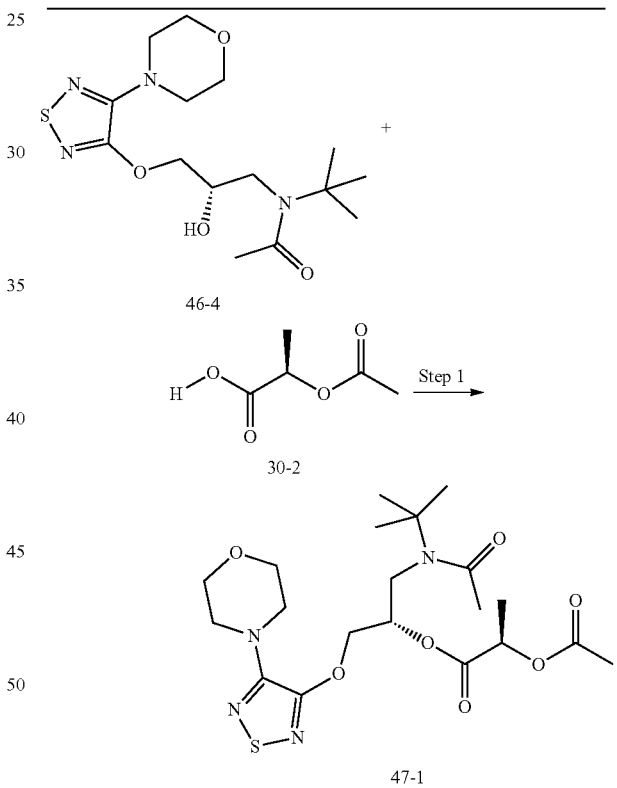

Step-1: Preparation of (R)-2-Acetoxy-propionic acid (S)-1-[(acetyl-tert-butyl-amino)-methyl]-2-(4-morpholin-4-yl-[1,2,5]thiadiazol-3-yloxy)-ethyl ester (47-1)

To a solution of (R)-2-acetoxy-propionic acid (30-2, 0.166 g, 1.26 mmol) in dichloromethane (3 mL) was added N,N-dicyclohexylcarbodiimide (0.312 g, 1.51 mmol), N-tert-butyl-N—[(S)-2-hydroxy-3-(4-morpholin-4-yl-[1,2,5]thiadiazol-3-yloxy)-propyl]-acetamide (46-4, 0.3 g, 0.84 mmol) and 4-dimethylaminopyridine (10 mg, 0.08 mmol) at 0° C. The reaction mixture was allowed to stir at 25-30° C. over a period of 1 h. The resulting reaction mass was quenched with water (100 mL) and extracted with dichloromethane (100×3 mL) The dichloromethane was dried over sodium sulfate, filtered and concentrated under reduced pressure. The crude product obtained upon evaporation of volatiles was purified through silica gel (230-400) column (60% ethylacetate in hexane) to obtain product 47-1 as a colorless wax 250 mg (63%). $^1$H-NMR (400 MHz, DMSO-d6) δ 5.44-5.32 (m, 1H), 4.96 (q, 1H), 4.56 (dd, 1H), 4.41 (dd, 1H), 3.82-3.60 (m, 6H), 3.43-3.34 (m, 4H), 2.08 (s, 3H), 2.02 (s, 3H), 1.38-1.30 (m, 12H). MS m/z [M+H]$^+$ 473.6.

Scheme 48: Synthesis of (S)-2-((S)-2-Acetoxy-propionyloxy)-propionic acid (S)-1-[(acetyl-tert-butyl-amino)-methyl]-2-(4-morpholin-4-yl-[1,2,5]thiadiazol-3-yloxy)-ethyl ester (48-1):

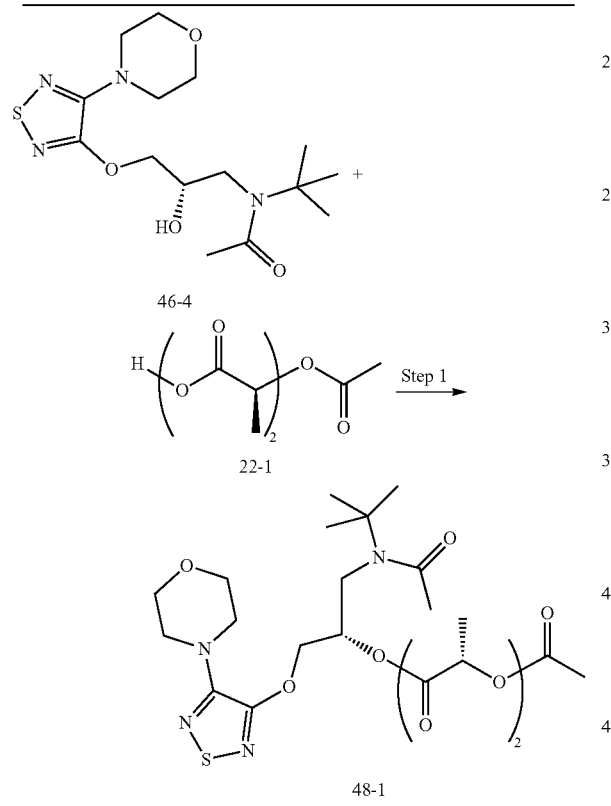

Step-1: Preparation of (S)-2-((S)-2-Acetoxy-propionyloxy)-propionic acid (S)-1-[(acetyl-tert-butyl-amino)-methyl]-2-(4-morpholin-4-yl-[1,2,5]thiadiazol-3-yloxy)-ethyl ester (48-1)

To a solution of (S)-2-((S)-2-acetoxy-propionyloxy)-propionic acid (22-1, 0.086 g, 0.42 mmol) in dichloromethane (1 mL) was added N,N'-dicyclohexylcarbodiimide (0.104 g, 0.5 mmol), N-tert-butyl-N—[(S)-2-hydroxy-3-(4-morpholin-4-yl-[1,2,5]thiadiazol-3-yloxy)-propyl]-acetamide (46-4, 0.1 g, 0.28 mmol) and 4-dimethylaminopyridine (4 mg, 0.03 mmol) at 0° C. The reaction mixture was allowed to stir at 25-30° C. over a period of 1 hour. The resulting reaction mass was quenched with water (50 mL) and extracted with dichloromethane (50×3 mL). The dichloromethane was dried over sodium sulfate, filtered and concentrated under reduced pressure. The crude product obtained upon evaporation of volatiles was purified through silica gel (230-400) column (63% ethyl acetate in hexane) to obtain product 48-1 as a colorless wax (100 mg, 66%). $^1$H-NMR (400 MHz, DMSO-d6) δ 5.48-5.40 (m, 1H), 5.09-5.00 (m, 2H), 4.56 (dd, 1H), 4.41 (dd, 1H), 3.79-3.63 (m, 6H), 3.42-3.34 (m, 4H), 2.09 (s, 3H), 2.04 (s, 3H), 1.43-1.35 (m, 6H), 1.34 (s, 9H). MS m/z [M+H]$^+$ 545.5.

Scheme 49: Synthesis of (R)-2-((R)-2-Acetoxy-propionyloxy)-propionic acid (R)-1-[(S)-1-[(acetyl-tert-butyl-amino)-methyl]-2-(4-morpholin-4-yl-[1,2,5]thiadiazol-3-yloxy)-ethoxycarbonyl]-ethyl ester (49-1):

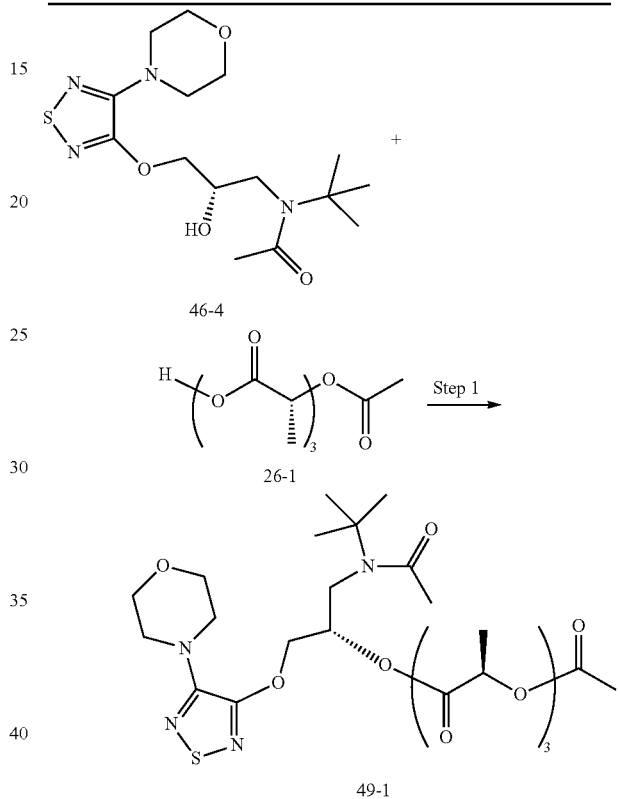

Step-1: Preparation of (R)-2-((R)-2-Acetoxy-propionyloxy)-propionic acid (R)-1-[(S)-1-[(acetyl-tert-butyl-amino)-methyl]-2-(4-morpholin-4-yl-[1,2,5]thiadiazol-3-yloxy)-ethoxycarbonyl]-ethyl ester (49-1)

To a solution of (R)-2-[(R)-2-((R)-2-acetoxy-propionyloxy)-propionyloxy]-propionic acid (26-3, 0.114 g, 0.42 mmol) in dichloromethane (1 mL) was added N,N-dicyclohexylcarbodiimide (0.104 g, 0.5 mmol), N-tert-butyl-N—[(S)-2-hydroxy-3-(4-morpholin-4-yl-[1,2,5]thiadiazol-3-yloxy)-propyl]-acetamide (46-4, 0.1 g, 0.28 mmol) and 4-dimethylaminopyridine (4 mg, 0.03 mmol) at 0° C. The reaction mixture was allowed to stir at 25-30° C. over a period of 1 hour. The resulting reaction mass was quenched with water (50 mL) and extracted with dichloromethane (50×3 mL). The dichloromethane was dried over sodium sulfate, filtered and concentrated under reduced pressure. The crude product obtained upon evaporation of volatiles was purified through silica gel (230-400) column (62% ethyl acetate in hexane) to obtain product 49-1 as a colorless wax (110 mg, 63.9%). $^1$H-NMR (400 MHz, DMSO-d6) δ 5.48-

5.39 (m, 1H), 5.20 (q, 1H), 5.09-4.94 (m, 2H), 4.55 (dd, 1H), 4.42 (dd, 1H), 3.79-3.62 (m, 6H), 3.41-3.36 (m, 4H), 2.10 (s, 3H), 2.06 (s, 3H), 1.44 (d, 3H), 1.39-1.33 (m, 15H). MS m/z [M+H]$^+$ 617.6.

(m, 6H), 3.41-3.35 (m, 4H), 2.08 (s, 3H), 2.06 (s, 3H), 1.44-1.34 (m, 12H), 1.33 (s, 9H). MS m/z [M+H]$^+$ 689.8.

Scheme 50: Synthesis of (S)-2-[(S)-2-((S)-2-Acetoxy-propionyloxy)-propionyloxy]-propionic acid (R)-1-[(S)-1-[(acetyl-tert-butyl-amino)-methyl]-2-(4-morpholin-4-yl-[1,2,5]thiadiazol-3-yloxy)-ethoxycarbonyl]-ethyl ester (50-1):

Scheme 51: Synthesis of (S)-2-{(2)-2-[(S)-2-((S)-2-Acetoxy-propionyloxy)-propionyloxy]-propionyloxy}-propionic acid (S)-1-[(S)-1-[(tert-butyl-formyl-amino)-methyl]-2-(4-morpholin-4-yl-[1,2,5]thiadiazol-3-yloxy)-ethoxycarbonyl]-ethyl ester (51-1):

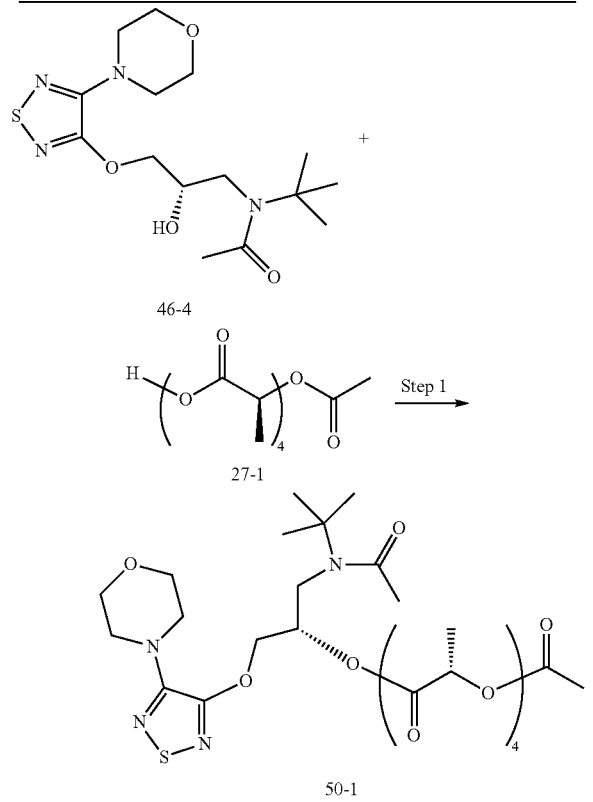

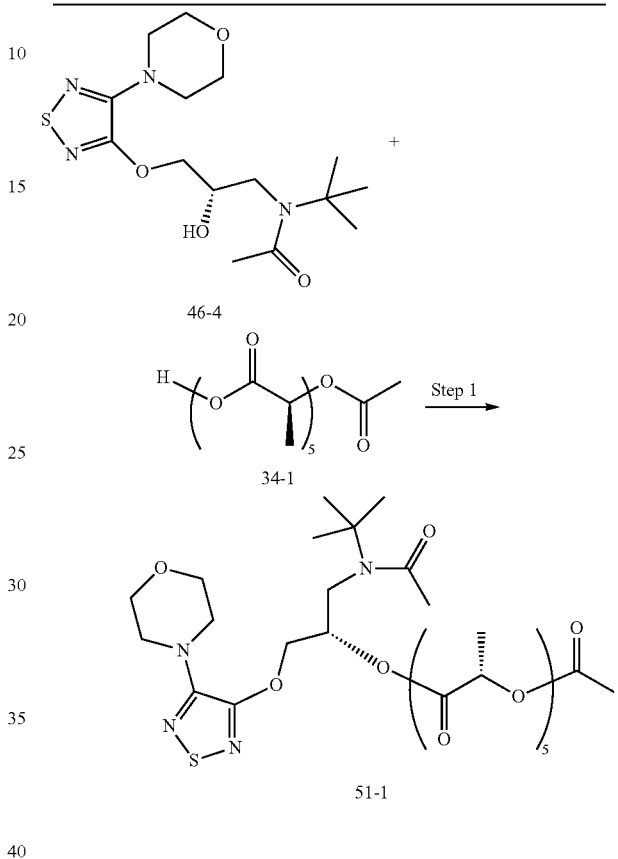

Step-1: Preparation of (S)-2-[(S)-2-((S)-2-Acetoxy-propionyloxy)-propionyloxy]-propionic acid (S)-1-[(S)-1-[(acetyl-tert-butyl-amino)-methyl]-2-(4-morpholin-4-yl-[1,2,5]thiadiazol-3-yloxy)-ethoxycarbonyl]-ethyl ester (50-1)

To a solution of (S)-2-{(S)-2-[(S)-2-((S)-2-acetoxy-propionyloxy)-propionyloxy]-propionyloxy}-propionic acid (27-1, 0.318 g, 0.91 mmol) in dichloromethane (2.5 mL) was added N,N'-dicyclohexylcarbodiimide (0.226 g, 1.09 mmol), N-tert-butyl-N—[(S)-2-hydroxy-3-(4-morpholin-4-yl-[1,2,5]thiadiazol-3-yloxy)-propyl]-acetamide (46-4, 0.25 g, 0.61 mmol) and 4-dimethylaminopyridine (7 mg, 0.06 mmol) at 0° C. The reaction mixture was allowed to stir at 25-30° C. over a period of 1 hour. The resulting reaction mass was quenched with water (50 mL) and extracted with dichloromethane (100×2 mL). The dichloromethane was dried over sodium sulfate, filtered and concentrated under reduced pressure. The crude product obtained upon evaporation of volatiles was purified through silica gel (230-400) column (60% ethyl acetate in hexane) to obtain product 50-1 as a colorless wax (170 mg, 40.4%). $^1$H-NMR (400 MHz, DMSO-d6) δ 5.48-5.39 (m, 1H), 5.21 (q, 1H), 5.14 (q, 1H), 5.09-5.00 (m, 2H), 4.55 (dd, 1H), 4.42 (dd, 1H), 3.80-3.62

Step-1: Preparation of (S)-2-{(S)-2-[(S)-2-((S)-2-Acetoxy-propionyloxy)-propionyloxy]-propionyloxy}-propionic acid (S)-1-[(S)-1-[(tert-butyl-formyl-amino)-methyl]-2-(4-morpholin-4-yl-[1,2,5]thiadiazol-3-yloxy)-ethoxycarbonyl]-ethyl ester (51-1)

To a solution of (S)-2-((S)-2-{(S)-2-[(S)-2-((S)-2-acetoxy-propionyloxy)-propionyloxy]-propionyloxy}-propionyloxy)-propionic acid (34-1, 0.529 g, 1.26 mmol) in dichloromethane (3 mL) was added N,N'-dicyclohexylcarbodiimide (0.312 g, 1.51 mmol), N-tert-butyl-N—[(S)-2-hydroxy-3-(4-morpholin-4-yl-[1,2,5]thiadiazol-3-yloxy)-propyl]-acetamide (46-4, 0.3 g, 0.84 mmol) and 4-dimethylaminopyridine (10 mg, 0.08 mmol) at 0° C. The reaction mixture was allowed to stir at 25-30° C. over a period of 1 hour. The resulting reaction mass was quenched with water (100 mL) and extracted with dichloromethane (100×3 mL). The dichloromethane extract was dried over sodium sulfate, filtered and concentrated under reduced pressure. The crude product obtained upon evaporation of volatiles was purified through silica gel (230-400) column (55% ethyl acetate in hexane) to obtain product 51-1 as a colorless wax (230 mg, 36.6%). $^1$H-NMR (400 MHz, DMSO-d6) δ 5.49-5.40 (m, 1H), 5.25-5.12 (m, 3H), 5.09-5.00 (m, 2H), 4.55 (dd, 1H), 4.42 (dd, 1H), 3.79-3.62 (m, 6H), 3.41-3.35 (m, 4H), 2.08 (s, 3H), 2.07 (s, 3H), 1.47-1.34 (m, 15H), 1.34 (s, 9H). MS m/z [M+H]$^+$ 761.9.

Scheme 52: Synthesis of Octadecanoic acid (S)-1-(tert-butylamino-methyl)-2-(4-morpholin-4-yl-[1,2,5]thiadiazol-3-yloxy)-ethyl ester maleate (52-2):

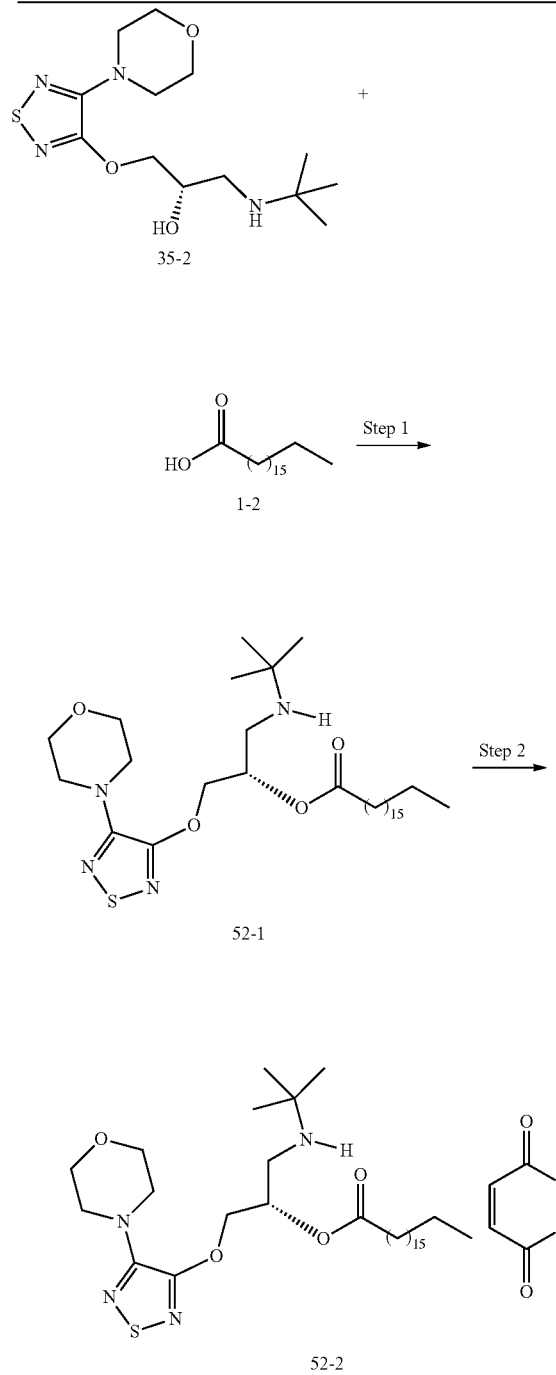

Step-1: Preparation of Octadecanoic acid (S)-1-(tert-butylamino-methyl)-2-(4-morpholin-4-yl-[1,2,5]thiadiazol-3-yloxy)-ethyl ester (52-1)

To a solution of stearic acid (1-2, 0.674 g, 2.37 mmol) in dichloromethane (5 mL) was added EDC.HCl (0.603 g, 3.16 mmol), Timolol (35-2, 0.5 g, 1.58 mmol) and 4-dimethyl-aminopyridine (19 mg, 0.16 mmol) at 0° C. The reaction mixture was allowed to stir at 25-30° C. over a period of 1 hour. The resulting reaction mass was quenched with water (100 mL) and extracted with dichloromethane (200×2 mL). The dichloromethane was dried over sodium sulfate, filtered and concentrated under reduced pressure. The crude product obtained upon evaporation of volatiles was purified through silica gel (230-400) column (35% ethyl acetate in hexane) to obtain product 52-1 as a colorless wax (500 mg, 54%). $^1$H NMR (400 MHz, DMSO-d6) δ 5.18-5.15 (m, 1H), 4.59 (dd, 1H), 4.47 (dd, 1H), 3.68 (t, 4H), 3.46-3.33 (4, 4H), 2.71-2.64 (m, 2H), 2.29-2.22 (m, 2H), 1.7-1.4 (m, 3H), 1.3-1.1 (m, 28H), 1.00 (s, 9H) 0.82 (t, 3H); MS m/z (M+H)$^+$ 583.7

Step-2: Preparation of Octadecanoic acid (S)-1-(tert-butylamino-methyl)-2-(4-morpholin-4-yl-[1,2,5]thiadiazol-3-yloxy)-ethyl ester maleate (52-2)

To a solution of octadecanoic acid (S)-1-(tert-butylamino-methyl)-2-(4-morpholin-4-yl-[1,2,5]thiadiazol-3-yloxy)-ethyl ester (52-1, 0.5 g, 0.86 mmol) in acetone (2.5 mL) was added maleic acid (95 mg, 0.82 mmol) at 0° C. The reaction mixture was allowed to stir at room temperature over a period of 20 minutes. The resulting reaction mixture was filtered to afford product 52-2 as a white solid (0.55 g, 91%). $^1$H-NMR (400 MHz, DMSO-d6) δ 8.56 (bs, 1H), 8.31 (bs, 1H), 6.02 (s, 2H), 5.46-5.36 (m, 1H), 4.65 (dd, 1H), 4.48 (dd, 1H), 3.72-3.63 (m, 4H), 3.48-3.12 (m, 6H), 2.33 (t, 2H), 1.51 (quintet, 2H), 1.31-1.13 (m, 37H), 0.85 (t, 3H). MS m/z [M+H]$^+$ 583.8.

Scheme 53: Synthesis of (4Z,7Z,10Z,13Z,16Z,19Z)-Docosa-4,7,10,13,16,19-hexaenoic acid(S)-1-(tert-butylamino-methyl)-2-(4-morpholin-4-yl [1,2,5]thiadiazol-3-yloxy)-ethylester maleate (53-3):

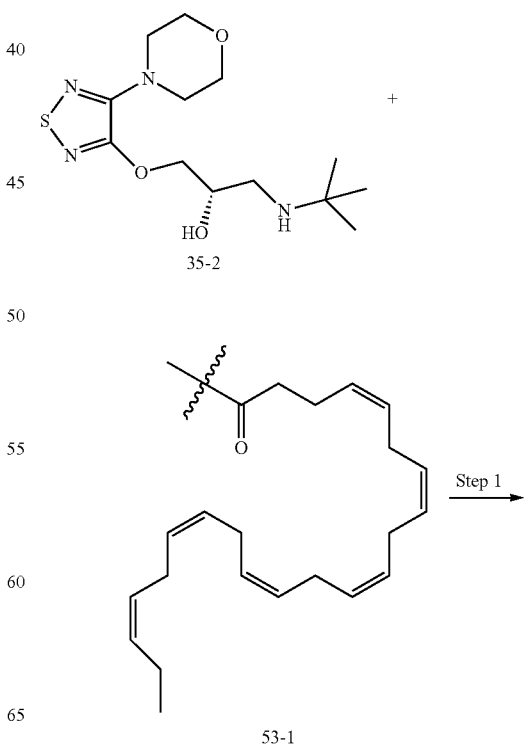

10H), 2.71-2.66 (m, 2H), 2.38-2.22 (m, 4H), 2.09-1.96 (m, 2H), 0.96 (s, 9H), 0.91 (t, 3H); MS m/z (M+H)+ 627.7

Step-2: Preparation of (4Z,7Z,10Z,13Z,16Z,19Z)-Docosa-4,7,10,13,16,19-hexaenoic acid (S)-1-(tert-butylamino-methyl)-2-(4-morpholin-4-yl-[1,2,5]thiadiazol-3-yloxy)-ethylester maleate (52-3)

To a solution of (4Z,7Z,10Z,13Z,16Z,19Z)-docosa-4,7,10,13,16,19-hexaenoic acid (S)-1-(tert-butylamino-methyl)-2-(4-morpholin-4-yl-[1,2,5]thiadiazol-3-yloxy)-ethyl ester (53-2, 0.28 g, 0.45 mmol) in acetone (1.4 mL) was added maleic acid (46 mg, 0.4 mmol) at 0° C. The mixture was allowed to stir at room temperature over a period of 20 minutes and was filtered to give product 53-3 as an off white low melting solid (0.27 g, 80%). 1H-NMR (400 MHz, DMSO-d6) δ 8.58 (bs, 1H), 8.33 (bs, 1H), 6.07 (s, 2H), 5.46-5.21 (m, 13H), 4.65 (dd, 1H), 4.48 (dd, 1H), 3.71-3.65 (m, 4H), 3.46-3.13 (m, 6H), 2.85-2.72 (m, 10H), 2.40 (t, 2H), 2.34-2.24 (m, 2H), 2.01 (quintet, 2H), 1.30 (s, 9H), 0.91 (t, 3H). MS m/z [M+H]+ 627.7.

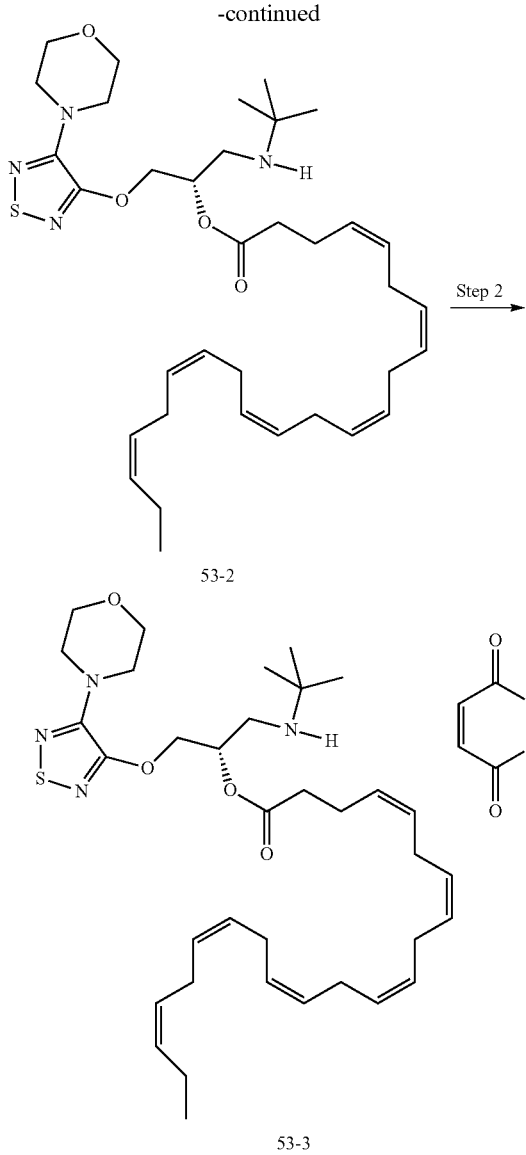

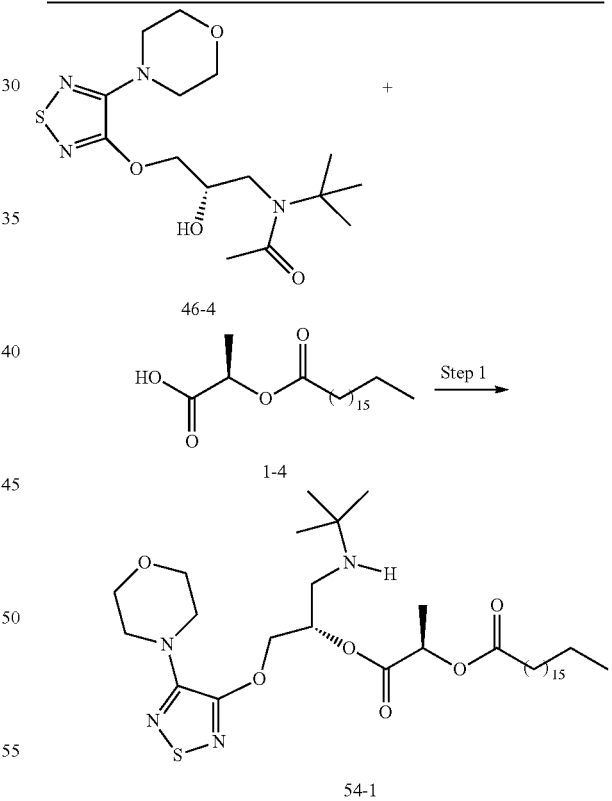

Scheme 54: Synthesis of Octadecanoic acid (R)-1-[(S)-1-[acetyl-tert-butyl-amino)-methyl]-2-(4-morpholin-4-yl-[1,2,5]thiadiazol-3-yloxy)-ethoxycarbonyl]-ethyl ester (54-1):

Step-1: Preparation of (4Z,7Z,10Z,13Z,16Z,19Z)-Docosa-4,7,10,13,16,19-hexaenoic acid (S)-1-(tert-butylamino-methyl)-2-(4-morpholin-4-yl-[1,2,5]thiadiazol-3-yloxy)-ethyl ester (53-2)

To a solution of docosahexaenoic acid (53-1, 0.519 g, 2.37 mmol) in dichloromethane (5 mL) was added EDC.HCl (0.603 g, 3.16 mmol), Timolol (35-2, 0.5 g, 1.58 mmol) and 4-dimethylaminopyridine (19 mg, 0.16 mmol) at 0° C. The reaction mixture was allowed to stir at 25-30° C. over a period of 1 hour. The resulting reaction mass was quenched with water (100 mL) and extracted with dichloromethane (200×2 mL). The dichloromethane was dried over sodium sulfate, filtered and concentrated under reduced pressure. The crude product obtained upon evaporation of volatiles was purified through silica gel (230-400) column (30% ethyl acetate in hexane) to obtain product 53-2 as a colorless wax (280 mg, 28%). 1H NMR (400 MHz, DMSO-d6) δ 5.41-5.22 (m, 12H), 5.18-5.06 (m, 1H), 4.62 (dd, 1H), 4.46 (dd, Hz, 1H), 3.70-3.63 (m, 4H), 3.47-3.31 (m, 6H), 2.87-2.73 (m, Step-1: Preparation of Octadecanoic acid (R)-1-[(S)-1-[(acetyl-tert-butyl-amino)-methyl]-2-(4-morpholin-4-yl-[1,2,5]thiadiazol-3-yloxy)-ethoxycarbonyl]-ethyl ester (54-1)

To a solution of octadecanoic acid (R)-1-carboxy-ethyl ester (1-4, 1.024 g, 1.47 mmol) in dichloromethane (3.5 mL) was added N,N'-dicyclohexylcarbodiimide (0.363 g, 1.76 mmol), N-tert-butyl-N—[(S)-2-hydroxy-3-(4-morpholin-4-yl-[1,2,5]thiadiazol-3-yloxy)-propyl]-acetamide (46-4, 0.35 g, 0.98 mmol) and 4-dimethylaminopyridine (11 mg, 0.09 mmol) at 0° C. The reaction mixture was allowed to stir at 25-30° C. over a period of 1 hour, quenched with water (100 mL) and extracted with dichloromethane (100×3 mL). The dichloromethane was dried over sodium sulfate, filtered and concentrated under reduced pressure. The crude product obtained upon evaporation of volatiles was purified through silica gel (230-400) column (30% ethyl acetate in hexane) to obtain product 54-1 as a colorless wax (280 mg, 41%). $^1$H-NMR (400 MHz, DMSO-d6) δ 5.44-5.36 (m, 1H), 4.97 (q, 1H), 4.53 (dd, 1H), 4.41 (dd, 1H), 3.78-3.61 (m, 6H), 3.45-3.36 (m, 4H), 2.30 (t, 2H), 2.08 (s, 3H), 1.5-1.15 (m, 42H) 0.84 (t, 3H). MS m/z [M+H]$^+$ 697.8.

Scheme 55: Synthesis of Octadecanoic acid (S)-1-{(S)-1-[(S)-1-[(acetyl-tert-butyl-amino)-methyl]-2-(4-morpholin-4-yl-[1,2,5]thiadiazol-3-yloxy)-ethoxycarbonyl]-ethoxycarbonyl}-ethyl ester (55-2):

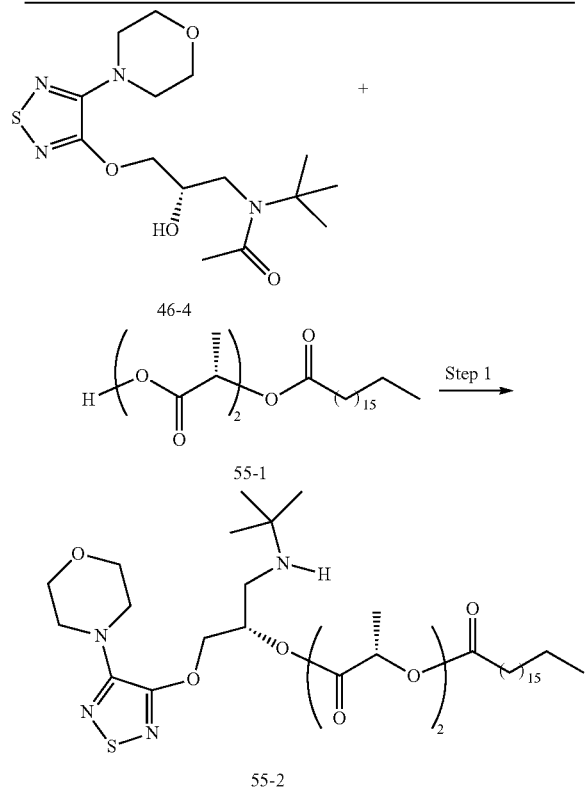

Step-1: Preparation of Octadecanoic acid (S)-1-{(S)-1-[(S)-1-[(acetyl-tert-butyl-amino)-methyl]-2-(4-morpholin-4-yl-[1,2,5]thiadiazol-3-yloxy)-ethoxycarbonyl]-ethoxycarbonyl}-ethyl ester (55-1)

To a solution of octadecanoic acid (S)-1-((S)-1-carboxy-ethoxycarbonyl)-ethyl ester (55-1, 0.539 g, 1.26 mmol) in dichloromethane (3 mL) was added N,N-dicyclohexylcarbodiimide (0.312 g, 1.51 mmol), N-tert-butyl-N—[(S)-2-hydroxy-3-(4-morpholin-4-yl-[1,2,5]thiadiazol-3-yloxy)-propyl]-acetamide (46-4, 0.3 g, 0.84 mmol) and 4-dimethylaminopyridine (10 mg, 0.08 mmol) at 0° C. The reaction mixture was allowed to stir at 25-30° C. over a period of 1 hour. The resulting reaction mass was quenched with water (100 mL) and extracted with dichloromethane (100×3 mL). The dichloromethane was dried over sodium sulfate, filtered and concentrated under reduced pressure. The crude product obtained upon evaporation of volatiles was purified through silica gel (230-400) column (35% ethyl acetate in hexane) to obtain product 55-2 as an colorless wax (300 mg, 46%). $^1$H-NMR (400 MHz, DMSO-d6) δ 5.47-5.37 (m, 1H), 5.09-5.01 (m, 2H), 4.55 (dd, 1H), 4.41 (dd, 1H), 3.78-3.62 (m, 6H), 3.42-3.35 (m, 4H), 2.30 (t, 2H), 2.08 (s, 3H), 1.55-1.15 (m, 45H) 0.85 (t, 3H). MS m/z [M+H]$^+$ 770.1.

Scheme 56: Synthesis of Octadecanoic acid (S)-1-[(S)-1-((S)-1-{(S)-1-[(S)-1-[(acetyl-tert-butyl-amino)-methyl]-2-(4-morpholin-4-yl-[1,2,5]thiadiazol-3-yloxy)-ethoxycarbonyl]-ethoxycarbonyl}-ethoxycarbonyl)-ethoxycarbonyl]-ethyl ester (56-1):

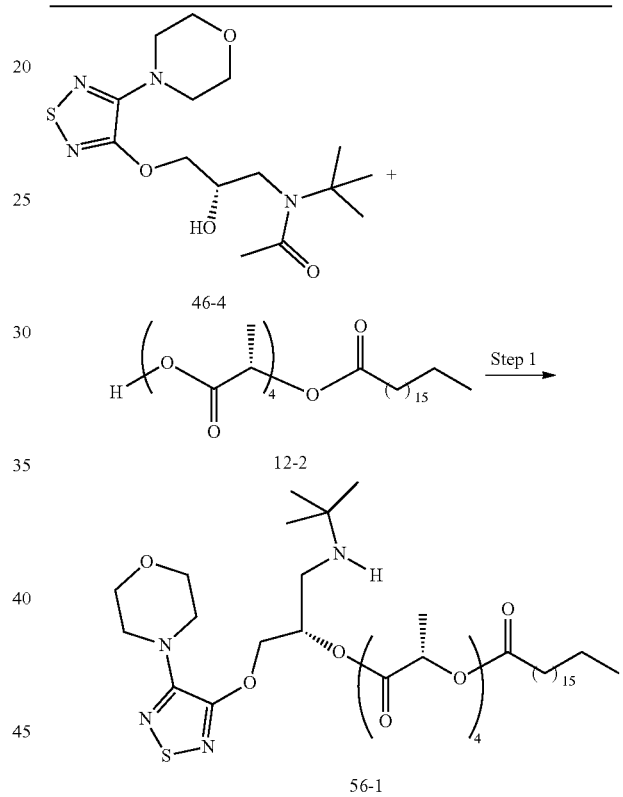

Step-1: Preparation of Octadecanoic acid (S)-1-[(S)-1-((S)-1-{(S)-1-[(S)-1-[(acetyl-tert-butyl-amino)-methyl]-2-(4-morpholin-4-yl-[1,2,5]thiadiazol-3-yloxy)-ethoxycarbonyl]-ethoxycarbonyl}-ethoxycarbonyl)-ethoxycarbonyl]-ethyl ester (56-1)

To a solution of octadecanoic acid (S)-1-{(S)-1-[(S)-1-((S)-1-carboxy-ethoxycarbonyl)-ethoxycarbonyl]-ethoxycarbonyl}-ethyl ester (12-2, 0.721 g, 1.26 mmol) in dichloromethane (3 mL) was added N,N'-dicyclohexylcarbodiimide (0.312 g, 1.51 mmol), N-tert-butyl-N—[(S)-2-hydroxy-3-(4-morpholin-4-yl-[1,2,5]thiadiazol-3-yloxy)-propyl]-acetamide (46-4, 0.3 g, 0.84 mmol) and 4-dimethylaminopyridine (10 mg, 0.08 mmol) at 0° C. The reaction mixture was allowed to stir at 25-30° C. over a period of 1 hour. The resulting reaction mass was quenched with water (100 mL) and extracted with dichloromethane (100×3 mL). The dichloromethane was dried over sodium sulfate, filtered and concentrated under reduced pressure. The crude product obtained upon evaporation of volatiles was purified through silica gel (230-400) column (32% ethyl acetate in hexane) to obtain product 56-1 as a colorless wax (300 mg, 39%). $^1$H-NMR (400 MHz, DMSO-d6) δ 5.46-5.39 (m, 1H), 5.22 (q, 1H), 5.13 (q, 1H), 5.08-5.01 (m, 2H), 4.55 (dd, 1H), 4.41 (dd, 1H), 3.80-3.64 (m, 6H), 3.41-3.36 (m, 4H), 2.33 (t, 2H), 2.08 (s, 3H), 1.55-1.18 (m, 51H) 0.85 (t, 3H). MS m/z [M+H]$^+$ 914.3.

Example 3. Synthesis of Bis-Prodrugs

Synthesis of Dorzolamide-Timolol Bis-Prodrugs

Scheme 56: Synthesis of (S)-2-Hydroxy-propionic acid (S)-2-((4S,6S)-4-ethylamino-6-methyl-7,7-dioxo-4,5,6,7-tetrahydro-7λ*6*-thieno[2,3-b]thiopyran-2-sulfonylamino)-1-methyl-2-oxo-ethyl eser (56-2):

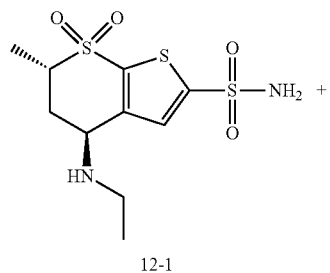

12-1

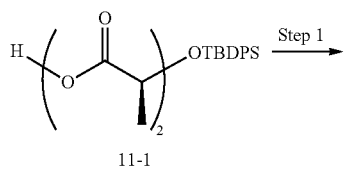

11-1

Step 1

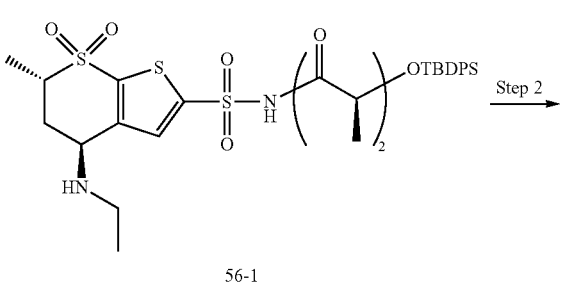

56-1

Step 2

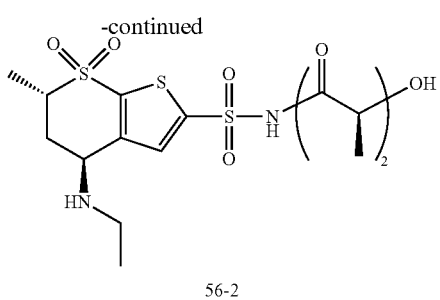

56-2

Step-1: Preparation of (S)-2-(tert-Butyl-diphenyl-silanyloxy)-propionic acid (S)-2-((4S,6S)-4-ethyl-amino-6-methyl-7,7-dioxo-4,5,6,7-tetrahydro-7λ*6*-thieno[2,3-b]thiopyran-2-sulfonylamino)-1-methyl-2-oxo-ethyl ester (56-1)

To a solution of Dorzolamide (12-1, 1.2 g, 3.33 mmol) in dichloromethane (12 mL) was added N,N-diisopropylethylamine (1.2 mL, 6.66 mmol) at 0° C. After 30 minutes, (S)-2-(tert-butyl-diphenyl-silanyloxy)-propionic acid (S)-1-carboxy-ethyl ester (11-4, 2.0 g, 5.01 mmol), EDC.HCl (1.27 g, 6.68 mmol) and 4-dimethylaminopyridine (0.04 g, 0.033 mmol) were added at 0° C. The reaction mixture was allowed to stir at 25-30° C. over a period of 1 hour. The resulting reaction mass was quenched with water (100 mL) and extracted with dichloromethane (200×3 mL). The dichloromethane was dried over sodium sulfate, filtered and concentrated under reduced pressure. The crude product obtained upon evaporation of volatiles was purified through silica gel (230-400) column (6% methanol in DCM) to obtain product 56-1 as a pale yellow solid (1.4 g, 60%).

Step-2: Preparation of (S)-2-Hydroxy-propionic acid (S)-2-((4S,6S)-4-ethylamino-6-methyl-7,7-dioxo-4,5,6,7-tetrahydro-7λ*6*-thieno[2,3-b]thiopyran-2-sulfonylamino)-1-methyl-2-oxo-ethyl ester (56-2)

To a solution of (S)-2-(tert-butyl-diphenyl-silanyloxy)-propionic acid (S)-1-[ethyl-((4S,6S)-6-methyl-7,7-dioxo-2-sulfamoyl-4,5,6,7-tetrahydro-7λ*6*-thieno[2,3-b]thiopyran-4-yl)-carbamoyl]-ethyl ester (56-1, 1.4 g, 1.98 mmol) in tetrahydrofuran (15 mL) was added tetra butyl ammonium fluoride (2.97 mL, 1.0 M, 2.97 mmol) and acetic acid (0.17 g, 2.97 mmol) at 0° C. The reaction mixture was allowed to stir at room temperature over a period of 12 hours. The resulting reaction mixture was concentrated under reduced pressure and crude product obtained upon evaporation of volatiles was purified through silica gel column chromatography (4% methanol in ethyl acetate) to give product 56-2 as an off white solid (850 mg, 92%).

Scheme 57: Synthesis of compound 57-4:
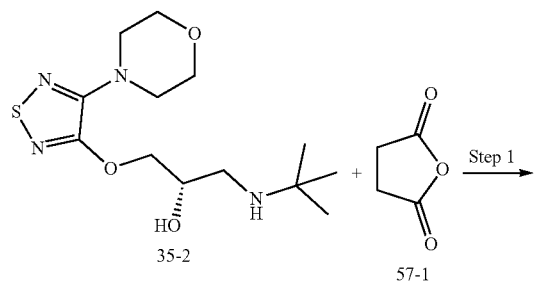
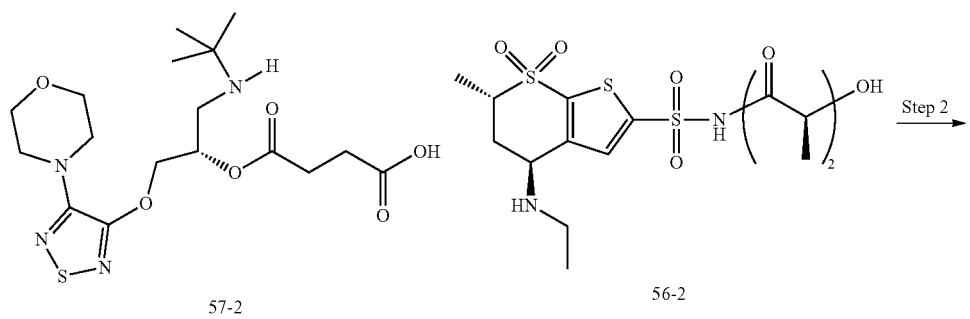
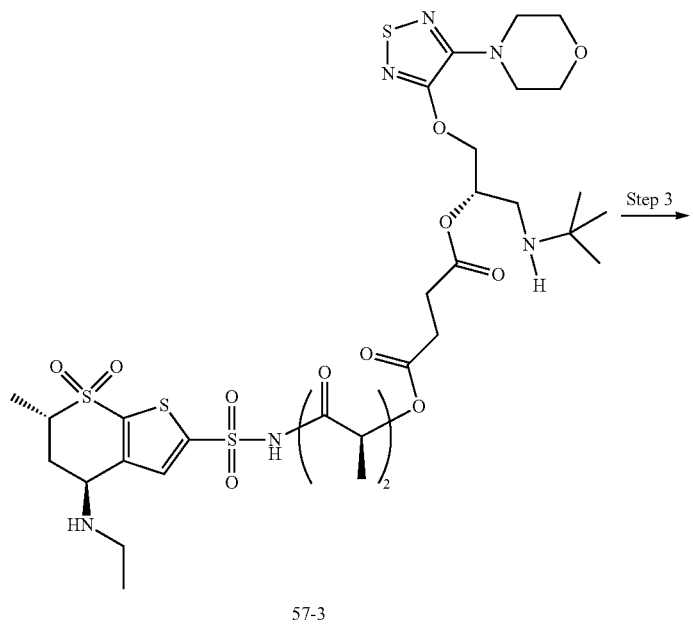

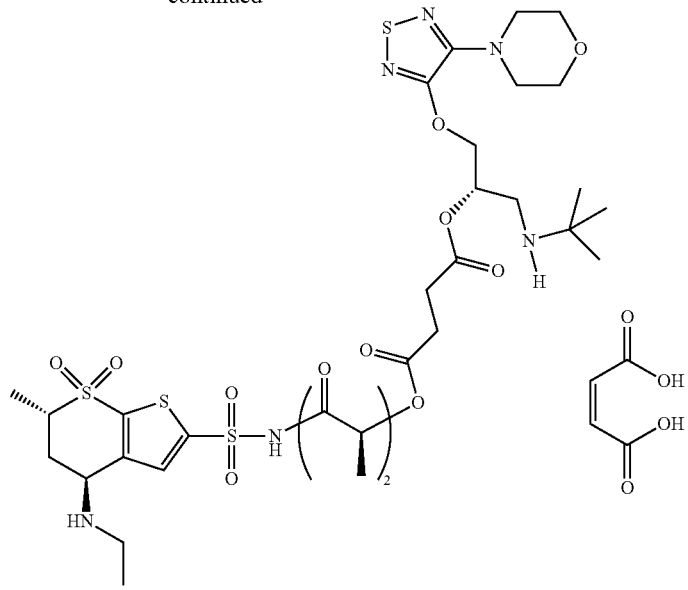

57-4

Step-1: Preparation of Succinic acid mono-[(S)-1-(tert-butylamino-methyl)-2-(4-morpholin-4-yl-[1,2,5]thiadiazol-3-yloxy)-ethyl] ester (57-2)

To a solution of (S)-1-tert-butylamino-3-(4-morpholin-4-yl-[1,2,5]thiadiazol-3-yloxy)-propan-2-ol (35-2, 1.0 g, 3.16 mmol) in dichloromethane (10 mL) was added dihydrofuran-2,5-dione (57-1, 0.35 g, 3.48 mmol) and 4-dimethylaminopyridine (0.039 g, 0.31 mmol) at 0° C. The reaction mixture was allowed to stir at room temperature over a period of 2 hours. The resulting reaction mixture was concentrated under reduced pressure to give product 57-2 as an off white solid (800 mg, 61%). $^1$H-NMR (400 MHz, DMSO-d6) δ 5.25-5.14 (m, 1H), 4.60 (dd, 1H), 4.46 (dd, 1H), 3.72-3.64 (m, 4H), 3.46-3.36 (m, 4H), 2.84-2.74 (m, 2H), 2.51-2.36 (m, 4H), 1.05 (s, 9H). MS m/z (M+H) 417.8.

Step-2: Preparation of Compound 57-3

To a solution of succinic acid mono-[(S)-1-(tert-butylamino-methyl)-2-(4-morpholin-4-yl-[1,2,5]thiadiazol-3-yloxy)-ethyl] ester (57-2, 0.71 g, 1.70 mmol) in dichloromethane (5 mL) were added EDC.HCl (0.4 g, 2.13 mmol), ((S)-2-hydroxy-propionic acid (S)-2-((4S,6S)-4-ethylamino-6-methyl-7,7-dioxo-4,5,6,7-tetrahydro-7*6*-thieno[2,3-b]thiopyran-2-sulfonylamino)-1-methyl-2-oxo-ethyl ester (56-2, 0.5 g, 1.06 mmol) and 4-dimethylaminopyridine (13 mg, 0.106 mmol) at 0° C. The reaction mixture was allowed to stir at 25-30° C. over a period of 1 hour. The resulting reaction mass was quenched with water (100 mL) and extracted with dichloromethane (200×3 mL). The dichloromethane was dried over sodium sulfate, filtered and concentrated under reduced pressure. The crude product obtained upon evaporation of volatiles was purified through silica gel (230-400) column (6% methanol in DCM) to obtain product 57-3 as an off white solid (0.3 g, 33%). $^1$H-NMR (400 MHz, DMSO-d6) δ 7.40 (s, 1H), 5.43-5.34 (m, 1H), 4.96 (q, J=7 Hz, 1H), 4.79 (q, J=7 Hz, 1H), 4.62 (dd, 1H), 4.48 (dd, 1H), 3.95-4.84 (m, 1H), 3.71-3.65 (m, 4H), 3.42-3.34 (m, 6H), 2.69-2.5 (m, 6H), 2.4-2.2 (m, 2H), 1.44 (d, J=7.0 Hz, 3H), 1.36-1.15 (m, 16H), 1.04 (t, 3H). MS m/z (M−H)⁻ 866.1.

Step-3: Preparation of Compound 57-4

To a solution of compound 57-3 (0.3 g, 0.346 mmol) in acetone (1.5 mL) was added maleic acid (36 mg, 0.311 mmol) at 0° C. The reaction mixture was allowed to stir at room temperature over a period of 20 minutes. The resulting reaction mixture was concentrated under reduced pressure to give product 57-4 as an off white solid (0.32 g, 94%). $^1$H-NMR (400 MHz, DMSO-d6) δ 8.75 (bs, 2H), 8.55 (bs, 1H), 8.28 (bs, 1H), 7.70 (s, 1H), 6.06 (s, 2H, Maleate), 5.46-5.36 (m, 1H), 4.96 (q, 1H), 4.80 (q, 1H), 4.66-4.58 (m, 2H), 4.48 (dd, 1H), 4.00-3.91 (m, 1H), 3.71-3.65 (m, 4H), 3.5-3.1 (m, 7H), 3.07-2.95 (m, 1H), 2.7-2.5 (m, 6H), 1.45 (d, 3H), 1.37 (d, 3H), 1.32-1.25 (m, 12H), 1.21 (t, 3H). MS m/z [M−H]⁻ 866.2.

Scheme 58

Synthesis of Compound 58-3:

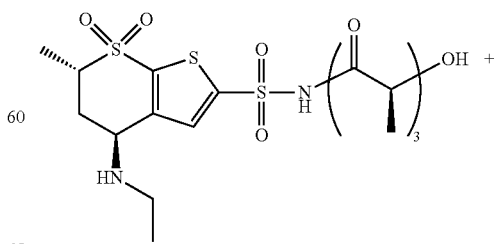

56-2

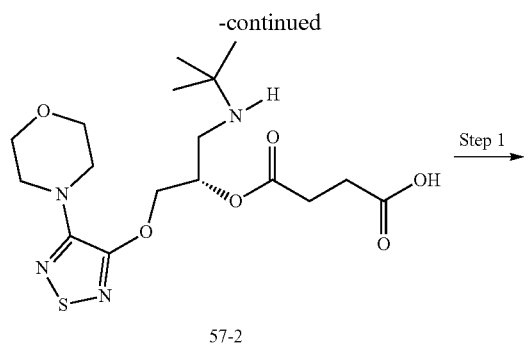

57-2

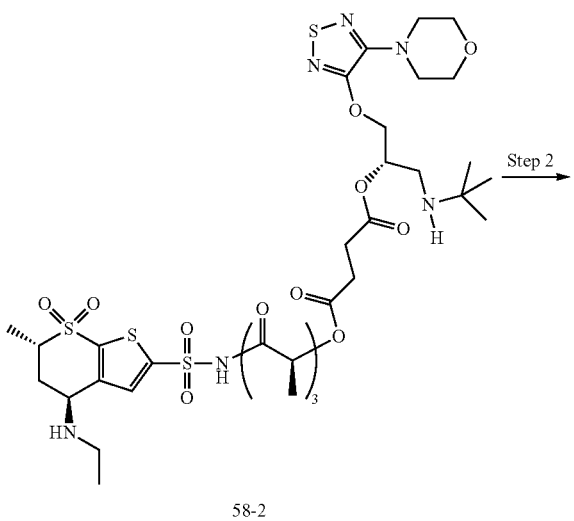

58-2

Step-1: Preparation of Compound 58-2

To a solution of succinic acid mono-[(S)-1-(tert-butylamino-methyl)-2-(4-morpholin-4-yl-[1,2,5]thiadiazol-3-yloxy)-ethyl] ester (57-2, 0.61 g, 1.48 mmol) in dichloromethane (5 mL) was added EDC.HCl (0.353 g, 1.85 mmol), 2-hydroxy-propionic acid 1-[2-((4S,6S)-4-ethyl-amino-6-methyl-7,7-dioxo-4,5,6,7-tetrahydro-7λ*6*-thieno[2,3-b]thiopyran-2-sulfonylamino)-1-methyl-2-oxo-ethoxycarbonyl]-ethyl ester (58-1, 0.5 g, 0.92 mmol) and 4-dimethylaminopyridine (11 mg, 0.092 mmol) at 0° C. The reaction mixture was allowed to stir at 25-30° C. over a period of 1 hour. The resulting reaction mass was quenched with water (100 mL) and extracted with dichloromethane (200×3 mL). The dichloromethane was dried over sodium sulfate, filtered and concentrated under reduced pressure. The crude product obtained upon evaporation of volatiles was purified through silica gel (230-400) column (4% methanol in DCM) to obtain product 58-2 as an off white solid (0.1 g, 11%). 1H-NMR (400 MHz, DMSO-d6) δ 8.55 (bs, 1H), 8.4 (bs, 1H), 7.40 (bs, 1H), 5.45-5.33 (m, 1H), 5.10-5.01 (m, 2H), 4.79 (q, 1H), 4.66-4.58 (dd, 1H), 4.48 (dd, 1H), 3.94-3.82 (m, 2H), 3.71-3.64 (m, 4H), 3.47-3.35 (m, 6H), 3.25-3.10 (m, 2H), 2.75-2.58 (m, 4H), 2.4-2.2 (m, 2H), 1.48 (d, 3H), 1.42 (d, 3H), 1.33-1.15 (m, 15H), 1.04 (t, 3H). MS m/z [M−H]⁻ 938.2.

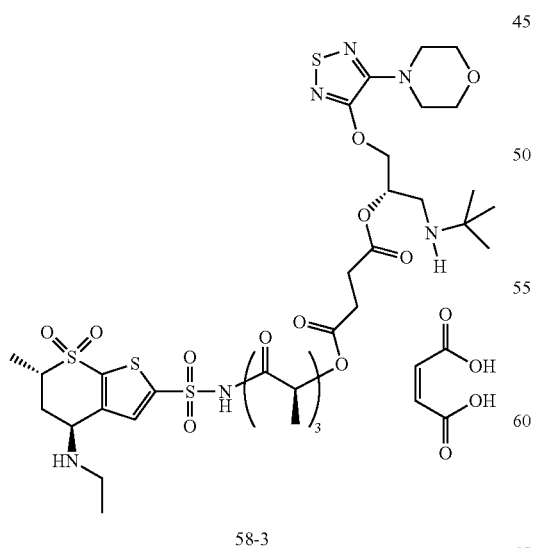

58-3

Step-2: Preparation of Compound 58-3

To a solution of compound 58-2 (0.1 g, 0.106 mmol) in acetone (1 mL) was added maleic acid (11 mg, 0.095 mmol) at 0° C. The reaction mixture was allowed to stir at room temperature over a period of 20 minutes. The resulting reaction mixture was concentrated under reduced pressure to give product 58-3 as an off white solid (0.1 g, 92%). ¹H-NMR (400 MHz, DMSO-d6) δ 8.75 (bs, 2H), 8.54 (bs, 1H), 8.29 (bs, 1H), 7.70 (s, 1H), 6.08 (s, 2H, Maleate), 5.46-5.36 (m, 1H), 5.11-5.01 (m, 2H), 4.81 (q, 1H), 4.66-4.56 (m, 2H), 4.48 (dd, 1H), 4.01-3.91 (m, 1H), 3.71-3.64 (m, 4H), 3.5-3.1 (m, 7H), 3.09-2.95 (m, 1H), 2.7-2.5 (m, 6H), 1.49 (d, 3H), 1.41 (d, 3H), 1.37 (d, 3H), 1.32-1.25 (m, 12H), 1.21 (t, 3H). MS m/z [M−H]⁻ 938.2.

Synthesis of Brinzolamide-Timolol Bis-Prodrugs
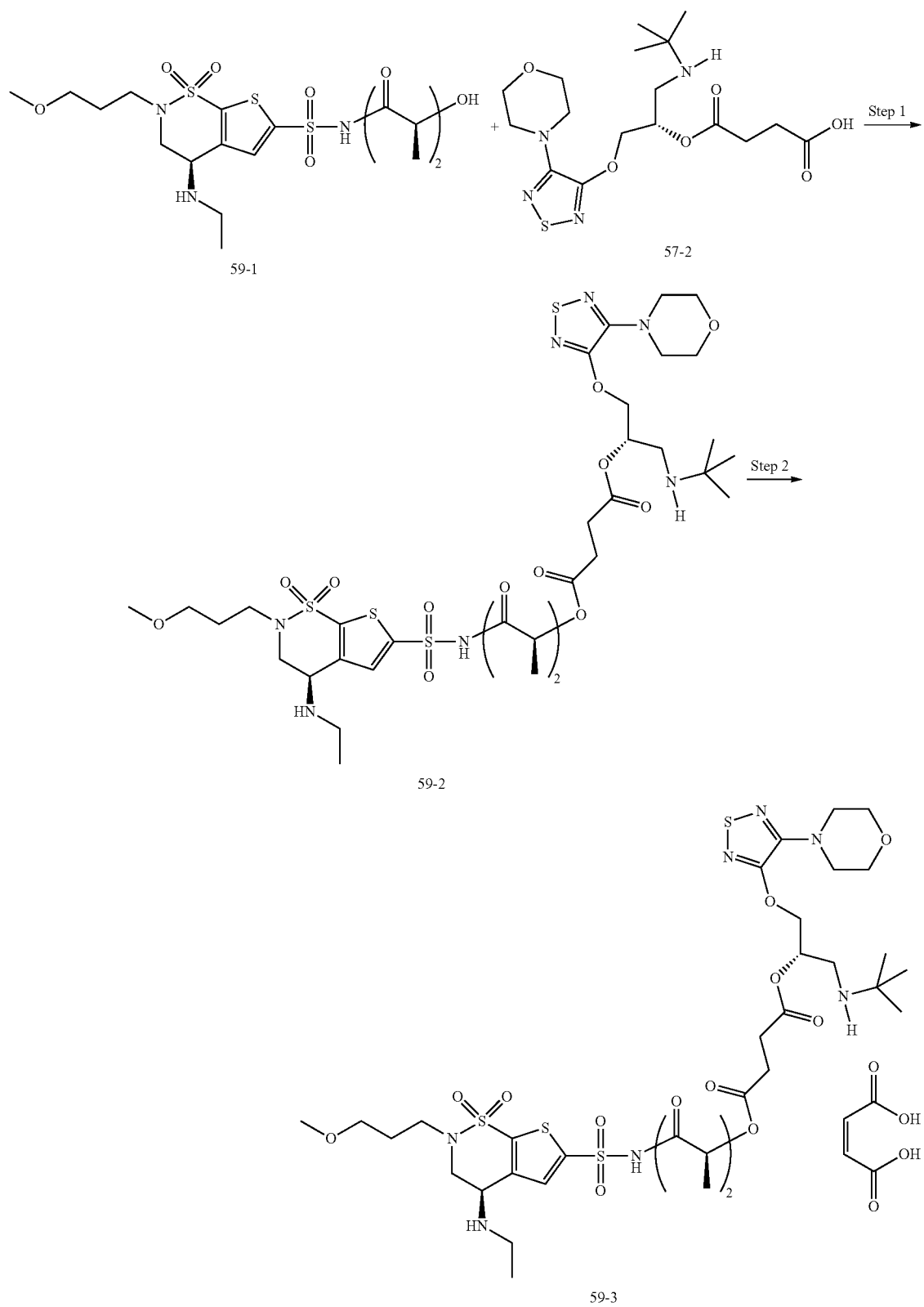

Step-1: Preparation of Compound 59-2

To a solution of succinic acid mono-[(S)-1-(tert-butylamino-methyl)-2-(4-morpholin-4-yl-[1,2,5]thiadiazol-3-yloxy)-ethyl] ester (57-2, 0.506 g, 1.22 mmol) in dichloromethane (5 mL) was added EDC.HCl (0.29 g, 1.59 mmol), 2-hydroxy-propionic acid 2-[(R)-4-ethylamino-2-(3-methoxy-propyl)-1,1-dioxo-1,2,3,4-tetrahydro-1λ*6*-thieno[3,2-e][1,2]thiazine-6-sulfonylamino]-1-methyl-2-oxo-ethyl ester (59-1, 0.4 g, 0.76 mmol) and 4-dimethylaminopyridine (10 mg, 0.012 mmol) at 0° C. The reaction mixture was allowed to stir at 25-30° C. over a period of 1 hour. The resulting reaction mass was quenched with water (100 mL) and extracted with dichloromethane (200×3 mL). The dichloromethane was dried over sodium sulfate, filtered and concentrated under reduced pressure. The crude product obtained upon evaporation of volatiles was purified through silica gel (230-400) column (4% methanol in DCM) to obtain product 59-2 as an off white solid (0.15 g (21%). $^1$H-NMR (400 MHz, DMSO-d6) δ 8.55 (bs, 1H), 8.29 (bs, 1H), 7.48 (s, 1H), 5.46-5.34 (m, 1H), 4.96 (q, 1H), 4.79 (q, 1H), 4.63 (dd, 1H), 4.48 (dd, 1H), 4.11-3.98 (m, 1H), 3.81-3.65 (m, 6H), 3.5-3.3 (m, 8H), 3.3-3.08 (m, 5H), 2.75-2.5 (m, 6H), 1.79 (quintet, 2H), 1.44 (d, 3H), 1.35-1.1 (m, 13H), 1.01 (t, 3H). MS m/z (M+H)$^+$ 926.8

Step-2: Preparation of Compound 59-3

To a solution of compound 59-2 (0.15 g, 0.161 mmol) in acetone (1 mL) was added maleic acid (17 mg, 0.145 mmol) at 0° C. The reaction mixture was allowed to stir at room temperature over a period of 10 minutes. The resulting reaction mixture was concentrated under reduced pressure to give product 59-3 as an off white solid (0.16 g, 94%). $^1$H-NMR (400 MHz, DMSO-d6) δ 9.1 (bs, 2H), 8.56 (bs, 1H), 8.29 (bs, 1H), 7.79 (s, 1H), 6.09 (s, 2H, Maleate), 5.46-5.36 (m, 1H), 4.96 (q, 1H), 4.86-4.77 (m, 2H), 4.62 (dd, 1H), 4.48 (dd, 1H), 4.11-3.96 (m, 1H), 3.71-3.65 (m, 4H), 3.5-3.3 (m, 8H), 3.3-3.0 (m, 7H), 2.73-2.59 (m, 4H), 1.89-1.77 (m, 2H), 1.45 (d, 3H), 1.32-1.25 (m, 12H), 1.21 (t, 3H). MS m/z [M+H]$^+$ 926.8.

Scheme 60: Synthesis of Compound 60-3:

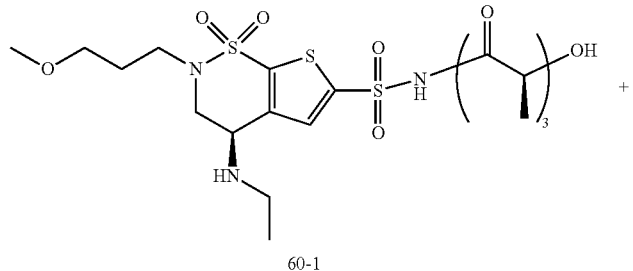

60-1

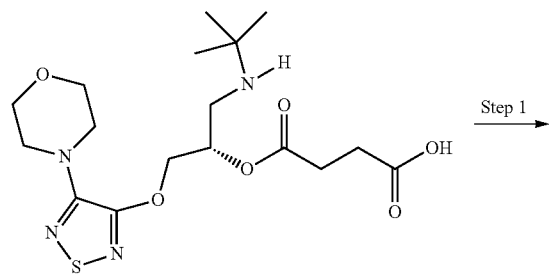

57-2

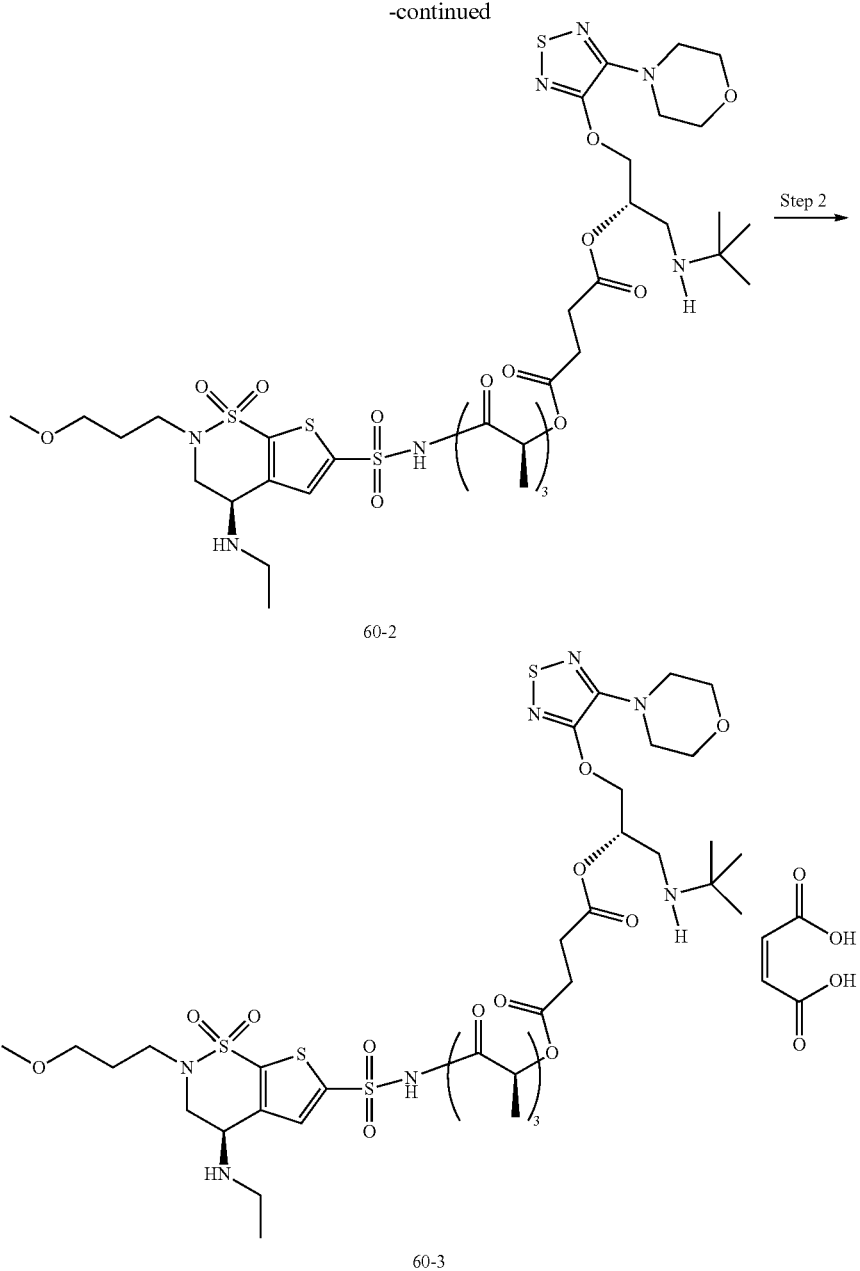

60-2

60-3

Step-1: Preparation of Compound 60-2

To a solution of succinic acid mono-[(S)-1-(tert-butylamino-methyl)-2-(4-morpholin-4-yl-[1,2,5]thiadiazol-3-yloxy)-ethyl] ester (57-2, 0.66 g, 1.60 mmol) in dichloromethane (6 mL) was added EDC.HCl (0.382 g, 2.0 mmol), 2-hydroxy-propionic acid 1-{2-[(R)-4-ethylamino-2-(3-methoxy-propyl)-1,1-dioxo-1,2,3,4-tetrahydro-1λ*6*-thieno[3,2-e][1,2]thiazine-6-sulfonylamino]-1-methyl-2-oxo-ethoxycarbonyl}-ethyl ester (60-1, 0.6 g, 1.00 mmol) and 4-dimethylaminopyridine (12 mg, 0.010 mmol) at 0° C. The reaction mixture was allowed to stir at 25-30° C. over a period of 1 hour. The resulting reaction mass was quenched with water (100 mL) and extracted with dichloromethane (200×3 mL). The dichloromethane was dried over sodium sulfate, filtered sulfate and concentrated under reduced pressure. The crude product obtained upon evaporation of volatiles was purified through silica gel (230-400) column (4% methanol in DCM) to obtain product 60-2 as an off white solid (0.13 g, 19%). $^1$H-NMR (400 MHz, DMSO-d6) δ 8.56 (bs, 1H), 8.27 (bs, 1H), 7.49 (bs, 1H), 5.40 (bs, 1H), 5.09-5.01 (m, 2H), 4.79 (q, 1H), 4.62 (dd, 1H), 4.48 (dd, 1H), 4.11-3.98 (m, 1H), 3.82-3.66 (m, 6H), 3.48-3.32 (m, 8H), 3.25-3.08 (m, 5H), 2.74-2.5 (m, 6H), 1.80 (quintet, 2H), 1.47 (d, 3H), 1.41 (d, 3H), 1.32-1.18 (m, 13H), 1.02 (t, 3H). MS m/z (M+H)$^+$ 999.1.

Step-2: Preparation of Compound 60-3

To a solution of compound 60-2 (0.13 g, 0.161 mmol) in acetone (1 mL) was added maleic acid (17 mg, 0.145 mmol) at 0° C. The reaction mixture was allowed to stir at room temperature over a period of 20 minutes. The resulting reaction mixture was concentrated under reduced pressure to afford product 60-3 as an off white solid (0.135 g, 93%). ¹H-NMR (400 MHz, DMSO-d6) δ 9.1 (bs, 2H), 8.59 (bs, 1H), 8.33 (bs, 1H), 7.78 (s, 1H), 6.05 (s, 2H, Maleate), 5.46-5.36 (m, 1H), 5.11-5.01 (m, 2H), 4.85-4.75 (m, 2H), 4.62 (dd, 1H), 4.48 (dd, 1H), 4.12-3.94 (m, 2H), 3.72-3.65 (m, 4H), 3.5-3.3 (m, 8H), 3.25-2.95 (m, 7H), 2.73-2.59 (m, 4H), 1.89-1.79 (m, 2H), 1.49 (d, 3H), 1.41 (d, 3H), 1.33-1.25 (m, 12H), 1.19 (t, 3H). MS m/z [M+H]⁺ 999.1.

Synthesis of Latanoprost:Sunitinib Bis-Prodrugs (Compounds of Formula VII)

EDC.HCl (0.132 g, 0.694 mmol), Latanoprost (61-2, 0.1 g, 0.231 mmol) and 4-dimethylaminopyridine (3 mg, 0.023 mmol) at 0° C. The reaction mixture was allowed to stir at 25-30° C. over a period of 2 hours. The resulting reaction mass was quenched with water (100 mL) and extracted with dichloromethane (200×3 mL). The dichloromethane was dried over sodium sulfate, filtered and concentrated under reduced pressure. The crude product obtained upon evaporation of volatiles was purified through silica gel (230-400) column (4% methanol in DCM) and further purified by preparative-HPLC to obtain product 61-3 as pale yellow solid (0.05 g, 20%). ¹H-NMR (400 MHz, DMSO-d6) δ

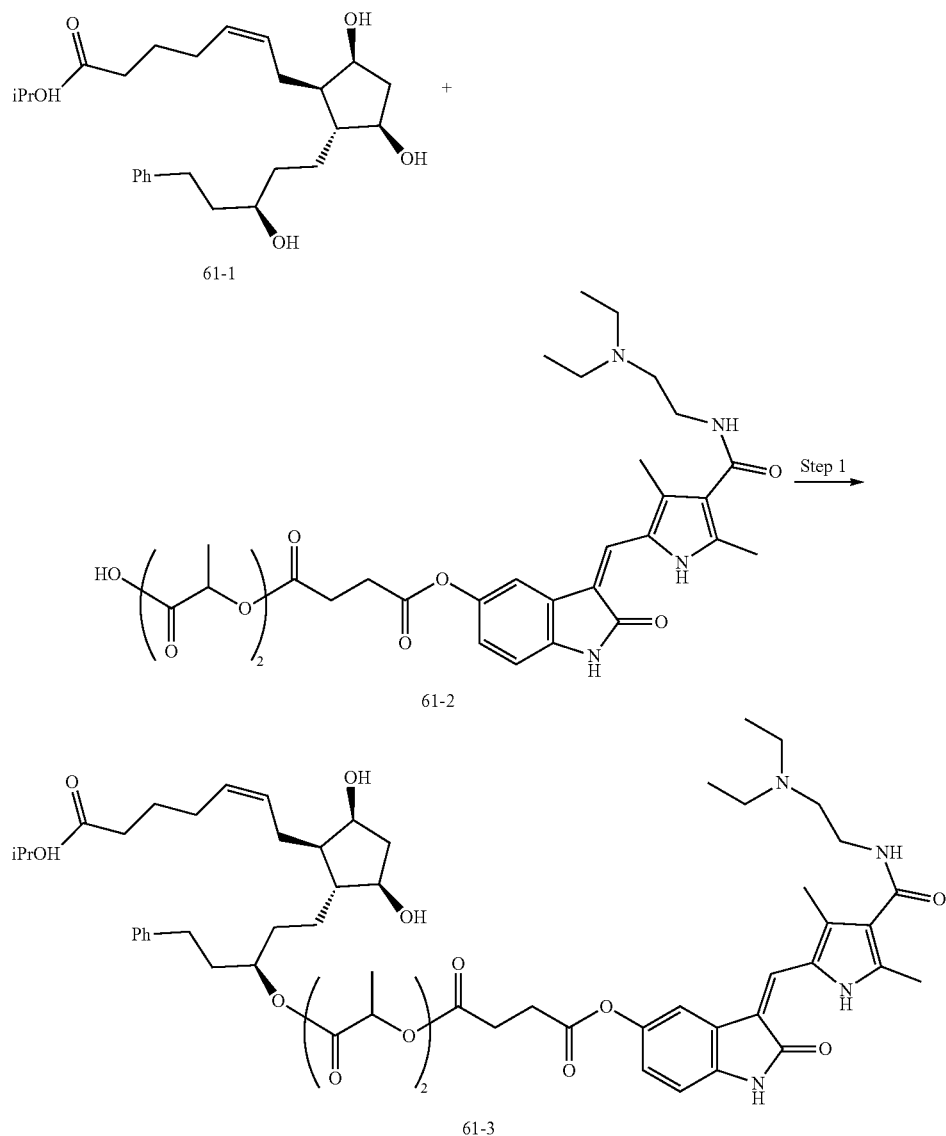

Step-1: Preparation of Compound 61-1

To a solution of (2S)-2-{[(2S)-2-[(4-{[(3Z)-3-[(4-{[2-(diethylamino)ethyl]carbamoyl}-3,5-dimethyl-1H-pyrrol-2-yl)methylidene]-2-oxo-2,3-dihydro-1H-indol-5-yl]oxy}-4-oxobutanoyl)oxy]propanoyl]oxy}propanoic acid (61-1, 0.3 g, 0.462 mmol) in dichloromethane (6 mL) was added 13.67 (s, 1H), 10.94 (s, 1H), 8.19 (s, 1H, formate), 7.67 (s, 1H), 7.59 (s, 1H), 7.48 (t, 1H), 7.30-7.21 (m, 2H), 7.20-7.10 (m, 3H), 6.90-6.78 (m, 2H), 5.5-4.7 (m, 6H), 4.6 (bs, 1H), 4.4 (bs, 1H), 3.9-3.3 (m, 4H), 2.9-2.5 (m, 12H), 2.44 (s, 3H), 2.40 (s, 3H), 2.25-1.8 (m, 7H), 1.7-1.1 (m, 17H), 1.13 (d, 6H), 0.98 (t, 6H). MS m/z (M+H)* 1056.4, (M+2H)++ 641.6.

Scheme 62: Synthesis of compound 62-6:
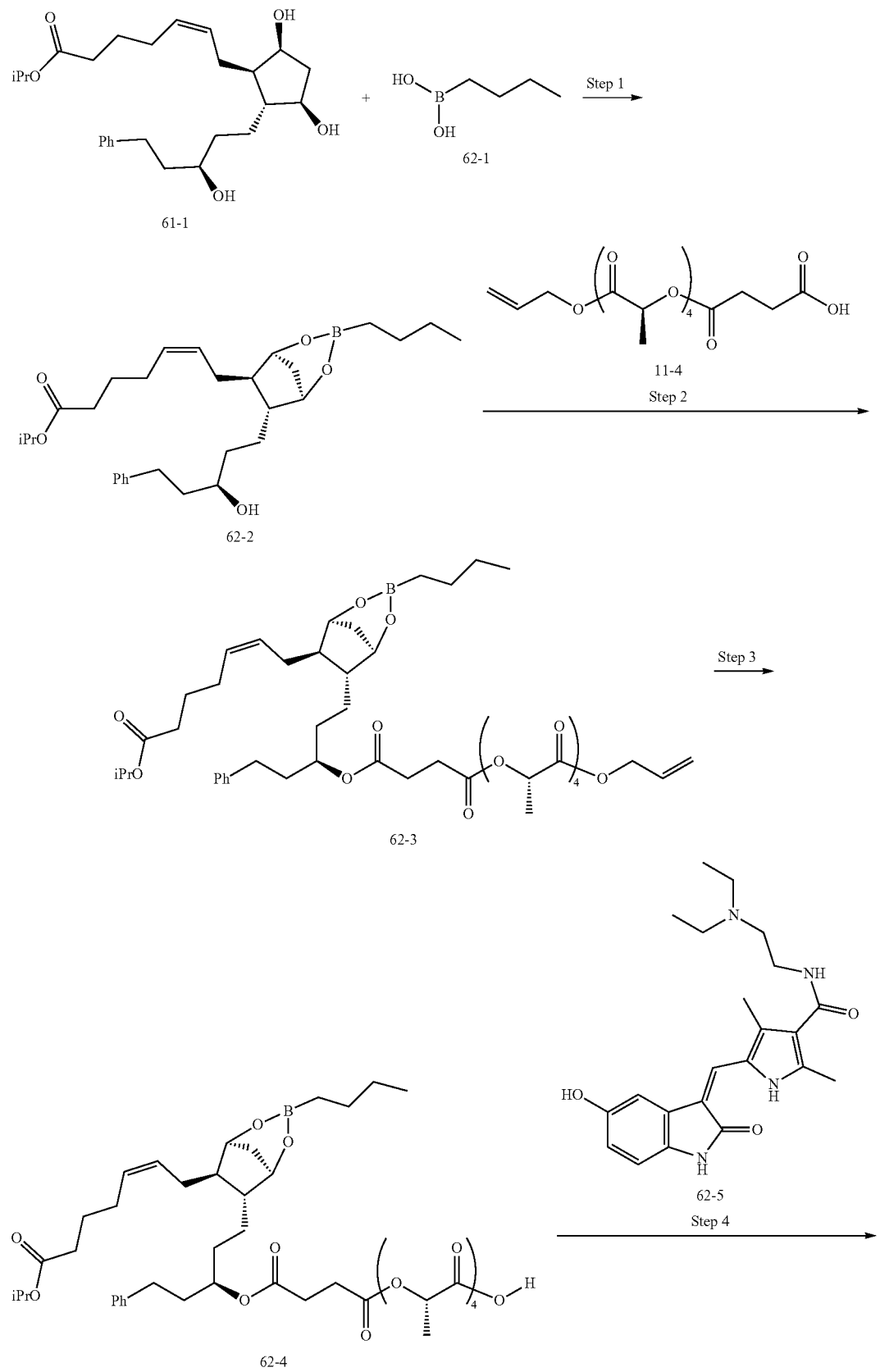

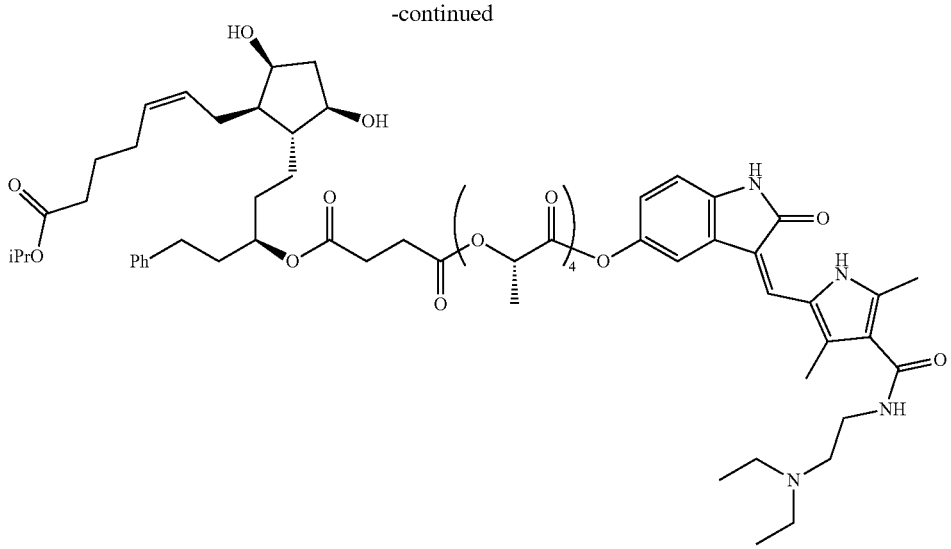

62-6

Step-1: Preparation of isopropyl (Z)-7-((1R,5S,6R, 7R)-3-butyl-7-((R)-3-hydroxy-5-phenylpentyl)-2,4-dioxa-3-borabicyclo[3.2.1]octan-6-yl)hept-5-enoate (62-2)

To a solution of Latanoprost (61-1, 3.0 g, 6.94 mmol) in anhydrous dichloromethane (30 mL) was added n-butylboronic acid (62-1, 0.778 g, 7.63 mmol). The mixture was heated at 45° C. for 1 hour under a nitrogen atmosphere. Solvent was removed and the residue was dried in vacuo. Additional anhydrous dichloromethane was added and removed in vacuo for an additional 3 hours. The residue was further heated in anhydrous dichloromethane at 45° C. for 16 hours and the solvent was removed under reduced pressure to obtain product 62-2 as a colorless oil (2.8 g, 80%). $^1$H-NMR (400 MHz, CDCl$_3$) δ 7.33-7.25 (m, 2H), 7.25-7.17 (m, 3H), 5.52-5.37 (m, 2H), 5.01 (quintet, 1H), 4.33-4.28 (m, 1H), 4.08-4.04 (m, 1H), 3.68-3.60 (m, 1H), 2.86-2.76 (m, 1H), 2.73-2.63 (m, 1H), 2.31-2.21 (m, 4H), 2.16-2.09 (m, 2H), 1.96-1.91 (m, 1H), 1.82-1.47 (m, 9H), 1.43-1.22 (m, 12H), 0.88 (t, 3H), 0.67 (t, 2H).

Step-2: Preparation of (62-3)

To a solution of succinic acid mono-((S)-1-{(S)-1-[(S)-1-((S)-1-allyloxycarbonyl-ethoxycarbonyl)-ethoxycarbonyl]-ethoxycarbonyl}-ethyl) ester (11-4, 3.58 g, 8.02 mmol) in dichloromethane (20 mL) was added N,N'-diisopropylcarbodiimide (1.26 mL, 8.02 mmol), (Z)-7-[(1S,5R,6R,7R)-3-butyl-7-((R)-3-hydroxy-5-phenyl-pentyl)-2,4-dioxa-3-borabicyclo[3.2.1]oct-6-yl]-hept-5-enoic acid isopropyl ester (62-2, 2.0 g, 4.01 mmol) and 4-dimethylaminopyridine (48 mg, 0.40 mmol) at 0° C. The reaction mixture was allowed to stir at 25-30° C. over a period of 2 hours. The resulting reaction mass was quenched with water (100 mL) and extracted with dichloromethane (200×3 mL). The dichloromethane was dried over sodium sulfate, filtered and concentrated under reduced pressure. The crude product obtained upon evaporation of volatiles was purified through silica gel (230-400) column (30% ethyl acetate in hexane) to obtain product 62-3 as colorless liquid (2.5 g, 67%).

Step-3: Preparation of (62-4)

To a solution succinic acid (R)-1-{(R)-1-[(R)-1-((R)-1-allyloxycarbonyl-ethoxycarbonyl)-ethoxycarbonyl]-ethoxycarbonyl}-ethyl ester (R)-3-[(1R,5S,6R,7R)-3-butyl-7-((Z)-6-isopropoxycarbonyl-hex-2-enyl)-2,4-dioxa-3-borabicyclo[3.2.1]oct-6-yl]-1-phenethyl-propyl ester (62-3, 2.5 g, 2.69 mmol) in tetrahydrofuran (25 mL) was added tetrakis(triphenylphosphine)palladium (0.31 g, 0.269 mmol) and pyrrolidine (0.22 mL, 2.56 mmol) at 0° C. The reaction mixture was allowed to stir at room temperature over a period of 2 hours. The resulting reaction mixture was concentrated under reduced pressure and crude product obtained upon evaporation of the volatiles was purified through silica gel column chromatography (8% methanol in dichloromethane) to afford product 62-4 as colorless liquid (1.2 g, 52%).

Step-4: Preparation of Compound 62-6

To a solution of succinic acid (R)-3-[(1R,5S,6R,7R)-3-butyl-7-((Z)-6-isopropoxycarbonyl-hex-2-enyl)-2,4-dioxa-3-bora-bicyclo[3.2.1]oct-6-yl]-1-phenethyl-propyl ester (R)-1-{(R)-1-[(R)-1-((R)-1-carboxy-ethoxycarbonyl)-ethoxycarbonyl]-ethoxycarbonyl}-ethyl ester (62-4, 0.45 g, 0.505 mmol) in dichloromethane (4 mL) was added N,N-diisopropylethylamine (0.12 mL, 0.631 mmol) at 0° C. After 5 minutes, EDC.HCl (0.12 g, 0.631 mmol), 5-hydroxy Sunitinib (62-5, 0.125 g, 0.315 mmol) and 4-dimethylaminopyridine (4 mg, 0.031 mmol) were added at 0° C. The reaction mixture was allowed to stir at 25-30° C. over a period of 1 hour. The resulting reaction mass was quenched with water (100 mL) and extracted with dichloromethane (200×3 mL). The dichloromethane was dried over sodium sulfate, filtered concentrated under reduced pressure. The crude product obtained upon evaporation of volatiles was purified was purified by preparative HPLC to obtain product 62-6 as a reddish yellow solid (40 mg, 10%). $^1$H-NMR (400 MHz, DMSO-d6) δ 13.74 (s, 1H), 11.01 (s, 1H), 7.8-7.6 (m, 3H), 7.29-7.22 (m, 2H), 7.19-7.12 (m, 3H), 6.92-6.81 (m, 2H), 5.5-4.7 (m, 8H), 4.48 (d, 1H), 4.26, (d, 1H), 3.9-3.8 (m, 1H), 3.6-3.5 (m, 1H), 3.3-3.1 (m, 2H), 2.7-2.4 (m, 18H), 2.3-1.9 (m, 7H), 1.8-1.3 (m, 23H), 1.3-1.0 (m, 12H). MS m/z [M+1] 1200.9

Synthesis of a Latanoprost:Brimonidine Bis-Prodrug

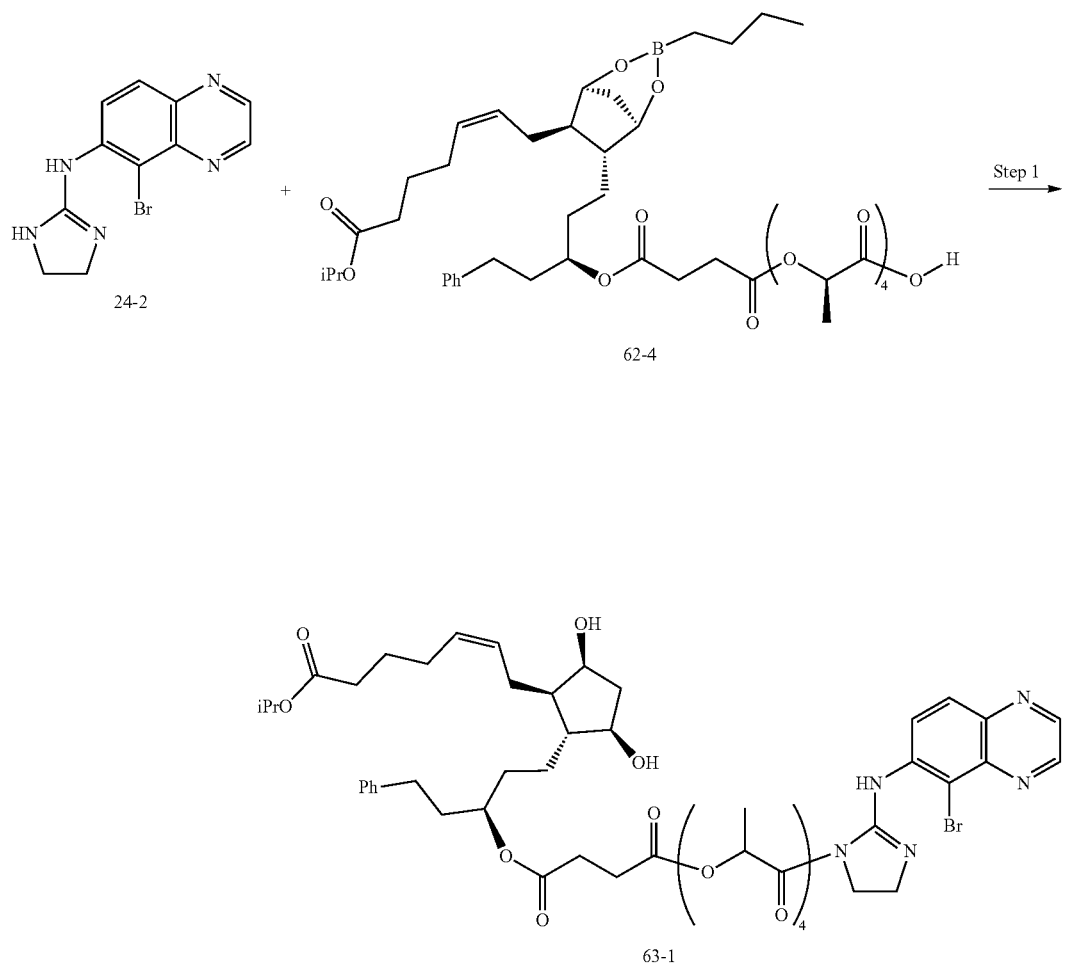

Scheme 63: Synthesis of compound 63-1:

Step-1: Preparation of Compound 63-1

To a solution of succinic acid 1-{1-[1-(1-carboxy-ethoxy-carbonyl)-ethoxycarbonyl]-ethoxy-carbonyl}-ethyl ester (R)-3-[(1R,2R,3R,5S)-3,5-dihydroxy-2-((Z)-6-isopropoxy-carbonyl-hex-2-enyl)-cyclopentyl]-1-phenethyl-propyl ester (62-4, 0.31 g, 0.385 mmol) in dichloromethane (3 mL) was added triethylamine (0.086 ml, 0.64 mmol), ethyl chloroformate (0.053 ml, 0.51 mmol), Brimonidine (24-2, 0.075 g, 0.256 mmol) and 4-dimethylaminopyridine (3 mg, 0.025 mmol) at 0° C. The reaction mixture was allowed to stir at 25-30° C. over a period of 1 hour. The resulting reaction mass was quenched with water (100 mL) and extracted with dichloromethane (200×2 mL). The dichloromethane was dried over sodium sulfate, filtered and concentrated under reduced pressure. The crude product obtained upon evaporation of volatiles was purified by preparative HPLC to obtain product 63-1 as a pale yellow solid (50 mg, 12%). $^1$H-NMR (400 MHz, DMSO-d6) δ 8.95 (d, J=2 Hz, 1H), 8.84 (d, J=2 Hz, 1H), 7.99 (d, J=9 Hz, 1H), 7.59 (d, J=9 Hz, 1H), 7.30-7.21 (m, 3H), 7.19-7.12 (m, 3H), 6.52 (q, 1H), 5.51-5.39 (m, 1H), 5.31-5.22 (m, 1H), 5.18 (q, 1H), 5.12 (q, 1H), 5.06 (q, 1H), 4.90-4.83 (m, 2H), 4.48 (d, 1H), 4.25 (d, 1H), 3.96-3.82 (m, 3H), 3.73-3.63 (m, 1H), 3.45-3.34 (m, 2H), 2.69-2.5 (m, 6H), 2.21 (t, 2H), 2.15-2.06 (m, 1H), 2.05-1.93 (m, 4H), 1.81-1.72 (m, 2H), 1.67-1.29 (m, 20H), 1.23-1.09 (m, 7H). MS m/z [M−H]⁻ 1094.2.

Example 4: Synthetic Examples to Describe Select Compounds of the Present Invention Scheme 64. Synthesis of Pentanedioic acid mono-[(S)-1-(tert-butylamino-methyl)-2-(4-morpholin-4-yl-[1,2,5]thiadiazol-3-yloxy)-ethyl] ester (64-2):

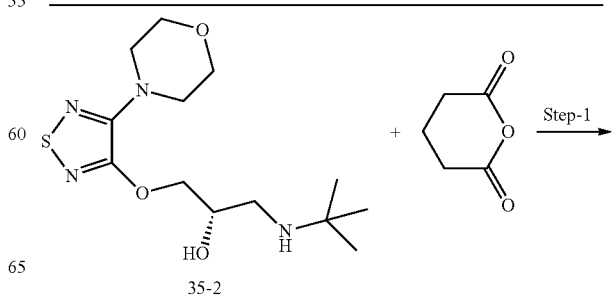

397
-continued

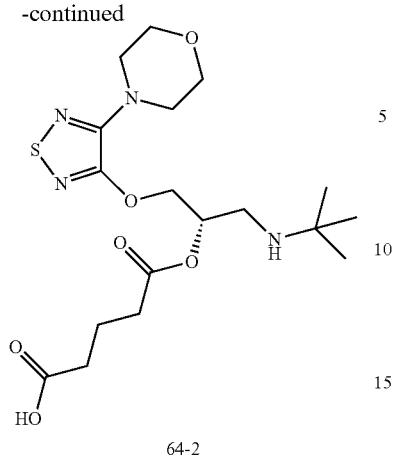

64-2

398

Step 1: Pentanedioic acid mono-[(S)-1-(tert-butylamino-methyl)-2-(4-morpholin-4-yl-[1,2,5]thiadiazol-3-yloxy)-ethyl] ester (64-2)

To a solution of (S)-1-tert-butylamino-3-(4-morpholin-4-yl-[1,2,5]thiadiazol-3-yloxy)-propan-2-ol 35-2 (2.0 g, 6.32 mmol) in dichloromethane (20 mL) were added dihydropyran-5,6-dione (0.86 g, 7.59 mmol) and 4-dimethylaminopyridine (0.079 g, 0.62 mmol) at 0° C. The reaction mixture was allowed to stir at room temperature over a period of 2 h. The resulting reaction mixture was concentrated under reduced pressure to afford product 64-2 as an off white solid 2.0 g (73%).

Scheme 65. Synthesis of Timolol-O-glutarate-PLA(n = 3)-Dorzolamide maleate salt (64-4):

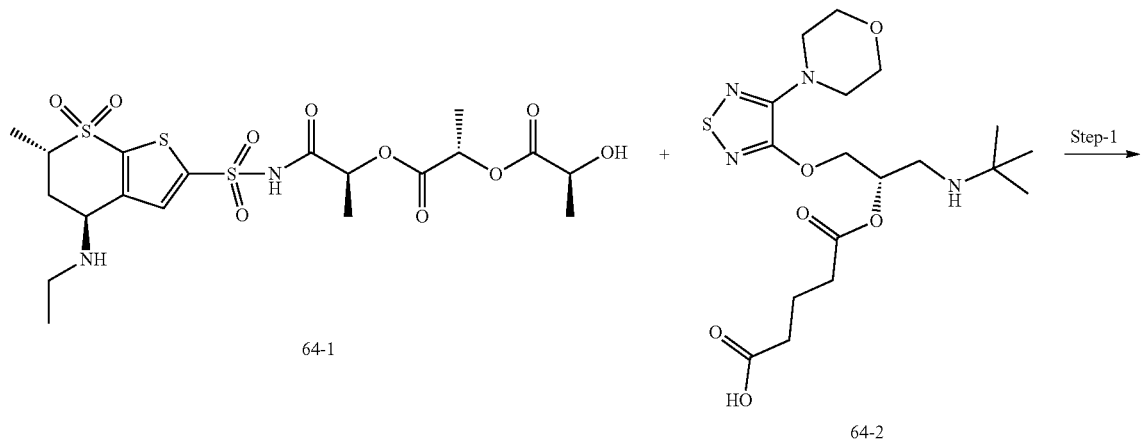

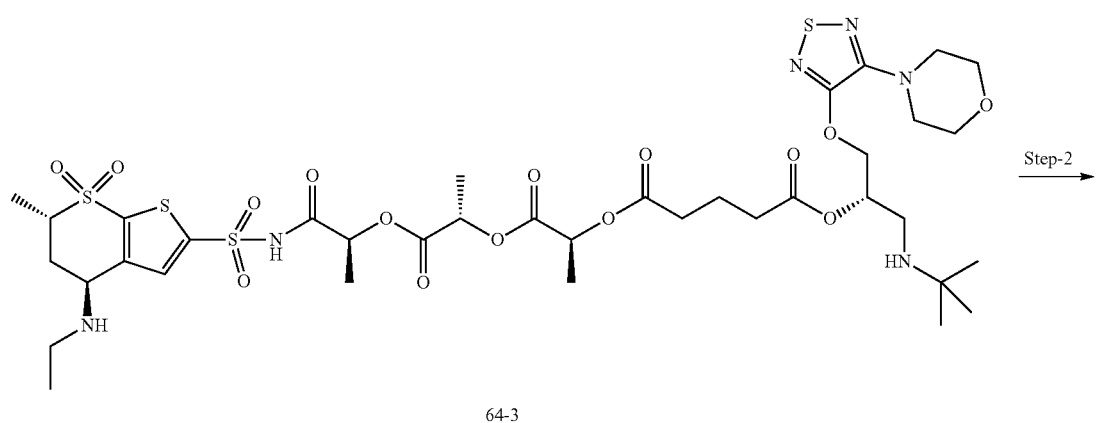

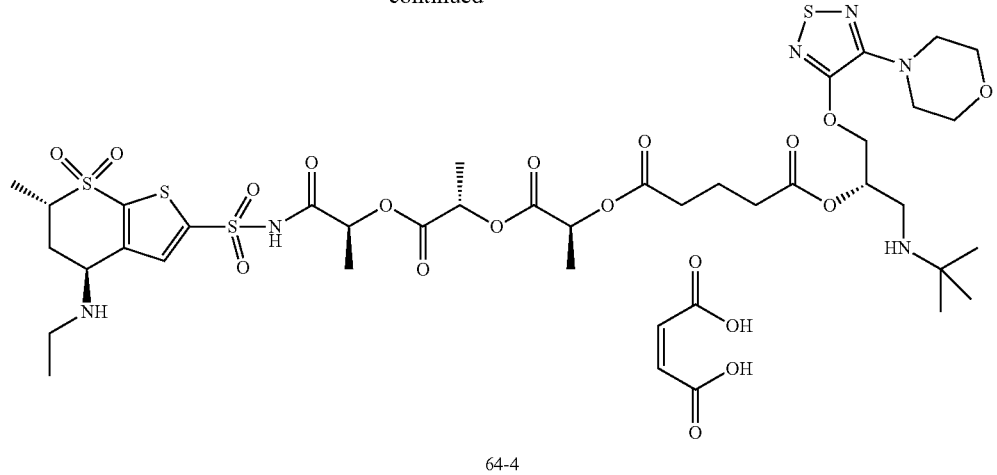

64-4

Step 1: Preparation of Timolol-O-glutarate-PLA(n=3)-Dorzolamide (64-3)

To a solution of pentanedioic acid mono-[(S)-1-(tert-butylamino-methyl)-2-(4-morpholin-4-yl-[1,2,5]thiadiazol-3-yloxy)-ethyl] ester 64-1 (0.61 g, 1.48 mmol) in dichloromethane (5 mL) was added EDC.HCl (0.35 g, 1.85 mmol), (S)-2-Hydroxy-propionic acid (S)-1-[(S)-2-((4S,6S)-4-ethylamino-6-methyl-7,7-dioxo-4,5,6,7-tetrahydro-7lambda*6*-thieno[2,3-b]thiopyran-2-sulfonylamino)-1-methyl-2-oxo-ethoxycarbonyl]-ethyl ester 64-2 (0.50 g, 0.92 mmol) and 4-dimethylaminopyridine (11 mg, 0.09 mmol) at 0° C. The reaction mixture was allowed to stir at 25-30° C. over a period of 2 hours. The resulting reaction mass was quenched with water (100 mL), extracted with dichloromethane (200×3 mL), dried over sodium sulfate and concentrated under reduced pressure. The crude product obtained upon evaporation of volatiles was purified through silica gel (230-400 mesh) column chromatography (4% methanol in DCM) to obtain product 64-3 as an off white solid 0.1 g (11%).

Step 2: Preparation of Timolol-O-glutarate-PLA(n=3)-Dorzolamide maleate salt (64-4)

To a solution of Timolol-O-glutarate-PLA(n=3)-Dorzolamide 64-3 (0.1 g, 0.10 mmol) in acetone (1 mL) was added maleic acid (11 mg, 0.09 mmol) at 0° C. The reaction mixture was allowed to stir at room temperature over a period of 20 minutes. The resulting reaction mixture was concentrated under reduced pressure and dried under vacuum to give product 64-4 as an off white solid 0.1 g (92%).

Scheme 66: Synthesis of Maleate salt of Succinic acid 1-{2-[2-(5-Bromo-quinoxalin-6-ylamino)-4,5-dihydro-imidazol-1-yl]-1-methyl-2-oxo-ethoxycarbonyl}-ethyl ester (S)-1-(tert-butylamino-methyl)-2-(4-morpholin-4-yl-[1,2,5]thiadiazol-3-yloxy)-ethyl ester (72-4):

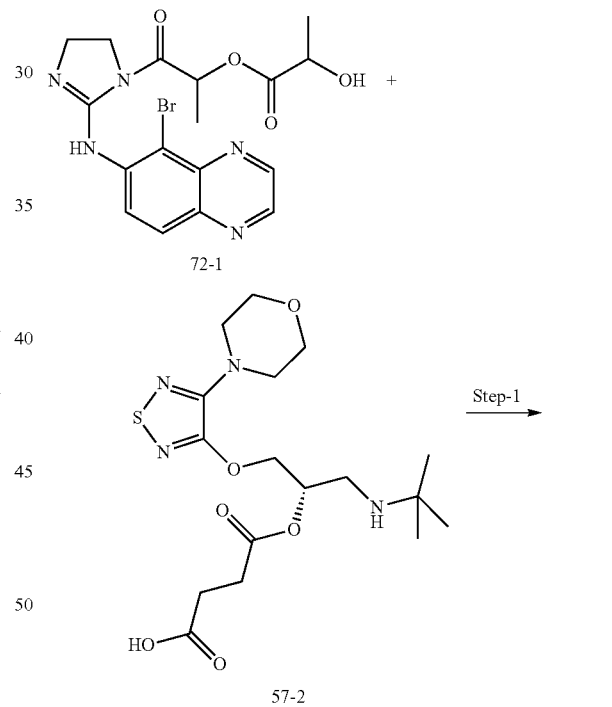

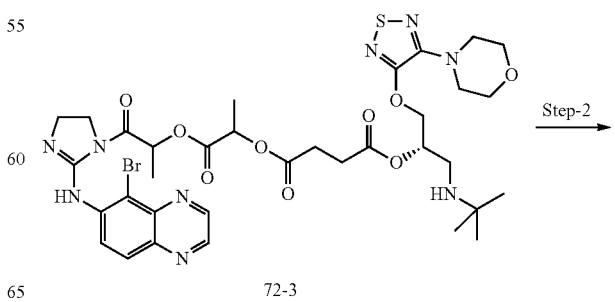

-continued

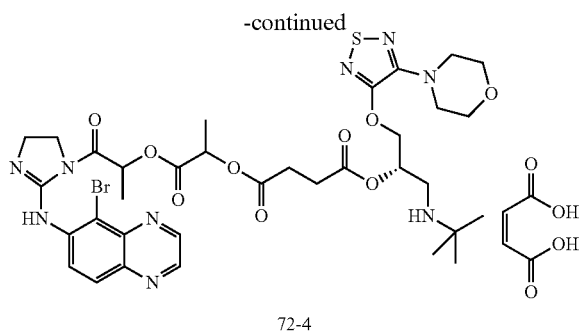

72-4

Step 1: Preparation of Succinic acid 1-{2-[2-(5-Bromo-quinoxalin-6-ylamino)-4,5-dihydro-imidazol-1-yl]-1-methyl-2-oxo-ethoxycarbonyl}-ethyl ester (S)-1-(tert-butylamino-methyl)-2-(4-morpholin-4-yl-[1,2,5]thiadiazol-3-yloxy)-ethyl ester (72-3)

To a solution of Succinic acid mono-[(S)-1-(tert-butylamino-methyl)-2-(4-morpholin-4-yl-[1,2,5] thiadiazol-3-yloxy)-ethyl]ester 57-2 (4.29 g, 10.32 mmol) in dichloromethane (30 mL) was added EDC.HCl (2.62 g, 13.75 mmol), 2-hydroxy-propionic acid 2-[2-(5-bromo-quinoxalin-6-ylamino)-4,5-dihydro-imidazol-1-yl]-1-methyl-2-oxo-ethyl ester 72-1 (3 g, 6.88 mmol), and 4-dimethylaminopyridine (0.083 g, 0.688 mmol) at 0° C. The reaction mixture was allowed to stir at 25-30° C. over a period of 2 hours. The resulting reaction mass was quenched with water (300 mL), extracted with dichloromethane (300×3 mL), dried over sodium sulfate and concentrated under reduced pressure. The crude product obtained upon evaporation of volatiles was purified through silica gel (230-400 mesh) column chromatography (3% 2-propanol in DCM) to obtain product 72-3 as a pale green solid 1.0 g (17%).

Step 2: Preparation of Maleate salt of Succinic acid 1-{2-[2-(5-Bromo-quinoxalin-6-ylamino)-4,5-dihydro-imidazol-1-yl]-1-methyl-2-oxo-ethoxycarbonyl}-ethyl ester (S)-1-(tert-butylamino-methyl)-2-(4-morpholin-4-yl-[1,2,5]thiadiazol-3-yloxy)-ethyl ester (72-4)

To a solution of Succinic acid 1-{2-[2-(5-Bromo-quinoxalin-6-ylamino)-4,5-dihydro-imidazol-1-yl]-1-methyl-2-oxo-ethoxycarbonyl}-ethyl ester (S)-1-(tert-butylamino-methyl)-2-(4-morpholin-4-yl-[1,2,5]thiadiazol-3-yloxy)-ethyl ester 72-3 (1 g, 1.19 mmol) in acetone (5 mL) was added maleic acid (0.125 g, 0.09 mmol) at 0° C. The reaction mixture was allowed to stir at room temperature over a period of 20 minutes. The resulting reaction mixture was concentrated under reduced pressure and dried under vacuum to give product 72-4 as a pale green solid 1.0 g (89%).

Scheme 67: Synthesis of Maleate salt of Succinic acid bis-[(S)-1-(tert-butylamino-methyl)-2-(4-morpholin-4-yl-[1,2,5]thiadiazol-3-yloxy)-ethyl] ester (76-4):

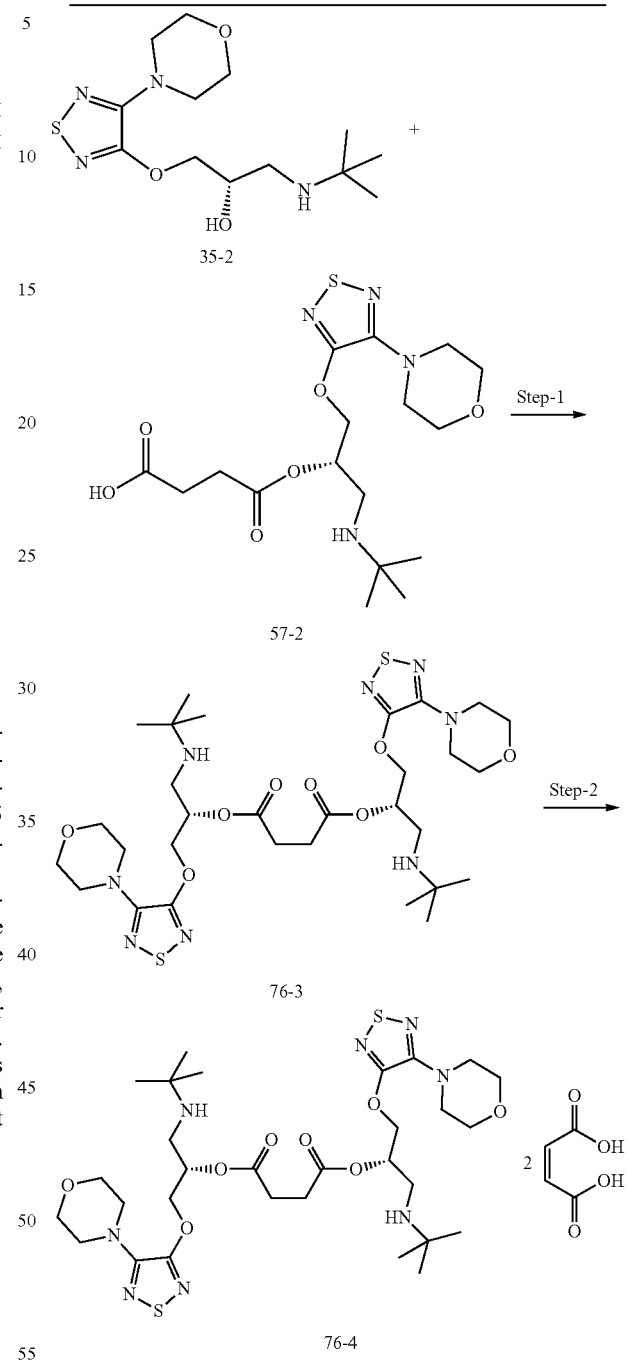

Step 1: Preparation of Succinic acid bis-[(S)-1-(tert-butylamino-methyl)-2-(4-morpholin-4-yl-[1,2,5]thiadiazol-3-yloxy)-ethyl] ester (76-3)

To a solution of Succinic acid mono-[(S)-1-(tert-butylamino-methyl)-2-(4-morpholin-4-yl-[1,2,5]thiadiazol-3-yloxy)-ethyl] ester 57-2 (7.24 g, 17.4 mmol) in dichloromethane (50 mL) was added EDC.HCl (4.53 g, 23.7 mmol), (S)-1-tert-Butylamino-3-(4-morpholin-4-yl-[1,2,5] thiadiazol-3-yloxy)-propan-2-ol 35-2 (5 g, 15.8 mmol), and 4-dimethylaminopyridine (0.19 g, 1.582 mmol) at 0° C. The reaction mixture was allowed to stir at 25-30° C. over a period of 2 hours. The resulting reaction mass was quenched with water (200 mL), extracted with dichloromethane (200×3 mL), dried over sodium sulfate and concentrated under reduced pressure. The crude product obtained upon evaporation of volatiles was purified through silica gel (230-400 mesh) column chromatography (40-50% ethyl acetate in hexane) to obtain product 76-3 as a colorless liquid 4.1 g (36%).

Step 2: Preparation of Maleate salt of Succinic acid bis-[(S)-1-(tert-butylamino-methyl)-2-(4-morpholin-4-yl-[1,2,5]thiadiazol-3-yloxy)-ethyl] ester (76-4)

To a solution of Succinic acid bis-[(S)-1-(tert-butylamino-methyl)-2-(4-morpholin-4-yl-[1,2,5]thiadiazol-3-yloxy)-ethyl] ester 76-3 (4.1 g, 5.74 mmol) in acetone (20 mL) was added maleic acid (0.559 g, 5.16 mmol) at 0° C. The reaction mixture was allowed to stir at room temperature over a period of 20 minutes. The resulting reaction mixture was concentrated under reduced pressure to afford product 76-4 as a white solid 3 g (63%).

Step 1: Preparation of 2-[2-(2-{2-[2,3-Dichloro-4-(2-methylene-butyryl)-phenoxy]-acetoxy}-propionyloxy)-propionyloxy]-propionic acid 2-[2-(5-bromo-quinoxalin-6-ylamino)-4,5-dihydro-imidazol-1-yl]-1-methyl-2-oxo-ethyl ester (79-3)

To a solution of ethacrynic acid 79-2 (2.44 g, 8.06 mmol) in dichloromethane (40 mL) was added EDC HCl (1.92 g, 10.08 mmol), 2-hydroxy-propionic acid 1-(1-{2-[2-(5-bromo-quinoxalin-6-ylamino)-4,5-dihydro-imidazol-1-yl]-1-methyl-2-oxo-ethoxycarbonyl}-ethoxycarbonyl)-ethyl ester 79-1 (3.9 g, 6.72 mmol) and 4-dimethylaminopyridine (0.082 g, 0.672 mmol) at 0° C. The reaction mixture was allowed to stir at 25-30° C. over a period of 2 hours. The resulting reaction mass was quenched with water (200 mL), extracted with dichloromethane (200×3 mL), dried over sodium sulfate and concentrated under reduced pressure. The crude product obtained upon evaporation of volatiles was purified through silica gel (230-400 mesh) column chromatography (12-15% ethyl acetate in dichloromethane) to obtain product 79-3 as a pale green solid 2.0 g (35%).

Scheme 68: Synthesis of 2-[2-(2-{2-[2,3-dichloro-4-(2-Methylene-butyryl)-phenoxy]-acetoxy}-propionyloxy)-propionyloxy]-propionic acid 2-[2-(5-bromo-quinoxalin-6-ylamino)-4,5-dihydro-imidazol-1-yl]-1-methyl-2-oxo-ethyl ester (79-3):

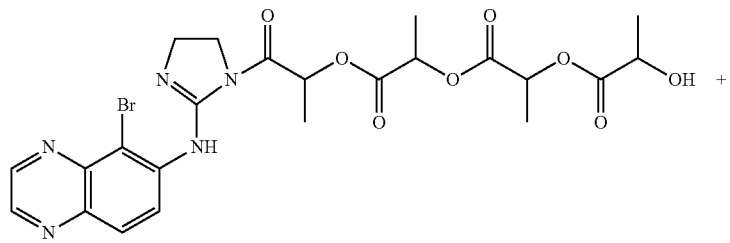

79-1

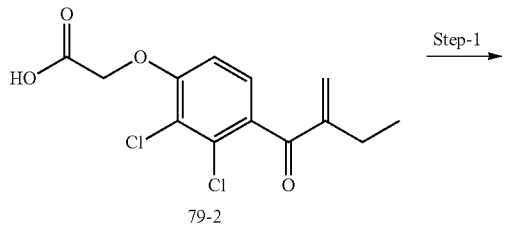

79-2

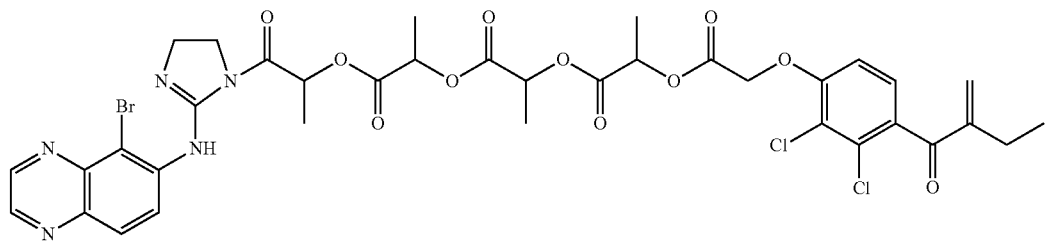

79-3

Scheme 69: Synthesis of (4S,6S)-4-Ethylamino-6-methyl-7,7-dioxo-4,5,6,7-tetrahydro-7 lambda*6*-thieno[2,3-b]thiopyran-2-sulfonic acid ((4Z,7Z,10Z,13Z,16Z,19Z)-docosa-4,7,10,13,16,19-hexaenoyl)-amide (80-3):

Step 1: Preparation of (4S,6S)-4-Ethylamino-6-methyl-7,7-dioxo-4,5,6,7-tetrahydro-7lambda*6*-thieno[2,3-b]thiopyran-2-sulfonic acid ((4Z,7Z,10Z,13Z,16Z,19Z)-docosa-4,7,10,13,16,19-hexaenoyl)-amide (80-3)

To a solution of Dorzolamide 12-1 (3.0 g, 8.35 mmol) in dichloromethane (30 mL) was added N,N-diisopropylethylamine (3.07 mL, 16.6 mmol) at 0° C. After 30 minutes, (4Z,7Z,10Z,13Z,16Z,19Z)-Docosa-4,7,10,13,16,19-hexaenoic acid 80-2 (3.5 g, 10.8 mmol), EDC.HCl (2.38 g, 12.5 mmol), benzotriazol-1-ol (0.23 g, 1.66 mmol) and 4-dimethylaminopyridine (0.1 g, 0.83 mmol) were added at 0° C. The reaction mixture was allowed to stir at 25-30° C. over a period of 1 hour. The resulting reaction mass was quenched with water (400 mL), extracted with dichloromethane (300×2 mL), dried over sodium sulfate and concentrated under reduced pressure. The crude product obtained upon evaporation of volatiles was purified through silica gel (230-400 mesh) column chromatography (2% methanol in DCM) to obtain product 80-3 as off white low melting solid 2.5 g (95%).

Scheme 70: Synthesis of Maleate salt of 4-[2-(5-Bromo-quinoxalin-6-ylamino)-4,5-dihydro-imidazol-1-yl]-4-oxo-butyric acid (S)-1-(tert-butylamino-methyl)-2-(4-morpholin-4-yl-[1,2,5]thiadiazol-3-yloxy)-ethyl ester (83-4):

-continued

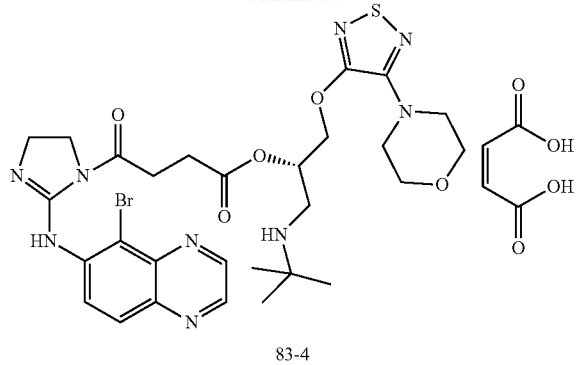

83-4

Step 1: Preparation of 4-[2-(5-Bromo-quinoxalin-6-ylamino)-4,5-dihydro-imidazol-1-yl]-4-oxo-butyric acid (S)-1-(tert-butylamino-methyl)-2-(4-morpholin-4-yl-[1,2,5]thiadiazol-3-yloxy)-ethyl ester (83-3)

To a solution of Succinic acid mono-[(S)-1-(tert-butylamino-methyl)-2-(4-morpholin-4-yl-[1,2,5] thiadiazol-3-yloxy)-ethyl] ester 57-2 (8.54 g, 20.5 mmol) in dichloromethane (40 mL) was added EDC.HCl (5.232 g, 27.3 mmol), Brimonidine 24-2 (4 g, 13.6 mmol), and 4-dimethylaminopyridine (0.167 g, 1.36 mmol) at 0° C. The reaction mixture was allowed to stir at 25-30° C. over a period of 2 hours. The resulting reaction mass was quenched with water (250 mL), extracted with dichloromethane (250×3 mL), dried over sodium sulfate and concentrated under reduced pressure. The crude product obtained upon evaporation of volatiles was purified through silica gel (230-400 mesh) column chromatography (3% 2-propanol in dichloromethane) to obtain product 83-3 as a pale yellow solid 3.0 g (31%).

Step 2: Preparation of maleate salt of 4-[2-(5-Bromo-quinoxalin-6-ylamino)-4,5-dihydro-imidazol-1-yl]-4-oxo-butyric acid (S)-1-(tert-butylamino-methyl)-2-(4-morpholin-4-yl-[1,2,5] thiadiazol-3-yloxy)-ethyl ester (83-4)

To a solution of 4-[2-(5-bromo-quinoxalin-6-ylamino)-4,5-dihydro-imidazol-1-yl]-4-oxo-butyric acid (S)-1-(tert-butylamino-methyl)-2-(4-morpholin-4-yl-[1,2,5] thiadiazol-3-yloxy)-ethyl ester 83-3 (3 g, 4.34 mmol) in acetone (15 mL) was added maleic acid (0.45 g, 3.91 mmol) at 0° C. The reaction mixture was allowed to stir at room temperature over a period of 20 minutes. The resulting reaction mixture was concentrated under reduced pressure to afford product 83-4 as a pale yellow solid 3 g (85%).

Scheme 71: Synthesis of 1-(2-Hydroxy-ethyl)-1-(3-methoxy-benzyl)-3-[4-(1H-pyrazol-4-yl)-phenyl]-urea (SR5834):

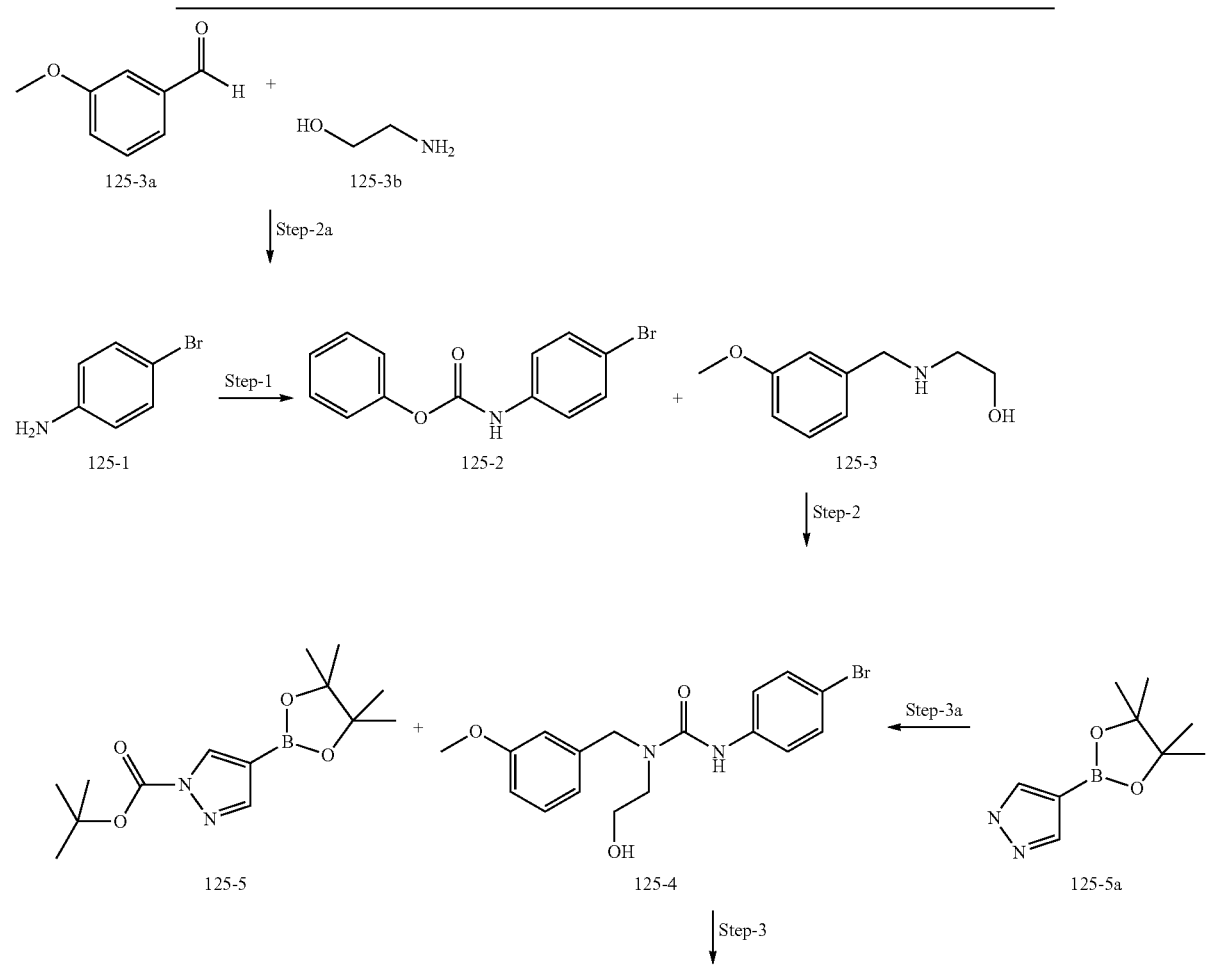

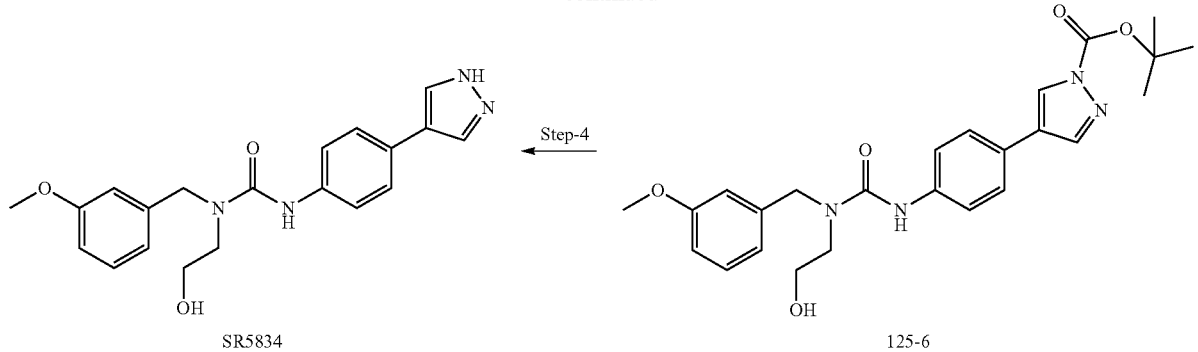

SR5834

125-6

Step 1: Preparation of (4-Bromo-phenyl)-carbamic acid phenyl ester (125-2)

To a solution of 4-bromo aniline 125-1 (50 g, 290 mmol) in dichloromethane (500 mL) was added N,N-diisopropylethylamine (148 mL, 871 mmol) followed by phenyl chloroformate (40.3 mL, 319 mmol) over a period of 30 min at 0° C. The reaction mixture was allowed to stir at 25° C. for 2 h. After the complete conversion of starting material as detected by TLC, the reaction mixture was concentrated completely under reduced pressure to give the crude 125-2 as light brown oil which was used in the next step without further purification.

Step 2a: Preparation of 2-(3-Methoxy-benzylamino)-ethanol (38-3)

To a solution of 3-methoxy-benzaldehyde 125-3a (30 g, 220 mmol) in methanol (300 mL) was added 2-aminoethanol 125-3b (13.45 g, 220 mmol). After stirring at room temperature for 15 min, the solution was cooled to 0° C. prior to the addition of sodium borohydride (4.16 g, 110 mmol). The resulting solution was stirred at room temperature for 1 h. After quenching with water (100 mL), methanol was removed under reduced pressure and the resulting aqueous phase was diluted with water (500 mL), extracted with 10% methanol in dichloromethane (2×500 mL). The combined extracts were dried over anhydrous $Na_2SO_4$ and concentrated under reduced pressure to give 125-3 as yellow oil 22 g (55%).

Step 2: Preparation of 3-(4-Bromo-phenyl)-1-(2-hydroxy-ethyl)-1-(3-methoxy-benzyl)-urea (125-4)

To a solution of (4-bromo-phenyl)-carbamic acid phenyl ester (125-2) (83 g, 284 mmol) in dimethyl sulfoxide (415 mL) was added N,N-diisopropylethylamine (96.6 mL, 568 mmol) followed by 2-(3-Methoxy-benzylamino)-ethanol 125-3 (51.47 g, 284 mmol) at 25° C. The reaction mixture was stirred for 1 h at 65° C. The reaction mixture was cooled to 25° C., diluted with water (2 L) and extracted with ethyl acetate (2×830 mL). The combined organic layer was dried over sodium sulfate, concentrated under reduced pressure and purified by recrystallization using 10% ethyl acetate in hexane to give 125-4 as an off white solid 71.14 g (66%).

Step 3a: Preparation of 4-(4,4,5,5-Tetramethyl-[1,3,2] dioxaborolan-2-yl)-pyrazole-1-carboxylic acid tert-butyl ester (125-5)

To a solution of 4-(4,4,5,5-tetramethyl-[1,3,2]dioxaborolan-2-yl)-1H-pyrazole 125-5a (100 g, 515 mmol) in N,N-dimethylformamide (500 mL, 5V) was added 4-dimethylaminopyridine (8.8 g, 72 mmol) followed by BOC anhydride (118 mL, 515 mmol) drop wise at 0° C. The reaction mixture was stirred for 16 h at 25° C. The reaction mixture was quenched with chilled water (2.5 L). The solid precipitate was collected by filtration and dried under vacuum to give ester 125-5 as a white solid 99 g (65%).

Step 3: Preparation of 4-{4-[3-(2-Hydroxy-ethyl)-3-(3-methoxy-benzyl)-ureido]-phenyl}-pyrazole-1-carboxylic acid tert-butyl ester (125-6)

3-(4-bromo-phenyl)-1-(2-hydroxy-ethyl)-1-(3-methoxy-benzyl)-urea 125-4 (25 g, 65 mmol) and 4-(4,4,5,5-tetramethyl-[1,3,2] dioxaborolan-2-yl)-pyrazole-1-carboxylic acid tert-butyl ester 38-5 (29 g, 98 mmol) and potassium carbonate (27.3 g, 197 mmol) were dissolved in degassed 5:1 dioxane/$H_2O$ (300 mL). Pd(PPh$_3$)$_4$ (7.6 g, 6.5 mmol) was then added under argon and the mixture was heated at 110° C. for 1 h. After cooling to room temperature, the mixture was diluted with water (500 mL) and extracted with ethyl acetate (500×2 mL). The combined organic extracts were washed with brine (500 mL), dried over anhydrous $Na_2SO_4$, and concentrated under reduced pressure to give crude 125-6 as a pale brown liquid which was used in the next step without further purification.

Step 4: Preparation of 1-(2-Hydroxy-ethyl)-1-(3-methoxy-benzyl)-3-[4-(1H-pyrazol-4-yl)-phenyl]-urea (SR5834)

To a solution of (4-bromo-phenyl)-carbamic acid phenyl ester 125-6 (30 g, 64 mmol) in 1,4-dioxane (150 mL) was added 4N hydrochloric acid in 1,4-dioxane (60 mL) dropwise at 0° C. The reaction mixture was stirred for 1 h at 65° C. The progress of the reaction was monitored by TLC. The reaction mixture was diluted with water (500 mL) and extracted with ethyl acetate (2×500 mL). The combined organic layer was dried over sodium sulfate and concentrated under reduced pressure. The residue was then recrystallized using dichloromethane to afford SR5834 as an off white solid 8 g.

Scheme 72: Synthesis of (S)-2-{(S)-2-[(S)-2-((S)-2-Acetoxy-propionyloxy)-propionyloxy]-propionyloxy}-propionic acid 2-{1-(3-methoxy-benzyl)-3-[4-(1H-pyrazol-4-yl)-phenyl]-ureido}-ethyl ester (88-3):

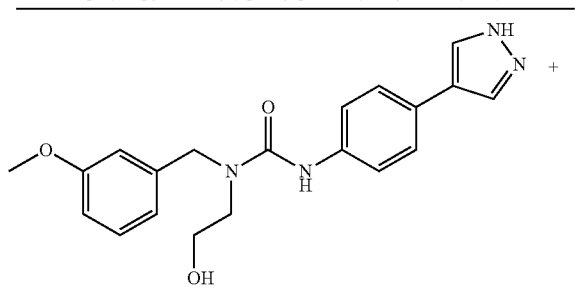

SR5834

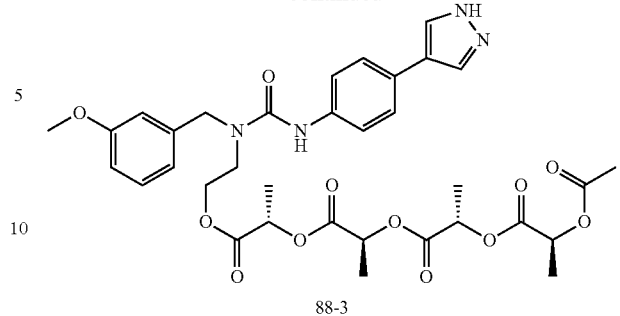

88-3

Step 1: Preparation of (S)-2-{(S)-2-[(S)-2-((S)-2-Acetoxy-propionyloxy)-propionyloxy]-propionyloxy}-propionic acid 2-{1-(3-methoxy-benzyl)-3-[4-(1H-pyrazol-4-yl)-phenyl]-ureido}-ethyl ester (88-3)

To a solution of (S)-2-{(S)-2-[(S)-2-((S)-2-Acetoxy-propionyloxy)-propionyloxy]-propionyloxy}-propionic acid 88-2 (1.56 g, 4.5 mmol) in dichloromethane (30 mL) were added EDC.HCl (0.78 g, 4.0 mmol), 1-(2-hydroxy-ethyl)-1-(3-methoxy-benzyl)-3-[4-(1H-pyrazol-4-yl)-phenyl]-urea SR8543 (1.5 g, 4.0 mmol) and 4-dimethylaminopyridine (50 mg, 0.40 mmol) at 25° C. The resulting reaction mixture was stirred at 25° C. for 48 hours. After the complete conversion of starting material as detected by TLC. The reaction mixture was quenched with water (100 mL) and extracted with dichloromethane (2×100 mL). The combined organic layer was dried over sodium sulfate, concentrated under reduced pressure and purified by silica gel (60-120 mesh) column chromatography (40-50% ethyl acetate in hexane) to give 88-31 as a yellow solid 500 mg (18%).

Scheme 73: Synthesis of (S)-2-{(S)-2-[(S)-2-((S)-2-Acetoxy-propionyloxy)-propionyloxy]-propionyloxy}-propionic acid (S)-1-[(S)-1-(2-{1-(3-methoxy-benzyl)-3-[4-(1H-pyrazol-4-yl)-phenyl]-ureido}-ethoxycarbonyl)-ethoxycarbonyl]-ethyl ester (89-3):

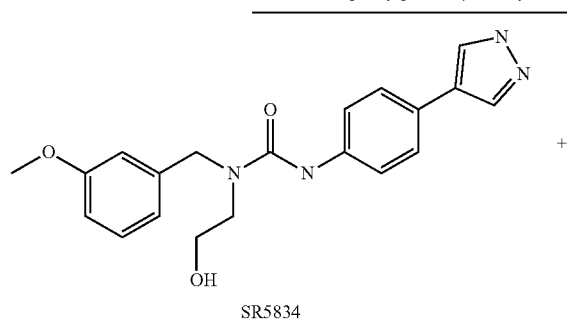

SR5834

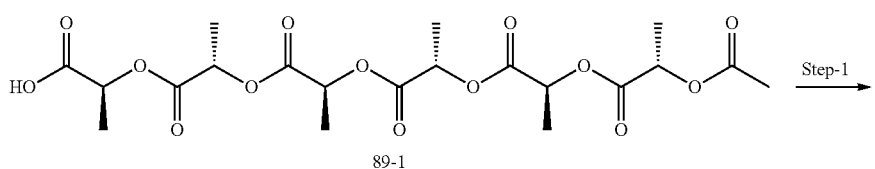

89-1

-continued

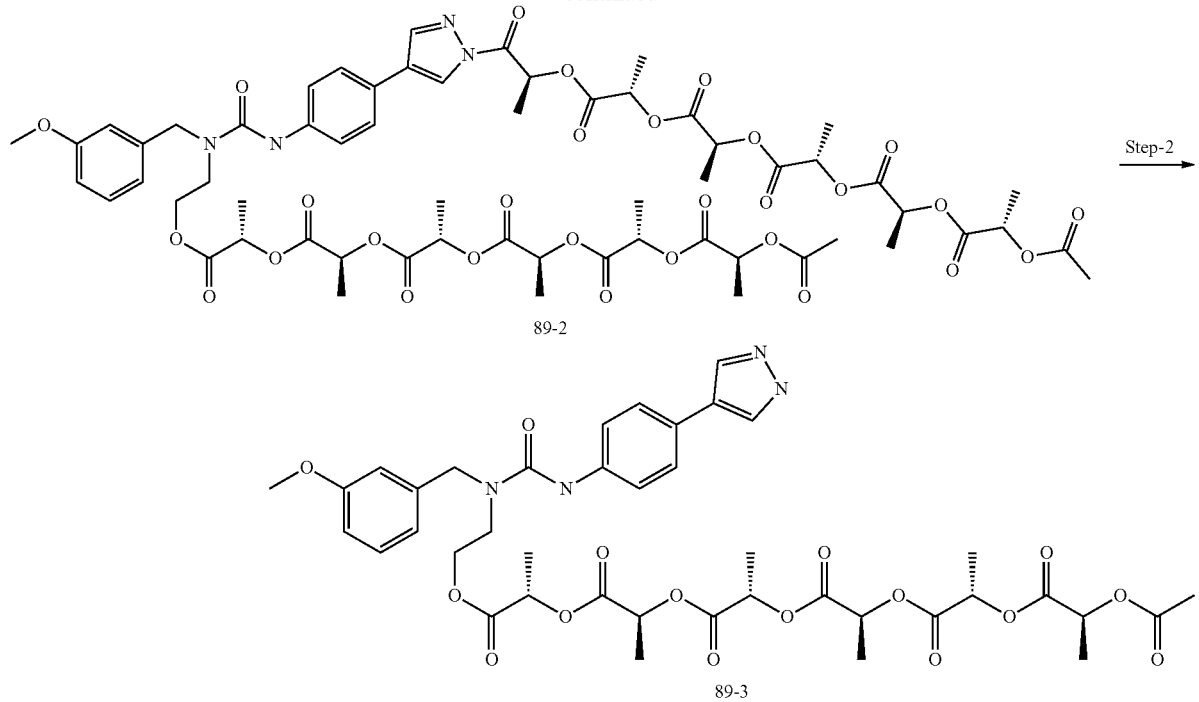

89-2

89-3

Step 1: Preparation of SR5834-Bis-PLA(n=6)-OAc (89-2)

To a solution of (S)-2-[(S)-2-((S)-2-{(S)-2-[(S)-2-((S)-2-Acetoxy-propionyloxy)-propionyloxy]-propionyloxy}-propionyloxy)-propionyloxy]-propionic acid 89-1 (1.6 g, 3.4 mmol) in dichloromethane (32 mL) were added EDC.HCl (0.65 g, 3.4 mmol), 1-(2-Hydroxy-ethyl)-1-(3-methoxy-benzyl)-3-[4-(1H-pyrazol-4-yl)-phenyl]-urea SR5834 (500 mg, 1.3 mmol) and 4-dimethylaminopyridine (17 mg, 0.13 mmol) at 0° C. The resulting reaction mixture was stirred at 25° C. for 16 hours. After the complete conversion of starting material as detected by TLC, the reaction mixture was quenched with water (100 mL) and extracted with dichloromethane (2×100 mL). The combined organic layer was dried over sodium sulfate, concentrated under reduced pressure to give crude 89-2 as a thick colorless oil 1.8 g.

Step 2: Preparation of (S)-2-{(S)-2-[(S)-2-((S)-2-Acetoxy-propionyloxy)-propionyloxy]-propionyloxy}-propionic acid (S)-1-[(S)-1-(2-{1-(3-methoxy-benzyl)-3-[4-(1H-pyrazol-4-yl)-phenyl]-ureido}-ethoxycarbonyl)-ethoxycarbonyl]-ethyl ester (89-3)

A solution of 89-2 (1.8 g, 1.189 mmol) in a mixture of water, ethanol and dichloromethane taken in the ratio (1:1:0.1, 10 V) was stirred at 25° C. for 16 h. The progress of the reaction was monitored by TLC and LCMS. The reaction mixture was concentrated completely to remove ethanol, diluted with water (20 mL) and extracted with dichloromethane (2×100 mL). The combined organic layer was dried over sodium sulfate, concentrated under reduced pressure and purified by silica gel (60-120 mesh) column chromatography (40-50% ethyl acetate in hexane) to obtain 89-3 as a white solid 700 mg (70%).

Scheme 74: Synthesis of 1-(2-Hydroxy-ethyl)-1-(3-methoxy-benzyl)-3-[4-(1H-pyrazol-4-yl)-2-(2-pyrrolidin-1-yl-ethoxy)-phenyl]-urea (RKI-H-1y):

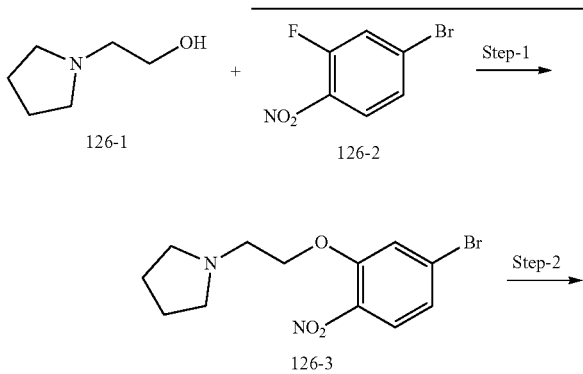

415
416
-continued
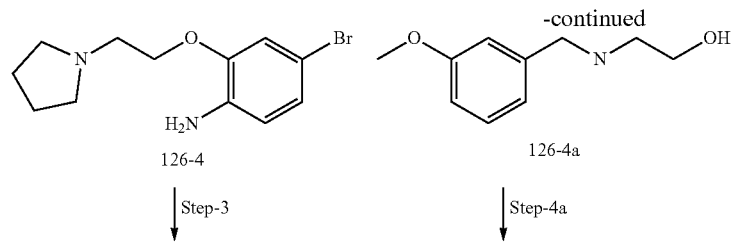
↓ Step-3          ↓ Step-4a
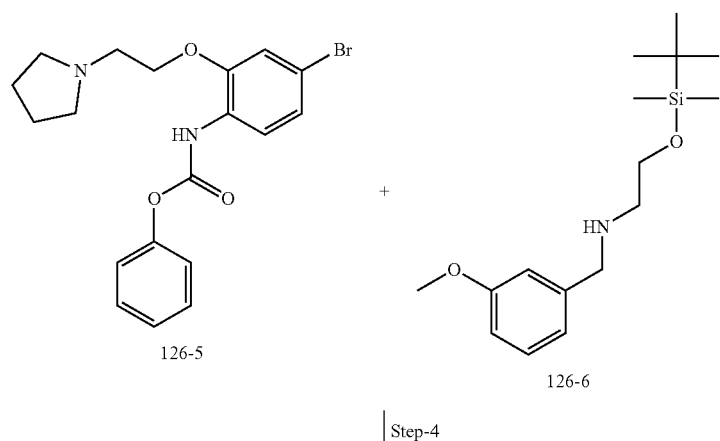
↓ Step-4
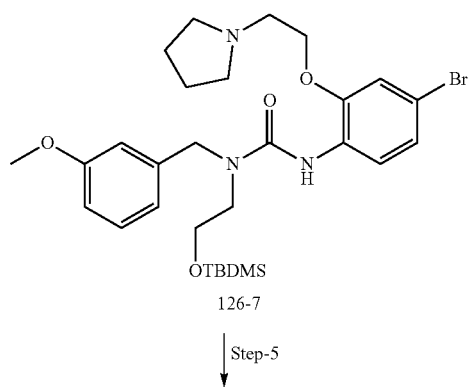
↓ Step-5
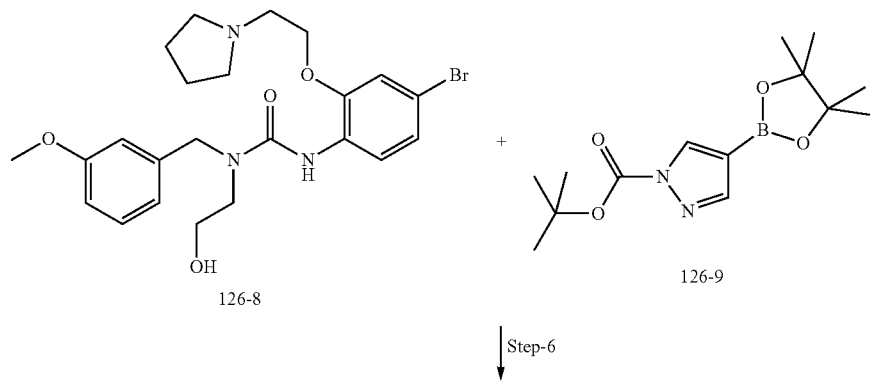
↓ Step-6

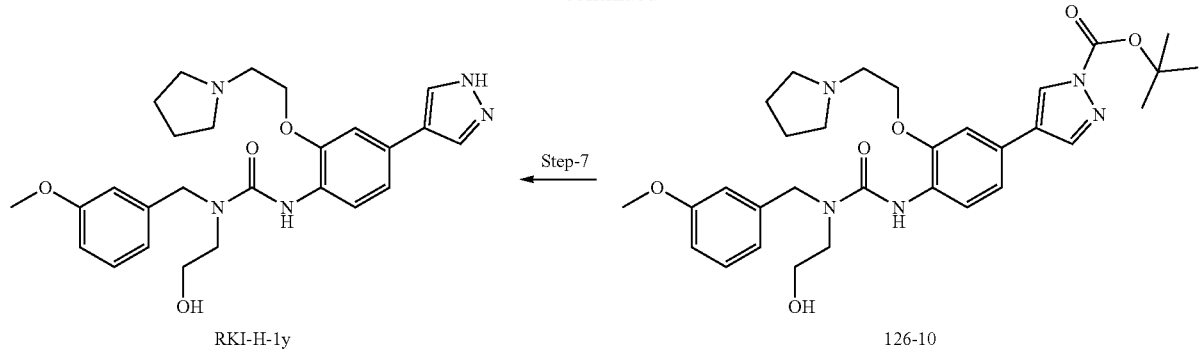

RKI-H-1y                126-10

Step 1: Preparation of 1-[2-(5-Bromo-2-nitro-phenoxy)-ethyl]-pyrrolidine (126-3)

To a solution of 4-bromo-2-fluoro-1-nitro-benzene 126-2 (38 g, 172 mmol) in N,N-dimethyl formamide (380 mL) was added cesium carbonate (168.83 g, 518 mmol) followed by 2-pyrrolidin-1-yl-ethanol 126-1 (22.18 g, 190 mmol) drop-wise at 0° C. The reaction mixture was stirred at 25° C. for 16 h. The progress of the reaction was monitored by TLC and LCMS. The reaction mixture was quenched with ice water (3.8 L). The solid precipitate was collected by filtration and dried over vacuum. The solid obtained was further suspended in hexane (190 mL) and stirred for 15 min, filtered and dried to obtain 126-3 as a yellow solid 41.9 g (77%).

Step 2: Preparation of 4-Bromo-2-(2-pyrrolidin-1-yl-ethoxy)-phenylamine (126-4)

To a solution of 1-[2-(5-bromo-2-nitro-phenoxy)-ethyl]-pyrrolidine 126-3 (38 g, 120 mmol) in ethyl acetate (380 mL) was added stannous chloride (114 g, 602 mmol) portion wise at 0° C. The reaction mixture was stirred for 6 h at 25° C. The progress of the reaction was monitored by TLC and LCMS. The reaction mixture was quenched with 10% sodium hydroxide solution and extracted with 10% methanol in dichloromethane (2×500 mL). The combined organic layer was dried over sodium sulfate and concentrated under reduced pressure to obtain 126-4 as a pale brown solid 23.8 g (69%).

Step 3: Preparation of [4-Bromo-2-(2-pyrrolidin-1-yl-ethoxy)-phenyl]-carbamic acid phenyl ester (126-5)

To a solution of 4-Bromo-2-(2-pyrrolidin-1-yl-ethoxy)-phenylamine 126-4 (9 g, 31 mmol) in dichloromethane (90 mL) was added N,N-diisopropylethylamine (16.1 mL, 94 mmol) followed by phenyl chloroformate (4.38 mL, 34 mmol) over a period of 5 min at 0° C. The reaction mixture was stirred for 2 h slowly raising the temperature to 25° C. The progress of the reaction was monitored by TLC and LCMS. The reaction mixture was concentrated completely under reduced pressure to give crude 126-5 as a pale yellow liquid which was used in the next step without further purification.

Step 4a: Preparation of 2-(tert-Butyl-dimethyl-silanyloxy)-ethyl]-(3-methoxy-benzyl)-amine (126-6)

To a solution of 2-(3-Methoxy-benzylamino)-ethanol 126-4a (32.8 g, 181 mmol) in dichloromethane (328 mL) was added imidazole (24.6 g, 362 mmol) followed by tertiary butyl dimethyl silyl chloride (29.86 g, 199 mmol) portion wise at 0° C. The reaction mixture was stirred at 0° C. for 1 h. The reaction mixture was diluted with water (1000 mL) and extracted with dichloromethane (2×1000 mL). The combined organic layer was dried over sodium sulfate and concentrated under reduced pressure to give 126-6 as a pale yellow liquid 50 g (93%).

Step 4: Preparation of 3-[4-Bromo-2-(2-pyrrolidin-1-yl-ethoxy)-phenyl]-1-(2-[tert-butyl dimethylsilyl)oxy]ethyl)-1-(3-methoxy-benzyl)-urea (126-7)

To a solution of [4-bromo-2-(2-pyrrolidin-1-yl-ethoxy)phenyl]-carbamic acid phenyl ester 126-5 (12 g, 29 mmol) in dimethyl sulphoxide (60 mL) was added N,N-diisopropylamine (10 mL, 59 mmol) followed by [2-(tert-Butyl-dimethyl-silanyloxy)-ethyl]-(3-methoxy-benzyl)-amine 126-6 (8.74 g, 29 mmol) at 25° C.

The reaction mixture was stirred at 65° C. for 1 h. The reaction mixture was cooled to 25° C., diluted with water (500 mL) and extracted with ethyl acetate (2×500 mL). The combined organic layer was dried over sodium sulfate, concentrated under reduced pressure to give crude 126-7 as pale brown liquid which was used in the next step without further purification.

Step 5: Preparation of 3-[4-Bromo-2-(2-pyrrolidin-1-yl-ethoxy)-phenyl]-1-(2-hydroxy-ethyl)-1-(3-methoxy-benzyl)-urea (126-8)

To a solution of 3-[4-bromo-2-(2-pyrrolidin-1-yl-ethoxy)-phenyl]-1-(2-[tert-butyl dimethylsilyl)oxy]ethyl)-1-(3-methoxy-benzyl)-urea 126-7 (14 g, 23 mmol) in tetrahydrofuran (140 mL) was added tetrabutyl ammonium fluoride (27.5 mL, 1.0M, 27 mmol) drop-wise at 0° C. and the reaction mixture was stirred at 25° C. for 1 h. The reaction mixture was diluted with water (500 mL) and extracted with ethyl acetate (2×500 mL). The combined organic layer was dried over sodium sulfate and concentrated under reduced pressure. The residue was recrystallized with methanol at 0° C. The resultant solid was filtered and dried over high vacuum to give 126-8 as an off white solid 5 g (53%).

Step 6: Preparation of 4-[4-[3-(2-Hydroxy-ethyl)-3-(3-methoxy-benzyl)-ureido]-3-(2-pyrrolidin-1-yl-ethoxy)-phenyl]-pyrazole-1-carboxylic acid tert-butyl ester (126-10)

3-[4-bromo-2-(2-pyrrolidin-1-yl-ethoxy)-phenyl]-1-(2-hydroxy-ethyl)-1-(3-methoxy-benzyl)-urea 126-8 (40 g, 81 mmol) and 4-(4,4,5,5-Tetramethyl-[1,3,2] dioxaborolan-2-yl)-pyrazole-1-carboxylic acid tert-butyl ester 126-5 (31 g, 105 mmol), and potassium carbonate (33.6 g, 243 mmol) were dissolved in degassed 5:1 dioxane/H₂O (400 mL). Pd(PPh₃)₄ (9.4 g, 8.1 mmol) was then added under argon and the mixture was heated at 110° C. for 1 h. After cooling to room temperature, the mixture was diluted with water (1000 mL) and extracted with ethyl acetate (1000 mL×2). The combined organic extracts were washed with brine (1000 mL), dried over anhydrous Na₂SO₄, concentrated under reduced pressure to give crude 126-10 as a pale brown liquid which was used in the next step without further purification.

Step 7: Preparation of 1-(2-Hydroxy-ethyl)-1-(3-methoxy-benzyl)-3-[4-(1H-pyrazol-4-yl)-2-(2-pyrrolidin-1-yl-ethoxy)-phenyl]-urea (RKI-H-1y)

To a solution of 4-[4-[3-(2-hydroxy-ethyl)-3-(3-methoxy-benzyl)-ureido]-3-(2-pyrrolidin-1-yl-ethoxy)-phenyl]-pyrazole-1-carboxylic acid tert-butyl ester 126-10 (45 g, 77 mmol) in methanol (450 mL) was added 4N hydrochloric acid in 1,4-dioxane (90 mL) drop-wise at 0° C. The reaction mixture was stirred at 25° C. 1 h. The progress of the reaction was monitored by TLC and LCMS. The reaction mixture was diluted with water (1000 mL) and washed with ethyl acetate (2×1000 mL). Aqueous layer was neutralized (pH=10) using sodium bicarbonate and extracted with 10% methanol in dichloromethane (2×1000 mL). The combined organic layer was dried over sodium sulfate and concentrated under reduced pressure to give RKI-H-1y as an off white solid 18 g (48%).

Scheme 75: Synthesis of (S)-2-{(S)-2-[(S)-2-((S)-2-Acetoxy-propionyloxy)-propionyloxy]-propionyloxy}-propionic acid 2-{1-(3-methoxy-benzyl)-3-[4-(1H-pyrazol-4-yl)-2-(2-pyrrolidin-1-yl-ethoxy)-phenyl]-ureido}-ethyl ester (90-2):

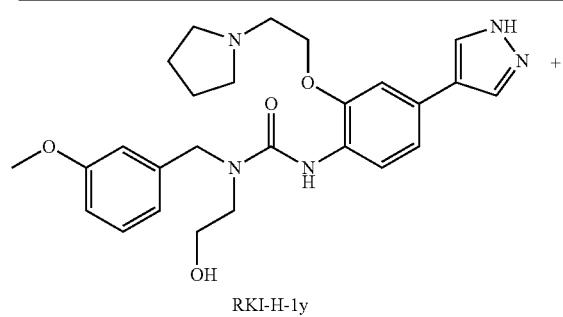

RKI-H-1y

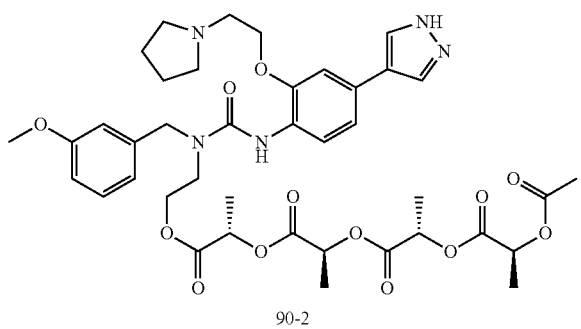

90-2

Step 1: Preparation of (S)-2-{(S)-2-[(S)-2-((S)-2-Acetoxy-propionyloxy)-propionyloxy]-propionyloxy}-propionic acid 2-{1-(3-methoxy-benzyl)-3-[4-(1H-pyrazol-4-yl)-2-(2-pyrrolidin-1-yl-ethoxy)-phenyl]-ureido}-ethyl ester (90-2)

To a solution of (S)-2-{(S)-2-[(S)-2-((S)-2-Acetoxy-propionyloxy)-propionyloxy]-propionyloxy}-propionic acid 90-1 (3.12 g, 2.710 mmol) in dichloromethane (13 mL) was added EDC.HCl (1.3 g, 6.776 mmol) followed by 4-dimethyl amino pyridine (33 mg, 0.217 mmol) at 0° C. After 5 min 1-(2-Hydroxy-ethyl)-1-(3-methoxy-benzyl)-3-[4-(1H-pyrazol-4-yl)-2-(2-pyrrolidin-1-yl-ethoxy)-phenyl]-urea RKI-H-1y (1.3 g, 2.710 mmol) was added and resulting reaction mixture was stirred at 25° C. for 4 days. The progress of the reaction was monitored by TLC and LCMS. The reaction mixture was quenched with water (250 mL) and extracted with dichloromethane (2×300 mL). The combined organic layer was dried over sodium sulfate, concentrated under reduced pressure and purified by combi-flash column to give 90-2 as an off white solid 300 mg (14%).

Scheme 76: Synthesis of 4-[2-(5-Bromo-quinoxalin-6-ylamino)-4,5-dihydro-imidazol-1-yl]-4-oxo-butyric acid 1-[1-(2-{1-(3-methoxy-benzyl)-3-[4-(1H-pyrazol-4-yl)-phenyl]-ureido}-ethoxycarbonyl)-ethoxycarbonyl]-ethyl ester (101-3):

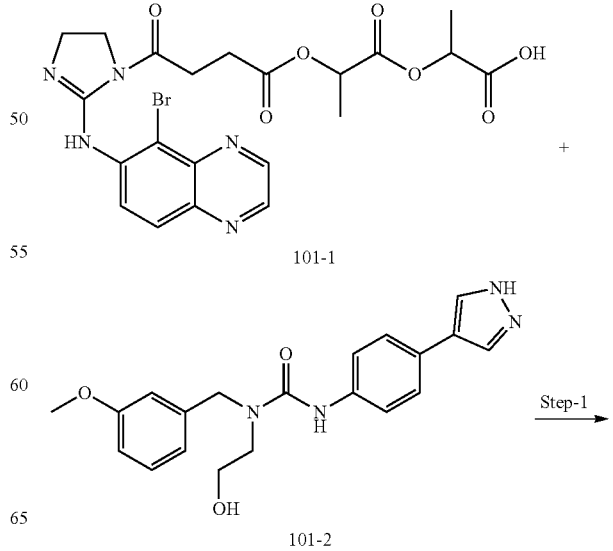

421
-continued

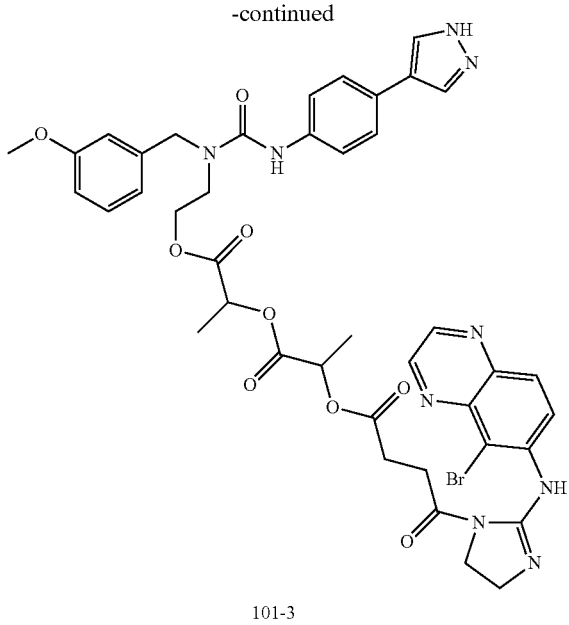

101-3

422

Step 1: Preparation of 4-[2-(5-Bromo-quinoxalin-6-ylamino)-4,5-dihydro-imidazol-1-yl]-4-oxo-butyric acid 1-[1-(2-{1-(3-methoxy-benzyl)-3-[4-(1H-pyrazol-4-yl)-phenyl]-ureido}-ethoxycarbonyl)-ethoxycarbonyl]-ethyl ester (101-3)

To a solution of 4-[2-(5-Bromo-quinoxalin-6-ylamino)-4,5-dihydro-imidazol-1-yl]-4-oxo-butyric acid 1-(1-carboxy-ethoxycarbonyl)-ethyl ester 101-1 (0.615 g, 1.14 mmol) in dichloromethane (10 mL) was added EDC.HCl (0.273 g, 1.43 mmol), 1-(2-Hydroxy-ethyl)-1-(3-methoxy-benzyl)-3-[4-(1H-pyrazol-4-yl)-phenyl]-urea 101-2 (0.35 g, 0.95 mmol), and 4-dimethylaminopyridine (0.01 g, 0.09 mmol) at 0° C. The reaction mixture was allowed to stir at 25-30° C. over a period of 16 hours. The resulting reaction mass was quenched with water (100 mL), extracted with dichloromethane (100×3 mL), dried over sodium sulfate and concentrated under reduced pressure. The crude product obtained upon evaporation of volatiles was purified through preparative HPLC to obtain product 101-3 as a pale yellow solid 60 mg (7%).

Scheme 77: Synthesis of (S)-2-{(S)-2-[(S)-2-((S)-2-Acetoxy-propionyloxy)-propionyloxyl-propionyloxy}-propionic acid (S)-1-{(S)-2-[2-(5-bromo-quinoxalin-6-ylamino)-4,5-dihydro-imidazol-1-yl]-1-methyl-2-oxo-ethoxycarbonyl}-ethyl ester (107-3):

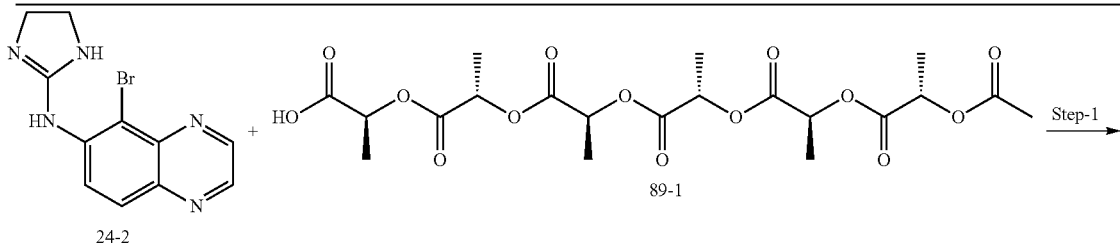

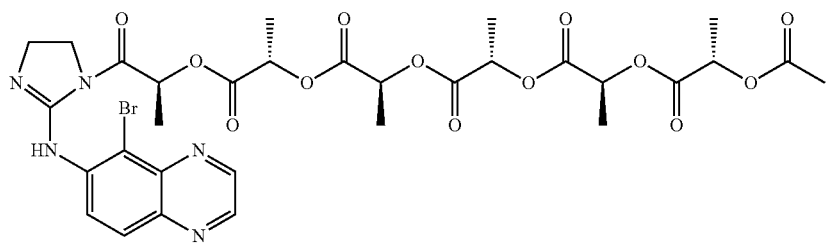

107-3

423

Step 1: Preparation of (S)-2-{(S)-2-[(S)-2-((S)-2-Acetoxy-propionyloxy)-propionyloxy]-propionyloxy}-propionic acid (S)-1-{(S)-2-[2-(5-bromo-quinoxalin-6-ylamino)-4,5-dihydro-imidazol-1-yl]-1-methyl-2-oxo-ethoxycarbonyl}-ethyl ester (107-3)

To a solution of (S)-2-[(S)-2-((S)-2-{(S)-2-[(S)-2-((S)-2-Acetoxy-propionyloxy)-propionyloxy]-propionyloxy}-propionyloxy)-propionyloxy]-propionic acid 89-1 (5.56 g, 11.3 mmol) in dimethyl sulfoxide (30 mL) were added EDC.HCl (2.55 g, 13.3 mmol), benzotriazol-1-ol (0.28 g, 2.05 mmol), Brimonidine 24-2 (3 g, 10.2 mmol) and 4-dimethylaminopyridine (0.125 g, 1.02 mmol) at 0° C. The reaction mixture was allowed to stir at 25-30° C. over a period of 2 h. The resulting reaction mass was quenched with water (400 mL), extracted with dichloromethane (500×2 mL), dried over sodium sulfate and concentrated under reduced pressure. The crude product obtained upon evaporation of volatiles was purified through silica gel (230-400 mesh) column chromatography (45% ethyl acetate in hexane) to obtain product 107-3 as a pale yellow solid 2.4 g (30.5%).

Scheme 78: Synthesis of 5-[5-(2,5-Dioxo-pyrrolidin-1-yl)-2-oxo-1,2-dihydro-indol-(3Z)-ylidenemethyl]-2,4-dimethyl-1H-pyrrole-3-carboxylic acid (2-diethylamino-ethyl)-amide (108-3):

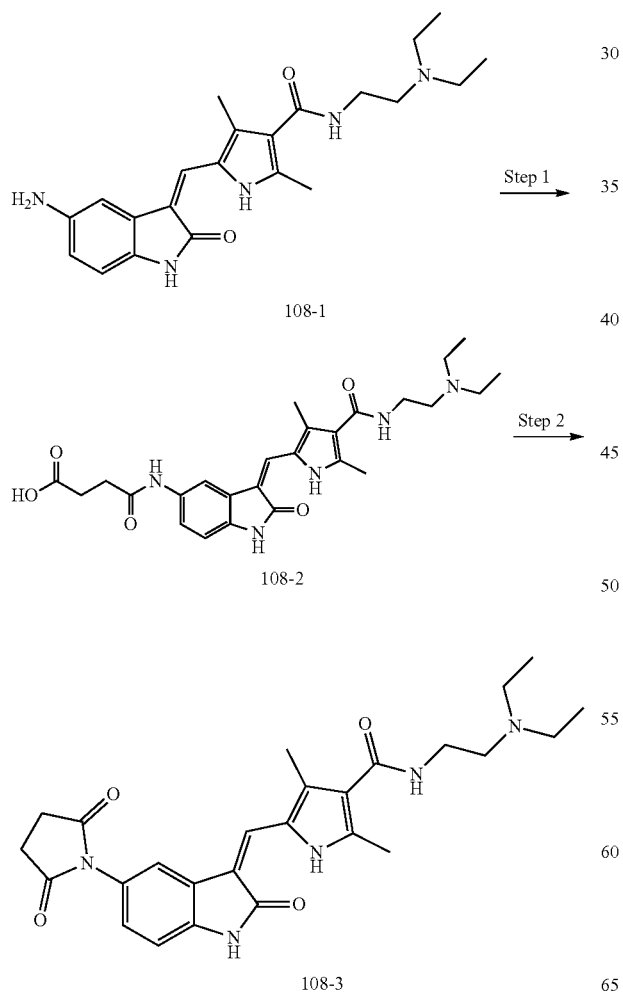

424

Step 1: Preparation of N-{3-[1-[4-(2-Diethylamino-ethylcarbamoyl)-3,5-dimethyl-1H-pyrrol-2-yl]-meth-(Z)-ylidene]-2-oxo-2,3-dihydro-1H-indol-5-yl}-succinamic acid (108-2)

To a solution of 5-[5-Amino-2-oxo-1,2-dihydro-indol-(3Z)-ylidenemethyl]-2,4-dimethyl-1H-pyrrole-3-carboxylic acid (2-diethylamino-ethyl)-amide 108-1 (7.0 g, 17.7 mmol) in dichloromethane (70 mL) were added dihydro-furan-2,5-dione (1.94 g, 19.49 mmol) and 4-dimethylaminopyridine (0.21 g, 1.77 mmol) at 0° C. The reaction mixture was allowed to stir at room temperature over a period of 16 h. The resulting reaction mixture was concentrated under reduced pressure to give product 108-2 as a brown solid 4.4 g (50%).

Step 2: Preparation of 5-[5-(2,5-Dioxo-pyrrolidin-1-yl)-2-oxo-1,2-dihydro-indol-(3Z)-ylidenemethyl]-2,4-dimethyl-1H-pyrrole-3-carboxylic acid (2-diethylamino-ethyl)-amide (108-3)

To a solution of N-{3-[1-[4-(2-Diethylamino-ethylcarbamoyl)-3,5-dimethyl-1H-pyrrol-2-yl]-meth-(Z)-ylidene]-2-oxo-2,3-dihydro-1H-indol-5-yl}-succinamic acid 108-2 (2.3 g, 4.65 mmol) in N,N-dimethylformamide (23 mL) were added N,N-diisopropylethylamine (1.28 mL, 6.97 mmol), HATU (2.1 g, 5.58 mmol), 4-dimethylaminopyridine (0.057 g, 0.46 mmol) at 0° C. The reaction mixture was allowed to stir at 25-30° C. over a period of 2 h. The resulting reaction mass was quenched with water (100 mL), extracted with ethyl acetate (200×2 mL), dried over sodium sulfate and concentrated under reduced pressure. The crude product was washed with diethyl ether (20×2 mL) to obtain product 108-3 as a pale yellow solid 1.2 g (54%).

Scheme 79: Synthesis of 9-(5-Bromo-quinoxalin-6-yl)-2,6,7,9-tetrahydro-3H-imidazo[1,2-a][1,3]diazepine-5,8-dione (110-3):

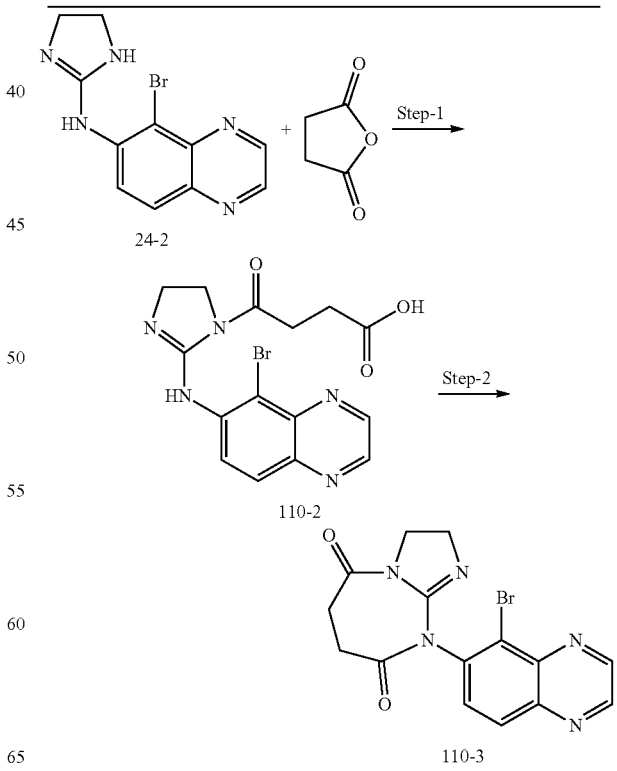

Step 1: Preparation of 4-[2-(5-Bromo-quinoxalin-6-ylamino)-4,5-dihydro-imidazol-1-yl]-4-oxo-butyric acid (110-2)

To a solution Brimonidine 24-2 (2 g, 6.84 mmol) in dimethyl sulfoxide (20 mL) were added dihydro-furan-2,5-dione (0.89 g, 8.90 mmol) and 4-dimethylaminopyridine (83 mg, 0.68 mmol) at 0° C. The reaction mixture was allowed to stir at room temperature over a period of 2 hours. The resulting reaction mixture was quenched with ice cold water and stirred for 10 min. The solid precipitate was filtered and dried under vacuum to obtain product 110-2 as yellow solid 1.8 g (67%).

Step 2: Preparation of 9-(5-Bromo-quinoxalin-6-yl)-2,6,7,9-tetrahydro-3H-imidazo[1,2-a][1,3]diazepine-5,8-dione (110-3)

To a solution of 4-[2-(5-Bromo-quinoxalin-6-ylamino)-4,5-dihydro-imidazol-1-yl]-4-oxo-butyric acid 110-2 (4 g, 10.20 mmol) in N,N-dimethylformamide (20 mL) were added N,N-diisopropylethylamine (2.82 mL, 15.30 mmol), HATU (5.04 g, 13.20 mmol), 4-dimethylaminopyridine (124 mg, 1.02 mmol) at 0° C. The reaction mixture was allowed to stir at 25-30° C. over a period of 2 h. The resulting reaction mixture was quenched with ice cold water and stirred for 10 min. The solid precipitate was filtered and dried under vacuum obtain product as 110-3 as an off white solid 2 g (52%).

Scheme 80: Synthesis of (S)-2-Acetoxy-propionic acid (S)-2-[3-[(S)-2-((S)-2-acetoxy-propionyloxy)-propionyl]-2-(5-bromo-quinoxalin-6-ylimino)-imidazolidin-1-yl]-1-methyl-2-oxo-ethyl ester (111-4):

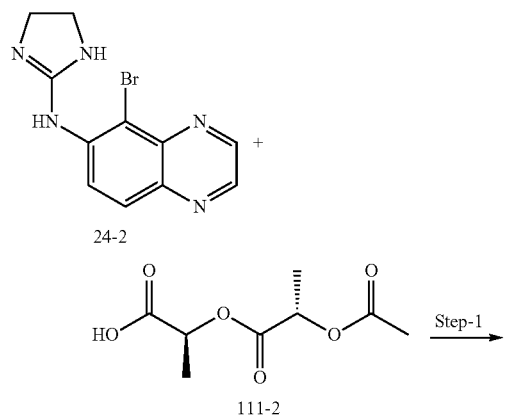

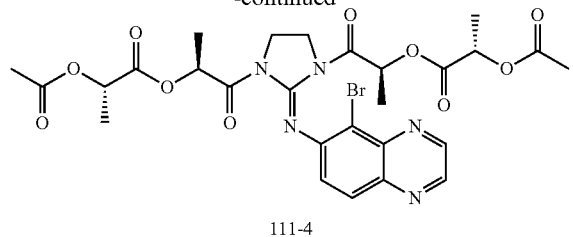

Step 1: Preparation of (S)-2-Acetoxy-propionic acid (S)-2-[2-(5-bromo-quinoxalin-6-ylamino)-4,5-dihydro-imidazol-1-yl]-1-methyl-2-oxo-ethyl ester (111-3)

To a solution of (S)-2-((S)-2-Acetoxy-propionyloxy)-propionic acid 111-2 (0.433 g, 2.12 mmol) in dimethyl sulfoxide were added EDC.HCl (0.487 g, 2.55 mmol), Brimonidine 24-2 (0.25 g, 0.85 mmol) and 4-dimethylaminopyridine (10 mg, 0.08 mmol) at 0° C. The reaction mixture was allowed to stir at 25-30° C. over a period of 2 hours. The resulting reaction mass was quenched with water (50 mL), extracted with ethyl acetate (100×2 mL), dried over sodium sulfate and concentrated under reduced pressure. The crude product obtained upon evaporation of volatiles was purified through silica gel (60-120 mesh) column chromatography (40% ethyl acetate in hexane) to obtain product 111-3 as a pale yellow solid 250 mg (62%).

Step 2: Preparation of (S)-2-Acetoxy-propionic acid (S)-2-[3-[(S)-2-((S)-2-acetoxy-propionyloxy)-propionyl]-2-(5-bromo-quinoxalin-6-ylimino)-imidazolidin-1-yl]-1-methyl-2-oxo-ethyl ester (111-4)

To a solution of (S)-2-((S)-2-Acetoxy-propionyloxy)-propionic acid 111-2 (1.92 g, 9.41 mmol) in dichloromethane (20 mL) were added oxalyl chloride (0.96 mL, 11.29 mmol) and N,N-dimethylformamide (0.3 mL) at 0° C. The reaction mixture was allowed to stir at room temperature over a period of 30 min. Concentrated the reaction mixture to dryness under nitrogen, diluted with dichloromethane (45 mL), was added triethylamine (1.92 mL, 14.11 mmol) followed by (S)-2-Acetoxy-propionic acid (S)-2-[2-(5-bromo-quinoxalin-6-ylamino)-4,5-dihydro-imidazol-1-yl]-1-methyl-2-oxo-ethyl ester 111-3 (4.5 g, 9.41 mmol) and 4-dimethylaminopyridine (0.114 g, 0.94 mmol) at 0° C. The reaction mixture was allowed to stir at room temperature over a period of 2 hours. The resulting reaction mass was quenched with water (200 mL), extracted with ethyl acetate (200×3 mL), dried over sodium sulfate and concentrated under reduced pressure and washed with ether (30 mL×2) to obtain product 111-4 as an off white solid 4.0 g (64%).

Scheme 81: Synthesis of (S)-2-Acetoxy-propionic acid (S)-2-{3-acetyl-2-[(Z)-5-bromo-quinoxalin-6-ylimino]-imidazolidin-1-yl}-1-methyl-2-oxo-ethyl ester (114-4):

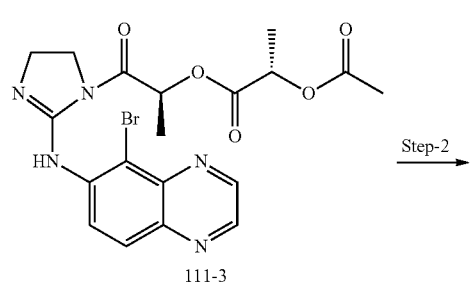

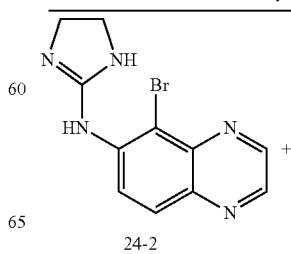

427

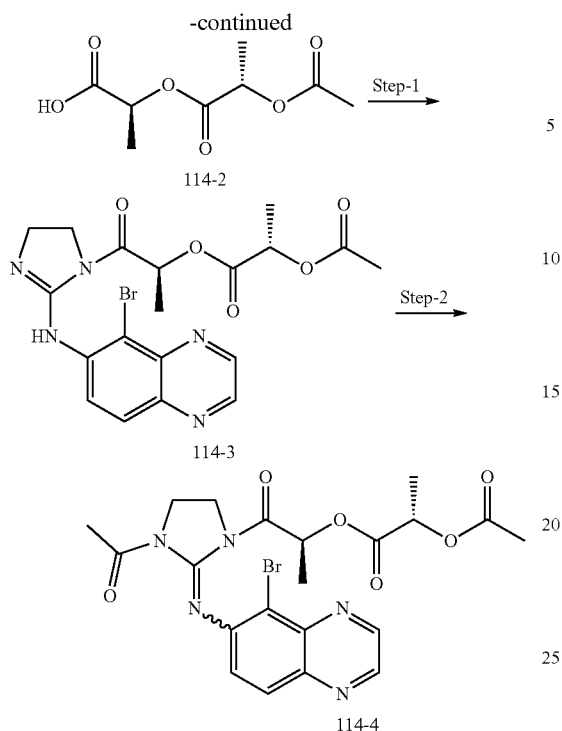

Step 1: Preparation of (S)-2-Acetoxy-propionic acid (S)-2-[2-(5-bromo-quinoxalin-6-ylamino)-4,5-dihydro-imidazol-1-yl]-1-methyl-2-oxo-ethyl ester (114-3)

To a solution of (S)-2-((S)-2-Acetoxy-propionyloxy)-propionic acid 114-2 (0.433 g, 2.12 mmol), in dimethyl sulfoxide (2.5 mL) were added EDC.HCl (0.487 g, 2.55 mmol), Brimonidine 24-2 (0.25 g, 0.85 mmol) and 4-dimethylaminopyridine (10 mg, 0.08 mmol) at 0° C. The reaction mixture was allowed to stir at 25-30° C. over a period of 1 h. The resulting reaction mass was quenched with water (50 mL), extracted with dichloromethane (100×2 mL), dried over sodium sulfate and concentrated under reduced pressure. The crude product obtained upon evaporation of volatiles was purified through silica gel (230-400 mesh) column chromatography (40% ethyl acetate in hexane) to obtain product 114-3 as a pale yellow solid 250 mg (62%).

Step 2: (S)-2-Acetoxy-propionic acid (S)-2-{3-acetyl-2-[(Z)-5-bromo-quinoxalin-6-ylimino]-imidazolidin-1-yl}-1-methyl-2-oxo-ethyl ester (114-4)

To a solution of (S)-2-Acetoxy-propionic acid (S)-2-[2-(5-bromo-quinoxalin-6-ylamino)-4,5-dihydro-imidazol-1-yl]-1-methyl-2-oxo-ethyl ester 114-3 (1 g, 2.09 mmol) in dichloromethane (20 mL) were added triethylamine (1.47 ml, 10.40 mmol), acetyl chloride (0.22 mL, 3.1 mmol) and 4-dimethylaminopyridine (0.025 g, 0.20 mmol) at 0° C. The reaction mixture stirred at 25-30° C. over a period of 1 h. The resulting reaction mixture was quenched with water (200 mL), extracted with dichloromethane (2×250 mL) and dried over sodium sulfate. Then volatiles were evaporated under reduced pressure. The crude product obtained upon evaporation of volatiles was purified through silica gel (230-400 mesh) column chromatography (40% ethyl acetate in hexane) to obtain product 114-4 as an off white solid 0.6 g.

428

Scheme 82: Synthesis of Succinic acid (S)-1-({[(S)-2-((S)-2-acetoxy-propionyloxy)-propionyl]-tert-butyl-amino}-methyl)-2-(4-morpholin-4-yl-[1,2,5]thiadiazol-3-yloxy)-ethyl ester ethyl ester (117-6):

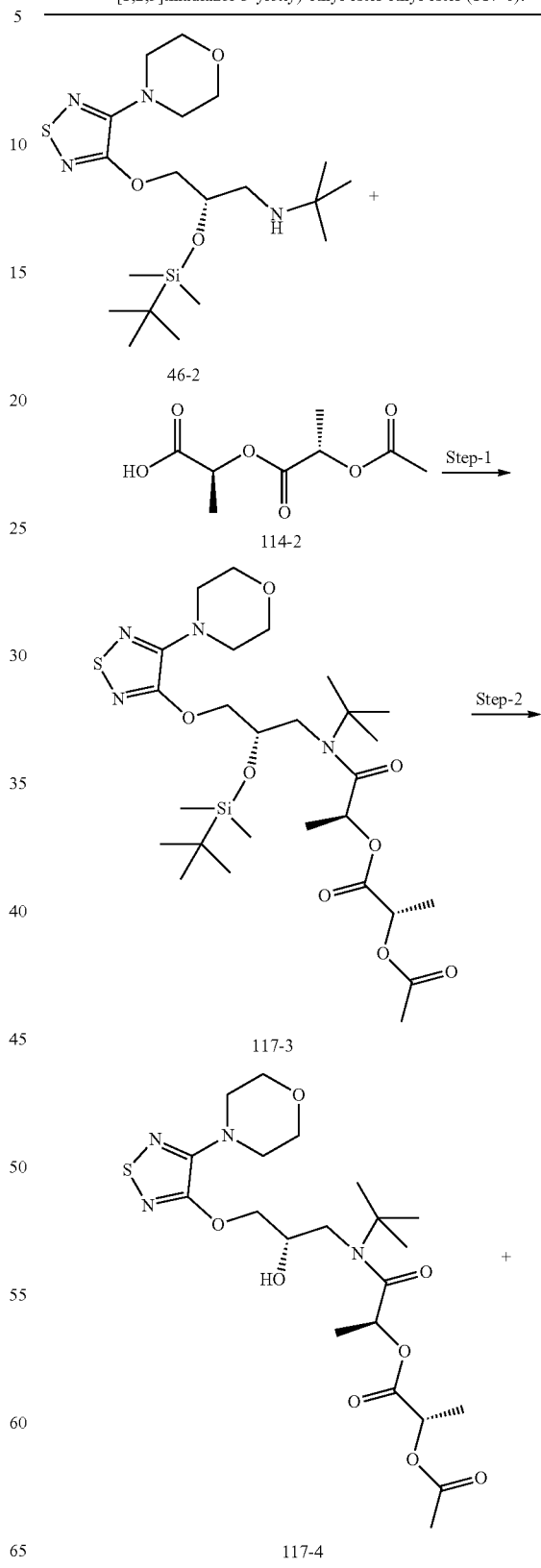

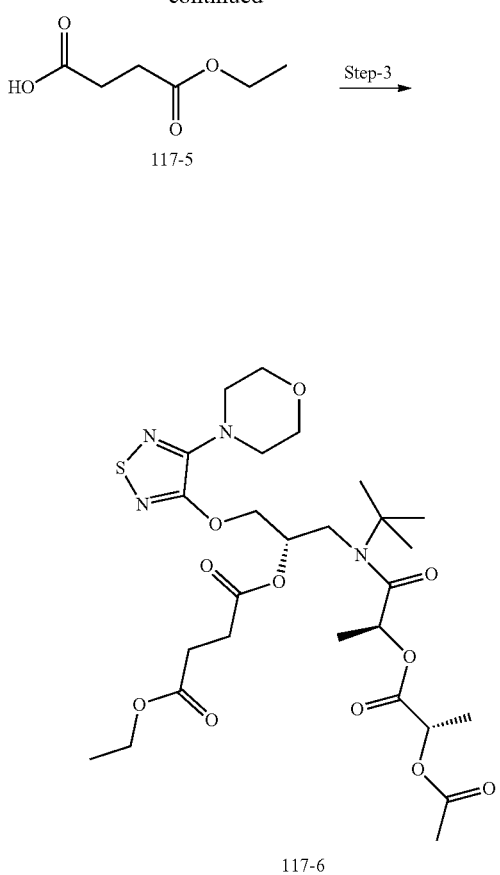

117-5

117-6

Step 1: Preparation of (S)-2-Acetoxy-propionic acid (S)-1-{tert-butyl-[(S)-2-(tert-butyl-dimethyl-silanyloxy)-3-(4-morpholin-4-yl-[1,2,5]thiadiazol-3-yloxy)-propyl]-carbamoyl}-ethyl ester (117-3)

To a solution of (S)-2-((S)-2-Acetoxy-propionyloxy)-propionic acid 114-2 (9.47 g, 46.4 mmol) in dichloromethane (100 mL) was added oxalyl chloride (5.97 mL, 69.6 mmol) and N,N-dimethylformamide (0.2 mL) at 0° C. The reaction mixture was allowed to stir at room temperature over a period of 30 minutes. The reaction mixture was concentrated to dryness under nitrogen, diluted with dichloromethane (100 mL), and N,N-diisopropylethylamine (17.1 mL, 92.8 mmol) followed by tert-Butyl-[(S)-2-(tert-butyl-dimethyl-silanyloxy)-3-(4-morpholin-4-yl-[1,2,5]thiadiazol-3-yloxy)-propyl]-amine 46-2 (10 g, 23.2 mmol) and 4-dimethylaminopyridine (0.02 g, 2.3 mmol) was added at 0° C. The reaction mixture was allowed to stir at room temperature over a period of 1 hour. The resulting reaction mass was quenched with water (500 mL), extracted with dichloromethane (500×2 mL), dried over sodium sulfate and concentrated under reduced pressure. The crude product obtained upon evaporation of volatiles was purified through silica gel (230-400 mesh) column chromatography (12% ethyl acetate in hexane) to obtain product 117-3 as colorless liquid 5.0 g (34%).

Step 2: Preparation of (S)-2-Acetoxy-propionic acid (S)-1-{tert-butyl-[(S)-2-hydroxy-3-(4-morpholin-4-yl-[1,2,5]thiadiazol-3-yloxy)-propyl]-carbamoyl}-ethyl ester (117-4)

To a solution of 2-Acetoxy-propionic acid 1-{tert-butyl-[(S)-2-(tert-butyl-dimethyl-silanyloxy)-3-(4-morpholin-4-yl-[1,2,5]thiadiazol-3-yloxy)-propyl]-carbamoyl}-ethyl ester 117-3 (5.0 g, 8.1 mmol) in tetrahydrofuran (50 mL) was added tetra butyl ammonium fluoride (12.1 mL, 1.0 M, 12.1 mmol) at 0° C. The reaction mixture was allowed to stir at room temperature over a period of 1 hour. The resulting reaction mixture was concentrated under reduced pressure and crude product obtained upon evaporation of the volatiles was purified through silica gel (230-400 mesh) column chromatography (25% ethyl acetate in hexane) to give product 117-4 as an colorless wax 1.3 g (31%).

Step 3: Preparation of Succinic acid (S)-1-({[(S)-2-((S)-2-acetoxy-propionyloxy)-propionyl]-tert-butyl-amino}-methyl)-2-(4-morpholin-4-yl-[1,2,5]thiadiazol-3-yloxy)-ethyl ester ethyl ester (117-6)

To a solution of Succinic acid monoethyl ester 117-5 (0.5 g, 3.50 mmol) in dichloromethane (15 mL) was added DCC (0.73 g, 3.58 mmol), (S)-2-Acetoxy-propionic acid (S)-1-{tert-butyl-[(S)-2-hydroxy-3-(4-morpholin-4-yl-[1,2,5]thiadiazol-3-yloxy)-propyl]-carbamoyl}-ethyl ester 117-4 (1.2 g, 2.38 mmol) and 4-dimethylaminopyridine (0.029 g, 0.23 mmol) at 0° C. The reaction mixture was allowed to stir at 25-30° C. over a period of 1 hour. The resulting reaction mass was quenched with water (100 mL), extracted with dichloromethane (200×2 mL), dried over sodium sulfate and concentrated under reduced pressure. The crude product obtained upon evaporation of volatiles was purified through silica gel (230-400 mesh) column chromatography (25% ethyl acetate in hexane) to obtain product 117-6 as colorless wax 0.8 g (52%).

Scheme 83: Synthesis of Timolol-Bis-PLA(n = 4)-OAc (119-6):

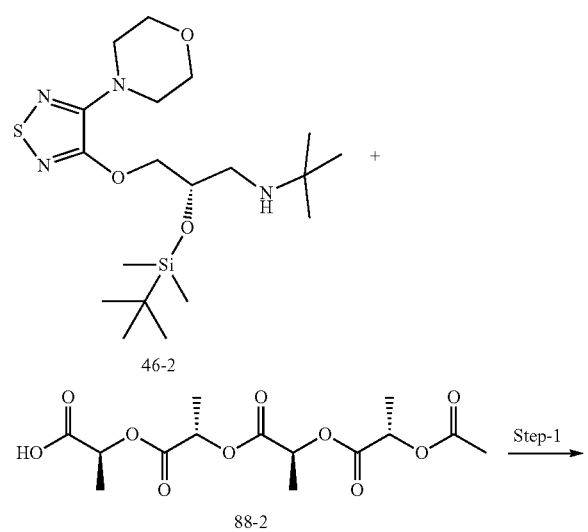

46-2

88-2

431
-continued

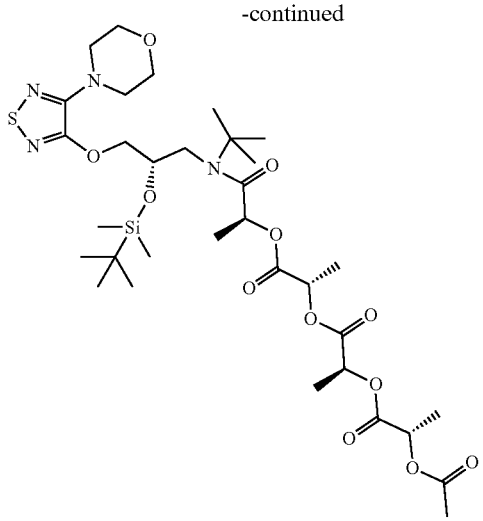

119-3

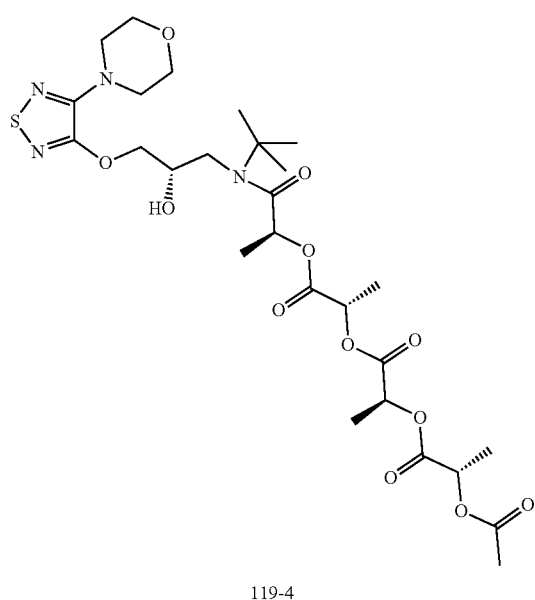

119-4

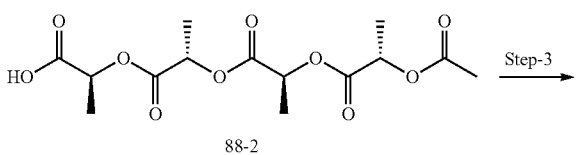

88-2

432
-continued

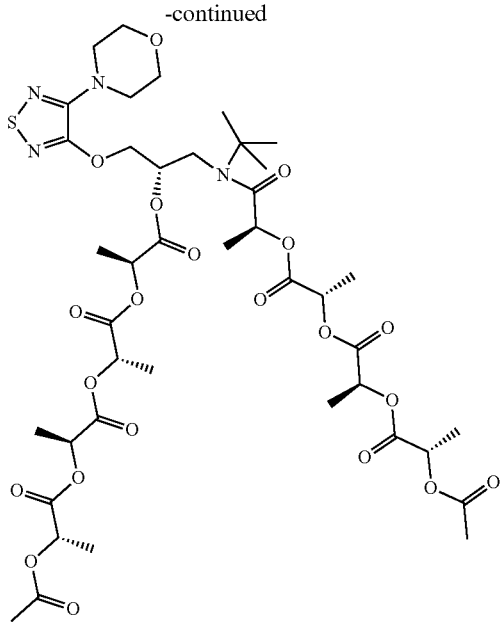

119-6

Step 1: Preparation of (S)-2-[(S)-2-((S)-2-Acetoxy-propionyloxy)-propionyloxy]-propionic acid (S)-1-{tert-butyl-[(S)-2-(tert-butyl-dimethyl-silanyloxy)-3-(4-morpholin-4-yl-[1,2,5]thiadiazol-3-yloxy)-propyl]-carbamoyl}-ethyl ester (119-3)

To a solution of (S)-2-{(S)-2-[(S)-2-((S)-2-Acetoxy-propionyloxy)-propionyloxy]-propionyloxy}-propionic acid 88-2 (14.5 g, 41.7 mmol) in dichloromethane (100 mL) was added oxalyl chloride (4.5 mL, 52.2 mmol) and N,N-dimethylformamide (0.2 mL) at 0° C. The reaction mixture was allowed to stir at room temperature over a period of 30 minutes. The reaction mixture was concentrated to dryness under nitrogen, diluted with dichloromethane (100 mL), and N,N-diisopropylethylamine (13.4 mL, 73.1 mmol) followed by tert-Butyl-[(S)-2-(tert-butyl-dimethyl-silanyloxy)-3-(4-morpholin-4-yl-[1,2,5]thiadiazol-3-yloxy)-propyl]-amine 46-2 (9 g, 20.8 mmol) and 4-dimethylaminopyridine (0.25 g, 2.0 mmol) was added at 0° C. The reaction mixture was allowed to stir at room temperature over a period of 1 hour. The resulting reaction mass was quenched with water (500 mL), extracted with dichloromethane (500×2 mL), dried over sodium sulfate and concentrated under reduced pressure. The crude product obtained upon evaporation of volatiles was purified through silica gel (230-400 mesh) column chromatography (16% ethyl acetate in hexane) to obtain product 119-3 as colorless wax 8.0 g (50%).

Step 2: Preparation of (S)-2-[(S)-2-((S)-2-Acetoxy-propionyloxy)-propionyloxy]-propionic acid (S)-1-{tert-butyl-[(S)-2-hydroxy-3-(4-morpholin-4-yl-[1,2,5]thiadiazol-3-yloxy)-propyl]-carbamoyl}-ethyl ester (119-4)

To a solution of (S)-2-[(S)-2-((S)-2-Acetoxy-propionyloxy)-propionyloxy]-propionic acid (S)-1-{tert-butyl-[(S)-2-(tert-butyl-dimethyl-silanyloxy)-3-(4-morpholin-4-yl-[1,2,5]thiadiazol-3-yloxy)-propyl]-carbamoyl}-ethyl ester 119-3 (7.0 g, 9.2 mmol) in tetrahydrofuran (70 mL) was added tetra butyl ammonium fluoride (14 mL, 1.0 M, 13.8 mmol) at 0° C. The reaction mixture was allowed to stir at room temperature over a period of 1 hour. The resulting reaction mixture was concentrated under reduced pressure and crude product obtained upon evaporation of the volatiles was purified through silica gel (230-400 mesh) column chromatography (25% ethyl acetate in hexane) to give product 119-4 as a colorless wax 1.2 g (20%).

Step 3: Preparation of Timolol-Bis-PLA(n=4)-OAc (119-6)

To a solution of (S)-2-{(S)-2-[(S)-2-((S)-2-Acetoxy-propionyloxy)-propionyloxy]-propionyloxy}-propionic acid 88-2 (0.8 g, 2.5 mmol) in dichloromethane (10 mL) was added DCC (0.63 g, 3.0 mmol), (S)-2-[(S)-2-((S)-2-Acetoxy-propionyloxy)-propionyloxy]-propionic acid (S)-1-{tert-butyl-[(S)-2-hydroxy-3-(4-morpholin-4-yl-[1,2,5]thiadiazol-3-yloxy)-propyl]-carbamoyl}-ethyl ester 119-4 (1.1 g, 1.7 mmol) and 4-dimethylaminopyridine (0.02 g, 0.17 mmol) at 0° C. The reaction mixture was allowed to stir at 25-30° C. over a period of 1 hour. The resulting reaction mass was quenched with water (100 mL), extracted with dichloromethane (200×2 mL), dried over sodium sulfate and concentrated under reduced pressure. The crude product obtained upon evaporation of volatiles was purified through combi-flash column chromatography (45% ethyl acetate in hexane) to obtain product 119-6 as colorless wax 0.7 g (42%).

Scheme 84: Synthesis of Octadecanoic acid (S)-1-{(S)-1-[(S)-1-(acetyl-tert-butyl-amino)-methyl]-2-(4-morpholin-4-yl-[1,2,5]thiadiazol-3-yloxy)-ethoxycarbonyl]-ethoxycarbonyl}-ethyl ester (121-3):

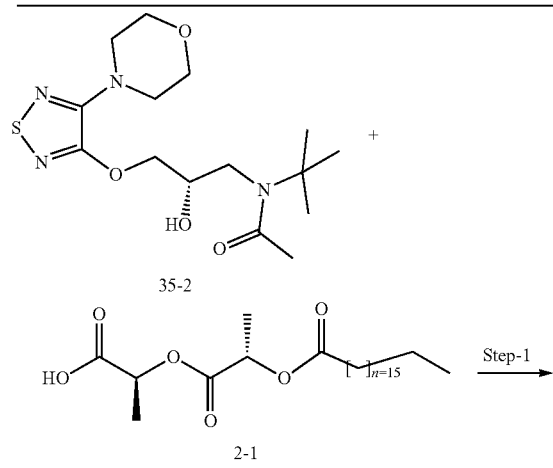

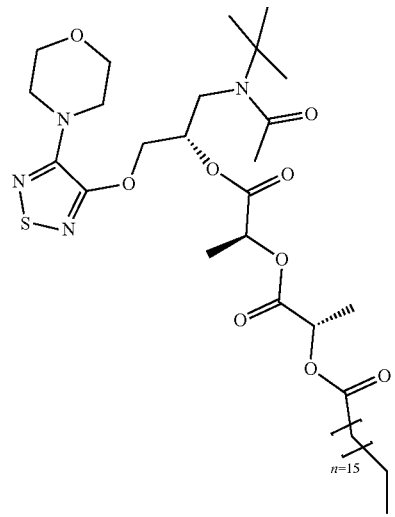

121-3

Step 1: Synthesis of Octadecanoic acid (S)-1-{(S)-1-[(S)-1-[(acetyl-tert-butyl-amino)-methyl]-2-(4-morpholin-4-yl-[1,2,5]thiadiazol-3-yloxy)-ethoxycarbonyl]-ethoxycarbonyl}-ethyl ester (121-3)

To a solution of octadecanoic acid (S)-1-((S)-1-carboxy-ethoxycarbonyl)-ethyl ester 2-1 (0.3 g, 0.83 mmol) in dichloromethane (6 mL) was added DCC (0.31 g, 1.50 mmol), N-tert-butyl-N—[(S)-2-hydroxy-3-(4-morpholin-4-yl-[1,2,5]thiadiazol-3-yloxy)-propyl]-acetamide 35-2 (0.53 g, 1.25 mmol) and 4-dimethylaminopyridine (0.01 g, 0.08 mmol) at 0° C. The reaction mixture was allowed to stir at 25-30° C. over a period of 2 hours. The resulting reaction mass was quenched with water (50 mL), extracted with dichloromethane (50×2 mL), dried over sodium sulfate and concentrated under reduced pressure. The crude product obtained upon evaporation of volatiles was purified through silica gel (230-400 mesh) column chromatography (60% ethyl acetate in hexane) to obtain product 121-3 as a thick oil 0.3 g (95%).

Scheme 85: Synthesis of 4-[2-(5-Bromo-quinoxalin-6-ylamino)-4,5-dihydro-imidazol-1-yl]-4-oxo-butyric acid (S)-1-((S)-1-carboxy-ethoxycarbonyl)-ethyl ester (122-4):

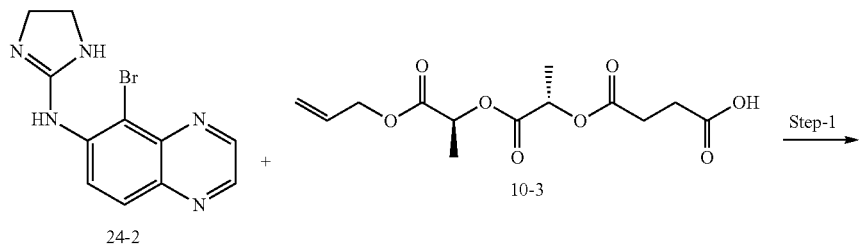

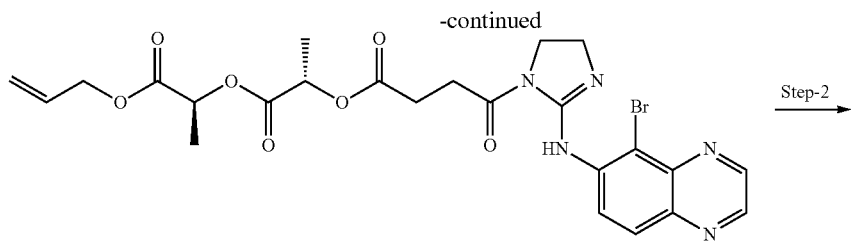

122-3

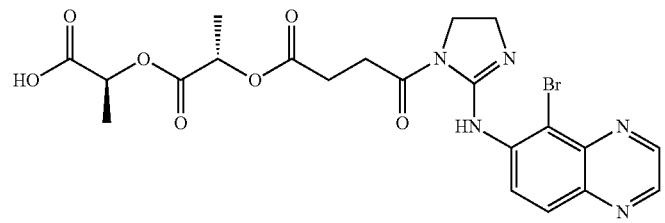

122-4

Step 1: Preparation of 4-[2-(5-Bromo-quinoxalin-6-ylamino)-4,5-dihydro-imidazol-1-yl]-4-oxo-butyric acid (S)-1-((S)-1-allyloxycarbonyl-ethoxycarbonyl)-ethyl ester (122-3)

To a solution of Succinic acid mono-[(S)-1-((5)-1-allyloxycarbonyl-ethoxycarbonyl)-ethyl] ester 10-3 (4.6 g, 15.4 mmol) in dimethyl sulfoxide (30 mL) was added EDC.HCl (3.5 g, 18.4 mmol), benzotriazol-1-ol (0.28 g, 2.05 mmol), Brimonidine 24-2 (3 g, 10.2 mmol) and 4-dimethylaminopyridine (0.12 g, 1.02 mmol) at 0° C. The reaction mixture was allowed to stir at 25-30° C. over a period of 2 h. The resulting reaction mass was quenched with water (400 mL), extracted with dichloromethane (500×2 mL), dried over sodium sulfate and concentrated under reduced pressure. The crude product obtained upon evaporation of volatiles was purified through silica gel (60-120 mesh) column chromatography (50% ethyl acetate in hexane) to obtain product 122-3 as a pale yellow solid 4.2 g (70%).

Step 2: Preparation of 4-[2-(5-Bromo-quinoxalin-6-ylamino)-4,5-dihydro-imidazol-1-yl]-4-oxo-butyric acid (S)-1-((S)-1-carboxy-ethoxycarbonyl)-ethyl ester (122-4)

To a solution 4-[2-(5-Bromo-quinoxalin-6-ylamino)-4,5-dihydro-imidazol-1-yl]-4-oxo-butyric acid (S)-1-((S)-1-allyloxycarbonyl-ethoxycarbonyl)-ethyl ester 122-3 (4 g, 6.94 mmol) in tetrahydrofuran (40 mL) were added tetrakis (triphenylphosphine) palladium (0.8 g, 0.69 mmol) and pyrrolidine (0.6 mL, 6.59 mmol) at 0° C. The reaction mixture was allowed to stir at room temperature over a period of 2 h. The resulting reaction mixture was concentrated under reduced pressure and crude product obtained upon evaporation of the volatiles was purified through silica gel (230-400 mesh) column chromatography (8% isopropyl alcohol in dichloromethane) to give product 122-4 as a greenish solid 2.3 g (62%).

Scheme 86: Synthesis of (S)-2-Hydroxy-propionic acid (S)-1-((S)-1-{(S)-2-[2-(5-bromo-quinoxalin-6-ylamino)-4,5-dihydro-imidazol-1-yl]-1-methyl-2-oxo-ethoxycarbonyl}-ethoxycarbonyl)-ethyl ester (123-4):

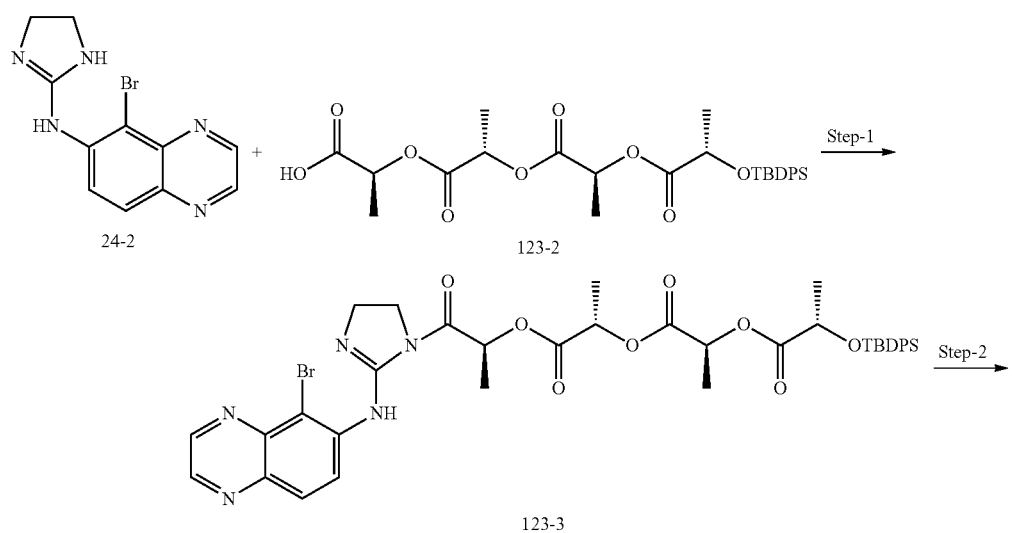

-continued

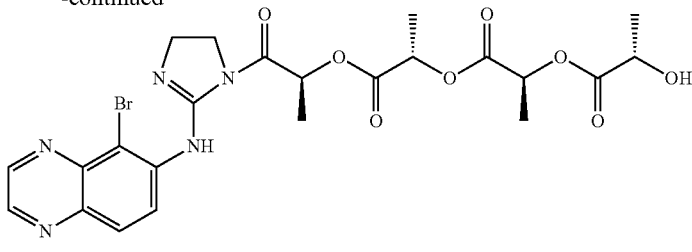

123-4

Step 1: Preparation of (S)-2-(tert-Butyl-diphenyl-silanyloxy)-propionic acid (S)-1-((S)-1-{(S)-2-[2-(5-bromo-quinoxalin-6-ylamino)-4,5-dihydro-imidazol-1-yl]-1-methyl-2-oxo-ethoxycarbonyl}-ethoxycarbonyl)-ethyl ester (123-3)

To a solution of (S)-2-(tert-Butyl-diphenyl-silanyloxy)-propionic acid (S)-1-[(S)-1-((S)-1-carboxy-ethoxycarbonyl)-ethoxycarbonyl]-ethyl ester 3-2 (11.1 g, 20.5 mmol) in dimethyl sulfoxide (20 mL) was added N,N-diisopropylethylamine (6 mL, 34.2 mmol), EDC.HCl (5.2 g, 27.3 mmol), benzotriazol-1-ol (0.37 g, 2.73 mmol), Brimonidine 24-2 (4 g, 13.60 mmol) and 4-dimethylaminopyridine (0.16 g, 1.36 mmol) at 0° C. The reaction mixture was allowed to stir at 25-30° C. over a period of 2 hours. The resulting reaction mass was quenched with water (400 mL), extracted with dichloromethane (500×2 mL), dried over sodium sulfate and concentrated under reduced pressure. The crude product obtained upon evaporation of volatiles was purified through silica gel (60-120 mesh) column chromatography (40% ethyl acetate in hexane) to obtain product 123-3 as a pale yellow solid 9.5 g (84%).

Step 2: Preparation of (S)-2-Hydroxy-propionic acid (S)-1-((S)-1-{(S)-2-[2-(5-bromo-quinoxalin-6-ylamino)-4,5-dihydro-imidazol-1-yl]-1-methyl-2-oxo-ethoxycarbonyl}-ethoxycarbonyl)-ethyl ester (123-4)

To a solution of (S)-2-(tert-Butyl-diphenyl-silanyloxy)-propionic acid (S)-1-((S)-1-{(S)-2-[2-(5-bromo-quinoxalin-6-ylamino)-4,5-dihydro-imidazol-1-yl]-1-methyl-2-oxo-ethoxycarbonyl}-ethoxycarbonyl)-ethyl ester 123-3 (8.0 g, 9.77 mmol) in tetrahydrofuran (80 mL) was added tetra butyl ammonium fluoride (14.6 mL, 1.0 M, 14.60 mmol) and acetic acid (0.85 mL, 14.60 mmol) at 0° C. The reaction mixture was allowed to stir at room temperature over a period of 3 hours. The resulting reaction mixture was concentrated under reduced pressure and crude product obtained upon evaporation of the volatiles was purified through silica gel (230-400 mesh) column chromatography (2% 2-propanol in DCM) to give product 123-4 as a pale yellow solid 4.0 g (70%).

Scheme 87: Synthesis of (S)-2-Hydroxy-propionic acid (S)-2-[2-(5-bromo-quinoxalin-6-ylamino)-4,5-dihydro-imidazol-1-yl]-1-methyl-2-oxo-ethyl ester (124-4):

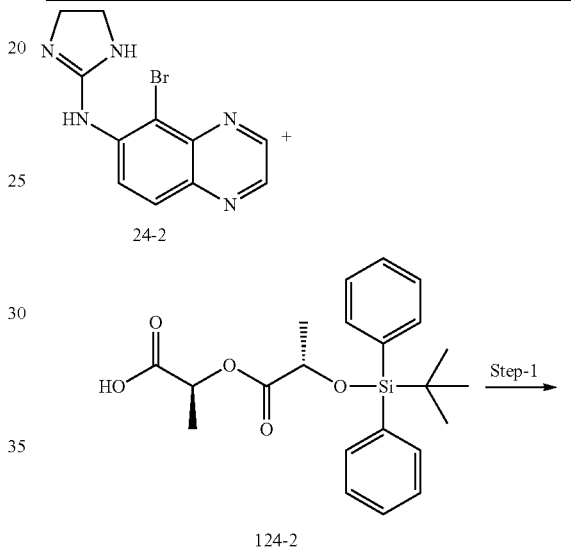

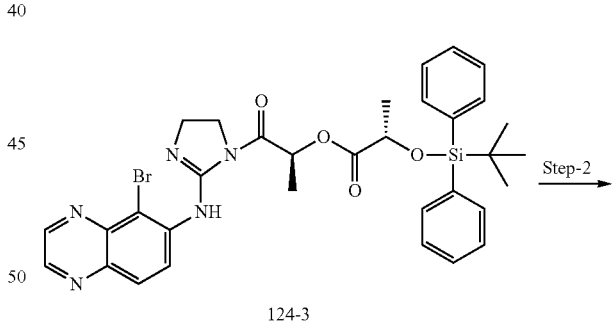

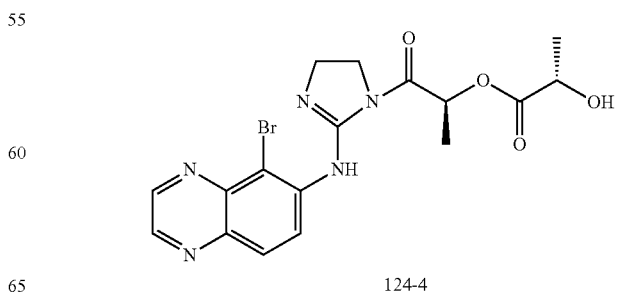

439

Step 1: Preparation of (S)-2-(tert-Butyl-diphenyl-silanyloxy)-propionic acid (S)-2-[2-(5-bromo-quinoxalin-6-ylamino)-4,5-dihydro-imidazol-1-yl]-1-methyl-2-oxo-ethyl ester (124-3)

To a solution of (S)-2-(tert-Butyl-diphenyl-silanyloxy)-propionic acid (S)-1-carboxy-ethyl ester 124-2 (24.6 g, 61.6 mmol) in dimethyl sulfoxide (120 mL) was added EDC.HCl (14.12 g, 73.9 mmol), Brimonidine 24-2 (12 g, 41.09 mmol) and 4-dimethylaminopyridine (0.5 g, 4.19 mmol) at 0° C. The reaction mixture was allowed to stir at 25-30° C. over a period of 2 hours. The resulting reaction mass was quenched with water (300 mL), extracted with ethyl acetate (500×2 mL), dried over sodium sulfate and concentrated under reduced pressure. The crude product obtained upon evaporation of volatiles was purified through silica gel (60-120 mesh) column chromatography (40% ethyl acetate in hexane) to obtain product 124-3 as a pale yellow solid 11.8 g (42%).

440

Step 2: Preparation of (S)-2-Hydroxy-propionic acid (S)-2-[2-(5-bromo-quinoxalin-6-ylamino)-4,5-dihydro-imidazol-1-yl]-1-methyl-2-oxo-ethyl ester (124-4)

To a solution of (S)-2-(tert-Butyl-diphenyl-silanyloxy)-propionic acid (S)-2-[2-(5-bromo-quinoxalin-6-ylamino)-4,5-dihydro-imidazol-1-yl]-1-methyl-2-oxo-ethyl ester 124-3 (11.8 g, 18.20 mmol) in tetrahydrofuran (118 mL) was added tetra butyl ammonium fluoride (36.4 mL, 1.0 M, 36.47 mmol) and acetic acid (2.2 mL, 36.47 mmol) at 0° C. The reaction mixture was allowed to stir at room temperature over a period of 3 h. The resulting reaction mixture was concentrated under reduced pressure and crude product obtained upon evaporation of the volatiles was purified through silica gel (230-400 mesh) column chromatography (2% 2-propanol in DCM) to give product 124-4 as pale yellow solid 3 g (37%).

Scheme 88: Synthesis of compound 240-6:

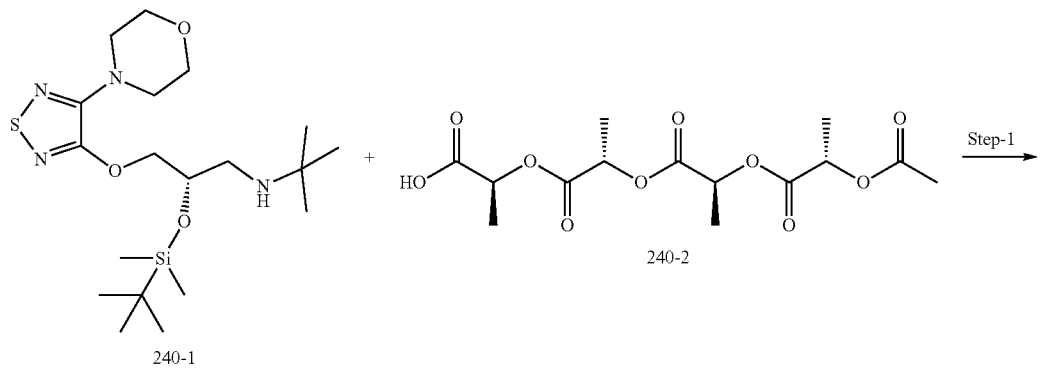

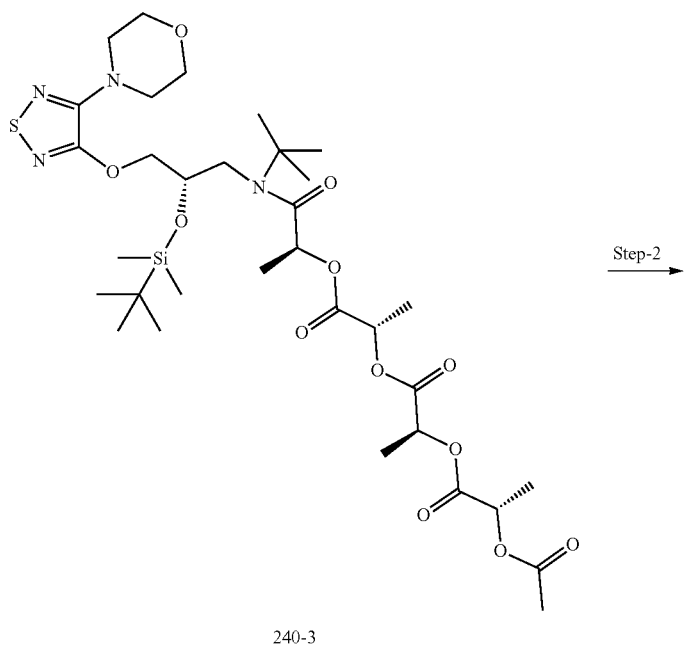

-continued

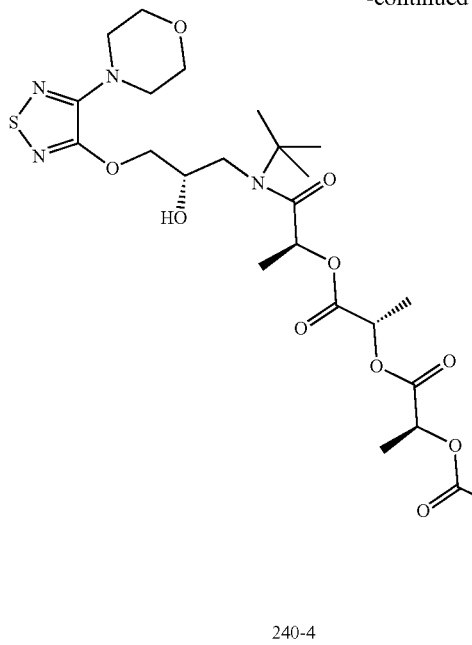

240-4

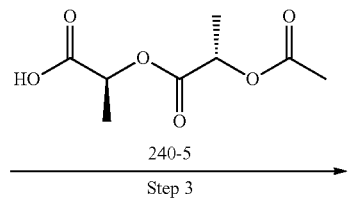

240-5

Step 3

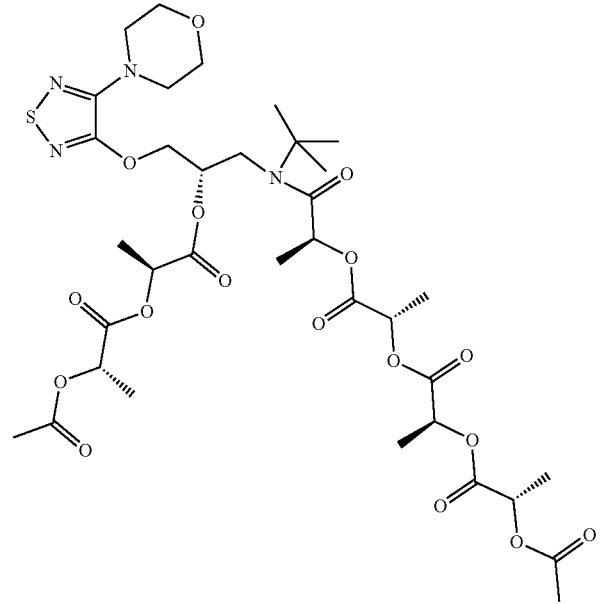

240-6

Step-1: Preparation of (S)-2-[(S)-2-((S)-2-Acetoxy-propionyloxy)-propionyloxy]-propionic acid (S)-1-{tert-butyl-[(S)-2-(tert-butyl-dimethyl-silanyloxy)-3-(4-morpholin-4-yl-[1,2,5]thiadiazol-3-yloxy)-propyl]-carbamoyl}-ethyl ester (240-3)

To a solution of (S)-2-{(S)-2-[(S)-2-((S)-2-acetoxy-propionyloxy)-propionyloxy]-propionyloxy}-propionic acid (240-2, 14.5 g, 41.7 mmol) in dichloromethane (100 mL) was added oxalyl chloride (4.5 mL, 52.2 mmol) and N,N-dimethylformamide (0.2 mL) at 0° C. The reaction mixture was allowed to stir at room temperature over a period of 30 minutes. The reaction was concentrated to dryness under nitrogen atmosphere, diluted with dichloromethane (100 mL), N,N-diisopropylethylamine (13.4 mL, 73.1 mmol) was added followed by tert-butyl-[(S)-2-(tert-butyl-dimethyl-silanyloxy)-3-(4-morpholin-4-yl-[1,2,5]thiadiazol-3-yloxy)-propyl]-amine (240-1, 9 g, 20.8 mmol) and 4-dimethylaminopyridine (0.25 g, 2.0 mmol) at 0° C. The reaction mixture was allowed to stir at room temperature over a period of 1 hour. The resulting reaction mixture was quenched with water (500 mL), extracted with dichloromethane (2×500 mL), dried over sodium sulfate and concentrated under reduced pressure. The crude product obtained upon evaporation of volatiles was purified through silica gel (230-400 mesh) column chromatography (16% ethyl acetate in hexane) to give 240-3 as a colorless wax (8.0 g, 50%).

Step-2: Preparation of (S)-2-[(S)-2-((S)-2-Acetoxy-propionyloxy)-propionyloxy]-propionic acid (S)-1-{tert-butyl-[(S)-2-hydroxy-3-(4-morpholin-4-yl-[1,2,5]thiadiazol-3-yloxy)-propyl]-carbamoyl}-ethyl ester (240-4)

To a solution of (S)-2-[(S)-2-((S)-2-acetoxy-propionyloxy)-propionyloxy]-propionic acid (S)-1-{tert-butyl-[(S)-2-(tert-butyl-dimethyl-silanyloxy)-3-(4-morpholin-4-yl-[1,2,5]thiadiazol-3-yloxy)-propyl]-carbamoyl}-ethyl ester (240-3, 7.0 g, 9.2 mmol) in tetrahydrofuran (70 mL) was added tetrabutylammonium fluoride (14 mL, 1.0 M, 13.8 mmol) at 0° C. The reaction mixture was allowed to stir at room temperature over a period of 1 hour. The resulting reaction mixture was concentrated under reduced pressure, and the crude product obtained upon evaporation of the volatiles was purified through silica gel (230-400 mesh) column chromatography (25% ethyl acetate in hexane) to give 240-4 as a colorless wax (1.2 g, 20%).

Step-3: Preparation of (2S)-1-{[(2S)-1-[(2S)-2-{[(2S)-2-{[(2S)-2-{[(2S)-2-(acetyloxy) propanoyl]oxy}propanoyl]oxy}propanoyl]oxy}-N-tert-butyl-propanamido]-3-{[4-(morpholin-4-yl)-1,2,5-thiadiazol-3-yl]oxy}propan-2-yl]oxy}-1-oxopropan-2-yl (2S)-2-(acetyloxy)propanoate (240-6)

To a solution of 240-5 (0.85 g, 4.18 mmol) in dichloromethane (15 mL) were added DCC (0.95 g, 4.64 mmol), (S)-2-[(S)-2-((S)-2-acetoxy-propionyloxy)-propionyloxy]-propionic acid (S)-1-{tert-butyl-[(S)-2-hydroxy-3-(4-morpholin-4-yl-[1,2,5]thiadiazol-3-yloxy)-propyl]-carbamoyl}-ethyl ester (240-4, 1.5 g, 2.32 mmol) and 4-dimethylaminopyridine (28 mg, 0.23 mmol) at 0° C. The reaction mixture was allowed to stir at 25-30° C. over a period of 2 hours. The resulting reaction mixture was quenched with water (100 mL), extracted with dichloromethane (250×2 mL), dried over sodium sulfate and concentrated under reduced pressure. The crude product obtained upon evaporation of volatiles was purified through silica gel (230-400 mesh) column (25% ethyl acetate in hexane) to give 240-6 as a colorless wax (0.75 g, 38%). $^1$H-NMR (400 MHz, DMSO-d6) δ 5.55-5.3 (m, 2H), 5.25-4.92 (m, 5H), 4.7-4.3 (m, 2H), 3.8-3.6 (m, 6H), 3.45-3.3 (m, 4H), 2.06 (s, 3H), 2.05 (s, 3H), 1.5-1.35 (m, 18H), 1.35 (s, 9H). MS m/z [M+Na]$^+$ 856.3.

Scheme 89: Synthesis of 242-3

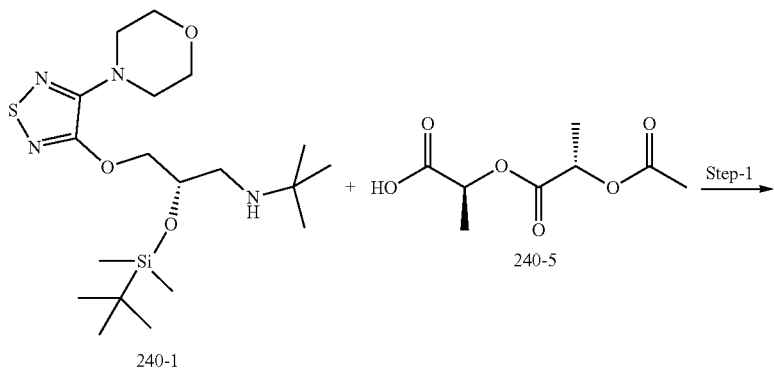

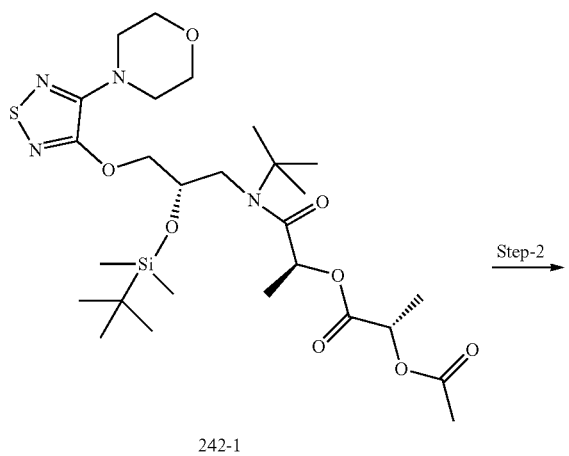

242-1

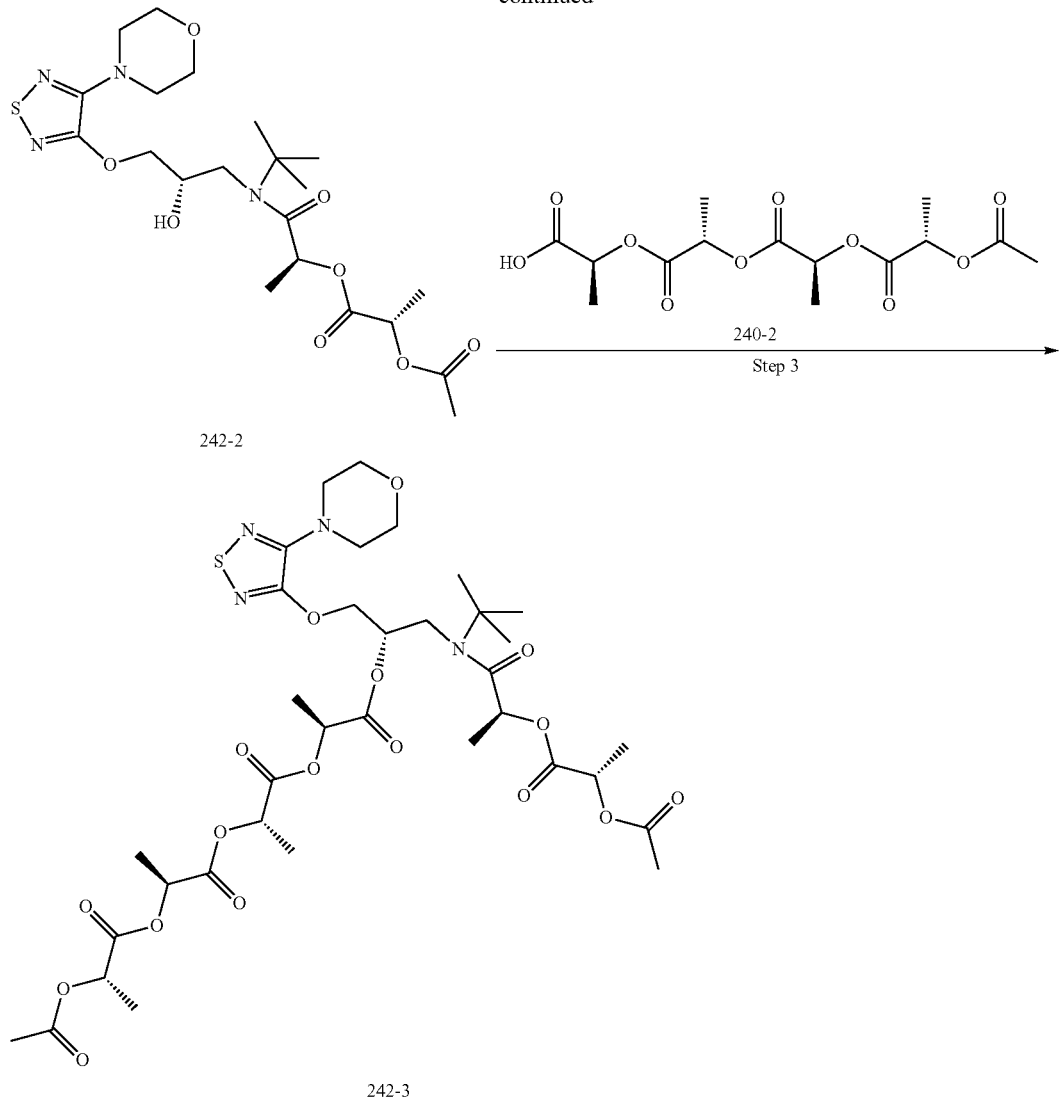

Step-1: Preparation of (S)-2-Acetoxy-propionic acid (S)-1-{tert-butyl-[(S)-2-(tert-butyl-dimethyl-silanyloxy)-3-(4-morpholin-4-yl-[1,2,5]thiadiazol-3-yloxy)-propyl]-carbamoyl}-ethyl ester (242-1)

To a solution of (S)-2-((S)-2-acetoxy-propionyloxy)-propionic acid (240-5, 9.47 g, 46.4 mmol) in dichloromethane (100 mL) were added oxalyl chloride (5.97 mL, 69.6 mmol) and N,N-dimethylformamide (0.2 mL) at 0° C. The reaction mixture was allowed to stir at room temperature over a period of 30 minutes. The reaction mixture was concentrated to dryness under nitrogen and diluted with dichloromethane (100 mL). N,N-diisopropylethylamine (17.1 mL, 92.8 mmol) was added followed by tert-butyl-[(S)-2-(tert-butyl-dimethyl-silanyloxy)-3-(4-morpholin-4-yl-[1,2,5]thiadiazol-3-yloxy)-propyl]-amine (240-1, 10 g, 23.2 mmol) and 4-dimethylaminopyridine (0.02 g, 2.3 mmol) at 0° C. The reaction mixture was allowed to stir at room temperature over a period of 1 hour. The resulting reaction mixture was quenched with water (500 mL), extracted with dichloromethane (2×500 mL), dried over sodium sulfate and concentrated under reduced pressure. The crude product obtained upon evaporation of volatiles was purified through silica gel (230-400 mesh) column (12% ethyl acetate in hexane) to give 242-1 as a colorless liquid (5.0 g, 34%).

Step-2: Preparation of (S)-2-Acetoxy-propionic acid (S)-1-{tert-butyl-[(S)-2-hydroxy-3-(4-morpholin-4-yl-[1,2,5]thiadiazol-3-yloxy)-propyl]-carbamoyl}-ethyl ester (242-2)

To a solution of 2-acetoxy-propionic acid 1-{tert-butyl-[(S)-2-(tert-butyl-dimethyl-silanyloxy)-3-(4-morpholin-4-yl-[1,2,5]thiadiazol-3-yloxy)-propyl]-carbamoyl}-ethyl ester (242-1, 5.0 g, 8.1 mmol) in tetrahydrofuran (50 mL), was added tetrabutylammonium fluoride (12.1 mL, 1.0 M, 12.1 mmol) at 0° C. The reaction mixture was allowed to stir at room temperature over a period of 1 hour. The resulting reaction mixture was concentrated under reduced pressure, and the crude product obtained upon evaporation of the volatiles was purified through silica gel (230-400 mesh) column chromatography (25% ethyl acetate in hexane) to give 242-2 as a colorless wax (1.3 g, 31%).

Step-3: Preparation of (2S)-1-{[(2S)-1-{[(2S)-1-{[(2S)-1-[(2S)-2-{[(2S)-2-(acetyloxy)propanoyl]oxy}-N-tert-butylpropanamido]-3-{[4-(morpholin-4-yl)-1,2,5-thiadiazol-3-yl]oxy} propan-2-yl]oxy}-1-oxopropan-2-yl]oxy}-1-oxopropan-2-yl]oxy}-1-oxopropan-2-yl (2S)-2-(acetyloxy)propanoate (242-3)

To a solution of 240-2 (1.99 g, 5.72 mmol) in dichloromethane (16 mL) were added DCC (1.31 g, 6.36 mmol), (S)-2-acetoxy-propionic acid (S)-1-{tert-butyl-[(S)-2-hydroxy-3-(4-morpholin-4-yl-[1,2,5]thiadiazol-3-yloxy)-propyl]-carbamoyl}-ethyl ester (242-2, 1.6 g, 3.18 mmol) and 4-dimethylaminopyridine (39 mg, 0.32 mmol) at 0° C. The reaction mixture was allowed to stir at 25-30° C. over a period of 2 hours.

The resulting reaction mixture was quenched with water (100 mL), extracted with ethyl acetate (100×3 mL), dried over sodium sulfate and concentrated under reduced pressure. The crude product obtained upon evaporation of volatiles was purified through silica gel (230-400 mesh) column chromatography (25% ethyl acetate in hexane) to give 242-3 as a colorless wax (0.75 g, 28%). $^1$H-NMR (400 MHz, DMSO-d6) δ 5.55-5.3 (m, 2H), 5.23-5.01 (m, 5H), 4.7-4.3 (m, 2H), 3.8-3.6 (m, 6H), 3.47-3.3 (m, 4H), 2.05 (s, 3H), 2.03 (s, 3H), 1.5-1.35 (m, 18H), 1.34 (s, 9H). MS m/z [M+Na]$^+$ 856.5.

Scheme 90: Synthesis of 253-3

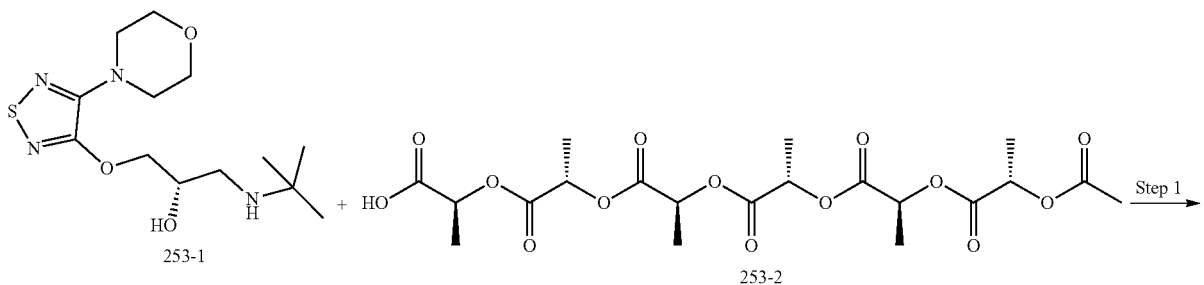

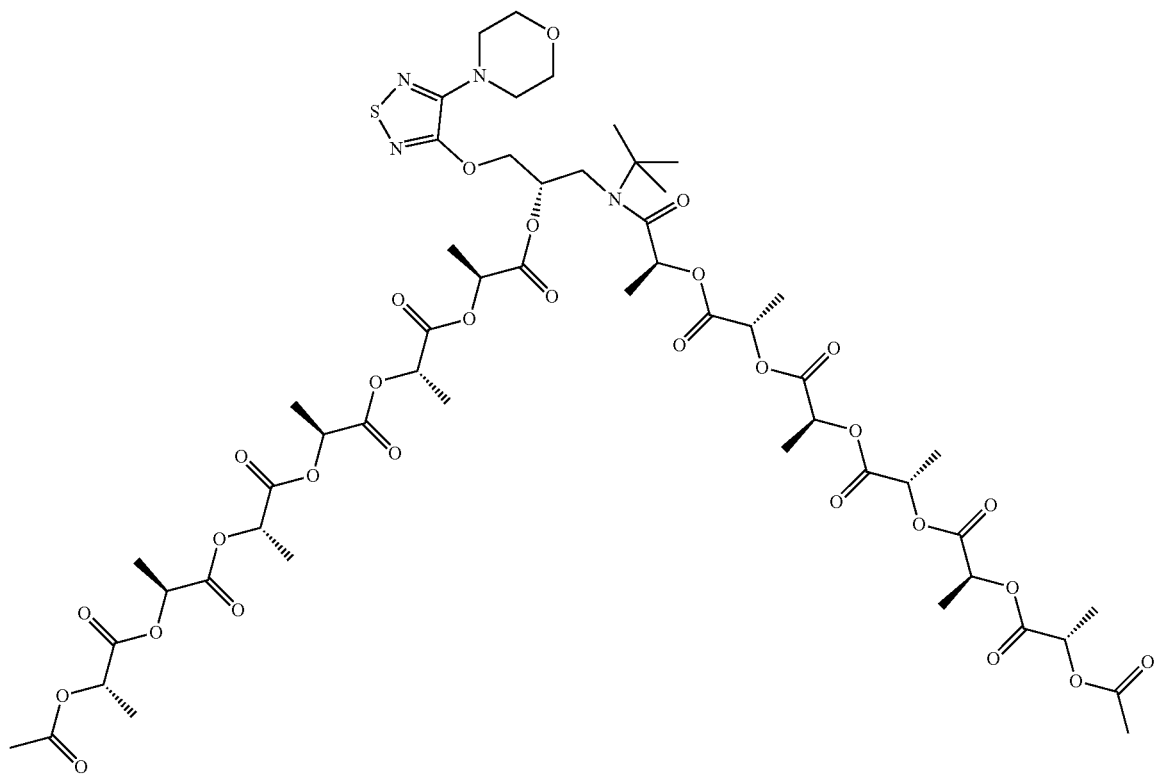

253-3

Step-1: Preparation of (2S)-1-{[(2S)-1-{[(2S)-1-{[(2S)-1-{[(2S)-1-{[(2S)-1-[(2S)- 2-{[(2S)-2-{[(2S)-2-{[(2S)-2-{[(2S)-2-(acetyloxy)propanoyl]oxy}propanoyl]oxy} propanoyl]oxy} propanoyl]oxy}propanoyl]oxy}-N-tert-butylpropanamido]-3-{[4-(morpholin-4-yl)-1,2,5-thiadiazol-3-yl]oxy}propan-2-yl]oxy}-1-oxopropan-2-yl]oxy}-1-oxopropan-2-yl]oxy}-1-oxopropan-2-yl]oxy}-1-oxopropan-2-yl (2S)-2-(acetyloxy)propanoate (253-3)

To a solution of (S)-2-[(S)-2-((S)-2-{(S)-2-[(S)-2-((S)-2-acetoxy-propionyloxy)-propionyloxy]-propionyloxy}-propionyloxy)-propionyloxy]-propionic acid (253-2, 2.72 g, 5.53 mmol) in dichloromethane (30 mL) were added oxalyl chloride (0.54 mL, 6.32 mmol) and N,N-dimethylformamide (0.1 mL) at 0° C. The reaction mixture was allowed to stir at room temperature over a period of 30 minutes. The reaction mixture was concentrated to dryness under nitrogen and diluted with dichloromethane (20 mL). N,N-diisopropylethylamine (1.38 mL, 7.9 mmol) was added followed by timolol (253-1, 0.5 g, 1.58 mmol) and 4-dimethylaminopyridine (0.02 g, 0.16 mmol) at 0° C. The reaction mixture was allowed to stir at room temperature over a period of 1 hour. The resulting reaction mixture was quenched with water (150 mL), extracted with ethyl acetate (300 mL), dried over sodium sulfate and concentrated under reduced pressure. The crude product obtained upon evaporation of volatiles was purified through silica gel (230-400 mesh) column (40% ethyl acetate in hexane) to give partially pure 253-3 as a colorless wax. The waxy residue was further purified by preparative HPLC and lyophilized to obtain pure product 253-3 as a colorless wax (350 mg, 17%). $^1$H-NMR (400 MHz, DMSO-d6) δ 5.55-5.3 (m, 2H), 5.3-5.0 (m, 1H), 4.7-4.3 (m, 2H), 3.8-3.6 (m, 6H), 3.45-3.3 (m, 4H), 2.07 (s, 6H), 1.5-1.35 (m, 36H), 1.33 (s, 9H). MS m/z [M+NH$_4$]$^+$ 1284.3.

Scheme 91: Synthesis of 234-3

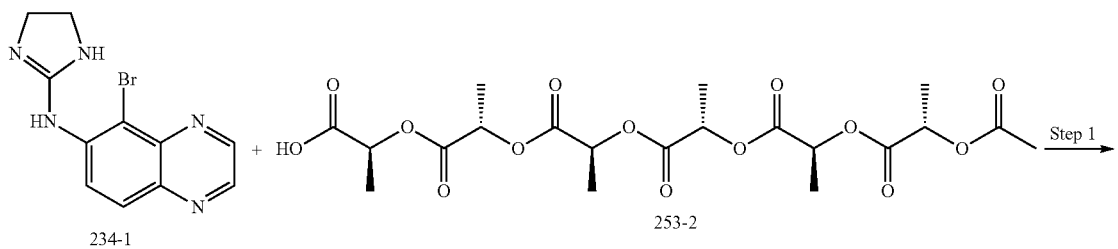

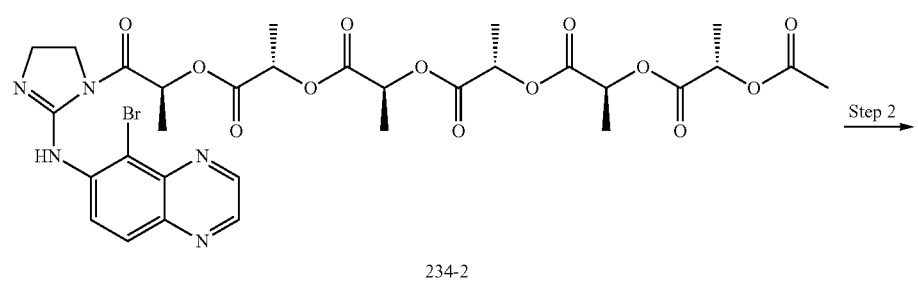

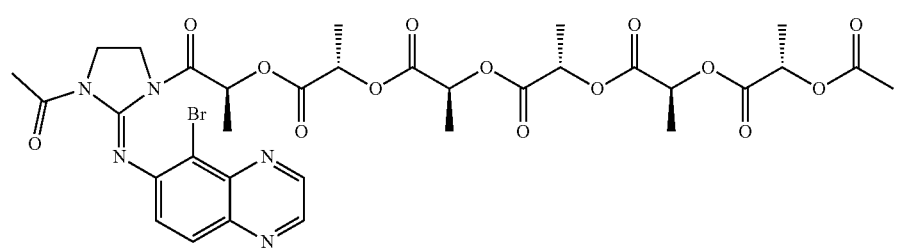

Step-1: Preparation of (S)-2-{(S)-2-[(S)-2-((S)-2-Acetoxy-propionyloxy)-propionyloxy]-propionyloxy}-propionic acid (S)-1-{(S)-2-[2-(5-bromo-quinoxalin-6-ylamino)-4,5-dihydro-imidazol-1-yl]-1-methyl-2-oxo-ethoxycarbonyl}-ethyl ester (234-2)

To a solution of (S)-2-[(S)-2-((S)-2-{(S)-2-[(S)-2-((S)-2-acetoxy-propionyloxy)-propionyloxy]-propionyloxy}-propionyloxy)-propionyloxy]-propionic acid (253-2, 5.5 g, 11.1 mmol) in dichloromethane (60 mL) were added EDC.HCl (1.89 g, 12.2 mmol), hydroxybenzotriazole (0.68 g, 5.08 mmol), brimonidine (234-1, 3.0 g, 10.1 mmol) and 4-dimethylaminopyridine (125 mg, 1.01 mmol) at 0° C. The reaction mixture was allowed to stir at 25-30° C. over a period of 2 hours. The resulting reaction mixture was quenched with water (250 mL), extracted with ethyl acetate (400×2 mL), dried over sodium sulfate and concentrated under reduced pressure. The crude product obtained upon evaporation of volatiles was purified through silica gel (230-400 mesh) column (40% Ethyl acetate in Hexane) to give 234-2 as a pale yellow solid (2.4 g, 30%).

Step-2: Preparation of (2S)-1-{[(2S)-1-{[(2S)-1-{[(2S)-1-{[(2S)-1-[(2Z)-3-acetyl-2-[(5-bromoquinoxalin-6-yl)imino]imidazolidin-1-yl]-1-oxopropan-2-yl]oxy}-1-oxopropan-2-yl]oxy}-1-oxopropan-2-yl]oxy}-1-oxopropan-2-yl]oxy}-1-oxopropan-2-yl (2S)-2-(acetyloxy)propanoate (234-3)

To a solution of (S)-2-{(S)-2-[(S)-2-((S)-2-acetoxy-propionyloxy)-propionyloxy]-propionyloxy}-propionic acid (S)-1-{(S)-2-[2-(5-bromo-quinoxalin-6-ylamino)-4,5-dihydro-imidazol-1-yl]-1-methyl-2-oxo-ethoxycarbonyl}-ethyl ester (234-2, 6.5 g, 8.47 mmol) in dichloromethane (65 mL) were added triethylamine (3.67 mL, 25.41 mmol), acetyl chloride (1.21 mL, 16.95 mmol) and 4-dimethylaminopyridine (103 mg, 0.84 mmol) at 0° C. The reaction mixture was allowed to stir at 25-30° C. over a period of 2 hours. The resulting reaction mixture was quenched with water (200 mL), extracted with ethyl acetate (2×200 mL), dried over sodium sulfate and concentrated under reduced pressure. The crude product obtained upon evaporation of volatiles was purified through silica gel (230-400 mesh) column (70% Ethyl acetate in Hexane) to give 234-3 as a pale yellow solid (3.0 g, 43%). $^1$H-NMR (400 MHz, DMSO-d6) δ 8.94 (d, J=2 Hz, 1H), 8.84 (d, J=2 Hz, 1H), 7.90 (d, J=9 Hz, 1H), 7.58 (d, J=9 Hz, 1H), 6.3-6.1 (m, 1H), 5.24-5.14 (m, 4H), 5.02 (q, 1H), 4.15-3.85 (m, 4H), 2.06 (s, 6H), 1.55-1.37 (m, 18H). MS m/z [M+H]$^+$ 808.6.

Scheme 92: Synthesis of 238-5

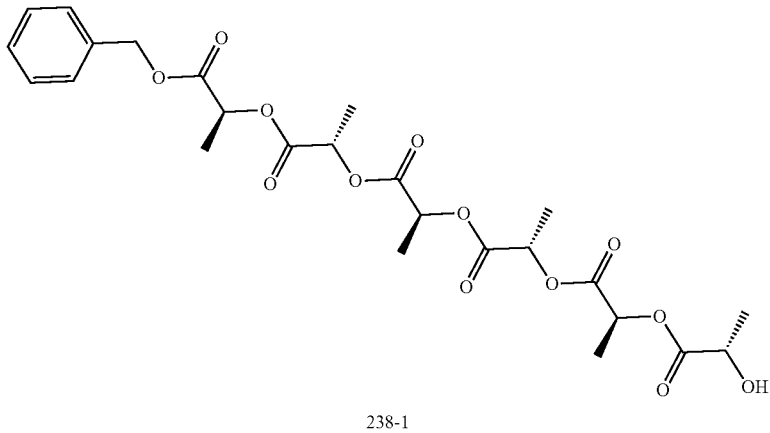

238-1

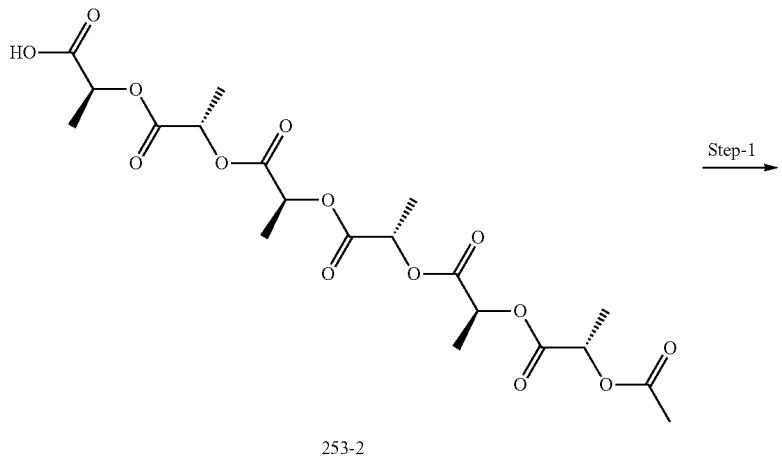

253-2

-continued
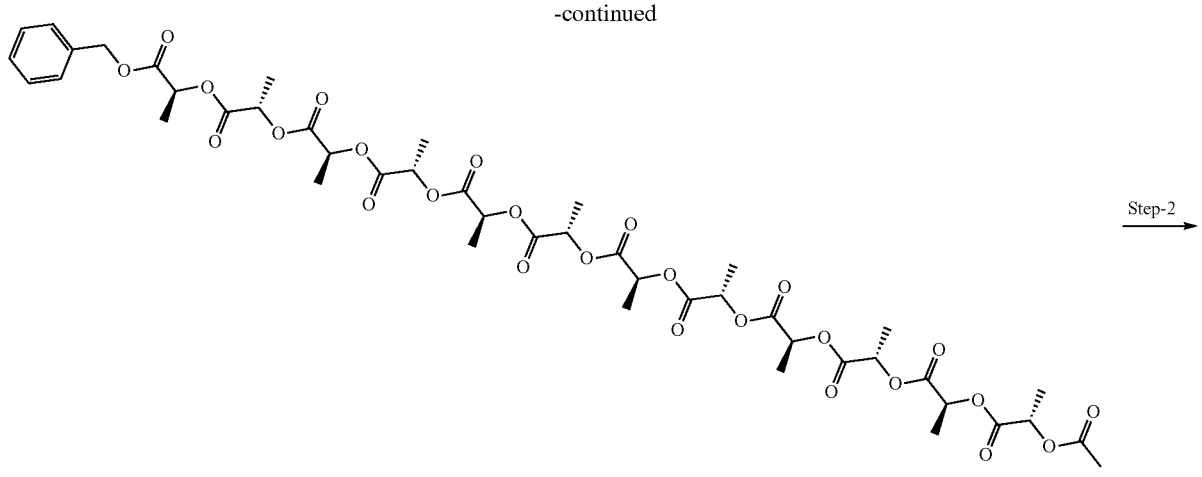
238-2
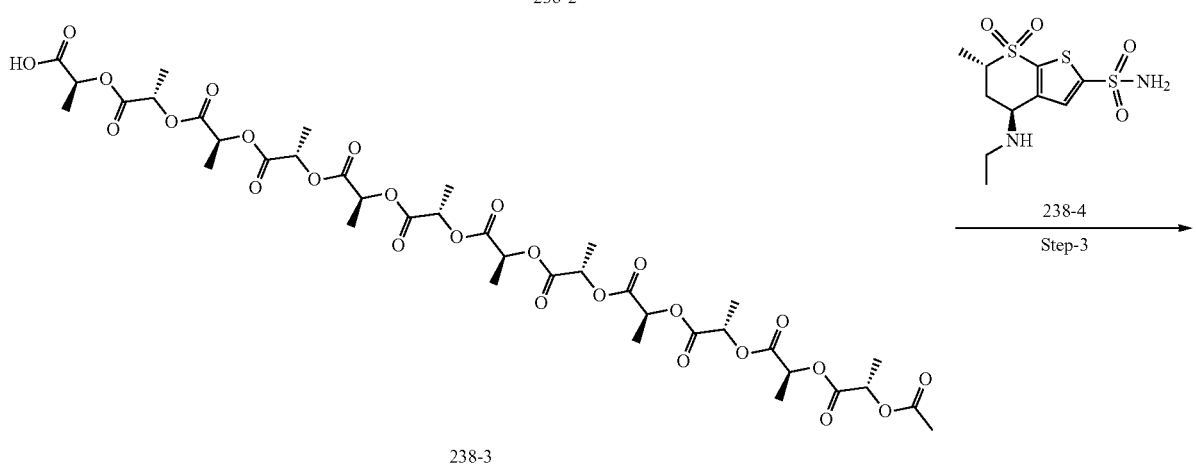
238-3
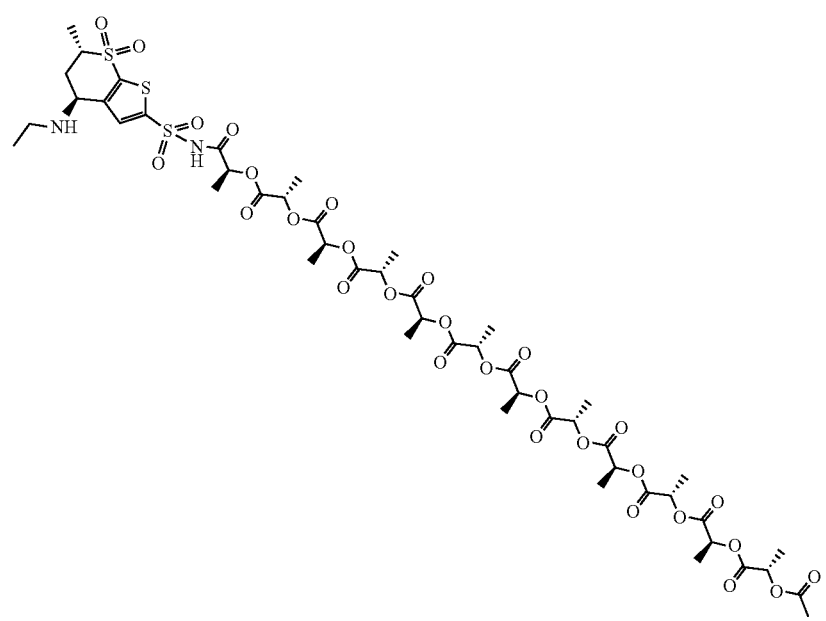
238-5

Step-1: Preparation of (2S)-1-{[(2S)-1-{[(2S)-1-{[(2S)-1-{[(2S)-1-{[(2S)-1-{[(2S)-1-{[(2S)-1-{[(2S)-1-{[(2S)-1-(benzyloxy)-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl (2S)-2-(acetyloxy)propanoate (238-2)

To a solution of (2S)-2-{[(2S)-2-{[(2S)-2-{[(2S)-2-{[(2S)-2-{[(2S)-2-(acetyloxy)propanoyl]oxy}propanoyl]oxy}propanoyl]oxy}propanoyl]oxy}propanoic acid (253-2, 2.7 g, 5.5 mmol) in dichloromethane (30 mL) was added EDC.HCl (0.98 g, 5.18 mmol), hydroxybenzotriazole (0.10 g, 0.174 mmol), (2S)-1-{[(2S)-1-{[(2S)-1-{[(2S)-1-{[(2S)-1-(benzyloxy)-1-oxopropan-2-yl]oxy}-1-oxopropan-2-yl]oxy}-1-oxopropan-2-yl]oxy}-1-oxopropan-2-yl]oxy}-1-oxopropan-2-yl (2S)-2-hydroxypropanoate (238-1, 2.0 g, 3.7 mmol) and 4-dimethylaminopyridine (0.045 g, 0.37 mmol) at 0° C. The reaction mixture was allowed to stir at 25-30° C. over a period of 1 hour. The resulting reaction mixture was quenched with water (250 mL), extracted with ethyl acetate (350×3 mL), dried over Na$_2$SO$_4$ and concentrated under reduced pressure. The crude product obtained upon evaporation of volatiles was purified through silica gel (230-400 mesh) column chromatography (17% ethyl acetate in hexane) to obtain product 238-2 as a colorless liquid (2.3 g, 62%).

Step-2: Preparation of (2S)-2-{[(2S)-2-{[(2S)-2-{[(2S)-2-{[(2S)-2-{[(2S)-2-{{(2S)-2-{[(2S)-2-{[(2S)-2-{[(2S)-2-{[(2S)-2-(acetyloxy)propanoyl]oxy}propanoyl]oxy}propanoyl]oxy}propanoyl]oxy}propanoyl]oxy}propanoyl]oxy}propanoyl]oxy}propanoic acid (238-3)

To a Parr hydrogenation vessel was added a solution of (2S)-1-{[(2S)-1-{[(2S)-1-{[(2S)-1-{[(2S)-1-{[(2S)-1-{[(2S)-1-{[(2S)- 1-{[(2S)-1-(benzyloxy)-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl (2S)-2-(acetyloxy) propanoate (238-2, 2.3 g, 2.26 mmol) in methanol (30 mL) and 10% Pd/C (0.57 g, 50% wet) at 25-30° C. The reaction mixture was stirred at room temperature under hydrogen pressure (5 kg/cm$^2$) over a period of 1 hour. After completion of the reaction, the reaction mixture was filtered through a celite bed and concentrated under reduced pressure to obtain 238-3 as a wax (1.4 g, 70%).

Step-3: Preparation of (2S)-1-{[(2S)-1-{[(2S)-1-{[(2S)-1-{[(2S)-1-{[(2S)-1-{[(2S)-1-{[(2S)-1-{[(2S)-1-{[(2S)-1-[(1S)-1-({[(2S,4S)-4-(ethylamino)-2-methyl-1,1-dioxo-2H,3H,4H-1λ$^6$-thieno[2,3-b]thiopyran-6-yl]sulfonyl}carbamoyl)ethoxy]-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl (2S)-2-(acetyloxy)propanoate (238-5)

To a suspension of dorzolamide (238-4, 0.38 g, 1.0 mmol) in dichloromethane (6 mL) was added N,N-diisopropylethylamine (0.38 mL, 2.11 mmol) at 0° C., and the reaction was stirred for 30 minutes. Then (2S)-2-{[(2S)-2-{[(2S)-2-{[(2S)-2-{[(2S)-2-{[(2S)-2-{[(2S)-2-{[(2S)-2-{[(2S)-2-{[(2S)-2-{[(2S)-2-(acetyloxy)propanoyl]oxy}propanoyl]oxy}propanoyl]oxy}propanoyl]oxy}propanoyl]oxy}propanoyl]oxy}propanoyl]oxy}propanoyl]oxy}propanoyl]oxy}propanoic acid (238-3, 1.39 g, 1.37 mmol), EDC.HCl (0.30 g, 1.58 mmol), hydroxybenzotriazole (0.029 g, 0.021 mmol) and 4-dimethylaminopyridine (0.012 g, 0.010 mmol) were added at 0° C. The reaction mixture was allowed to stir at 25-30° C. over a period of 2 hours. The resulting reaction mass was quenched with water (100 mL), extracted with ethyl acetate (3×150 mL), dried over sodium sulfate and concentrated under reduced pressure. The crude product obtained upon evaporation of volatiles was purified through silica gel (230-400 mesh) column (100% ethyl acetate) to obtain product 238-5 as an off white solid (550 mg, 42%). $^1$H-NMR (400 MHz, DMSO-d6) δ 7.37 (s, 1H), 5.26-5.13 (m, 9H), 5.13-5.00 (m, 2H), 4.79 (q, 1H), 3.94-3.75 (m, 2H), 2.7-2.5 (m, 2H), 2.32-2.2 (m, 2H), 2.07 (s, 3H), 1.51-1.38 (m, 33H), 1.35-1.25 (m, 6H), 1.02 (t, 3H); MS m/z (M+H)$^+$ 1232.4.

Scheme 93: Synthesis of 248-7

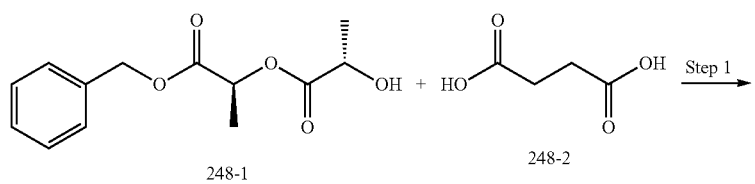

248-1    248-2

-continued
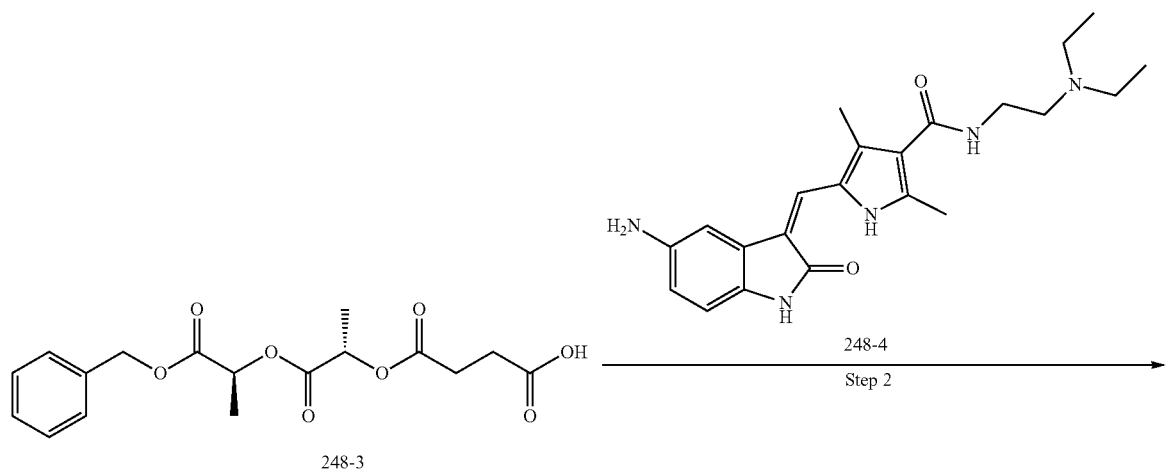
248-3    248-4 Step 2
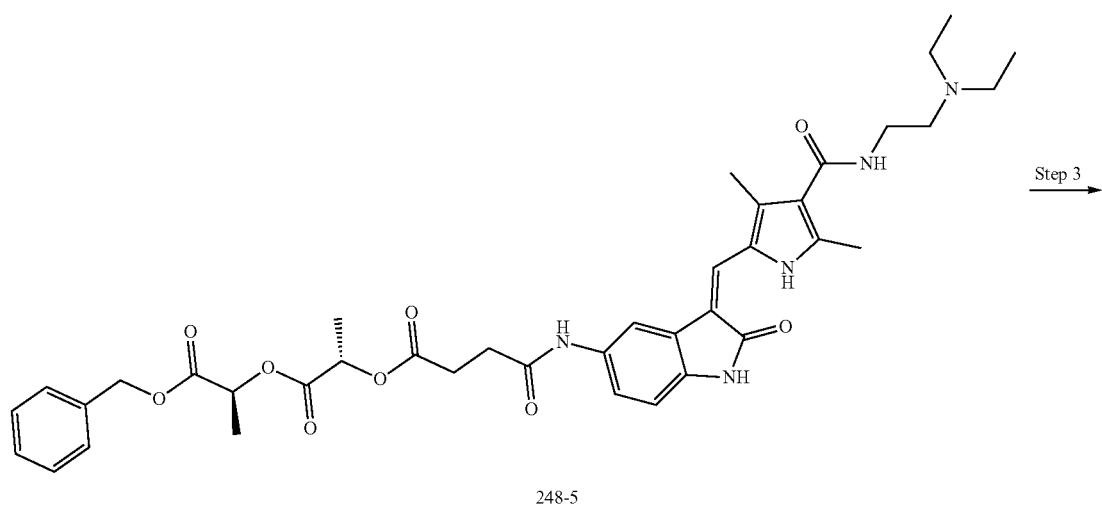
248-5    Step 3
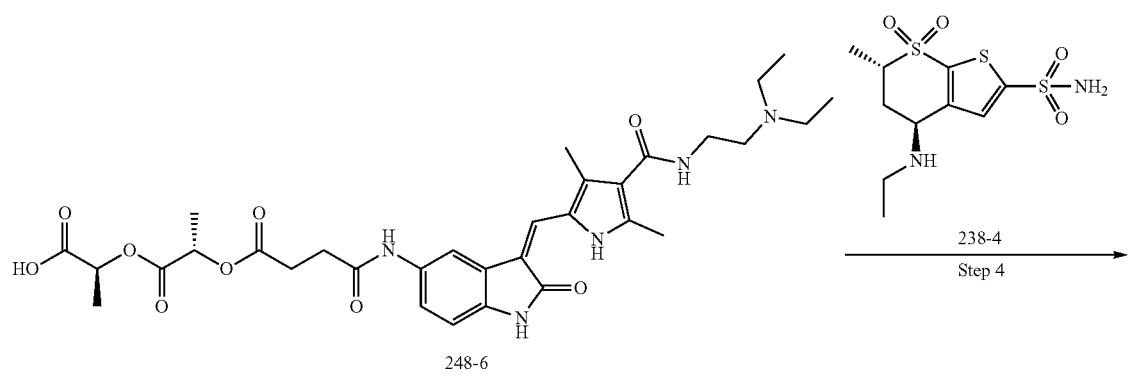
248-6    238-4 Step 4

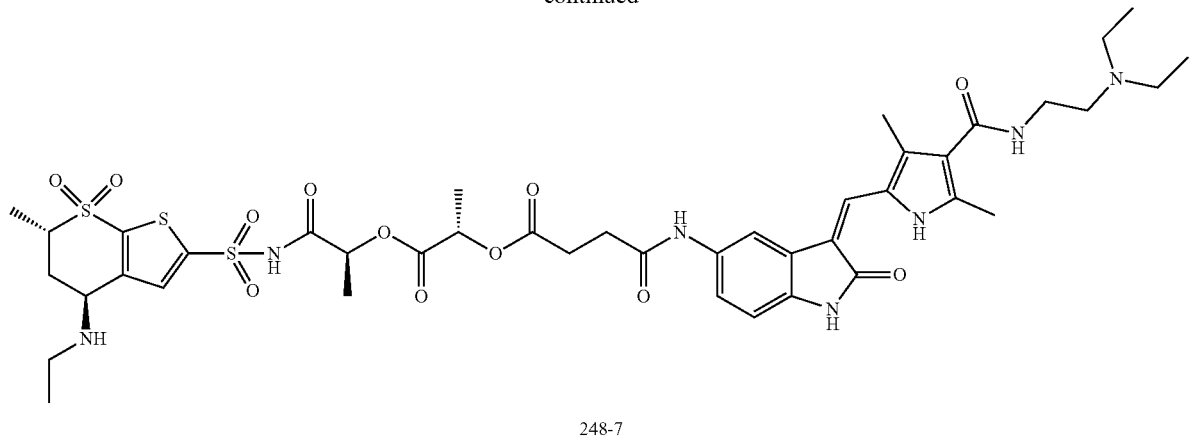 [SMILES: CCN[C@H]1C[C@H](C)S(=O)(=O)c2sc(S(=O)(=O)NC(=O)[C@H](C)OC(=O)[C@H](C)OC(=O)CCC(=O)Nc3ccc4c(c3)/C(=C/c3[nH]c(C)c(C(=O)NCCN(CC)CC)c3C)C(=O)N4)cc21]

248-7

Step-1 Preparation 4-{[(2S)-1-{[(2S)-1-(benzyloxy)-1-oxopropan-2-yl]oxy}-1-oxopropan-2-yl]oxy}-4-oxobutanoic acid (248-3)

To a solution of succinic acid (248-2, 28 g, 237 mmol) in dichloromethane (300 mL) was added N,N-diisopropylethylamine (52 mL, 295 mmol), EDC.HCl (56.9 g, 295 mmol), hydroxybenzotriazole (3.2 g, 23 mmol), 2-hydroxy-propionic acid 1-benzyloxycarbonyl-ethyl ester (248-1, 30 g, 118 mmol) and 4-dimethylaminopyridine (1.45 g, 11 mmol) at 0° C. The reaction mixture was allowed to stir at 25-30° C. over a period of 1 hour. The resulting reaction mixture was quenched with water (300 mL), extracted with dichloromethane (2×200 mL), dried over sodium sulfate and concentrated under reduced pressure. The crude product obtained upon evaporation of volatiles was purified through silica gel (230-400 mesh) column (35% ethyl acetate in hexane) to obtain product 248-3 as a colorless liquid (25 g, 65%).

Step-2: Preparation of (2S)-1-{[(2S)-1-(benzyloxy)-1-oxopropan-2-yl]oxy}-1-oxopropan-2-yl 3-{[(3Z)-3-[(4-{[2-(diethylamino)ethyl]carbamoyl}-3,5-dimethyl-1H-pyrrol-2-yl)methylidene]-2-oxo-2,3-dihydro-1H-indol-5-yl]carbamoyl}propanoate (248-5)

To a solution of succinic acid mono-[1-(1-benzyloxycarbonyl-ethoxycarbonyl)-ethyl] ester (248-3, 10.4 g, 19 mmol) in N,N-dimethylformamide (100 mL) were added N,N-diisopropylethylamine (6.8 mL, 39 mmol), HATU (11.2 g, 29 mmol) and 5-amino sunitinib (248-4, 10 g, 19 mmol) at 0° C. The reaction mixture was allowed to stir at 25-30° C. over a period of 3 hours. The resulting reaction mixture was quenched with water (500 mL), extracted with dichloromethane (2×250 mL), dried over sodium sulfate and concentrated under reduced pressure. The crude product obtained was purified by recrystallization using ethyl acetate/diethyl ether to obtain product 248-5 as a reddish brown solid (11 g, 76%).

Step-3: Preparation of (2S)-2-{[(2S)-2-[(3-{[(3Z)-3-[(4-{[2-(diethylamino)ethyl]carbamoyl}-3,5-dimethyl-1H-pyrrol-2-yl)methylidene]-2-oxo-2,3-dihydro-1H-indol-5-yl]carbamoyl}propanoyl)oxy]propanoyl]oxy}propanoic acid (248-6)

To a 100 mL autoclave vessel were added a solution of N-{3-[1-[4-(2-diethylamino-ethylcarbamoyl)-3,5-dimethyl-1H-pyrrol-2-yl]-meth-(Z)-ylidene]-2-oxo-2,3-dihydro-1H-indol-5-yl}-succinamic acid 1-(1-benzyl oxy carbonyl-ethoxycarbony 1)-ethyl ester (248-5, 11 g, 15 mmol) in a mixture of methanol (220 mL) and dichloromethane (22 mL) followed by 10% Pd/C (2.2 g, 50% wet) at 25-30° C. The reaction mixture was stirred at room temperature under hydrogen pressure (1 kg/cm$^2$) over a period of 30 minutes. After completion of the reaction, the reaction mixture was filtered through a celite bed. Then volatiles were evaporated under reduced pressure to obtain product 248-6 as a reddish orange solid (8.4 g, 87%).

Step-4: Preparation of (2S)-1-[(1S)-1-({[(2S,4S)-4-(ethylamino)-2-methyl-1,1-dioxo-2H,3H,4H-1λ$^6$-thieno[2,3-b]thiopyran-6-yl]sulfonyl}carbamoyl)ethoxy]-1-oxopropan-2-yl 3-{[(3Z)-3-[(4-{[2-(diethylamino)ethyl]carbamoyl}-3,5-dimethyl-1H-pyrrol-2-yl)methylidene]-2-oxo-2,3-dihydro-1H-indol-5-yl]carbamoyl}propanoate (248-7)

To a suspension of dorzolamide (238-4, 300 mg, 0.833 mmol) in dichloromethane (6 mL) was added N,N-diisopropylethylamine (0.2 mL, 1.333 mmol) at 0° C. and stirred for 30 minutes. Then (2S)-2-{[(2S)-2-[(3-{[(3Z)-3-[(4-{[2-(diethylamino)ethyl]carbamoyl}-3,5-dimethyl-1H-pyrrol-2-yl)methylidene]-2-oxo-2,3-dihydro-1H-indol-5-yl]carbamoyl}propanoyl)oxy]propanoyl]oxy}propanoic acid (248-6, 533 mg, 0.833 mmol), EDC.HCl (255 mg, 1.333 mmol), hydroxybenzotriazole (23 mg, 0.166 mmol) and 4-dimethylaminopyridine (10 mg, 0.083 mmol) were added at 0° C. The reaction mixture was allowed to stir at 25-30° C. over a period of 2 hours. The resulting reaction mixture was quenched with water (50 mL), extracted with dichloromethane (3×50 mL), dried over sodium sulfate and concentrated under reduced pressure. The crude product obtained upon evaporation of volatiles was purified by preparative HPLC and lyophilized to obtain the monoformate salt of product 248-7 as an orange solid (197 mg, 25%)) $^1$H-NMR (400 MHz, DMSO-d6) δ 13.71 (s, 1H), 10.87 (s, 1H), 9.88 (s, 1H), 8.14 (s, 1H), 7.94 (d, J=2 Hz, 1H), 7.69 (t, 1H), 7.5-7.4 (m, 2H), 7.17 (dd, J=2 Hz, J=8 Hz, 1H), 6.81 (d, J=8 Hz, 1H), 4.99 (q, 1H), 4.80 (q, 1H), 4.1-3.8 (m, 2H), 3.5-3.4 (m, 2H), 3.1-2.95 (m, 6H), 2.8-2.5 (m, 6H), 2.46 (s, 3H), 2.42 (s, 3H), 2.4-2.2 (m, 2H), 1.46 (d, 3H), 1.4-1.3 (m, 6H), 1.16 (t, 6H), 1.06 (t, 3H); MS m/z [M+H]$^+$ 947.4.

Scheme 94
Synthesis of 246-4
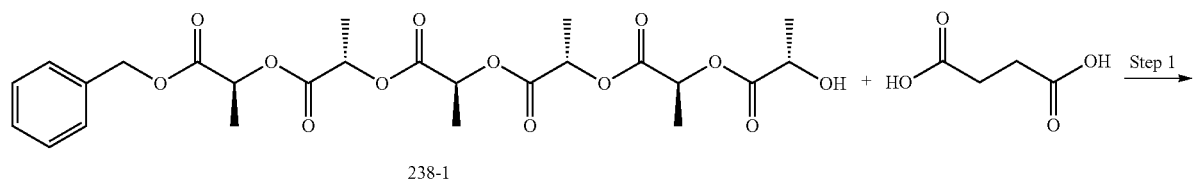
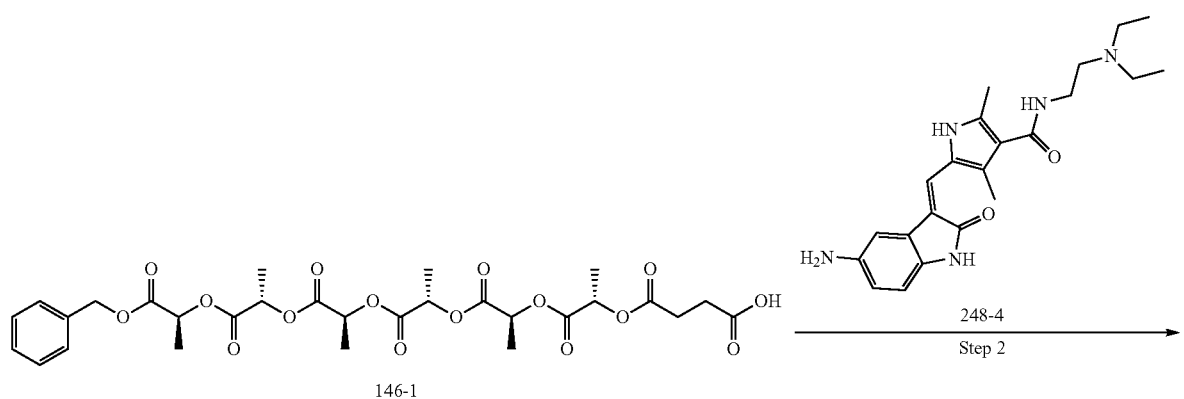
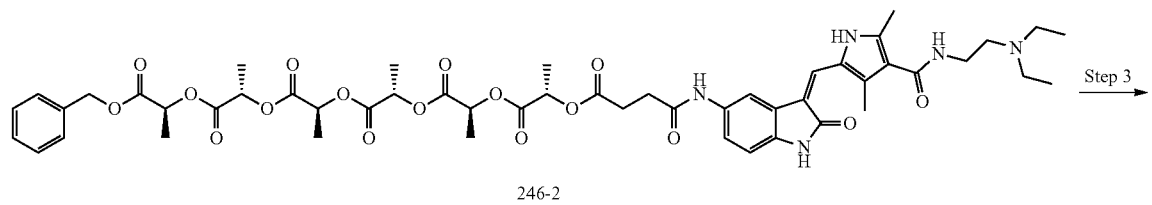
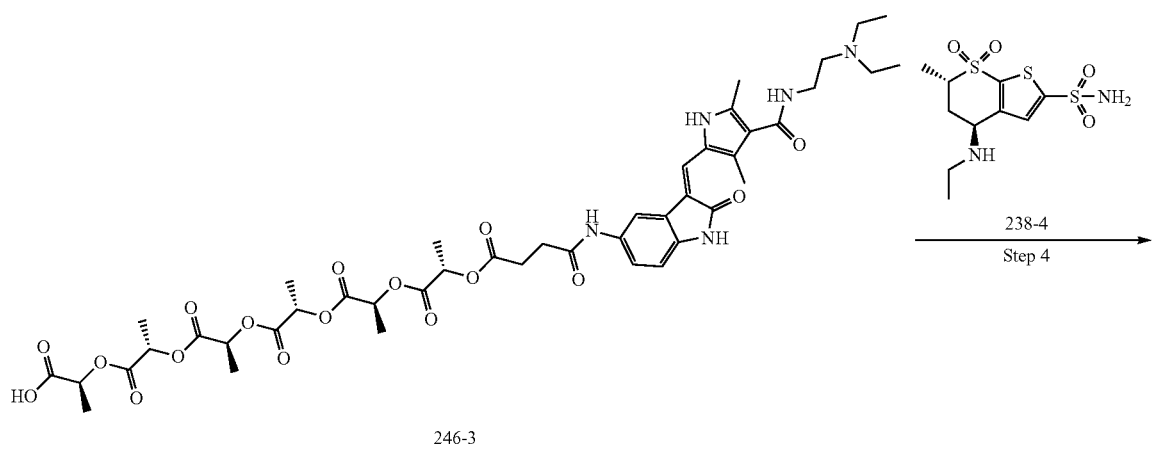

-continued

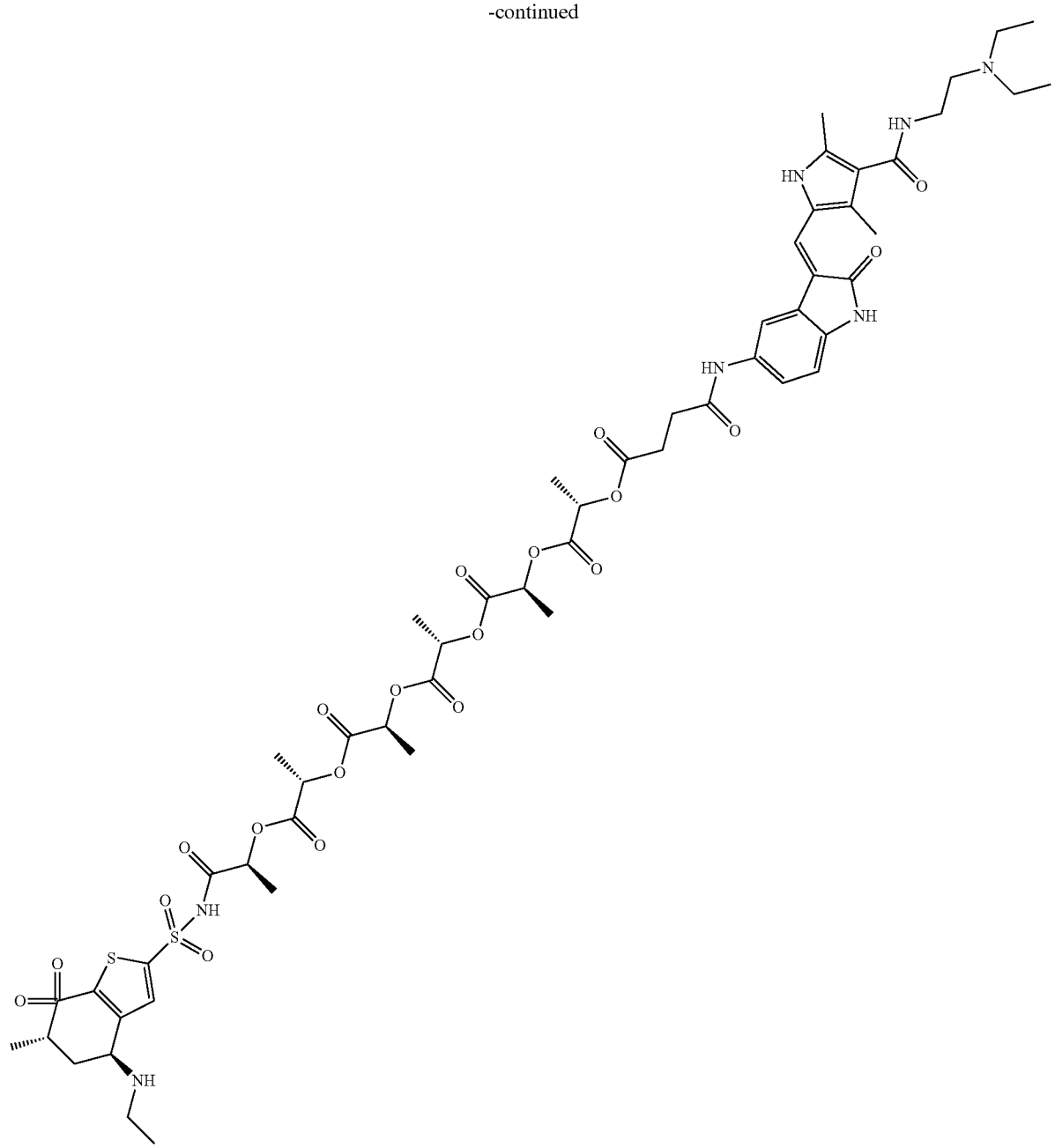

246-4

Step-1: Preparation of 4-{{(2S)-1-{[(2S)-1-{[(2S)-1-{[(2S)-1-{[(2S)-1-{[(2S)-1-(benzyloxy)-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-4-oxobutanoic acid (246-1)

To a solution of succinic acid (248-2, 3.01 g, 25.5 mmol) in dichloromethane (60 mL) was added N,N-diisopropylethylamine (5.1 mL, 27.7 mmol), EDC.HCl (5.3 g, 27.7 mmol), hydroxybenzotriazole (0.30 g, 2.2 mmol), (S)-2-hydroxy-propionic acid (S)-1-((S)-1-{(S)-1-[(S)-1-((S)-1-benzyloxycarbonyl-ethoxycarbonyl)-ethoxycarbonyl]-ethoxycarbonyl}-ethoxycarbonyl)-ethyl ester (238-1, 6 g, 11 mmol) and 4-dimethylaminopyridine (0.135 g, 1.1 mmol) at 0° C. The reaction mixture was allowed to stir at 25-30° C. over a period of 2 hours. The resulting reaction mixture was quenched with water (200 mL), extracted with dichloromethane (2×200 mL), dried over sodium sulfate and concentrated under reduced pressure. The crude product obtained upon evaporation of volatiles was purified through silica gel (230-400 mesh) column (2-5% methanol in DCM) to obtain product 246-1 as a colorless liquid (4.7 g, 66%).

Step-2: Preparation of (2S)-1-{[(2S)-1-{[(2S)-1-{[(2S)-1-{[(2S)-1-{[(2S)-1-(benzyloxy)-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl 3-{[(3Z)-3-[(4-{[2-(diethylamino)ethyl]carbamoyl}-3,5-dimethyl-1H-pyrrol-2-yl)methylidene]-2-oxo-2,3-dihydro-1H-indol-5-yl]carbamoyl}propanoate (246-2)

To a solution of 4-{[(2S)-1-{[(2S)-1-{[(2S)-1-{[(2S)-1-{[(2S)-1-{[(2S)-1-(benzyloxy)-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-4-oxobutanoic acid (246-1, 4.59 g, 7.17 mmol) in N,N-dimethylformamide (25 mL) were added N,N-diisopropylethylamine (1.76 mL, 9.56 mmol), HATU (2.72 g, 7.17 mmol) and 5-amino sunitinib (248-4, 1.89 g, 4.78 mmol) at 0° C. The reaction mixture was allowed to stir at 25-30° C. over a period of 1 hour. The resulting reaction mixture was quenched with water (100 mL), extracted with dichloromethane (2×250 mL), dried over sodium sulfate and concentrated under reduced pressure. The crude product obtained was purified by recrystallization using ethyl acetate/diethyl ether and hexane to obtain 246-2 as a reddish brown solid (3.3 g, 67%).

Step-3: Preparation of (2S)-2-{[(2S)-2-{[(2S)-2-{[(2S)-2-{[(2S)-2-{[(2S)-2-[(3- {[(3Z)-3-[(4-{[2-(diethylamino)ethyl]carbamoyl}-3,5-dimethyl-1H-pyrrol-2-yl)methylidene]-2-oxo-2,3-dihydro-1H-indol-5-yl]carbamoyl}propanoyl)oxy]propanoyl]oxy}propanoyl]oxy}propanoyl]oxy}propanoyl]oxy}propanoic acid (246-3)

To a Parr hydrogenation vessel were added a solution of (2S)-1-{[(2S)-1-{[(2S)-1-{[(2S)-1-{[(2S)-1-{[(2S)-1-(benzyloxy)-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl 3-{[(3Z)-3-[(4-{[2-(diethylamino)ethyl]carbamoyl}-3,5-dimethyl-1H-pyrrol-2-yl)methylidene]-2-oxo-2,3-dihydro-1H-indol-5-yl]carbamoyl}propanoate (246-2, 3.3 g, 3.2 mmol) in a combination of methanol (27 mL) and dichloromethane (3 mL) followed by 10% Pd/C (0.33 g, 50% wet) at 25-30° C. The reaction mixture was stirred at room temperature under hydrogen pressure (1 kg/cm2) over a period of 30 minutes. After completion of the reaction, the reaction mixture was filtered through a celite bed. The volatiles were evaporated under reduced pressure to obtain 246-3 as a reddish orange solid (2.5 g, 83%).

Step-4: Preparation of (2S)-1-{[(2S)-1-{[(2S)-1-{1 [(2S)-1-{[(2S)-1-[(1S)-1-({[(2S,4S)-4-(ethylamino)-2-methyl-1,1-dioxo-2H,3H,4H-1$\lambda^6$-thieno[2,3-b]thiopyran-6-yl]sulfonyl}carbamoyl)ethoxy]-1-oxopropan-2-yl]oxy}-1-oxopropan-2-yl]oxy}-1-oxopropan-2-yl]oxy}-1-oxopropan-2-yl]oxy}-1-oxopropan-2-yl]oxy}-1-oxopropan-2-yl 3-{[(3Z)-3-[(4-{[2-(diethylamino)ethyl]carbamoyl}-3,5-dimethyl-1H-pyrrol-2-yl)methylidene]-2-oxo-2,3-dihydro-1H-indol-5-yl]carbamoyl}propanoate (246-4)

To a suspension of dorzolamide (238-4, 750 mg, 2.0 mmol) in dichloromethane (10 mL) was added N,N-diisopropylethylamine (0.61 mL, 3.3 mmol) at 0° C. and stirred for 30 minutes. Then 246-3 (2.5 g, 2.7 mmol), EDC.HCl (635 mg, 3.3 mmol), hydroxybenzotriazole (57 mg, 0.41 mmol) and 4-dimethylaminopyridine (25 mg, 0.20 mmol) were added at 0° C. The reaction mixture was allowed to stir at 25-30° C. over a period of 2 hours. The resulting reaction mixture was concentrated under reduced pressure and slurried with water (10 mL), and the resulting precipitate was collected by filtration. The crude compound was further purified by preparative HPLC and lyophilized to obtain the monoformate salt of 246-4 as an orange solid (900 mg, 36%). $^1$H-NMR (400 MHz, DMSO-d6) δ 13.71 (s, 1H), 10.86 (s, 1H), 9.88 (s, 1H), 8.14 (s, 1H), 7.94 (d, J=2 Hz, 1H), 7.68 (t, 1H), 7.5-7.4 (m, 2H), 7.17 (dd, J=2 Hz, J=8 Hz, 1H), 6.81 (d, J=8 Hz, 1H), 5.25-5.0 (m, 5H), 4.79 (q, 1H), 4.1-3.8 (m, 2H), 3.55-3.4 (m, 2H), 3.15-2.9 (m, 6H), 2.8-2.5 (m, 6H), 2.46 (s, 3H), 2.41 (s, 3H), 2.4-2.2 (m, 2H), 1.55-1.4 (m, 15H), 1.36-1.24 (m, 6H), 1.16 (t, 6H), 1.06 (t, 3H); MS m/z [M+H]$^+$ 1235.6, [M+2H]$^{2+}$ 619.8.

Scheme 95
Synthesis of 249-3

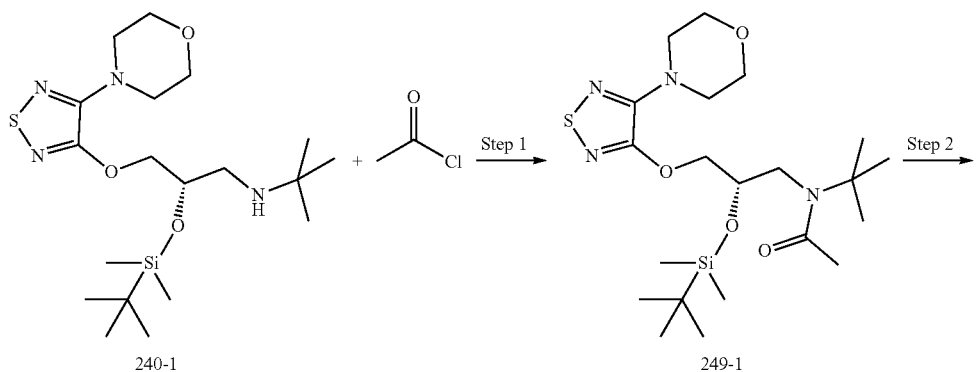

240-1     249-1

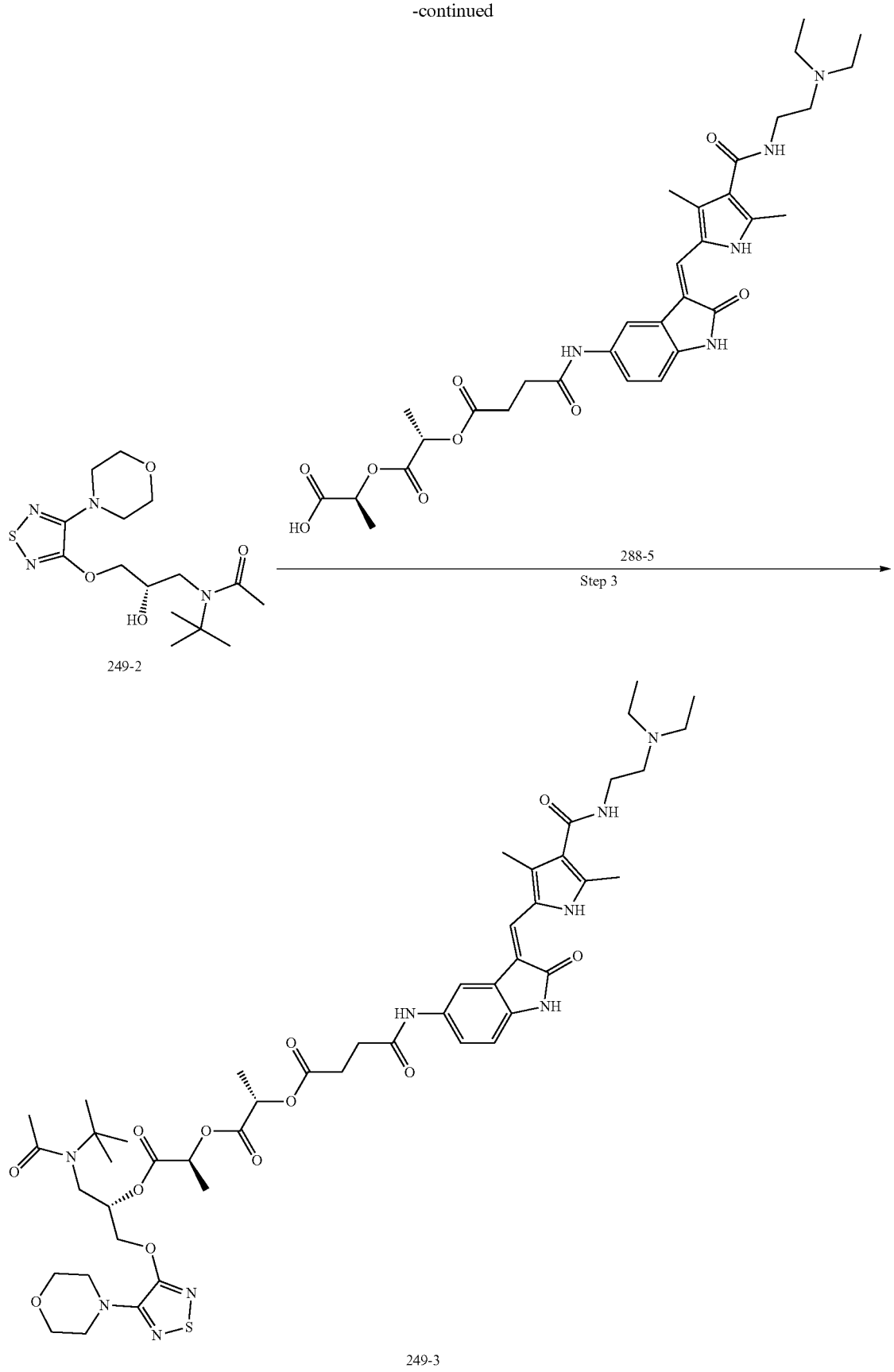

Step-1: Preparation of N-tert-Butyl-N—[(S)-2-(tert-butyl-dimethyl-silanyloxy)-3-(4-morpholin-4-yl-[1,2,5]thiadiazol-3-yloxy)-propyl]-acetamide (249-1)

To a solution of tert-butyl-[(S)-2-(tert-butyl-dimethyl-silanyloxy)-3-(4-morpholin-4-yl-[1,2,5]thiadiazol-3-yloxy)-propyl]-amine (240-1, 4 g, 9.29 mmol) in chloroform (40 mL) were added triethylamine (1.9 ml, 13.93 mmol) and acetyl chloride (0.99 mL, 13.93 mmol) at 0° C. The reaction mixture was stirred at 25-30° C. over a period of 12 hours. The resulting reaction mixture was quenched with water (100 mL), extracted with dichloromethane (2×200 mL) and dried over sodium sulfate. The volatiles were evaporated under reduced pressure to obtain product 249-1 as a colorless liquid (3.3 g, 75%).

Step-2: Preparation of N-tert-butyl-N—[(S)-2-hydroxy-3-(4-morpholin-4-yl-[1,2,5]thiadiazol-3-yloxy)-propyl]-acetamide (249-2)

To a solution of N-tert-butyl-N—[(S)-2-(tert-butyl-dimethyl-silanyloxy)-3-(4-morpholin-4-yl-[1,2,5]thiadiazol-3-yloxy)-propyl]-acetamide (249-1, 3.3 g, 6.98 mmol) in tetrahydrofuran (33 mL) was added tetrabutylammonium fluoride (10.4 mL, 1.0 M, 10.47 mmol) at 0° C. The reaction mixture was allowed to stir at room temperature over a period of 1 hour. The resulting reaction mixture was concentrated under reduced pressure. The crude product obtained upon evaporation of the volatiles was purified through silica gel (60-120 mesh) column chromatography (60% ethyl acetate in hexane) to give product 249-2 as an off white solid (1.3 g, 52%).

Step-3: Preparation of (2S)-1-{[(2S)-1-{[(2S)-1-(N-tert-butylacetamido)-3-{[4-(morpholin-4-yl)-1,2,5-thiadiazol-3-yl]oxy}propan-2-yl]oxy}-1-oxopropan-2-yl]oxy}-1-oxopropan-2-yl 3-{[(3Z)-3-[(4-{[2-(diethylamino)ethyl]carbamoyl}-3,5-dimethyl-1H-pyrrol-2-yl)methylidene]-2-oxo-2,3-dihydro-1H-indol-5-yl]carbamoyl}propanoate (249-3)

The mixture of (2S)-2-{[(2S)-2-[(3-{[(3Z)-3-[(4-{[2-(diethylamino)ethyl]carbamoyl}-3,5-dimethyl-1H-pyrrol-2-yl)methylidene]-2-oxo-2,3-dihydro-1H-indol-5-yl]carbamoyl}propanoyl)oxy]propanoyl]oxy}propanoic acid (288-5, 3.48 g, 5.45 mmol) and N-tert-butyl-N—[(S)-2-hydroxy-3-(4-morpholin-4-yl-[1,2,5]thiadiazol-3-yloxy)-propyl]-acetamide 25-4 (249-2, 1.5 g, 4.19 mmol) was stripped with N,N-dimethylformamide (3×15 mL). The residue was brought up in N,N-dimethylformamide (15 mL) and dried molecular sieves (4 A°), EDC.HCl (1.2 g, 6.28 mmol), hydroxybenzotriazole (0.11 g, 0.83 mmol) and 4-dimethylaminopyridine (0.05 g, 0.42 mmol) were added at 0° C. The reaction mixture was allowed to stir at 25-30° C. over a period of 16 hours. The resulting reaction mixture was diluted with ethyl acetate (100 mL) and filtered to remove insoluble material. The filtrate was washed with water (2×50 mL), dried over sodium sulfate and concentrated under reduced pressure. The crude product obtained upon evaporation of volatiles was purified by preparative HPLC and lyophilized to obtain product 249-3 as an orange solid (250 mg, 6%). $^1$H-NMR (400 MHz, DMSO-d6) δ 13.64 (s, 1H), 10.84 (s, 1H), 9.87 (s, 1H), 7.89 (d, J=2 Hz, 1H), 7.47 (t, 1H), 7.43 (s, 1H), 7.21 (dd, J=2 Hz, J=8 Hz, 1H), 6.81 (d, J=8 Hz, 1H), 5.48-5.36 (m, 1H), 5.12-4.97 (m, 2H), 4.54 (dd, 1H), 4.41 (dd, 1H), 3.8-3.6 (m, 6H), 3.5-3.3 (m, 6H), 2.7-2.5 (m, 8H), 2.44 (s, 3H), 2.39 (s, 3H), 2.09 (s, 3H), 1.5-1.3 (m, 15H), 0.99 (t, 6H); MS m/z [M+H]$^+$ 981.4.

Example 5. Synthetic Examples to Describe Linker Moieties Utilized Above

Scheme 96: Synthesis of (S)-2-{(S)-2-[(S)-2-((S)-2-acetoxy-propionyloxy)-propionyloxyl]-propionyloxy}-propionic acid (88-2):

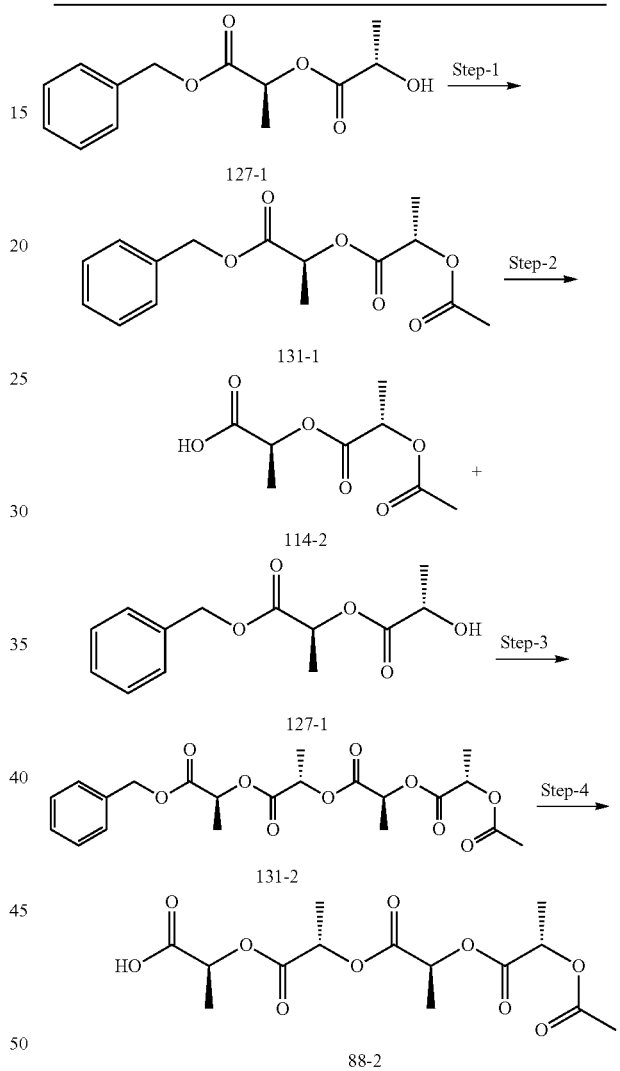

Step-1: Preparation of (S)-2-((S)-2-acetoxy-propionyloxy)-propionic acid benzyl ester (131-1)

To a solution of (S)-2-hydroxy-propionic acid (S)-1-benzyloxycarbonyl-ethyl ester 127-1 (5 g, 19.84 mmol) in dichloromethane (50 mL) was added 4-dimethylaminopyridine (0.24 g, 1.98 mmol) and acetic anhydride (2.8 mL, 29.76 mmol) at 0° C. The reaction mixture stirred at 25-30° C. over a period of 3 h. The resulting reaction mixture was quenched with water (200 mL), extracted with ethyl acetate (2×200 mL) and dried over sodium sulfate. The volatiles were evaporated under reduced pressure to obtain product 131-1 as a pale yellow liquid (7.3 g, 73%).

Step-2: Preparation of (S)-2-((S)-2-acetoxy-propionyloxy)-propionic acid (114-2)

To a 250 mL autoclave vessel were added a solution of (S)-2-((S)-2-acetoxy-propionyloxy)-propionic acid benzyl ester 131-1 (7.3 g, 24.82) in methanol (40 mL) and 10% Pd/C (1.5 g, 50% wet) at 25-30° C. The reaction mixture was stirred at room temperature under hydrogen pressure (5 kg/cm$^2$) over a period of 2 h. After completion of the reaction, the reaction mixture was filtered through a celite bed. Then volatiles were evaporated under reduced pressure to obtain product 114-2 as a pale yellow liquid 4.4 g (81%).

Step-3: Preparation of (S)-2-{(S)-2-[(S)-2-((S)-2-acetoxy-propionyloxy)-propionyloxy]-propionyloxy}-propionic acid benzyl ester (131-2)

To a solution of (S)-2-((S)-2-acetoxy-propionyloxy)-propionic acid 114-2 (4.3 g, 20.83 mmol) and (S)-2-hydroxy-propionic acid (S)-1-benzyloxycarbonyl-ethyl ester 127-1 (3.5 g, 13.88 mmol) in dichloromethane (50 mL) were added EDC HCl (5.3 g, 27.76 mmol), 4-dimethylaminopyridine (169 mg, 1.38 mmol) at 0° C. The reaction mixture was allowed to stir at 25-30° C. over a period of 1 h. The resulting reaction mass was quenched with water (100 mL), extracted with dichloromethane (200×3 mL), dried over sodium sulfate and concentrated under reduced pressure. The crude product obtained upon evaporation of volatiles was purified through silica gel (230-400 mesh) column chromatography (8% ethyl acetate in hexane) to obtain product 131-2 as a pale yellow liquid 2.2 g (36%).

Step-4: Preparation of (S)-2-{(S)-2-[(S)-2-((S)-2-acetoxy-propionyloxy)-propionyloxy]-propionyloxy}-propionic acid (88-2)

To a 100 mL autoclave vessel were added a solution of (S)-2-{(S)-2-[(S)-2-((S)-2-acetoxy-propionyloxy)-propionyloxy]-propionyloxy}-propionic acid benzyl ester 131-2 (2.2 g, 5.08 mmol) in methanol (15 mL) and 10% Pd/C (0.45 g, 50% wet) at 25-30° C. The reaction mixture was stirred at room temperature under hydrogen pressure (5 kg/cm$^2$) over a period of 2 h. After completion of the reaction, the reaction mixture was filtered through a celite bed. The volatiles were evaporated under reduced pressure to give 88-2 as a pale yellow liquid 1.1 g (65%).

Scheme 97: Synthesis of (S)-2-[(S)-2-((S)-2-{(S)-2-[(S)-2-((S)-2-acetoxy-propionyloxy)-propionyloxy]-propionyloxy}-propionyloxy)-propionyloxy]-propionic acid (89-1):

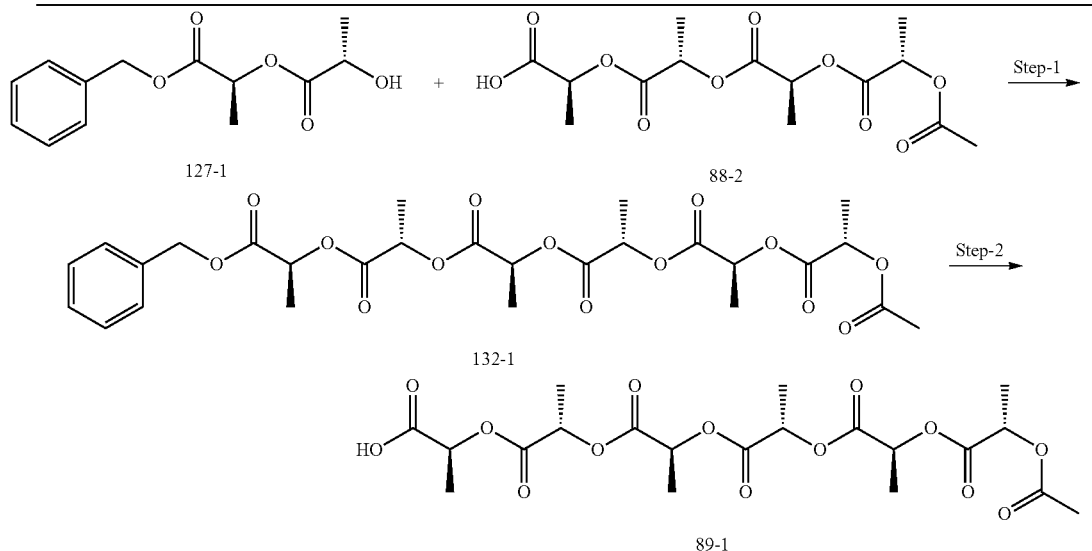

Step-1: Preparation of (S)-2-[(S)-2-((S)-2-{(S)-2-[(S)-2-((S)-2-acetoxy-propionyloxy)-propionyloxy]-propionyloxy}-propionyloxy)-propionyloxy]-propionic acid benzyl ester (132-1)

To a solution of (S)-2-{(S)-2-[(S)-2-((S)-2-acetoxy-propionyloxy)-propionyloxy]-propionyloxy}-propionic acid 88-2 (12.4 g, 35.71 mmol) and (S)-2-hydroxy-propionic acid (S)-1-benzyloxycarbonyl-ethyl ester 127-1 (6.0 g, 23.80 mmol) in dichloromethane (60 mL) were added EDC.HCl (9.09 g, 47.60 mmol), 4-dimethylaminopyridine (290 mg, 2.38 mmol) at 0° C. The reaction mixture was allowed to stir at 25-30° C. over a period of 1 h. The resulting reaction mass was quenched with water (100 mL), extracted with dichloromethane (200×3 mL), dried over sodium sulfate and concentrated under reduced pressure. The crude product obtained upon evaporation of volatiles was purified through silica gel (230-400 mesh) column chromatography (6% ethyl acetate in hexane) to obtain product 132-1 as a pale yellow liquid 8.3 g (60%).

Step-2: Preparation of (S)-2-[(S)-2-((S)-2-{(S)-2-[(S)-2-((S)-2-acetoxy-propionyloxy)-propionyloxy]-propionyloxy}-propionyloxy)-propionyloxy]-propionic acid (89-1)

To a 250 mL autoclave vessel were added a solution of (S)-2-[(S)-2-((S)-2-{(S)-2-[(S)-2-((S)-2-acetoxy-propionyloxy)-propionyloxy]-propionyloxy}-propionyloxy)-propionyloxy]-propionic acid benzyl ester 132-1 (8.3 g, 14.26 mmol) in methanol (50 mL) and 10% Pd/C (1.65 g, 50% wet) at 25-30° C. The reaction mixture was stirred at room temperature under hydrogen pressure (5 kg/cm²) over a period of 2 h. After completion of the reaction, the reaction mixture was filtered through a celite bed. Then volatiles were evaporated under reduced pressure to obtain product 89-1 as a pale yellow liquid 5.7 g (81%).

concentrated under reduced pressure. The crude product obtained upon evaporation of volatiles was purified through silica gel (60-120 mesh) column chromatography (10% methanol in dichloromethane) to obtain product 123-2 as a pale yellow liquid 5.8 g (94%).

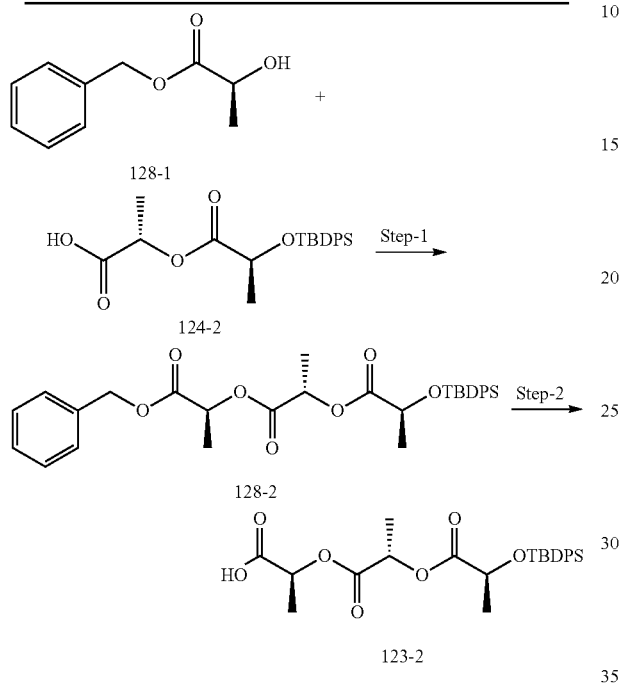

Scheme 98: Synthesis of (S)-2-(tert-butyl-diphenyl-silanyloxy)-propionic acid (S)-1-((S)-1-carboxy-ethoxycarbonyl)-ethyl ester (123-2):

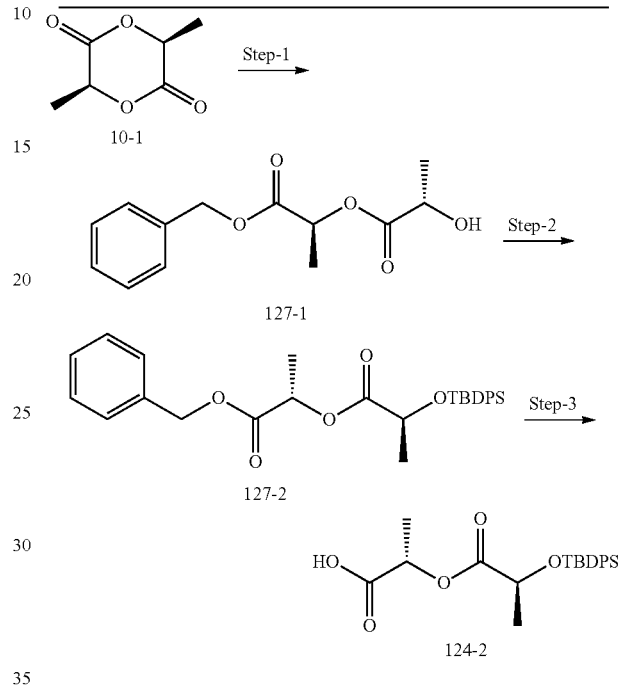

Scheme 99: Synthesis of (S)-2-(tert-butyl-diphenyl-silanyloxy)-propionic acid (S)-1-carboxy-ethyl ester (124-2):

Step-1: Preparation of (S)-2-(tert-butyl-diphenyl-silanyloxy)-propionic acid (S)-1-((S)-1-benzyloxy-carbonyl-ethoxycarbonyl)-ethyl ester (128-2)

To a solution of (S)-2-(tert-Butyl-diphenyl-silanyloxy)-propionic acid (S)-1-carboxy-ethyl ester 124-2 (5.17 g, 7.22 mmol) in dichloromethane (10 mL) were added EDC.HCl (2.12 g, 11.11 mmol), (S)-2-hydroxy-propionic acid benzyl ester 128-1 (1 g, 5.55 mmol) and 4-dimethylaminopyridine (670 mg, 0.55 mmol) at 0° C. The reaction mixture was allowed to stir at ambient temperature over a period of 1 h. Resulting reaction mixture was diluted with ethyl acetate (300 mL) and washed with water (2×50 mL). The crude product obtained upon evaporation of volatiles was purified through silica gel (230-400 mesh) column chromatography (3% ethyl acetate in hexane) to give product 128-2 as a colorless liquid 4.3 g (88%).

Step-2: Preparation of (S)-2-(tert-butyl-diphenyl-silanyloxy)-propionic acid (S)-1-((S)-1-carboxy-ethoxycarbonyl)-ethyl ester (123-2)

To a 100 mL autoclave vessel were added a solution of (S)-2-(tert-butyl-diphenyl-silanyloxy)-propionic acid (S)-1-((S)-1-benzyloxycarbonyl-ethoxycarbonyl)-ethyl ester 128-2 (7.0 g, 12.45) in methanol (40 mL) and 10% Pd/C (1.4 g, 50% wet) at 25-30° C. The reaction mixture was stirred at room temperature under hydrogen pressure (5 kg/cm²) over a period of 2 h. After completion of the reaction, the reaction mixture was filtered through a celite bed and

Step-1: Preparation of (S)-2-hydroxy-propionic acid (S)-1-benzyloxycarbonyl-ethyl ester (127-1)

To a solution of (3S,6S)-3,6-dimethyl-[1,4]dioxane-2,5-dione 10-1 (5.0 g, 34.72 mmol) in toluene (100 mL) was added benzyl alcohol (3.2 mL, 31.72 mmol) and camphor sulfonic acid (0.8 g, 3.47 mmol) at 25-30° C. The reaction mixture was allowed to stir at 80° C. over a period of 2 hours and the resulting reaction mixture was diluted with ethyl acetate (800 mL) and washed with water (2×400 mL). The crude product obtained upon evaporation of volatiles was purified through preparative HPLC to obtain product 127-1 as a pale yellow liquid 5.5 g (63%).

Step-2: Preparation of (S)-2-(tert-butyl-diphenyl-silanyloxy)-propionic acid (S)-1 benzyloxycarbonyl-ethyl ester (127-2)

To a solution of (S)-2-hydroxy-propionic acid (S)-1-benzyloxycarbonyl-ethyl ester 127-1 (0.1 g, 0.23 mmol) in dichloromethane (5 mL) were added triethylamine (0.23 mL, 1.61 mmol), TBDPS-Cl (0.43 mL, 1.618 mmol) and catalytic amount of 4-dimethylaminopyridine at 0° C. The reaction mixture was stirred at room temperature over period of 8 h. Resulting reaction mixture was quenched with water (20 mL) and extracted with ethyl acetate (2×50 mL). Then volatiles were evaporated under reduced pressure to obtain product 127-2 as a colorless liquid 200 mg (74%).

Step-3: Preparation of (S)-2-(tert-butyl-diphenyl-silanyloxy)-propionic acid (S)-1-carboxy-ethyl ester (124-2)

To a 100 mL autoclave vessel were added a solution of (S)-2-(tert-butyl-diphenyl-silanyloxy)-propionic acid (S)-1-benzyloxycarbonyl-ethyl ester 127-2 (1.5 g) in methanol (20 mL) and 10% Pd/C (0.3 g, 50% wet) at 25-30° C. The reaction mixture was stirred at room temperature under hydrogen pressure (5 kg/cm$^2$) over a period of 2 h. After completion of the reaction, the reaction mixture was filtered through a celite bed and concentrated under reduced pressure. The crude product obtained upon evaporation of volatiles was purified through silica gel (60-120 mesh) column chromatography (10% methanol in dichloromethane) to obtain product 124-2 as colorless liquid 700 mg (58%).

Scheme 100: Synthesis of (S)-2-(tert-bytyl-diphenyl-silanyloxy)-propionic acid (S)-1-[(S)-1-((S)-1carboxy-ethoxycarbonyl)-ethoxycarbonyl]-ethyl ester (129-2):

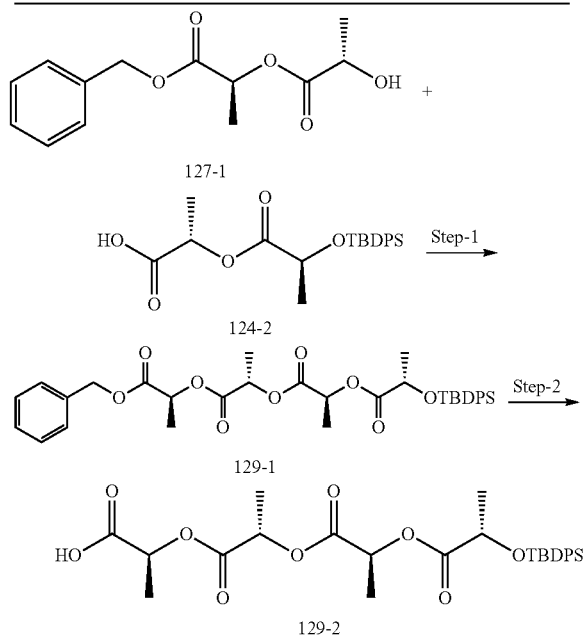

Step-1: Preparation of (S)-2-(tert-butyl-diphenyl-silanyloxy)-propionic acid (S)-1-[(S)-1-((S)-1-benzyloxycarbonyl-ethoxycarbonyl)-ethoxycarbonyl]-ethyl ester (129-1)

To a solution of (S)-2-hydroxy-propionic acid (S)-1-benzyloxycarbonyl-ethyl ester 127-1 (6.0 g, 33.2 mmol) and (S)-2-(tert-butyl-diphenyl-silanyloxy)-propionic acid (S)-1-carboxy-ethyl ester 124-2 (17.3 g, 7.77 mmol) in dichloromethane (60 mL) were added EDC.HCl (8.2 g, 43.2 mmol), 4-dimethylaminopyridine (405 mg, 3.3 mmol) at 0° C. The reaction mixture was allowed to stir at 25-30° C. over a period of 1 h. The resulting reaction mass was quenched with water (200 mL), extracted with dichloromethane (250×3 mL), dried over Na$_2$SO$_4$ and concentrated under reduced pressure. The crude product obtained upon evaporation of volatiles was purified through silica gel (230-400 mesh) column chromatography (10% methanol in dichloromethane) to obtain product 129-1 as a pale yellow liquid 5.8 g (94%).

Step-2: Preparation of (S)-2-(tert-butyl-diphenyl-silanyloxy)-propionic acid (S)-1-[(S)-1-((S)-1-carboxy-ethoxycarbonyl)-ethoxycarbonyl]-ethyl ester (129-2)

To a 100 mL autoclave vessel were added a solution of (S)-2-(tert-Butyl-diphenyl-silanyloxy)-propionic acid (S)-1-[(S)-1-((S)-1-benzyloxycarbonyl-ethoxycarbonyl)-ethoxycarbonyl]-ethyl ester 129-1 (700 mg, 1.10 mmol) in methanol (10 mL) and 10% Pd/C (140 mg, 50% wet) at 25-30° C. The reaction mixture was stirred at room temperature under hydrogen pressure (5 kg/cm$^2$) over a period of 2 h. After completion of the reaction, the reaction mixture was filtered through a celite bed and concentrated under reduced pressure. The crude product obtained upon evaporation of volatiles was purified through silica gel (60-120 mesh) column chromatography (10% methanol in dichloromethane) to obtain product 129-2 as a pale yellow liquid 420 mg (78%).

Scheme 101: Synthesis of (S)-2-(tert-butyl-diphenyl-silanyloxy)-propionic acid (130-2):

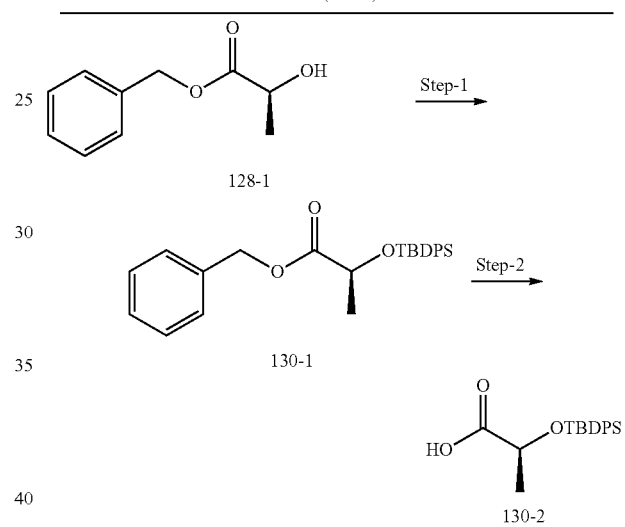

Step-1: Preparation of (S)-2-(tert-Butyl-diphenyl-silanyloxy)-propionic acid benzyl ester (130-1)

To a solution of (S)-2-hydroxy-propionic acid benzyl ester 128-1 (5 g, 27.77 mmol) in dichloromethane (50 mL) were added triethylamine (7.8 mL, 55.55 mmol), TBDPS-Cl (14.6 mL, 55.55 mmol) and catalytic amount of 4-dimethylaminopyridine at 0° C. The reaction mixture was stirred at room temperature over period of 8 h. Resulting reaction mixture was quenched with water (200 mL) and extracted with ethyl acetate (2×150 mL). Then volatiles were evaporated under reduced pressure to obtain product 130-1 as a pale yellow liquid 8.2 g (70%).

Step-2: Preparation of (S)-2-(tert-butyl-diphenyl-silanyloxy)-propionic acid (130-2)

To a 250 mL autoclave vessel were added a solution of (S)-2-(tert-Butyl-diphenyl-silanyloxy)-propionic acid benzyl ester 130-1 (8.2 g, 19.61 mmol) in methanol (50 mL) and 10% Pd/C (1.6 g, 50% wet) at 25-30° C. The reaction mixture was stirred at room temperature under hydrogen pressure (5 kg/cm$^2$) over a period of 2 h. After completion of the reaction, the reaction mixture was filtered through a celite bed. The volatiles were evaporated under reduced pressure to obtain product 130-2 as a pale yellow liquid 4.9 g (76%).

Scheme: 102: Synthesis of (S)-2-[(S)-2-((S)-2-{(S)-2-((S)-2-acetoxy-propionyloxy)-propionyloxy]-propionyloxy}-propionyloxy)-propionyloxy]-propionic acid (133-3):

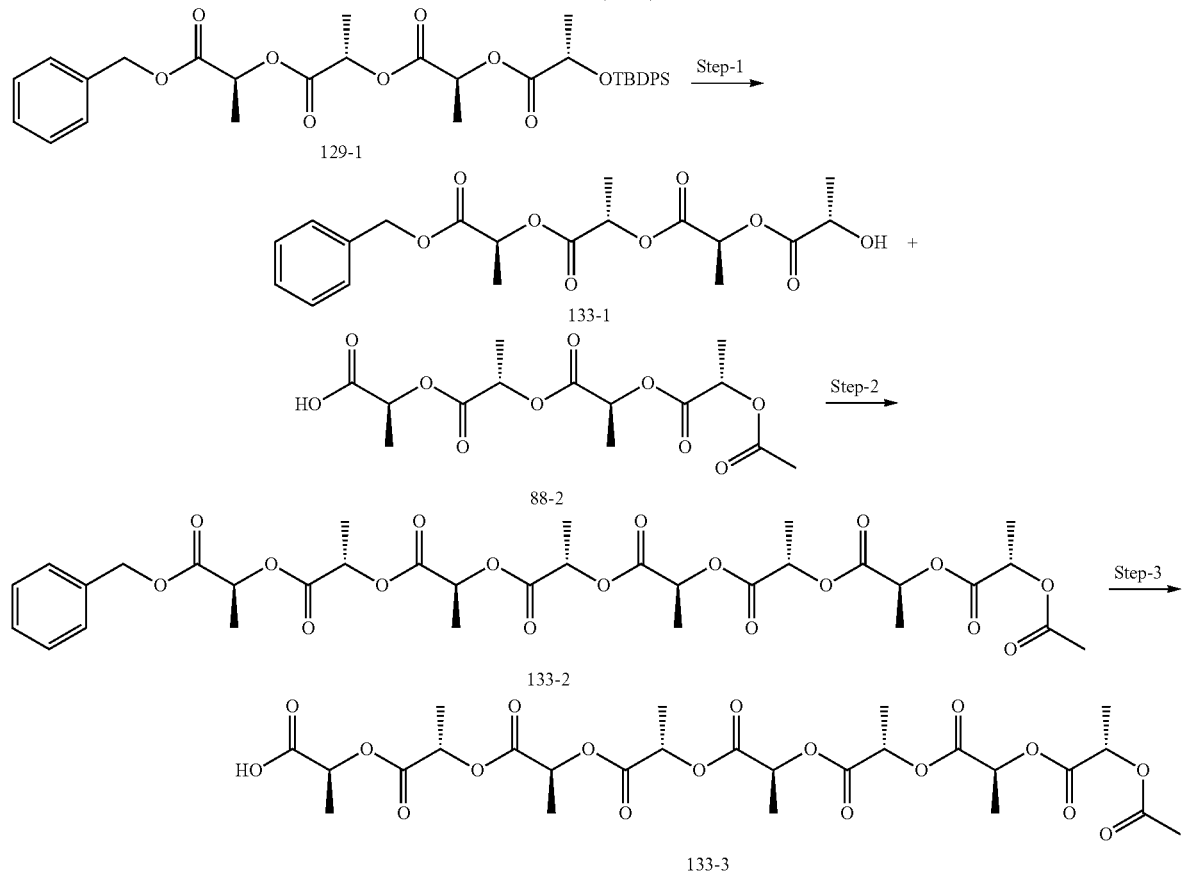

Step-1: Preparation of (S)-2-Hydroxy-propionic acid (S)-1-[(S)-1-((S)-1-benzyloxycarbonyl-ethoxycarbonyl)-ethoxycarbonyl]-ethyl ester (129-1)

To a solution of (S)-2-(tert-Butyl-diphenyl-silanyloxy)-propionic acid (S)-1-[(S)-1-((S)-1-benzyloxycarbonyl-ethoxycarbonyl)-ethoxycarbonyl]-ethyl ester 129-1 (2.0 g, 31.54 mmol) in tetrahydrofuran (20 mL) were added tetra butyl ammonium fluoride (4.73 mL, 1.0M, 47.31 mmol) and acetic acid (2.86 g, 47.31 mmol) at 0° C. The reaction mixture was allowed to stir at room temperature over a period of 1 h. The resulting reaction mixture was concentrated under reduced pressure and crude product obtained upon evaporation of the volatiles was purified through silica gel (230-400 mesh) column chromatography (13% ethyl acetate in hexane) to give product 133-1 as a colorless liquid 1.3 g (41.9%).

Step-2: Preparation of (S)-2-{(S)-2-[(S)-2-((S)-2-Acetoxy-propionyloxy)-propionyloxy]-propionyloxy}-propionic acid (S)-1-{(S)-1-[(S)-1-((S)-1-benzyloxycarbonyl-ethoxycarbonyl)-ethoxycarbonyl]-ethoxycarbonyl}-ethyl ester (133-2)

To a solution of (S)-2-{(S)-2-[(S)-2-((S)-2-acetoxy-propionyloxy)-propionyloxy]-propionyloxy}-propionic acid 88-2 (1.315 g, 3.78 mmol) and (S)-2-Hydroxy-propionic acid (S)-1-[(S)-1-((S)-1-benzyloxycarbonyl-ethoxycarbonyl)-ethoxycarbonyl]-ethyl ester 133-1 (1.0 g, 2.52 mmol) in dichloromethane (10 mL) were added EDC.HCl (0.866 g, 4.53 mmol), 4-dimethylaminopyridine (31 mg, 0.25 mmol) at 0° C. The reaction mixture was allowed to stir at 25-30° C. over a period of 1 h. The resulting reaction mass was quenched with water (100 mL), extracted with dichloromethane (300 mL), dried over sodium sulfate and concentrated under reduced pressure. The crude product obtained upon evaporation of volatiles was purified through silica gel (230-400 mesh) column chromatography (12% ethyl acetate in hexane) to obtain product 133-2 as a pale yellow liquid 1.2 g (65%).

Step-3: Preparation of (S)-2-((S)-2-{(S)-2-[(S)-2-((S)-2-{(S)-2-[(S)-2-((S)-2-Acetoxy-propionyloxy)-propionyloxy]-propionyloxy}-propionyloxy]-propionyloxy}-propionyloxy)-propionic acid (133-3)

To a 250 mL autoclave vessel were added a solution of (S)-2-((S)-2-{(S)-2-[(S)-2-((S)-2-{(S)-2-[(S)-2-((S)-2-Acetoxy-propionyloxy)-propionyloxy]-propionyloxy}-propionyloxy]-propionyloxy}-propionyloxy)-propionic acid 133-2 (1.2 g, 2.06 mmol) in methanol (12 mL) and 10% Pd/C (0.3 g, 10% wet) at 25-30° C. The reaction mixture was stirred at room temperature under hydrogen pressure (5 kg/cm$^2$) over a period of 2 h.

After completion of the reaction, the reaction mixture was filtered through a celite bed. The volatiles were evaporated under reduced pressure to give 133-3 as a pale yellow liquid 0.8 g (76%).

carbonyl)-ethyl ester 134-1 (18 g, 34.74 mmol) in methanol (90 mL) and 10% Pd/C (3.6 g, 50% wet) at 25-30° C. The reaction mixture was stirred at room temperature under hydrogen pressure (5 kg/cm$^2$) over a period of 2 h. After

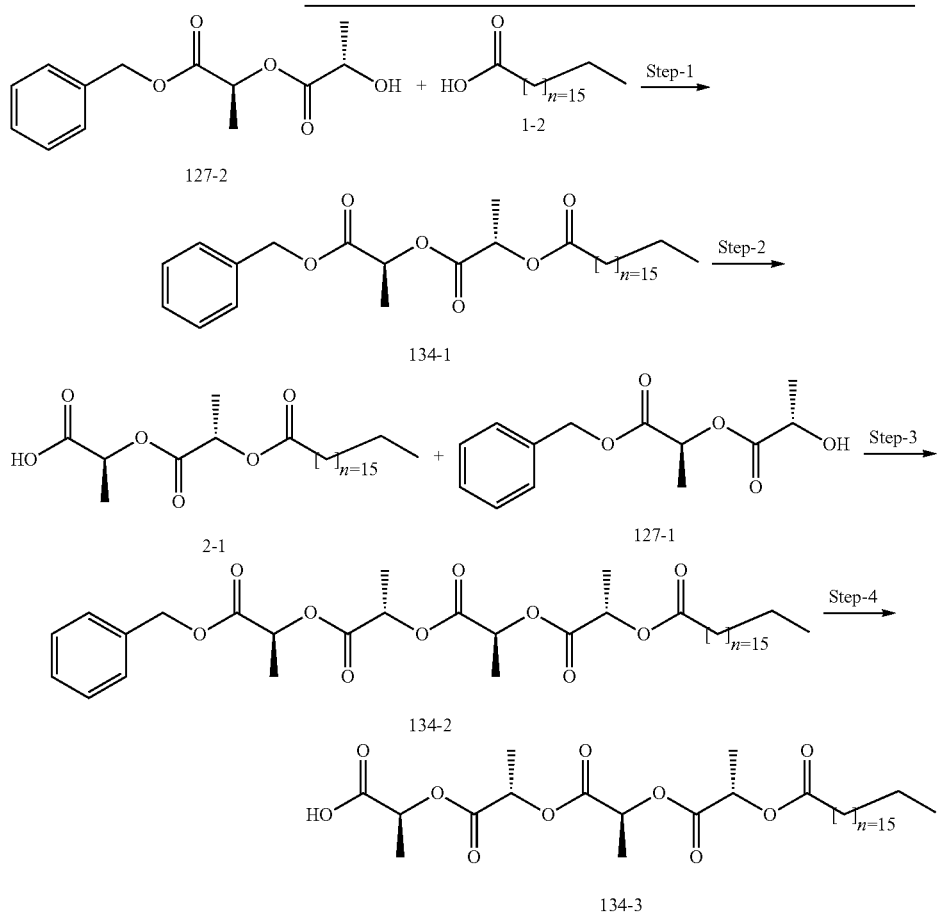

Scheme 103: Synthesis of octadecanoic acid (S)-1-{(S)-1-[(S)-1-((S)-1-carboxy-ethoxycarbonyl)-ethoxy carbonyl]-ethoxycarbonyl}-ethyl ester (134-3):

Step-1: Preparation of octadecanoic acid (S)-1-((S)-1-benzyloxycarbonyl-ethoxycarbonyl)-ethyl ester (134-1)

To a solution of octadecanoic acid 1-2 (23.4 g, 82.53 mmol) and (S)-2-hydroxy-propionic acid (S)-1-benzyloxycarbonyl-ethyl ester 127-1 (16.0 g, 63.49 mmol) in dichloromethane (160 mL) were added EDC.HCl (24.2 g, 126.90 mmol), 4-dimethylaminopyridine (770 mg, 6.34 mmol) at 0° C. The reaction mixture was allowed to stir at 25-30° C. over a period of 1 h. The resulting reaction mass was quenched with water (500 mL), extracted with dichloromethane (500×3 mL), dried over sodium sulfate and concentrated under reduced pressure. The crude product obtained upon evaporation of volatiles was purified through silica gel (230-400 mesh) column chromatography (2% ethyl acetate in hexane) to obtain product 134-1 as a pale yellow liquid 18 g (55%).

Step-2: Preparation of octadecanoic acid (S)-1-((S)-1-carboxy-ethoxycarbonyl)-ethyl ester (2-1)

To a 500 mL autoclave vessel were added a solution of octadecanoic acid (S)-1-((S)-1-benz yloxycarbonyl-ethoxycompletion of the reaction, the reaction mixture was filtered through a celite bed. The volatiles were evaporated under reduced pressure to obtain product 2-1 as a colorless low melting solid 12.5 g (84%).

Step-3: Preparation of octadecanoic acid (S)-1-{(S)-1-[(S)-1-((S)-1-benzyloxycarbonyl-ethoxycarbonyl)-ethoxycarbonyl]-ethoxycarbonyl}-ethyl ester (134-2)

To a solution of octadecanoic acid (S)-1-((S)-1-carboxy-ethoxycarbonyl)-ethyl ester 2-1 (10.2 g, 23.80 mmol) and (S)-2-hydroxy-propionic acid (S)-1-benzyloxycarbonyl-ethyl ester 127-1 (4.0 g, 15.87 mmol) in dichloromethane (40 mL) were added EDC.HCl (6.06 g, 31.74 mmol), hydroxybenzotriazole (428 mg, 3.17 mmol) and 4-dimethylaminopyridine (193 mg, 1.58 mmol) and at 0° C. The reaction mixture was allowed to stir at 25-30° C. over a period of 1 h. The resulting reaction mass was quenched with water (500 mL), extracted with dichloromethane (500×3 mL), dried over sodium sulfate and concentrated under reduced pressure. The crude product obtained upon evaporation of volatiles was purified through silica gel (230-400 mesh) column chromatography (3% ethyl acetate in hexane) to obtain product 134-2 as a pale yellow liquid 6.1 g (58%).

Step-4: Preparation of octadecanoic acid (S)-1-{(S)-1-[(S)-1-((S)-1-carboxy-ethoxycarbonyl)-ethoxy carbonyl]-ethoxycarbonyl}-ethyl ester (134-3)

To a 250 mL autoclave vessel were added a solution of octadecanoic acid (S)-1-{(S)-1-[(S)-1-((S)-1-benzyloxycarbonyl-ethoxycarbonyl)-ethoxycarbonyl]-ethoxycarbonyl}-ethyl ester 134-2 (6.1 g, 9.21 mmol) in methanol (40 mL) and 10% Pd/C (1.2 g, 50% wet) at 25-30° C. The reaction mixture was stirred at room temperature under hydrogen pressure (5 kg/cm$^2$) over a period of 2 h. After completion of the reaction, the reaction mixture was filtered through a celite bed. The volatiles were evaporated under reduced pressure to obtain product 134-3 as a colorless low melting solid 4.5 g (85%).

Scheme 105: Synthesis of (S)-2-Hydroxy-propionic acid (S)-1-ethoxycarbonyl-ethyl ester (133-2):

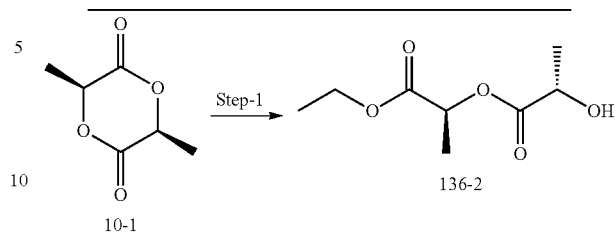

Step-1: Preparation of (S)-2-Hydroxy-propionic acid (S)-1-ethoxycarbonyl-ethyl ester (136-2)

To a solution of (3S,6S)-3,6-dimethyl-[1,4]dioxane-2,5-dione 10-1 (5.0 g, 34.72 mmol) in toluene (100 mL) was added ethanol (1.92 mL, 31.98 mmol) and camphor sulfonic acid (0.8 g, 3.47 mmol) at 25-30° C. The reaction mixture was allowed to stir at 80° C. over a period of 2 h. The resulting reaction mixture was diluted with ethyl acetate Scheme 104: Synthesis of succinic acid mono-((S)-1-{(S)-1-((S)-1-benzyloxycarbonyl-ethoxycarbonyl)-ethoxycarbonyl]-ethoxycarbonyl}-ethyl ester (135-1):

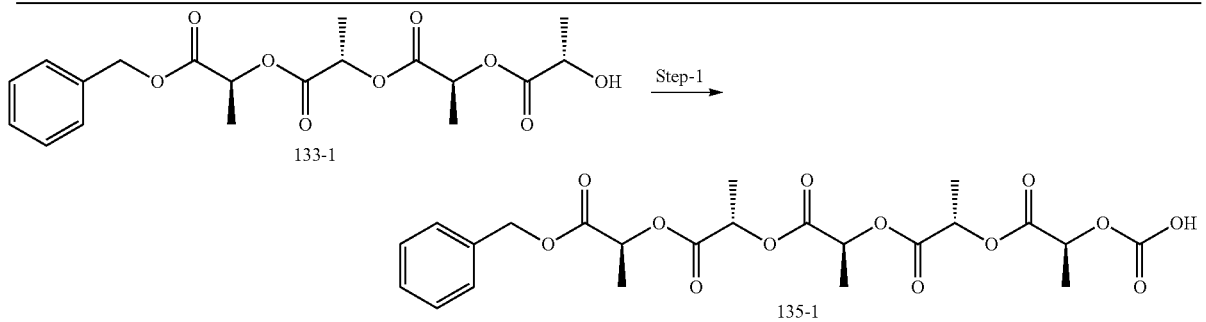

Step-1: Preparation of succinic acid mono-((S)-1-{(S)-1-[(S)-1-((S)-1-benzyloxycarbonyl-ethoxycarbonyl)-ethoxycarbonyl]-ethoxycarbonyl}-ethyl) ester (135-1)

To a solution of succinic acid (2.8 g, 23.71 mmol) in dichloromethane (50 mL) were added EDC.HCl (6.79 g, 35.55 mmol), hydroxybenzotriazole (0.327 g, 2.37 mmol), (S)-2-hydroxy-propionic acid (S)-1-[(S)-1-((S)-1-benzyloxycarbonyl-ethoxycarbonyl)-ethoxycarbonyl]-ethyl ester 133-1 (4.7 g, 11.85 mmol) and 4-dimethylaminopyridine (144 mg, 1.18 mmol) at 0° C. The reaction mixture was allowed to stir at 25-30° C. over a period of 1 h. The resulting reaction mixture was quenched with water (250 mL), extracted with dichloromethane (500×3 mL), dried over sodium sulfate and concentrated under reduced pressure. The crude product obtained upon evaporation of volatiles was purified through silica gel (230-400 mesh) column chromatography (40% ethyl acetate in hexane) to obtain product 135-1 as a pale yellow liquid 3.1 g (53%).

(800 mL) and washed with water (2×200 mL). The crude product obtained upon evaporation of volatiles was purified through silica gel (230-400 mesh) column chromatography (13% ethyl acetate in hexane) to obtain product 136-2 as a colorless liquid 6.6 g (60%).

Scheme 106: Synthesis of (S)-2-Hydroxy-propionic acid (S)-1-[(S)-1-((S)-1-ethoxycarbonyl-ethoxycarbonyl)-ethoxycarbonyl]-ether ester (137-2):

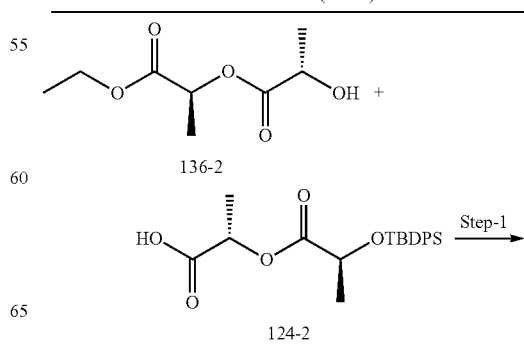

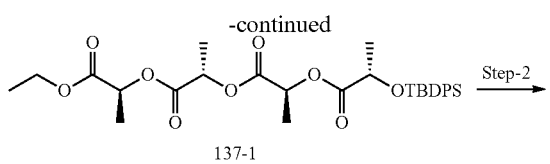

137-1

Step-2

Step-2: Preparation of (S)-2-Hydroxy-propionic acid (S)-1-[(S)-1-((S)-1-ethoxycarbonyl-ethoxycarbonyl)-ethoxycarbonyl]-ethyl ester (137-2)

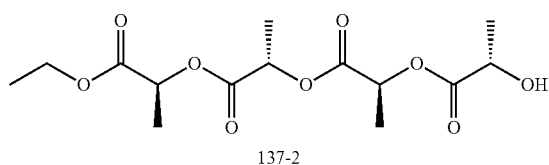

137-2

To a solution of (S)-2-(tert-Butyl-diphenyl-silanyloxy)-propionic acid (S)-1-[(S)-1-((S)-1-ethoxycarbonyl-ethoxycarbonyl)-ethoxycarbonyl]-ethyl ester 137-1 (4 g, 6.99 mmol) in tetrahydrofuran (40 mL) was added tetra butyl ammonium fluoride (10.49 mL, 1.0M, 10.49 mmol) and acetic acid (0.63 g, 10.49 mmol) at 0° C. The reaction mixture was allowed to stir at room temperature over a period of 1 h. The resulting reaction mixture was concentrated under reduced pressure and crude product obtained upon evaporation of the volatiles was purified through silica gel (230-400 mesh) column chromatography (12% ethyl acetate in hexane) to give product 137-2 as a colorless liquid 1.0 g (43%).

Scheme 107: Synthesis of (S)-2-Hydroxy-propionic acid (S)-1-((S)-1-{(S)-1-[(S)-1-((S)-1-ethoxycarbonyl-ethoxycarbonyl)-ethoxycarbonyl]-ethoxycarbonyl}-ethoxycarbonyl)ethyl ester (138-2):

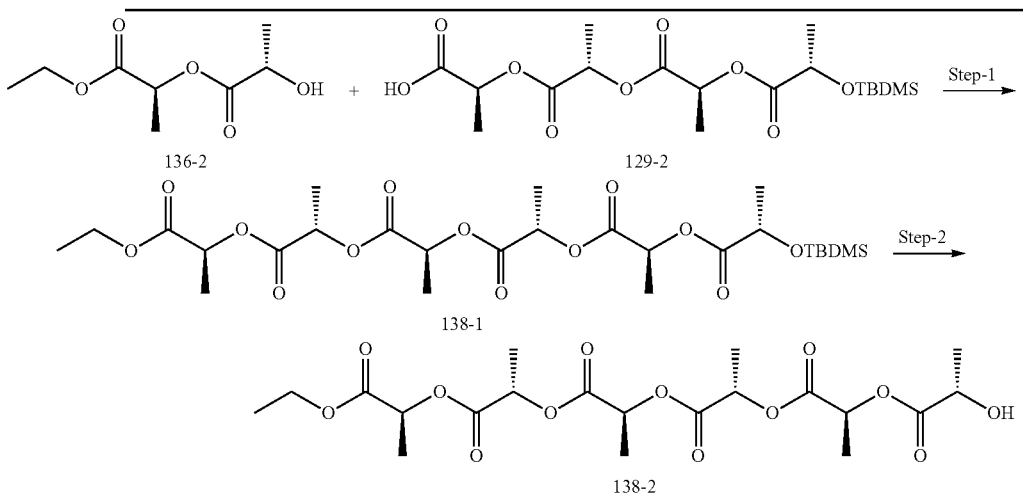

Step-1: Preparation of (S)-2-(tert-Butyl-diphenyl-silanyloxy)-propionic acid (S)-1-[(S)-1-((S)-1-ethoxycarbonyl-ethoxycarbonyl)-ethoxycarbonyl]-ethyl ester (137-1)

To a solution of (S)-2-(tert-Butyl-diphenyl-silanyloxy)-propionic acid (S)-1-carboxy-ethyl ester 124-2 (5.4 g, 13.68 mmol) in dichloromethane (60 mL) was that added EDC.HCl (3.0 g, 15.78 mmol), (S)-2-Hydroxy-propionic acid (S)-1-ethoxycarbonyl-ethyl ester (2.0 g, 10.52 mmol) and 4-dimethylaminopyridine (0.12 g, 1.05 mmol) at 0° C. The reaction mixture was allowed to stir at 25-30° C. over a period of 1 h. The resulting reaction mass was quenched with water (200 mL), extracted with dichloromethane (250×3 mL), dried over Na₂SO₄ and concentrated under reduced pressure. The crude product obtained upon evaporation of volatiles was purified through silica gel (230-400 mesh) column chromatography (3% ethyl acetate in hexane) to obtain product 137-1 as a colorless liquid 4.2 g (70%).

Step-1: Preparation of (S)-2-(tert-Butyl-diphenyl-silanyloxy)-propionic acid (S)-1-((S)-1-{(S)-1-[(S)-1-((S)-1-ethoxycarbonyl-ethoxycarbonyl)-ethoxycarbonyl]-ethoxycarbonyl}-ethoxycarbonyl)-ethyl ester (138-1)

To a solution of (S)-2-(tert-Butyl-diphenyl-silanyloxy)-propionic acid (S)-1-[(S)-1-((S)-1-carboxy-ethoxycarbonyl)-ethoxycarbonyl]-ethyl ester 129-2 (7.44 g, 13.68 mmol) in dichloromethane (20 mL) was added EDC.HCl (2.411 g, 12.62 mmol), (S)-2-Hydroxy-propionic acid (S)-1-ethoxycarbonyl-ethyl ester (2 g, 10.52 mmol) 136-2 and 4-dimethylaminopyridine (128 mg, 1.05 mmol) at 0° C. The reaction mixture was allowed to stir at 25-30° C. over a period of 1 h. The resulting reaction mass was quenched with water (200 mL), extracted with dichloromethane (250×2 mL), dried over Na₂SO₄ and concentrated under reduced pressure. The crude product obtained upon evaporation of volatiles was purified through silica gel (230-400 mesh) column chromatography (5% ethyl acetate in hexane) to obtain product 138-1 as a colorless liquid 6.0 g (79%).

Step-2 Preparation of (S)-2-Hydroxy-propionic acid (S)-1-((S)-1-{(S)-1-[(S)-1-((S)-1-ethoxycarbonyl-ethoxycarbonyl)-ethoxycarbonyl]-ethoxycarbonyl}-ethoxycarbonyl)-ethyl ester (15-2)

To a solution of (S)-2-(tert-Butyl-diphenyl-silanyloxy)-propionic acid (S)-1-((S)-1-{(S)-1-[(S)-1-((S)-1-ethoxycarbonyl-ethoxycarbonyl)-ethoxycarbonyl]-ethoxycarbonyl}-ethoxycarbonyl)-ethyl ester 138-1 (7 g, 9.78 mmol) in tetrahydrofuran (70 mL) were added tetra butyl ammonium fluoride (14.64 mL, 1.0M, 14.66 mmol) and acetic acid (0.88 g, 14.66 mmol) at 0° C. The reaction mixture was allowed to stir at room temperature over a period of 1 h. The resulting reaction mixture was concentrated under reduced pressure and crude product obtained upon evaporation of the volatiles was purified through silica gel (230-400 mesh) column chromatography (14% ethyl acetate in hexane) to give product 138-2 as a colorless liquid 3.0 g (64%).

Step-2: Preparation of (S)-2-Hydroxy-propionic acid (S)-1-{(S)-1-[(S)-1-((S)-1-{(S)-1-[(s)-1-((S)-1-ethoxycarbonyl-ethoxycarbonyl)-ethoxycarbonyl]-ethoxycarbonyl}-ethoxycarbonyl)-ethoxycarbonyl]-ethoxycarbonyl}-ethyl ester (139-2)

To a solution of (S)-2-(tert-Butyl-diphenyl-silanyloxy)-propionic acid (S)-1-{(S)-1-[(S)-1-((S)-1-{(S)-1-[(S)-1-((S)-1-ethoxycarbonyl-ethoxycarbonyl)-ethoxycarbonyl]-ethoxycarbonyl}-ethoxycarbonyl)-ethoxycarbonyl]-ethoxycarbonyl}-ethyl ester 139-1 (10.0 g, 11.63 mmol) in tetrahydrofuran (100 mL) were added tetra butyl ammonium fluoride (17.44 mL, 1.0M, 17.44 mmol) and acetic acid (0.88 g, 17.44 mmol) at 0° C. The reaction mixture was allowed to stir at room temperature over a period of 1 h. The resulting reaction mixture was concentrated under reduced pressure and crude product obtained upon evaporation of the volatiles was purified through silica gel (230-400 mesh) column Scheme 108: Synthesis of (S)-2-Hydroxy-propionic acid (S)-1-{(S)-1-[(S)-1-((S)-1-{(S)-1-[(S)-1-((S)-1-ethoxycarbonyl-ethoxycarbonyl)-ethoxycarbonyl]-ethoxycarbonyl}-ethoxycarbonyl)-ethoxycarbonyl]-ethoxycarbonyl}-ethyl ester (139-2):

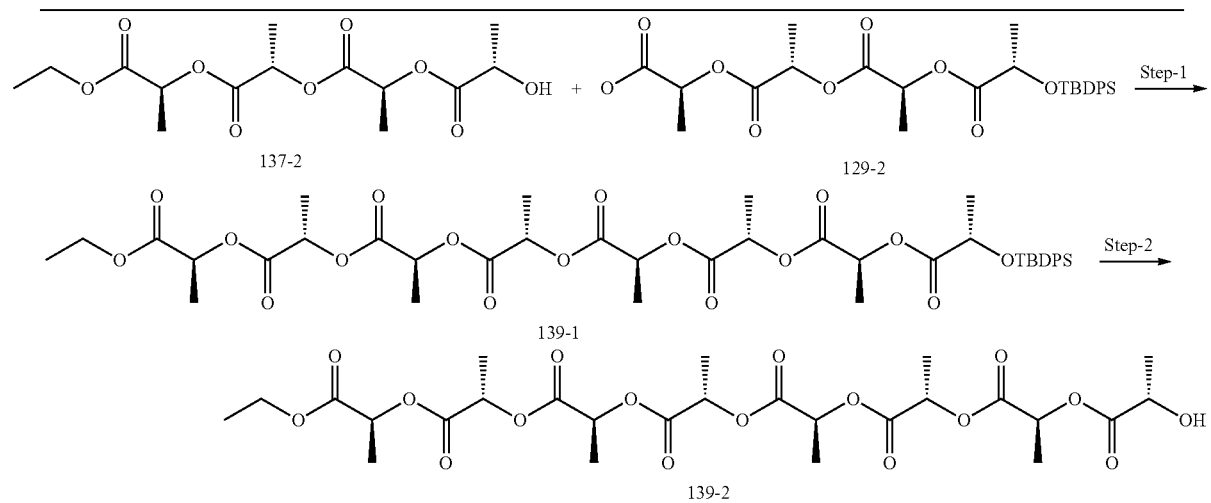

chromatography (14% ethyl acetate in hexane) to give product 139-2 as a colorless liquid 4.5 g (62%).

Step-1: Preparation of (S)-2-(tert-Butyl-diphenyl-silanyloxy)-propionic acid (S)-1-{(S)-1-[(S)-1-((S)-1-{(S)-1-[(S)-1-((S)-1-ethoxycarbonyl-ethoxycarbonyl)-ethoxycarbonyl]-ethoxycarbonyl}-ethoxycarbonyl)-ethoxycarbonyl]-ethoxycarbonyl}-ethyl ester (139-1)

To a solution of (S)-2-(tert-Butyl-diphenyl-silanyloxy)-propionic acid (S)-1-[(S)-1-((S)-1-carboxy-ethoxycarbonyl)-ethoxycarbonyl]-ethyl ester 129-2 (17.78 g, 32.69 mmol) in dichloromethane (84 mL) were added EDC.HCl (7.2 g, 37.72 mmol), (S)-2-Hydroxy-propionic acid (S)-1-[(S)-1-((S)-1-ethoxycarbonyl-ethoxycarbonyl)-ethoxycarbonyl]-ethyl ester 137-2 (8.4 g, 25.15 mmol) and 4-dimethylaminopyridine (0.30 g, 2.51 mmol) at 0° C. The reaction mixture was allowed to stir at 25-30° C. over a period of 1 h. The resulting reaction mass was quenched with water (500 mL), extracted with dichloromethane (250×4 mL), dried over Na$_2$SO$_4$ and concentrated under reduced pressure. The crude product obtained upon evaporation of volatiles was purified through silica gel (230-400 mesh) column chromatography (8% ethyl acetate in hexane) to obtain product 139-1 as a colorless liquid 10.0 g (47.6%).

Scheme 109: Synthesis of Succinic acid monoethyl ester (140-1):

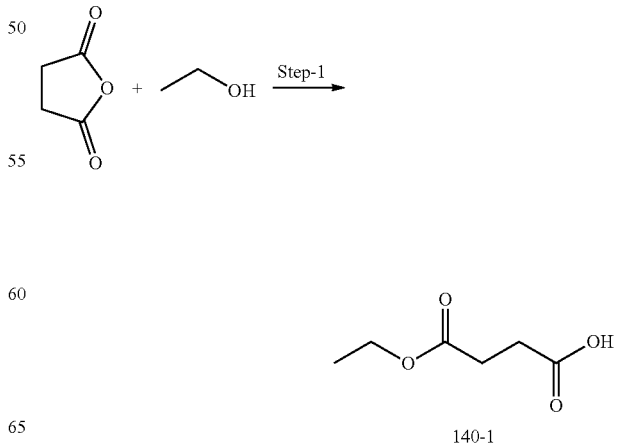

Step-1: Preparation of Succinic acid monoethyl ester (140-1)

A solution of dihydro-furan-2,5-dione (20 g, 20 mmol) in ethanol (100 mL) was allowed to stir at 80° C. over a period of 16 h. The resulting reaction mixture was directly concentrated under reduced pressure. The residue was diluted with DCM (600 mL) and washed with saturated sodium bicarbonate solution (300 mL). The aqueous layer was separated from organic, acidified with 1.5N HCl (pH=2) and extracted with DCM (300×2 mL), dried over $Na_2SO_4$ and concentrated under reduced pressure to obtain product 140-1 as a colorless liquid 11.5 g (39.3%).

Scheme 110: Synthesis of (Z)-But-2-enedioic acid monoethyl ester (141-1):

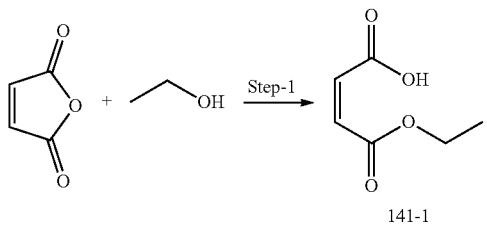

141-1

Step-1: Preparation of (Z)-But-2-enedioic acid monoethyl ester (141-1)

A solution of furan-2,5-dione (5 g, 51.02 mmol) in ethanol (50 mL) was allowed to stir at 100° C. over a period of 16 h. The resulting reaction mixture was directly concentrated under reduced pressure. Then residue was diluted with DCM (450 mL) and washed with saturated sodium bicarbonate solution (200 mL). The aqueous layer was separated from organic, acidified with 1.5N HCl (pH=2) and extracted with DCM (150×3 mL), dried over $Na_2SO_4$ and concentrated under reduced pressure to obtain product 141-1 as a colorless liquid 3.3 g (45.2%).

Scheme 103: Synthesis of (Z)-But-2-enedioic acid monododecyl ester (142-1):

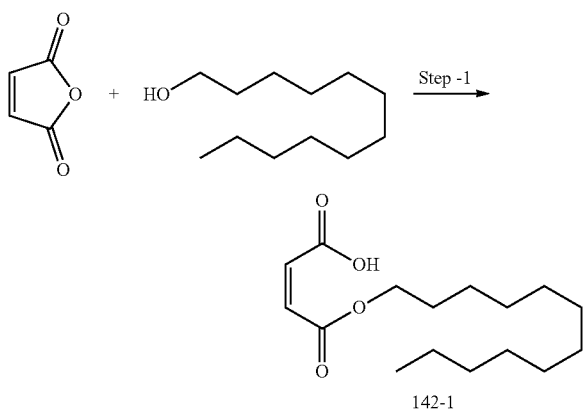

142-1

Step-1: Preparation of (Z)-But-2-enedioic acid monododecyl ester (142-1)

To a solution of dodecan-1-ol (1.0 g, 5.37 mmol) in toluene (10 mL) was added furan-2,5-dione (0.526 g, 5.37 mmol) at 25-30° C. The resulting mixture was allowed to stir at 100° C. over a period of 16 h. The reaction mixture was diluted with ethyl acetate (300 mL) and basified (pH=10) with sodium hydroxide solution (100 mL). The aqueous layer was separated from organic, acidified with 1.5N HCl (pH=2), extracted with ethyl acetate (100×3 mL), dried over $Na_2SO_4$ and concentrated under reduced pressure to obtain product 142-1 as a white solid 1.1 g (73%).

Scheme 111: Synthesis of (Z)-But-2-enedioic acid monooctadecyl ester (143-1):

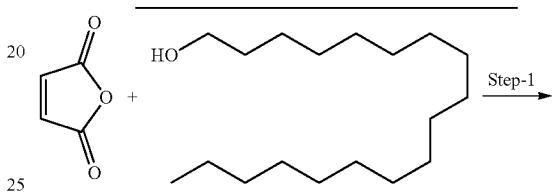

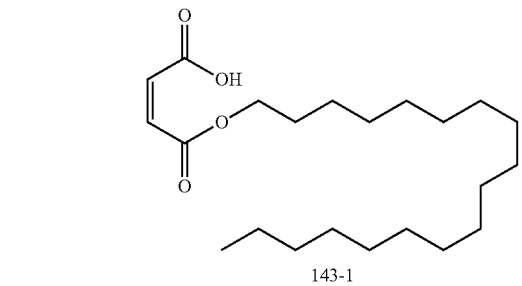

143-1

Step-1: Preparation of (Z)-But-2-enedioic acid monooctadecyl ester (143-1)

To a solution of octadecan-1-ol (1.0 g, 3.70 mmol) in toluene (10 mL) was added furan-2,5-dione (0.362 g, 3.70 mmol) at 25-30° C. The resulting mixture was allowed to stir at 100° C. over a period of 16 h. The reaction mixture was diluted with ethyl acetate (300 mL) and basified (pH=10) with sodium hydroxide solution (100 mL). That aqueous layer was separated from organic, acidified with 1.5N HCl (pH=2), extracted with ethyl acetate (100×3 mL), dried over $Na_2SO_4$ and concentrated under reduced pressure to obtained product 143-1 as a white solid 0.8 g (58.8%

Scheme 112: Synthesis of (4Z,7Z,10Z,13Z,16Z,19Z)-Docosa-4,7,10,13,16,19-hexaenoic acid (S)-1-((S)-1-carboxy-ethoxycarbonyl)-ethyl ester (144-2):

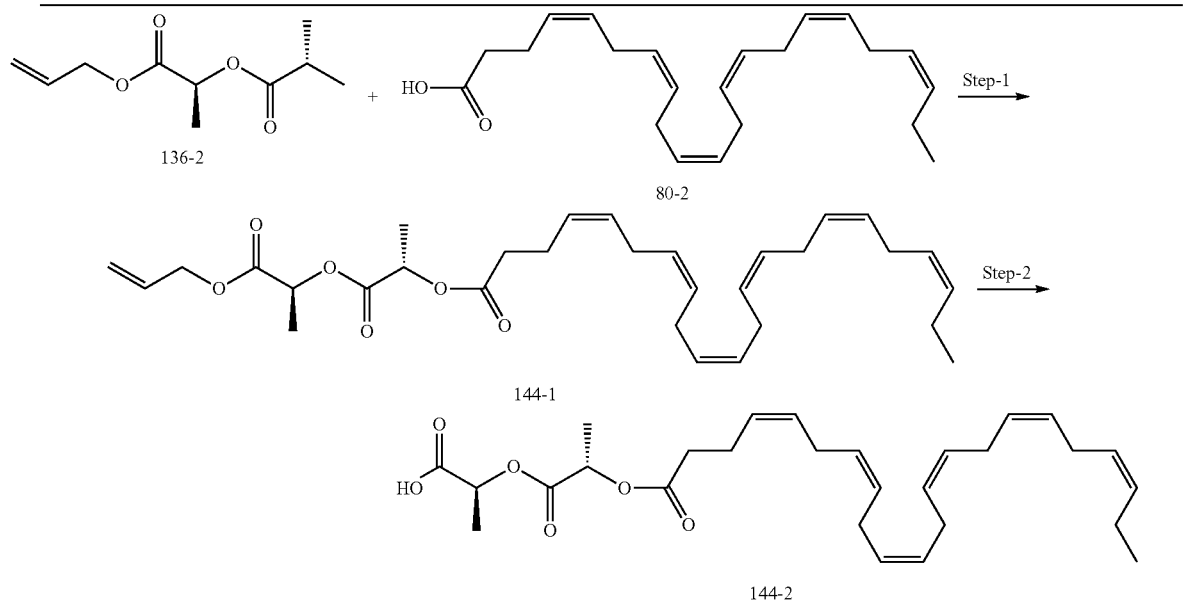

Step-1: Preparation of (4Z,7Z,10Z,13Z,16Z,19Z)-Docosa-4,7,10,13,16,19-hexaenoic acid (S)-1-((S)-1-allyloxycarbonyl-ethoxycarbonyl)-ethyl ester (144-1)

To a solution of (4Z,7Z,10Z,13Z,16Z,19Z)-Docosa-4,7,10,13,16,19-hexaenoic acid 80-2 (3.11 g, 9.47 mmol) in dichloromethane (15 mL) were added EDC.HCl (2.26 g, 11.83 mmol), (S)-2-Hydroxy-propionic acid (S)-1-allyloxycarbonyl-ethyl ester (13-1) (1.5 g, 7.89 mmol) and 4-dimethylaminopyridine (96 mg, 0.79 mmol) at 0° C. The reaction mixture was allowed to stir at 25-30° C. over a period of 2 h. The resulting reaction mass was quenched with water (100 mL), extracted with dichloromethane (250×2 mL), dried over Na$_2$SO$_4$ and concentrated under reduced pressure. The crude product obtained upon evaporation of volatiles was purified through silica gel (230-400 mesh) column chromatography (4% ethyl acetate in hexane) to obtain product 144-1 as a brown liquid 1.5 g (37%).

Step-2: Preparation of (4Z,7Z,10Z,13Z,16Z,19Z)-Docosa-4,7,10,13,16,19-hexaenoic acid (S)-1-((S)-1-carboxy-ethoxycarbonyl)-ethyl ester (144-2)

To a solution of (4Z,7Z,10Z,13Z,16Z,19Z)-Docosa-4,7,10,13,16,19-hexaenoic acid (S)-1-((S)-1-allyloxycarbonyl-ethoxycarbonyl)-ethyl ester 80-2 (1.5 g, 2.92 mmol) in tetrahydrofuran (15 mL) were added palladium tetrakis (0.338 g, 0.29 mmol) and pyrrolidine (0.19 g, 2.77 mmol) at 0° C. The reaction mixture was allowed to stir at room temperature over a period of 1 h. The resulting reaction mixture was concentrated under reduced pressure and crude product obtained upon evaporation of the volatiles was purified through silica gel (230-400 mesh) column chromatography (2% methanol in dichloromethane) to give 144-2 as a brown wax 0.5 g (36%).

Scheme 113: Synthesis of (4Z,7Z,10Z,13Z,16Z,19Z)-Docosa-4,7,10,13,16,19-hexaenoic acid (S)-1-{(S)-1-[(S)-1-((S)-1-carboxy-ethoxycarbonyl)-ethoxycarbonyl]-ethoxycarbonyl}-ethyl

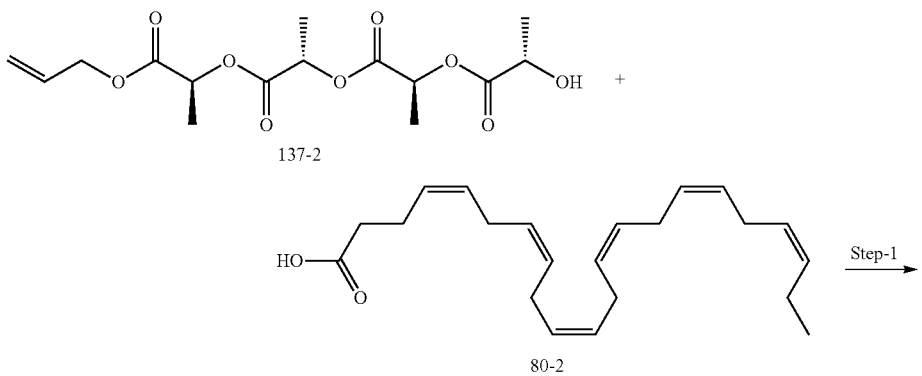

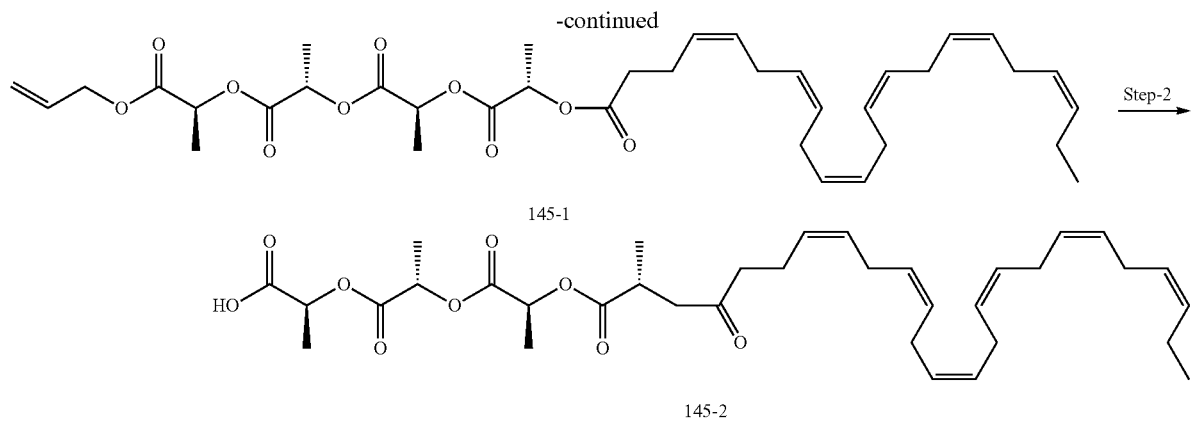

145-1

145-2

Step-1: Preparation (4Z,7Z,10Z,13Z,16Z,19Z)-Docosa-4,7,10,13,16,19-hexaenoic acid (S)-1-{(S)-1-[(S)-1-((S)-1-allyloxycarbonyl-ethoxycarbonyl)-ethoxycarbonyl]-ethoxycarbonyl}-ethyl ester (145-1)

To a solution of (4Z,7Z,10Z,13Z,16Z,19Z)-Docosa-4,7,10,13,16,19-hexaenoic acid 80-2 (1.14 g, 3.7 mmol) in dichloromethane (10 mL) were added DCC (0.893 g, 4.33 mmol), (S)-2-hydroxy-propionic acid (S)-1-[(S)-1-((S)-1-allyloxycarbonyl-ethoxycarbonyl)-ethoxy carbonyl]-ethyl ester 137-2 (1.0 g, 2.89 mmol) and 4-dimethylaminopyridine (35 mg, 0.29 mmol) at 0° C. The reaction mixture was allowed to stir at 25-30° C. over a period of 2 h. The resulting reaction mass was quenched with water (100 mL), extracted with dichloromethane (100×3 mL), dried over Na$_2$SO$_4$ and concentrated under reduced pressure. The crude product obtained upon evaporation of volatiles was purified through silica gel (230-400 mesh) column chromatography (5% ethyl acetate in hexane) to obtain product 145-1 as a brown liquid 0.9 g (47.6%).

Step-2: Preparation of (4Z,7Z,10Z,13Z,16Z,19Z)-Docosa-4,7,10,13,16,19-hexaenoic acid (S)-1-{(S)-1-[(S)-1-((S)-1-carboxy-ethoxycarbonyl)-ethoxycarbonyl]-ethoxycarbonyl}-ethyl ester (145-2)

To a solution of (4Z,7Z,10Z,13Z,16Z,19Z)-Docosa-4,7,10,13,16,19-hexaenoic acid (S)-1-{(S)-1-[(S)-1-((S)-1-allyloxycarbonyl-ethoxycarbonyl)-ethoxycarbonyl]-ethoxycarbonyl}-ethyl ester 145-1 (0.9 g, 1.37 mmol) in tetrahydrofuran (9 mL) were added palladium tetrakis (0.162 g, 0.14 mmol) and pyrrolidine (0.09 g, 1.3 mmol) at 0° C. The reaction mixture was allowed to stir at room temperature over a period of 1 h. The resulting reaction mixture was concentrated under reduced pressure. The crude product obtained upon evaporation of the volatiles was purified through silica gel (230-400 mesh) column chromatography (2% MeOH in DCM) to give product 145-2 as a brown wax 0.4 g (46%).

Example 6. Analytical Method Development for Select Compounds

Analytical Method Development for Timolol Prodrugs
Determination of Maximal Absorptive Wavelength Timolol maleate (35-1) and prodrugs of Timolol were dissolved in DMSO at a concentration of 100 μg/mL. The samples were scanned at a wavelength range of 200-800 nm using a Genesys 105 UV-VIS spectrophotometer (Thermo Scientific). Maximum absorption wavelength was 298 nm.

HPLC Method for Timolol and PLA-Conjugated Timolol

Chromatographic separation of native Timolol and its PLA conjugated derivatives was achieved using an Agilent 1260 Infinity HPLC equipped with a diode array and a multiple wavelength detector with an XTERRA C8 column (5 μm, 4.6 mm×150 mm) as the stationary phase. The gradient separation method is outlined in Table 1A. The analysis was performed at an injection volume of 40 μL, a flow rate of 0.8 mL/min and a detection wavelength of 298 nm at 25° C. Retention times for Timolol and PLA-conjugated compounds are illustrated in Table 1B.

TABLE 1A

HPLC Gradient Method for Separation of Timolol Derivatives

| Time (min) | A (water + 0.1% FA) | B (MeCN + 0.1% FA) |
|---|---|---|
| 0 | 95 | 5 |
| 4 | 5 | 95 |
| 5 | 5 | 95 |
| 5.5 | 95 | 5 |
| 9 | 95 | 5 |

TABLE 1B

Relative Retention Times of Timolol and Derivatives

| PLA Repeat Units | Timolol RRT (min) |
|---|---|
| Parent | 4.27 |
| Acetyl, n = 1 | 4.64 |
| Acetyl, n = 4 | 4.83 |
| Stearyl, n = 1 | 5.78 |
| Stearyl, n = 4 | 5.94 |
| Stearyl, n = 6 | 6.27 | n = the number of LA repeat units conjugated to the parent compound.

Analytical Method Development for ROCK Inhibitor Prodrugs

Chromatographic separation of SR5834 and RKI-H-1y and their prodrugs was achieved using an Agilent 1260 Infinity HPLC with an XTERRA C8 column (5 μm, 4.6 mm×150 mm) as the stationary phase and a gradient method utilizing acetonitrile and water as the mobile phase. The gradient separation method is outlined in Table 2. The analysis was performed at an injection volume of 10 μL, a flow rate of 0.8 mL/min and a detection wavelength of 270 nm at 25° C.

TABLE 2

| HPLC Gradient Method for separation of Rock Inhibitor Prodrugs | | |
|---|---|---|
| Time (min) | A (water + 0.1% FA) | B (MeCN + 0.1% FA) |
| 0 | 95 | 5 |
| 4 | 20 | 80 |
| 5 | 5 | 95 |
| 5.5 | 95 | 5 |
| 7 | 95 | 5 |

Example 7. Determination of Drug Solubility

For each test, approximately 5-10 mg was transferred to a 10 mL glass vial. Aqueous or organic solvent was added to each vial to achieve an overall concentration of 50 mg/mL. After vortexing aggressively for 2-3 minutes and sonicating in a bath sonicator for 5 minutes, undissolved drug was spun down at 1200 rpm for 5 minutes to generate a pellet. The supernatant was collected and filtered through a 0.2 μm nylon syringe filter into HPLC vials for drug content analysis. Drug concentration was determined by comparing against a standard calibration curve.

Drug solubility in aqueous and organic solvent can inform on the potential for said drug to be encapsulated within microparticles and its release kinetics once it has been encapsulated. Herein, drug solubility was evaluated to better predict and select compounds that may be amenable to particle encapsulation. The solubility of PLA-Brinzolamide monoprodrugs, PLA-Dorzolamide monoprodrugs, Tris-PLA Latanoprost prodrugs, Sunitinib-related prodrugs, Brimonidine monoprodrugs, Timolol monoprodrugs, and bisprodrugs are shown in Table 3A and Table 3B.

All prodrugs of Brimonidine, rock inhibitors, and bifunctional conjugates of Sunitinib exhibited low aqueous solubility and high organic solubility (less than 1 mg/mL in aqueous solution and greater than 50 mg/mL in DMSO), respectively.

Solubility of Timolol prodrugs was controlled by a number of parameters including the linker, the terminal end-group, the number of PLA repeat units, and the salt form. Increasing PLA repeat units enhanced hydrophobicity of the compound, resulting in a decrease in the aqueous solubility. The aqueous solubility of Timolol-stearyl PLA(n=4) (41-2) decreased from greater than 50 mg/mL to 6.25 when the PLA repeat units was increased from n=4 (compound 41-2) to n=6, (compound 43-1) respectively. In general, HCL salts of the Timolol-prodrugs was more water soluble than the maleate salt forms.

TABLE 3A

| Solubility of Mono-prodrugs and Bifunctional Prodrugs | | | | |
|---|---|---|---|---|
| | | | Solubility | |
| | Compound Name | Water | DMSO | DCM |
| Brinzolamide Parent | Brinzolamide | <1.0 | >50 | <7.5 |
| | Brinzolamide-PLA (n = 5) (18-3) | <25 | >50 | >50 |
| | Brinzolamide-PLA (n = 10) (19-3) | <1.0 | >50 | >50 |
| | Brinzolamide-PLA (n = 12) (20-2) | <1.0 | >50 | >50 |
| | Brinzolamide-Stearyl PLA (n = 4) (15-2) | <1.0 | >50 | — |
| | Brinzolamide-Stearyl PLA (n = 6) | <0.1 | >50 | — |
| | Brinzolamide-Stearyl PLA (n = 8) | <0.1 | >50 | — |
| | Brinzolamide-Stearyl PLA (n = 12) (16-1) | <0.1 | >50 | — |
| | Brinzolamide-Stearyl PLA (n = 14) (17-1) | <0.1 | >50 | — |
| Dorzolamide Parent | Dorzolamide | >50 | <1.0 | <1.0 |
| PLA-Dorzolamide Mono Prodrugs | Dorzolamide-PLA (n = 1) | >50 | <1.0 | — |
| | Dorzolamide-Stearyl PLA(n = 4) (12-3) | <0.1 | >50 | >50 |
| | Dorzolamide-Stearyl PLA(n = 6) | <0.1 | >50 | >50 |
| | Dorzolamide-Stearyl PLA(n = 8) | <0.1 | >50 | >50 |
| | Dorzolamide-Stearyl PLA(n = 12) (13-2) | <1.0 | >50 | >50 |
| | Dorzolamide-Stearyl PLA(n = 14) (14-2) | <1.0 | >50 | >50 |
| Latanoprost Parent | Latanoprost | <1.0 | >50 | >50 |
| Tris-PLA Latanoprost Prodrugs | Latanoprost-Acetyl PLA (n = 6) | <1.0 | <50 | — |
| Sunitinib Related Prodrugs | 5-Amino Sunitinib | <1.0 | >50 | — |
| | Acetyl PLA(n = 2)-5-hydroxy Sunitinib | >50 | >50 | — |
| | Acetyl PLA(n = 3)-5-hydroxy Sunitinib | >50 | >50 | — |
| | Acetyl PLA(n = 4)-5-hydroxy Sunitinib | >50 | >50 | — |
| | Acetyl PLA(n = 5)-5-hydroxy Sunitinib | >10 | >50 | — |
| | 5-hydroxy Sunitinib-PLA(n = 3)-Etacrynic acid | <1.0 | >50 | — |
| Brimonidine Mono Prodrugs | Brimonidine-PLA(n = 2)-Acetate (25-2) | <1.0 | >50 | — |
| | Brimonidine-PLA(n = 3)-Acetate (26-2) | <1.0 | >50 | — |
| | Brimonidine-PLA(n = 4)-Acetate (27-2) | <1.0 | >50 | — |
| | Brimonidine-PLA(n = 3)-Stearate (28-2) | <1.0 | >50 | — |
| | Brimonidine-PLA(n = 4)-Stearate (29-2) | <1.0 | >50 | — |
| | Brimonidine-Acetyl PLA(n = 8) (109-1) | <0.1 | >50 | — |
| | Brimonidine-Bis-Acetyl PLA(n = 2) (111-4) | <1.0 | >50 | — |
| | Brimonidine-Acetyl PLA(n = 2)-N-acetate (114-4) | 1.0 | 100 | — |
| | Brimonidine-Acetyl PLA(n = 4)-N-acetate (115-1) | <0.2 | 100 | — |
| | Brimonidine-Bis-Acetyl PLA (n = 4) (116-1) | <0.003 | 100 | — |
| Timolol Mono Prodrugs | Timolol-O-Acetate Maleate (35-4) | <1.0 | >50 | — |
| | Timolol-O-Boc (36-2) | <1.0 | >50 | — |
| | Timolol-O-Boc-N-Acetate (37-2) | <1.0 | >50 | — |

TABLE 3A-continued

Solubility of Mono-prodrugs and Bifunctional Prodrugs

| Compound Name | Solubility | | |
|---|---|---|---|
| | Water | DMSO | DCM |
| Timolol-Acetyl PLA(n = 1) Maleate (44-2) | <1.0 | >50 | — |
| Timolol-Stearyl PLA(n = 1) Maleate (38-2) | <1.0 | >50 | — |
| Timolol-Stearyl PLA(n = 1) HCL (39-1) | <25 | >50 | — |
| Timolol-Acetyl PLA(n = 4) Maleate (45-2) | <1.0 | >50 | — |
| Timolol-Stearyl PLA(n = 4) Maleate (40-2) | <1.0 | >50 | — |
| Timolol-Stearyl (n = 4) HCL (41-2) | >50 | >50 | — |
| Timolol-Stearyl (n = 6) Maleate (42-2) | <1.0 | >50 | — |
| Timolol-Stearyl (n = 6) HCL (43-1) | 6.25 | >50 | — |

TABLE 3B

Solubility Data of Additional Mono-prodrugs and Bifunctional Prodrugs

| | Compound Name | Solubility | | |
|---|---|---|---|---|
| | | Water | DMSO | DCM |
| Brinzolamide Parent | Brinzolamide | <1.0 | >50 | <7.5 |
| PLA-Brinzolamide Prodrugs | Brinzolamide (n = 1) | >50 | >50 | >50 |
| Dorzolamide Parent | Dorzolamide | >50 | <1.0 | <1.0 |
| PLA-Dorzolamide Prodrugs | Dorzolamide-PLA (n = 5) | <1.0 | >50 | >50 |
| | Dorzolamide-PLA(n = 10) | <0.1 | >50 | >50 |
| | Dorzolamide-PLA(n = 12) | <0.1 | >50 | >50 |
| | Dorzolamide-PLA(n = 14) | <0.1 | >50 | >50 |
| | Dorzolamide-DHA (80-3) | <1.0 | >100 | >50 |
| Timolol Mono Prodrugs | Timolol-DHA Maleate (53-3) | <1.0 | >100 | — |
| | N-Acyl-Timolol-PLA (n = 1) Stearate (65-1) | <1.0 | >100 | — |
| | N-Acyl-Timolol-PLA (n = 2) Stearate (66-1) | <1.0 | >100 | — |
| | N-Acyl-Timolol-PLA (n = 4) Stearate (67-1) | <1.0 | 70 | — |
| | N-Acyl-Timolol-DHA (68-1) | <1.0 | >100 | — |
| | N-Acyl-Timolol-PLA (n = 2) DHA | <1.0 | >100 | |
| | N-Acyl-Timolol-PLA (n = 4) DHA | <1.0 | >100 | |
| | N-Acyl-Timolol-PLA (n = 4) (69-1) | <6.3 | >100 | |
| | Timolol-O-Linoleic Acid-Maleate (70-1) | <0.01 | >50 | — |
| | Timolol-O-Linoleic Acid-HCl (71-1) | >25 | >50 | — |
| | Timolol-Bis-Acetyl-PLA (n = 2) (118-1) | <0.1 | >50 | — |
| | Timolol-Bis-Acetyl-PLA (n = 4) (119-1) | <0.00005 | >50 | — |
| | Timolol-Bis-N-Acetyl-PLA (n = 4)-O-Ethyl-succinate (120-1) | <1.0 | >50 | — |
| | Timolol-Bis-N-Acetyl-PLA (n = 4)-O-Acetyl PLA (n = 2) (229) | <0.006 | >50 | — |
| | Timolol-Bis-N-Acetyl-PLA (n = 2)-O-Acetyl PLA (n = 4) (230) | <0.007 | >50 | — |
| | Timolol-Sebacic Acid-Timolol Maleate (75-1) | <1.0 | >100 | |
| Timolol Bis Prodrugs | Timolol-Succinic Acid-Timolol Maleate (76-4) | >6.25 | >100 | |
| | Timolol-Glutaric Acid-Timolol Maleate (77-1) | <1.0 | >100 | |
| | Timolol-Fumurate-Timolol Maleate (78-1) | <1.0 | >100 | |
| | Timolol-Bis-N-Acetyl-PLA (n = 2)-O-Ethyl-succinate (117-6) | <1.0 | >50 | — |
| Rock Inhibitor Mono Prodrugs | RKI-1y | <1.0 | >100 | — |
| | RKI-H-1y | <1.0 | >100 | — |
| | SR5834 | <1.0 | >100 | — |
| | SR5834-Acetyl PLA(n = 4) (88-3) | <0.001 | >50 | — |
| | SR5834-Bis-Acetyl PLA(n = 4) (113-1) | <1.0 | 50 | — |
| | RKI-H-ly-Acetyl PLA (n = 4) (90-3) | <0.3 | >100 | — |

Example 8. In Vitro Stability of Prodrugs

Prodrugs of interest were dissolved in PBS (pH 7) containing 10% DMSO (v/v) at a concentration of 0.1 mg/mL. The samples were incubated at 37° C. or 50° C. to simulate physiological and accelerated degradation conditions, respectively. At various time points, 500 μL of the solution was collected, filtered through a 0.2 μm nylon syringe filter and analyzed by RP-HPLC.

In Vitro Stability of Timolol NCEs

Figure 2:
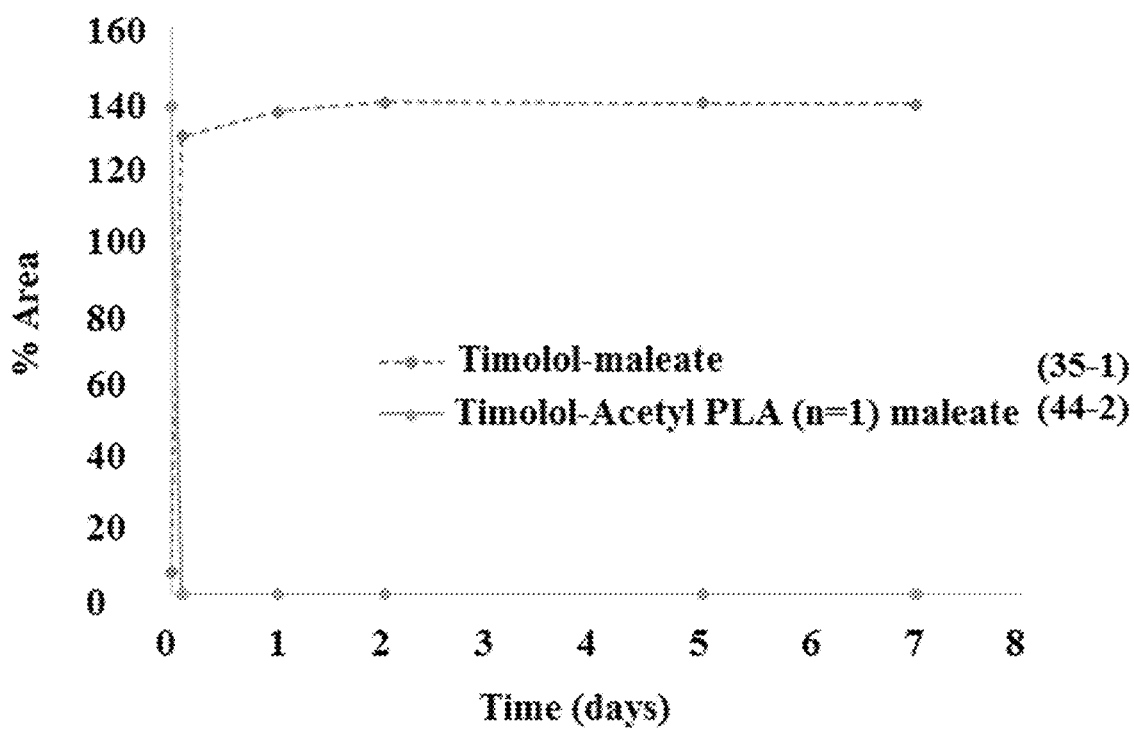
FIG. 2 is a graph depicting the percentage of Timolol-acetyl PLA (n=1) maleate (44-2) that is degraded to parent Timolol maleate (35-1) over the course of 8 days as described in Example 8. The x-axis represents time measured in days and the y-axis represents the amount of undegraded of Timolol-acetyl PLA (n=1) maleate (44-2) as a percentage of the total amount of Timolol-maleate.
Figure 3:
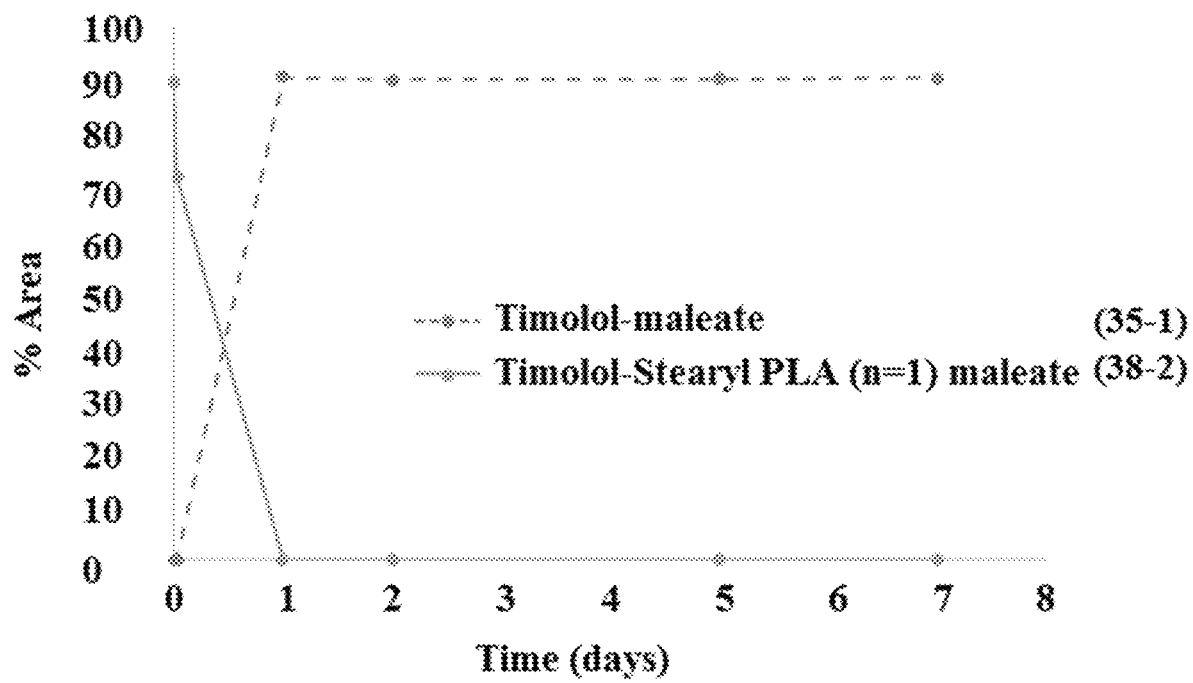
FIG. 3 is a graph depicting the percentage of Timolol-stearyl PLA (n=1) maleate (38-2) that is degraded to parent Timolol maleate (35-1) over the course of 8 days as described in Example 8. The x-axis represents time measured in days and the y-axis represents the amount of undegraded Timolol-stearyl PLA (n=1) maleate (38-2) as a percentage of the total amount of Timolol-maleate.
Figure 4:
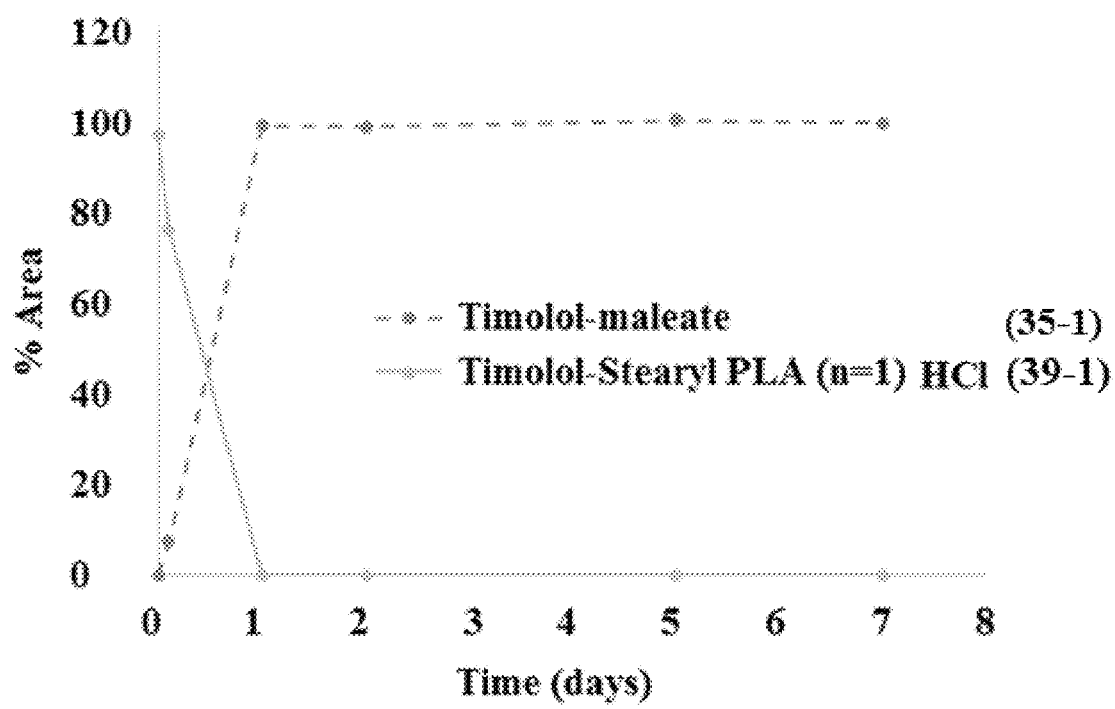
FIG. 4 is a graph depicting the percentage of Timolol-stearyl PLA (n=1) HCl (39-1) that is degraded to parent Timolol maleate (35-1) over the course of 8 days as described in Example 8. The x-axis represents time measured in days and the y-axis represents the amount of undegraded Timolol-stearyl PLA (n=1) HCl (39-1) as a percentage of the total amount of Timolol-maleate.
Figure 5:
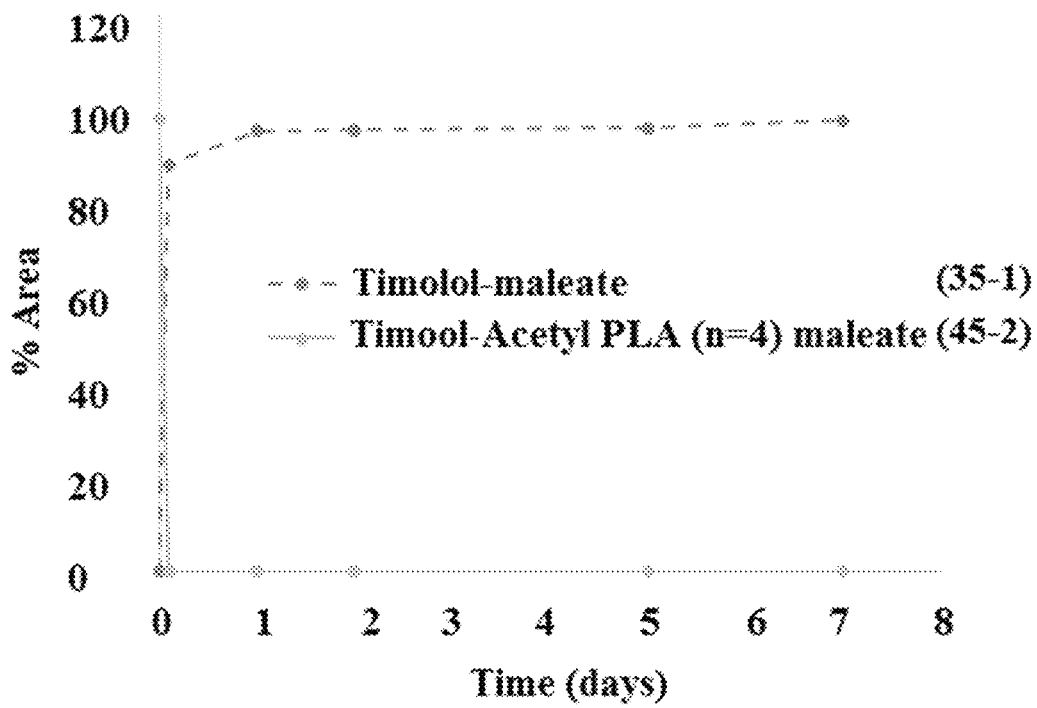
FIG. 5 is a graph depicting the percentage of Timolol-acetyl PLA (n=4) maleate (45-2) that is degraded to parent Timolol maleate (35-1) over the course of 8 days as described in Example 8. The x-axis represents time measured in days and the y-axis represents the amount of undegraded Timolol-acetyl PLA (n=4) maleate (45-2) as a percentage of the total amount of Timolol-maleate.
Figure 6:
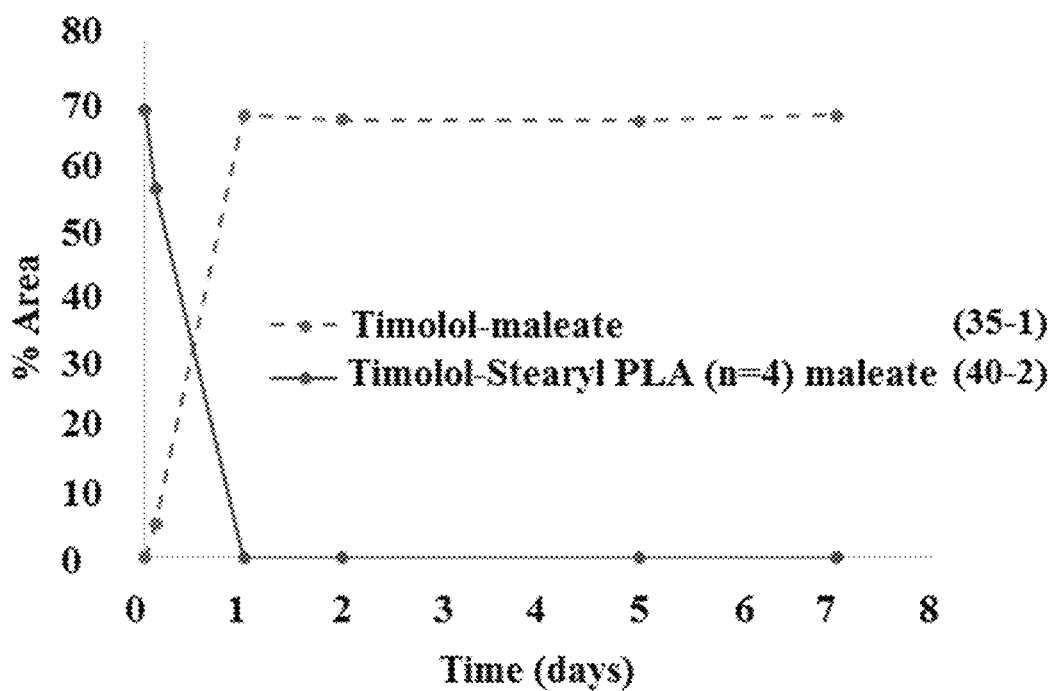
FIG. 6 is a graph depicting the percentage of Timolol-stearyl PLA (n=4) maleate (40-2) that is degraded to parent Timolol maleate (35-1) over the course of 8 days as described in Example 8. The x-axis represents time measured in days and the y-axis represents the amount of undegraded Timolol-stearyl PLA (n=4) maleate (40-2) as a percentage of the total amount of Timolol-maleate.
Figure 7:
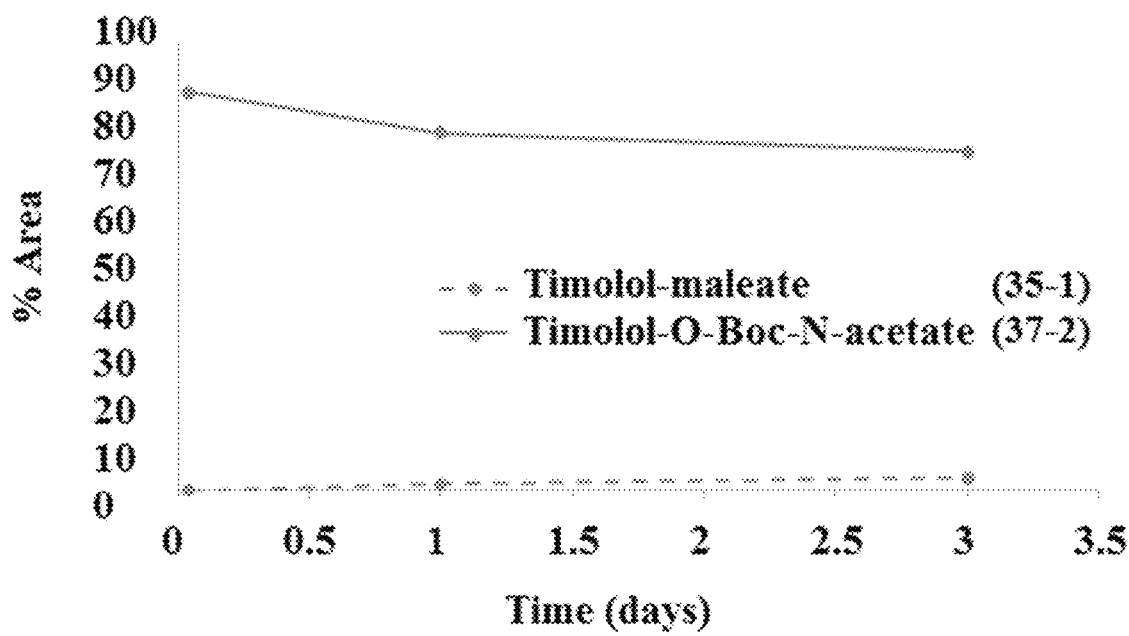
FIG. 7 is a graph depicting the percentage of Timolol-O-Boc-N-acetate (37-2) that is degraded to parent Timolol maleate (35-1) over the course of 3.5 days as described in Example 8. The x-axis represents time measured in days and the y-axis represents the amount of undegraded Timolol-O-Boc-N-acetate (37-2) as a percentage of the total amount of Timolol-maleate.

The degradation kinetics of Timolol maleate (FIG. 1) and prodrugs of Timolol (FIG. 2, FIG. 3, FIG. 4, FIG. 5, and FIG. 6) was evaluated. Rapid degradation to the parent compound was observed for Timolol prodrugs with O-PLA (n)-O-Acetyl functionalization in a 1% Tween/PBS buffer solution at 37° C. (FIG. 2, FIG. 3). Within less than one hour, 100% conversion to the parent compound was observed. In addition, esters with alkoxy substitutes in the alpha position were more labile than alkyl acids. In comparison, O-PLA (n)-O-stearyl prodrugs of Timolol (FIG. 1, FIG. 6) were significantly more stable than their acetylated forms, with 100% conversion to the parent compound within 24 hours after incubation. Timolol prodrugs with O-Boc-N-Acetyl functionalization were very stable and resistant to hydrolysis with greater than 75% of the prodrug remaining in solution after 1 week of incubation (FIG. 7). In addition, the rate of hydrolysis was independent of salt form (FIG. 3 vs. FIG. 4).

Figure 8:
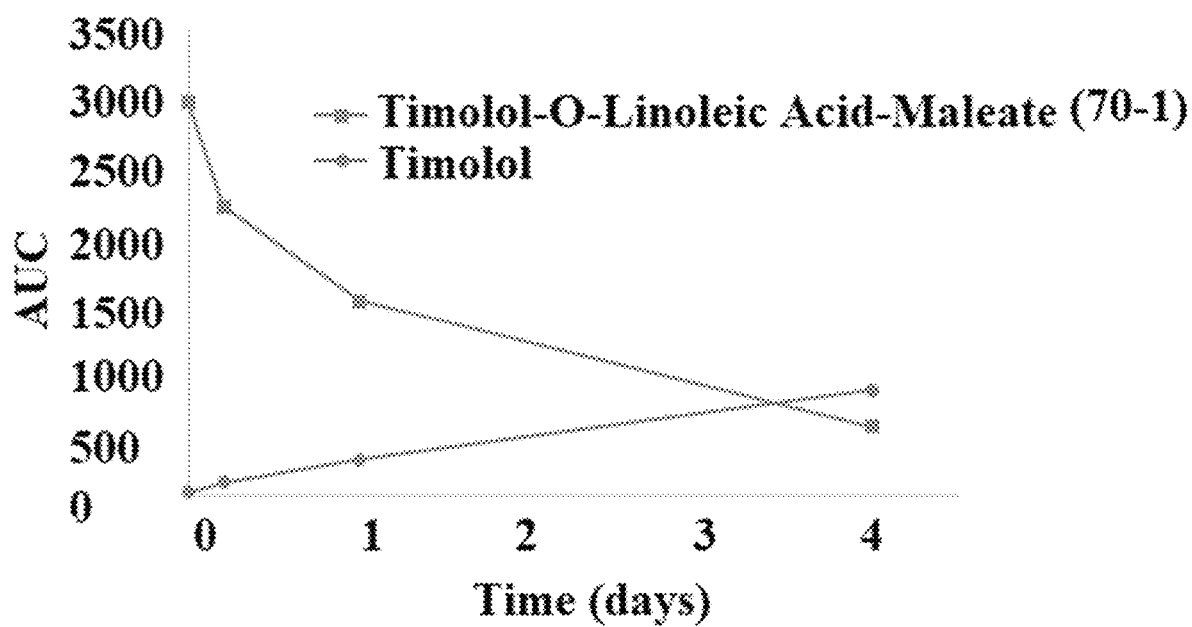
FIG. 8 is a graph measuring the stability of Timolol-O-linoleic acid maleate (70-1) as the prodrug degrades to parent Timolol at 37° C. as described in Example 8. Over the course of 4 days, the prodrug exhibited steady generation of the parent Timolol. The x-axis is the time measured in days and the y-axis is intensity measured as area under the curve (AUC).
Figure 9:
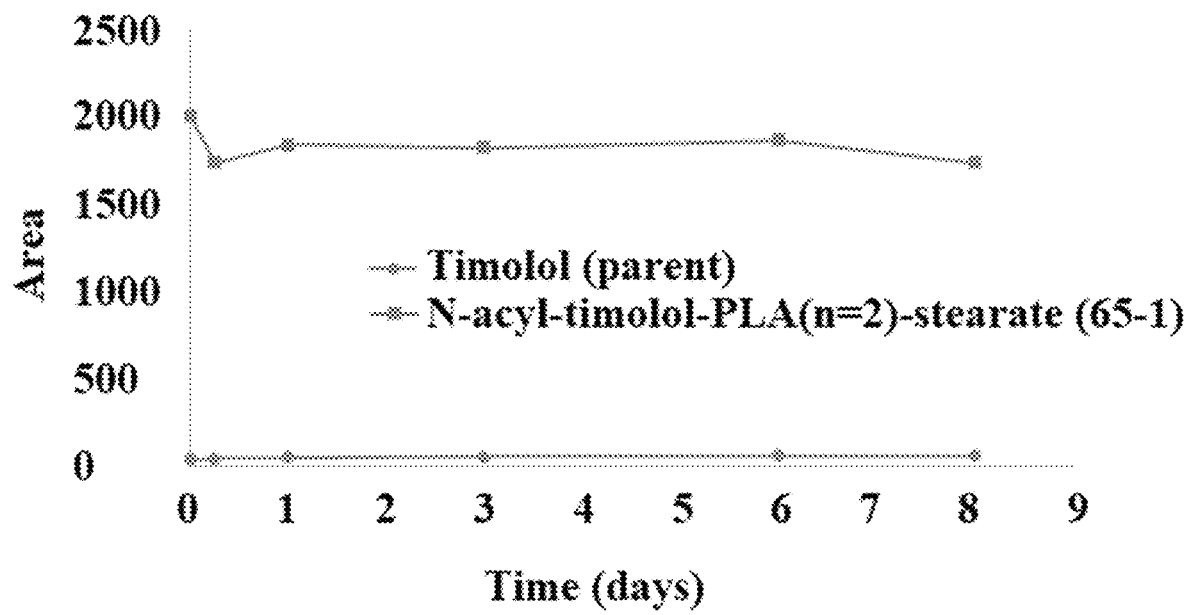
FIG. 9 is a graph measuring the stability of N-acyl-Timolol-PLA (n=2)-stearate (65-1) over 8 hours at 37° C. as described in Example 8. The concentration of 65-1 does not decreases as the prodrug is resistant to hydrolysis. The x-axis is the time measured in days and the y-axis is intensity measured as area under the curve (AUC).
Figure 10:
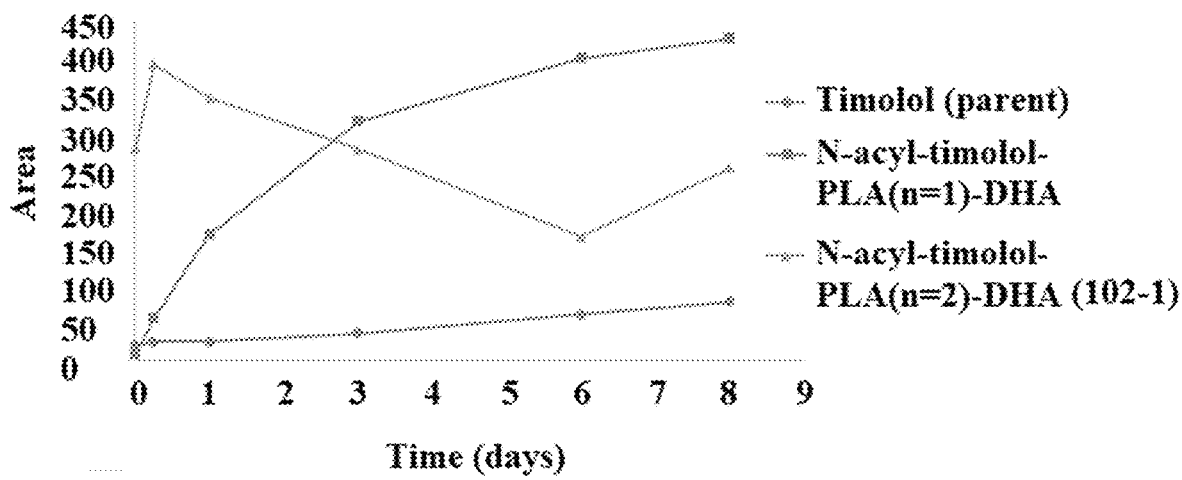
FIG. 10 is a graph measuring the stability of N-acyl-Timolol-PLA (n=2)-DHA (102-1) as the prodrug degrades to N-acyl-Timolol-PLA (n=1)-DHA and parent Timolol at 37° C. as described in Example 8. Over the course of 8 days, the prodrug exhibited steady generation of the intermediate N-acyl-Timolol-PLA (n=1)-DHA and slow hydrolysis to parent Timolol. The x-axis is the time measured in days and the y-axis is intensity measured as area under the curve (AUC).
Figure 11:
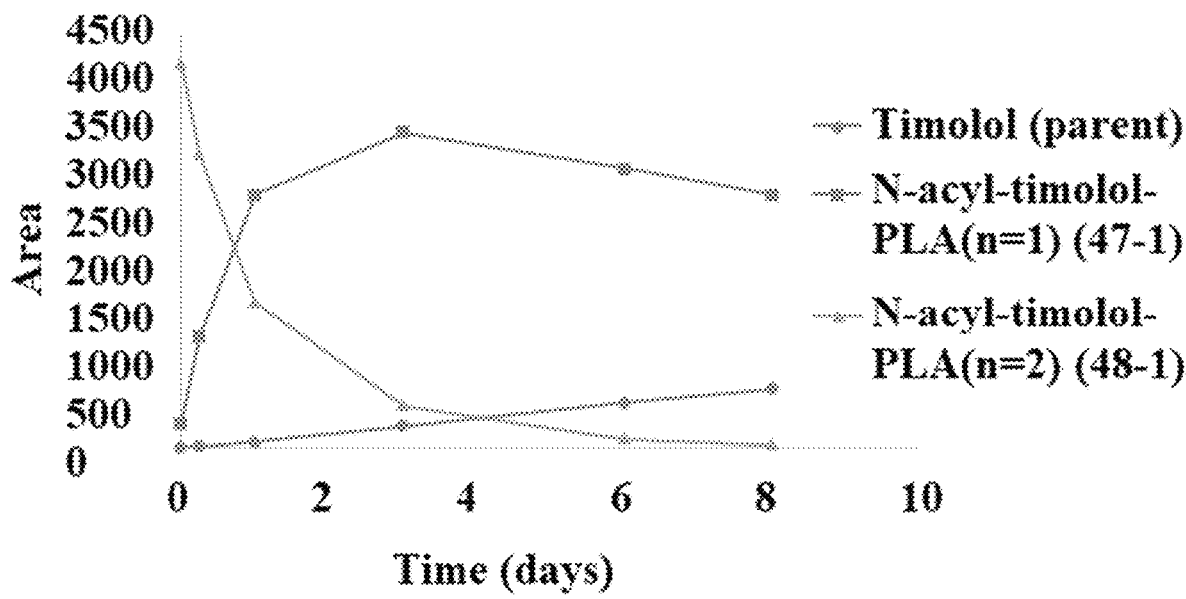
FIG. 11 is a graph measuring the stability of N-acyl-Timolol-PLA (n=2) (48-1) as the prodrug degrades to N-acyl-Timolol-PLA (n=1) (47-1) and parent Timolol at 37° C. as described in Example 8. Over the course of 8 days, the prodrug exhibited steady generation of the intermediate (47-1) and slow hydrolysis to parent Timolol. The x-axis is the time measured in days and the y-axis is intensity measured as area under the curve (AUC).
Figure 12:
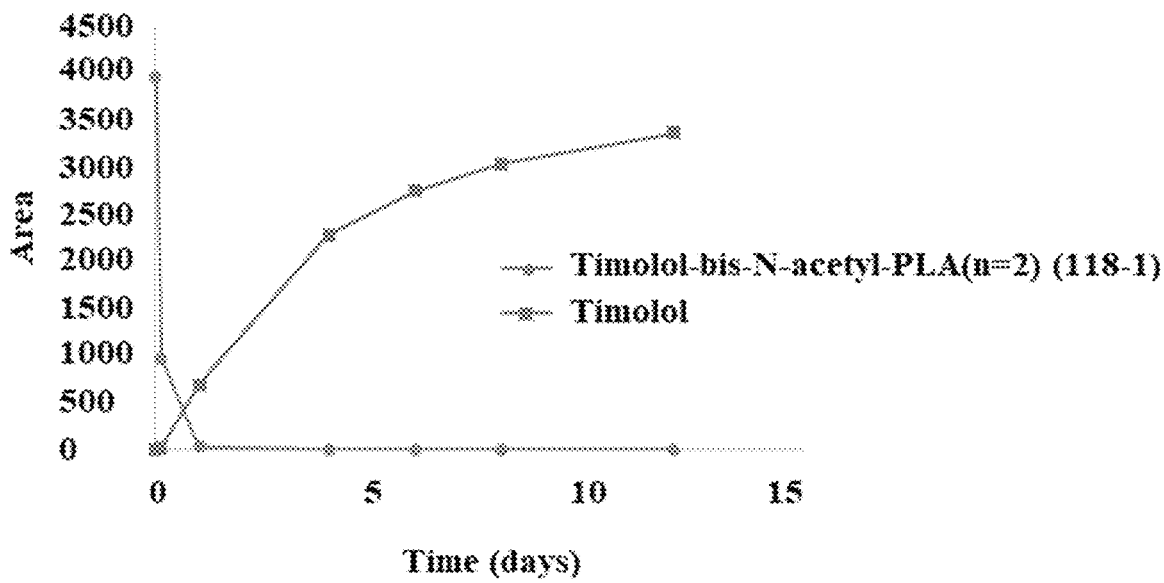
FIG. 12 is a graph measuring the stability of Timolol-bis-N-acetyl-PLA(n=2) (118-1) as the prodrug degrades to parent Timolol at 37° C. as described in Example 8. The x-axis is the time measured in days and the y-axis is intensity measured as area under the curve (AUC).
Figure 13:
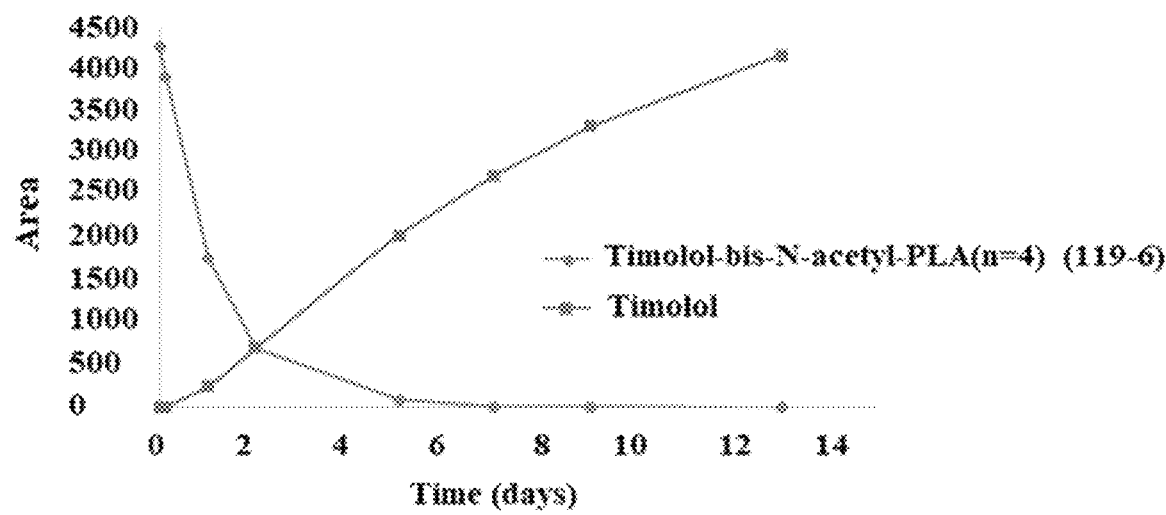
FIG. 13 is a graph measuring the stability of Timolol-bis-N-acetyl-PLA(n=4) (119-6) as the prodrug degrades to parent Timolol at 37° C. as described in Example 8. The x-axis is the time measured in days and the y-axis is intensity measured as area under the curve (AUC).
Figure 14:
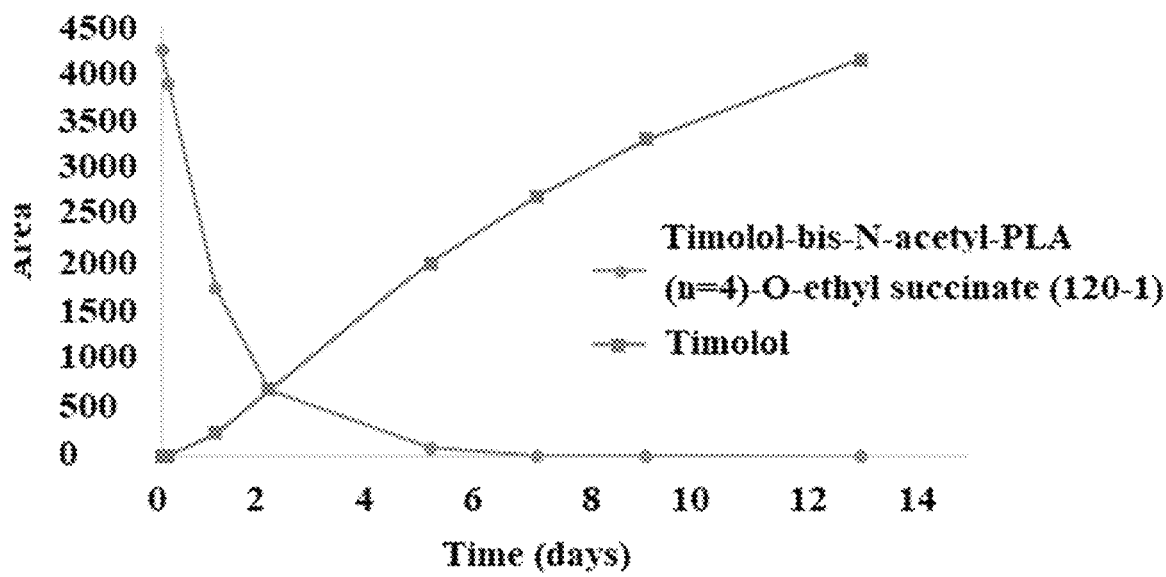
FIG. 14 is a graph measuring the stability of Timolol-bis-N-acetyl-PLA(n=4)-O-ethyl succinate (120-1) as the prodrug degrades to parent Timolol at 37° C. as described in Example 8. The x-axis is the time measured in days and the y-axis is intensity measured as area under the curve (AUC).
Figure 15:
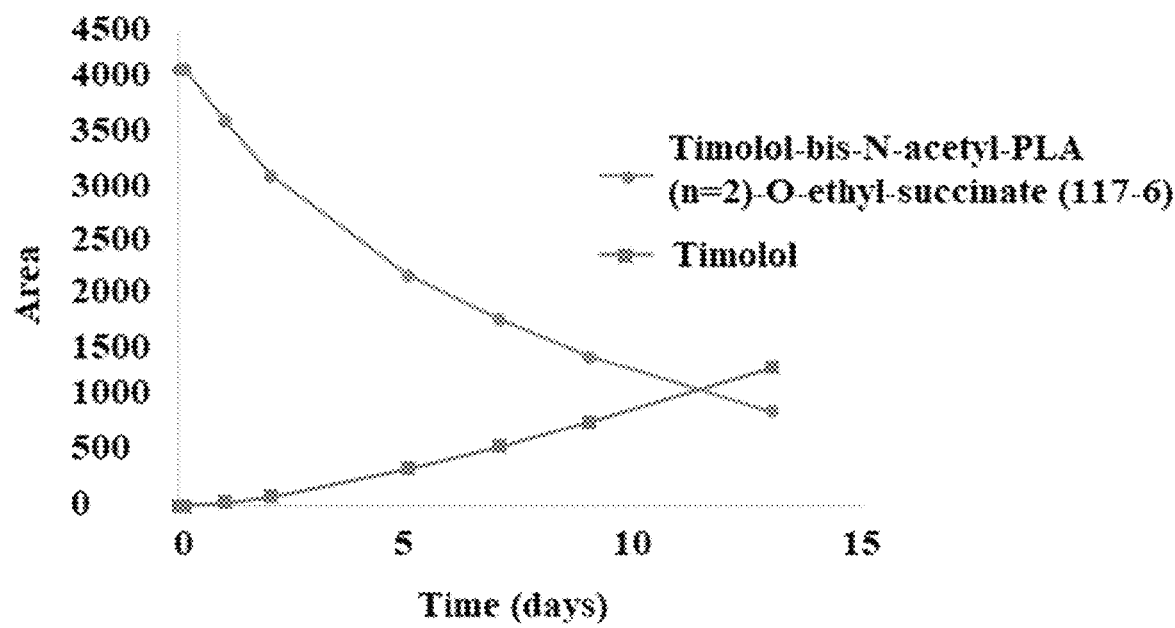
FIG. 15 is a graph measuring the stability of Timolol-bis-N-acetyl-PLA(n=2)-O-ethyl-succinate (117-6) as the prodrug degrades to parent Timolol at 37° C. as described in Example 8. The x-axis is the time measured in days and the y-axis is intensity measured as area under the curve (AUC).
Figure 16:
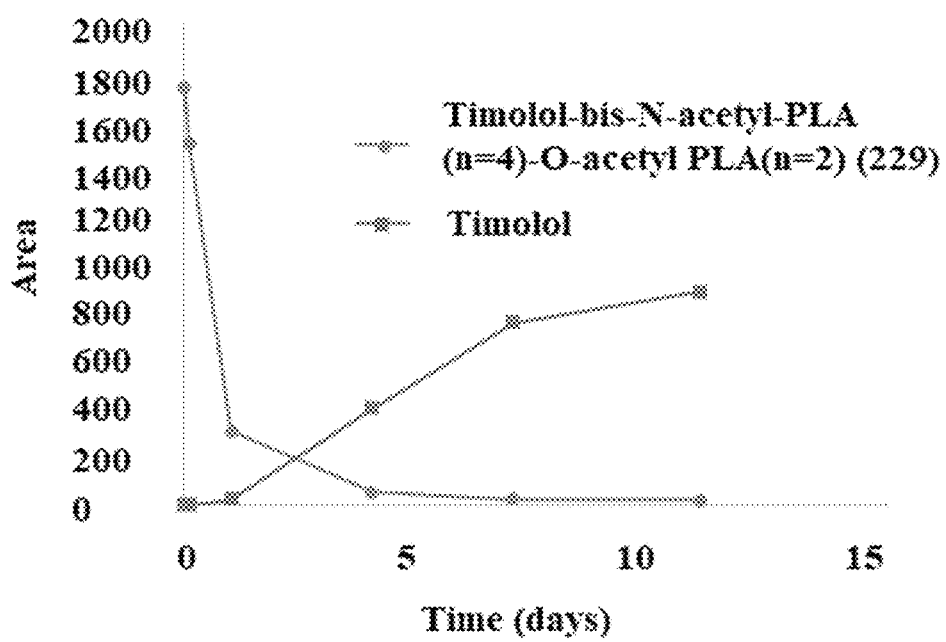
FIG. 16 is a graph measuring the stability of Timolol-bis-N-acetyl-PLA(n=4)-O-acetyl PLA(n=2) (229) as the prodrug degrades to parent Timolol at 37° C. as described in Example 8. The x-axis is the time measured in days and the y-axis is intensity measured as area under the curve (AUC).
Figure 17:
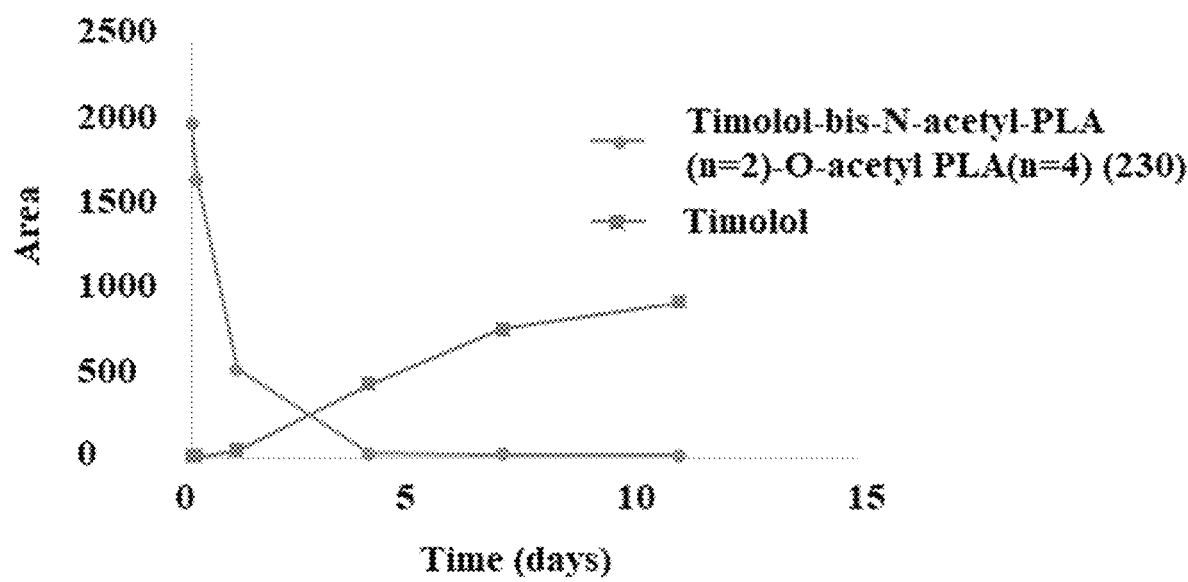
FIG. 17 is a graph measuring the stability of Timolol-bis-N-acetyl-PLA(n=2)-O-acetyl PLA(n=4) (230) as the prodrug degrades to parent Timolol at 37° C. as described in Example 8. The x-axis is the time measured in days and the y-axis is intensity measured as area under the curve (AUC).

The degradation kinetics of N-acyl Timolol prodrugs was evaluated. Linoleic acid prodrug of Timolol (70-1) degraded steadily over the 4-day period, releasing parent Timolol in a linear rate (FIG. 8). As shown in FIG. 9, acyl-Timolol-PLA (n=2) stearate (65-1) was resistant to hydrolysis and failed to release the parent over the course of the study. Without wishing to be bound by any one theory, the long stearate chain serves to protect the prodrug from degradation. In contrast, N-Acyl-Timolol-PLA(n=2)-DHA (102-1) (FIG. 10) exhibited steady generation of intermediate degradants and slow hydrolysis to the parent compound. A similar trend was observed for N-acyl-Timolol-PLA(n=2) (48-1) (FIG. 11). Timolol-bis-N-acetyl PLA(n=2) (118-1) (FIG. 12) degraded slightly faster than a Timolol-bis-N-acetyl PLA (n=4) (119-6) (FIG. 13) as the number of intermediate processes leading to the release of free Timolol is less. In contrast Timolol-bis-N-acetyl-PLA(n=4)-O-ethyl-succinate (120-1) (FIG. 14) degraded to free Timolol incompletely by day 13. Timolol-bis-N-acetyl-PLA(n=2)-O-ethyl-succinate (117-6) (FIG. 15) degraded to free Timolol faster, yet by day 13 only approximately 50% of the polymer was hydrolyzed to release free Timolol. Bis prodrugs of Timolol wherein the —N and —O functional groups were modified with PLA polymers exhibited rapid hydrolysis of the polymer generating intermediates and releasing free Timolol in a linear rate (FIG. 16 and FIG. 17).

In Vitro Stability of Dorzolamide NCEs

Figure 18A:
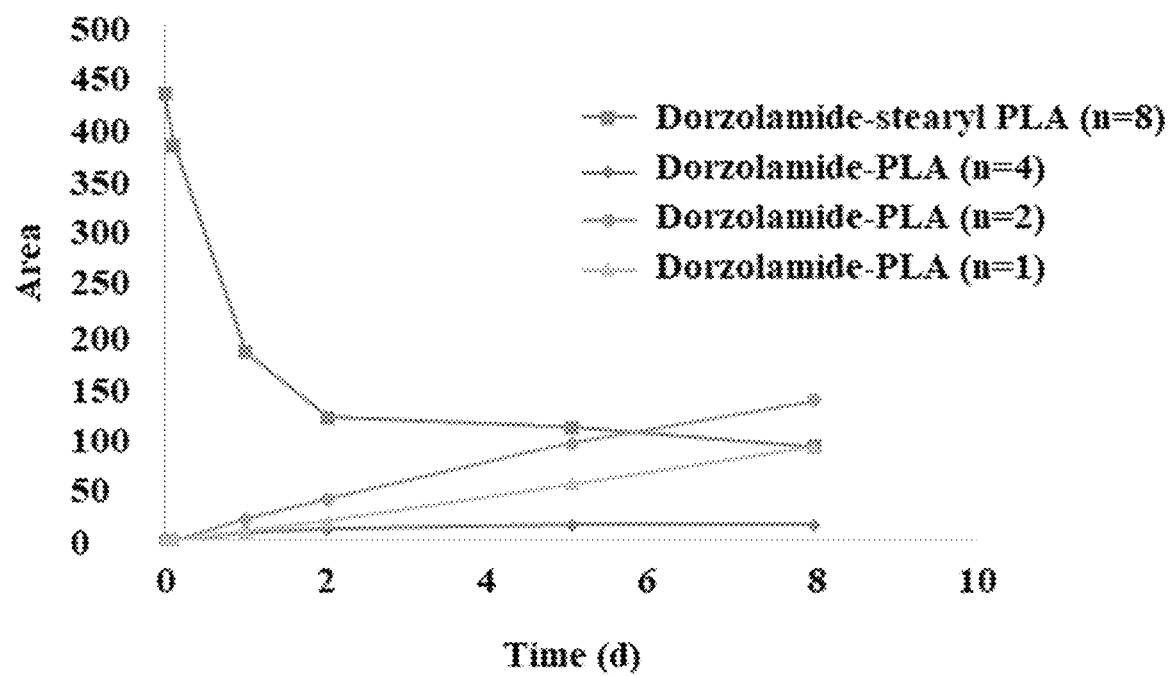
FIG. 18A is a graph measuring the stability of dorzolamide-stearyl PLA (n=8) as the prodrug degrades to dorzolamide-PLA (n=4), dorzolamide-PLA (n=2), and dorzolamide-PLA (n=1) at 37° C. as described in Example 8. The x-axis is the time measured in days and the y-axis is intensity measured as area under the curve (AUC).
Figure 18B:
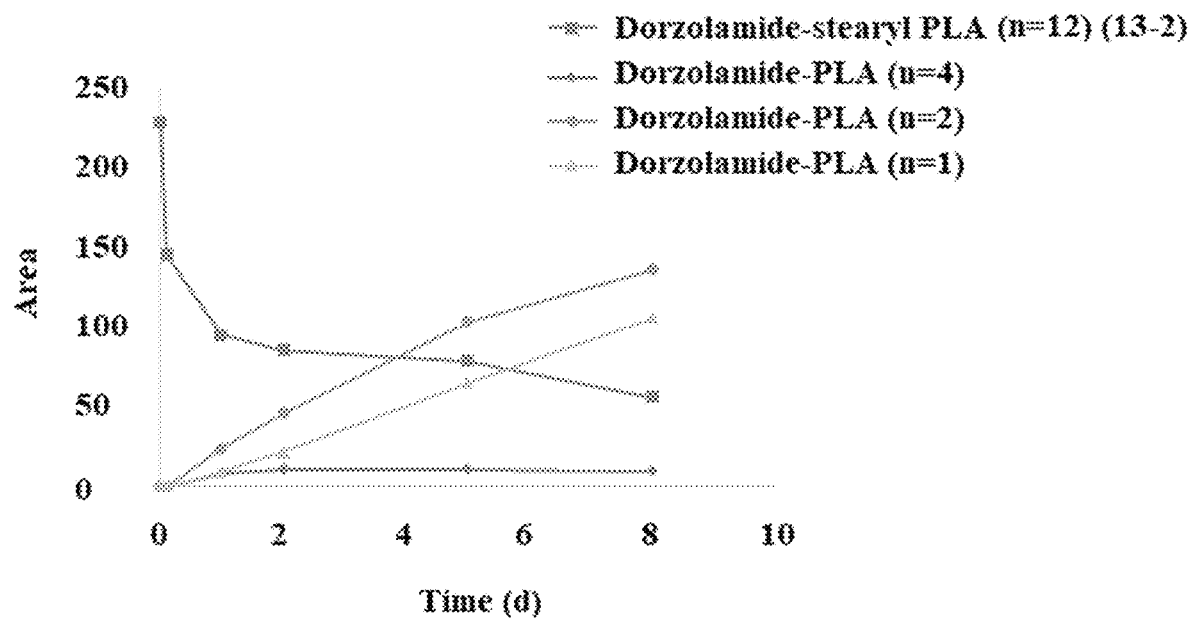
FIG. 18B is a graph measuring the stability of dorzolamide-stearyl PLA (n=12) (13-2) as the prodrug degrades to dorzolamide-PLA (n=4), dorzolamide-PLA (n=2), and dorzolamide-PLA (n=1) at 37° C. as described in Example 8. The x-axis is the time measured in days and the y-axis is intensity measured as area under the curve (AUC).
Figure 18C:
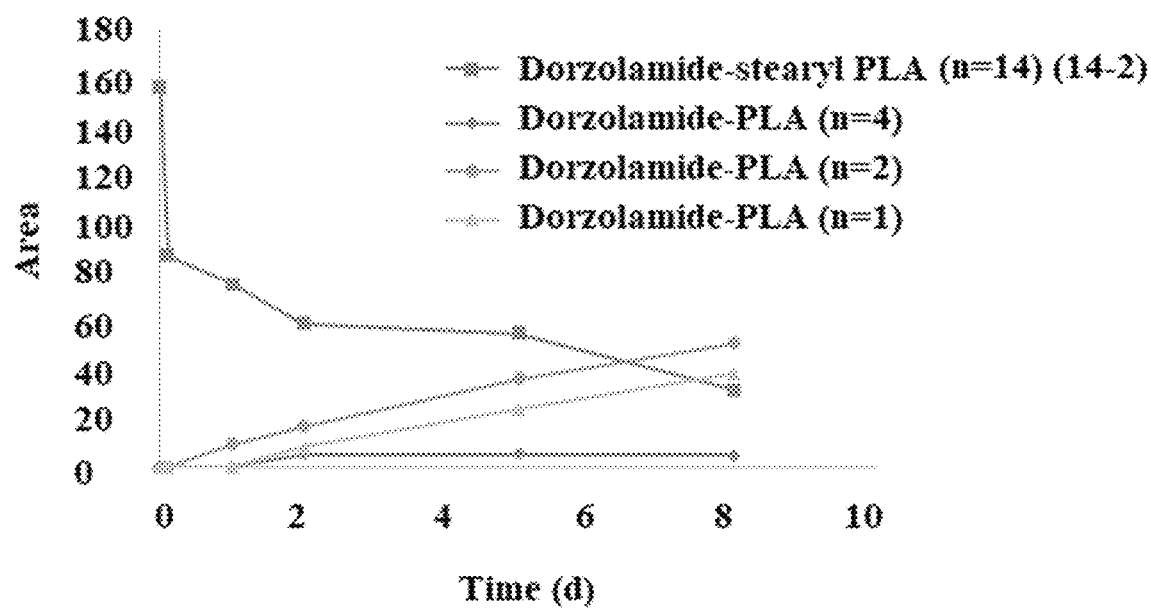
FIG. 18C is a graph measuring the stability of dorzolamide-stearyl PLA (n=14) (14-2) as the prodrug degrades to dorzolamide-PLA (n=4), dorzolamide-PLA (n=2), and dorzolamide-PLA (n=1) at 37° C. as described in Example 8. The x-axis is the time measured in days and the y-axis is intensity measured as area under the curve (AUC).
Figure 19A:
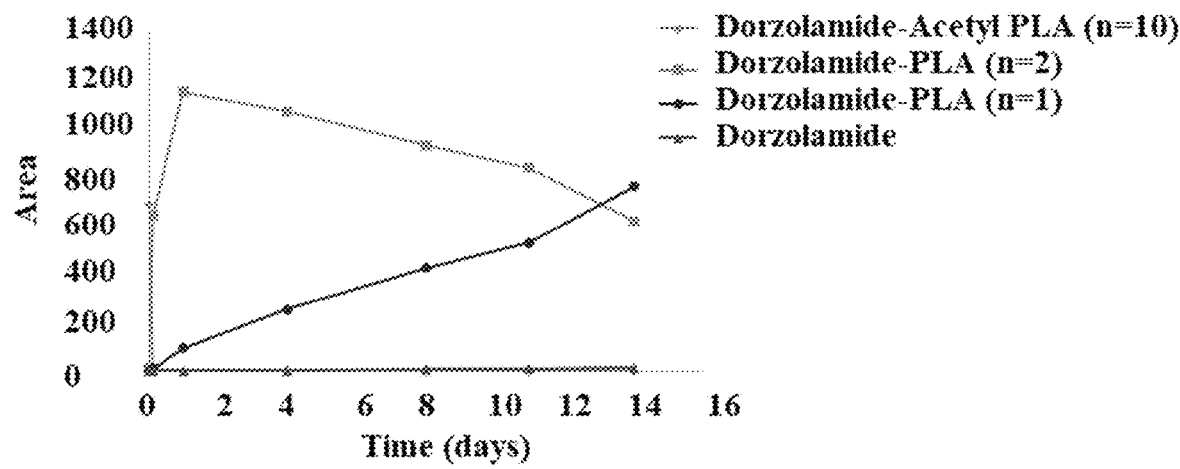
FIG. 19A is a graph measuring the stability of dorzolamide-Acetyl PLA (n=10) as the prodrug degrades to dorzolamide-PLA (n=2), dorzolamide-PLA (n=1), and parent dorzolamide at 37° C. as described in Example 8. The x-axis is the time measured in days and the y-axis is intensity measured as area under the curve (AUC).
Figure 19B:
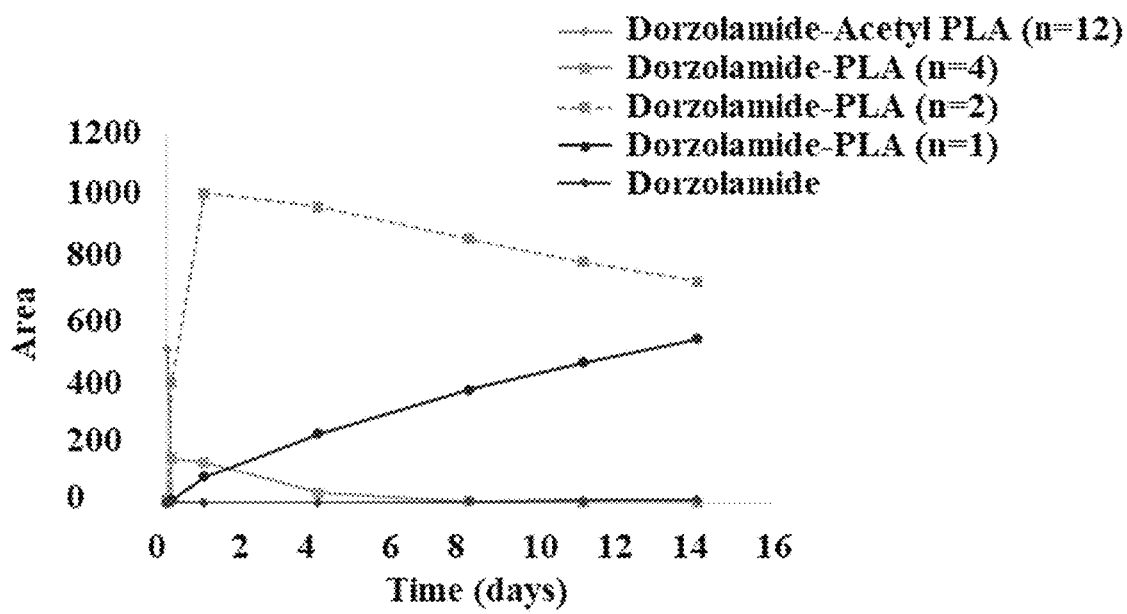
FIG. 19B is a graph measuring the stability of dorzolamide-acetyl PLA (n=12) as the prodrug degrades to dorzolamide-PLA (n=4), dorzolamide-PLA (n=2), dorzolamide-PLA (n=1), and parent dorzolamide at 37° C. as described in Example 8. The x-axis is the time measured in days and the y-axis is intensity measured as area under the curve (AUC).
Figure 20:
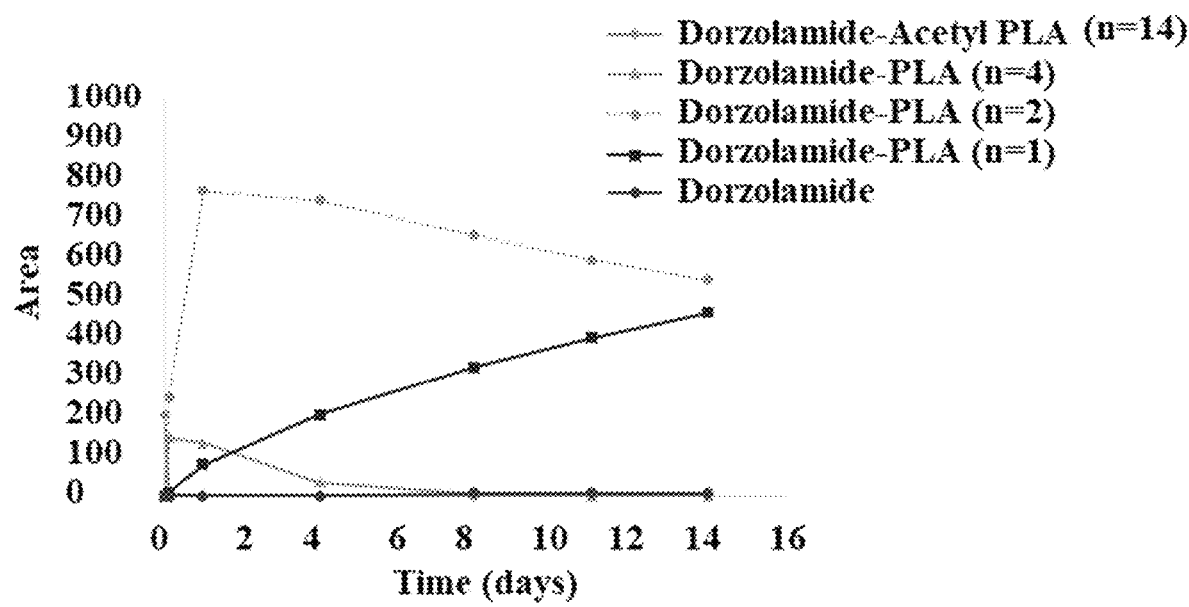
FIG. 20 is a graph measuring the stability of dorzolamide-acetyl PLA (n=14) as the prodrug degrades to dorzolamide-PLA (n=4), dorzolamide-PLA (n=2), dorzolamide-PLA (n=1), and parent dorzolamide at 37° C. as described in Example 8. The x-axis is the time measured in days and the y-axis is intensity measured as area under the curve (AUC).
Figure 21:
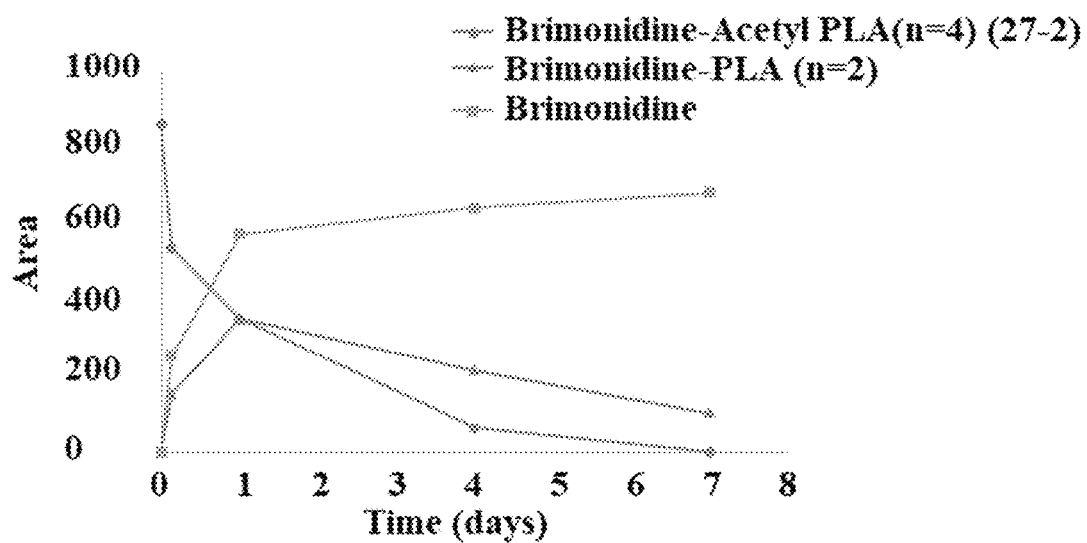
FIG. 21 is a graph measuring the stability of Brimonidine-acetyl PLA(n=4) (27-2) as the prodrug degrades to Brimonidine-PLA (n=2) and parent Brimonidine at 37° C. as described in Example 8. The x-axis is the time measured in hours and the y-axis is intensity measured as area under the curve (AUC).
Figure 22:
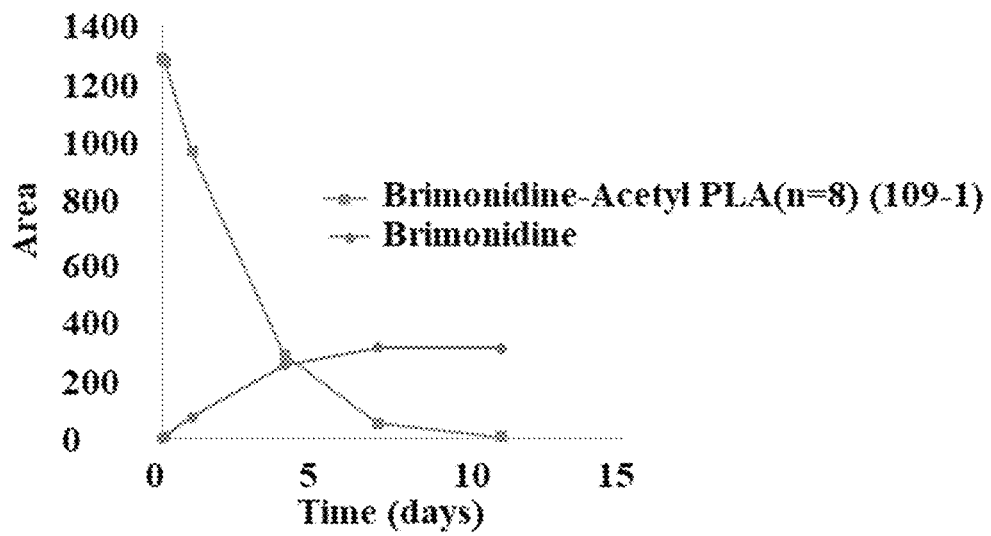
FIG. 22 is a graph measuring the stability of Brimonidine-acetyl PLA(n=8) (109-1) as the prodrug degrades to parent Brimonidine at 37° C. as described in Example 8. The x-axis is the time measured in days and the y-axis is intensity measured as area under the curve (AUC).
Figure 23:
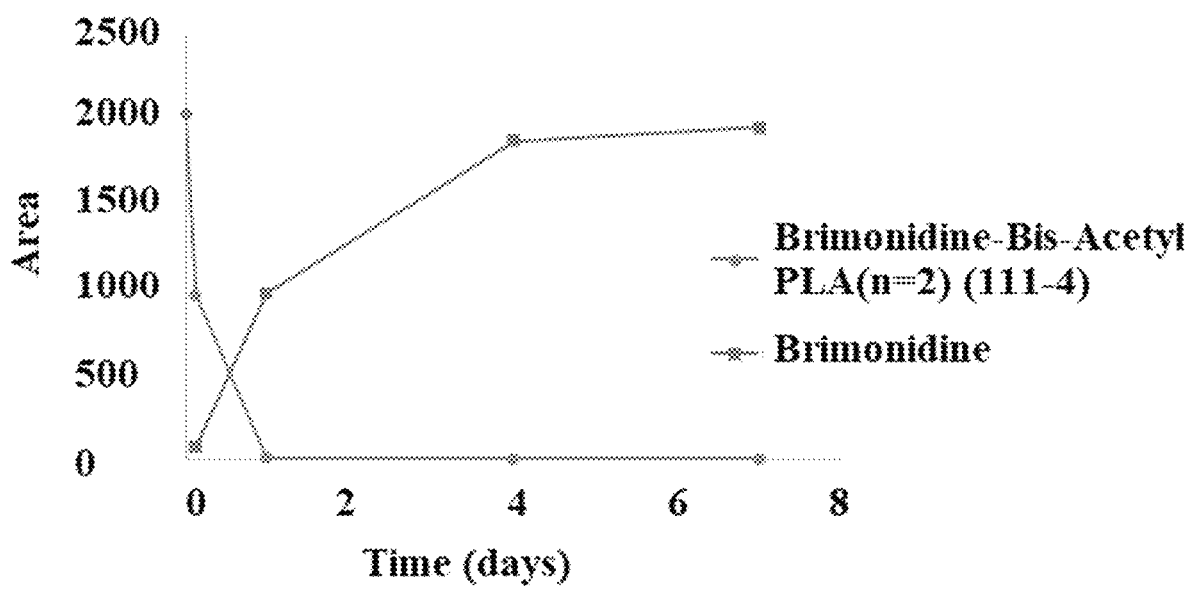
FIG. 23 is a graph measuring the stability of Brimonidine-bis-acetyl PLA(n=2) (111-4) as the prodrug degrades to parent Brimonidine at 37° C. as described in Example 8. The x-axis is the time measured in days and the y-axis is intensity measured as area under the curve (AUC).
Figure 24:
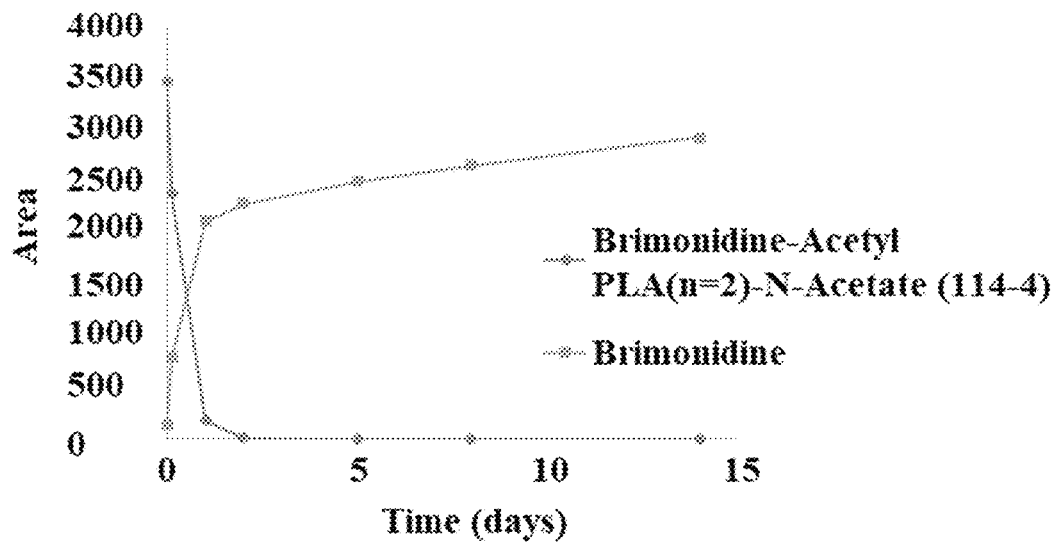
FIG. 24 is a graph measuring the stability of Brimonidine-acetyl PLA(n=2)-N-Acetate (114-4) as the prodrug degrades to parent Brimonidine at 37° C. as described in Example 8. The x-axis is the time measured in days and the y-axis is intensity measured as area under the curve (AUC).
Figure 25:
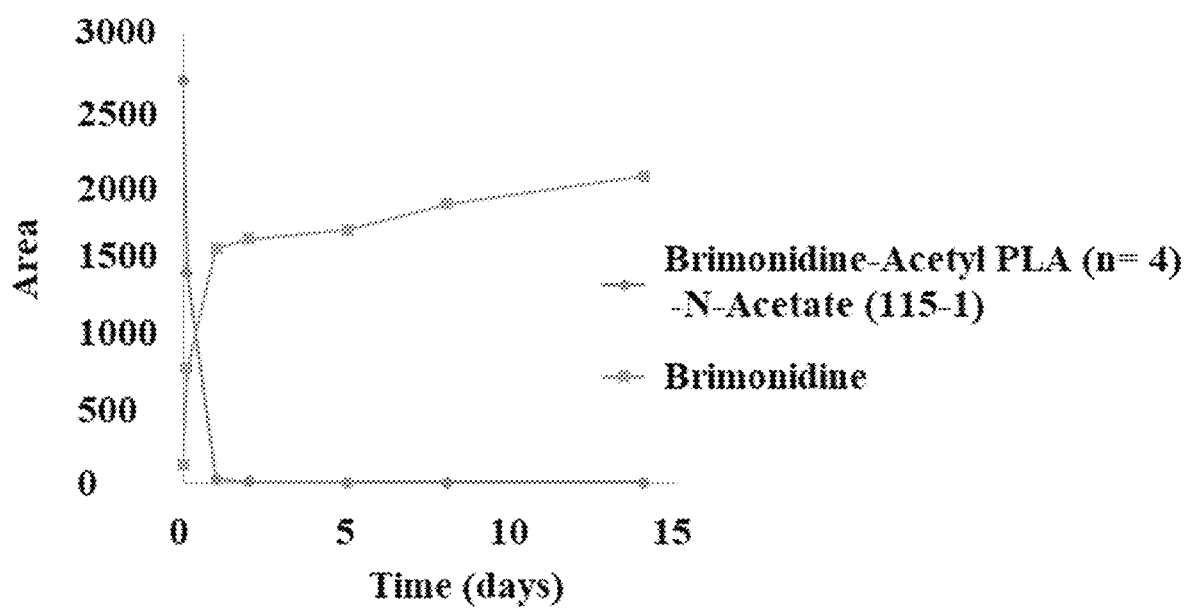
FIG. 25 is a graph measuring the stability of Brimonidine-acetyl PLA(n=4)-N-Acetate (115-1) as the prodrug degrades to parent Brimonidine at 37° C. as described in Example 8. The x-axis is the time measured in days and the y-axis is intensity measured as area under the curve (AUC).

Stearyl capped prodrugs were more stable and less prone to ester hydrolysis than acetylated prodrugs (FIG. 18A, FIG. 18B, and FIG. 18C) and LA units were hydrolyzed in pairs (FIG. 19A, FIG. 19B, and FIG. 20).

In Vitro Stability of Prodrugs of Brimonidine NCEs

Figure 26:
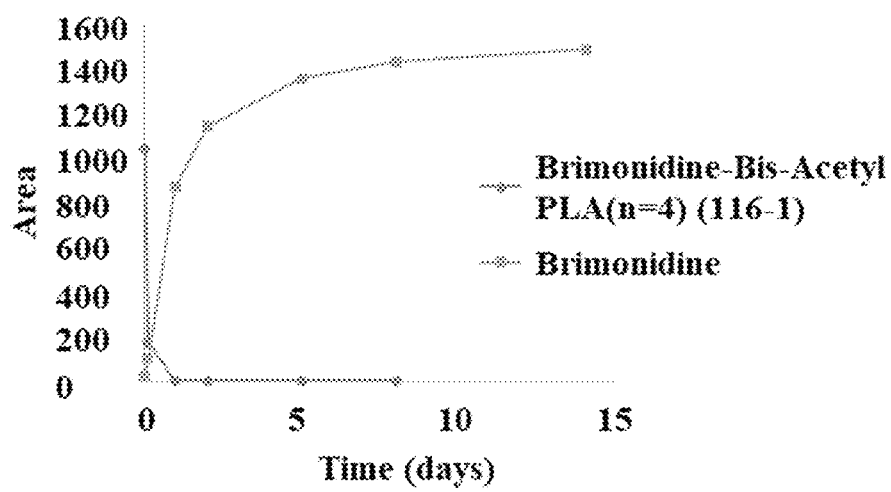
FIG. 26 is a graph measuring the stability of Brimonidine-bis-acetyl PLA(n=4) (116-1) as the prodrug degrades to parent Brimonidine at 37° C. as described in Example 8. The x-axis is the time measured in days and the y-axis is intensity measured as area under the curve (AUC).

Prodrugs of Brimonidine rapidly hydrolyze to release the parent compound in aqueous solution under physiological conditions. All compounds tested exhibit rapid degradation to the parent compound at one day followed by a more prolonged phase of hydrolysis to the parent (FIG. 21, FIG. 22, FIG. 23, FIG. 24, and FIG. 25). The rate of degradation back to the parent decreased with increasing number of lactide units on the polymer linker. In addition, the kinetics of degradation to the parent compound was slowed further by the conjugation of Bis-PLA (FIG. 26).

In Vitro Stability of Prodrugs of Rock Inhibitors

Figure 27:
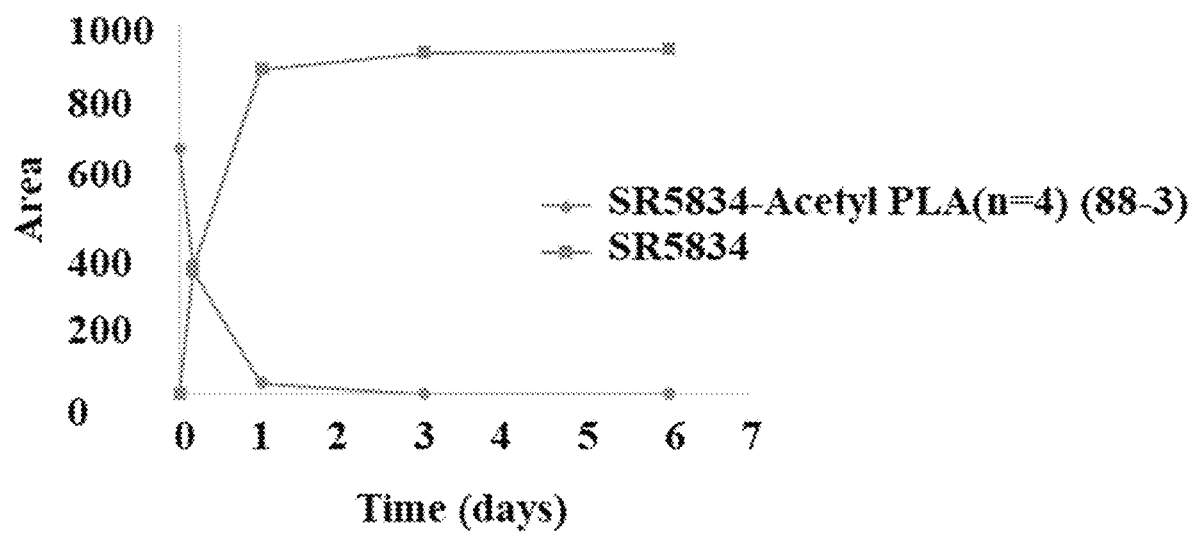
FIG. 27 is a graph measuring the stability of SR5834-acetyl PLA(n=4) (88-3) as the prodrug degrades to parent SR5834 at 37° C. as described in Example 8. The x-axis is the time measured in days and the y-axis is intensity measured as area under the curve (AUC).
Figure 28:
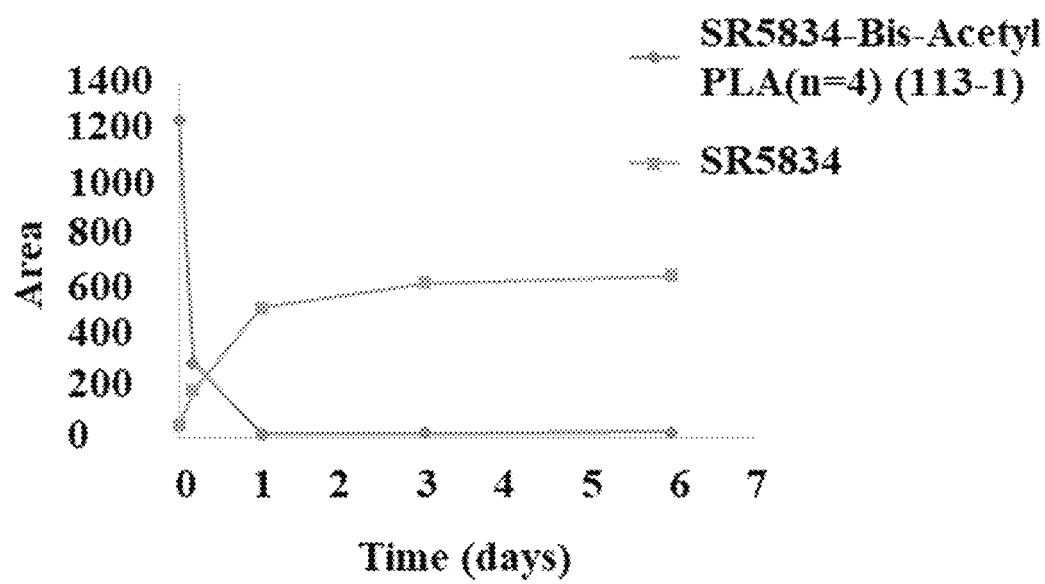
FIG. 28 is a graph measuring the stability of SR5834-bis-acetyl PLA(n=4) (113-1) as the prodrug degrades to parent SR5834 at 37° C. as described in Example 8. The x-axis is the time measured in days and the y-axis is intensity measured as area under the curve (AUC).
Figure 29:
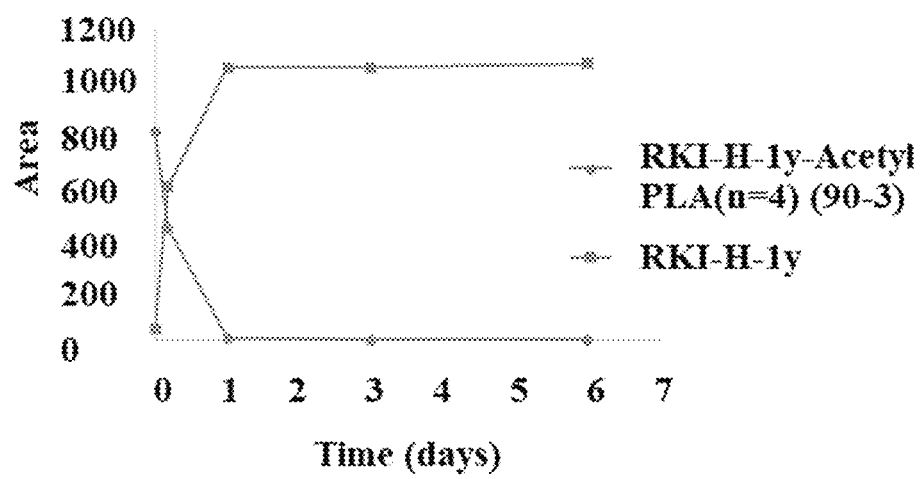
FIG. 29 is a graph measuring the stability of RKI-H-1y-acetyl PLA(n=4) (90-3) as the prodrug degrades to parent RKI-H-1y at 37° C. as described in Example 8. The x-axis is the time measured in days and the y-axis is intensity measured as area under the curve (AUC).

Evaluation of the stability and kinetics of degradation of the prodrug revealed rapid hydrolysis of the polymer and degradation to the parent drug for all prodrugs of rock inhibitors tested (FIG. 27, FIG. 28, and FIG. 29). The bis-modified prodrug (FIG. 28) exhibited comparably rapid degradation of the primary prodrug; however, the rate of generation of the parent was half of that observed in prodrugs modified at one functional site.

In Vitro Stability of Timolol-Dorzolamide Bi-Functional Prodrugs

Timolol-succinate-(PLA)$_3$-Dorzolamide (58-2) was prepared as shown in Scheme 58 and Timolol-glutarate-(PLA)$_3$-Dorzolamide (64-4) was prepared as shown in Scheme 64.

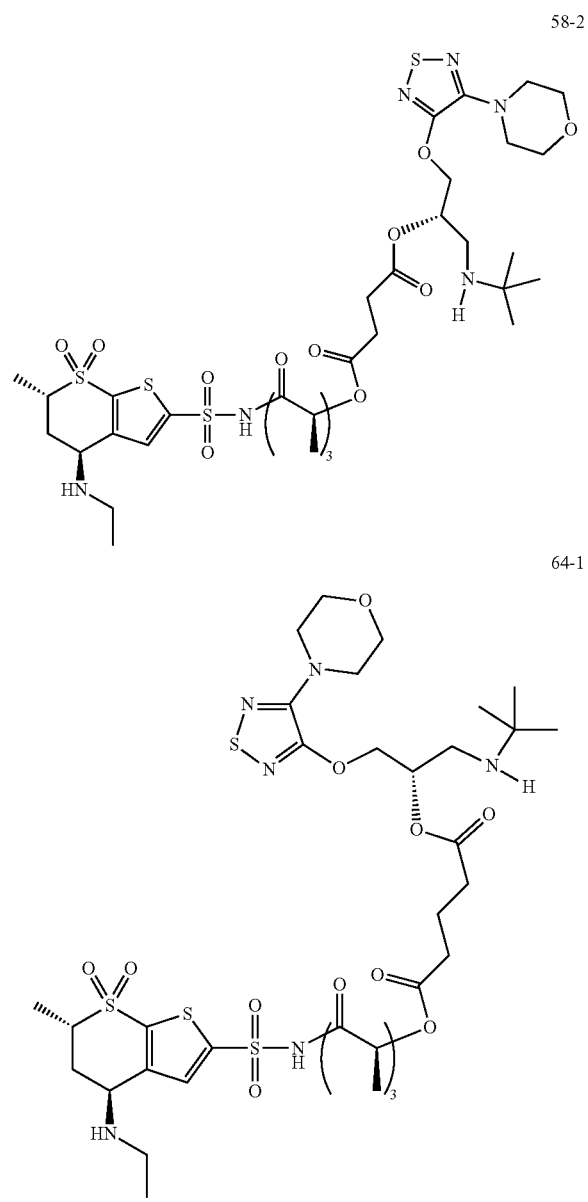

Figure 30A:
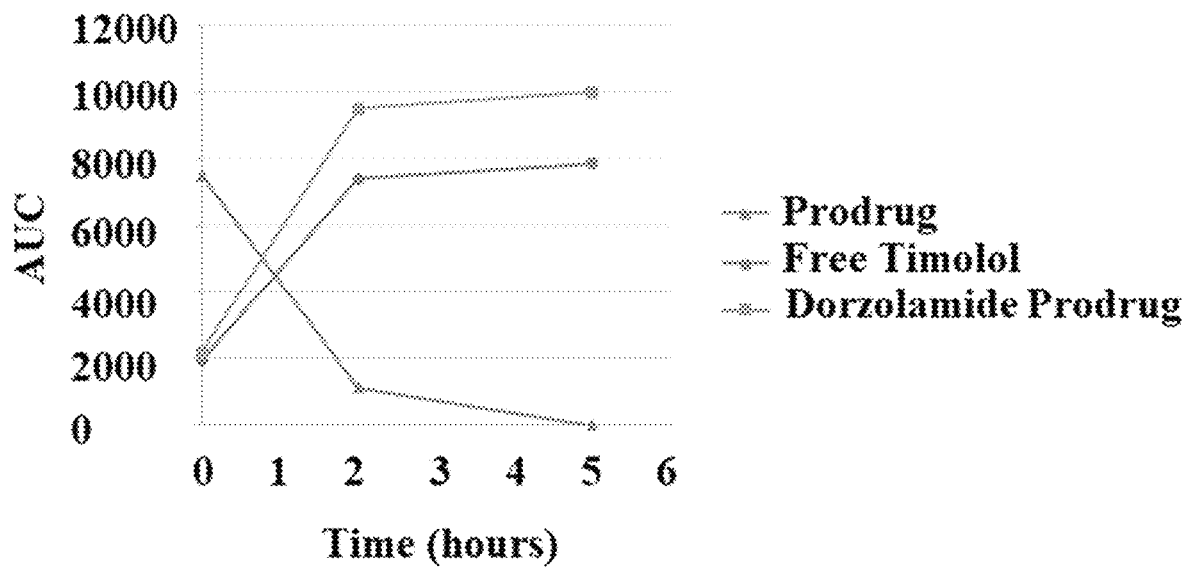
FIG. 30A is a graph measuring the stability of Timolol-Dorzolamide prodrug (58-2) over 5 hours at 37° C. as described in Example 8. The concentration of 58-2 decreases as the prodrug cleaves to afford free Timolol and Dorzolamide linked with 1-3 PLA moieties (Dorzolamide Prodrug). The x-axis is the time measured in hours and the y-axis is intensity measured as area under the curve (AUC).
Figure 30B:
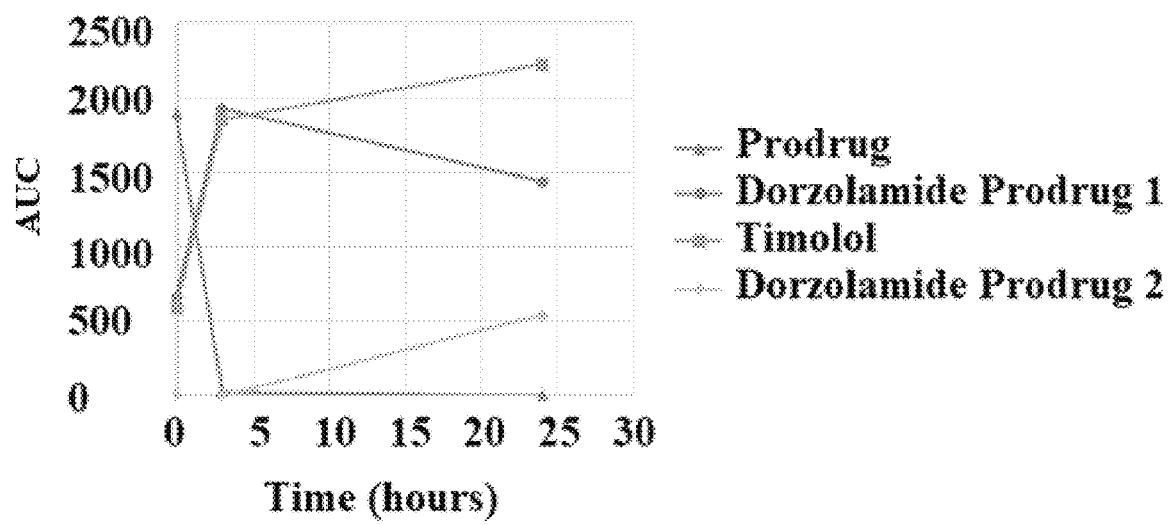
FIG. 30B is a graph measuring the stability of Timolol-Dorzolamide prodrug (64-4) over 25 hours at 37° C. as described in Example 8. The concentration of 64-4 decreases as the prodrug cleaves to afford free Timolol and Dorzolamide linked with 1-3 PLA moieties (Dorzolamide Prodrug 1 and Dorzolamide Prodrug 2). Prodrug 64-4 cleaves to afford the active moieties in less than 5 hours. The x-axis is the time measured in hours and the y-axis is intensity measured as area under the curve (AUC).
Figure 31A:
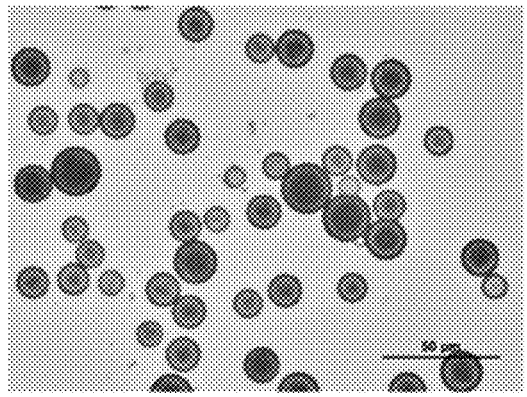
FIG. 31A is a light microscopy image at 40× magnification of particles encapsulating Brinzolamide-acetyl PLA (n=5) (18-3) as described in Example 9. Particles were found to be spherical in nature.
Figure 31B:
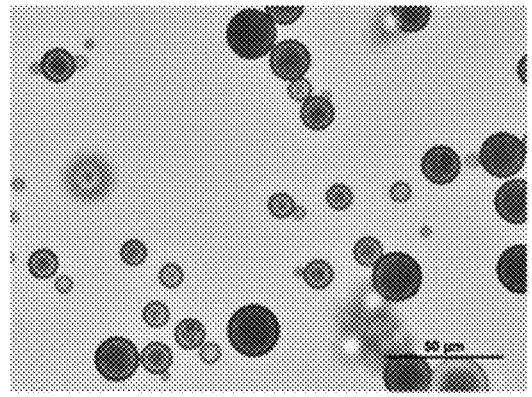
FIG. 31B is a light microscopy image at 40× magnification of particles encapsulating Dorzolamide-acetyl PLA (n=5) as described in Example 9. Particles were found to be spherical in nature.
Figure 31C:
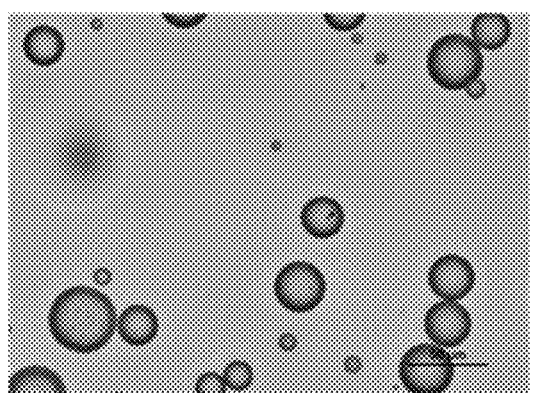
FIG. 31C is a light microscopy image at 40× magnification of particles encapsulating Latanoprost-acetyl PLA (n=5) as described in Example 9. Particles were found to be spherical in nature.
Figure 31D:
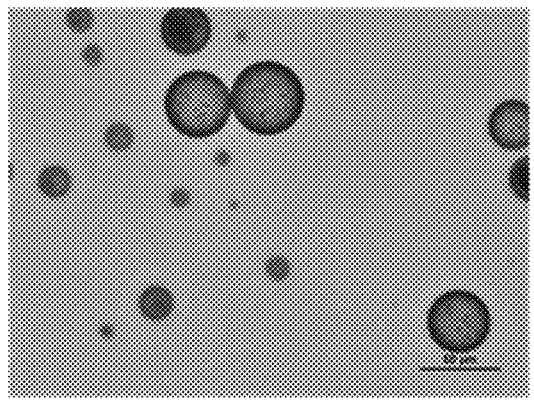
FIG. 31D is a light microscopy image at 40× magnification of particles encapsulating Timolol-acetyl PLA (n=5) (45-2) as described in Example 9. Particles were found to be spherical in nature.

Timolol-Dorzolamide bi-functional prodrugs were dissolved in a mixture of DMSO and PBS and incubated at 37° C. The solution was aliquoted and analyzed by HPLC at pre-determined time points. Timolol-Dorzolamide bi-functional prodrugs were stable for about 3 hours as evidenced by the significant reduction of prodrug peaks in HPLC after 2-3 hours (FIG. 30A and FIG. 30B). Timolol parent drug was detected as the bi-functional prodrug degraded, whereas Dorzolamide appeared in the form of prodrugs, i.e., Dorzolamide linked with 1-3 PLA units.

Example 9. Encapsulation of Conjugates in Polymer Microparticles

Materials poly(D,L-lactic-co-glycolic acid (PLGA, 75:25 lactic acid to glycolic acid ratio, 4A, Evonik)
poly(D,L-lactic-co-glycolic acid (PLGA, 50:50 lactic acid to glycolic acid ratio)-poly(ethylene glycol)5000
poly(D,L-lactide, 4A, Evonik)
poly vinyl alcohol (Mr~25K, 88% hydrolyzed, Polysciences)
D-α-tocopherol poly(ethylene glycol)$_{1000}$ succinate (Sigma Aldrich)
Phosphate-buffered saline (pH 7.4)
Ultrapure cell culture grade water
All other chemicals were A.C.S. reagent grade (VWR)

Microparticle Preparation

Microparticles containing prodrugs of Brinzolamide, Dorzolamide, Timolol, Latanoprost or bimatoprost were formulated using an oil-in-water solvent evaporation microencapsulation method. The polymer was initially dissolved in a water immiscible organic solvent to which dissolved drug was added. Briefly, PLGA (LA:GA=75:25, 4A) or PLA (140-200 mg/mL) and PLGA$_{50/50}$-PEG$_{5k}$ (1.4-2 mg/mL) was dissolved in 2 mL of methylene chloride. The prodrug (13.8-50% theoretical loading) was dissolved in 1 mL of DMSO or ethyl acetate after vigorous vortexing and ultrasonication in a bath sonicator and added to the polymer solution. The aqueous phase consisted of 200 mL of PBS or water with 1% PVA or D-α-tocopherol poly(ethylene glycol)$_{1000}$ succinate as a surfactant to stabilize the emulsification. The aqueous phase was mixed at 5000 rpms using a Silverson L5A-M benchtop mixer. The dispersed phase was rapidly added to the aqueous phase and allowed to mix at 5000 rpms for 1 minute to generate an oil-in-water emulsion and disperse the materials as droplets. The organic solution was allowed to evaporate under constant stirring at 500 rpms for 2 hours under ambient temperatures or at 4° C. in an ice bath. The particle suspension was allowed to settle for 30 min, after which the solution was decanted and remaining particles were collected, suspended in distilled deionized water, and washed 3 times using water via centrifugation at 1000 rpms for 5 minutes to remove any residual solvent. The pellet was collected and lyophilized overnight.

Particle Size

Particle size and size distribution was determined using a Beckman Coulter Multsizer IV with a 100 μm diameter aperture based on a sample size of at least 50,000 counts. Particle size was expressed as volume-weighted mean diameters. Briefly, 2-5 mg of particles were suspended in 1 mL of double distilled water and added to a beaker containing 100 mL of ISOTON II solution. Measurements were obtained once the coincidence of particles reached 6-10%. Table 5 and Table 8 outlines the size and size distribution of the microparticles generated for each test compound. Particle size can vary depending upon a number of variables including polymer concentration, mixing-speed, mixing-time, dispersed/aqueous phase ratio, etc. Particles were formulated with volume-weighted mean diameters ranging from approximately 19 μm to 34 μm depending on the formulation parameters.

Drug Loading

To determine the % drug loading (DL), 10 mg of particles was weighed into a glass scintillation vial and dissolved with 10 mL of MeCN:water (1:1, v/v). The solution was filtered through a 0.2 μm nylon syringe filter and the drug content was determined by RP-HPLC referenced against a standard calibration curve. The drug loading results are presented in Table 5 and Table 8. All particles generated at ambient temperature with 1% PVA in the aqueous phase exhibited low drug loading regardless of the encapsulated drug (<1.0% DL), but results in Table 8 suggest that loading is influenced by the presence of the functional group on the terminal lactate. Loading of acetylated test compounds was approximately 5-fold higher than those with uncapped hydroxyl on the terminal lactate units (0.14 vs. 1.00 and 0.22 vs. 0.98%, respectively for Brinzolamide and Dorzolamide).

Loading was also dependent on the rate of solidification of the particles and the surfactant used in the emulsification process. Preparing particles at 4° C. and with D-α-tocopherol poly(ethylene glycol)$_{1000}$ succinate to stabilize the emulsification resulted in significant enhancement in drug loading. For example, % DL of Brinzolamide-acetyl PLA (n=5) (18-3) was 0.73% when particles were formulated at room temperature using 1% PVA as the surfactant compared to 7.39% when particles were formulated at 4° C. using D-α-tocopherol poly(ethylene glycol)$_{1000}$ succinate as the surfactant. In addition, increasing polymer concentration also resulted in an increase in % DL. Brinzolamide-acetyl PLA (n=5) (38-1) content increased from 7.39% to 8.89% when the polymer concentration increased from 140 mg/mL to 200 mg/mL, respectively.

Increased theoretical loading (% drug mass/polymer mass) in the dispersed phase can increase % DL within the formed particles. This is evidenced in the case of Timolol bis prodrugs (Table 6 and Table 7) and Brimonidine prodrugs (Table 4 and Table 5).

TABLE 4

Polymer, Polymer concentration, and percent theoretical loading of prodrugs of Brinzolamide, Dorzolamide, Latanoprost, and Brimonidine encapsulated microparticles

| Compound Name | Backbone Polymer | Polymer Conc (mg/mL) | % Theoretical Loading |
|---|---|---|---|
| Brinzolamide-PLA (n = 4) | PLGA7525 4A + 1% PEG-PLGA5050 | 140 | 13.8 |
| Brinzolamide-PLA(n = 4) | PLGA7525 4A + 1% PEG-PLGA5050 | 180 | 13.8 |
| Brinzolamide-PLA(n = 4) | PLA 4.5A + 1% PEG-PLGA5050 | 180 | 13.8 |
| Brinzolamide-Acetyl PLA(n = 4) | PLGA7525 4A + 1% PEG-PLGA5050 | 140 | 13.8 |
| Brinzolamide-Acetyl PLA(n = 5) | PLGA7525 4A + 1% PEG-PLGA5050 | 140 | 13.8 |

TABLE 4-continued

Polymer, Polymer concentration, and percent theoretical loading of prodrugs of Brinzolamide, Dorzolamide, Latanoprost, and Brimonidine encapsulated microparticles

| Compound Name | Backbone Polymer | Polymer Conc (mg/mL) | % Theoretical Loading |
|---|---|---|---|
| Brinzolamide-Acetyl PLA(n = 5) | PLGA7525 4A + 1% PEG-PLGA5050 | 140 | 13.8 |
| Brinzolamide-Acetyl PLA(n = 5) | PLGA7525 4A + 1% PEG-PLGA5050 | 200 | 13.8 |
| Brinzolamide-Acetyl PLA(n = 5) | PLA 4.5A + 1% PEG-PLGA5050 | 180 | 13.8 |
| Brinzolamide-Acetyl PLA(n = 5) | PLA 4.5A + 1% PEG-PLGA5050 | 180 | 13.8 |
| Dorzolamide-PLA(n = 4) | PLGA7525 4A + 1% PEG-PLGA5050 | 140 | 13.8 |
| Dorzolamide-PLA(n = 4) | PLGA7525 4A + 1% PEG-PLGA5050 | 180 | 13.8 |
| Dorzolamide-PLA(n = 4) | PLA 4.5A + 1% PEG-PLGA5050 | 180 | 13.8 |
| Dorzolamide-PLA(n = 4) | PLGA7525 4A + 1% PEG-PLGA5050 | 180 | 13.8 |
| Dorzolamide-Acetyl PLA(n = 4) | PLGA7525 4A + 1% PEG-PLGA5050 | 140 | 13.8 |
| Dorzolamide-Acetyl PLA(n = 5) | PLGA7525 4A + 1% PEG-PLGA5050 | 140 | 13.8 |
| Dorzolamide-Acetyl PLA(n = 5) | PLGA7525 4A + 1% PEG-PLGA5050 | 200 | 13.8 |
| Dorzolamide-Acetyl PLA(n = 5) | PLA 4.5A + 1% PEG-PLGA5050 | 180 | 13.8 |
| Dorzolamide-PLA(n = 10) | PLGA7525 4A + 1% PEG-PLGA5050 | 260 | 15.0 |
| Dorzolamide-PLA(n = 10) | 77/22 (PLA 4.5A/PLGA7525 4A + 1% PEG-PLGA5050 | 260 | 15.0 |
| Dorzolamide-PLA(n = 12) | PLGA7525 4A + 1% PEG-PLGA5050 | 260 | 15.0 |
| Dorzolamide-PLA(n = 12) | 77/22 (PLA 4.5A/PLGA7525 4A + 1% PEG-PLGA5050 | 260 | 15.0 |
| Dorzolamide-PLA(n = 14) | PLGA7525 4A + 1% PEG-PLGA5050 | 260 | 15.0 |
| Dorzolamide-PLA(n = 14) | 77/22 (PLA 4.5A/PLGA7525 4A + 1% PEG-PLGA5050 | 260 | 15.0 |
| Latanoprost-Acetyl PLA(n = 4) | PLGA + 1% PEG-PLGA5050 | 140 | 13.8 |
| Latanoprost-Acetyl PLA(n = 4) | PLA + 1% PEG-PLGA5050 | 180 | 13.8 |
| Latanoprost-Acetyl PLA(n = 4) | PLGA + 1% PEG-PLGA5050 | 200 | 13.8 |
| Latanoprost-Acetyl PLA(n = 4) | PLGA + 1% PEG-PLGA5050 | 200 | 15 |
| Latanoprost-Acetyl PLA(n = 4) | PLGA + 1% PEG-PLGA5050 | 200 | 30 |
| Latanoprost-Acetyl PLA(n = 4) | PLGA + 1% PEG-PLGA5050 | 200 | 50 |
| Latanoprost-Acetyl PLA(n = 4) | PLGA + 1% PEG-PLGA5050 | 200 | 40 |
| Latanoprost-tris Acetyl PLA(n = 6) | PLGA + 1% PEG-PLGA5050 | 200 | 13.8 |
| Brimonidine-Acetyl PLA(n = 2)-N-Acetate (114-4) | PLGA7525 4A + 1% PEG-PLGA5050 | 200 | 15.0 |
| Brimonidine-Acetyl PLA(n = 2)-N-Acetate (114-4) | PLGA8515 5A + 1% PEG-PLGA5050 | 200 | 15.0 |
| Brimonidine-Acetyl PLA(n = 2)-N-Acetate (114-4) | PLA 4.5A + 1% PEG-PLGA5050 | 200 | 15.0 |
| Brimonidine-Acetyl PLA(n = 4)-N-Acetate (115-1) | PLGA7525 4A + 1% PEG-PLGA5050 | 200 | 15.0 |
| Brimonidine-Acetyl PLA(n = 4)-N-Acetate (115-1) | PLGA8515 5A + 1% PEG-PLGA5050 | 200 | 15.0 |
| Brimonidine-Acetyl PLA(n = 4)-N-Acetate (115-1) | PLA 4.5A + 1% PEG-PLGA5050 | 200 | 15.0 |

TABLE 4-continued

Polymer, Polymer concentration, and percent theoretical loading of prodrugs of Brinzolamide, Dorzolamide, Latanoprost, and Brimonidine encapsulated microparticles

| Compound Name | Backbone Polymer | Polymer Conc (mg/mL) | % Theoretical Loading |
|---|---|---|---|
| Brimonidine-Acetyl PLA(n = 4)-N-Acetate (115-1) | 77/22 (PLA 4.5A/PLGA8515 5A) + 1% PEG-PLGA5050 | 200 | 15.0 |
| Brimonidine-Acetyl PLA(n = 4)-N-Acetate (115-1) | 77/22 (PLA 4.5A/PLGA8515 5A) + 1% PEG-PLGA5050 | 200 | 20.0 |
| Brimonidine-Acetyl PLA(n = 4)-N-Acetate (115-1) | 77/22 (PLA 4.5A/PLGA8515 5A) + 1% PEG-PLGA5050 | 200 | 30.0 |

TABLE 5

Formulation parameters and physicochemical properties of prodrugs of Brinzolamide, Dorzolamide, Latanoprost, and Brimonidine encapsulated microparticles

| Compound Name | Surfactant | Formulation Temp | Mean Particle Size (μm) | SD | % DL |
|---|---|---|---|---|---|
| Brinzolamide-PLA (n = 4) | A | RT | 25.8 | 7.48 | 0.14 |
| Brinzolamide-PLA(n = 4) | B | ice bath | 27.56 | 8.51 | 8.11 |
| Brinzolamide-PLA(n = 4) | B | ice bath | 25.76 | 8.18 | 8.05 |
| Brinzolamide-Acetyl PLA(n = 4) | A | RT | 24.9 | 8.27 | 1.01 |
| Brinzolamide-Acetyl PLA(n = 5) | A | RT | 23.58 | 7.73 | 0.156 |
| Brinzolamide-Acetyl PLA(n = 5) | B | ice bath | 26.5 | 7.98 | 7.39 |
| Brinzolamide-Acetyl PLA(n = 5) | B | ice bath | 27.4 | 7.86 | 8.89 |
| Brinzolamide-Acetyl PLA(n = 5) | B | ice bath | 27.12 | 10.3 | 9.09 |
| Brinzolamide-Acetyl PLA(n = 5) | A | ice bath | 26.38 | 8.92 | 10.5 |
| Dorzolamide-PLA(n = 4) | A | RT | 26.83 | 8.53 | 0.22 |
| Dorzolamide-PLA(n = 4) | B | ice bath | 28.42 | 9.34 | 8.28 |
| Dorzolamide-PLA(n = 4) | B | ice bath | 26.22 | 8.15 | 8.34 |
| Dorzolamide-PLA(n = 4) | A | ice bath | 27.89 | 9.18 | 7.98 |
| Dorzolamide-Acetyl PLA(n = 4) | A | RT | 26.4 | 8.94 | 0.98 |
| Dorzolamide-Acetyl PLA(n = 5) | A | RT | 23.14 | 8.06 | 0.991 |
| Dorzolamide-Acetyl PLA(n = 5) | B | ice bath | 19.7 | 9.45 | 8.71 |
| Dorzolamide-Acetyl PLA(n = 5) | A | ice bath | 30.37 | 11.2 | 10.1 |
| Dorzolamide-PLA(n = 10) | A | RT | 26.59 | 18.4 | 15.3 |
| Dorzolamide-PLA(n = 10) | A | RT | 24.37 | 13.6 | 11.8 |
| Dorzolamide-PLA(n = 12) | A | RT | 28.73 | 11.0 | 11.7 |
| Dorzolamide-PLA(n = 12) | A | RT | 24.14 | 10.5 | 12.5 |
| Dorzolamide-PLA(n = 14) | A | RT | 25. | 13.3 | 14.7 |
| Dorzolamide-PLA(n = 14) | A | RT | 24.76 | 10.2 | 13.6 |
| Latanoprost-Acetyl PLA(n = 4) | A | RT | 28.1 | 8.58 | 0.53 |
| Latanoprost-Acetyl PLA(n = 4) | A | ice bath | 32.16 | 11.3 | 3.1 |
| Latanoprost-Acetyl PLA(n = 4) | A | ice bath | 27.78 | 8.12 | 8.59 |
| Latanoprost-Acetyl PLA(n = 4) | A | ice bath | 27.86 | 8.81 | 8.57 |
| Latanoprost-Acetyl PLA(n = 4) | A | ice bath | 27.46 | 8.08 | 21.15 |
| Latanoprost-Acetyl PLA(n = 4) | A | ice bath | 32.12 | 10.6 | 36.4 |
| Latanoprost-Acetyl PLA(n = 4) | A | ice bath | 30.92 | 10.3 | 30.98 |
| Latanoprost-tris Acetyl PLA(n = 6) | B | ice bath | 26.44 | 9.18 | 3.57 |
| Brimonidine-Acetyl PLA(n = 2)-N-Acetate (114-4) | A | RT | 23.9 | 9.38 | 4.54 |

TABLE 5-continued

Formulation parameters and physicochemical properties of prodrugs of Brinzolamide, Dorzolamide, Latanoprost, and Brimonidine encapsulated microparticles

| Compound Name | Surfactant | Formulation Temp | Mean Particle Size (μm) | SD | % DL |
|---|---|---|---|---|---|
| Brimonidine-Acetyl PLA(n = 2)-N-Acetate (114-4) | A | RT | 29.31 | 9.45 | 4.83 |
| Brimonidine-Acetyl PLA(n = 2)-N-Acetate (114-4) | A | RT | 22.67 | 9.18 | 3.81 |
| Brimonidine-Acetyl PLA(n = 4)-N-Acetate (115-1) | A | RT | 22.59 | 8.16 | 12.7 |
| Brimonidine-Acetyl PLA(n = 4)-N-Acetate (115-1) | C | RT | 24.57 | 8.55 | 13.72 |
| Brimonidine-Acetyl PLA(n = 4)-N-Acetate (115-1) | C | RT | 32.1 | 12.5 | 14.72 |
| Brimonidine-Acetyl PLA(n = 4)-N-Acetate (115-1) | C | RT | 24.15 | 7.09 | 13.37 |
| Brimonidine-Acetyl PLA(n = 4)-N-Acetate (115-1) | C | RT | 22.61 | 7.10 | 18.72 |
| Brimonidine-Acetyl PLA(n = 4)-N-Acetate (115-1) | C | RT | 24.1 | 7.04 | 27.49 |

Surfactant- A) 1% PVA in PBS; B) 1% alpha-tocopherol-$PEG_{1k}$-succinate in PBS; C) 1% PVA in $H_2O$.

TABLE 6

Backbone polymer, Polymer concentration, and percent theoretical loading of PLA-Timolol, ROCK Inhibitors, and bifunctional prodrug encapsulated microparticles

| Compound Name | Backbone Polymer | Polymer Conc (mg/mL) | % Theoretical Loading |
|---|---|---|---|
| Timolol-stearyl PLA (n = 4) maleate (40-2) | PLGA7525 4A + 1% PEG-PLGA5050 | 200 | 13.8 |
| Timolol-stearyl PLA (n = 4) maleate (40-2) | PLGA7525 4A + 1% PEG-PLGA5050 | 200 | 13.8 |
| Timolol-stearyl PLA (n = 4) maleate (40-2) | PLA 4.5A + 1% PEG-PLGA5050 | 200 | 13.8 |
| Timolol-stearyl PLA (n = 4) HCL (41-2) | PLGA7525 4A + 1% PEG-PLGA5050 | 200 | 13.8 |
| Timolol-stearyl PLA (n = 4) HCL (41-2) | PLA 4.5A + 1% PEG-PLGA5050 | 200 | 13.8 |
| Timolol-stearyl PLA (n = 4) HCL (41-2) | PLGA8515 5A + 1% PEG-PLGA5050 | 200 | 13.8 |
| Timolol-stearyl PLA (n = 4) HCL (41-2) | PLA 4.5A + 1% PEG-PLGA5050 | 200 | 13.8 |
| Timolol-Acetyl PLA (n = 4) maleate (45-2) | PLGA7525 4A + 1% PEG-PLGA5050 | 200 | 13.8 |
| Timolol-stearyl PLA (n = 4) HCL (41-2) | PLGA5050 2A + 1% PEG-PLGA5050 | 200 | 13.8 |
| Timolol-Acetyl PLA (n = 4) maleate (45-2) | PLA 4.5A + 1% PEG-PLGA5050 | 200 | 13.8 |
| Timolol-Succinic acid-Timolol Maleate (76-4) | 77/22 (PLA 4.5A/PLGA8515 5A) + 1% PEG-PLGA5050 | 260 | 15.0 |
| Timolol-Glutaric acid-Timolol Maleate (77-1) | 77/22 (PLA 4.5A/PLGA8515 5A) + 1% PEG-PLGA5050 | 260 | 15.0 |
| Timolol-Fumarate-Timolol Maleate (78-1) | 77/22 (PLA 4.5A/PLGA8515 5A) + 1% PEG-PLGA5050 | 260 | 15.0 |
| Timolol-Bis-Acetyl PLA(n = 4) (119-6) | 64/20/15 (PLA 4.5A/PLGA8515 5A/PLGA5050 4A) + 1% PEG-PLGA5050 | 260 | 15.0 |
| Timolol-Bis-Acetyl PLA(n = 4) (119-6) | 77/22 (PLA 4.5A/PLGA8515 5A) + 1% PEG-PLGA5050 | 260 | 15.0 |
| Timolol-Bis-Acetyl PLA(n = 4) (119-6) | 77/22 (PLA 4.5A/PLGA8515 5A) + 1% PEG-PLGA5050 | 260 | 20.0 |
| Timolol-Bis-Acetyl PLA(n = 4) (119-6) | 77/22 (PLA 4.5A/PLGA8515 5A) + 1% PEG-PLGA5050 | 260 | 30.0 |

TABLE 6-continued

Backbone polymer, Polymer concentration, and percent theoretical loading of PLA-Timolol, ROCK Inhibitors, and bifunctional prodrug encapsulated microparticles

| Compound Name | Backbone Polymer | Polymer Conc (mg/mL) | % Theoretical Loading |
|---|---|---|---|
| Timolol-Bis-N-Acetyl PLA(n = 4)-O-Acetyl PLA (n = 2) (229) | PLA 4.5A + 1% PEG-PLGA5050 | 260 | 15.0 |
| Timolol-Bis-N-Acetyl PLA(n = 4)-O-Acetyl PLA(n = 2) (229) | 77/22 (PLA 4.5A/PLGA8515 5A) + 1% PEG-PLGA5050 | 260 | 15.0 |
| Timolol-Bis-N-Acetyl PLA(n = 4)-O-Acetyl PLA(n = 2) (229) | 64/20/15 (PLA 4.5A/PLGA8515 5A/PLGA5050 4A) + 1% PEG-PLGA5050 | 260 | 15.0 |
| Timolol-Bis-N-Acetyl PLA(n = 2)-O-Acetyl PLA(n = 4) (230) | PLA 4.5A + 1% PEG-PLGA5050 | 260 | 15.0 |
| Timolol-Bis-N-Acetyl PLA(n = 2)-O-Acetyl PLA(n = 4) (230) | 77/22 (PLA 4.5A/PLGA8515 5A) + 1% PEG-PLGA5050 | 260 | 15.0 |
| Timolol-Bis-N-Acetyl PLA(n = 2)-O-Acetyl PLA(n = 4) (230) | 64/20/15 (PLA 4.5A/PLGA8515 5A/PLGA5050 4A) + 1% PEG-PLGA5050 | 260 | 15.0 |
| SR5834 | 69/30 (PLA 4.5A/PLGA7525 6E) + 1% PEG-PLGA5050 | 260 | 15.0 |
| SR5834 | 77/22 (PLA 4.5A/PLGA8515 5A) + 1% PEG-PLGA5050 | 260 | 15.0 |
| SR5834 | 74/20/5 (PLA 4.5A/PLGA8515 5A/PLGA5050 4A) + 1% PEG-PLGA5050 | 260 | 15.0 |
| SR5834 | 69/20/10 (PLA 4.5A/PLGA8515 5A/PLGA5050 4A) + 1% PEG-PLGA5050 | 260 | 15.0 |
| SR5834 | PLGA7525 4A + 1% PEG-PLGA5050 | 260 | 15.0 |
| SR5834 | PLGA7525 6E + 1% PEG-PLGA5050 | 260 | 15.0 |
| SR5834 | 74/20/5 (PLA 4.5A/PLGA7525 4A/PLGA5050 4A) + 1% PEG-PLGA5050 | 260 | 15.0 |
| SR5834 | 69/20/10 (PLA 4.5A/PLGA7525 4A/PLGA5050 4A) + 1% PEG-PLGA5050 | 260 | 15.0 |
| SR5834 | PLGA8515 5A + 1% PEG-PLGA5050 | 260 | 15.0 |
| SR5834 | PLA 4.5A + 1% PEG-PLGA5050 | 260 | 15.0 |
| SR5834-PLA(n = 4) | PLGA7525 4A + 1% PEG-PLGA5050 | 260 | 15.0 |
| RKI-H-1y malate | 69/30 (PLA 4.5A/PLGA7525 6E) + 1% PEG-PLGA5050 | 260 | 15.0 |
| RKI-H-1y malate | 69/30 (PLA 4.5A/PLGA7525 8E) + 1% PEG-PLGA5050 | 260 | 15.0 |
| RKI-H-1y malate | 69/30 (PLA 4.5A/PLGA8515 5A) + 1% PEG-PLGA5050 | 260 | 15.0 |
| RKI-H-1y malate | 69/25/5 (PLA 4.5A/PLGA8515 5A/PLGA5050 4A) + 1% PEG-PLGA5050 | 260 | 15.0 |
| RKI-H-1y malate | PLGA7525 4A + 1% PEG-PLGA5050 | 260 | 15.0 |
| RKI-H-1y malate | PLGA7525 6E + 1% PEG-PLGA5050 | 260 | 15.0 |
| RKI-H-1y malate | PLGA8515 5A + 1% PEG-PLGA5050 | 260 | 15.0 |
| RKI-H-1y malate | PLA 4.5A + 1% PEG-PLGA5050 | 260 | 15.0 |

TABLE 6-continued

Backbone polymer, Polymer concentration, and percent theoretical loading of PLA-Timolol, ROCK Inhibitors, and bifunctional prodrug encapsulated microparticles

| Compound Name | Backbone Polymer | Polymer Conc (mg/mL) | % Theoretical Loading |
|---|---|---|---|
| Hydroxy-1y-Acetyl PLA(n = 4) (90-3) | PLGA7525 4A + 1% PEG-PLGA5050 | 260 | 15.0 |
| Dorzolamide-PLA(n = 4)-succinate-5-hydroxy-Sunitinib | PLA 4.5A + 1% PEG-PLGA5050 | 180 | 13.8 |
| Brinzolamide-PLA(n = 4)-succinate-5-hydroxy-Sunitinib | PLA 4.5 A + 1% PEG-PLGA5050 | 180 | 13.8 |

PLGA$^x$ (85:15 lactic acid to glycolic acid ratio, 5A, Evonik)
PLGA$^y$ (50:50 lactic acid to glycolic acid ratio, 2A, Evonik)

TABLE 7

Formulation parameters and physicochemical properties of PLA-Timolol prodrugs and bifunctional prodrugs

| Compound Name | Surfactant | Formulation Temp | Mean Particle Size (µm) | SD | % DL |
|---|---|---|---|---|---|
| Timolol-Stearyl PLA (n = 4) maleate (40-2) | 1% PVA in PBS | ice bath | 34.17 | 12.1 | 10.18 |
| Timolol-Stearyl PLA (n = 4) maleate (40-2) | 1% PVA in PBS | RT | 31.51 | 11 | 12.7 |
| Tiraolol-stearyl PLA (n = 4) maleate (40-2) | 1% PVA in PBS | ice bath | 34.74 | 12.9 | 12.13 |
| Timolol-Stearyl PLA (n = 4) HCL (41-2) | 1% PVA in PBS | RT | 33.12 | 12 | 12.09 |
| Timolol-Stearyl PLA (n = 4) HCL (41-2) | 1% PVA in PBS | ice bath | 36.2 | 12.8 | 11.09 |
| Timolol-Stearyl PLA (n = 4) HCL (41-2) | 1% PVA in PBS | RT | 34.03 | 11.9 | 12.6 |
| Timolol-Stearyl PLA (n = 4) HCL (41-2) | 1% PVA in PBS | RT | 27.99 | 8.13 | 12.26 |
| Timolol-Acetyl PLA (n = 4) maleate (45-2) | 1% PVA in PBS | RT | 31.2 | 11.7 | 10.63 |
| Timolol-Stearyl PLA (n = 4) HCL (41-2) | 1% PVA in PBS | RT | 25.33 | 8.77 | 12.51 |
| Timolol-Acetyl PLA (n = 4) maleate (45-2) | 1% PVA in PBS | RT | 27.85 | 8.23 | 8.76 |
| Timolol-Succinic acid-Timolol-Maleate (76-4) | 1% PVA in PBS | RT | 28.74 | 11.0 | 7.45 |
| Timolol-Glutaric acid-Timolol-Maleate (77-1) | 1% PVA in PBS | RT | 27.29 | 11.0 | 7.94 |
| Timolol-Fumarate-Timolol-Maleate (78-1) | 1% PVA in PBS | RT | 27.45 | 10.3 | 9.61 |
| Timolol-Bis-Acetyl PLA(n = 4) (119-6) | 1% PVA in H$_2$O | RT | 26.52 | 8.46 | 6.8 |
| Timolol-Bis-Acetyl PLA(n = 4) (119-6) | 1% PVA in H$_2$O | RT | 28.0 | 8.47 | 7.38 |
| Timolol-Bis-Acetyl PLA(n = 4) (119-6) | 1% PVA in H$_2$O | RT | 29.27 | 7.84 | 10.41 |
| Timolol-Bis-Acetyl PLA(n = 4) (119-6) | 1% PVA in H$_2$O | RT | 28.17 | 7.97 | 13.10 |
| Timolol-Bis-N-Acetyl PLA(n = 4)-O-Acetyl PLA(n = 2) | 1% PVA in H$_2$O | RT | 28.17 | 7.52 | 13.36 |
| Timolol-Bis-N-Acetyl PLA(n = 4)-O-Acetyl PLA(n = 2) | 1% PVA in H$_2$O | RT | 27.29 | 8.25 | 14.06 |
| Timolol-Bis-N-Acetyl PLA(n = 4)-O-Acetyl PLA(n = 2) | 1% PVA in H$_2$O | RT | 26.87 | 8.05 | 13.4 |
| Timolol-Bis-N-Acetyl PLA(n = 2)-O-Acetyl PLA(n = 4) | 1% PVA in H$_2$O | RT | 28.24 | 7.62 | 12.65 |
| Timolol-Bis-N-Acetyl PLA(n = 2)-O-Acetyl PLA(n = 4) | 1% PVA in H$_2$O | RT | 27.31 | 8.33 | 16.33 |

TABLE 7-continued

Formulation parameters and physicochemical properties of PLA-Timolol prodrugs and bifunctional prodrugs

| Compound Name | Surfactant | Formulation Temp | Mean Particle Size (μm) | SD | % DL |
|---|---|---|---|---|---|
| Timolol-Bis-N-Acetyl PLA(n = 2)-O-Acetyl PLA(n = 4) | 1% PVA in H₂O | RT | 27.6 | 8.29 | 12.6 |
| SR5834 | 1% PVA in PBS | RT | 25.28 | 7.9 | 7.19 |
| SR5834 | 1% PVA in PBS | RT | 23.91 | 7.91 | 6.31 |
| SR5834 | 1% PVA in PBS | RT | 24.21 | 7.8 | 6.81 |
| SR5834 | 1% PVA in PBS | RT | 23.71 | 7.7 | 6.22 |
| SR5834 | 1% PVA in PBS | RT | 22.24 | 7.83 | 6.56 |
| SR5834 | 1% PVA in PBS | RT | 27.23 | 8.73 | 7.69 |
| SR5834 | 1% PVA in PBS | RT | 22.86 | 7.90 | 6.29 |
| SR5834 | 1% PVA in PBS | RT | 22.74 | 7.53 | 6.54 |
| SR5834 | 1% PVA in PBS | RT | 25.07 | 7.66 | 6.89 |
| SR5834 | 1% PVA in PBS | RT | 24.3 | 7.41 | 6.36 |
| SR5834-PLA(n = 4) | 1% PVA in PBS | RT | 30.41 | 10.5 | 12.88 |
| RKI-H-1y malate | 1% PVA in PBS | RT | 24.25 | 8.23 | 17.31 |
| RKI-H-1y malate | 1% PVA in PBS | RT | 25.43 | 8.15 | 16.91 |
| RKI-H-1y malate | 1% PVA in PBS | RT | 26.42 | 7.98 | 17.17 |
| RKI-H-1y malate | 1% PVA in PBS | RT | 24.52 | 8.80 | 17 |
| RKI-H-1y malate | 1% PVA in PBS | RT | 29.42 | 10.1 | 17.03 |
| RKI-H-1y malate | 1% PVA in PBS | RT | 27.42 | 9.94 | 16.95 |
| RKI-H-1y malate | 1% PVA in PBS | RT | 26.93 | 10.4 | 17.17 |
| RKI-H-1y malate | 1% PVA in PBS | RT | 25.35 | 8.94 | 17.48 |
| Hydroxy-1y-Acetyl PLA(n = 4) (90-3) | 1% PVA in PBS | RT | 23.76 | 8.48 | 12.84 |
| Dorzolamide-PLA(n = 4)-succinate-5-hydroxy-Sunitinib | 1% PVA in PBS | RT | 26.91 | 10.8 | 11.62 |
| Brinzolamide-PLA(n = 4)-succinate-5-hydroxy-Sunitinib | 1% PVA in PBS | RT | 33.83 | 11.5 | 8.47 |

Surfactant: A) 1% PVA in PBS

Particle Morphology

Particle morphology was assessed using a Nikon Eclipse TS-100 light microscope. Briefly, 3-5 mg of particles were suspended in 1 mL of water. A volume of 10 uL of the particle suspension was transferred onto a glass slide and imaged directly. In general, particles were found to be spherical in morphology (FIG. 31A, FIG. 31B, FIG. 31C, and FIG. 31D).

Drug Release

In vitro drug release kinetics were evaluated in a release medium of PBS and 1% Tween 20 (pH 7.4). Briefly, 10 mg of particles were transferred to glass scintillation vials and 4 mL of the release medium was added to suspend the particles. Samples were prepared in duplicate. The particles were mixed by gentle vortexing and incubated on an orbital shaker at 150 rpm at 37° C. At various time points, 3 mL of release media was collected and analyzed for drug content and 3 mL of fresh media was added to replace the sample that was collected. Collected release samples were frozen and stored at −80° C. until analysis for drug content. The collected samples were filtered through a 0.2 μm syringe filter and analyzed by RP-HPLC.

Figure 32:
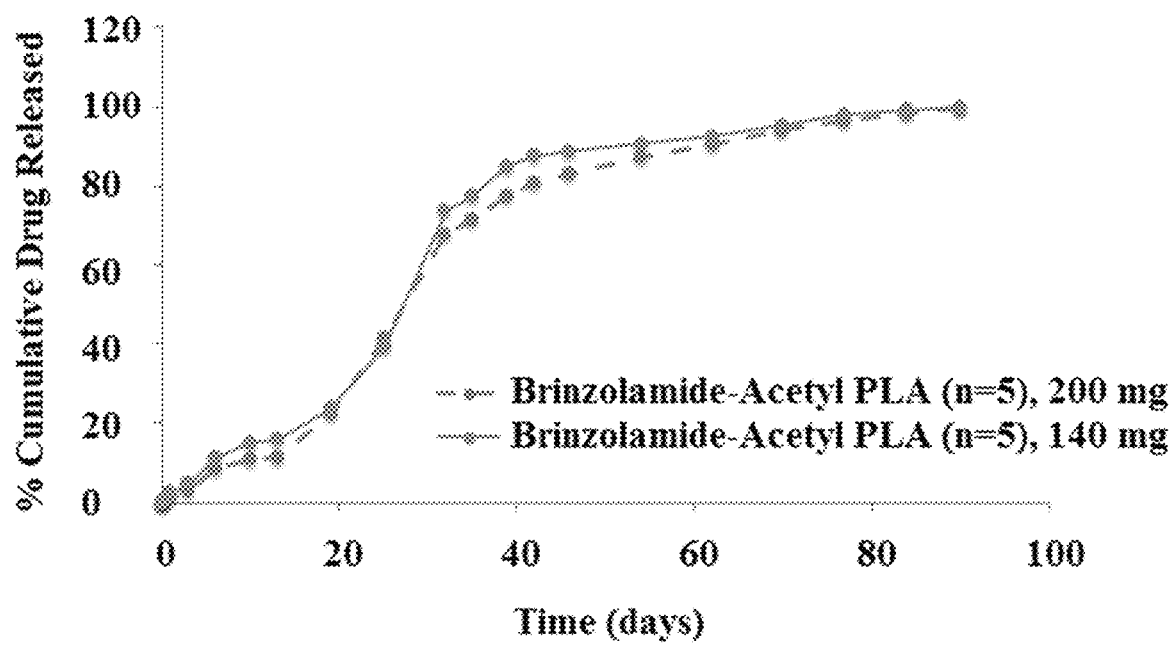
FIG. 32 is a graph depicting the drug release kinetics of Brinzolamide-acetyl PLA (n=5) from particles prepared with a polymer concentration of 140 mg/mL and 200 mg/mL over the course of 100 days as described in Example 9. The x-axis represents time measured in days and the y-axis represents cumulative drug release measured in percent.

FIG. 32 illustrates the cumulative release profile for particles with polymer concentrations of 140 mg/mL and 200 mg/mL encapsulating Brinzolamide-acetyl PLA (n=5). The cumulative release profiles of both formulations exhibited relatively low initial burst release (0.65% and 0.32% released at 3 hours, respectively). However, by day 3, particles prepared with a higher polymer concentration exhibited significantly slower burst release than particles prepared at 140 mg/mL concentration (2.85% vs. 4.92%, respectively). By day 42, particles prepared at a polymer concentration of 140 mg/mL had released 87.6% of the drug whereas particles prepared at a concentration of 200 mg/mL had released only 80.7%. Thus, by increasing the polymer concentration from 140 mg/mL to 200 mg/mL, the burst and overall rate of release of Brinzolamide-Acetyl PLA (n=5) from the particles was decreased. Without wishing to be bound to any one theory, the rate of release of Brinzolamide-acetyl PLA (n=5) may be attributed to its high hydrophobicity and hydrophobic interactions between the drug and the polymer matrix. Increasing the hydrophobicity of the polymer by selecting a higher LA:GA ratio of polymer or PLA may further decrease the rate of release.

Figure 33:
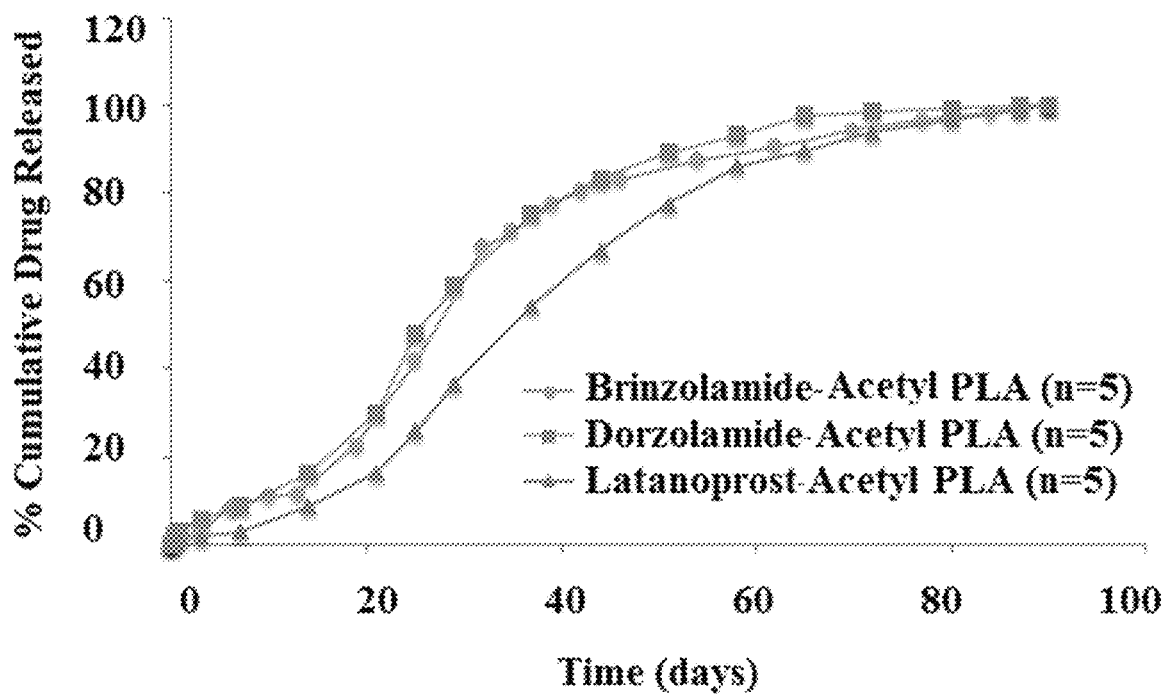
FIG. 33 is a graph comparing the drug release kinetics of Brinzolamide-acetyl PLA (n=5) (18-3), Dorzolamide-acetyl PLA (n=5), and Latanoprost-acetyl PLA (n=5) over the course of 100 days as described in Example 9. The x-axis represents time measured in days and the y-axis represents cumulative drug release measured in percent.

In vitro release profiles of Brinzolamide-acetyl PLA (n=5), Dorzolamide-acetyl PLA (n=5) and Latanoprost-acetyl PLA (n=5) are shown in FIG. 33. The release kinetics of acetylated Brinzolamide and Dorzolamide with five LA repeat units were comparable. The release kinetics for Brinzolamide-acetyl PLA (n=5) and Dorzolamide-acetyl PLA (n=5) was significantly faster than Latanoprost-acetyl PLA (n=5); approximately 75.3% of Dorzolamide-acetyl PLA (n=5) was released after 37 days compared to 54.3% for Latanoprost-acetyl PLA (n=5). Without wishing to be bound to any one theory, this may be attributed to the differences in hydrophobicity between CAIs and Latanoprost. Burst release was also significantly higher for Dorzolamide-acetyl PLA (n=5) than Latanoprost-acetyl PLA (n=5). At 3 hours, approximately 1.20% of Dorzolamide-acetyl PLA (n=5) had been released compared to 0.55% for Latanoprost-acetyl PLA (n=5).

Figure 34:
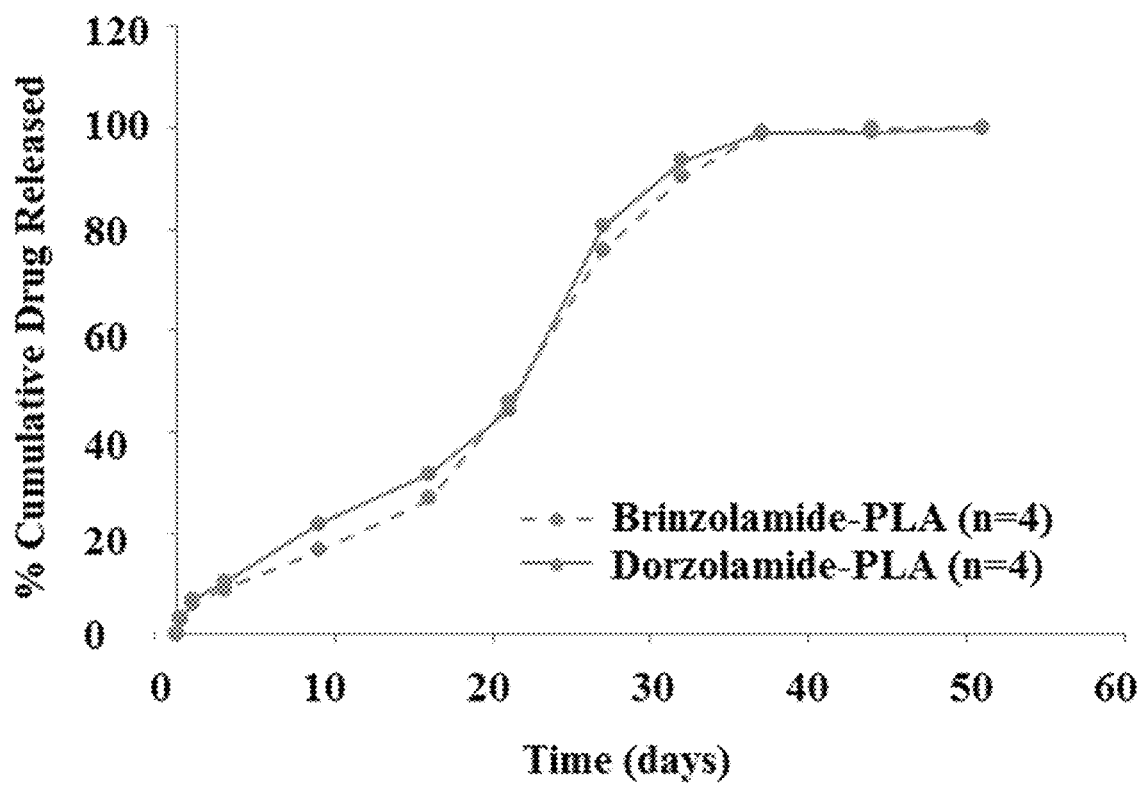
FIG. 34 is a graph comparing the drug release kinetics of Brinzolamide PLA (n=4) and Dorzolamide PLA (n=4) over the course of 60 days as described in Example 9. The x-axis represents time measured in days and the y-axis represents cumulative drug release measured in percent.

Release kinetics for uncapped Brinzolamide-PLA(n=4) and Dorzolamide-PLA(n=4) is illustrated in FIG. 34. A cursory evaluation of the release kinetics between acetylated vs non-acetylated carbonic anhydrase inhibiting NCEs reveal acetylation of the terminal lactate unit significantly decreased the release kinetics of the NCE from the microparticles. For example, approximately 97% of Dorzolamide-Acetyl PLA(n=5) was released by day 63 whereas approximately 99% of non-acetylated Dorzolamide-PLA(n=4) was released by day 37, respectively. Without wishing to be bound to any one theory, this may be attributed to the large difference in aqueous solubility between the acetylated compounds (low aqueous solubility) and the un-acetylated compounds (high aqueous solubility).

Figure 36:
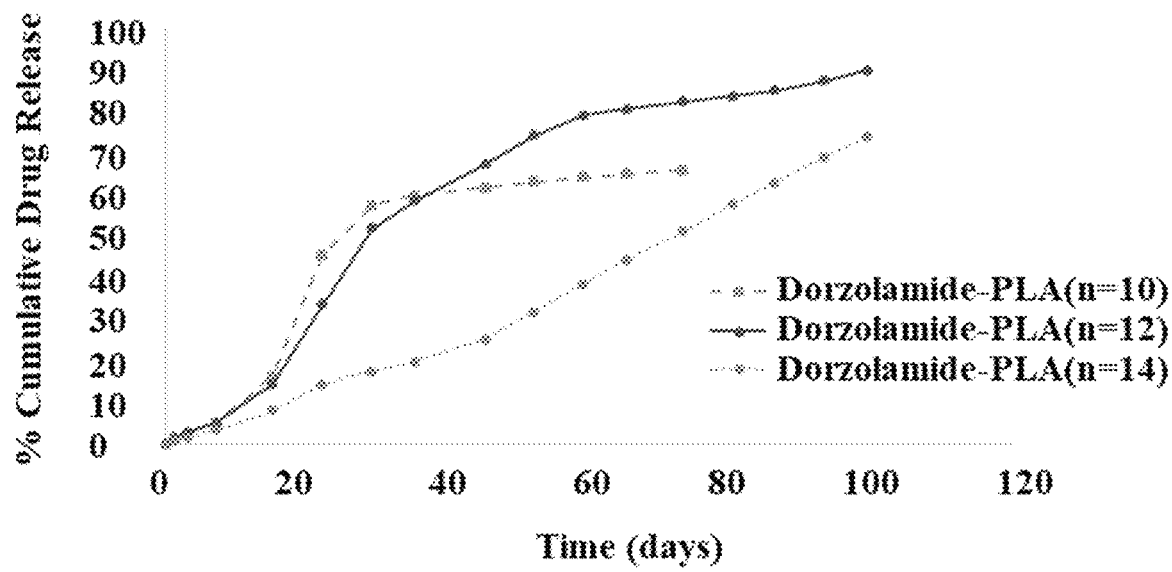
FIG. 36 is a graph comparing the drug release kinetics of Dorzolamide-PLA(n=10), Dorzolamide-PLA (n=12), and Dorzolamide-PLA (n=14) encapsulated in PLGA7525 4A particles over the course of 100 days as described in Example 9. The x-axis represents time measured in days and the y-axis represents cumulative drug release measured in percent.
Figure 37:
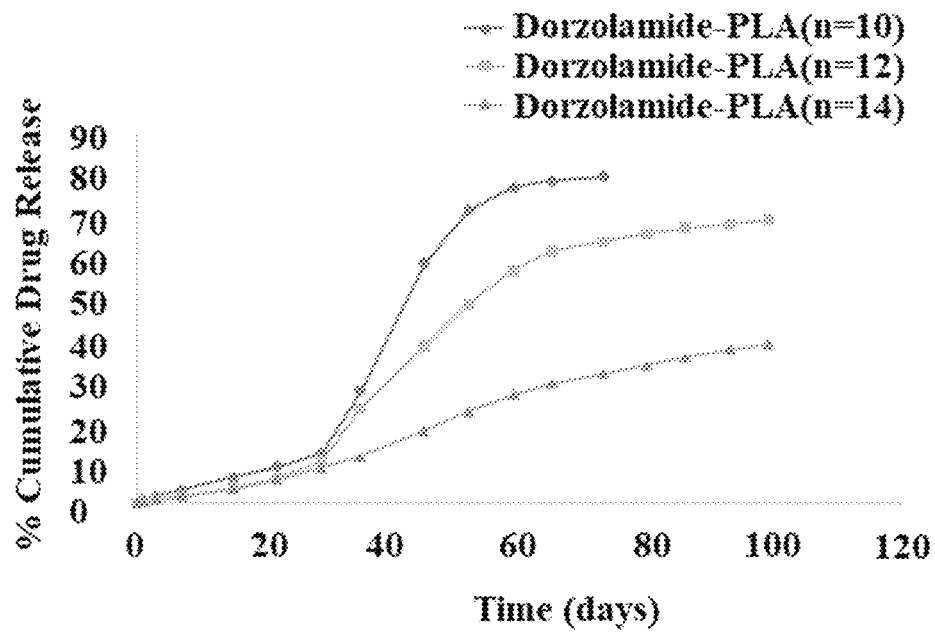
FIG. 37 is a graph comparing the drug release kinetics of Dorzolamide-PLA(n=10), Dorzolamide-PLA (n=12), and Dorzolamide-PLA (n=14) encapsulated in PLA 4.5A/PLGA8515 5A particles over the course of 100 days as described in Example 9. The x-axis represents time measured in days and the y-axis represents cumulative drug release measured in percent.

Increasing the number of PLA repeat units on the Dorzolamide prodrug resulted in a significant increase in the duration of release (FIG. 36 and FIG. 37).

Figure 35:
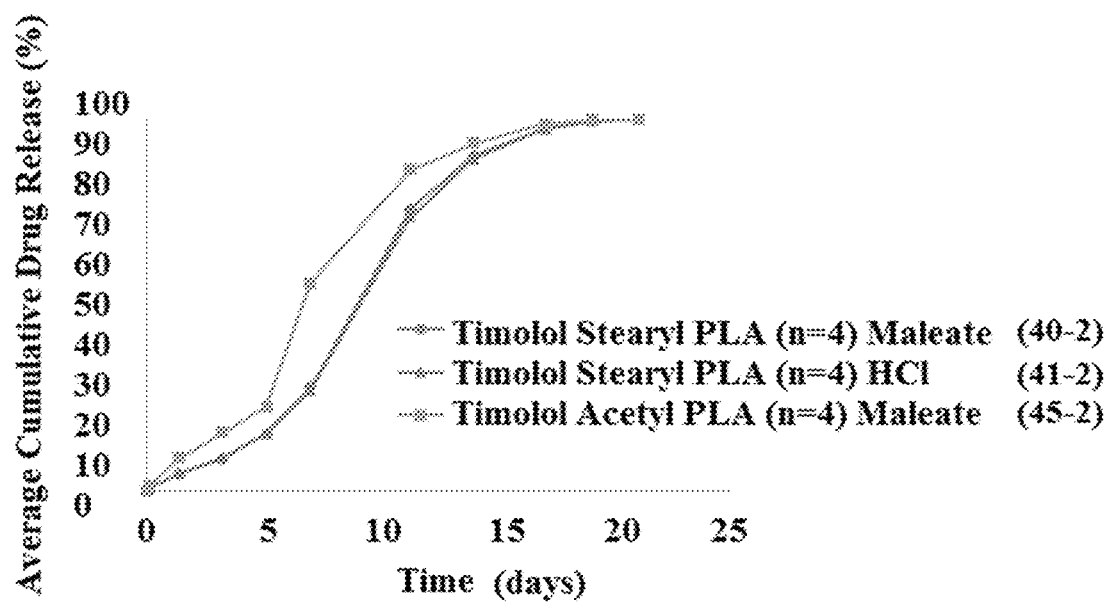
FIG. 35 is a graph comparing the drug release kinetics of Timolol stearyl PLA (n=4) maleate (40-2), Timolol stearyl PLA (n=4) HCl (41-2), and Timolol acetyl PLA (n=4) (45-2) over the course of 25 days as described in Example 9. The x-axis represents time measured in days and the y-axis represents cumulative drug release measured in percent.
Figure 38:
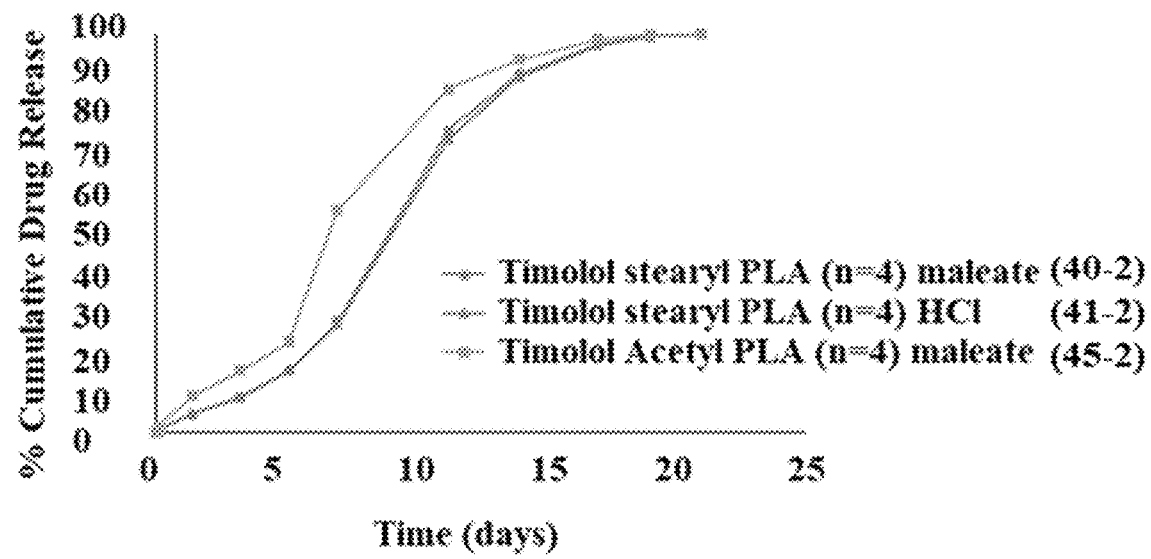
FIG. 38 is a graph comparing the drug release kinetics of Timolol-stearyl PLA (n=4) maleate (40-2), Timolol-stearyl PLA (n=4) HCl (41-2), and Timolol-acetyl PLA (n=4) maleate (45-2) as described in Example 9. The x-axis represents time measured in days and the y-axis represents cumulative drug release measured in percent.
Figure 39:
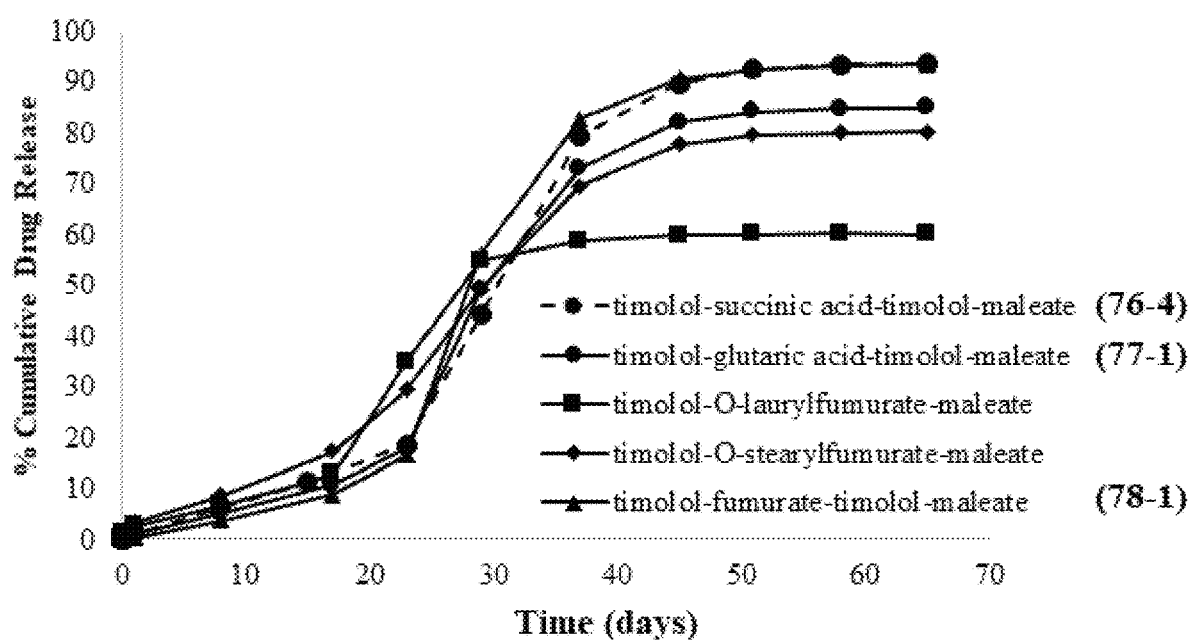
FIG. 39 is a graph comparing the drug release kinetics of bis-Timolol prodrugs Timolol-succinic acid-Timolol-maleate (76-4), Timolol-glutaric acid-Timolol-maleate (77-1), and Timolol-fumurate-Timolol-maleate (78-1) to mono-Timolol prodrugs Timolol-O-laurylfumurate-maleate and Timolol-O-stearylfumurate-maleate as described in Example 9. The x-axis represents time measured in days and the y-axis represents cumulative drug release measured in percent.

Analysis of the cumulative release profile of prodrug derivatives of Timolol (FIG. 35 and FIG. 38) revealed that the nature of the endcap group on the terminal lactate unit has an effect on the release kinetics of the NCE. Particles encapsulating Timolol-Stearyl PLA(n=4) maleate (40-2) were found to release the NCE at a much slower rate than particles encapsulating Timolol-Acetyl PLA(n=4) maleate (45-2). The rate of release was independent of the salt form. For Timolol, endcapping the terminal lactide with a stearyl chain decreased the rate of drug release over acetylation of the terminal lactide (FIG. 38). Comparative evaluation of blended particles with the same polymer composition encapsulating 5 different mono and bis prodrugs of Timolol (FIG. 39) revealed only minor differences between the release rates of the 5 particle formulations. Thus, release rate is not solely dictated by the physicochemical properties of the linker but rather must be attributed to a combination of parameters that may include linker type and site of linker conjugation.

Figure 40:
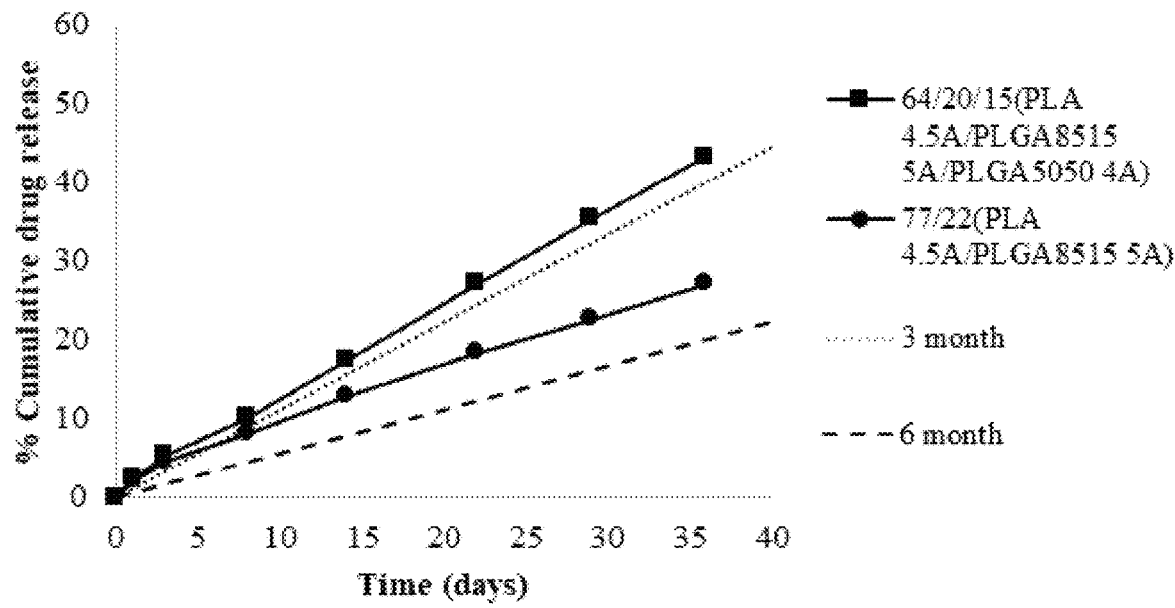
FIG. 40 is a graph comparing the drug release kinetics of Timolol-bis-Acetyl PLA(n=4) (119-6) from particles generated from different blends of PLA and PLGA polymers as described in Example 9. The x-axis represents time measured in days and the y-axis represents cumulative drug release measured in percent.
Figure 41:
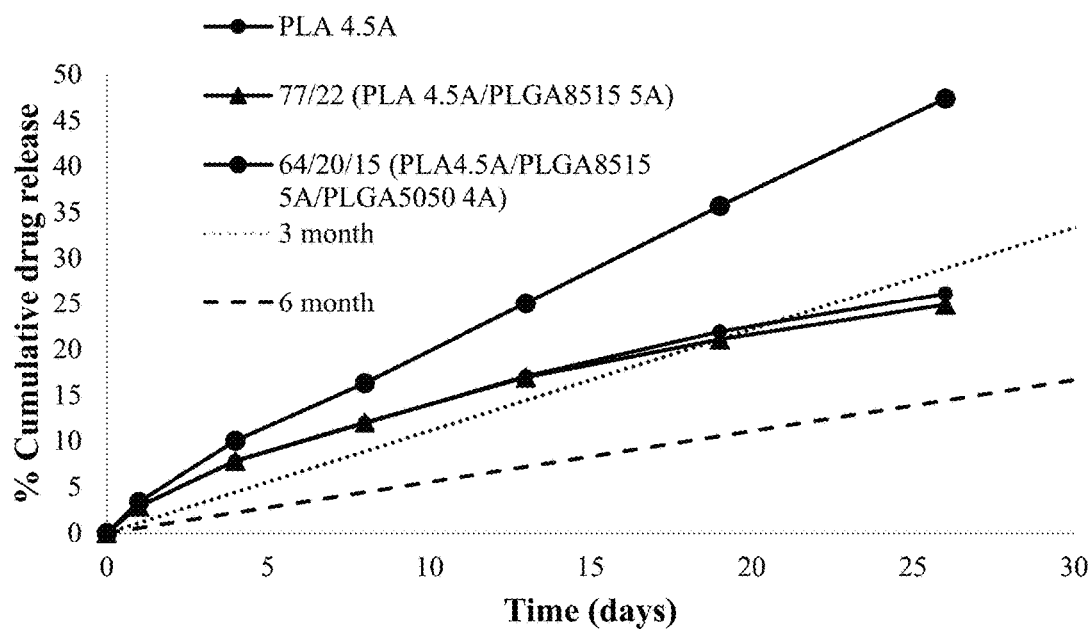
FIG. 41 is a graph comparing the drug release kinetics of Timolol-Bis-N-Acetyl-PLA (n=4)-O-Acetyl PLA (n=2) (229) from particles with varying polymer blends as described in Example 9. The x-axis represents time measured in days and the y-axis represents cumulative drug release measured in percent.
Figure 42:
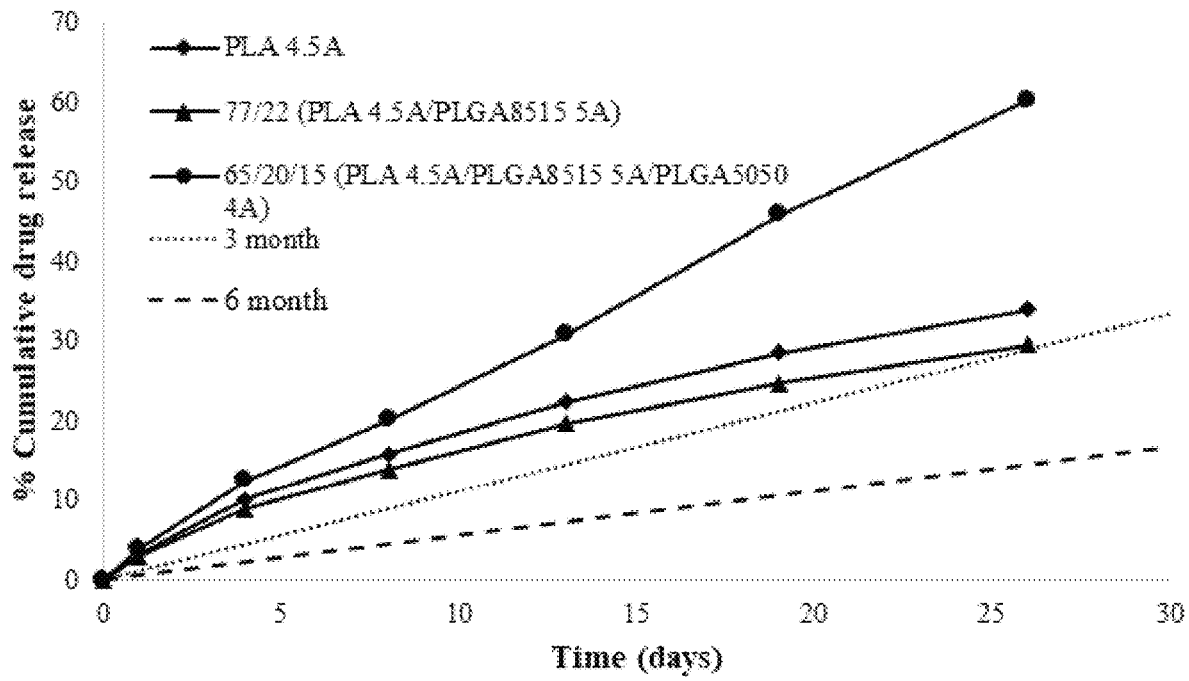
FIG. 42 is a graph comparing the drug release kinetics of Timolol-Bis-N-Acetyl-PLA (n=2)-O-Acetyl PLA (n=4) (230) from particles with varying polymer blends as described in Example 9. The x-axis represents time measured in days and the y-axis represents cumulative drug release measured in percent.

The effect of polymer composition including monomer ratio and molecular weight, polymer end-groups (ester or acid), inherent viscosity and polymer blend ratios on particle degradation and drug release kinetics was evaluate and illustrated in FIG. 40. The rate of particle degradation was slowed and drug release was prolonged when the mole % of DL-lactide over glycolide was increased. By incorporating polymers with different monomer ratios (i.e. PLA, PLGA8515, PLGA525, PLGA5050; wherein 8515 refers to 85% DL-lactide and 15% glycolide) into the particles, it is possible to fine-tune the degradation rate of the particles to achieve a linear rate of drug release from the particles to minimize burst or lag and to extend the duration of release. End-group modification of the polymer from the acid form to the ester form exhibited a similar effect at slowing particle degradation and drug release. Interestingly, blending a number of different polymers with different monomer ratios, end groups and molecular weights enabled optimization of release kinetics to achieve a linear 3-6 month release profile. Based on the current evidence, the 78/22 (PLA 5A/PLGA8515 4.5A) and 65/20/15 (PLA 4A/PLGA6515 4.5A/PLGA5050 4A) polymer blends generated ideal particles for a 3-6 month linear release formulation for Timolol-bis-Acetyl-PLA(n=4) (119-6) (FIG. 40). Particles of 100% PLA 4.5A and 77/22 (PLA 4.5A/PLGA8515 5A) blends exhibited comparable slow release of encapsulated Timolol-Bis-N-acetyl-PLA (n=4)-O-acetyl PLA (n=2) (229) in comparison to particles comprised of 65/20/15 (PLA 4A/PLGA6515 4.5A/PLGA5050 4A) polymer blends (FIG. 41). This trend was mirrored for particles encapsulating Timolol-Bis-N-acetyl-PLA (n=2)-O-acetyl PLA (n=4) (230) (FIG. 42).

Figure 43:
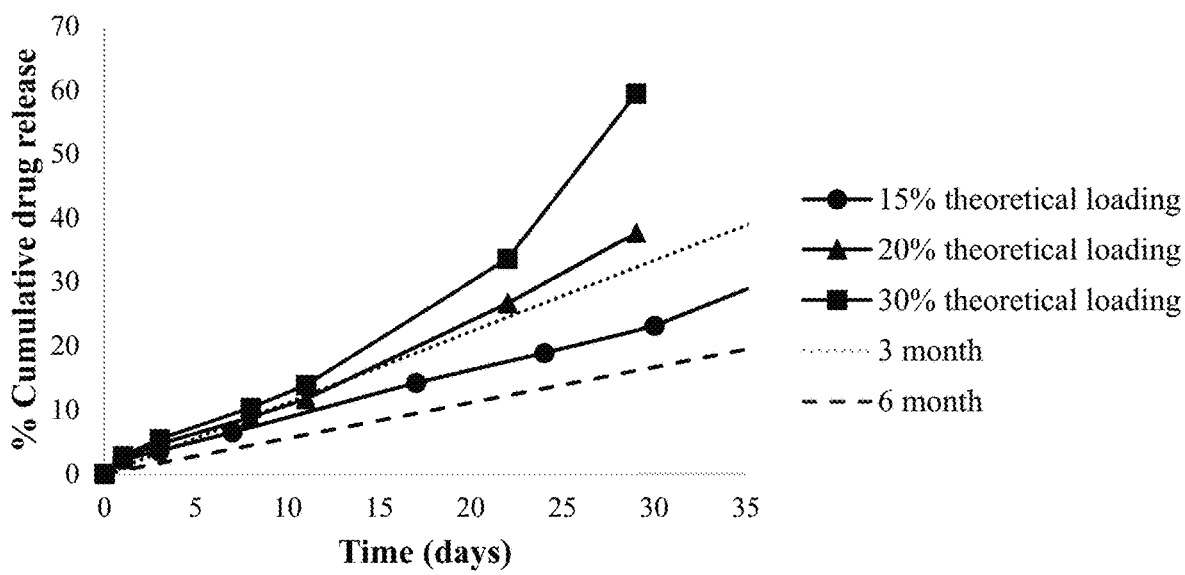
FIG. 43 is a graph of the drug release kinetics of Brimonidine-PLA(n=4)-N-acetate (115-1) from particles with 15, 20 and 30% theoretical drug loading as described in Example 9. The x-axis represents time measured in days and the y-axis represents cumulative drug release measured in percent.

As evidenced in FIG. 43, a correlation between % theoretical loading and drug release rate can be observed for Brimonidine-Acetyl PLA(n=4)-N-acetate (115-1). Increasing the amount of drug loaded into the particles resulted in an increase in the rate of drug release.

Figure 44:
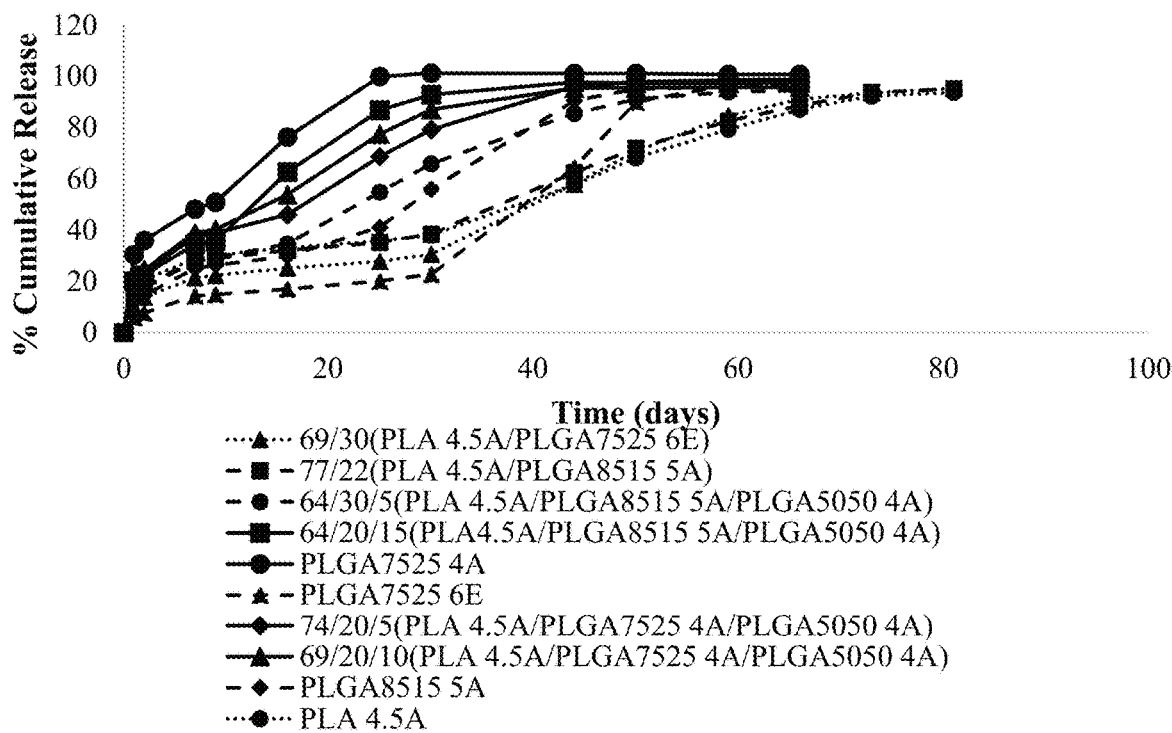
FIG. 44 is a graph of the drug release kinetics of SR5834 from particles of different polymer blends as described in Example 9. The x-axis represents time measured in days and the y-axis represents cumulative drug release measured in percent.
Figure 45:
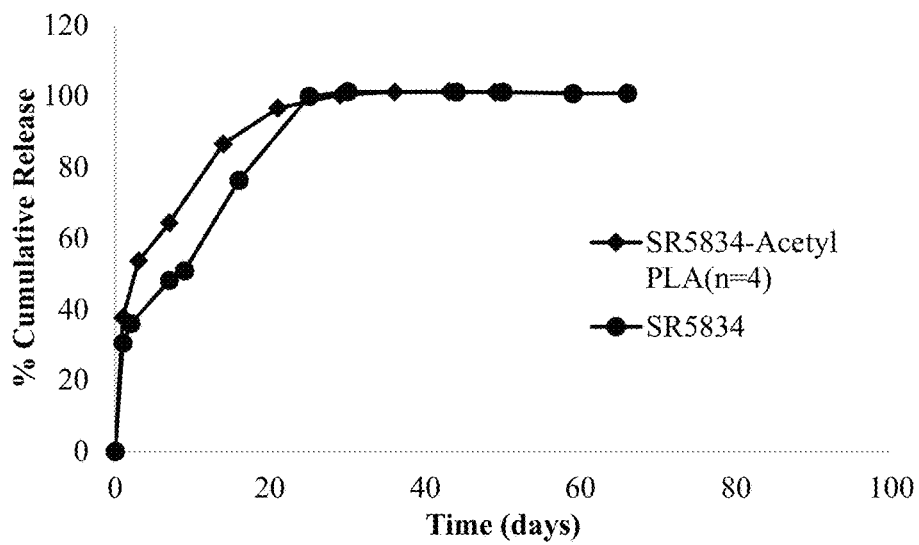
FIG. 45 is a graph comparing the drug release kinetics of SR5834 and SR5834-Acetyl PLA(n=4) (88-3) from PLGA7525 4A microparticles as described in Example 9. The x-axis represents time measured in days and the y-axis represents cumulative drug release measured in percent.
Figure 46:
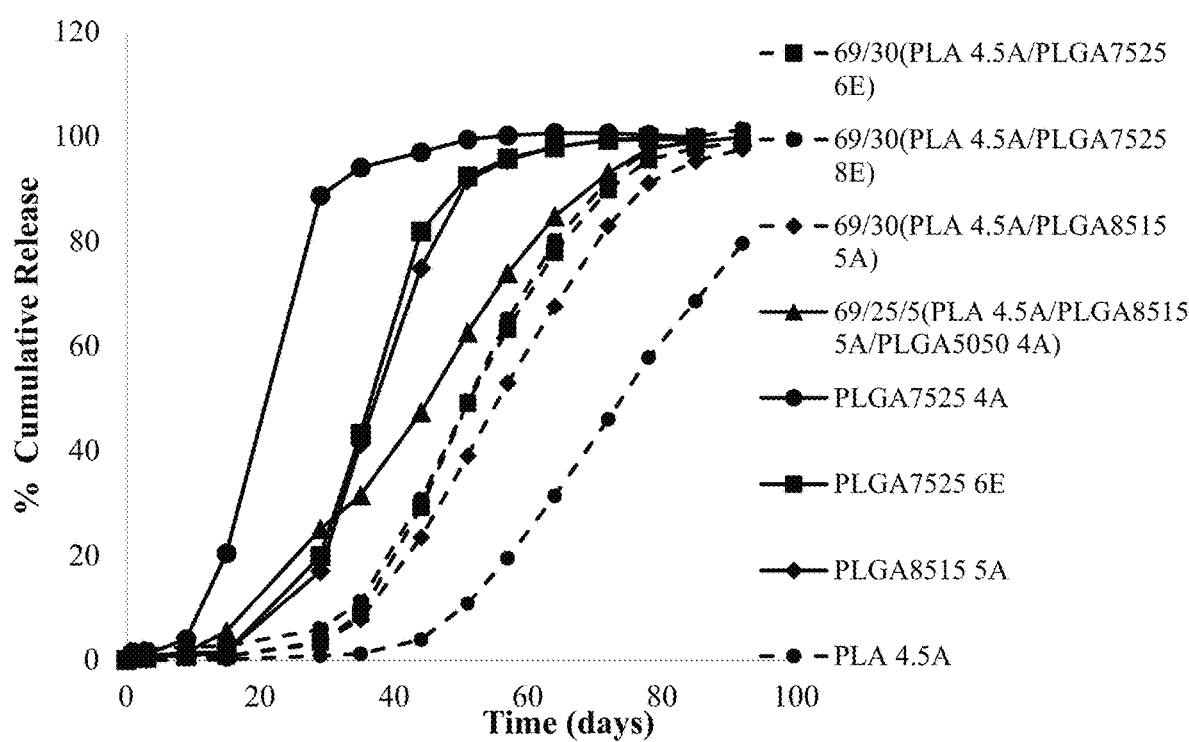
FIG. 46 is a graph of the drug release kinetics of native RKI-H-1y from particles of different polymer blends as described in Example 9. The x-axis represents time measured in days and the y-axis represents cumulative drug release measured in percent.

Evaluation of particle formulations of SR5834 composed of different polymer blends revealed three formulations that exhibit sustained release for a period of 90 days (FIG. 44). Modification of the rock inhibitor into a prodrug via facile conjugation to Acetyl-PLA(n=4) (compound 88-3) did not result in any significant effect on the release kinetics (FIG. 45). Similarly, sustained release formulations for RKI-II-1y was prepared with varying copolymer compositions and blends (FIG. 46).

The microparticle compositions described herein have demonstrated the potential to load and release one or more prodrugs for the management of elevated intraocular pressure for a prolonged period (>1 month).

Encapsulation of Timolol-Dorzolamide prodrugs in polymeric microspheres and concurrent dual drug release from prodrug-loaded microspheres Timolol-Dorzolamide bi-functional prodrugs 58-2 and 64-4 were encapsulated in polymeric microspheres using w/o emulsion, solvent evaporation techniques described in Example 9. Prodrugs were successfully encapsulated into microspheres with drug loading between 10-20 w/w %. Various formulation parameters, such as target drug loading, polymer concentration, formulation temperature, polymer composition, disperse phase and continuous phase ratio, etc., were investigated to optimize drug loading.

Figure 47:
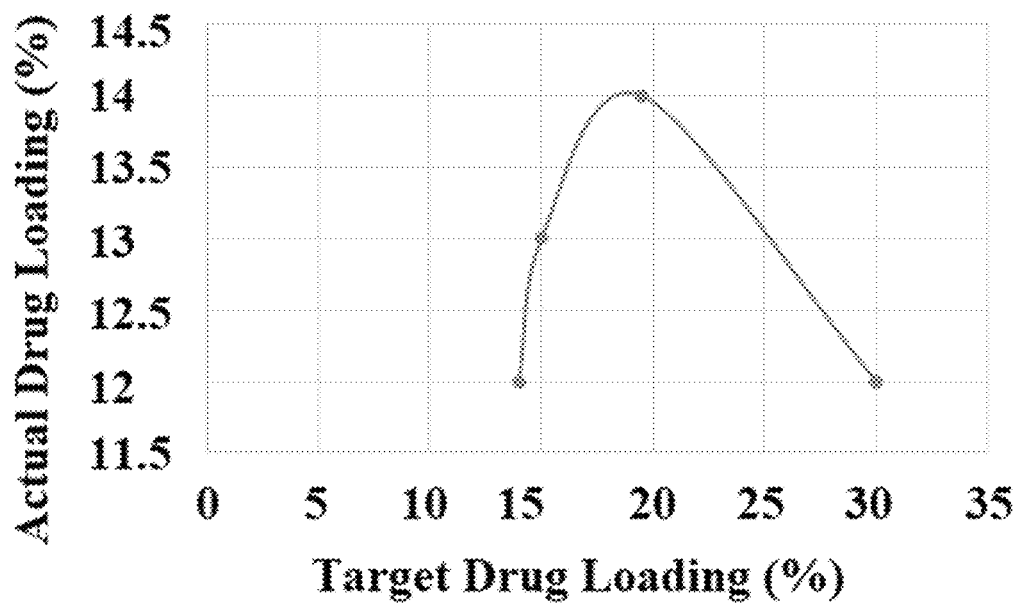
FIG. 47 is a graph comparing the actual drug-loading and the target drug-loading of Timolol-Dorzolamide prodrug 58-2 as described in Example 8. As the target drug-loading increases from 15% to 30%, the actual drug-loading initially increases and then begins to decline. The x-axis is target drug-loading measured in percent and the y-axis is actual drug-loading measured in percent.
Figure 48:
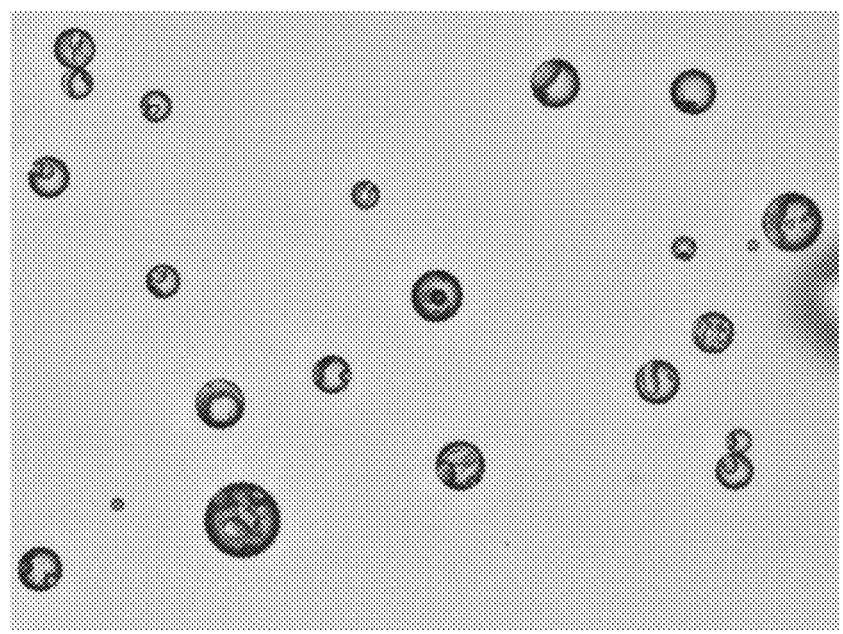
FIG. 48 is an image of microspheres with a target drug-loading of 30% Timolol-Dorzolamide prodrug 58-2. As described in Example 8, as the target drug-loading exceeds 20%, the drug tends to disrupt the physical integrity of the polymer matrix.

Target drug loading has a direct impact on the actual drug loading. Actual drug loading first increased with target drug loading and then reduced after target drug loading exceeded 20%. (FIG. 47). Without being bound to any one theory, the initial positive correlation between actual drug loading and target drug loading is probably due to more drug being added to the system and thus encapsulated. However, as the target drug loading exceeds 20%, the excessive drug disrupts the physical integrity of the polymer matrix and yields a low drug loading due to drug leakage. This is evidenced by the highly porous structure of the microspheres. (FIG. 48)

Parent Timolol and Dorzolamide prodrugs (Dorzolamide linked with 1-3 PLA units) were released concurrently from the bi-functional prodrug-loaded microspheres. Two important factors that impacted drug release kinetics, namely polymer composition and target drug loading, are described below.

(i) Polymer composition vs. release kinetics

Figure 49A:
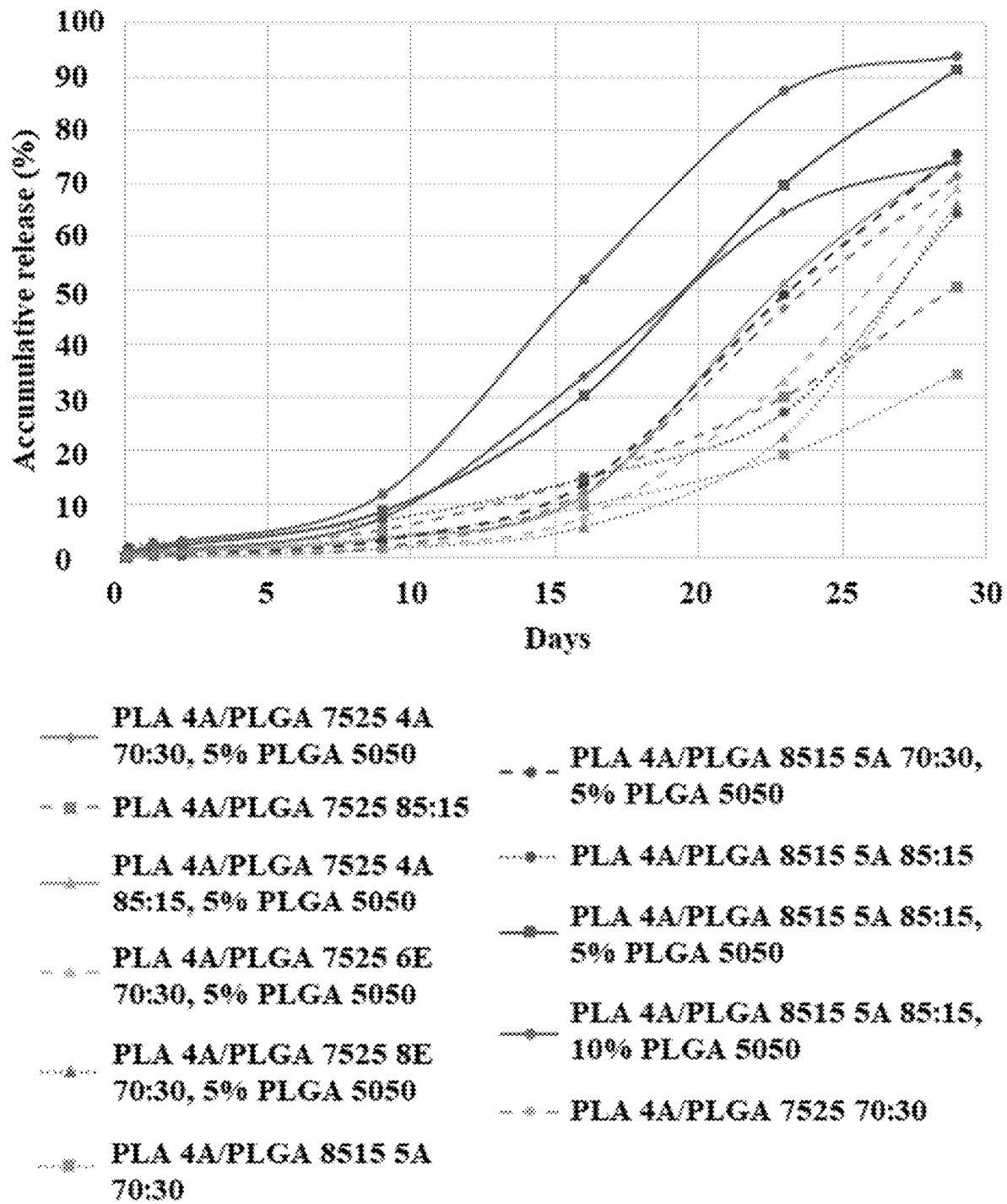
FIGS. 49A and 49B are graphs comparing the percent release of free Timolol (FIG. 16A) and Dorzolamide linked with PLA moieties (FIG. 16B) that is released from microparticles encapsulating Timolol-Dorzolamide prodrug 58-2. Prodrug 58-2 was encapsulated in microparticles with fast degrading polymer matrices (PLGA 5050 4A) and slow-degrading polymer matrices (PLA 4A and PLFA 7525 8E) as described in Example 8. The x-axis is time measured in days and the y-axis is accumulative release measured in percent.
Figure 49B:
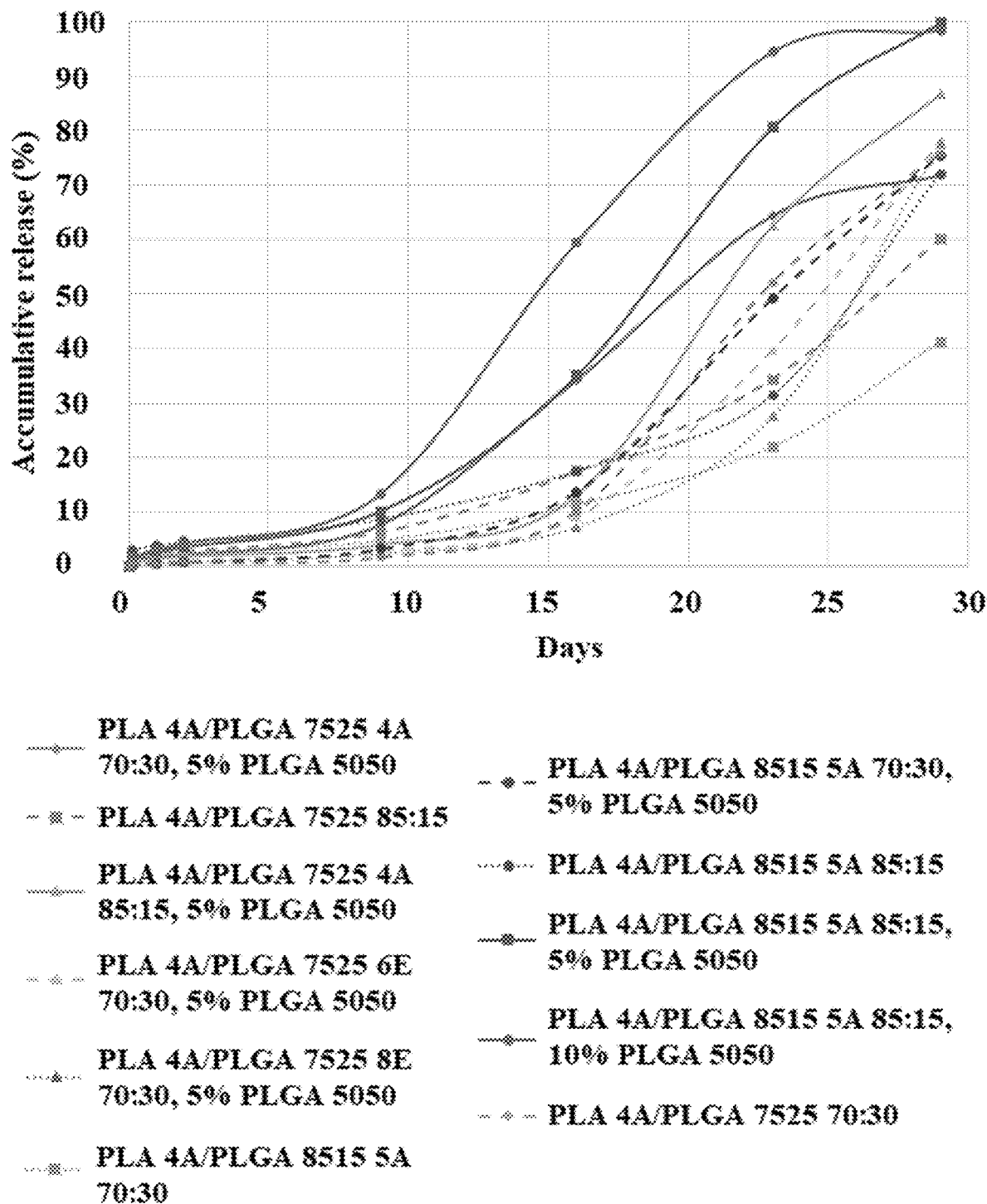

Different polymer compositions were investigated to encapsulate Timolol-succinate-PLA (n=3)-Dorzolamide (58-2). When a fast-degrading polymer (PLGA50:50 4A) was incorporated into the polymer matrix, the drug release rate was increased. When the microspheres were composed of slow-degrading polymers (e.g., PLA 4A and PLGA75:25 8E), the drug release rates were reduced. (FIG. 49A and FIG. 49B).

(ii) Drug loading vs. release kinetics

Drug release from polymeric microspheres usually exhibit a lag period where minimal amount of drugs are released in the first few days or even weeks of the study. This is usually undesirable in clinical applications when initial patient response is required because the drug released in this period may not reach therapeutic effective level.

Figure 50:
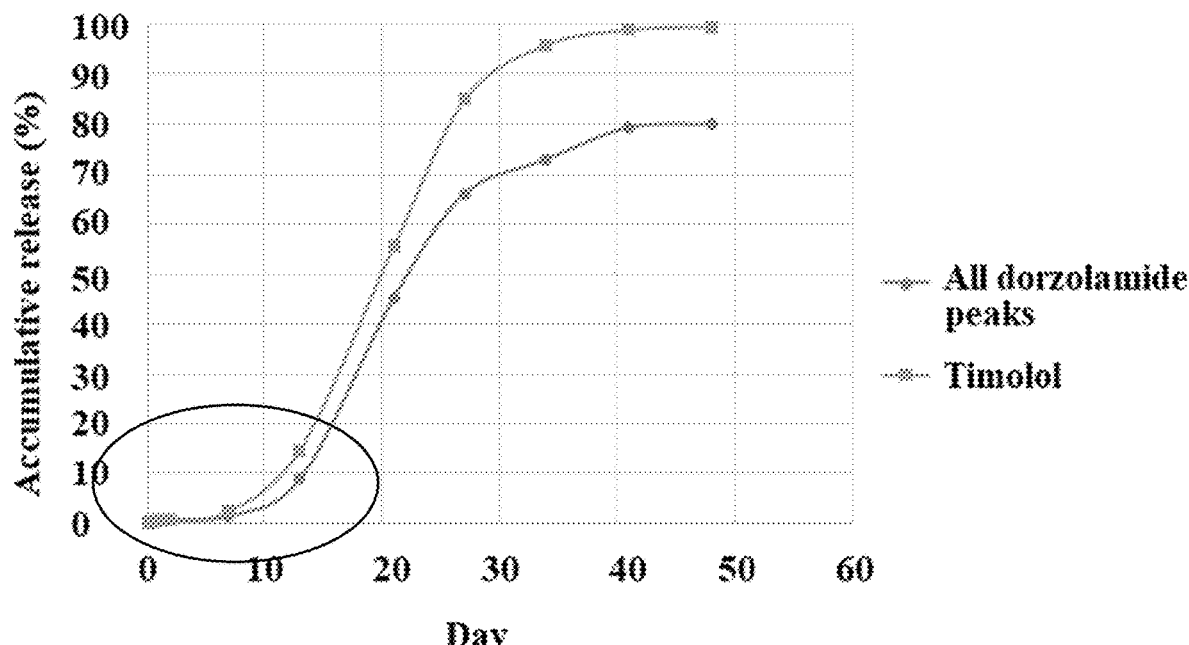
FIG. 50 is a graph of measuring the percent release of free Timolol and Dorzolamide linked with PLA moieties that is released from microparticles encapsulating Timolol-Dorzolamide prodrug 58-2 at a target drug-loading of 15%. As described in Example 8, a lag period of about 10 days was observed.
Figure 51:
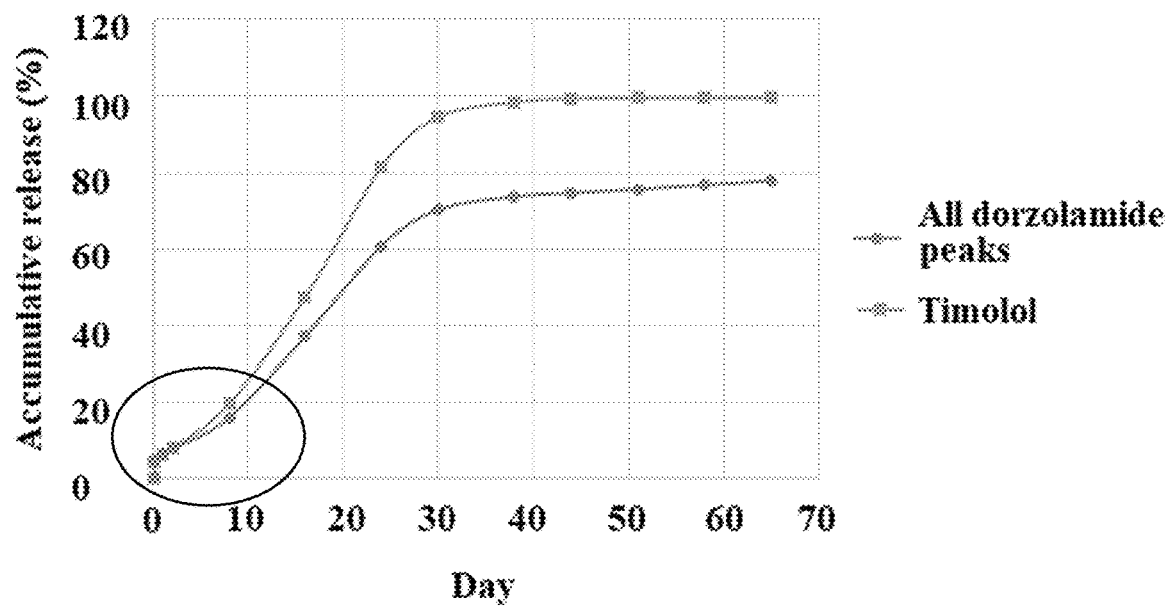
FIG. 51 is a graph of measuring the percent release of free Timolol and Dorzolamide linked with PLA moieties that is released from microparticles encapsulating Timolol-Dorzolamide prodrug 58-2 at a target drug-loading of 20%. As described in Example 8, no lag period in release was observed.
Figure 52A:
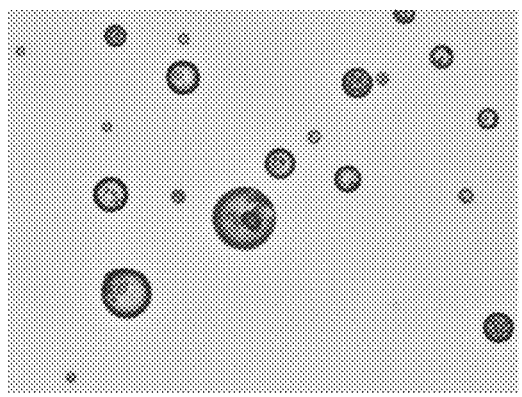
FIG. 52A is an image of microsphere encapsulating Timolol-Dorzolamide prodrug 58-2 at a target drug-loading of 20% as described in Example 8. Small pores were observed at the microsphere surface.
Figure 52B:
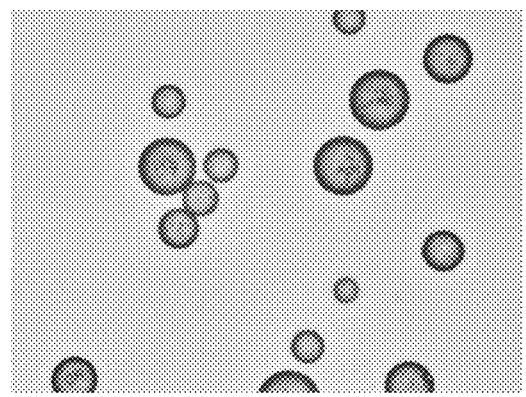
FIG. 52B is an image of microspheres encapsulating Timolol-Dorzolamide prodrug 58-2 at a target drug-loading of 15% as described in Example 8. Microspheres have smooth surface with minimal pores at the surface.
Figure 53:
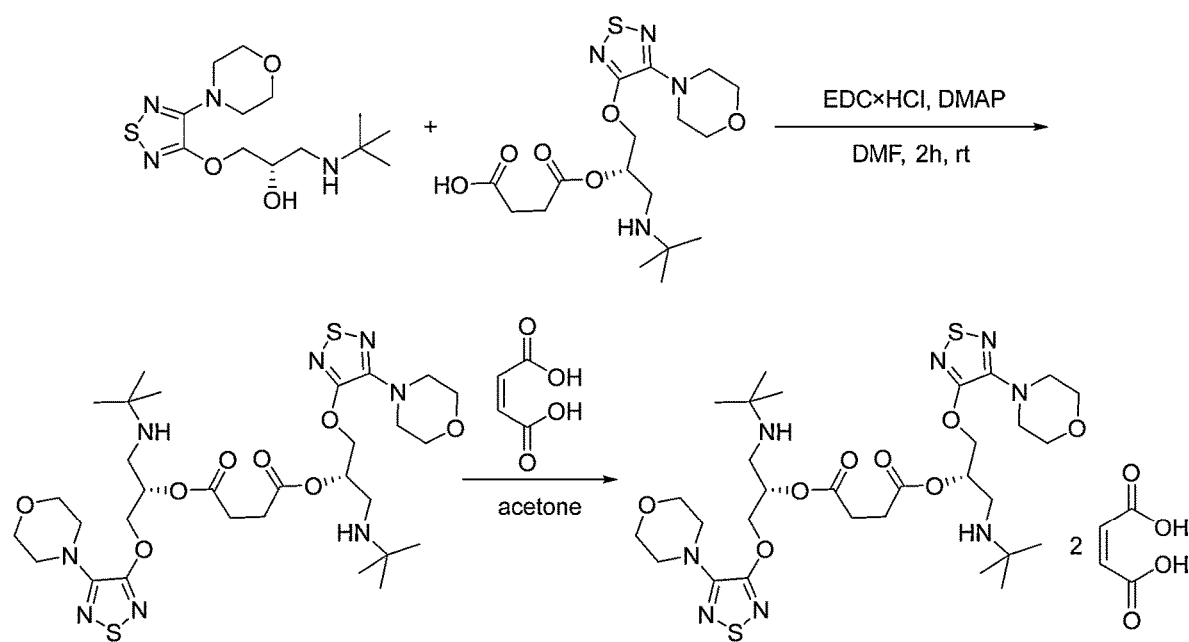
FIG. 53 is the synthesis of compound 76-4, a bis-prodrug of the beta-blocker Timolol.
Figure 54:
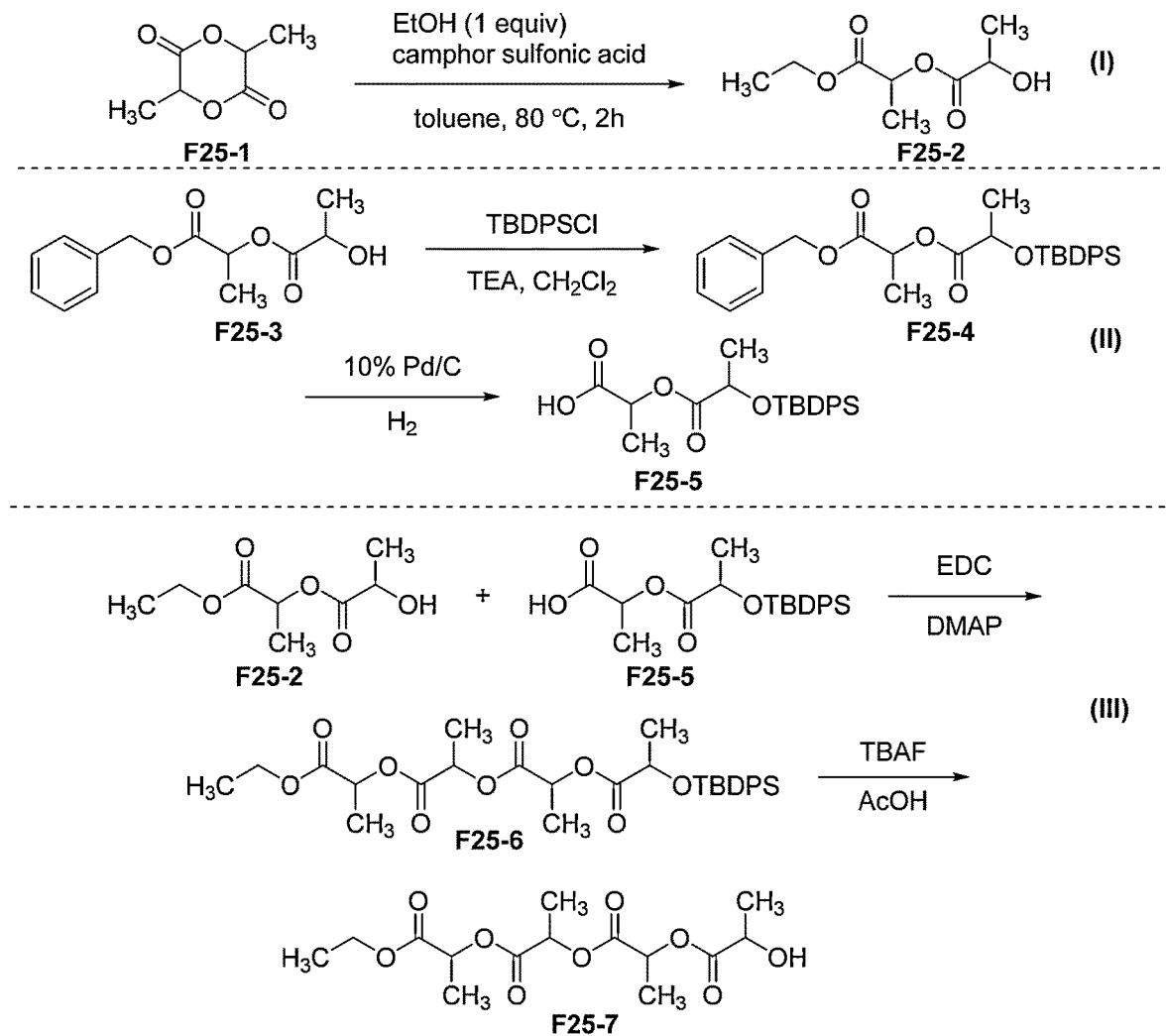
FIG. 54 is the synthesis of 1-ethoxy-1-oxopropan-2-yl 2-((2-((2-hydroxypropanoyl)oxy)propanoyl)oxy)propanoate (F25-7). In the first reaction (I), 1-ethoxy-1-oxopropan-2-yl 2-hydroxypropanoate (F25-2) is generated and in the second reaction (II), 2-((2-((tert-butyldiphenylsilyl)oxy)propanoyl)oxy)propanoic acid is generated (F25-5). Finally, F25-2 and F25-5 are combined in the third reaction (III) to afford F25-7, a PLA derivative used in the synthesis of mono- and bis-prodrugs. F25-1 was converted to F25-2 on a 32 g scale and formation of compound F25-2 was confirmed by LC-MS. Compound F25-2 was isolated on a 49.5 g scale (Crude). F25-2 to was converted to F25-3 on a 49.5 g scale and the formation of compound F25-3 was confirmed by NMR and LC-MS. Compound F25-3 on a 29.5 g scale. F25-4 was converted to F25-5 on a 12.5 g scale and formation of compound F25-5 was confirmed by NMR and LC-MS. Compound F25-5 was isolated on a 27.5 g scale. Compound F25-5 was converted to F25-6 on a 27.5 g scale and formation of F25-6 was confirmed by NMR and LC-MS. Compound F25-6 was isolated on a 10.5 g scale.
Figure 55:
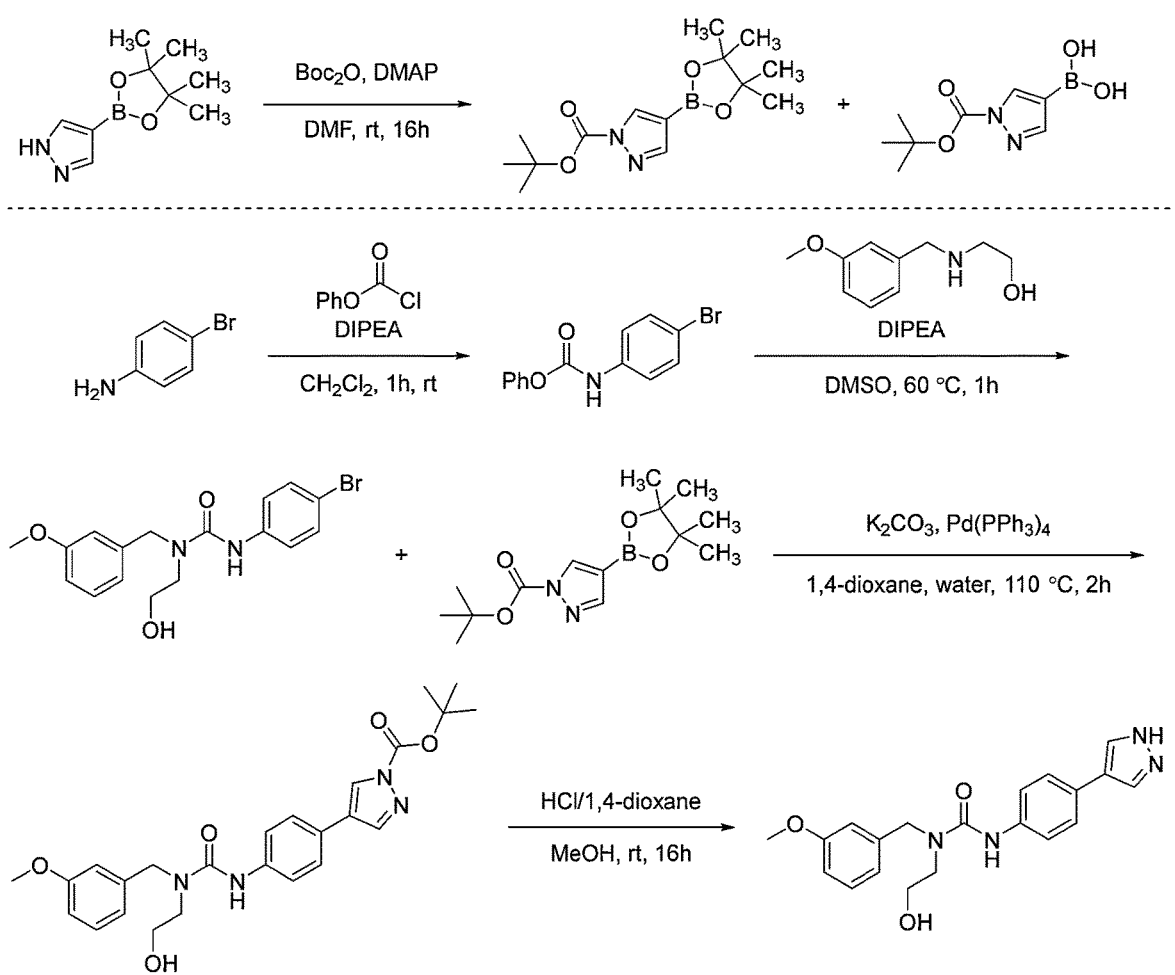
FIG. 55 is the synthesis of the ROCK inhibitor SR5834. SR5832 is synthesized by first generating (1-(tert-butoxycarbonyl)-1H-pyrazol-4-yl)boronic acid as an intermediate.
Figure 56:
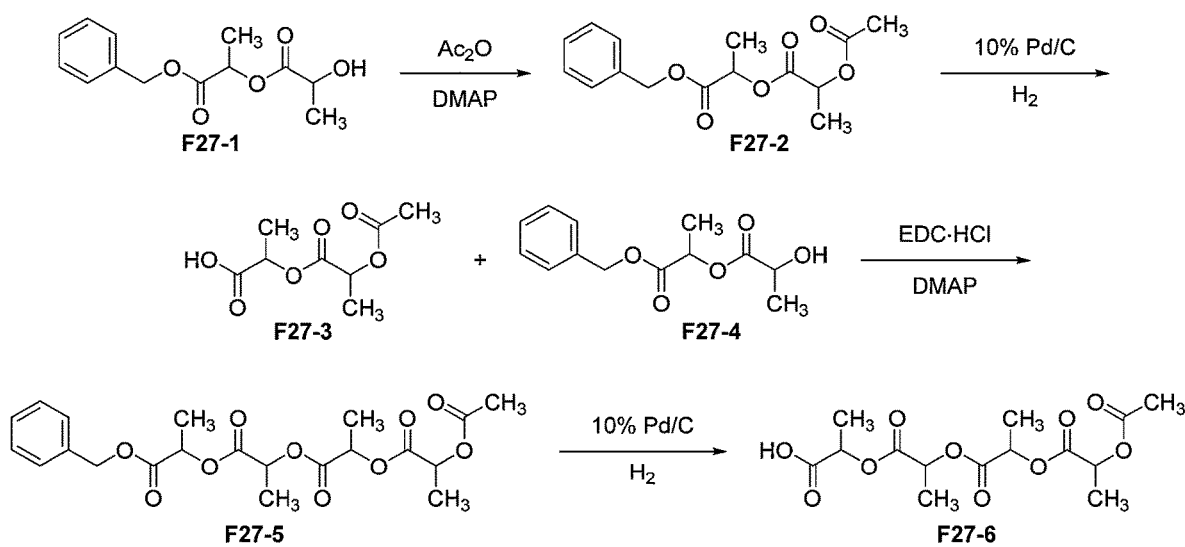
FIG. 56 is the synthesis of PLA derivative, 2,5,8,11-tetramethyl-4,7,10,13-tetraoxo-3,6,9,12-tetraoxatetradecanoic acid (F27-6). Compound F27-1 was converted to F27-2 on a 35 g scale and formation of compound F27-2 was confirmed by NMR and LC-MS. Compound F27-2 was isolated on a 39 g scale. Compound F27-2 was converted to F27-3 on a 39 g scale and formation of compound F27-3 was confirmed by NMR and MS. Compound F27-3 was isolated on a 21.5 g scale. Compound F27-4 was converted to F27-5 on a 21.5 g scale and formation of compound F27-5 was confirmed by NMR and LC-MS. Compound F27-5 was isolated on a 26 g scale. Compound F27-5 was converted to F27-6 on a 26 g scale and formation of compound F27-6 was confirmed by NMR and MS. Compound F27-6 was isolated on a 19.5 g scale.
Figure 57:
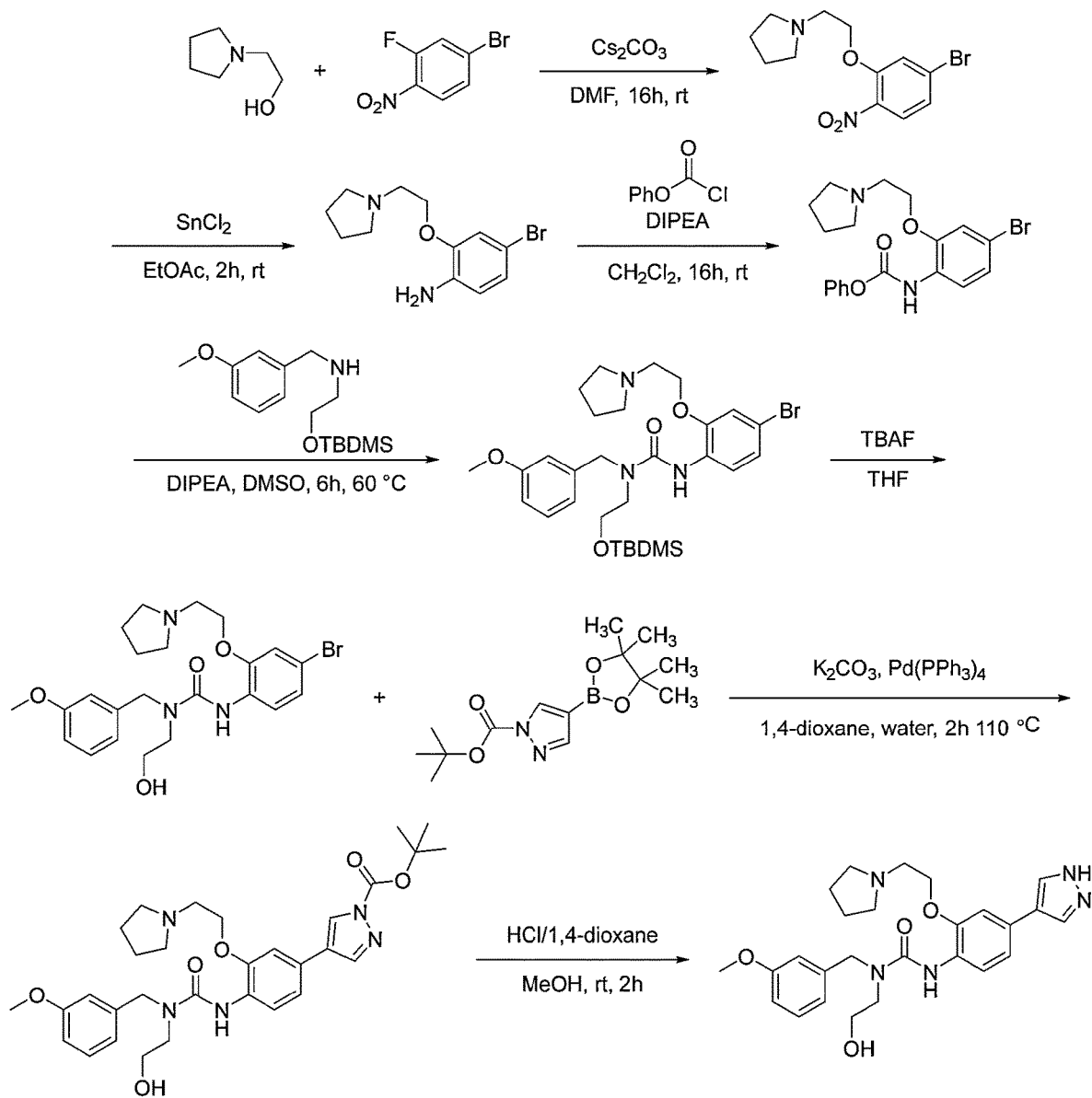
FIG. 57 is the synthesis of ROCK inhibitor RKI-H-1y.
Figure 58:
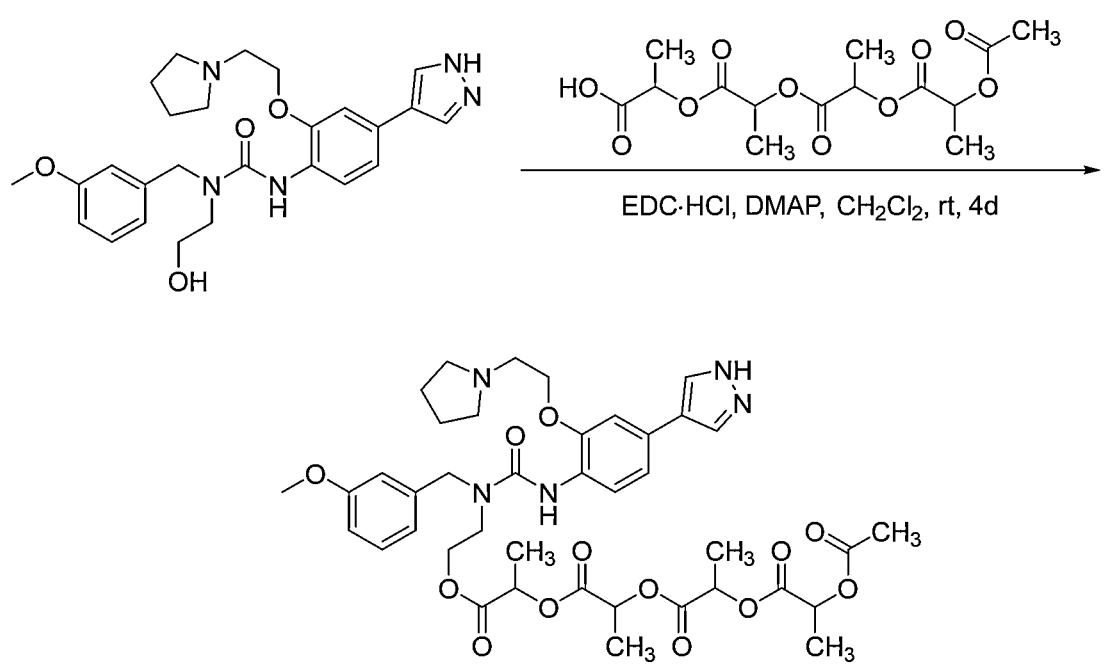
FIG. 58 is the synthesis of ROCK inhibitor compound 90-1 via a coupling reaction of the PLA derivative F27-6 and ROCK inhibitor RKI-H-1y. Compound 91-1 is synthesized in a similar manner.
Figure 59:
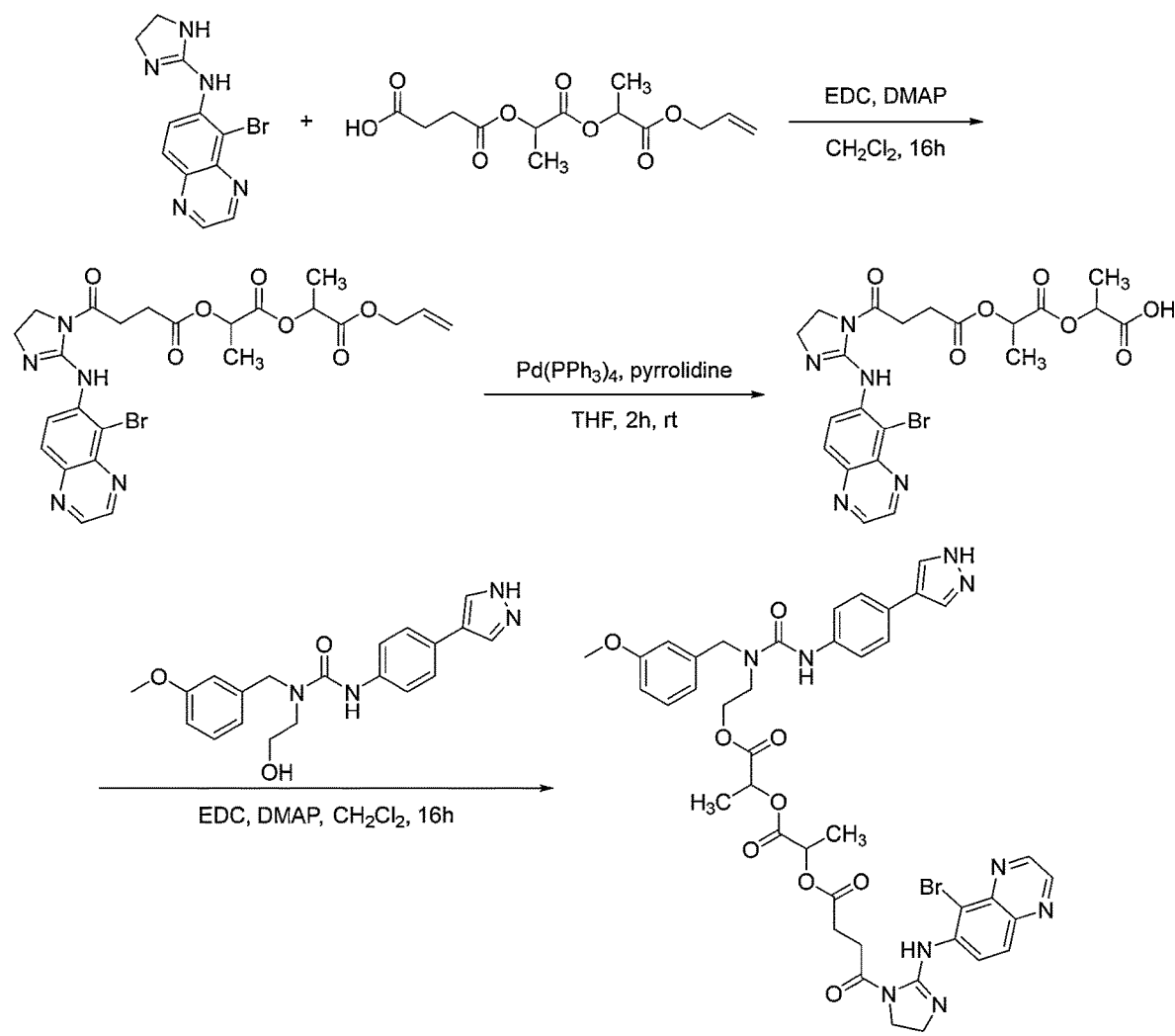
FIG. 59 is the synthesis of compound 101-3, a bis-prodrug of a ROCK inhibitor and Brimonidine.
Figure 60:
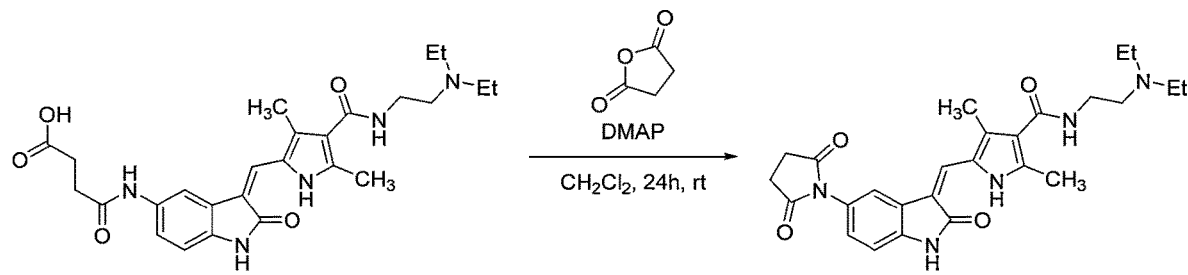
FIG. 60 is the synthesis of compound 108-1, a Sunitinib derivative.
Figure 61:
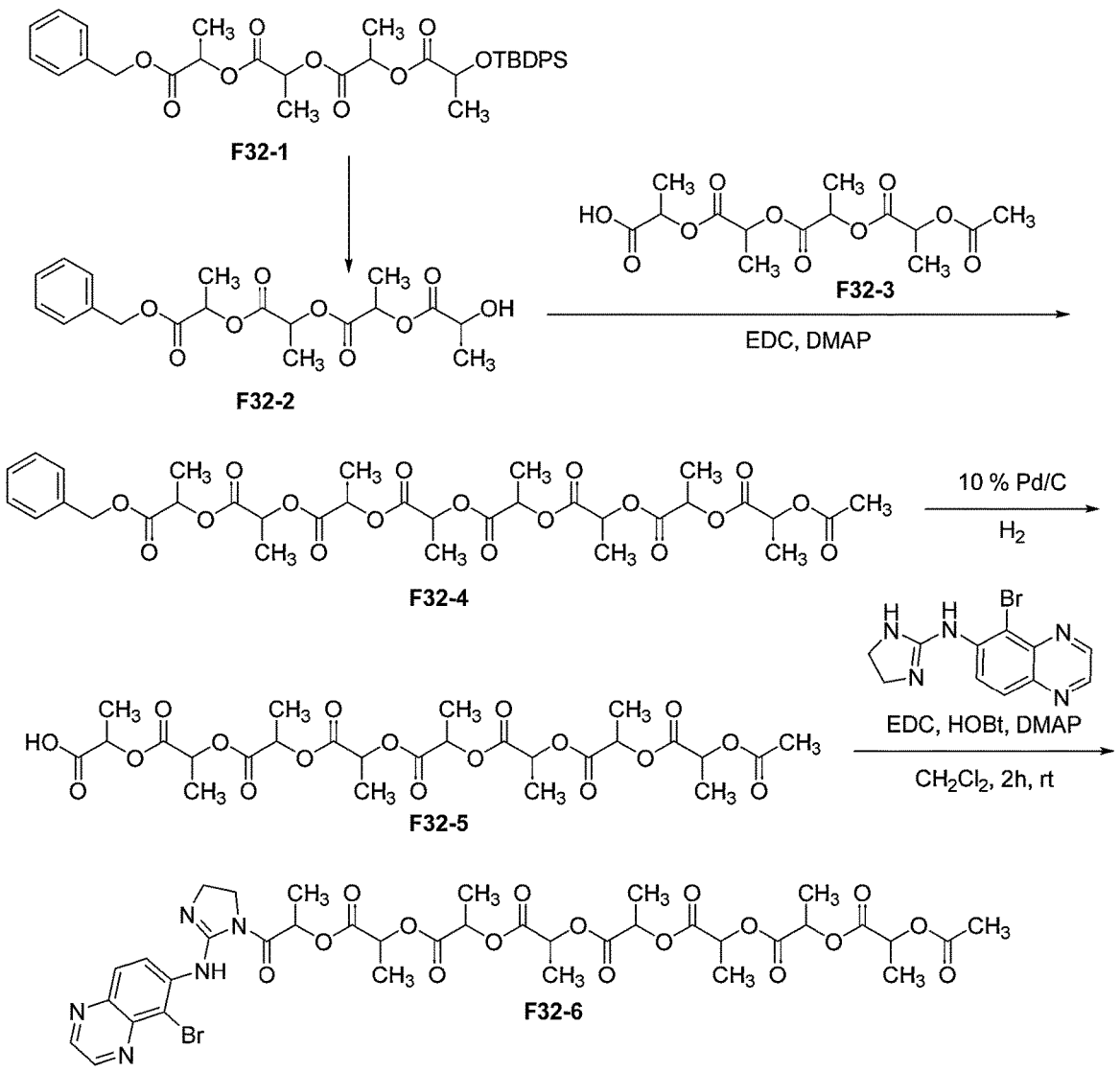
FIG. 61 is the synthesis of compound F32-6, a Brimonidine mono-prodrug. Compound F32-1 was converted to F32-2 on a 14.0 g scale. Formation of compound F32-2 was confirmed by NMR and LC-MS and compound F32-2 was isolated on a 4.8 g scale. Compound F32-2 was converted to F32-4 on a 4.8 g scale. Formation of compound F32-4 was confirmed by NMR and LC-MS and compound F32-4 was isolated on a 8.2 g scale. Compound F32-4 was converted to F32-5 on a 8.2 g scale. Formation of compound F32-5 was confirmed by NMR and LC-MS and compound F32-6 was isolated on a 5.7 g scale.
Figure 62:
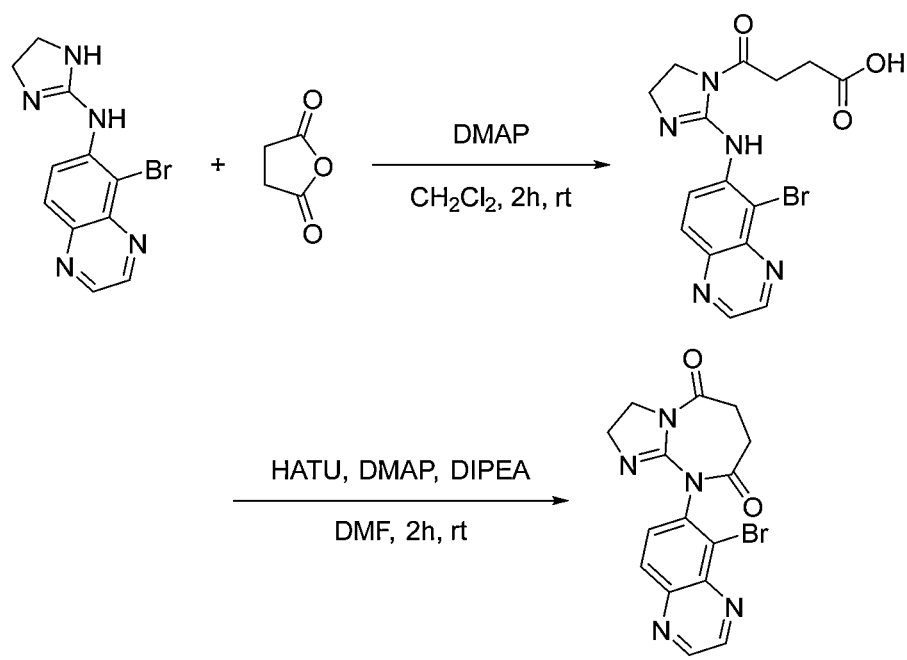
FIG. 62 is the synthesis of compound 110-1, a Brimonidine derivative.
Figure 63:
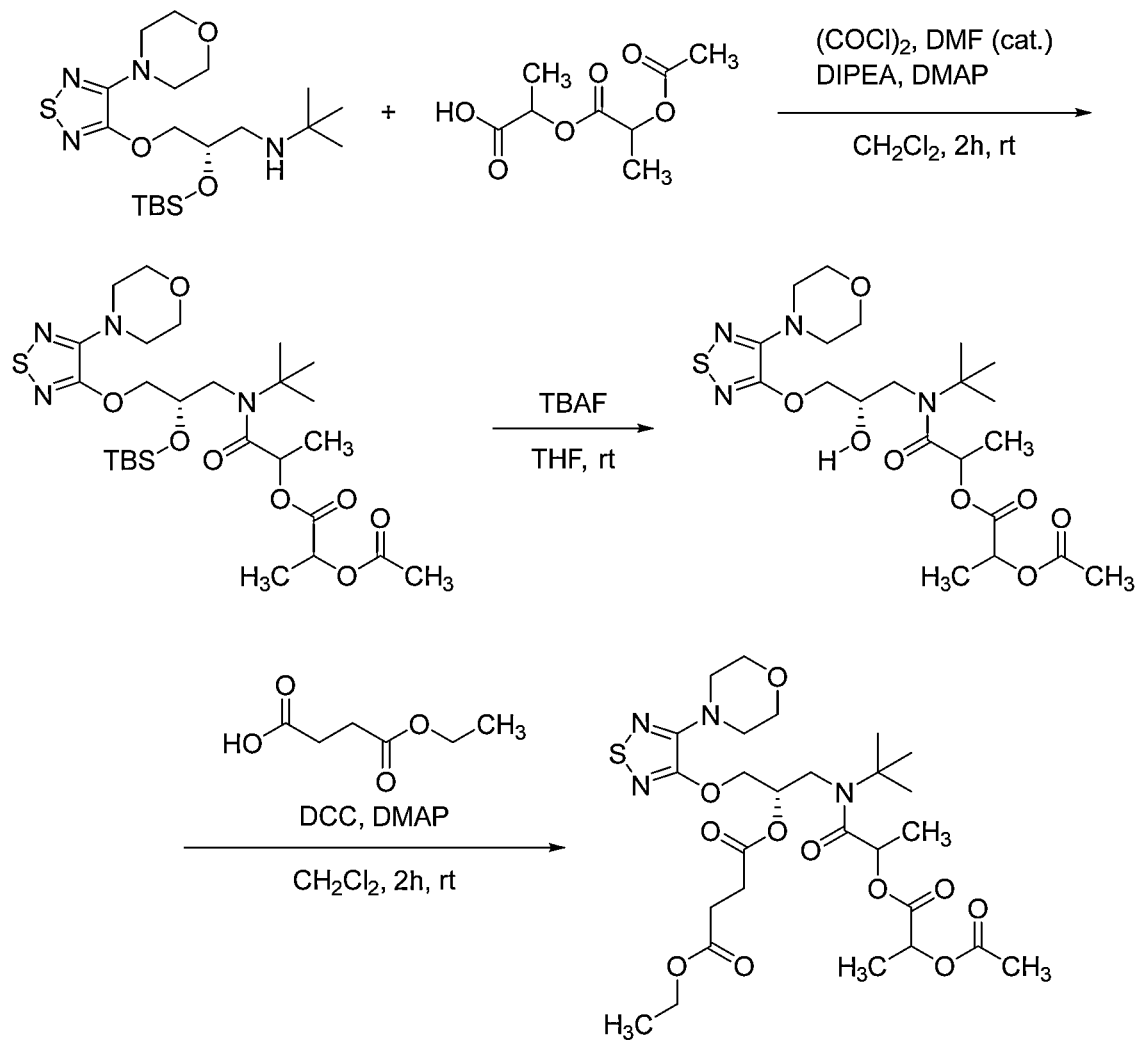
FIG. 63 is the synthesis of compound 117-6, a Timolol mono-prodrug.
Figure 64:
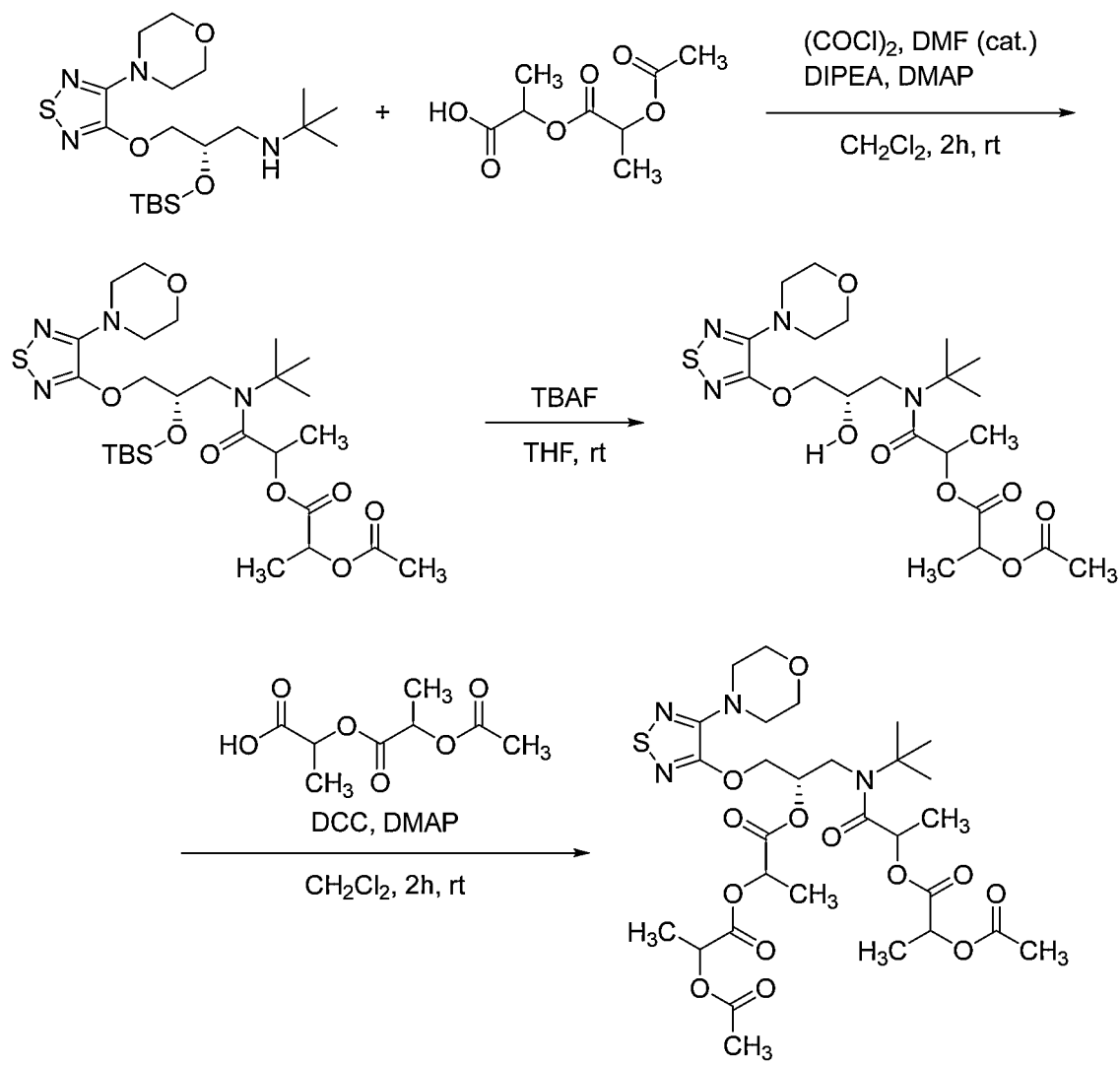
FIG. 64 is the synthesis of compound 118-1, a Timolol mono-prodrug. Compound 119-6 is synthesized in a similar manner.
Figure 65:
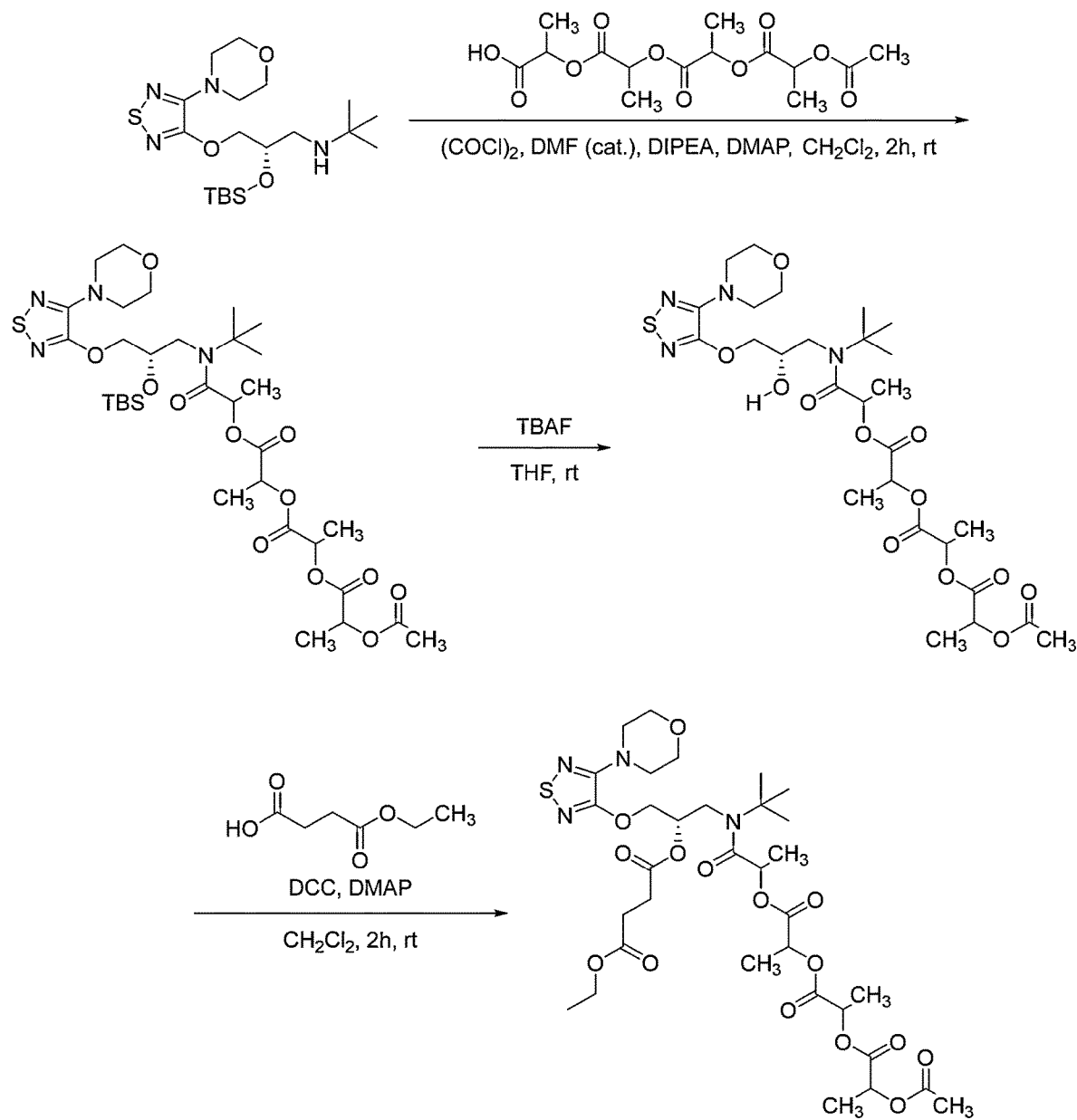
FIG. 65 is the synthesis of compound 120-1, a Timolol mono-prodrug.

A lag period of about 10 days was observed for microspheres with a target drug loading of 15%. (FIG. 50) However, when the target drug loading was increased to 20%, no lag period was observed. (FIG. 51). Without wishing to be bound to any one theory, this is probably due to the slightly porous structure of the microspheres caused by the higher target drug loading. (FIG. 52A and FIG. 52B)

Example 10. Non-Limiting Examples of Compounds of Formula I
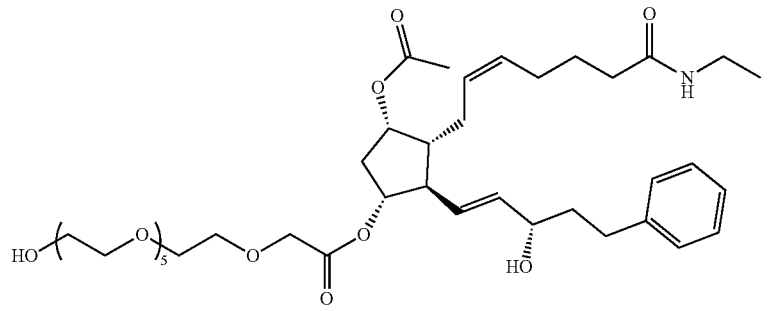
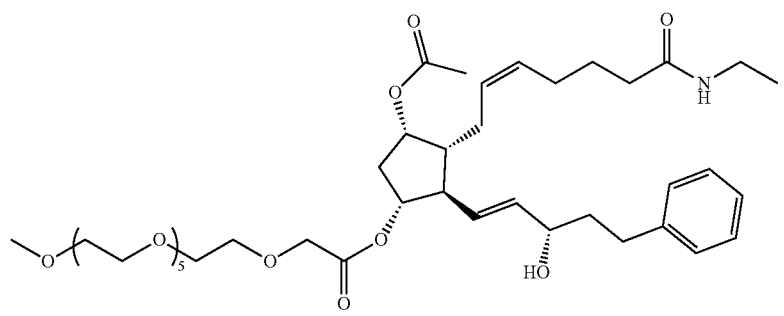
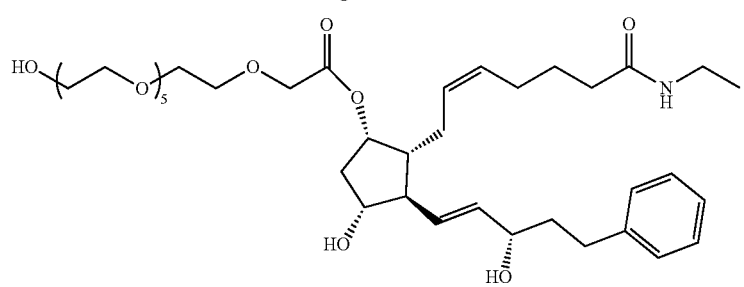
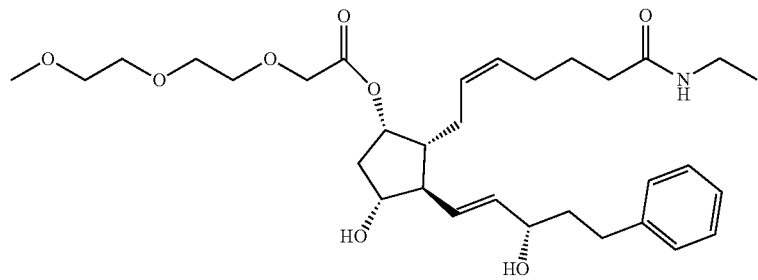
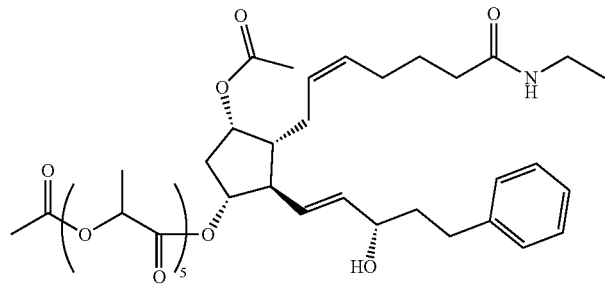

-continued
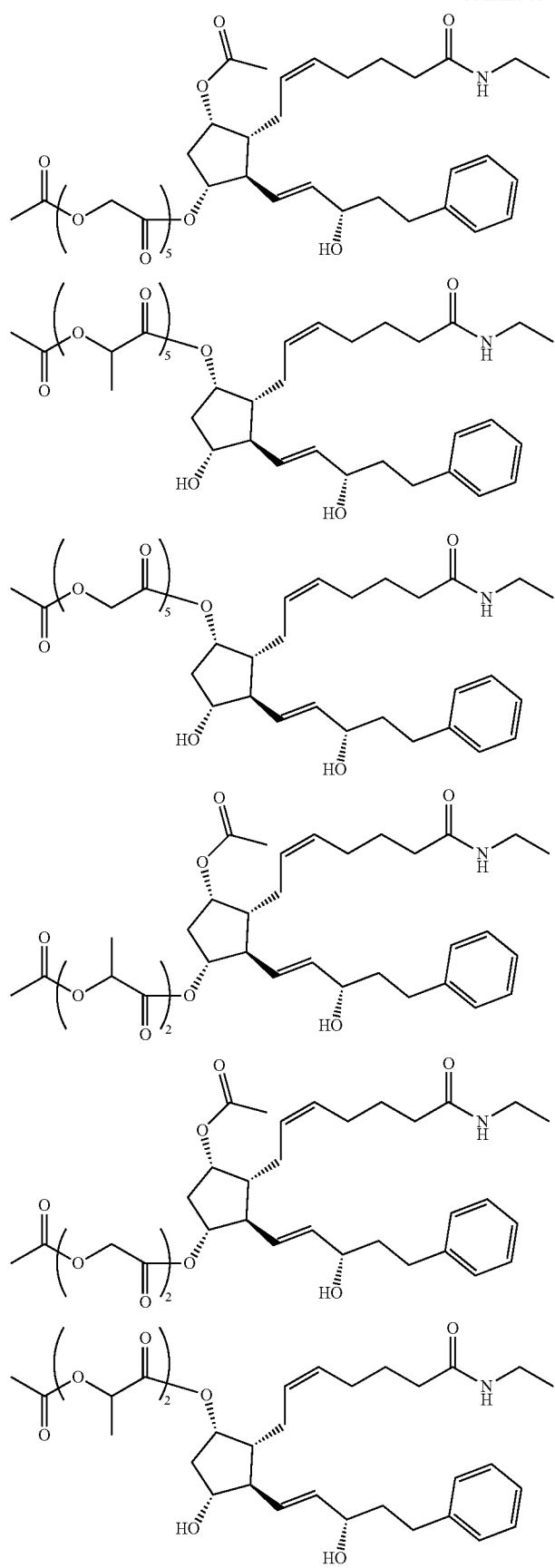

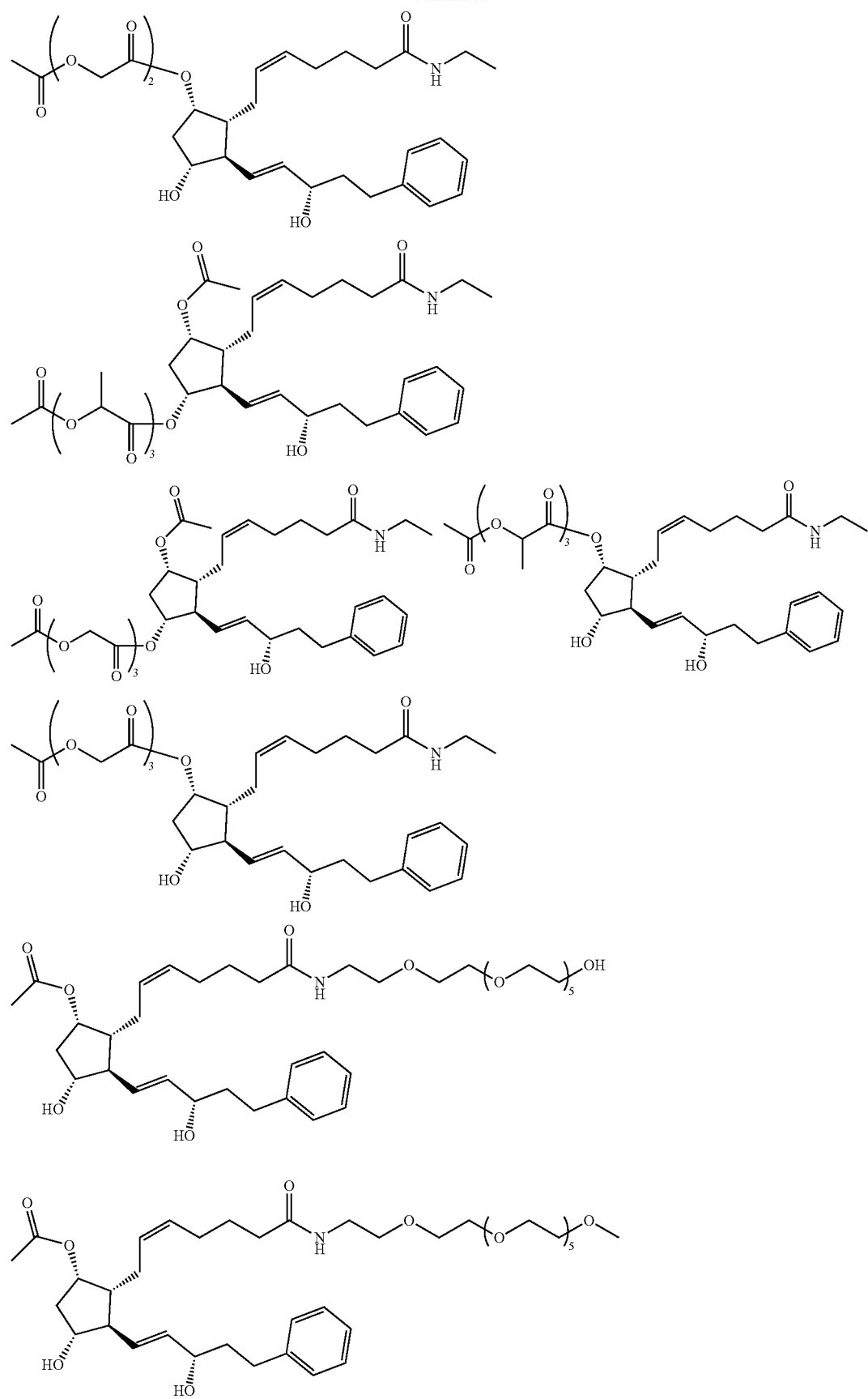

521
-continued
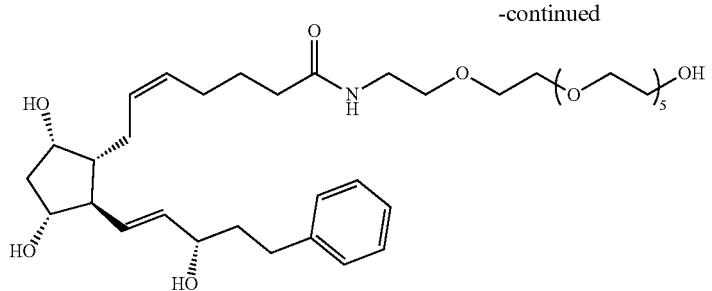
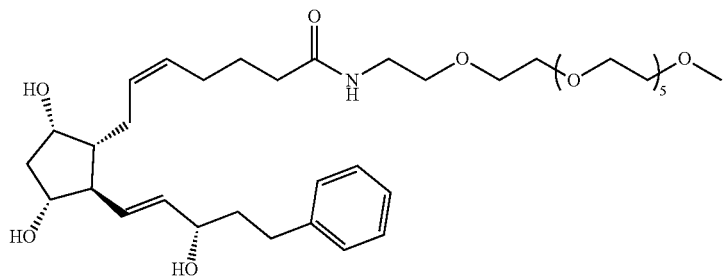
Example 11. Non-Limiting Examples of Compounds of Formula II
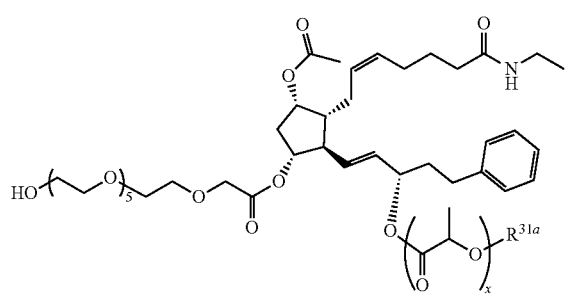
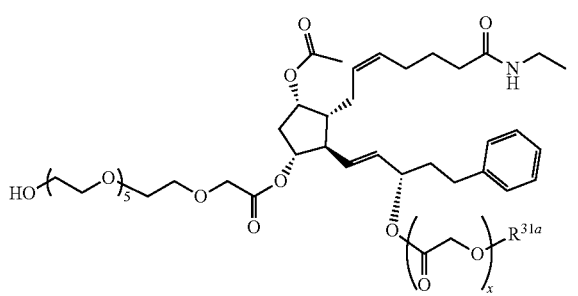
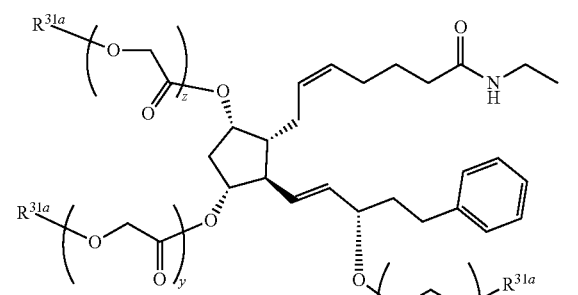
522
-continued
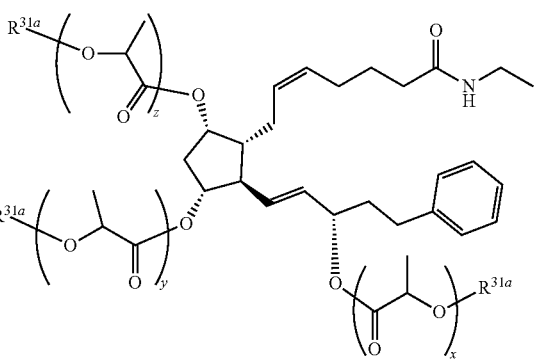
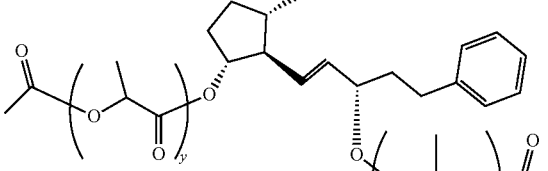

523
-continued
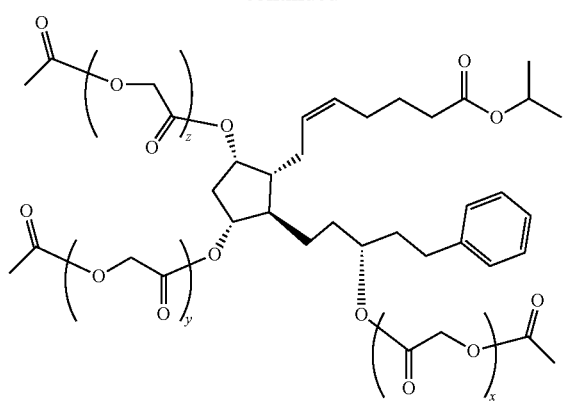
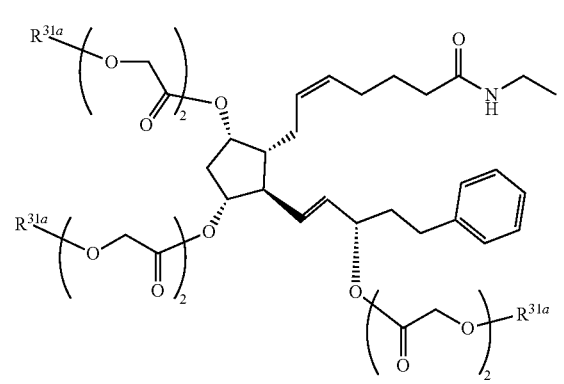
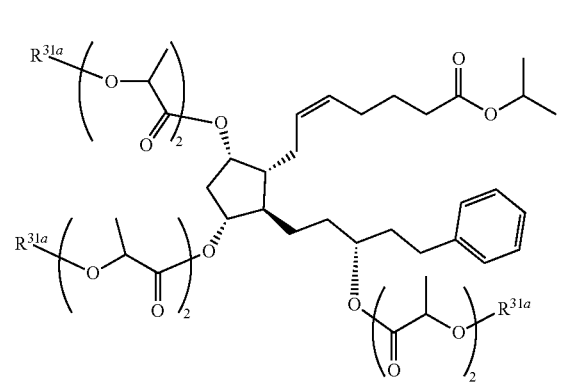
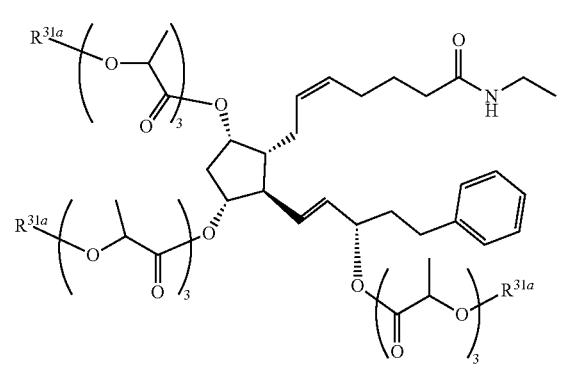
524
-continued
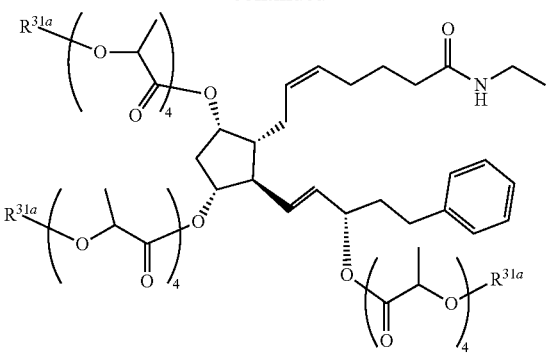
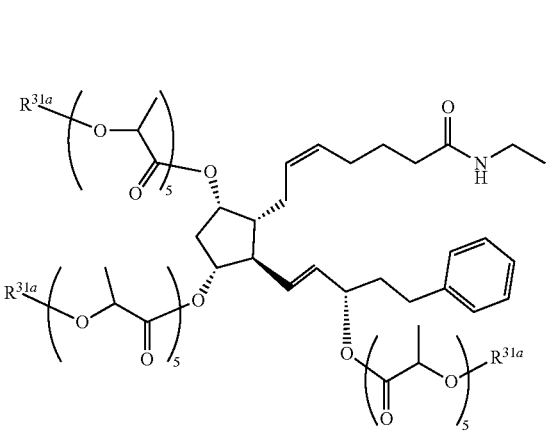
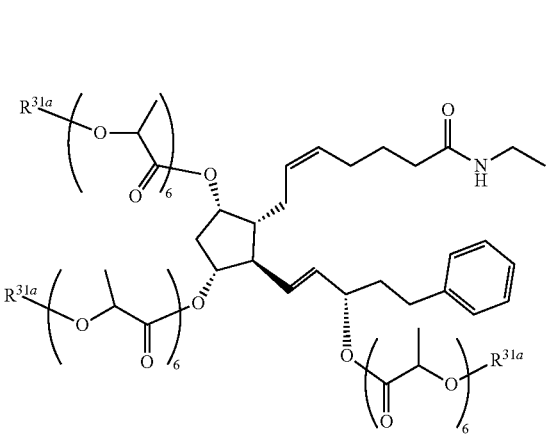
Example 12. Non-Limiting Examples of Compounds of Formula III
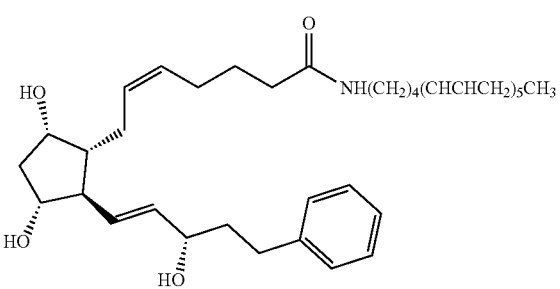

-continued
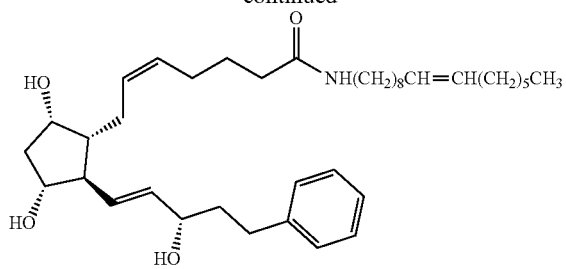
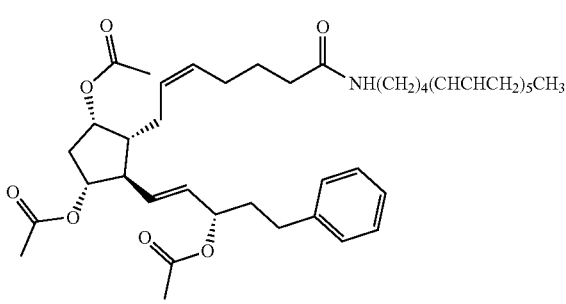
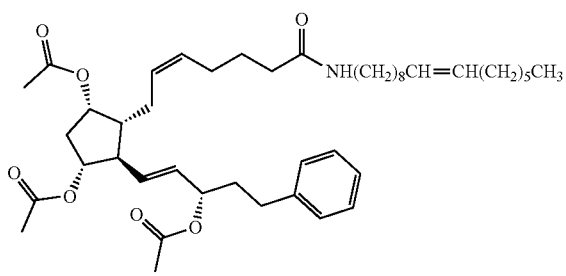
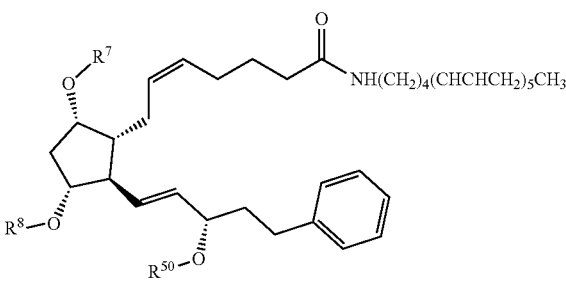
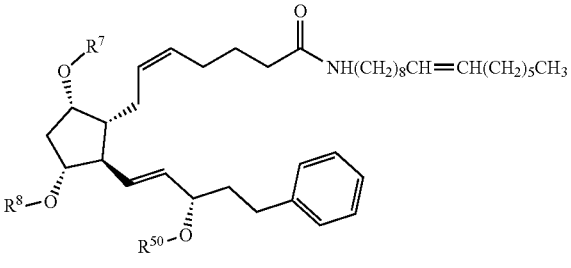
Example 13. Non-Limiting Examples of Compounds of Formula IV
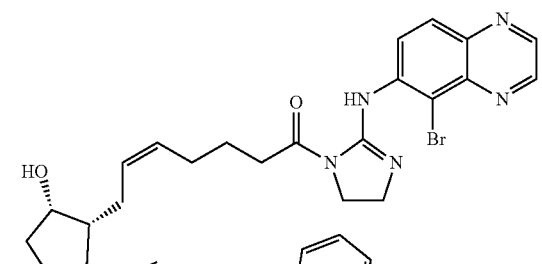
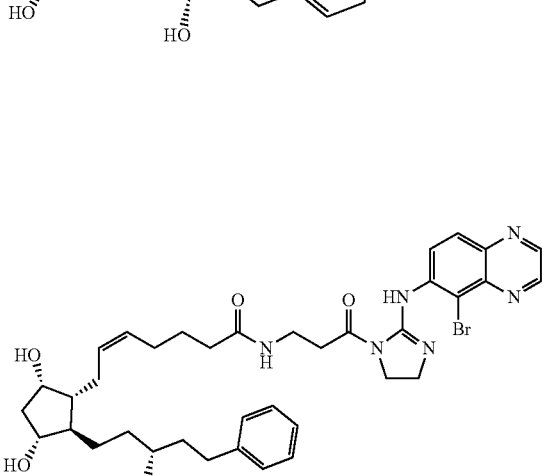
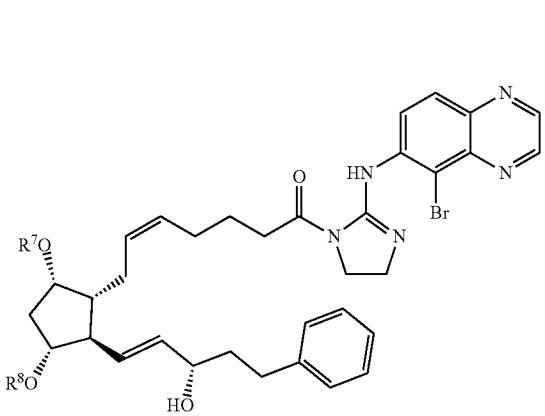
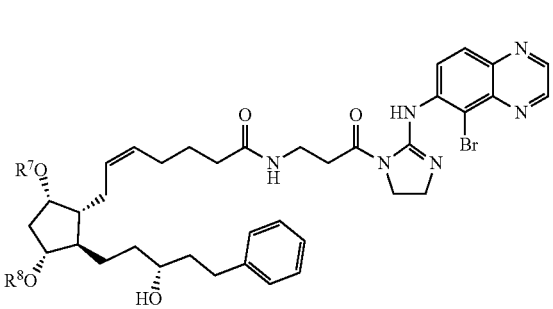

527
-continued
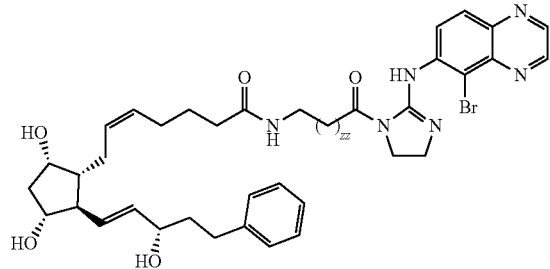
528
-continued
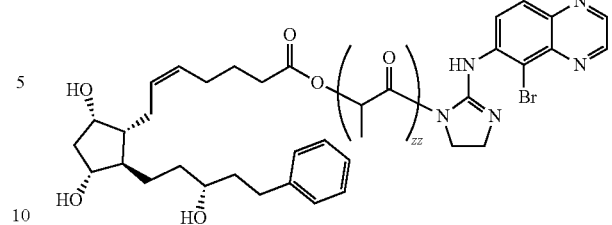
Example 14. Non-Limiting Examples of Formula V and VI
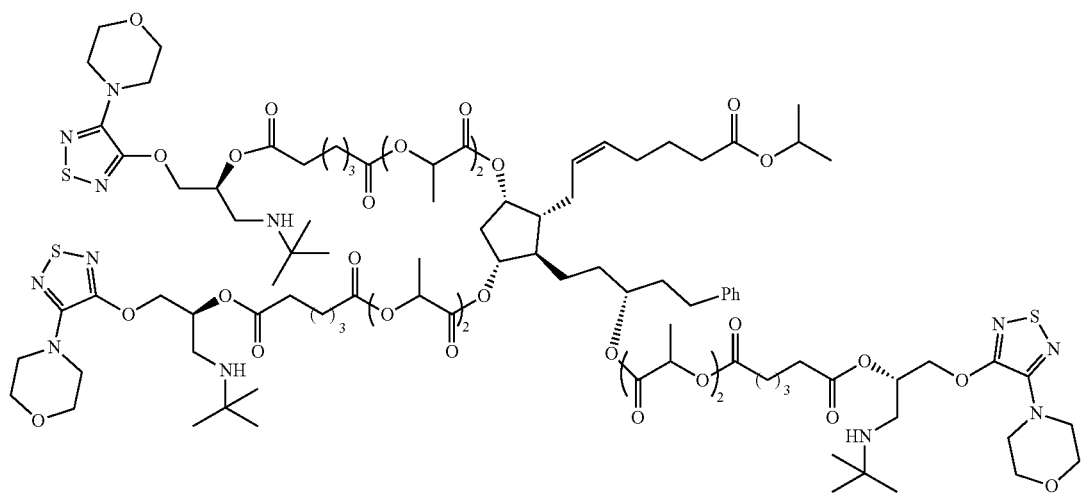
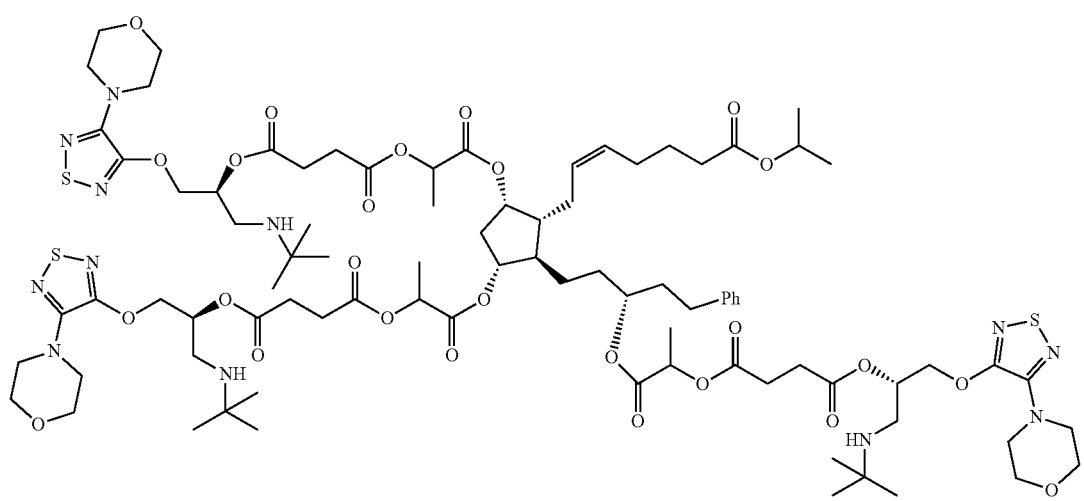

-continued
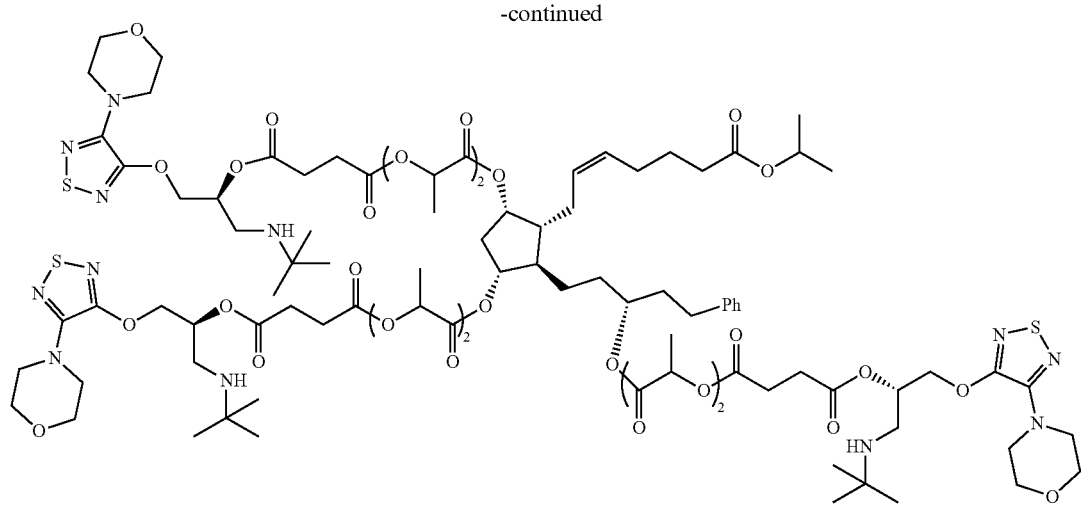
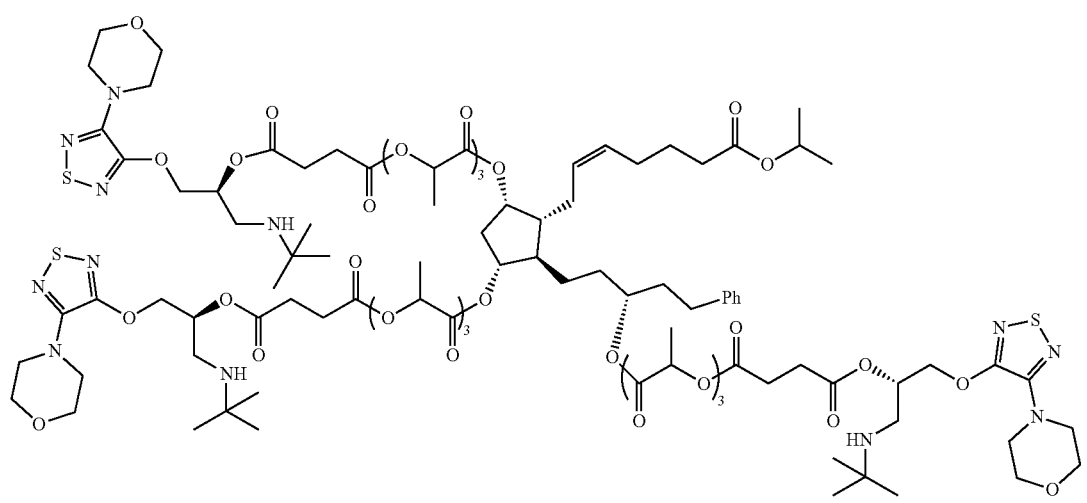
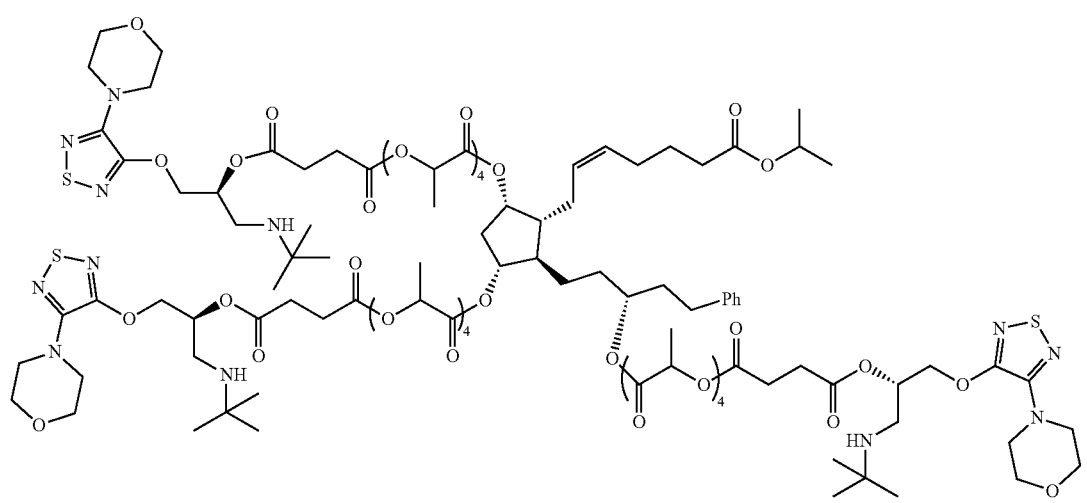

531
532
-continued
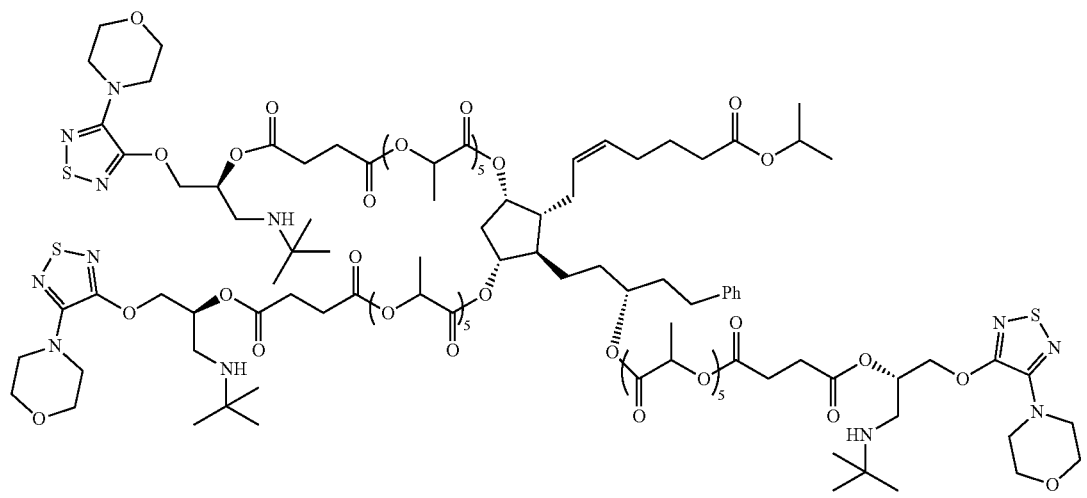
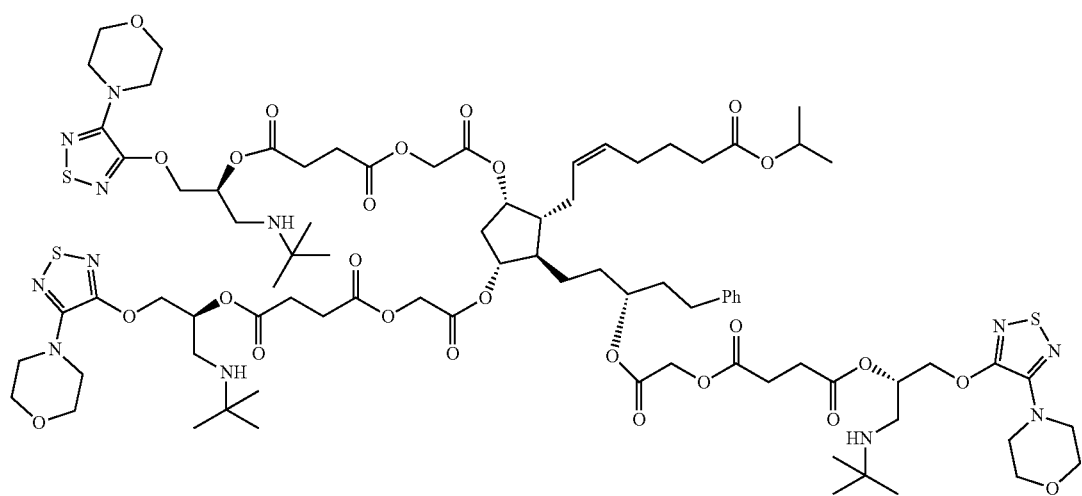
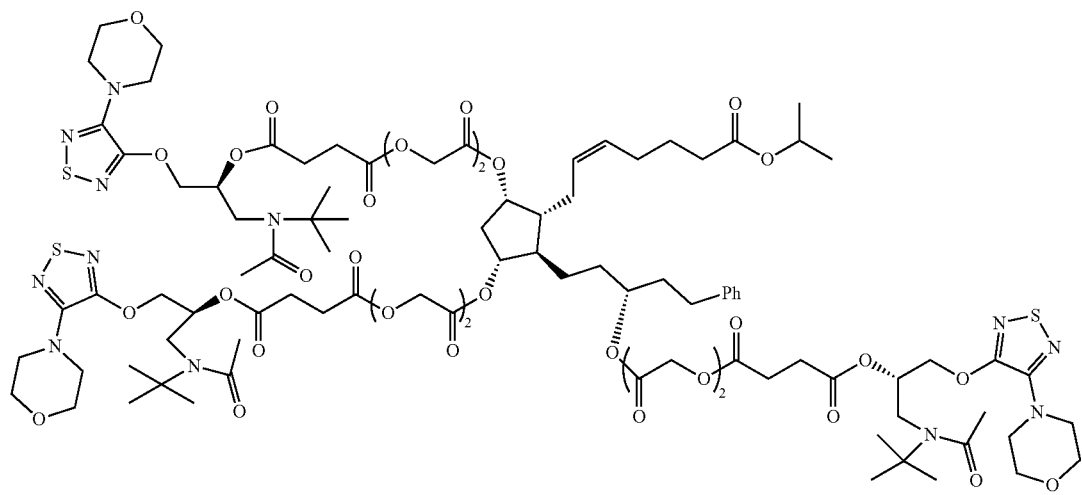

533
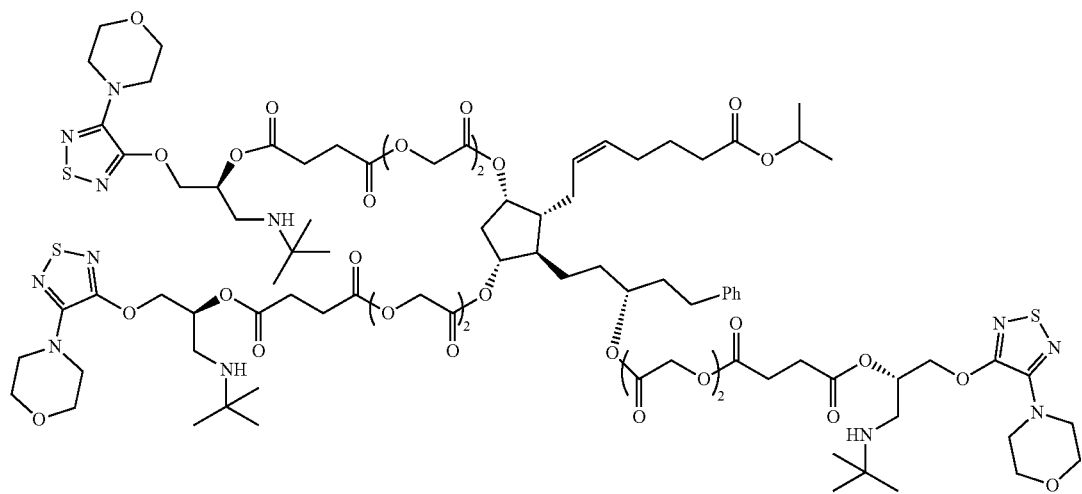
534
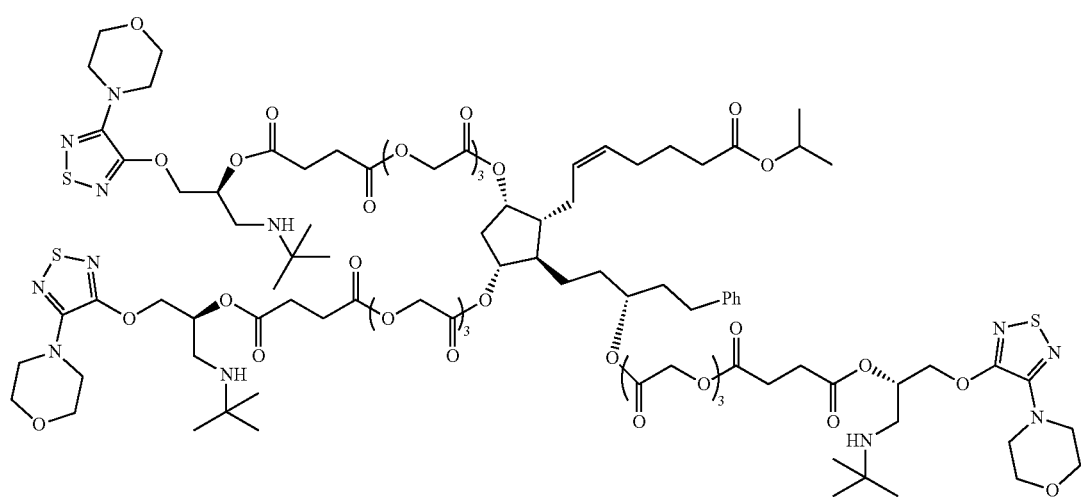
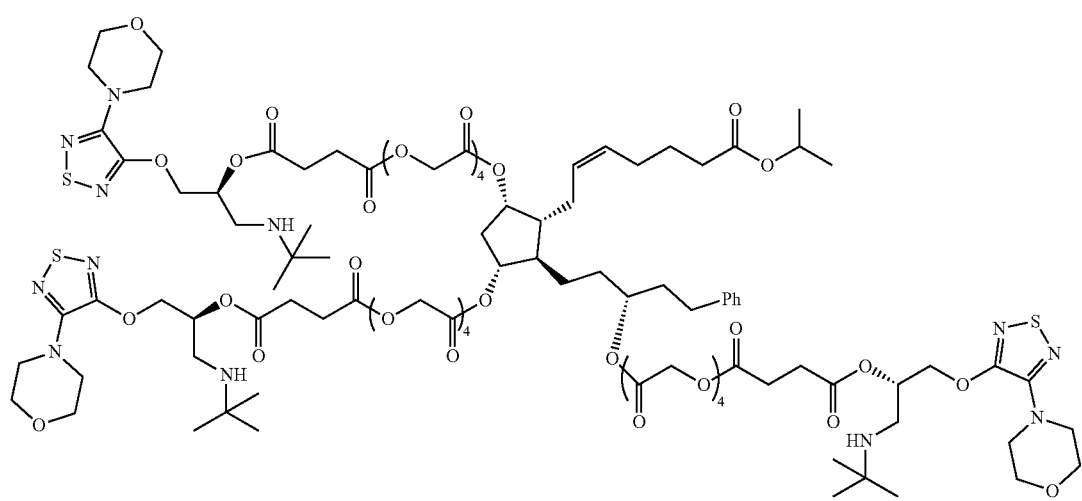

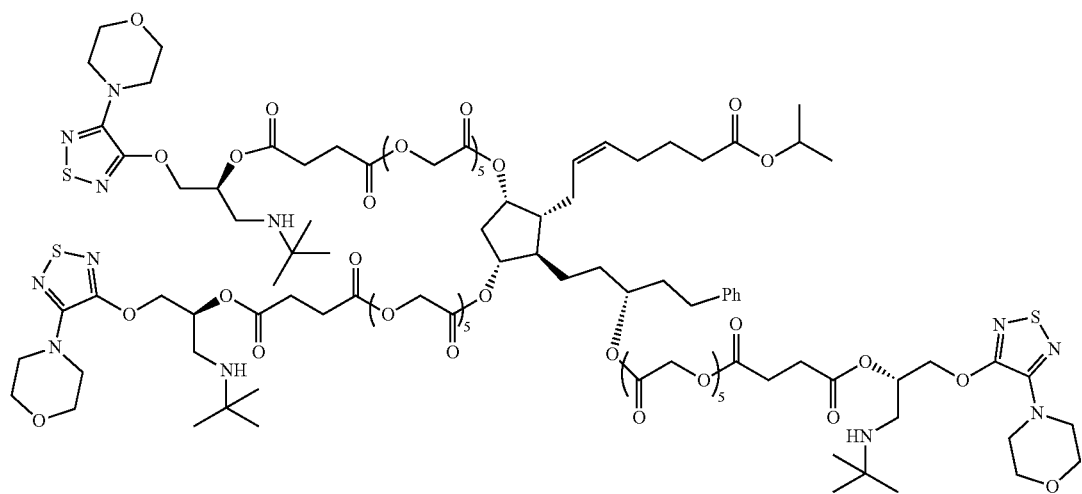
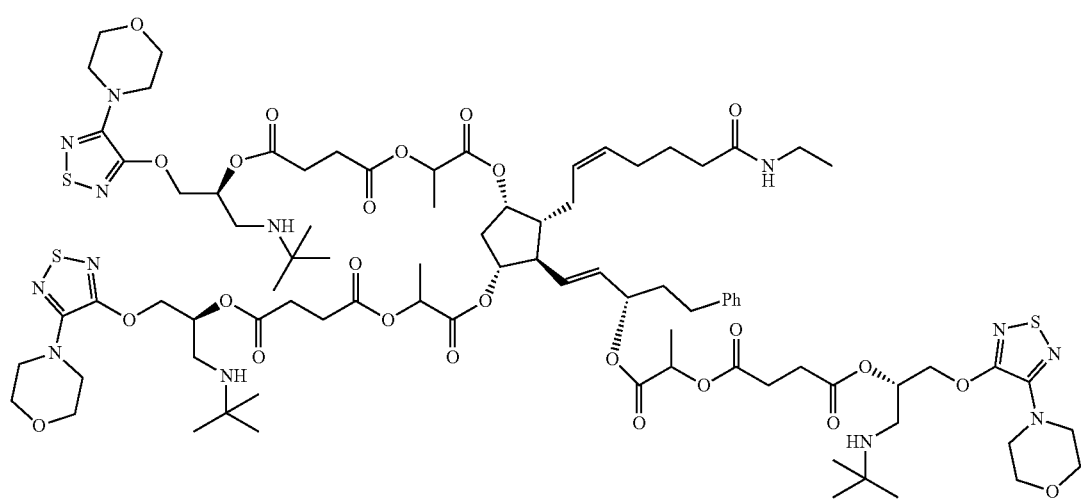
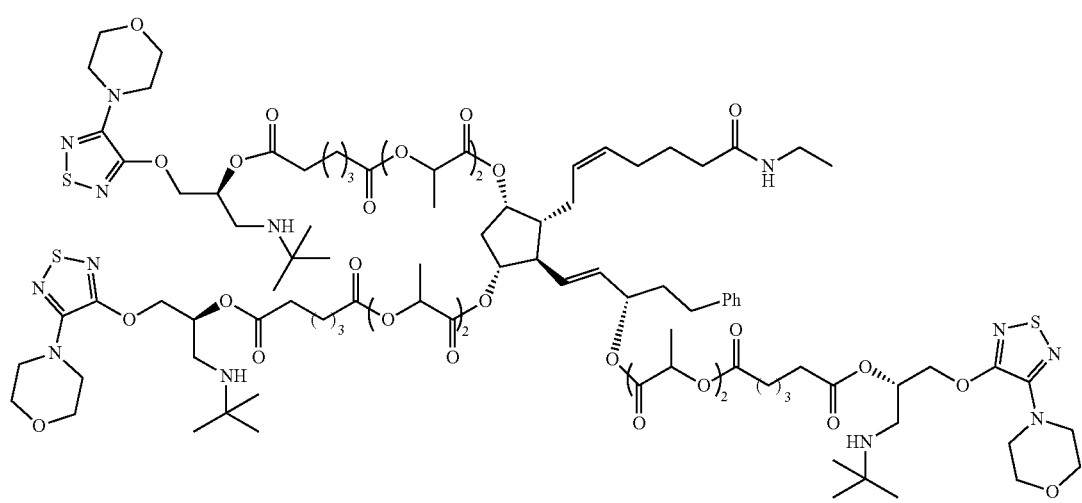

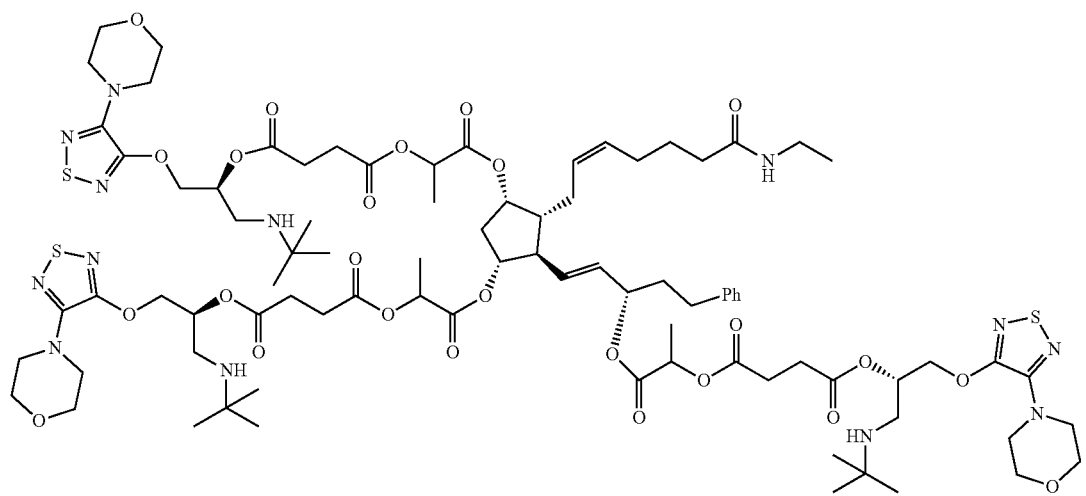
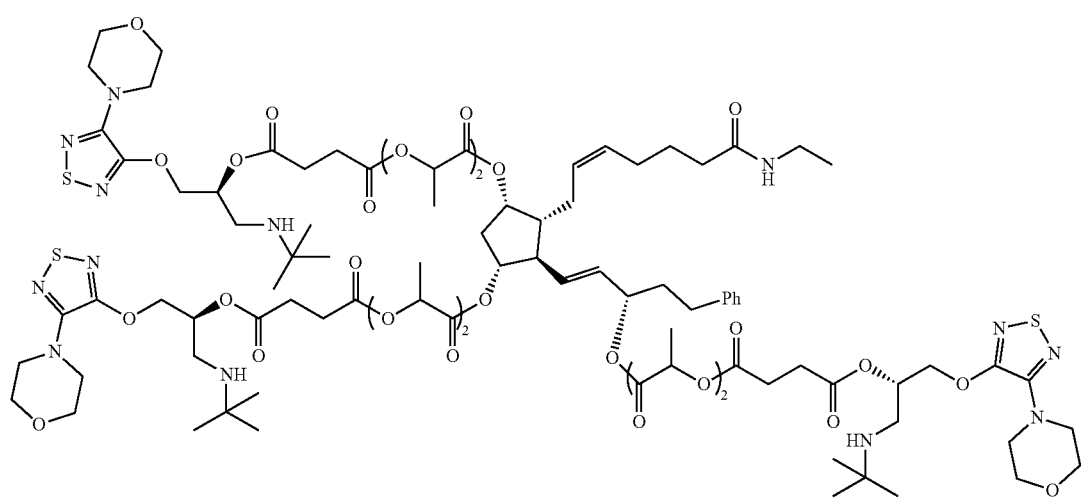
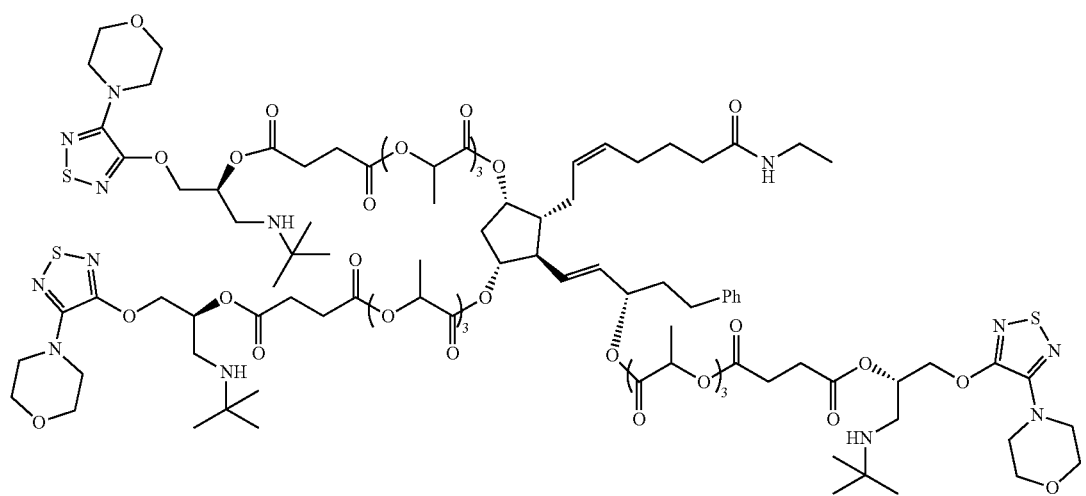

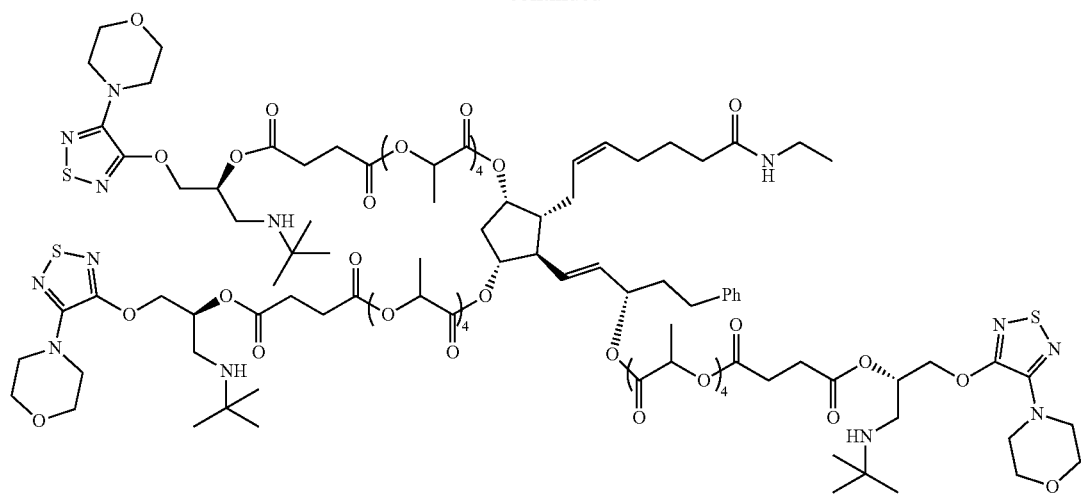
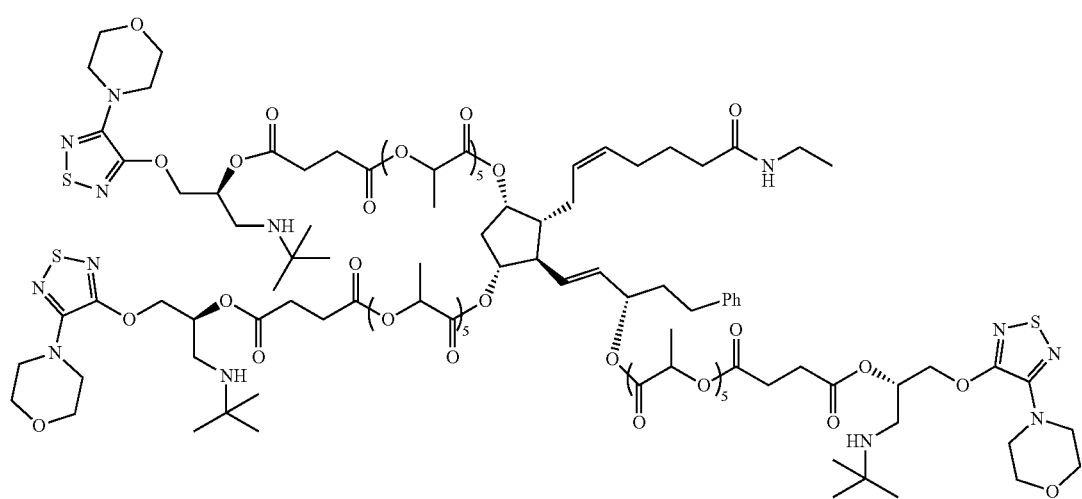
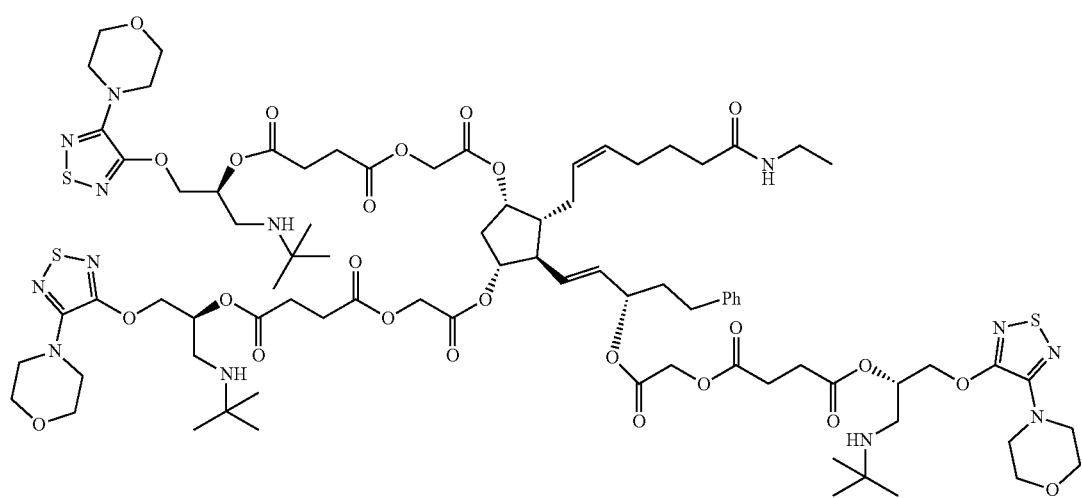

541
542
-continued
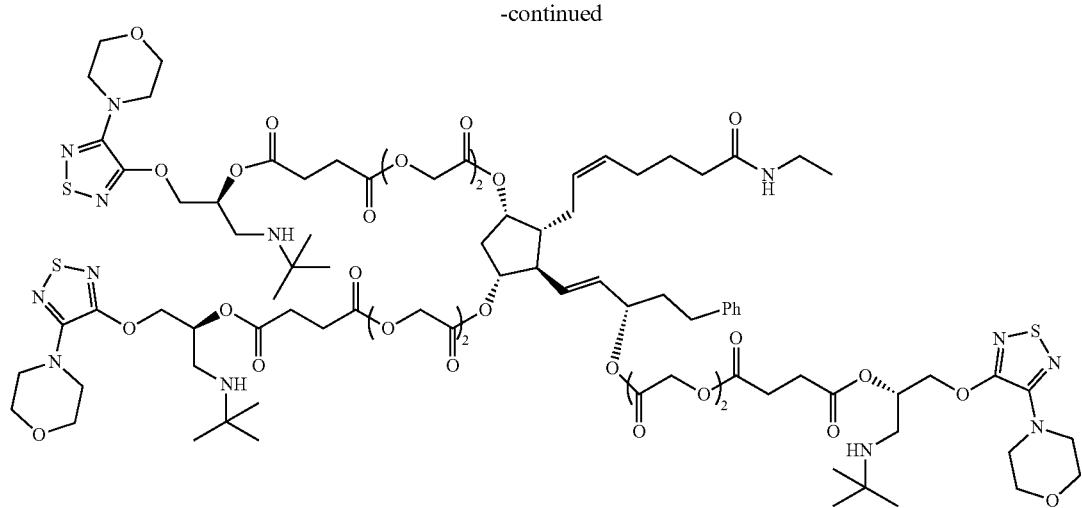
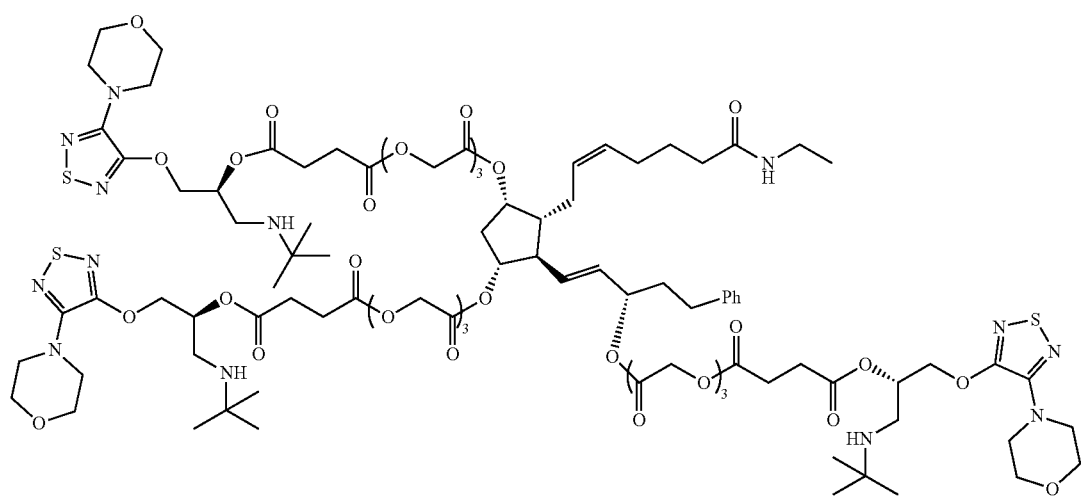
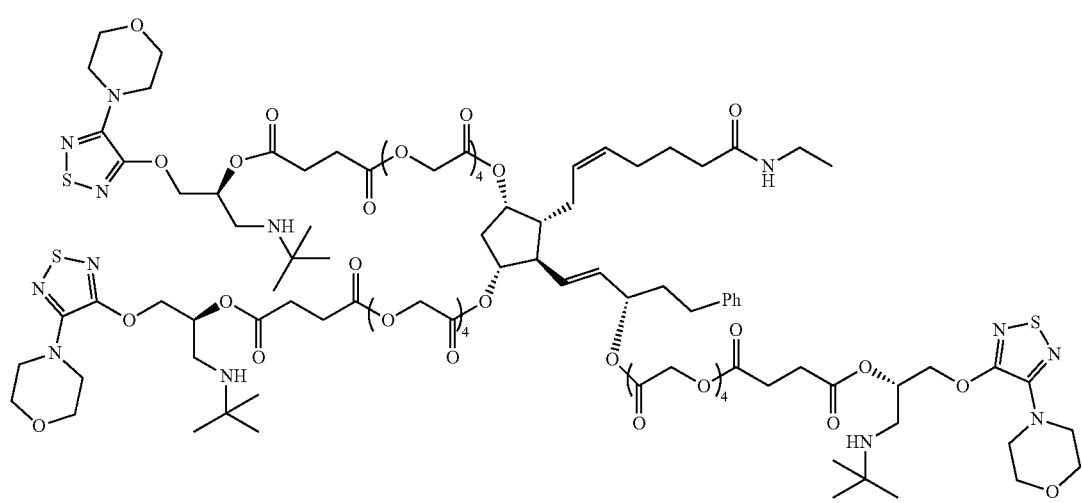

-continued
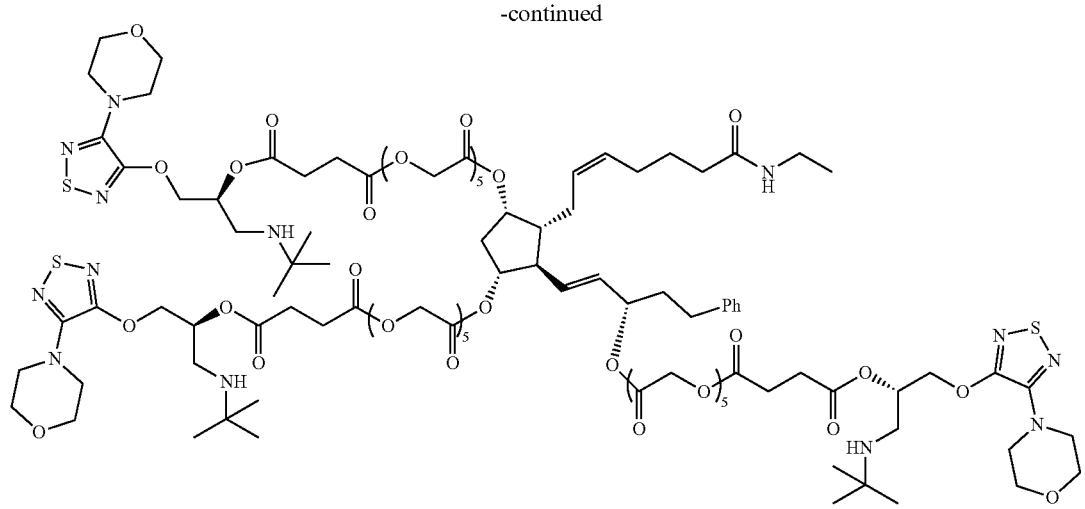
Example 15. Non-Limiting Examples of Formula VII and VIII
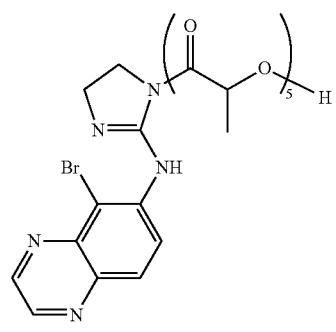
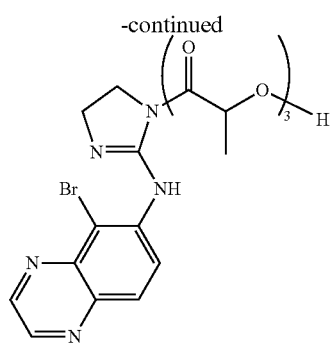
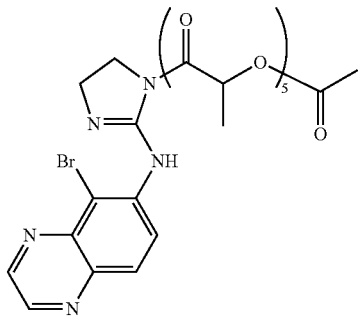
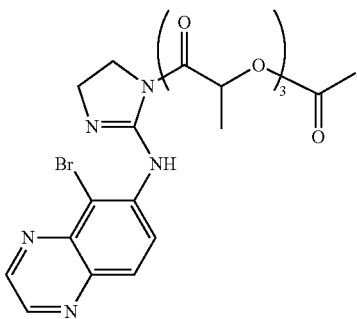
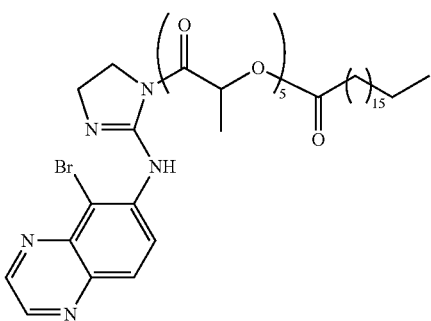
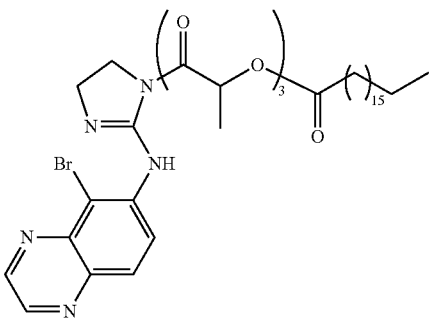

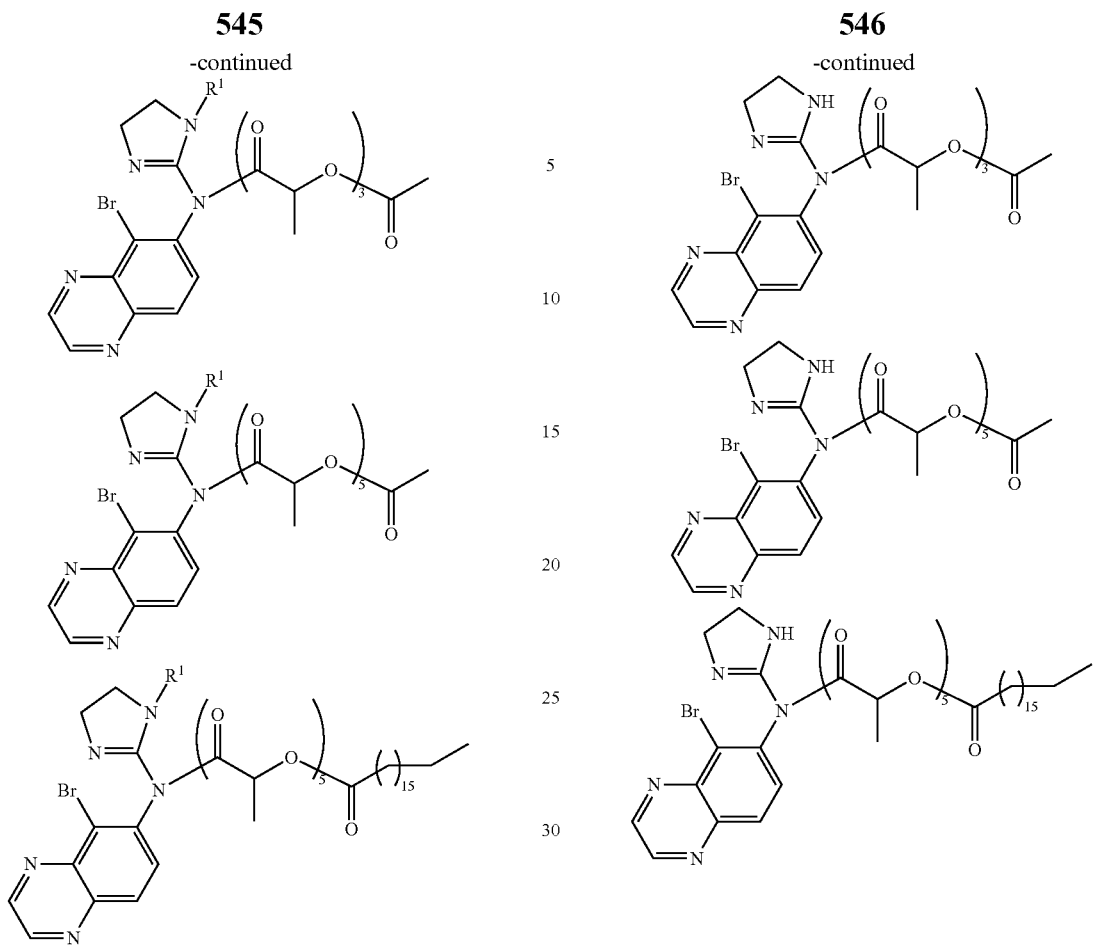
Example 16. Non-Limiting Examples of Formula IX and IX'
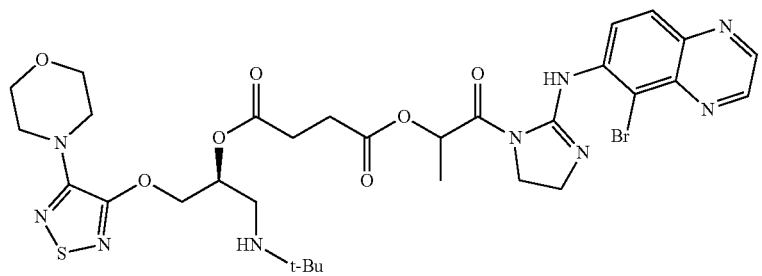
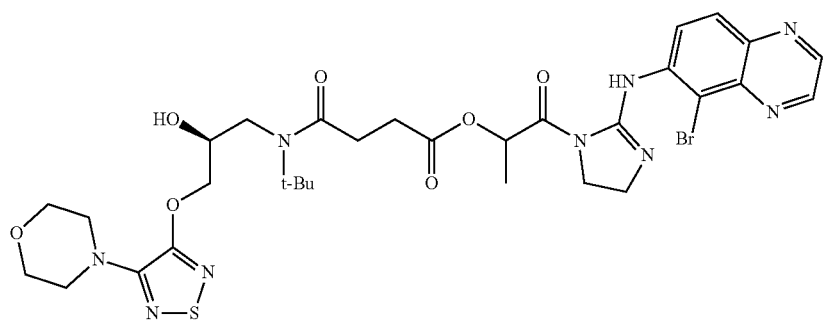

-continued
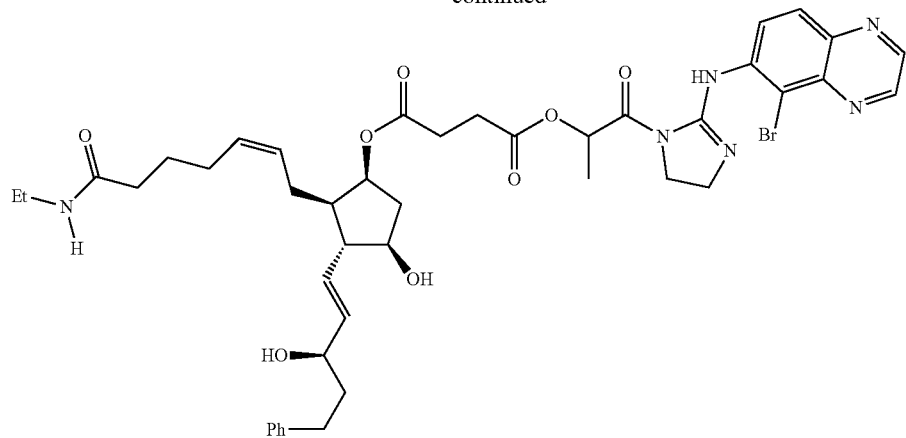
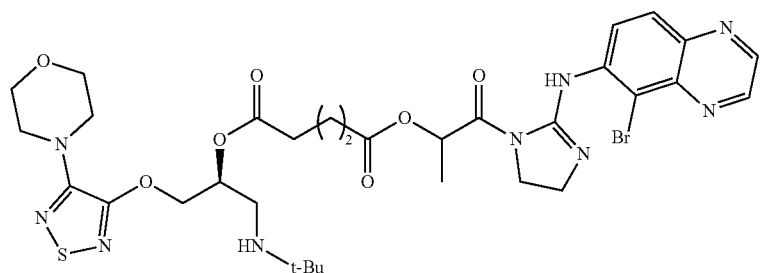
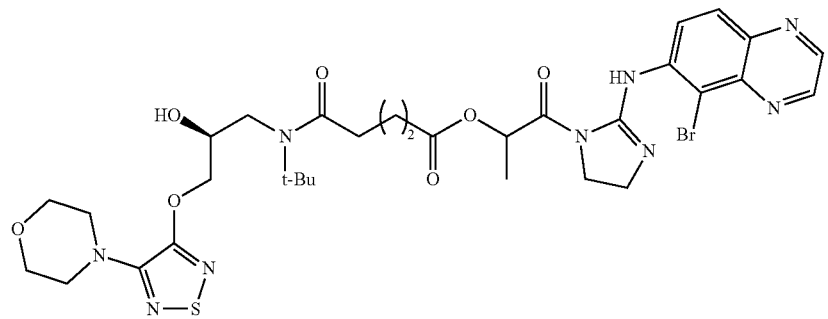
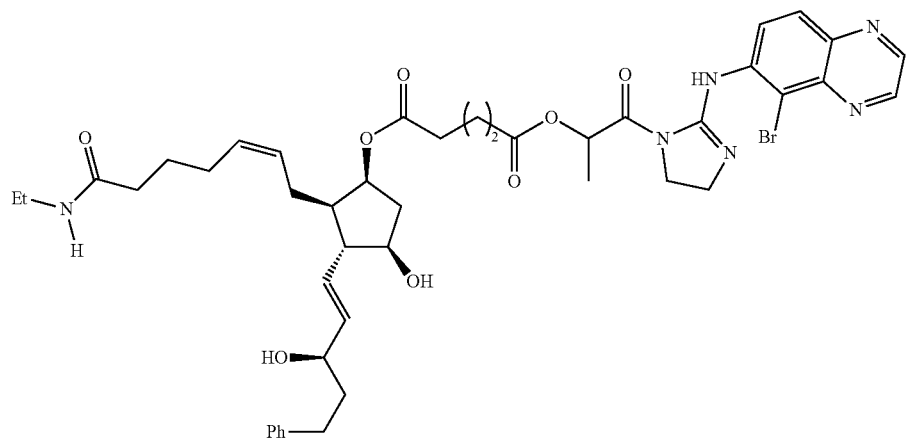

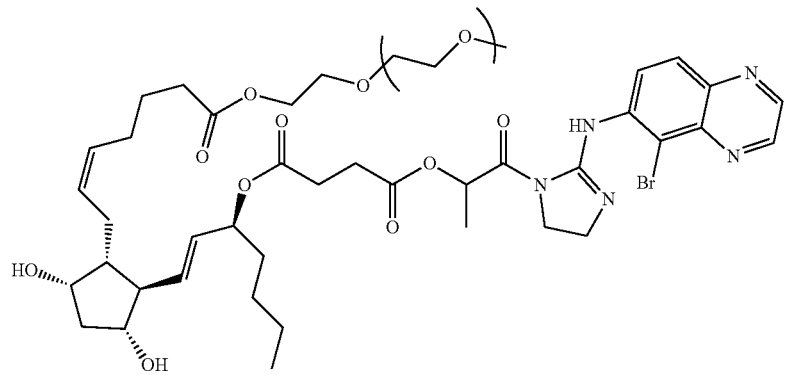
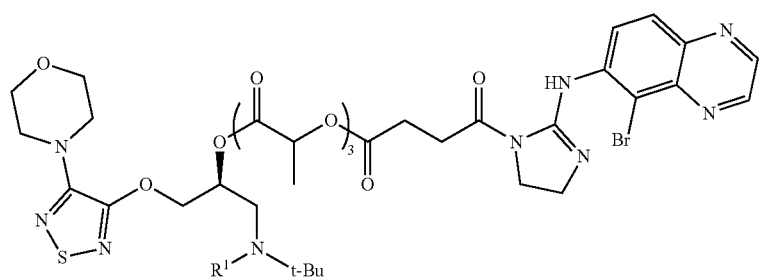
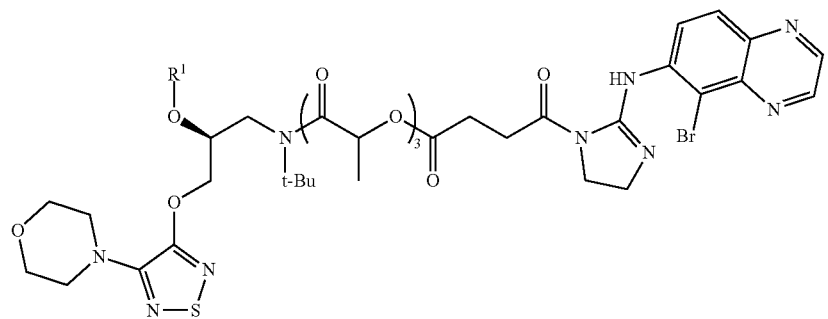
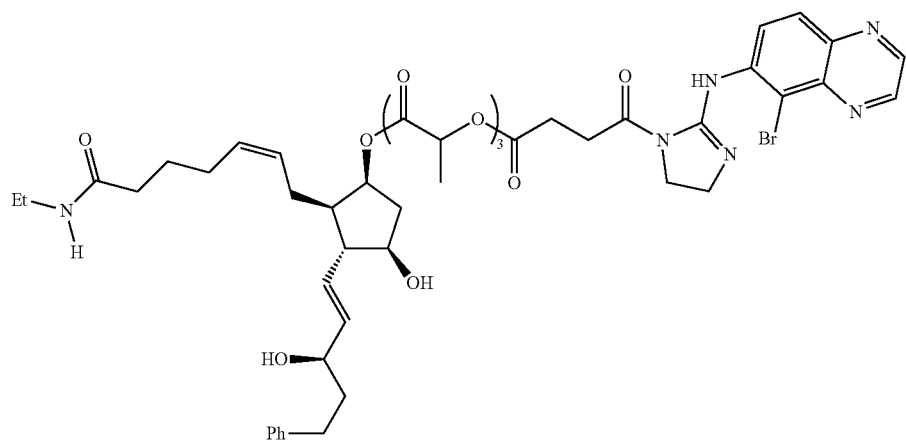

551
-continued
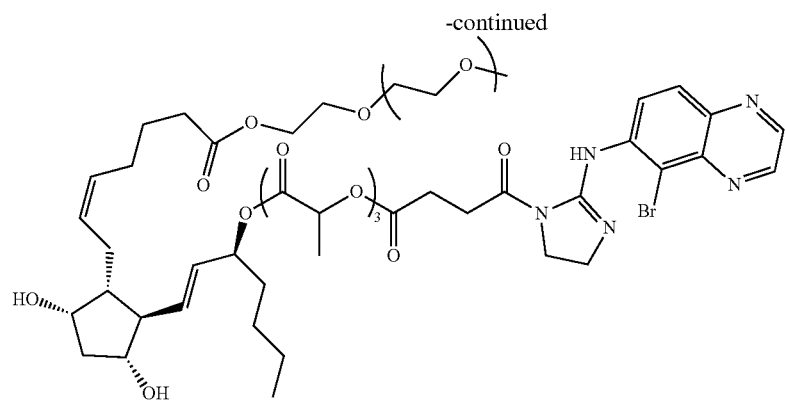
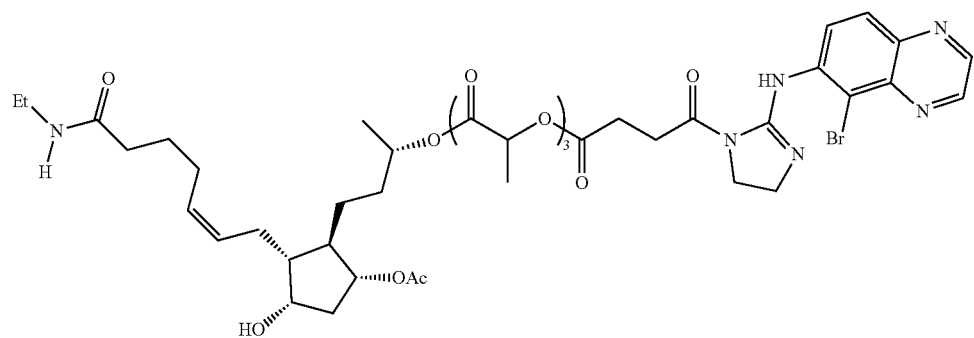
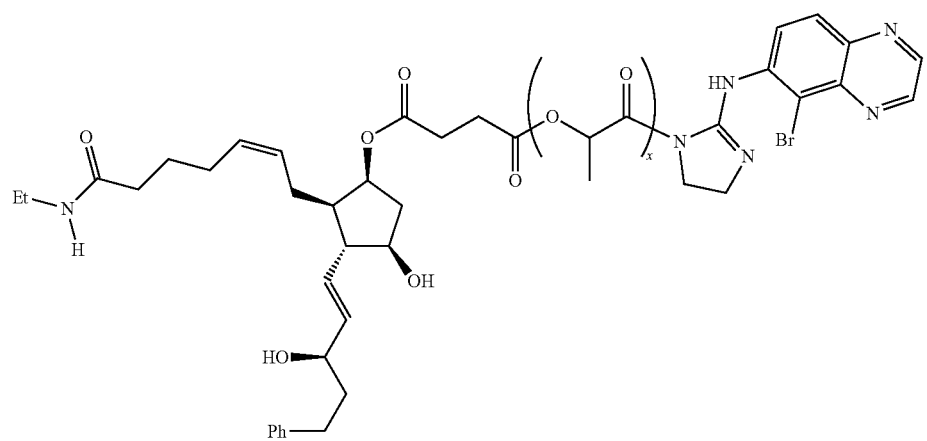
552

553
Example 17. Non-Limiting Examples of Formula X
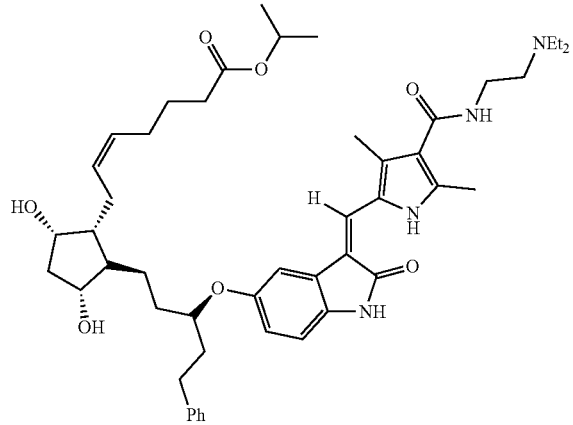
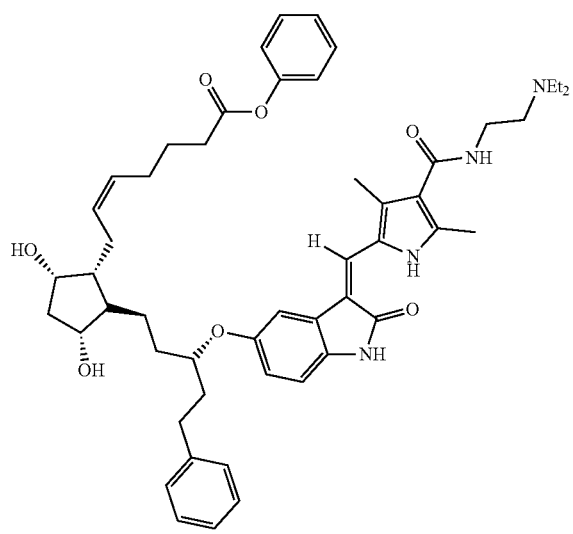
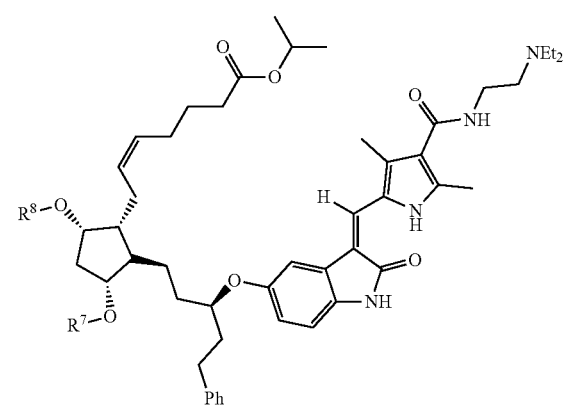
554
-continued
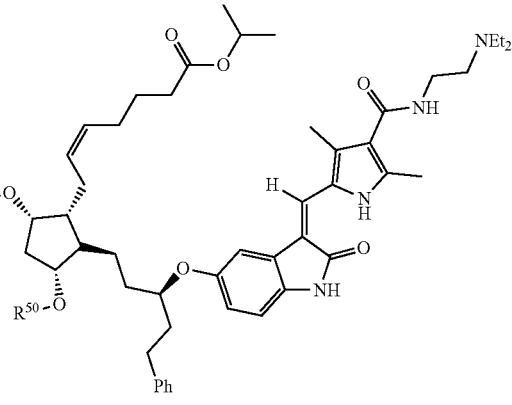
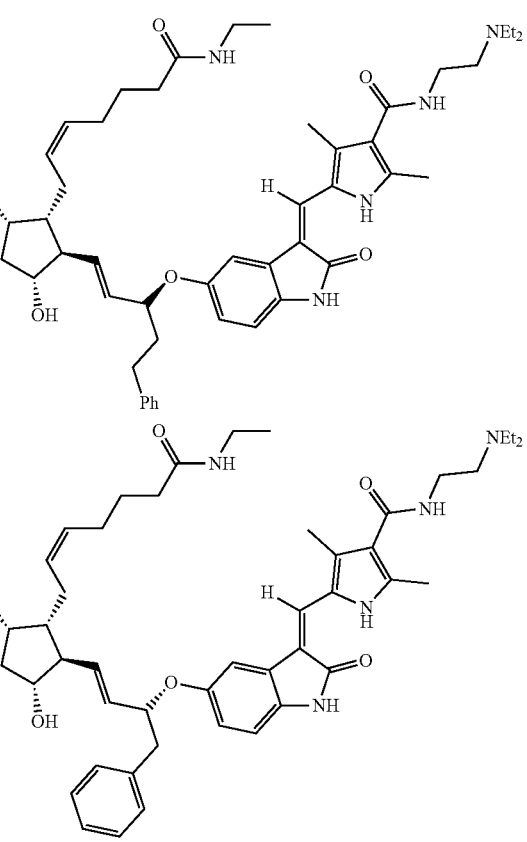

555
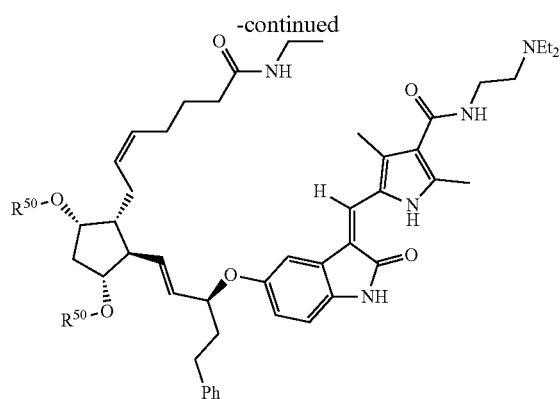
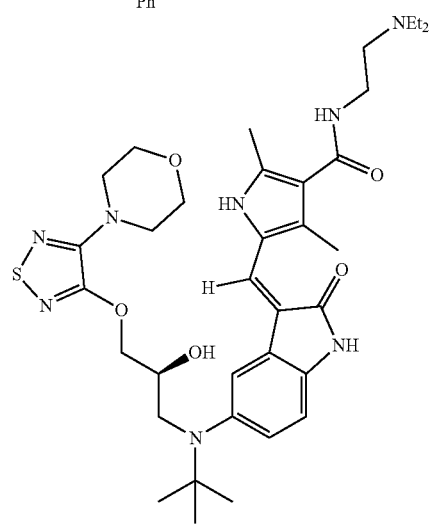
556
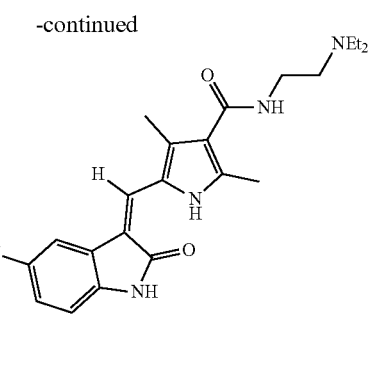
Example 18. Non-Limiting Examples of Formula XI
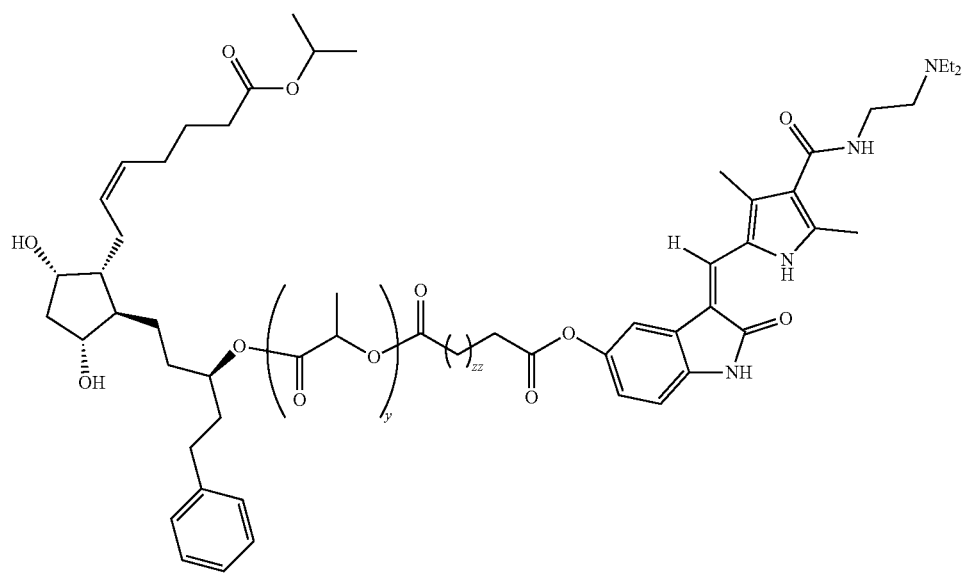

557
558
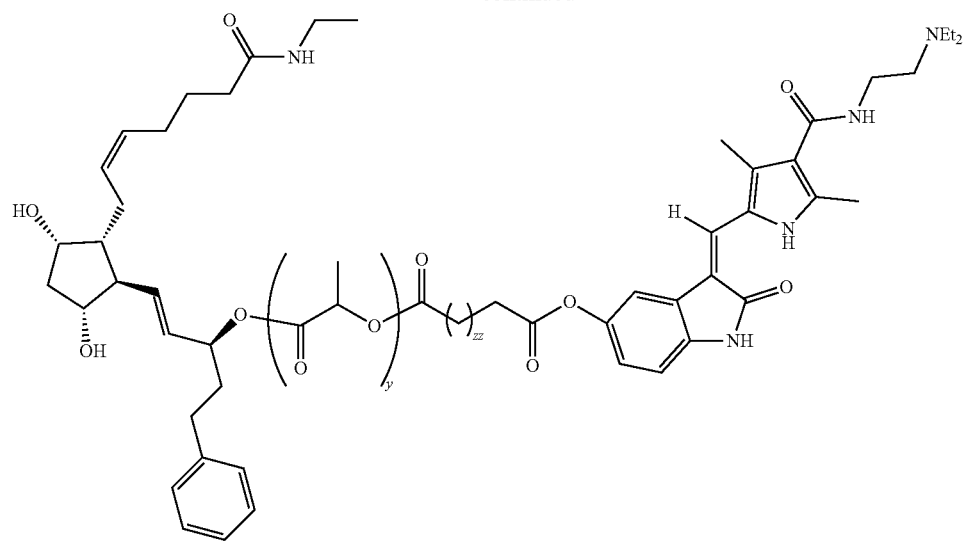
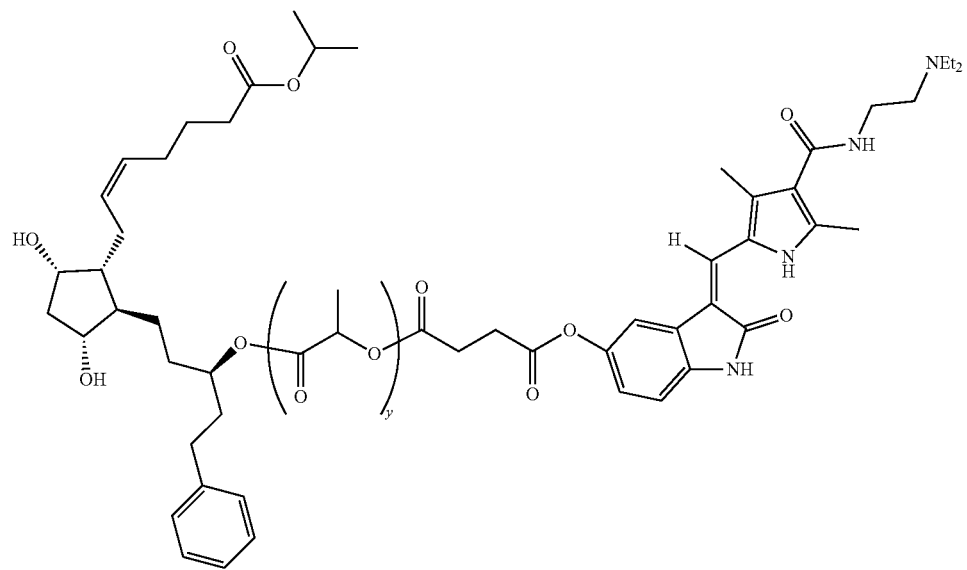
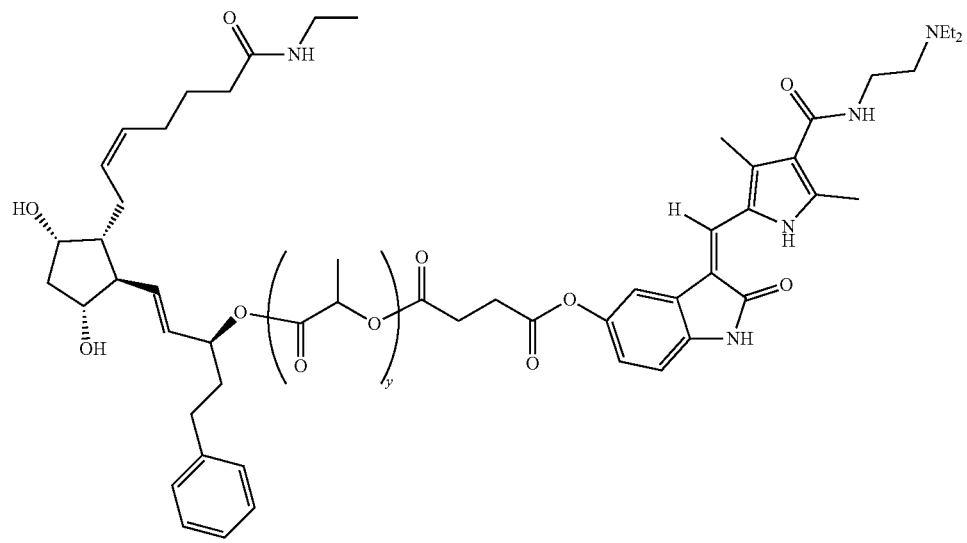

-continued
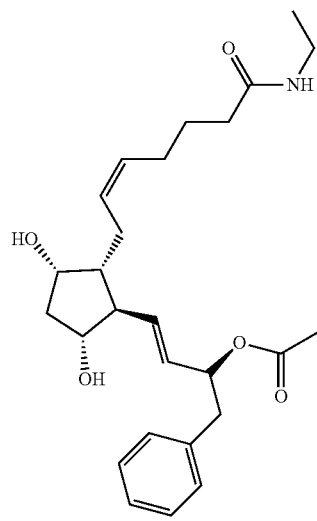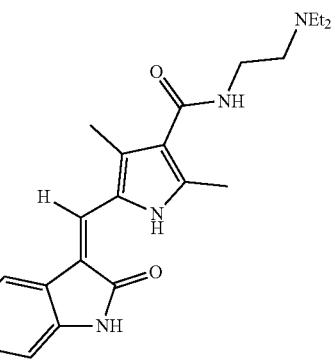
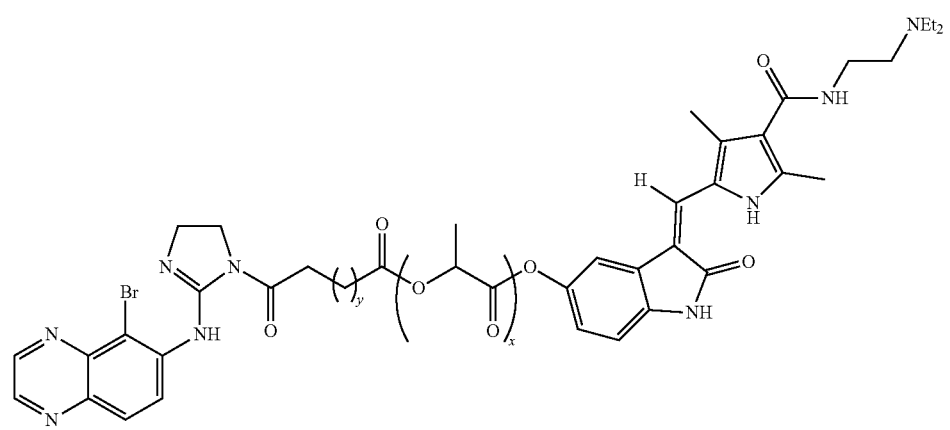
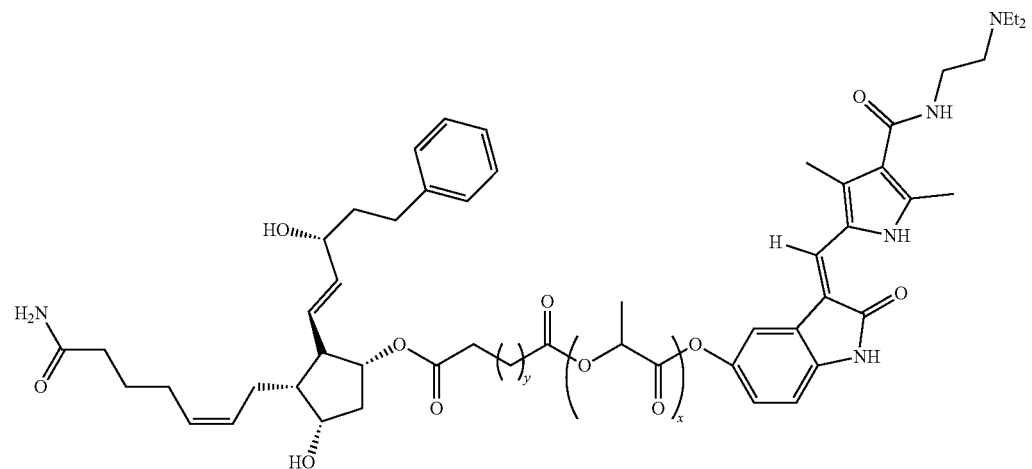

Example 19. Non-Limiting Examples of Formula XII
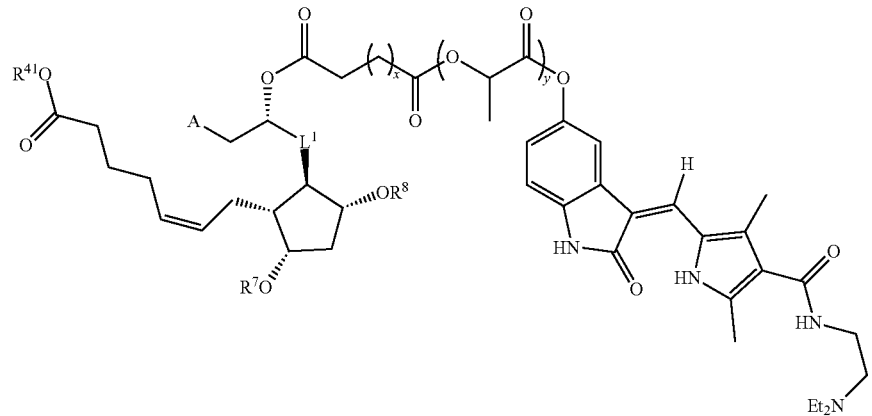
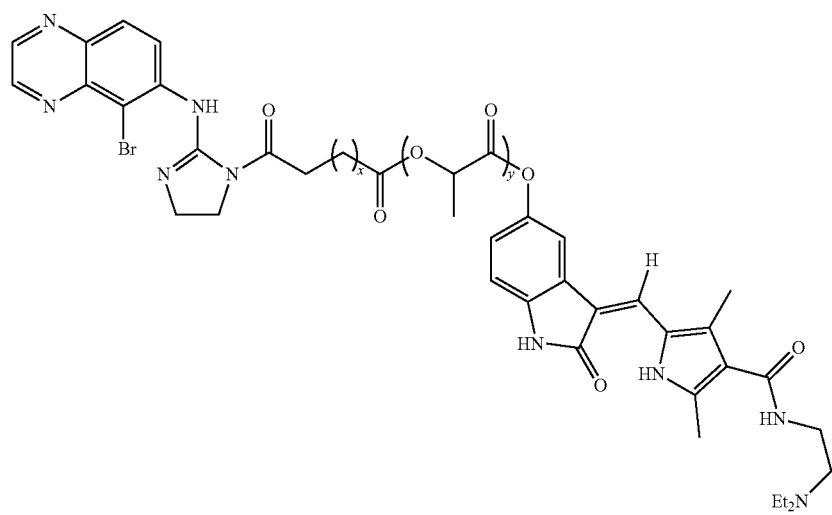
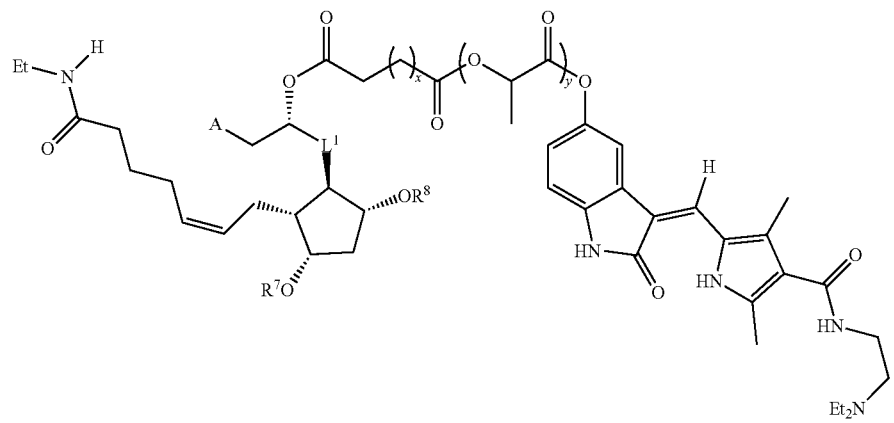

Example 20. Non-Limiting Examples of Formula XIII
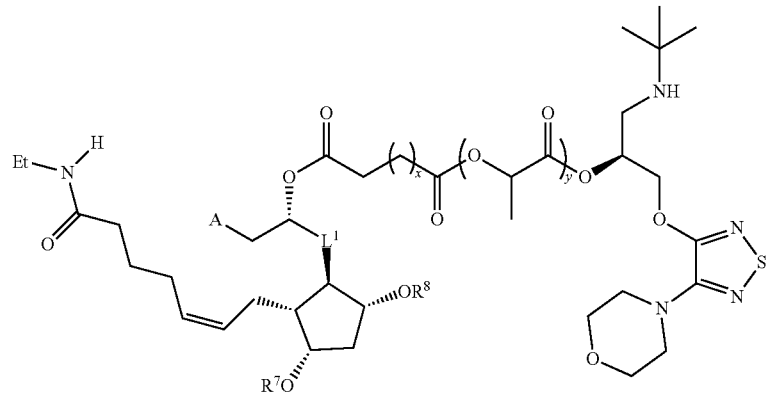
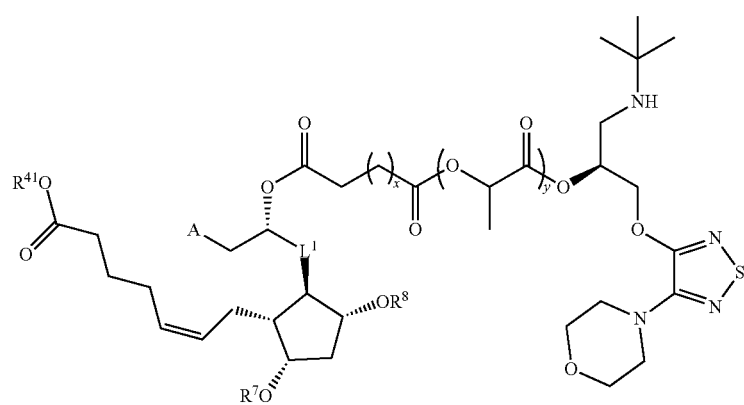
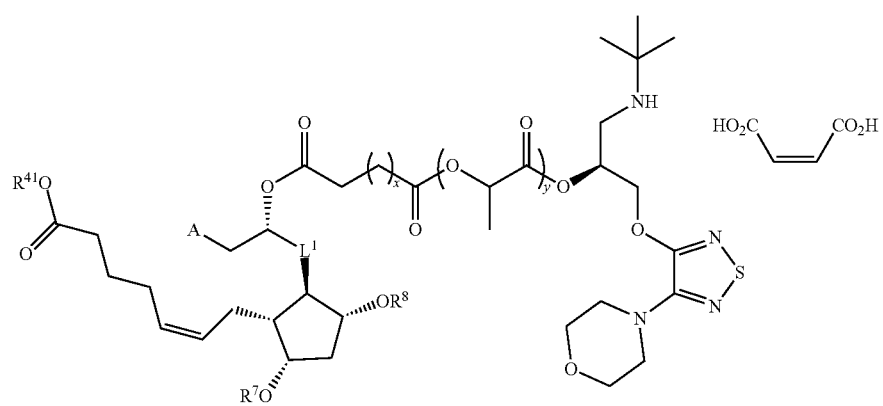
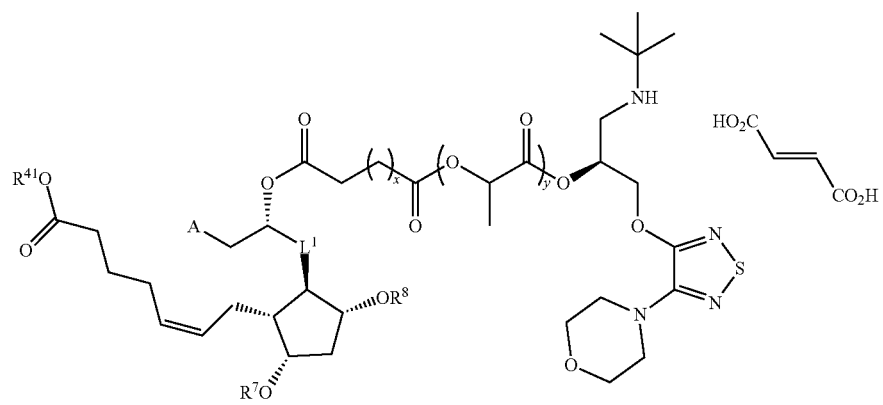

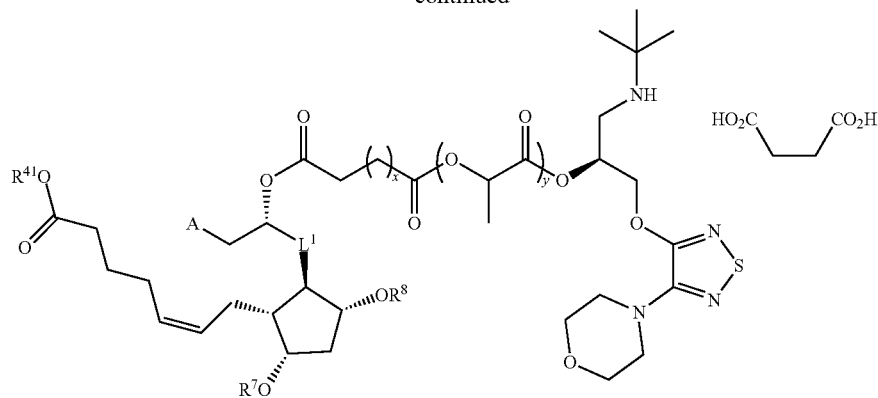
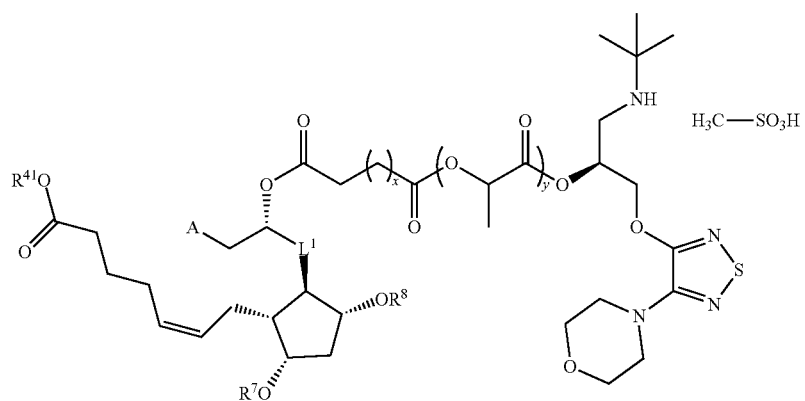
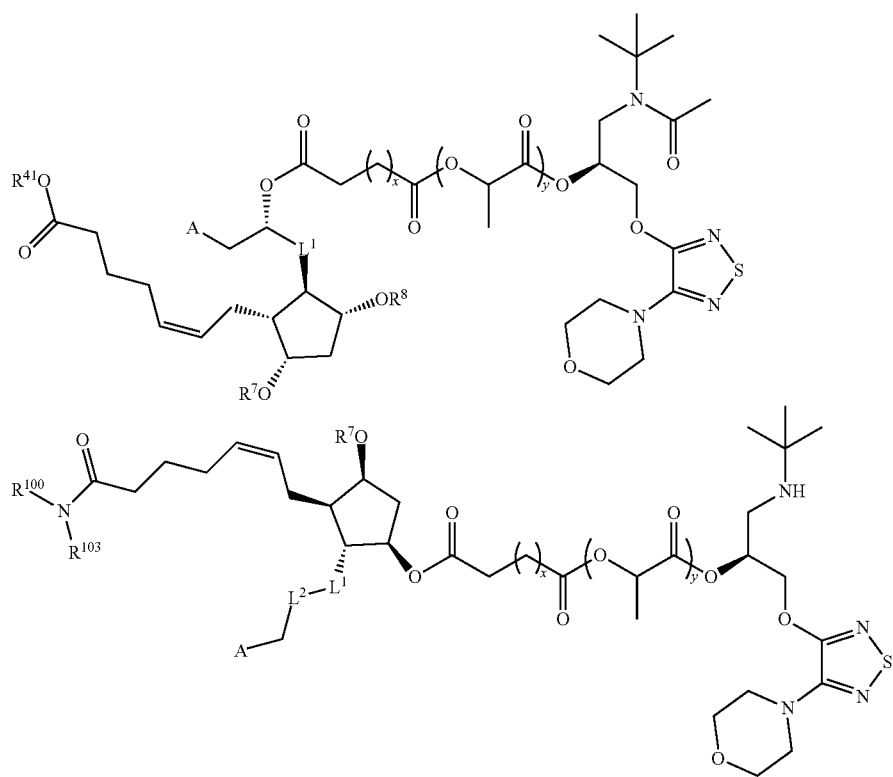

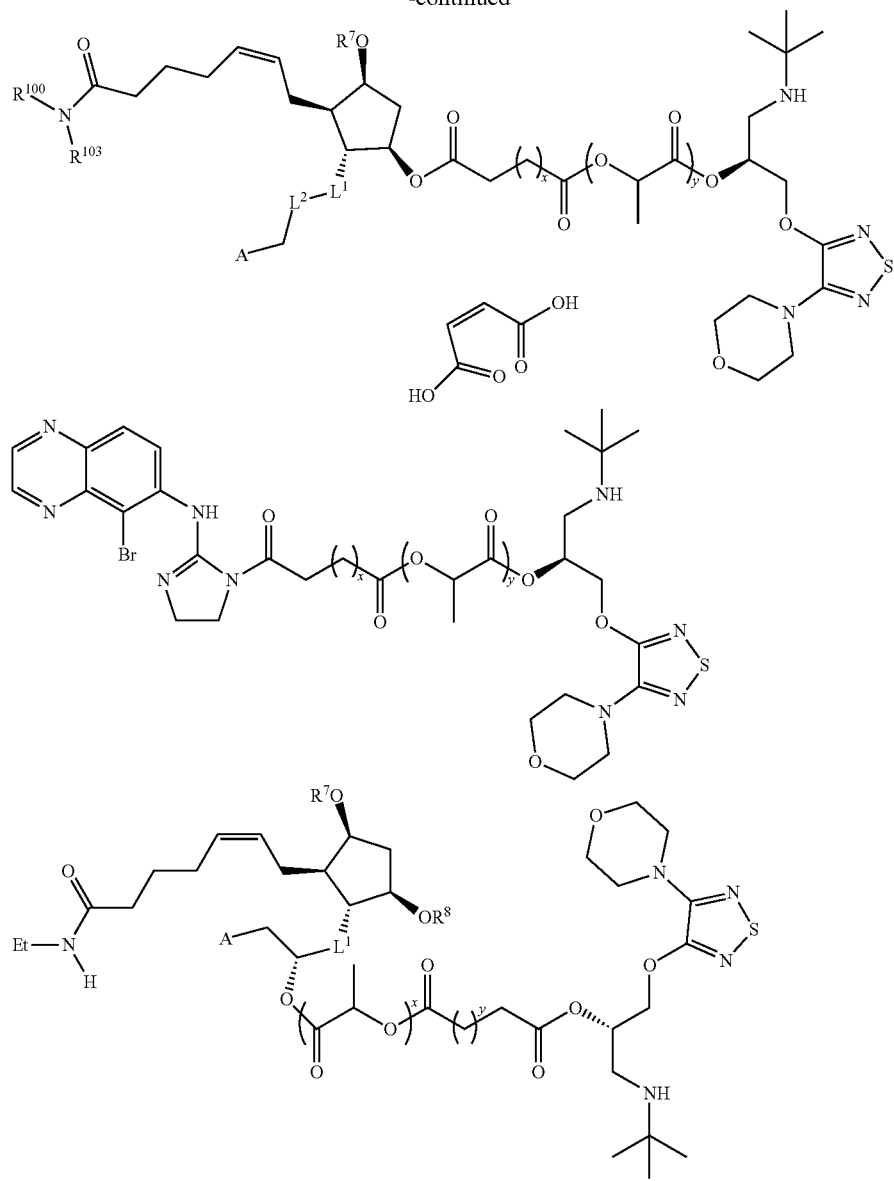
Example 21. Non-Limiting Examples of Formula XIV
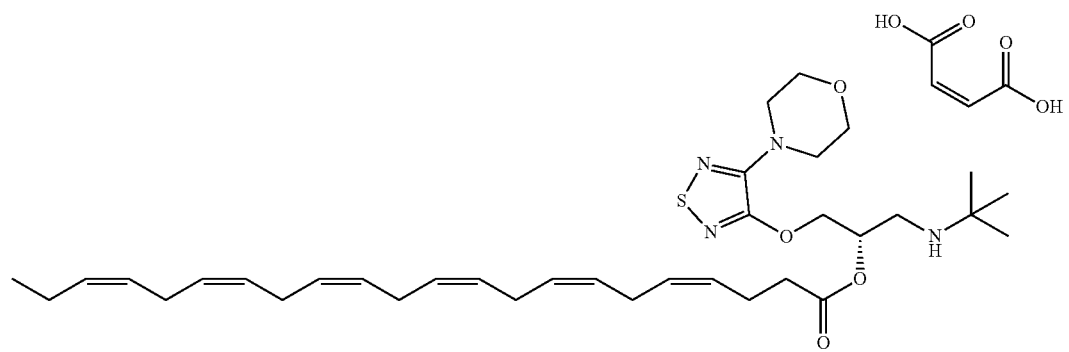

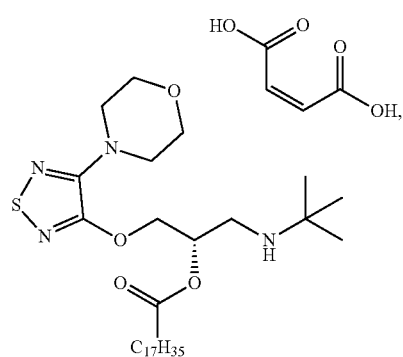
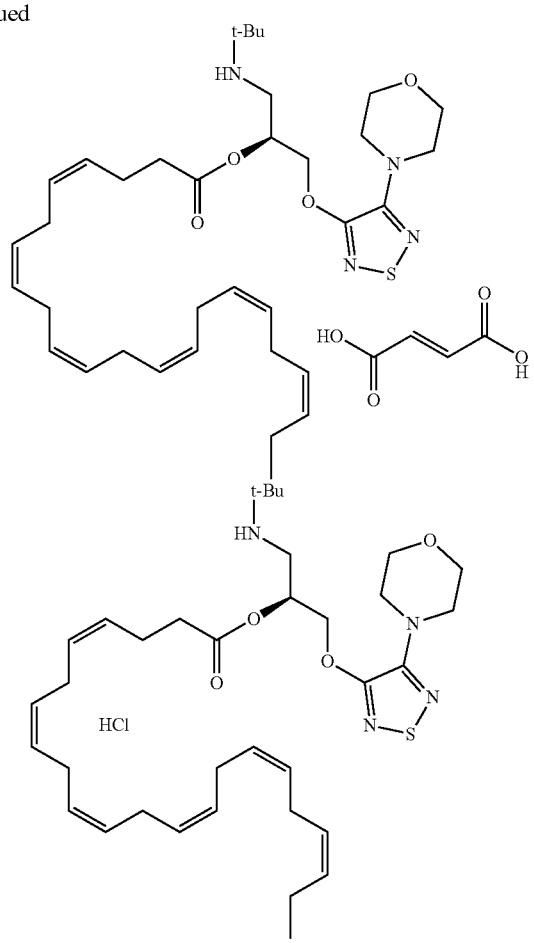
Example 22. Non-Limiting Examples of Formula XV
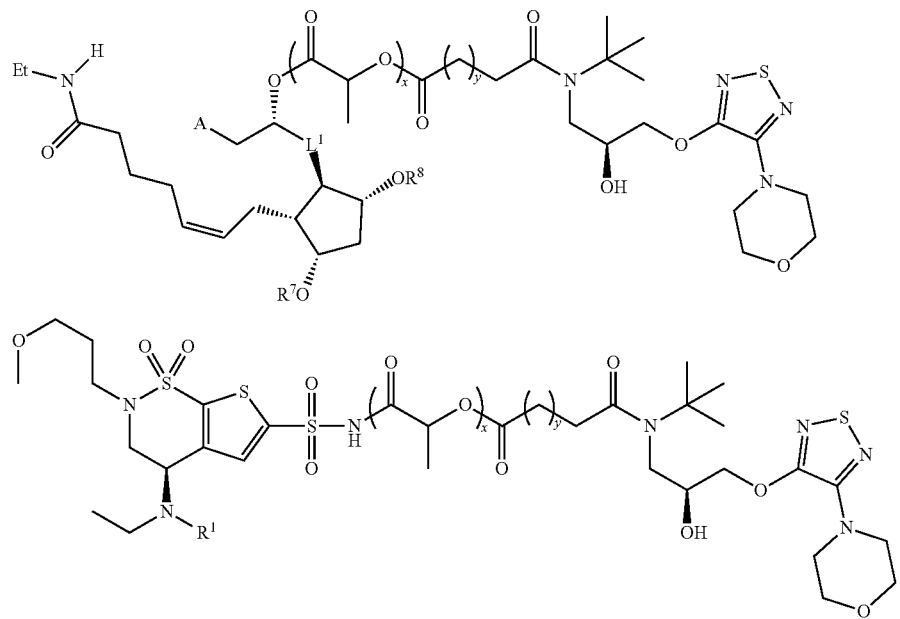

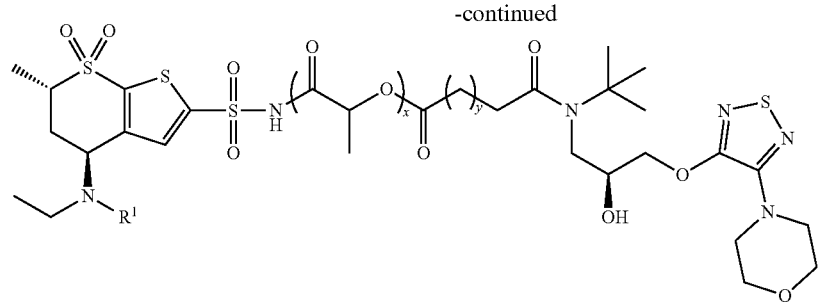
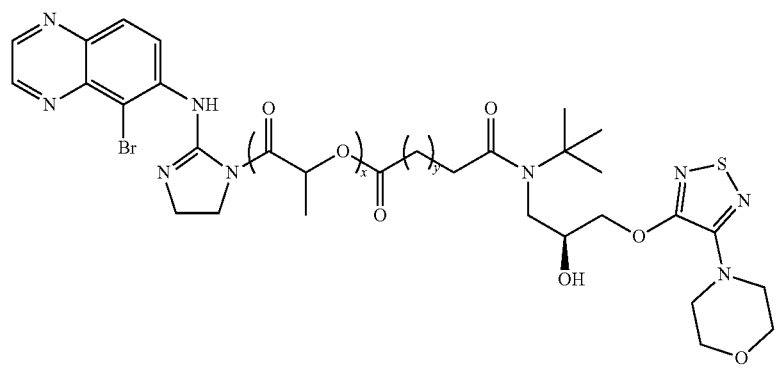
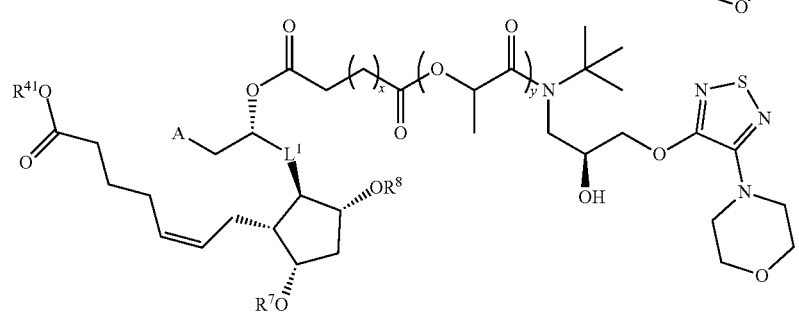
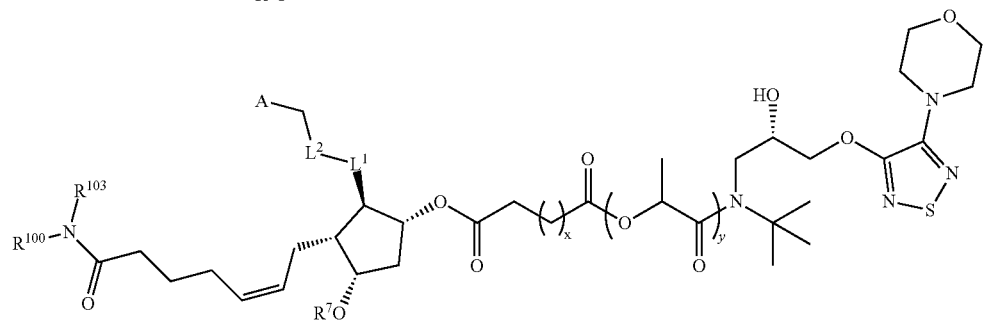
Example 23. Non-Limiting Example of Formula XVI
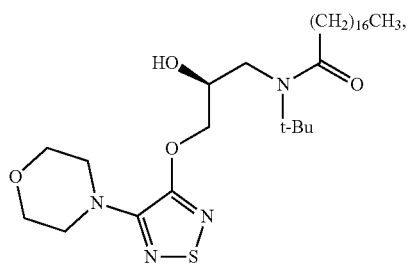
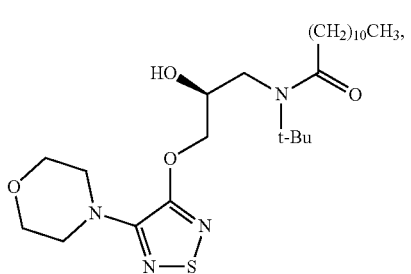

573
-continued
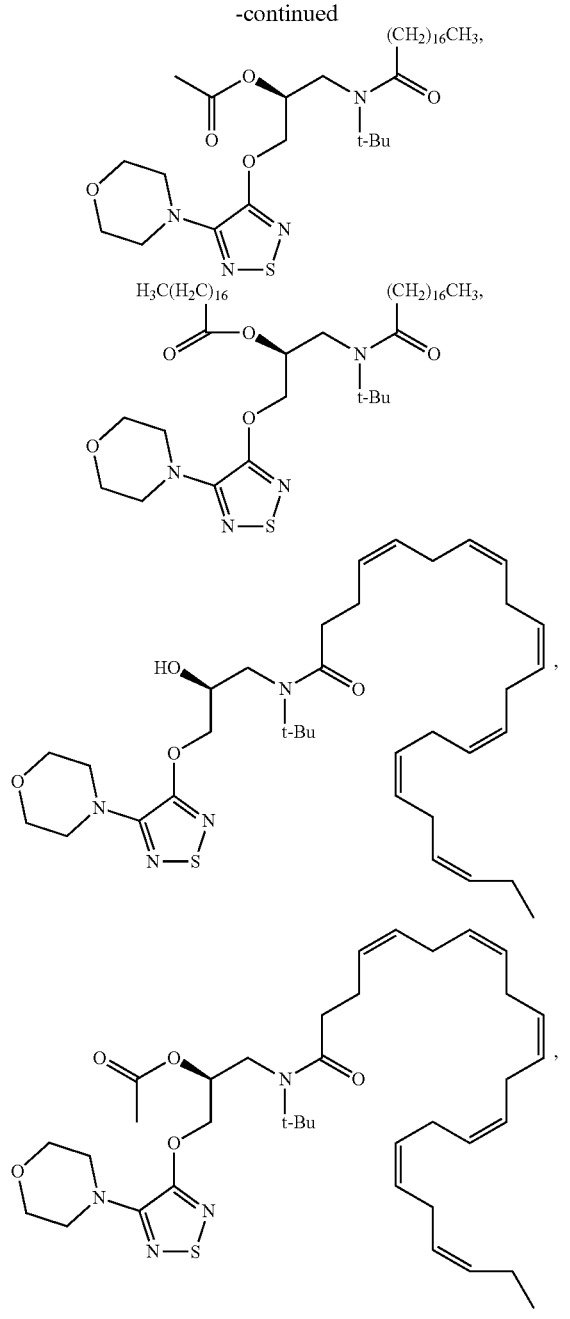
Example 24. Non-Limiting Examples of Formula XVII
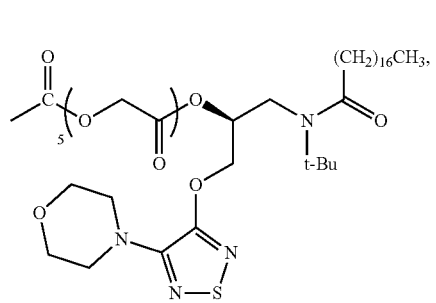
574
-continued
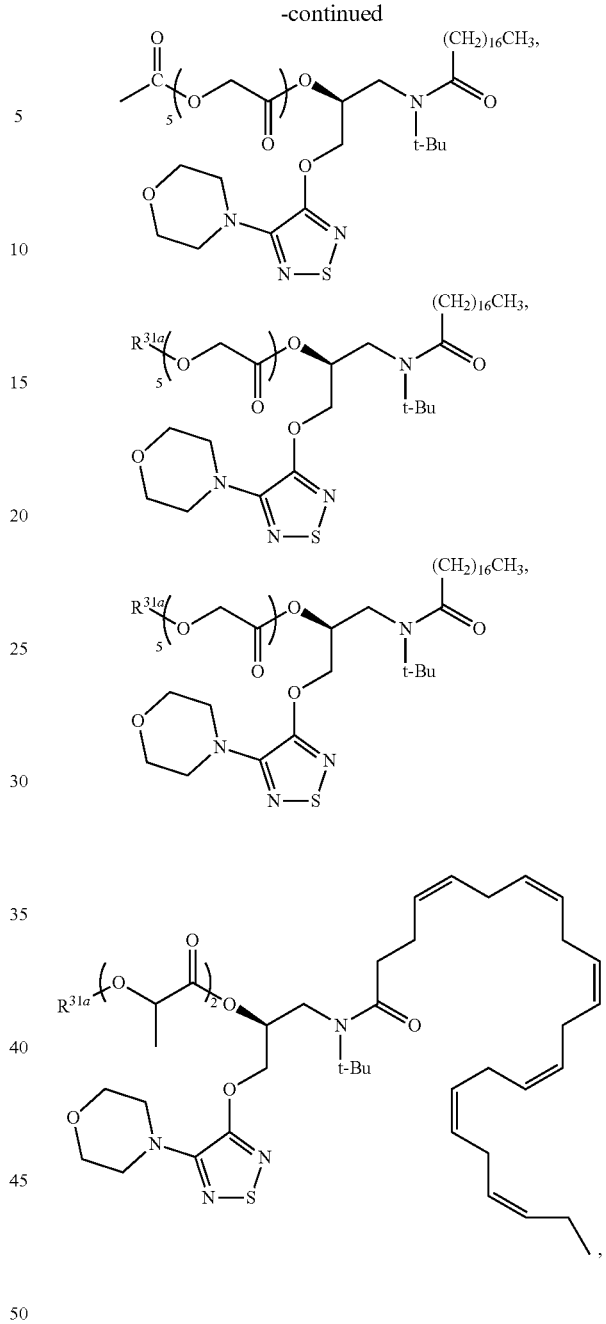

575
-continued
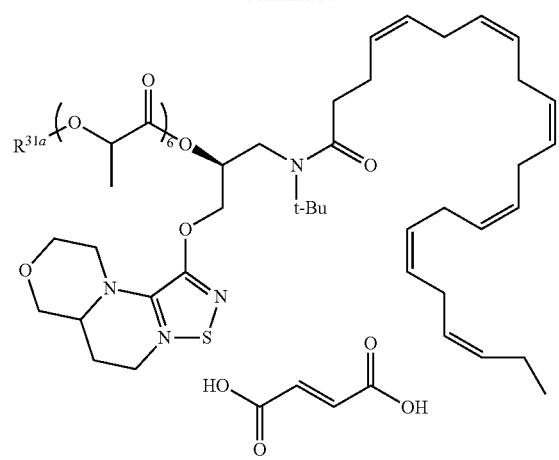
576
-continued
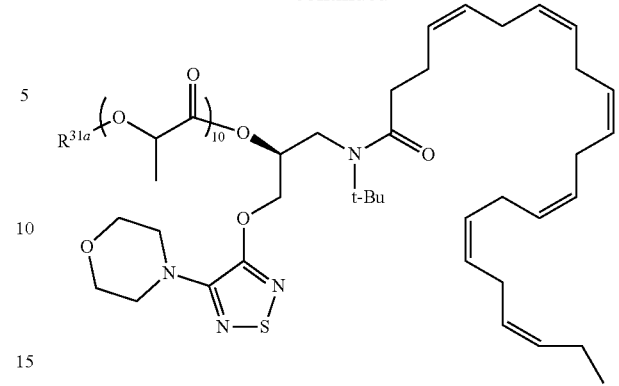
Example 25. Non-Limiting Examples of Formula XVIII, XIX, XX, XXII
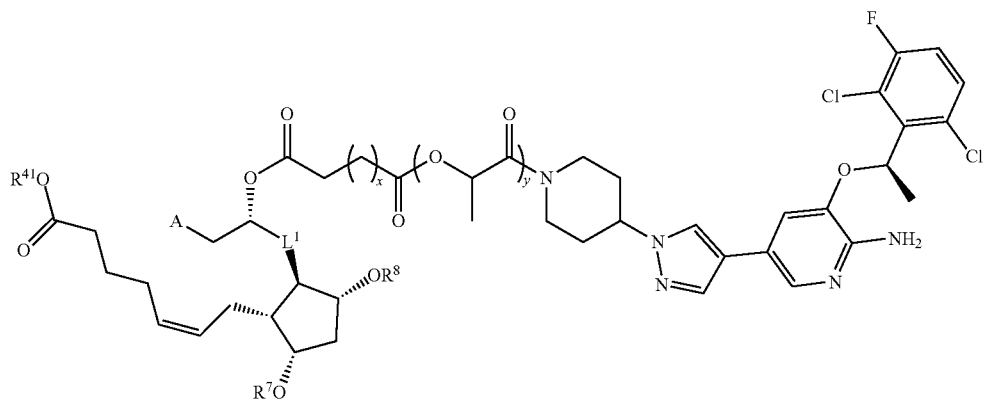
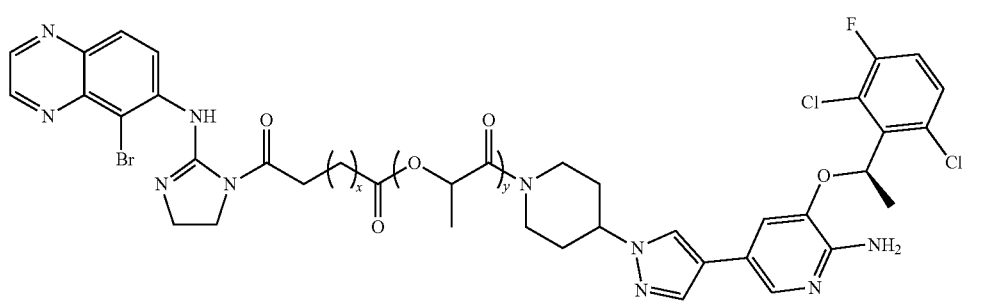
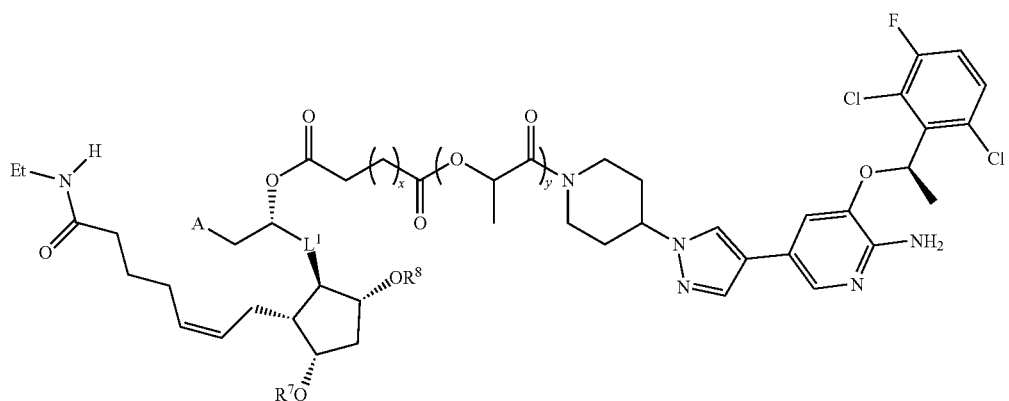

-continued
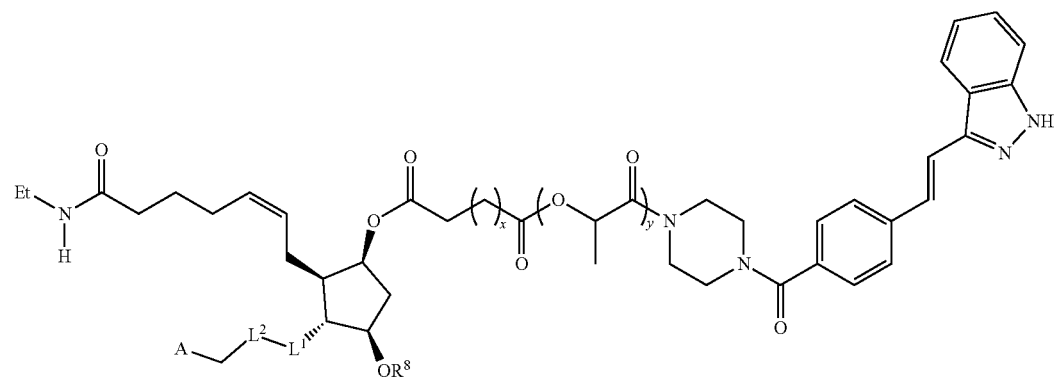
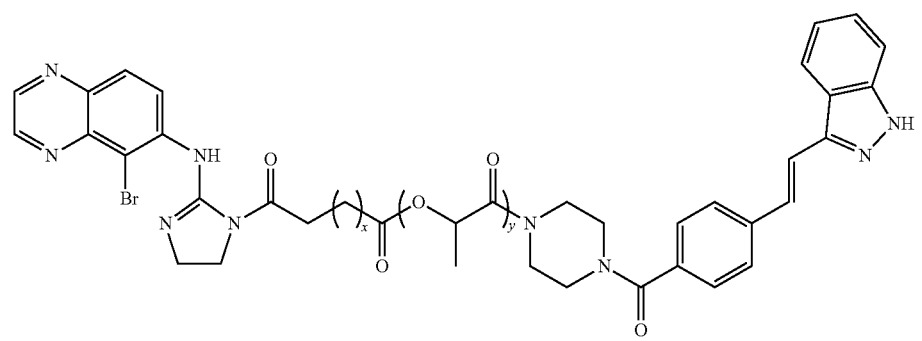
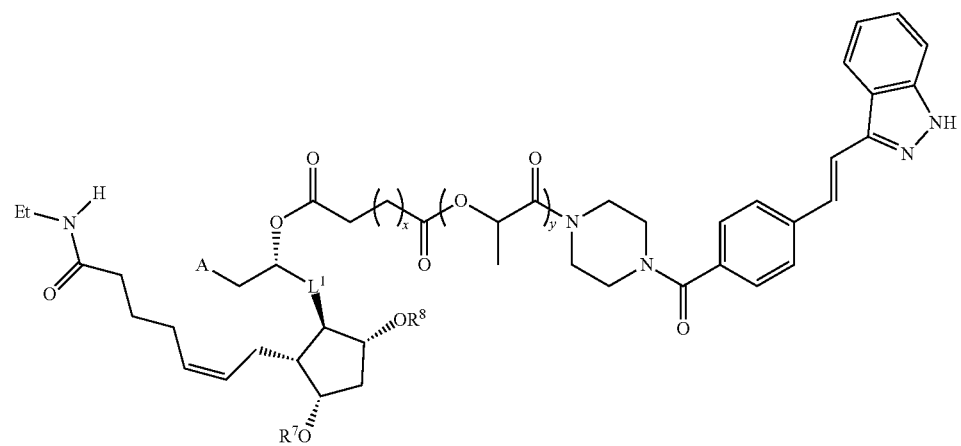
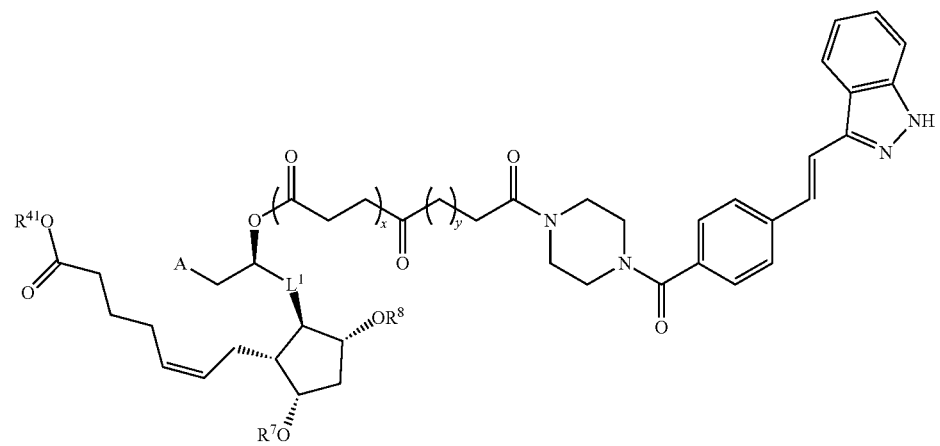

-continued
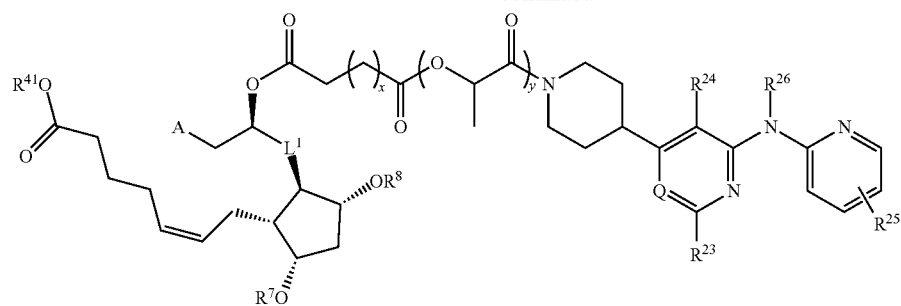
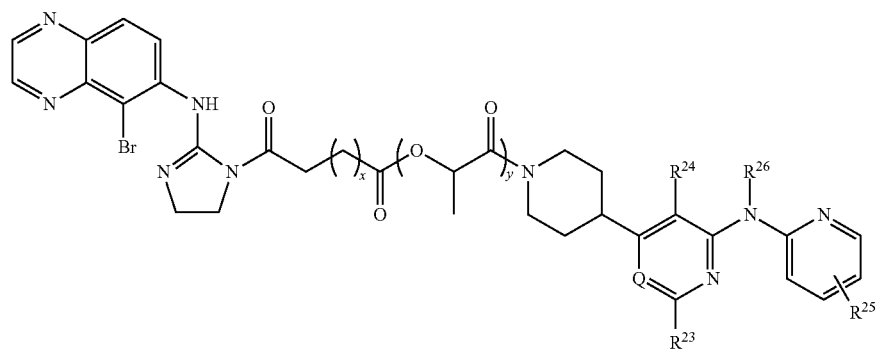
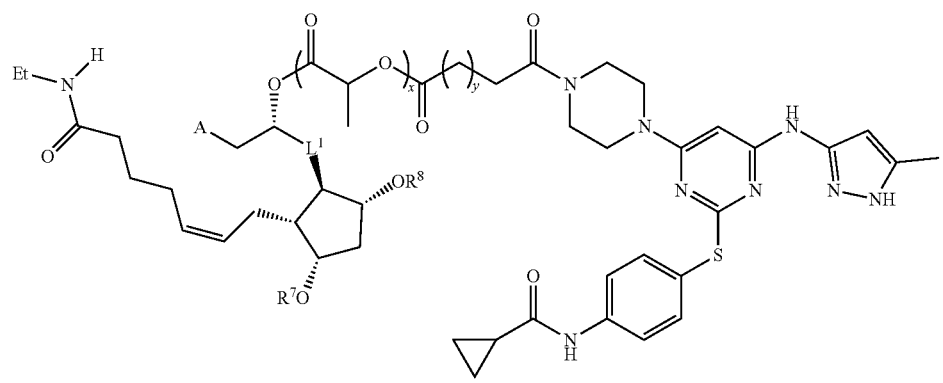
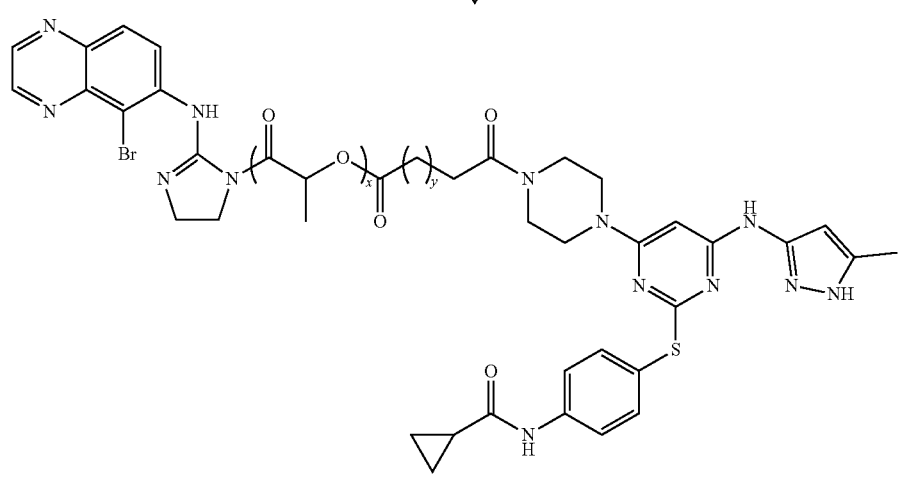

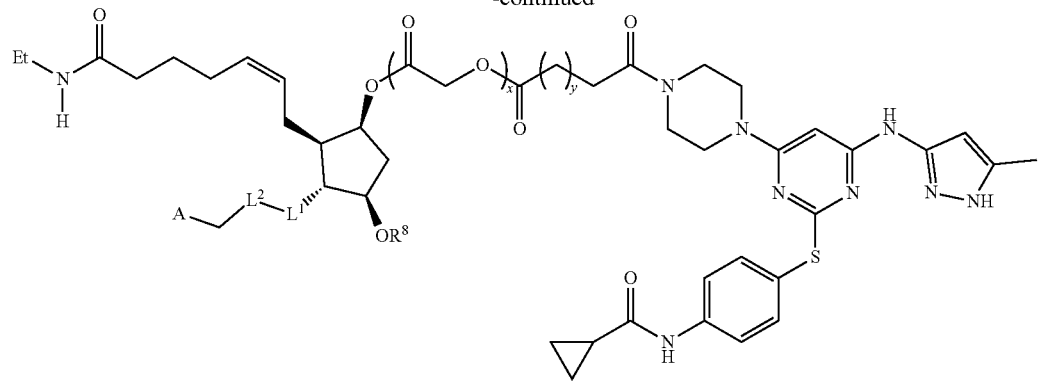
Example 26. Non-Limiting Examples of Formula XXII, XXIII, XXIV, XXV, XVI, and XXVII
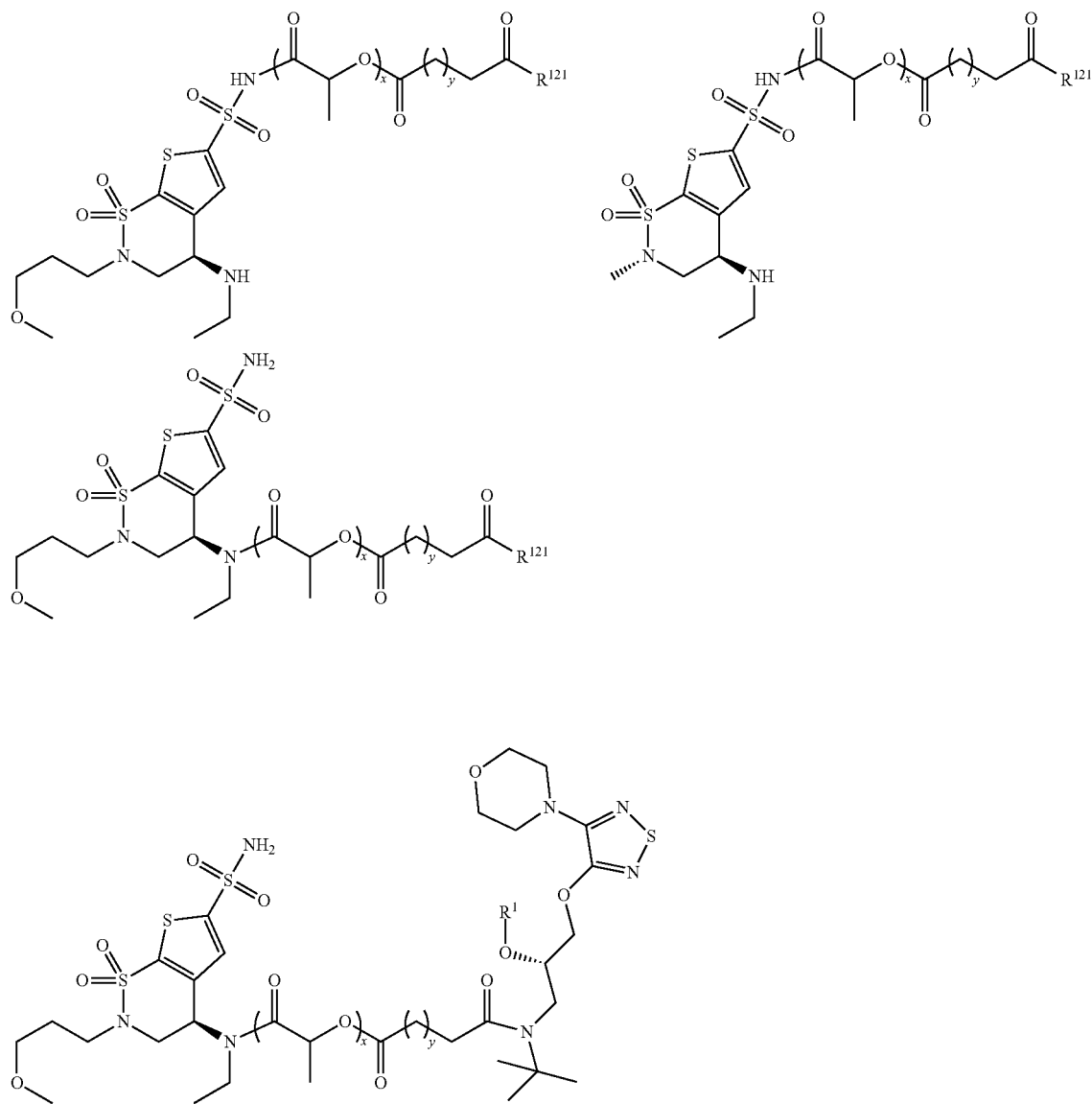

583
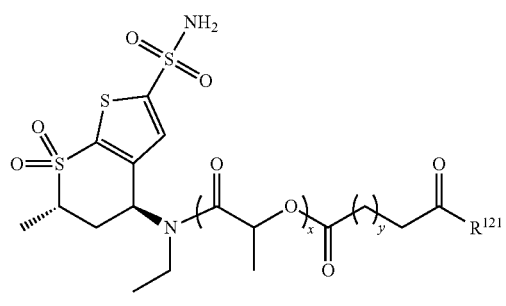
584 -continued
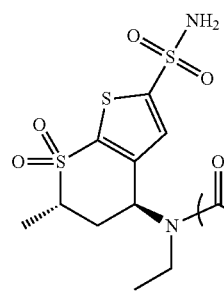
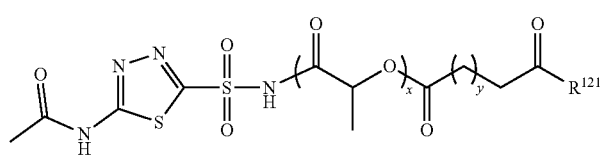
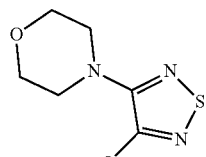
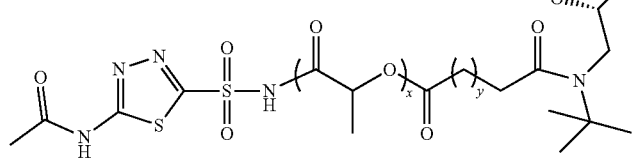
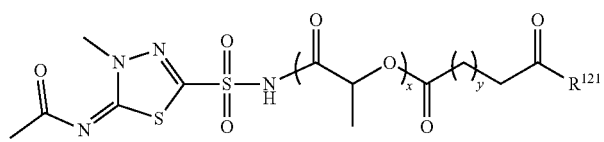
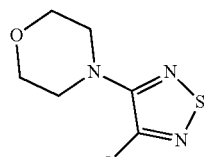
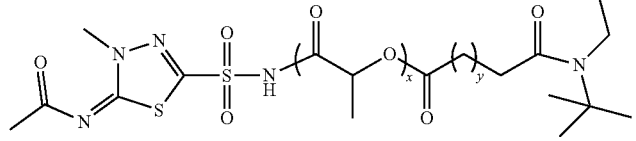
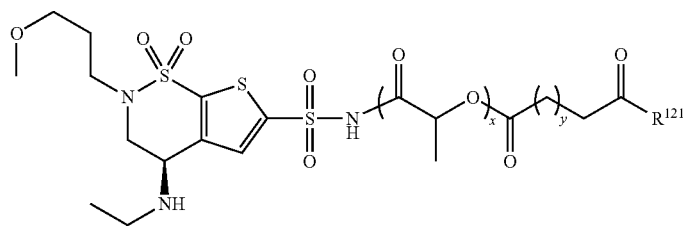

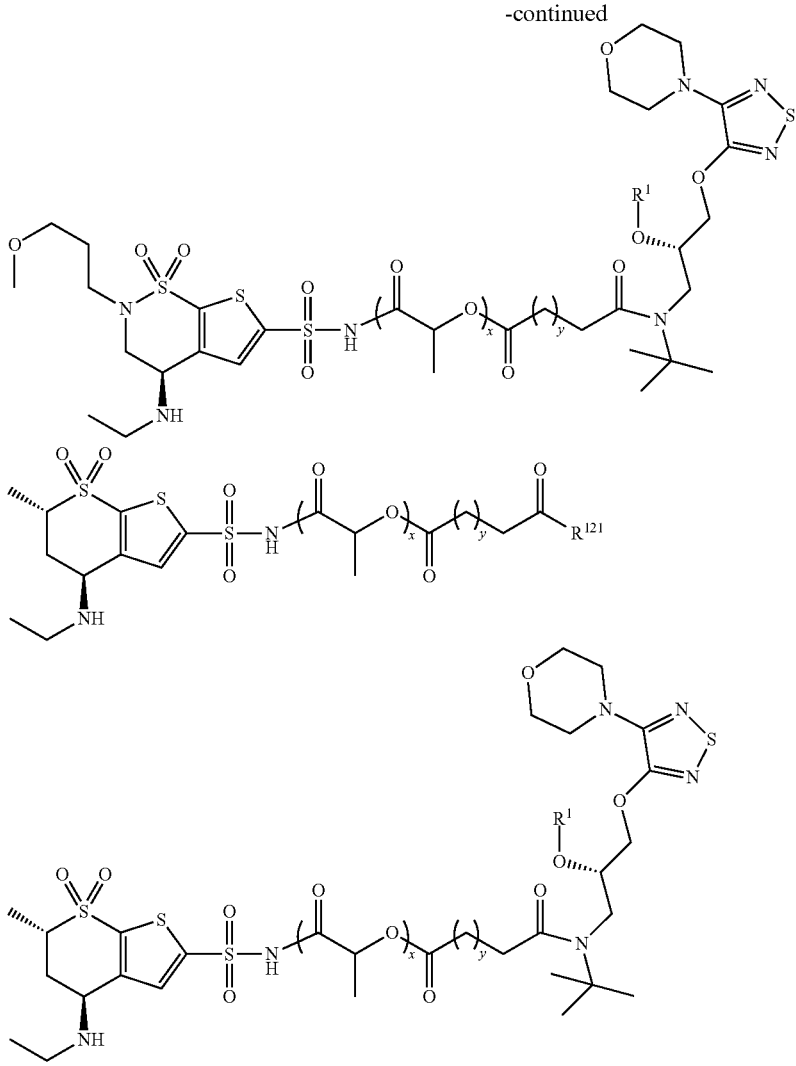
Example 27. Non-Limiting Examples of Formula XXVIII, XXIX, XXX, XXXI, XXXII, and XXXIII
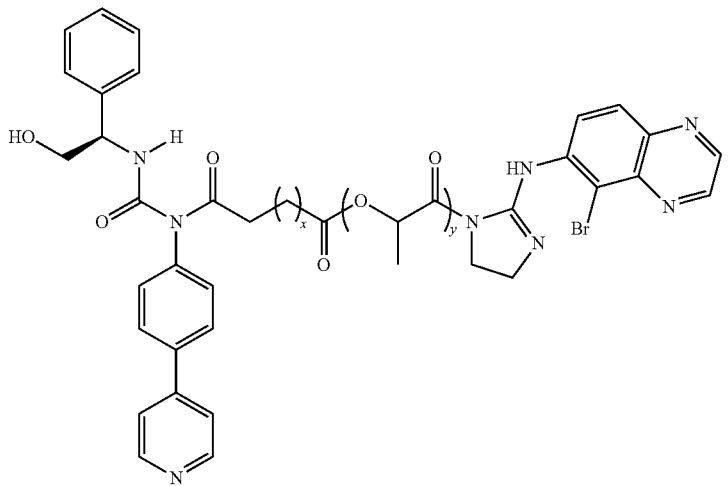

-continued
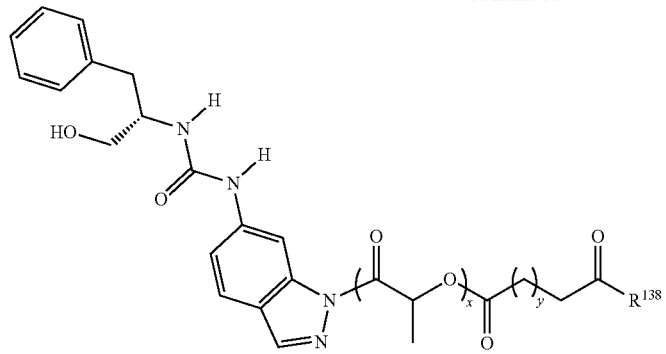
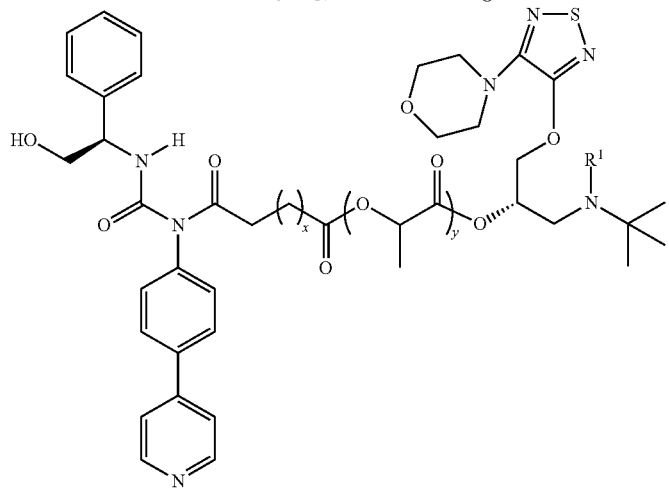
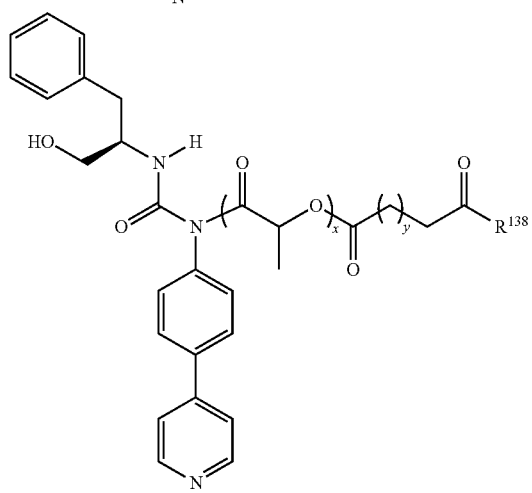
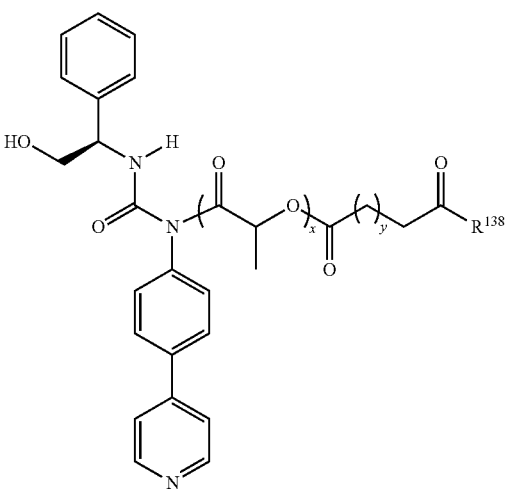
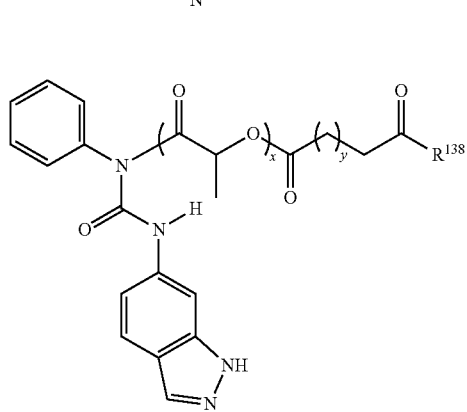
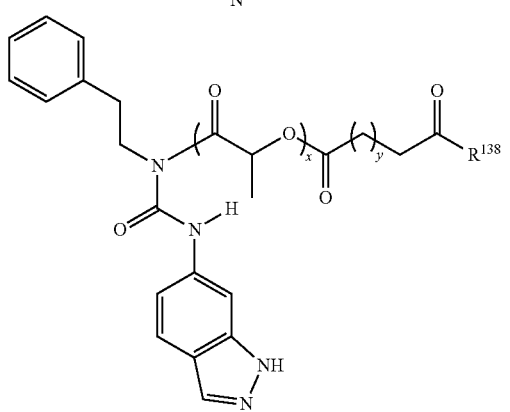

-continued
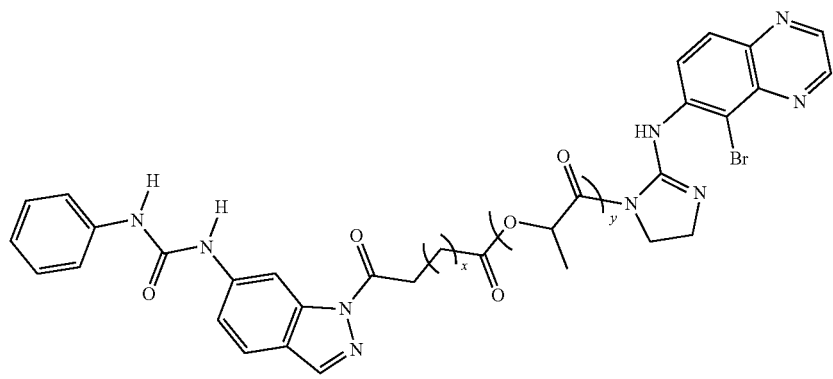
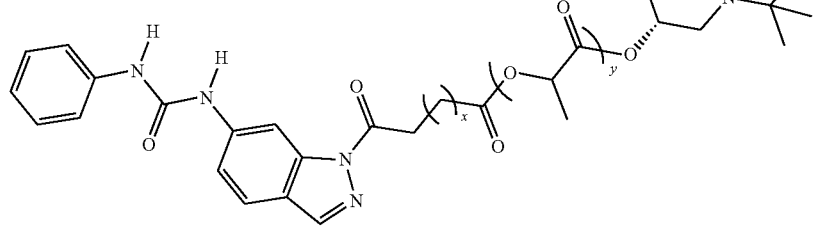
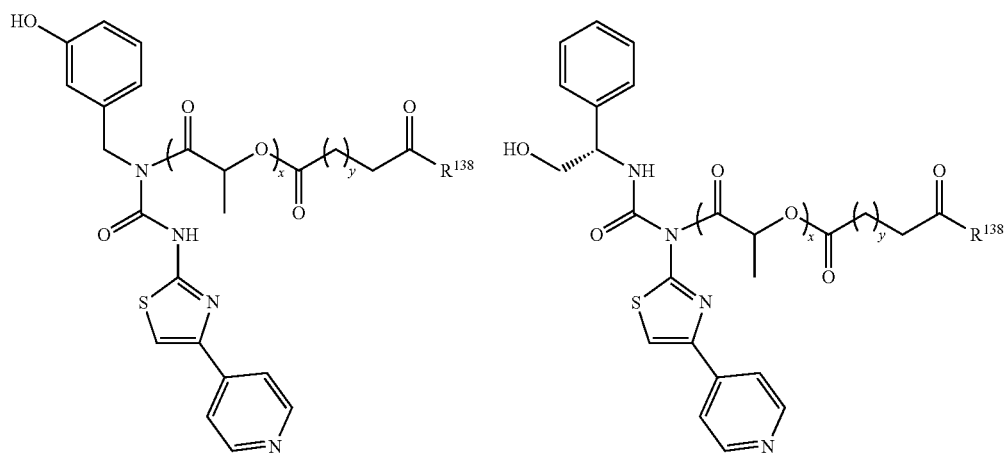
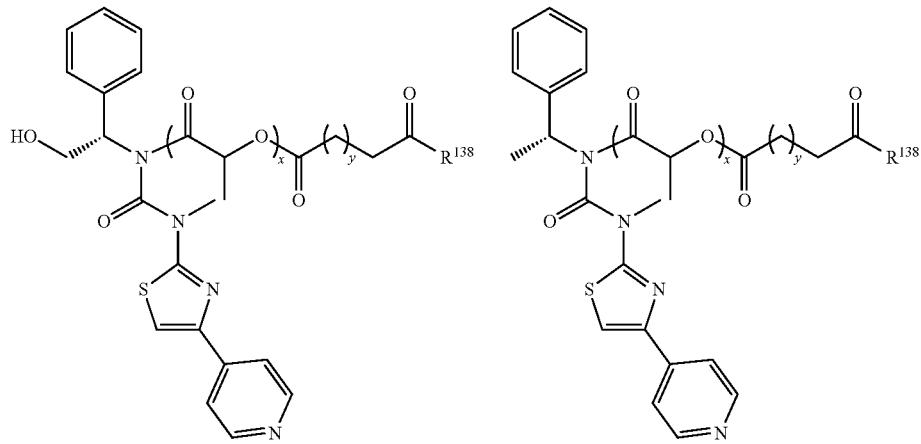

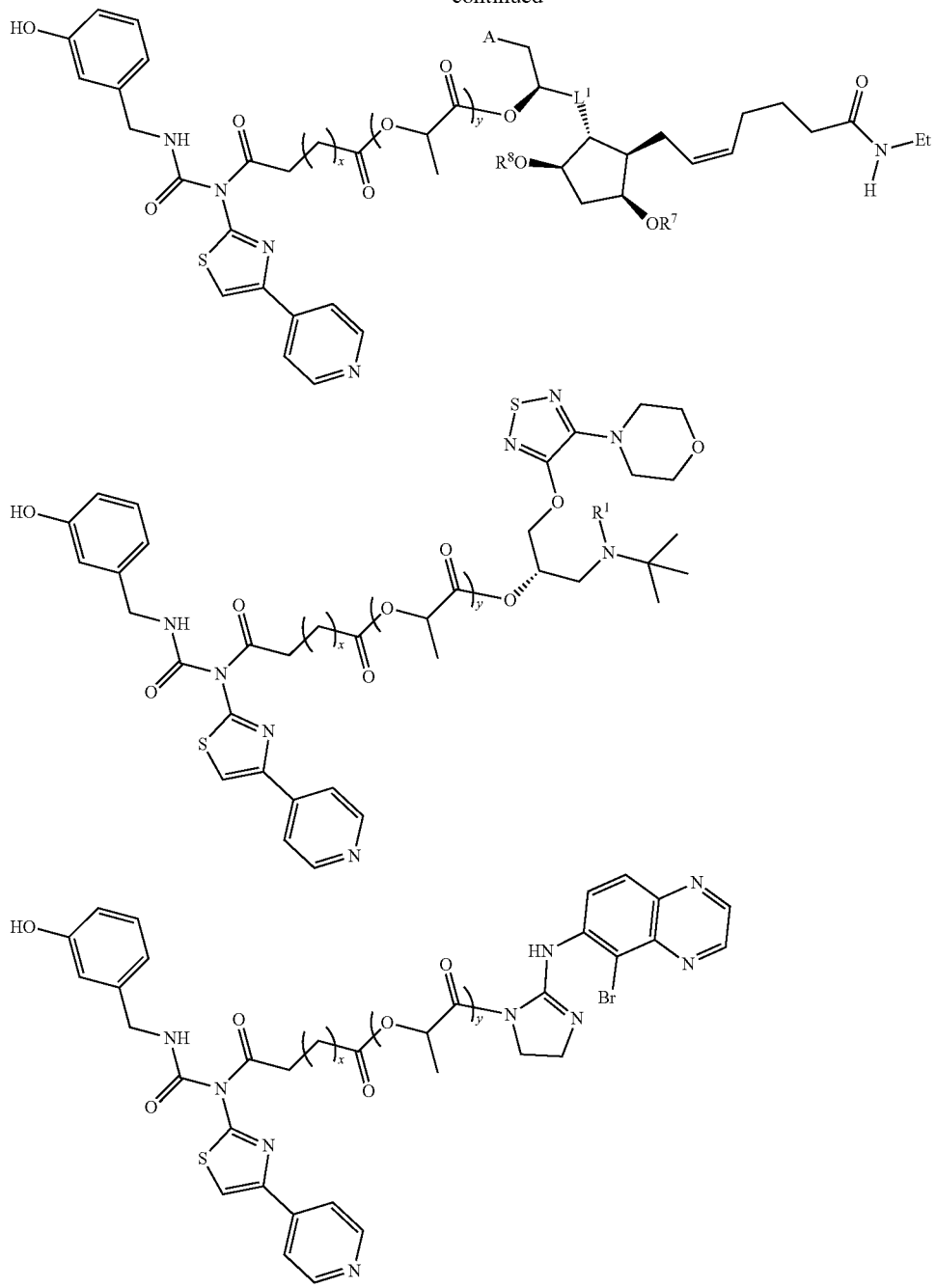
Example 28. Non-Limiting Examples of Formula XXXIV and XXXV
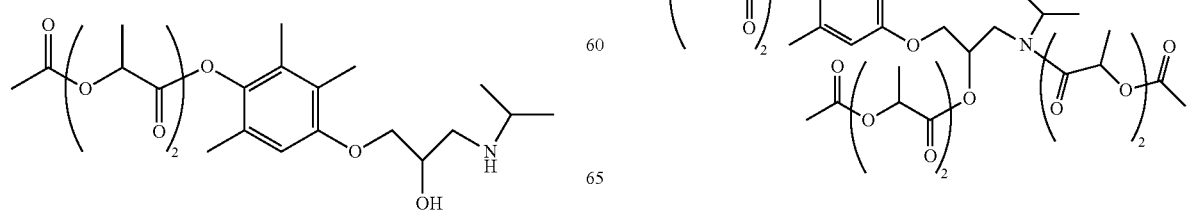

593
-continued
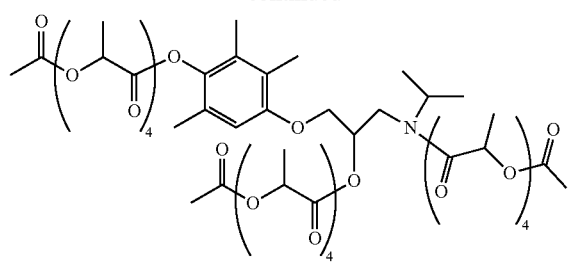
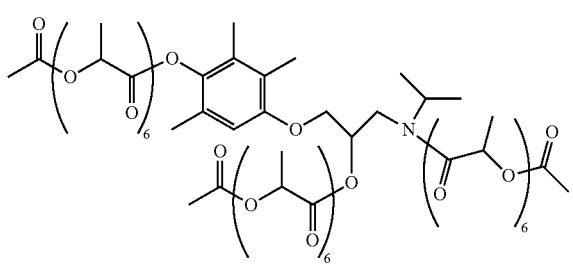
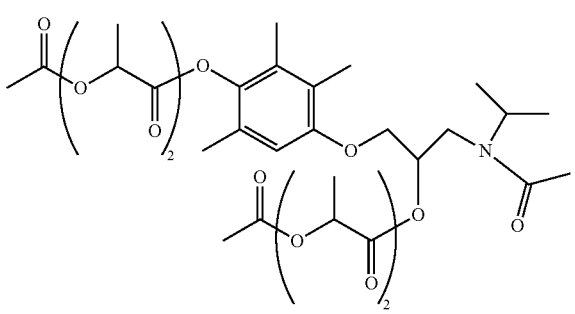
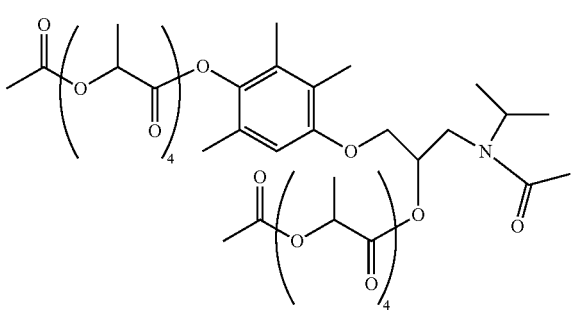
594
-continued
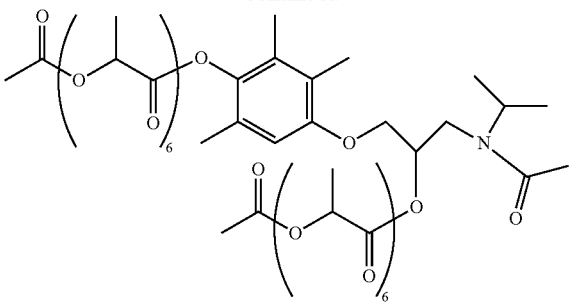
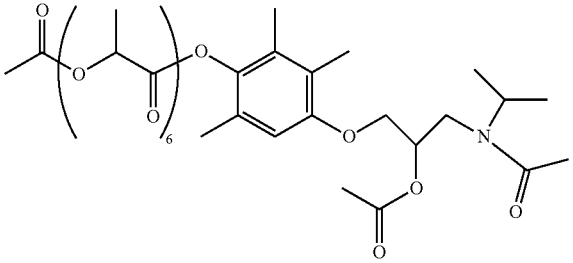
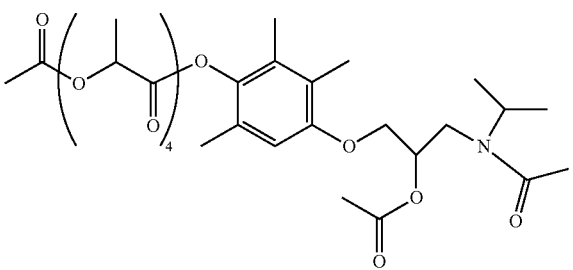
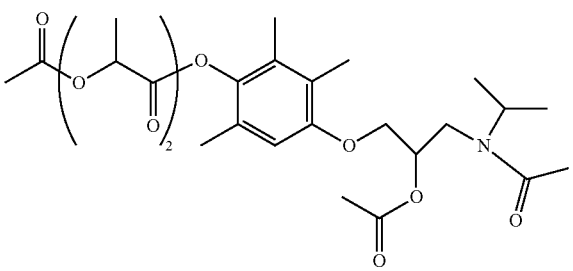
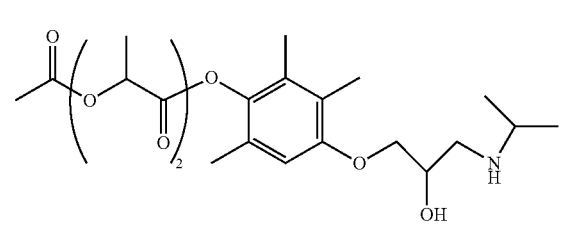

Example 29. Non-Limiting Examples of Formula XXXVI
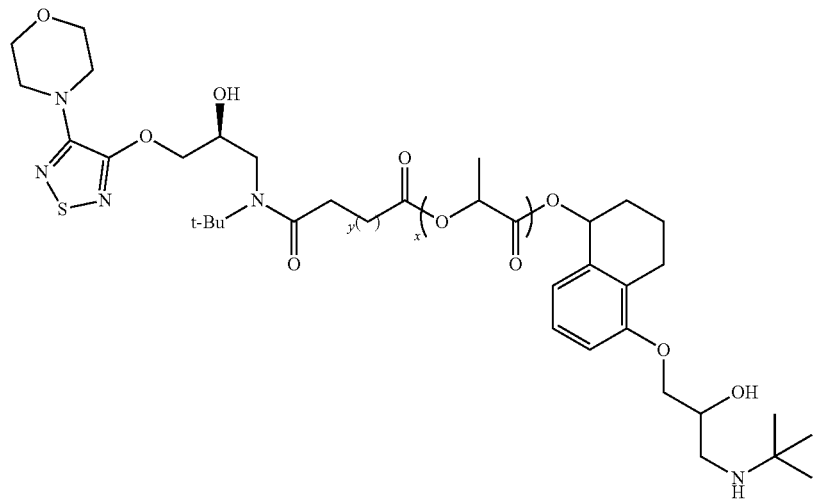
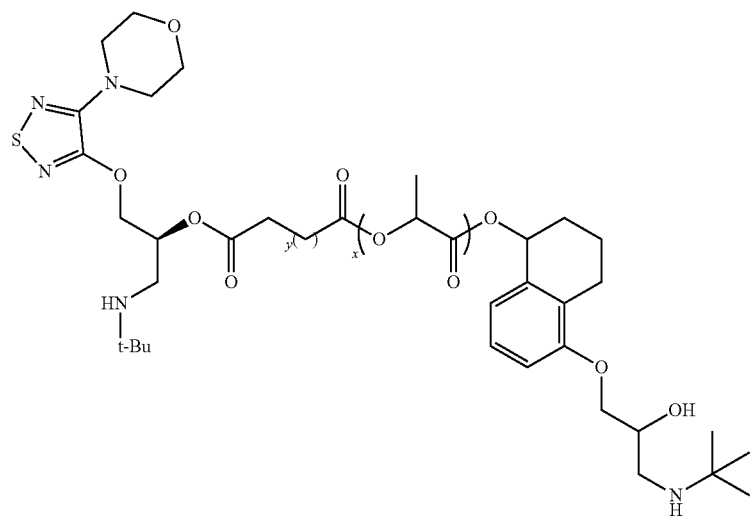
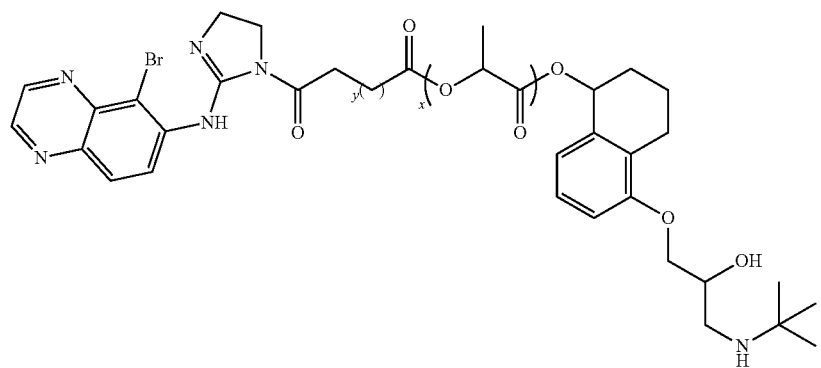

-continued
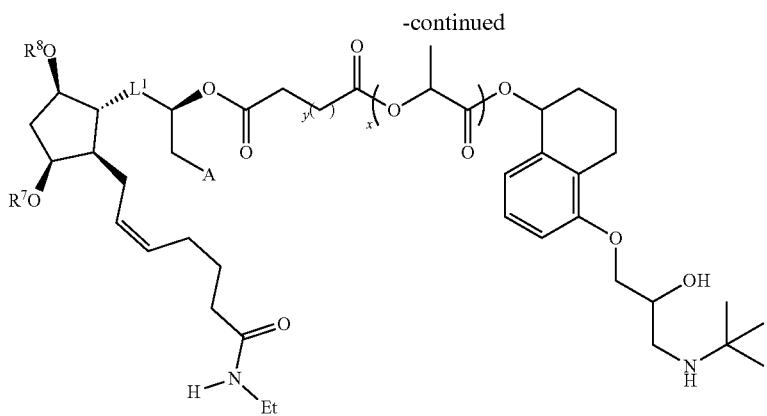
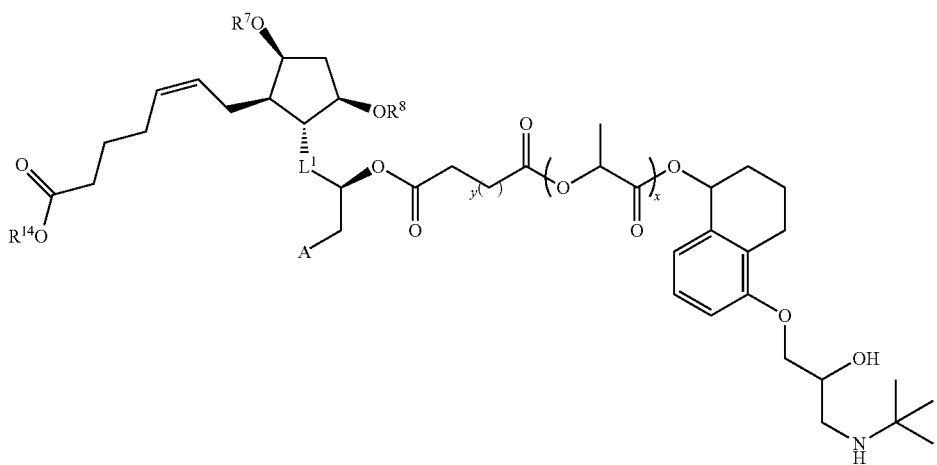
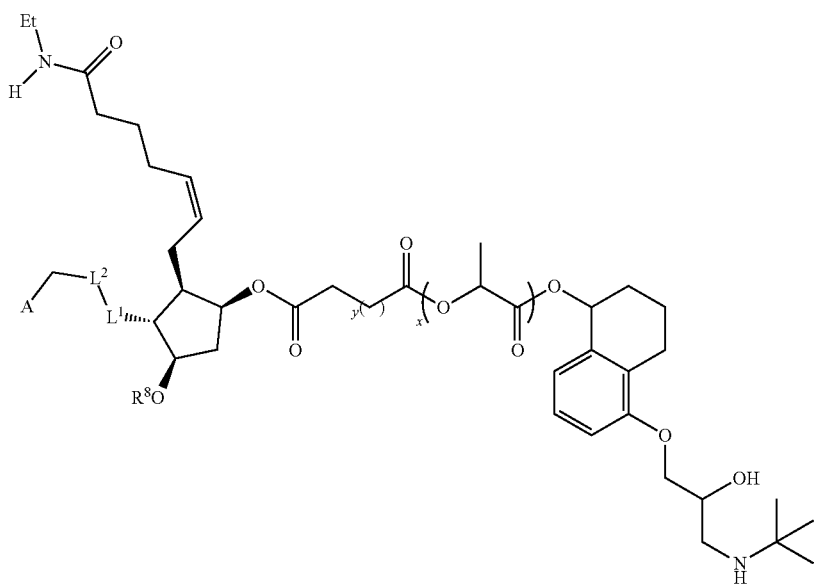

Example 30. Non-Limiting Examples of Formula XXXVII
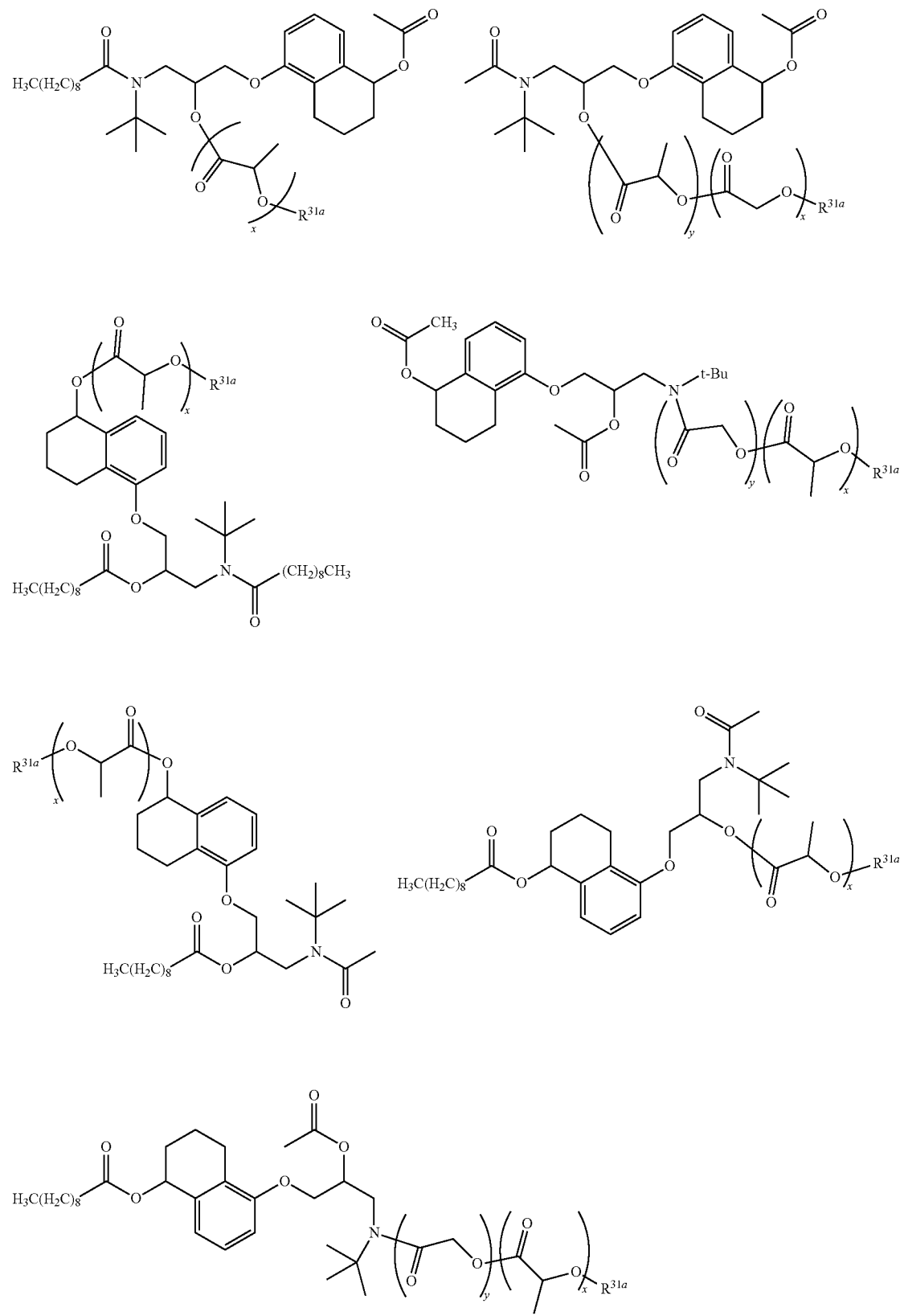

601
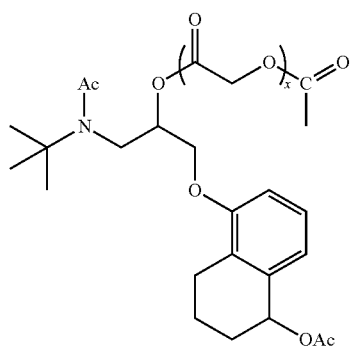
602
-continued
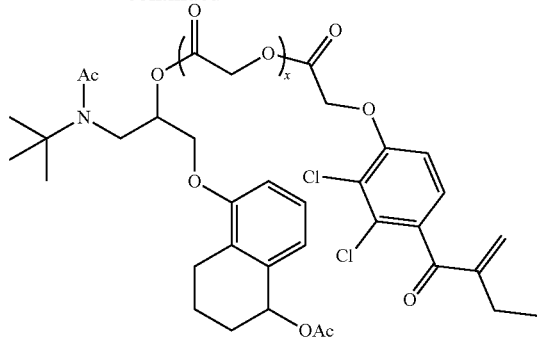
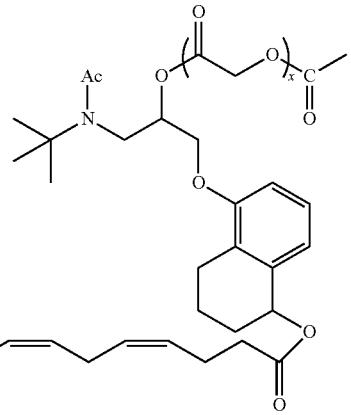
Example 31. Non-Limiting Examples of Formula XXXVIII
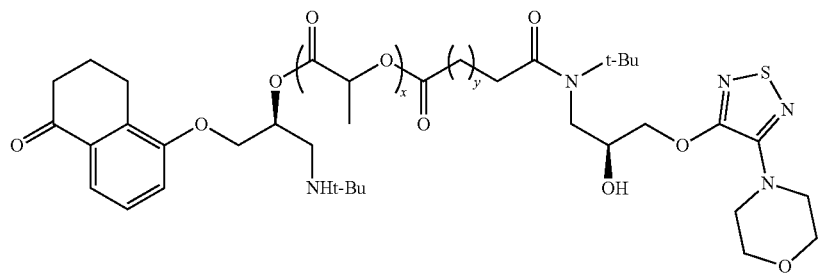
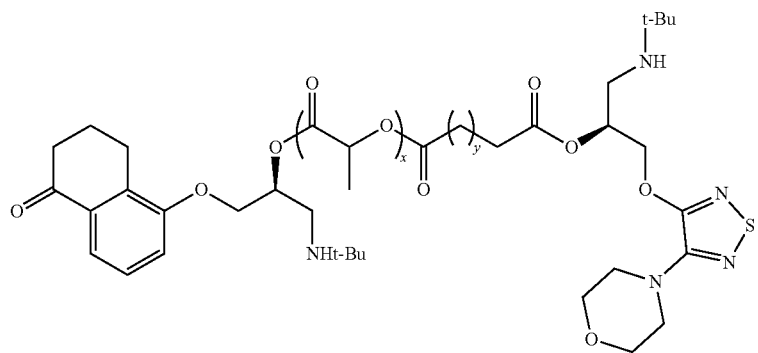

-continued
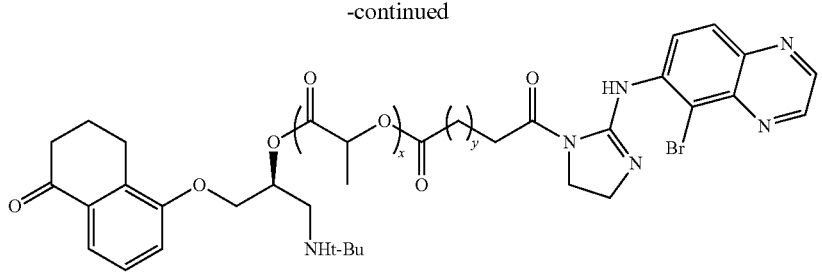
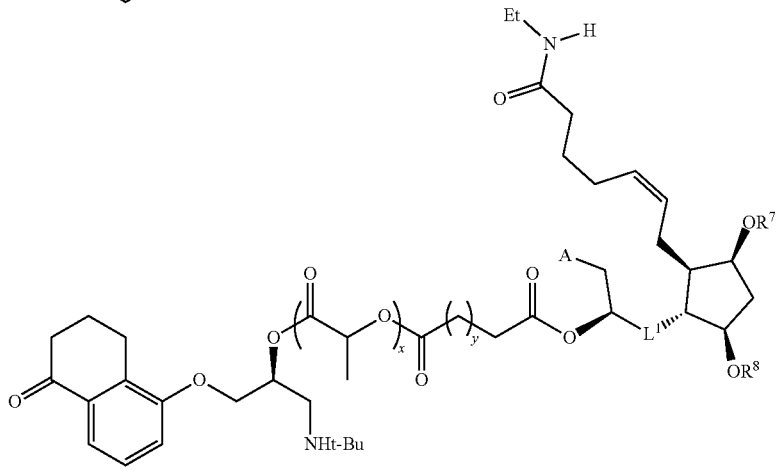
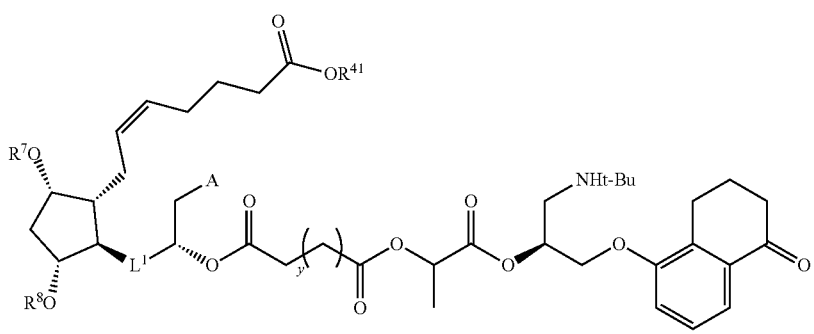
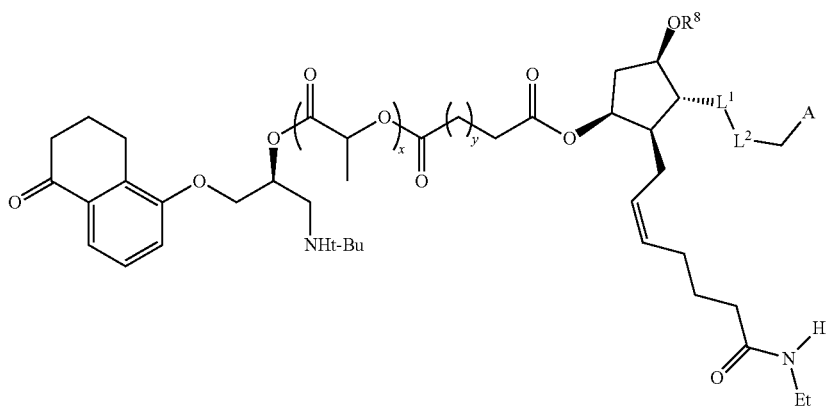

Example 32. Non-Limiting Examples of Formula XXXIX
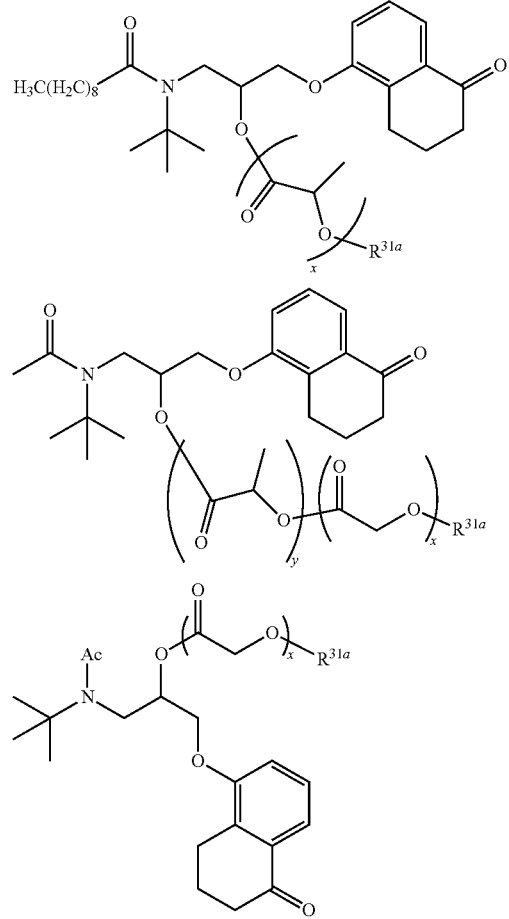
Example 33. Non-Limiting Examples of Formula XLI
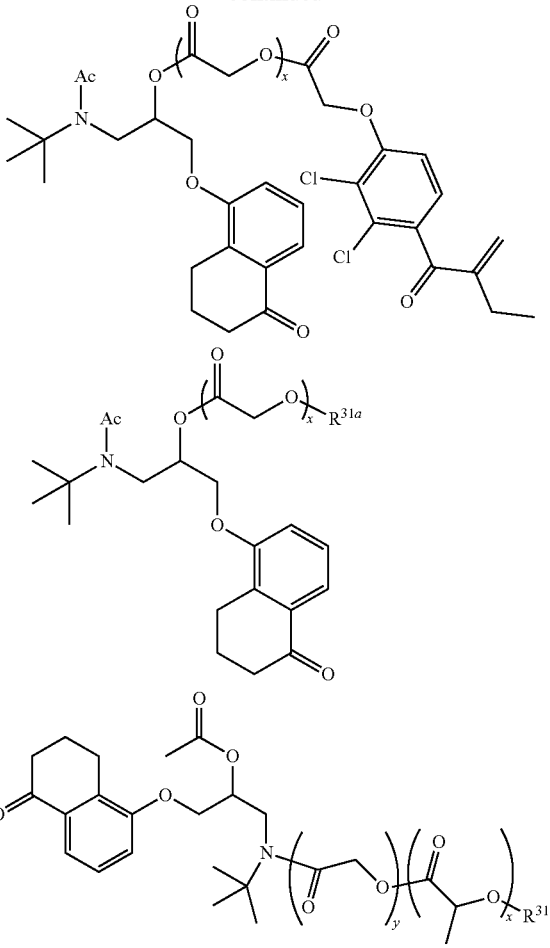
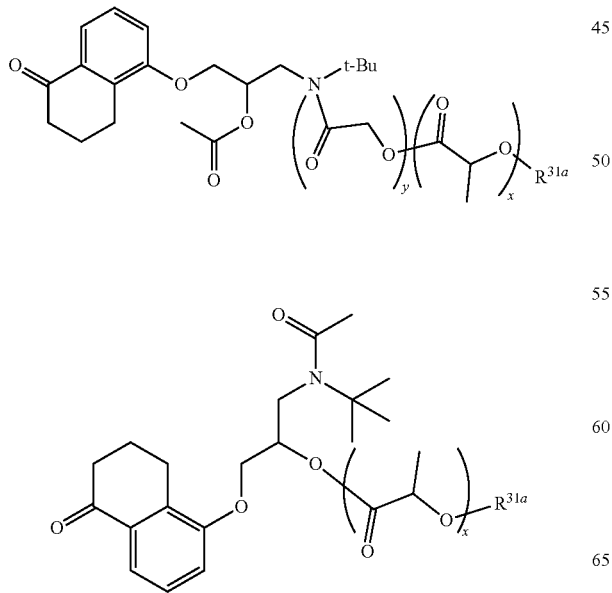
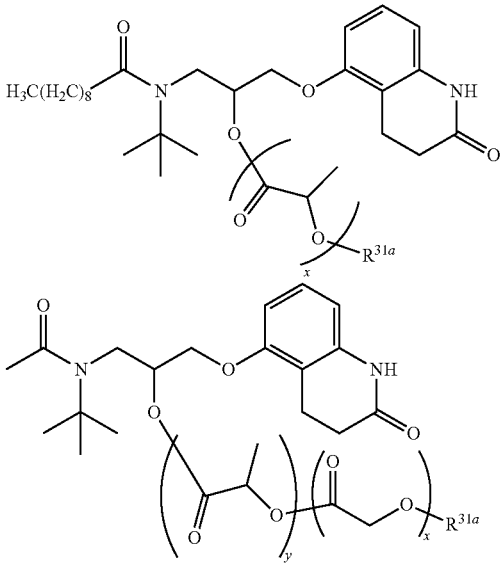

607
-continued
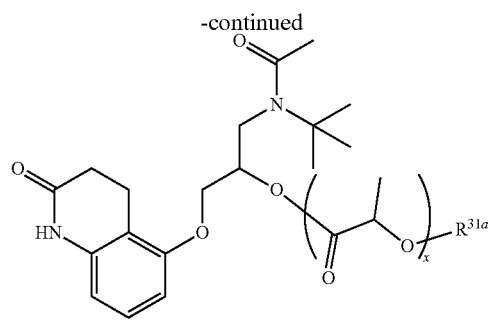
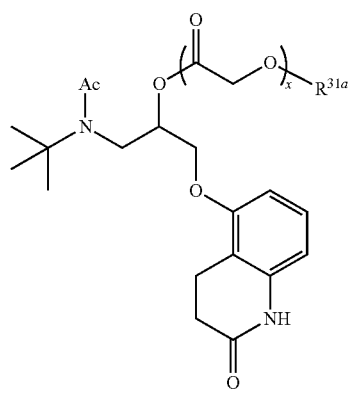
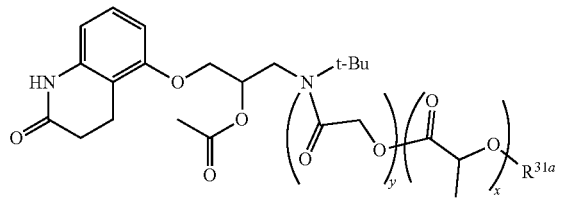
608
-continued
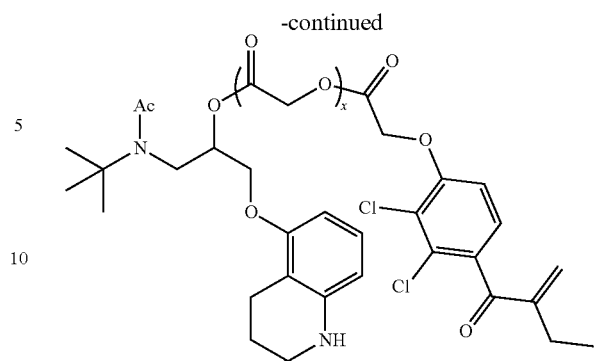
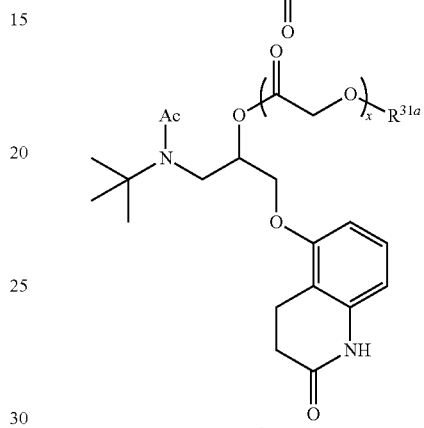
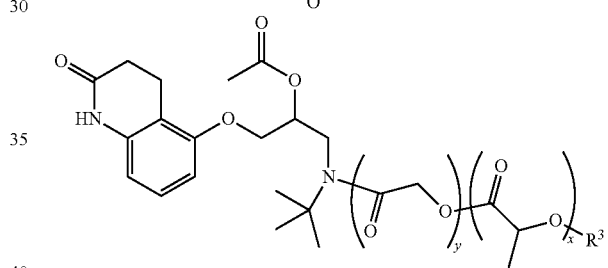
Example 34. Non-Limiting Examples of Formula XLIII
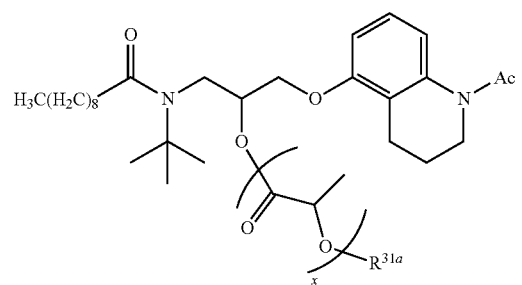
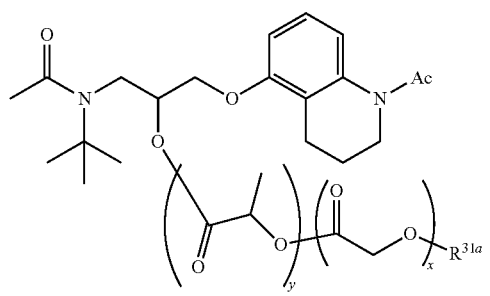

609
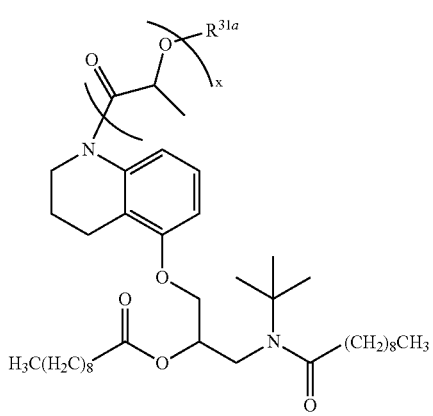
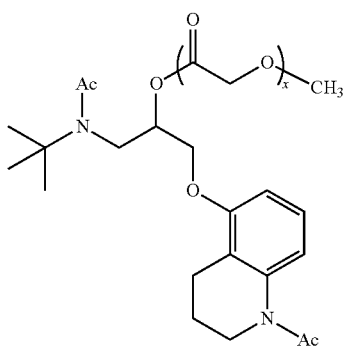
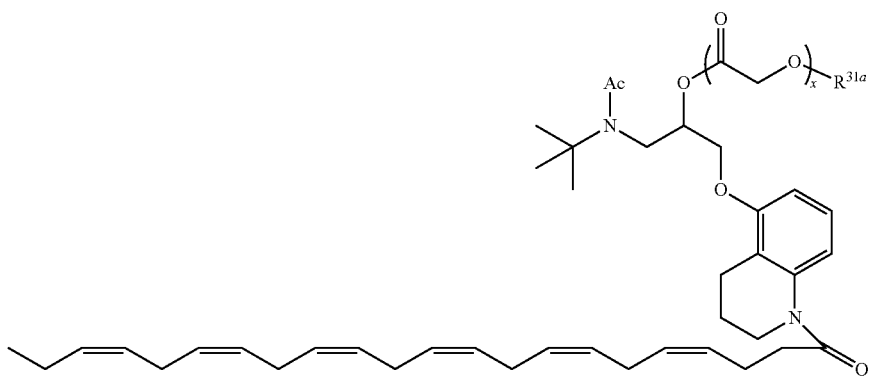
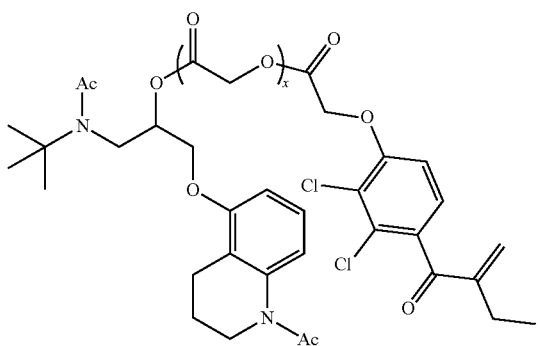
610
-continued
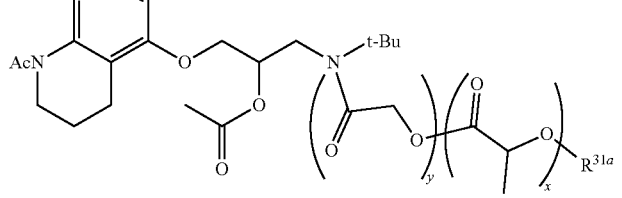
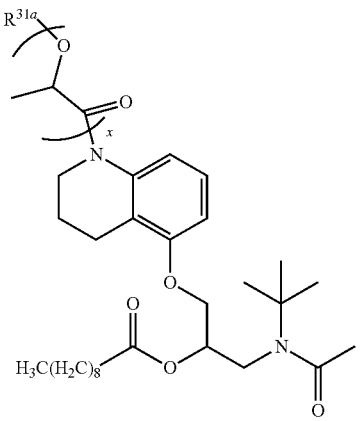
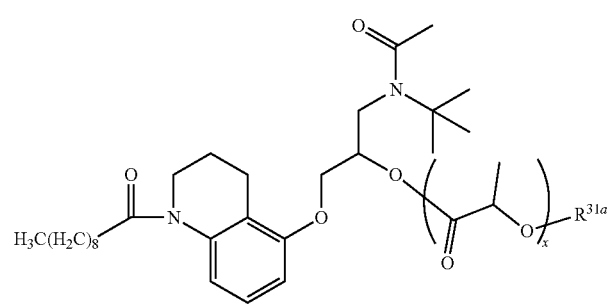

-continued

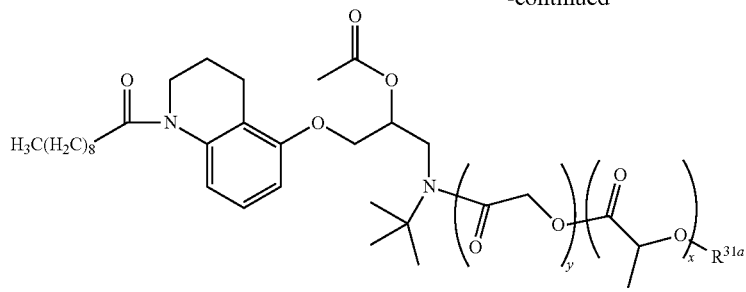

Example 35. Examples of Compounds of the Present Invention

This invention is intended to include all combinations of each of the active moieties and linkers shown in each of FIGS. 66A to 66I as if each combination were explicitly illustrated.

In FIGS. 66A to 66I, x', and y' are each independently selected from 0, 1, 2, 3, 4, 5, 6, 7, 8, 9, and 10, and wherein if x' and y' are within the linker then x' and y' cannot both be 0.

Example 36. Examples of Compounds of the Present Invention

Figure 66A:
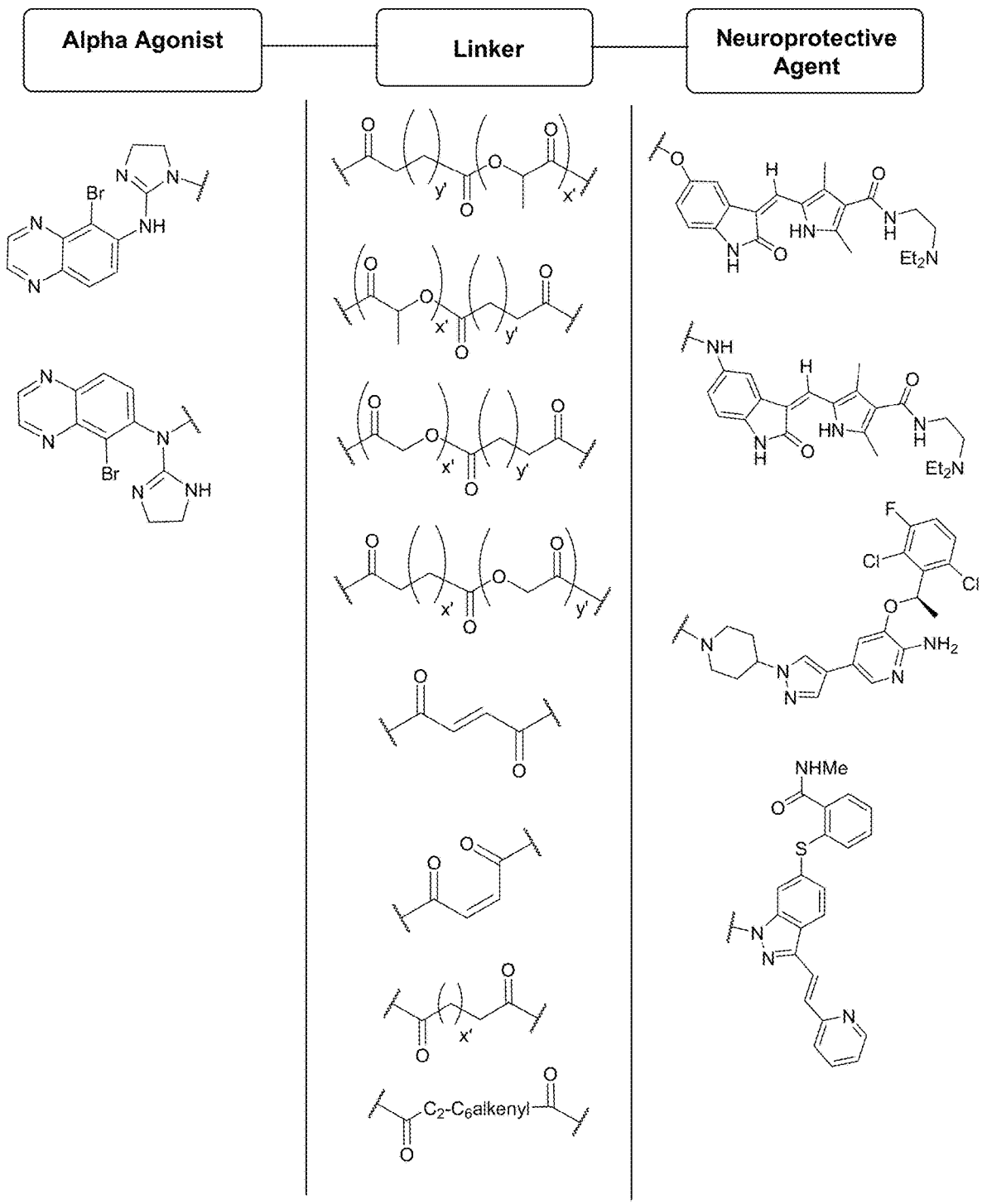
FIG. 66A illustrates non-limiting combinations of active moieties (alpha agonist and neuroprotective agent) and linkers in compounds according to the invention.
Figure 66B:
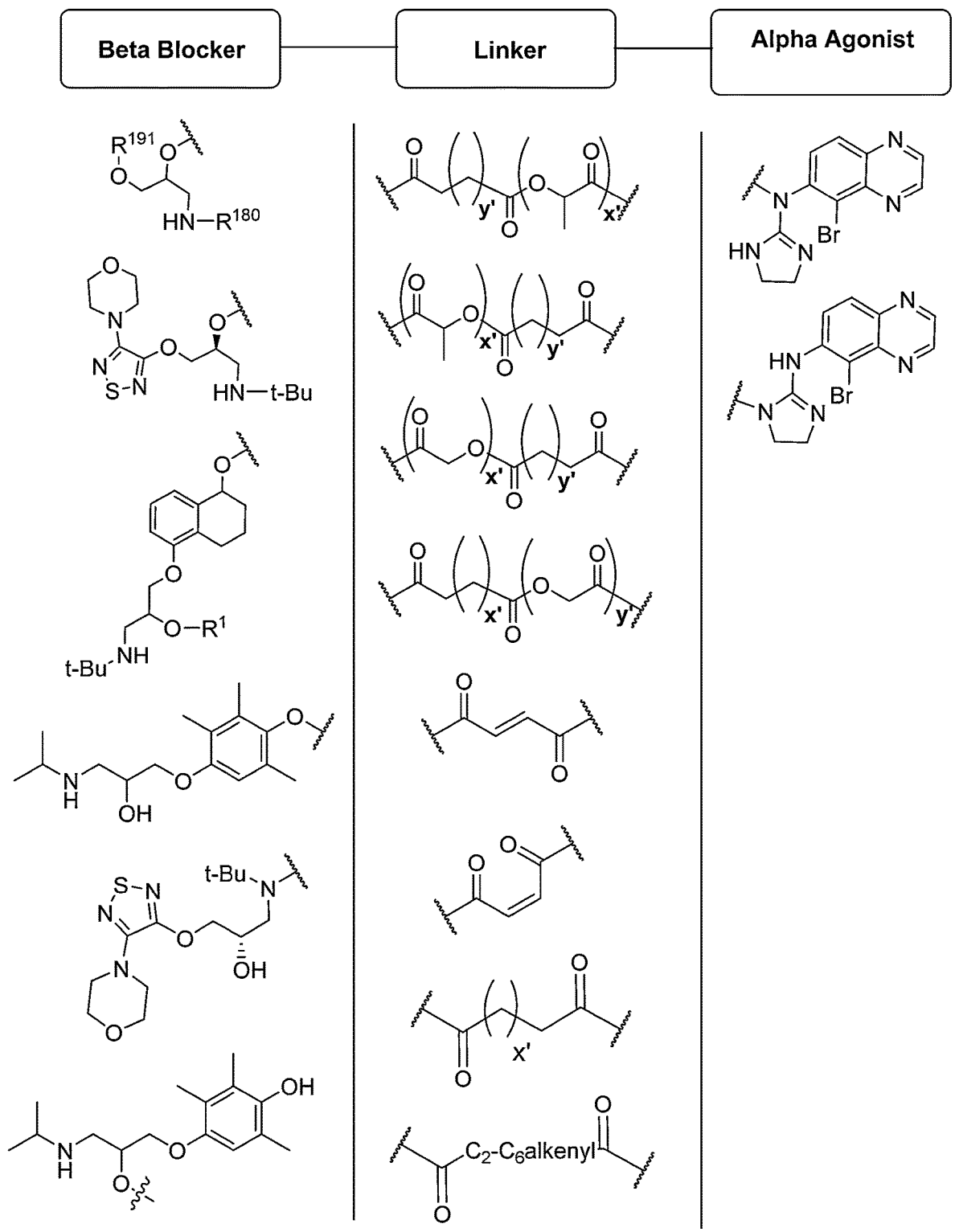
FIG. 66B illustrates non-limiting combinations of active moieties (alpha agonist and neuroprotective agent) and linkers in compounds according to the invention.
Figure 66C:
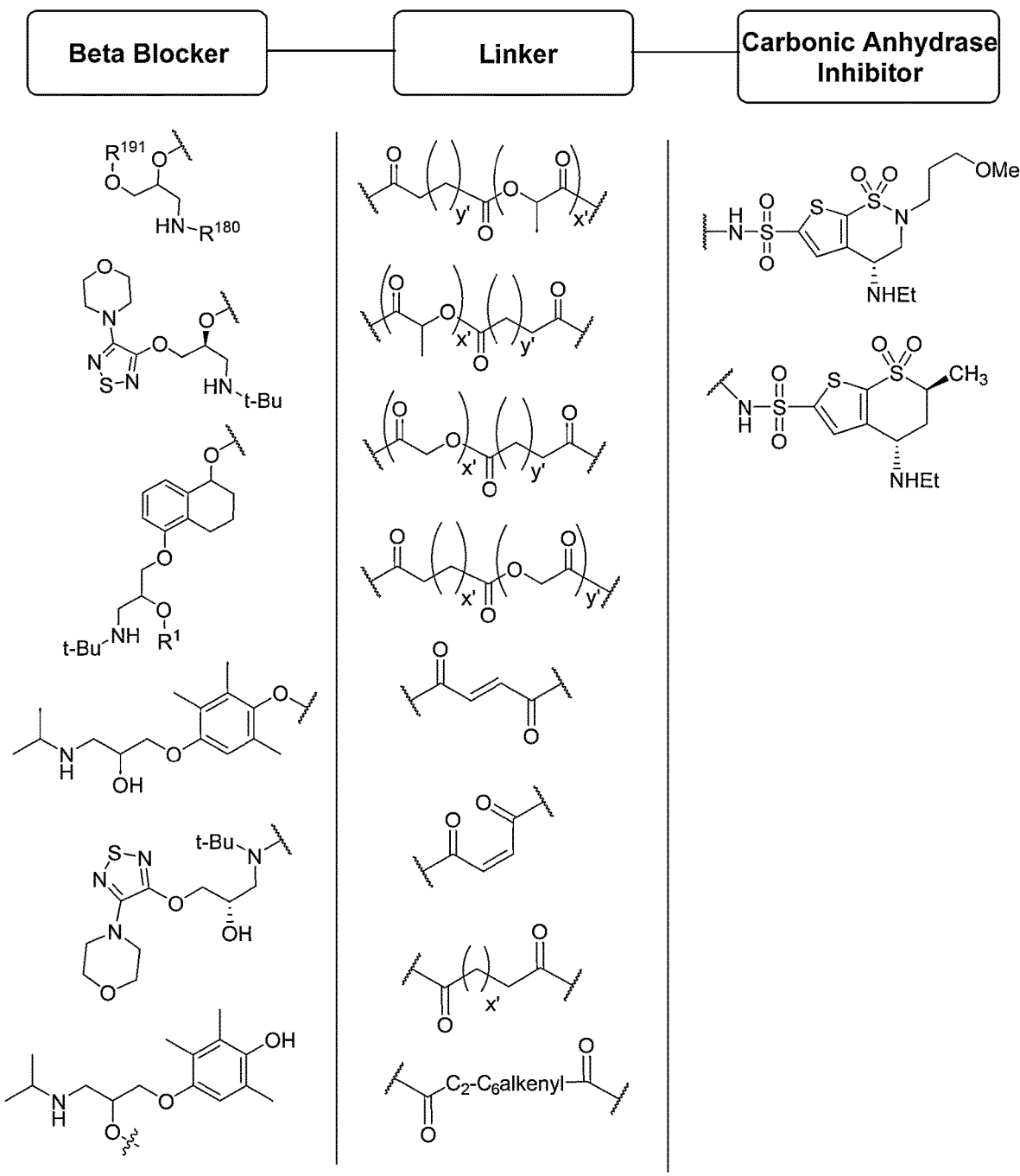
FIG. 66C illustrates non-limiting combinations of active moieties (alpha agonist and neuroprotective agent) and linkers in compounds according to the invention.
Figure 66D:
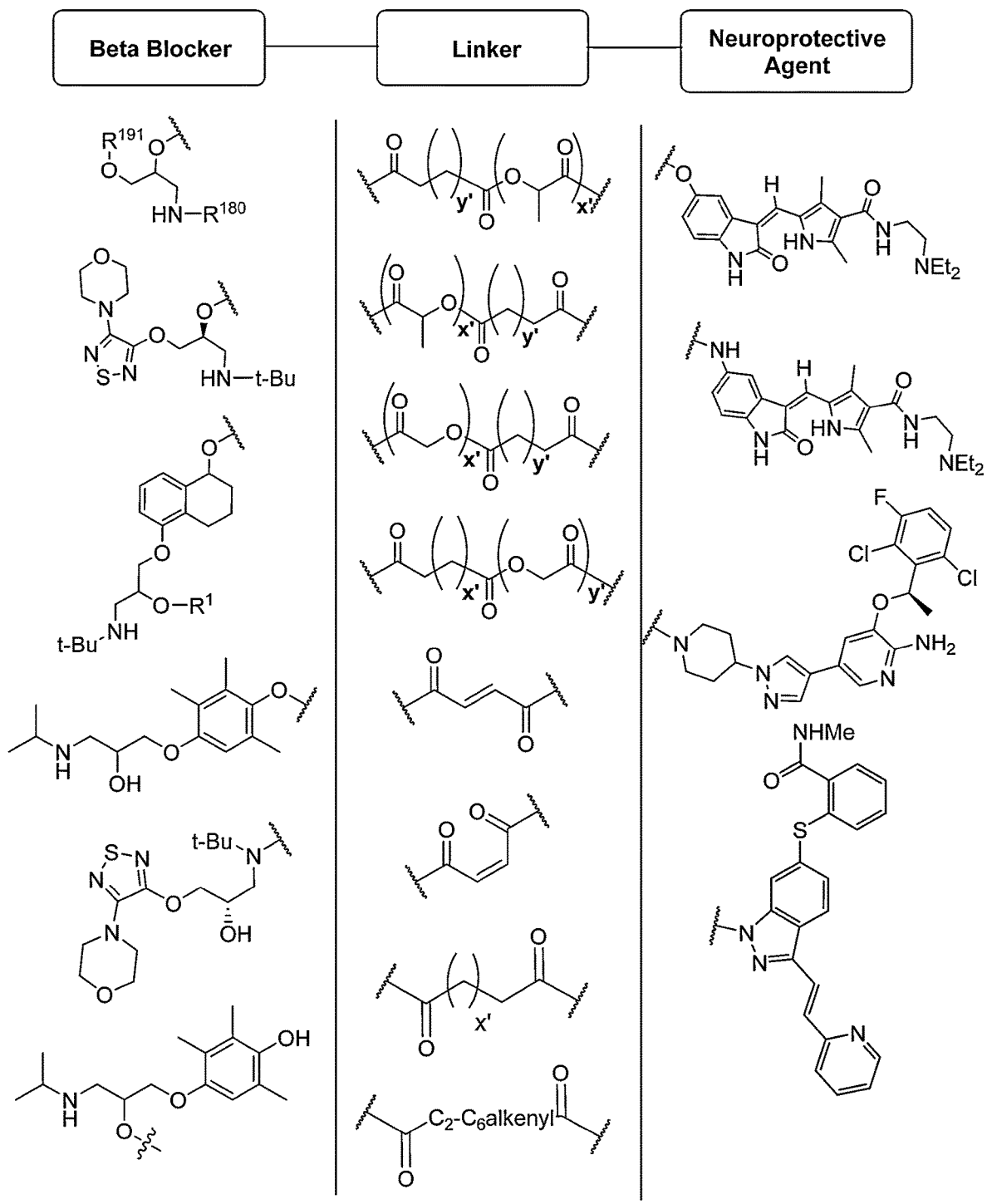
FIG. 66D illustrates non-limiting combinations of active moieties (alpha agonist and neuroprotective agent) and linkers in compounds according to the invention.
Figure 66E:
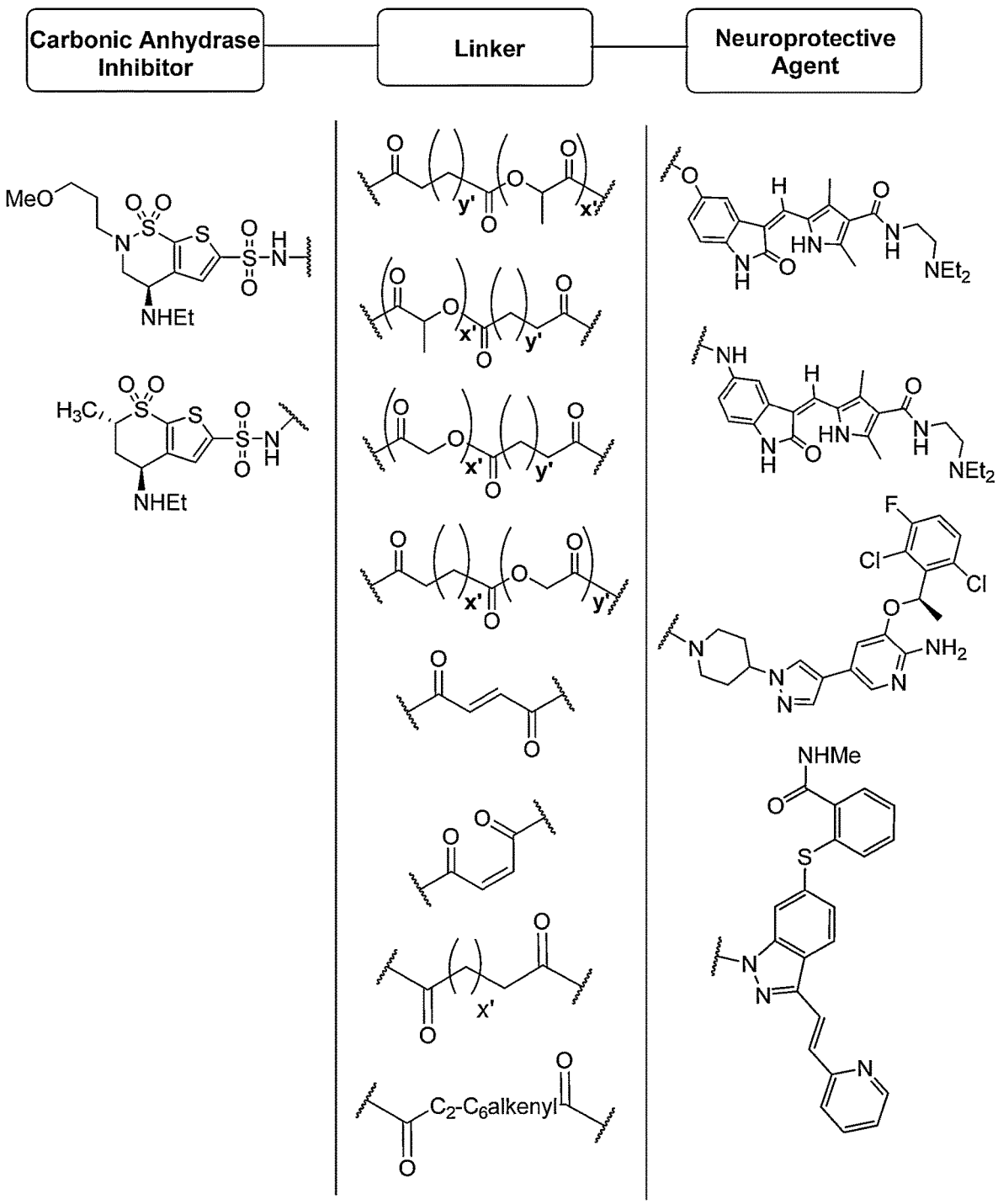
FIG. 66E illustrates non-limiting combinations of active moieties (alpha agonist and neuroprotective agent) and linkers in compounds according to the invention.
Figure 66F:
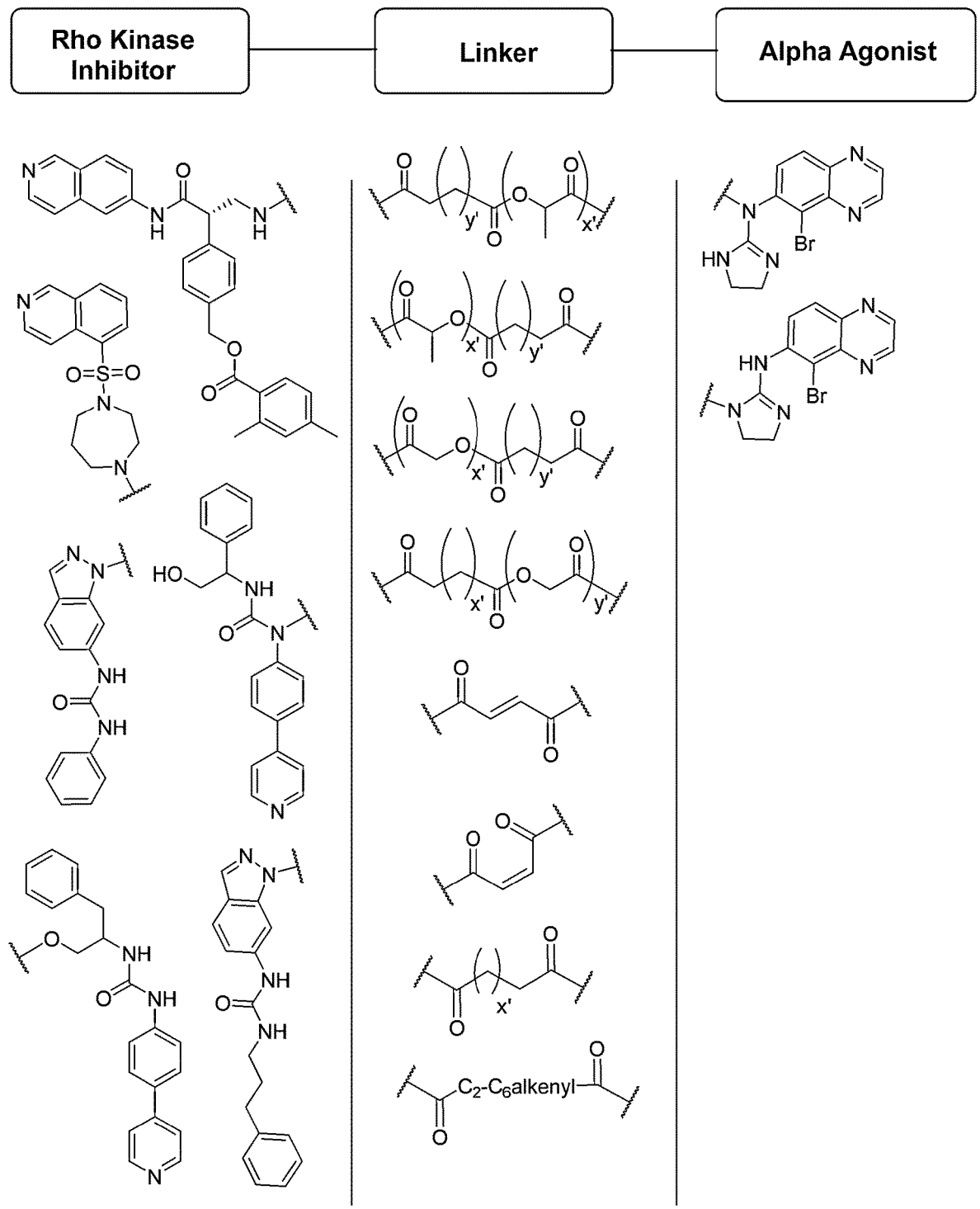
FIG. 66F illustrates non-limiting combinations of active moieties (alpha agonist and neuroprotective agent) and linkers in compounds according to the invention.
Figure 66G:
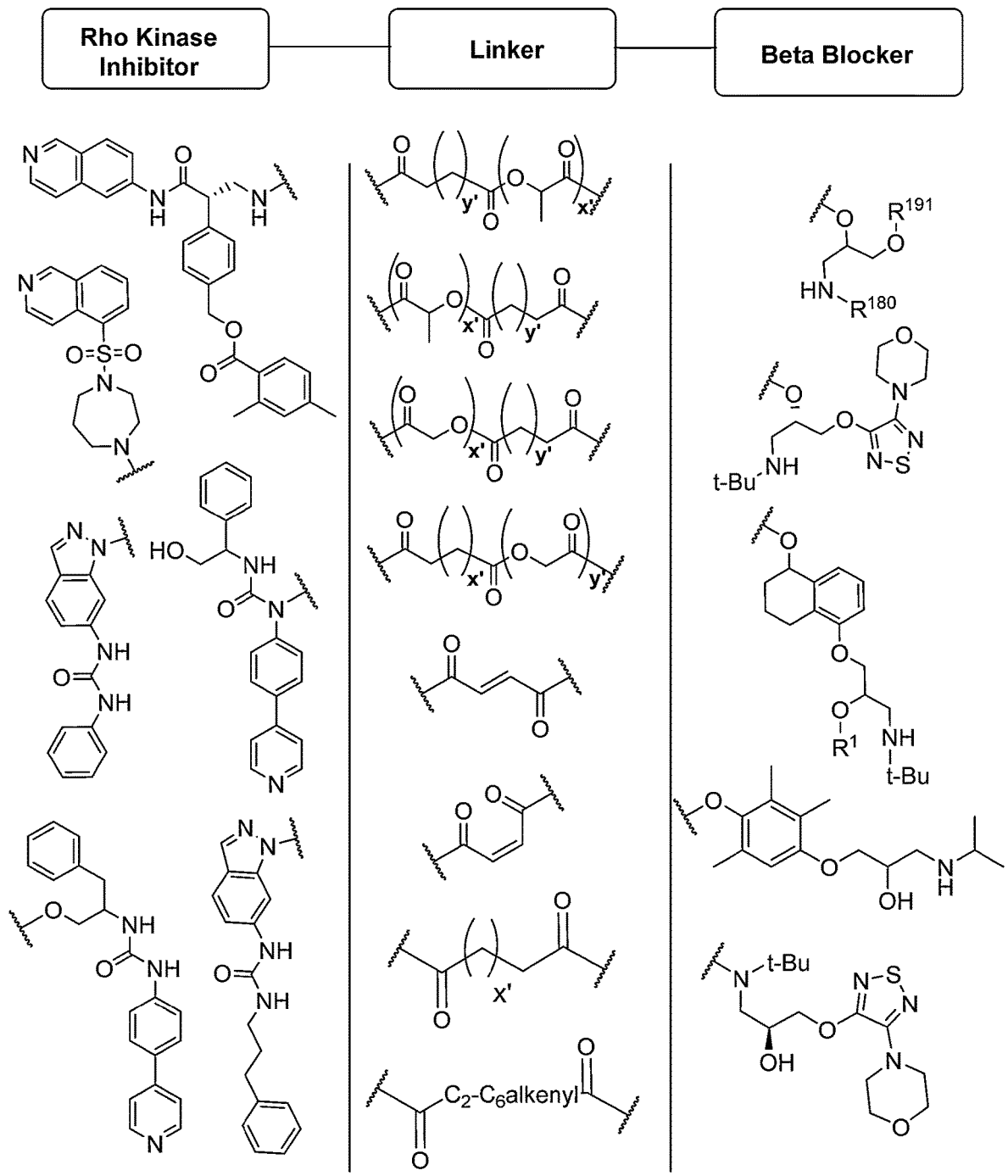
FIG. 66G illustrates non-limiting combinations of active moieties (alpha agonist and neuroprotective agent) and linkers in compounds according to the invention.
Figure 66H:
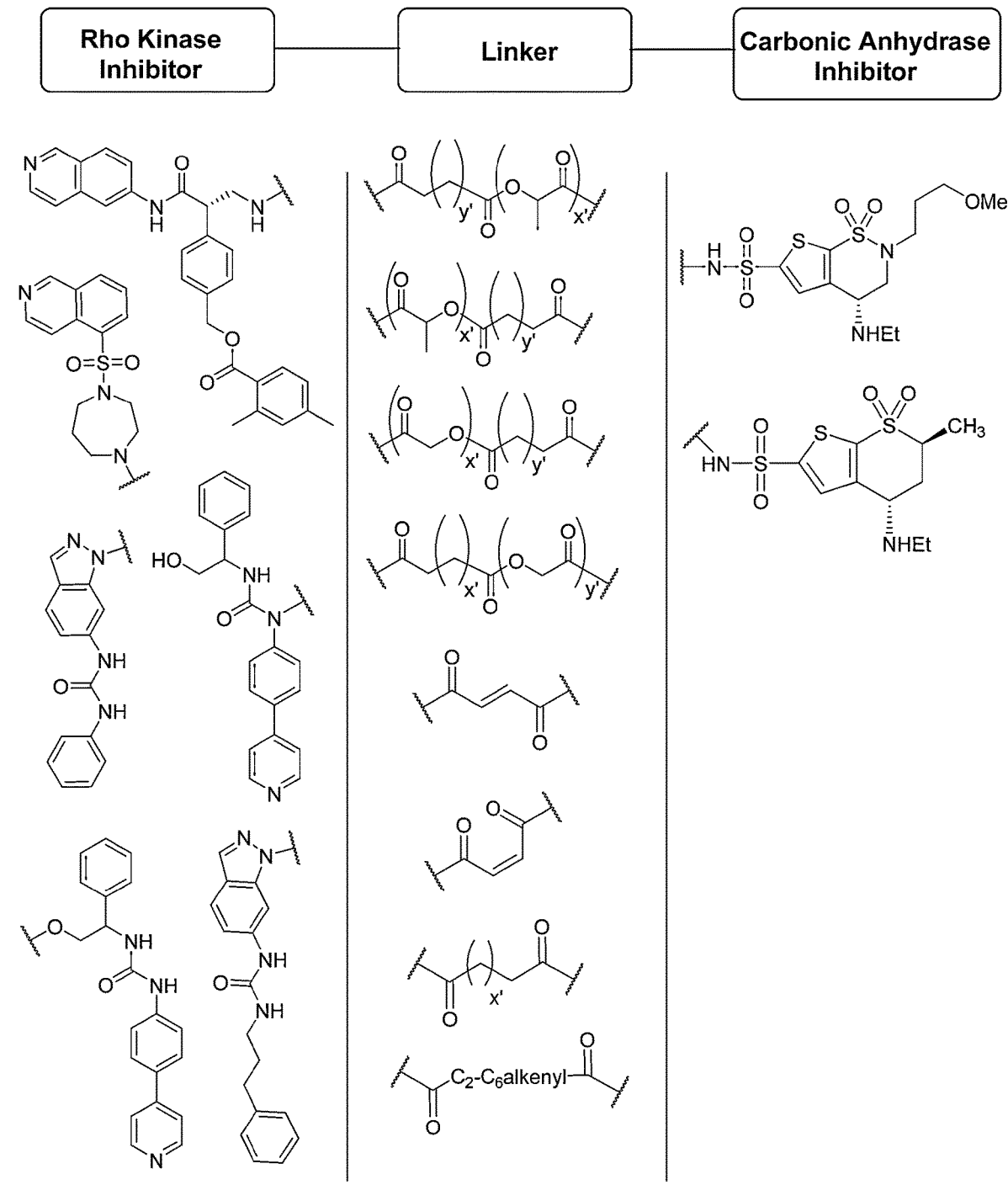
FIG. 66H illustrates non-limiting combinations of active moieties (alpha agonist and neuroprotective agent) and linkers in compounds according to the invention.
Figure 66I:
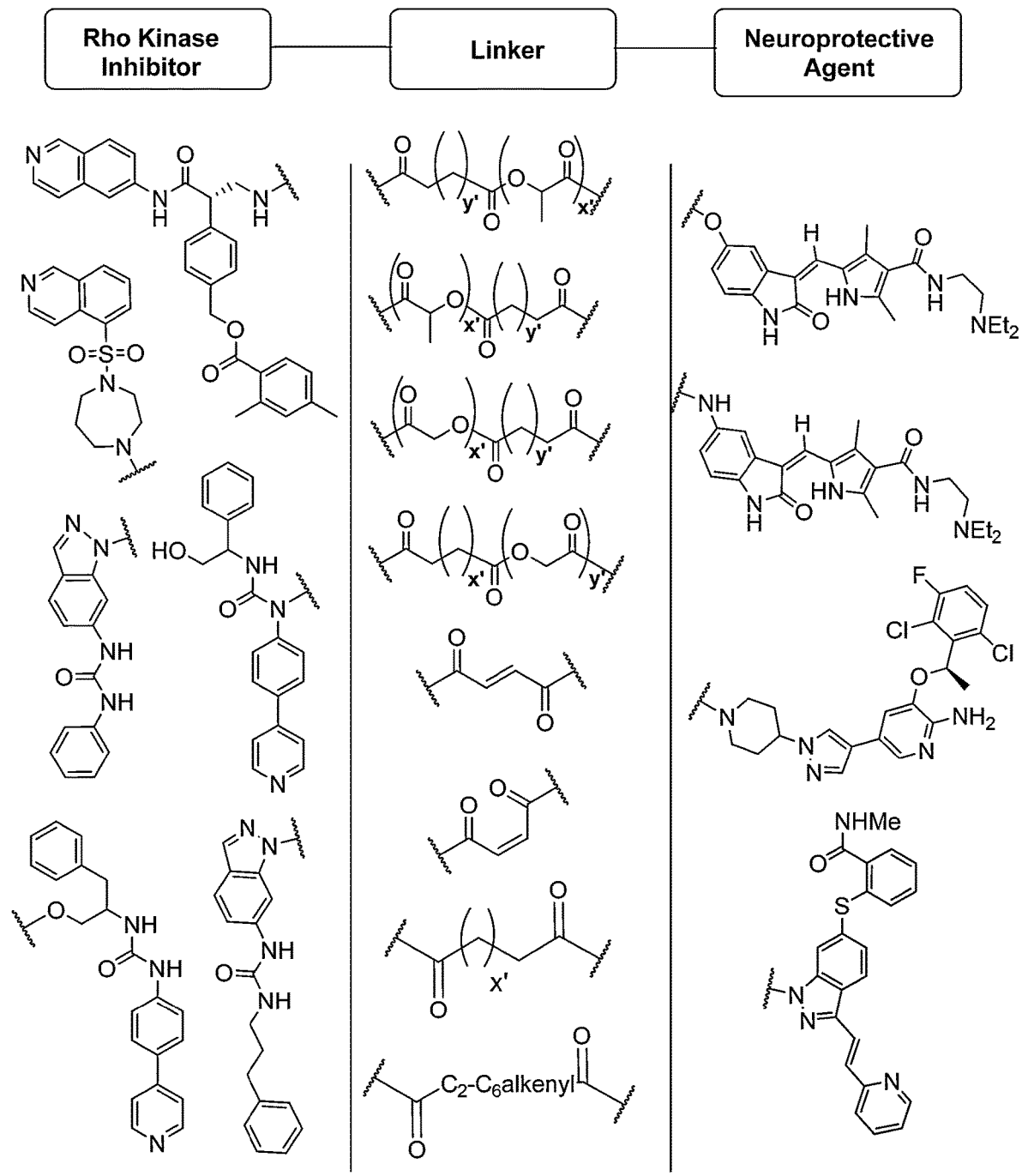
FIG. 66I illustrates non-limiting combinations of active moieties (alpha agonist and neuroprotective agent) and linkers in compounds according to the invention.
Figure 66J:
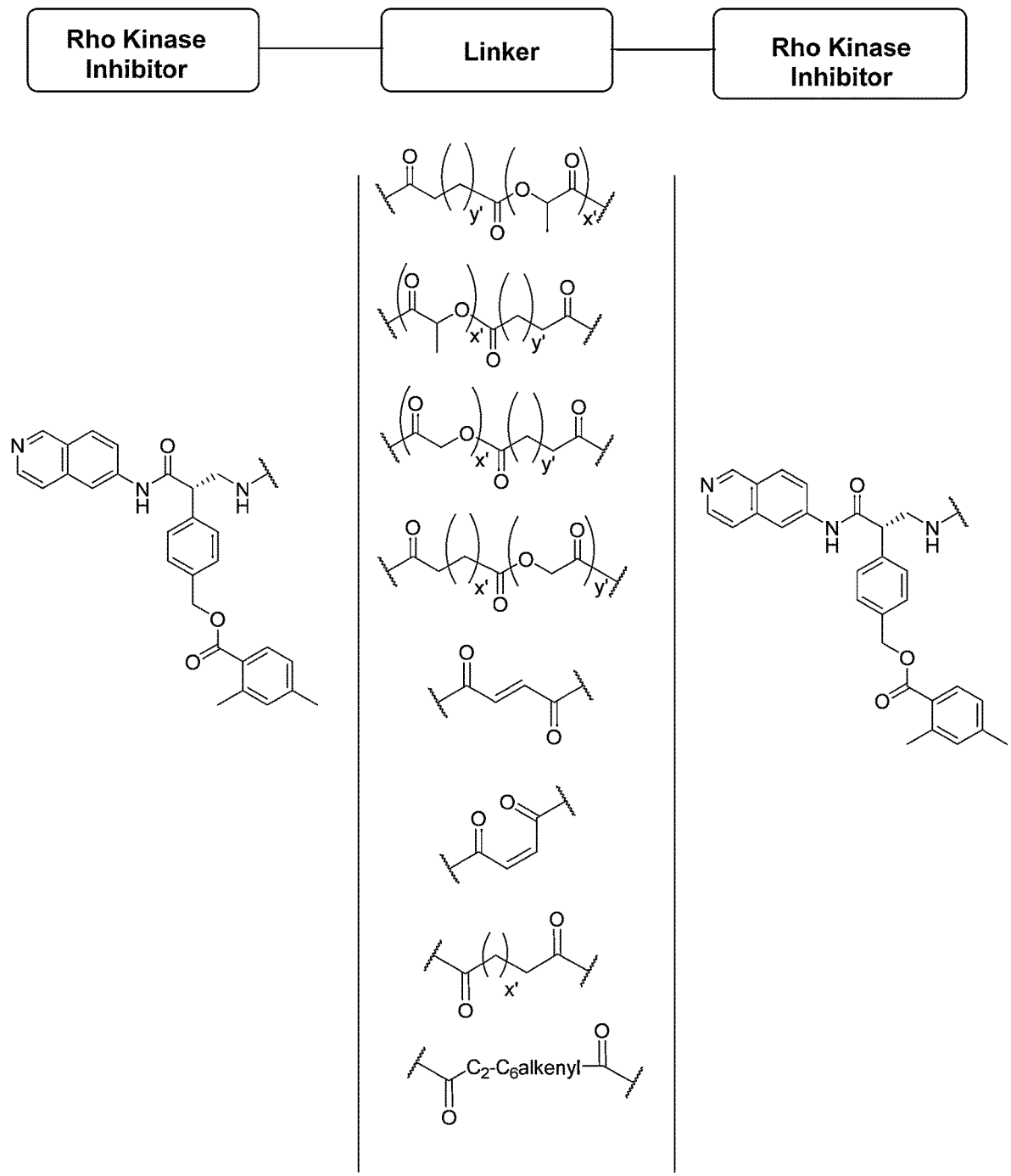
FIG. 66J illustrates non-limiting combinations of active moieties (alpha agonist and neuroprotective agent) and linkers in compounds according to the invention.
Figure 66K:
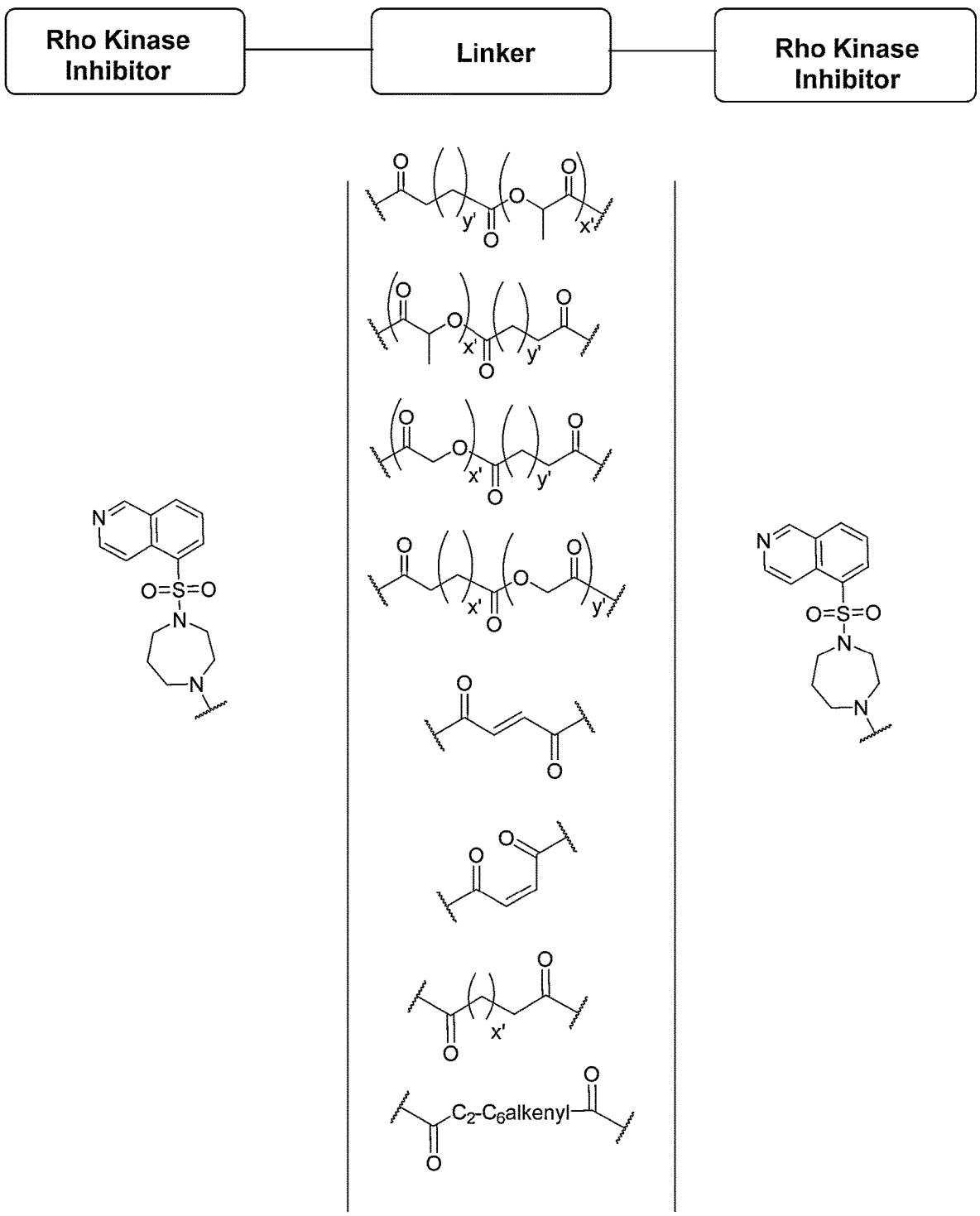
FIG. 66K illustrates non-limiting combinations of active moieties (alpha agonist and neuroprotective agent) and linkers in compounds according to the invention.
Figure 66L:
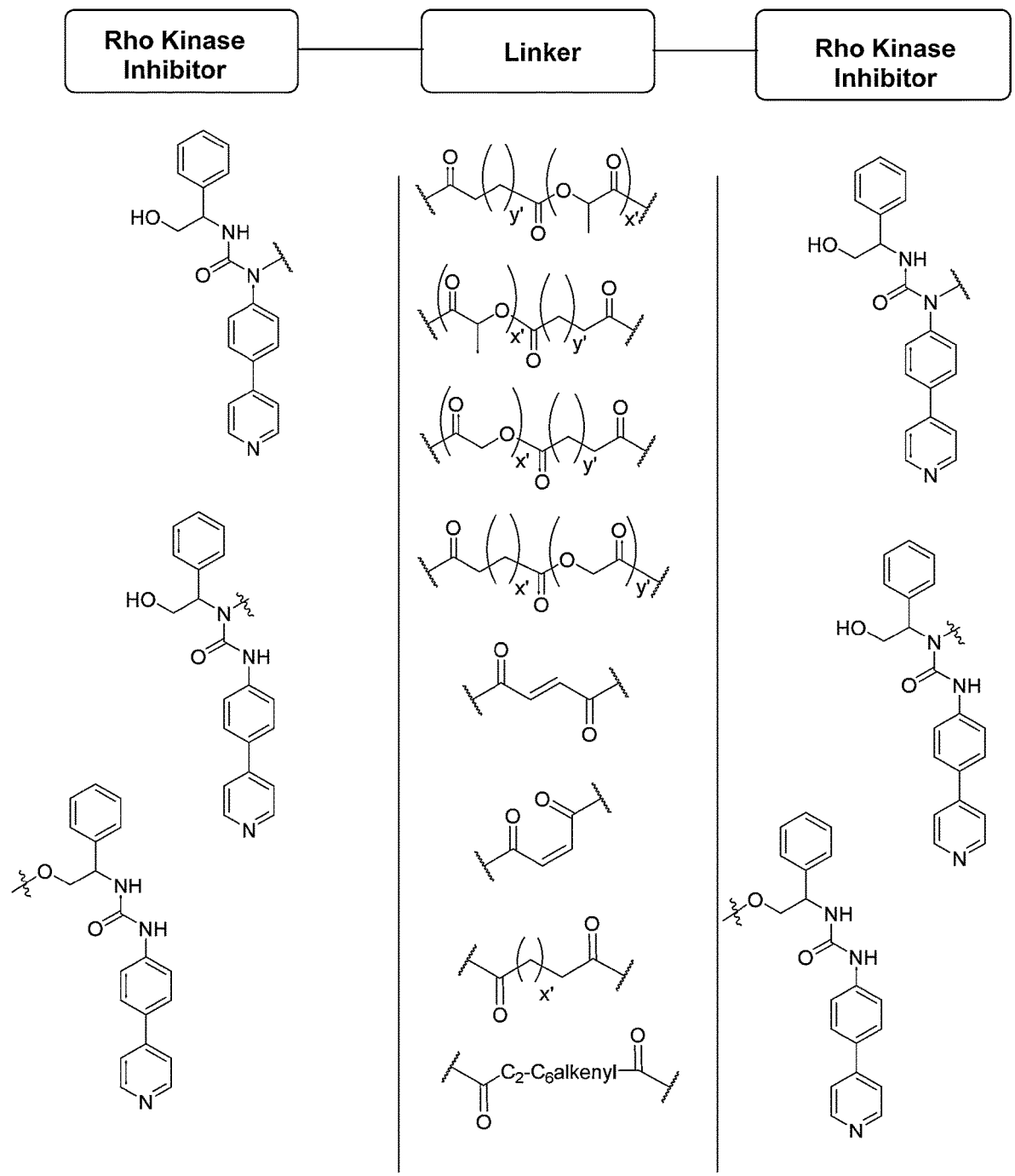
FIG. 66L illustrates non-limiting combinations of active moieties (alpha agonist and neuroprotective agent) and linkers in compounds according to the invention.
Figure 66M:
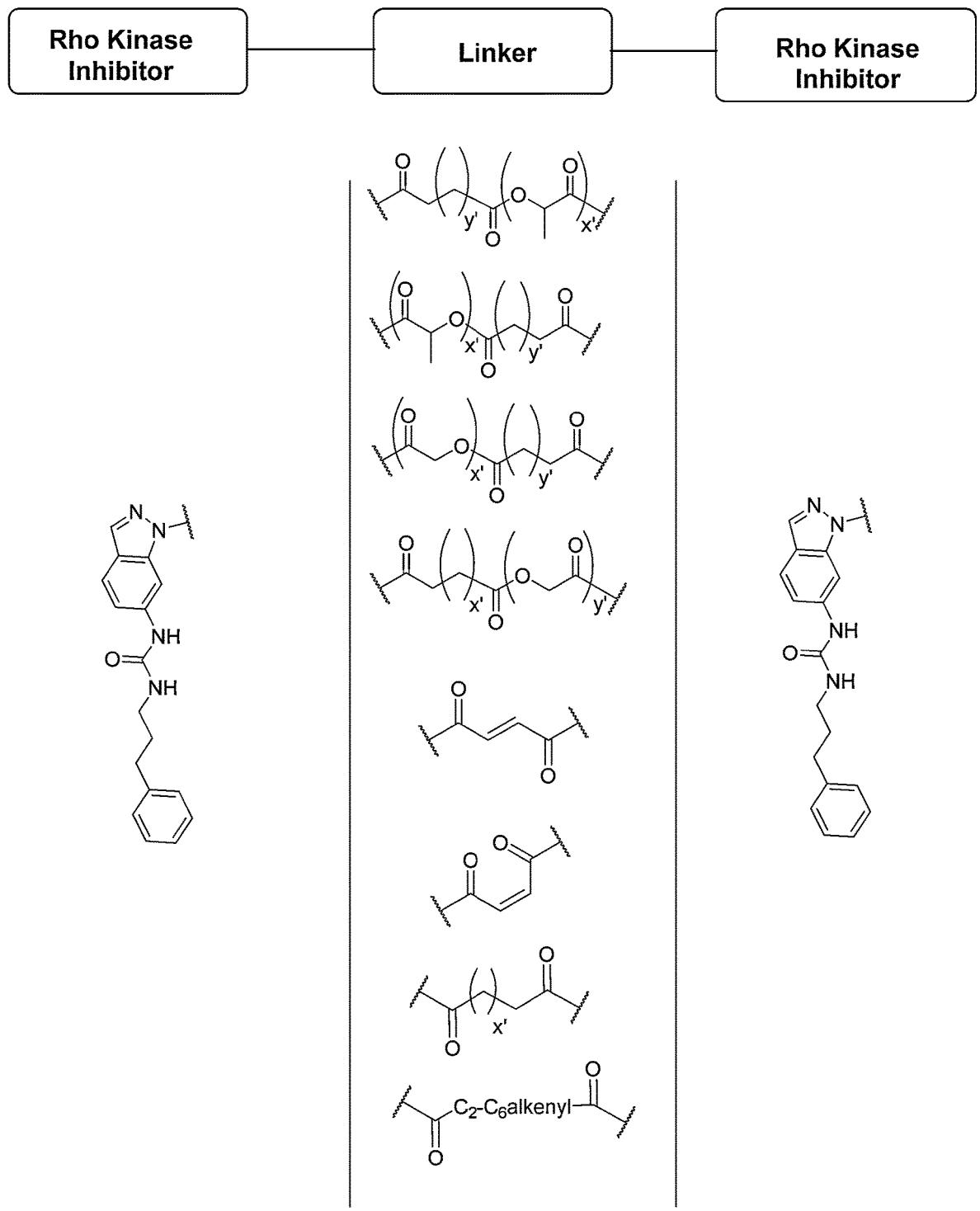
FIG. 66M illustrates non-limiting combinations of active moieties (alpha agonist and neuroprotective agent) and linkers in compounds according to the invention.
Figure 66N:
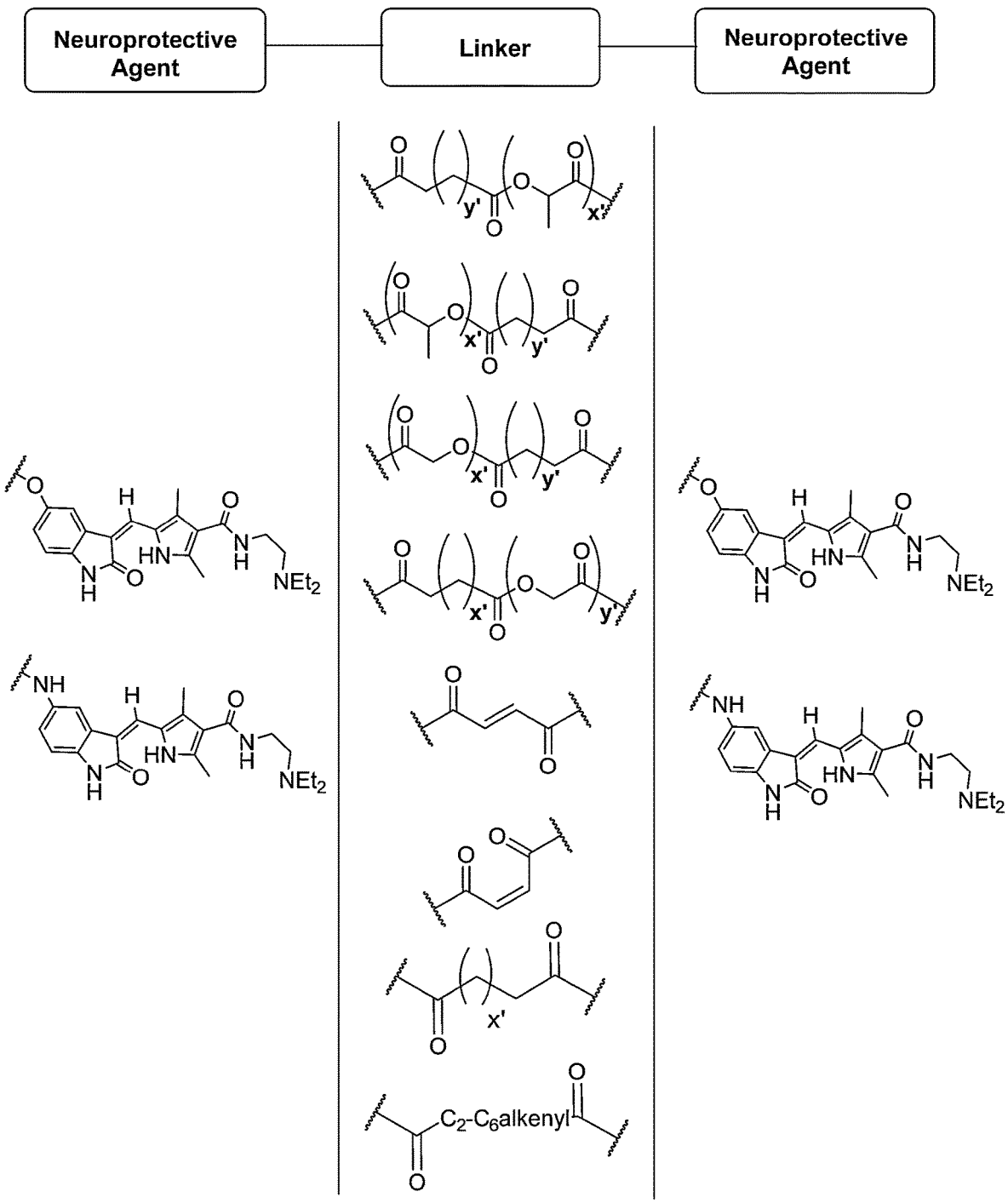
FIG. 66N illustrates non-limiting combinations of active moieties (alpha agonist and neuroprotective agent) and linkers in compounds according to the invention.
Figure 66O:
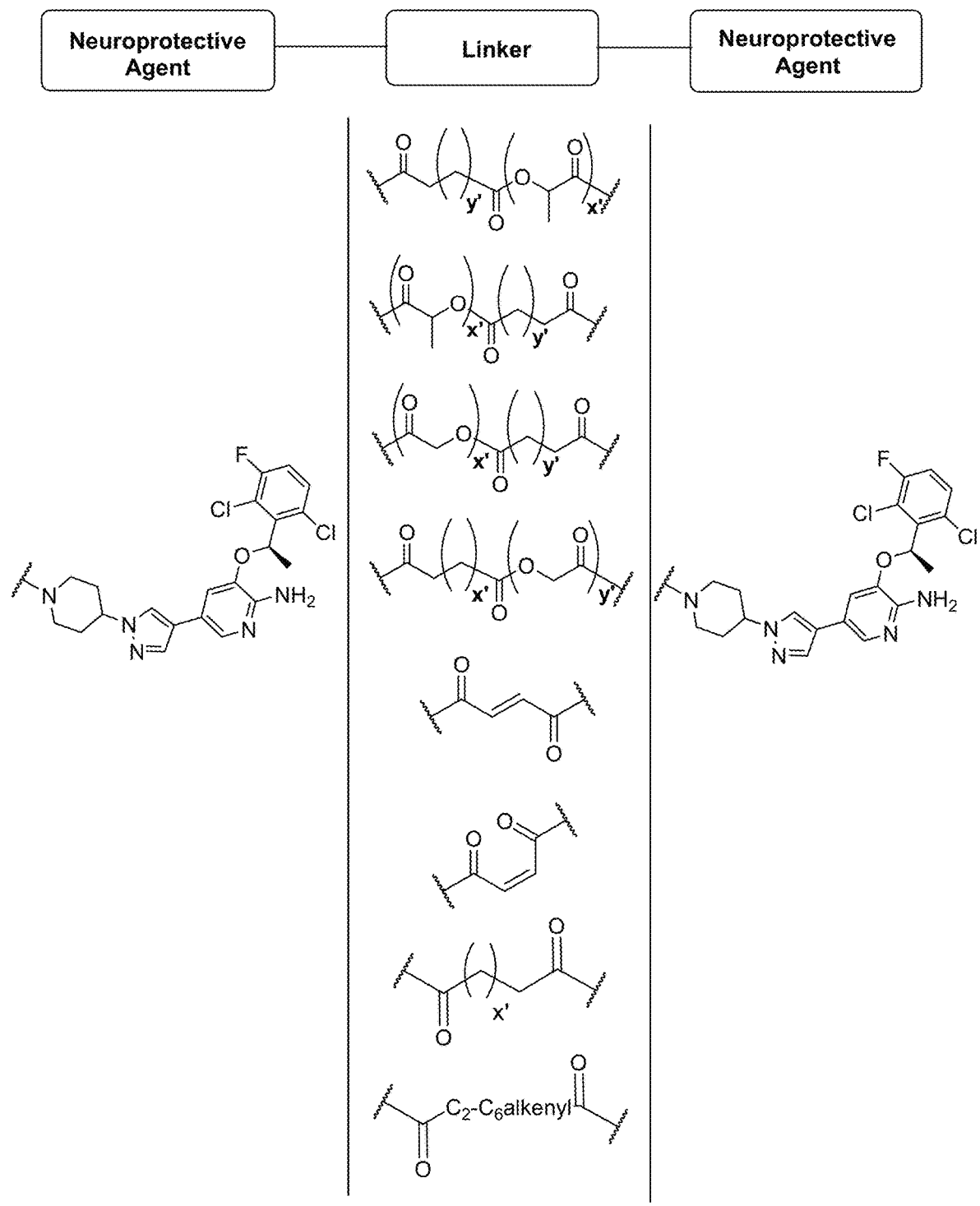
FIG. 66O illustrates non-limiting combinations of active moieties (alpha agonist and neuroprotective agent) and linkers in compounds according to the invention.
Figure 66P:
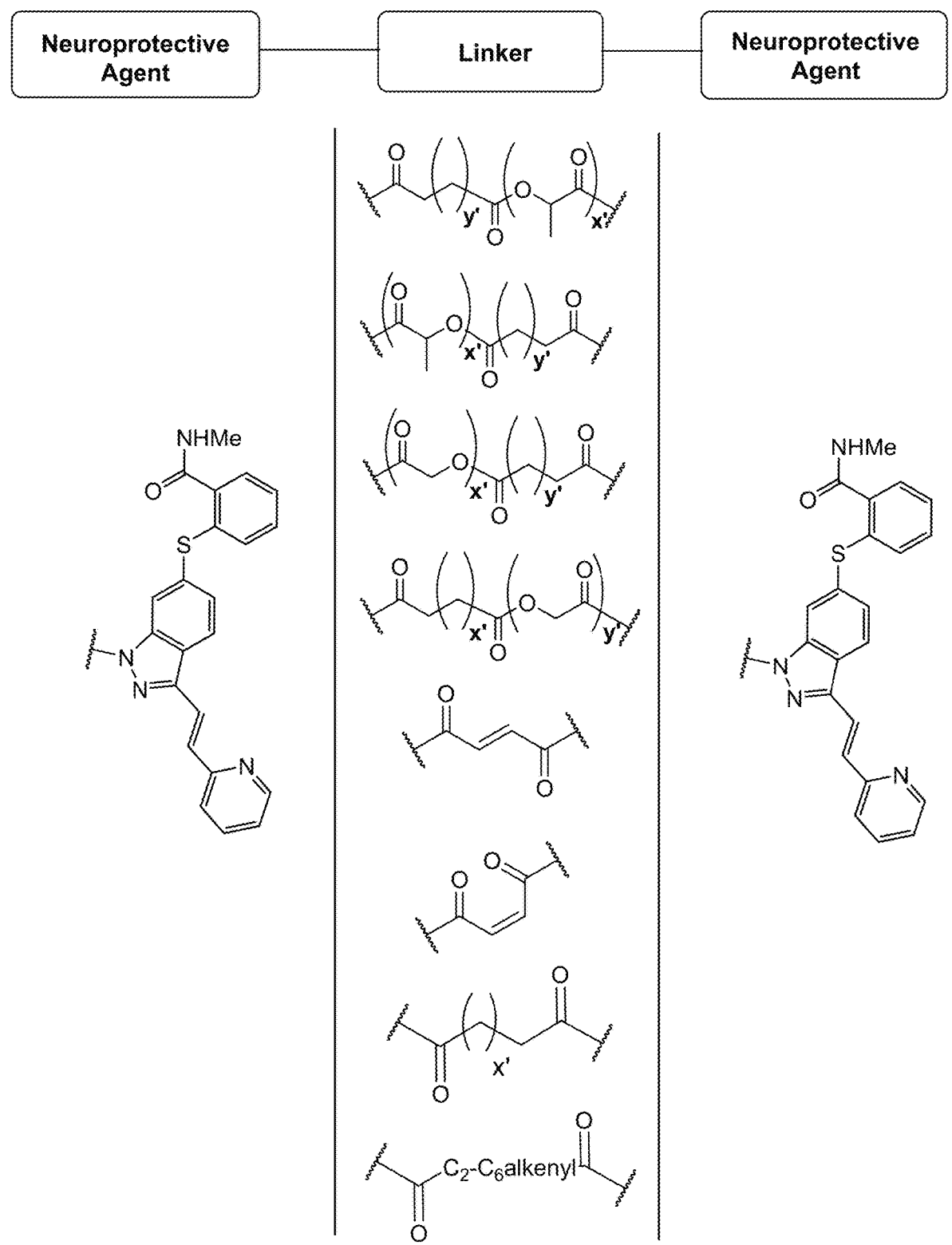
FIG. 66P illustrates non-limiting combinations of active moieties (alpha agonist and neuroprotective agent) and linkers in compounds according to the invention.
Figure 66Q:
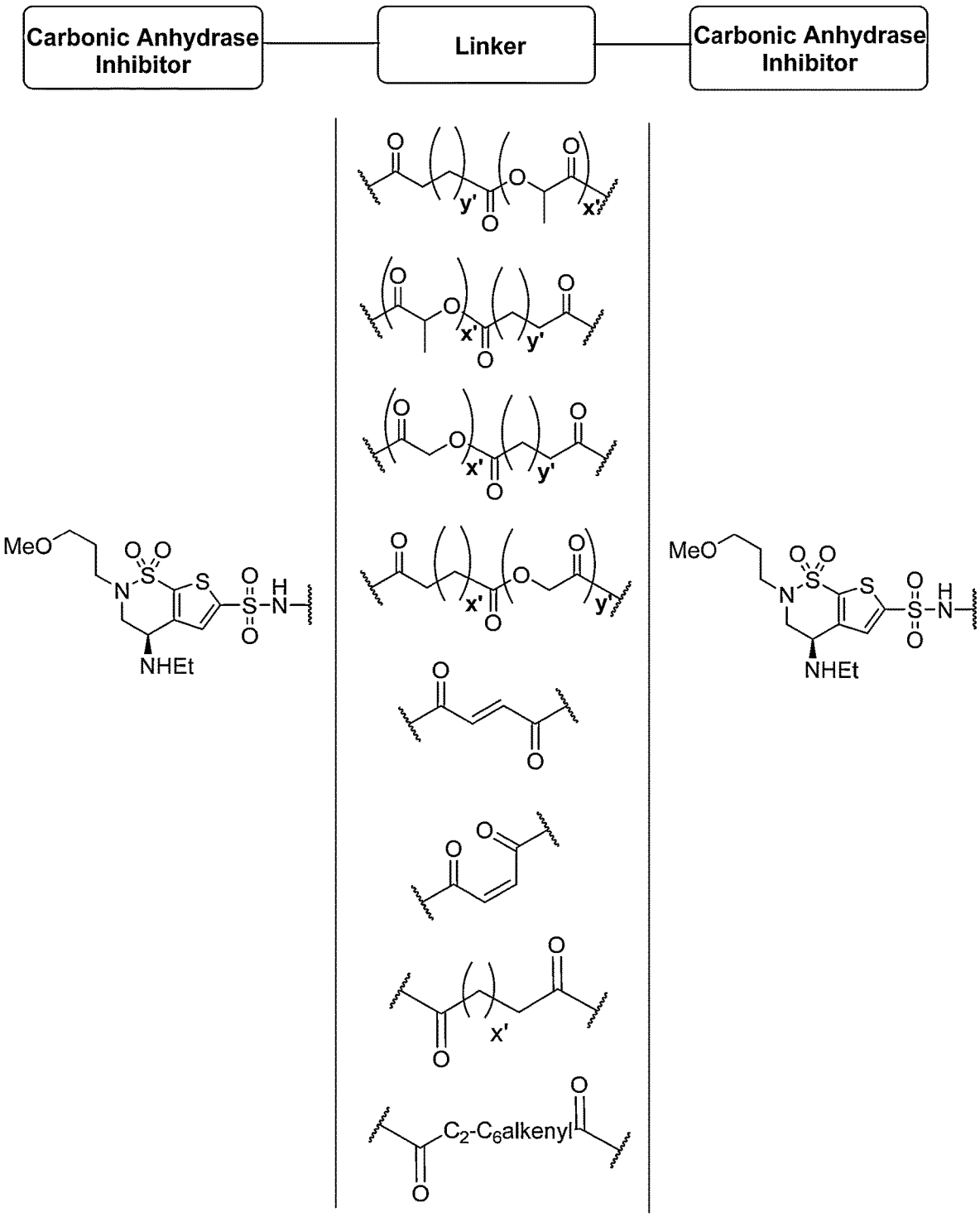
FIG. 66Q illustrates non-limiting combinations of active moieties (alpha agonist and neuroprotective agent) and linkers in compounds according to the invention.
Figure 66R:
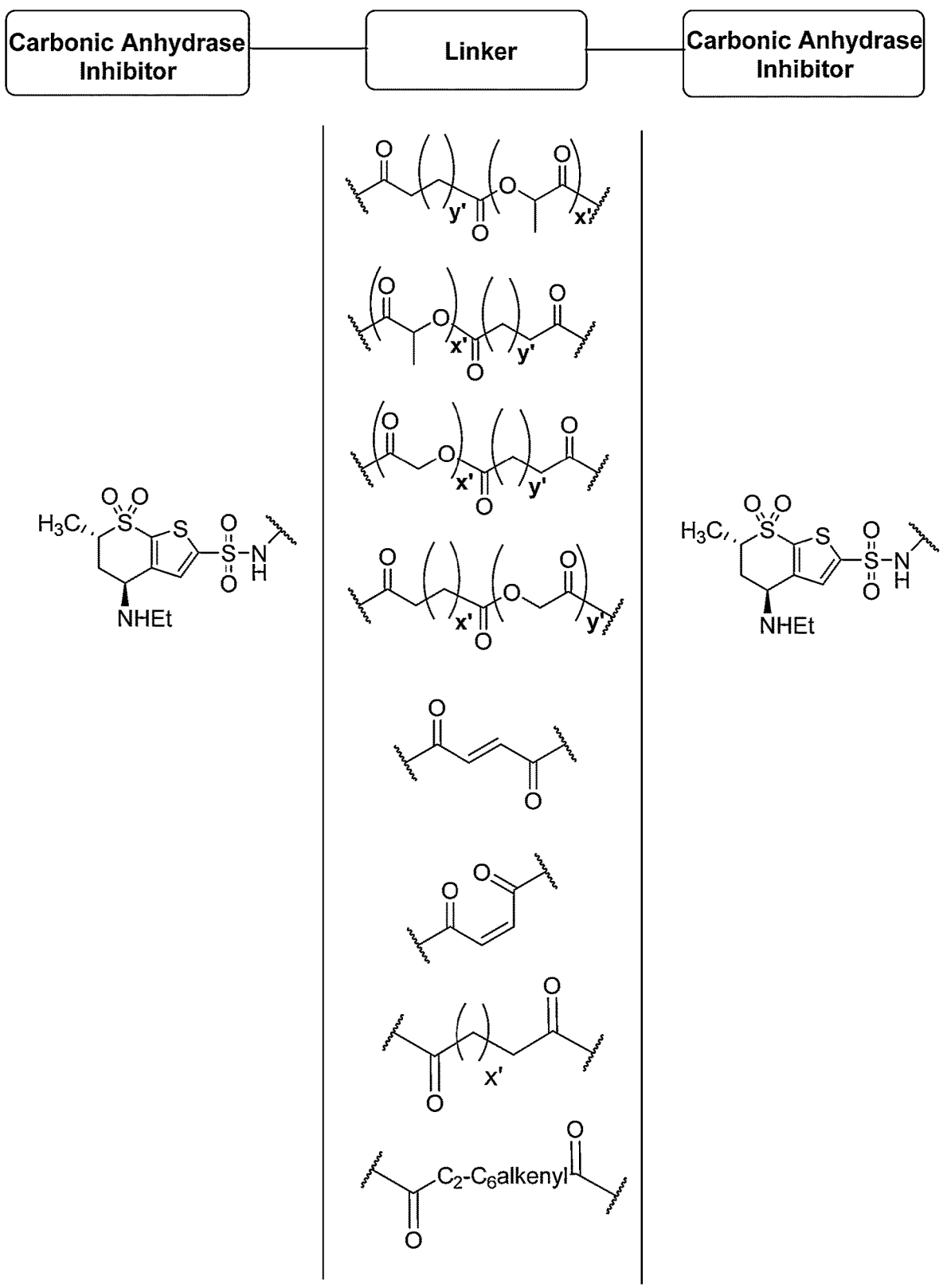
FIG. 66R illustrates non-limiting combinations of active moieties (alpha agonist and neuroprotective agent) and linkers in compounds according to the invention.
Figure 66S:
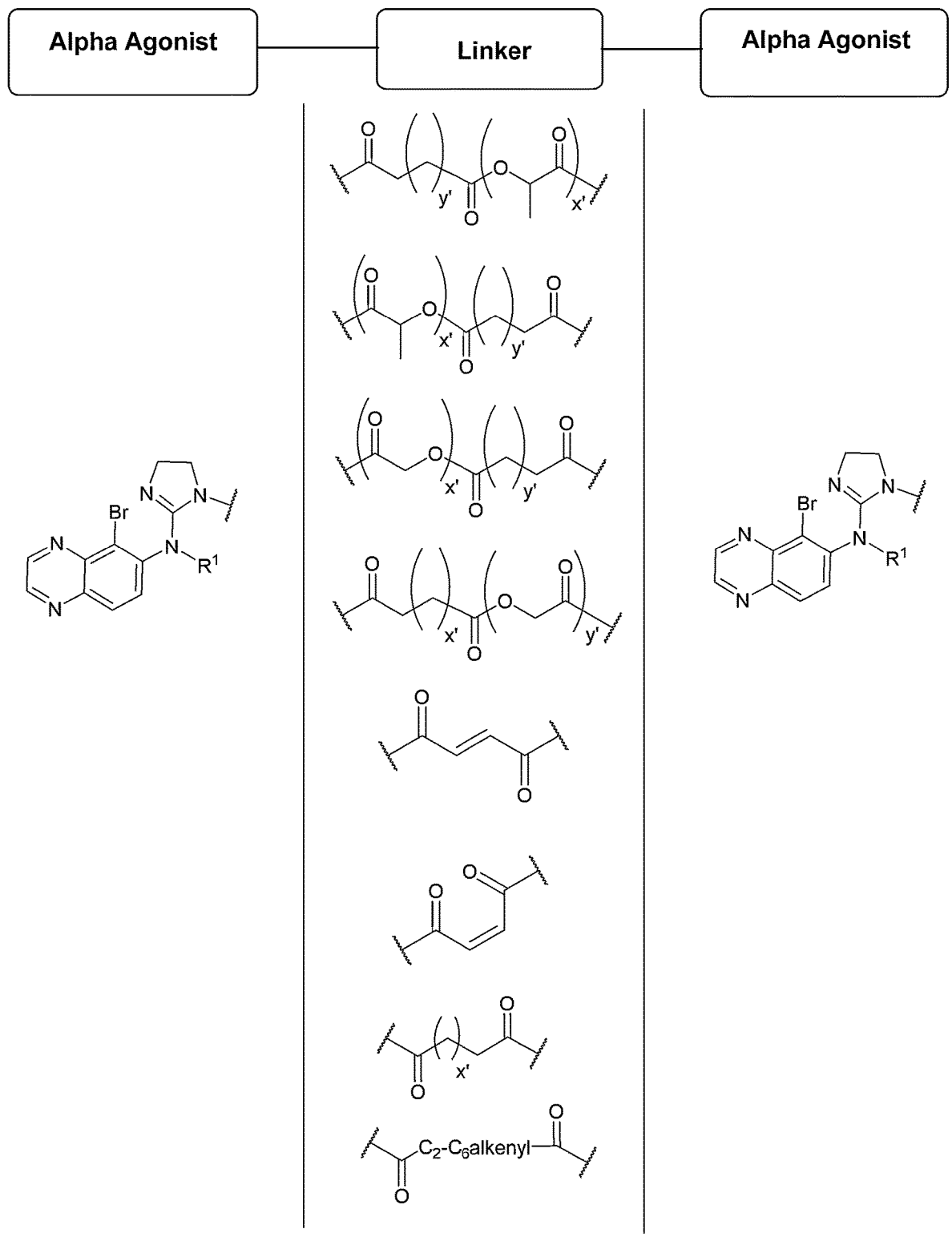
FIG. 66S illustrates non-limiting combinations of active moieties (alpha agonist and neuroprotective agent) and linkers in compounds according to the invention.
Figure 66T:
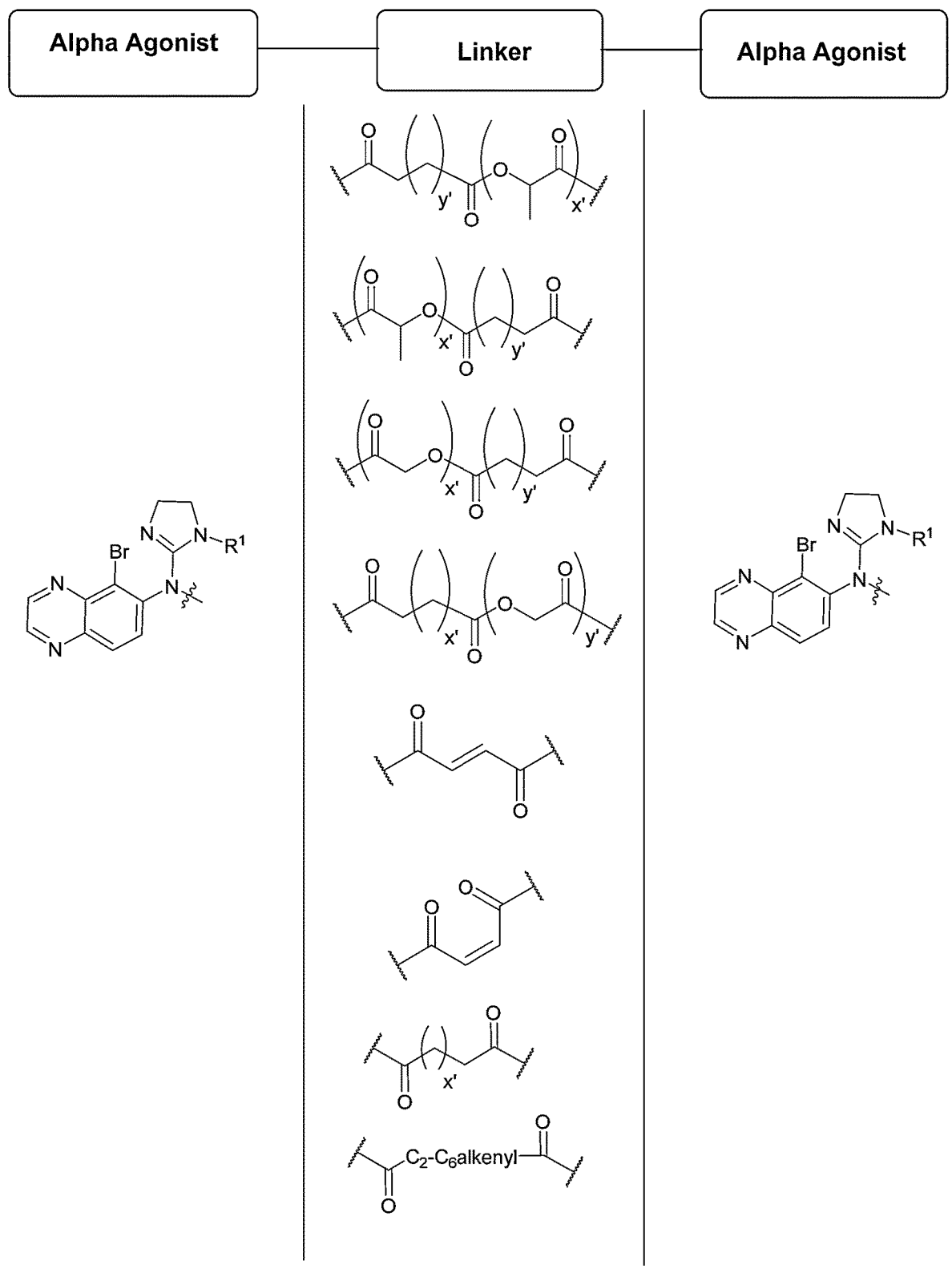
FIG. 66T illustrates non-limiting combinations of active moieties (alpha agonist and neuroprotective agent) and linkers in compounds according to the invention.
Figure 66U:
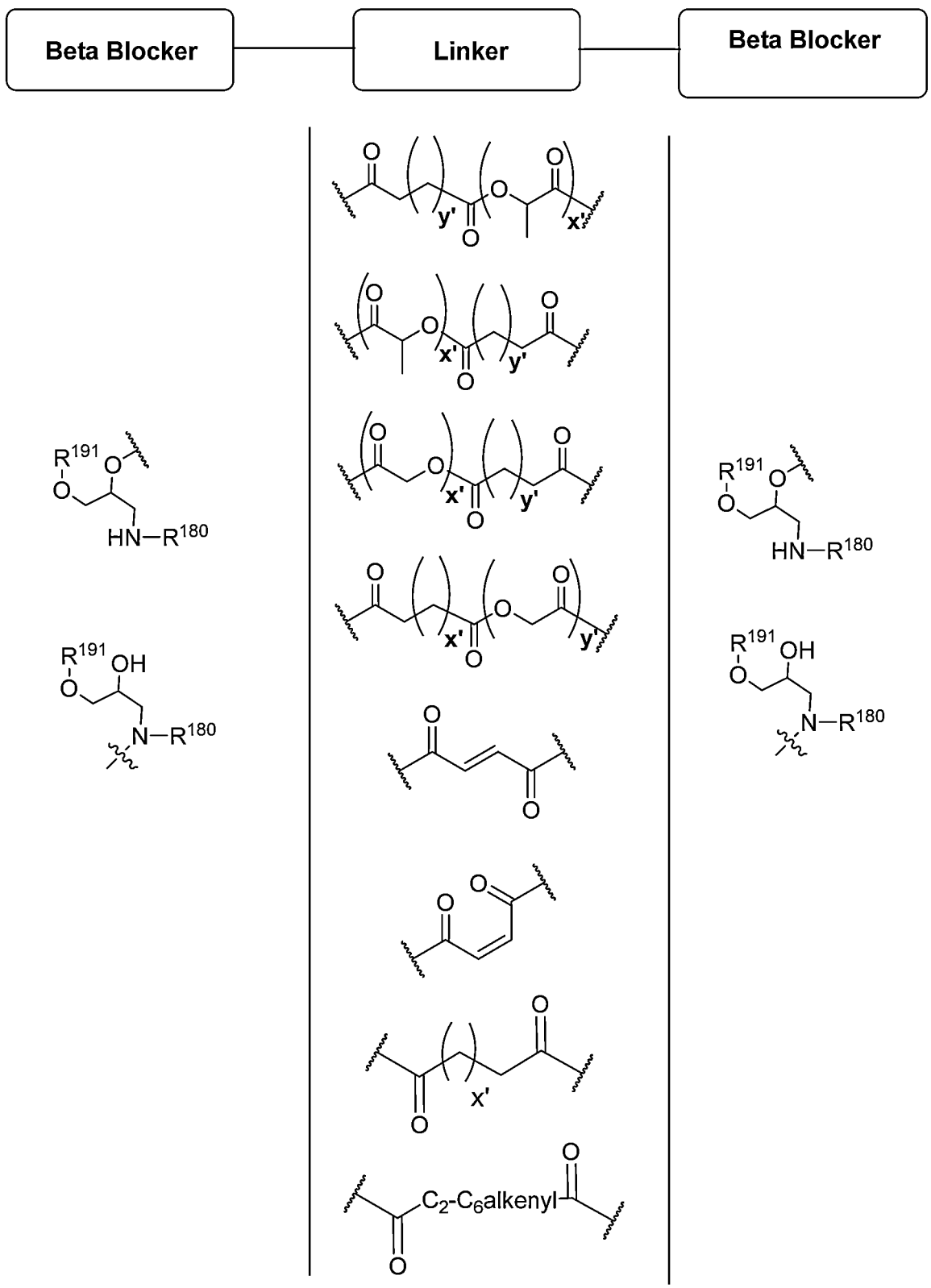
FIG. 66U illustrates non-limiting combinations of active moieties (alpha agonist and neuroprotective agent) and linkers in compounds according to the invention.
Figure 66V:
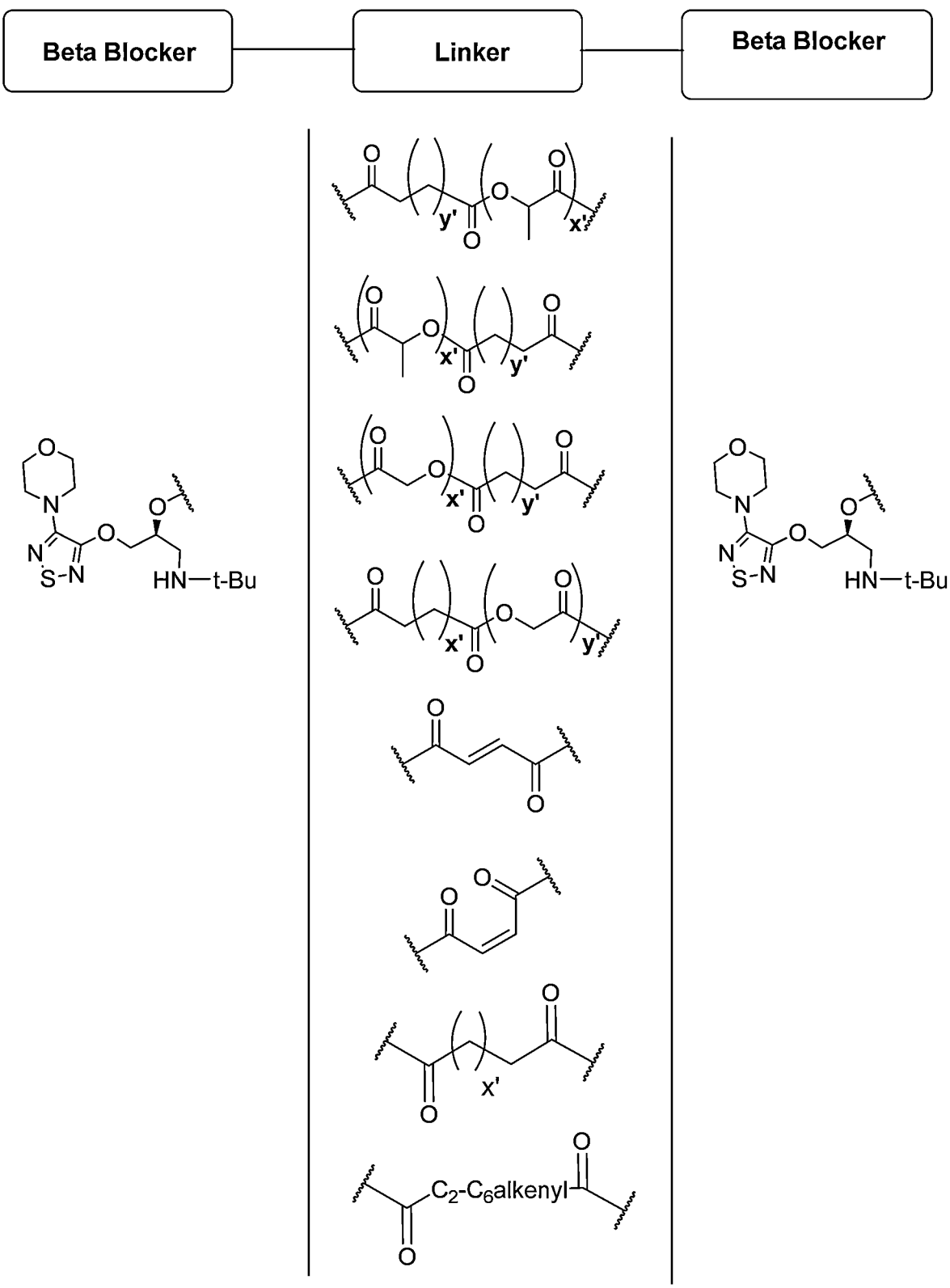
FIG. 66V illustrates non-limiting combinations of active moieties (alpha agonist and neuroprotective agent) and linkers in compounds according to the invention.
Figure 66W:
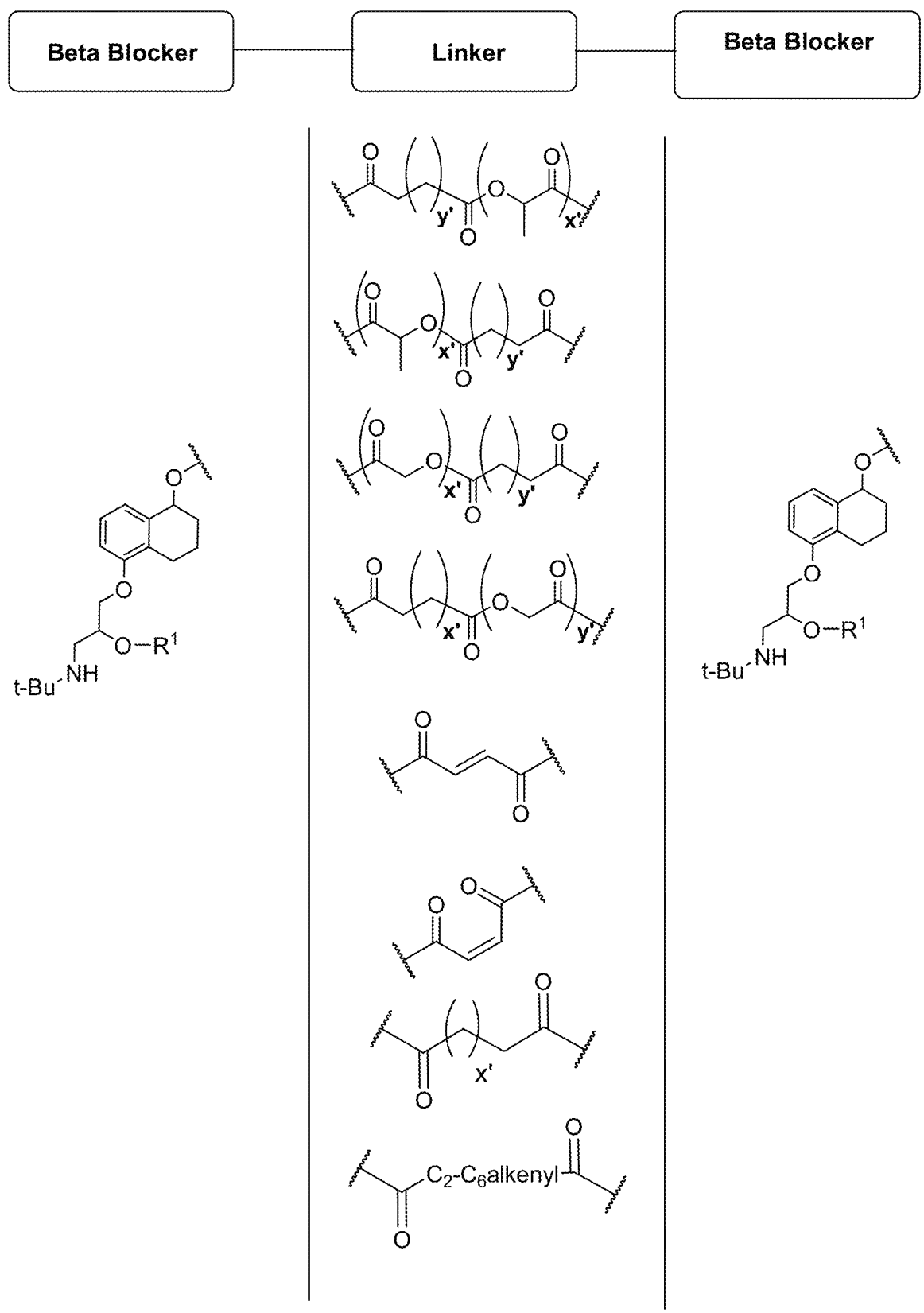
FIG. 66W illustrates non-limiting combinations of active moieties (alpha agonist and neuroprotective agent) and linkers in compounds according to the invention.
Figure 66X:
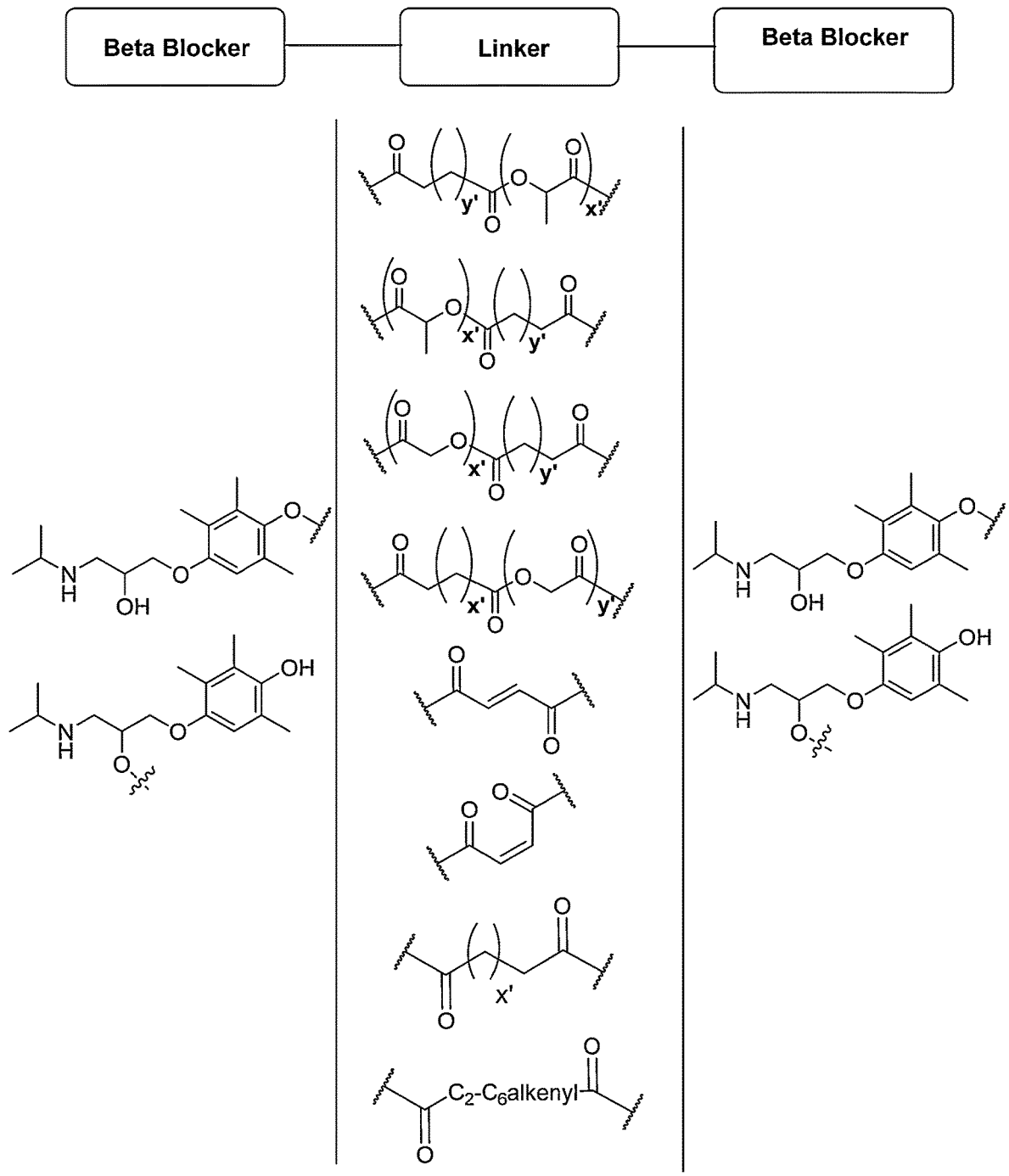
FIG. 66X illustrates non-limiting combinations of active moieties (alpha agonist and neuroprotective agent) and linkers in compounds according to the invention.
Figure 66Y:
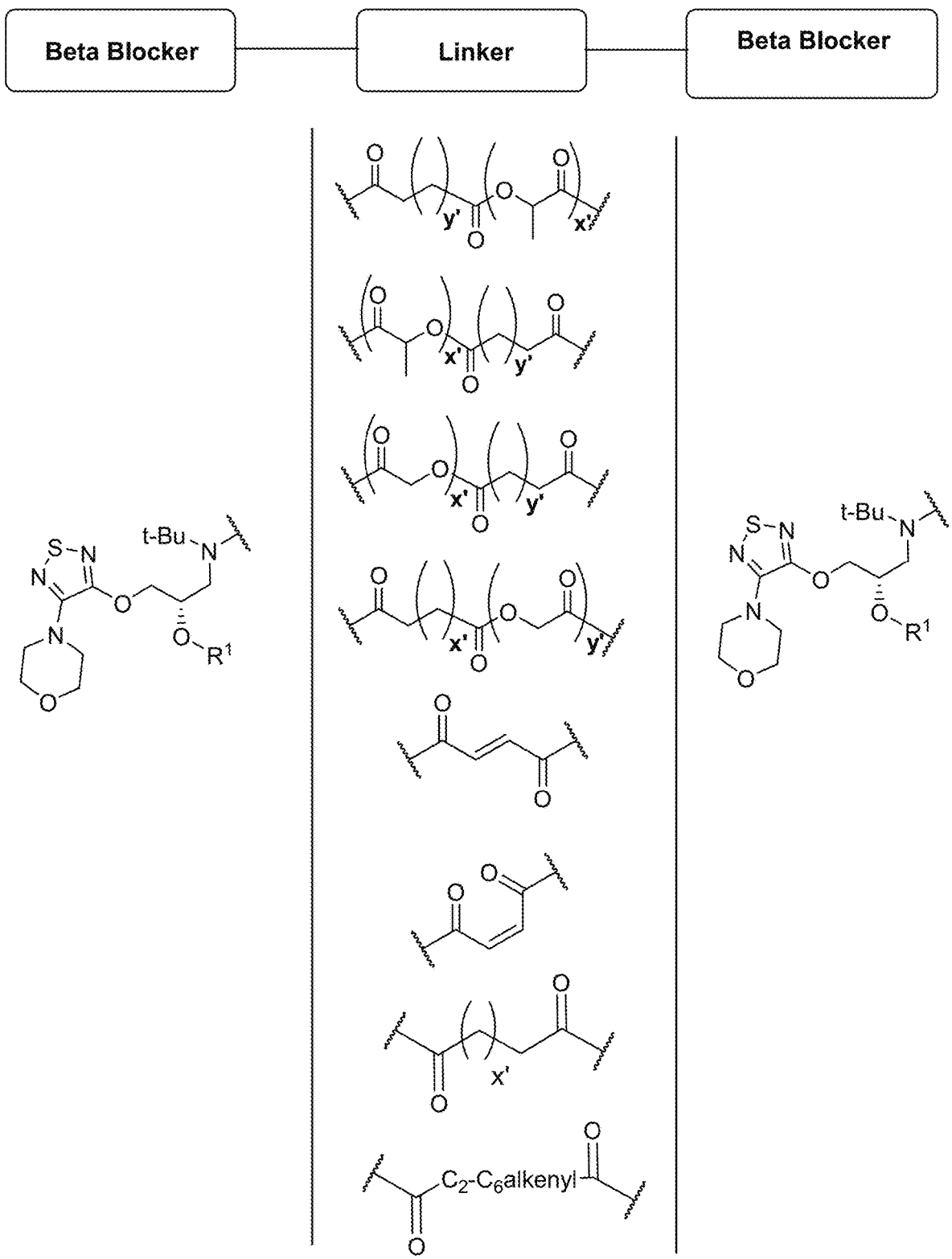
FIG. 66Y illustrates non-limiting combinations of active moieties (alpha agonist and neuroprotective agent) and linkers in compounds according to the invention.

This invention includes the specific combinations of each species and each linker shown in each of FIGS. 66J to 66Y with each other as if each compound were explicitly described.

In FIGS. 66J to 66Y, x', y', and z' are each independently selected from 0, 1, 2, 3, 4, 5, 6, 7, 8, 9, and 10.

Example 37. Compounds of the Present Invention

In one embodiment the compound of the present invention is selected from:

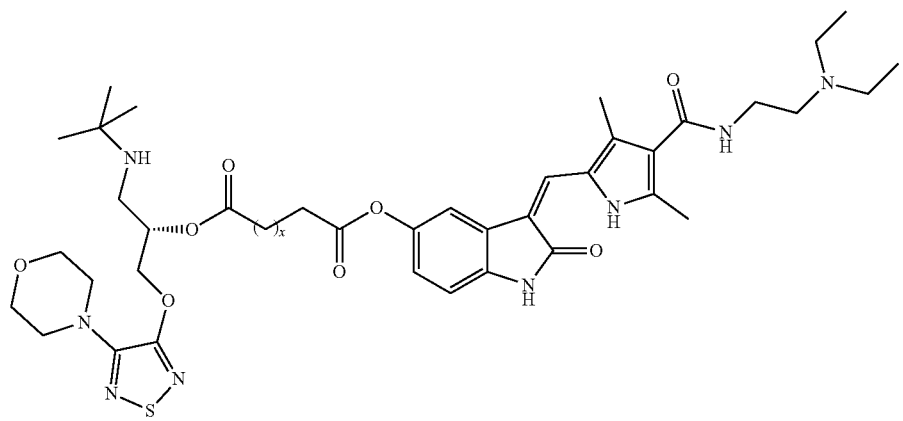

and

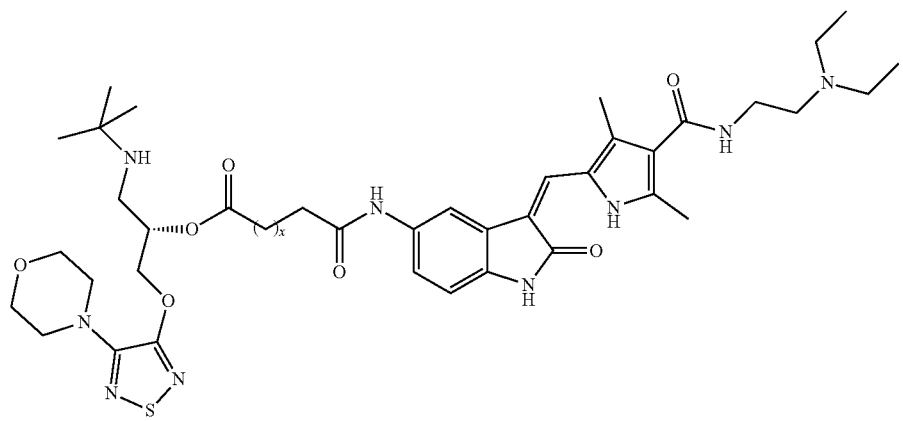

;

wherein x is 1, 2, 3, 4, 5, 6, 7, 8, or 9.

In one embodiment the compound of the present invention is selected from:

613
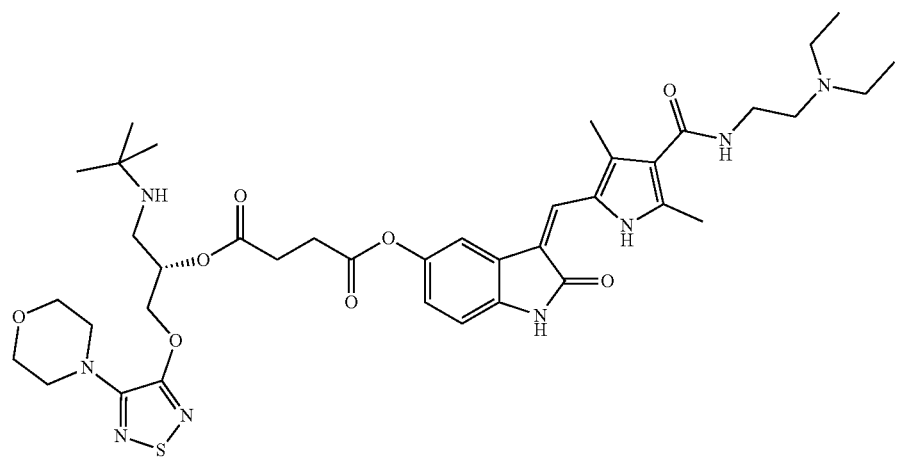
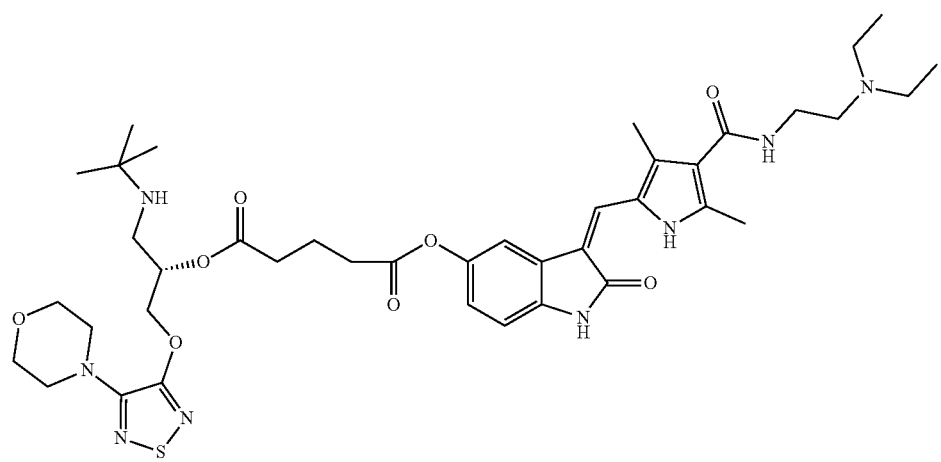
614
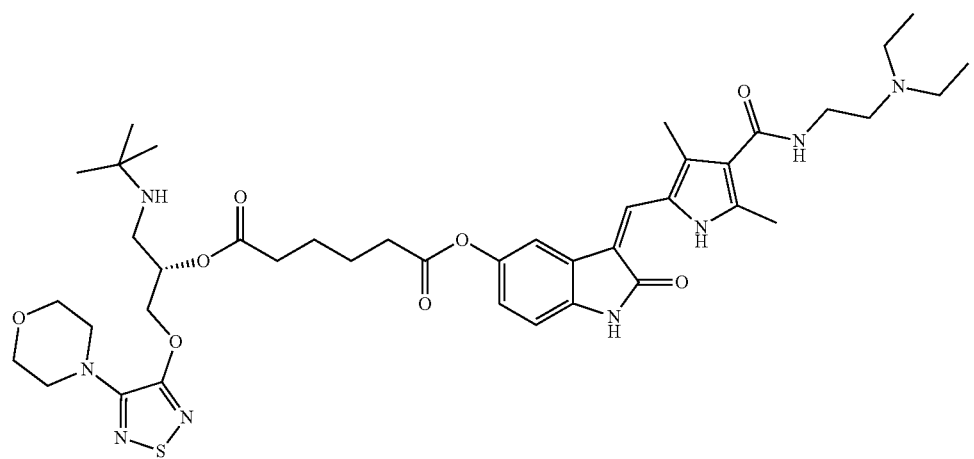

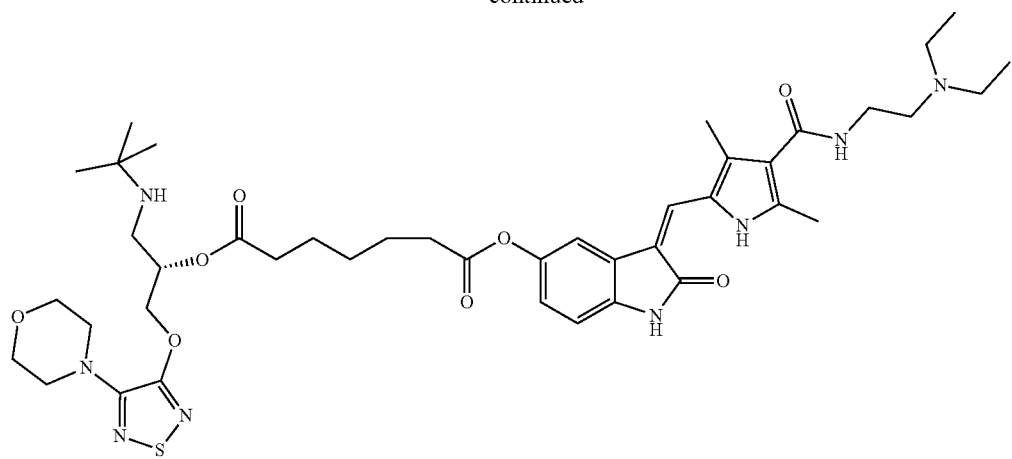
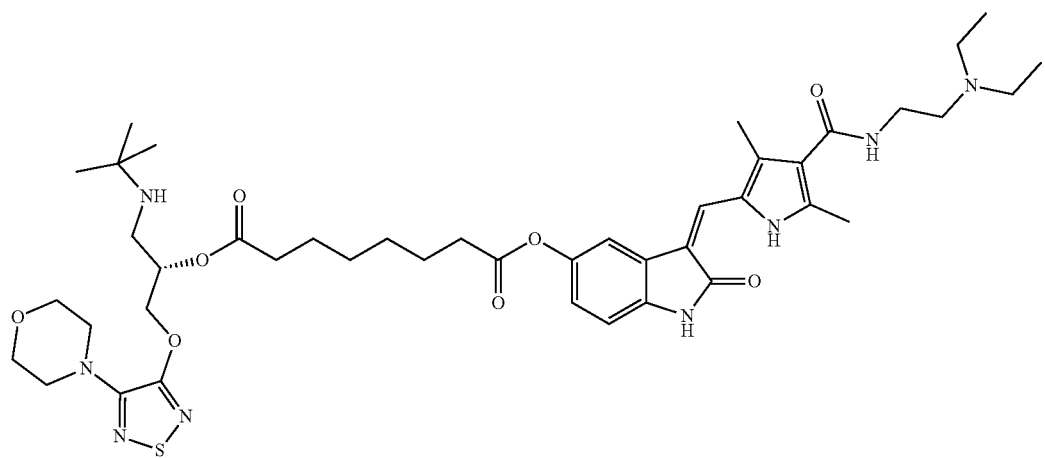
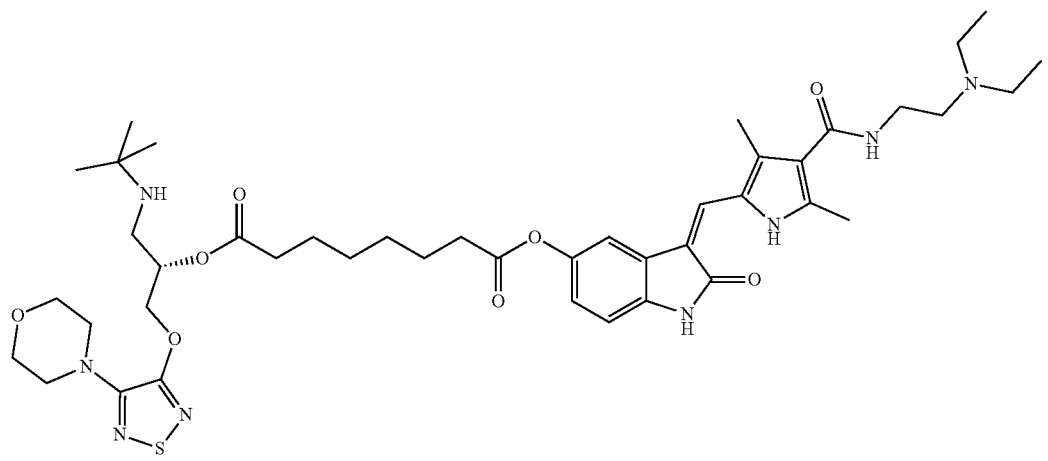

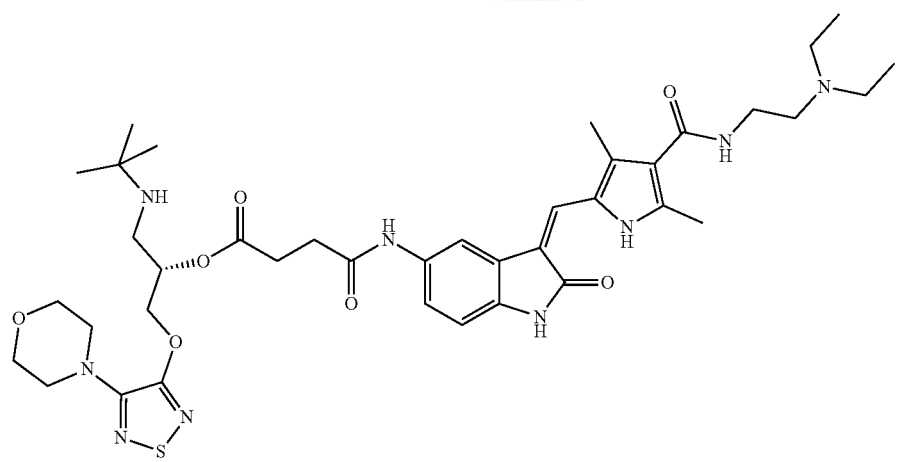
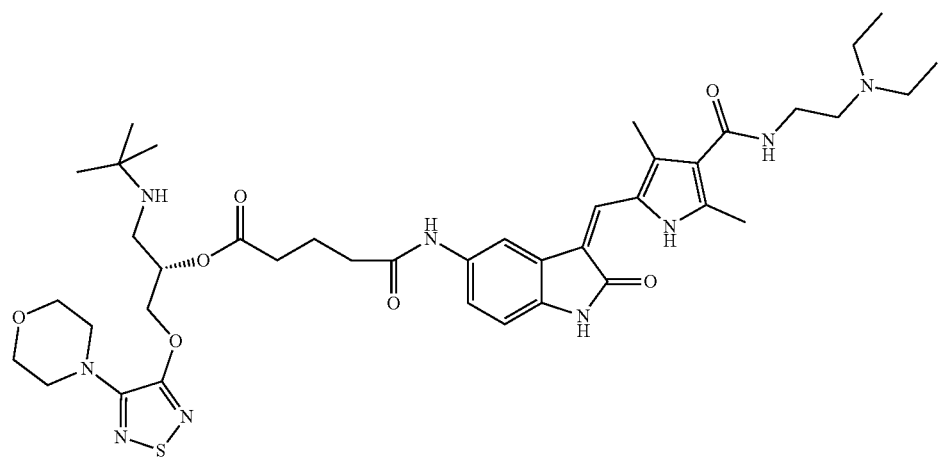
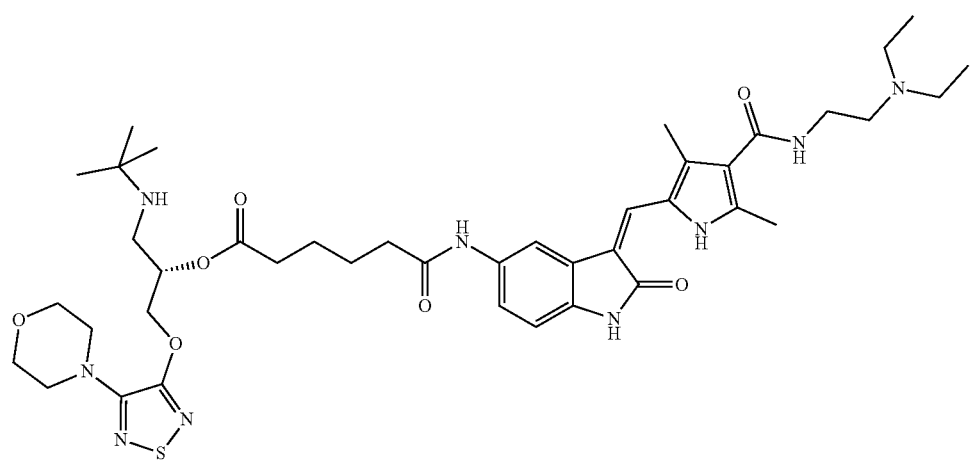
and

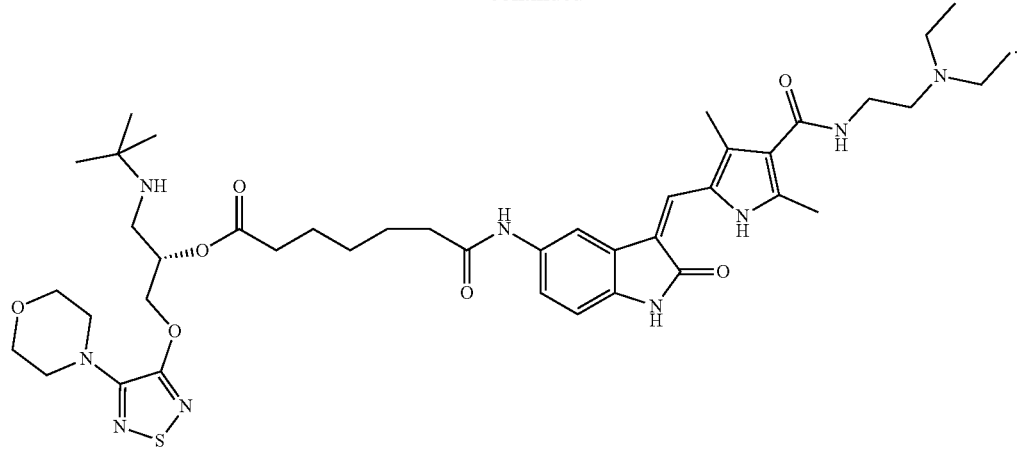
In one embodiment the compound of the present invention is selected from:
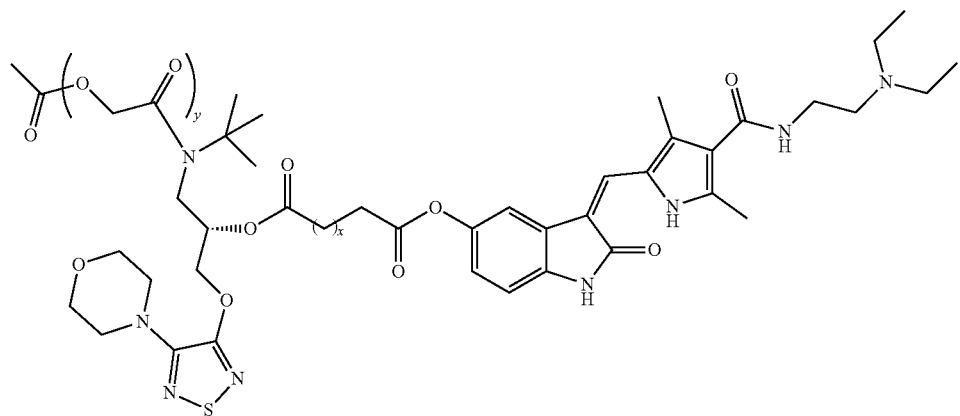
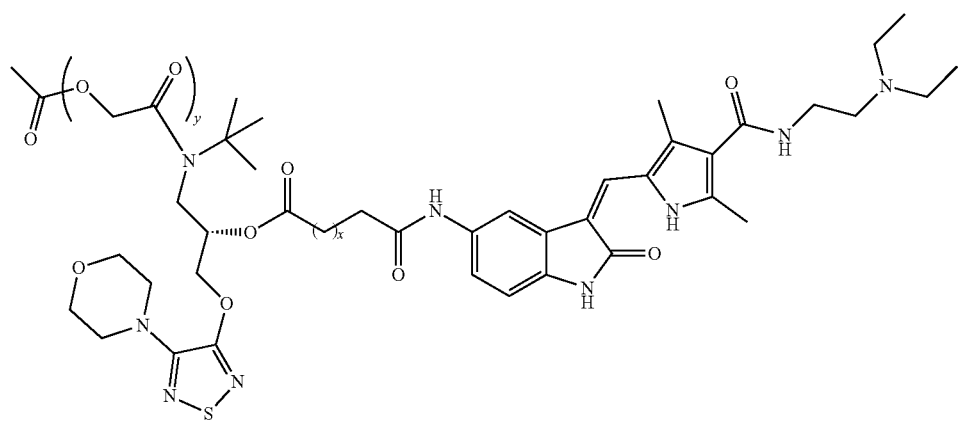

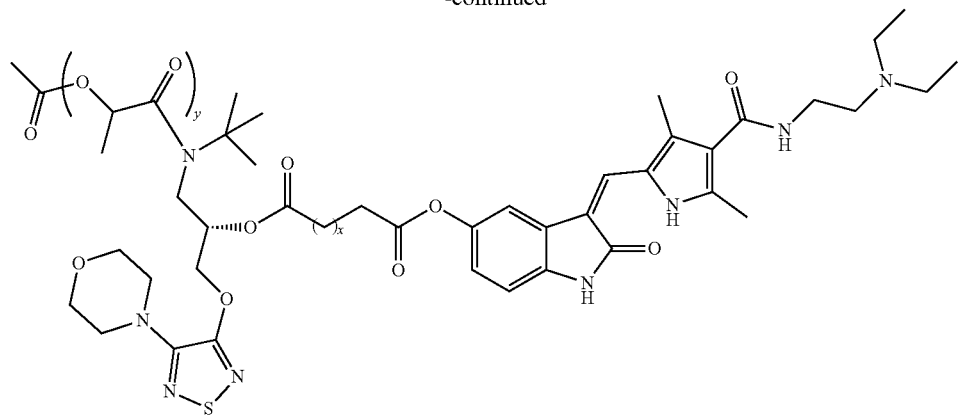
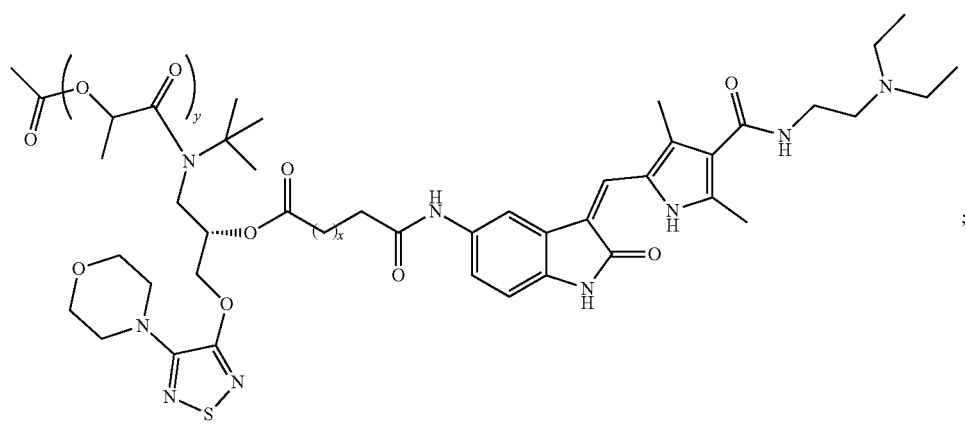
wherein x and y are independently 1, 2, 3, 4, 5, 6, 7, 8, or 9.
In one embodiment the compound of the present invention is selected from:
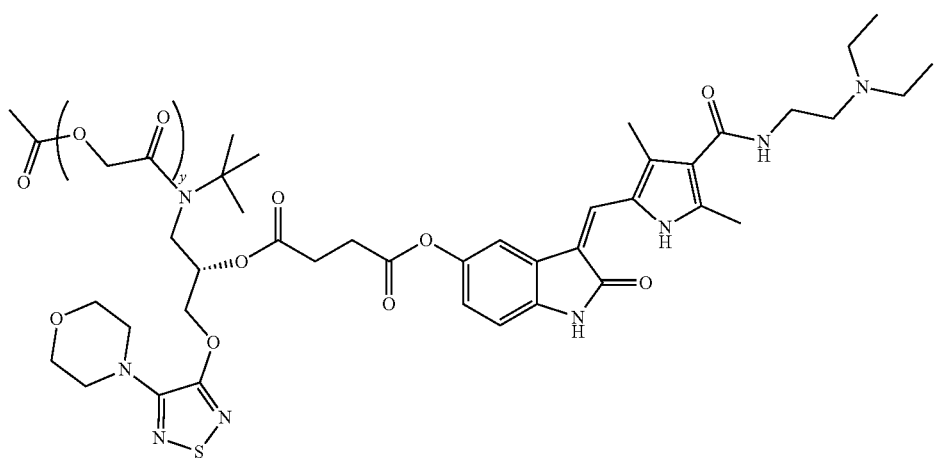

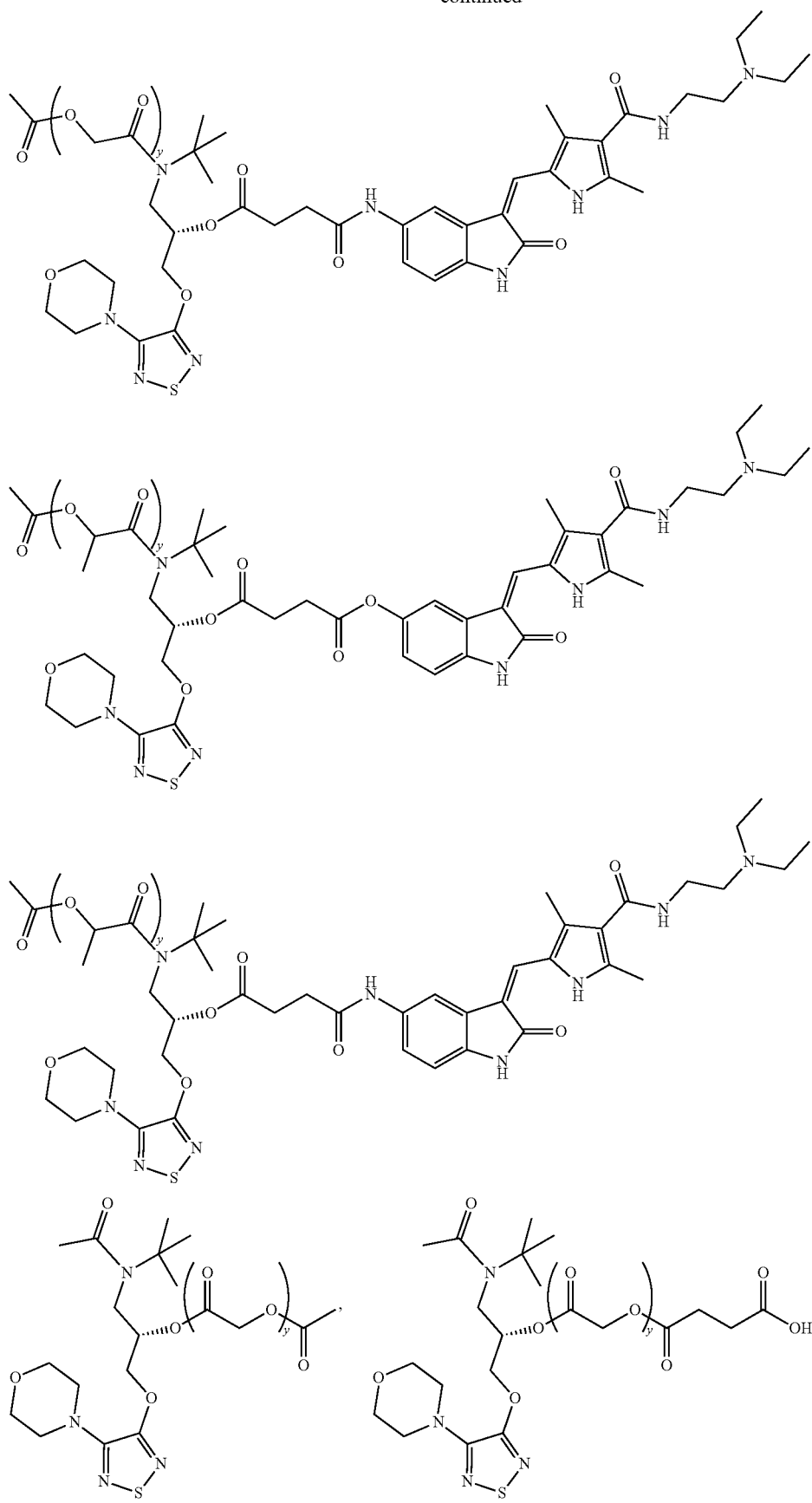

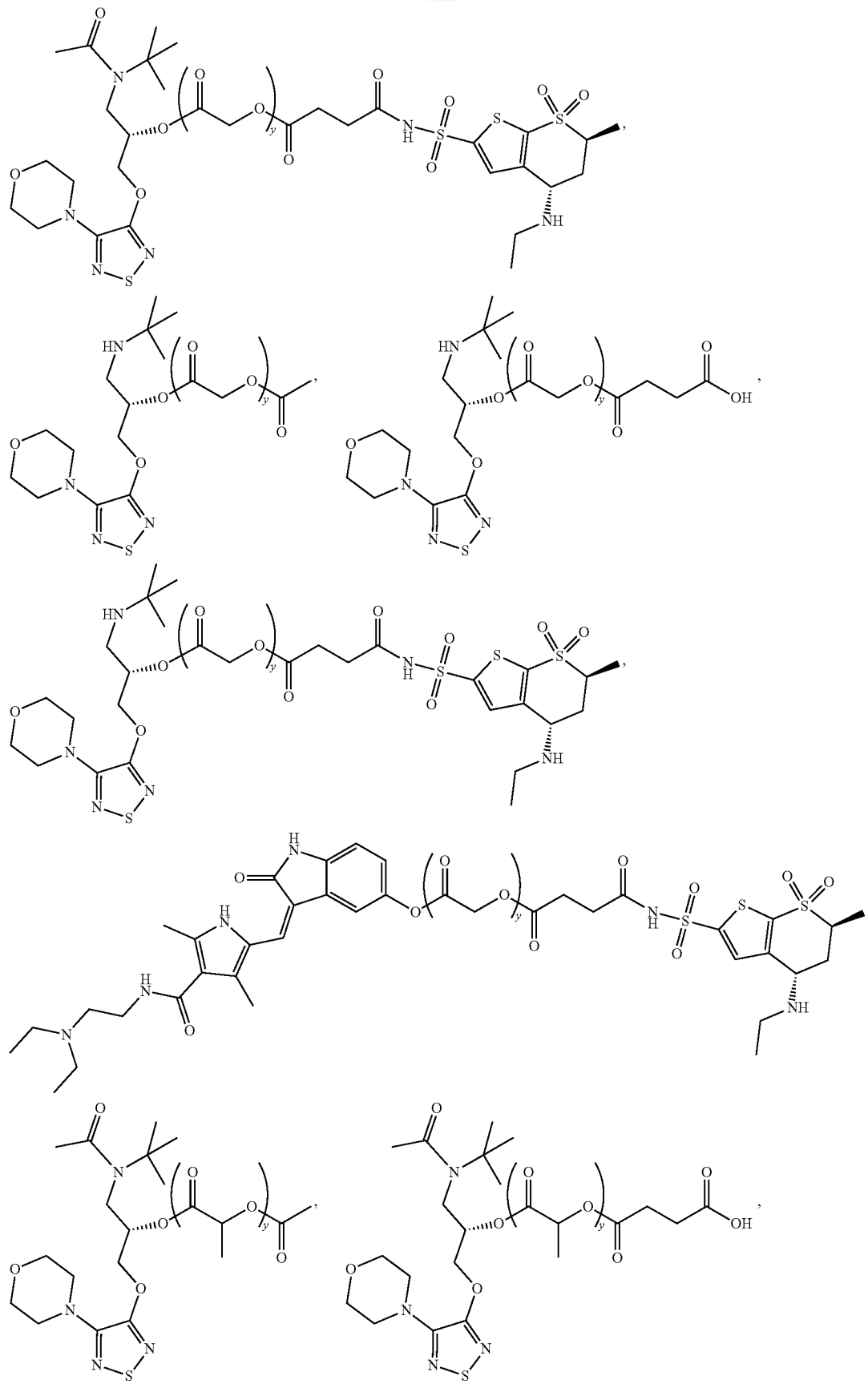

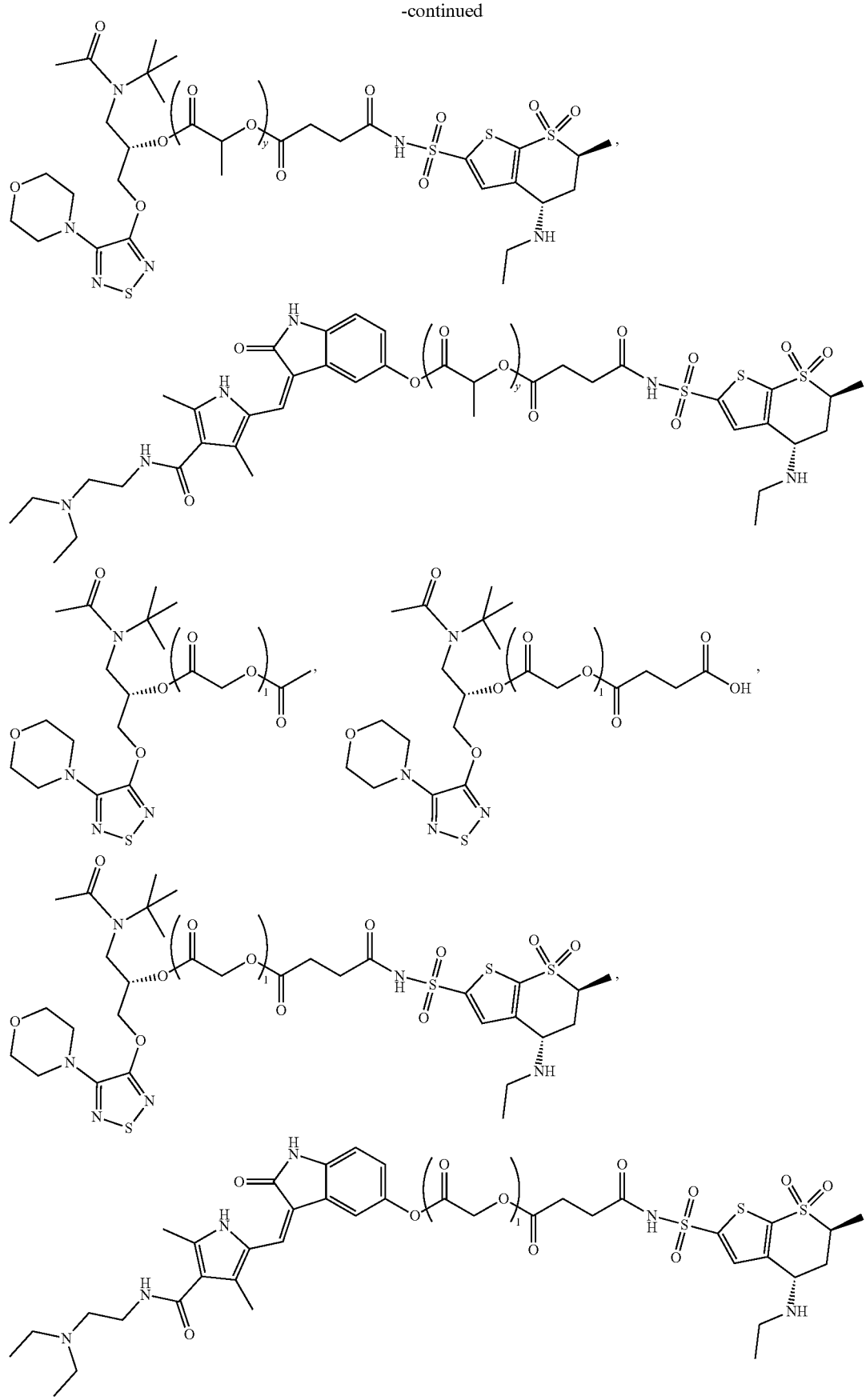

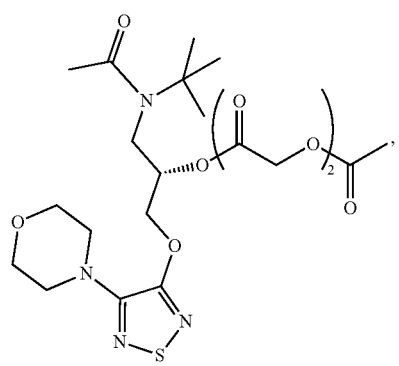
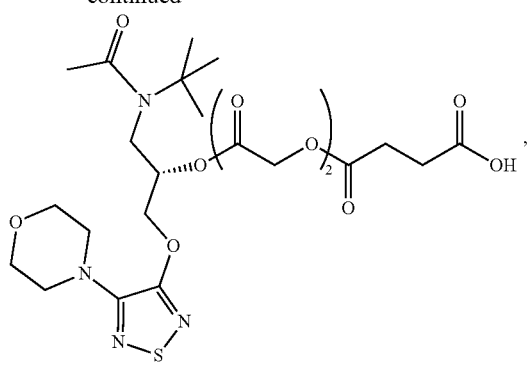
-continued
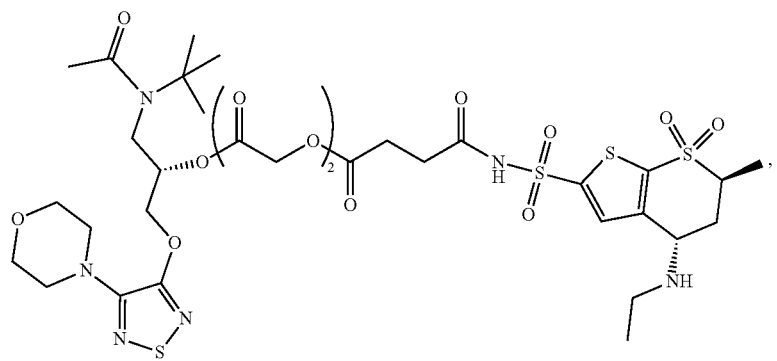
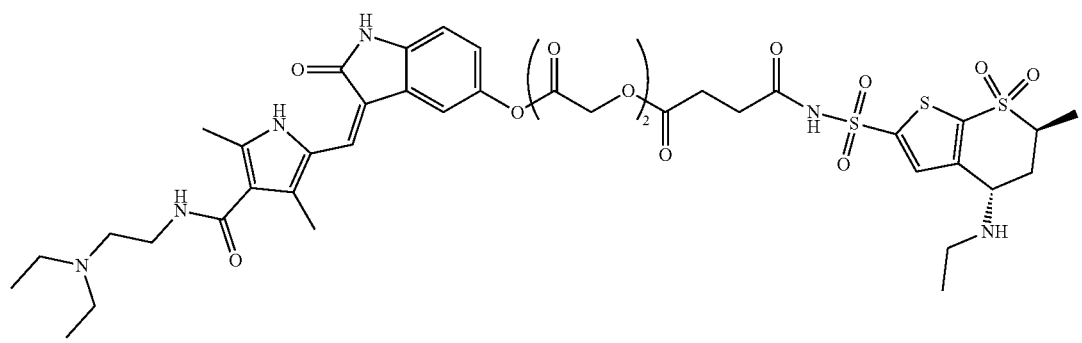
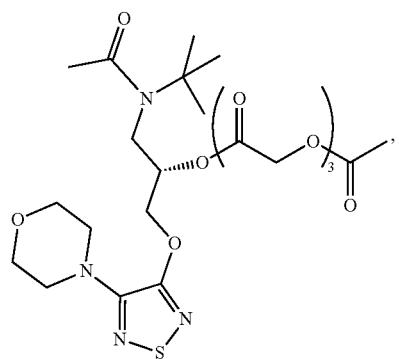
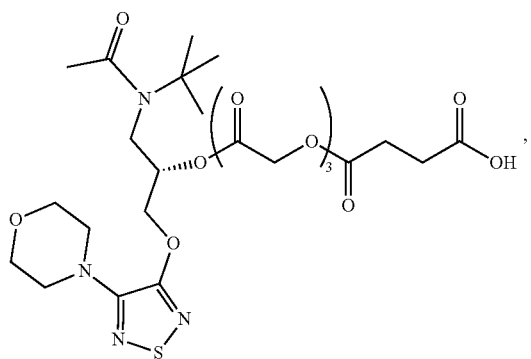

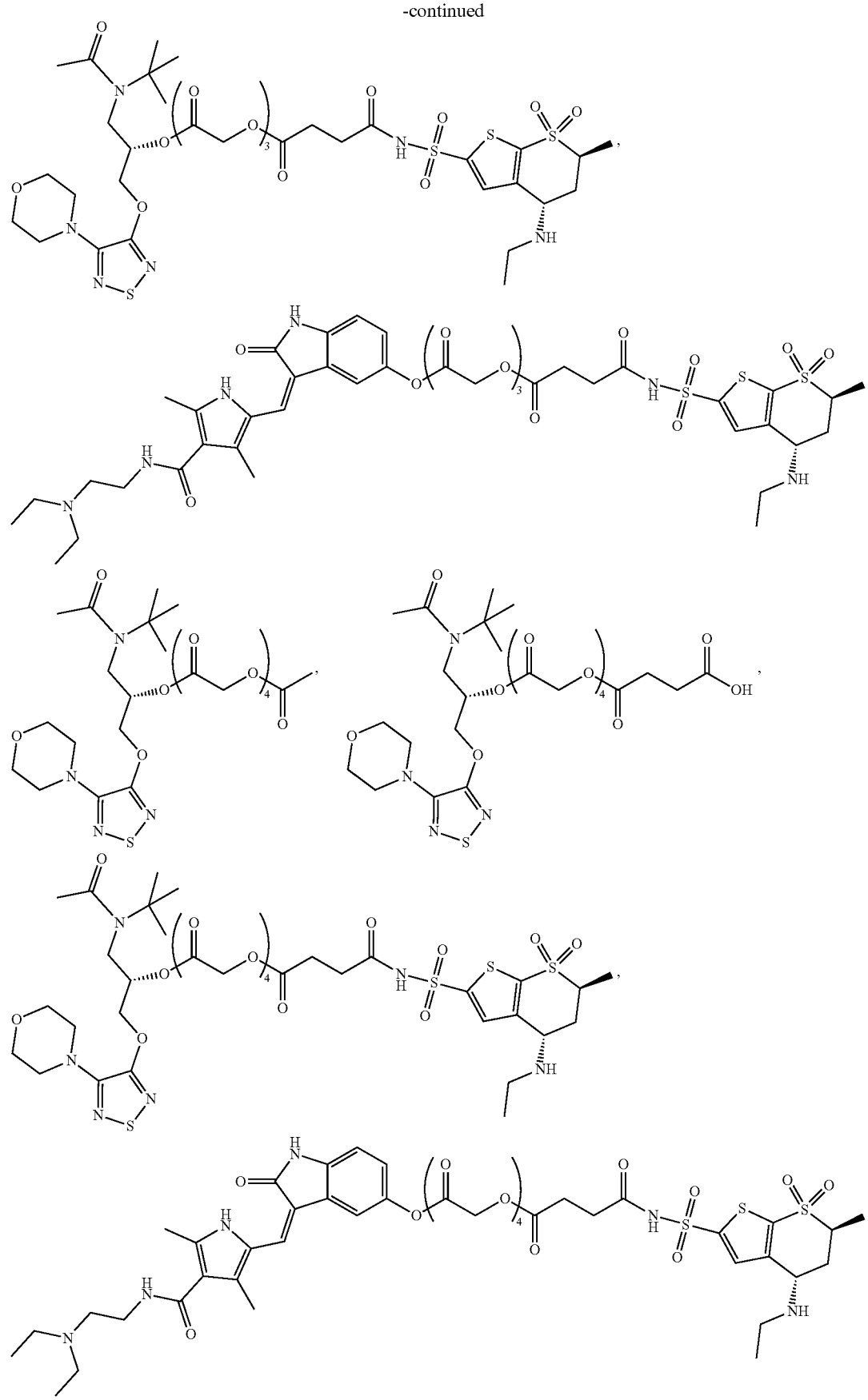

633 634
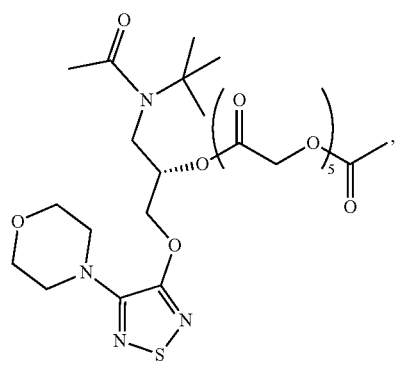
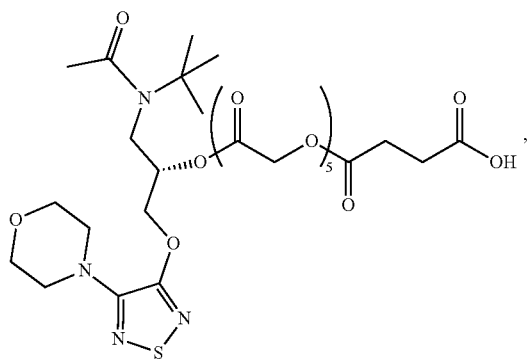
-continued
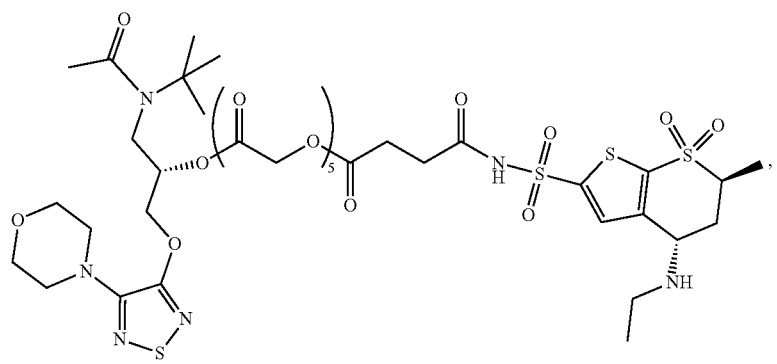
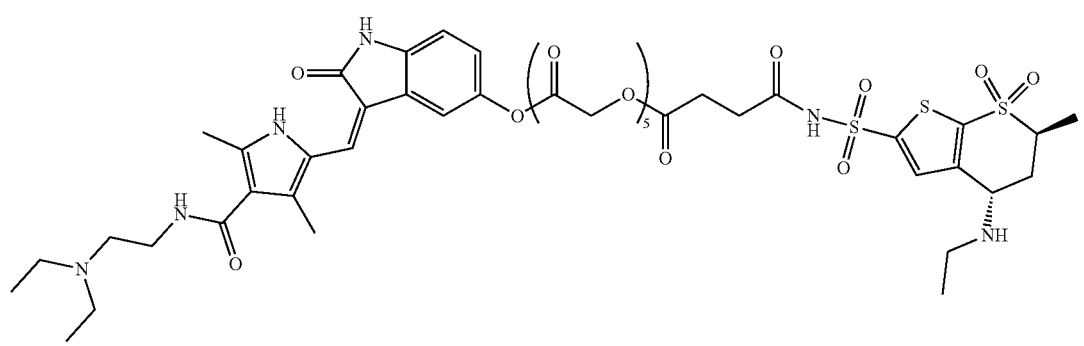
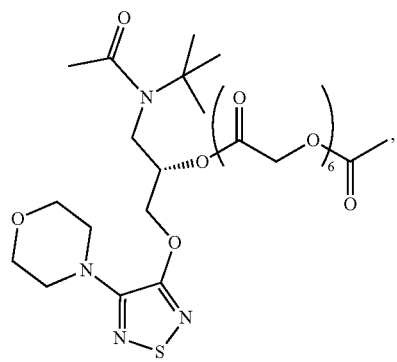

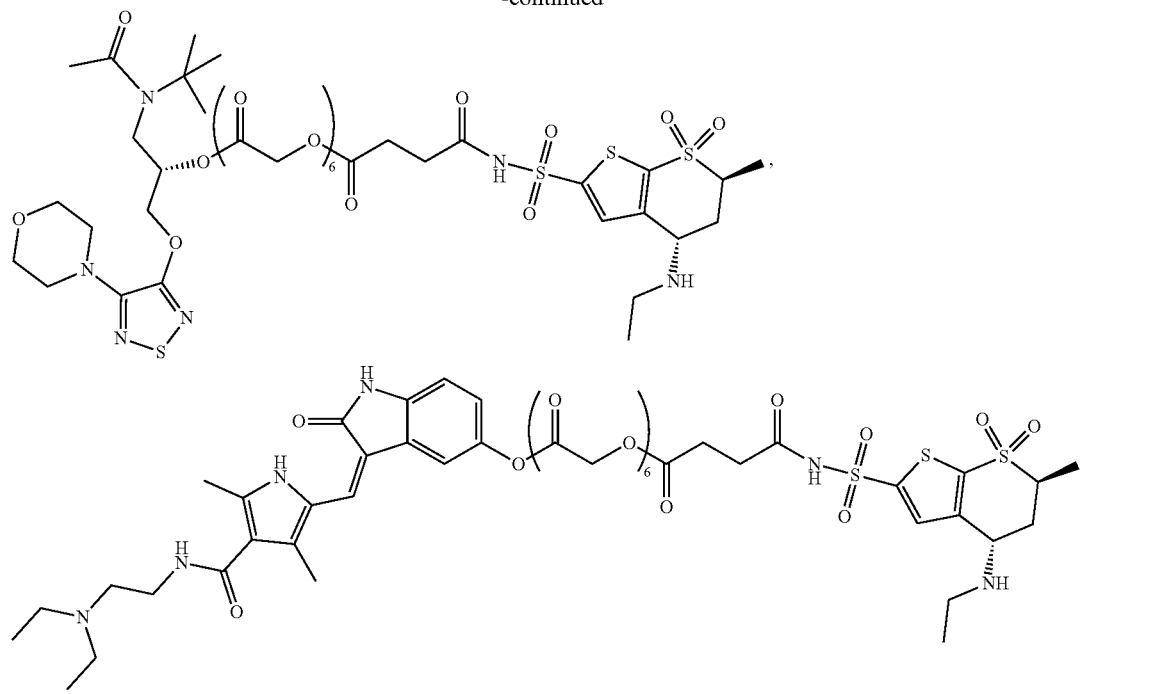
In another embodiment of the above structures,
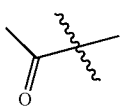 [SMILES: *C(C)=O]
is replaced with
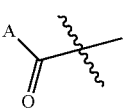
wherein A is defined above.
In another embodiment of the above structure,
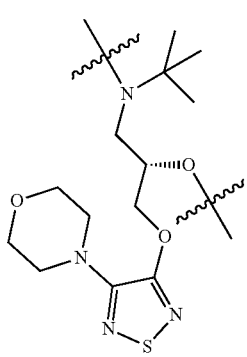 [SMILES: *O[C@H](COc1nsnc1N1CCOCC1)CN(*)C(C)(C)C]
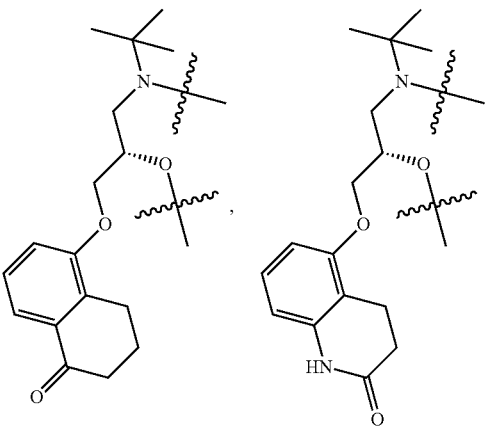
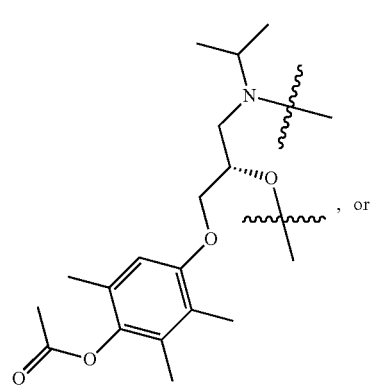

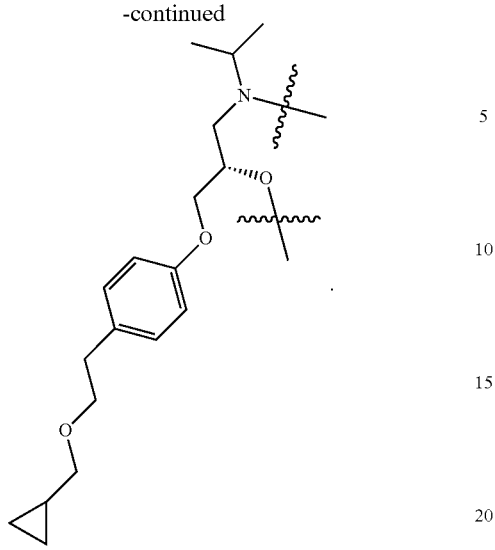
In another embodiment the compound of the present invention is selected from:
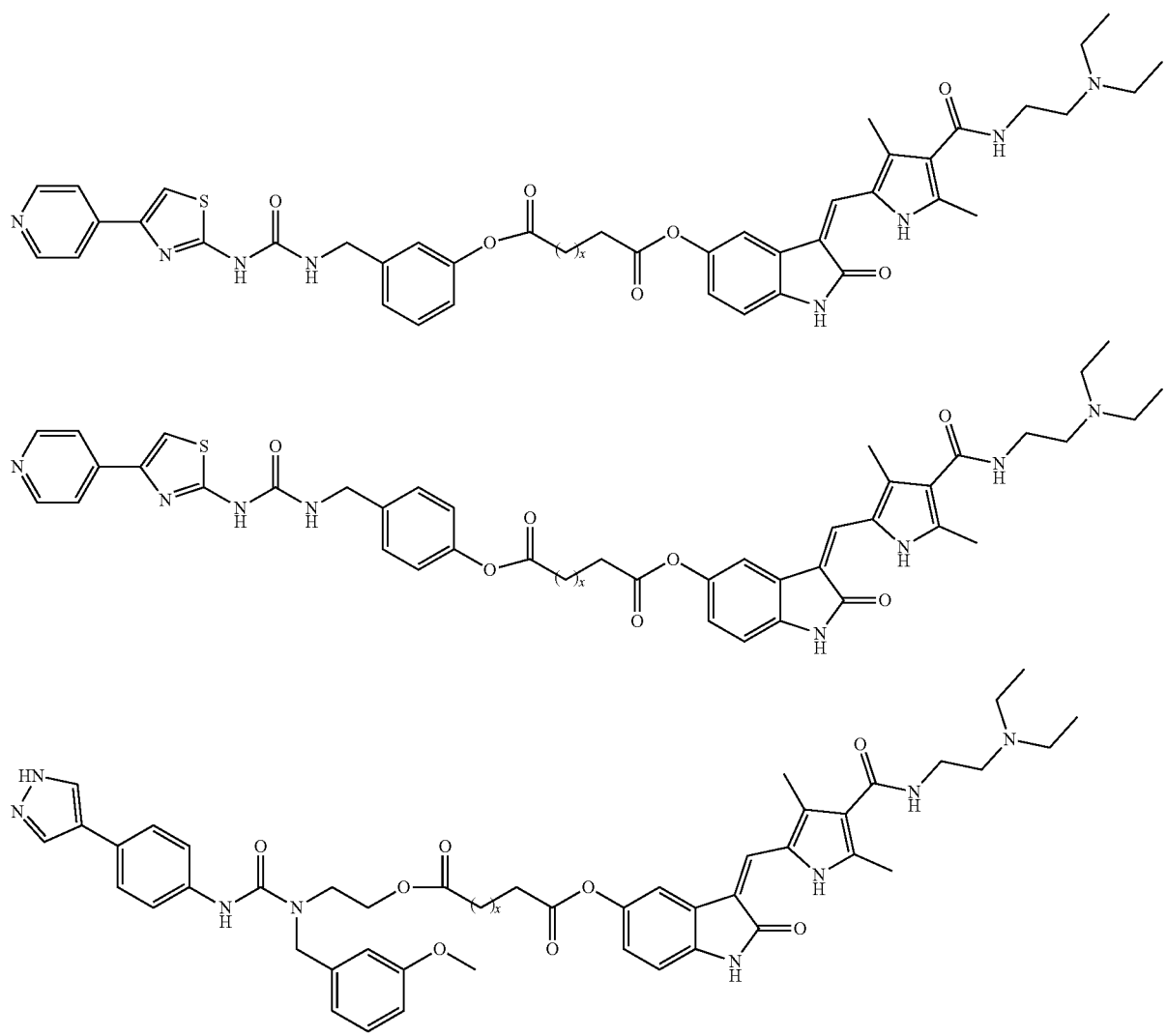

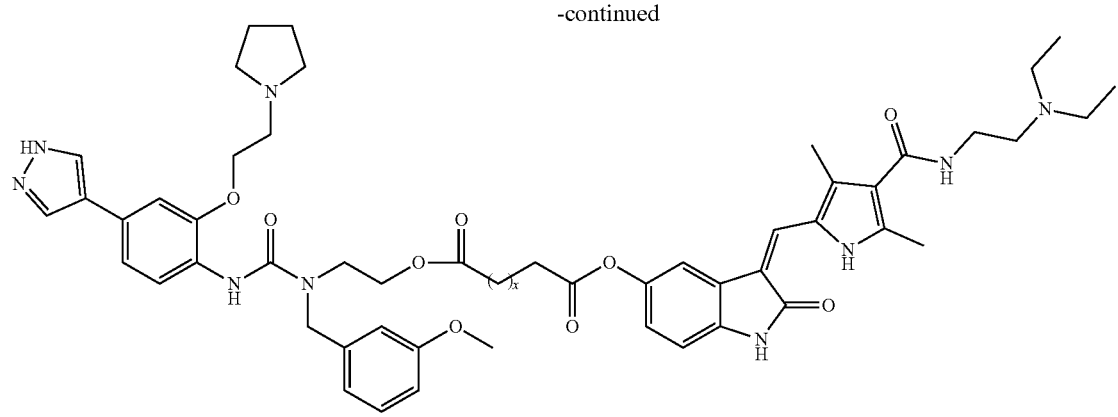
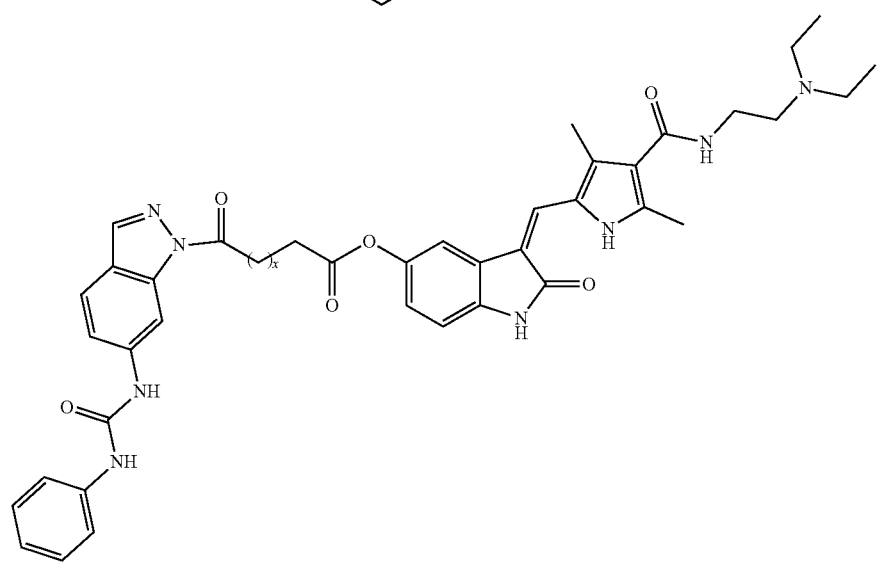
and
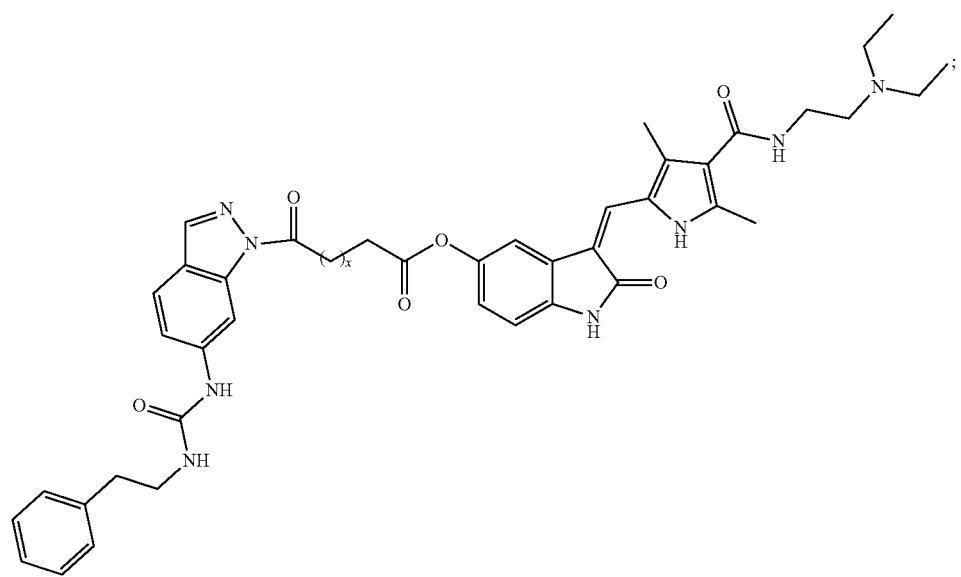
wherein x is 1, 2, 3, 4, 5, 6, 7, 8, or 9.
In one embodiment the compound of the present invention is selected from:

641 642
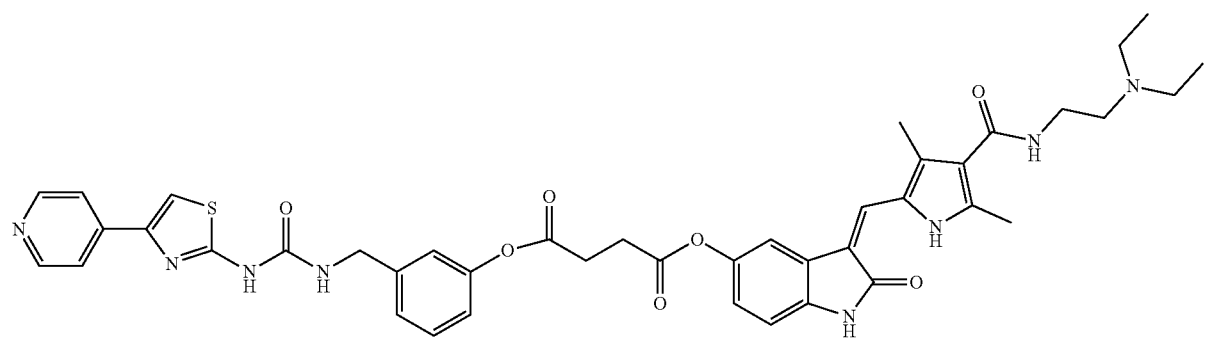
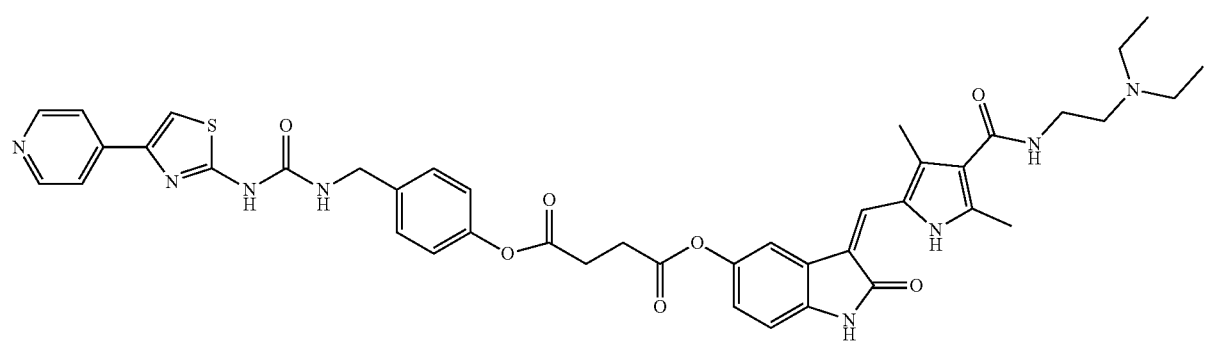
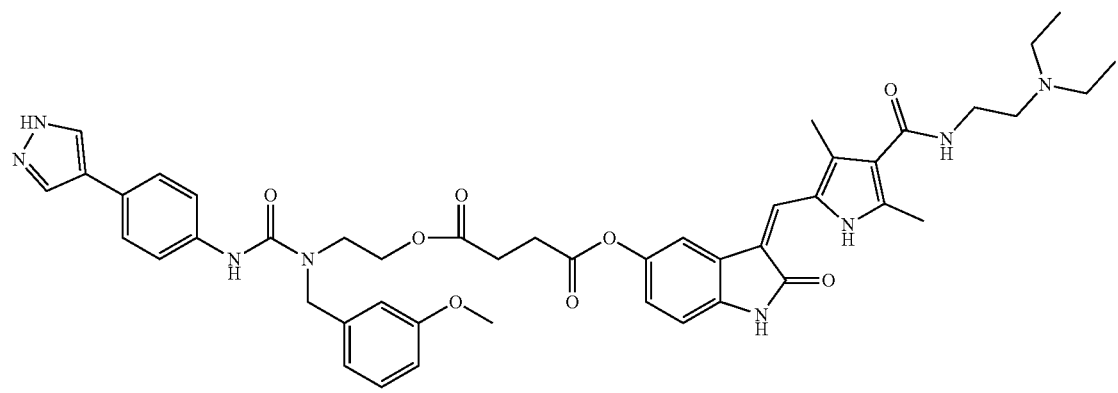
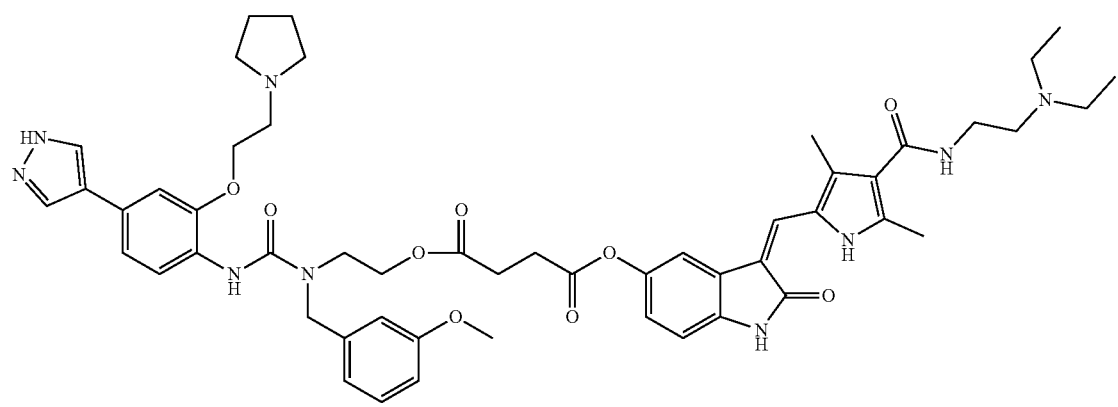

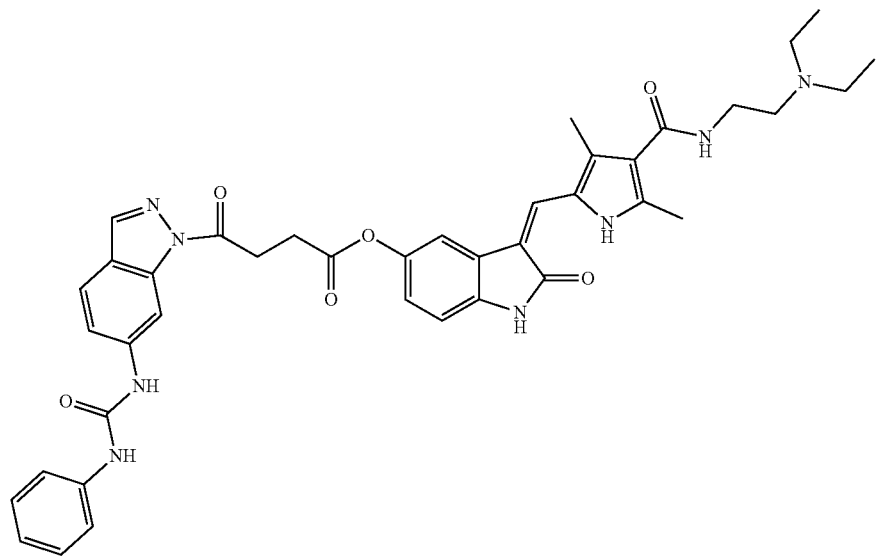
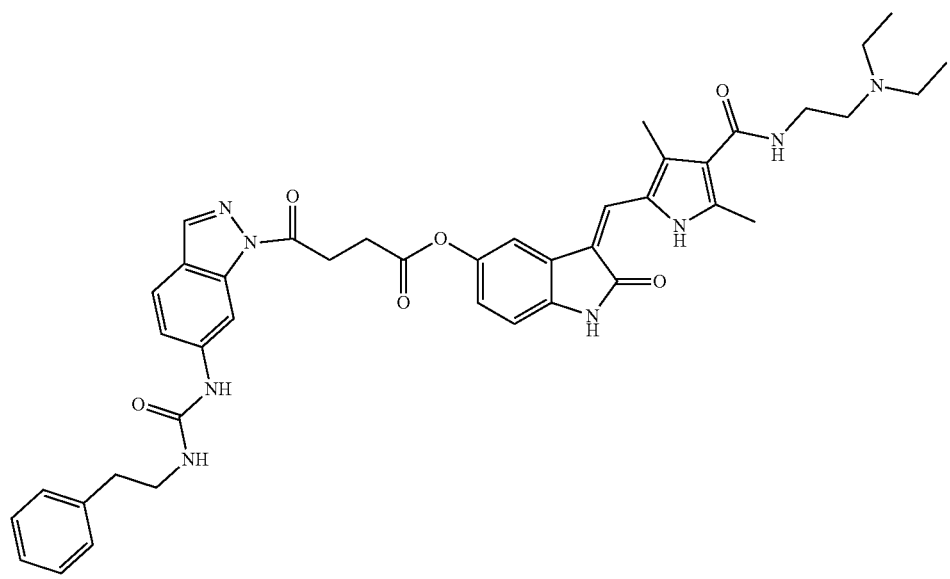
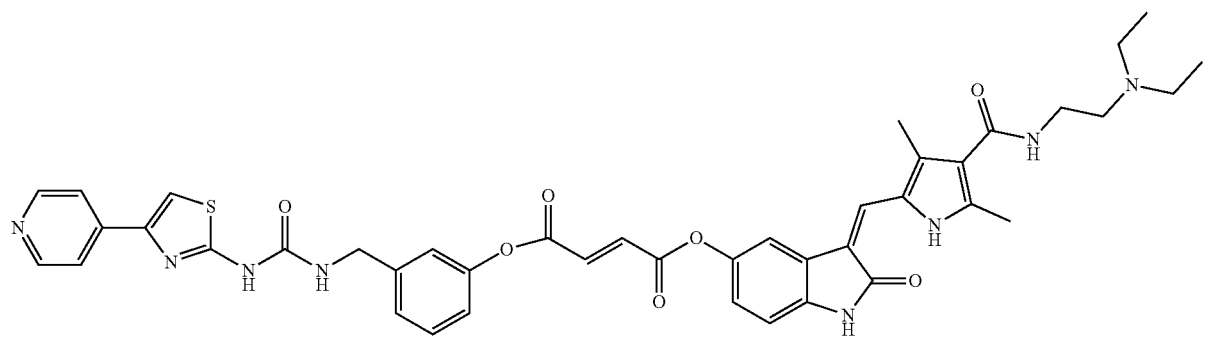

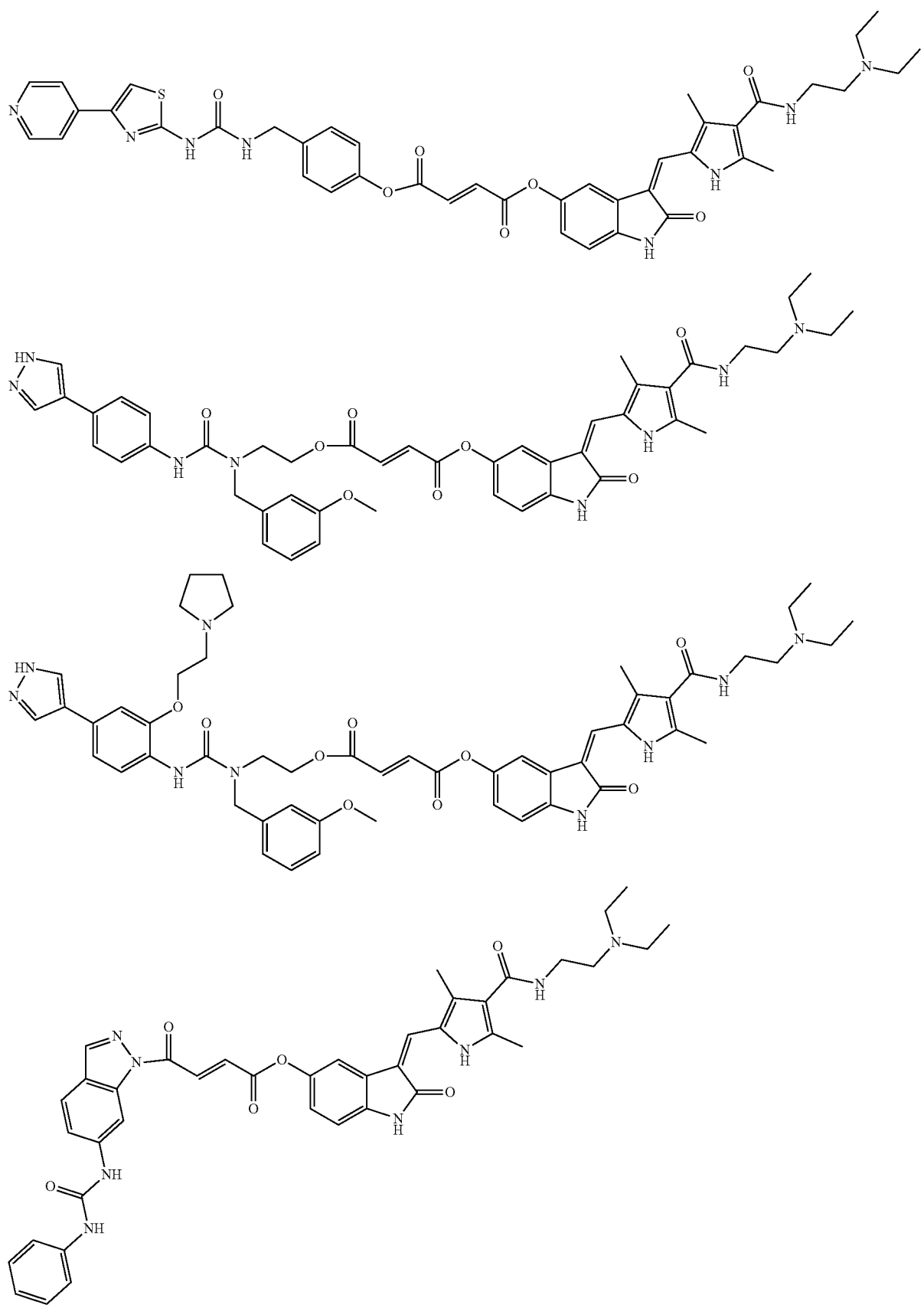

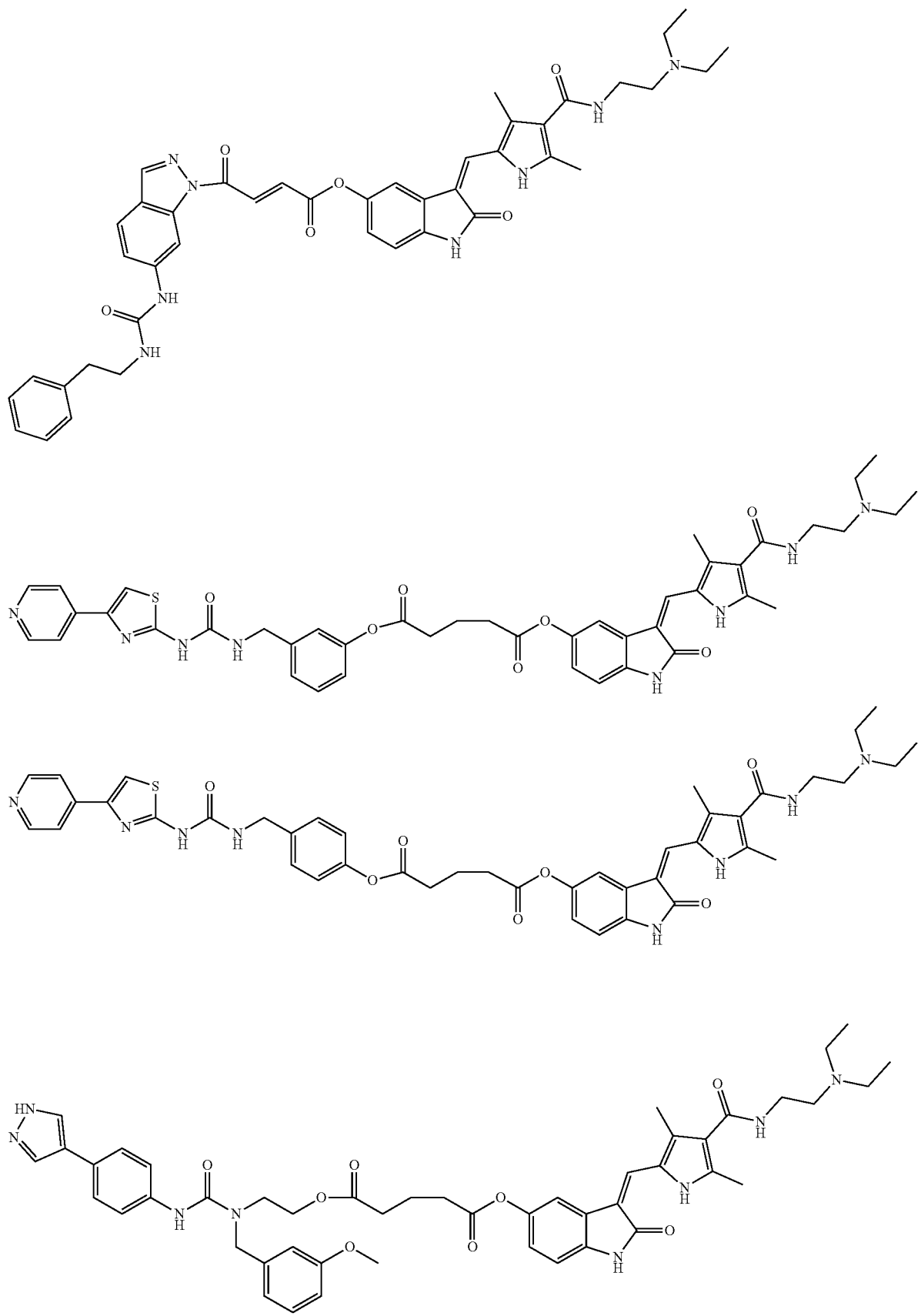

649 650
-continued
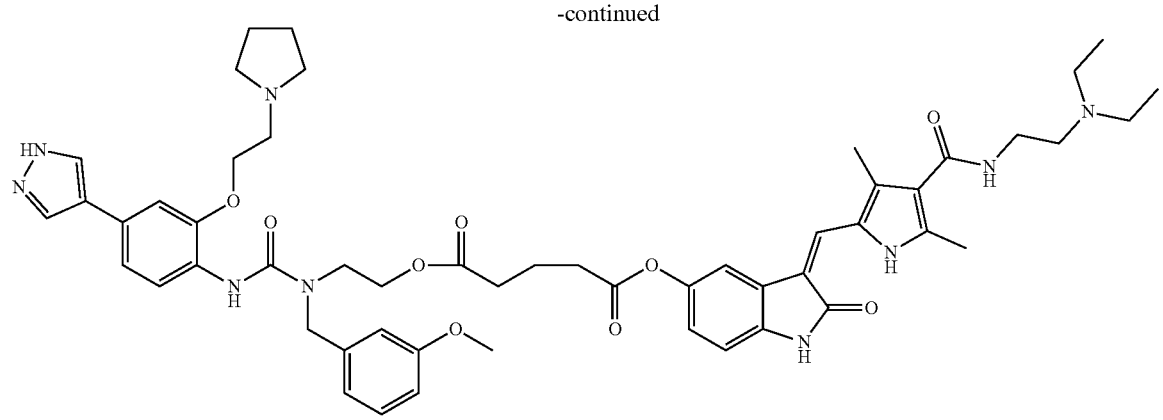
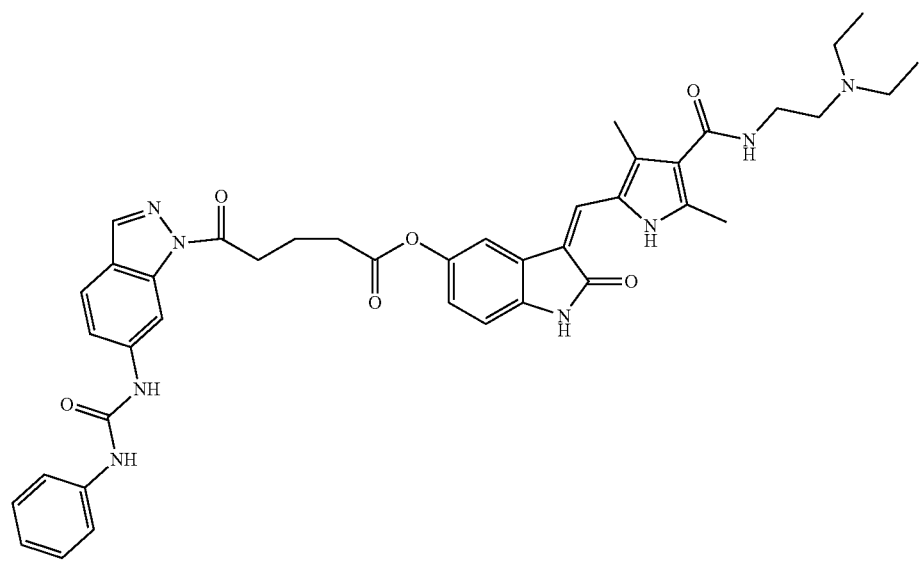
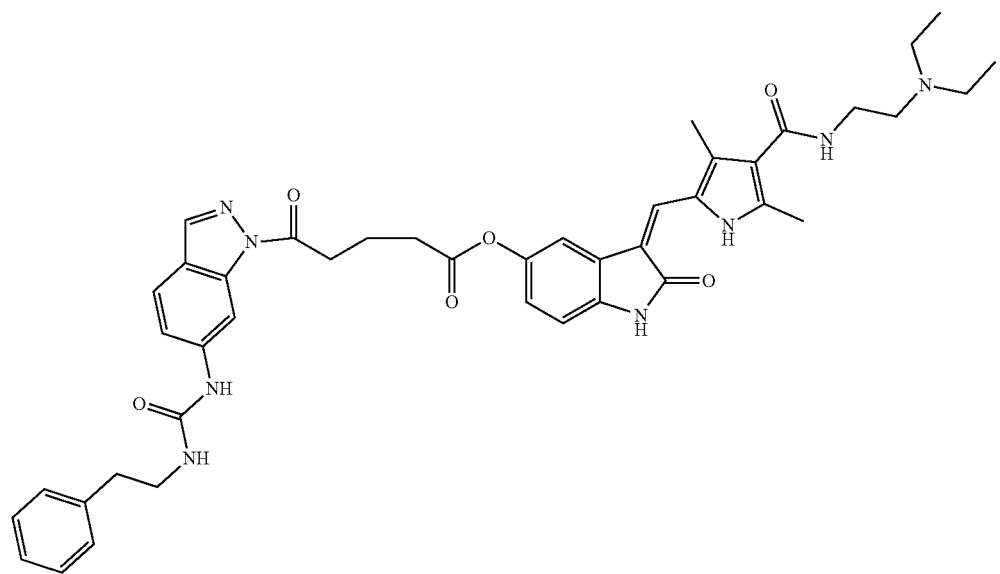

651 652
-continued
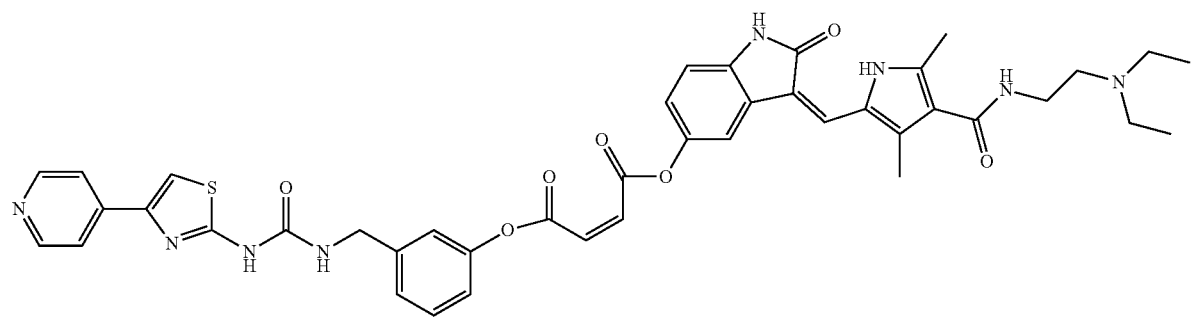
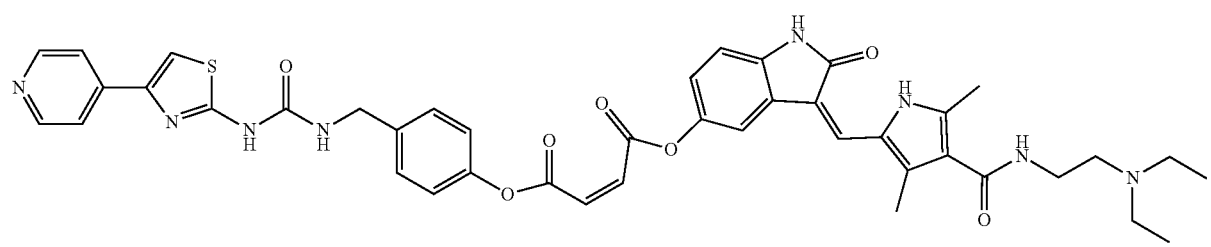
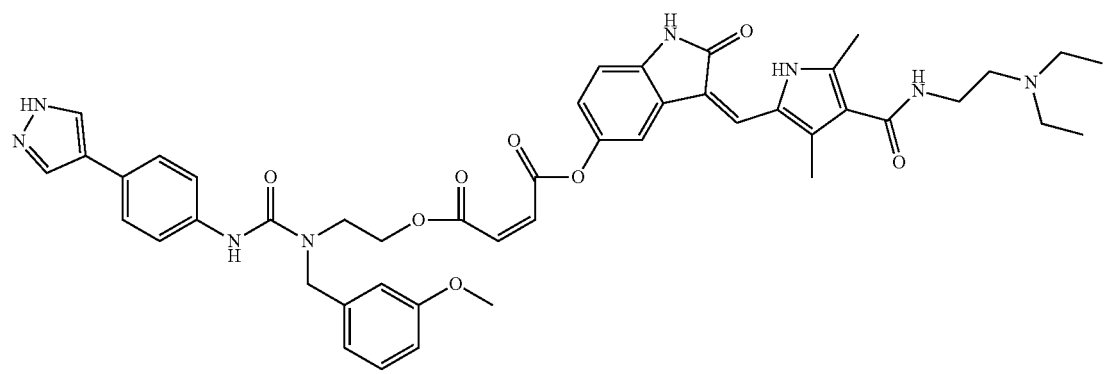
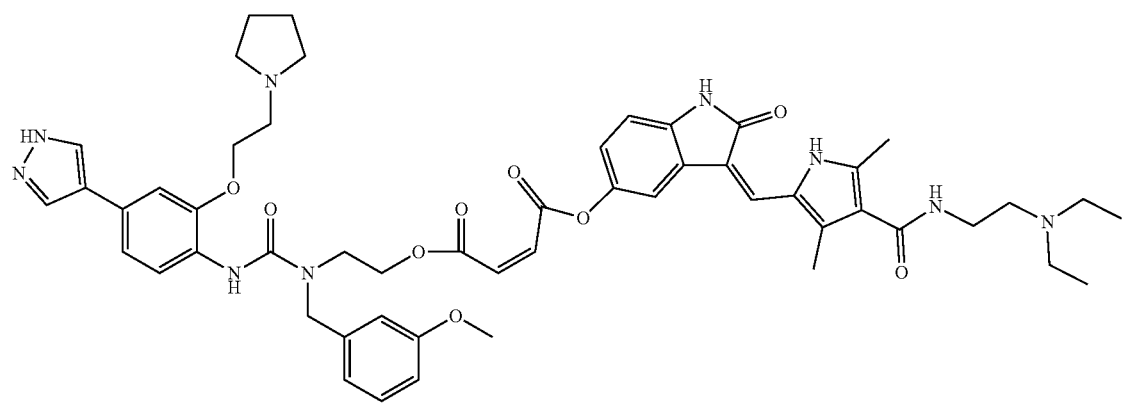

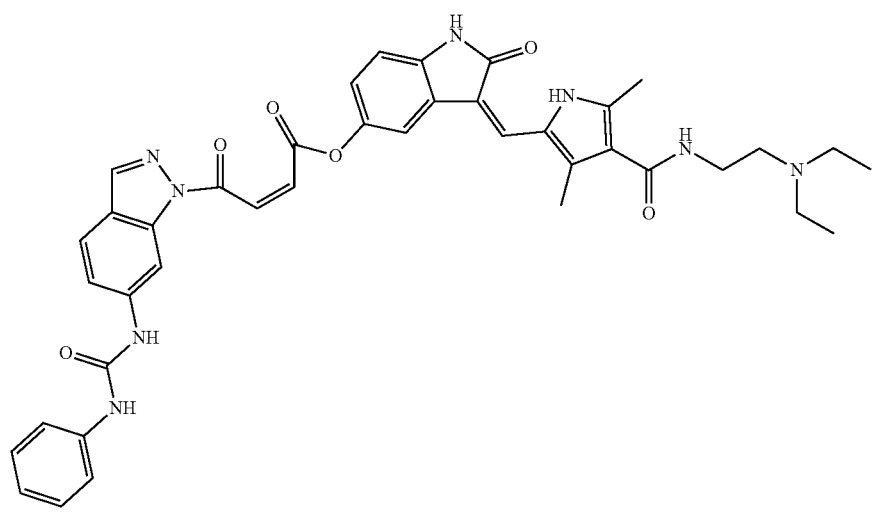
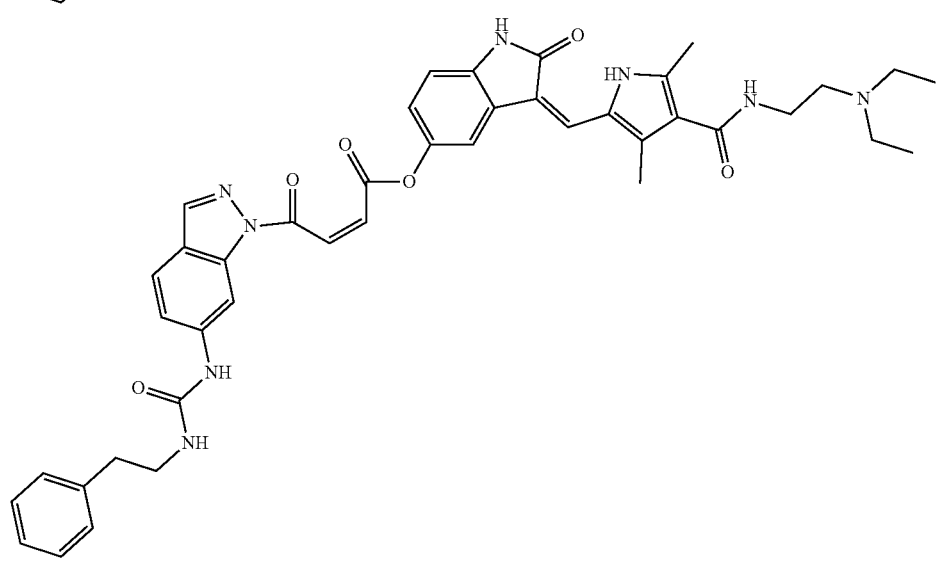
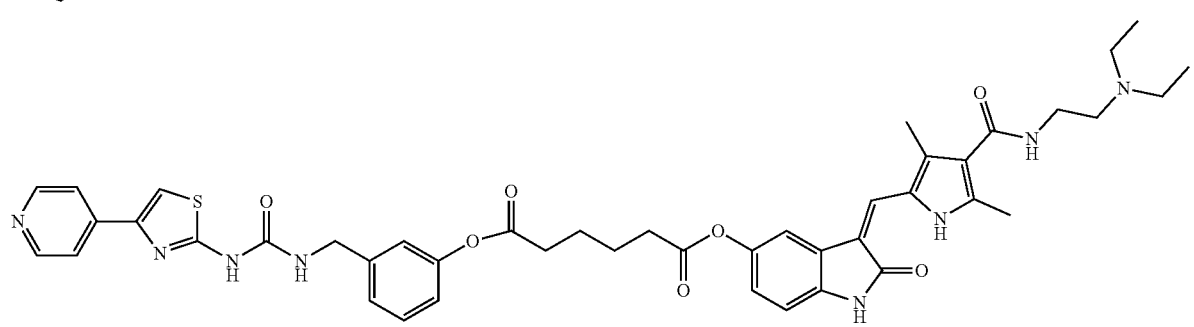
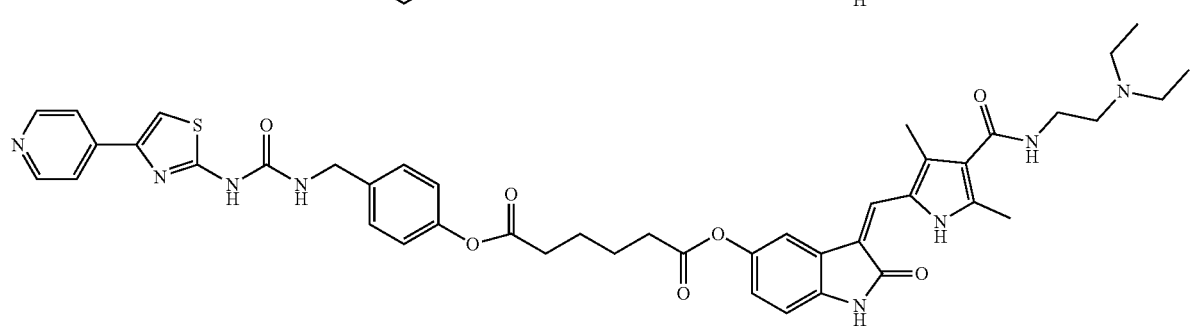

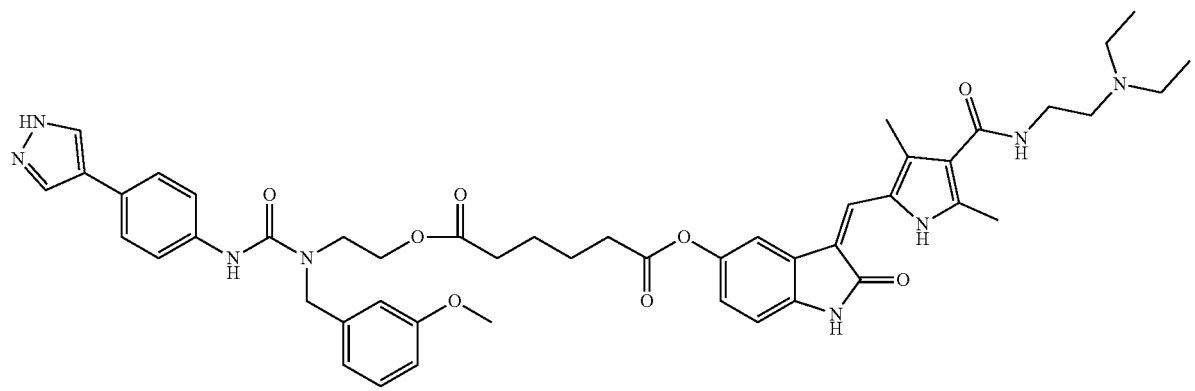
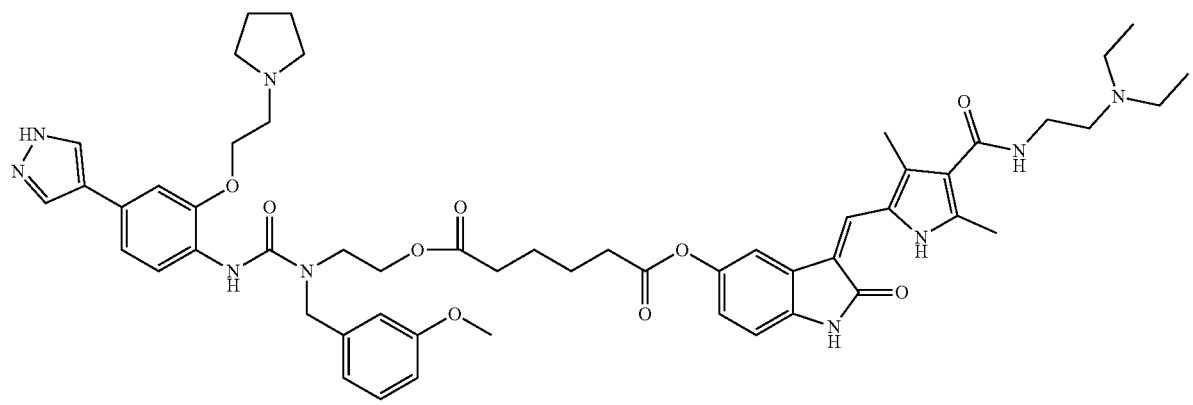
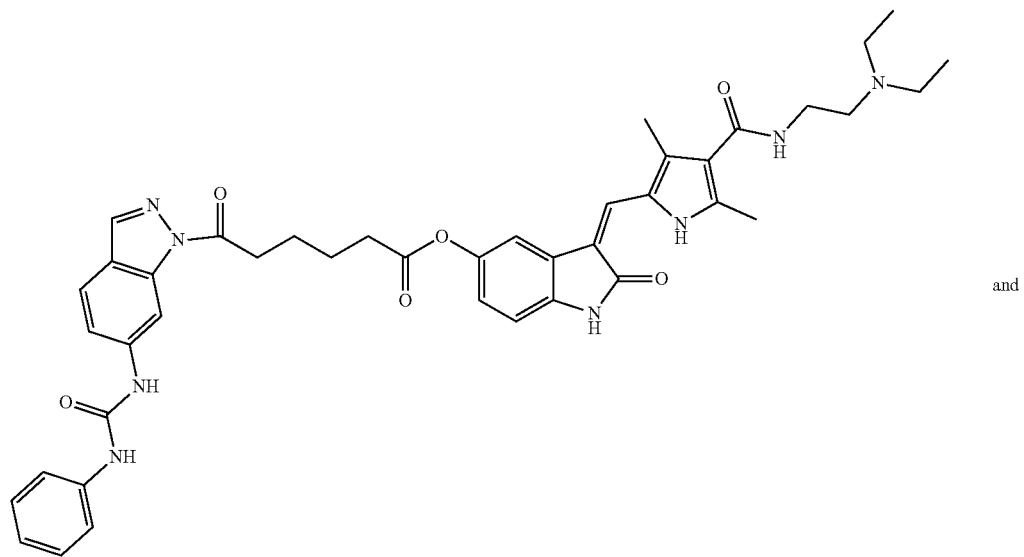
and

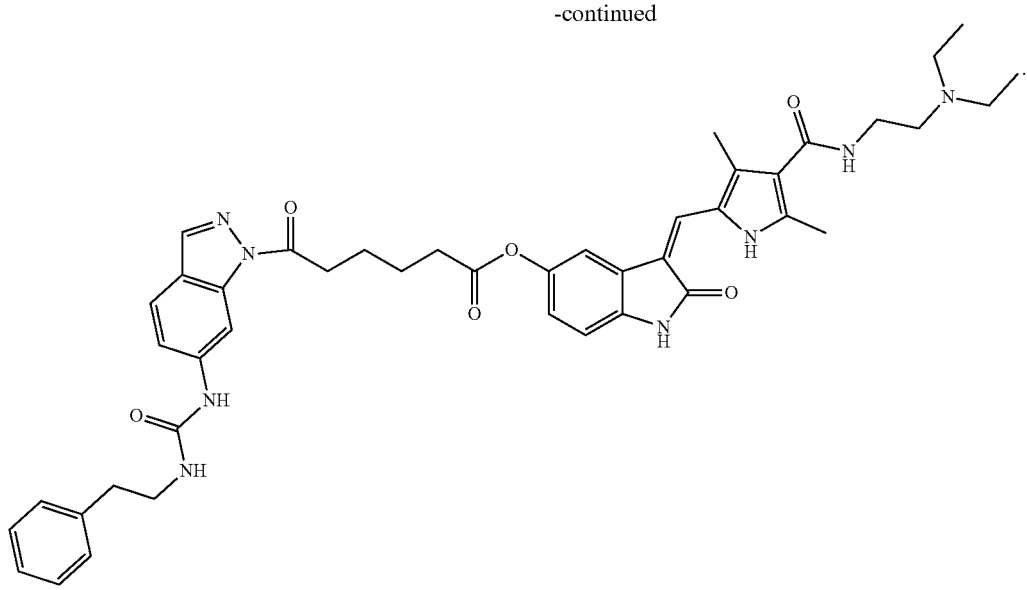
In another embodiment the compound of the present invention is selected from:
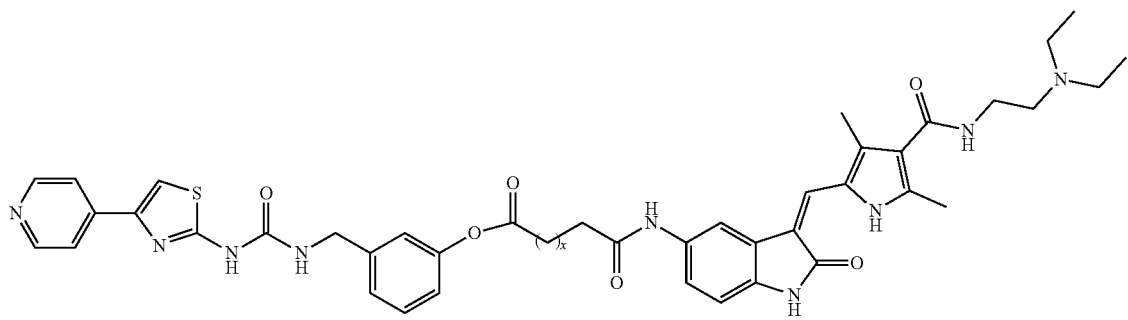
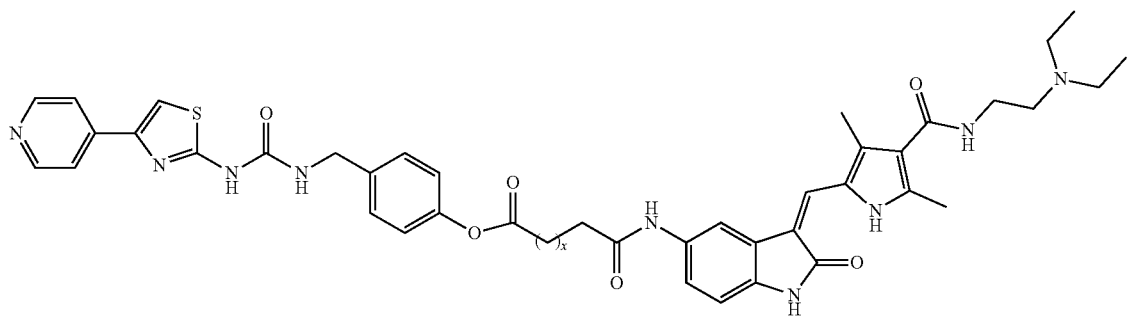

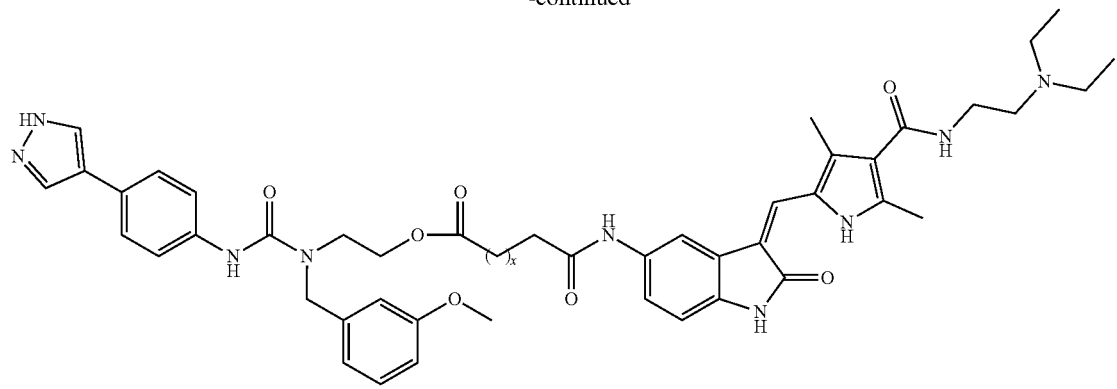
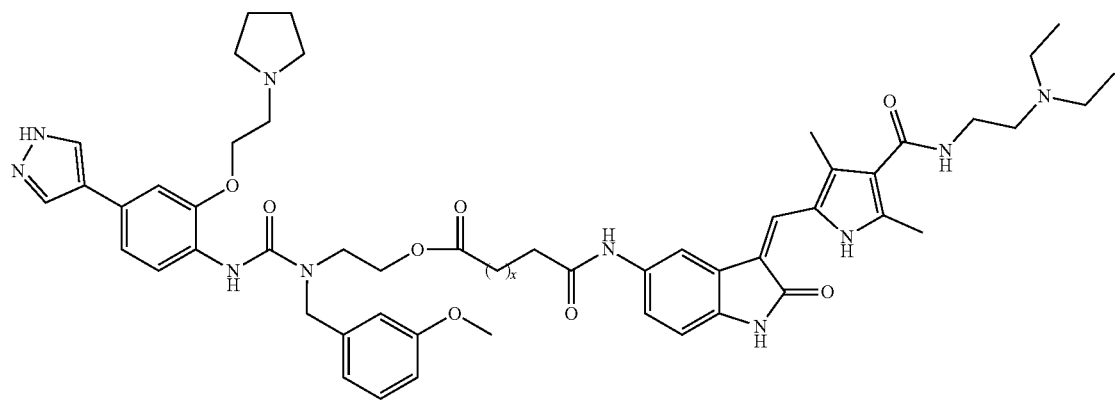
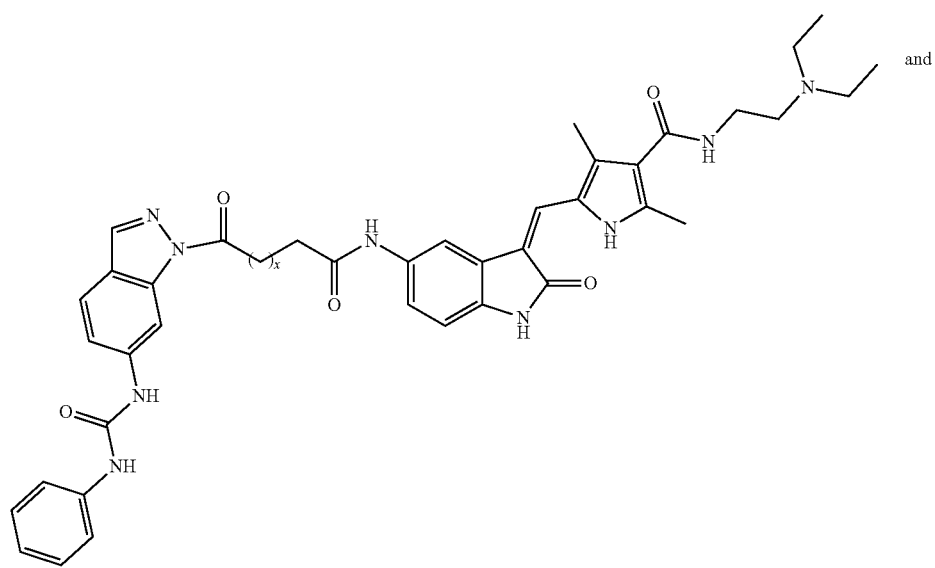
and

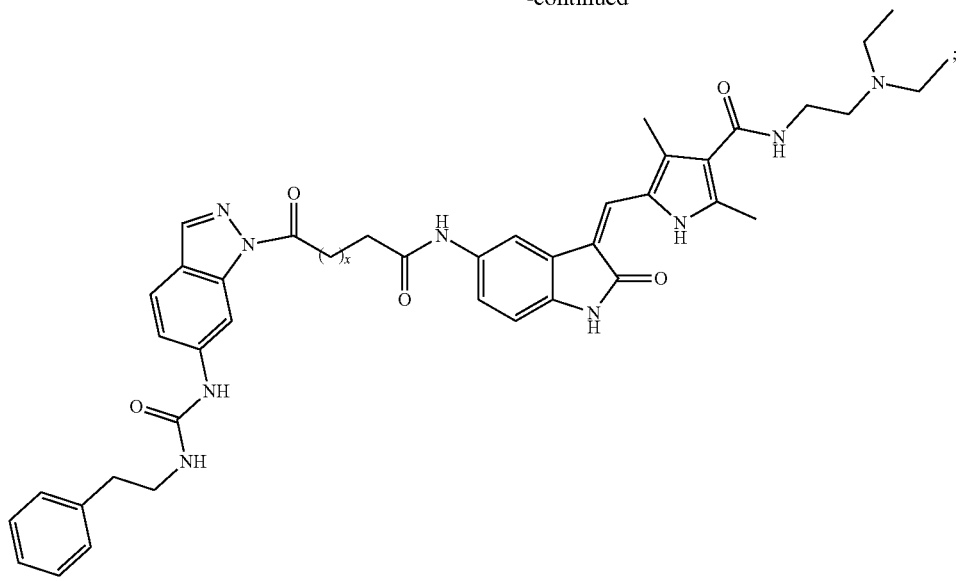
wherein x is 1, 2, 3, 4, 5, 6, 7, 8, or 9.
In one embodiment the compound of the present invention is selected from:
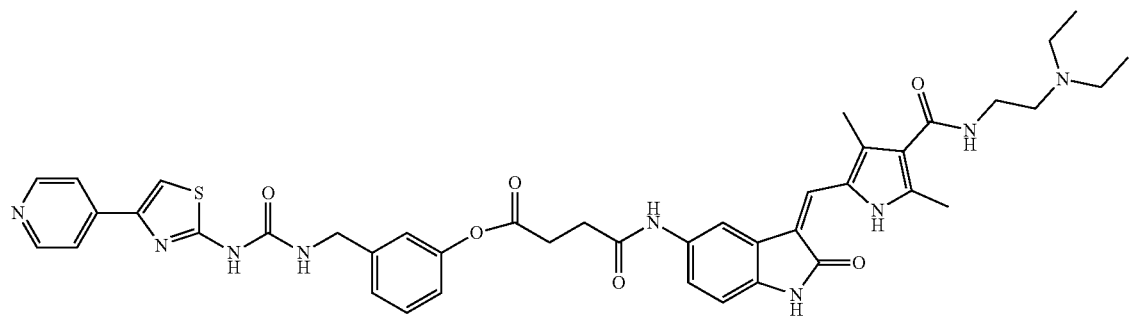
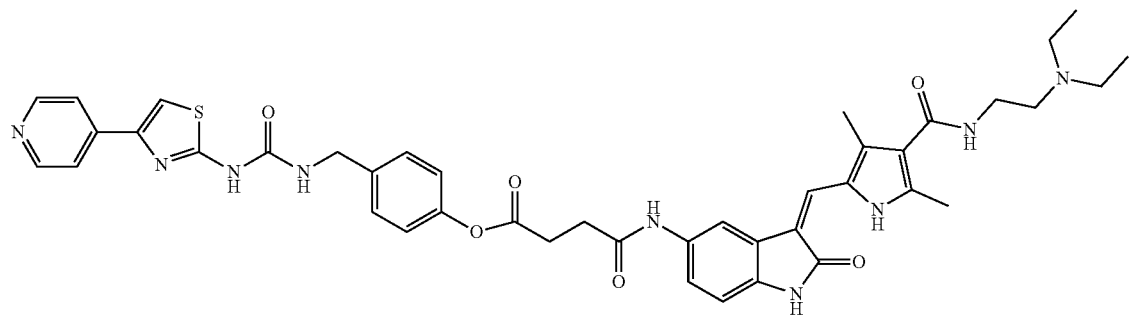

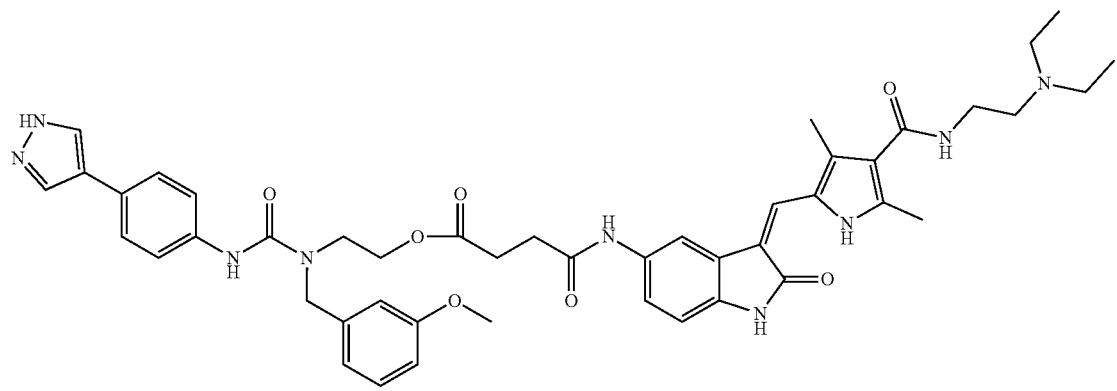
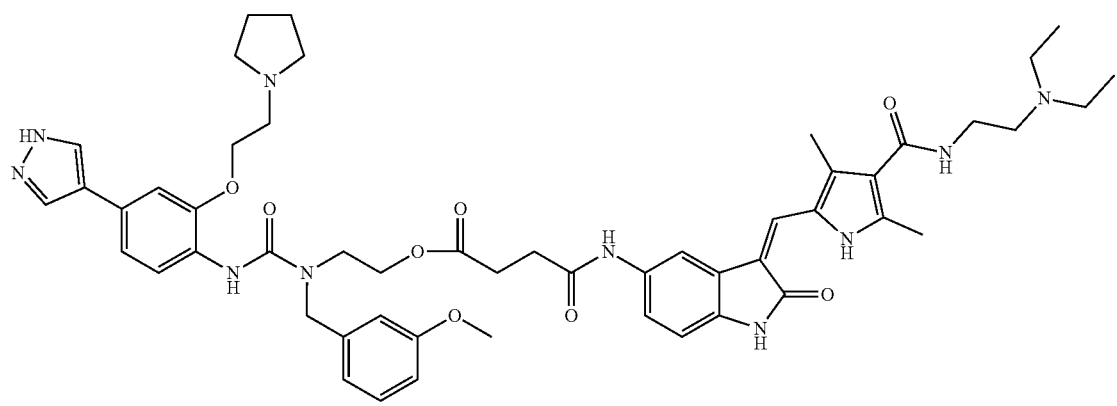
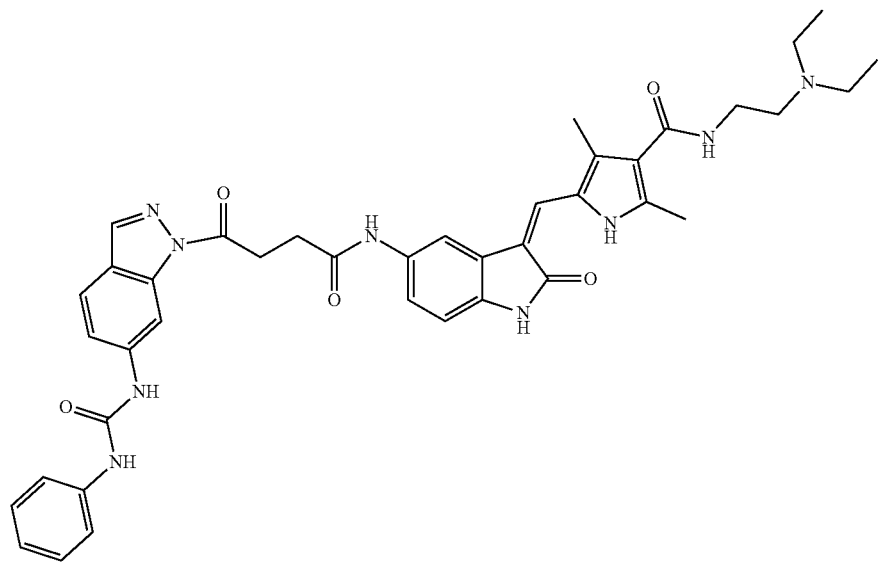

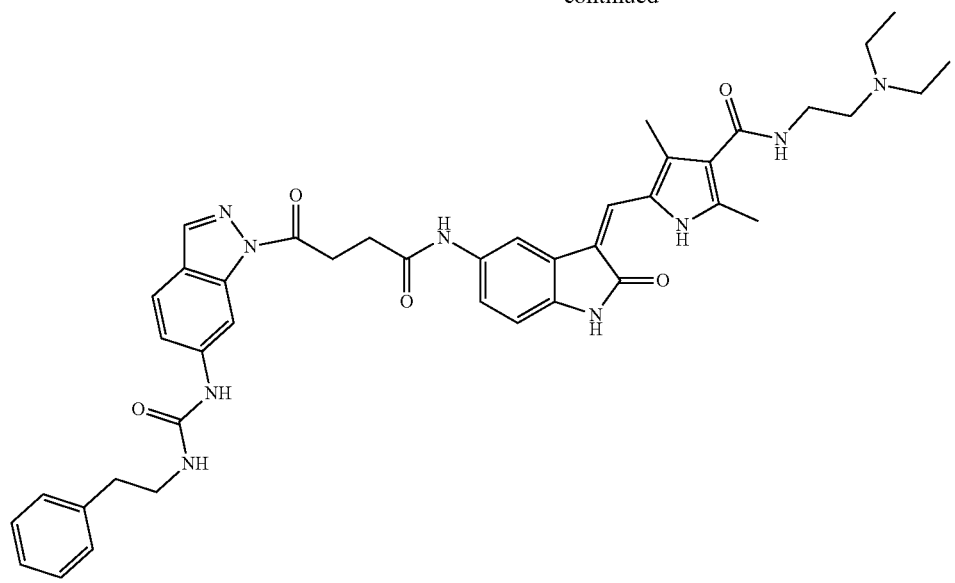
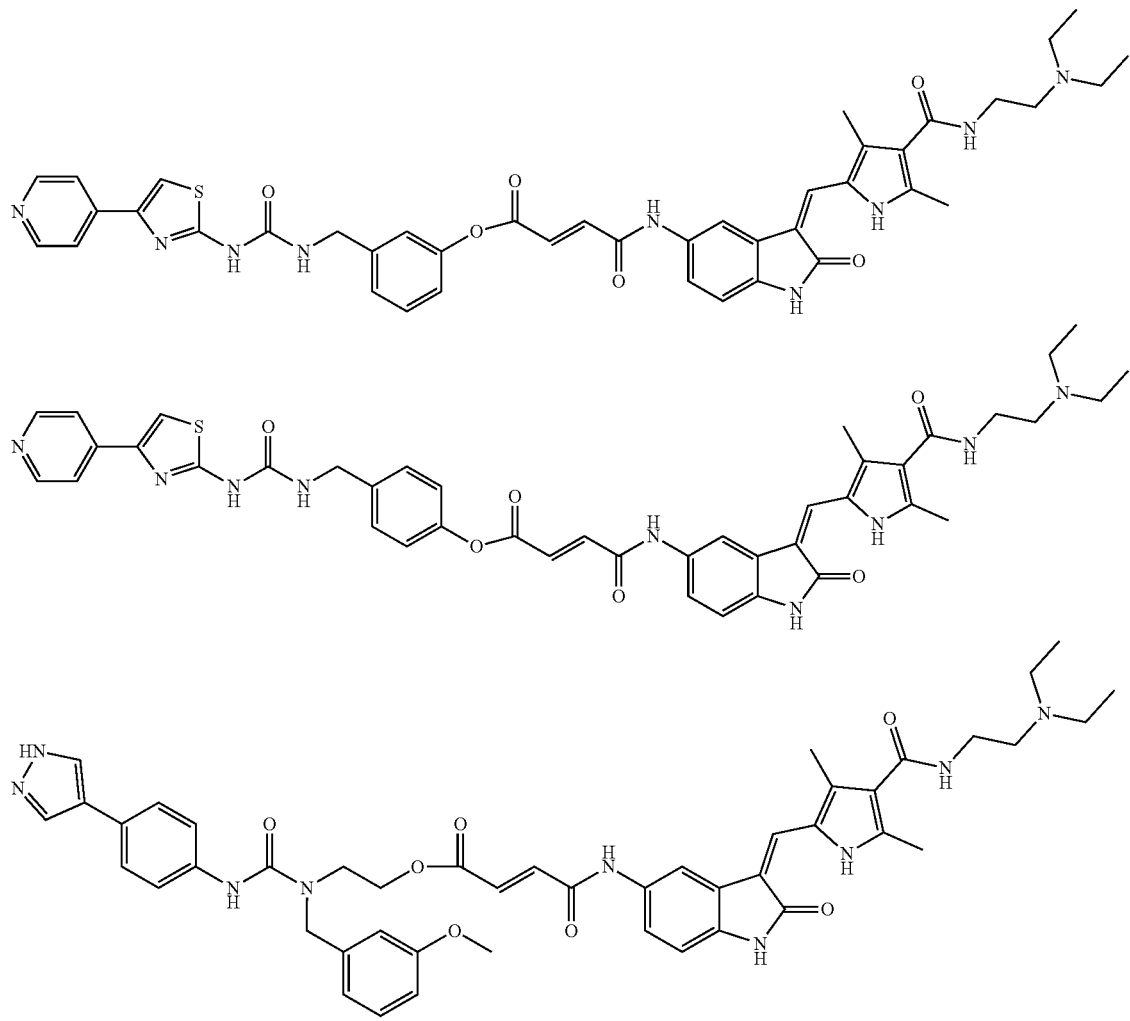

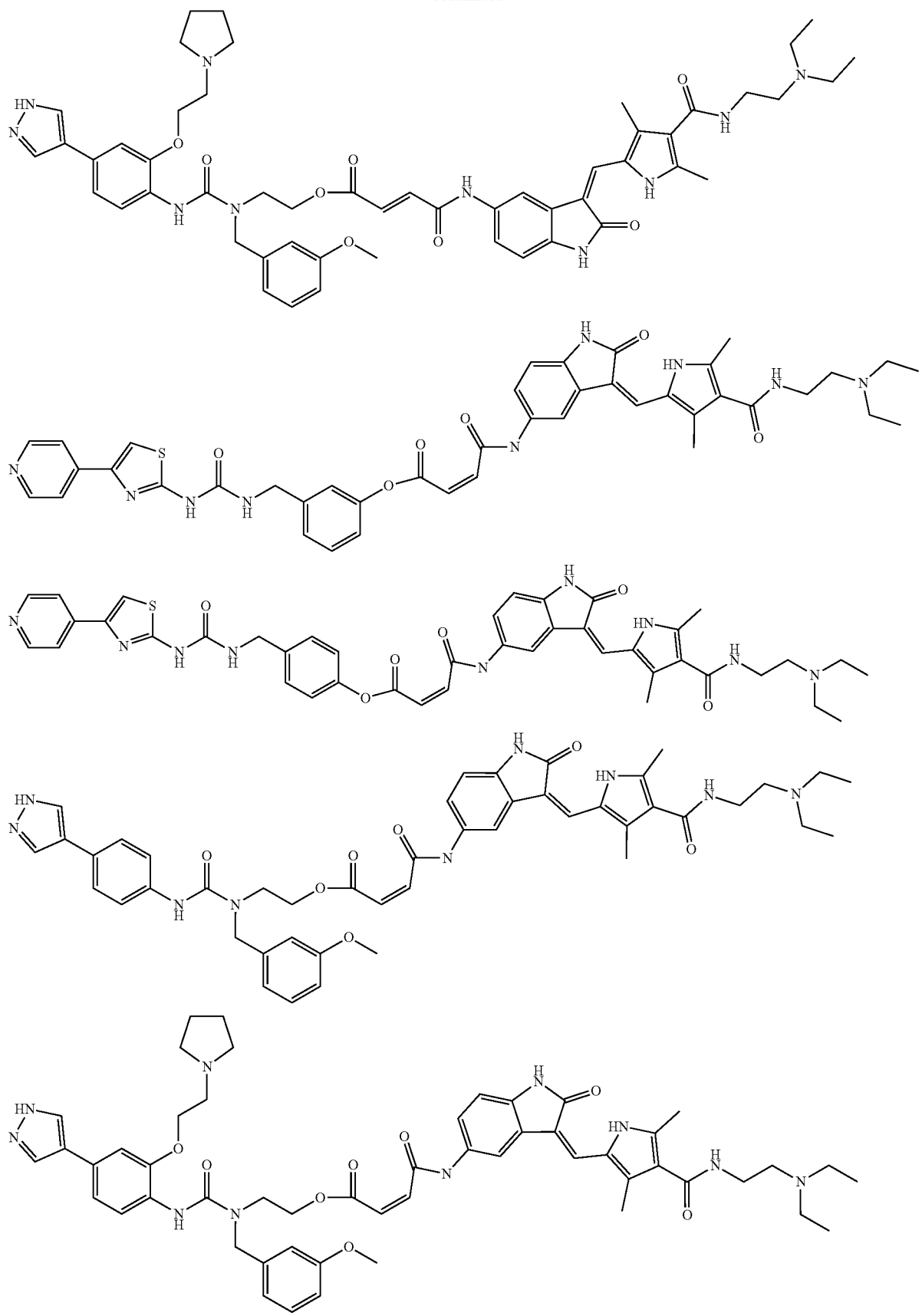

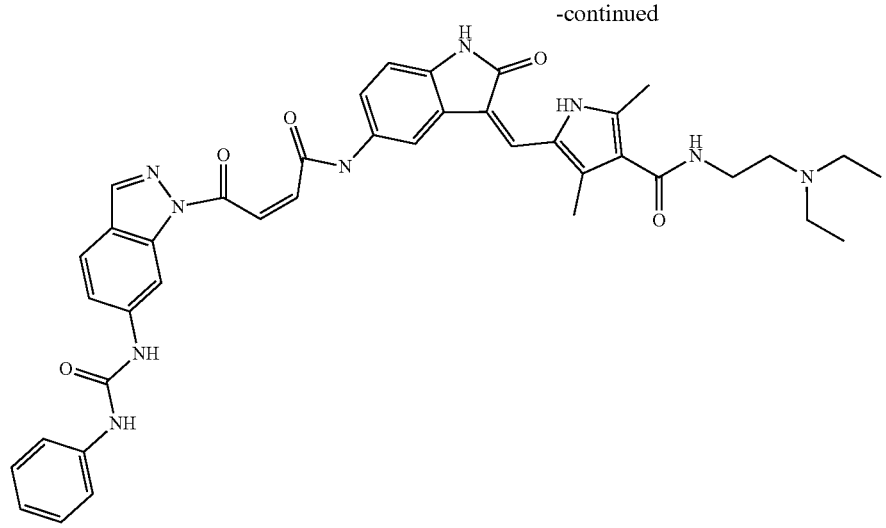
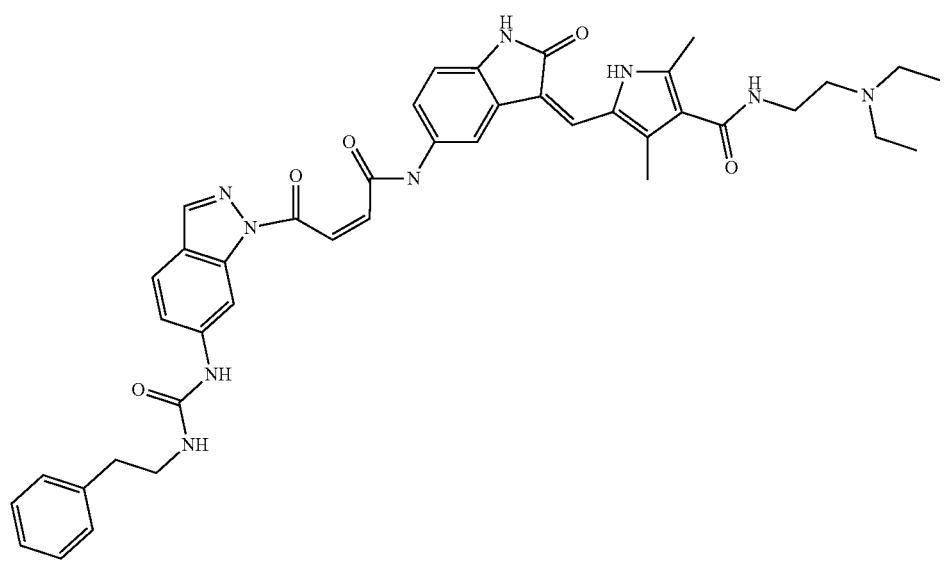
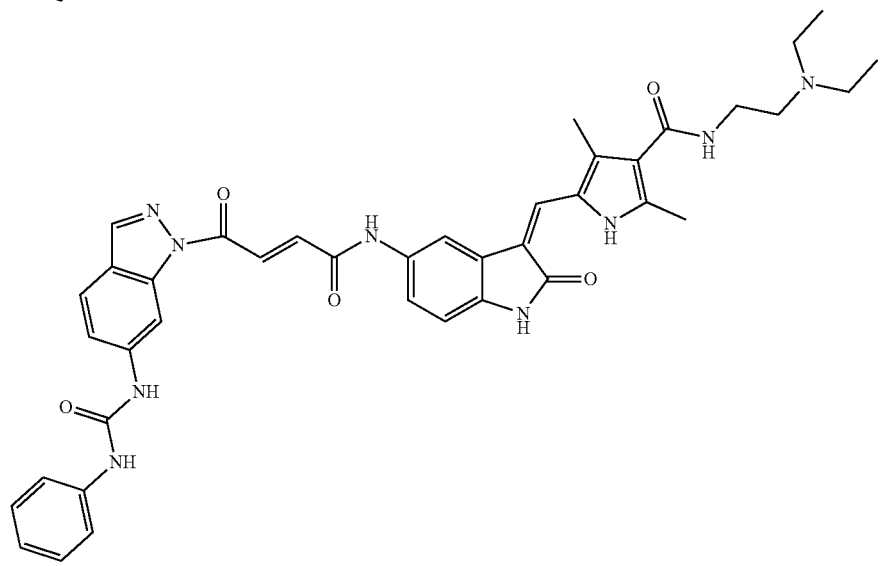

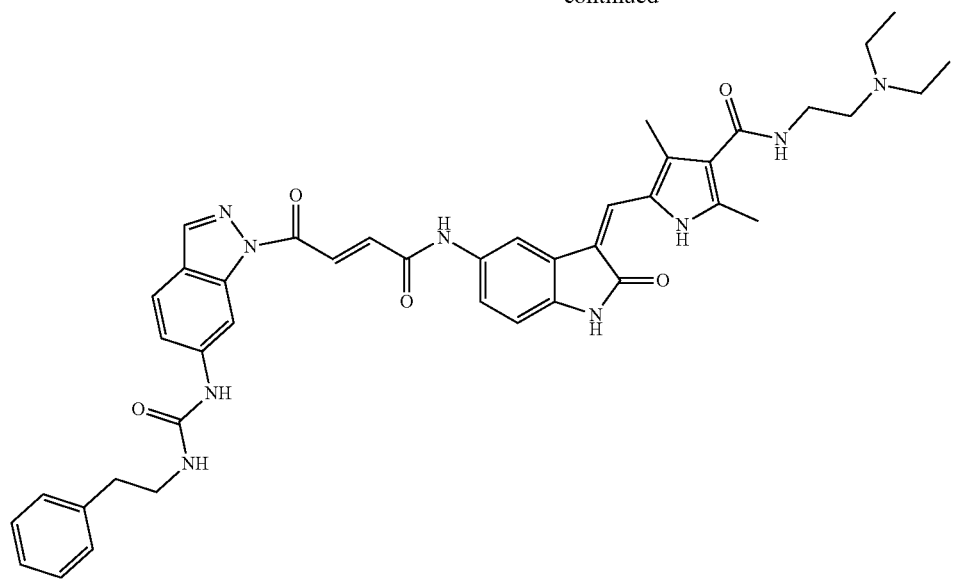
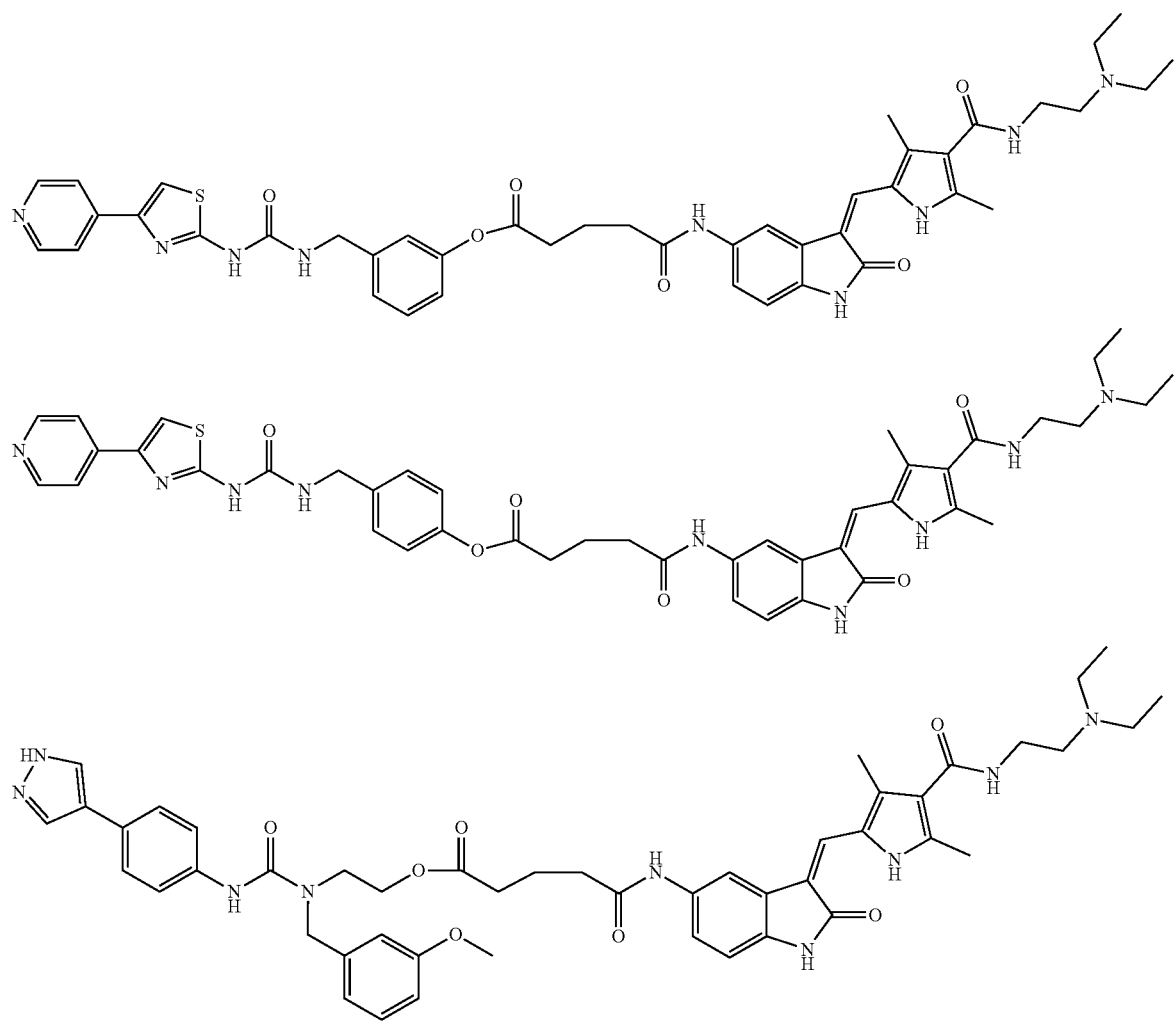

673
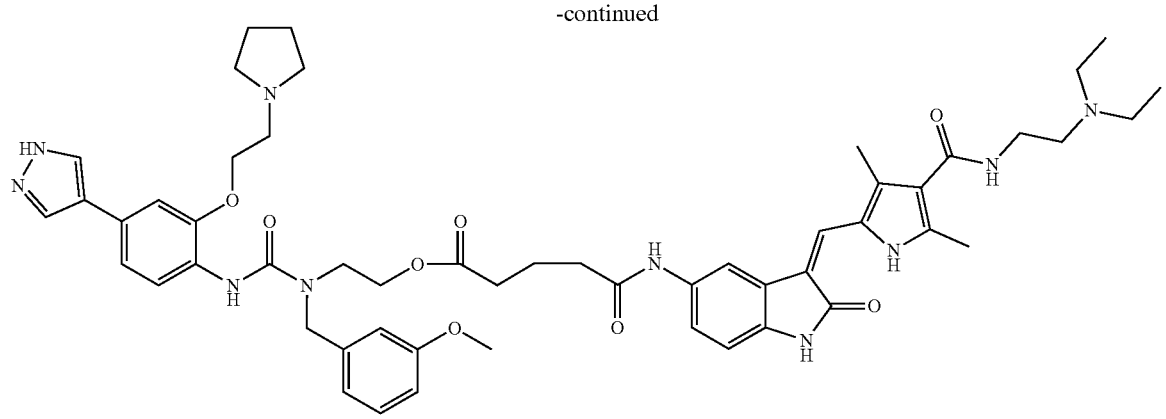
674
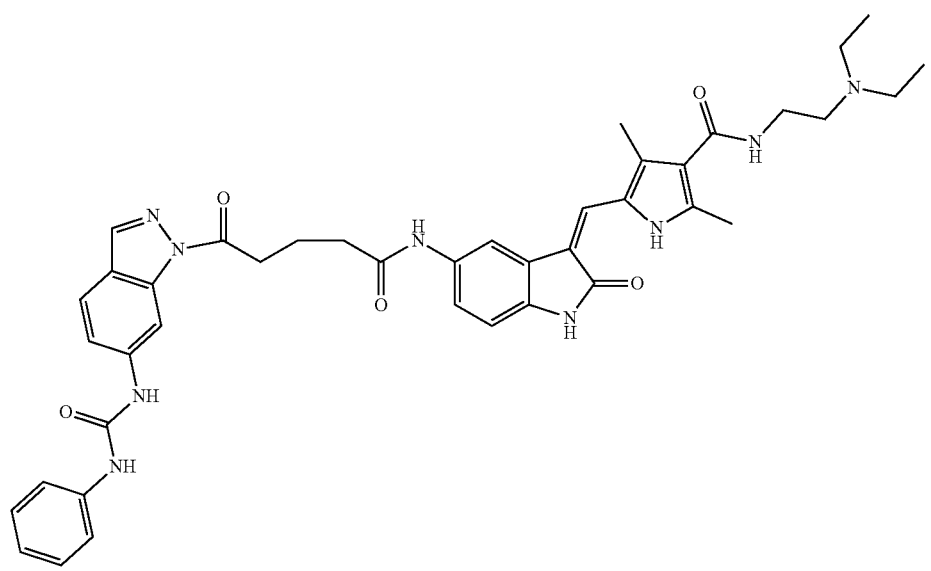
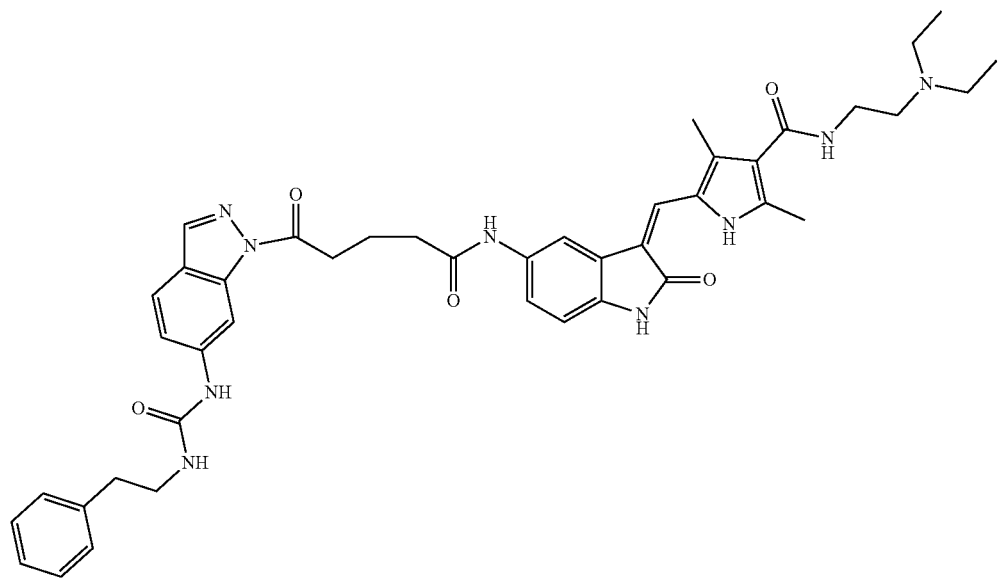

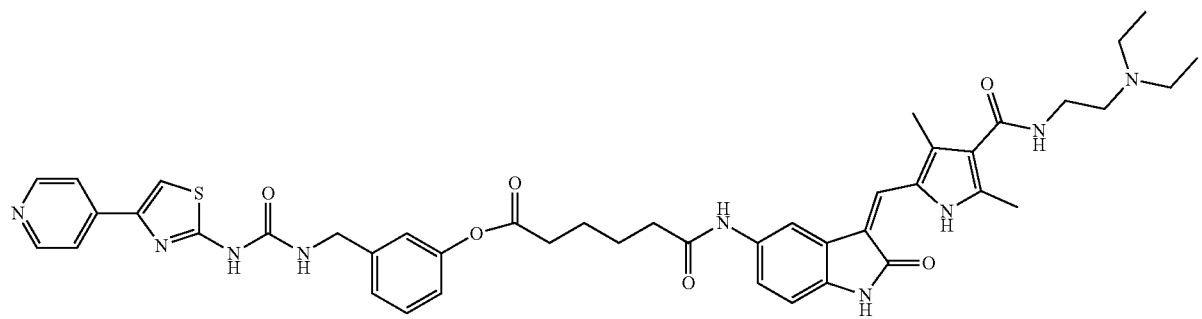
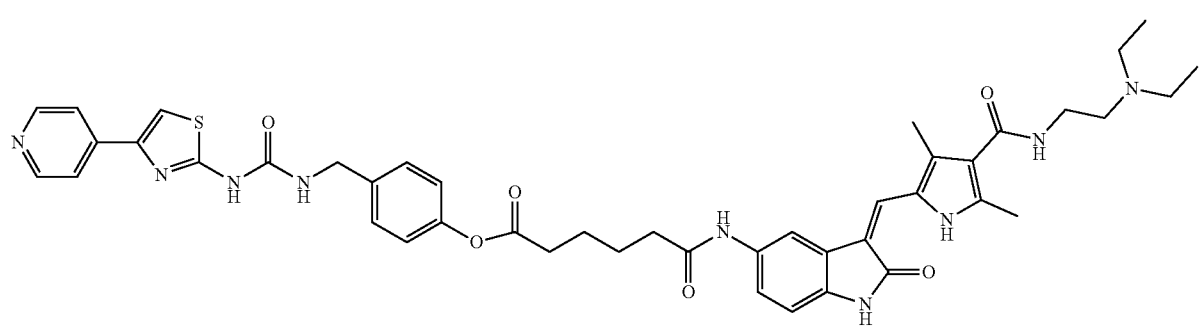
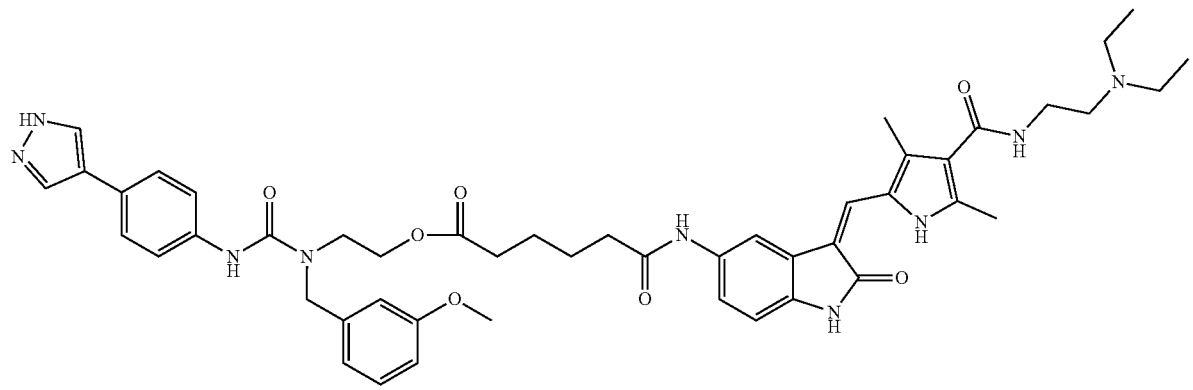
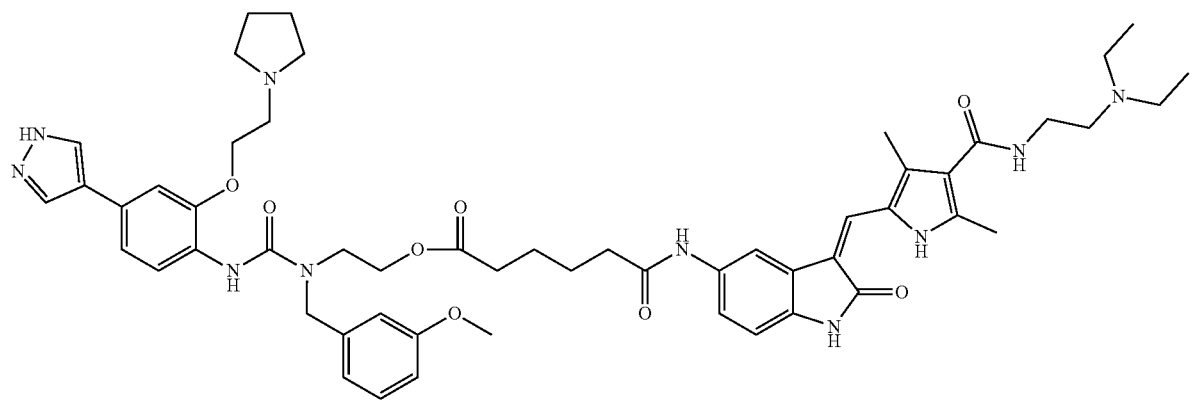

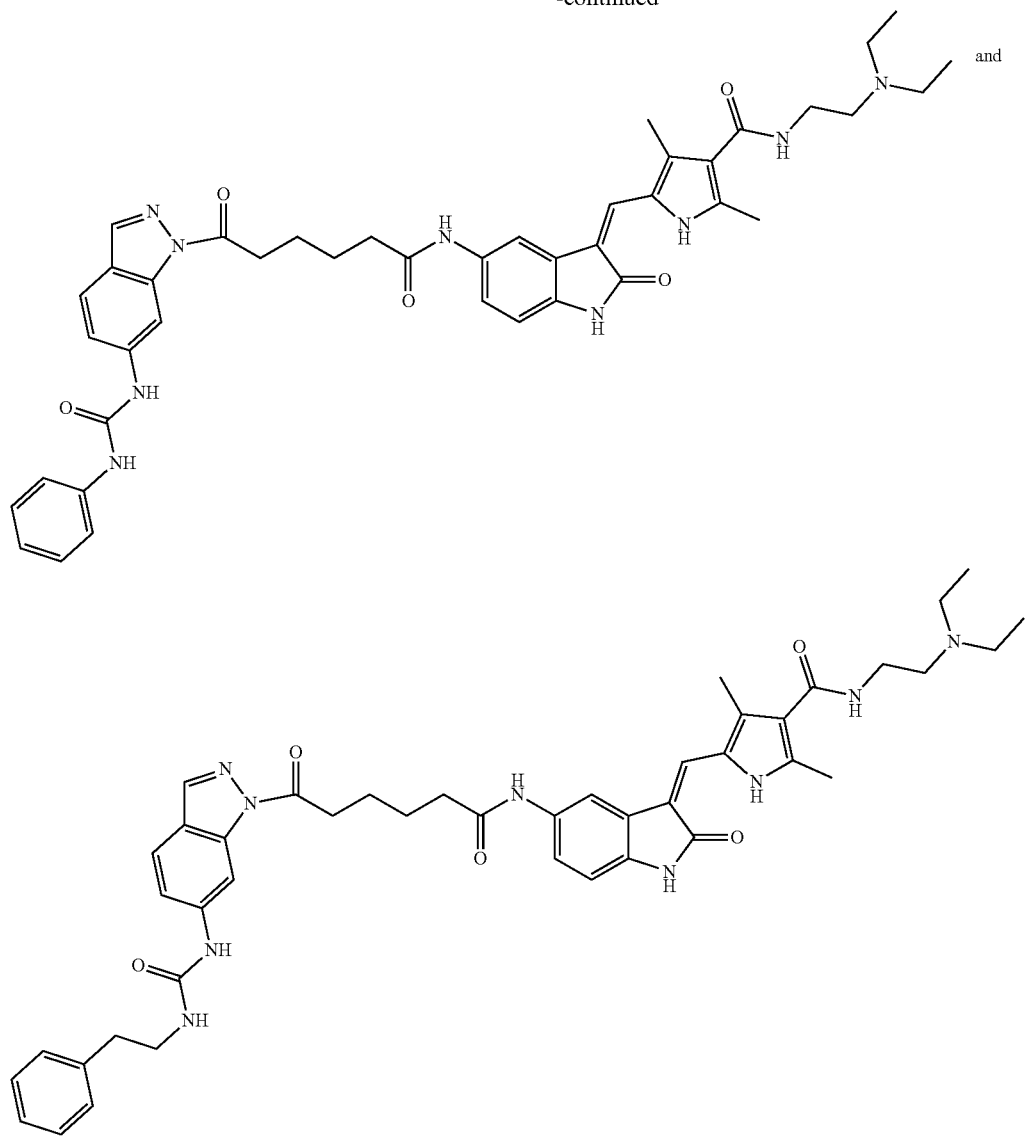
Example 38. Non-Limiting Examples of Dorzolamide Mono-Prodrugs
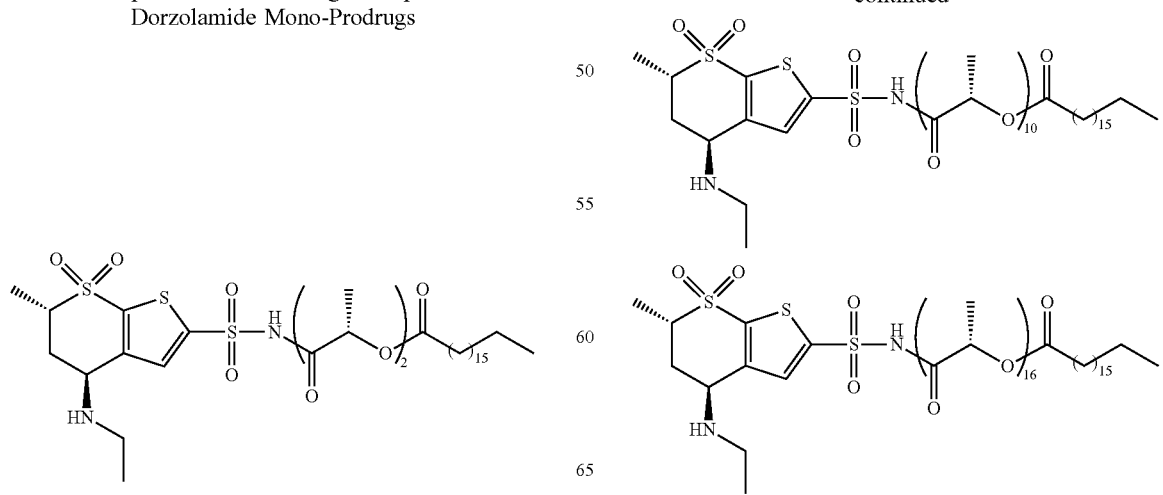

679
-continued
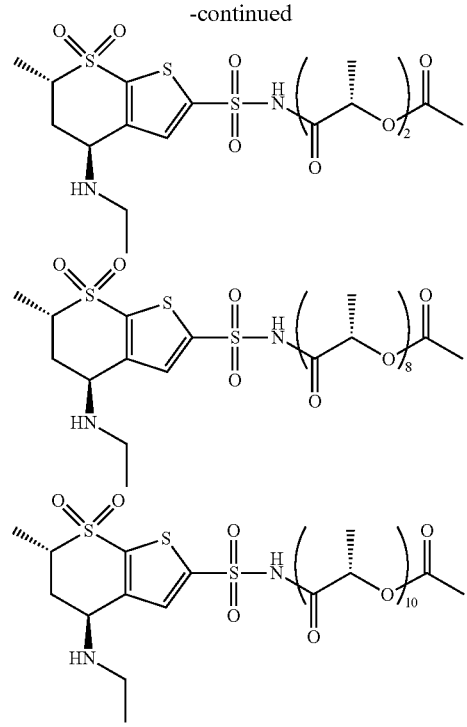
Example 39. Non-Limiting Examples of Brinzolamide Mono-Prodrugs
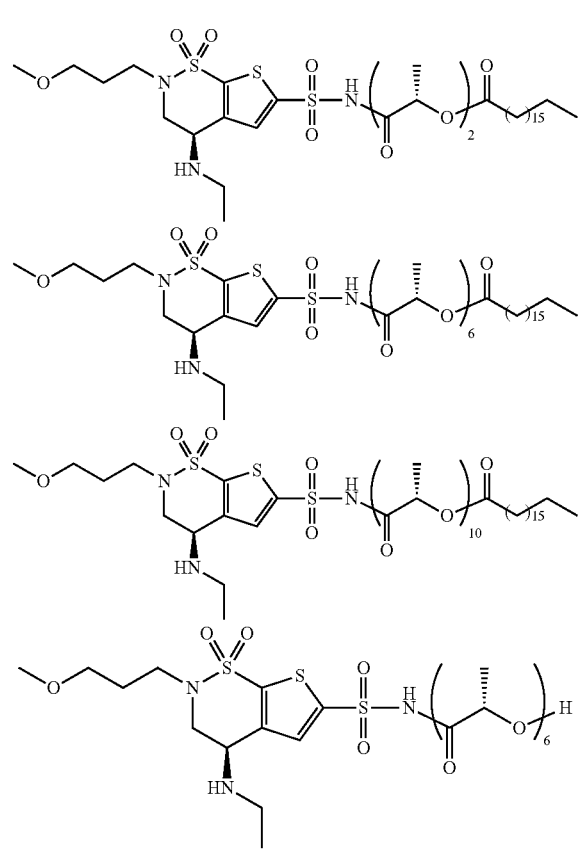
680
-continued
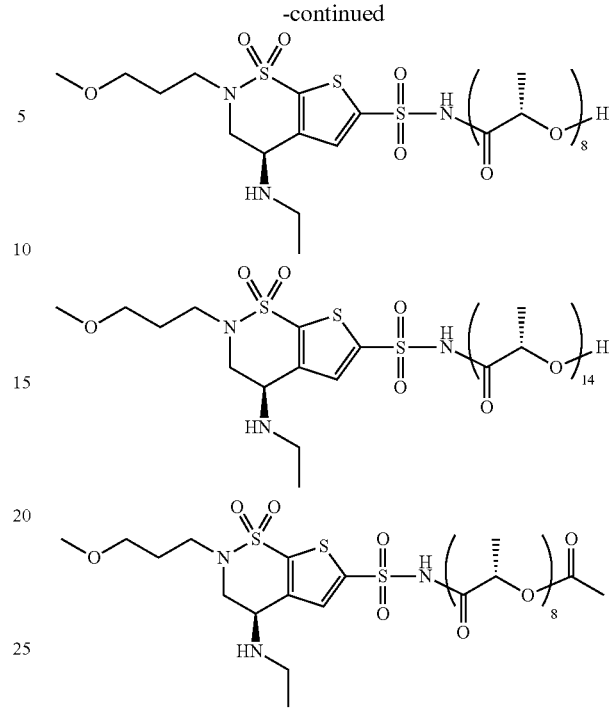
Example 40. Non-limiting Examples of Compounds of the Present Invention
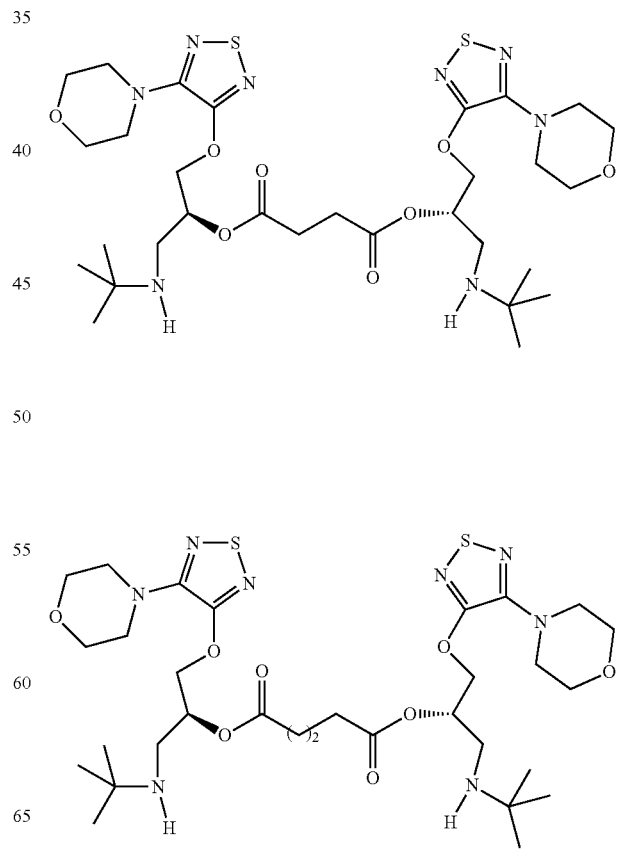

681
-continued
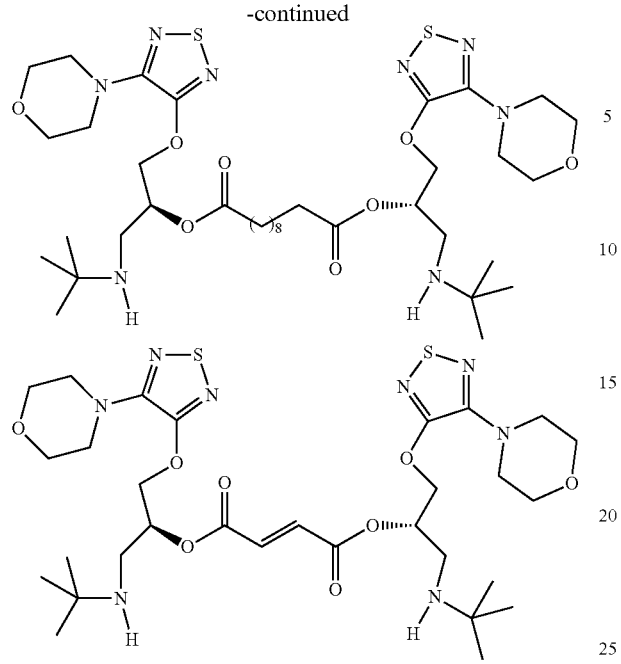
Example 41. Non-Limiting Examples of Compounds of Formula L
682
-continued
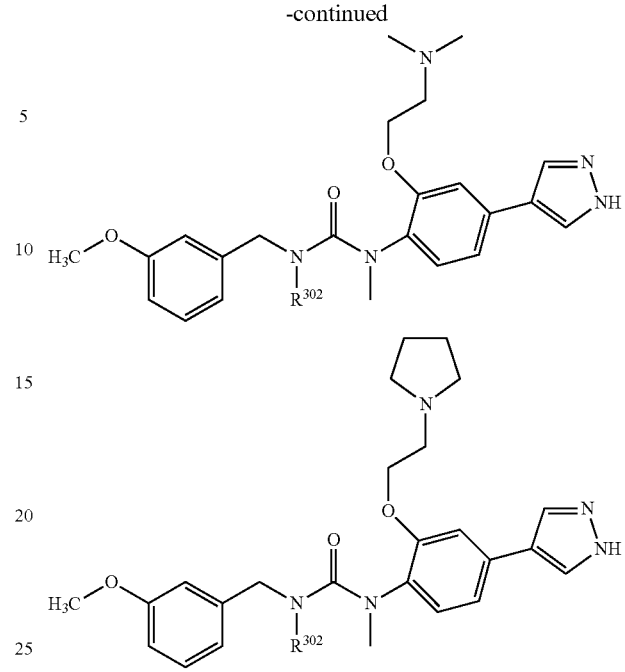
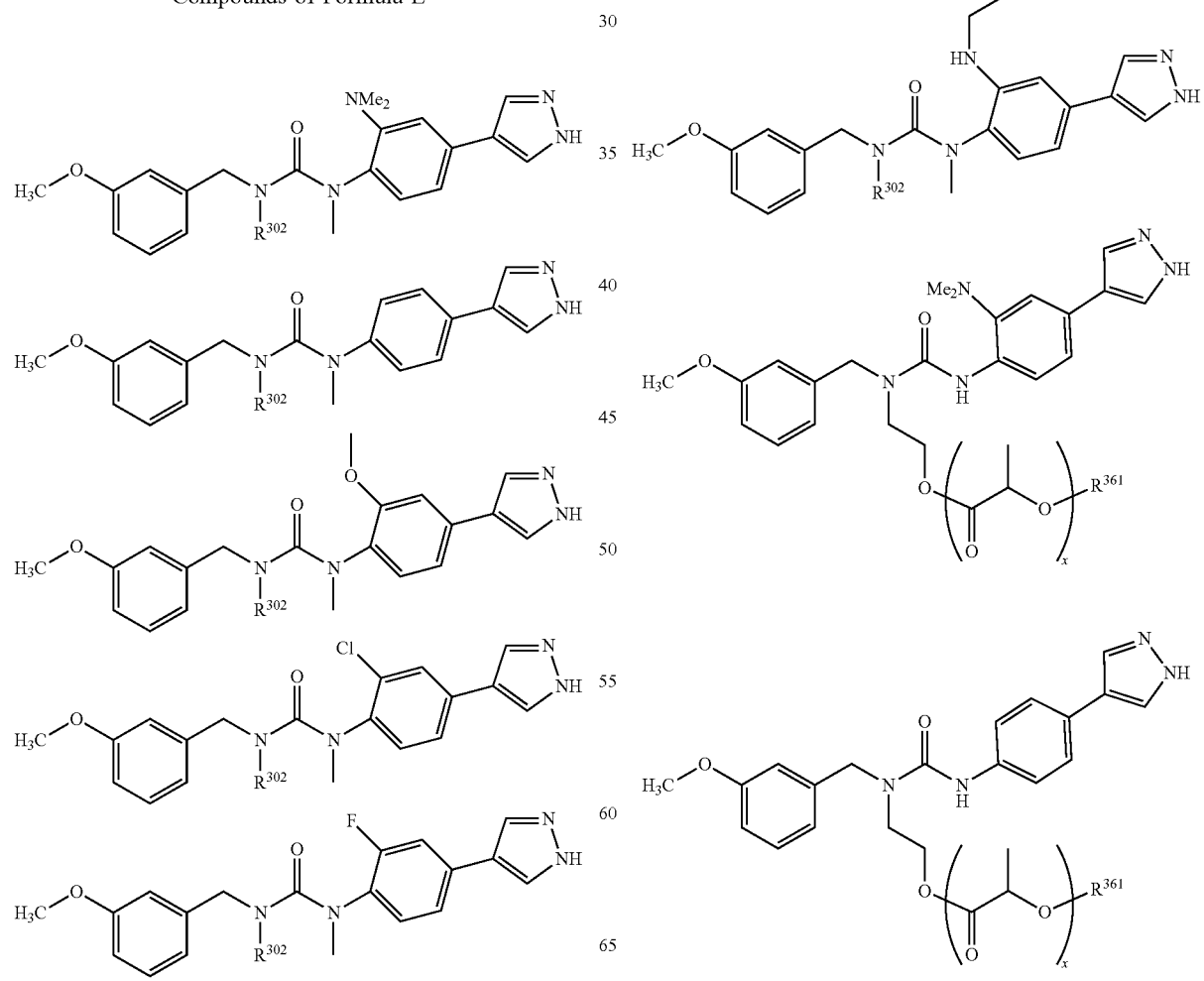

683
-continued
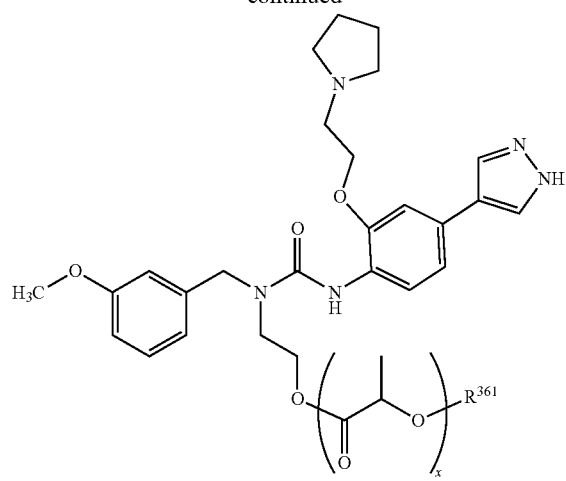
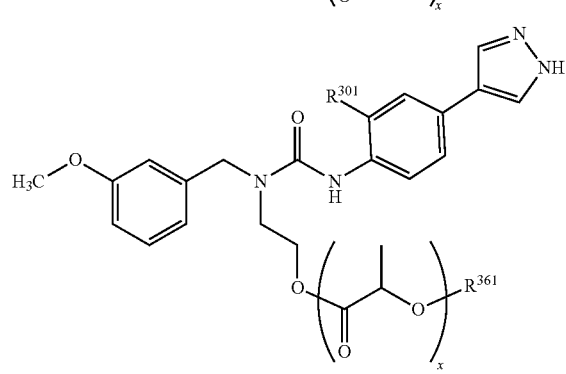
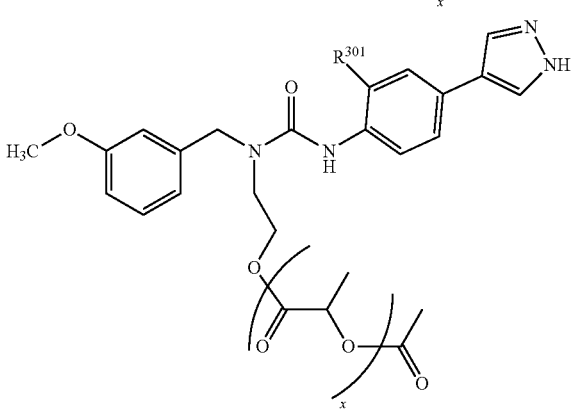
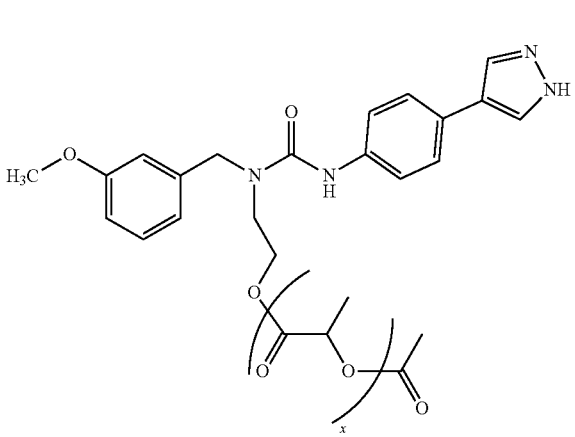
684
-continued
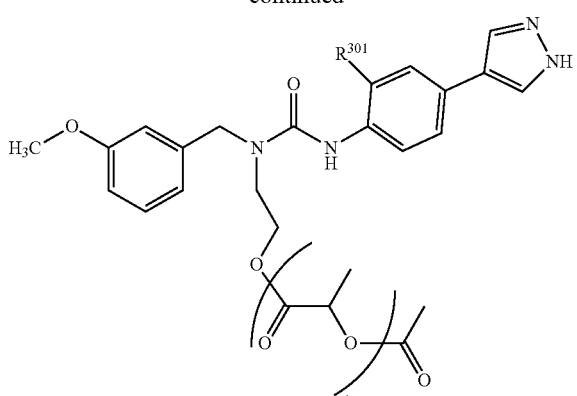
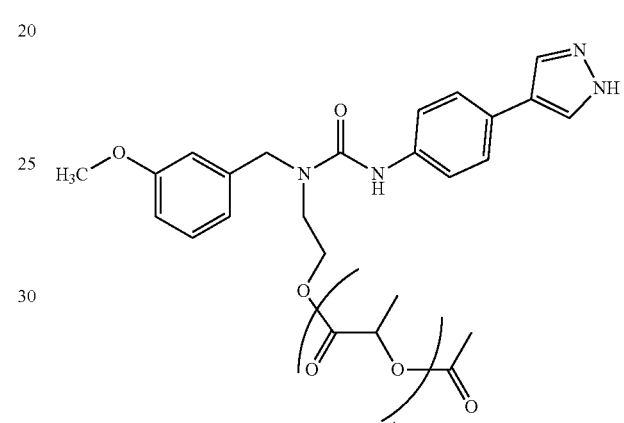
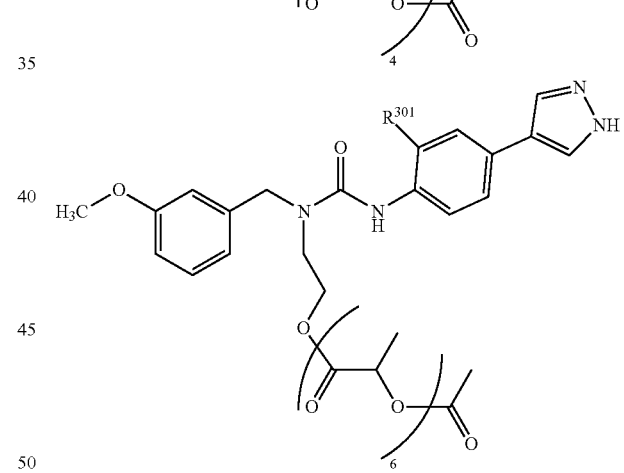
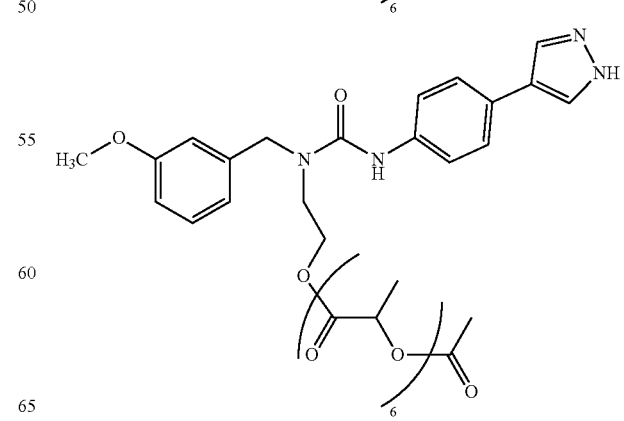

685
-continued
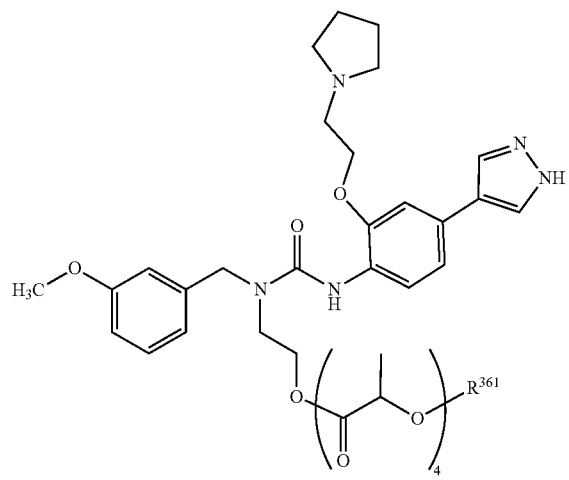
686
-continued
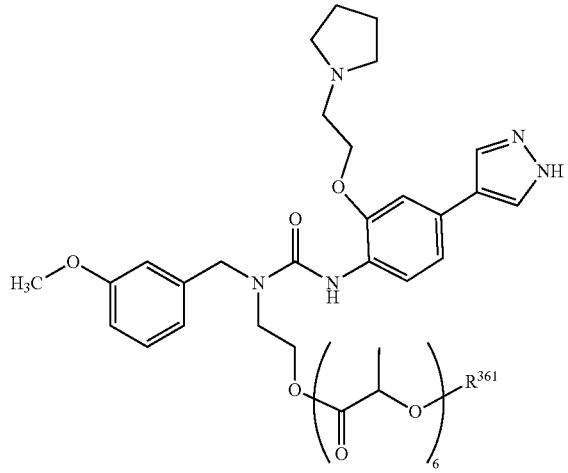
Example 42. Non-Limiting Examples of Compounds of Formula LII
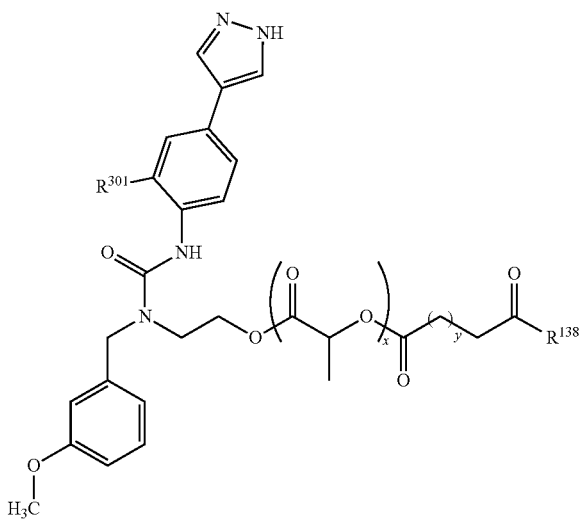
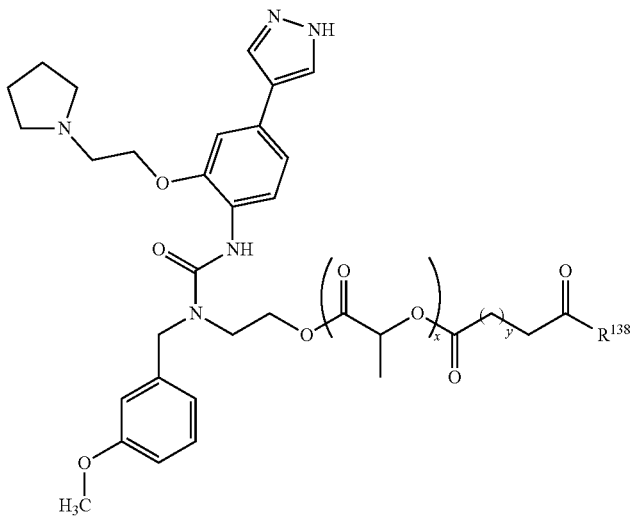

-continued
687
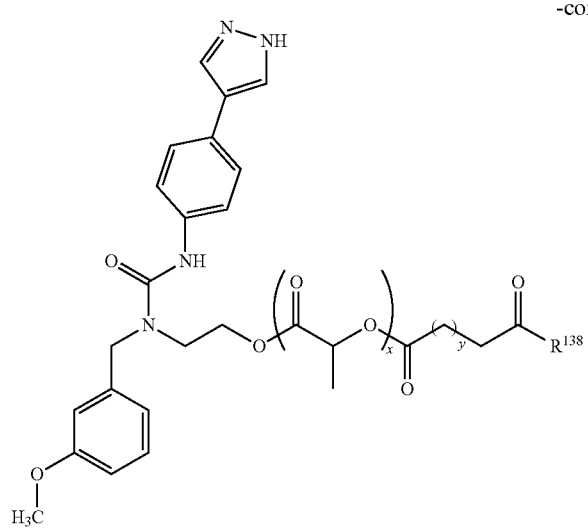
688
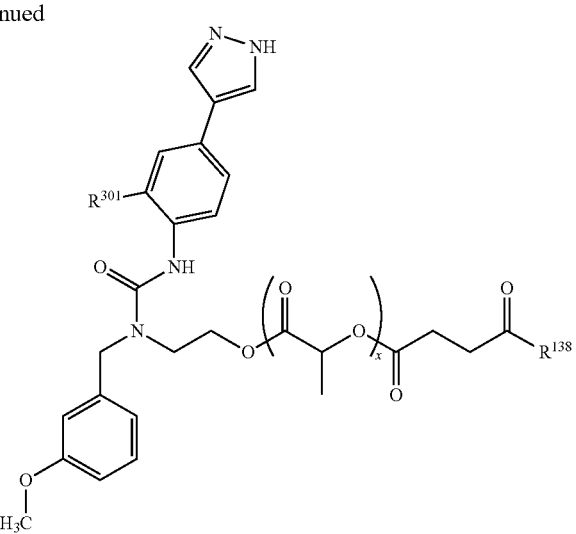
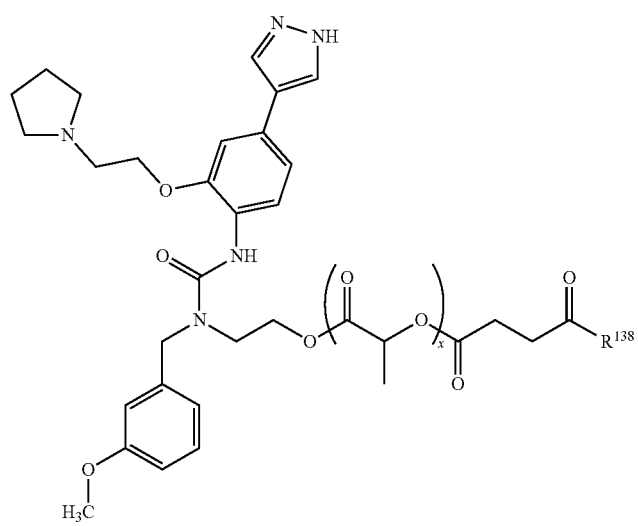
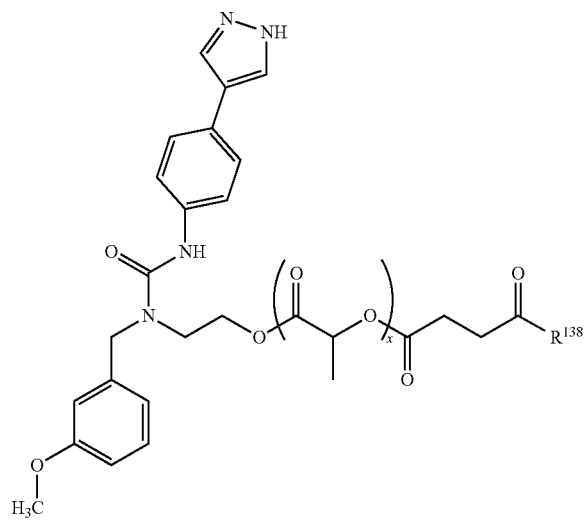

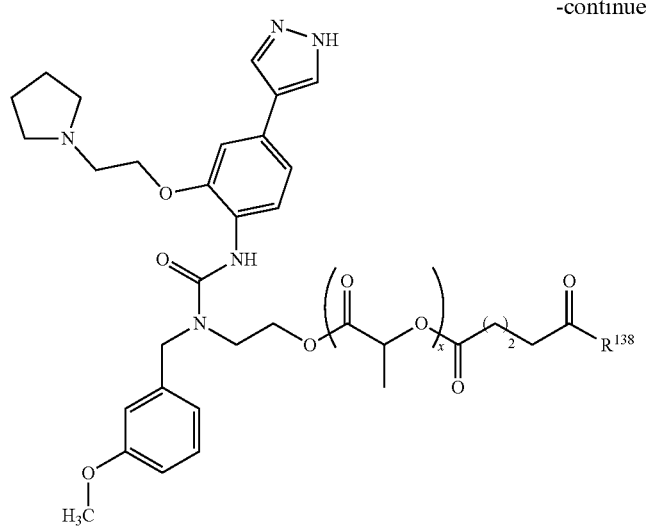
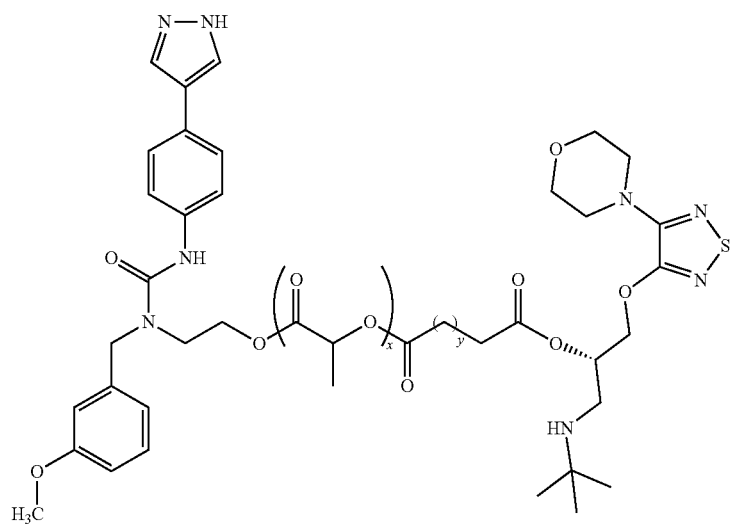
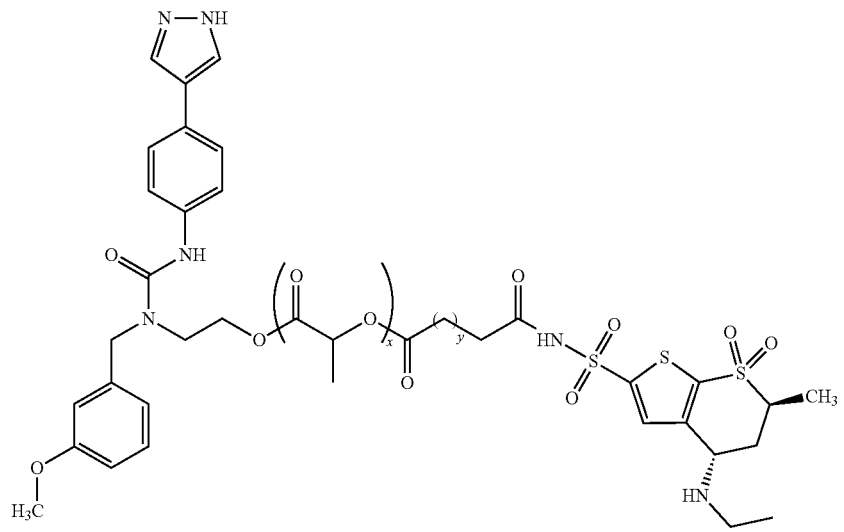

-continued
691
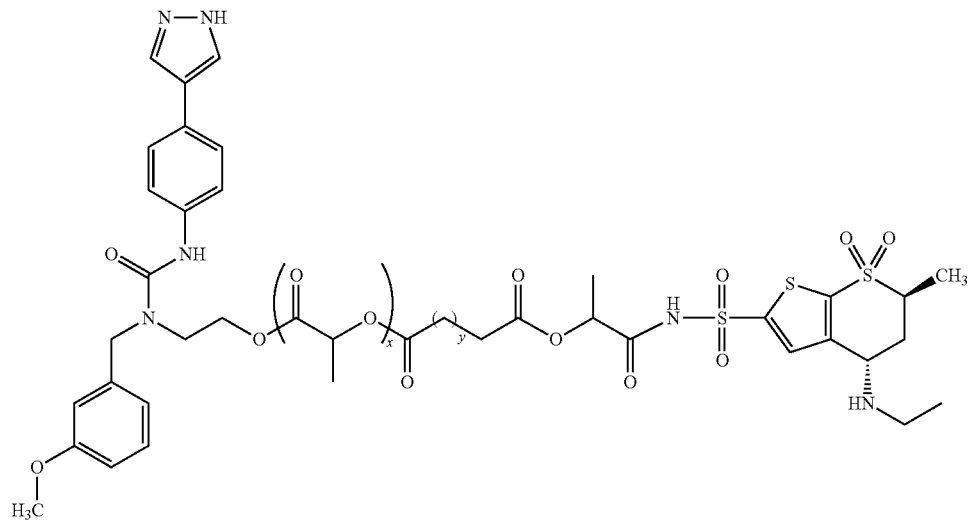
692
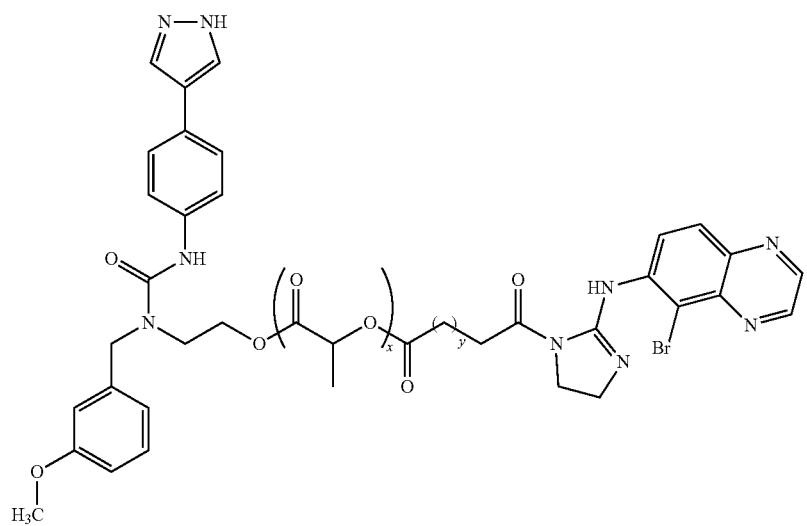
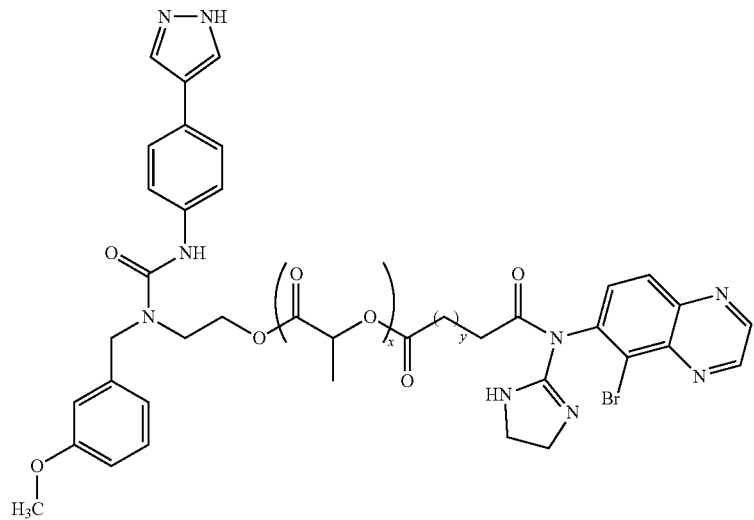

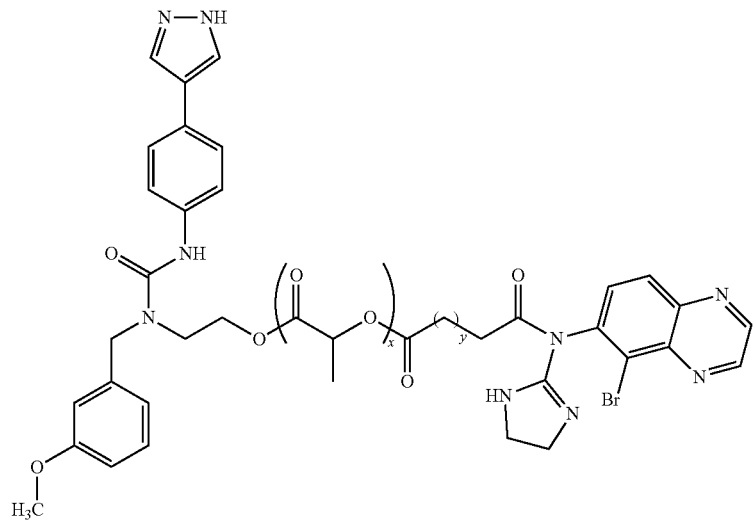
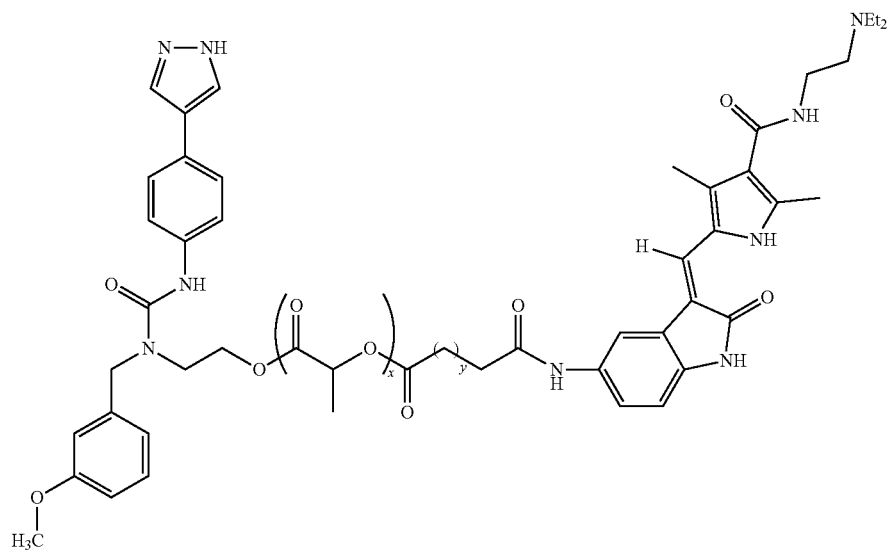
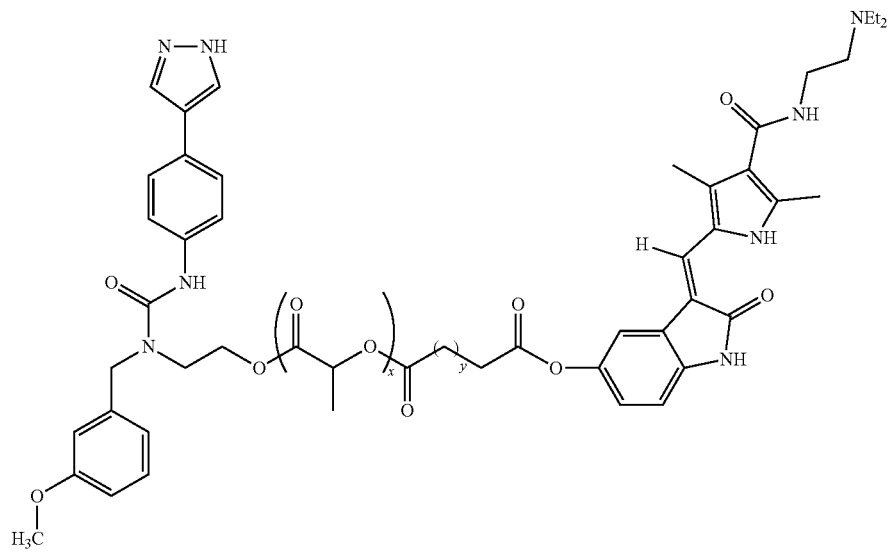

695
696
-continued
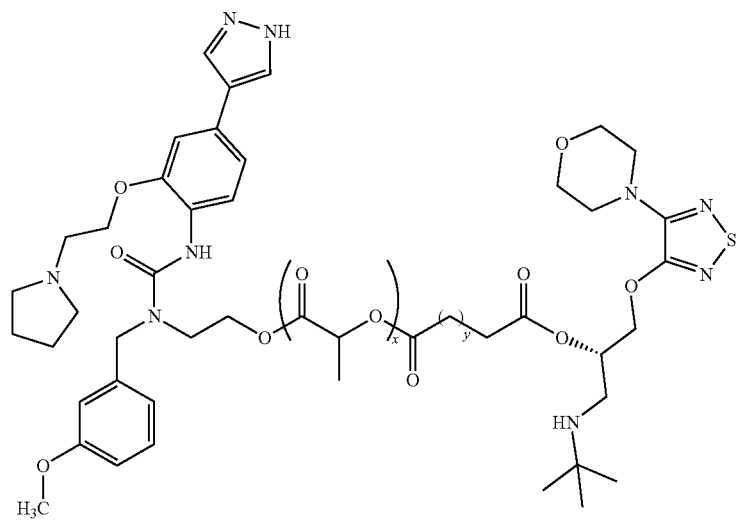
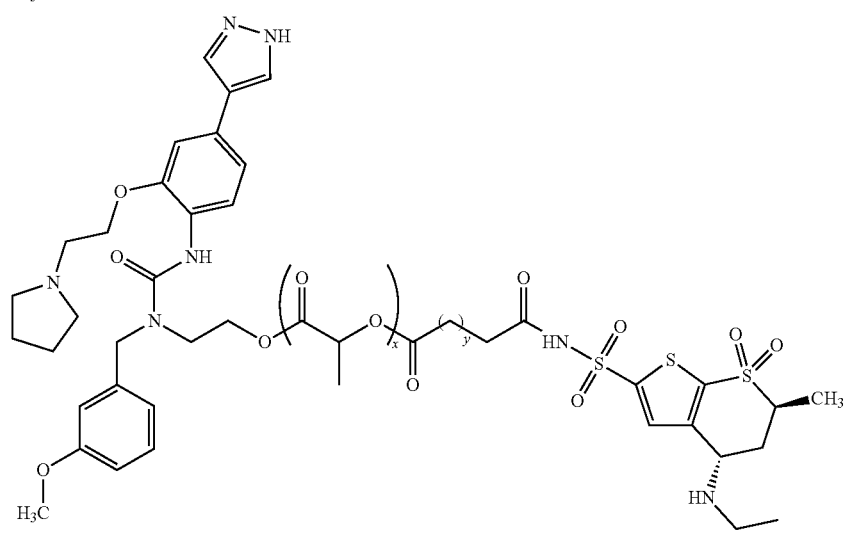
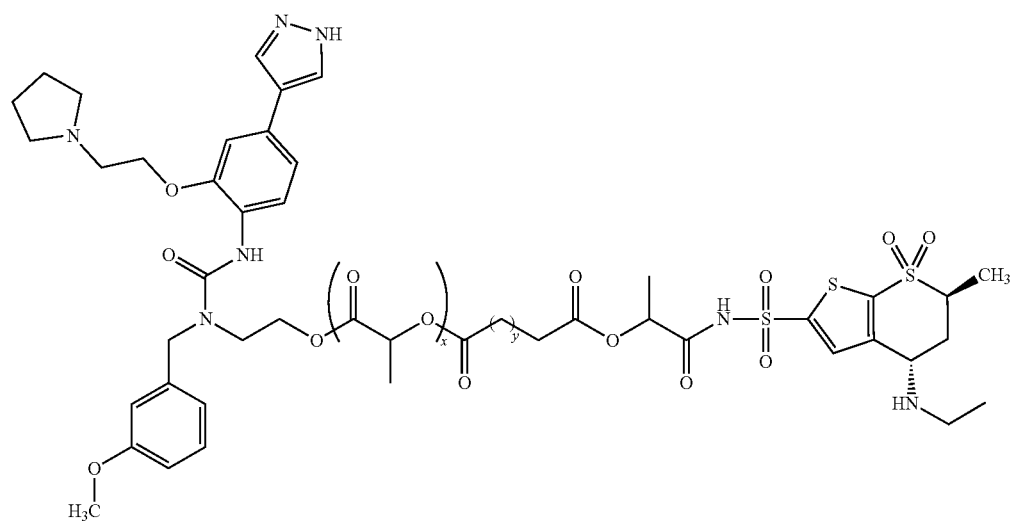

-continued
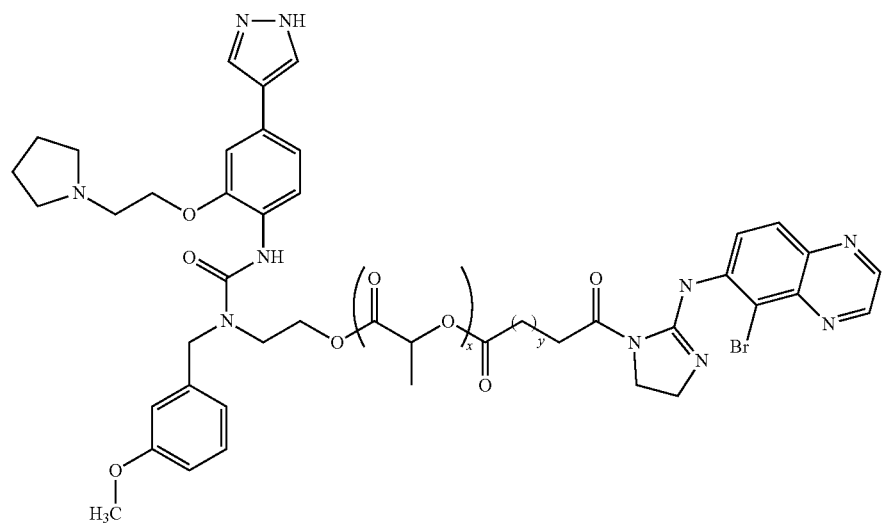
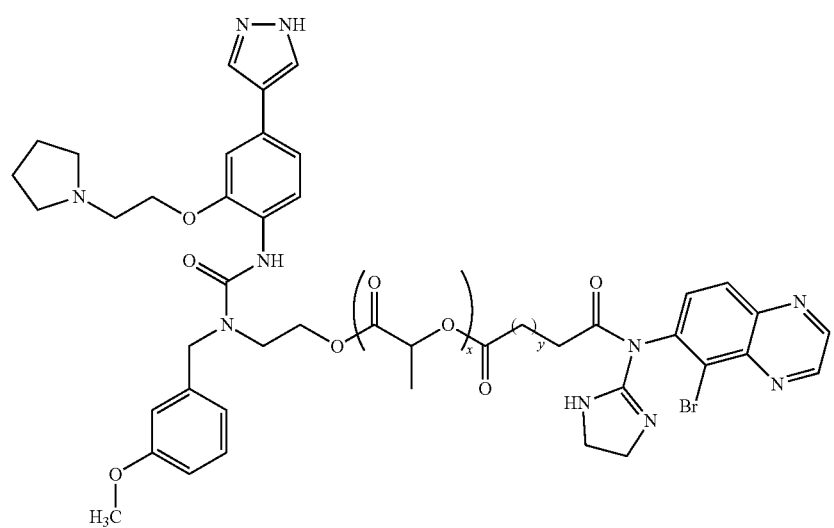
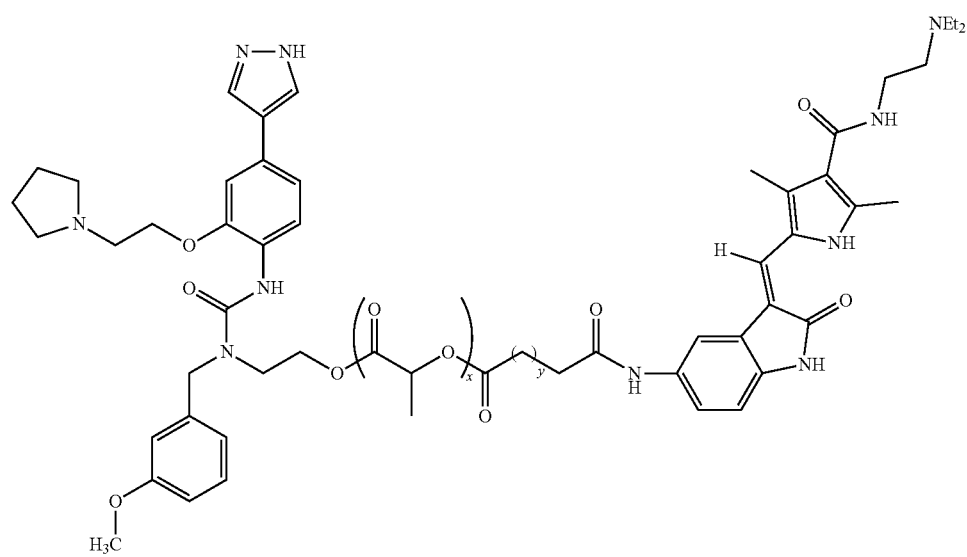

699
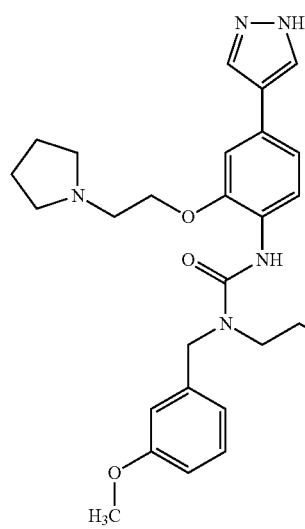
700
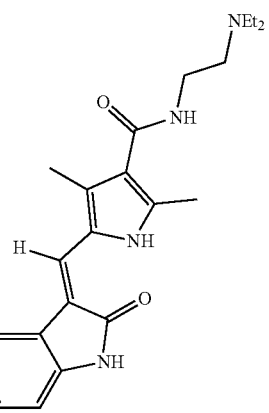
Example 43. Non-Limiting Examples of Compounds of Formula XVII
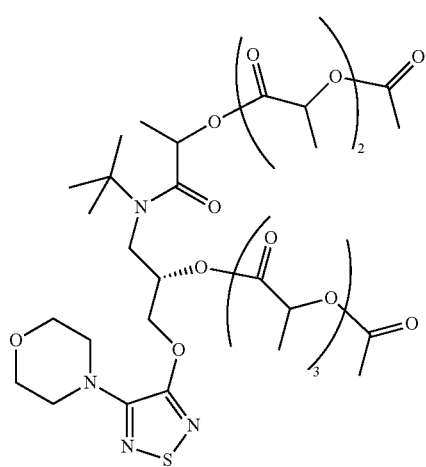
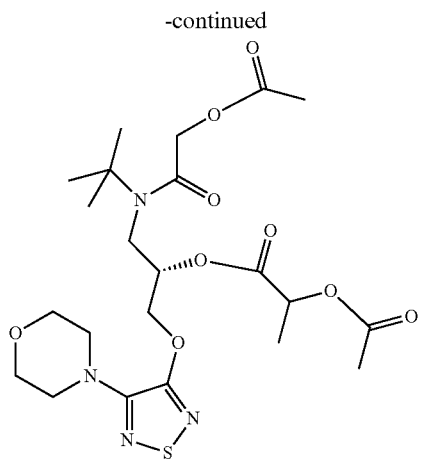
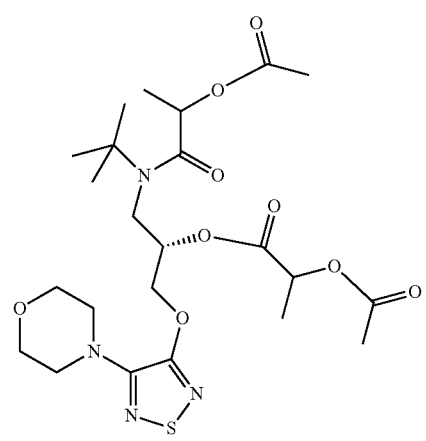
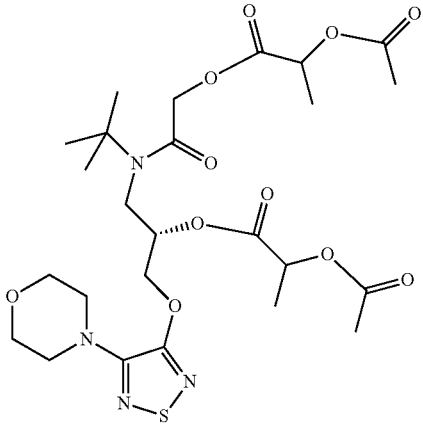

701
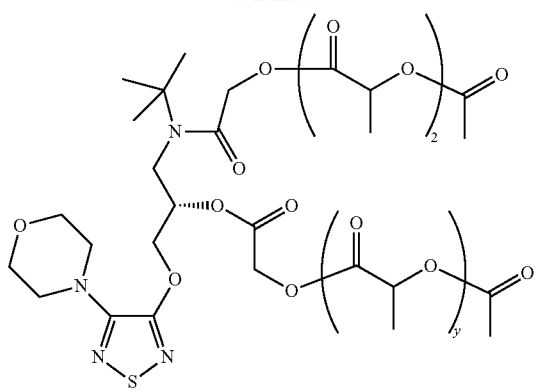
702
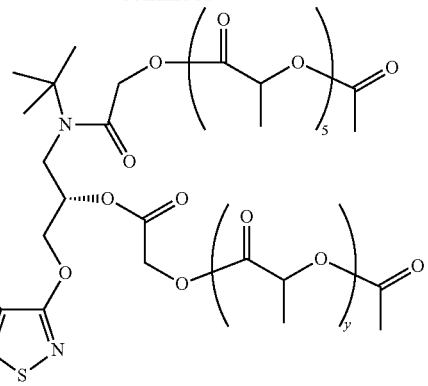
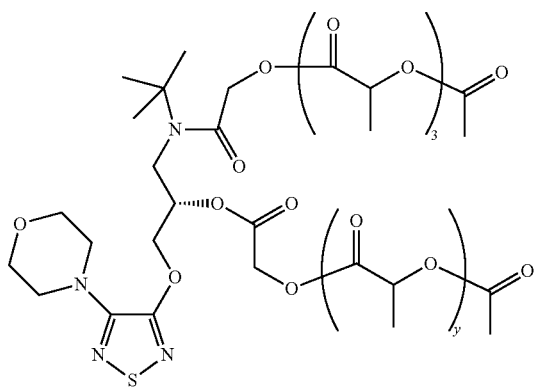
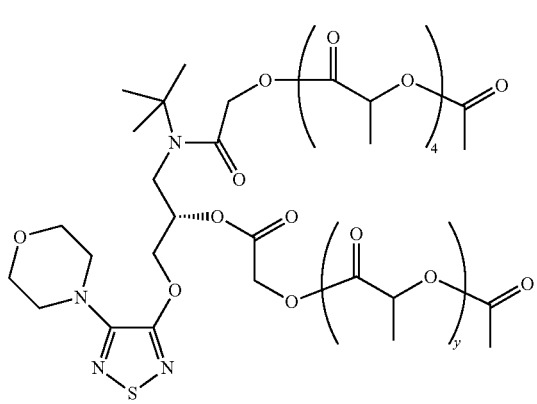
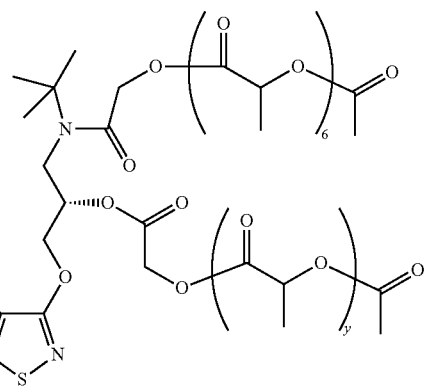

Example 44. Non-limiting Examples of Compounds of Formula XV'
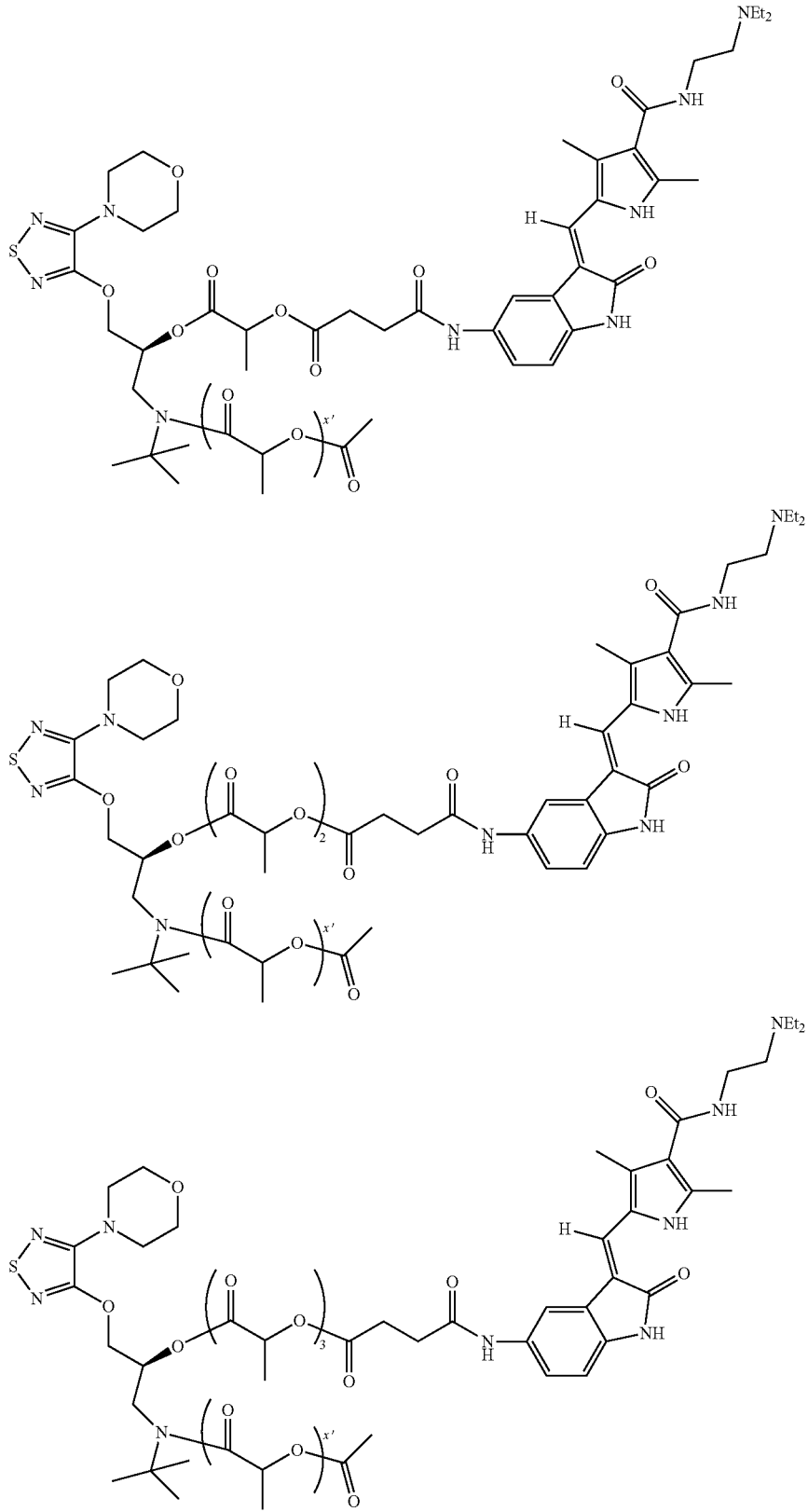

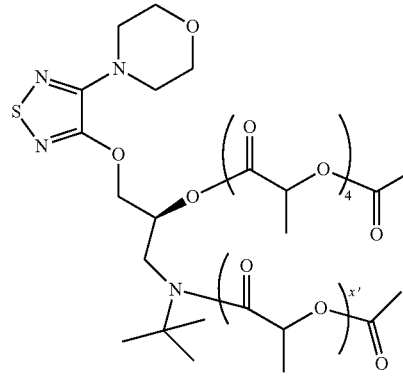
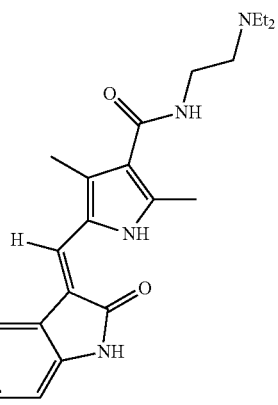
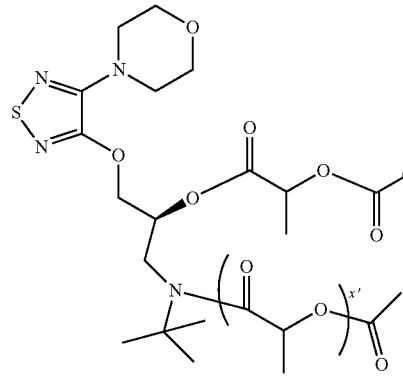
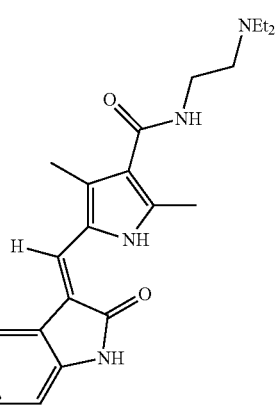
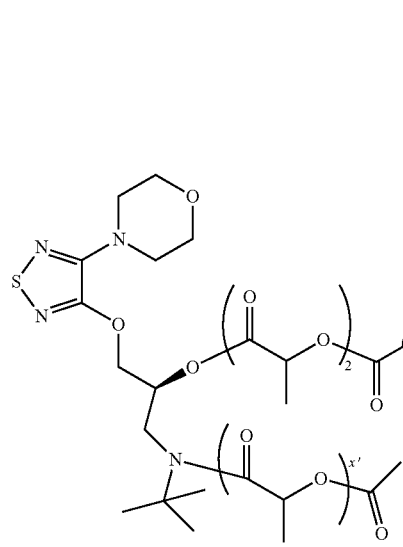
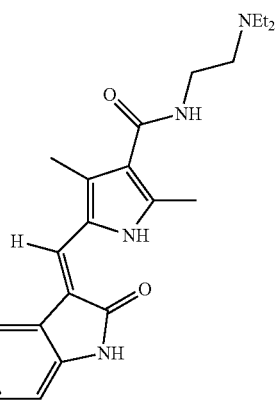

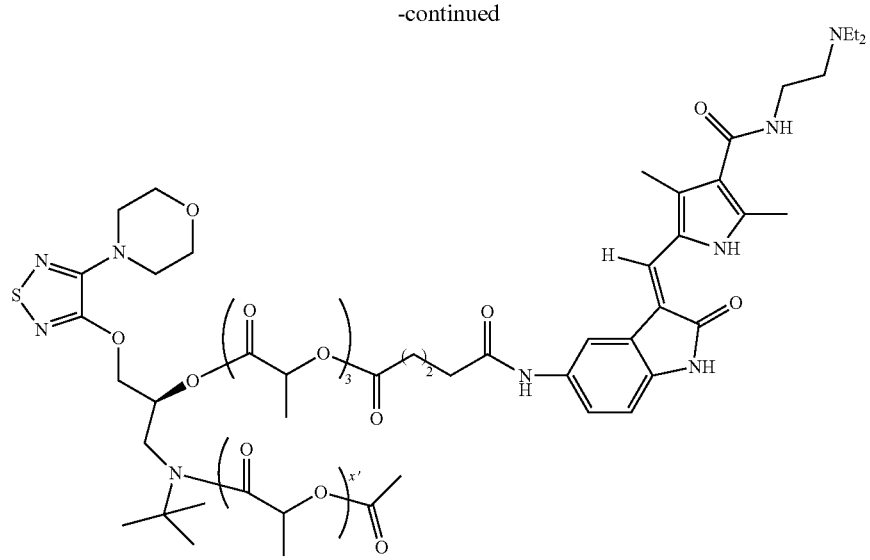
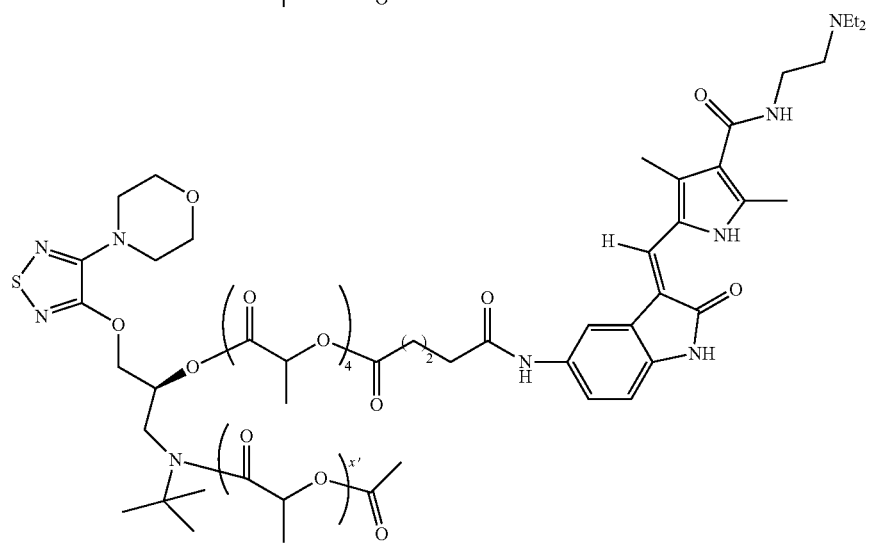
Example 45. Non-Limiting Examples of Compounds of Formula LIV
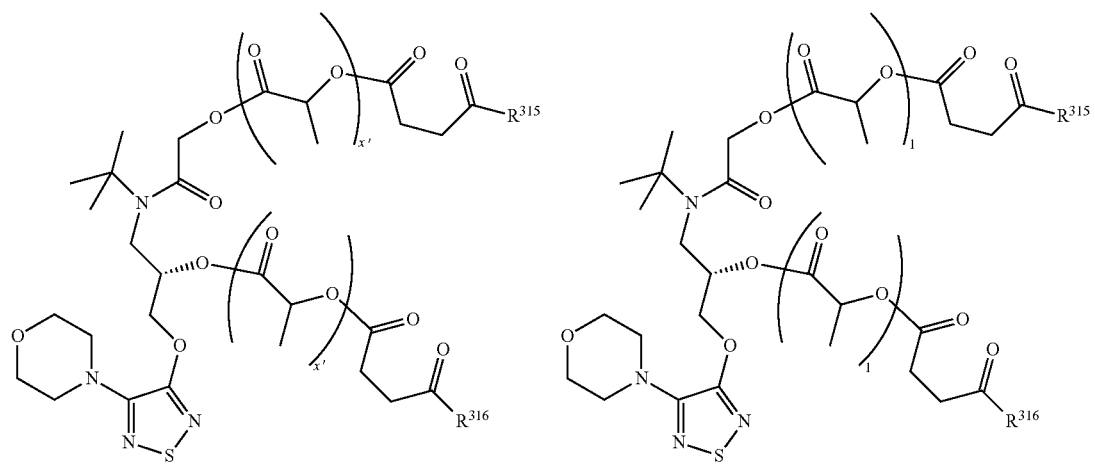

709                                710
-continued
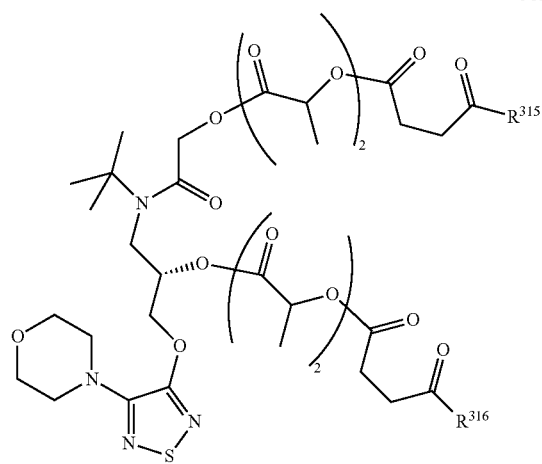 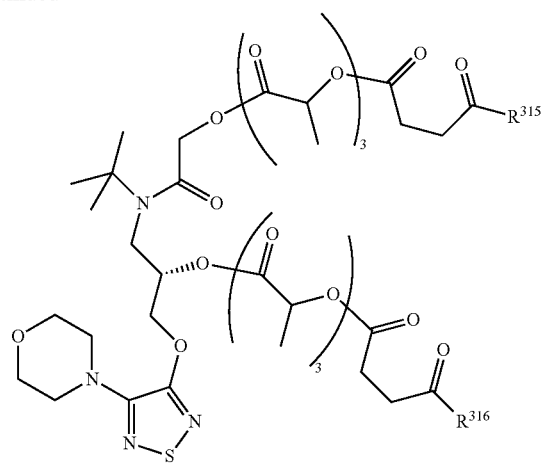
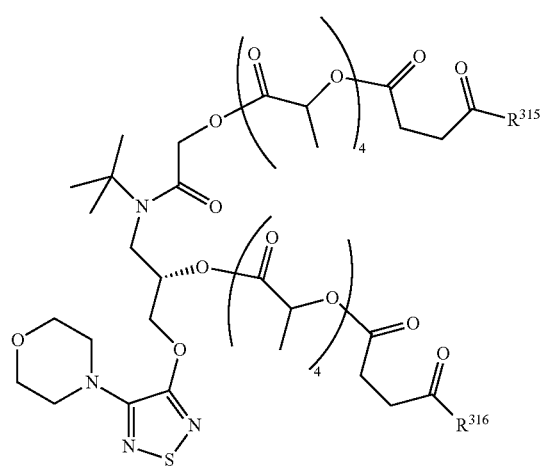 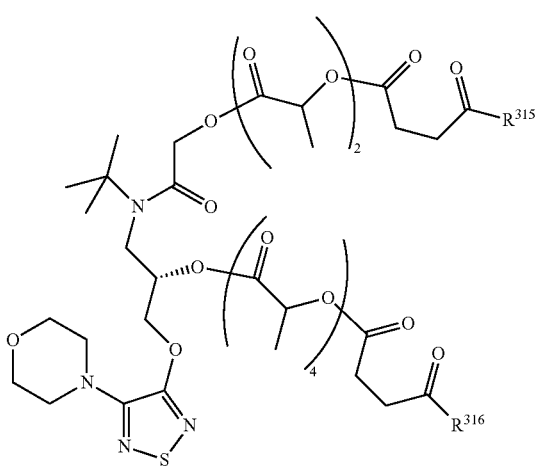
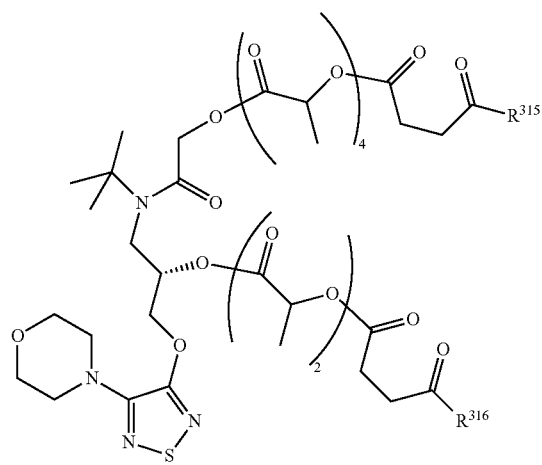 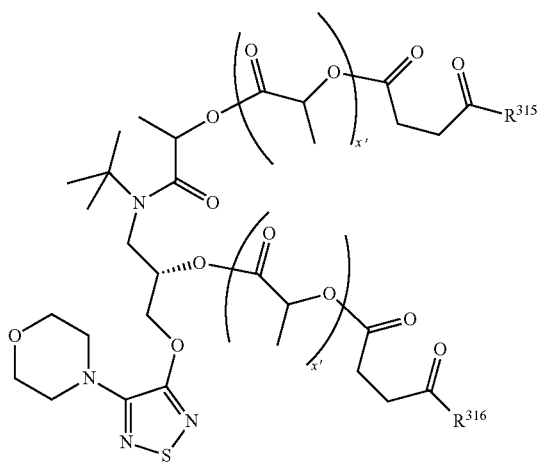

711
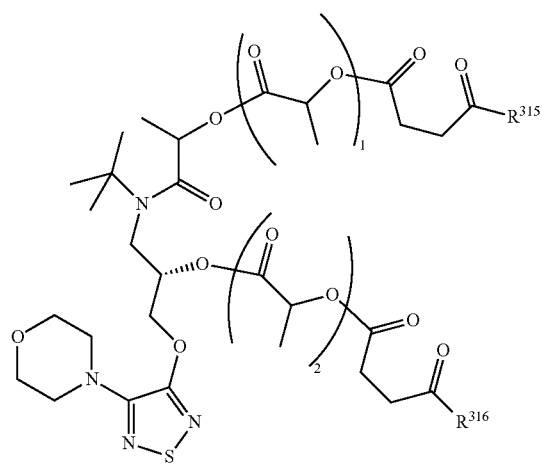
712
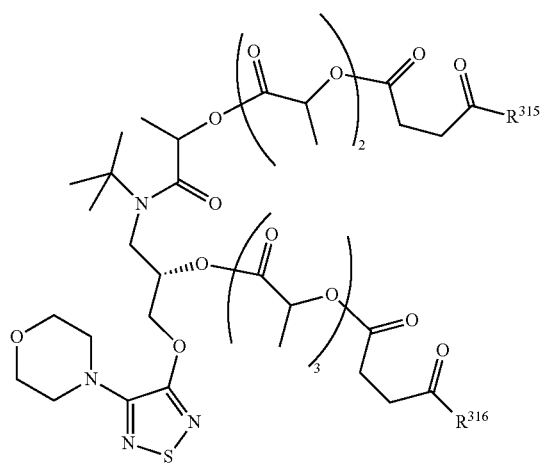
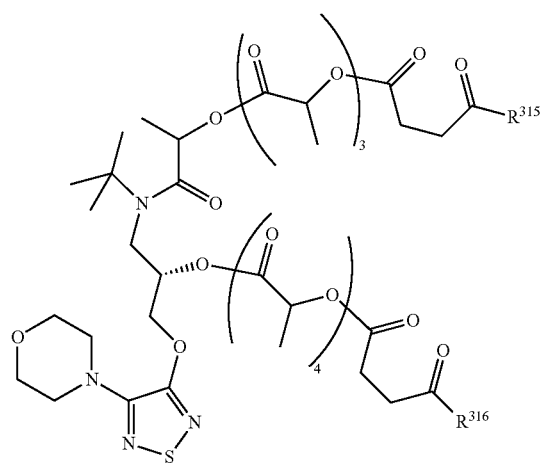
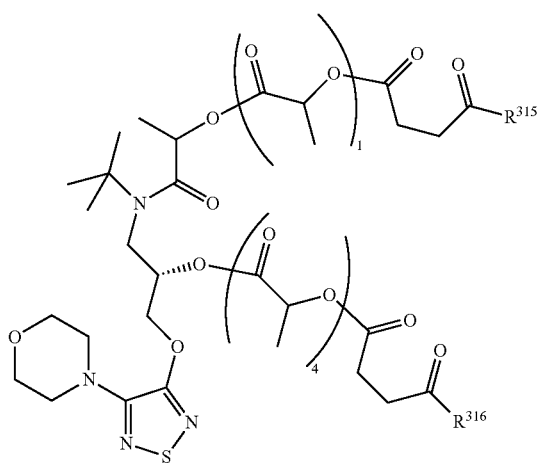
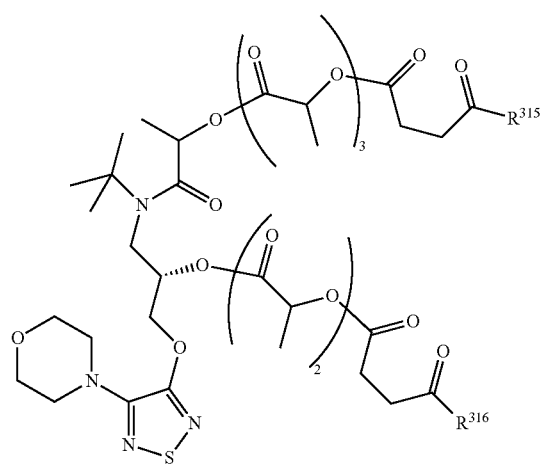

-continued
713
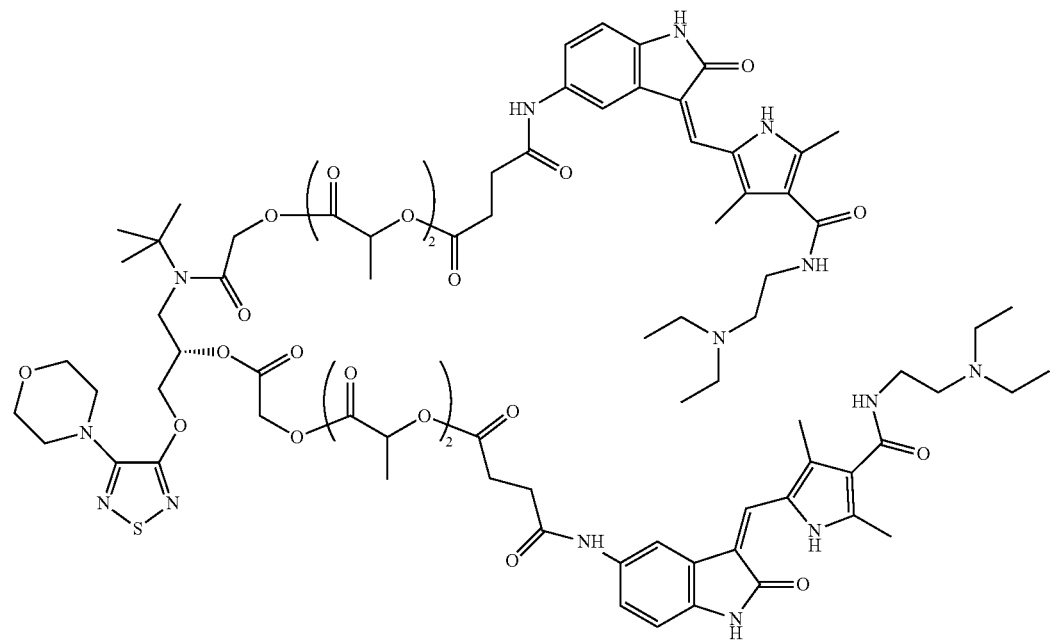
714
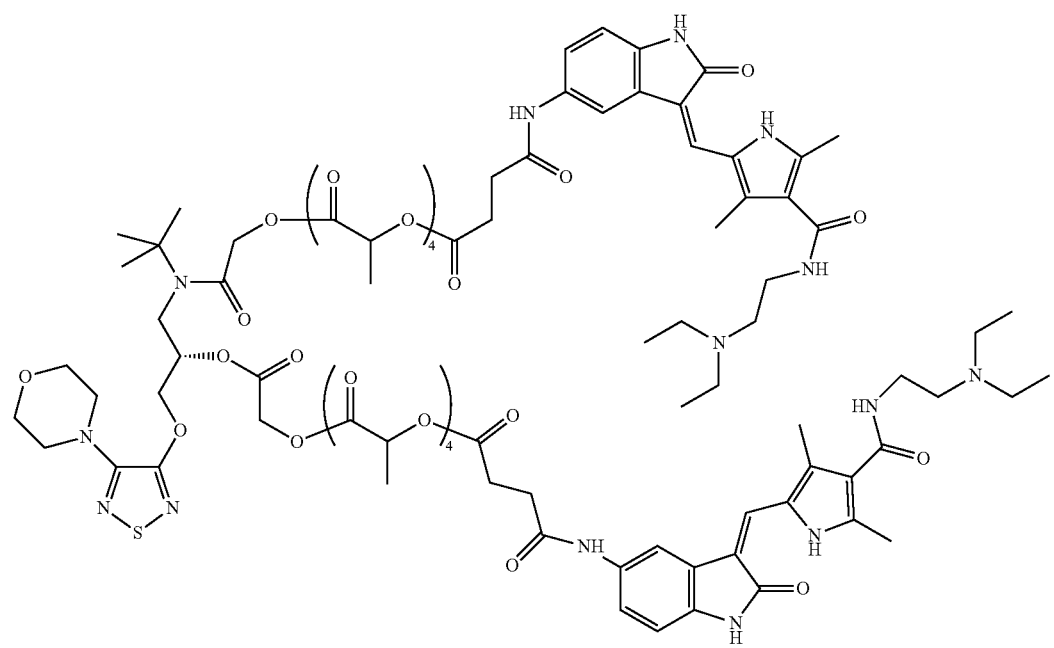

715
-continued
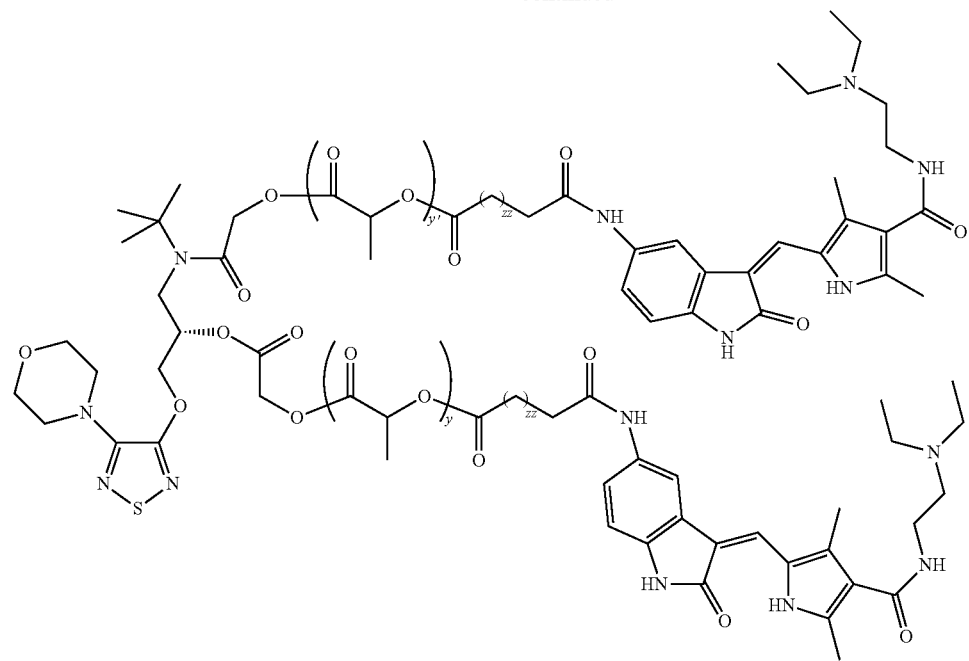
716
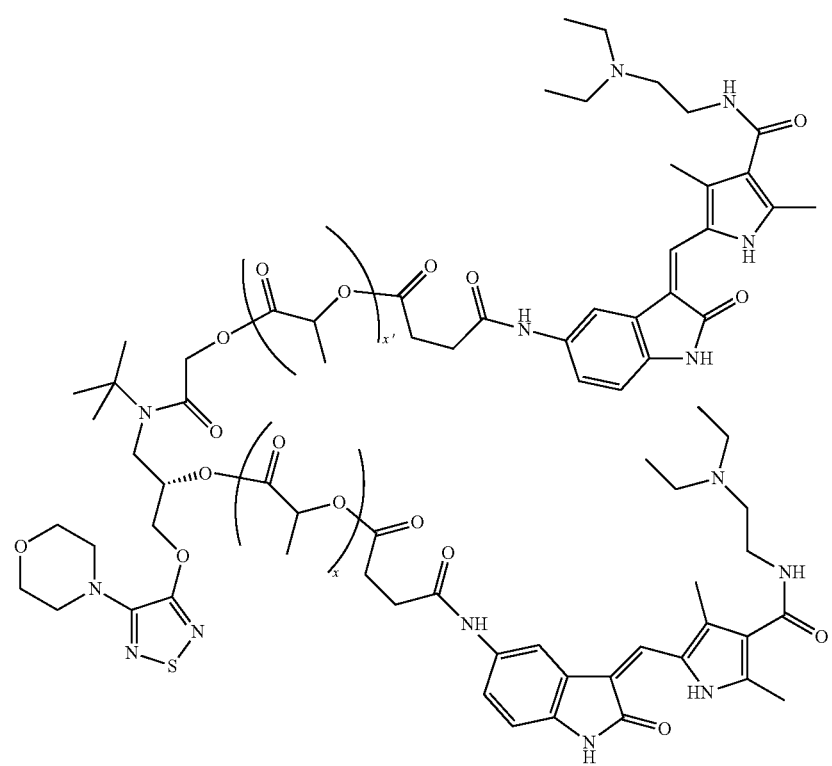

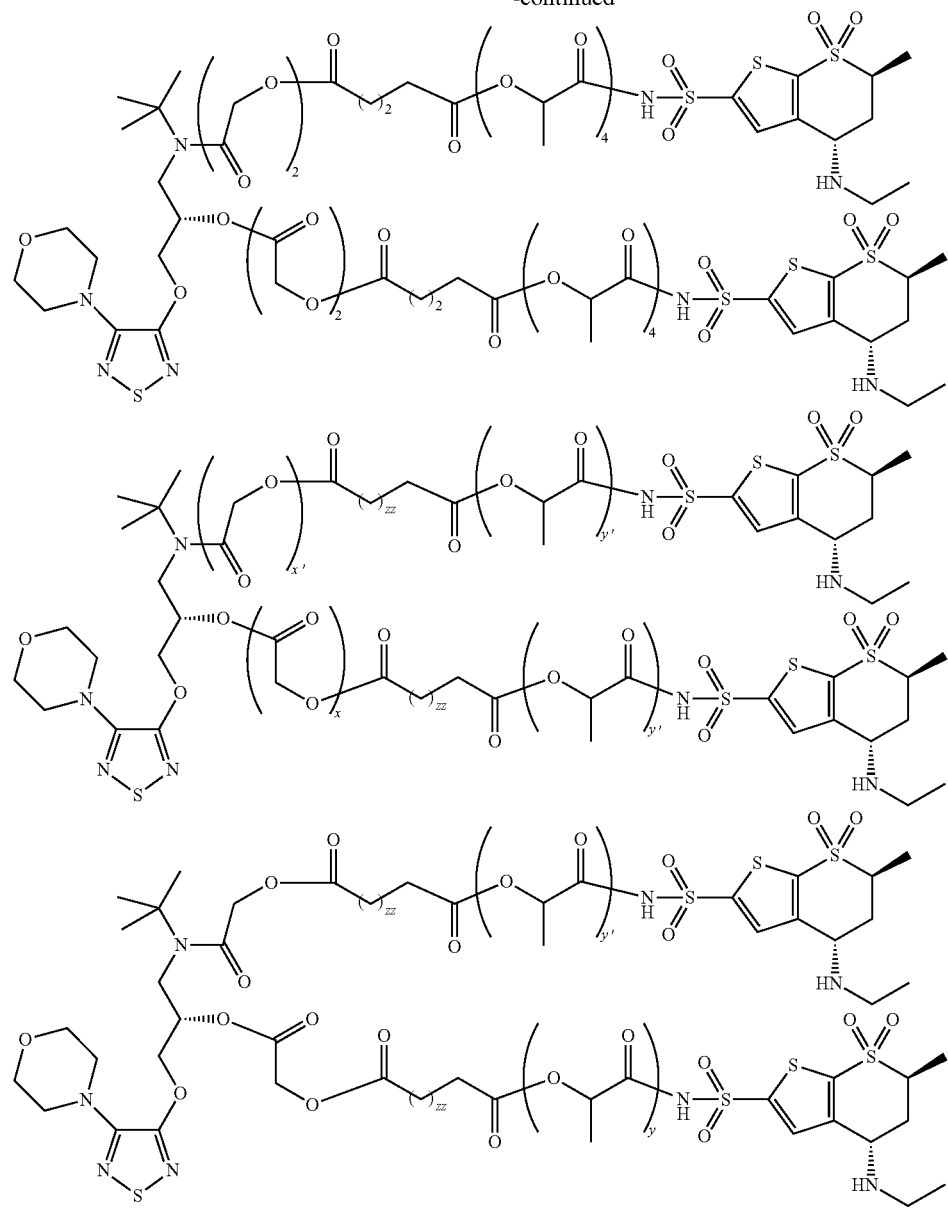
Example 46. Non-Limiting Examples of Compounds of Formula VIII', IX, IX' and IX"
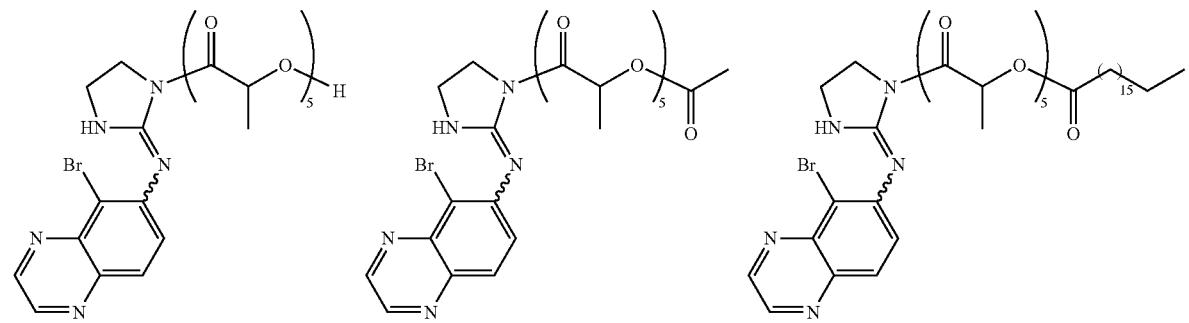

719
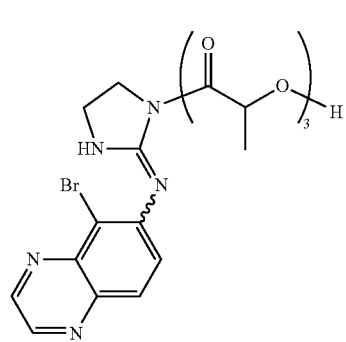
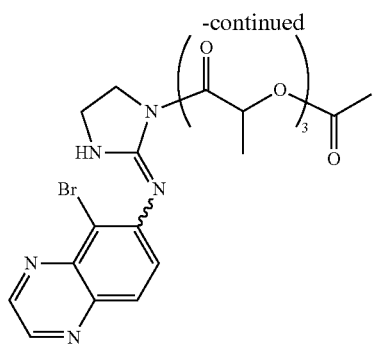
-continued
720
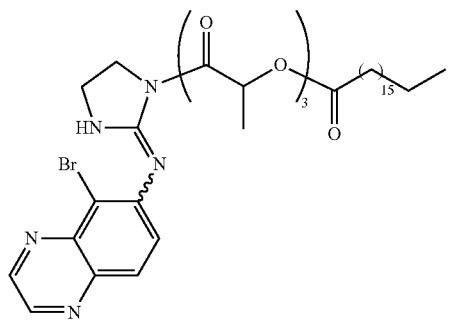
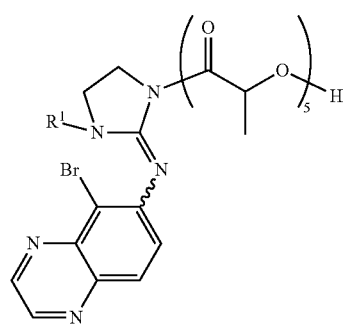
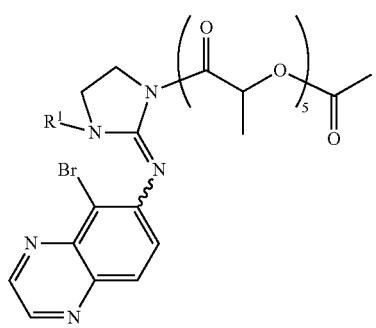
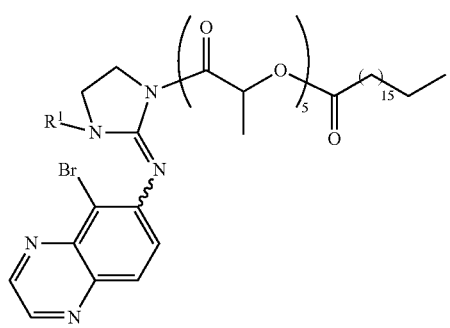
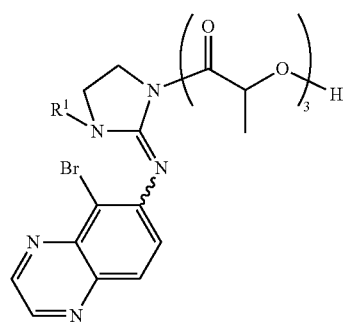
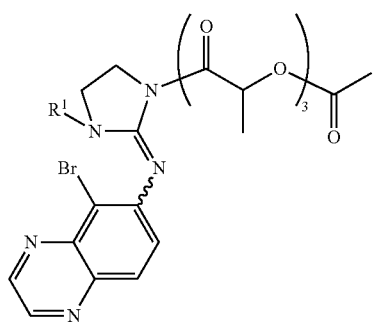
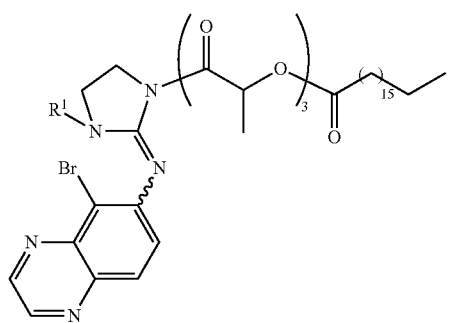
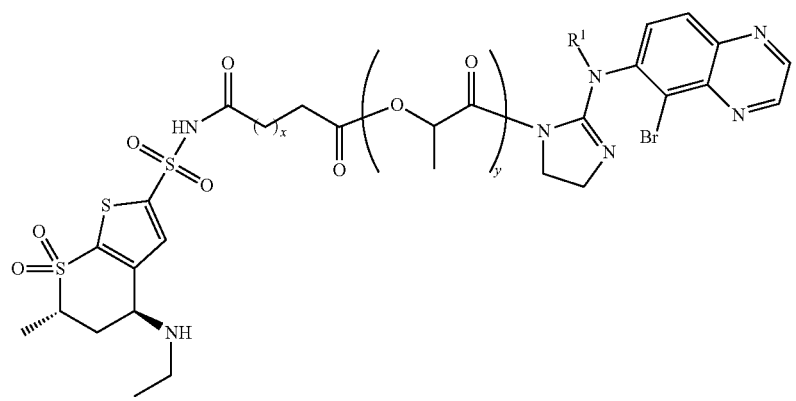

-continued
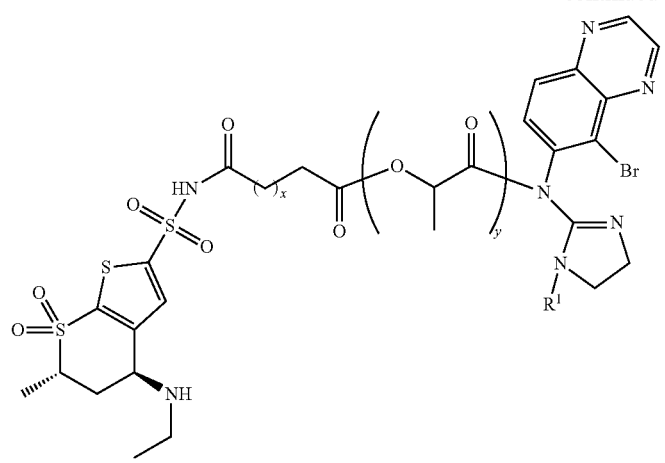
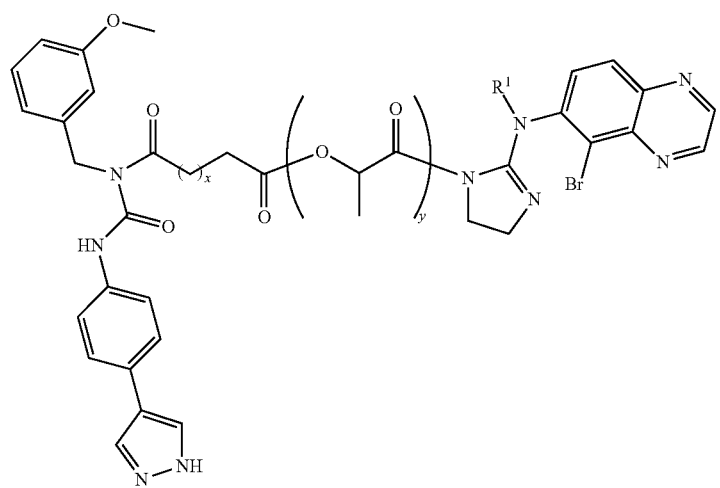
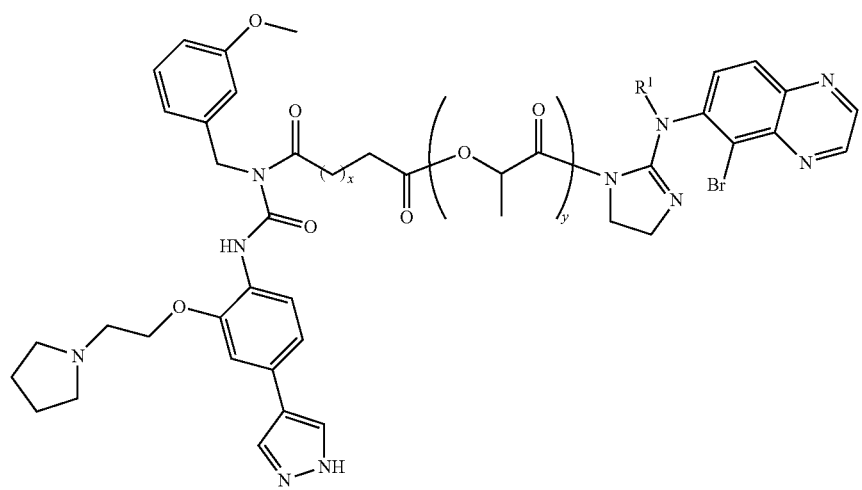

-continued
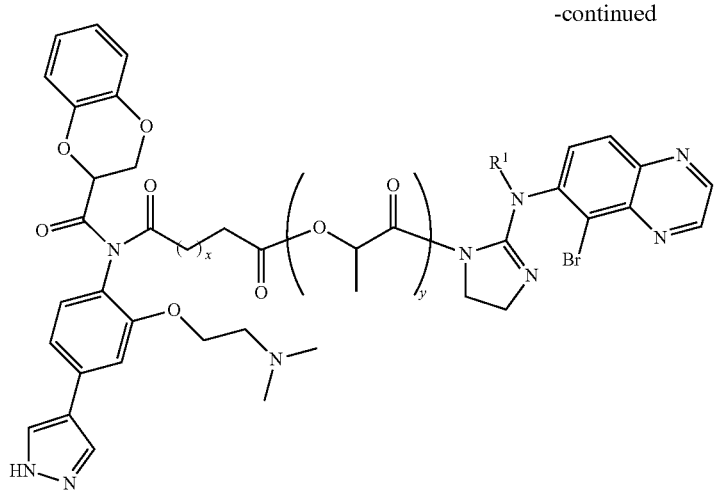
Example 47. Non-Limiting Examples of Compounds of Formula XI
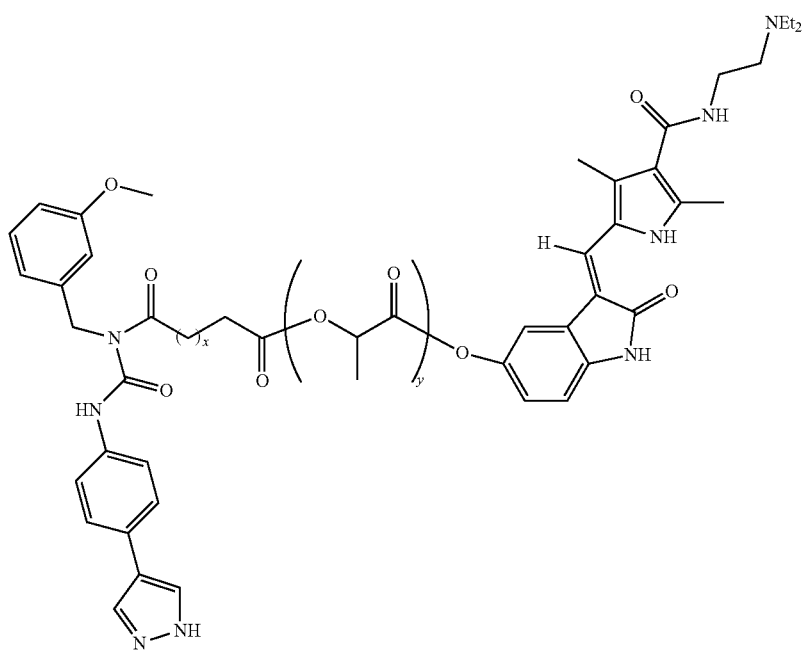

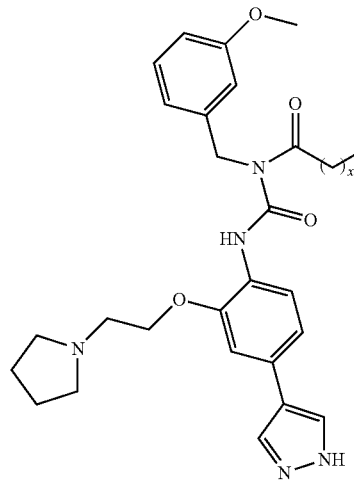
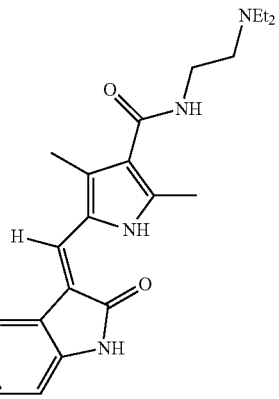
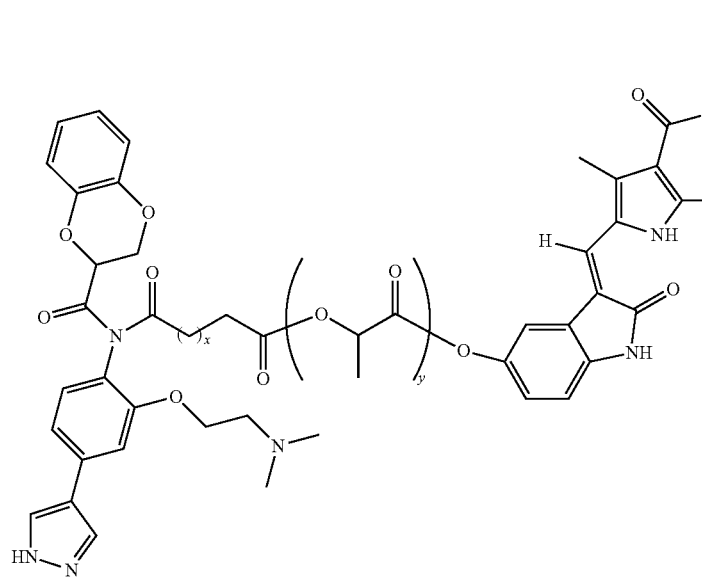
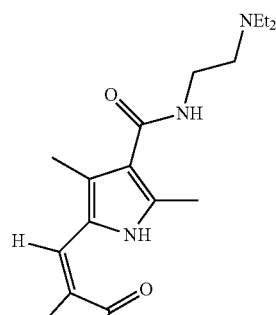

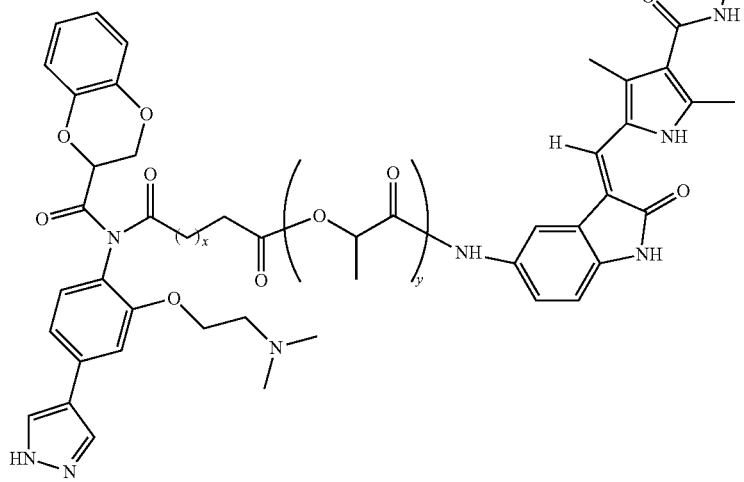
Example 48. Non-Limiting Examples of Compounds of Formula LIII
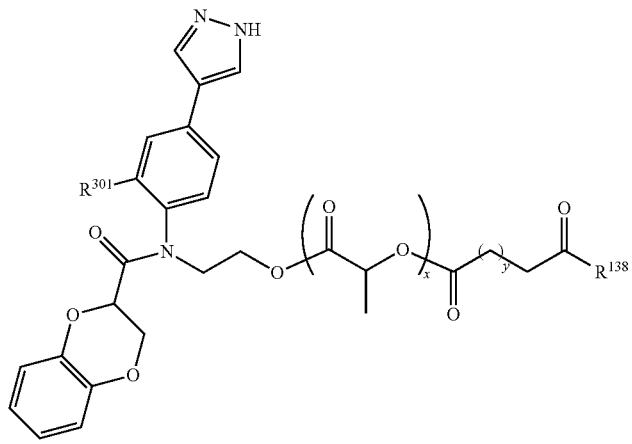
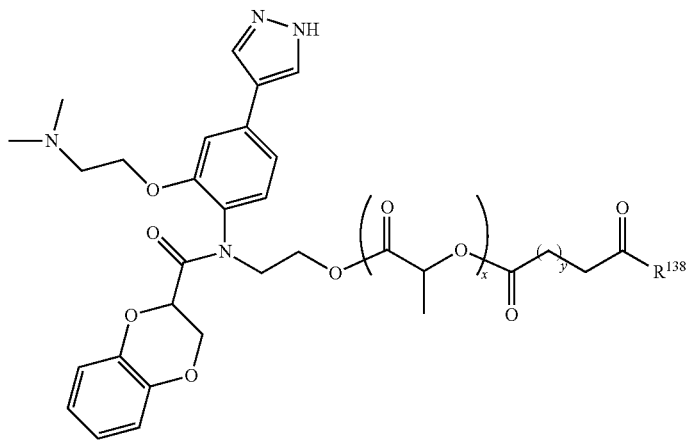

-continued
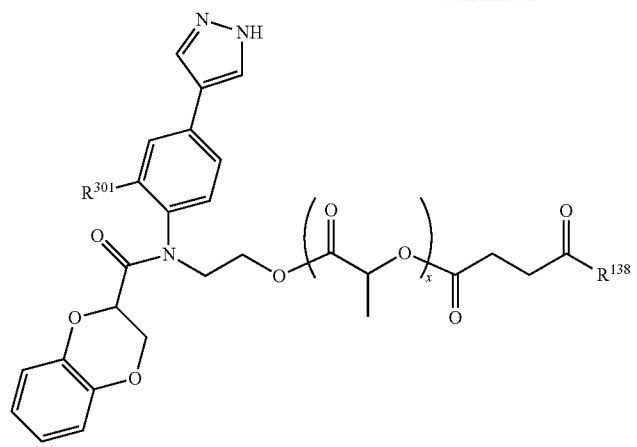
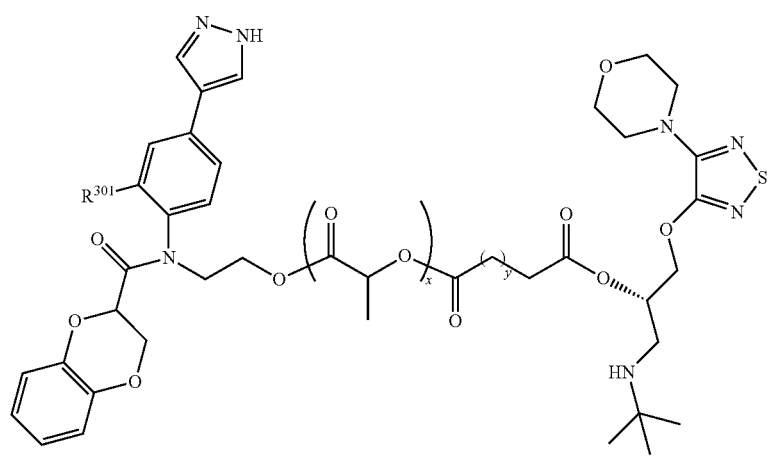
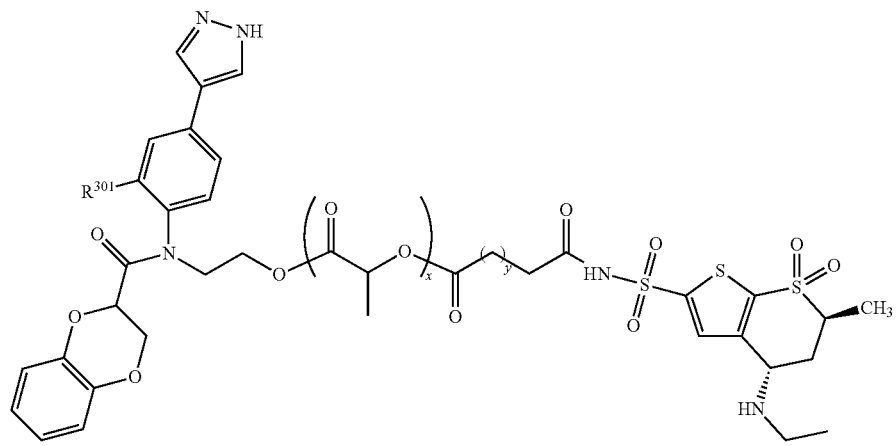

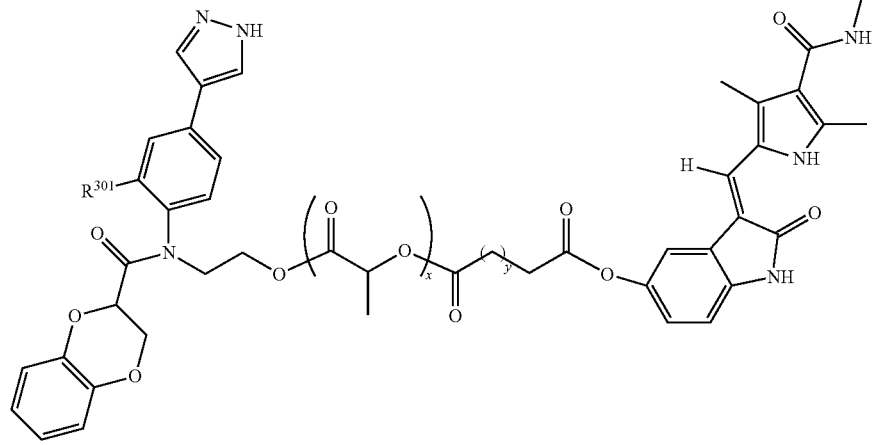
Example 49. Non-Limiting Examples of Compounds of the Present Invention
Table 8A, Table 8B, Table 8C, Table 8D, Table 8E present illustrative compounds of the present invention. Table 8F presents characterization data for select compounds of the present invention.
TABLE 8A
Non-limiting Examples of compounds of Formula II, VII, IX, XI, XIV, XV, and XVII
12-3
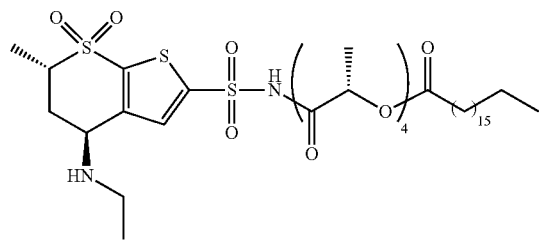
13-2
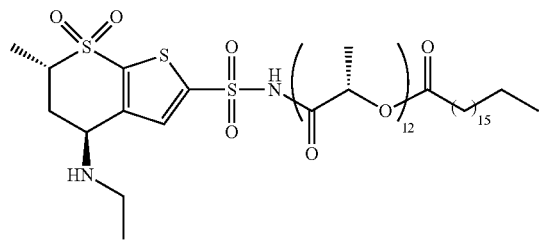
14-2
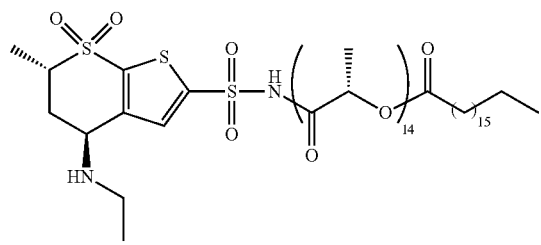

TABLE 8A-continued
Non-limiting Examples of compounds of Formula II, VII, IX, XI, XIV, XV, and XVII
15-2 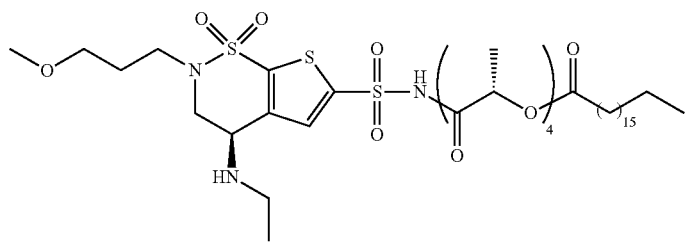
16-1 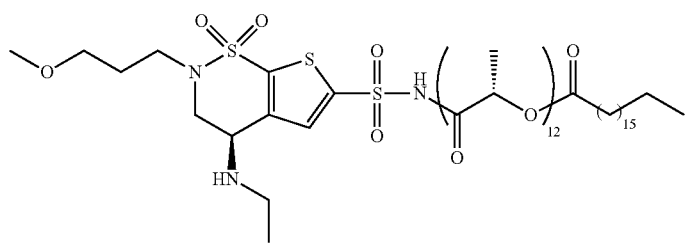
17-1 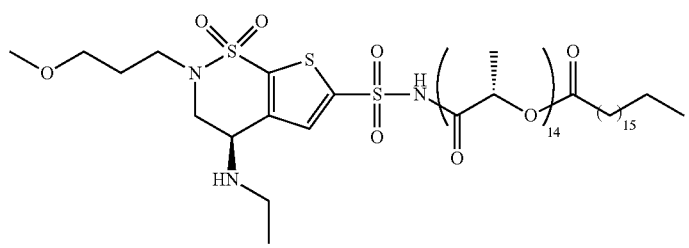
18-3 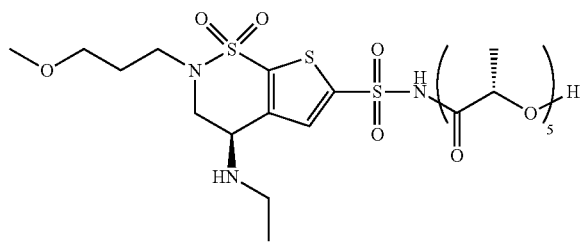
19-3 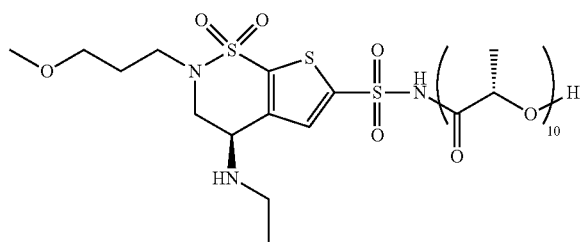
20-3 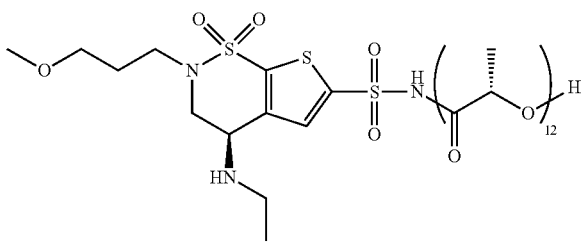

US 11,548,861 B2
TABLE 8A-continued
Non-limiting Examples of compounds of Formula II, VII, IX, XI, XIV, XV, and XVII
21-3 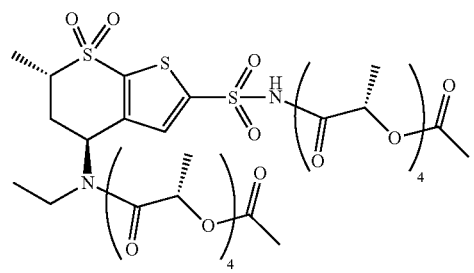
22-3 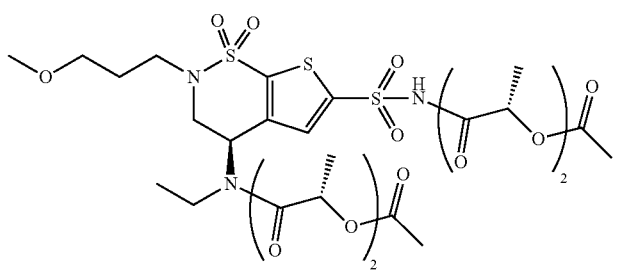
23-3 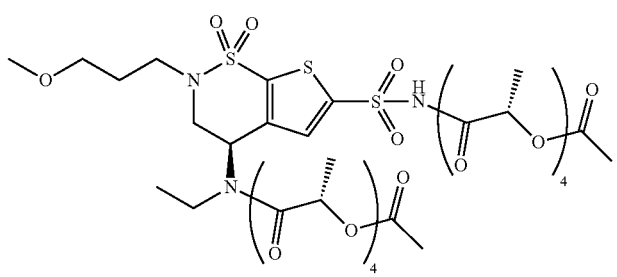
25-2 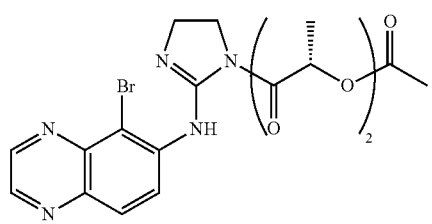
26-2 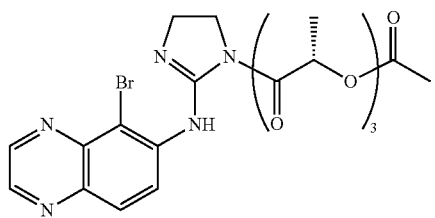
27-2 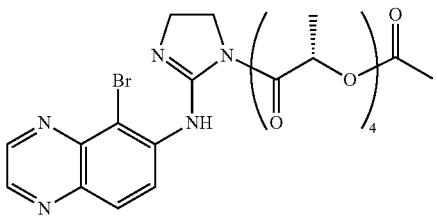

TABLE 8A-continued
Non-limiting Examples of compounds of Formula II, VII, IX, XI, XIV, XV, and XVII
28-2
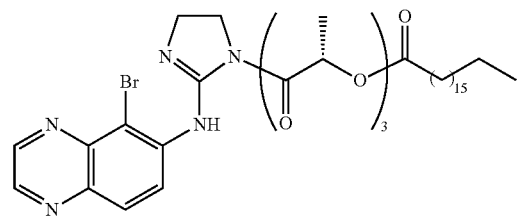
29-2
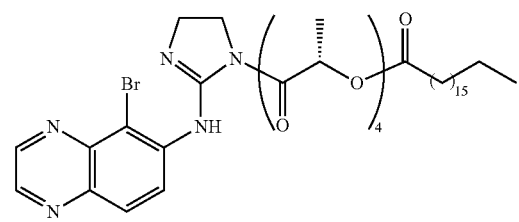
30-3
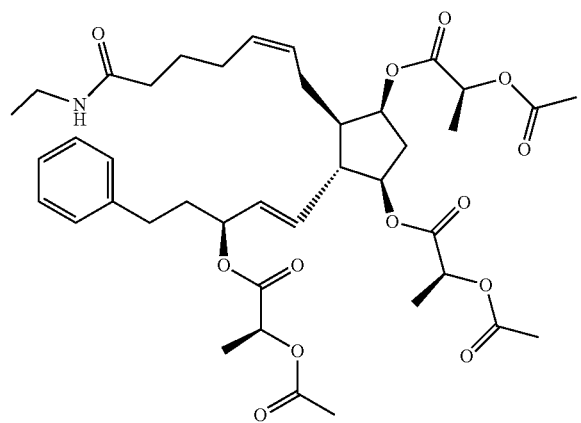 [SMILES: CCNC(=O)CCC/C=C\C[C@@H]1[C@@H](/C=C/[C@H](CCc2ccccc2)OC(=O)[C@H](C)OC(C)=O)[C@H](OC(=O)[C@H](C)OC(C)=O)C[C@@H]1OC(=O)[C@H](C)OC(C)=O]
31-2
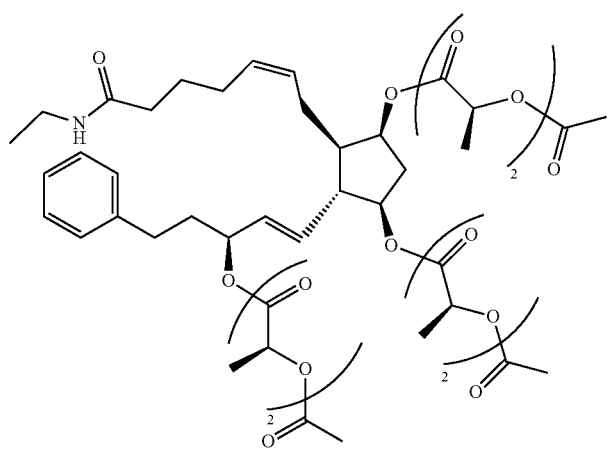

TABLE 8A-continued
Non-limiting Examples of compounds of Formula II, VII, IX, XI, XIV, XV, and XVII
32-2
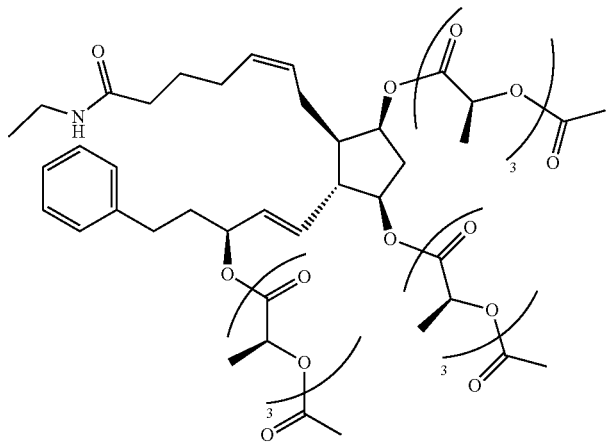
33-2
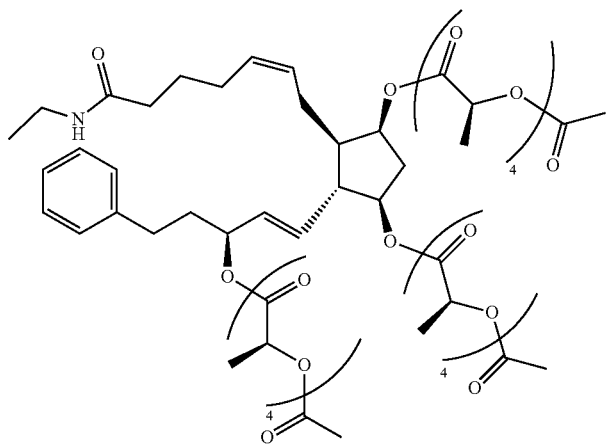
34-2
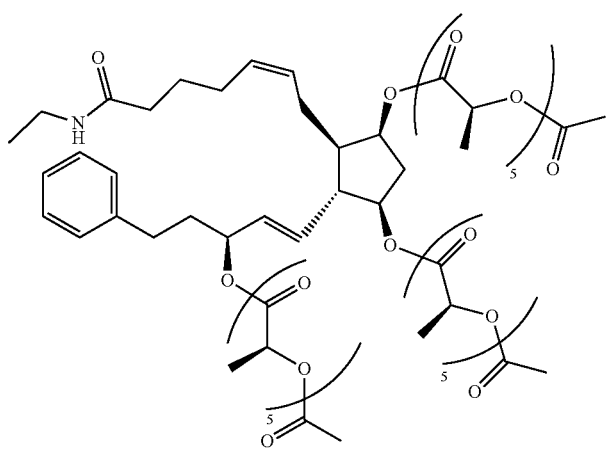

TABLE 8A-continued
Non-limiting Examples of compounds of Formula II, VII, IX, XI, XIV, XV, and XVII
35-4
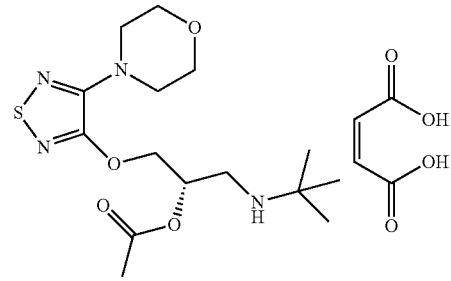
36-2
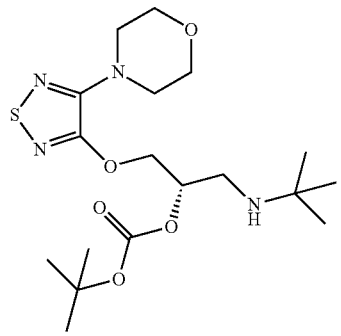 [SMILES: CC(C)(C)NC[C@@H](COc1nsnc1N1CCOCC1)OC(=O)OC(C)(C)C]
37-2
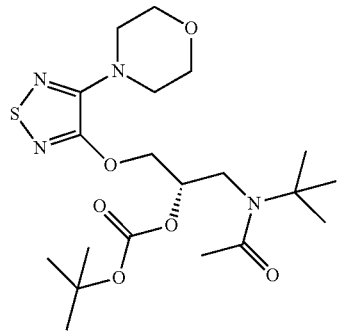 [SMILES: CC(=O)N(C[C@@H](COc1nsnc1N1CCOCC1)OC(=O)OC(C)(C)C)C(C)(C)C]
38-2
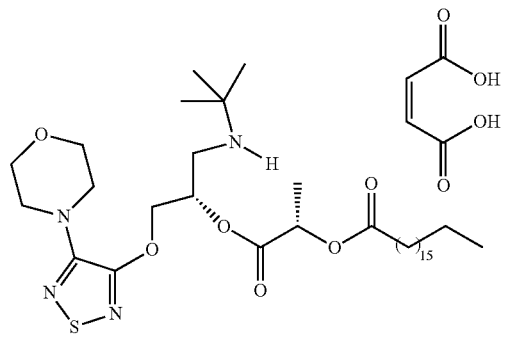
39-1
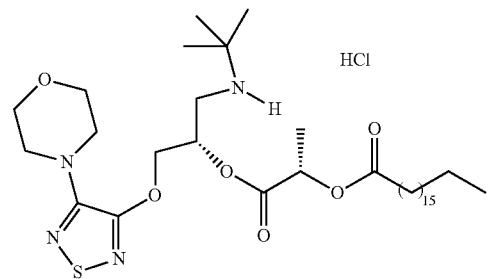

TABLE 8A-continued
Non-limiting Examples of compounds of Formula II, VII, IX, XI, XIV, XV, and XVII
40-2
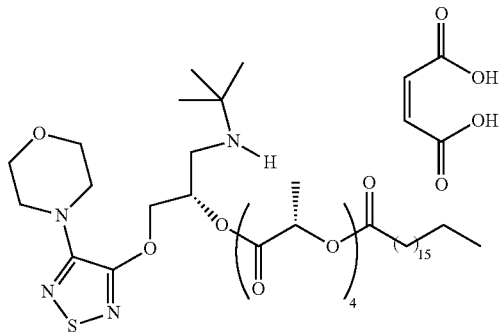
41-2
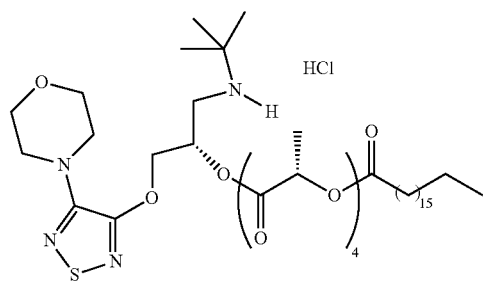
42-2
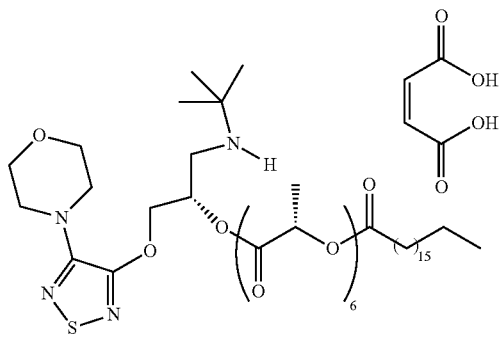
43-1
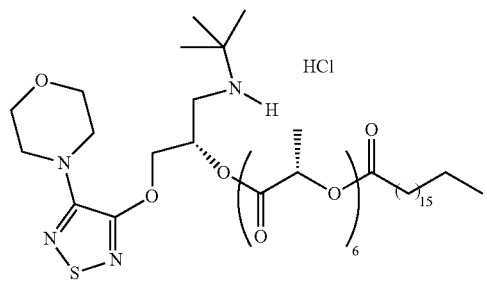

TABLE 8A-continued
Non-limiting Examples of compounds of Formula II, VII, IX, XI, XIV, XV, and XVII
44-2
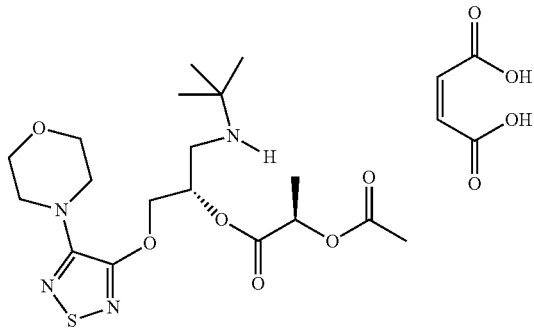 [SMILES: CC(=O)O[C@H](C)C(=O)O[C@@H](CNC(C)(C)C)COc1nsnc1N1CCOCC1 ; O=C(O)/C=C\C(=O)O]
45-2
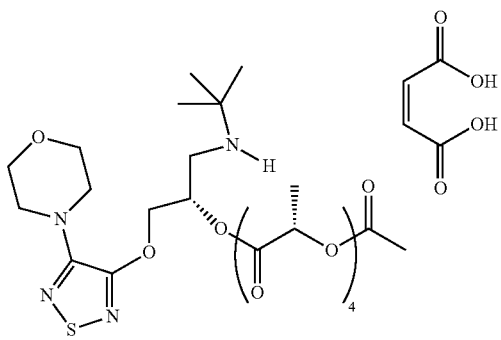
46-4
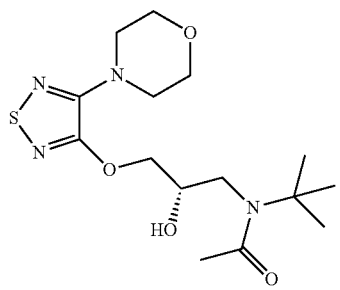 [SMILES: CC(=O)N(C[C@H](O)COc1nsnc1N1CCOCC1)C(C)(C)C]
47-1
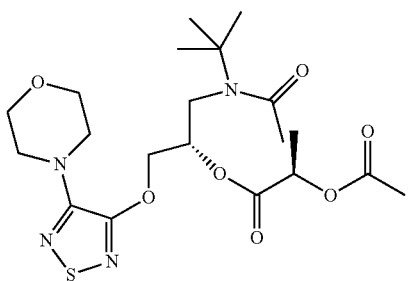 [SMILES: CC(=O)O[C@H](C)C(=O)O[C@H](COc1nsnc1N1CCOCC1)CN(C(C)=O)C(C)(C)C]
48-1
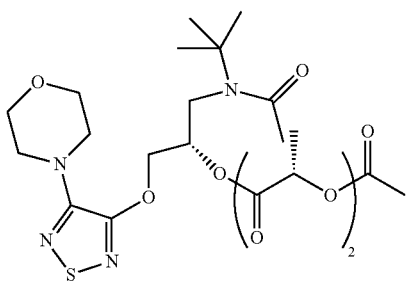

TABLE 8A-continued
Non-limiting Examples of compounds of Formula II, VII, IX, XI, XIV, XV, and XVII
49-1
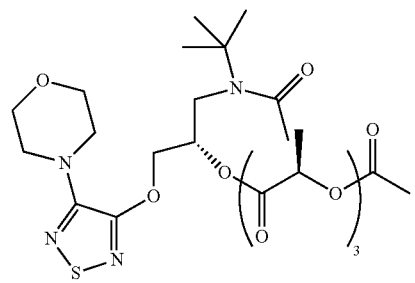
50-1
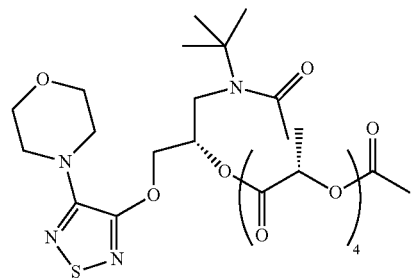
51-1
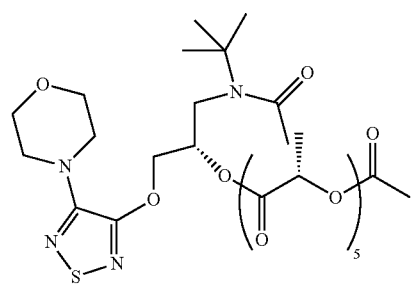
52-2
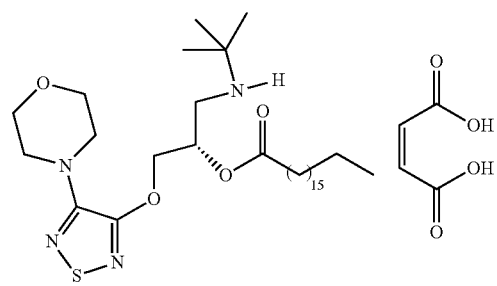

TABLE 8A-continued
Non-limiting Examples of compounds of Formula II, VII, IX, XI, XIV, XV, and XVII
53-3
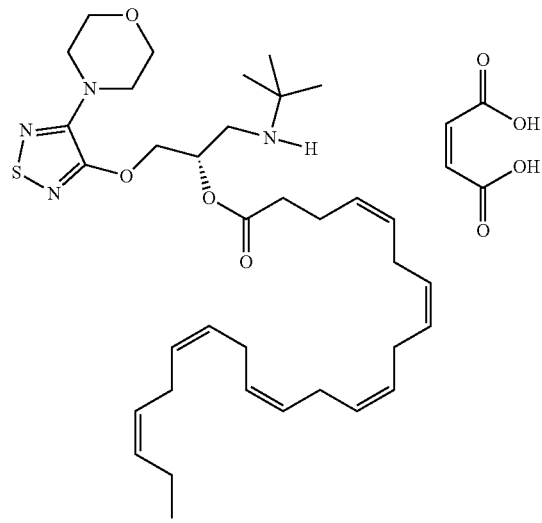 [SMILES: CC/C=C\C/C=C\C/C=C\C/C=C\C/C=C\C/C=C\CCC(=O)O[C@@H](CNC(C)(C)C)COc1nsnc1N1CCOCC1 ; O=C(O)/C=C\C(=O)O]
54-1
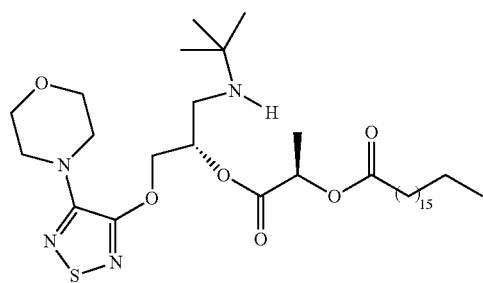
55-2
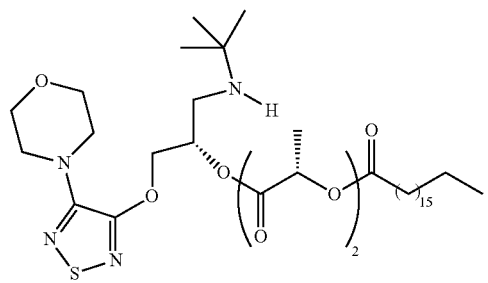
56-1
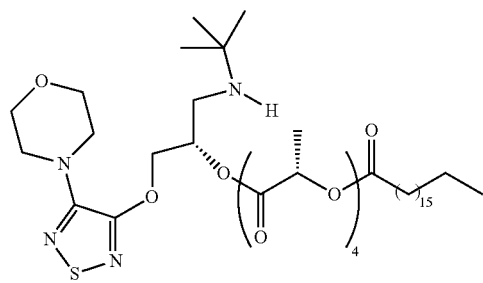

TABLE 8A-continued
Non-limiting Examples of compounds of Formula II, VII, IX, XI, XIV, XV, and XVII
56-2 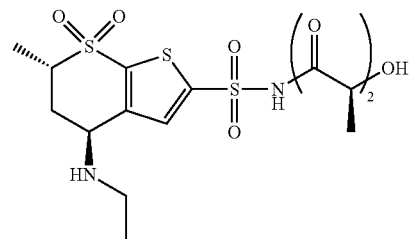
57-4 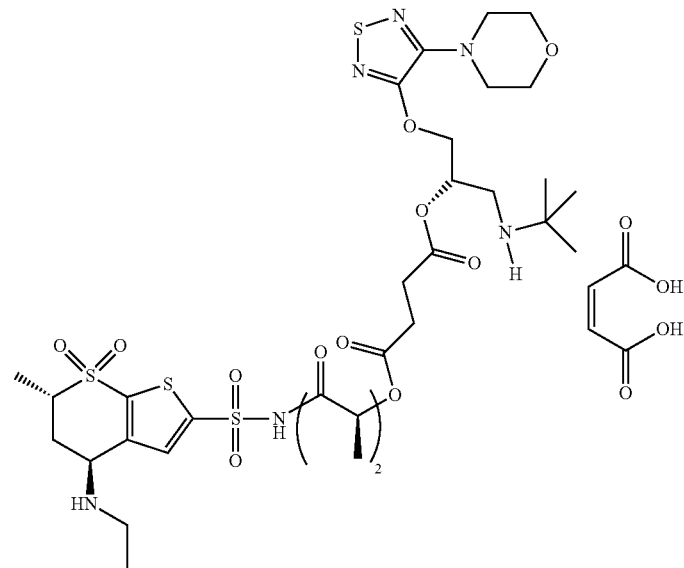
58-3 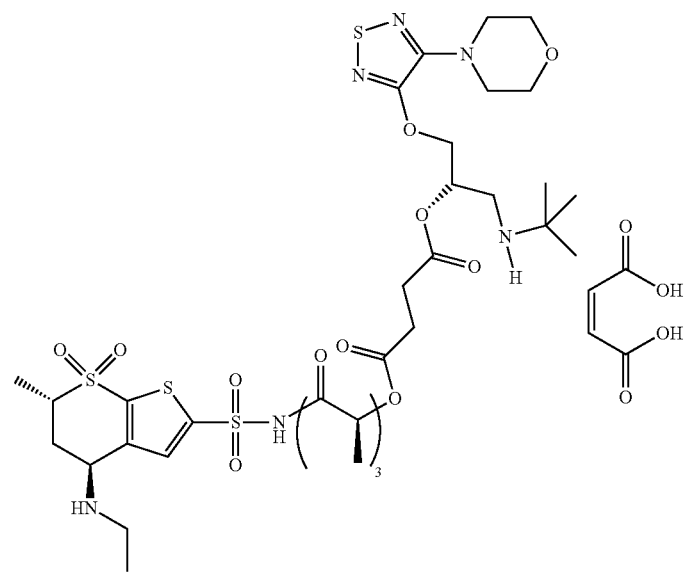

TABLE 8A-continued
Non-limiting Examples of compounds of Formula II, VII, IX, XI, XIV, XV, and XVII
59-3
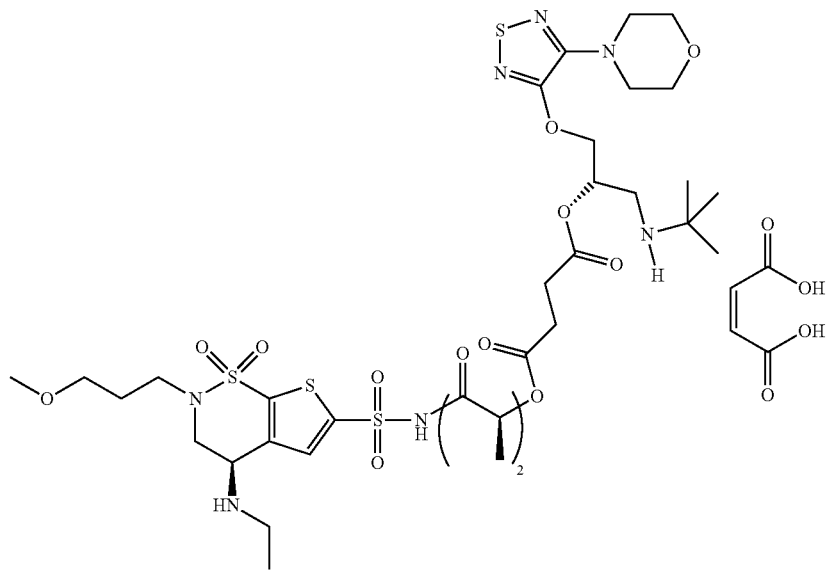
60-3
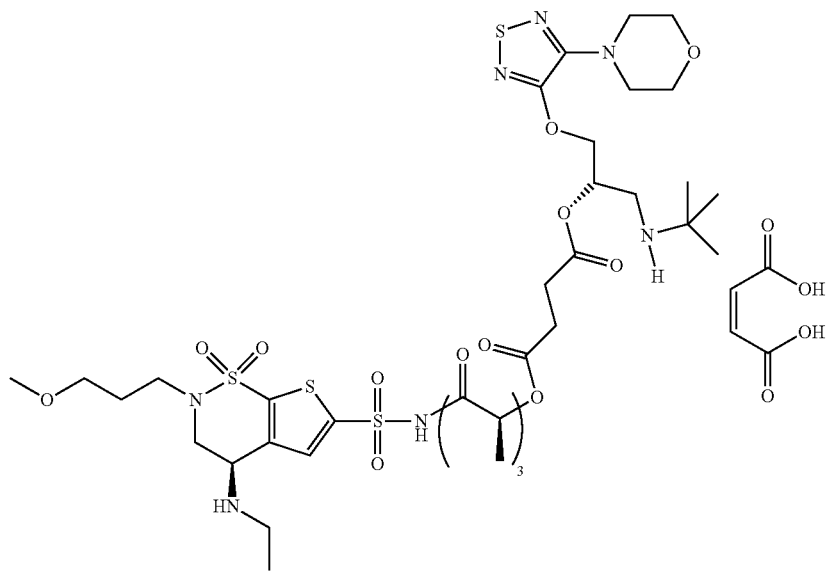
61-3
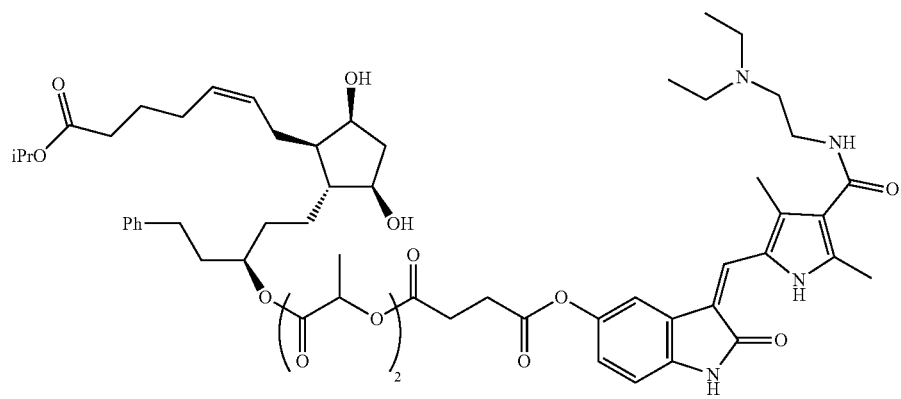

TABLE 8A-continued
Non-limiting Examples of compounds of Formula II, VII, IX, XI, XIV, XV, and XVII
62-6
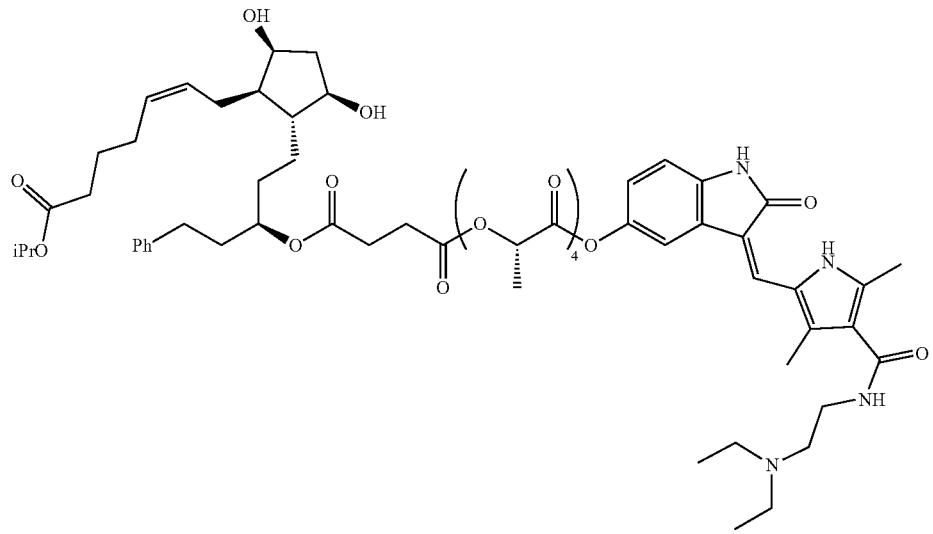
63-1
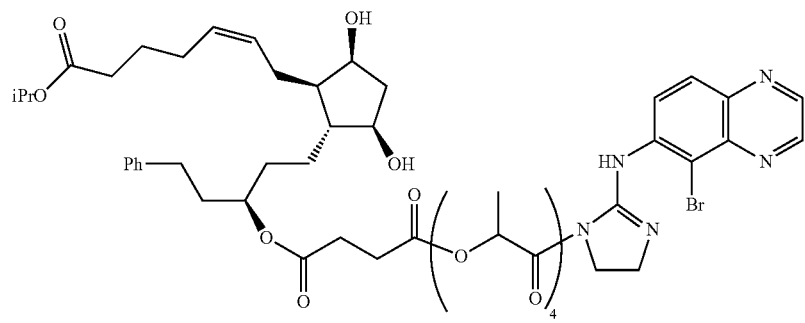
TABLE 8B
Additional Non-limiting Examples of compounds of the Present Invention
57-2
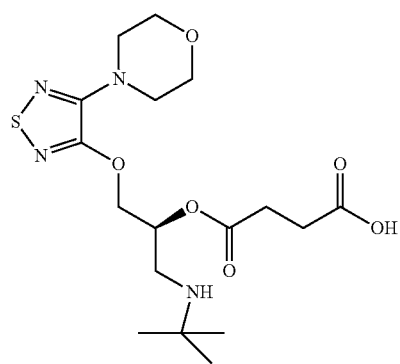 [SMILES: CC(C)(C)NC[C@@H](COc1nsnc1N1CCOCC1)OC(=O)CCC(=O)O]

TABLE 8B-continued
Additional Non-limiting Examples of compounds of the Present Invention
64-4
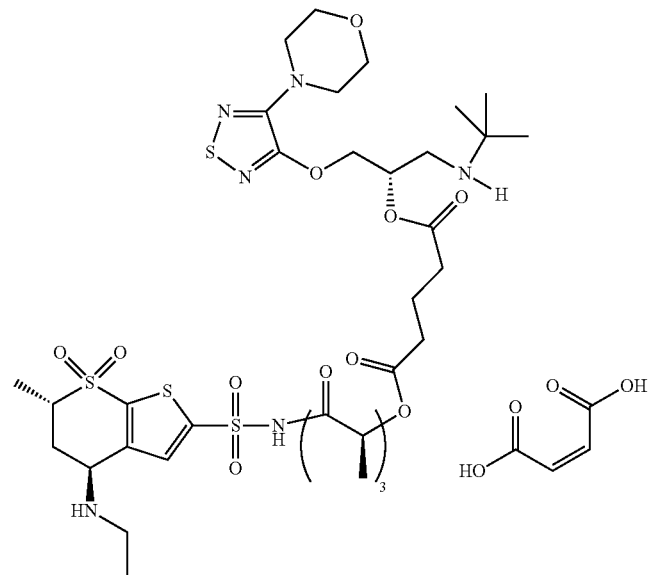
65-1
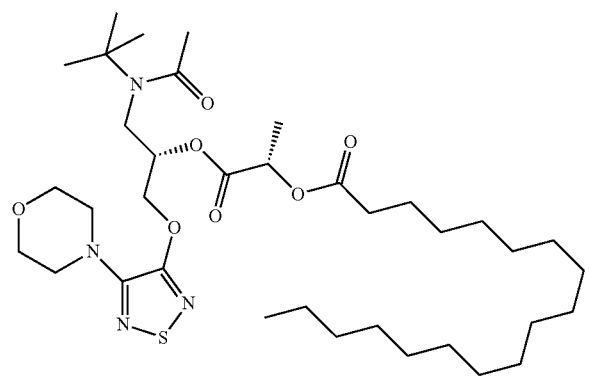 [SMILES: CCCCCCCCCCCCCCCCCC(=O)O[C@@H](C)C(=O)O[C@H](COc1nsnc1N1CCOCC1)CN(C(C)=O)C(C)(C)C]
66-1
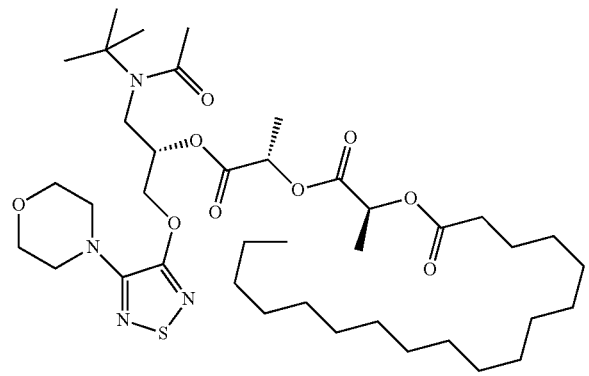 [SMILES: CCCCCCCCCCCCCCCCCC(=O)O[C@@H](C)C(=O)O[C@@H](C)C(=O)O[C@H](COc1nsnc1N1CCOCC1)CN(C(C)=O)C(C)(C)C]

TABLE 8B-continued
Additional Non-limiting Examples of compounds of the Present Invention
67-1
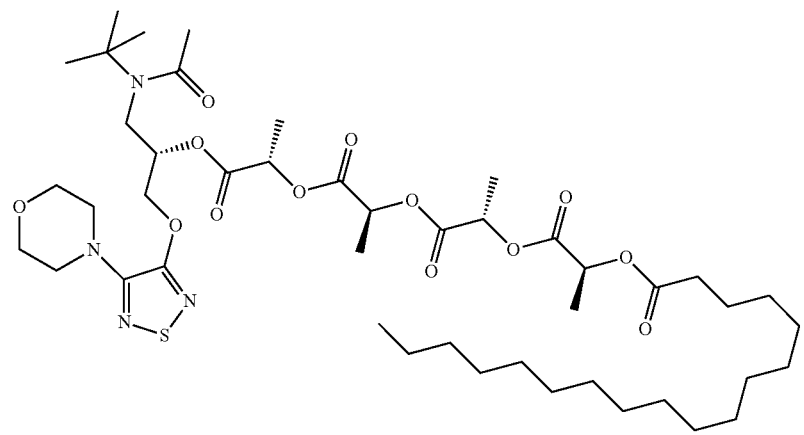 [SMILES: CCCCCCCCCCCCCCCCCC(=O)O[C@@H](C)C(=O)O[C@@H](C)C(=O)O[C@@H](C)C(=O)O[C@@H](C)C(=O)O[C@H](COc1nsnc1N1CCOCC1)CN(C(C)=O)C(C)(C)C]
68-1
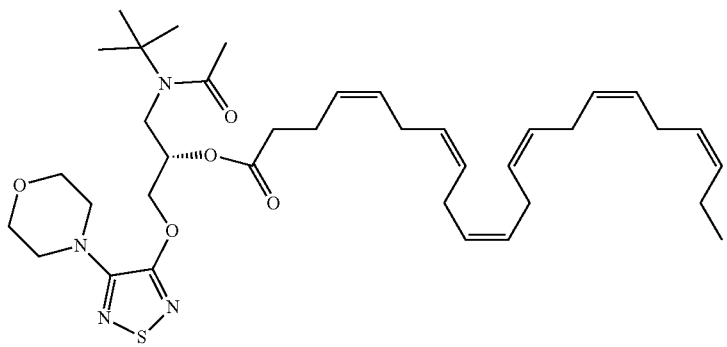 [SMILES: CC/C=C\C/C=C\C/C=C\C/C=C\C/C=C\C/C=C\CCC(=O)O[C@H](COc1nsnc1N1CCOCC1)CN(C(C)=O)C(C)(C)C]
69-1
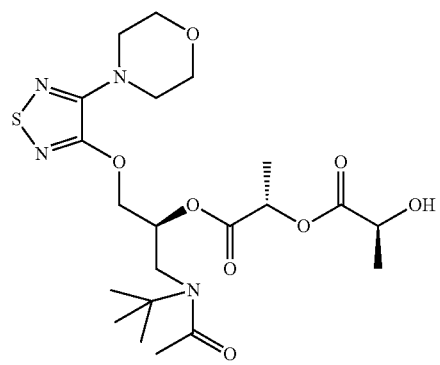 [SMILES: CC(=O)N(C[C@@H](COc1nsnc1N1CCOCC1)OC(=O)[C@H](C)OC(=O)[C@H](C)O)C(C)(C)C]
70-1
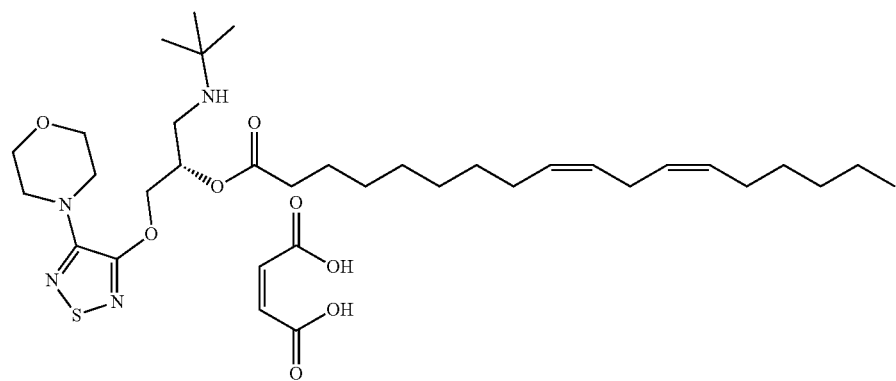

TABLE 8B-continued
Additional Non-limiting Examples of compounds of the Present Invention
71-1
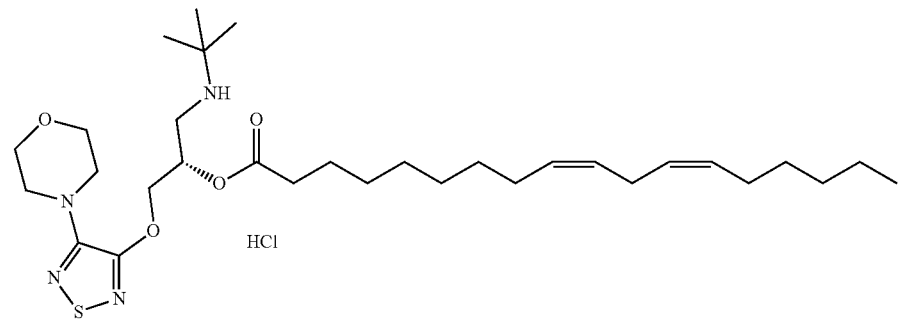 [SMILES: CCCCC/C=C\C/C=C\CCCCCCCC(=O)O[C@@H](CNC(C)(C)C)COc1nsnc1N1CCOCC1 ; Cl]
72-4
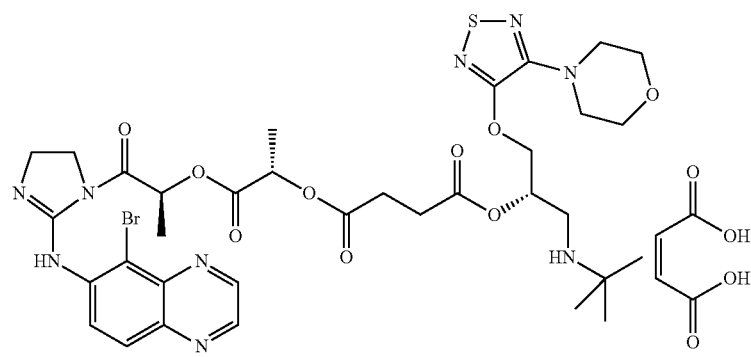
72-4a
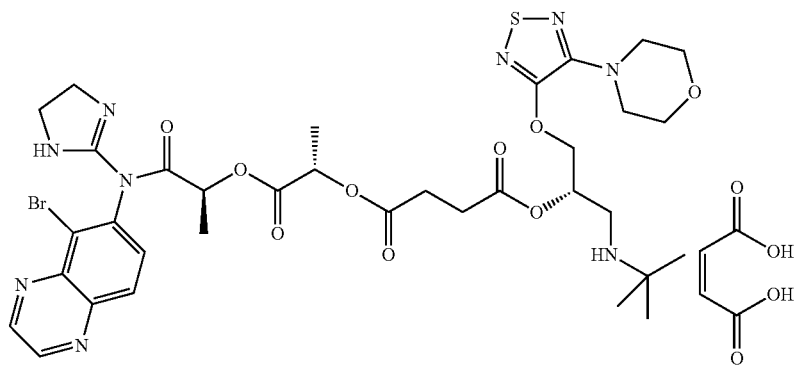
72-4b
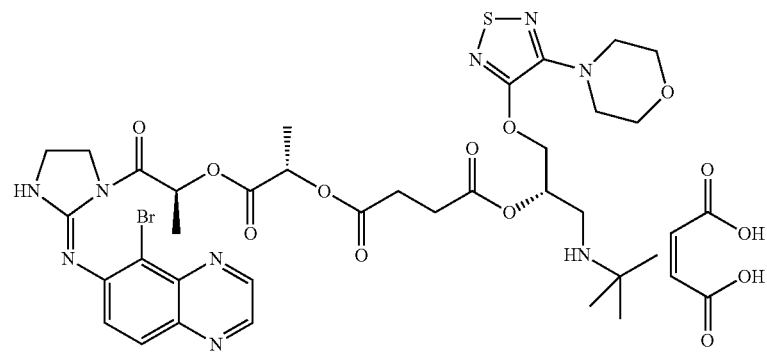

763 764
TABLE 8B-continued
Additional Non-limiting Examples of compounds of the Present Invention
72-4c
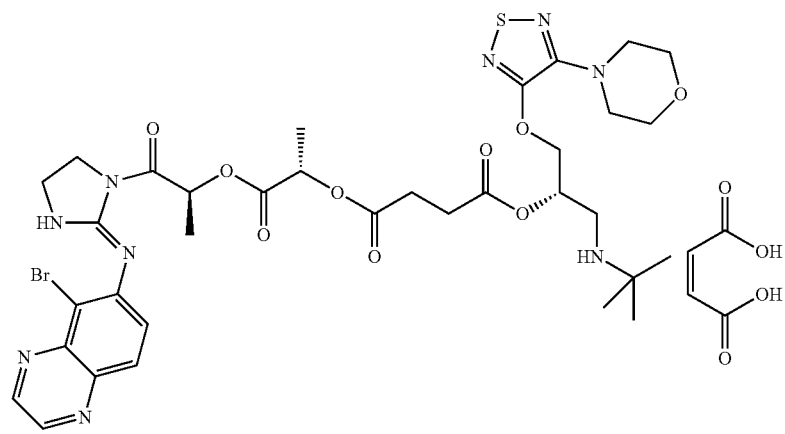
73-1
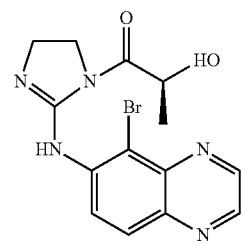 [SMILES: C[C@H](O)C(=O)N1CCN=C1Nc1ccc2nccnc2c1Br]
73-1a
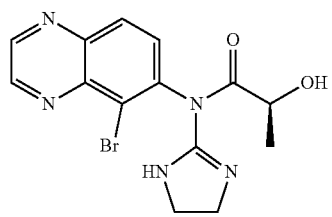 [SMILES: C[C@H](O)C(=O)N(C1=NCCN1)c1ccc2nccnc2c1Br]
73-1b
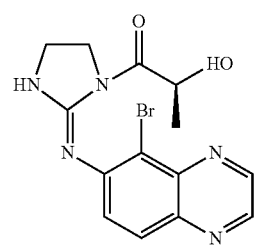 [SMILES: C[C@H](O)C(=O)N1CCN/C1=N/c1ccc2nccnc2c1Br]
73-1c
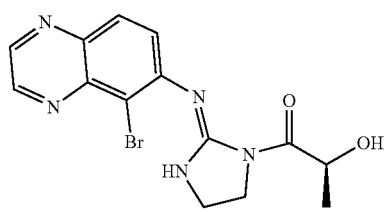 [SMILES: C[C@H](O)C(=O)N1CCN/C1=N\c1ccc2nccnc2c1Br]

TABLE 8B-continued
Additional Non-limiting Examples of compounds of the Present Invention
74-1
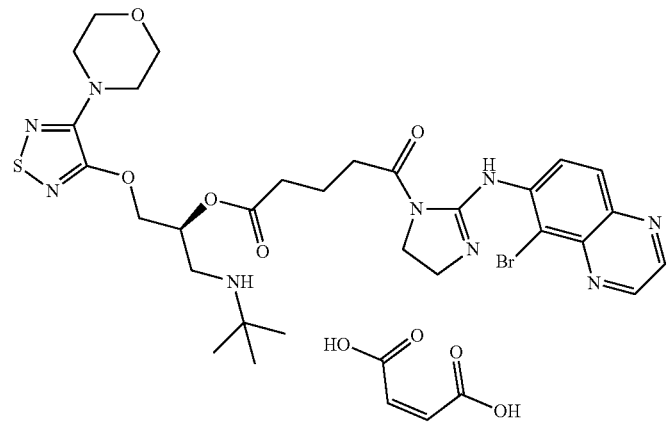
74-1a
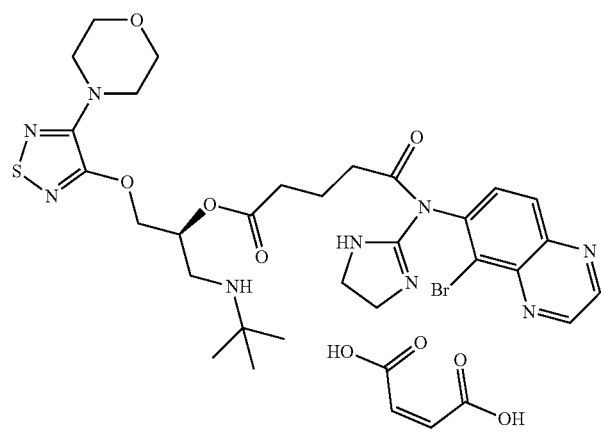
74-1b
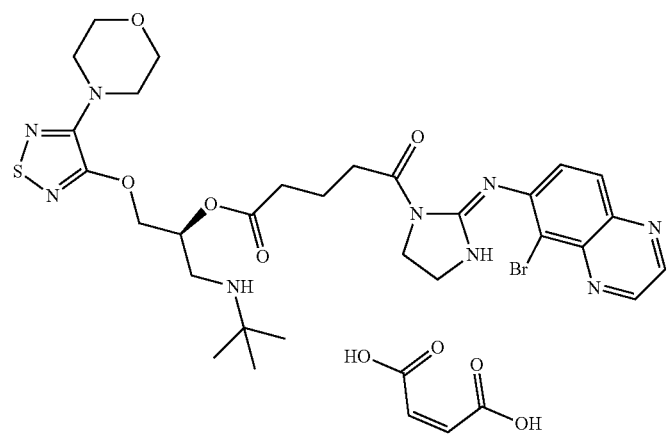 [SMILES: CC(C)(C)NC[C@@H](COc1nsnc1N1CCOCC1)OC(=O)CCCC(=O)N1CCN/C1=N\c1ccc2nccnc2c1Br ; O=C(O)/C=C\C(=O)O]

TABLE 8B-continued
Additional Non-limiting Examples of compounds of the Present Invention
74-1c 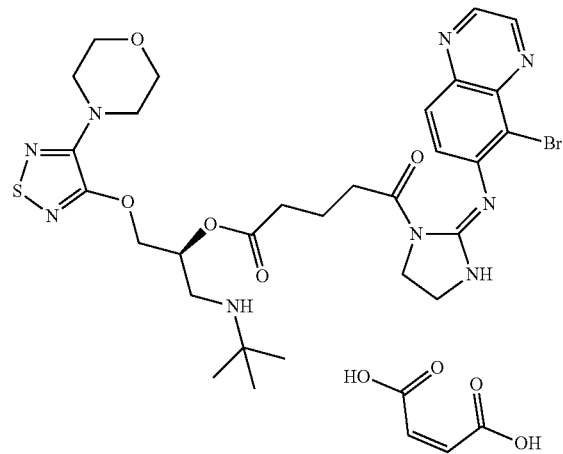 [SMILES: CC(C)(C)NC[C@@H](COc1nsnc1N1CCOCC1)OC(=O)CCCC(=O)N1CCN/C1=N/c1ccc2nccnc2c1Br ; O=C(O)/C=C\C(=O)O] 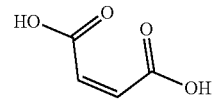
75-1 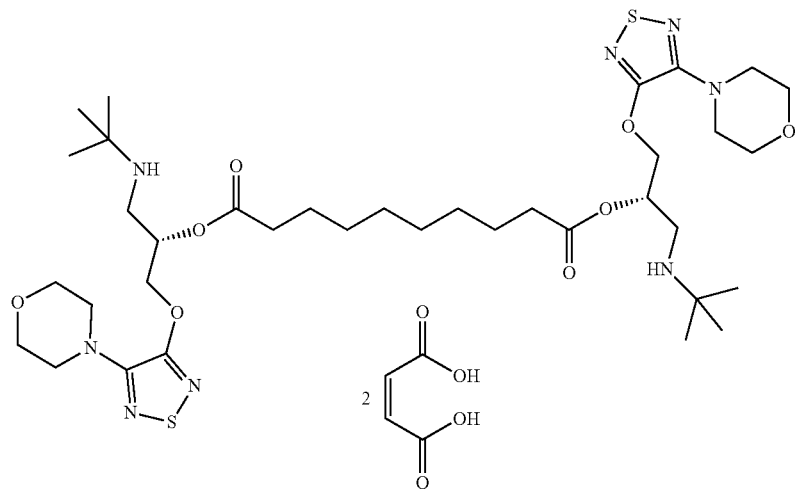 [SMILES: CC(C)(C)NC[C@@H](COc1nsnc1N1CCOCC1)OC(=O)CCCCCCCCC(=O)O[C@@H](CNC(C)(C)C)COc1nsnc1N1CCOCC1 ; O=C(O)/C=C\C(=O)O] 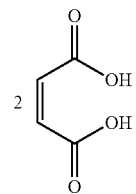
76-4 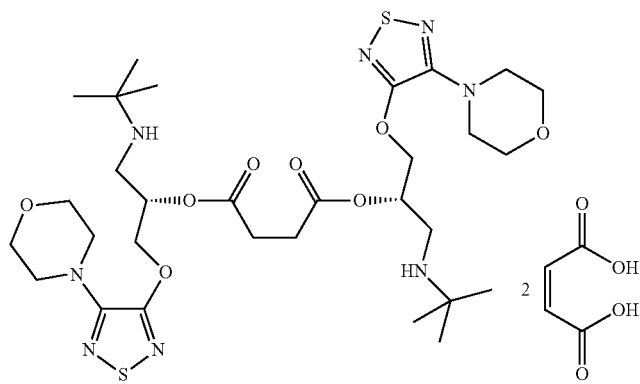 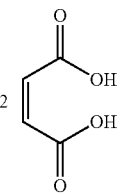

TABLE 8B-continued
Additional Non-limiting Examples of compounds of the Present Invention
77-1
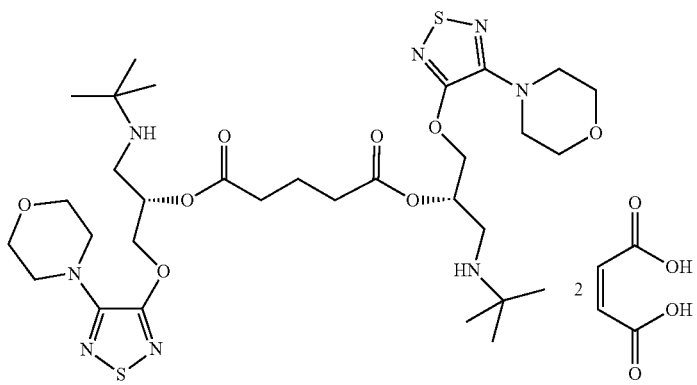
78-1
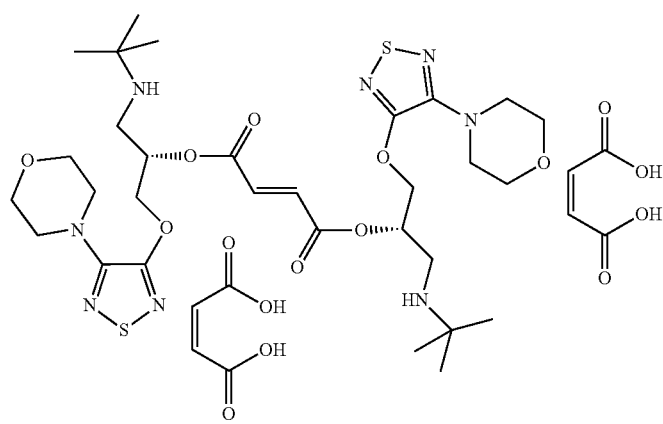
79-3
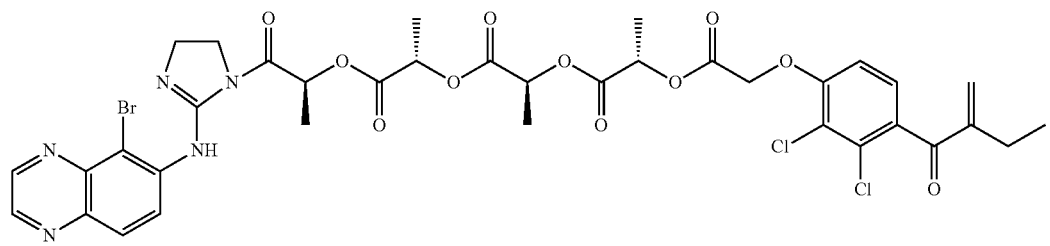 [SMILES: C=C(CC)C(=O)c1ccc(OCC(=O)O[C@@H](C)C(=O)O[C@@H](C)C(=O)O[C@@H](C)C(=O)O[C@@H](C)C(=O)N2CCN=C2Nc2ccc3nccnc3c2Br)c(Cl)c1Cl]
79-3a
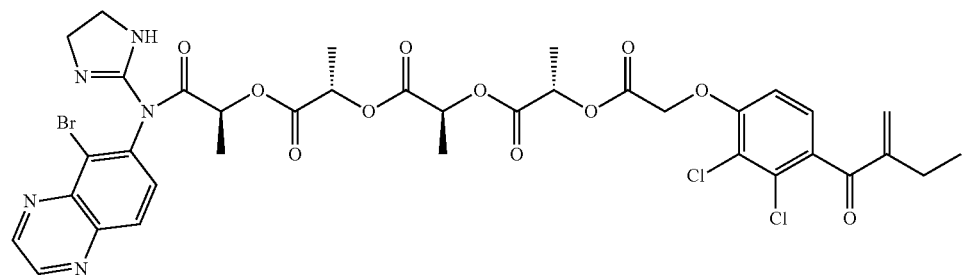 [SMILES: C=C(CC)C(=O)c1ccc(OCC(=O)O[C@@H](C)C(=O)O[C@@H](C)C(=O)O[C@@H](C)C(=O)O[C@@H](C)C(=O)N(C2=NCCN2)c2ccc3nccnc3c2Br)c(Cl)c1Cl]
79-31b
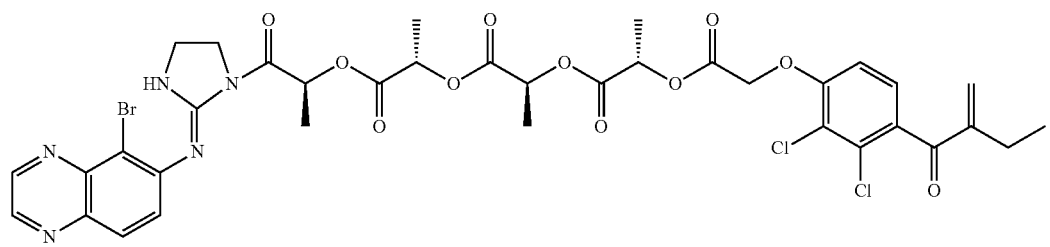 [SMILES: C=C(CC)C(=O)c1ccc(OCC(=O)O[C@@H](C)C(=O)O[C@@H](C)C(=O)O[C@@H](C)C(=O)O[C@@H](C)C(=O)N2CCN/C2=N\c2ccc3nccnc3c2Br)c(Cl)c1Cl]

TABLE 8B-continued
Additional Non-limiting Examples of compounds of the Present Invention
79-3c 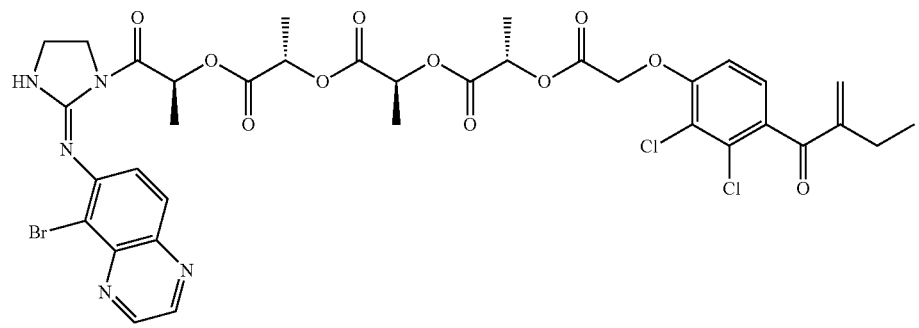 [SMILES: C=C(CC)C(=O)c1ccc(OCC(=O)O[C@@H](C)C(=O)O[C@@H](C)C(=O)O[C@@H](C)C(=O)O[C@@H](C)C(=O)N2CCN/C2=N/c2ccc3nccnc3c2Br)c(Cl)c1Cl]
80-3 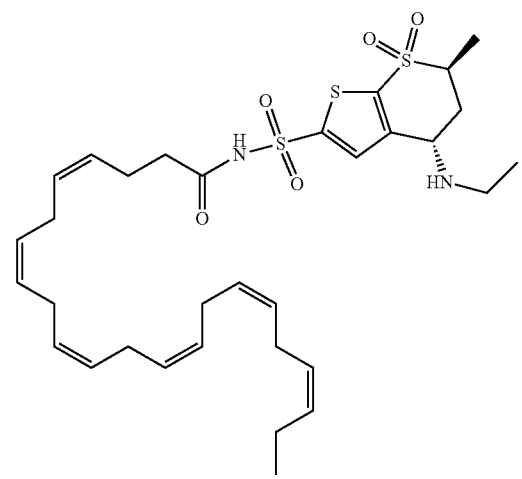 [SMILES: CC/C=C\C/C=C\C/C=C\C/C=C\C/C=C\C/C=C\CCC(=O)NS(=O)(=O)c1cc2c(s1)S(=O)(=O)[C@@H](C)C[C@@H]2NCC]
81-1 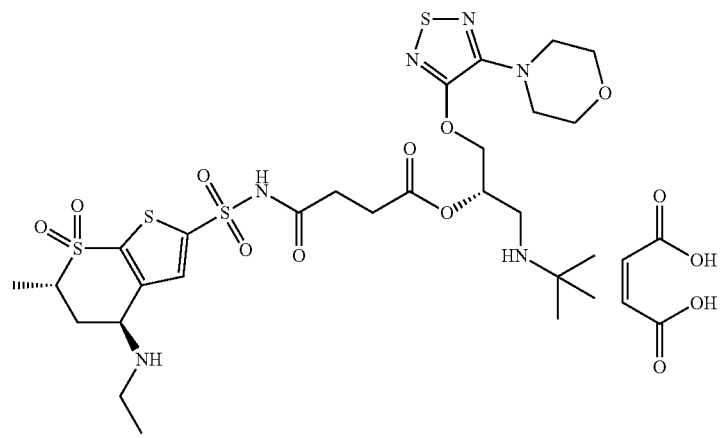
82-1 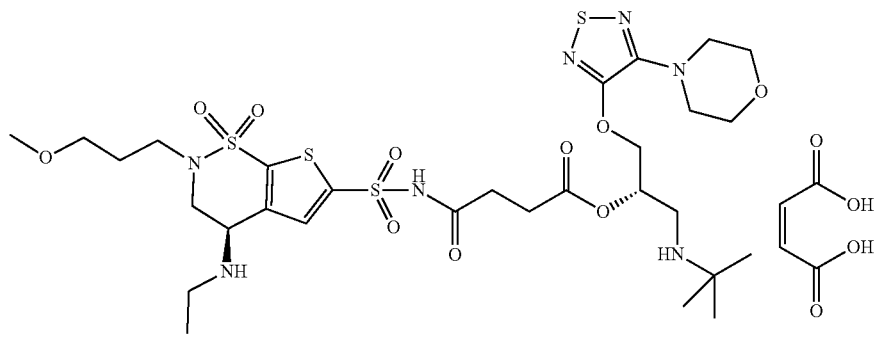

TABLE 8B-continued
Additional Non-limiting Examples of compounds of the Present Invention
83-4
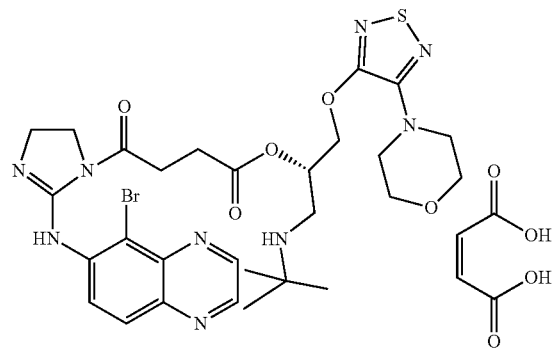
83-4a
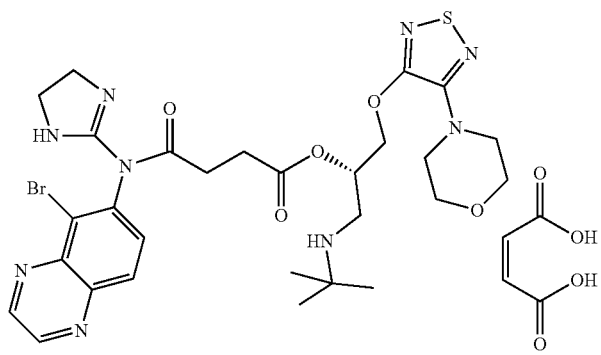
83-4b
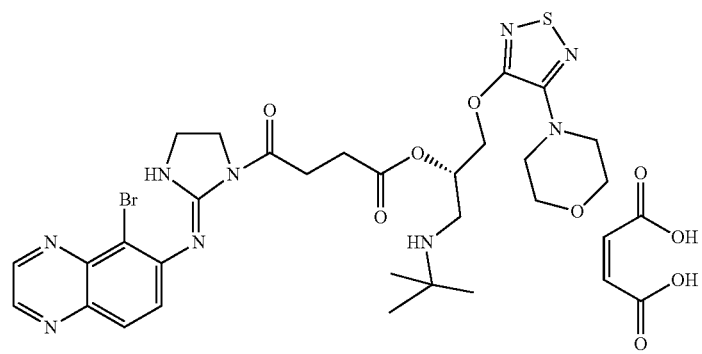
83-4c
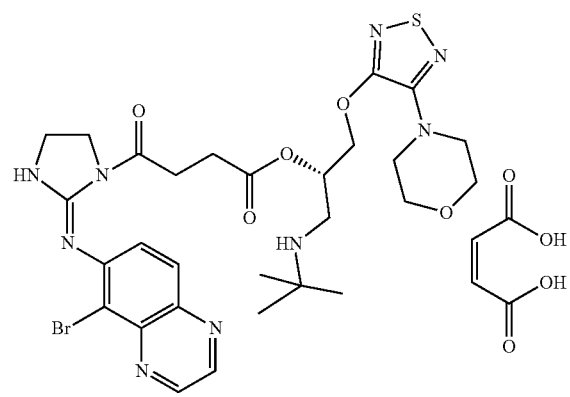

TABLE 8B-continued
Additional Non-limiting Examples of compounds of the Present Invention
84-1
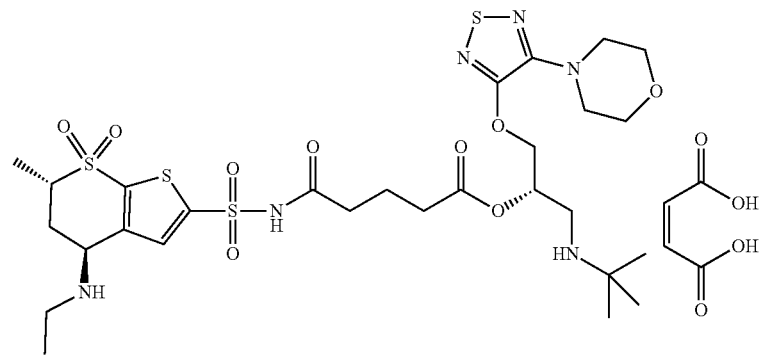
85-1
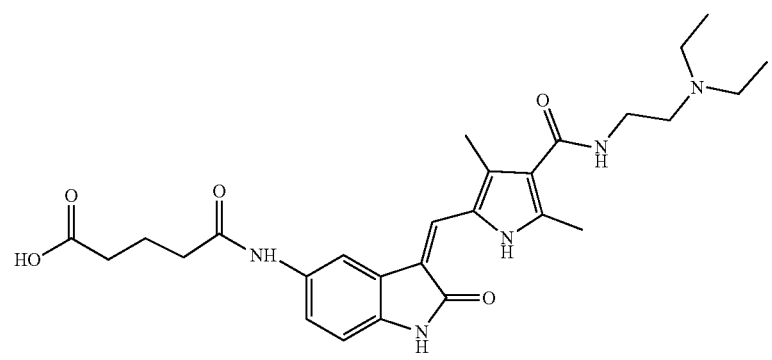 [SMILES: CCN(CC)CCNC(=O)c1c(C)[nH]c(/C=C2\C(=O)Nc3ccc(NC(=O)CCCC(=O)O)cc32)c1C]
86-1
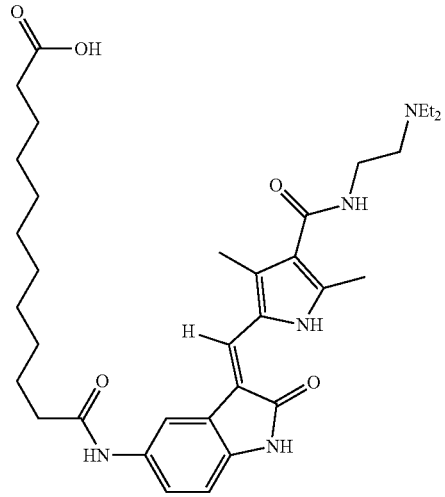
87-1
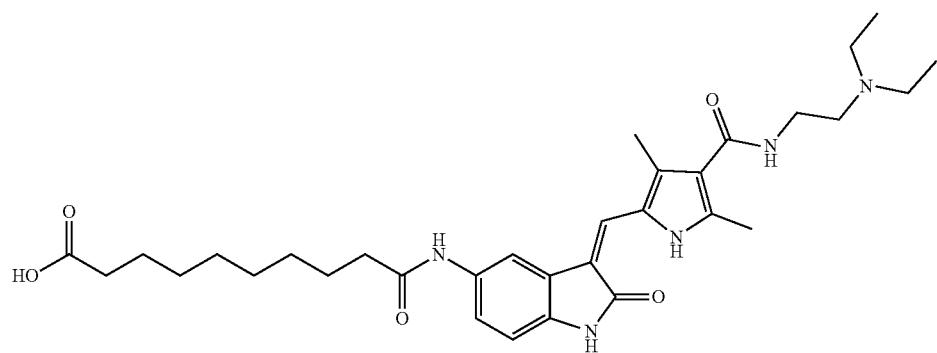 [SMILES: CCN(CC)CCNC(=O)c1c(C)[nH]c(/C=C2\C(=O)Nc3ccc(NC(=O)CCCCCCCCC(=O)O)cc32)c1C]

TABLE 8B-continued
Additional Non-limiting Examples of compounds of the Present Invention
88-3 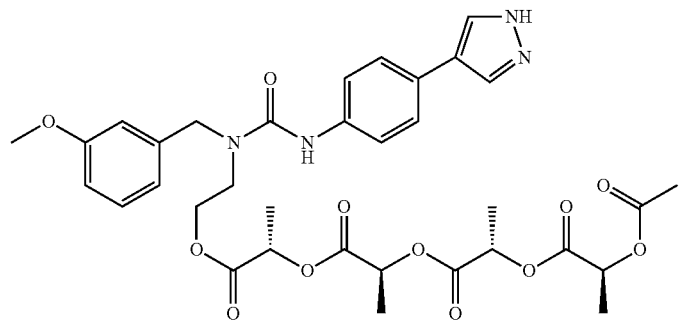 [SMILES: COc1cccc(CN(CCOC(=O)[C@H](C)OC(=O)[C@H](C)OC(=O)[C@H](C)OC(=O)[C@H](C)OC(C)=O)C(=O)Nc2ccc(-c3cn[nH]c3)cc2)c1]
89-3 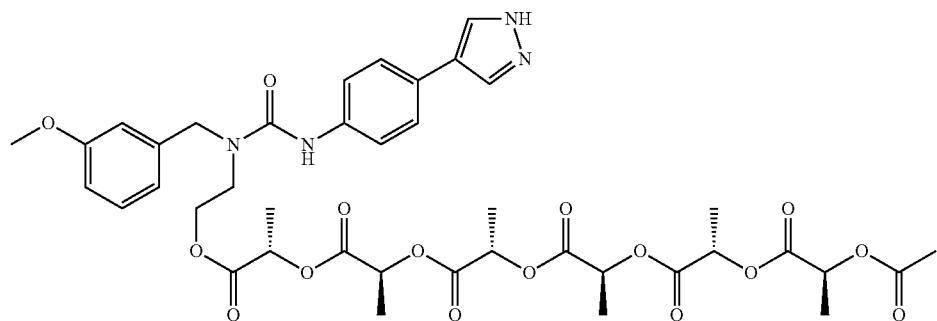 [SMILES: COc1cccc(CN(CCOC(=O)[C@H](C)OC(=O)[C@H](C)OC(=O)[C@H](C)OC(=O)[C@H](C)OC(=O)[C@H](C)OC(=O)[C@H](C)OC(C)=O)C(=O)Nc2ccc(-c3cn[nH]c3)cc2)c1]
90-1 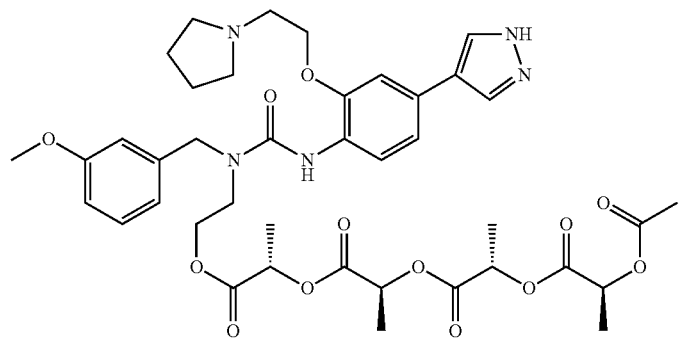 [SMILES: COc1cccc(CN(CCOC(=O)[C@H](C)OC(=O)[C@H](C)OC(=O)[C@H](C)OC(=O)[C@H](C)OC(C)=O)C(=O)Nc2ccc(-c3cn[nH]c3)cc2OCCN2CCCC2)c1]
91-2 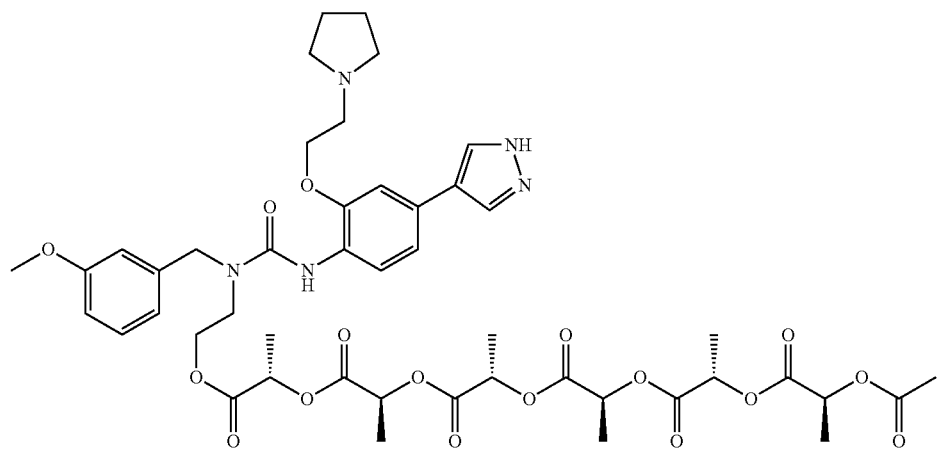 [SMILES: COc1cccc(CN(CCOC(=O)[C@H](C)OC(=O)[C@H](C)OC(=O)[C@H](C)OC(=O)[C@H](C)OC(=O)[C@H](C)OC(=O)[C@H](C)OC(C)=O)C(=O)Nc2ccc(-c3cn[nH]c3)cc2OCCN2CCCC2)c1]

TABLE 8B-continued
Additional Non-limiting Examples of compounds of the Present Invention
92-1
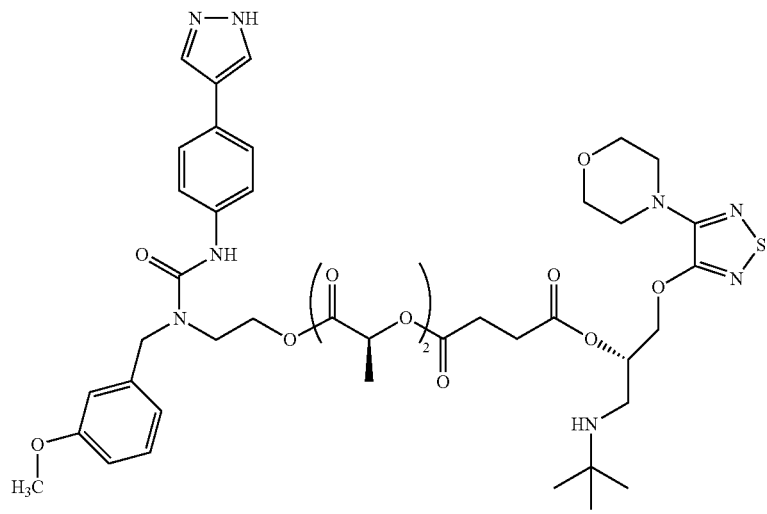
93-1
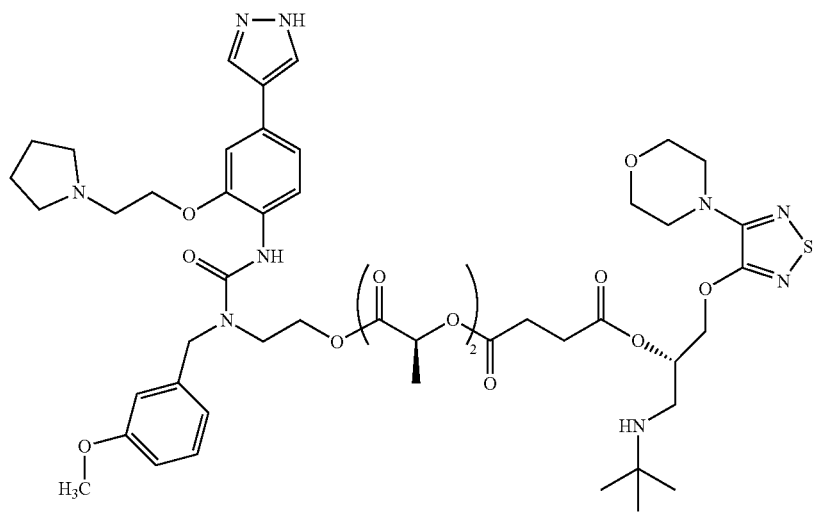
94-1
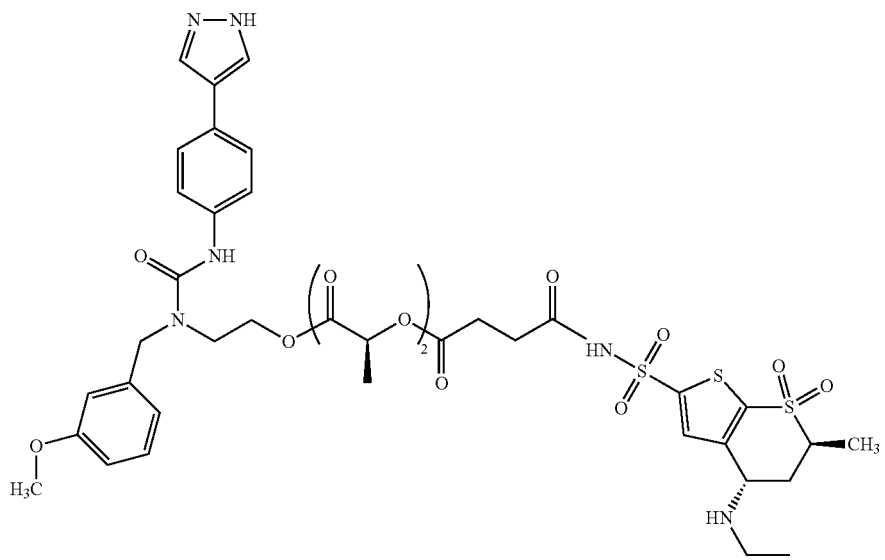

TABLE 8B-continued
Additional Non-limiting Examples of compounds of the Present Invention
95-1
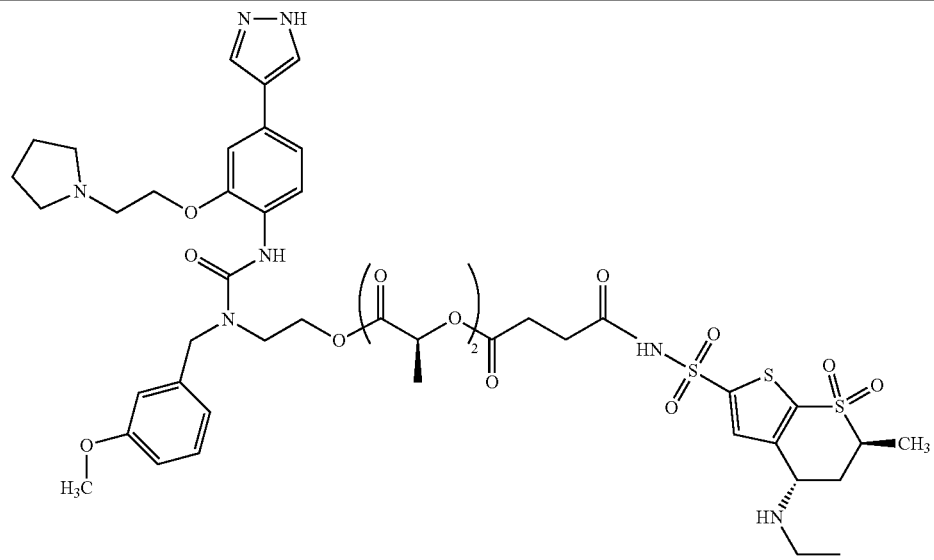
96-1
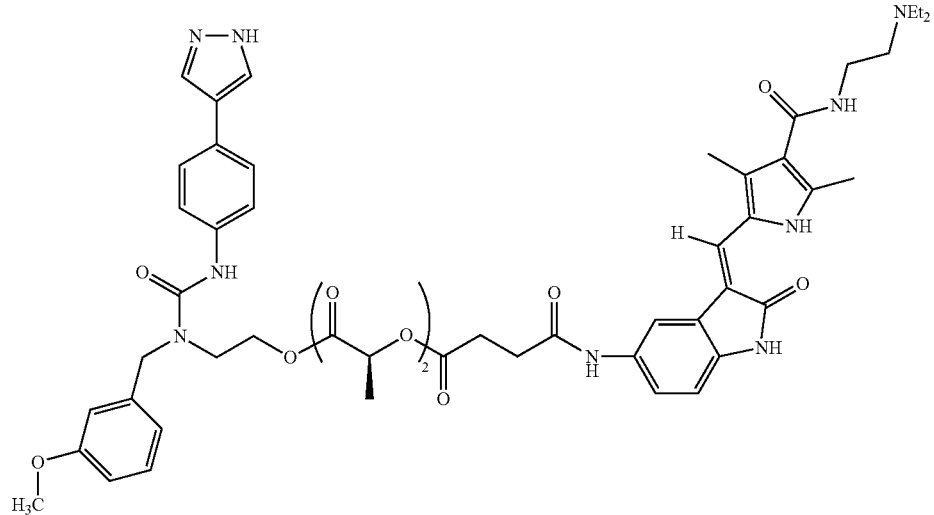
97-1
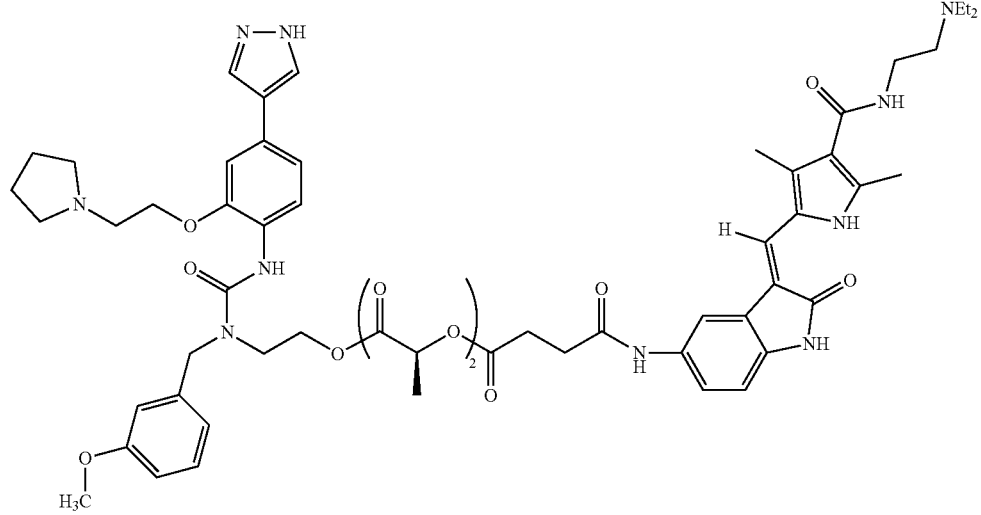

TABLE 8B-continued
Additional Non-limiting Examples of compounds of the Present Invention
98-1 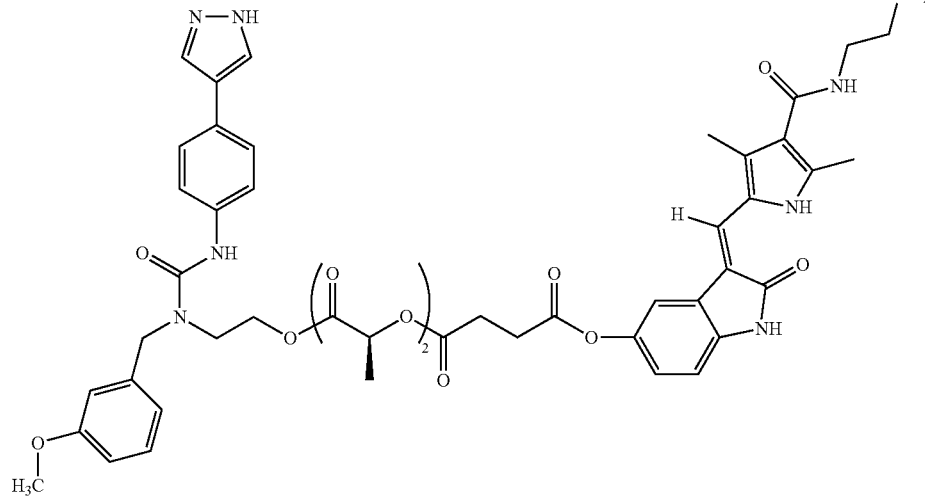
99-1 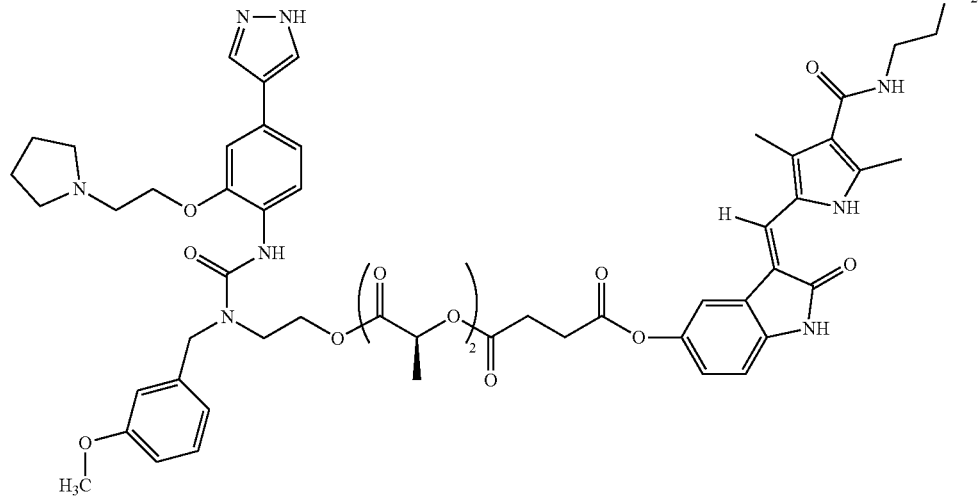

TABLE 8B-continued
Additional Non-limiting Examples of compounds of the Present Invention
100-1
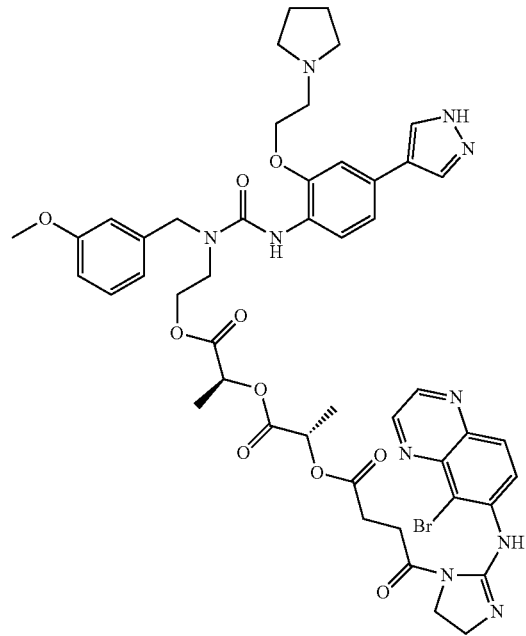 [SMILES: COc1cccc(CN(CCOC(=O)[C@H](C)OC(=O)[C@H](C)OC(=O)CCC(=O)N2CCN=C2Nc2ccc3nccnc3c2Br)C(=O)Nc2ccc(-c3cn[nH]c3)cc2OCCN2CCCC2)c1]
100-1a
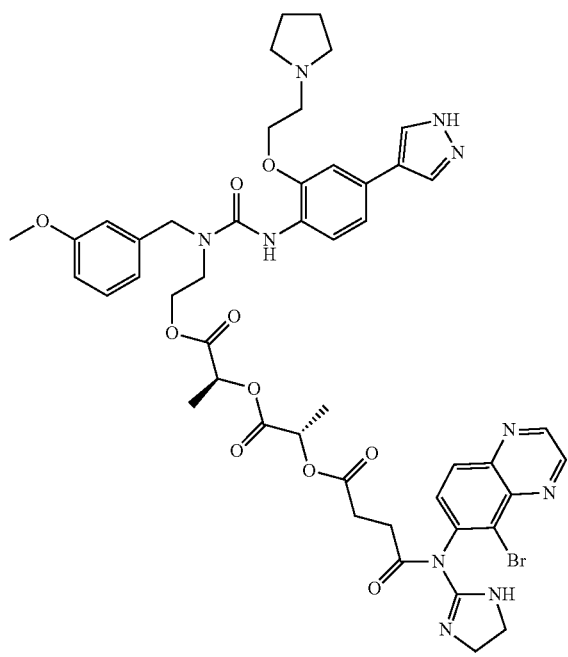 [SMILES: COc1cccc(CN(CCOC(=O)[C@H](C)OC(=O)[C@H](C)OC(=O)CCC(=O)N(C2=NCCN2)c2ccc3nccnc3c2Br)C(=O)Nc2ccc(-c3cn[nH]c3)cc2OCCN2CCCC2)c1]

TABLE 8B-continued
Additional Non-limiting Examples of compounds of the Present Invention
100-1b
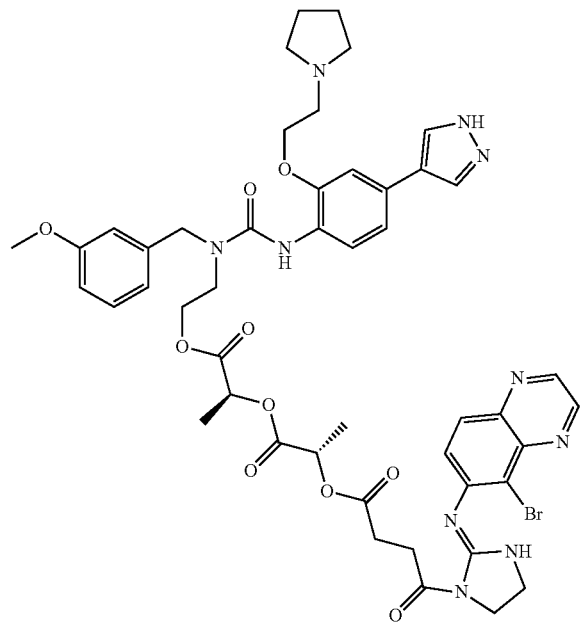 [SMILES: COc1cccc(CN(CCOC(=O)[C@H](C)OC(=O)[C@H](C)OC(=O)CCC(=O)N2CCN/C2=N\c2ccc3nccnc3c2Br)C(=O)Nc2ccc(-c3cn[nH]c3)cc2OCCN2CCCC2)c1]
100-1c
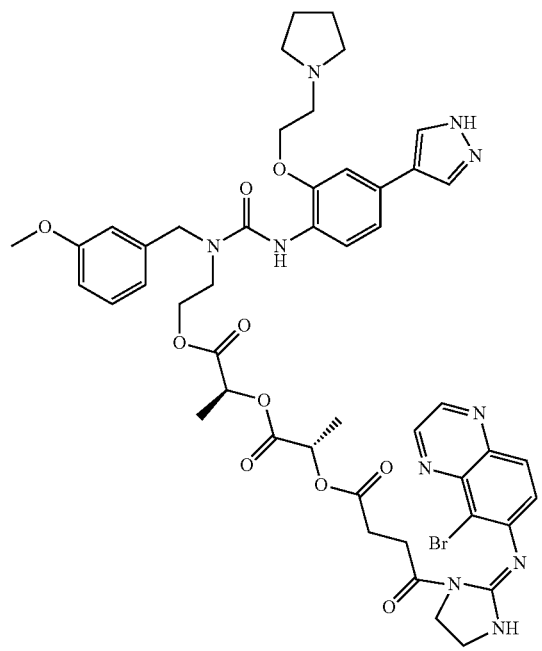 [SMILES: COc1cccc(CN(CCOC(=O)[C@H](C)OC(=O)[C@H](C)OC(=O)CCC(=O)N2CCN/C2=N/c2ccc3nccnc3c2Br)C(=O)Nc2ccc(-c3cn[nH]c3)cc2OCCN2CCCC2)c1]

TABLE 8B-continued
Additional Non-limiting Examples of compounds of the Present Invention
101-3
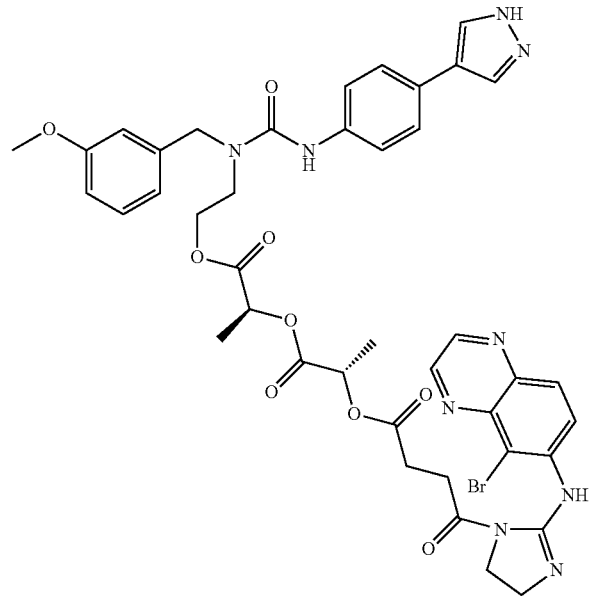 [SMILES: COc1cccc(CN(CCOC(=O)[C@H](C)OC(=O)[C@H](C)OC(=O)CCC(=O)N2CCN=C2Nc2ccc3nccnc3c2Br)C(=O)Nc2ccc(-c3cn[nH]c3)cc2)c1]
101-3a
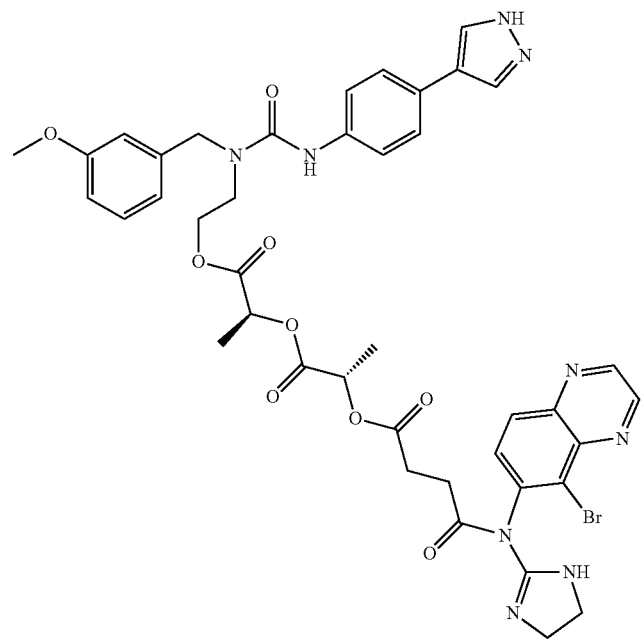 [SMILES: COc1cccc(CN(CCOC(=O)[C@H](C)OC(=O)[C@H](C)OC(=O)CCC(=O)N(C2=NCCN2)c2ccc3nccnc3c2Br)C(=O)Nc2ccc(-c3cn[nH]c3)cc2)c1]

TABLE 8B-continued
Additional Non-limiting Examples of compounds of the Present Invention
101-3b
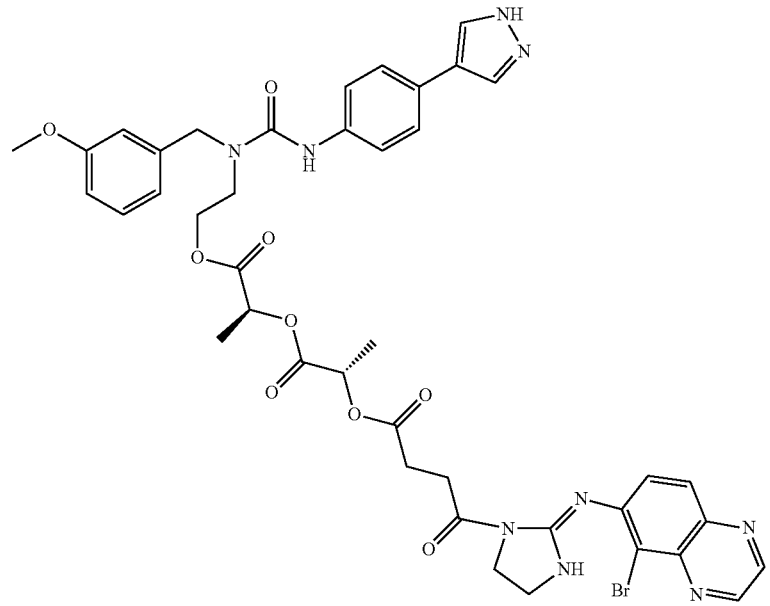 [SMILES: COc1cccc(CN(CCOC(=O)[C@H](C)OC(=O)[C@H](C)OC(=O)CCC(=O)N2CCN/C2=N\c2ccc3nccnc3c2Br)C(=O)Nc2ccc(-c3cn[nH]c3)cc2)c1]
101-3c
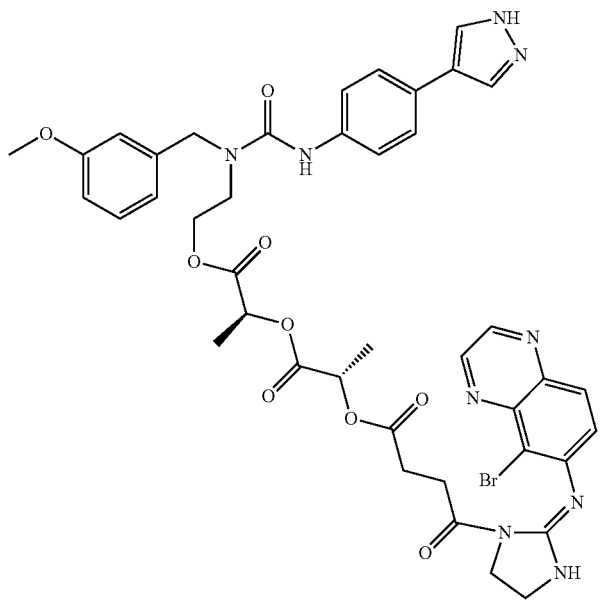 [SMILES: COc1cccc(CN(CCOC(=O)[C@H](C)OC(=O)[C@H](C)OC(=O)CCC(=O)N2CCN/C2=N/c2ccc3nccnc3c2Br)C(=O)Nc2ccc(-c3cn[nH]c3)cc2)c1]
102-1
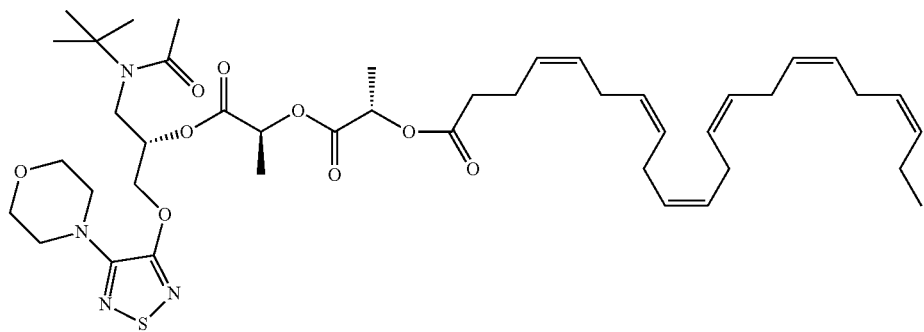 [SMILES: CC/C=C\C/C=C\C/C=C\C/C=C\C/C=C\C/C=C\CCC(=O)O[C@@H](C)C(=O)O[C@@H](C)C(=O)O[C@H](COc1nsnc1N1CCOCC1)CN(C(C)=O)C(C)(C)C]

TABLE 8B-continued
Additional Non-limiting Examples of compounds of the Present Invention
103-1
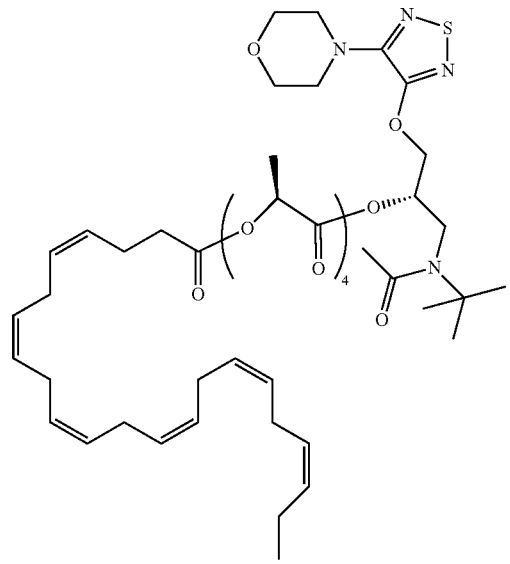
104-1
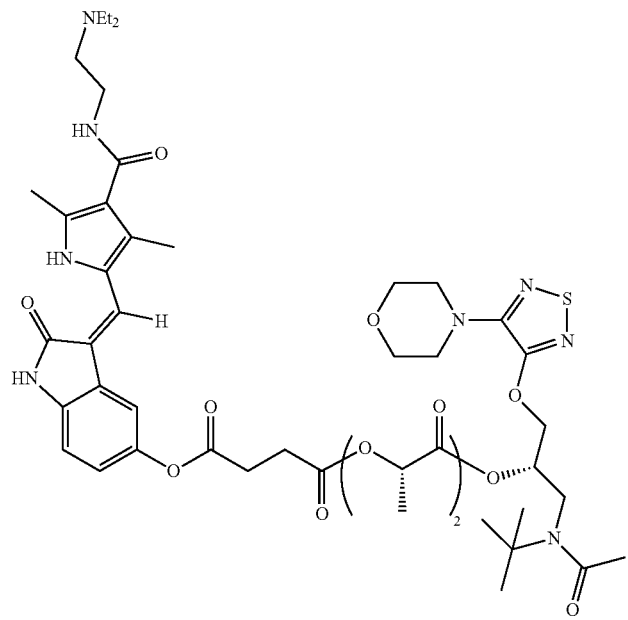

TABLE 8B-continued
Additional Non-limiting Examples of compounds of the Present Invention
105-1
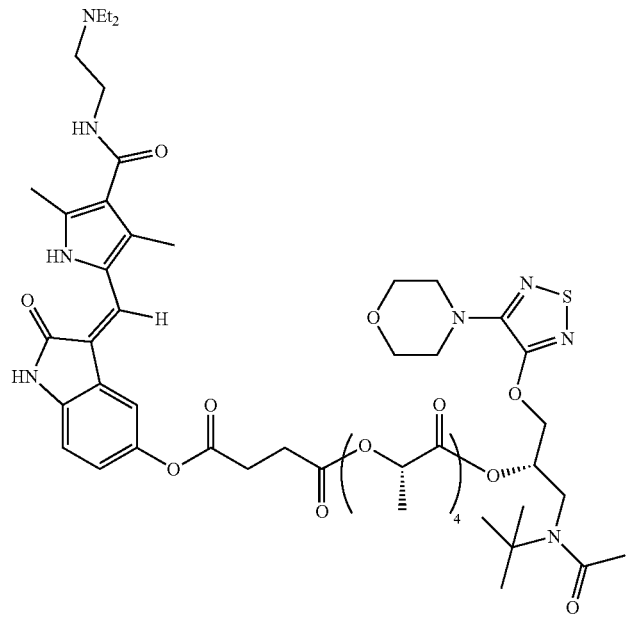
106-1
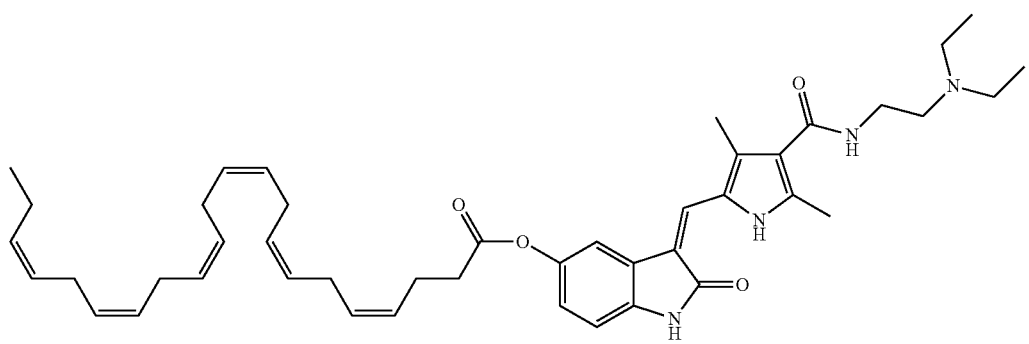 [SMILES: CC/C=C\C/C=C\C/C=C\C/C=C\C/C=C\C/C=C\CCC(=O)Oc1ccc2c(c1)/C(=C/c1[nH]c(C)c(C(=O)NCCN(CC)CC)c1C)C(=O)N2]
107-4
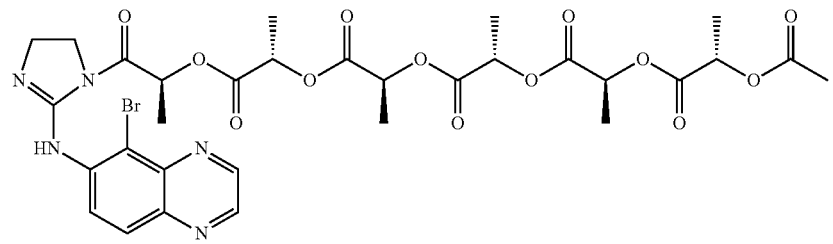 [SMILES: CC(=O)O[C@@H](C)C(=O)O[C@@H](C)C(=O)O[C@@H](C)C(=O)O[C@@H](C)C(=O)O[C@@H](C)C(=O)O[C@@H](C)C(=O)N1CCN=C1Nc1ccc2nccnc2c1Br]
107-4a
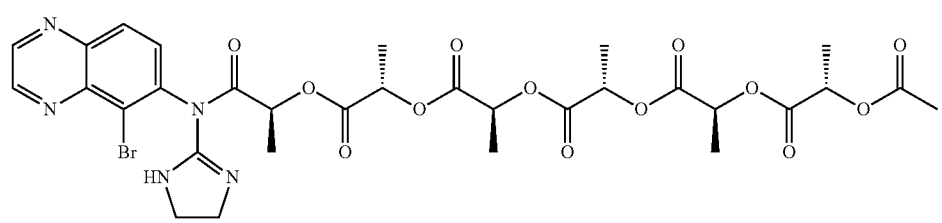 [SMILES: CC(=O)O[C@@H](C)C(=O)O[C@@H](C)C(=O)O[C@@H](C)C(=O)O[C@@H](C)C(=O)O[C@@H](C)C(=O)O[C@@H](C)C(=O)N(C1=NCCN1)c1ccc2nccnc2c1Br]

US 11,548,861 B2
TABLE 8B-continued
Additional Non-limiting Examples of compounds of the Present Invention
107-4b 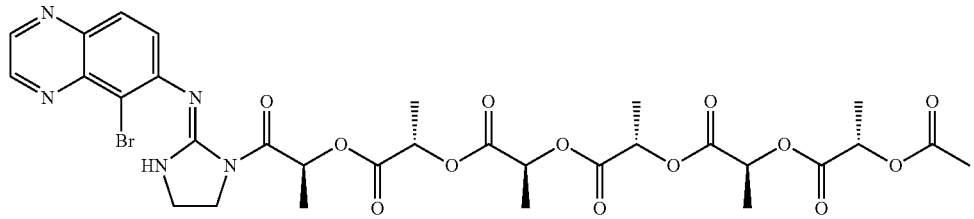 [SMILES: CC(=O)O[C@@H](C)C(=O)O[C@@H](C)C(=O)O[C@@H](C)C(=O)O[C@@H](C)C(=O)O[C@@H](C)C(=O)O[C@@H](C)C(=O)N1CCN/C1=N\c1ccc2nccnc2c1Br]
107-4c 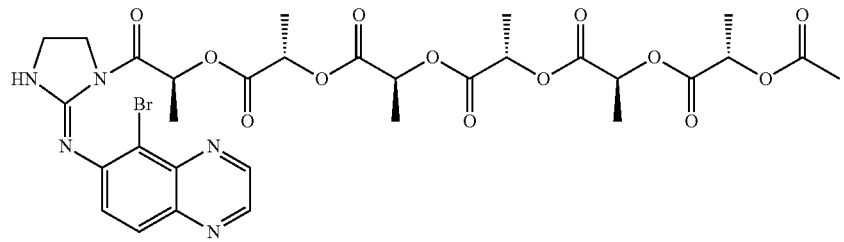 [SMILES: CC(=O)O[C@@H](C)C(=O)O[C@@H](C)C(=O)O[C@@H](C)C(=O)O[C@@H](C)C(=O)O[C@@H](C)C(=O)O[C@@H](C)C(=O)N1CCN/C1=N/c1ccc2nccnc2c1Br]
108-3 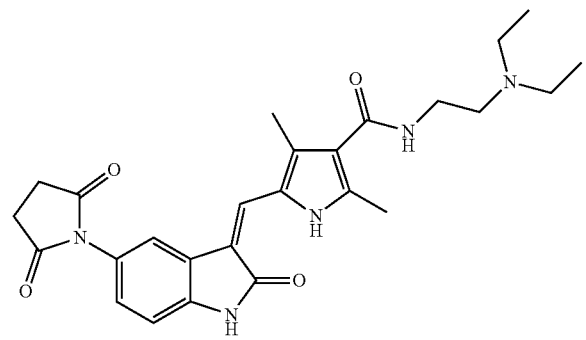 [SMILES: CCN(CC)CCNC(=O)c1c(C)[nH]c(/C=C2\C(=O)Nc3ccc(N4C(=O)CCC4=O)cc32)c1C]
109-1 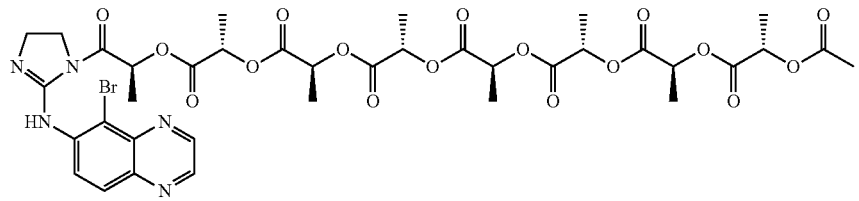 [SMILES: CC(=O)O[C@@H](C)C(=O)O[C@@H](C)C(=O)O[C@@H](C)C(=O)O[C@@H](C)C(=O)O[C@@H](C)C(=O)O[C@@H](C)C(=O)O[C@@H](C)C(=O)O[C@@H](C)C(=O)N1CCN=C1Nc1ccc2nccnc2c1Br]
109-1a 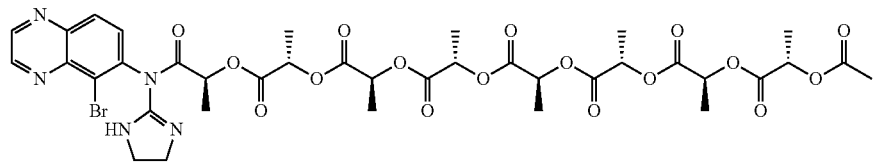 [SMILES: CC(=O)O[C@@H](C)C(=O)O[C@@H](C)C(=O)O[C@@H](C)C(=O)O[C@@H](C)C(=O)O[C@@H](C)C(=O)O[C@@H](C)C(=O)O[C@@H](C)C(=O)O[C@@H](C)C(=O)N(C1=NCCN1)c1ccc2nccnc2c1Br]
109-1b 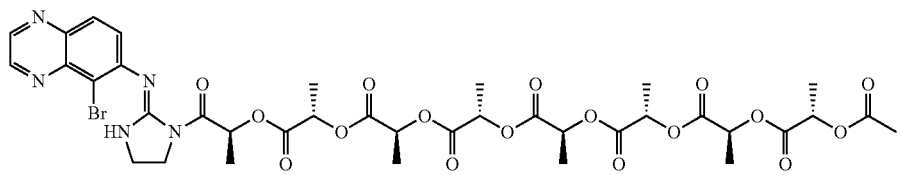 [SMILES: CC(=O)O[C@@H](C)C(=O)O[C@@H](C)C(=O)O[C@@H](C)C(=O)O[C@@H](C)C(=O)O[C@@H](C)C(=O)O[C@@H](C)C(=O)O[C@@H](C)C(=O)O[C@@H](C)C(=O)N1CCN/C1=N\c1ccc2nccnc2c1Br]
109-1c 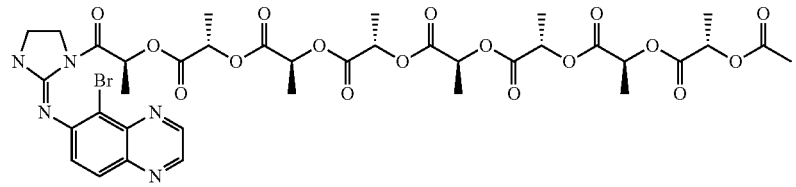 [SMILES: CC(=O)O[C@@H](C)C(=O)O[C@@H](C)C(=O)O[C@@H](C)C(=O)O[C@@H](C)C(=O)O[C@@H](C)C(=O)O[C@@H](C)C(=O)O[C@@H](C)C(=O)O[C@@H](C)C(=O)N1CCN/C1=N/c1ccc2nccnc2c1Br]

TABLE 8B-continued
Additional Non-limiting Examples of compounds of the Present Invention
110-3 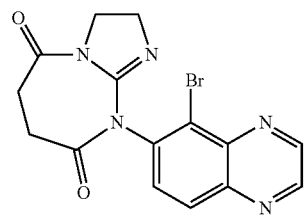 [SMILES: O=C1CCC(=O)N(c2ccc3nccnc3c2Br)C2=NCCN12]
111-4 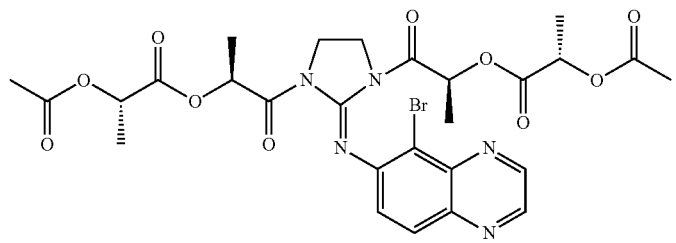 [SMILES: CC(=O)O[C@@H](C)C(=O)O[C@@H](C)C(=O)N1CCN(C(=O)[C@H](C)OC(=O)[C@H](C)OC(C)=O)C1=Nc1ccc2nccnc2c1Br]
111-4a 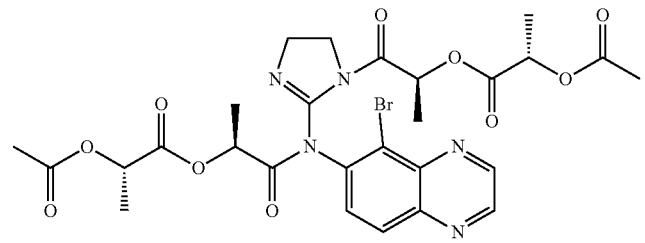 [SMILES: CC(=O)O[C@@H](C)C(=O)O[C@@H](C)C(=O)N1CCN=C1N(C(=O)[C@H](C)OC(=O)[C@H](C)OC(C)=O)c1ccc2nccnc2c1Br]
112-1 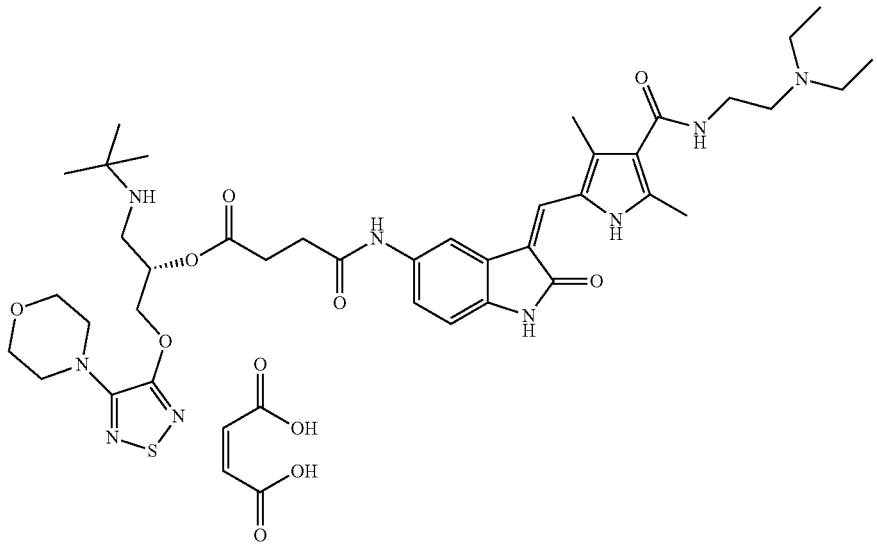
113-1 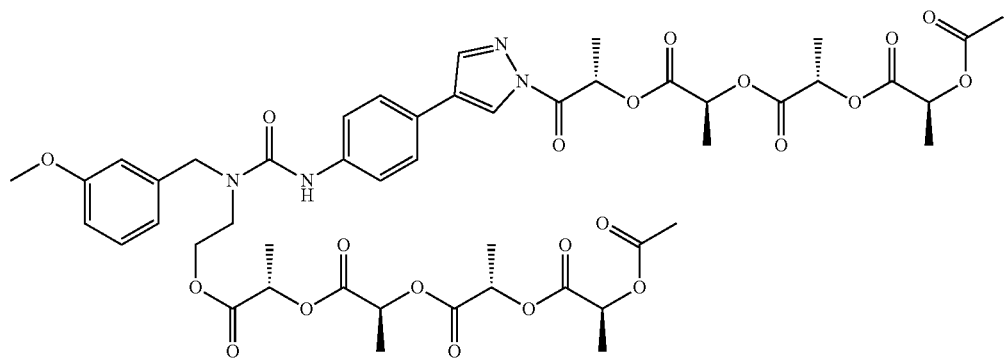 [SMILES: COc1cccc(CN(CCOC(=O)[C@H](C)OC(=O)[C@H](C)OC(=O)[C@H](C)OC(=O)[C@H](C)OC(C)=O)C(=O)Nc2ccc(-c3cnn(C(=O)[C@H](C)OC(=O)[C@H](C)OC(=O)[C@H](C)OC(=O)[C@H](C)OC(C)=O)c3)cc2)c1]

TABLE 8B-continued
Additional Non-limiting Examples of compounds of the Present Invention
114-4 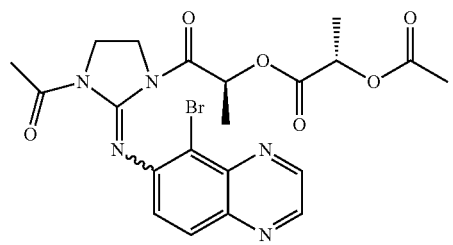
114-4a 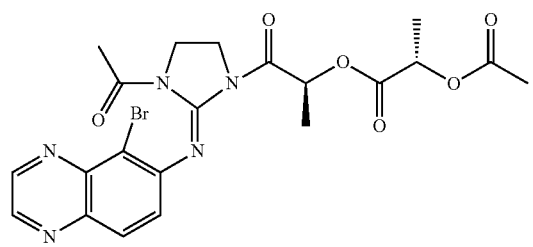 [SMILES: CC(=O)O[C@@H](C)C(=O)O[C@@H](C)C(=O)N1CCN(C(C)=O)/C1=N\c1ccc2nccnc2c1Br]
114-4b 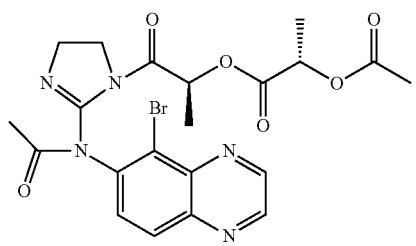 [SMILES: CC(=O)O[C@@H](C)C(=O)O[C@@H](C)C(=O)N1CCN=C1N(C(C)=O)c1ccc2nccnc2c1Br]
114-4c 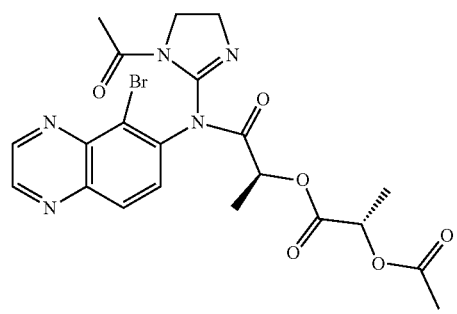 [SMILES: CC(=O)O[C@@H](C)C(=O)O[C@@H](C)C(=O)N(C1=NCCN1C(C)=O)c1ccc2nccnc2c1Br]
114-4d 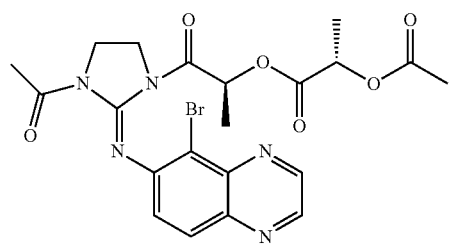 [SMILES: CC(=O)O[C@@H](C)C(=O)O[C@@H](C)C(=O)N1CCN(C(C)=O)/C1=N/c1ccc2nccnc2c1Br]
115-1 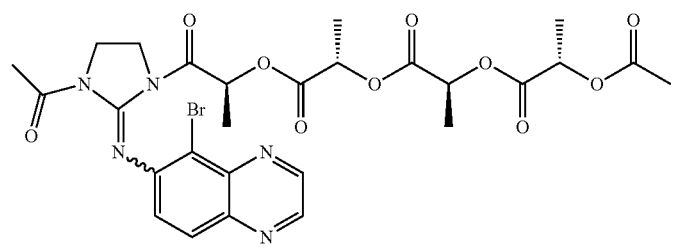 [SMILES: CC(=O)O[C@@H](C)C(=O)O[C@@H](C)C(=O)O[C@@H](C)C(=O)O[C@@H](C)C(=O)N1CCN(C(C)=O)C1=Nc1ccc2nccnc2c1Br]

TABLE 8B-continued
Additional Non-limiting Examples of compounds of the Present Invention
115-1a
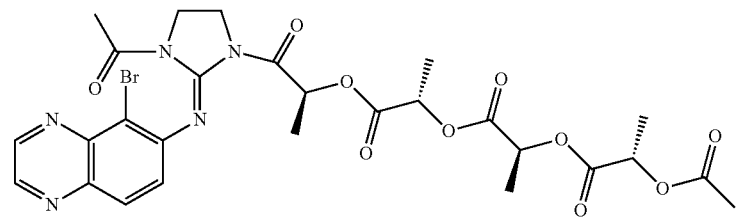 [SMILES: CC(=O)O[C@@H](C)C(=O)O[C@@H](C)C(=O)O[C@@H](C)C(=O)O[C@@H](C)C(=O)N1CCN(C(C)=O)/C1=N\c1ccc2nccnc2c1Br]
115-1b
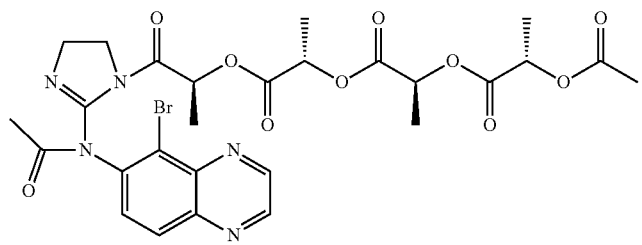 [SMILES: CC(=O)O[C@@H](C)C(=O)O[C@@H](C)C(=O)O[C@@H](C)C(=O)O[C@@H](C)C(=O)N1CCN=C1N(C(C)=O)c1ccc2nccnc2c1Br]
115-1c
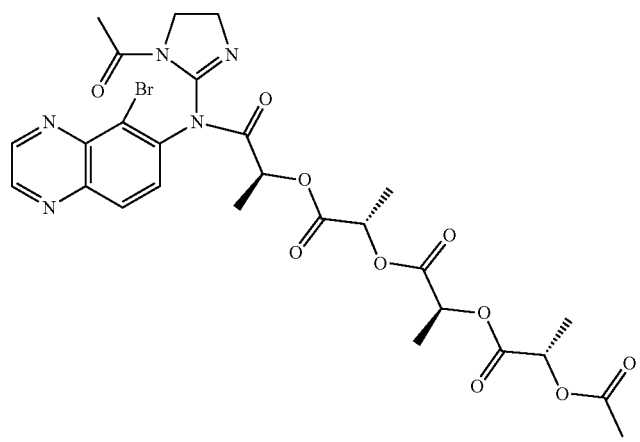 [SMILES: CC(=O)O[C@@H](C)C(=O)O[C@@H](C)C(=O)O[C@@H](C)C(=O)O[C@@H](C)C(=O)N(C1=NCCN1C(C)=O)c1ccc2nccnc2c1Br]
115-1d
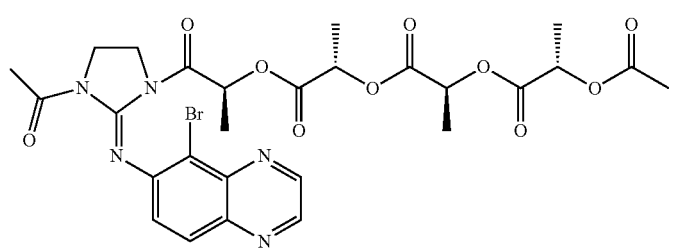
116-1
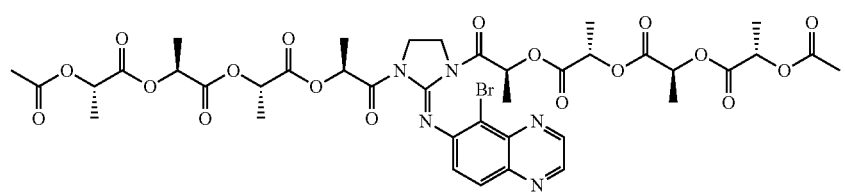 [SMILES: CC(=O)O[C@@H](C)C(=O)O[C@@H](C)C(=O)O[C@@H](C)C(=O)O[C@@H](C)C(=O)N1CCN(C(=O)[C@H](C)OC(=O)[C@H](C)OC(=O)[C@H](C)OC(=O)[C@H](C)OC(C)=O)C1=Nc1ccc2nccnc2c1Br]
116-1a
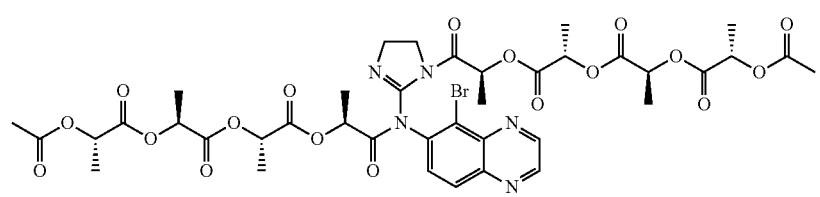 [SMILES: CC(=O)O[C@@H](C)C(=O)O[C@@H](C)C(=O)O[C@@H](C)C(=O)O[C@@H](C)C(=O)N1CCN=C1N(C(=O)[C@H](C)OC(=O)[C@H](C)OC(=O)[C@H](C)OC(=O)[C@H](C)OC(C)=O)c1ccc2nccnc2c1Br]

TABLE 8B-continued
Additional Non-limiting Examples of compounds of the Present Invention
117-6
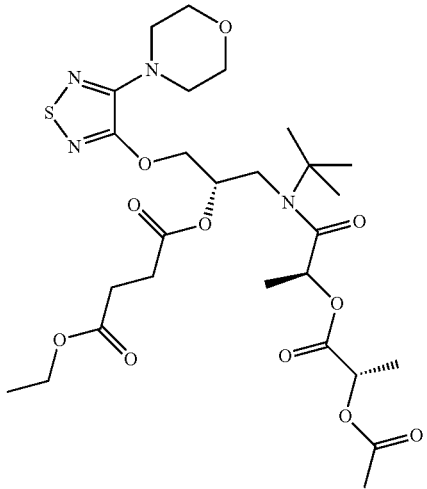 [SMILES: CCOC(=O)CCC(=O)O[C@H](COc1nsnc1N1CCOCC1)CN(C(=O)[C@H](C)OC(=O)[C@H](C)OC(C)=O)C(C)(C)C]
118-1
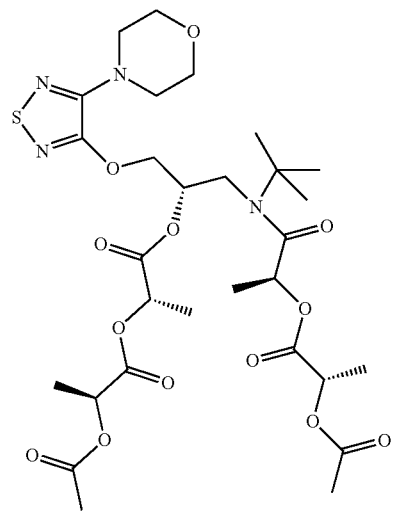 [SMILES: CC(=O)O[C@@H](C)C(=O)O[C@@H](C)C(=O)O[C@H](COc1nsnc1N1CCOCC1)CN(C(=O)[C@H](C)OC(=O)[C@H](C)OC(C)=O)C(C)(C)C]

TABLE 8B-continued
Additional Non-limiting Examples of compounds of the Present Invention
119-6
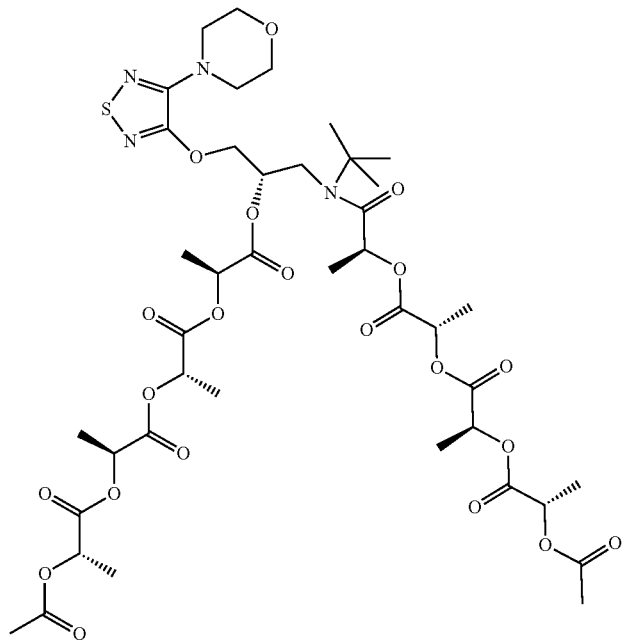 [SMILES: CC(=O)O[C@@H](C)C(=O)O[C@@H](C)C(=O)O[C@@H](C)C(=O)O[C@@H](C)C(=O)O[C@H](COc1nsnc1N1CCOCC1)CN(C(=O)[C@H](C)OC(=O)[C@H](C)OC(=O)[C@H](C)OC(=O)[C@H](C)OC(C)=O)C(C)(C)C]
120-1
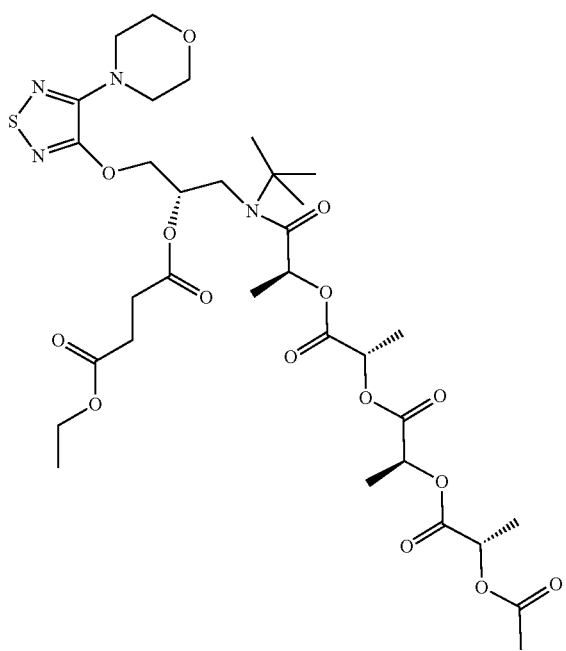 [SMILES: CCOC(=O)CCC(=O)O[C@H](COc1nsnc1N1CCOCC1)CN(C(=O)[C@H](C)OC(=O)[C@H](C)OC(=O)[C@H](C)OC(=O)[C@H](C)OC(C)=O)C(C)(C)C]

TABLE 8B-continued
Additional Non-limiting Examples of compounds of the Present Invention
121-3 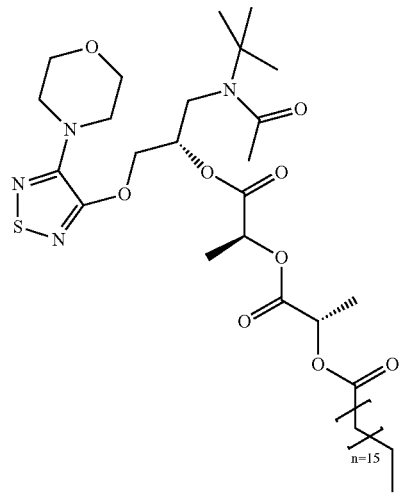
122-4 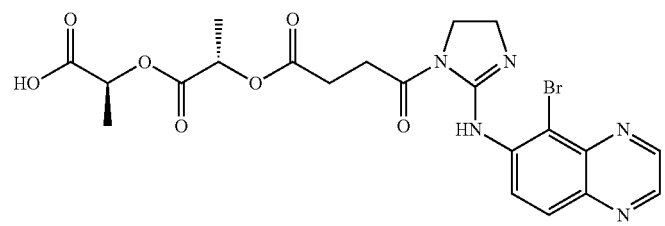 [SMILES: C[C@H](OC(=O)[C@H](C)OC(=O)CCC(=O)N1CCN=C1Nc1ccc2nccnc2c1Br)C(=O)O]
122-4a 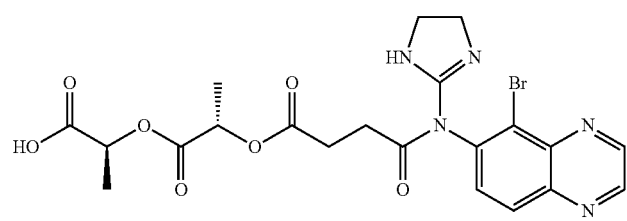 [SMILES: C[C@H](OC(=O)[C@H](C)OC(=O)CCC(=O)N(C1=NCCN1)c1ccc2nccnc2c1Br)C(=O)O]
122-4b 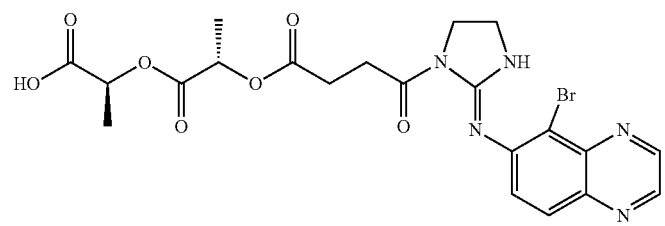 [SMILES: C[C@H](OC(=O)[C@H](C)OC(=O)CCC(=O)N1CCN/C1=N\c1ccc2nccnc2c1Br)C(=O)O]

TABLE 8B-continued
*Additional Non-limiting Examples of compounds of the Present Invention*
122-4c
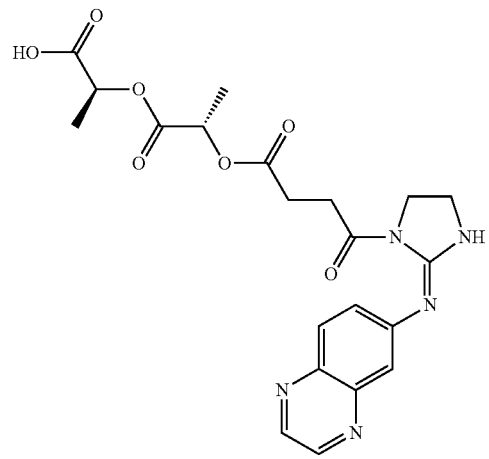 [SMILES: C[C@H](OC(=O)[C@H](C)OC(=O)CCC(=O)N1CCN/C1=N/c1ccc2nccnc2c1)C(=O)O]
123-4
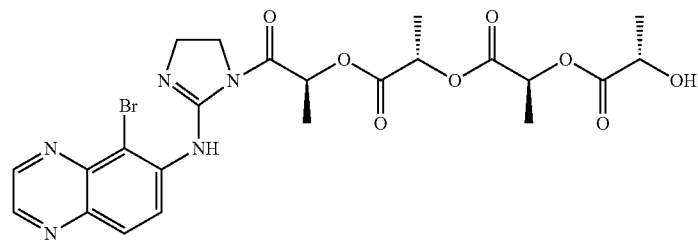 [SMILES: C[C@H](O)C(=O)O[C@@H](C)C(=O)O[C@@H](C)C(=O)O[C@@H](C)C(=O)N1CCN=C1Nc1ccc2nccnc2c1Br]
123-4a
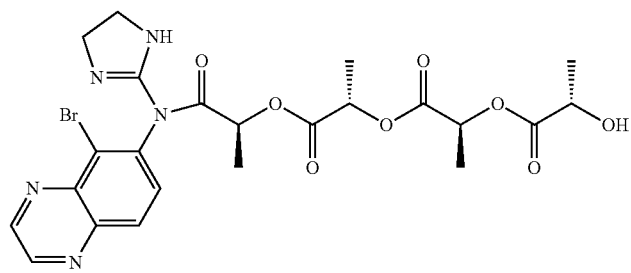 [SMILES: C[C@H](O)C(=O)O[C@@H](C)C(=O)O[C@@H](C)C(=O)O[C@@H](C)C(=O)N(C1=NCCN1)c1ccc2nccnc2c1Br]
123-4b
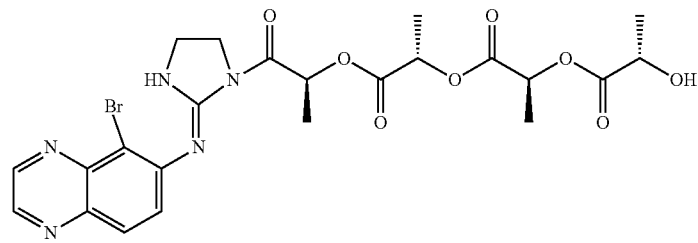 [SMILES: C[C@H](O)C(=O)O[C@@H](C)C(=O)O[C@@H](C)C(=O)O[C@@H](C)C(=O)N1CCN/C1=N\c1ccc2nccnc2c1Br]
123-4c
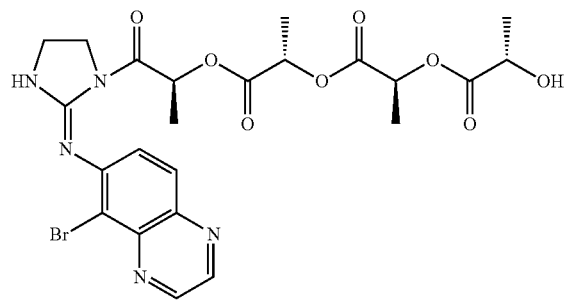 [SMILES: C[C@H](O)C(=O)O[C@@H](C)C(=O)O[C@@H](C)C(=O)O[C@@H](C)C(=O)N1CCN/C1=N/c1ccc2nccnc2c1Br]

TABLE 8B-continued
*Additional Non-limiting Examples of compounds of the Present Invention*
124-4
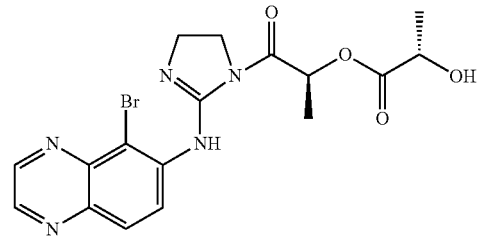 [SMILES: C[C@H](O)C(=O)O[C@@H](C)C(=O)N1CCN=C1Nc1ccc2nccnc2c1Br]
124-4a
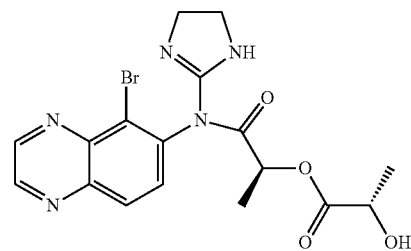 [SMILES: C[C@H](O)C(=O)O[C@@H](C)C(=O)N(C1=NCCN1)c1ccc2nccnc2c1Br]
124-4b
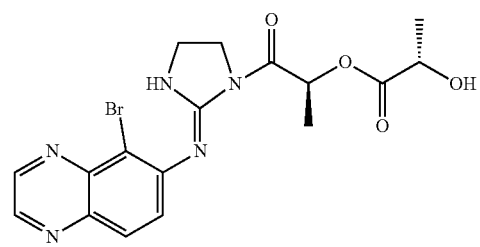 [SMILES: C[C@H](O)C(=O)O[C@@H](C)C(=O)N1CCN/C1=N\c1ccc2nccnc2c1Br]
124-4c
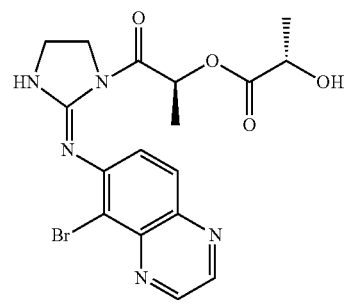

TABLE 8C
Select Compounds of the Present Invention
150 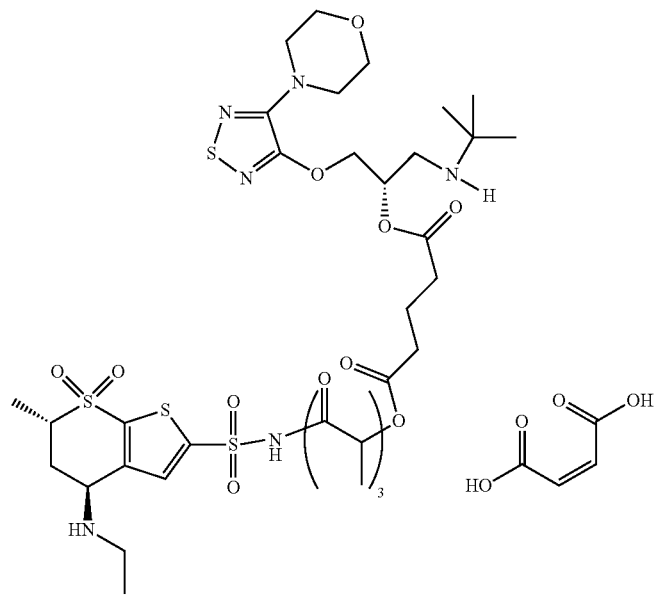
151 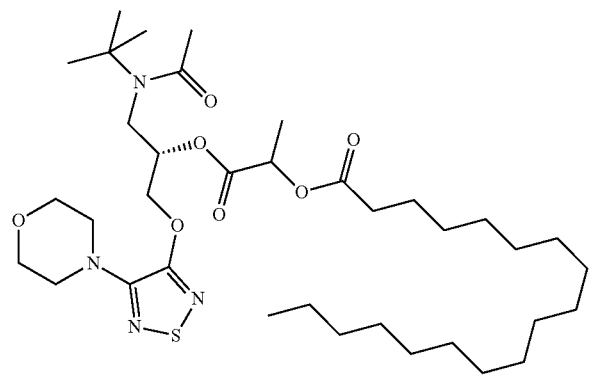 [SMILES: CCCCCCCCCCCCCCCCCC(=O)OC(C)C(=O)O[C@H](COc1nsnc1N1CCOCC1)CN(C(C)=O)C(C)(C)C]
152 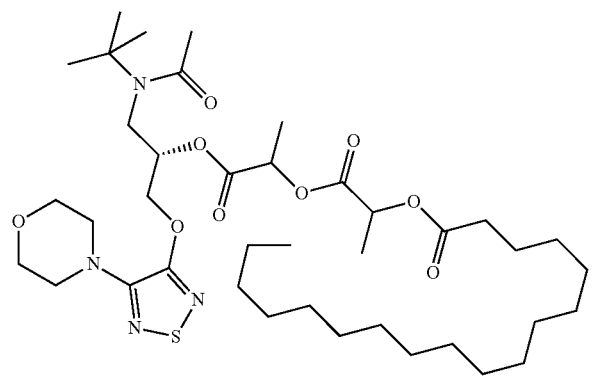 [SMILES: CCCCCCCCCCCCCCCCCC(=O)OC(C)C(=O)OC(C)C(=O)O[C@H](COc1nsnc1N1CCOCC1)CN(C(C)=O)C(C)(C)C]

TABLE 8C-continued
Select Compounds of the Present Invention
153 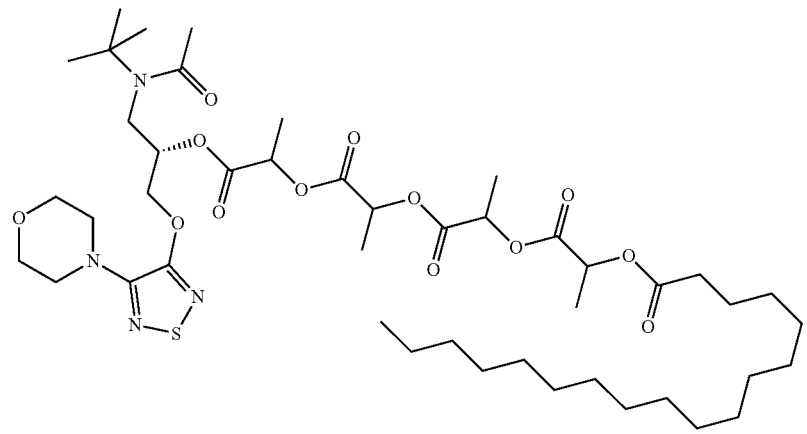 [SMILES: CCCCCCCCCCCCCCCCCC(=O)OC(C)C(=O)OC(C)C(=O)OC(C)C(=O)OC(C)C(=O)O[C@H](COc1nsnc1N1CCOCC1)CN(C(C)=O)C(C)(C)C]
154 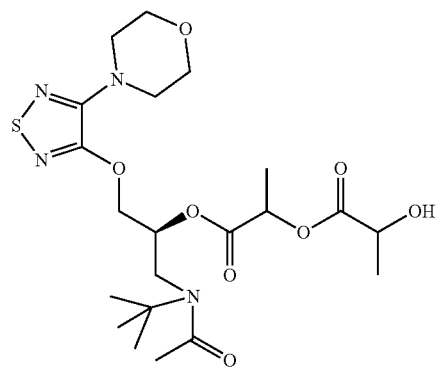 [SMILES: CC(=O)N(C[C@@H](COc1nsnc1N1CCOCC1)OC(=O)C(C)OC(=O)C(C)O)C(C)(C)C]
155 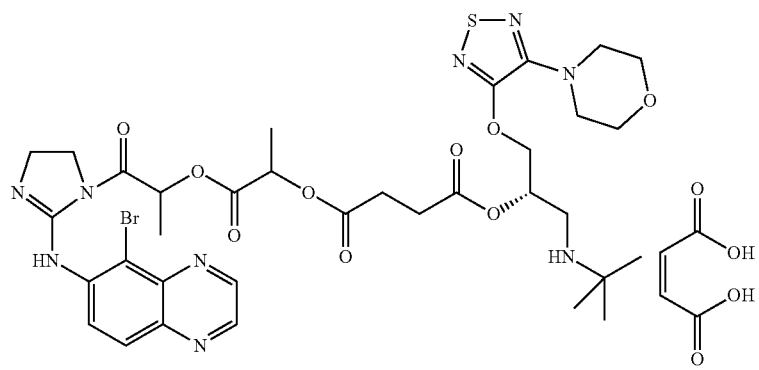
156 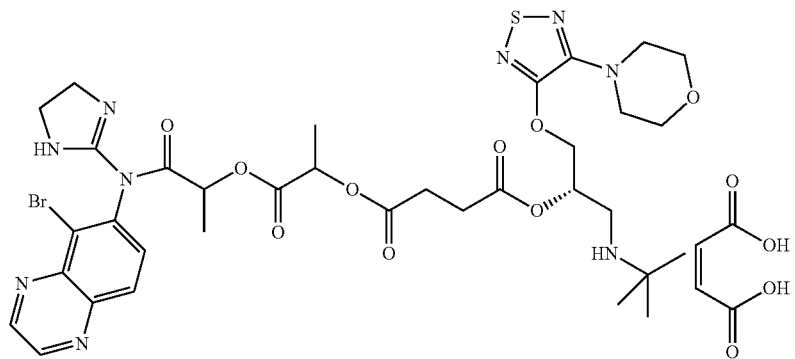

TABLE 8C-continued
Select Compounds of the Present Invention
157 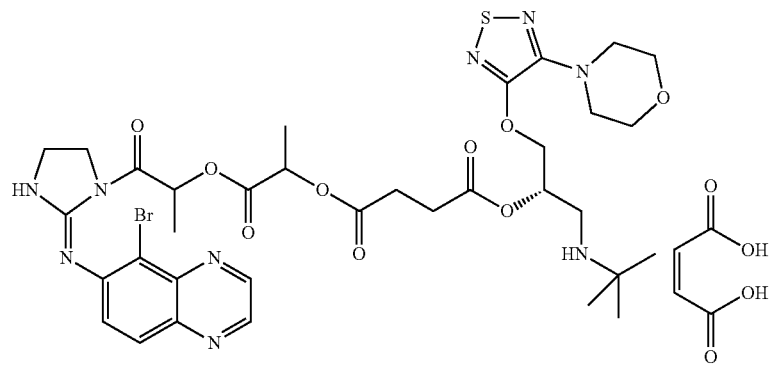
158 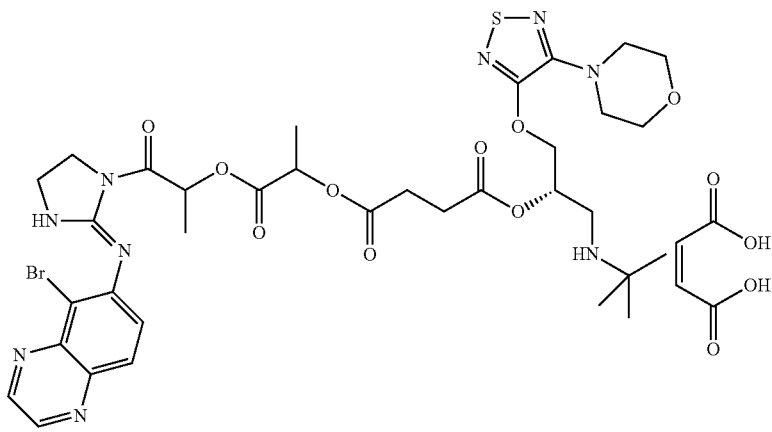
159 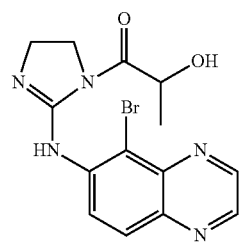 [SMILES: CC(O)C(=O)N1CCN=C1Nc1ccc2nccnc2c1Br]
160 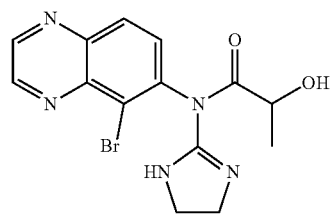 [SMILES: CC(O)C(=O)N(C1=NCCN1)c1ccc2nccnc2c1Br]
161 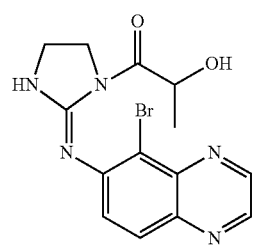 [SMILES: CC(O)C(=O)N1CCN/C1=N/c1ccc2nccnc2c1Br]

TABLE 8C-continued
Select Compounds of the Present Invention
162 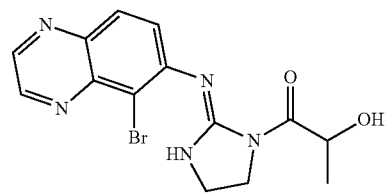 [SMILES: CC(O)C(=O)N1CCN/C1=N\c1ccc2nccnc2c1Br]
163 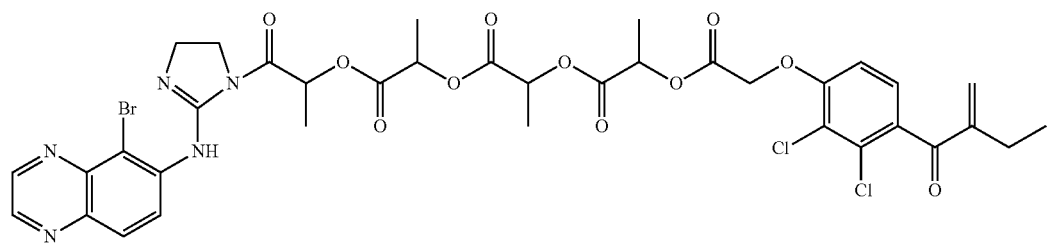 [SMILES: C=C(CC)C(=O)c1ccc(OCC(=O)OC(C)C(=O)OC(C)C(=O)OC(C)C(=O)OC(C)C(=O)N2CCN=C2Nc2ccc3nccnc3c2Br)c(Cl)c1Cl]
164 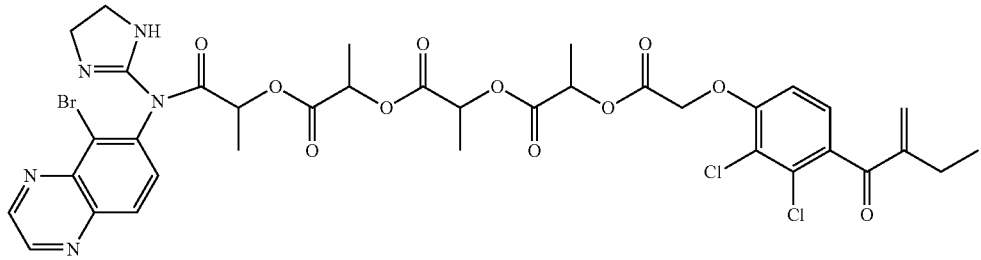 [SMILES: C=C(CC)C(=O)c1ccc(OCC(=O)OC(C)C(=O)OC(C)C(=O)OC(C)C(=O)OC(C)C(=O)N(C2=NCCN2)c2ccc3nccnc3c2Br)c(Cl)c1Cl]
165 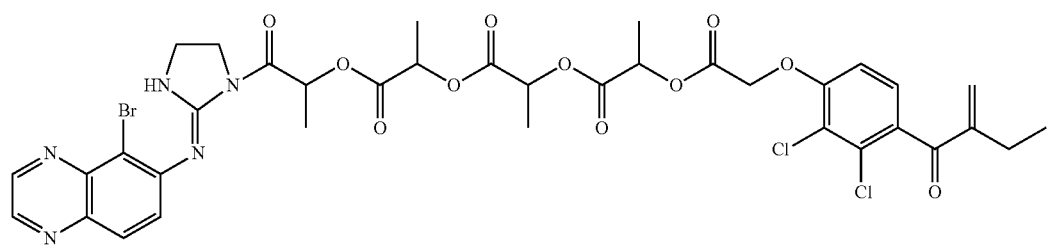 [SMILES: C=C(CC)C(=O)c1ccc(OCC(=O)OC(C)C(=O)OC(C)C(=O)OC(C)C(=O)OC(C)C(=O)N2CCN/C2=N\c2ccc3nccnc3c2Br)c(Cl)c1Cl]
166 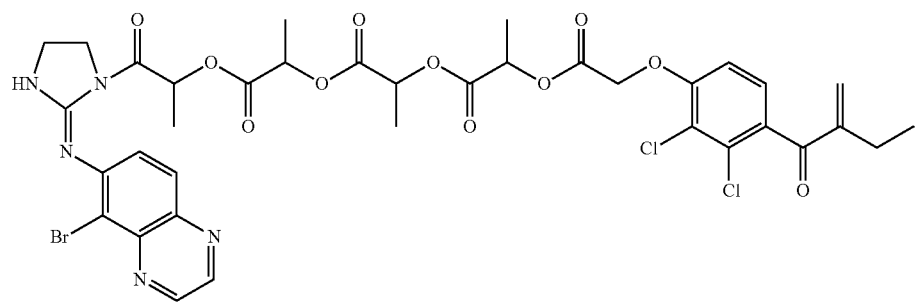 [SMILES: C=C(CC)C(=O)c1ccc(OCC(=O)OC(C)C(=O)OC(C)C(=O)OC(C)C(=O)OC(C)C(=O)N2CCN/C2=N/c2ccc3nccnc3c2Br)c(Cl)c1Cl]

TABLE 8C-continued
Select Compounds of the Present Invention
167
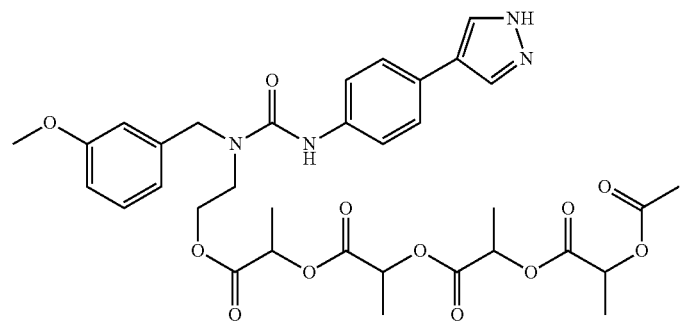 [SMILES: COc1cccc(CN(CCOC(=O)C(C)OC(=O)C(C)OC(=O)C(C)OC(=O)C(C)OC(C)=O)C(=O)Nc2ccc(-c3cn[nH]c3)cc2)c1]
168
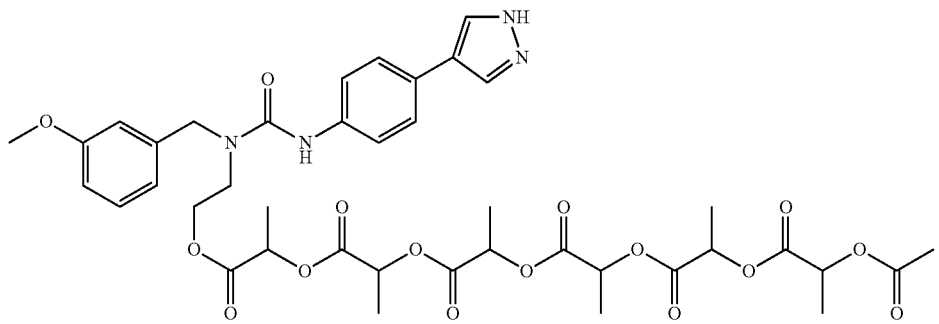 [SMILES: COc1cccc(CN(CCOC(=O)C(C)OC(=O)C(C)OC(=O)C(C)OC(=O)C(C)OC(=O)C(C)OC(=O)C(C)OC(C)=O)C(=O)Nc2ccc(-c3cn[nH]c3)cc2)c1]
169
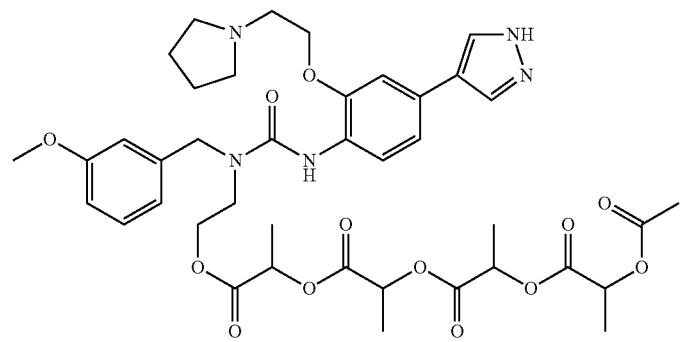 [SMILES: COc1cccc(CN(CCOC(=O)C(C)OC(=O)C(C)OC(=O)C(C)OC(=O)C(C)OC(C)=O)C(=O)Nc2ccc(-c3cn[nH]c3)cc2OCCN2CCCC2)c1]
170
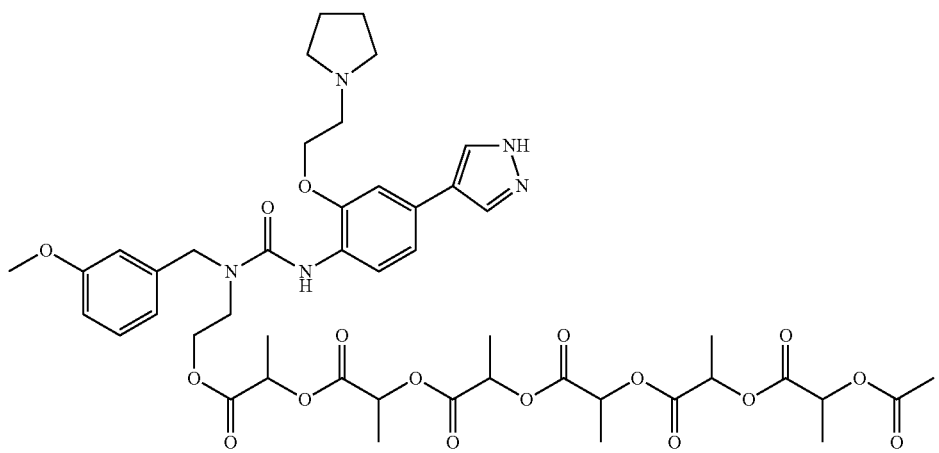 [SMILES: COc1cccc(CN(CCOC(=O)C(C)OC(=O)C(C)OC(=O)C(C)OC(=O)C(C)OC(=O)C(C)OC(=O)C(C)OC(C)=O)C(=O)Nc2ccc(-c3cn[nH]c3)cc2OCCN2CCCC2)c1]

TABLE 8C-continued
Select Compounds of the Present Invention
171 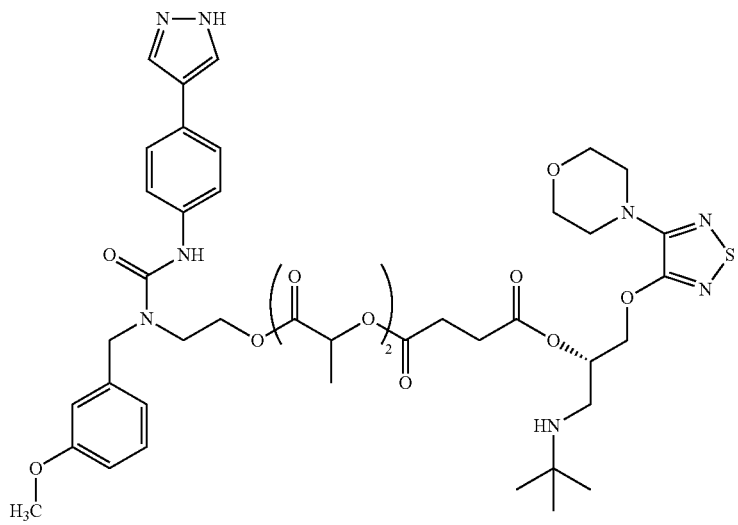
172 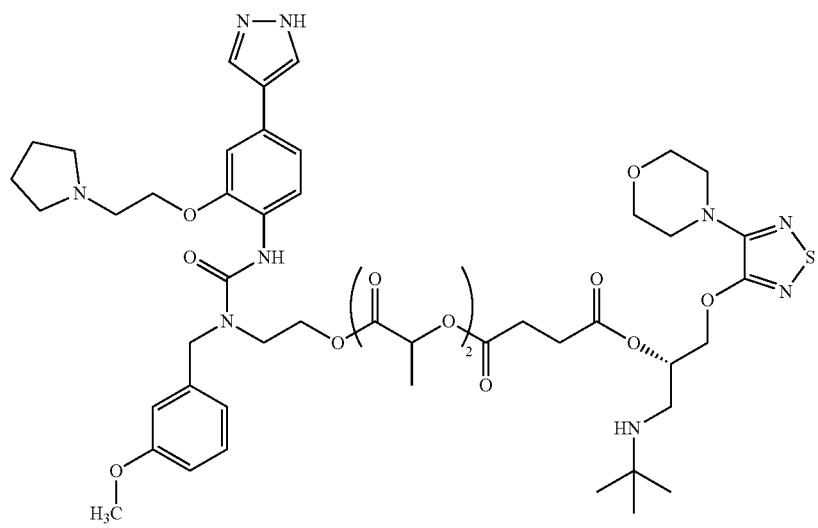
173 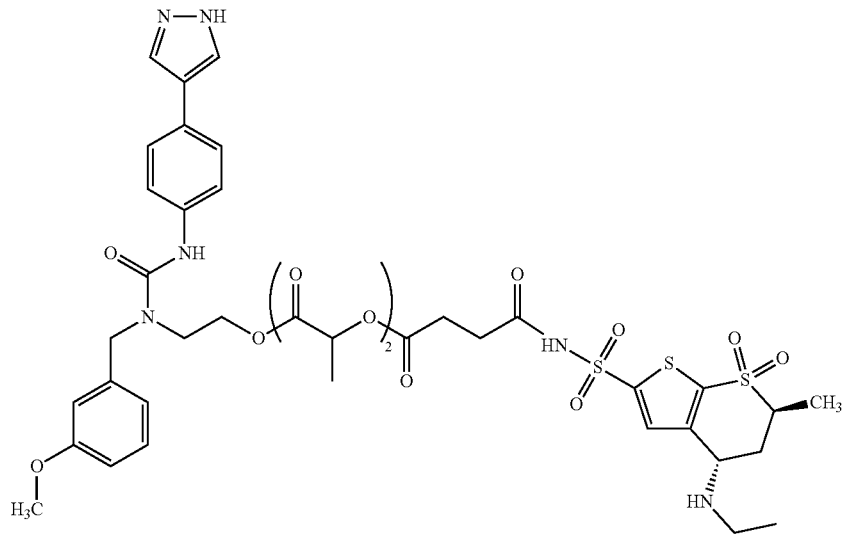

US 11,548,861 B2
827                                                                 828
TABLE 8C-continued
Select Compounds of the Present Invention
174
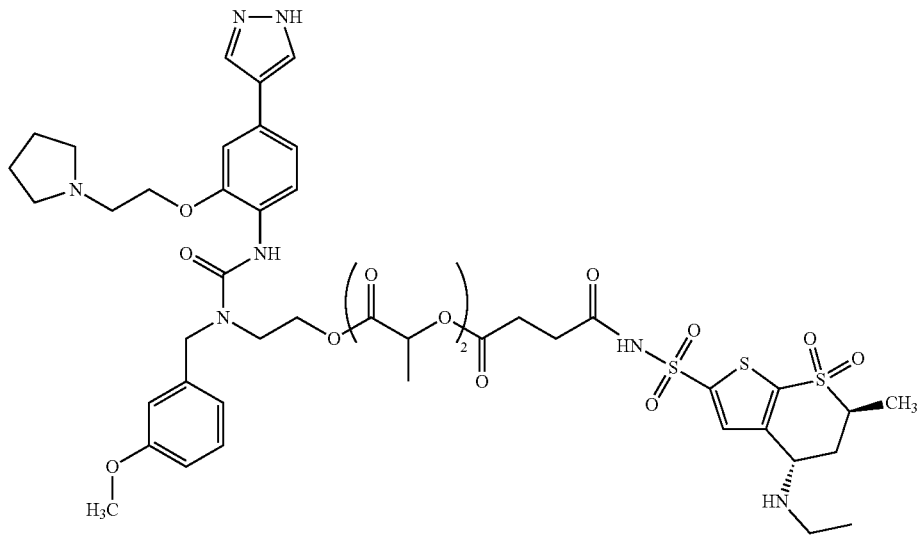
175
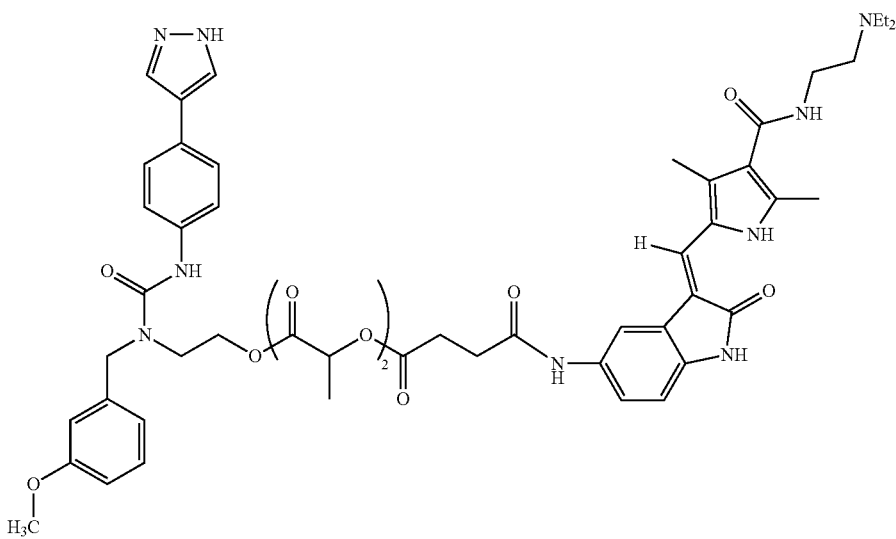
176
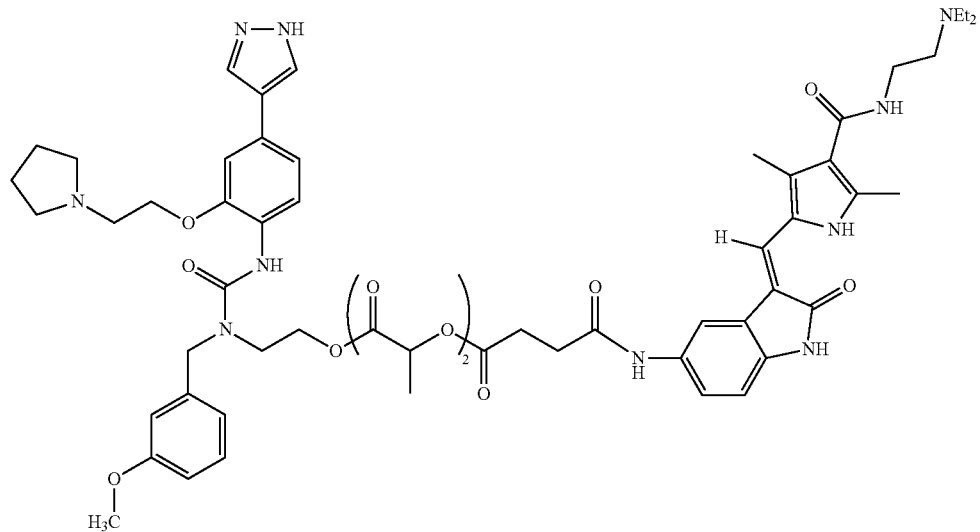

829
TABLE 8C-continued
Select Compounds of the Present Invention
177
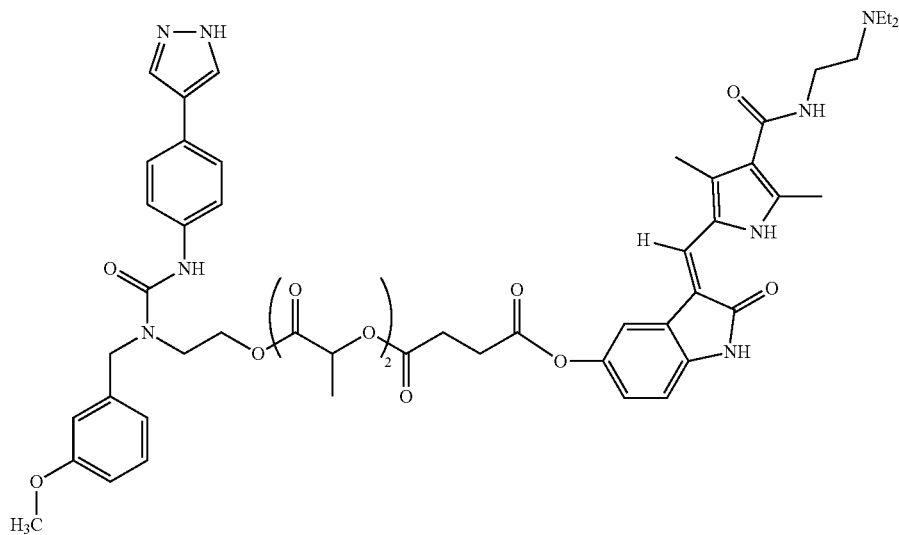
178
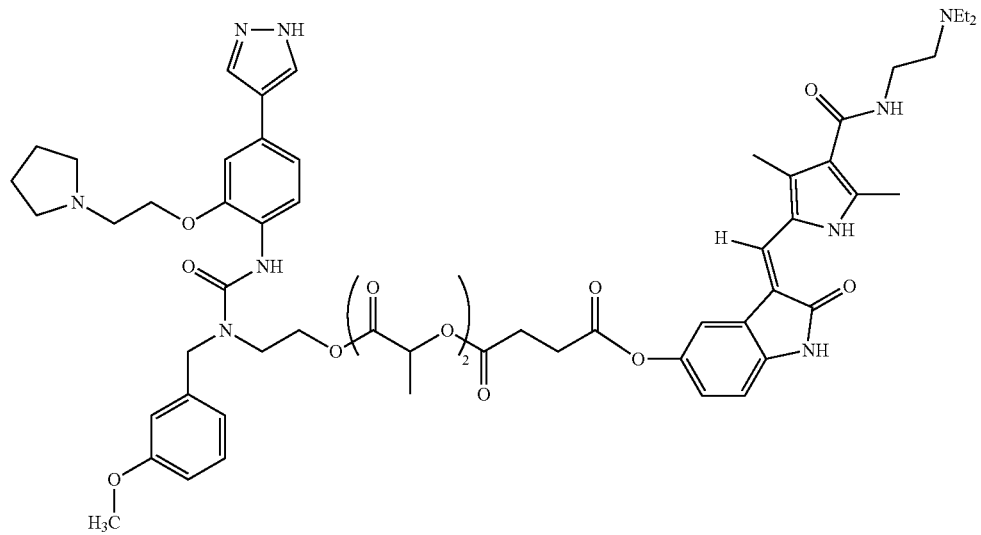
830

TABLE 8C-continued
Select Compounds of the Present Invention
179 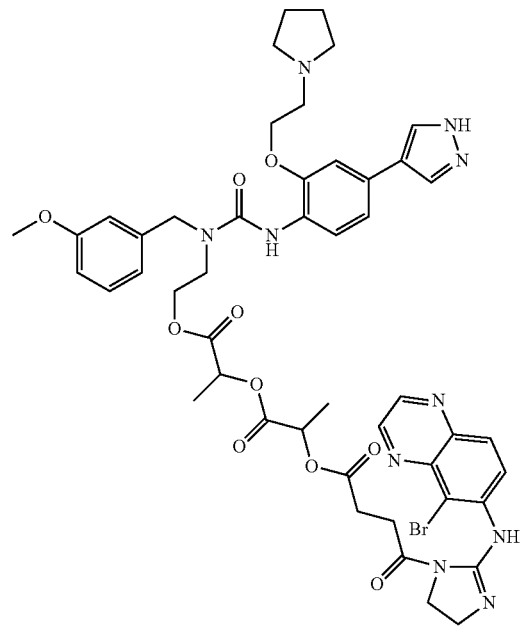 [SMILES: COc1cccc(CN(CCOC(=O)C(C)OC(=O)C(C)OC(=O)CCC(=O)N2CCN=C2Nc2ccc3nccnc3c2Br)C(=O)Nc2ccc(-c3cn[nH]c3)cc2OCCN2CCCC2)c1]
180 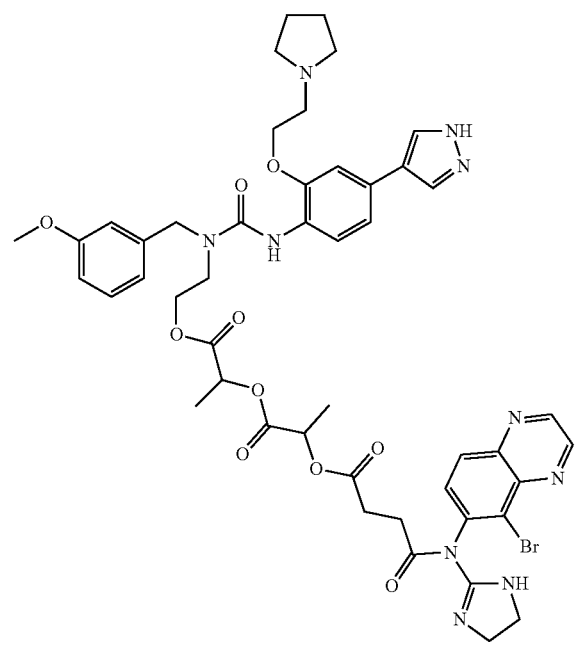 [SMILES: COc1cccc(CN(CCOC(=O)C(C)OC(=O)C(C)OC(=O)CCC(=O)N(C2=NCCN2)c2ccc3nccnc3c2Br)C(=O)Nc2ccc(-c3cn[nH]c3)cc2OCCN2CCCC2)c1]

TABLE 8C-continued
Select Compounds of the Present Invention
181
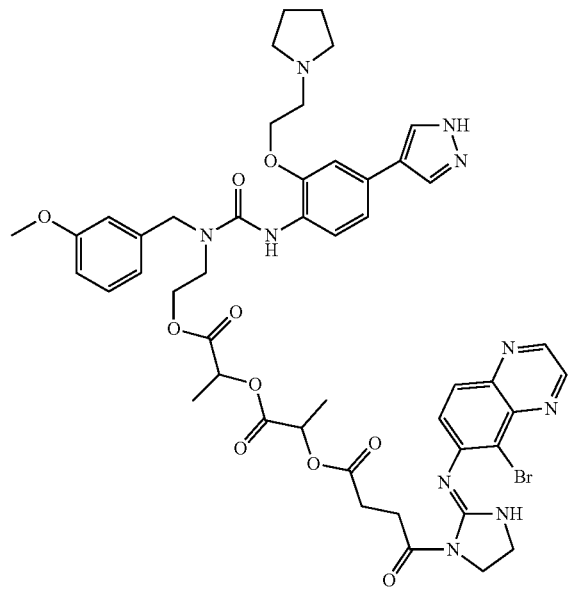 [SMILES: COc1cccc(CN(CCOC(=O)C(C)OC(=O)C(C)OC(=O)CCC(=O)N2CCN/C2=N\c2ccc3nccnc3c2Br)C(=O)Nc2ccc(-c3cn[nH]c3)cc2OCCN2CCCC2)c1]
182
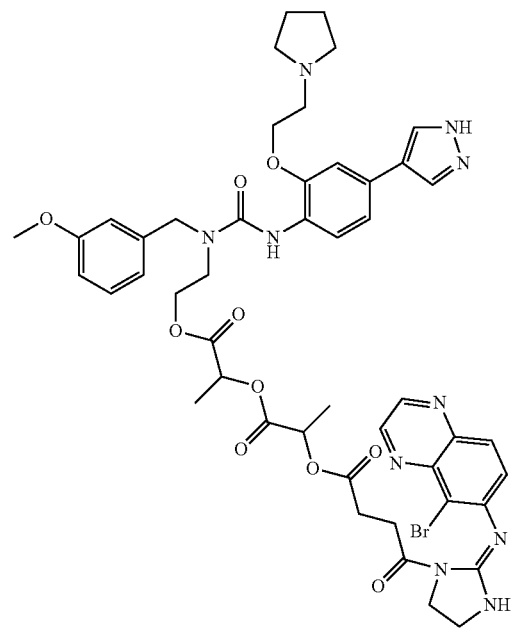 [SMILES: COc1cccc(CN(CCOC(=O)C(C)OC(=O)C(C)OC(=O)CCC(=O)N2CCN/C2=N/c2ccc3nccnc3c2Br)C(=O)Nc2ccc(-c3cn[nH]c3)cc2OCCN2CCCC2)c1]

TABLE 8C-continued
Select Compounds of the Present Invention
183
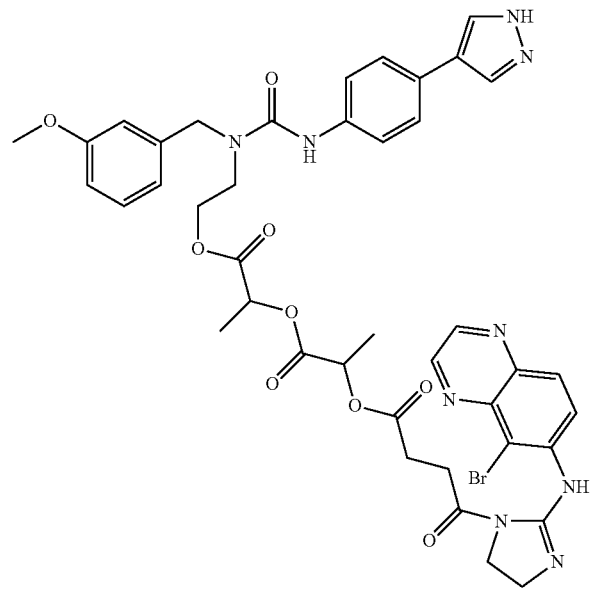 [SMILES: COc1cccc(CN(CCOC(=O)C(C)OC(=O)C(C)OC(=O)CCC(=O)N2CCN=C2Nc2ccc3nccnc3c2Br)C(=O)Nc2ccc(-c3cn[nH]c3)cc2)c1]
184
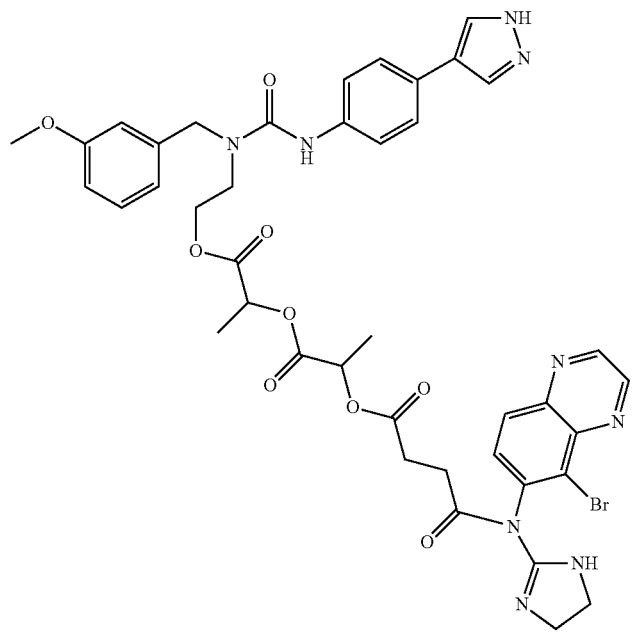 [SMILES: COc1cccc(CN(CCOC(=O)C(C)OC(=O)C(C)OC(=O)CCC(=O)N(C2=NCCN2)c2ccc3nccnc3c2Br)C(=O)Nc2ccc(-c3cn[nH]c3)cc2)c1]

TABLE 8C-continued
Select Compounds of the Present Invention
185
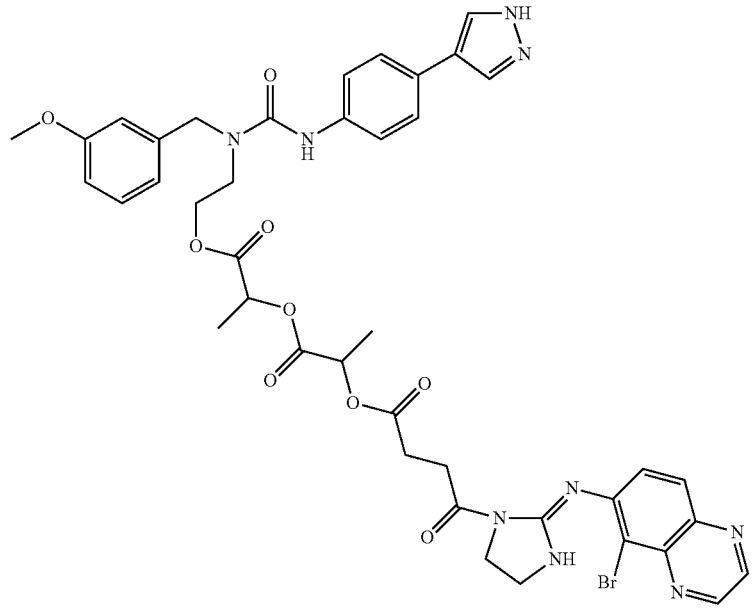 [SMILES: COc1cccc(CN(CCOC(=O)C(C)OC(=O)C(C)OC(=O)CCC(=O)N2CCN/C2=N\c2ccc3nccnc3c2Br)C(=O)Nc2ccc(-c3cn[nH]c3)cc2)c1]
186
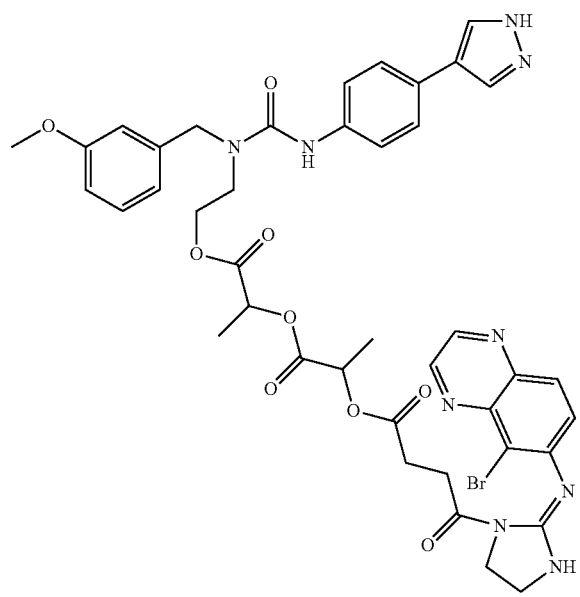 [SMILES: COc1cccc(CN(CCOC(=O)C(C)OC(=O)C(C)OC(=O)CCC(=O)N2CCN/C2=N/c2ccc3nccnc3c2Br)C(=O)Nc2ccc(-c3cn[nH]c3)cc2)c1]
187
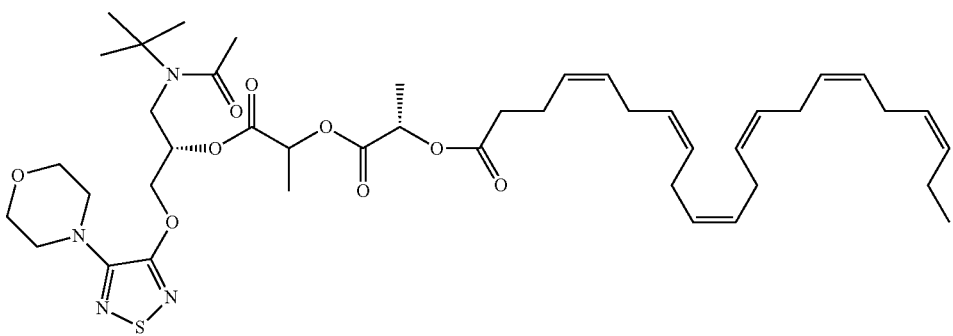 [SMILES: CC/C=C\C/C=C\C/C=C\C/C=C\C/C=C\C/C=C\CCC(=O)O[C@@H](C)C(=O)OC(C)C(=O)O[C@H](COc1nsnc1N1CCOCC1)CN(C(C)=O)C(C)(C)C]

TABLE 8C-continued
Select Compounds of the Present Invention
188
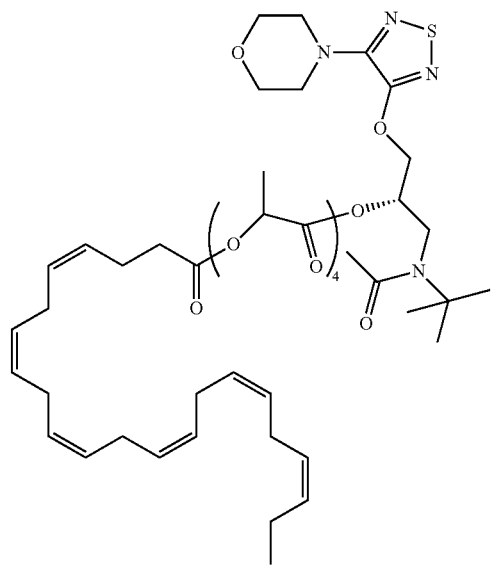
189
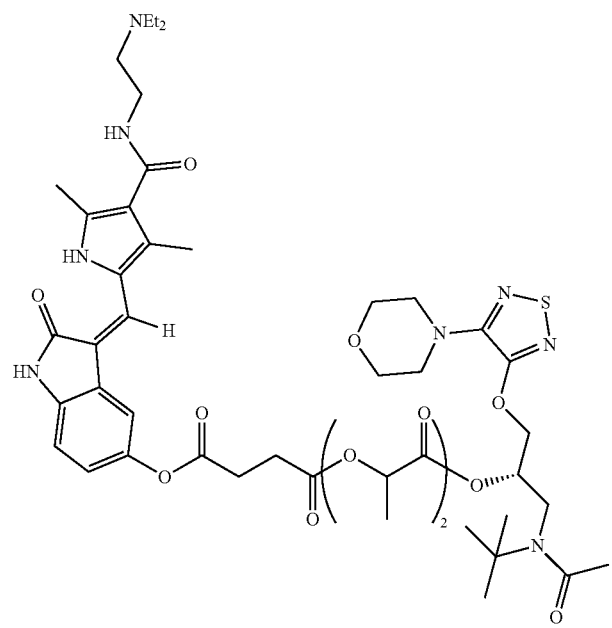

TABLE 8C-continued
Select Compounds of the Present Invention
190 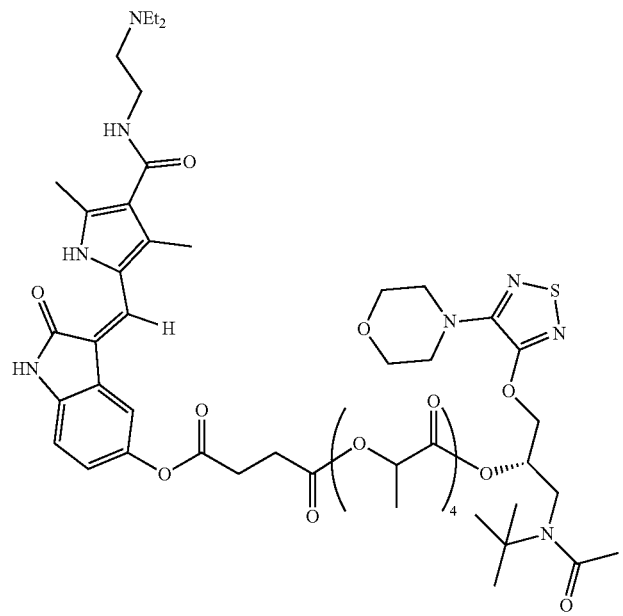
191 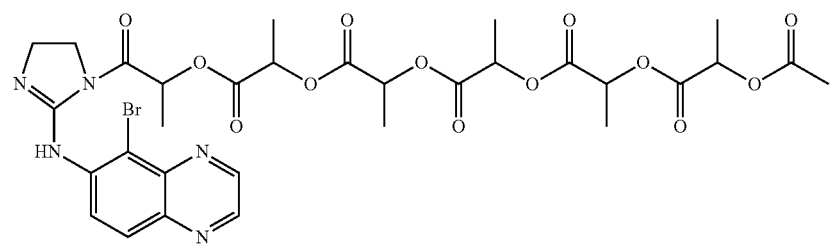 [SMILES: CC(=O)OC(C)C(=O)OC(C)C(=O)OC(C)C(=O)OC(C)C(=O)OC(C)C(=O)OC(C)C(=O)N1CCN=C1Nc1ccc2nccnc2c1Br]
192 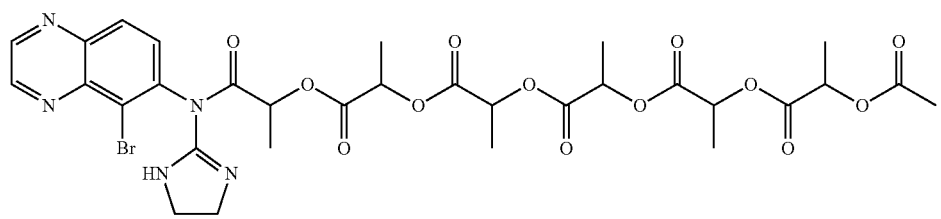 [SMILES: CC(=O)OC(C)C(=O)OC(C)C(=O)OC(C)C(=O)OC(C)C(=O)OC(C)C(=O)OC(C)C(=O)N(C1=NCCN1)c1ccc2nccnc2c1Br]
193 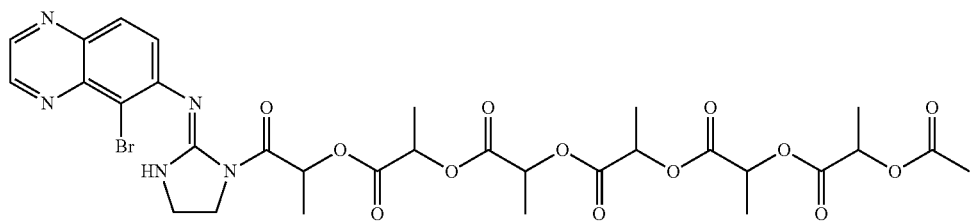 [SMILES: CC(=O)OC(C)C(=O)OC(C)C(=O)OC(C)C(=O)OC(C)C(=O)OC(C)C(=O)OC(C)C(=O)N1CCN/C1=N\c1ccc2nccnc2c1Br]
194 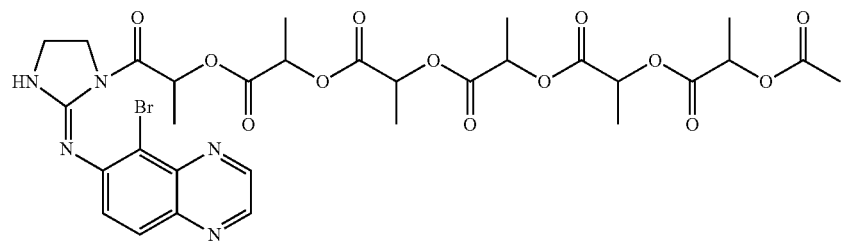 [SMILES: CC(=O)OC(C)C(=O)OC(C)C(=O)OC(C)C(=O)OC(C)C(=O)OC(C)C(=O)OC(C)C(=O)N1CCN/C1=N/c1ccc2nccnc2c1Br]

TABLE 8C-continued
Select Compounds of the Present Invention
195 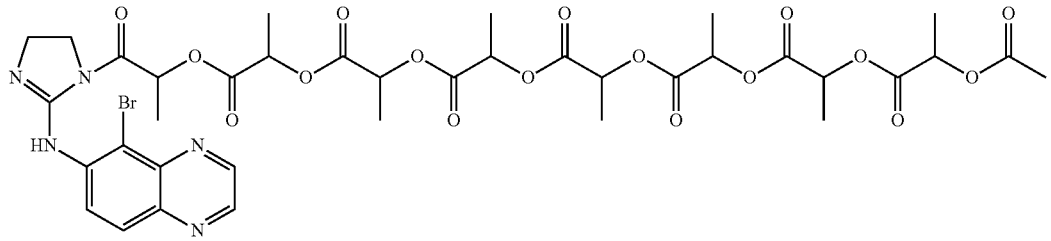 [SMILES: CC(=O)OC(C)C(=O)OC(C)C(=O)OC(C)C(=O)OC(C)C(=O)OC(C)C(=O)OC(C)C(=O)OC(C)C(=O)OC(C)C(=O)N1CCN=C1Nc1ccc2nccnc2c1Br]
196 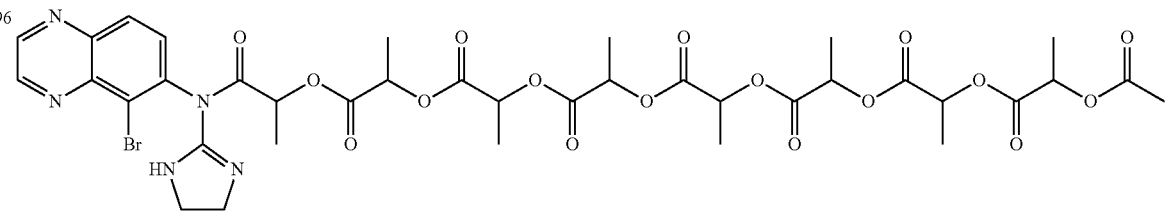
197 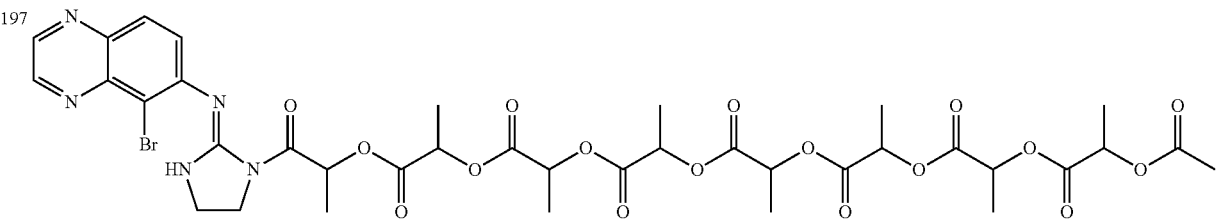
198 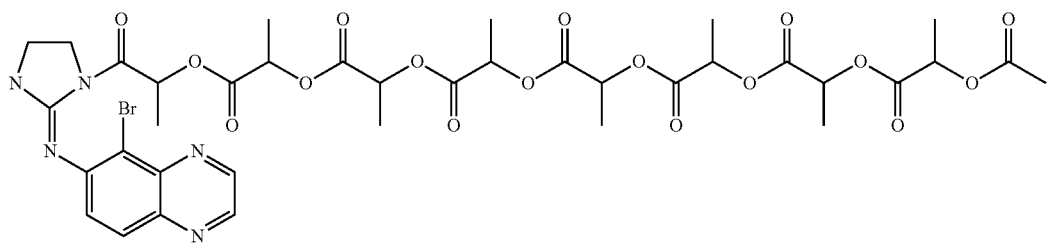 [SMILES: CC(=O)OC(C)C(=O)OC(C)C(=O)OC(C)C(=O)OC(C)C(=O)OC(C)C(=O)OC(C)C(=O)OC(C)C(=O)OC(C)C(=O)N1CCN/C1=N/c1ccc2nccnc2c1Br]
199 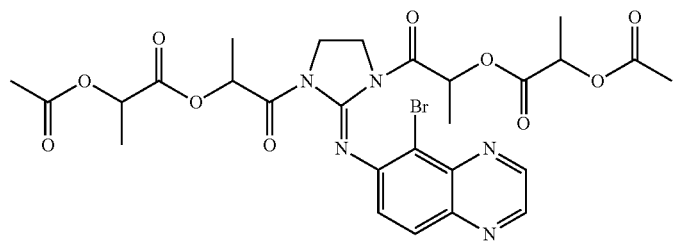 [SMILES: CC(=O)OC(C)C(=O)OC(C)C(=O)N1CCN(C(=O)C(C)OC(=O)C(C)OC(C)=O)C1=Nc1ccc2nccnc2c1Br]
200 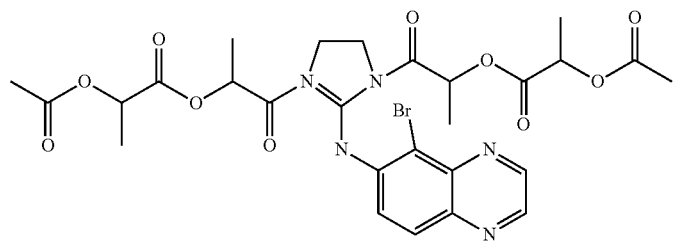

TABLE 8C-continued
Select Compounds of the Present Invention
201 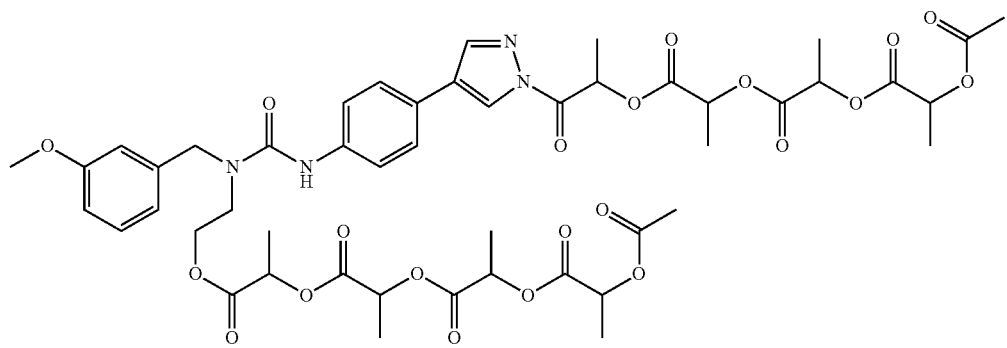 [SMILES: COc1cccc(CN(CCOC(=O)C(C)OC(=O)C(C)OC(=O)C(C)OC(=O)C(C)OC(C)=O)C(=O)Nc2ccc(-c3cnn(C(=O)C(C)OC(=O)C(C)OC(=O)C(C)OC(=O)C(C)OC(C)=O)c3)cc2)c1]
202 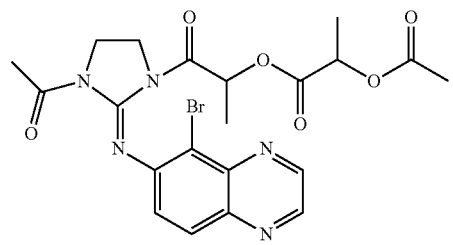 [SMILES: CC(=O)OC(C)C(=O)OC(C)C(=O)N1CCN(C(C)=O)/C1=N/c1ccc2nccnc2c1Br]
203 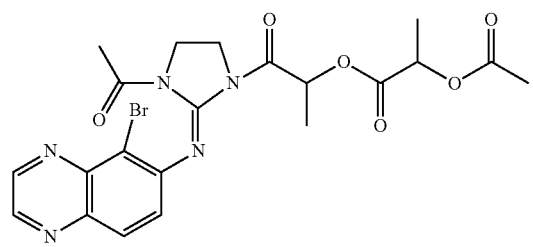 [SMILES: CC(=O)OC(C)C(=O)OC(C)C(=O)N1CCN(C(C)=O)/C1=N\c1ccc2nccnc2c1Br]
204 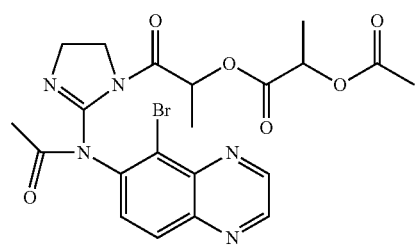 [SMILES: CC(=O)OC(C)C(=O)OC(C)C(=O)N1CCN=C1N(C(C)=O)c1ccc2nccnc2c1Br]
205 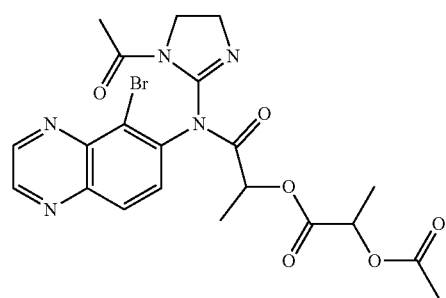 [SMILES: CC(=O)OC(C)C(=O)OC(C)C(=O)N(C1=NCCN1C(C)=O)c1ccc2nccnc2c1Br]

TABLE 8C-continued
Select Compounds of the Present Invention
206 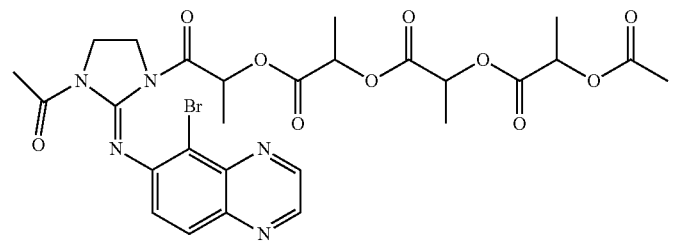 [SMILES: CC(=O)OC(C)C(=O)OC(C)C(=O)OC(C)C(=O)OC(C)C(=O)N1CCN(C(C)=O)/C1=N/c1ccc2nccnc2c1Br]
207 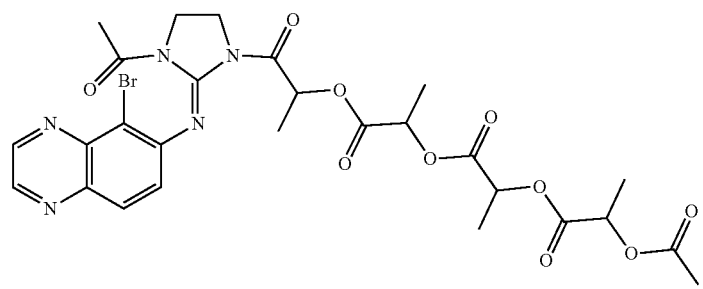 [SMILES: CC(=O)OC(C)C(=O)OC(C)C(=O)OC(C)C(=O)OC(C)C(=O)N1CCN(C(C)=O)/C1=N\c1ccc2nccnc2c1Br]
208 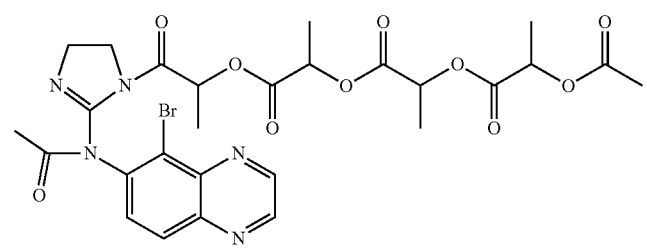 [SMILES: CC(=O)OC(C)C(=O)OC(C)C(=O)OC(C)C(=O)OC(C)C(=O)N1CCN=C1N(C(C)=O)c1ccc2nccnc2c1Br]
209 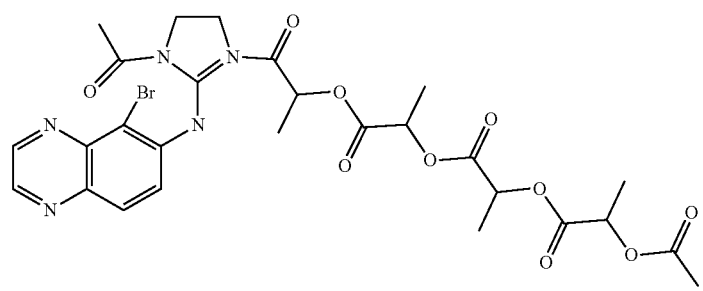
210 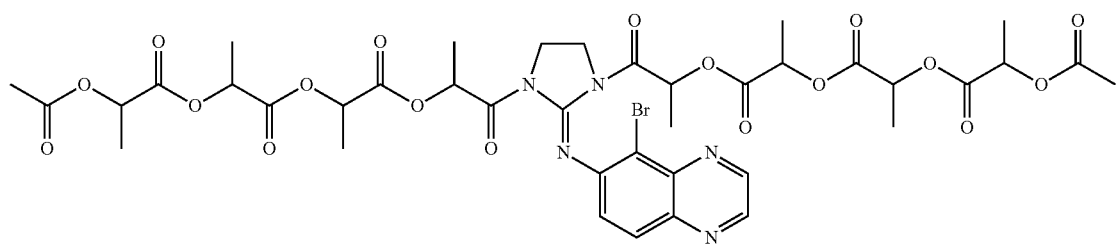 [SMILES: CC(=O)OC(C)C(=O)OC(C)C(=O)OC(C)C(=O)OC(C)C(=O)N1CCN(C(=O)C(C)OC(=O)C(C)OC(=O)C(C)OC(=O)C(C)OC(C)=O)C1=Nc1ccc2nccnc2c1Br]
211 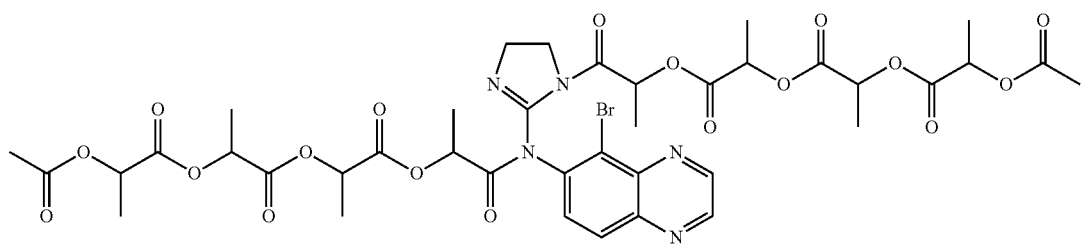 [SMILES: CC(=O)OC(C)C(=O)OC(C)C(=O)OC(C)C(=O)OC(C)C(=O)N1CCN=C1N(C(=O)C(C)OC(=O)C(C)OC(=O)C(C)OC(=O)C(C)OC(C)=O)c1ccc2nccnc2c1Br]

TABLE 8C-continued
Select Compounds of the Present Invention
212 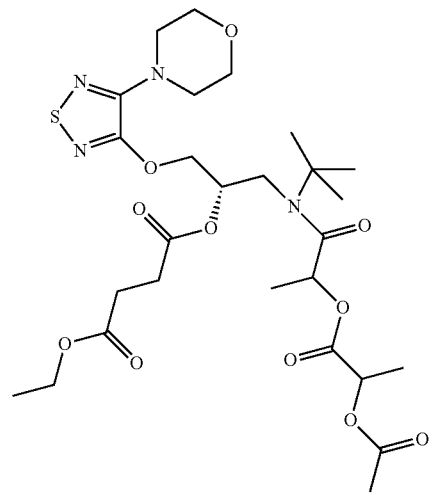 [SMILES: CCOC(=O)CCC(=O)O[C@H](COc1nsnc1N1CCOCC1)CN(C(=O)C(C)OC(=O)C(C)OC(C)=O)C(C)(C)C]
213 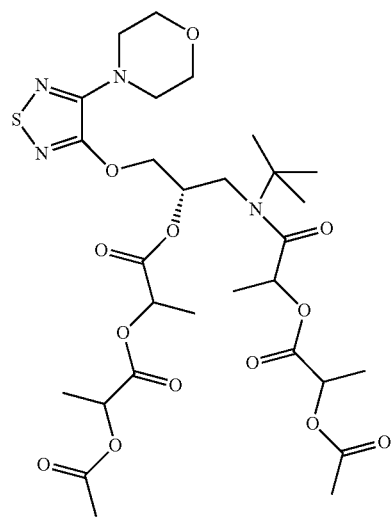 [SMILES: CC(=O)OC(C)C(=O)OC(C)C(=O)O[C@H](COc1nsnc1N1CCOCC1)CN(C(=O)C(C)OC(=O)C(C)OC(C)=O)C(C)(C)C]

TABLE 8C-continued
Select Compounds of the Present Invention
214
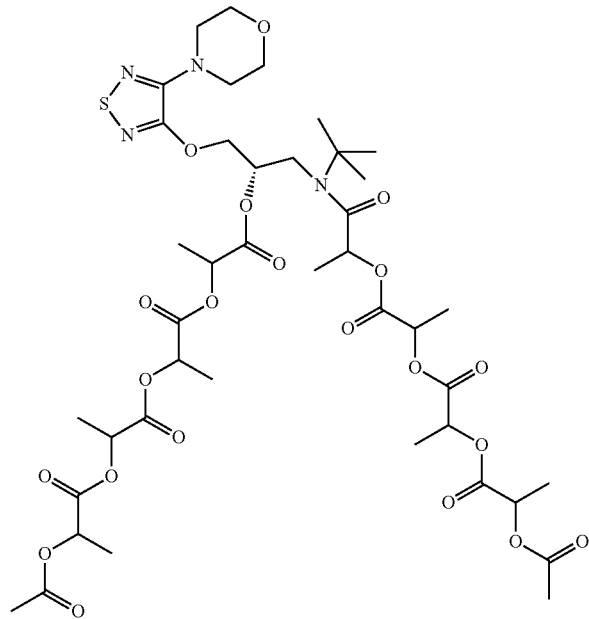 [SMILES: CC(=O)OC(C)C(=O)OC(C)C(=O)OC(C)C(=O)OC(C)C(=O)O[C@H](COc1nsnc1N1CCOCC1)CN(C(=O)C(C)OC(=O)C(C)OC(=O)C(C)OC(=O)C(C)OC(C)=O)C(C)(C)C]
215
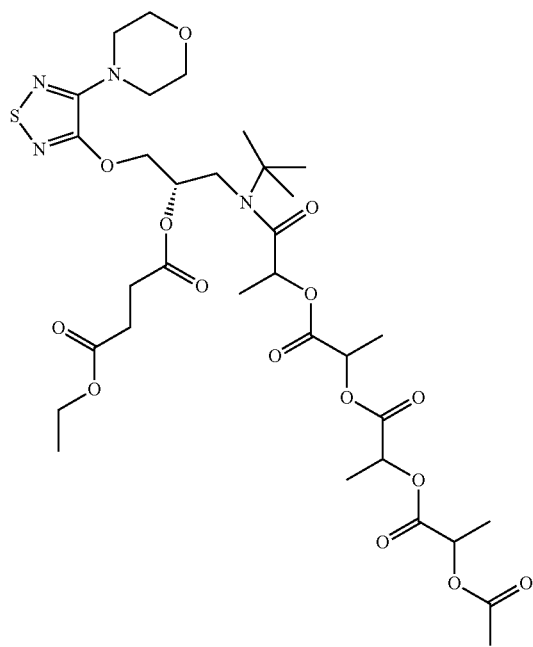 [SMILES: CCOC(=O)CCC(=O)O[C@H](COc1nsnc1N1CCOCC1)CN(C(=O)C(C)OC(=O)C(C)OC(=O)C(C)OC(=O)C(C)OC(C)=O)C(C)(C)C]

TABLE 8C-continued
Select Compounds of the Present Invention
216
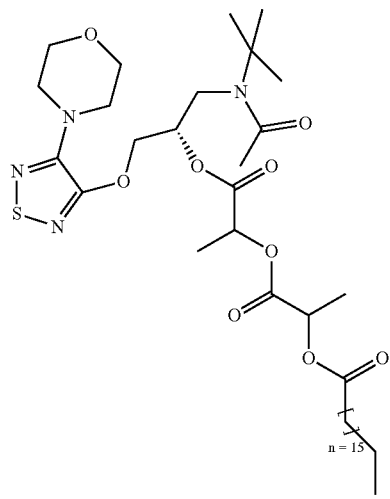
217
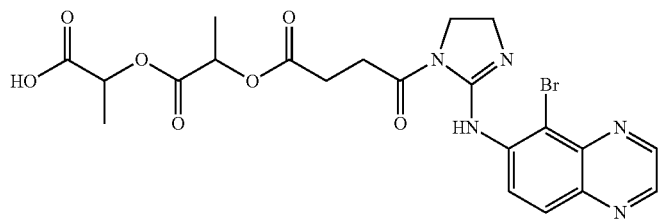 [SMILES: CC(OC(=O)C(C)OC(=O)CCC(=O)N1CCN=C1Nc1ccc2nccnc2c1Br)C(=O)O]
218
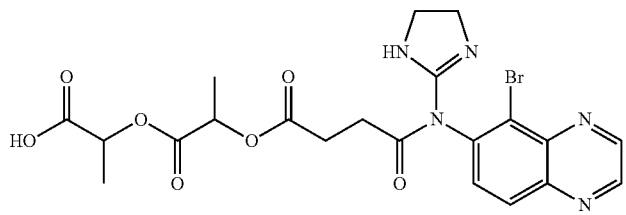 [SMILES: CC(OC(=O)C(C)OC(=O)CCC(=O)N(C1=NCCN1)c1ccc2nccnc2c1Br)C(=O)O]
219
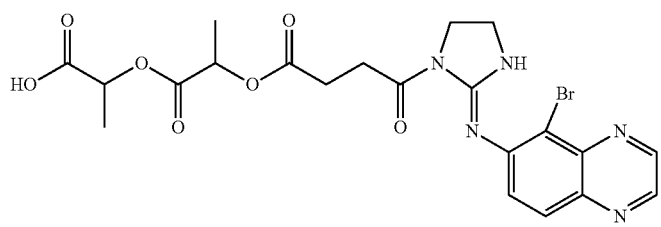 [SMILES: CC(OC(=O)C(C)OC(=O)CCC(=O)N1CCN/C1=N\c1ccc2nccnc2c1Br)C(=O)O]

TABLE 8C-continued
Select Compounds of the Present Invention
220
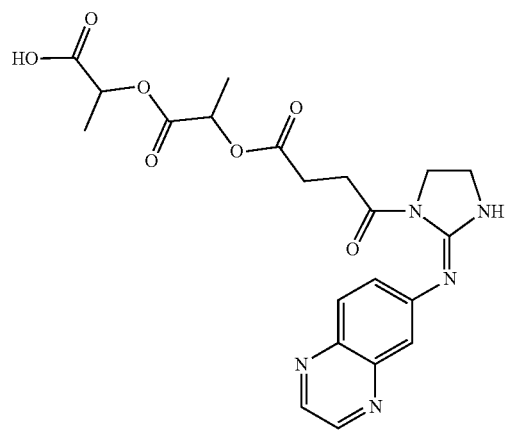 [SMILES: CC(OC(=O)C(C)OC(=O)CCC(=O)N1CCN/C1=N/c1ccc2nccnc2c1)C(=O)O]
221
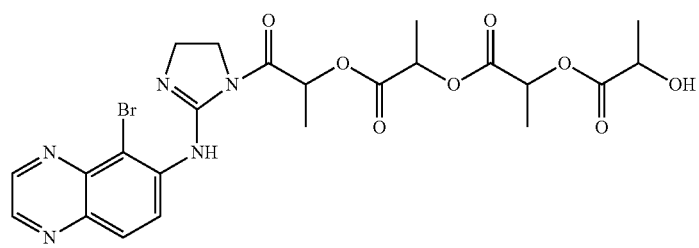 [SMILES: CC(O)C(=O)OC(C)C(=O)OC(C)C(=O)OC(C)C(=O)N1CCN=C1Nc1ccc2nccnc2c1Br]
222
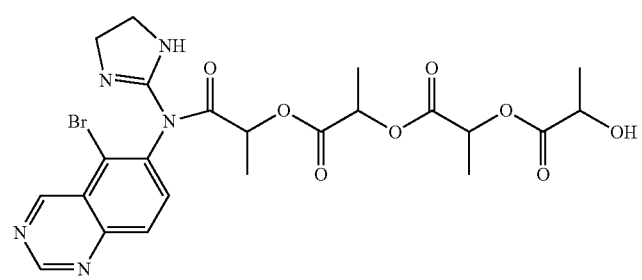 [SMILES: CC(O)C(=O)OC(C)C(=O)OC(C)C(=O)OC(C)C(=O)N(C1=NCCN1)c1ccc2ncncc2c1Br]
223
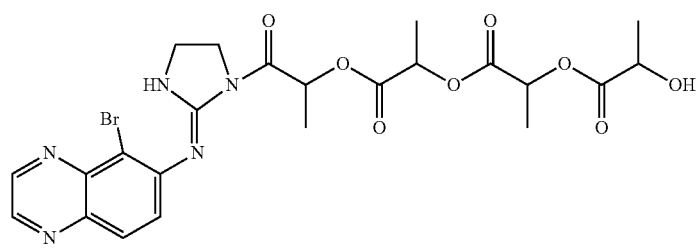 [SMILES: CC(O)C(=O)OC(C)C(=O)OC(C)C(=O)OC(C)C(=O)N1CCN/C1=N\c1ccc2nccnc2c1Br]
224
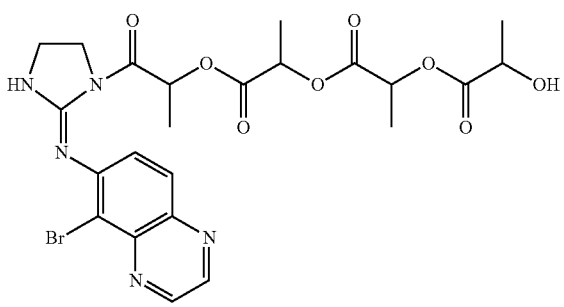 [SMILES: CC(O)C(=O)OC(C)C(=O)OC(C)C(=O)OC(C)C(=O)N1CCN/C1=N/c1ccc2nccnc2c1Br]

TABLE 8C-continued

Select Compounds of the Present Invention

225
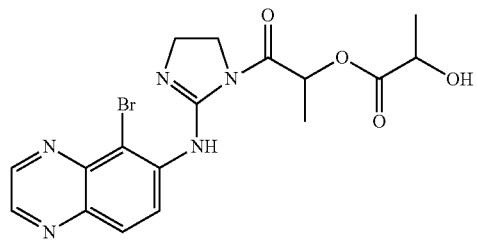 [SMILES: CC(O)C(=O)OC(C)C(=O)N1CCN=C1Nc1ccc2nccnc2c1Br]

226
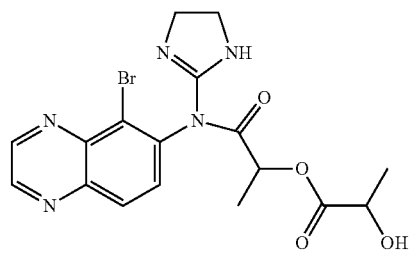 [SMILES: CC(O)C(=O)OC(C)C(=O)N(C1=NCCN1)c1ccc2nccnc2c1Br]

227
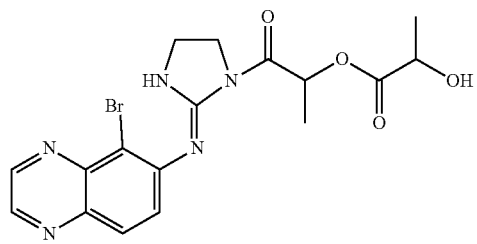 [SMILES: CC(O)C(=O)OC(C)C(=O)N1CCN/C1=N\c1ccc2nccnc2c1Br]

228
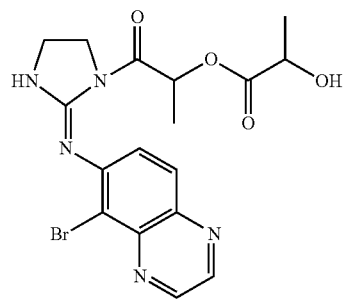 [SMILES: CC(O)C(=O)OC(C)C(=O)N1CCN/C1=N/c1ccc2nccnc2c1Br]

TABLE 8D

I Non-limiting Examples of Compounds of the Present Invention

| Active Moiety | General Name | Mw | Mw w/Salt | Molecular Formula |
|---|---|---|---|---|
| Timolol | N-acyl-Timolol-DHA | 668.95 | NA | $C_{37}H_{56}N_4O_5S$ |
| Timolol | N-acyl-Timolol-PLA (n = 2)-DHA | 813.07 | NA | $C_{43}H_{64}N_4O_9S$ |
| Timolol | N-acyl-Timolol-PLA (n = 4)-DHA | 957.2 | NA | $C_{49}H_{72}N_4O_{13}S$ |
| Timolol | N-acyl-Timolol-PLA (n = 2) | 502.59 | NA | $C_{21}H_{34}N_4O_8S$ |
| Timolol, Sunitinib | N-acyl-Timolol-PLA (n = 2)-succinate-Sunitinib | 981.14 | NA | $C_{47}H_{64}N_8O_{13}S$ |
| Timolol, Sunitinib | N-acyl-Timolol-PLA (n = 4)-succinate-Sunitinib | 1125.27 | NA | $C_{53}H_{72}N_8O_{17}S$ |
| Ethacrynic acid | Ethacrynic acid-PLA (n = 4)-Ethyl ester | 619.45 | NA | $C_{27}H_{32}C_{12}O_{12}$ |
| Ethacrynic acid | Ethacrynic acid-PLA (n = 2)-Ethyl ester | 475.33 | NA | $C_{21}H_{24}C_{12}O_8$ |
| Timolol | Timolol-O-Succinate | 416.5 | NA | $C_{17}H_{28}N_4O_6S$ |
| Timolol | Timolol-O-Ethylsuccinate-Maleate | 444.55 | 560.62 (Maleate salt) | $C_{19}H_{32}N_4O_6S \cdot C_4H_4O_4$ |

TABLE 8D-continued

I Non-limiting Examples of Compounds of the Present Invention

| Active Moiety | General Name | Mw | Mw w/Salt | Molecular Formula |
|---|---|---|---|---|
| Timolol | Timolol-O-Ethylsuccinate-HCl salt | 444.55 | 481.01 (HCl salt) | $C_{19}H_{32}N_4O_6S \cdot HCl$ |
| Timolol | Timolol-O-Maleate | 414.48 | NA | $C_{17}H_{26}N_4O_6S$ |
| Timolol | Timolol-O-Ethylmaleate-Maleic acid salt | 442.54 | 558.61 (Maleate salt) | $C_{19}H_{30}N_4O_6S \cdot C_4H_4O_4$ |
| Timolol | Timolol-O-Ethylmaleate-HCl salt | 442.54 | 479.0 (HCl salt) | $C_{19}H_{30}N_4O_6S \cdot HCl$ |
| Timolol | Timolol-O-Linoleic acid-Maleate | 578.86 | 694.93 (Maleate salt) | $C_{31}H_{54}N_4O_4S \cdot C4H4O4$ |
| Timolol | Timolol-O-Linoleic acid-HCl salt | 578.86 | 615.32 (HCl salt) | $C_{31}H_{54}N_4O_4S \cdot HCl$ |
| DHA | DHA | 328.5 | NA | $C_{22}H_{32}O_2$ |
| Brinzolamide | N-Methyl-Brinzolamide | 397.54 | NA | $C_{13}H_{23}N_3O_5S_3$ |
| Brinzolamide | N-Methyl-Dorzolamide | 338.47 | NA | $C_{11}H_{18}N_2O_4S_3$ |
| Dorzolamide | Dorzolamide-DHA conjugate | 634.93 | NA | $C_{32}H_{46}N_2O_5S_3$ |
| Timolol, Dorzolamide | Timolol-succinate-Dorzolamide-maleate | 722.93 | 839.00 (Maleate salt) | $C_{27}H_{42}N_6O_9S_4 \cdot C_4H_4O_4$ |
| Timolol, Brinzolamide | Timolol-succinate-Brinzolamide-maleate | 781.99 | 898.06 (Maleate salt) | $C_{29}H_{47}N_7O_{10}S_4 \cdot C_4H_4O_4$ |
| Timolol, Brimonidine | Brimonidine-Succinate-Timolol-maleate | 690.62 | 806.69 (Maleate salt) | $C_{28}H_{36}BrN_9O_5S \cdot C_4H_4O_4$ |
| Sunitinib | 5-Hydroxy Sunitinib-DHA | 706.98 | NA | $C_{44}H_{58}N_4O_4$ |
| Timolol | Timolol-Succinate-Ethyl-PLA (n = 4)-Maleate | 732.81 | 848.81 (Maleate salt) | $C_{31}H_{48}N_4O_{14}S \cdot C_4H_4O_4$ |
| Timolol, Brimonidine | Timolol-succinate-PLA (n = 2)-Brimonidine | 834.75 | 950.82 (Maleate salt) | $C_{34}H_{44}BrN_9O_9S \cdot C_4H_4O_4$ |
| Brimonidine | Brimonidine-PLA (n = 1) | 364.2 | NA | $C_{14}H_{14}BrN_5O_2$ |
| Timolol, Dorzolamide | Timolol-Glutarate-Dorzolamide-maleate | 736.95 | 853.02 (Maleate salt) | $C_{28}H_{44}N_6O_9S_4 \cdot C_4H_4O_4$ |
| SA12590 | SA12590 | 307.35 | NA | $C_{19}H_{17}NO_3$ |
| Timolol, Dorzolamide | Timolol-O-Glutarate-PLA (n = 3)-Dorzolamide-maleate | 953.15 | 1069.22 (Maleate salt) | $C_{37}H_{56}N_6O_{15}S_4 \cdot C_4H_4O_4$ |
| Sorafenib | Sorafenib acid | 451.79 | NA | $C_{20}H_{13}ClF_3N_3O_4$ |
| Timolol, Brimonidine | Timolol-O-Glutarate-Brimonidine-Maleate | 704.65 | 820.72 (Maleate salt) | $C_{29}H_{38}BrN_9O_5S \cdot C_4H_4O_4$ |
| Timolol | Timolol-Sebacic acid-Timolol-Maleate | 799.07 | 1031.21 (Maleate salt) | $C_{36}H_{62}N_8O_8S_2 \cdot 2C_4H_4O_4$ |
| Sunitinib | 5-Amino-Sunitinib-Glutarate | 509.61 | NA | $C_{27}H_{35}N_5O_5$ |
| Sunitinib | 5-Amino-Sunitinib-Dodecanedioic acid | 607.8 | 838.1 (Dodecanedioic acid salt) | $C_{34}H_{49}N_5O_5 \cdot C_{12}H_{22}O_4$ |
| Timolol | Timolol-O-Ethylmaleate-HCl salt | 442.54 | 479.0 (HCl salt) | $C_{19}H_{30}N_4O_6S \cdot HCl$ |
| Dorzolamide | Dorzolamaide-Ethylfumarate | 450.55 | NA | $C_{16}H_{22}N_2O_7S_3$ |
| Sunitinib | 5-Amino-Sunitinib-Sebacic acid | 579.75 | 693.77 (TFA salt) | $C_{32}H_{45}N_5O_5 \cdot C_2HF_3O_2$ |
| Timolol | Timolol-Succinic acid-Timolol-Maleate | 714.91 | 947.05 (Maleate salt) | $C_{30}H_{50}N_8O_8S_2 \cdot 2C_4H_4O_4$ |
| Timolol | Timolol-Glutaric acid-Timolol-Maleate | 728.94 | 961.08 (Maleate salt) | $C_{31}H_{52}N_8O_8S_2 \cdot 2C_4H_4O_4$ |
| Dorzolamide | Dorzolamide-Stearylfumarate | 674.99 | NA | $C_{32}H_{54}N_2O_7S_3$ |
| Dorzolamide | Dorzolamide-Laurylmaleate | 590.83 | NA | $C_{24}H_{42}N_2O_7S_3$ |
| Timolol | Timolol-O-Laurylfumarate-maleate | 582.81 | 698.88 (Maleate salt) | $C_{29}H_{50}N_4O_6S \cdot C_4H_4O_4$ |
| Timolol | Timolol-O-Stearylfumarate-maleate | 666.97 | 783.04 (Maleate salt) | $C_{35}H_{62}N_4O_6S \cdot C_4H_4O_4$ |

TABLE 8D-continued

| | I Non-limiting Examples of Compounds of the Present Invention | | | |
|---|---|---|---|---|
| Active Moiety | General Name | Mw | Mw w/Salt | Molecular Formula |
| Timolol | Timolol-Fumarate-Timolol-Maleate | 712.89 | 945.03 (Maleate salt) | $C_{30}H_{48}N_8O_8S_2 \cdot 2C_4H_4O_4$ |
| Ethacrynic acid, Brimonidine | Brimonidine-PLA (n = 4)-Etacrynic acid | 865.53 | NA | $C_{36}H_{36}BrCl_2N_5O_{11}$ |
| RKI 1y | ROCK inhibitor-1y | 463.58 | NA | $C_{26}H_{33}N_5O_3$ |
| RKI Hydroxy 1y | 1-(2-hydroxyethyl)-1-[(3-methoxyphenyl)methyl]-3-[4-(1H-pyrazol-4-yl)-2-[2-(pyrrolidin-1-yl)ethoxy]phenyl]urea (RKI-Hydroxy-1y) | 479.58 | NA | $C_{26}H_{33}N_5O_4$ |
| SR5834 | 1-(2-hydroxyethyl)-1-[(3-methoxyphenyl)methyl]-3-[4-(1H-pyrazol-4-yl)phenyl]urea (RKI SR5834) | 366.42 | NA | $C_{20}H_{22}N_4O_3$ |
| Ethacrynic acid, Dorzolamide | Dorzolamide-PLA (n = 4)-Etacrynic acid | 897.83 | NA | $C_{35}H_{42}Cl_2N_2O_{15}S_3$ |
| Brimonidine | Brimonidine-Acetyl PLA(n = 6) | 766.56 | NA | $C_{31}H_{36}BrN_5O_{13}$ |
| Sunitinib | 5-Amino-Sunitinib-Succinamide | 477.57 | NA | $C_{26}H_{31}N_5O_4$ |
| Brimonidine | Brimonidine-Acetyl PLA(n = 8) | 910.69 | NA | $C_{37}H_{44}BrN_5O_{17}$ |
| Brimonidine | Brimonidine-Succinamide | 374.2 | NA | $C_{15}H_{12}BrN_5O_2$ |
| Brimonidine | Brimonidine-Bis-Acetyl PLA(n = 2) | 664.47 | NA | $C_{27}H_{30}BrN_5O_{10}$ |
| Ethacrynic acid | Ethyl PLA (n = 6)- Etacrynic acid | 763.58 | NA | $C_{33}H_{40}C_{12}O_{16}$ |
| Ethacrynic acid | Ethyl PLA (n = 8)- Etacrynic acid | 907.71 | NA | $C_{39}H_{48}C_{12}O_{20}$ |
| Ethacrynic acid, Sunitinib | 5-Amino Sunitinib-Etacrynic acid | 680.64 | NA | $C_{35}H_{39}Cl_2N_5O_5$ |
| Timolol, Sunitinib | Timolol-Succinate-5-Amino Sunitinib-maleate | 793.99 | 910.06 (Maleate salt) | $C_{26}H_{31}N_5O_4$ |
| SR5834 | SR5834-Acetyl PLA(n = 4) | 696.72 | NA | $C_{34}H_{40}N_4O_{12}$ |
| SR5834 | SR5834-Bis-Acetyl PLA(n = 4) | 1027.01 | NA | $C_{48}H_{58}N_4O_{21}$ |
| RKI Hydroxy ly | RKI-Hydroxy-ly-Acetyl PLA (n = 4) | 809.88 | NA | $C_{40}H_{51}N_5O_{13}$ |
| SR5834 | 1-(2-{[(3-methoxyphenyl)methyl]({[4-(1H-pyrazol-4-yl)phenyl]carbamoyl})amino}ethoxy)-1-oxopropan-2-yl 2-{[2-({2-[(2-{[2-(acetyloxy)propanoyl]oxy}propanoyl)oxy]propanoyl}oxy)propanoyl]oxy} propanoate | 840.85 | NA | $C_{40}H_{48}N_4O_{16}$ |
| Brimonidine | Brimonidine-Acetyl PLA(n = 2)-N-acetate | 520.34 | NA | $C_{21}H_{22}BrN_5O_6$ |
| Brimonidine | Brimonidine-Acetyl PLA(n = 4)-N-acetate | 664.47 | NA | $C_{27}H_{30}BrN_5O_{10}$ |
| Brimonidine | Brimonidine-Bis-Acetyl PLA (n = 4) | 952.73 | NA | $C_{39}H_{46}BrN_5O_{18}$ |
| Timolol, Ethacrynic acid | Timolol-Etacrynic acid-maleate | 601.55 | 717.62 (Maleate salt) | $C_{26}H_{34}C_{12}N_4O_6S \cdot C_4H_4O_4$ |
| Timolol | Timolol-Bis-N-Acetyl-PLA (n = 2)-O-Ethyl-succinate | 630.72 | NA | $C_{27}H_{42}N_4O_{11}S$ |
| Timolol | Timolol-Bis-Acetyl-PLA (n = 2) | 688.76 | NA | $C_{29}H_{44}N_4O_{13}S$ |
| SR5834, Brimonidine | SR5834-PLA(n = 2)-succinate-Brimonidine | 884.75 | NA | $C_{41}H_{42}BrN_9O_9$ |
| Ethacrynic acid, Sunitinib | 5-Amino Sunitinib-1,2-propyleneglycol-Etacrynic acid | 838.79 | NA | $C_{42}H_{49}C_{12}N_5O_9$ |
| Timolol | Timolol-Bis-Acetyl-PLA (n = 4) | 977.01 | NA | $C_{41}H_{60}N_4O_{21}S$ |
| Timolol | Timolol-Bis-N-Acetyl-PLA (n = 4)-O-Ethyl-succinate | 774.85 | NA | $C_{33}H_{50}N_4O_{15}S$ |

TABLE 8E
Select Compounds of the Present Invention
229
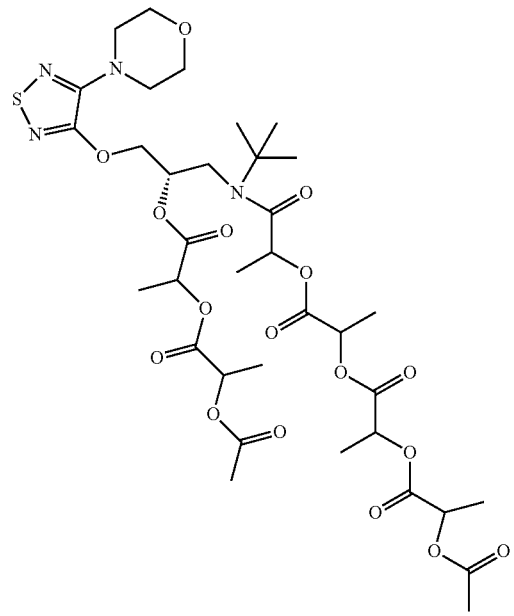 [SMILES: CC(=O)OC(C)C(=O)OC(C)C(=O)OC(C)C(=O)OC(C)C(=O)N(C[C@@H](COc1nsnc1N1CCOCC1)OC(=O)C(C)OC(=O)C(C)OC(C)=O)C(C)(C)C]
230
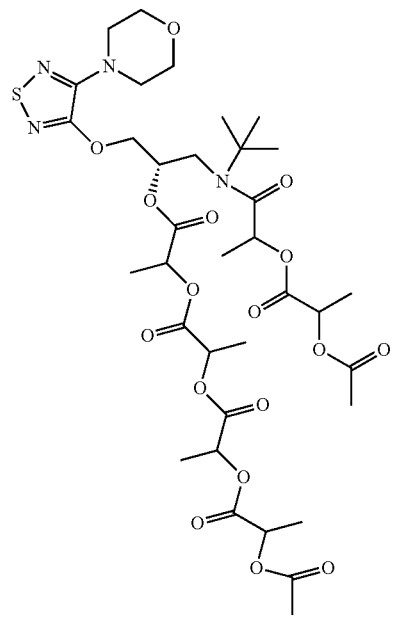 [SMILES: CC(=O)OC(C)C(=O)OC(C)C(=O)OC(C)C(=O)OC(C)C(=O)O[C@H](COc1nsnc1N1CCOCC1)CN(C(=O)C(C)OC(=O)C(C)OC(C)=O)C(C)(C)C]
231
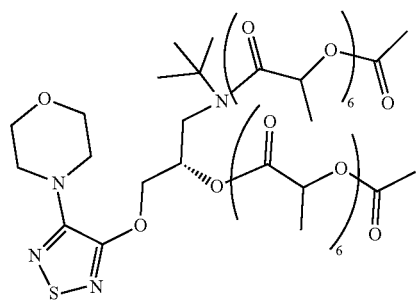

TABLE 8E-continued
Select Compounds of the Present Invention
232 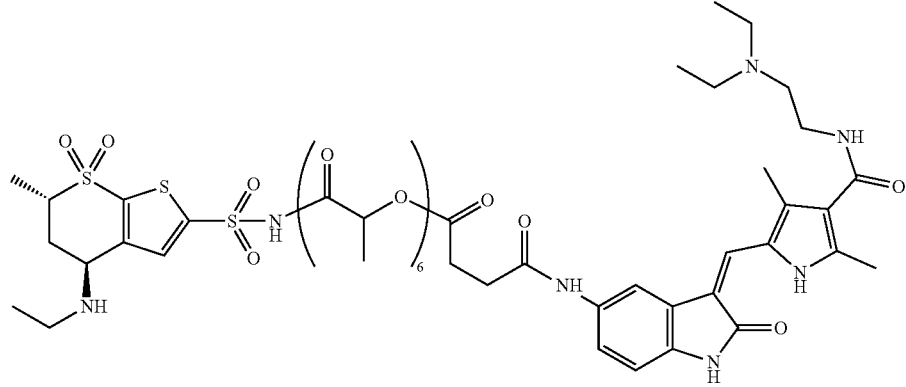
233 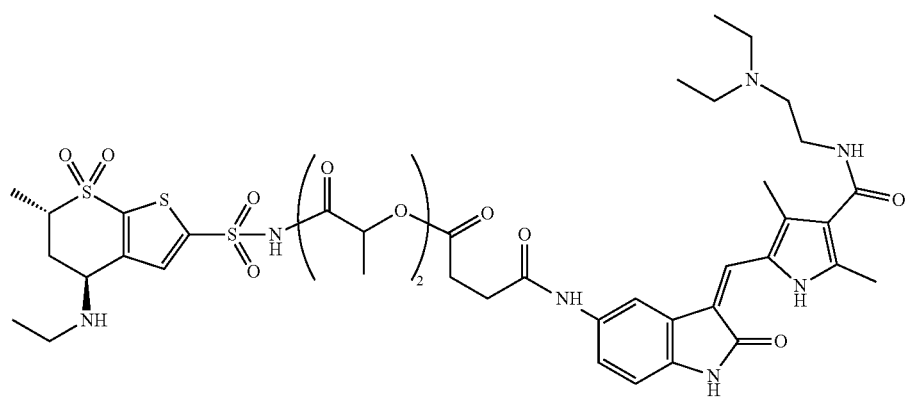
234-3 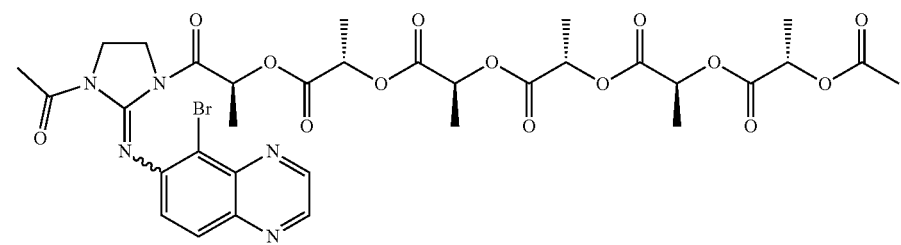 [SMILES: CC(=O)O[C@@H](C)C(=O)O[C@@H](C)C(=O)O[C@@H](C)C(=O)O[C@@H](C)C(=O)O[C@@H](C)C(=O)O[C@@H](C)C(=O)N1CCN(C(C)=O)C1=Nc1ccc2nccnc2c1Br]
234-3a 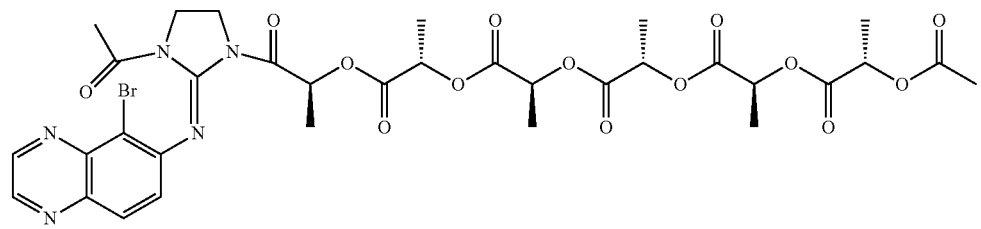 [SMILES: CC(=O)O[C@@H](C)C(=O)O[C@@H](C)C(=O)O[C@@H](C)C(=O)O[C@@H](C)C(=O)O[C@@H](C)C(=O)O[C@@H](C)C(=O)N1CCN(C(C)=O)/C1=N\c1ccc2nccnc2c1Br]
234-3b 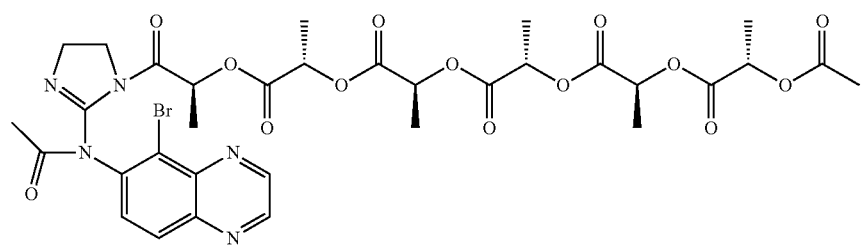 [SMILES: CC(=O)O[C@@H](C)C(=O)O[C@@H](C)C(=O)O[C@@H](C)C(=O)O[C@@H](C)C(=O)O[C@@H](C)C(=O)O[C@@H](C)C(=O)N1CCN=C1N(C(C)=O)c1ccc2nccnc2c1Br]

TABLE 8E-continued
Select Compounds of the Present Invention
234-3c 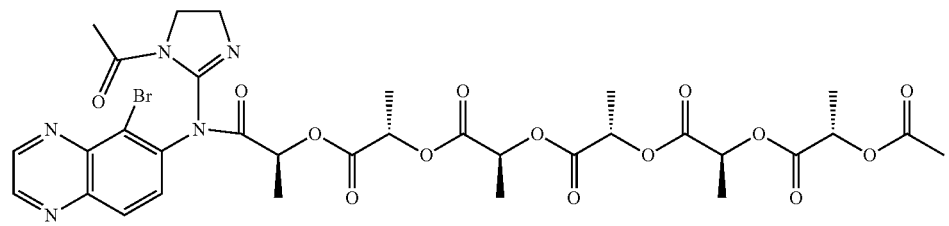 [SMILES: CC(=O)O[C@@H](C)C(=O)O[C@@H](C)C(=O)O[C@@H](C)C(=O)O[C@@H](C)C(=O)O[C@@H](C)C(=O)O[C@@H](C)C(=O)N(C1=NCCN1C(C)=O)c1ccc2nccnc2c1Br]
234-3d 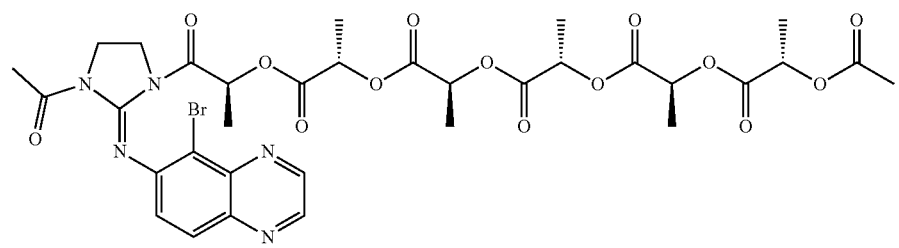
235 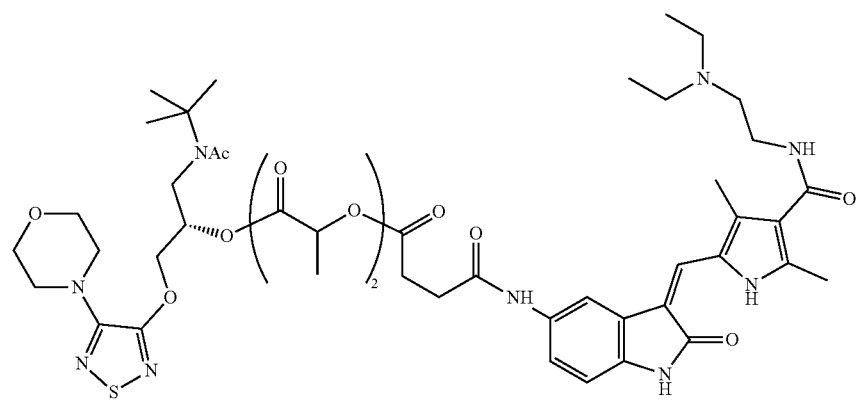
236 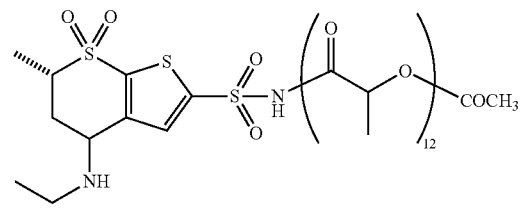
237 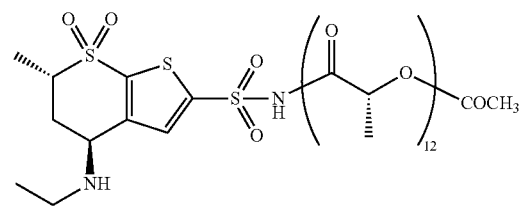
238-5 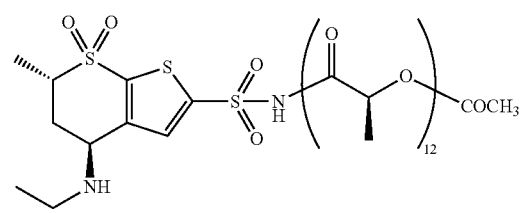

TABLE 8E-continued
Select Compounds of the Present Invention
239 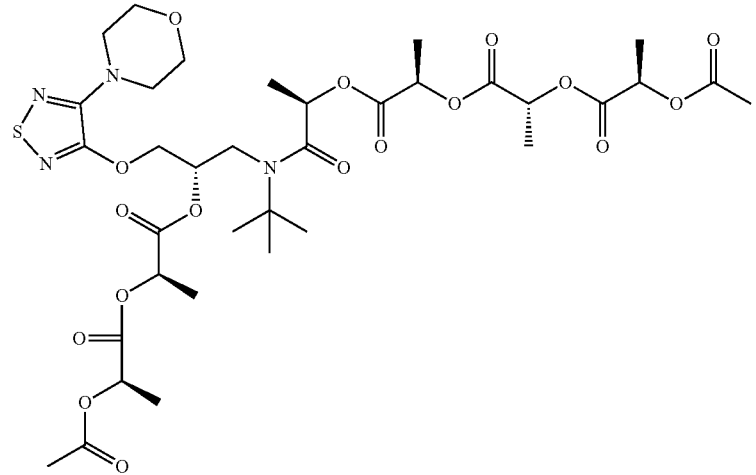 [SMILES: CC(=O)O[C@H](C)C(=O)O[C@H](C)C(=O)O[C@H](COc1nsnc1N1CCOCC1)CN(C(=O)[C@@H](C)OC(=O)[C@@H](C)OC(=O)[C@@H](C)OC(=O)[C@@H](C)OC(C)=O)C(C)(C)C]
240-6 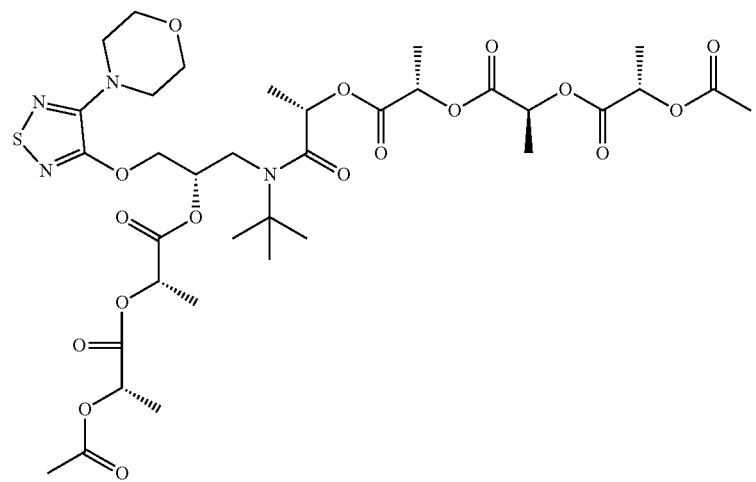 [SMILES: CC(=O)O[C@@H](C)C(=O)O[C@@H](C)C(=O)O[C@H](COc1nsnc1N1CCOCC1)CN(C(=O)[C@H](C)OC(=O)[C@H](C)OC(=O)[C@H](C)OC(=O)[C@H](C)OC(C)=O)C(C)(C)C]
241 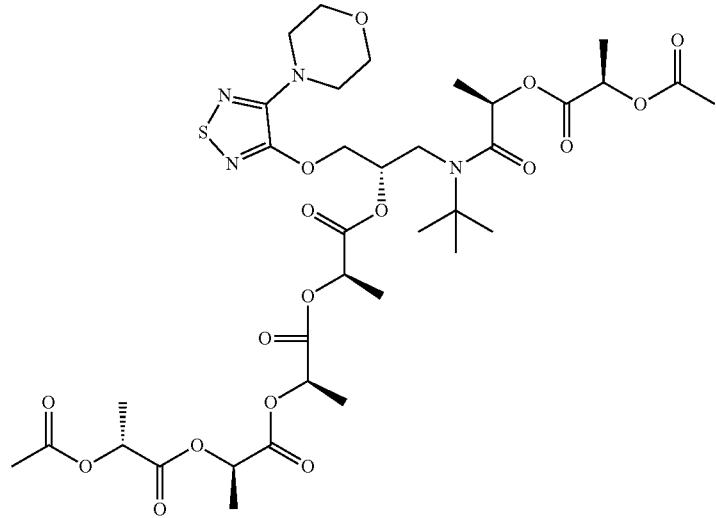 [SMILES: CC(=O)O[C@H](C)C(=O)O[C@H](C)C(=O)O[C@H](C)C(=O)O[C@H](C)C(=O)O[C@H](COc1nsnc1N1CCOCC1)CN(C(=O)[C@@H](C)OC(=O)[C@@H](C)OC(C)=O)C(C)(C)C]

TABLE 8E-continued
Select Compounds of the Present Invention
242-3
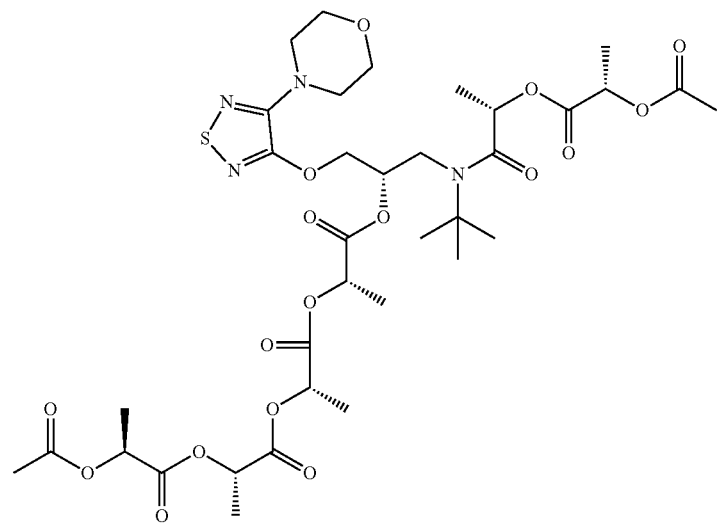 [SMILES: CC(=O)O[C@@H](C)C(=O)O[C@@H](C)C(=O)O[C@@H](C)C(=O)O[C@@H](C)C(=O)O[C@H](COc1nsnc1N1CCOCC1)CN(C(=O)[C@H](C)OC(=O)[C@H](C)OC(C)=O)C(C)(C)C]
243
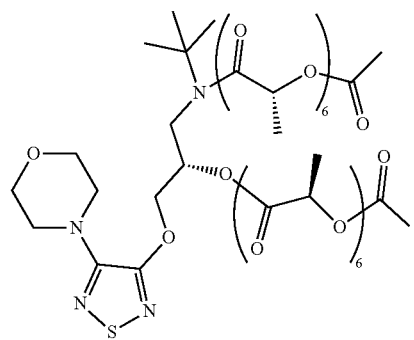
244
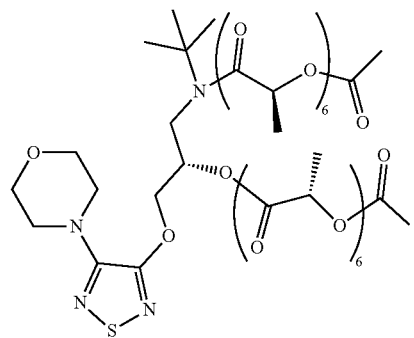

TABLE 8E-continued
Select Compounds of the Present Invention
245
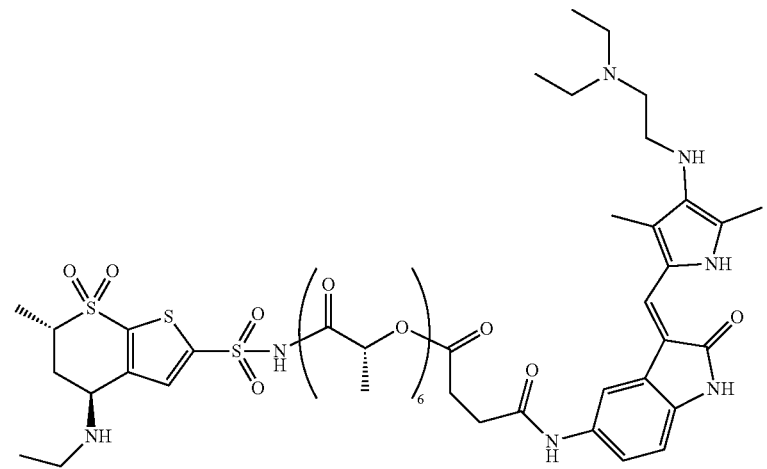
246-4
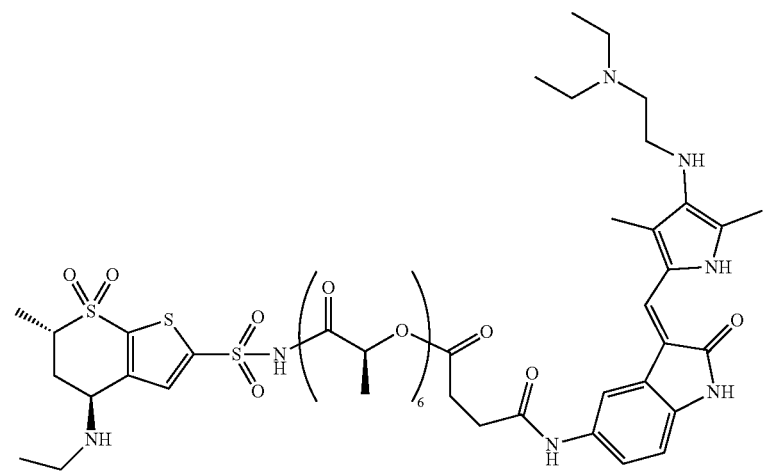
247
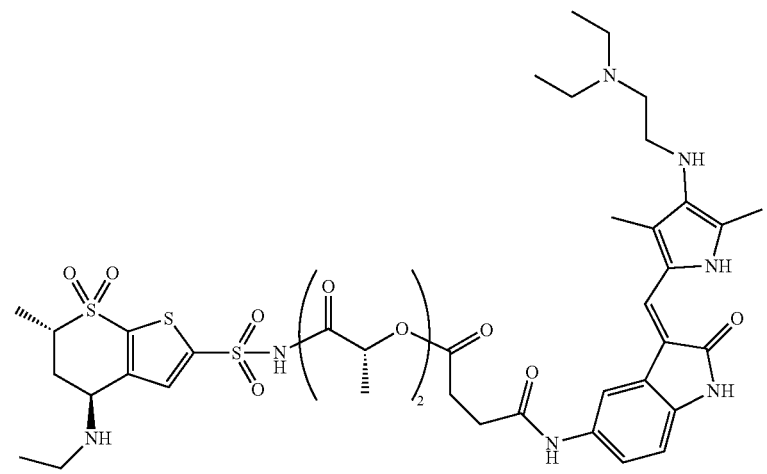

US 11,548,861 B2
875                                                                     876
TABLE 8E-continued
Select Compounds of the Present Invention
248-7
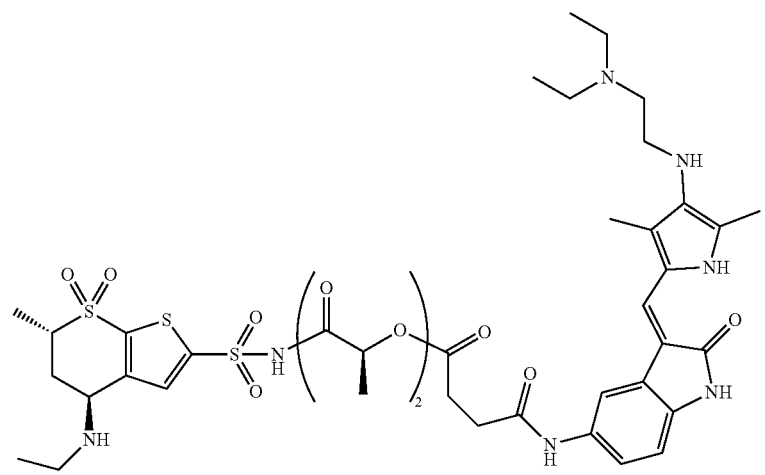
249-3
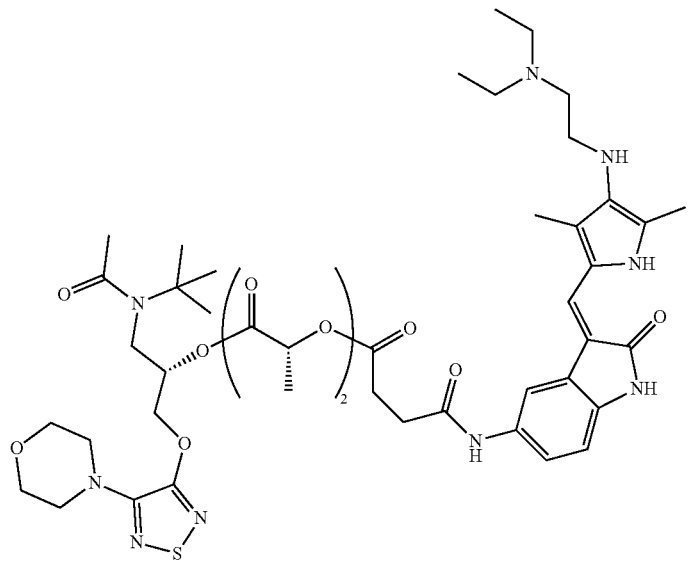
250
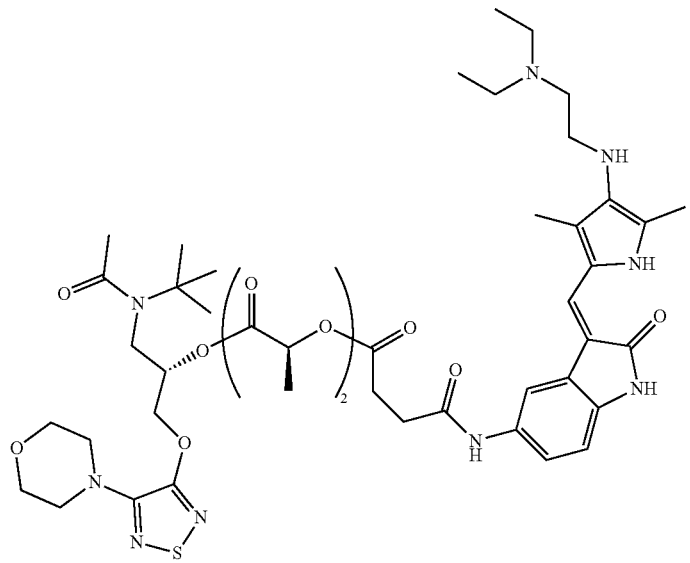

US 11,548,861 B2
TABLE 8E-continued
Select Compounds of the Present Invention
251 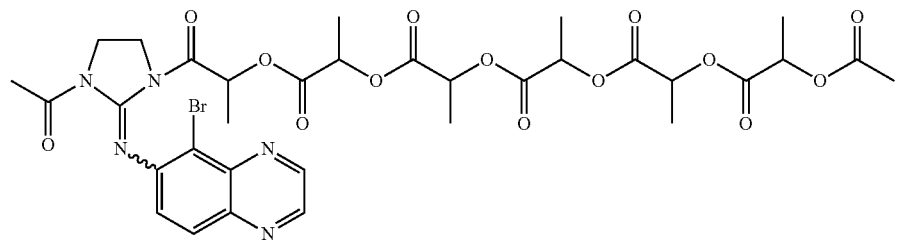 [SMILES: CC(=O)OC(C)C(=O)OC(C)C(=O)OC(C)C(=O)OC(C)C(=O)OC(C)C(=O)OC(C)C(=O)N1CCN(C(C)=O)C1=Nc1ccc2nccnc2c1Br]
251a 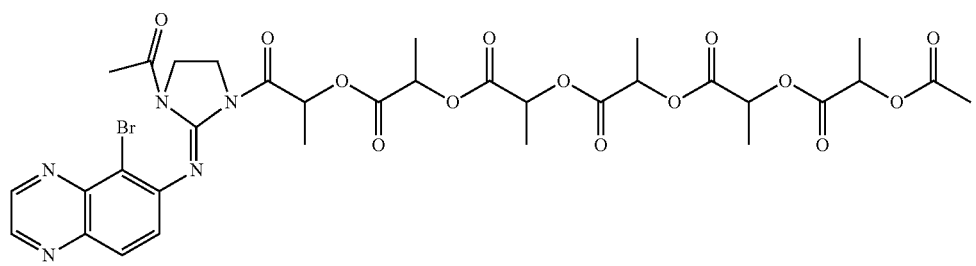 [SMILES: CC(=O)OC(C)C(=O)OC(C)C(=O)OC(C)C(=O)OC(C)C(=O)OC(C)C(=O)OC(C)C(=O)N1CCN(C(C)=O)/C1=N\c1ccc2nccnc2c1Br]
251b 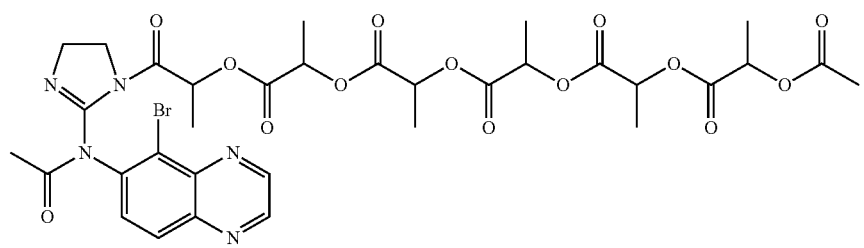 [SMILES: CC(=O)OC(C)C(=O)OC(C)C(=O)OC(C)C(=O)OC(C)C(=O)OC(C)C(=O)OC(C)C(=O)N1CCN=C1N(C(C)=O)c1ccc2nccnc2c1Br]
251c 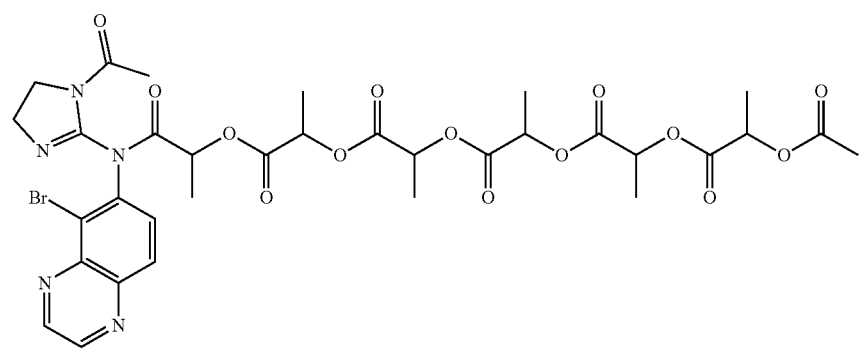 [SMILES: CC(=O)OC(C)C(=O)OC(C)C(=O)OC(C)C(=O)OC(C)C(=O)OC(C)C(=O)OC(C)C(=O)N(C1=NCCN1C(C)=O)c1ccc2nccnc2c1Br]
251d 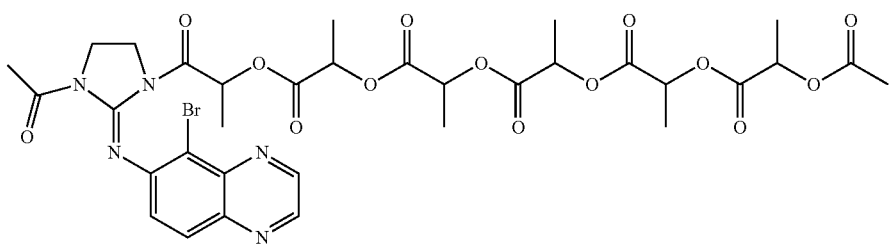 [SMILES: CC(=O)OC(C)C(=O)OC(C)C(=O)OC(C)C(=O)OC(C)C(=O)OC(C)C(=O)OC(C)C(=O)N1CCN(C(C)=O)/C1=N/c1ccc2nccnc2c1Br]
252 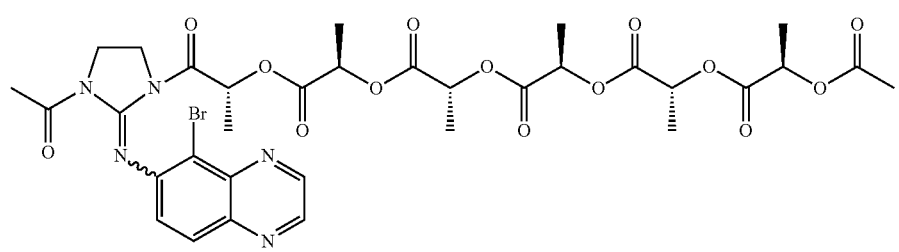 [SMILES: CC(=O)O[C@H](C)C(=O)O[C@H](C)C(=O)O[C@H](C)C(=O)O[C@H](C)C(=O)O[C@H](C)C(=O)O[C@H](C)C(=O)N1CCN(C(C)=O)C1=Nc1ccc2nccnc2c1Br]

TABLE 8E-continued
Select Compounds of the Present Invention
252a
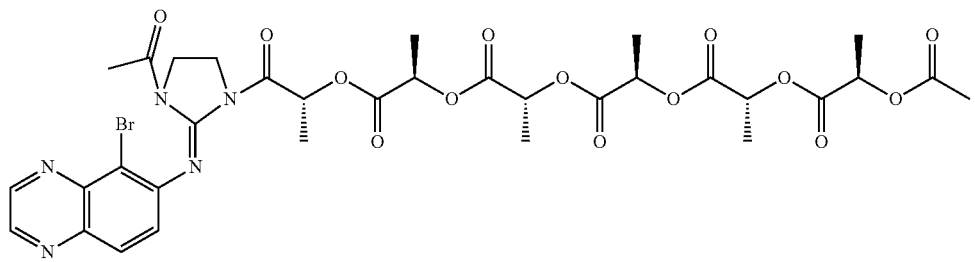 [SMILES: CC(=O)O[C@H](C)C(=O)O[C@H](C)C(=O)O[C@H](C)C(=O)O[C@H](C)C(=O)O[C@H](C)C(=O)O[C@H](C)C(=O)N1CCN(C(C)=O)/C1=N\c1ccc2nccnc2c1Br]
252b
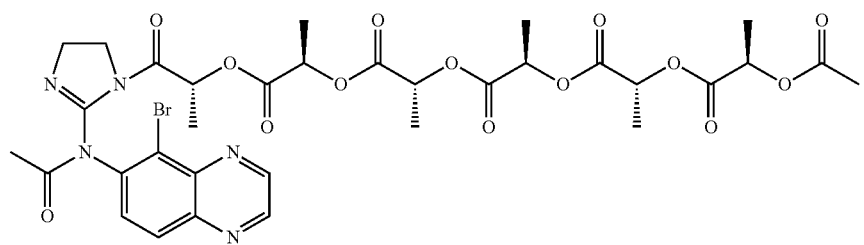 [SMILES: CC(=O)O[C@H](C)C(=O)O[C@H](C)C(=O)O[C@H](C)C(=O)O[C@H](C)C(=O)O[C@H](C)C(=O)O[C@H](C)C(=O)N1CCN=C1N(C(C)=O)c1ccc2nccnc2c1Br]
252c
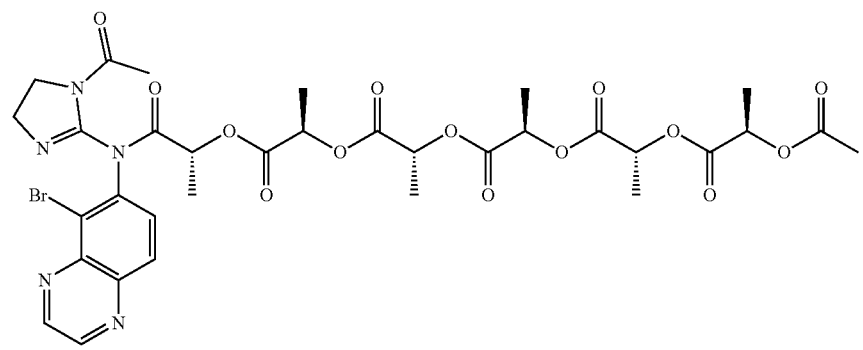 [SMILES: CC(=O)O[C@H](C)C(=O)O[C@H](C)C(=O)O[C@H](C)C(=O)O[C@H](C)C(=O)O[C@H](C)C(=O)O[C@H](C)C(=O)N(C1=NCCN1C(C)=O)c1ccc2nccnc2c1Br]
252d
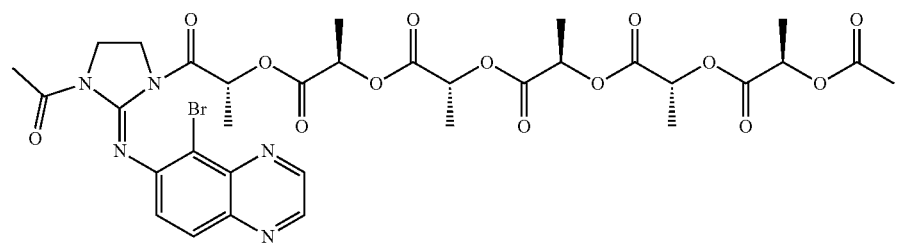 [SMILES: CC(=O)O[C@H](C)C(=O)O[C@H](C)C(=O)O[C@H](C)C(=O)O[C@H](C)C(=O)O[C@H](C)C(=O)O[C@H](C)C(=O)N1CCN(C(C)=O)/C1=N/c1ccc2nccnc2c1Br]

TABLE 8E-continued

Select Compounds of the Present Invention 253-3

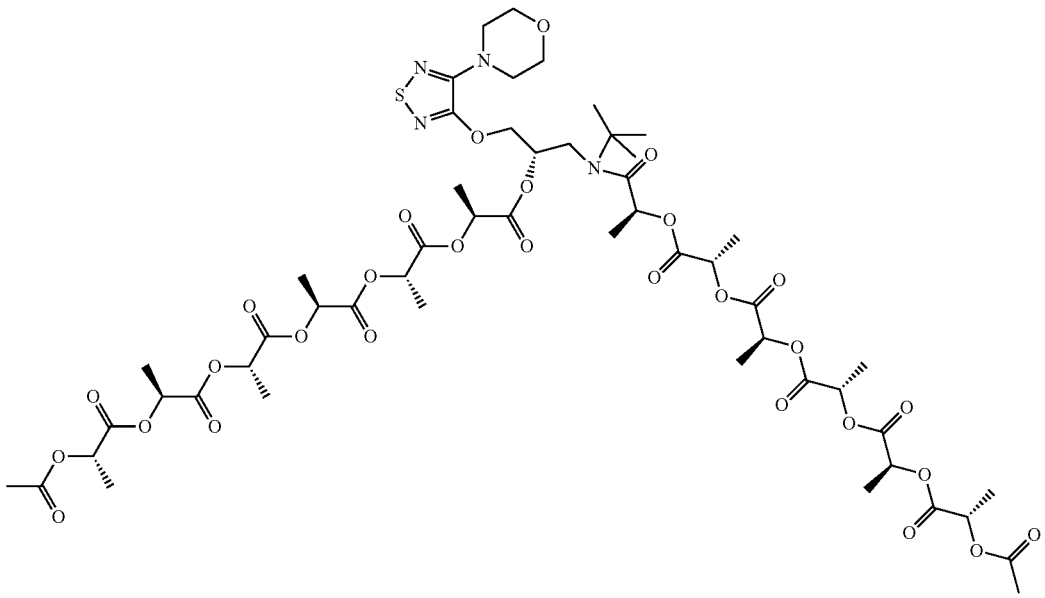 [SMILES: CC(=O)O[C@@H](C)C(=O)O[C@@H](C)C(=O)O[C@@H](C)C(=O)O[C@@H](C)C(=O)O[C@@H](C)C(=O)O[C@@H](C)C(=O)O[C@H](COc1nsnc1N1CCOCC1)CN(C(=O)[C@H](C)OC(=O)[C@H](C)OC(=O)[C@H](C)OC(=O)[C@H](C)OC(=O)[C@H](C)OC(=O)[C@H](C)OC(C)=O)C(C)(C)C]

TABLE 8F

Characterization Data of Select Compounds of the Present Invention 57-2  $^1$H-NMR (400 MHz, DMSO-d6) δ 5.19 (quintet, 1H), 4.59 (dd, 1H), 4.47 (dd, 1H), 3.72-3.65 (m, 4H), 3.45-3.28 (m, 4H), 2.82-2.72 (m, 2H), 2.5-2.35 (m, 4H), 1.04 (s, 9H). MS m/z [M + H]$^+$ 417.7.

64-3  $^1$H-NMR (400 MHz, DMSO-d6) δ 8.9-8.2 (bm, 4H), 7.71 (s, 1H), 6.10 (s, 2H), 5.5-5.4 (m, 1H), 5.12-5.0 (m, 2H), 4.80 (q, 1H), 4.7-4.5 (m, 2H), 4.47 (dd, 1H), 4.0-3.9 (m, 1H), 3.74-3.66 (m, 4H), 3.5-2.9 (m, 8H), 2.65-2.2 (m, 6H), 1.84-1.72 (m, 2H), 1.49 (d, 3H), 1.42 (d, 3H), 1.37 (d, 3H), 1.35-1.25 (m, 12H), 1.21 (t, 3H), MS m/z [M − H]$^−$ 952.3.

65-1  $^1$H-NMR (400 MHz, DMSO-d6) δ 5.44-5.36 (m, 1H), 4.97 (q, 1H), 4.53 (dd, 1H), 4.41 (dd, 1H), 3.78-3.61 (m, 6H), 3.45-3.36 (m, 4H), 2.30 (t, 2H), 2.08 (s, 3H), 1.5-1.15 (m, 42H) 0.84 (t, 3H). MS m/z [M + H]$^+$ 697.8.

66-1  $^1$H-NMR (400 MHz, DMSO-d6) δ 5.47-5.37 (m, 1H), 5.09-5.01 (m, 2H), 4.55 (dd, 1H), 4.41 (dd, 1H), 3.78-3.62 (m, 6H), 3.42-3.35 (m, 4H), 2.30 (t, 2H), 2.08 (s, 3H), 1.55-1.15 (m, 45H) 0.85 (t, 3H). MS m/z [M + H]$^+$ 770.1.

67-1  $^1$H-NMR (400 MHz, DMSO-d6) δ 5.46-5.39 (m, 1H), 5.22 (q, 1H), 5.13 (q, 1H), 5.08-5.01 (m, 2H), 4.55 (dd, 1H), 4.41 (dd, 1H), 3.80-3.64 (m, 6H), 3.41-3.36 (m, 4H), 2.33 (t, 2H), 2.08 (s, 3H), 1.55-1.18 (m, 51H) 0.85 (t, 3H). MS m/z [M + H]$^+$ 914.3.

68-1  $^1$H-NMR (400 MHz, DMSO-d6) δ 5.4-5.2 (m, 13H), 4.56 (dd, 1H), 4.43 (dd, 1H), 3.76-3.60 (m, 6H), 3.47-3.32 (m, 4H), 2.85-2.7 (m, 10H), 2.4-2.2 (m, 4H), 2.07 (s, 3H), 2.03 (quintet, 2H), 1.34 (s, 9H), 0.91 (t, 3H). MS m/z [M + H]$^+$ 669.9.

69-1  $^1$H-NMR (400 MHz, DMSO-d6) δ 5.58-5.47 (m, 2H), 5.00 (q, 1H), 4.54 (dd, 1H), 4.41 (dd, 1H), 4.18 (quintet, 1H), 3.8-3.6 (m, 6H), 3.45-3.35 (m, 4H), 2.09 (s, 3H), 1.4-1.2 (m, 15H). MS m/z [M + H]$^+$ 502.7.

70-1  $^1$H-NMR (400 MHz, DMSO-d6) δ 8.57 (bs, 1H), 8.33 (bs, 1H), 6.07 (s, 2H), 5.48-5.39 (m, 1H), 5.37-5.24 (m, 4H), 4.65 (dd, 1H), 4.48 (dd, 1H), 3.72-3.65 (m, 4H), 3.5-3.15 (m, 6H), 2.73 (t, 2H), 2.33 (t, 2H), 2.06-1.94 (m, 4H), 1.57-1.44 (m, 2H), 1.35-1.17 (m, 23H), 0.86 (t, 3H). MS m/z [M + H]$^+$ 579.9.

71-1  $^1$H-NMR (400 MHz, DMSO-d6) δ 8.96 (bs, 1H), 8.53 (bs, 1H), 5.49-5.42 (m, 1H), 5.37-5.23 (m, 4H), 4.65 (dd, 1H), 4.48 (dd, 1H), 3.72-3.65 (m, 4H), 3.44-3.30 (m, 5H), 3.23-3.13 (m, 1H), 2.72 (t, 2H), 2.33 (t, 2H), 2.06-1.94 (m, 4H), 1.56-1.43 (m, 2H), 1.35-1.17 (m, 23H), 0.85 (t, 3H). MS m/z [M + H]$^+$ 579.9.

72-4  $^1$H-NMR (400 MHz, DMSO-d6) δ 8.95 (d, J = 2 Hz, 1H), 8.84 (d, J = 2 Hz, 1H), 8.53 (bs, 1H), 8.25 (bs, 1H), 7.99 (d, J = 9 Hz, 1H), 7.58 (d, J = 9 Hz, 1H), 7.30 (s, 1H), 6.53 (q, 1H), 6.03 (s, 2H), 5.46-5.36 (m, 1H), 5.05 (q, 1H), 4.63 (dd, 1H), 4.47 (dd, 1H), 3.89 (t, 2H), 3.72-3.63 (m, 5H), 3.45-3.3.1 (m, 7H), 2.72-2.56 (m, 4H), 1.64 (d, 3H), 1.50 (d, 3H), 1.27 (s, 9H). MS m/z [M + H]$^+$ 835.7.

73-1  $^1$H-NMR (400 MHz, DMSO-d6) δ 8.96 (d, J = 2 Hz, 1H), 8.85 (d, J = 2 Hz, 1H), 8.00 (d, J = 9 Hz, 1H), 7.63 (d, J = 9 Hz, 1H), 7.32 (s, 1H), 5.75 (d, 1H), 5.26 (quintet, 1H), 3.97-3.85 (m, 2H), 3.43-3.30 (m, 2H), 1.35 (d, 3H). MS m/z [M + H]$^+$ 366.4.

TABLE 8F-continued

Characterization Data of Select Compounds of the Present Invention 74-1    1H-NMR (400 MHz, DMSO-d6) δ 8.93 (d, J = 2 Hz, 1H), 8.83 (d, J = 2 Hz, 1H), 8.54 (bs, 1H), 8.26 (bs, 1H), 7.97 (d, J = 9 Hz, 1H), 7.54 (d, J = 9 Hz, 1H), 7.09 (s, 1H), 6.02 (s, 2H), 5.46-5.36 (m, 1H), 4.64 (dd, 1H), 4.45 (dd, 1H), 3.88 (t, 2H), 3.72-3.62 (m, 5H), 3.55-3.3.1 (m, 7H), 2.6-2.4 (m, 4H), 1.92 (quintet, 2H), 1.27 (s, 9H). MS m/z [M + H]$^+$ 705.5.

75-1    1H-NMR (400 MHz, DMSO-d6) δ 8.6 (bs, 2H), 8.3 (bs, 2H), 6.03 (s, 4H), 5.46-5.36 (m, 2H), 4.64 (dd, 2H), 4.46 (dd, 2H), 3.72-3.63 (m, 8H), 3.45-3.1 (m, 12H), 2.4-2.2 (m, 4H), 1.48 (quintet, 4H), 1.33 (s, 18H), 1.3-1.1 (m, 8H). MS m/z [M + H]$^+$ 799.8.

76-4    1H-NMR (400 MHz, DMSO-d6) δ 8.6 (bs, 2H), 8.3 (bs, 2H), 6.03 (s, 4H), 5.46-5.34 (m, 2H), 4.64 (dd, 2H), 4.49 (dd, 2H), 3.73-3.634 (m, 8H), 3.48-3.13 (m, 12H), 2.74-2.54 (m, 4H), 1.29 (s, 18H). MS m/z [M + H]$^+$ 715.7.

77-1    1H-NMR (400 MHz, DMSO-d6) δ 8.6 (bs, 2H), 8.4 (bs, 2H), 6.03 (s, 4H), 5.48-5.36 (m, 2H), 4.65 (dd, 2H), 4.46 (dd, 2H), 3.75-3.65 (m, 8H), 3.5-3.1 (m, 12H), 2.5-2.3 (m, 4H), 1.77 (quintet, 2H), 1.29 (s, 18H). MS m/z [M + H]$^+$ 730.1.

78-1    1H-NMR (400 MHz, DMSO-d6) δ 8.66 (bs, 2H), 8.33 (bs, 2H), 6.88 (s, 2H), 6.12 (s, 2H), 5.65-5.53 (m, 2H), 4.74 (dd, 2H), 4.52 (dd, 2H), 3.7-3.55 (m, 10H), 3.55-3.1 (m, 10H), 1.30 (s, 18H). MS m/z [M + H]$^+$ 713.9, [M + 2H]$^{2+}$ 358.0.

79-3    1H-NMR (400 MHz, DMSO-d6) δ 8.95 (d, J = 2 Hz, 1H), 8.85 (d, J = 2 Hz, 1H), 7.99 (d, J = 9 Hz, 1H), 7.59 (d, J = 9 Hz, 1H), 7.34-7.29 (m, 2H), 7.15 (d, J = 9 Hz, 1H,), 6.52 (q, 1H), 6.06 (s, 1H), 5.55 (s, 1H), 5.27-5.11 (m, 5H), 3.96-3.83 (m, 2H), 3.43-3.33 (m, 2H), 2.36 (q, 2H), 1.64 (d, 3H), 1.52-1.42 (m, 9H), 1.07 (t, 3H),. MS m/z [M + H]$^+$ 886.8.

80-3    1H-NMR (400 MHz, DMSO-d6) δ 8.8 (bs, 2H), 7.71 (s, 1H), 5.4-5.2 (m, 12H), 4.59 (bs, 1H), 4.0-3.9 (m, 1H), 3.25-3.1 (m, 1H), 3.1-2.9 (m, 1H), 2.9-2.7 (m, 10H), 2.65-2.4 (m, 2H), 2.18 (q, 2H), 2.1-1.96 (m, 4H), 1.36 (d, 3H), 1.3-1.1 (m, 3H), 0.91 (t, 3H). MS m/z [M + H]$^+$ 635.7.

81-1    1H-NMR (400 MHz, DMSO-d6) δ 9.0-7.9 (bm, 4H), 7.69 (s, 1H), 6.05 (s, 2H), 5.5-5.4 (m, 1H), 4.68-4.55 (m, 2H), 4.49 (dd, 1H), 4.0-3.9 (m, 1H), 3.71-3.63 (m, 4H), 3.5-3.1 (m, 7H), 3.05-2.95 (m, 1H), 2.7-2.3 (m, 6H), 1.1-1.4 (m, 15H), MS m/z [M + H]$^+$ 723.6.

82-1    1H-NMR (400 MHz, DMSO-d6) δ 9.0 (bs, 2H), 8.6 (bs, 1H), 8.0 (bs, 1H), 7.77 (s, 1H), 6.07 (s, 2H), 5.5-5.4 (m, 1H), 4.87-4.6 (m, 1H), 4.65 (dd, 1H), 4.49 (dd, 1H), 4.08-3.96 (m, 2H), 3.71-3.65 (m, 4H), 3.5-2.9 (m, 15H), 2.6-2.3 (m, 4H), 1.81 (quintet, 2H), 1.35-1.1 (m, 12H), MS m/z [M + H]$^+$ 780.9.

83-3    1H-NMR (400 MHz, DMSO-d6) δ 8.94 (d, J = 2 Hz, 1H), 8.82 (d, J = 2 Hz, 1H), 7.97 (d, J = 9 Hz, 1H), 7.55 (d, J = 9 Hz, 1H), 7.09 (s, 1H), 5.20-5.10 (m, 1H), 4.59 (dd, 1H), 4.45 (dd, 1H), 3.82 (t, 2H), 3.69-3.61 (m, 4H), 3.45-3.30 (m, 8H), 2.77-2.59 (m, 4H), 0.98 (s, 9H). MS m/z [M + H]$^+$ 692.1.

83-4    1H-NMR (400 MHz, DMSO-d6) δ 8.94 (d, J = 2 Hz, 1H), 8.83 (d, J = 2 Hz, 1H), 8.6 (bs, 1H), 8.3 (bs, 1H), 7.98 (d, J = 9 Hz, 1H), 7.55 (d, J = 9 Hz, 1H), 7.12 (s, 1H), 6.04 (s, 2H), 5.48-5.39 (m, 1H), 4.62 (dd, 1H), 4.48 (dd, 1H), 3.9-3.7 (m, 2H), 3.70-3.60 (m, 4H), 3.56-3.15 (m, 8H), 2.72 (t, 2H), 1.29 (s, 9H). MS m/z [M + H]$^+$ 692.3.

84-1    1H-NMR (400 MHz, DMSO-d6) δ 9.1-8.3 (bm, 4H), 7.69 (s, 1H), 6.04 (s, 2H), 5.5-5.4 (m, 1H), 4.7-4.5 (m, 2H), 4.48 (dd, 1H), 4.0-3.9 (m, 1H), 3.74-3.62 (m, 4H), 3.5-2.9 (m, 8H), 2.65-2.2 (m, 4H), 2.15-1.95 (m, 2H), 1.8-1.6 (m, 2H), 1.36 (d, 3H), 1.28 (s, 9H), 1.20 (t, 3H), MS m/z [M − H]$^−$ 735.9.

85-1    1H-NMR (400 MHz, DMSO-d6) δ 13.73 (s, 1H), 12.12 (bs, 1H), 10.88 (s, 1H), 9.79 (s, 1H), 9.29 (bs, 1H), 7.95 (s, 1H), 7.80 (t, 1H), 7.47 (s, 1H), 7.20 (d, J = 8 Hz, 1H), 6.82 (d, J = 8 Hz, 1H), 3.6-3.5 (m, 2H), 3.3-3.1 (m, 6H), 2.46, (s, 3H), 2.40 (s, 3H), 2.36-2.22 (m, 4H), 1.85-1.75 (m, 2H), 1.21 (t, 6H). MS m/z [M + H]$^+$ 510.7.

86-1    1H-NMR (400 MHz, DMSO-d6) δ 13.72 (s, 1H), 12.03 (bs, 2H), 10.86 (s, 1H), 9.73 (s, 1H), 7.93 (s, 1H), 7.73 (t, 1H), 7.46 (s, 1H), 7.21 (d, J = 8 Hz, 1H), 6.81 (d, J = 8 Hz, 1H), 3.6-3.5 (m, 2H), 3.3-3.0 (m, 6H), 2.46, (s, 3H), 2.42 (s, 3H), 2.3-2.1 (m, 4H), 1.6-1.4 (m, 4H), 1.3-1.1 (m, 18H). MS m/z [M + H]$^+$ 608.9.

87-1    1H-NMR (400 MHz, DMSO-d6) δ 13.73 (s, 1H), 12.0 (bs, 1H), 10.88 (s, 1H), 9.76 (s, 1H), 9.34 (bs, 1H), 7.96 (s, 1H), 7.81 (t, 1H), 7.47 (s, 1H), 7.22 (d, J = 8 Hz, 1H), 6.81 (d, J = 8 Hz, 1H), 3.65-3.5 (m, 2H), 3.3-3.1 (m, 6H), 2.47, (s, 3H), 2.42 (s, 3H), 2.3-2.1 (m, 4H), 1.65-1.4 (m, 4H), 1.35-1.15 (m, 14H). MS m/z [M + H]$^+$ 580.9.

88-3    1H-NMR (400 MHz, DMSO-d6) δ 12.81 (s, 1H), 8.46 (s, 1H), 8.2-7.7 (m, 2H), 7.7-7.4 (m, 4H), 7.29-7.20 (m, 1H), 6.86-6.70 (m, 3H), 5.24-4.98 (m, 4H), 4.68-4.54 (m, 2H), 4.32-4.13 (m, 2H), 3.73 (s, 3H), 3.58 (t, 2H), 2.06 (s, 3H), 1.50-1.34 (m, 12H). MS m/z [M + H]$^+$ 697.9.

89-3    1H-NMR (400 MHz, DMSO-d6) δ 12.82 (s, 1H), 8.46 (s, 1H), 8.07 (bs, 1H), 7.82 (bs, 1H), 7.50-7.40 (m, 4H), 7.29-7.20 (m, 1H), 6.86-6.77 (m, 3H), 5.24-4.98 (m, 6H), 4.68-4.54 (m, 2H), 4.32-4.13 (m, 2H), 3.73 (s, 3H), 3.58 (t, 2H), 2.06 (s, 3H), 1.51-1.34 (m, 18H). MS m/z [M + H]$^+$ 842.1.

90-1    1H-NMR (400 MHz, DMSO-d6) δ 8.1-7.9 (m, 2H), 7.75-7.6 (m, 2H), 7.34-7.26 (m, 1H), 7.25 (s, 1H), 7.15 (d, 1H), 6.90-6.83 (m, 3H), 5.25-4.98 (m, 4H), 4.68-4.54 (m, 2H), 4.35-4.12 (m, 2H), 3.74 (s, 3H), 3.63 (t, 2H), 3.4-3.3 (m, 2H), 3.9-3.4 (m, 6H), 2.06 (s, 3H), 1.75-1.66 (m, 4H), 1.50-1.36 (tn, 12H). MS m/z [M + H]$^+$ 811.1.

TABLE 8F-continued

Characterization Data of Select Compounds of the Present Invention

| | |
|---|---|
| 91-2 | $^1$H-NMR (400 MHz, DMSO-d6) δ 12.9 (bs, 1H), 8.1-7.9 (m, 2H), 7.9-7.5 (m, 2H), 7.36-7.2 (m, 2H), 7.17 (d, 1H), 6.90-6.83 (m, 3H), 5.24-4.95 (m, 6H), 4.72-4.54 (m, 2H), 4.4-4.2 (m, 4H), 3.75 (s, 3H), 3.63 (t, 2H), 3.3-2.6 (m, 6H), 2.06 (s, 3H), 1.9-1.7 (m, 4H), 1.50-1.36 (m, 18H). MS m/z [M + H]$^+$ 955.1. |
| 101-3 | $^1$H-NMR (400 MHz, DMSO-d6) δ 12.8 (bs, 1H), 8.94 (d, J = 2 Hz, 1H), 8.83 (d, J = 2 Hz, 1H), 8.46 (s, 1H), 8.15-7.8 (m, 3H), 7.56 (d, 1H), 7.50-7.40 (m, 4H), 7.29-7.21 (m, 1H), 7.10 (s, 1H), 6.86-6.77 (m, 3H), 5.14-5.02 (m, 2H), 4.67-4.54 (m, 2H), 4.32-4.12 (m, 2H), 4.9-4.8 (m, 2H), 3.72 (s, 3H), 3.58 (t, 2H), 3.45-3.25 (m, 2H), 2.8-2.4 (m, 4H), 1.43 (d, 3H), 1.38 (d, 3H). MS m/z [M + H]$^+$ 883.7. |
| 102-1 | $^1$H-NMR (400 MHz, DMSO-d6) δ 5.5-5.4 (m, 1H), 5.4-5.2 (m, 12H), 5.1-5.0 (m, 2H), 4.56 (dd, 1H), 4.44 (dd, 1H), 3.8-3.63 (m, 6H), 3.42-3.34 (m, 4H), 2.85-2.73 (m, 10H), 2.4-2.2 (m, 4H), 2.09 (s, 3H), 2.02 (quintet, 2H), 1.45-1.32 (m, 15H), 0.91 (t, 3H). MS m/z [M + H]$^+$ 814.3. |
| 103-1 | $^1$H-NMR (400 MHz, DMSO-d6) δ 5.5-5.4 (m, 1H), 5.4-5.0 (m, 16H), 4.55 (dd, 1H), 4.42 (dd, 1H), 3.8-3.63 (m, 6H), 3.42-3.34 (m, 4H), 2.85-2.74 (m, 10H), 2.42-2.37 (m, 2H), 2.36-2.24 (m, 2H), 2.08 (s, 3H), 2.02 (quintet, 2H), 1.45-1.32 (m, 21H), 0.91 (t, 3H). MS m/z [M + H]$^+$ 957.7. |
| 104-1 | $^1$H-NMR (400 MHz, DMSO-d6) δ 13.74 (s, 1H), 10.98 (s, 1H), 9.1 (bs, 1H), 7.77 (t, 1H), 7.68 (s, 1H), 7.61 (d, 1H), 6.9-6.8 (m, 2H), 5.5-5.4 (m, 1H), 5.2-5.0 (m, 2H), 4.56 (dd, 1H), 4.44 (dd, 1H), 3.8-3.6 (m, 6H), 3.6-3.5 (m, 2H), 3.5-3.1 (m, 10H), 2.85-2.65 (m, 4H), 2.47 (s, 3H), 2.44 (s, 3H), 2.07 (s, 3H), 1.44-1.32 (m, 15H), 1.20 (t, 6H); MS m/z [M + H]$^+$ 982.3 |
| 105-1 | $^1$H-NMR (400 MHz, DMSO-d6) δ 13.74 (s, 1H), 10.99 (s, 1H), 9.1 (bs, 1H), 7.77 (t, 1H), 7.69 (s, 1H), 7.61 (d, 1H), 6.9-6.8 (m, 2H), 5.5-5.4 (m, 1H), 5.26-4.98 (m, 4H), 4.56 (dd, 1H), 4.43 (dd, 1H), 3.8-3.6 (m, 6H), 3.6-3.5 (m, 2H), 3.5-3.18 (m, 10H), 2.9-2.7 (m, 4H), 2.47 (s, 3H), 2.44 (s, 3H), 2.08 (s, 3H), 1.5-1.3 (m, 21H), 1.23 (t, 6H); MS m/z [M + H]$^+$ 1126.7. |
| 106-1 | $^1$H-NMR (400 MHz, DMSO-d6) δ 13.74 (s, 1H), 10.97 (s, 1H), 7.75 (t, 1H), 7.65 (s, 1H), 7.61 (d, 1H), 6.9-6.8 (m, 2H), 5.5-5.2 (m, 12H), 3.6-3.5 (m, 2H), 3.3-3.15 (m, 6H), 2.9-2.7 (m, 12H), 2.7-2.6 (m, 2H), 2.47 (s, 3H), 2.42 (s, 3H), 2.02 (quintet, 2H), 1.23 (t, 6H), 0.90 (t, 3H); MS m/z [M + H]$^+$ 708.2. |
| 107-4 | $^1$H-NMR (400 MHz, DMSO-d6) δ 8.96 (d, J = 2 Hz, 1H), 8.85 (d, J = 2 Hz, 1H), 7.99 (d, J = 9 Hz, 1H), 7.59 (d, J = 9 Hz, 1H), 7.30 (s, 1H), 6.52 (q, 1H), 5.26-5.16 (m, 4H), 5.03 (q, 1H), 3.95-3.84 (m, 2H), 3.44-3.34 (m, 2H), 2.06 (s, 3H), 1.64 (d, 3H), 1.52-1.39 (m, 15H). MS m/z [M + H]$^+$ 767.1. |
| 108-3 | $^1$H-NMR (400 MHz, DMSO-d6) δ 13.68 (s, 1H), 11.10 (s, 1H), 7.71 (t, 1H), 7.65 (s, 2H), 6.97 (s, 2H), 3.55-3.45 (m, 2H), 3.3-3.0 (m, 6H), 2.81 (s, 4H), 2.47 (s, 3H), 2.42 (s, 3H), 1.18 (t, 6H); MS m/z [M + H]$^+$ 478.7. |
| 109-1 | $^1$H-NMR (400 MHz, DMSO-d6) δ 8.96 (d, J = 2 Hz, 1H), 8.85 (d, J = 2 Hz, 1H), 7.99 (d, J = 9 Hz, 1H), 7.59 (d, J = 9 Hz, 1H), 7.29 (s, 1H), 6.52 (q, 1H), 5.25-5.14 (m, 6H), 5.04 (q, 1H), 3.97-3.85 (m, 2H), 3.44-3.34 (m, 2H), 2.06 (s, 3H), 1.63 (d, 3H), 1.54-1.36 (m, 21H). MS m/z [M + H]$^+$ 911.6. |
| 110-3 | $^1$H-NMR (400 MHz, DMSO-d6) δ 9.08 (d, J = 2H, 1H), 9.07 (d, J = 2 Hz, 1H), 8.19 (d, J = 9 Hz, 1H), 7.97 (d, J = 9 Hz, 1H), 4.14-3.91 (m, 2H), 3.63-3.46 (m, 2H), 3.21-3.12 (m, 1H), 3.04-2.85 (m, 3H). MS m/z [M + H]$^+$ 376.1. |
| 111-4 | $^1$H-NMR (400 MHz, DMSO-d6) δ 8.96 (d, J = 2 Hz, 1H), 8.86 (d, J = 2 Hz, 1H), 7.93-7.87 (m, 1H), 7.63-7.54 (m, 1H), 6.2-5.6 (m, 2H), 5.05-4.93 (m, 2H), 4.2-3.9 (m, 4H), 2.05 (s, 3H), 2.03 (s, 3H), 1.5-1.2 (m, 12H). MS m/z [M + H]$^+$ 738.6. |
| 112-1 | $^1$H-NMR (400 MHz, DMSO-d6, TFA) δ 13.74 (s, 1H), 10.87 (s, 1H), 9.99 (s, 1H), 9.25 (bs, 1H), 8.74 (bt, 1H), 8.25 (bt, 1H), 7.86 (d, 1H), 7.80 (t, 1H), 7.43 (s, 1H), 7.17 (dd, 1H), 6.80 (d, 1H), 6.25 (s, 2H), 5.51-5.43 (m, 1H), 4.64 (dd, 1H), 4.46 (dd, 1H), 3.7-3.5 (m, 6H), 3.5-3.3 (m, 6H), 3.3-3.1 (m, 6H), 2.75-2.55 (m, 4H), 2.46 (s, 3H), 2.40 (s, 3H) 1.27 (s, 9H), 1.22, (t, 6H); MS m/z [M + H]$^+$ 795.0. |
| 113-1 | $^1$H-NMR (400 MHz, DMSO-d6) δ 8.82 (s, 1H), 8.59 (s, 1H), 8.47 (s, 1H), 7.68 (d, J = 9 Hz, 2H), 7.54 (d, J = 9 Hz, 2H), 7.29-7.22 (m, 1H), 6.86-6.77 (m, 3H), 6.09 (q, 1H), 5.31-4.99 (m, 7H), 4.68-4.54 (m, 2H), 4.32-4.15 (m, 2H), 3.73 (s, 3H), 3.58 (t, 2H), 2.06 (s, 6H), 1.60 (d, 3H), 1.52 (d, 3H), 1.50-1.34 (m, 18H). MS m/z [M + H]$^+$ 1028.5. |
| 114-4 | $^1$H-NMR (400 MHz, DMSO-d6) δ 8.95 (d, J = 2 Hz, 1H), 8.84 (d, J = 2 Hz, 1H), 7.90 (d, J = 9 Hz, 1H), 7.59 (d, J = 9 Hz, 1H), 6.3-6.1 (m, 1H), 5.02 (q, 1H), 4.14-3.85 (m, 4H), 2.09 (bs, 3H), 1.99 (s, 3H), 1.55-1.37 (m, 6H). MS m/z [M + H]$^+$ 521.2. |
| 115-1 | $^1$H-NMR (400 MHz, DMSO-d6) δ 8.95 (d, J = 2 Hz, 1H), 8.84 (d, J = 2 Hz, 1H), 7.90 (d, J = 9 Hz, 1H), 7.59 (d, J = 9 Hz, 1H), 6.3-6.1 (m, 1H), 5.23-5.13 (m, 2H), 5.01 (q, 1H), 4.15-3.85 (m, 4H), 2.06 (s, 6H), 1.55-1.37 (m, 12H). MS m/z [M + H]$^+$ 665.8. |
| 116-1 | $^1$H-NMR (400 MHz, DMSO-d6) δ 8.96 (d, J = 2 Hz, 1H), 8.85 (d, J = 2 Hz, 1H), 7.93-7.86 (m, 1H), 7.62-7.54 (m, 1H), 6.1-5.7 (m, 2H), 5.24-4.96 (m, 6H), 4.2-3.9 (m, 4H), 2.06 (s, 6H), 1.5-1.2 (m, 24H). MS m/z [M + H]$^+$ 954.1. |

TABLE 8F-continued

Characterization Data of Select Compounds of the Present Invention

| | |
|---|---|
| 117-6 | $^1$H-NMR (400 MHz, DMSO-d6) δ 5.5-5.3 (m, 2H), 4.98 (q, 1H), 4.65-4.4 (m, 2H), 4.06-3.9 (m, 2H), 3.85-3.55 (m, 6H), 3.46-3.33 (m, 4H), 2.6-2.4 (m, 4H), 2.06 (s, 3H), 1.45-1.28 (m, 15H), 1.2-1.05 (m, 3H). MS m/z [M + H]$^+$ 632.2. |
| 118-1 | $^1$H-NMR (400 MHz, DMSO-d6) δ 5.5-5.3 (m, 2H), 5.15-4.94 (m, 3H), 4.7-4.5 (m, 1H), 4.5-4.35 (m, 1H), 3.8-3.6 (m, 6H), 3.46-3.3 (m, 4H), 2.06 (s, 3H), 2.05 (s, 3H), 1.45-1.28 (m, 21H). MS m/z [M + H]$^+$ 691.7, [M + Na]$^+$ 712.1. |
| 119-6 | $^1$H-NMR (400 MHz, DMSO-d6) δ 5.55-5.3 (m, 2H), 5.4-5.0 (m, 7H), 4.7-4.5 (m, 1H), 4.5-4.35 (m, 1H), 3.8-3.6 (m, 6H), 3.46-3.3 (m, 4H), 2.06 (s, 6H), 1.45-1.28 (m, 33H). MS m/z [M + H]$^+$ 998.0, [M + Na]$^+$ 1000.5. |
| 120-1 | $^1$H-NMR (400 MHz, DMSO-d6) δ 5.55-5.3 (m, 2H), 5.23-5.01 (m, 3H), 4.65-4.4 (m, 2H), 4.1-3.95 (m, 3H), 3.85-3.55 (m, 5H), 3.5-3.3 (m, 4H), 2.6-2.4 (m, 4H), 2.07 (s, 3H), 1.4-1.2 (m, 21H), 1.2-1.05 (m, 3H). MS m/z [M + H]$^+$ 776.7. |
| 234-3 | $^1$H-NMR (400 MHz, DMSO-d6) δ 8.94 (d, J = 2 Hz, 1H), 8.84 (d, J = 2 Hz, 1H), 7.90 (d, J = 9 Hz, 1H), 7.58 (d, J = 9 Hz, 1H), 6.3-6.1 (m, 1H), 5.24-5.14 (m, 4H), 5.02 (q, 1H), 4.15-3.85 (m, 4H), 2.06 (s, 6H), 1.55-1.37 (m, 18H). MS m/z [M + H]$^+$ 808.6. |
| 238-5 | $^1$H-NMR (400 MHz, DMSO-d6) δ 7.37 (s, 1H), 5.26-5.13 (m, 9H), 5.13-5.00 (m, 2H), 4.79 (q, 1H), 3.94-3.75 (m, 2H), 2.7-2.5 (m, 2H), 2.32-2.2 (m, 2H), 2.07 (s, 3H), 1.51-1.38 (m, 33H), 1.35-1.25 (m, 6H), 1.02 (t, 3H); MS m/z (M + H)$^+$ 1232.4. |
| 240-6 | $^1$H-NMR (400 MHz, DMSO-d6) δ 5.55-5.3 (m, 2H), 5.25-4.92 (m, 5H), 4.7-4.3 (m, 2H), 3.8-3.6 (m, 6H), 3.45-3.3 (m, 4H), 2.06 (s, 3H), 2.05 (s, 3H), 1.5-1.35 (m, 18H), 1.35 (s, 9H). MS m/z [M + Na]$^+$ 856.3. |
| 242-3 | $^1$H-NMR (400 MHz, DMSO-d6) δ 5.55-5.3 (m, 2H), 5.23-5.01 (m, 5H), 4.7-4.3 (m, 2H), 3.8-3.6 (m, 6H), 3.47-3.3 (m, 4H), 2.05 (s, 3H), 2.03 (s, 3H), 1.5-1.35 (m, 18H), 1.34 (s, 9H). MS m/z [M + Na]$^+$ 856.5. |
| 244 | $^1$H-NMR (400 MHz, DMSO-d6) δ 5.55-5.3 (m, 2H), 5.3-5.0 (m, 11H), 4.7-4.3 (m, 2H), 3.8-3.6 (m, 6H), 3.45-3.3 (m, 4H), 2.07 (s, 6H), 1.5-1.35 (m, 36H), 1.33 (s, 9H). MS m/z [M + NH$_4$]$^+$ 1284.3. |
| 246-4 | $^1$H-NMR (400 MHz, DMSO-d6) δ 13.71 (s, 1H), 10.86 (s, 1H), 9.88 (s, 1H), 8.14 (s, 1H), 7.94 (d, J = 2 Hz, 1H), 7.68 (t, 1H), 7.5-7.4 (m, 2H), 7.17 (dd, J = 2 Hz, J = 8 Hz, 1H), 6.81 (d, J = 8 Hz, 1H), 5.25-5.0 (m, 5H), 4.79 (q, 1H), 4.1-3.8 (m, 2H), 3.55-3.4 (m, 2H), 3.15-2.9 (m, 6H), 2.8-2.5 (m, 6H), 2.46 (s, 3H), 2.41 (s, 3H), 2.4-2.2 (m, 2H), 1.55-1.4 (m, 15H), 1.36-1.24 (m, 6H), 1.16 (t, 6H), 1.06 (t, 3H); MS m/z [M + H]$^+$ 1235.6, [M + 2H]$^{2+}$ 619.8. (As mono-formate salt) |
| 248-7 | $^1$H-NMR (400 MHz, DMSO-d6) δ 13.71 (s, 1H), 10.87 (s, 1H), 9.88 (s, 1H), 8.14 (s, 1H), 7.94 (d, J = 2 Hz, 1H), 7.69 (t, 1H), 7.5-7.4 (m, 2H), 7.17 (dd, J = 2 Hz, J = 8 Hz, 1H), 6.81 (d, J = 8 Hz, 1H), 4.99 (q, 1H), 4.80 (q, 1H), 4.1-3.8 (m, 2H), 3.5-3.4 (m, 2H), 3.1-2.95 (m, 6H), 2.8-2.5 (m, 6H), 2.46 (s, 3H), 2.42 (s, 3H), 2.4-2.2 (m, 2H), 1.46 (d, 3H), 1.4-1.3 (m, 6H), 1.16 (t, 6H), 1.06 (t, 3H); MS m/z [M + H]$^+$ 947.4 (As mono-formate salt) |
| 249-3 | $^1$H-NMR (400 MHz, DMSO-d6) δ 13.64 (s, 1H), 10.84 (s, 1H), 9.87 (s, 1H), 7.89 (d, J = 2 Hz, 1H), 7.47 (t, 1H), 7.43 (s, 1H), 7.21 (dd, J = 2 Hz, J = 8 Hz, 1H), 6.81 (dd, J = 8 Hz, 1H), 5.48-5.36 (m, 1H), 5.12-4.97 (m, 2H), 4.54 (dd, 1H), 4.41 (dd, 1H), 3.8-3.6 (m, 6H), 3.5-3.3 (m, 6H), 2.7-2.5 (m, 8H), 2.44 (s, 3H), 2.39 (s, 3H). 2.09 (s, 3H), 1.5-1.3 (m, 15H), 0.99 (t, 6H); MS m/z [M + H]$^+$ 981.4. |
| 253-3 | $^1$H-NMR (400 MHz, DMSO-d6) δ 5.55-5.3 (m, 2H), 5.3-5.0 (m, 11H), 4.7-4.3 (m, 2H), 3.8-3.6 (m, 6H), 3.45-3.3 (m, 4H), 2.07 (s, 6H), 1.5-1.35 (m, 36H), 1.33 (s, 9H). MS m/z [M + NH$_4$]$^+$ 1284.3. |

This specification has been described with reference to embodiments of the invention. However, one of ordinary skill in the art appreciates that various modifications and changes can be made without departing from the scope of the invention as set forth herein. Accordingly, the specification is to be regarded in an illustrative rather than a restrictive sense, and all such modifications are intended to be included within the scope of invention.

Example 49. Non-Limiting Examples of Compounds of the Present Invention

Table 8A, Table 8B, Table 8C, Table 8D, Table 8E present illustrative compounds of the present invention. Table 8F presents characterization data for select compounds of the present invention.

What is claimed is:

1. A compound of the formula:

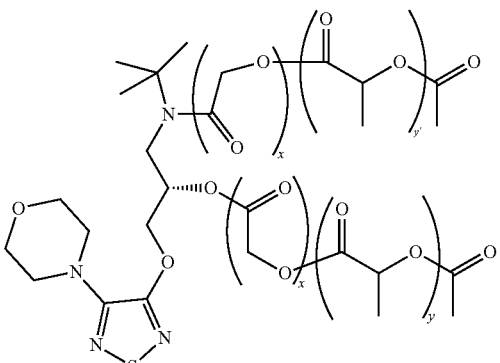

or a pharmaceutically acceptable salt thereof;
wherein x and x' are 1; and
y and y' are selected from 2, 3, 4, 5, and 6.

2. The compound of claim 1, wherein y and y' are independently selected from 2, 3, and 4, or a pharmaceutically acceptable salt thereof.

3. The compound of claim 2, wherein y is 2 and y' is 2.
4. The compound of claim 2, wherein y is 2 and y' is 3.
5. The compound of claim 2, wherein y is 2 and y' is 4.
6. The compound of claim 2, wherein y is 3 and y' is 2.
7. The compound of claim 2, wherein y is 3 and y' is 3.
8. The compound of claim 2, wherein y is 3 and y' is 4.
9. The compound of claim 2, wherein y is 4 and y' is 2.
10. The compound of claim 2, wherein y is 4 and y' is 3.
11. The compound of claim 2 wherein y is 4 and y' is 4.

* * * * *